United States Patent
Bacon et al.

(10) Patent No.: US 11,066,414 B2
(45) Date of Patent: *Jul. 20, 2021

(54) COT MODULATORS AND METHODS OF USE THEREOF

(71) Applicant: Gilead Sciences, Inc., Foster City, CA (US)

(72) Inventors: Elizabeth M. Bacon, Burlingame, CA (US); Gayatri Balan, Bellevue, WA (US); Chien-Hung Chou, Dublin, CA (US); Christopher T. Clark, Seattle, WA (US); Jeromy J. Cottell, Redwood City, CA (US); Musong Kim, Bellevue, WA (US); Thorsten A. Kirschberg, San Carlos, CA (US); John O. Link, San Francisco, CA (US); Gary Phillips, Issaquah, WA (US); Scott D. Schroeder, Union City, CA (US); Neil H. Squires, San Francisco, CA (US); Kirk L. Stevens, Bothell, WA (US); James G. Taylor, Burlingame, CA (US); William J. Watkins, Saratoga, CA (US); Nathan E. Wright, Foster City, CA (US); Sheila M. Zipfel, San Mateo, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/717,074

(22) Filed: Dec. 17, 2019

(65) Prior Publication Data

US 2020/0123172 A1 Apr. 23, 2020

Related U.S. Application Data

(63) Continuation of application No. 15/891,163, filed on Feb. 7, 2018, now abandoned, which is a continuation of application No. 15/199,534, filed on Jun. 30, 2016, now abandoned.

(60) Provisional application No. 62/269,060, filed on Dec. 17, 2015, provisional application No. 62/189,158, filed on Jul. 6, 2015.

(51) Int. Cl.
| | | |
|---|---|---|
| *C07D 401/14* | (2006.01) | |
| *C07D 498/04* | (2006.01) | |
| *C07D 405/14* | (2006.01) | |
| *C07D 413/14* | (2006.01) | |
| *C07D 401/12* | (2006.01) | |
| *C07D 409/14* | (2006.01) | |
| *C07D 417/14* | (2006.01) | |
| *C07D 471/04* | (2006.01) | |
| *C07D 495/04* | (2006.01) | |
| *C07B 59/00* | (2006.01) | |

(52) U.S. Cl.
CPC .......... *C07D 498/04* (2013.01); *C07B 59/002* (2013.01); *C07D 401/12* (2013.01); *C07D 401/14* (2013.01); *C07D 405/14* (2013.01); *C07D 409/14* (2013.01); *C07D 413/14* (2013.01); *C07D 417/14* (2013.01); *C07D 471/04* (2013.01); *C07D 495/04* (2013.01); *C07B 2200/05* (2013.01)

(58) Field of Classification Search
CPC .................................................. C07D 401/14
See application file for complete search history.

(56) References Cited

U.S. PATENT DOCUMENTS

| | | |
|---|---|---|
| 3,845,770 A | 11/1974 | Theeuwes et al. |
| 4,326,525 A | 4/1982 | Swanson et al. |
| 4,902,514 A | 2/1990 | Barclay et al. |
| 4,992,445 A | 2/1991 | Lawter et al. |
| 5,001,139 A | 3/1991 | Lawter et al. |
| 5,023,252 A | 6/1991 | Hseih |
| 5,616,345 A | 4/1997 | Geoghegan et al. |
| 7,297,795 B2 | 11/2007 | Sutherland et al. |
| 7,432,279 B2 | 10/2008 | Green et al. |
| 7,741,354 B2 | 6/2010 | Thormann et al. |
| 8,008,481 B2 | 8/2011 | Ericsson et al. |
| 9,815,818 B2 * | 11/2017 | Bacon ..................... A61P 35/00 |
| 9,878,995 B2 | 1/2018 | Bacon et al. |
| 9,878,996 B2 * | 1/2018 | Silverman ............ C07D 401/14 |
| 10,059,695 B2 | 8/2018 | Balan et al. |
| 10,316,017 B2 | 6/2019 | Bacon et al. |
| 10,577,352 B2 | 3/2020 | Balan et al. |
| 2005/0043537 A1 | 2/2005 | Sutherland et al. |
| 2006/0264460 A1 | 11/2006 | Green et al. |
| 2013/0225579 A1 | 8/2013 | Zhang et al. |
| 2015/0297573 A1 | 10/2015 | Dalle et al. |
| 2017/0152240 A1 | 6/2017 | Bacon et al. |
| 2017/0268069 A1 | 9/2017 | Garraway et al. |

(Continued)

FOREIGN PATENT DOCUMENTS

| | | |
|---|---|---|
| WO | WO-1998/43960 A1 | 10/1998 |
| WO | WO 00/18740 | 4/2000 |

(Continued)

OTHER PUBLICATIONS

Chemical Abstract Registry No. 1349435-18-2, indexed in the Registry File on STN CAS Online Dec. 6, 2011.

(Continued)

*Primary Examiner* — Rei Tsang Shiao

(74) *Attorney, Agent, or Firm* — Fish & Richardson P.C.

(57) ABSTRACT

The present disclosure relates generally to modulators of Cot (cancer Osaka thyroid) and methods of use and manufacture thereof.

9 Claims, No Drawings

(56) References Cited

U.S. PATENT DOCUMENTS

| | | |
|---|---|---|
| 2017/0362201 A1 | 12/2017 | Bacon et al. |
| 2018/0237455 A1 | 8/2018 | Bacon et al. |
| 2019/0016705 A1 | 1/2019 | Balan et al. |
| 2020/0392170 A1 | 12/2020 | Canales et al. |

FOREIGN PATENT DOCUMENTS

| | | |
|---|---|---|
| WO | WO-2005/019201 A2 | 3/2005 |
| WO | WO 2005/082891 | 9/2005 |
| WO | WO-2006/124692 A2 | 11/2006 |
| WO | WO-2008/055950 A1 | 5/2008 |
| WO | WO-2017/007689 A1 | 1/2017 |
| WO | WO-2017/007694 A1 | 1/2017 |
| WO | WO-2018/005435 A1 | 1/2018 |
| WO | WO 2020/252151 | 12/2020 |

OTHER PUBLICATIONS

Cohen, P. et al. (2009), "Targeting protein kinases for the development of anti-inflammatory drugs", Curr Opin Cell Biol., 21:317-24.

Cusack, K. et al. (2009) "Identification of a selective thieno[2,3-c]pyridine inhibitor of COT kinase and TNF-∝ production" *Bioorganic & Medicinal Chemistry Letters* 19:1722-25.

Detz, R. et al. (2008) "Enantioselective Copper-Catalyzed Propargylic Amination" *Angew. Chem. Int. Ed.* 47:3777-80.

Eisenberg, R. et al. (2009), "Why can't we find a new treatment for SLE?", J Autoimmun, 32:223-30.

Exam Report dated Nov. 30, 2018 for Pakastani Appl. No. 401/2016.

Exam Report dated Dec. 21, 2018 for New Zealand Appl. No. 738525.

Exam Report dated Jul. 25, 2019 for Indian Appl. No. 201817004204.

Exam Report dated Oct. 24, 2019 for Australian Appl. No. 2019203122.

Gantke, T. et al. (2010) "Regulation and function of TPL-2, an IkB kinase-regulated MAP kinase kinase kinase" Cell Res. 21(1):131-45.

Garofalo, A. et al. (2013) "Discovery of 4-alkylamino-7-aryl-3-cyanoquinoline LRRK2 kinase inhibitors" Bioorganic & Medicianl Chemistry Letters 23:1974-1977.

Gavrin, L. et al. (2005) "Inhibition of Tpl2 kinase and TNF-∝ production with 1,7-naphthyridine-3-carbonitriles: Synthesis and structure-activity relationships" Bioorganic & Medicinal Chemistry Letters 15:5288-5292.

George, D. et al. (2008) "Discovery of thieno[2,3-c]pyridines as potent COT inhibitors" Bioorganic & Medicinal Chemistry Letters 18:4952-4955.

George, D. et al. (2009) "Cot/Tpl-2 Protein Kinase as a Target for the Treatment of Inflammatory Disease" Current Topics in Medicinal Chemistry 9:611-622.

Gianatassio, R. et al. (2016) "Strain Release Amination" Science 351(6270):241-246.

Glatthar, R. et al. (2016) "Discovery of Imidazoquinolines as a Novel Class of Potent, Selective, and in Vivo Efficacious Cancer Osaka Thyroid (COT) Kinase Inhibitors" Journal of Medicinal Chemistry 59:7544-7560.

Goyal, R. et al.(2011), "Models for anti-inflammatory activity of 8-substituted-4-anilino-6-aminoquinoline-3-carbonitriles", Med Chem Res, 21:1044-55.

Green, N. et al. (2007) "Inhibitors of Tumor Progression Loci-2 (Tpl2) Kinase and Tumor Necrosis Factor ∝ (Tnf-∝) Production: Selectivity and in Vivo Antiinflammatory Activity of Novel 8-Substituted-4-anilino-6-aminoquinoline-3-carbonitriles" J. Med. Chem. 50:4728-4745.

Gupta, B. et al., (1988) "Homolytic displacement at carbon. Part 3. First example of alpha-attack on the allenyl- and prop-2-ynyl-cobaloximes" *J. Chem. Soc.* 1377-1383.

Hall, J. et al. (2007) "Pharmacologic Inhibition of Tpl2 Blocks Inflammatory Responses in Primary Human Monocytes, Synoviocytes, and Blood" The Journal of Biological Chemistry 282(46):33295-33304.

Hirata, K. et al. (2010) "Inhibition of tumor progression locus 2 protein kinase decreases lipopolysaccharide-induced tumor necrosis factor alpha production due to the inhibition of the tip-associated protein induction in RAW264.7 cells", Biol Pharm Bull, 33(7):1233-7.

Hu, Y. et al. (2006) "Inhibition of Tpl2 kinase and TNFa production with quinoline-3-carbonitriles for the treatment of rheumatoid arthritis" Bioorganic & Medicinal Chemistry Letters 16:6067-6072.

Hu, Y. et al. (2011) "Discovery of indazoles as inhibitors of Tpl2 kinase" Bioorganic & Medicinal Chemistry Letters 1-4 (article in press; doi: 10.1016).

Int'l Search Report—Written Opinion dated Aug. 16, 2016 for PCT/US2016/040520.

Int'l Search Report—Written Opinion dated Sep. 23, 2016 for PCT/US2016/040552.

Int'l Search Report—Written Opinion dated Sep. 20, 2017 for PCT/US2017/039418.

Kaila, N. et al. (2007) "Identification of a novel class of selective Tpl2 kinase inhibitors: 4-Alkylamino-[1,7]naphthyridine-3-carbonitriles" Bioorganic & Medicinal Chemistry 15:6425-6442.

Kitamura, M. et al. (2014) "A reagent for safe and efficient diazo-transfer to primary amines: 2-azido-1,3-dimethylimidazolinium hexafluorophosphate" Org. Biomol. Chem. 12:4397-4406.

McMahon, G. et al., (2000) "VEGF Receptor Signaling in Tumor Angiogensis", The Oncologist, 5: 3-10.

Notice of Allowance dated Jun. 9, 2017 for U.S. Appl. No. 15/199,779.

Notice of Allowance dated Oct. 25, 2017 for U.S. Appl. No. 15/429,086.

Notice of Allowance dated Apr. 26, 2018 for U.S. Appl. No. 15/634,314.

Notice of Allowance dated Mar. 14, 2019 for U.S. Appl. No. 15/697,755.

Office Action dated Mar.23, 2017 for U.S. Appl. No. 15/429,086.

Office Action dated Jun. 30, 2017 for U.S. Appl. No. 15/429,086.

Office Action dated Sep. 7, 2017 for U.S. Appl. No. 15/199,534.

Office action dated Oct. 18, 2017 for Taiwan Appl. No. 105121281.

Office Action dated Dec. 18, 2017 for U.S. Appl. No. 15/634,314.

Office Action dated Jul. 5, 2018 for U.S. Appl. No. 15/697,755.

Office Action dated Feb. 14, 2019 for Chilean Appl. No. 201703356.

Office Action dated Apr. 25, 2019 for Panamanian Appl. No. 91923.

Office Action dated Jun. 19, 2019 for U.S. Appl. No. 16/045,518.

Office Action dated Aug. 2, 2019 for Mexican Appl No. MX/a/2017/004737.

Office Action dated Aug. 7, 2019 for Taiwanese Appl No. 107117905.

Office Action dated Aug. 26, 2019 for India Appl. No. 201817004197.

Office Action dated Sep. 27, 2019 for European Appl. No. 16741446.5.

Office Action dated Oct. 4, 2019 for U.S. Appl. No. 15/891,163.

Office Action dated Mar. 12, 2020 for Ukranian Appl. No. a201712984.

Office Action dated Jan. 10, 2018 for Colombian Appl. No. NC2017/0013351.

Pinedo, H.M. et al., (2000) "Translational Research: The Role of VEGF in Tumor Angiogensis", The Oncologist, 5: 1-2.

Preliminary Rejection dated Jun. 17, 2019 for Korean Appl. No. 10-2018-7003220.

PubChem Database (2006) 4-Chloro-3-cyano-7-ethoxy-6-nitroquinoline, CID11011305, 8 pages.

PubChem Database (2006) 4-Chloro-6-nitro-quinoline-3-carbonitrile, CID11085690, 7 pages.

PubChem Database (2006) 4-Chloro-7-methoxy-6-nitroquinoline-3-carbonitrile, CID11139975, 7 pages.

PubChem Database (2006) 4-Chloro-8-methoxy-6-nitro-quinoline-3-carbonitrile, CID11129151, 7 pages.

PubChem Database (2007) 4,8-Dichloro-6-nitroquinoline-3-carbonitrile, CID17759323, 7 pages.

PubChem Database (2007) 4-Chloro-8-methyl-6-nitro-3-quinolinecarbonitrile, CID22466621, 7 pages.

PubChem Database (2013) 4-Chloro-7-[3-(morpholin-4-yl)propoxy]-6-nitroquinoline-3-carbonitrile, CID71425067, 6 pages.

Restriction Requirement dated Feb. 16, 2017 for U.S. Appl. No. 15/199,534.

Restriction Requirement dated Mar. 8, 2017 for U.S. Appl. No. 15/199,779.

(56) References Cited

OTHER PUBLICATIONS

Restriction Requirement dated Aug. 11, 2017 for U.S. Appl. No. 15/634,314.
Restriction Requirement dated Mar. 26, 2018 for U.S. Appl. No. 15/697,755.
Restriction Requirement dated Jun. 29, 2018 for U.S. Appl. No. 15/891,163.
Restriction Requirement dated Feb. 8, 2019 for U.S. Appl. No. 16/045,518.
Search Report dated Feb. 5, 2019 for European Appl. No. 18186568.4.
Teli, M. et al. (2011) "Pharmacophore generation and atom-based 3D-QSAR of novel quinoline-3-carbonitrile derivatives as Tpl2 kinase inhibitors" *Journal of Enzyme Inhibition and Medicinal Chemistry,* 1-13.
Wissner, A. et al. (2004) "Syntheses and EGFR kinase inhibitory activity of 6-substituted-4-anilino [1,7] and [1,8] naphthyridine-3-carbonitriles" *Bioorg Med Checm Lett.* 14(6):1411-6.
Wu, J. et al. (2009) "Selective inhibitors of tumor progression loci-2 (Tpl2) kinase with potent inhibition of TNF-∝ production in human whole blood" Bioorganic & Medicinal Chemistry Letters 19:3485-3488.
Zhu, L. et al., (2010), "Anti-TNF-alpha therapies in systemic lupus erythematosus", J Biomed Biotechnol., Article ID: 465898.
Akriviadis, E. et al. (2016) "Treatment of alcoholic hepatitis: is this a "dead-end"?" Ann Gastroenterol., 29(2): 236-237.
Chemical Abstract Registry No. 1092351-39-7, dated Dec. 31, 2008, retrieved on Mar. 25, 2020.
Chemical Abstract Registry No. 1415564-65-6, dated Dec. 27, 2012, retrieved on Mar. 25, 2020.
Exam Report in Pakistani Appln. No. 401/2016, dated Nov. 30, 2019, 2 pages.
Foster, A. (1984) "Deuterium Isotope Effects in Studies of Drug Metabolism," Trends Pharmacol. Sci., 5(12):524-527.
GenBank Accession No. NP_004985, "matrix metalloproteinase-9 preproprotein [*Homo sapiens*]," Jul. 4, 2020, 3 pages.
Green, N. et al. (2007) "Inhibitors of Tumor Progression Loci-2 (Tpl2) Kinase and Tumor Necrosis Factor oc (Tnf-oc) Production: Selectivity and in Vivo Anti-inflammatory Activity of Novel 8-Substituted-4-anilino-6-aminoquinoline-3-carbonitriles" J. Med. Chem. 50:4728-4745.
Gu, Z. et al. (2005) "A highly specific inhibitor of matrix metalloproteinase-9 rescues laminin from proteolysis and neurons from apoptosis in transient focal cerebral ischemia," The Journal of Neuroscience, 25(27):6401-6408.
Gupta, B. et al. (1988) "Homolytic displacement at carbon. Part 3. First example of alpha-attack on the allenyl- and prop-2-ynyl-cobaloximes" J. Chem. Soc., Perkin Trans. 2, 1377-1383.
Guyatt, G. et al.(1989) "A new measure of health status for clinical trials in inflammatory bowel disease," Gastroenterology, 96:804-810.
Nathubhai, A. et al. (2011) "N3-alkylation during formation of quinazolin-4-ones from condensation of anthranilamides and orthoamides," Organic and Biomolecular Chemistry, 9(17):6089-6099.
Office Action dated Aug. 22, 2019 for U.S. Appl. No. 16/391,673, 7 pages.
Office Action in AR Appln. No. 20160102051, dated Jun. 1, 2020, 7pages (with English translation).
Office Action in ARIPO Appln. No. AP/P/2017/010402, dated Jun. 16, 2020, 5 pages.
Office Action in EP Appln. No. 18186568.4, dated May 5, 2020, 4 pages.
Office Action in GC Appln. No. 2016-31644, dated May 6, 2020, 3 pages.
Office Action in JP Appln. No. 2018-171794, dated Jun. 23, 2020, 6 pages (with English translation).
Office Action in JP Appln. No. 2019-137759, dated Jun. 16, 2020, 4 pages (with English translation).
Office Action in PH Appln. No. 1-2018-500031, dated Jun. 23, 2020, 4 pages.
Office Action in SA Appln. No. 517381350, dated Sep. 20, 2020, 7 pages (with English translation).
PCT International Search Report and Written Opinion in International Appln. No. PCT/US2020/037214, dated Aug. 25, 2020, 13 pages.
Perugorria, M. J. et al., "Tumor progression locus 2/Cot is required for activation of extracellular regulated kinase in liver injury and toll-like receptor-induced TIMP-1 gene transcription in hepatic stellate cells in mice," Hepatology, 2013, 57:1238-1249.
Vyrla, D. et. al. (2016) "TPL2 Kinase Is a Crucial Signaling Factor and Mediator of NKT Effector Cytokine Expression in Immune-Mediated Liver Injury," The Journal of Immunology, 196(10):4298-310.
Truelove, S. C. et al. (1955) "Cortisone in ulcerative colitis; final report on a therapeutic trial," Br Med J., 2(4947):1041-1048.
Office Action in CN Appln. No. 201910292757.5, dated Dec. 23, 2020, 15 pages (with English translation).
Office Action in CR Appln. No. 2017-0599, dated Oct. 28, 2020, 17 pages (with English translation).
Office Action in DO Appln. No. 2017-0311, dated Aug. 24, 2020, 5 pages (with English translation).
Office Action in MX Appln. No. MX_a_2020-000232, dated Oct. 8, 2020, 5 pages (with English translation).

* cited by examiner

COT MODULATORS AND METHODS OF USE THEREOF

CROSS REFERENCE TO RELATED APPLICATIONS

This application is a Continuation of application Ser. No. 15/891,163 filed on Feb. 7, 2018. Application Ser. No. 15/891,163 is a Continuation of application Ser. No. 15/199,534 filed on Jun. 30, 2016. Application Ser. No. 15/199,534 claims the benefit of U.S. Provisional Application 62/269,060 filed on Dec. 17, 2015. Application Ser. No. 15/199,534 claims the benefit of U.S. Provisional Application 62/189,158 filed on Jul. 6, 2015. The entire contents of these applications are incorporated herein by reference in their entirety.

FIELD

The present disclosure relates generally to modulators of Cot (cancer Osaka thyroid) and methods of use and manufacture thereof.

BACKGROUND

Cot (cancer Osaka thyroid) protein is a serine/threonine kinase that is a member of the MAP kinase kinase kinase (MAP3K) family. It is also known as "Tpl2" (tumor progression locus), "MAP3K8" (mitogen-activated protein kinase kinase kinase 8) or "EST" (Ewing sarcoma transformant). Cot was identified by its oncogenic transforming activity in cells and has been shown to regulate oncogenic and inflammatory pathways.

Cot is known to be upstream in the MEK-ERK pathway and is essential for LPS induced tumor necrosis factor-α (TNF-α) production. Cot has been shown to be involved in both production and signaling of TNFα. TNFα is a pro-inflammatory cytokine and plays an important role in inflammatory diseases, such as rheumatoid arthritis (RA), multiple sclerosis (MS), inflammatory bowel disease (IBD), diabetes, sepsis, psoriasis, misregulated TNFα expression and graft rejection.

Agents and methods that modulate the expression or activity of Cot, therefore, may be useful for preventing or treating such diseases.

SUMMARY

The present disclosure provides compounds that modulate the expression or activity of Cot. The disclosure also provides compositions, including pharmaceutical compositions, kits that include the compounds, and methods of using (or administering) and making the compounds. The compounds provided herein are useful in treating diseases, disorders, or conditions that are mediated by Cot. The disclosure also provides compounds for use in therapy. The disclosure further provides compounds for use in a method of treating a disease, disorder, or condition that is mediated by Cot. Moreover, the disclosure provides uses of the compounds in the manufacture of a medicament for the treatment of a disease, disorder or condition that is mediated by (or meadiated, at least in part, by) Cot.

In one aspect, provided is a compound having the structure of Formula I:

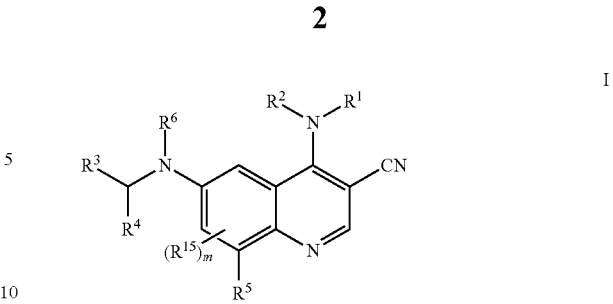

wherein
$R^1$ is hydrogen, —O—$R^7$, —N($R^8$)($R^9$), —C(O)—$R^7$, —S(O)$_2$—$R^7$, —C$_{1-9}$ alkyl, C$_{2-6}$ alkenyl, C$_{2-6}$ alkynyl, C$_{3-15}$ cycloalkyl, heterocyclyl, aryl, or heteroaryl;
wherein each C$_{1-9}$ alkyl, C$_{2-6}$ alkenyl, C$_{2-6}$ alkynyl, C$_{3-15}$ cycloalkyl, heterocyclyl, aryl, and heteroaryl may be optionally substituted with one to four $Z^1$;
$R^2$ is hydrogen, —C(O)—$R^7$, —C(O)O—$R^7$, —C(O)N($R^7$)$_2$, C$_{1-9}$ alkyl, C$_{2-6}$ alkenyl, C$_{2-6}$ alkynyl, C$_{1-6}$ haloalkyl, C$_{3-15}$ cycloalkyl, aryl, heterocyclyl, or heteroaryl;
wherein each C$_{1-9}$ alkyl, C$_{2-6}$ alkenyl, C$_{2-6}$ alkynyl, C$_{1-6}$ haloalkyl, C$_{3-15}$ cycloalkyl, aryl, heterocyclyl, and heteroaryl may be optionally substituted with one to four $Z^2$;
or $R^1$ and $R^2$ together with the nitrogen to which they are attached to form a heterocyclyl or heteroaryl, wherein each heterocyclyl or heteroaryl is optionally substituted with one to four $Z^2$;
$R^3$ is heterocyclyl or heteroaryl, wherein each heterocyclyl or heteroaryl is optionally substituted with one to four $Z^3$;
$R^4$ is heterocyclyl or heteroaryl, wherein each heterocyclyl or heteroaryl is optionally substituted with one to four $Z^4$;
$R^5$ is hydrogen, halo, —CN, —NO$_2$, —N($R^8$)($R^9$), —S(O)—$R^7$, —S(O)$_2$$R^7$, —S(O)$_2$N($R^7$)$_2$, —C(O)$R^7$, —OC(O)—$R^7$, —C(O)O—$R^7$, —OC(O)O—$R^7$, —OC(O)N($R^{10}$)($R^{11}$), —C(O)N($R^7$)$_2$, —N($R^7$)C(O)($R^7$), C$_{1-9}$ alkyl, C$_{2-6}$ alkenyl, C$_{2-6}$ alkynyl, C$_{1-9}$ alkylthio, C$_{1-6}$ haloalkyl, C$_{3-15}$ cycloalkyl, aryl, heterocyclyl, or heteroaryl;
wherein each C$_{1-9}$ alkyl, C$_{2-6}$ alkenyl, C$_{2-6}$ alkynyl, C$_{1-9}$ alkylthio, C$_{1-6}$ haloalkyl, C$_{3-15}$ cycloalkyl, aryl, heterocyclyl, and heteroaryl may be optionally substituted with one to four $Z^5$;
$R^6$ is hydrogen, —C(O)—$R^7$, —C(O)O—$R^7$, —C(O)N($R^7$)$_2$, C$_{1-9}$ alkyl, C$_{2-6}$ alkenyl, C$_{2-6}$ alkynyl, C$_{1-6}$ haloalkyl, C$_{3-15}$ cycloalkyl, aryl, heterocyclyl, or heteroaryl;
wherein each C$_{1-9}$ alkyl, C$_{2-6}$ alkenyl, C$_{2-6}$ alkynyl, C$_{1-6}$ haloalkyl, C$_{3-15}$ cycloalkyl, aryl, heterocyclyl, and heteroaryl may be optionally substituted with one to four $Z^6$;
each $R^7$ is independently hydrogen, C$_{1-9}$ alkyl, C$_{2-6}$ alkenyl, C$_{2-6}$ alkynyl, C$_{1-6}$ haloalkyl, C$_{3-15}$ cycloalkyl, aryl, heterocyclyl, or heteroaryl;
wherein each C$_{1-9}$ alkyl, C$_{2-6}$ alkenyl, C$_{2-6}$ alkynyl, C$_{1-6}$ haloalkyl, C$_{3-15}$ cycloalkyl, aryl, heterocyclyl, and heteroaryl may be optionally substituted with one to four $Z^7$;
$R^8$ and $R^9$ at each occurrence are independently hydrogen, —S(O)$_2$$R^{10}$, —C(O)—$R^{10}$, —C(O)O—$R^{10}$, —C(O)N($R^{10}$)($R^{11}$), C$_{1-9}$ alkyl, C$_{2-6}$ alkenyl, C$_{2-6}$ alkynyl, C$_{1-6}$ haloalkyl, C$_{3-15}$ cycloalkyl, aryl, heterocyclyl, or heteroaryl;
wherein each C$_{1-9}$ alkyl, C$_{2-6}$ alkenyl, C$_{2-6}$ alkynyl, C$_{1-6}$ haloalkyl, C$_{3-15}$ cycloalkyl, aryl, heterocyclyl, or heteroaryl may be optionally substituted with one to four $Z^8$;

$R^{10}$ and $R^{11}$ at each occurrence are independently hydrogen, $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl, wherein each $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, and heteroaryl optionally is substituted with one to four $Z^{1b}$;

each $Z^1$, $Z^2$, $Z^3$, $Z^4$, $Z^5$, $Z^6$, $Z^7$, and $Z^8$ is independently hydrogen, oxo, halo, —$NO_2$, —$N_3$, —CN, thioxo, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —C(O)—$R^{12}$, —C(O)O—$R^{12}$, —C(O)—N($R^{13}$)($R^{14}$), —N($R^{13}$)($R^{14}$), —N($R^{13}$)$_2$($R^{14}$)$^+$, —N($R^{12}$)C(O)—$R^{12}$, —N($R^{12}$)C(O)O—$R^{12}$, —N($R^{12}$)C(O)N($R^{13}$)($R^{14}$), —N($R^{12}$)S(O)$_2$($R^{12}$), —N$R^{12}$S(O)$_2$N($R^{13}$)($R^{14}$), —N$R^{12}$S(O)$_2$O($R^{12}$), —OC(O)$R^{12}$, —OC(O)—N($R^{13}$)($R^{14}$), —P(O)(O$R^{12}$)$_2$, —OP(O)(O$R^{12}$)$_2$, —CH$_2$P(O)(O$R^{12}$)$_2$, —OCH$_2$P(O)(O$R^{12}$)$_2$, —C(O)OCH$_2$P(O)(O$R^{12}$)$_2$, —P(O)($R^{12}$)(O$R^{12}$), —OP(O)($R^{12}$)(O$R^{12}$), —CH$_2$P(O)($R^{12}$)(O$R^{12}$), —OCH$_2$P(O)($R^{12}$)(O$R^{12}$), —C(O)OCH$_2$P(O)($R^{12}$)(O$R^{12}$), —P(O)(N($R^{12}$)$_2$)$_2$, —OP(O)(N($R^{12}$)$_2$)$_2$, —CH$_2$P(O)(N($R^{12}$)$_2$)$_2$, —OCH$_2$P(O)(N($R^{12}$)$_2$)$_2$, —C(O)OCH$_2$P(O)(N($R^{12}$)$_2$)$_2$, —P(O)(N($R^{12}$)$_2$)(O$R^{12}$), —OP(O)(N($R^{12}$)$_2$)(O$R^{12}$), —CH$_2$P(O)(N($R^{12}$)$_2$)(O$R^{12}$), —OCH$_2$P(O)(N($R^{12}$)$_2$)(O$R^{12}$), —C(O)OCH$_2$P(O)(N($R^{12}$)$_2$)(O$R^{12}$), —P(O)($R^{12}$)(N($R^{12}$)$_2$), —OP(O)($R^{12}$)(N($R^{12}$)$_2$), —CH$_2$P(O)($R^{12}$)(N($R^{12}$)$_2$), —OCH$_2$P(O)($R^{12}$)(N($R^{12}$)$_2$), —C(O)OCH$_2$P(O)($R^{12}$)(N($R^{12}$)$_2$), —Si($R^{12}$)$_3$, —S—$R^{12}$, —S(O)$R^{12}$, —S(O)(NH)$R^{12}$, —S(O)$_2R^{12}$ or —S(O)$_2$N($R^{13}$)($R^{14}$);

wherein any alkyl, alkenyl, alkynyl, cycloalkyl, haloalkyl, aryl, heteroaryl or heterocyclyl is optionally substituted with one to four $Z^{1a}$ groups;

each $Z^{1a}$ is independently oxo, halo, thioxo, —$NO_2$, —CN, —$N_3$, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O—$R^{12}$, —C(O)$R^{12}$, —C(O)O—$R^{12}$, —C(O)N($R^{13}$)($R^{14}$), —N($R^{13}$)($R^{14}$), —N($R^{13}$)$_2$($R^{14}$)$^+$, —N($R^{12}$)—C(O)$R^{12}$, —N($R^{12}$)C(O)O($R^{12}$), —N($R^{12}$)C(O)N($R^{13}$)($R^{14}$), —N($R^{12}$)S(O)$_2$($R^{12}$), —N($R^{12}$)S(O)$_2$—N($R^{13}$)($R^{14}$), —N($R^{12}$)S(O)$_2$O($R^{12}$), —OC(O)$R^{12}$, —OC(O)O$R^{12}$, —OC(O)—N($R^{13}$)($R^{14}$), —Si($R^{12}$)$_3$, —S—$R^{12}$, —S(O)$R^{12}$, —S(O)(NH)$R^{12}$, —S(O)$_2R^{12}$ or —S(O)$_2$N($R^{13}$)($R^{14}$);

wherein any alkyl, alkenyl, alkynyl, cycloalkyl, aryl, heteroaryl or heterocyclyl is optionally substituted with one to four $Z^{1b}$ groups;

each $R^{12}$ is independently hydrogen, $C_{1-9}$ alkyl, $C_{2-6}$ alkenyl, $C_{2-6}$ alkynyl, $C_{3-15}$ cycloalkyl, aryl, heteroaryl or heterocyclyl, wherein any alkyl, alkenyl, alkynyl, cycloalkyl, aryl, heteroaryl or heterocyclyl is optionally substituted with one to four $Z^{1b}$ groups;

$R^{13}$ and $R^{14}$ at each occurrence are each independently hydrogen, $C_{1-9}$ alkyl, $C_{2-6}$ alkenyl, $C_{2-6}$ alkynyl, $C_{3-15}$ cycloalkyl, aryl, heteroaryl or heterocyclyl;

wherein any alkyl, alkenyl, alkynyl, cycloalkyl, aryl, heteroaryl or heterocyclyl is optionally substituted with one to four $Z^{1b}$ groups, or $R^{13}$ and $R^{14}$ together with the nitrogen to which they are attached form a heterocyclyl, wherein said heterocyclyl is optionally substituted with one to four $Z^{1b}$ groups;

each $R^{15}$ is independently halo, —CN, —$NO_2$, —O—$R^7$, —N($R^8$)($R^9$), —S(O)—$R^7$, —S(O)$_2R^7$, —S(O)$_2$N($R^7$)$_2$, —C(O)$R^7$, —OC(O)—$R^7$, —C(O)O—$R^7$, —OC(O)O—$R^7$, —OC(O)N($R^{10}$)($R^{11}$), —C(O)N($R^7$)$_2$, —N(R)C(O) ($R^7$), $C_{1-9}$ alkyl, $C_{2-6}$ alkenyl, $C_{2-6}$ alkynyl, $C_{1-9}$ alkylthio, $C_{1-6}$ haloalkyl, $C_{3-15}$ cycloalkyl, aryl, heterocyclyl, or heteroaryl; and each $Z^{1b}$ is independently oxo, thioxo, hydroxy, halo, —$NO_2$, —$N_3$, —CN, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O($C_{1-9}$ alkyl), —O($C_{2-6}$ alkenyl), —O($C_{2-6}$ alkynyl), —O($C_{3-15}$ cycloalkyl), —O($C_{1-8}$ haloalkyl), —O(aryl), —O(heteroaryl), —O(heterocyclyl), —$NH_2$, —NH($C_{1-9}$ alkyl), —NH($C_{2-6}$ alkenyl), —NH($C_{2-6}$ alkynyl), —NH($C_{3-15}$ cycloalkyl), —NH($C_{1-8}$ haloalkyl), —NH(aryl), —NH(heteroaryl), —NH(heterocyclyl), —N($C_{1-9}$ alkyl)$_2$, —N($C_{3-15}$ cycloalkyl)$_2$, —N($C_{2-6}$ alkenyl)$_2$, —N($C_{2-6}$ alkynyl)$_2$, —N($C_{3-15}$ cycloalkyl)$_2$, —N($C_{1-8}$ haloalkyl)$_2$, —N(aryl)$_2$, —N(heteroaryl)$_2$, —N(heterocyclyl)$_2$, —N($C_{1-9}$ alkyl)($C_{3-15}$ cycloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)($C_{1-8}$ haloalkyl), —N($C_{1-9}$ alkyl)(aryl), —N($C_{1-9}$ alkyl)(heteroaryl), —N($C_{1-9}$ alkyl)(heterocyclyl), —C(O)($C_{1-9}$ alkyl), —C(O)($C_{2-6}$ alkenyl), —C(O)($C_{2-6}$ alkynyl), —C(O)($C_{3-15}$ cycloalkyl), —C(O)($C_{1-8}$ haloalkyl), —C(O)(aryl), —C(O)(heteroaryl), —C(O)(heterocyclyl), —C(O)O($C_{1-9}$ alkyl), —C(O)O($C_{2-6}$ alkenyl), —C(O)O($C_{2-6}$ alkynyl), —C(O)O($C_{3-15}$ cycloalkyl), —C(O)O($C_{1-8}$ haloalkyl), —C(O)O(aryl), —C(O)O(heteroaryl), —C(O)O(heterocyclyl), —C(O)$NH_2$, —C(O)NH($C_{1-9}$ alkyl), —C(O)NH($C_{2-6}$ alkenyl), —C(O)NH($C_{2-6}$ alkynyl), —C(O)NH($C_{3-15}$ cycloalkyl), —C(O)NH($C_{1-8}$ haloalkyl), —C(O)NH(aryl), —C(O)NH(heteroaryl), —C(O)NH(heterocyclyl), —C(O)N($C_{1-9}$ alkyl)$_2$, —C(O)N($C_{3-15}$ cycloalkyl)$_2$, —C(O)N($C_{2-6}$ alkenyl)$_2$, —C(O)N($C_{2-6}$ alkynyl)$_2$, —C(O)N($C_{3-15}$ cycloalkyl)$_2$, —C(O)N($C_{1-8}$ haloalkyl)$_2$, —C(O)N(aryl)$_2$, —C(O)N(heteroaryl)$_2$, —C(O)N(heterocyclyl)$_2$, —NHC(O)($C_{1-9}$ alkyl), —NHC(O)($C_{2-6}$ alkenyl), —NHC(O)($C_{2-6}$ alkynyl), —NHC(O)($C_{3-15}$ cycloalkyl), —NHC(O)($C_{1-8}$ haloalkyl), —NHC(O)(aryl), —NHC(O)(heteroaryl), —NHC(O)(heterocyclyl), —NHC(O)O($C_{1-9}$ alkyl), —NHC(O)O($C_{2-6}$ alkenyl), —NHC(O)O($C_{2-6}$ alkynyl), —NHC(O)O($C_{3-15}$ cycloalkyl), —NHC(O)O($C_{1-8}$ haloalkyl), —NHC(O)O(aryl), —NHC(O)O(heteroaryl), —NHC(O)O(heterocyclyl), —NHC(O)NH($C_{1-9}$ alkyl), —NHC(O)NH($C_{2-6}$ alkenyl), —NHC(O)NH($C_{2-6}$ alkynyl), —NHC(O)NH($C_{3-15}$ cycloalkyl), —NHC(O)NH($C_{1-8}$ haloalkyl), —NHC(O)NH(aryl), —NHC(O)NH(heteroaryl), —NHC(O)NH(heterocyclyl), —SH, —S($C_{1-9}$ alkyl), —S($C_{2-6}$ alkenyl), —S($C_{2-6}$ alkynyl), —S($C_{3-15}$ cycloalkyl), —S($C_{1-8}$ haloalkyl), —S(aryl), —S(heteroaryl), —S(heterocyclyl), —NHS(O)($C_{1-9}$ alkyl), —N($C_{1-9}$ alkyl)(S(O)($C_{1-9}$ alkyl), —S(O)N($C_{1-9}$ alkyl)$_2$, —S(O)($C_{1-9}$ alkyl), —S(O)(NH)($C_{1-9}$ alkyl), —S(O)($C_{2-6}$ alkenyl), —S(O)($C_{2-6}$ alkynyl), —S(O)($C_{3-15}$ cycloalkyl), —S(O)($C_{1-8}$ haloalkyl), —S(O)(aryl), —S(O)(heteroaryl), —S(O)(heterocyclyl), —S(O)$_2$($C_{1-9}$ alkyl), —S(O)$_2$($C_{2-6}$ alkenyl), —S(O)$_2$($C_{2-6}$ alkynyl), —S(O)$_2$($C_{3-15}$ cycloalkyl), —S(O)$_2$($C_{1-8}$ haloalkyl), —S(O)$_2$(aryl), —S(O)$_2$(heteroaryl), —S(O)$_2$(heterocyclyl), —S(O)$_2$NH($C_{1-9}$ alkyl), or —S(O)$_2$N($C_{1-9}$ alkyl)$_2$;

wherein any alkyl, cycloalkyl, aryl, heteroaryl, or heterocyclyl is optionally substituted with one to four halo, $C_{1-9}$ alkyl, $C_{1-8}$ haloalkyl, —OH, —$NH_2$, —NH($C_{1-9}$ alkyl), —NH($C_{3-15}$ cycloalkyl), —NH($C_{1-8}$ haloalkyl), —NH(aryl), —NH(heteroaryl), —NH(heterocyclyl), —N($C_{1-9}$ alkyl)$_2$, —N($C_{3-15}$ cycloalkyl)$_2$, —NHC(O) ($C_{3-15}$ cycloalkyl), —NHC(O)($C_{1-8}$ haloalkyl), —NHC(O)(aryl), —NHC(O)(heteroaryl), —NHC(O)(heterocyclyl), —NHC(O)O(C$_{1-9}$ alkyl), —NHC(O)O(C$_{2-6}$ alkynyl), —NHC(O)O(C$_{3-15}$ cycloalkyl), —NHC(O)O(C$_{1-8}$ haloalkyl), —NHC(O)O(aryl), —NHC(O)O(heteroaryl), —NHC(O)O(heterocyclyl), —NHC(O)NH(C$_{1-9}$ alkyl), —S(O)(NH)(C$_{1-9}$ alkyl), S(O)$_2$(C$_{1-9}$ alkyl), —S(O)$_2$(C$_{3-15}$ cycloalkyl), —S(O)$_2$(C$_{1-8}$ haloalkyl), —S(O)$_2$(aryl), —S(O)$_2$(heteroaryl), —S(O)$_2$(heterocyclyl), —S(O)$_2$NH(C$_{1-9}$ alkyl), —S(O)$_2$N(C$_{1-9}$ alkyl)$_2$, —O(C$_{3-15}$ cycloalkyl), —O(C$_{1-8}$ haloalkyl), —O(aryl), —O(heteroaryl), —O(heterocyclyl), or —O(C$_{1-9}$ alkyl); and m is 0, 1, or 2;

or a pharmaceutically acceptable salt, tautomer, stereoisomer, mixture of stereoisomers, prodrug, or deuterated analog thereof.

Some embodiments provide a method of using (or administering) the compounds of Formula I, or additional Formula (s) described throughout, in the treatment of a disease or condition in a mammal, particularly a human, that is amenable to treatment by an Cot modulator.

In certain embodiments, the disclosure provides pharmaceutical compositions comprising a therapeutically effective amount of a compound of the disclosure (e.g. a compound of Formula I or additional Formulas described throughout), and at least one pharmaceutically acceptable excipient.

DETAILED DESCRIPTION

Definitions and General Parameters

The following description sets forth exemplary methods, parameters and the like. It should be recognized, however, that such description is not intended as a limitation on the scope of the present disclosure but is instead provided as a description of exemplary embodiments.

As used in the present specification, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —C(O)NH$_2$ is attached through the carbon atom. A dash at the front or end of a chemical group is a matter of convenience; chemical groups may be depicted with or without one or more dashes without losing their ordinary meaning. A wavy line drawn through a line in a structure indicates a point of attachment of a group. Unless chemically or structurally required, no directionality is indicated or implied by the order in which a chemical group is written or named.

The prefix "C$_{u-v}$" indicates that the following group has from u to v carbon atoms. For example, "C$_{1-6}$ alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount±10%. In other embodiments, the term "about" includes the indicated amount±5%. In certain other embodiments, the term "about" includes the indicated amount±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., C$_{1-20}$ alkyl), 1 to 8 carbon atoms C$_{1-8}$ alkyl), 1 to 6 carbon atoms (i.e., C$_{1-6}$ alkyl), or 1 to 4 carbon atoms (i.e., C$_{1-4}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e. —(CH$_2$)$_3$CH$_3$), sec-butyl (i.e. —CH(CH$_3$)CH$_2$CH$_3$), isobutyl (i.e. —CH$_2$CH(CH$_3$)$_2$) and tert-butyl (i.e. —C(CH$_3$)$_3$); and "propyl" includes n-propyl (i.e. —(CH$_2$)$_2$CH$_3$) and isopropyl (i.e. —CH(CH$_3$)$_2$).

"Alkenyl" refers to an alkyl group containing at least one carbon-carbon double bond and having from 2 to 20 carbon atoms (i.e., C$_{2-20}$ alkenyl), 2 to 8 carbon atoms (i.e., C$_{2-8}$ alkenyl), 2 to 6 carbon atoms (i.e., C$_{2-6}$ alkenyl), or 2 to 4 carbon atoms (i.e., C$_{2-4}$ alkenyl). Examples of alkenyl groups include ethenyl, propenyl, butadienyl (including 1,2-butadienyl and 1,3-butadienyl).

"Alkynyl" refers to an alkyl group containing at least one carbon-carbon triple bond and having from 2 to 20 carbon atoms (i.e., C$_{2-20}$ alkynyl), 2 to 8 carbon atoms (i.e., C$_{2-8}$ alkynyl), 2 to 6 carbon atoms (i.e., C$_{2-6}$ alkynyl), or 2 to 4 carbon atoms (i.e., C$_{2-4}$ alkynyl). The term "alkynyl" also includes those groups having one triple bond and one double bond.

"Alkoxy" refers to the group "alkyl-O—". Examples of alkoxy groups include methoxy, ethoxy, n-propoxy, isopropoxy, n-butoxy, tert-butoxy, sec-butoxy, n-pentoxy, n-hexoxy, and 1,2-dimethylbutoxy.

"Haloalkoxy" refers to an alkoxy group as defined above, wherein one or more hydrogen atoms are replaced by a halogen.

"Alkylthio" refers to the group "alkyl-S—".

"Acyl" refers to a group —C(O)R, wherein R is hydrogen, alkyl, cycloalkyl, heterocyclyl, aryl, heteroalkyl, or heteroaryl; each of which may be optionally substituted, as defined herein. Examples of acyl include formyl, acetyl, cylcohexylcarbonyl, cyclohexylmethyl-carbonyl, and benzoyl.

"Amido" refers to both a "C-amido" group which refers to the group —C(O)NR$^y$R$^z$ and an "N-amido" group which refers to the group —NR$^y$C(O)R$^z$, wherein R$^y$ and R$^z$ are independently selected from the group consisting of hydrogen, alkyl, aryl, haloalkyl, or heteroaryl; each of which may be optionally substituted.

"Amino" refers to the group —NR$^y$R$^z$ wherein R$^y$ and R$^z$ are independently selected from the group consisting of hydrogen, alkyl, haloalkyl, aryl, or heteroaryl; each of which may be optionally substituted.

"Amidino" refers to C(NH)(NH$_2$).

"Aryl" refers to an aromatic carbocyclic group having a single ring (e.g. monocyclic) or multiple rings (e.g. bicyclic or tricyclic) including fused systems. As used herein, aryl has 6 to 20 ring carbon atoms (i.e., C$_{6-20}$ aryl), 6 to 12 carbon ring atoms (i.e., C$_{6-12}$ aryl), or 6 to 10 carbon ring atoms (i.e., C$_{6-10}$ aryl). Examples of aryl groups include phenyl, naphthyl, fluorenyl, and anthryl. Aryl, however, does not encompass or overlap in any way with heteroaryl defined below. If one or more aryl groups are fused with a heteroaryl, the resulting ring system is heteroaryl. If one or more aryl groups are fused with a heterocyclyl, the resulting ring system is heterocyclyl.

"Azido" refers to $N_3$.

"Carbamoyl" refers to both an "O-carbamoyl" group which refers to the group —O—C(O)NR$^y$R$^z$ and an "N-carbamoyl" group which refers to the group —NR$^y$C(O)OR$^z$, wherein R$^y$ and R$^z$ are independently selected from the group consisting of hydrogen, alkyl, aryl, haloalkyl, or heteroaryl; each of which may be optionally substituted.

"Carboxyl" refers to —C(O)OH.

"Carboxyl ester" refers to both —OC(O)R and —C(O)OR, wherein R is hydrogen, alkyl, cycloalkyl, heterocyclyl, aryl, heteroalkyl, or heteroaryl; each of which may be optionally substituted, as defined herein.

"Cyano" or "carbonitrile" refers to the group —CN.

"Cycloalkyl" refers to a saturated or partially unsaturated cyclic alkyl group having a single ring or multiple rings including fused, bridged, and spiro ring systems. The term "cycloalkyl" includes cycloalkenyl groups (i.e. the cyclic group having at least one double bond). As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Examples of cycloalkyl groups include cyclopropyl, cyclobutyl, cyclopentyl, and cyclohexyl.

"Guanidino" refers to —NHC(NH)(NH$_2$).

"Hydrazino" refers to —NHNH$_2$.

"Imino" refers to a group —C(NR)R, wherein each R is alkyl, cycloalkyl, heterocyclyl, aryl, heteroalkyl, or heteroaryl; each of which may be optionally substituted, as defined herein.

"Halogen" or "halo" includes fluoro, chloro, bromo, and iodo. "Haloalkyl" refers to an unbranched or branched alkyl group as defined above, wherein one or more hydrogen atoms are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include difluoromethyl (—CHF$_2$) and trifluoromethyl (—CF$_3$).

"Heteroalkyl" refers to an alkyl group in which one or more of the carbon atoms (and any associated hydrogen atoms) are each independently replaced with the same or different heteroatomic group. The term "heteroalkyl" includes unbranched or branched saturated chain having carbon and heteroatoms. By way of example, 1, 2 or 3 carbon atoms may be independently replaced with the same or different heteroatomic group. Heteroatomic groups include, but are not limited to, —NR—, —O—, —S—, —S(O)—, —S(O)$_2$—, and the like, where R is H, alkyl, aryl, cycloalkyl, heteroalkyl, heteroaryl or heterocyclyl, each of which may be optionally substituted. Examples of heteroalkyl groups include —OCH$_3$, —CH$_2$OCH$_3$, —SCH$_3$, —CH$_2$SCH$_3$, —NRCH$_3$, and —CH$_2$NRCH$_3$, where R is hydrogen, alkyl, aryl, arylalkyl, heteroalkyl, or heteroaryl, each of which may be optionally substituted. As used herein, heteroalkyl include 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to an aromatic group having a single ring, multiple rings, or multiple fused rings, with one or more ring heteroatoms independently selected from nitrogen, oxygen, and sulfur. As used herein, heteroaryl includes 1 to 20 ring carbon atoms (i.e., $C_{1-20}$ heteroaryl), 3 to 12 ring carbon atoms $C_{3-12}$ heteroaryl), or 3 to 8 carbon ring atoms (i.e., $C_{3-8}$ heteroaryl); and 1 to 5 heteroatoms, 1 to 4 heteroatoms, 1 to 3 ring heteroatoms, 1 to 2 ring heteroatoms, or 1 ring heteroatom independently selected from nitrogen, oxygen, and sulfur. Examples of heteroaryl groups include pyrimidinyl, purinyl, pyridyl, pyridazinyl, benzothiazolyl, and pyrazolyl. Examples of the fused-heteroaryl rings include, but are not limited to, benzo[d]thiazolyl, quinolinyl, isoquinolinyl, benzo[b]thiophenyl, indazolyl, benzo[d]imidazolyl, pyrazolo[1,5-a]pyridinyl, and imidazo[1,5-a]pyridinyl, where the heteroaryl can be bound via either ring of the fused system. Any aromatic ring, having a single or multiple fused rings, containing at least one heteroatom, is considered a heteroaryl regardless of the attachment to the remainder of the molecule (i.e., through any one of the fused rings). Heteroaryl does not encompass or overlap with aryl as defined above.

"Heterocyclyl" refers to a saturated or unsaturated cyclic alkyl group, with one or more ring heteroatoms independently selected from nitrogen, oxygen and sulfur. The term "heterocyclyl" includes heterocycloalkenyl groups (i.e. the heterocyclyl group having at least one double bond), bridged-heterocyclyl groups, fused-heterocyclyl groups, and spiro-heterocyclyl groups. A heterocyclyl may be a single ring or multiple rings wherein the multiple rings may be fused, bridged, or spiro. Any non-aromatic ring containing at least one heteroatom is considered a heterocyclyl, regardless of the attachment (i.e., can be bound through a carbon atom or a heteroatom). Further, the term heterocyclyl is intended to encompass any non-aromatic ring containing at least one heteroatom, which ring may be fused to an aryl or heteroaryl ring, regardless of the attachment to the remainder of the molecule. As used herein, heterocyclyl has 2 to 20 ring carbon atoms (i.e., $C_{2-20}$ heterocyclyl), 2 to 12 ring carbon atoms (i.e., $C_{2-12}$ heterocyclyl), 2 to 10 ring carbon atoms (i.e., $C_{2-10}$ heterocyclyl), 2 to 8 ring carbon atoms (i.e., $C_{2-8}$ heterocyclyl), 3 to 12 ring carbon atoms (i.e., $C_{3-12}$ heterocyclyl), 3 to 8 ring carbon atoms (i.e., $C_{3-8}$ heterocyclyl), or 3 to 6 ring carbon atoms (i.e., $C_{3-6}$ heterocyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. A heterocyclyl may contain one or more oxo and/or thioxo groups. Examples of heterocyclyl groups include pyrrolidinyl, piperidinyl, piperazinyl, oxetanyl, dioxolanyl, azetidinyl, and morpholinyl. As used herein, the term "bridged-heterocyclyl" refers to a four- to ten-membered cyclic moiety connected at two non-adjacent atoms of the heterocyclyl with one or more (e.g. 1 or 2) four- to ten-membered cyclic moiety having at least one heteroatom where each heteroatom is independently selected from nitrogen, oxygen, and sulfur. As used herein, bridged-heterocyclyl includes bicyclic and tricyclic ring systems. Also used herein, the term "spiro-heterocyclyl" refers to a ring system in which a three- to ten-membered heterocyclyl has one or more additional ring, wherein the one or more additional ring is three- to ten-membered cycloalkyl or three- to ten-membered heterocyclyl, where a single atom of the one or more additional ring is also an atom of the three- to ten-membered heterocyclyl. Examples of the spiro-heterocyclyl rings include bicyclic and tricyclic ring systems, such as 2-oxa-7-azaspiro[3.5]nonanyl, 2-oxa-6-azaspiro[3.4]octanyl, and 6-oxa-1-azaspiro[3.3]heptanyl. Examples of the fused-heterocyclyl rings include, but are not limited to, 1,2,3,4-tetrahydroisoquinolinyl, 1-oxo-1,2,3,4-tetrahydroisoquinolinyl, 1-oxo-1,2-dihydroisoquinolinyl, 4,5,6,7- tetrahydrothieno[2,3-c]pyridinyl, indolinyl, and isoindolinyl, where the heterocyclyl can be bound via either ring of the fused system.

"Hydroxy" or "hydroxyl" refers to the group —OH. "Hydroxyalkyl" refers to an unbranched or branched alkyl group as defined above, wherein one or more hydrogen atoms are replaced by a hydroxyl.

"Oxo" refers to the group (=O) or (O).

"Nitro" refers to the group $NO_2$.

"Sulfonyl" refers to the group —$S(O)_2R$, where R is alkyl, haloalkyl, heterocyclyl, cycloalkyl, heteroaryl, or aryl. Examples of sulfonyl are methylsulfonyl, ethylsulfonyl, phenyl sulfonyl, and toluenesulfonyl.

"Alkylsulfonyl" refers to the group —$S(O)_2R$, where R is alkyl.

"Alkylsulfinyl" refers to the group —S(O)R, where R is alkyl.

"Thiocyanate"—SCN.

"Thiol" refers to the group —SR, where R is alkyl, haloalkyl, heterocyclyl, cycloalkyl, heteroaryl, or aryl.

"Thioxo" or "thione" refer to the group (=S) or (S).

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless indicated explicitly otherwise, where combinations of groups are referred to herein as one moiety, e.g. arylalkyl, the last mentioned group contains the atom by which the moiety is attached to the rest of the molecule.

The terms "optional" or "optionally" means that the subsequently described event or circumstance may or may not occur, and that the description includes instances where said event or circumstance occurs and instances in which it does not. Also, the term "optionally substituted" refers to any one or more hydrogen atoms on the designated atom or group may or may not be replaced by a moiety other than hydrogen.

Some of the compounds exist as tautomers. Tautomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

Any formula or structure given herein, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2H$ (deuterium, D), $^3H$ (tritium) $^{11}C$, $^{13}C$, $^{14}C$, $^{15}N$, $^{18}F$, $^{31}P$, $^{32}P$, $^{35}S$, $^{36}Cl$ and $^{125}I$. Various isotopically labeled compounds of the present disclosure, for example those into which radioactive isotopes such as $^3H$, $^{13}C$ and $^{14}C$ are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes "deuterated analogues" of compounds of Formula I in which from 1 to n hydrogens attached to a carbon atom is/are replaced by deuterium, in which n is the number of hydrogens in the molecule. Such compounds exhibit increased resistance to metabolism and are thus useful for increasing the half-life of any compound of Formula I when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}F$ labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of Formula I.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

In many cases, the compounds of this disclosure are capable of forming acid and/or base salts by virtue of the presence of amino and/or carboxyl groups or groups similar thereto.

Provided are also pharmaceutically acceptable salts, hydrates, solvates, tautomeric forms, polymorphs, and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The term "pharmaceutically acceptable salt" of a given compound refers to salts that retain the biological effectiveness and properties of the given compound, and which are not biologically or otherwise undesirable. "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts. Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. Likewise, pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines (i.e., $NH_2$(alkyl)), dialkyl amines (i.e., HN(alkyl)$_2$), trialkyl amines (i.e., N(alkyl)$_3$), substituted alkyl amines (i.e., $NH_2$(substituted alkyl)), di(substituted alkyl) amines (i.e., HN(substituted alkyl)$_2$), tri (substituted alkyl) amines (i.e., N(substituted alkyl)$_3$), alkenyl amines (i.e., $NH_2$(alkenyl)), dialkenyl amines (i.e., HN(alkenyl)$_2$), trialkenyl amines (i.e., N(alkenyl)$_3$), substituted alkenyl amines (i.e., $NH_2$(substituted alkenyl)), di(substituted alkenyl) amines (i.e., HN(substituted alkenyl)$_2$), tri(substituted alkenyl) amines (i.e., N(substituted alkenyl)$_3$, mono-, di- or tri-cycloalkyl amines (i.e., $NH_2$(cycloalkyl), HN(cycloalkyl)$_2$, N(cycloalkyl)$_3$), mono-, di- or tri-arylamines (i.e., $NH_2$(aryl), HN(aryl)$_2$, N(aryl)$_3$), or mixed amines, etc. Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine, and the like.

The term "substituted" means that any one or more hydrogen atoms on the designated atom or group is replaced with one or more substituents other than hydrogen, provided that the designated atom's normal valence is not exceeded. The one or more substituents include, but are not limited to, alkyl, alkenyl, alkynyl, alkoxy, acyl, amino, amino, amidino, aryl, azido, carbamoyl, carboxyl, carboxyl ester, cyano, guanidino, halo, haloalkyl, haloalkoxy, heteroalkyl, heteroaryl, heterocyclyl, hydroxy, hydrazino, imino, oxo, nitro, alkyl sulfinyl, sulfonic acid, alkyl sulfonyl, thiocyanate, thiol, thione, or combinations thereof. Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl)substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. Unless specified otherwise, where a group is described as optionally substituted, any substituents of the group are themselves unsubstituted. For example, in some embodiments, the term "substituted alkyl" refers to an alkyl group having one or more substituents including hydroxyl, halo, alkoxy, cycloalkyl, heterocyclyl, aryl, and heteroaryl. In other embodiments, the one or more substituents may be further substituted with halo, alkyl, haloalkyl, hydroxyl, alkoxy, cycloalkyl, heterocyclyl, aryl, or heteroaryl, each of which is substituted. In other embodiments, the substituents may be further substituted with halo, alkyl, haloalkyl, alkoxy, hydroxyl, cycloalkyl, heterocyclyl, aryl, or heteroaryl, each of which is unsubstituted.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

A "solvate" is formed by the interaction of a solvent and a compound. Solvates of salts of the compounds described herein are also provided. Hydrates of the compounds described herein are also provided.

LIST OF ABBREVIATIONS AND ACRONYMS

| Abbreviation | Meaning |
| --- | --- |
| °C | Degree Celsius |
| Ac | Acetyl |
| aq. | Aqueous |
| ATP | Adenosine triphosphate |
| BOC | tert-Butoxycarbonyl |
| br | Broad |
| BSA | Bovine serum albumin |
| Cbz | Carboxybenzyl |
| COD | Cyclooctadiene |
| COPD | Chronic obstructive pulmonary disease |
| Cot | Cancer Osaka Thyroid |
| Cp | Cyclopentadienyl |
| d | Doublet |
| DABCO | 1,4-Diazabicyclo[2.2.2]octane |
| DBU | 1,8-Diazabicyclo[5.4.0]undec-7-ene |
| DCE | Dichloroethene |
| DCM | Dichloromethane |
| dd | Doublet of doublets |
| DEF | N,N-Diethylformamide |
| DMF | Dimethylformamide |
| DMSO | Dimethylsulfoxide |
| dppf | 1,1'-Bis(diphenylphosphino)ferrocene |
| dt | Doublet-triplet |
| DTT | Dithiothreitol |
| $EC_{50}$ | The half maximal effective concentration |
| EGFR | Epidermal growth factor receptor |
| eq | Equivalents |
| ES/MS | Electrospray mass spectrometry |
| Et | Ethyl |

-continued

| Abbreviation | Meaning |
|---|---|
| FBS | Fetal bovine serum |
| g | Grams |
| HEPES | 2-[4-(2-hydroxyethyl)piperazin-1-yl]ethanesulfonic acid |
| HPLC | High pressure liquid chromatography |
| hrs | Hours |
| Hz | Hertz |
| IBD | Inflammatory bowel disease |
| i-pr | Isopropyl |
| J | Coupling constant (MHz) |
| Kg/kg | Kilogram |
| LCMS | Liquid chromatography - mass spectrometry |
| LPS | Lipopolysaccharide |
| M | Molar |
| m | multiplet |
| M+ | Mass peak |
| M+H+ | Mass peak plus hydrogen |
| Me | Methyl |
| mg | Milligram |
| MHz | Megahertz |
| min | Minute |
| ml/mL | Milliliter |
| mM | Millimolar |
| mmol | Millimole |
| MOPS | 3-Morpholinopropane-1-sulfonic acid |
| MS | Mass spectroscopy |
| Ms | Mesyl |
| nBu/Bu | Butyl |
| nL | Nanoliter |
| nm | Nanometer |
| NMR | Nuclear magnetic resonance |
| NP-40 | Nonyl phenoxypolyethoxylethanol |
| Ns | Nosyl |
| Pd-C/Pd/C | Palladium on Carbon |
| pg | Pictogram |
| Ph | Phenyl |
| PPTS | Pyridinium p-toluenesulfonate |
| PS | Polystyrene |
| p-TSOH/pTSA | p-Toluenesulfonic acid |
| q | Quartet |
| q.s. | Quantity sufficient to achieve a stated function |
| RBF | Round bottom flask |
| RP | Reverse phase |
| RPMI | Roswell Park Memorial Institute medium |
| rt | Room temperature |
| s | Singlet |
| sat. | Saturated |
| t | Triplet |
| TBAF | Tetra-n-butylammonium fluoride |
| TBS | tert-Butyldimethylsilyl |
| t-Bu | tert-Butyl |
| TC | Thiophene-2-carboxylate |
| TEA | Triethanolamine |
| Tf | Trifluoromethanesulfonyl |
| TFA | Trifluoroacetic acid |
| THF | Tetrahydrofuran |
| Tpl2 | Tumor Progression Locus 2 |
| TR-FRET | Time-resolved fluorescence energy transfer |
| Ts | Tosyl |
| δ | Chemical shift (ppm) |
| μL/μl | Microliter |
| μM | Micromolar |

Compounds

Provided herein are compounds that function as modulators of Cot. In one aspect, provided is a compound having structure of Formula I:

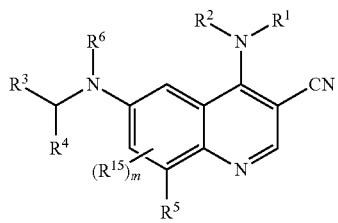

wherein
$R^1$ is hydrogen, $-O-R^7$, $-N(R^8)(R^9)$, $-C(O)-R^7$, $-S(O)_2-R^7$, $-C_{1-9}$ alkyl, $C_{2-6}$ alkenyl, $C_{2-6}$ alkynyl, $C_{3-15}$ cycloalkyl, heterocyclyl, aryl, or heteroaryl;
wherein each $C_{1-9}$ alkyl, $C_{2-6}$ alkenyl, $C_{2-6}$ alkynyl, $C_{3-15}$ cycloalkyl, heterocyclyl, aryl, and heteroaryl may be optionally substituted with one to four $Z^1$;
$R^2$ is hydrogen, $-C(O)-R^7$, $-C(O)O-R^7$, $-C(O)N(R^7)_2$, $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl;
wherein each $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, and heteroaryl may be optionally substituted with one to four $Z^2$;
or $R^1$ and $R^2$ together with the nitrogen to which they are attached to form a heterocyclyl or heteroaryl, wherein each heterocyclyl or heteroaryl is optionally substituted with one to four $Z^2$;
$R^3$ is heterocyclyl or heteroaryl, wherein each heterocyclyl or heteroaryl is optionally substituted with one to four $Z^3$;
$R^4$ is heterocyclyl or heteroaryl, wherein each heterocyclyl or heteroaryl is optionally substituted with one to four $Z^4$;
$R^5$ is hydrogen, halo, $-CN$, $-NO_2$, $-O-R^7$, $-N(R^8)(R^9)$, $-S(O)-R^7$, $-S(O)_2R^7$, $-S(O)_2N(R^7)_2$, $-C(O)R^7$, $-OC(O)-R^7$, $-C(O)O-R^7$, $-OC(O)O-R^7$, $-OC(O)N(R^{10})(R^{11})$, $-C(O)N(R^7)_2$, $-N(R^7)C(O)(R^7)$, $C_{1-9}$ alkyl, $C_{2-6}$ alkenyl, $C_{2-6}$ alkynyl, $C_{1-9}$ alkylthio, $C_{1-6}$ haloalkyl, $C_{3-15}$ cycloalkyl, aryl, heterocyclyl, or heteroaryl;
wherein each $C_{1-9}$ alkyl, $C_{2-6}$ alkenyl, $C_{2-6}$ alkynyl, $C_{1-9}$ alkylthio, $C_{1-6}$ haloalkyl, $C_{3-15}$ cycloalkyl, aryl, heterocyclyl, and heteroaryl may be optionally substituted with one to four $Z^5$;
$R^6$ is hydrogen, $-C(O)-R^7$, $-C(O)O-R^7$, $-C(O)N(R^7)_2$, $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl;
wherein each $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, and heteroaryl may be optionally substituted with one to four $Z^6$;
each $R^7$ is independently hydrogen, $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl;
wherein each $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, and heteroaryl may be optionally substituted with one to four $Z^7$;
$R^8$ and $R^9$ at each occurrence are independently hydrogen, $-S(O)_2R^{10}$, $-C(O)-R^{10}$, $-C(O)O-R^{10}$, $-C(O)N(R^{10})(R^{11})$, $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl;
wherein each $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl may be optionally substituted with one to four $Z^8$;

$R^{10}$ and $R^{11}$ at each occurrence are independently hydrogen, $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl, wherein each $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, and heteroaryl optionally is substituted with one to four $Z^{1b}$;

each $Z^1$, $Z^2$, $Z^3$, $Z^4$, $Z^5$, $Z^6$, $Z^7$, and $Z^8$ is independently hydrogen, oxo, halo, —NO$_2$, —N$_3$, —CN, thioxo, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O—$R^{12}$, —C(O)—$R^{12}$, —C(O)O—$R^{12}$, —C(O)—N($R^{13}$)($R^{14}$), —N($R^{13}$)($R^{14}$), —N($R^{13}$)$_2$($R^{14}$)$^+$, —N($R^{12}$)C(O)—$R^{12}$, —N($R^{12}$)C(O)O—$R^{12}$, —N($R^{12}$)C(O)N($R^{13}$)($R^{14}$), —N($R^{12}$)S(O)$_2$($R^{12}$), —NR$^{12}$S(O)$_2$N($R^{13}$)($R^{14}$), —NR$^{12}$S(O)$_2$O($R^{12}$), —OC(O)$R^{12}$, —OC(O)—N($R^{13}$)($R^{14}$), —P(O)(O$R^{12}$)$_2$, —OP(O)(O$R^{12}$)$_2$, —CH$_2$P(O)(O$R^{12}$)$_2$, —OCH$_2$P(O)(O$R^{12}$)$_2$, —C(O)OCH$_2$P(O)(O$R^{12}$)$_2$, —P(O)($R^{12}$)(O$R^{12}$), —OP(O)($R^{12}$)(O$R^{12}$), —CH$_2$P(O)($R^{12}$)(O$R^{12}$), —OCH$_2$P(O)($R^{12}$)(O$R^{12}$), —C(O)OCH$_2$P(O)($R^{12}$)(O$R^{12}$), —P(O)(N($R^{12}$)$_2$)$_2$, —OP(O)(N($R^{12}$)$_2$)$_2$, —CH$_2$P(O)(N($R^{12}$)$_2$)$_2$, —OCH$_2$P(O)(N($R^{12}$)$_2$)$_2$, —C(O)OCH$_2$P(O)(N($R^{12}$)$_2$)$_2$, —P(O)(N($R^{12}$)$_2$)(O$R^{12}$), —OP(O)(N($R^{12}$)$_2$)(O$R^{12}$), —CH$_2$P(O)(N($R^{12}$)$_2$)(O$R^{12}$), —OCH$_2$P(O)(N($R^{12}$)$_2$)(O$R^{12}$), —C(O)OCH$_2$P(O)(N($R^{12}$)$_2$)(O$R^{12}$), —P(O)($R^{12}$)(N($R^{12}$)$_2$), —OP(O)($R^{12}$)(N($R^{12}$)$_2$), —CH$_2$P(O)($R^{12}$)(N($R^{12}$)$_2$), —OCH$_2$P(O)($R^{12}$)(N($R^{12}$)$_2$), —C(O)OCH$_2$P(O)($R^{12}$)(N($R^{12}$)$_2$), —Si($R^{12}$)$_3$, —S—$R^{12}$, —S(O)$R^{12}$, —S(O)(NH)$R^{12}$, —S(O)$_2$$R^{12}$ or —S(O)$_2$N($R^{13}$)($R^{14}$);

wherein any alkyl, alkenyl, alkynyl, cycloalkyl, haloalkyl, aryl, heteroaryl or heterocyclyl is optionally substituted with one to four $Z^{1a}$ groups;

each $Z^{1a}$ is independently oxo, halo, thioxo, —NO$_2$, —CN, —N$_3$, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O—$R^{12}$, —C(O)$R^{12}$, —C(O)O—$R^{12}$, —C(O)N($R^{13}$)($R^{14}$), —N($R^{13}$)($R^{14}$), —N($R^{13}$)$_2$($R^{14}$)$^+$, —N($R^{12}$)—C(O)$R^{12}$, —N($R^{12}$)C(O)O($R^{12}$), —N($R^{12}$)C(O)N($R^{13}$)($R^{14}$), —N($R^{12}$)S(O)$_2$($R^{12}$), —N($R^{12}$)S(O)$_2$—N($R^{13}$)($R^{14}$), —N($R^{12}$)S(O)$_2$O($R^{12}$), —OC(O)$R^{12}$, —OC(O)O$R^{12}$, —OC(O)—N($R^{13}$)($R^{14}$), —Si($R^{12}$)$_3$, —S—$R^{12}$, —S(O)$R^{12}$, —S(O)(NH)$R^{12}$, —S(O)$_2$$R^{12}$ or —S(O)$_2$N($R^{13}$)($R^{14}$);

wherein any alkyl, alkenyl, alkynyl, cycloalkyl, aryl, heteroaryl or heterocyclyl is optionally substituted with one to four $Z^{1b}$ groups;

each $R^{12}$ is independently hydrogen, $C_{1-9}$ alkyl, $C_{2-6}$ alkenyl, $C_{2-6}$ alkynyl, $C_{3-15}$ cycloalkyl, aryl, heteroaryl or heterocyclyl, wherein any alkyl, alkenyl, alkynyl, cycloalkyl, aryl, heteroaryl or heterocyclyl is optionally substituted with one to four $Z^{1b}$ groups;

$R^{13}$ and $R^{14}$ at each occurrence are each independently hydrogen, $C_{1-9}$ alkyl, $C_{2-6}$ alkenyl, $C_{2-6}$ alkynyl, $C_{3-15}$ cycloalkyl, aryl, heteroaryl or heterocyclyl;

wherein any alkyl, alkenyl, alkynyl, cycloalkyl, aryl, heteroaryl or heterocyclyl is optionally substituted with one to four $Z^{1b}$ groups, or $R^{13}$ and $R^{14}$ together with the nitrogen to which they are attached form a heterocyclyl, wherein said heterocyclyl is optionally substituted with one to four $Z^{1b}$ groups;

each $R^{15}$ is independently halo, —CN, —NO$_2$, —O—$R^7$, —N($R^8$)($R^9$), —S(O)—$R^7$, —S(O)$_2$$R^7$, —S(O)$_2$N($R^7$)$_2$, —C(O)$R^7$, —OC(O)—$R^7$, —C(O)O—$R^7$, —OC(O)O—$R^7$, —OC(O)N($R^{10}$)($R^{11}$), —C(O)N($R^7$)$_2$, —N(R)C(O)

($R^7$), $C_{1-9}$ alkyl, $C_{2-6}$ alkenyl, $C_{2-6}$ alkynyl, $C_{1-9}$ alkylthio, $C_{1-6}$ haloalkyl, $C_{3-15}$ cycloalkyl, aryl, heterocyclyl, or heteroaryl;

each $Z^{1b}$ is independently oxo, thioxo, hydroxy, halo, —NO$_2$, —N$_3$, —CN, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O($C_{1-9}$ alkyl), —O($C_{2-6}$ alkenyl), —O($C_{2-6}$ alkynyl), —O($C_{3-15}$ cycloalkyl), —O($C_{1-8}$ haloalkyl), —O(aryl), —O(heteroaryl), —O(heterocyclyl), —NH$_2$, —NH($C_{1-9}$ alkyl), —NH($C_{2-6}$ alkenyl), —NH($C_{2-6}$ alkynyl), —NH($C_{3-15}$ cycloalkyl), —NH($C_{1-8}$ haloalkyl), —NH(aryl), —NH(heteroaryl), —NH(heterocyclyl), —N($C_{1-9}$ alkyl)$_2$, —N($C_{3-15}$ cycloalkyl)$_2$, —N($C_{2-6}$ alkenyl)$_2$, —N($C_{2-6}$ alkynyl)$_2$, —N($C_{3-15}$ cycloalkyl)$_2$, —N($C_{1-8}$haloalkyl)$_2$, —N(aryl)$_2$, —N(heteroaryl)$_2$, —N(heterocyclyl)$_2$, —N($C_{1-9}$ alkyl)($C_{3-15}$ cycloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)($C_{1-8}$ haloalkyl), —N($C_{1-9}$ alkyl)(aryl), —N($C_{1-9}$ alkyl)(heteroaryl), —N($C_{1-9}$ alkyl)(heterocyclyl), —C(O)($C_{1-9}$ alkyl), —C(O)($C_{2-6}$ alkenyl), —C(O)($C_{2-6}$ alkynyl), —C(O)($C_{3-15}$ cycloalkyl), —C(O)($C_{1-8}$ haloalkyl), —C(O)(aryl), —C(O)(heteroaryl), —C(O)(heterocyclyl), —C(O)O($C_{1-9}$ alkyl), —C(O)O($C_{2-6}$ alkenyl), —C(O)O($C_{2-6}$ alkynyl), —C(O)O($C_{3-15}$ cycloalkyl), —C(O)O($C_{1-8}$ haloalkyl), —C(O)O(aryl), —C(O)O(heteroaryl), —C(O)O(heterocyclyl), —C(O)NH$_2$, —C(O)NH($C_{1-9}$ alkyl), —C(O)NH($C_{2-6}$ alkenyl), —C(O)NH($C_{2-6}$ alkynyl), —C(O)NH($C_{3-15}$ cycloalkyl), —C(O)NH($C_{1-8}$ haloalkyl), —C(O)NH(aryl), —C(O)NH(heteroaryl), —C(O)NH(heterocyclyl), —C(O)N($C_{1-9}$ alkyl)$_2$, —C(O)N($C_{3-15}$ cycloalkyl)$_2$, —C(O)N($C_{2-6}$ alkenyl)$_2$, —C(O)N($C_{2-6}$ alkynyl)$_2$, —C(O)N($C_{3-15}$ cycloalkyl)$_2$, —C(O)N($C_{2-8}$haloalkyl)$_2$, —C(O)N(aryl)$_2$, —C(O)N(heteroaryl)$_2$, —C(O)N(heterocyclyl)$_2$, —NHC(O)($C_{1-9}$ alkyl), —NHC(O)($C_{2-6}$ alkenyl), —NHC(O)($C_{2-6}$ alkynyl), —NHC(O)($C_{3-15}$ cycloalkyl), —NHC(O)($C_{1-8}$ haloalkyl), —NHC(O)(aryl), —NHC(O)(heteroaryl), —NHC(O)(heterocyclyl), —NHC(O)O($C_{1-9}$ alkyl), —NHC(O)O($C_{2-6}$ alkenyl), —NHC(O)O($C_{2-6}$ alkynyl), —NHC(O)O($C_{3-15}$ cycloalkyl), —NHC(O)O($C_{1-8}$ haloalkyl), —NHC(O)O(aryl), —NHC(O)O(heteroaryl), —NHC(O)O(heterocyclyl), —NHC(O)NH($C_{1-9}$ alkyl), —NHC(O)NH($C_{2-6}$ alkenyl), —NHC(O)NH($C_{2-6}$ alkynyl), —NHC(O)NH($C_{3-15}$ cycloalkyl), —NHC(O)NH($C_{1-8}$ haloalkyl), —NHC(O)NH(aryl), —NHC(O)NH(heteroaryl), —NHC(O)NH(heterocyclyl), —SH, —S($C_{1-9}$ alkyl), —S($C_{2-6}$ alkenyl), —S($C_{2-6}$ alkynyl), —S($C_{3-15}$ cycloalkyl), —S($C_{1-8}$ haloalkyl), —S(aryl), —S(heteroaryl), —S(heterocyclyl), —NHS(O)($C_{1-9}$ alkyl), —N($C_{1-9}$ alkyl)(S(O)($C_{1-9}$ alkyl), —S(O)N($C_{1-9}$ alkyl)$_2$, —S(O)($C_{1-9}$ alkyl), —S(O)(NH)($C_{1-9}$ alkyl), —S(O)($C_{2-6}$ alkenyl), —S(O)($C_{2-6}$ alkynyl), —S(O)($C_{3-15}$ cycloalkyl), —S(O)($C_{1-8}$ haloalkyl), —S(O)(aryl), —S(O)(heteroaryl), —S(O)(heterocyclyl), —S(O)$_2$($C_{1-9}$ alkyl), —S(O)$_2$($C_{2-6}$ alkenyl), —S(O)$_2$($C_{2-6}$ alkynyl), —S(O)$_2$($C_{3-15}$ cycloalkyl), —S(O)$_2$($C_{1-8}$ haloalkyl), —S(O)$_2$(aryl), —S(O)$_2$(heteroaryl), —S(O)$_2$(heterocyclyl), —S(O)$_2$NH($C_{1-9}$ alkyl), or —S(O)$_2$N($C_{1-9}$ alkyl)$_2$;

wherein any alkyl, cycloalkyl, aryl, heteroaryl, or heterocyclyl is optionally substituted with one to four halo, $C_{1-9}$ alkyl, $C_{1-8}$ haloalkyl, —OH, —NH$_2$, —NH($C_{1-9}$ alkyl), —NH($C_{3-15}$ cycloalkyl), —NH($C_{1-8}$ haloalkyl), —NH(aryl), —NH(heteroaryl), —NH(heterocyclyl), —N($C_{1-9}$ alkyl)$_2$, —N($C_{3-15}$ cycloalkyl)$_2$, —NHC(O)($C_{3-15}$ cycloalkyl), —NHC(O)($C_{1-8}$ haloalkyl), —NHC(O)(aryl), —NHC(O)(heteroaryl), —NHC(O)(heterocyclyl), —NHC(O)O($C_{1-9}$ alkyl), —NHC(O)O($C_{2-6}$ alkynyl), —NHC(O)O($C_{3-15}$ cycloalkyl), —NHC(O)O ($C_{1-8}$ haloalkyl), —NHC(O)O(aryl), —NHC(O)O(heteroaryl), —NHC(O)O(heterocyclyl), —NHC(O)NH ($C_{1-9}$ alkyl), —S(O)(NH)($C_{1-9}$ alkyl), S(O)$_2$($C_{1-9}$ alkyl), —S(O)$_2$($C_{3-15}$ cycloalkyl), —S(O)$_2$($C_{1-8}$ haloalkyl), —S(O)$_2$(aryl), —S(O)$_2$(heteroaryl), —S(O)$_2$(heterocyclyl), —S(O)$_2$NH($C_{1-9}$ alkyl), —S(O)$_2$N($C_{1-9}$ alkyl)$_2$, —O($C_{3-15}$ cycloalkyl), —O($C_{1-8}$ haloalkyl), —O(aryl), —O(heteroaryl), —O(heterocyclyl), or —O($C_{1-9}$ alkyl); and m is 0, 1, or 2;

or a pharmaceutically acceptable salt, tautomer, stereoisomer, mixture of stereoisomers, prodrug, or deuterated analog thereof.

In another aspect, provided is a compound having structure of Formula I:

wherein $R^1$ is hydrogen, —O—$R^7$, —N($R^8$)($R^9$), —C(O)—$R^7$, —S(O)$_2$—$R^7$, —$C_{1-9}$ alkyl, $C_{2-6}$ alkenyl, $C_{2-6}$ alkynyl, $C_{3-15}$ cycloalkyl, heterocyclyl, aryl, or heteroaryl;
  wherein each $C_{1-9}$ alkyl, $C_{2-6}$ alkenyl, $C_{2-6}$ alkynyl, $C_{3-15}$ cycloalkyl, heterocyclyl, aryl, and heteroaryl may be optionally substituted with one to four $Z^1$;

$R^2$ is hydrogen, —C(O)—$R^7$, —C(O)O—$R^7$, —C(O)N($R^7$)$_2$, $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl;
  wherein each $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, and heteroaryl may be optionally substituted with one to four $Z^2$;

or $R^1$ and $R^2$ together with the nitrogen to which they are attached to form a heterocyclyl or heteroaryl, wherein each heterocyclyl or heteroaryl is optionally substituted with one to four $Z^2$;

$R^3$ is heterocyclyl or heteroaryl, wherein each heterocyclyl or heteroaryl is optionally substituted with one to four $Z^3$;

$R^4$ is heterocyclyl or heteroaryl, wherein each heterocyclyl or heteroaryl is optionally substituted with one to four $Z^4$;

$R^5$ is hydrogen, halo, —CN, —NO$_2$, —N($R^8$)($R^9$), —S(O)—$R^7$, —S(O)$_2$$R^7$, —S(O)$_2$N($R^7$)$_2$, —C(O)$R^7$, —OC(O)—$R^7$, —C(O)O—$R^7$, —OC(O)O—$R^7$, —OC(O)N($R^{10}$)($R^{11}$), —C(O)N($R^7$)$_2$, —N($R^7$)C(O)($R^7$), $C_{1-9}$ alkyl, $C_{2-6}$ alkenyl, $C_{2-6}$ alkynyl, $C_{1-9}$ alkylthio, $C_{1-6}$ haloalkyl, $C_{3-15}$ cycloalkyl, aryl, heterocyclyl, or heteroaryl;
  wherein each $C_{1-9}$ alkyl, $C_{2-6}$ alkenyl, $C_{2-6}$ alkynyl, $C_{1-9}$ alkylthio, $C_{1-6}$ haloalkyl, $C_{3-15}$ cycloalkyl, aryl, heterocyclyl, and heteroaryl may be optionally substituted with one to four $Z^5$;

$R^6$ is hydrogen, —C(O)—$R^7$, —C(O)O—$R^7$, —C(O)N($R^7$)$_2$, $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl;
  wherein each $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, and heteroaryl may be optionally substituted with one to four $Z^6$;

each $R^7$ is independently hydrogen, $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl;
  wherein each $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, and heteroaryl may be optionally substituted with one to four $Z^7$;

$R^8$ and $R^9$ at each occurrence are independently hydrogen, —S(O)$_2$$R^{10}$, —C(O)—$R^{10}$, —C(O)O—$R^{10}$, —C(O)N($R^{10}$)($R^{11}$), $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl;
  wherein each $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl may be optionally substituted with one to four $Z^8$;

$R^{10}$ and $R^{11}$ at each occurrence are independently hydrogen, $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl,
  wherein each $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, and heteroaryl optionally is substituted with one to four $Z^{1b}$;

each $Z^1$, $Z^2$, $Z^3$, $Z^4$, $Z^5$, $Z^6$, $Z^7$, and $Z^8$ is independently hydrogen, oxo, halo, —NO$_2$, —N$_3$, —CN, thioxo, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O—$R^{12}$, —C(O)—$R^{12}$, —C(O)O—$R^{12}$, —C(O)—N($R^{13}$)($R^{14}$), —N($R^{13}$)($R^{14}$), —N($R^{13}$)$_2$($R^{14}$)$^+$, —N($R^{12}$)C(O)—$R^{12}$, —N($R^{12}$)C(O)O—$R^{12}$, —N($R^{12}$)C(O)N($R^{13}$)($R^{14}$), —N($R^{12}$)S(O)$_2$($R^{12}$), —NR$^{12}$S(O)$_2$N($R^{13}$)($R^{14}$), —NR$^{12}$S(O)$_2$O($R^{12}$), —OC(O)R$^{12}$, —OC(O)—N($R^{13}$)($R^{14}$), —P(O)(OR$^{12}$)$_2$, —OP(O)(OR$^{12}$)$_2$, —CH$_2$P(O)(OR$^{12}$)$_2$, —OCH$_2$P(O)(OR$^{12}$)$_2$, —C(O)OCH$_2$P(O)(OR$^{12}$)$_2$, —P(O)($R^{12}$)(OR$^{12}$), —OP(O)($R^{12}$)(OR$^{12}$), —CH$_2$P(O)($R^{12}$)(OR$^{12}$), —OCH$_2$P(O)($R^{12}$)(OR$^{12}$), —C(O)OCH$_2$P(O)($R^{12}$)(OR$^{12}$), —P(O)(N($R^{12}$)$_2$)$_2$, —OP(O)(N($R^{12}$)$_2$)$_2$, —CH$_2$P(O)(N($R^{12}$)$_2$)$_2$, —OCH$_2$P(O)(N($R^{12}$)$_2$)$_2$, —C(O)OCH$_2$P(O)(N($R^{12}$)$_2$)$_2$, —P(O)(N($R^{12}$)$_2$)(OR$^{12}$), —OP(O)(N($R^{12}$)$_2$)(OR$^{12}$), —CH$_2$P(O)(N($R^{12}$)$_2$)(OR$^{12}$), —OCH$_2$P(O)(N($R^{12}$)$_2$)(OR$^{12}$), —C(O)OCH$_2$P(O)(N($R^{12}$)$_2$)(OR$^{12}$), —P(O)($R^{12}$)(N($R^{12}$)$_2$), —OP(O)($R^{12}$)(N($R^{12}$)$_2$), —CH$_2$P(O)($R^{12}$)(N($R^{12}$)$_2$), —OCH$_2$P(O)($R^{12}$)(N($R^{12}$)$_2$), —C(O)OCH$_2$P(O)($R^{12}$)(N($R^{12}$)$_2$), —Si($R^{12}$)$_3$, —S—$R^{12}$, —S(O)$R^{12}$, —S(O)(NH)$R^{12}$, —S(O)$_2$$R^{12}$ or —S(O)$_2$N($R^{13}$)($R^{14}$);

wherein any alkyl, alkenyl, alkynyl, cycloalkyl, haloalkyl, aryl, heteroaryl or heterocyclyl is optionally substituted with one to four $Z^{1a}$ groups;

each $Z^{1a}$ is independently oxo, halo, thioxo, —NO$_2$, —CN, —N$_3$, $C_{1-9}$ alkyl, $C_{2-6}$ alkenyl, $C_{2-6}$ alkynyl, $C_{3-15}$ cycloalkyl, $C_{1-8}$ haloalkyl, $C_{1-8}$ hydroxyalkyl, aryl, heteroaryl, heterocyclyl, —O—$R^{12}$, —C(O)$R^{12}$, —C(O)O—$R^{12}$, —C(O)N($R^{13}$)($R^{14}$), —N($R^{13}$)($R^{14}$), —N($R^{13}$)$_2$($R^{14}$)$^+$, —N($R^{12}$)—C(O)$R^{12}$, —N($R^{12}$)C(O)O($R^{12}$), —N($R^{12}$)C(O)N($R^{13}$)($R^{14}$), —N($R^{12}$)S(O)$_2$($R^{12}$), —N($R^{12}$)S(O)$_2$—N($R^{13}$)($R^{14}$), —N($R^{12}$)S(O)$_2$O($R^{12}$), —OC(O)R$^{12}$, —OC(O)OR$^{12}$, —OC(O)—N($R^{13}$)($R^{14}$), —C(O)N($R^{12}$)—S(O)$_2$$R^{12}$, —Si($R^{12}$)$_3$, —S—$R^{12}$, —S(O)$R^{12}$, —S(O)(NH)$R^{12}$, —S(O)$_2$$R^{12}$ or —S(O)$_2$N($R^{13}$)($R^{14}$);

wherein any alkyl, alkenyl, alkynyl, cycloalkyl, aryl, heteroaryl or heterocyclyl is optionally substituted with one to four $Z^{1b}$ groups;

each $R^{12}$ is independently hydrogen, $C_{1-9}$ alkyl, $C_{2-6}$ alkenyl, $C_{2-6}$ alkynyl, $C_{3-15}$ cycloalkyl, aryl, heteroaryl or heterocyclyl,
  wherein any alkyl, alkenyl, alkynyl, cycloalkyl, aryl, heteroaryl or heterocyclyl is optionally substituted with one to four $Z^{1b}$ groups;
$R^{13}$ and $R^{14}$ at each occurrence are each independently hydrogen, $C_{1-9}$ alkyl, $C_{2-6}$ alkenyl, $C_{2-6}$ alkynyl, $C_{3-15}$ cycloalkyl, aryl, heteroaryl or heterocyclyl;
  wherein any alkyl, alkenyl, alkynyl, cycloalkyl, aryl, heteroaryl or heterocyclyl is optionally substituted with one to four $Z^{1b}$ groups, or $R^{13}$ and $R^{14}$ together with the nitrogen to which they are attached form a heterocyclyl, wherein said heterocyclyl is optionally substituted with one to four $Z^{1b}$ groups;
each $R^{15}$ is independently halo, —CN, —NO$_2$, —O—R$^7$, —N(R$^8$)(R$^9$), —S(O)—R$^7$, —S(O)$_2$R$^7$, —S(O)$_2$N(R$^7$)$_2$, —C(O)R$^7$, —OC(O)—R$^7$, —C(O)O—R$^7$, —OC(O)O—R$^7$, —OC(O)N(R$^{10}$)(R$^{11}$), —C(O)N(R$^7$)$_2$, —N(R)C(O) (R$^7$), $C_{1-9}$ alkyl, $C_{2-6}$ alkenyl, $C_{2-6}$ alkynyl, $C_{1-9}$ alkylthio, $C_{1-6}$ haloalkyl, $C_{3-15}$ cycloalkyl, aryl, heterocyclyl, or heteroaryl; and
each $Z^{1b}$ is independently oxo, thioxo, hydroxy, halo, —NO$_2$, —N$_3$, —CN, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O(C$_{1-9}$ alkyl), —O(C$_{2-6}$ alkenyl), —O(C$_{2-6}$ alkynyl), —O(C$_{3-15}$ cycloalkyl), —O(C$_{1-8}$ haloalkyl), —O(aryl), —O(heteroaryl), —O(heterocyclyl), —NH$_2$, —NH(C$_{1-9}$ alkyl), —NH(C$_{2-6}$ alkenyl), —NH(C$_{2-6}$ alkynyl), —NH(C$_{3-15}$ cycloalkyl), —NH(C$_{1-8}$ haloalkyl), —NH(aryl), —NH(heteroaryl), —NH(heterocyclyl), —N(C$_{1-9}$ alkyl)$_2$, —N(C$_{3-15}$ cycloalkyl)$_2$, —N(C$_{2-6}$ alkenyl)$_2$, —N(C$_{2-6}$ alkynyl)$_2$, —N(C$_{3-15}$ cycloalkyl)$_2$, —N(C$_{1-8}$ haloalkyl)$_2$, —N(aryl)$_2$, —N(heteroaryl)$_2$, —N(heterocyclyl)$_2$, —N(C$_{1-9}$ alkyl)(C$_{3-15}$ cycloalkyl), —N(C$_{1-9}$ alkyl)(C$_{2-6}$ alkenyl), —N(C$_{1-9}$ alkyl)(C$_{2-6}$ alkynyl), —N(C$_{1-9}$ alkyl)(C$_{3-15}$ cycloalkyl), —N(C$_{1-9}$ alkyl)(C$_{1-8}$ haloalkyl), —N(C$_{1-9}$ alkyl)(aryl), —N(C$_{1-9}$ alkyl)(heteroaryl), —N(C$_{1-9}$ alkyl)(heterocyclyl), —C(O)(C$_{1-9}$ alkyl), —C(O)(C$_{2-6}$ alkenyl), —C(O)(C$_{2-6}$ alkynyl), —C(O)(C$_{3-15}$ cycloalkyl), —C(O)(C$_{1-8}$ haloalkyl), —C(O)(aryl), —C(O)(heteroaryl), —C(O)(heterocyclyl), —C(O)O(C$_{1-9}$ alkyl), —C(O)O(C$_{2-6}$ alkenyl), —C(O)O(C$_{2-6}$ alkynyl), —C(O)O(C$_{3-15}$ cycloalkyl), —C(O)O(C$_{1-8}$ haloalkyl), —C(O)O(aryl), —C(O)O(heteroaryl), —C(O)O(heterocyclyl), —C(O)NH$_2$, —C(O)NH(C$_{1-9}$ alkyl), —C(O)NH(C$_{2-6}$ alkenyl), —C(O)NH(C$_{2-6}$ alkynyl), —C(O)NH(C$_{3-15}$ cycloalkyl), —C(O)NH(C$_{1-8}$ haloalkyl), —C(O)NH(aryl), —C(O)NH(heteroaryl), —C(O)NH(heterocyclyl), —C(O)N(C$_{1-9}$ alkyl)$_2$, —C(O)N(C$_{3-15}$ cycloalkyl)$_2$, —C(O)N(C$_{2-6}$ alkenyl)$_2$, —C(O)N(C$_{2-6}$ alkynyl)$_2$, —C(O)N(C$_{3-15}$ cycloalkyl)$_2$, —C(O)N(C$_{2-8}$ haloalkyl)$_2$, —C(O)N(aryl)$_2$, —C(O)N(heteroaryl)$_2$, —C(O)N(heterocyclyl)$_2$, —NHC(O)(C$_{1-9}$ alkyl), —NHC(O)(C$_{2-6}$ alkenyl), —NHC(O)(C$_{2-6}$ alkynyl), —NHC(O)(C$_{3-15}$ cycloalkyl), —NHC(O)(C$_{1-8}$ haloalkyl), —NHC(O)(aryl), —NHC(O)(heteroaryl), —NHC(O)(heterocyclyl), —NHC(O)O(C$_{1-9}$ alkyl), —NHC(O)O(C$_{2-6}$ alkenyl), —NHC(O)O(C$_{2-6}$ alkynyl), —NHC(O)O(C$_{3-15}$ cycloalkyl), —NHC(O)O(C$_{1-8}$ haloalkyl), —NHC(O)O(aryl), —NHC(O)O(heteroaryl), —NHC(O)O(heterocyclyl), —NHC(O)NH(C$_{1-9}$ alkyl), —NHC(O)NH(C$_{2-6}$ alkenyl), —NHC(O)NH(C$_{2-6}$ alkynyl), —NHC(O)NH(C$_{3-15}$ cycloalkyl), —NHC(O)NH(C$_{2-8}$ haloalkyl), —NHC(O)NH(aryl), —NHC(O)NH(heteroaryl), —NHC(O)NH(heterocyclyl), —SH, —S(C$_{1-9}$ alkyl), —S(C$_{2-6}$ alkenyl), —S(C$_{2-6}$ alkynyl), —S(C$_{3-15}$ cycloalkyl), —S(C$_{1-8}$ haloalkyl), —S(aryl), —S(heteroaryl), —S(heterocyclyl), —NHS(O)(C$_{1-9}$ alkyl), —N(C$_{1-9}$ alkyl)(S(O)(C$_{1-9}$ alkyl), —S(O)N(C$_{1-9}$ alkyl)$_2$, —S(O)(C$_{1-9}$ alkyl), —S(O)(NH)(C$_{1-9}$ alkyl), —S(O)(C$_{2-6}$ alkenyl), —S(O)(C$_{2-6}$ alkynyl), —S(O)(C$_{3-15}$ cycloalkyl), —S(O)(C$_{1-8}$ haloalkyl), —S(O)(aryl), —S(O)(heteroaryl), —S(O)(heterocyclyl), —S(O)$_2$(C$_{1-9}$ alkyl), —S(O)$_2$(C$_{2-6}$ alkenyl), —S(O)$_2$(C$_{2-6}$ alkynyl), —S(O)$_2$(C$_{3-15}$ cycloalkyl), —S(O)$_2$(C$_{1-8}$ haloalkyl), —S(O)$_2$(aryl), —S(O)$_2$(heteroaryl), —S(O)$_2$(heterocyclyl), —S(O)$_2$NH(C$_{1-9}$ alkyl), or —S(O)$_2$N(C$_{1-9}$ alkyl)$_2$;
  wherein any alkyl, cycloalkyl, aryl, heteroaryl, or heterocyclyl is optionally substituted with one to four halo, $C_{1-9}$ alkyl, $C_{1-8}$ haloalkyl, —OH, —NH$_2$, —NH(C$_{1-9}$ alkyl), —NH(C$_{3-15}$ cycloalkyl), —NH(C$_{1-8}$ haloalkyl), —NH(aryl), —NH(heteroaryl), —NH(heterocyclyl), —N(C$_{1-9}$ alkyl)$_2$, —N(C$_{3-15}$ cycloalkyl)$_2$, —NHC(O) (C$_{3-15}$ cycloalkyl), —NHC(O)(C$_{1-8}$ haloalkyl), —NHC(O)(aryl), —NHC(O)(heteroaryl), —NHC(O)(heterocyclyl), —NHC(O)O(C$_{1-9}$ alkyl), —NHC(O)O(C$_{2-6}$ alkynyl), —NHC(O)O(C$_{3-15}$ cycloalkyl), —NHC(O)O(C$_{1-8}$ haloalkyl), —NHC(O)O(aryl), —NHC(O)O(heteroaryl), —NHC(O)O(heterocyclyl), —NHC(O)NH(C$_{1-9}$ alkyl), —S(O)(NH)(C$_{1-9}$ alkyl), S(O)$_2$(C$_{1-9}$ alkyl), —S(O)$_2$(C$_{3-15}$ cycloalkyl), —S(O)$_2$(C$_{1-8}$ haloalkyl), —S(O)$_2$(aryl), —S(O)$_2$(heteroaryl), —S(O)$_2$(heterocyclyl), —S(O)$_2$NH(C$_{1-9}$ alkyl), —S(O)$_2$N(C$_{1-9}$ alkyl)$_2$, —O(C$_{3-15}$ cycloalkyl), —O(C$_{1-8}$ haloalkyl), —O(aryl), —O(heteroaryl), —O(heterocyclyl), or —O(C$_{1-9}$ alkyl);

m is 0, 1, or 2;
or a pharmaceutically acceptable salt, tautomer, stereoisomer, mixture of stereoisomers, prodrug, or deuterated analog thereof.

In certain embodiments, the compound of Formula I is represented by Formula IA:

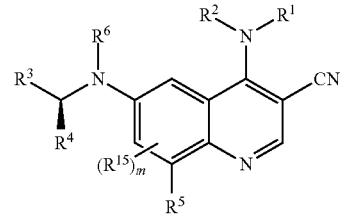

IA wherein $R^1$-$R^6$, $R^{15}$ and m are as described herein.

In certain embodiments, the compound of Formula I is represented by Formula IB:

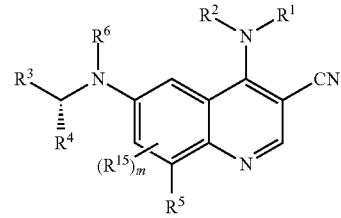

IB wherein $R^1$-$R^6$, $R^{15}$ and in are as described herein.

In certain embodiments, m is 0. In certain embodiments, $R^2$ is hydrogen.

In certain embodiments, provided is a compound of Formula II:

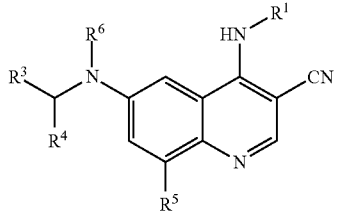

II wherein $R^1$, $R^3$, $R^4$, $R^5$ and $R^6$ are as defined herein.

In certain embodiments, provided is a compound of Formula IIA:

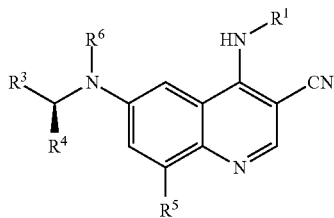

IIA wherein $R^1$, $R^3$, $R^4$, $R^5$ and $R^6$ are as defined herein.

In certain embodiments, provided is a compound of Formula III:

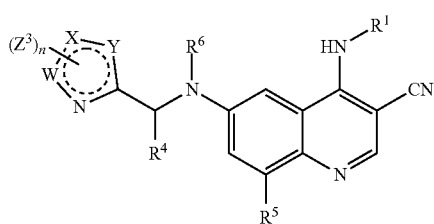

III wherein $R^1$, $R^4$, $R^5$ and $R^6$ are as defined herein,
W, X and Y are each independently N or C;
n is 1, 2, or 3;
each $Z^3$ is independently hydrogen, oxo, halo, —NO$_2$, —N$_3$, —CN, thioxo, C$_{1-9}$ alkyl, C$_{2-6}$ alkenyl, C$_{2-6}$ alkynyl, C$_{3-15}$ cycloalkyl, C$_{1-8}$ haloalkyl, aryl, heteroaryl, heterocyclyl, —O—R$^{12}$, —C(O)—R$^{12}$, —C(O)O—R$^{12}$, —C(O)—N(R$^{13}$)(R$^{14}$), —N(R$^{13}$)(R$^{14}$), —N(R$^{13}$)$_2$(R$^{14}$)$^+$, —N(R$^{12}$)C(O)—R$^{12}$, —N(R$^{12}$)C(O)O—R$^{12}$, —N(R$^{12}$)C(O)N(R$^{13}$)(R$^{14}$), —N(R$^{12}$)S(O)$_2$(R$^{12}$), —NR$^{12}$S(O)$_2$N(R$^{13}$)(R$^{14}$), —NR$^{12}$S(O)$_2$O(R$^{12}$), —OC(O)R$^{12}$, —OC(O)—N(R$^{13}$)(R$^{14}$), —P(O)(OR$^{12}$)$_2$, —OP(O)(OR$^{12}$)$_2$, —CH$_2$P(O)(OR$^{12}$)$_2$, —OCH$_2$P(O)(OR$^{12}$)$_2$, —C(O)OCH$_2$P(O)(OR$^{12}$)$_2$, —P(O)(R$^{12}$)(OR$^{12}$), —OP(O)(R$^{12}$)(OR$^{12}$), —CH$_2$P(O)(R$^{12}$)(OR$^{12}$), —OCH$_2$P(O)(R$^{12}$)(OR$^{12}$), —C(O)OCH$_2$P(O)(R$^{12}$)(OR$^{12}$), —P(O)(N(R$^{12}$)$_2$)$_2$, —OP(O)(N(R$^{12}$)$_2$)$_2$, —CH$_2$P(O)(N(R$^{12}$)$_2$)$_2$, —OCH$_2$P(O)(N(R$^{12}$)$_2$)$_2$, —C(O)OCH$_2$P(O)(N(R$^{12}$)$_2$)$_2$, —P(O)(N(R$^{12}$)$_2$)(OR$^{12}$), —OP(O)(N(R$^{12}$)$_2$)(OR$^{12}$), —CH$_2$P(O)(N(R$^{12}$)$_2$)(OR$^{12}$), —OCH$_2$P(O)(N(R$^{12}$)$_2$)(OR$^{12}$), —C(O)OCH$_2$P(O)(N(R$^{12}$)$_2$)(OR$^{12}$), —P(O)(R$^{12}$)(N(R$^{12}$)$_2$), —OP(O)(R$^{12}$)(N(R$^{12}$)$_2$), —CH$_2$P(O)(R$^{12}$)(N(R$^{12}$)$_2$), —OCH$_2$P(O)(R$^{12}$)(N(R$^{12}$)$_2$), —C(O)OCH$_2$P(O)(R$^{12}$)(N(R$^{12}$)$_2$), —Si(R$^{12}$)$_3$, —S—R$^{12}$, —S(O)R$^{12}$, —S(O)(NH)R$^{12}$, —S(O)$_2$R$^{12}$ or —S(O)$_2$N(R$^{13}$)(R$^{14}$);

wherein any alkyl, alkenyl, alkynyl, cycloalkyl, haloalkyl aryl, heteroaryl or heterocyclyl is optionally substituted with one to four $Z^{1a}$ groups;

each $Z^{1a}$ is independently oxo, halo, thioxo, —NO$_2$, —CN, —N$_3$, C$_{1-9}$ alkyl, C$_{2-6}$ alkenyl, C$_{2-6}$ alkynyl, C$_{3-15}$ cycloalkyl, C$_{1-8}$ haloalkyl, C$_{1-8}$ hydroxyalkyl, aryl, heteroaryl, heterocyclyl, —O—R$^{12}$, —C(O)R$^{12}$, —C(O)O—R$^{12}$, —C(O)N(R$^{13}$)(R$^{14}$), —N(R$^{13}$)(R$^{14}$), —N(R$^{13}$)$_2$(R$^{14}$)$^+$, —C(O)N(R$^{12}$)—S(O)$_2$R$^{12}$, —N(R$^{12}$)—C(O)R$^{12}$, —N(R$^{12}$)C(O)O(R$^{12}$), —N(R$^{12}$)C(O)N(R$^{13}$)(R$^{14}$), —N(R$^{12}$)S(O)$_2$(R$^{12}$), —N(R$^{12}$)S(O)$_2$—N(R$^{13}$)(R$^{14}$), —N(R$^{12}$)S(O)$_2$O(R$^{12}$), —OC(O)R$^{12}$, —OC(O)OR$^{12}$, —OC(O)—N(R$^{13}$)(R$^{14}$), —Si(R$^{12}$)$_3$, —S—R$^{12}$, —S(O)R$^{12}$, —S(O)(NH)R$^{12}$, —S(O)$_2$R$^{12}$ or —S(O)$_2$N(R$^{13}$)(R$^{14}$);

wherein any alkyl, alkenyl, alkynyl, cycloalkyl, aryl, heteroaryl or heterocyclyl is optionally substituted with one to four $Z^{1b}$ groups;

each $R^{12}$ is independently hydrogen, C$_{1-9}$ alkyl, C$_{2-6}$ alkenyl, C$_{2-6}$ alkynyl, C$_{3-15}$ cycloalkyl, aryl, heteroaryl or heterocyclyl, wherein any alkyl, alkenyl, alkynyl, cycloalkyl, aryl, heteroaryl or heterocyclyl is optionally substituted with one to four $Z^{1b}$ groups;

$R^{13}$ and $R^{14}$ at each occurrence are each independently hydrogen, C$_{1-9}$ alkyl, C$_{2-6}$ alkenyl, C$_{2-6}$ alkynyl, C$_{3-15}$ cycloalkyl, aryl, heteroaryl or heterocyclyl;

wherein any alkyl, alkenyl, alkynyl, cycloalkyl, aryl, heteroaryl or heterocyclyl is optionally substituted with one to four $Z^{1b}$ groups, or $R^{13}$ and $R^{14}$ together with the nitrogen to which they are attached form a heterocyclyl, wherein said heterocyclyl is optionally substituted with one to four $Z^{1b}$ groups; and each $Z^{1b}$ is independently oxo, thioxo, hydroxy, halo, —NO$_2$, —N$_3$, —CN, C$_{1-9}$ alkyl, C$_{2-6}$ alkenyl, C$_{2-6}$ alkynyl, C$_{3-15}$ cycloalkyl, C$_{1-8}$ haloalkyl, aryl, heteroaryl, heterocyclyl, —O(C$_{1-9}$ alkyl), —O(C$_{2-6}$ alkenyl), —O(C$_{2-6}$ alkynyl), —O(C$_{3-15}$ cycloalkyl), —O(C$_{1-8}$ haloalkyl), —O(aryl), —O(heteroaryl), —O(heterocyclyl), —NH$_2$, —NH(C$_{1-9}$ alkyl), —NH(C$_{2-6}$ alkenyl), —NH(C$_{2-6}$ alkynyl), —NH(C$_{3-15}$ cycloalkyl), —NH(C$_{1-8}$ haloalkyl), —NH(aryl), —NH(heteroaryl), —NH(heterocyclyl), —N(C$_{1-9}$ alkyl)$_2$, —N(C$_{3-15}$ cycloalkyl)$_2$, —N(C$_{2-6}$ alkenyl)$_2$, —N(C$_{2-6}$ alkynyl)$_2$, —N(C$_{3-15}$ cycloalkyl)$_2$, —N(C$_{1-8}$ haloalkyl)$_2$, —N(aryl)$_2$, —N(heteroaryl)$_2$, —N(heterocyclyl)$_2$, —N(C$_{1-9}$ alkyl)(C$_{3-15}$ cycloalkyl), —N(C$_{1-9}$ alkyl)(C$_{2-6}$ alkenyl), —N(C$_{1-9}$ alkyl)(C$_{2-6}$ alkynyl), —N(C$_{1-9}$ alkyl)(C$_{3-15}$ cycloalkyl), —N(C$_{1-9}$ alkyl)(C$_{1-8}$ haloalkyl), —N(C$_{1-9}$ alkyl)(aryl), —N(C$_{1-9}$ alkyl)(heteroaryl), —N(C$_{1-9}$ alkyl)(heterocyclyl), —C(O)(C$_{1-9}$ alkyl), —C(O)(C$_{2-6}$ alkenyl), —C(O)(C$_{2-6}$ alkynyl), —C(O)(C$_{3-15}$ cycloalkyl), —C(O)(C$_{1-8}$ haloalkyl), —C(O)(aryl), —C(O)(heteroaryl), —C(O)(heterocyclyl), —C(O)O(C$_{1-9}$ alkyl), —C(O)O(C$_{2-6}$ alkenyl), —C(O)O(C$_{2-6}$ alkynyl), —C(O)O(C$_{3-15}$ cycloalkyl), —C(O)O(C$_{1-8}$ haloalkyl), —C(O)O(aryl), —C(O)O(heteroaryl), —C(O)O(heterocyclyl), —C(O)NH$_2$, —C(O)NH(C$_{1-9}$ alkyl), —C(O)NH(C$_{2-6}$ alkenyl), —C(O)NH(C$_{2-6}$ alkynyl), —C(O)NH(C$_{3-15}$ cycloalkyl), —C(O)NH(C$_{1-8}$ haloalkyl), —C(O)NH(aryl), —C(O)NH(heteroaryl), —C(O)NH(heterocyclyl), —C(O)N(C$_{1-9}$ alkyl)$_2$, —C(O)N(C$_{3-15}$ cycloalkyl)$_2$, —C(O)N(C$_{2-6}$ alkenyl)$_2$, —C(O)N(C$_{2-6}$ alkynyl)$_2$, —C(O)N(C$_{3-15}$ cycloalkyl)$_2$, —C(O)N(C$_{2-8}$ haloalkyl)$_2$, —C(O)N(aryl)$_2$, —C(O)N(heteroaryl)$_2$, —C(O)N(heterocyclyl)$_2$, —NHC(O)(C$_{1-9}$ alkyl), —NHC(O)(C$_{2-6}$ alkenyl), —NHC(O)(C$_{2-6}$ alkynyl), —NHC(O)(C$_{3-15}$ cycloalkyl), —NHC(O)(C$_{1-8}$ haloalkyl), —NHC(O)(aryl), —NHC(O)(heteroaryl), —NHC(O)(heterocyclyl), —NHC(O)O(C$_{1-9}$ alkyl), —NHC(O)O(C$_{2-6}$ alkenyl), —NHC(O)O(C$_{2-6}$ alkynyl), —NHC(O)O(C$_{3-15}$ cycloalkyl), —NHC(O)O(C$_{1-8}$ haloalkyl), —NHC(O)O(aryl), —NHC(O)O(heteroaryl), —NHC(O)O(heterocyclyl), —NHC(O)NH(C$_{1-9}$ alkyl), —NHC(O)NH(C$_{2-6}$ alkenyl), —NHC(O)NH(C$_{2-6}$ alkynyl), —NHC(O)NH(C$_{3-15}$ cycloalkyl), —NHC(O)NH(C$_{2-8}$ haloalkyl), —NHC(O)NH(aryl), —NHC(O)NH(heteroaryl), —NHC(O)NH(heterocyclyl), —SH, —S(C$_{1-9}$ alkyl), —S(C$_{2-6}$ alkenyl), —S(C$_{2-6}$ alkynyl), —S(C$_{3-15}$ cycloalkyl), —S(C$_{1-8}$ haloalkyl), —S(aryl), —S(heteroaryl), —S(heterocyclyl), —NHS(O)(C$_{1-9}$ alkyl), —N(C$_{1-9}$ alkyl)(S(O)(C$_{1-9}$ alkyl), —S(O)N(C$_{1-9}$ alkyl)$_2$, —S(O)(C$_{1-9}$ alkyl), —S(O)(NH)(C$_{1-9}$ alkyl), —S(O)(C$_{2-6}$ alkenyl), —S(O)(C$_{2-6}$ alkynyl), —S(O)(C$_{3-15}$ cycloalkyl), —S(O)(C$_{1-8}$ haloalkyl), —S(O)(aryl), —S(O)(heteroaryl), —S(O)(heterocyclyl), —S(O)$_2$(C$_{1-9}$ alkyl), —S(O)$_2$(C$_{2-6}$ alkenyl), —S(O)$_2$(C$_{2-6}$ alkynyl), —S(O)$_2$(C$_{3-15}$ cycloalkyl), —S(O)$_2$(C$_{1-8}$ haloalkyl), —S(O)$_2$(aryl), —S(O)$_2$(heteroaryl), —S(O)$_2$(heterocyclyl), —S(O)$_2$NH(C$_{1-9}$ alkyl), or —S(O)$_2$N(C$_{1-9}$ alkyl)$_2$;

wherein any alkyl, cycloalkyl, aryl, heteroaryl, or heterocyclyl is optionally substituted with one to four halo, C$_{1-9}$ alkyl, C$_{1-8}$ haloalkyl, —OH, —NH$_2$, —NH(C$_{1-9}$ alkyl), —NH(C$_{3-15}$ cycloalkyl), —NH(C$_{1-8}$ haloalkyl), —NH(aryl), —NH(heteroaryl), —NH(heterocyclyl), —N(C$_{1-9}$ alkyl)$_2$, —N(C$_{3-15}$ cycloalkyl)$_2$, —NHC(O)(C$_{3-15}$ cycloalkyl), —NHC(O)(C$_{1-8}$ haloalkyl), —NHC(O)(aryl), —NHC(O)(heteroaryl), —NHC(O)(heterocyclyl), —NHC(O)O(C$_{1-9}$ alkyl), —NHC(O)O(C$_{2-6}$ alkynyl), —NHC(O)O(C$_{3-15}$ cycloalkyl), —NHC(O)O(C$_{1-8}$ haloalkyl), —NHC(O)O(aryl), —NHC(O)O(heteroaryl), —NHC(O)O(heterocyclyl), —NHC(O)NH(C$_{1-9}$ alkyl), —S(O)(NH)(C$_{1-9}$ alkyl), S(O)$_2$(C$_{1-9}$ alkyl), —S(O)$_2$(C$_{3-15}$ cycloalkyl), —S(O)$_2$(C$_{1-8}$ haloalkyl), —S(O)$_2$(aryl), —S(O)$_2$(heteroaryl), —S(O)$_2$(heterocyclyl), —S(O)$_2$NH(C$_{1-9}$ alkyl), —S(O)$_2$N(C$_{1-9}$ alkyl)$_2$, —O(C$_{3-15}$ cycloalkyl), —O(C$_{1-8}$ haloalkyl), —O(aryl), —O(heteroaryl), —O(heterocyclyl), or —O(C$_{1-9}$ alkyl);

or a pharmaceutically acceptable salt, tautomer, stereoisomer, mixture of stereoisomers, prodrug, or deuterated analog thereof.

In certain embodiments, provided is a compound of Formula IIIA:

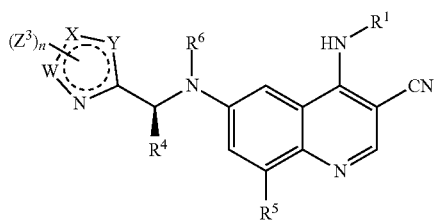

IIIA wherein R$^1$, R$^4$, R$^5$ and R$^6$ are as defined herein,
W, X and Y are each independently N or C;
n is 1, 2, or 3;
each Z$^3$ is independently hydrogen, oxo, halo, —NO$_2$, —N$_3$, —CN, thioxo, C$_{1-9}$ alkyl, C$_{2-6}$ alkenyl, C$_{2-6}$ alkynyl, C$_{3-15}$ cycloalkyl, C$_{1-8}$ haloalkyl, aryl, heteroaryl, heterocyclyl, —O—R$^{12}$, —C(O)—R$^{12}$, —C(O)O—R$^{12}$, —C(O)—N(R$^{13}$)(R$^{14}$), —N(R$^{13}$)(R$^{14}$), —N(R$^{13}$)$_2$(R$^{14}$)$^+$, —N(R$^{12}$)C(O)—R$^{12}$, —N(R$^{12}$)C(O)O—R$^{12}$, —N(R$^{12}$)C(O)N(R$^{13}$)(R$^{14}$), —N(R$^{12}$)S(O)$_2$(R$^{12}$), —NR$^{12}$S(O)$_2$N(R$^{13}$)(R$^{14}$), —NR$^{12}$S(O)$_2$O(R$^{12}$), —OC(O)R$^{12}$, —OC(O)—N(R$^{13}$)(R$^{14}$), —P(O)(OR$^{12}$)$_2$, —OP(O)(OR$^{12}$)$_2$, —CH$_2$P(O)(OR$^{12}$)$_2$, —OCH$_2$P(O)(OR$^{12}$)$_2$, —C(O)OCH$_2$P(O)(OR$^{12}$)$_2$, —P(O)(R$^{12}$)(OR$^{12}$), —OP(O)(R$^{12}$)(OR$^{12}$), —CH$_2$P(O)(R$^{12}$)(OR$^{12}$), —OCH$_2$P(O)(R$^{12}$)(OR$^{12}$). —C(O)OCH$_2$P(O)(R$^{12}$)(OR$^{12}$), —P(O)(N(R$^{12}$)$_2$)$_2$, —OP(O)(N(R$^{12}$)$_2$)$_2$, —CH$_2$P(O)(N(R$^{12}$)$_2$)$_2$, —OCH$_2$P(O)(N(R$^{12}$)$_2$)$_2$, —C(O)OCH$_2$P(O)(N(R$^{12}$)$_2$)$_2$, —P(O)(N(R$^{12}$)$_2$)(OR$^{12}$), —OP(O)(N(R$^{12}$)$_2$)(OR$^{12}$), —CH$_2$P(O)(N(R$^{12}$)$_2$)(OR$^{12}$), —OCH$_2$P(O)(N(R$^{12}$)$_2$)(OR$^{12}$), —C(O)OCH$_2$P(O)(N(R$^{12}$)$_2$)(OR$^{12}$), —P(O)(R$^{12}$)(N(R$^{12}$)$_2$), —OP(O)(R$^{12}$)(N(R$^{12}$)$_2$), —CH$_2$P(O)(R$^{12}$)(N(R$^{12}$)$_2$), —OCH$_2$P(O)(R$^{12}$)(N(R$^{12}$)$_2$), —C(O)OCH$_2$P(O)(R$^{12}$)(N(R$^{12}$)$_2$), —Si(R$^{12}$)$_3$, —S—R$^{12}$, —S(O)R$^{12}$, —S(O)(NH)R$^{12}$, —S(O)$_2$R$^{12}$ or —S(O)$_2$N(R$^{13}$)(R$^{14}$);

wherein any alkyl, alkenyl, alkynyl, cycloalkyl, haloalkyl aryl, heteroaryl or heterocyclyl is optionally substituted with one to four Z$^{1a}$ groups;

each Z$^{1a}$ is independently oxo, halo, thioxo, —NO$_2$, —CN, —N$_3$, C$_{1-9}$ alkyl, C$_{2-6}$ alkenyl, C$_{2-6}$ alkynyl, C$_{3-15}$ cycloalkyl, C$_{1-8}$ haloalkyl, aryl, heteroaryl, heterocyclyl, —O—R$^{12}$, —C(O)R$^{12}$, —C(O)O—R$^{12}$, —C(O)N(R$^{13}$)(R$^{14}$), —N(R$^{13}$)(R$^{14}$), —N(R$^{13}$)$_2$(R$^{14}$)$^+$, —N(R$^{12}$)—C(O)R$^{12}$, —N(R$^{12}$)C(O)O(R$^{12}$), —N(R$^{12}$)C(O)N(R$^{13}$)(R$^{14}$), —N(R$^{12}$)S(O)$_2$(R$^{12}$), —N(R$^{12}$)S(O)$_2$—N(R$^{13}$)(R$^{14}$), —N(R$^{12}$)S(O)$_2$O(R$^{12}$), —OC(O)R$^{12}$, —OC(O)OR$^{12}$, —OC(O)—N(R$^{13}$)(R$^{14}$), —Si(R$^{12}$)$_3$, —S—R$^{12}$, —S(O)R$^{12}$, —S(O)(NH)R$^{12}$, —S(O)$_2$R$^{12}$ or —S(O)$_2$N(R$^{13}$)(R$^{14}$);

wherein any alkyl, alkenyl, alkynyl, cycloalkyl, aryl, heteroaryl or heterocyclyl is optionally substituted with one to four Z$^{1b}$ groups;

each R$^{12}$ is independently hydrogen, C$_{1-9}$ alkyl, C$_{2-6}$ alkenyl, C$_{2-6}$ alkynyl, C$_{3-15}$ cycloalkyl, aryl, heteroaryl or heterocyclyl, wherein any alkyl, alkenyl, alkynyl, cycloalkyl, aryl, heteroaryl or heterocyclyl is optionally substituted with one to four Z$^{1b}$ groups;

R$^{13}$ and R$^{14}$ at each occurrence are each independently hydrogen, C$_{1-9}$ alkyl, C$_{2-6}$ alkenyl, C$_{2-6}$ alkynyl, C$_{3-15}$ cycloalkyl, aryl, heteroaryl or heterocyclyl;

wherein any alkyl, alkenyl, alkynyl, cycloalkyl, aryl, heteroaryl or heterocyclyl is optionally substituted with one to four Z$^{1b}$ groups, or R$^{13}$ and R$^{14}$ together with the nitrogen to which they are attached form a heterocyclyl, wherein said heterocyclyl is optionally substituted with one to four Z$^{1b}$ groups; and each Z$^{1b}$ is independently oxo, thioxo, hydroxy, halo, —NO$_2$, —N$_3$, —CN, C$_{1-9}$ alkyl, C$_{2-6}$ alkenyl, C$_{2-6}$ alkynyl, C$_{3-15}$ cycloalkyl, C$_{1-8}$ haloalkyl, aryl, heteroaryl, heterocyclyl, —O(C$_{1-9}$ alkyl), —O(C$_{2-6}$ alkenyl), —O(C$_{2-6}$ alkynyl), —O(C$_{3-15}$ cycloalkyl), —O(C$_{1-8}$ haloalkyl), —O(aryl), —O(heteroaryl), —O(heterocyclyl), —NH$_2$, —NH(C$_{1-9}$ alkyl), —NH(C$_{2-6}$ alkenyl), —NH(C$_{2-6}$ alkynyl), —NH(C$_{3-15}$ cycloalkyl), —NH(C$_{1-8}$ haloalkyl), —NH(aryl), —NH(heteroaryl), —NH(heterocyclyl), —N(C$_{1-9}$ alkyl)$_2$, —N(C$_{3-15}$ cycloalkyl)$_2$, —N(C$_{2-6}$ alkenyl)$_2$, —N(C$_{2-6}$ alkynyl)$_2$, —N(C$_{3-15}$ cycloalkyl)$_2$, —N(C$_{1-8}$ haloalkyl)$_2$, —N(aryl)$_2$, —N(heteroaryl)$_2$, —N(heterocyclyl)$_2$, —N(C$_{1-9}$ alkyl)(C$_{3-15}$ cycloalkyl), —N(C$_{1-9}$ alkyl)(C$_{2-6}$ alkenyl), —N(C$_{1-9}$ alkyl)(C$_{2-6}$ alkynyl), —N(C$_{1-9}$ alkyl)(C$_{3-15}$ cycloalkyl), —N(C$_{1-9}$ alkyl)(C$_{1-8}$ haloalkyl), —N(C$_{1-9}$ alkyl)(aryl), —N(C$_{1-9}$ alkyl)(heteroaryl), —N(C$_{1-9}$ alkyl)(heterocyclyl), —C(O)(C$_{1-9}$ alkyl), —C(O)(C$_{2-6}$ alkenyl), —C(O)(C$_{2-6}$ alkynyl), —C(O)(C$_{3-15}$ cycloalkyl), —C(O)(C$_{1-8}$ haloalkyl), —C(O)(aryl), —C(O)(heteroaryl), —C(O)(heterocyclyl), —C(O)O(C$_{1-9}$ alkyl), —C(O)O(C$_{2-6}$ alkenyl), —C(O)O(C$_{2-6}$ alkynyl), —C(O)O(C$_{3-15}$ cycloalkyl), —C(O)O(C$_{1-8}$ haloalkyl), —C(O)O(aryl), —C(O)O(heteroaryl), —C(O)O(heterocyclyl), —C(O)NH$_2$, —C(O)NH(C$_{1-9}$ alkyl), —C(O)NH(C$_{2-6}$ alkenyl), —C(O)NH(C$_{2-6}$ alkynyl), —C(O)NH(C$_{3-15}$ cycloalkyl), —C(O)NH(C$_{1-8}$ haloalkyl), —C(O)NH(aryl), —C(O)NH(heteroaryl), —C(O)NH(heterocyclyl), —C(O)N(C$_{1-9}$ alkyl)$_2$, —C(O)N(C$_{3-15}$ cycloalkyl)$_2$, —C(O)N(C$_{2-6}$ alkenyl)$_2$, —C(O)N(C$_{2-6}$ alkynyl)$_2$, —C(O)N(C$_{3-15}$ cycloalkyl)$_2$, —C(O)N(C$_{2-8}$ haloalkyl)$_2$, —C(O)N(aryl)$_2$, —C(O)N(heteroaryl)$_2$, —C(O)N(heterocyclyl)$_2$, —NHC(O)(C$_{1-9}$ alkyl), —NHC(O)(C$_{2-6}$ alkenyl), —NHC(O)(C$_{2-6}$ alkynyl), —NHC(O)(C$_{3-15}$ cycloalkyl), —NHC(O)(C$_{1-8}$ haloalkyl), —NHC(O)(aryl), —NHC(O)(heteroaryl), —NHC(O)(heterocyclyl), —NHC(O)O(C$_{1-9}$ alkyl), —NHC(O)O(C$_{2-6}$ alkenyl), —NHC(O)O(C$_{2-6}$ alkynyl), —NHC(O)O(C$_{3-15}$ cycloalkyl), —NHC(O)O(C$_{1-8}$ haloalkyl), —NHC(O)O(aryl), —NHC(O)O(heteroaryl), —NHC(O)O(heterocyclyl), —NHC(O)NH(C$_{1-9}$ alkyl), —NHC(O)NH(C$_{2-6}$ alkenyl), —NHC(O)NH(C$_{2-6}$ alkynyl), —NHC(O)NH(C$_{3-15}$ cycloalkyl), —NHC(O)NH(C$_{2-8}$ haloalkyl), —NHC(O)NH(aryl), —NHC(O)NH(heteroaryl), —NHC(O)NH(heterocyclyl), —SH, —S(C$_{1-9}$ alkyl), —S(C$_{2-6}$ alkenyl), —S(C$_{2-6}$ alkynyl), —S(C$_{3-15}$ cycloalkyl), —S(C$_{1-8}$ haloalkyl), —S(aryl), —S(heteroaryl), —S(heterocyclyl), —NHS(O)(C$_{1-9}$ alkyl), —N(C$_{1-9}$ alkyl)(S(O)(C$_{1-9}$ alkyl), —S(O)N(C$_{1-9}$ alkyl)$_2$, —S(O)(C$_{1-9}$ alkyl), —S(O)(NH)(C$_{1-9}$ alkyl), —S(O)(C$_{2-6}$ alkenyl), —S(O)(C$_{2-6}$ alkynyl), —S(O)(C$_{3-15}$ cycloalkyl), —S(O)(C$_{1-8}$ haloalkyl), —S(O)(aryl), —S(O)(heteroaryl), —S(O)(heterocyclyl), —S(O)$_2$(C$_{1-9}$ alkyl), —S(O)$_2$(C$_{2-6}$ alkenyl), —S(O)$_2$(C$_{2-6}$ alkynyl), —S(O)$_2$(C$_{3-15}$ cycloalkyl), —S(O)$_2$(C$_{1-8}$ haloalkyl), —S(O)$_2$(aryl), —S(O)$_2$(heteroaryl), —S(O)$_2$(heterocyclyl), —S(O)$_2$NH(C$_{1-9}$ alkyl), or —S(O)$_2$N(C$_{1-9}$ alkyl)$_2$;

wherein any alkyl, cycloalkyl, aryl, heteroaryl, or heterocyclyl is optionally substituted with one to four halo, C$_{1-9}$ alkyl, C$_{1-8}$ haloalkyl, —OH, —NH$_2$, —NH(C$_{1-9}$ alkyl), —NH(C$_{3-15}$ cycloalkyl), —NH(C$_{1-8}$ haloalkyl), —NH(aryl), —NH(heteroaryl), —NH(heterocyclyl), —N(C$_{1-9}$ alkyl)$_2$, —N(C$_{3-15}$ cycloalkyl)$_2$, —NHC(O)(C$_{3-15}$ cycloalkyl), —NHC(O)(C$_{1-8}$ haloalkyl), —NHC(O)(aryl), —NHC(O)(heteroaryl), —NHC(O)(heterocyclyl), —NHC(O)O(C$_{1-9}$ alkyl), —NHC(O)O(C$_{2-6}$ alkynyl), —NHC(O)O(C$_{3-15}$ cycloalkyl), —NHC(O)O(C$_{1-8}$ haloalkyl), —NHC(O)O(aryl), —NHC(O)O(heteroaryl), —NHC(O)O(heterocyclyl), —NHC(O)NH(C$_{1-9}$ alkyl), —S(O)(NH)(C$_{1-9}$ alkyl), S(O)$_2$(C$_{1-9}$ alkyl), —S(O)$_2$(C$_{3-15}$ cycloalkyl), —S(O)$_2$(C$_{1-8}$ haloalkyl), —S(O)$_2$(aryl), —S(O)$_2$(heteroaryl), —S(O)$_2$(heterocyclyl), —S(O)$_2$NH(C$_{1-9}$ alkyl), —S(O)$_2$N(C$_{1-9}$ alkyl)$_2$, —O(C$_{3-15}$ cycloalkyl), —O(C$_{1-8}$ haloalkyl), —O(aryl), —O(heteroaryl), —O(heterocyclyl), or —O(C$_{1-9}$ alkyl);

or a pharmaceutically acceptable salt, tautomer, stereoisomer, mixture of stereoisomers, prodrug, or deuterated analog thereof.

In certain embodiments, provided is a compound of Formula IIIA:

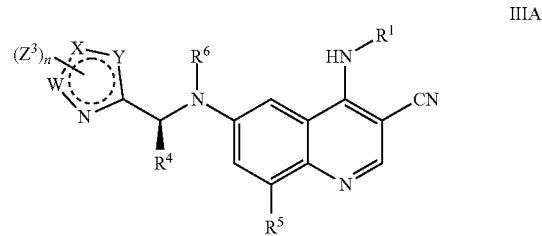

IIIA wherein R$^1$, R$^4$, R$^5$ and R$^6$ are as defined in claim 1,
W, X and Y are each independently N or C;
n is 1, 2, or 3;
each Z$^3$ is independently hydrogen, oxo, halo, —NO$_2$, —N$_3$, —CN, thioxo, C$_{1-9}$ alkyl, C$_{2-6}$ alkenyl, C$_{2-6}$ alkynyl, C$_{3-15}$ cycloalkyl, C$_{1-8}$ haloalkyl, aryl, heteroaryl, heterocyclyl, —O—R$^{12}$, —C(O)—R$^{12}$, —C(O)O—R$^{12}$, —C(O)—N(R$^{13}$)(R$^{14}$), —N(R$^{13}$)(R$^{14}$), —N(R$^{13}$)$_2$(R$^{14}$)$^+$, —N(R$^{12}$)C(O)—R$^{12}$, —N(R$^{12}$)C(O)O—R$^{12}$, —N(R$^{12}$)C(O)N(R$^{13}$)(R$^{14}$), —N(R$^{12}$)S(O)$_2$(R$^{12}$), —NR$^{12}$S(O)$_2$N(R$^{13}$)(R$^{14}$), —NR$^{12}$S(O)$_2$O(R$^{12}$), —OC(O)R$^{12}$, —OC(O)—N(R$^{13}$)(R$^{14}$), —P(O)(OR$^{12}$)$_2$, —OP(O)(OR$^{12}$)$_2$, —CH$_2$P(O)(OR$^{12}$)$_2$, —OCH$_2$P(O)(OR$^{12}$)$_2$, —C(O)OCH$_2$P(O)(OR$^{12}$)$_2$, —P(O)(R$^{12}$)(OR$^{12}$), —OP(O)(R$^{12}$)(OR$^{12}$), —CH$_2$P(O)(R$^{12}$)(OR$^{12}$), —OCH$_2$P(O)(R$^{12}$)(OR$^{12}$), —C(O)OCH$_2$P(O)(R$^{12}$)(OR$^{12}$), —P(O)(N(R$^{12}$)$_2$)$_2$, —OP(O)(N(R$^{12}$)$_2$)$_2$, —CH$_2$P(O)(N(R$^{12}$)$_2$)$_2$, —OCH$_2$P(O)(N(R$^{12}$)$_2$)$_2$, —C(O)OCH$_2$P(O)(N(R$^{12}$)$_2$)$_2$, —P(O)(N(R$^{12}$)$_2$)(OR$^{12}$), —OP(O)(N(R$^{12}$)$_2$)(OR$^{12}$), —CH$_2$P(O)(N(R$^{12}$)$_2$)(OR$^{12}$), —OCH$_2$P(O)(N(R$^{12}$)$_2$)(OR$^{12}$), —C(O)OCH$_2$P(O)(N(R$^{12}$)$_2$)(OR$^{12}$), —P(O)(R$^{12}$)(N(R$^{12}$)$_2$), —OP(O)(R$^{12}$)(N(R$^{12}$)$_2$), —CH$_2$P(O)(R$^{12}$)(N(R$^{12}$)$_2$), —OCH$_2$P(O)(R$^{12}$)(N(R$^{12}$)$_2$), —C(O)OCH$_2$P(O)(R$^{12}$)(N(R$^{12}$)$_2$), —Si(R$^{12}$)$_3$, —S—R$^{12}$, —S(O)R$^{12}$, —S(O)(NH)R$^{12}$, —S(O)$_2$R$^{12}$ or —S(O)$_2$N(R$^{13}$)(R$^{14}$);

wherein any alkyl, alkenyl, alkynyl, cycloalkyl, haloalkyl aryl, heteroaryl or heterocyclyl is optionally substituted with one to four Z$^{1a}$ groups;

each Z$^{1a}$ is independently oxo, halo, thioxo, —NO$_2$, —CN, —N$_3$, C$_{1-9}$ alkyl, C$_{2-6}$ alkenyl, C$_{2-6}$ alkynyl, C$_{3-15}$ cycloalkyl, C$_{1-8}$ haloalkyl, C$_{1-8}$ hydroxyalkyl, aryl, heteroaryl, heterocyclyl, —O—R$^{12}$, —C(O)R$^{12}$, —C(O)O—R$^{12}$, —C(O)N(R$^{13}$)(R$^{14}$), —N(R$^{13}$)(R$^{14}$), —N(R$^{13}$)$_2$(R$^{14}$)$^+$, —C(O)N(R$^{12}$)—S(O)$_2$R$^{12}$, —N(R$^{12}$)—C(O)R$^{12}$, —N(R$^{12}$)C(O)O(R$^{12}$), —N(R$^{12}$)C(O)N(R$^{13}$)(R$^{14}$), —N(R$^{12}$)S(O)$_2$(R$^{12}$), —N(R$^{12}$)S(O)$_2$—N(R$^{13}$)(R$^{14}$), —N(R$^{12}$)S(O)$_2$O(R$^{12}$), —OC(O)R$^{12}$, —OC(O)OR$^{12}$, —OC(O)—N(R$^{13}$)(R$^{14}$), —Si(R$^{12}$)$_3$, —S—R$^{12}$, —S(O)R$^{12}$, —S(O)(NH)R$^{12}$, —S(O)$_2$R$^{12}$ or —S(O)$_2$N(R$^{13}$)(R$^{14}$);

wherein any alkyl, alkenyl, alkynyl, cycloalkyl, aryl, heteroaryl or heterocyclyl is optionally substituted with one to four Z$^{1b}$ groups;

each R$^{12}$ is independently hydrogen, C$_{1-9}$ alkyl, C$_{2-6}$ alkenyl, C$_{2-6}$ alkynyl, C$_{3-15}$ cycloalkyl, aryl, heteroaryl or heterocyclyl, wherein any alkyl, alkenyl, alkynyl, cycloalkyl, aryl, heteroaryl or heterocyclyl is optionally substituted with one to four Z$^{1b}$ groups;

R$^{13}$ and R$^{14}$ at each occurrence are each independently hydrogen, C$_{1-9}$ alkyl, C$_{2-6}$ alkenyl, C$_{2-6}$ alkynyl, C$_{3-15}$ cycloalkyl, aryl, heteroaryl or heterocyclyl;

wherein any alkyl, alkenyl, alkynyl, cycloalkyl, aryl, heteroaryl or heterocyclyl is optionally substituted with one to four Z$^{1b}$ groups, or R$^{13}$ and R$^{14}$ together with the nitrogen to which they are attached form a heterocyclyl, wherein said heterocyclyl is optionally substituted with one to four $Z^{1b}$ groups; and each $Z^{1b}$ is independently oxo, thioxo, hydroxy, halo, —$NO_2$, —$N_3$, —CN, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O($C_{1-9}$ alkyl), —O($C_{2-6}$ alkenyl), —O($C_{2-6}$ alkynyl), —O($C_{3-15}$ cycloalkyl), —O($C_{1-8}$ haloalkyl), —O(aryl), —O(heteroaryl), —O(heterocyclyl), —$NH_2$, —NH($C_{1-9}$ alkyl), —NH($C_{2-6}$ alkenyl), —NH($C_{2-6}$ alkynyl), —NH($C_{3-15}$ cycloalkyl), —NH(C haloalkyl), —NH(aryl), —NH(heteroaryl), —NH(heterocyclyl), —N($C_{1-9}$ alkyl)$_2$, —N($C_{3-15}$ cycloalkyl)$_2$, —N($C_{2-6}$ alkenyl)$_2$, —N($C_{2-6}$ alkynyl)$_2$, —N($C_{3-15}$ cycloalkyl)$_2$, —N($C_{1-8}$ haloalkyl)$_2$, —N(aryl)$_2$, —N(heteroaryl)$_2$, —N(heterocyclyl)$_2$, —N($C_{1-9}$ alkyl)($C_{3-15}$ cycloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)($C_{1-8}$ haloalkyl), —N($C_{1-9}$ alkyl)(aryl), —N($C_{1-9}$ alkyl)(heteroaryl), —N($C_{1-9}$ alkyl)(heterocyclyl), —C(O)($C_{1-9}$ alkyl), —C(O)($C_{2-6}$ alkenyl), —C(O)($C_{2-6}$ alkynyl), —C(O)($C_{3-15}$ cycloalkyl), —C(O)($C_{1-8}$ haloalkyl), —C(O)(aryl), —C(O)(heteroaryl), —C(O)(heterocyclyl), —C(O)O($C_{1-9}$ alkyl), —C(O)O($C_{2-6}$ alkenyl), —C(O)O($C_{2-6}$ alkynyl), —C(O)O($C_{3-15}$ cycloalkyl), —C(O)O($C_{1-8}$ haloalkyl), —C(O)O(aryl), —C(O)O(heteroaryl), —C(O)O(heterocyclyl), —C(O)$NH_2$, —C(O)NH($C_{1-9}$ alkyl), —C(O)NH($C_{2-6}$ alkenyl), —C(O)NH($C_{2-6}$ alkynyl), —C(O)NH($C_{3-15}$ cycloalkyl), —C(O)NH($C_{1-8}$ haloalkyl), —C(O)NH(aryl), —C(O)NH(heteroaryl), —C(O)NH(heterocyclyl), —C(O)N($C_{1-9}$ alkyl)$_2$, —C(O)N($C_{3-15}$ cycloalkyl)$_2$, —C(O)N($C_{2-6}$ alkenyl)$_2$, —C(O)N($C_{2-6}$ alkynyl)$_2$, —C(O)N($C_{3-15}$ cycloalkyl)$_2$, —C(O)N($C_{2-8}$ haloalkyl)$_2$, —C(O)N(aryl)$_2$, —C(O)N(heteroaryl)$_2$, —C(O)N(heterocyclyl)$_2$, —NHC(O)($C_{1-9}$ alkyl), —NHC(O)($C_{2-6}$ alkenyl), —NHC(O)($C_{2-6}$ alkynyl), —NHC(O)($C_{3-15}$ cycloalkyl), —NHC(O)($C_{1-8}$ haloalkyl), —NHC(O)(aryl), —NHC(O)(heteroaryl), —NHC(O)(heterocyclyl), —NHC(O)O($C_{1-9}$ alkyl), —NHC(O)O($C_{2-6}$ alkenyl), —NHC(O)O($C_{2-6}$ alkynyl), —NHC(O)O($C_{3-15}$ cycloalkyl), —NHC(O)O($C_{1-8}$ haloalkyl), —NHC(O)O(aryl), —NHC(O)O(heteroaryl), —NHC(O)O(heterocyclyl), —NHC(O)NH($C_{1-9}$ alkyl), —NHC(O)NH($C_{2-6}$ alkenyl), —NHC(O)NH($C_{2-6}$ alkynyl), —NHC(O)NH($C_{3-15}$ cycloalkyl), —NHC(O)NH($C_{2-8}$ haloalkyl), —NHC(O)NH(aryl), —NHC(O)NH(heteroaryl), —NHC(O)NH(heterocyclyl), —SH, —S($C_{1-9}$ alkyl), —S($C_{2-6}$ alkenyl), —S($C_{2-6}$ alkynyl), —S($C_{3-15}$ cycloalkyl), —S($C_{1-8}$ haloalkyl), —S(aryl), —S(heteroaryl), —S(heterocyclyl), —NHS(O)($C_{1-9}$ alkyl), —N($C_{1-9}$ alkyl)(S(O)($C_{1-9}$ alkyl), —S(O)N($C_{1-9}$ alkyl)$_2$, —S(O)($C_{1-9}$ alkyl), —S(O)(NH)($C_{1-9}$ alkyl), —S(O)($C_{2-6}$ alkenyl), —S(O)($C_{2-6}$ alkynyl), —S(O)($C_{3-15}$ cycloalkyl), —S(O)($C_{1-8}$ haloalkyl), —S(O)(aryl), —S(O)(heteroaryl), —S(O)(heterocyclyl), —S(O)$_2$($C_{1-9}$ alkyl), —S(O)$_2$($C_{2-6}$ alkenyl), —S(O)$_2$($C_{2-6}$ alkynyl), —S(O)$_2$($C_{3-15}$ cycloalkyl), —S(O)$_2$($C_{1-8}$ haloalkyl), —S(O)$_2$(aryl), —S(O)$_2$(heteroaryl), —S(O)$_2$(heterocyclyl), —S(O)$_2$NH($C_{1-9}$ alkyl), or —S(O)$_2$N($C_{1-9}$ alkyl)$_2$;

wherein any alkyl, cycloalkyl, aryl, heteroaryl, or heterocyclyl is optionally substituted with one to four halo, $C_{1-9}$ alkyl, $C_{1-8}$ haloalkyl, —OH, —$NH_2$, —NH($C_{1-9}$ alkyl), —NH($C_{3-15}$ cycloalkyl), —NH($C_{1-8}$ haloalkyl), —NH(aryl), —NH(heteroaryl), —NH(heterocyclyl), —N($C_{1-9}$ alkyl)$_2$, —N($C_{3-15}$ cycloalkyl)$_2$, —NHC(O)($C_{3-15}$ cycloalkyl), —NHC(O)($C_{1-8}$ haloalkyl), —NHC(O)(aryl), —NHC(O)(heteroaryl), —NHC(O)(heterocyclyl), —NHC(O)O($C_{1-9}$ alkyl), —NHC(O)O($C_{2-6}$ alkynyl), —NHC(O)O($C_{3-15}$ cycloalkyl), —NHC(O)O($C_{1-8}$ haloalkyl), —NHC(O)O(aryl), —NHC(O)O(heteroaryl), —NHC(O)O(heterocyclyl), —NHC(O)NH($C_{1-9}$ alkyl), —S(O)(NH)($C_{1-9}$ alkyl), S(O)$_2$($C_{1-9}$ alkyl), —S(O)$_2$($C_{3-15}$ cycloalkyl), —S(O)$_2$($C_{1-8}$ haloalkyl), —S(O)$_2$(aryl), —S(O)$_2$(heteroaryl), —S(O)$_2$(heterocyclyl), —S(O)$_2$NH($C_{1-9}$ alkyl), —S(O)$_2$N($C_{1-9}$ alkyl)$_2$, —O($C_{3-15}$ cycloalkyl), —O($C_{1-8}$ haloalkyl), —O(aryl), —O(heteroaryl), —O(heterocyclyl), or —O($C_{1-9}$ alkyl);

or a pharmaceutically acceptable salt, tautomer, stereoisomer, mixture of stereoisomers, prodrug, or deuterated analog thereof.

In certain embodiments, W is N, X is N—$Z^3$, and Y is C—$Z^3$. In certain embodiments, W is C—$Z^3$, X is N—$Z^3$, and Y is C—$Z^3$.

In certain embodiments, the compound of Formula I is represented by Formula IV:

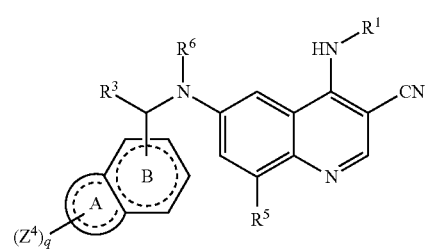

IV wherein $R^1$, $R^3$, $R^5$, $R^6$ and $Z^4$ are as defined herein, q is 0, 1, 2, 3 or 4, ring A is a 5- or 6-membered cycloalkyl, heterocyclyl or heteroaryl ring, and ring B is a 6-membered cycloalkyl, heterocyclyl or heteroaryl ring, provided that at least one heteroatom is present in ring A or ring B such that $R^4$ is an optionally substituted bicyclic heterocyclyl or optionally substituted bicyclic heteroaryl. In the above, the wavy line indicates the point of attachment to the remainder of the molecule, where the attachment can through either ring (i.e., ring A or ring B) of the optionally substituted bicyclic heterocyclyl or optionally substituted bicyclic heteroaryl. In some embodiments, ring A and/or ring B comprises an oxo (=O).

In certain embodiments, provided is a compound of Formula IVA:

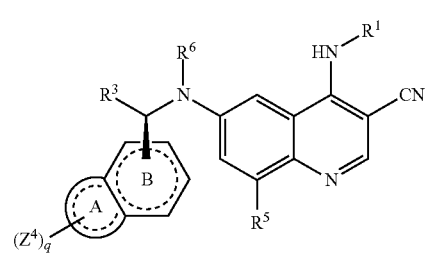

IVA wherein $R^1$, $R^3$, $R^5$, $R^6$, $Z^4$, q, ring A and ring B are as defined herein.

In certain embodiments, provided is a compound of Formula V:

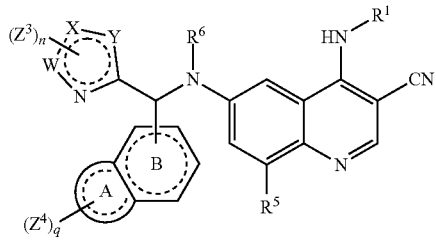

V wherein W, X, Y, $R^1$, $R^5$, $R^6$, $Z^3$, $Z^4$, q, n, ring A and ring B are as defined herein.

In certain embodiments, provided is a compound of Formula VA:

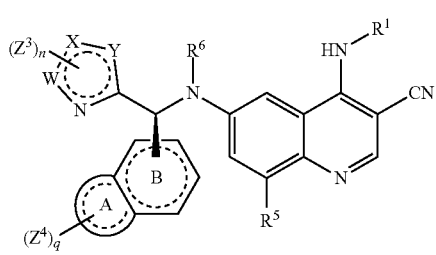

VA wherein W, X, Y, $R^1$, $R^5$, $R^6$, $Z^3$, $Z^4$, q, n, ring A and ring B are as defined herein.

In certain embodiments, the compound of Formula I is represented by Formula VI:

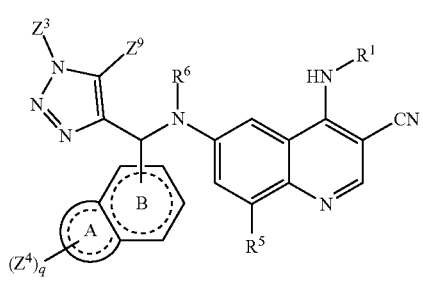

VI wherein $R^1$, $R^5$, $R^6$, $Z^3$, $Z^4$, q, n, ring A and ring B are as defined herein and $Z^9$ is hydrogen, halo, —CN, or —O—$R^{12}$.

In certain embodiments, the compound of Formula I is represented by Formula VIA:

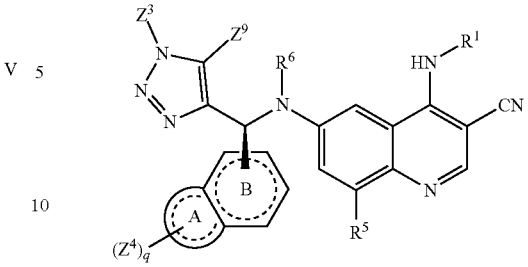

VIA wherein $R^1$, $R^5$, $R^6$, $Z^3$, $Z^4$, q, n, ring A and ring B are as defined herein and $Z^9$ is hydrogen, halo, —CN, or —O—$R^{12}$.

In certain embodiments, the compound of Formula I is represented by Formula VII:

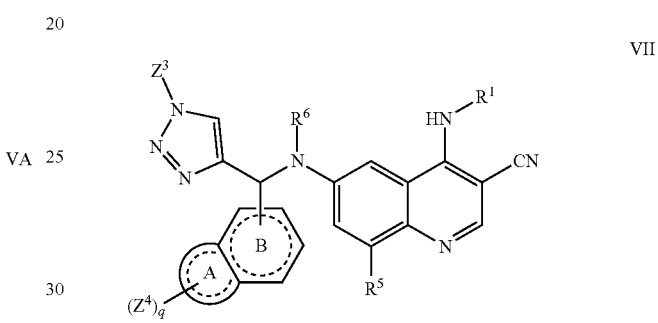

VII wherein $R^1$, $R^5$, $R^6$, $Z^3$, $Z^4$, q, n, ring A and ring B are as defined herein.

In certain embodiments, the compound of Formula I is represented by Formula VIIA:

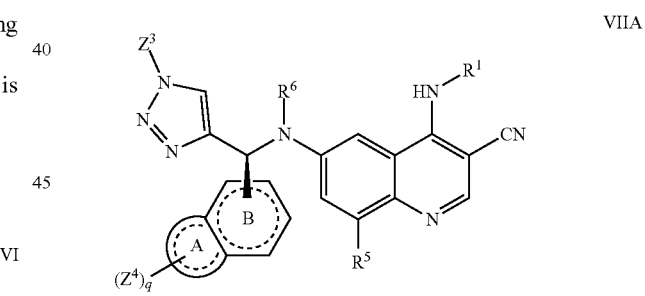

VIIA wherein $R^1$, $R^5$, $R^6$, $Z^3$, $Z^4$, q, n, ring A and ring B are as defined herein.

In certain embodiments, the compound of Formula I is represented by Formula VIII or IX:

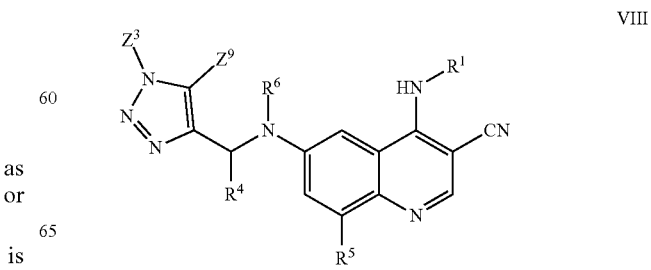

VIII

-continued

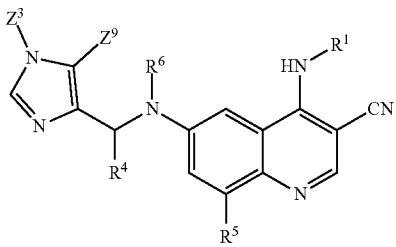

IX wherein $Z^3$, $R^1$, $R^4$, $R^5$ and $R^6$ are as defined herein and $Z^9$ is hydrogen, halo, —CN, or —O—$R^{12}$.

In certain embodiments, the compound of Formula I is represented by Formula VIIIA or IXA:

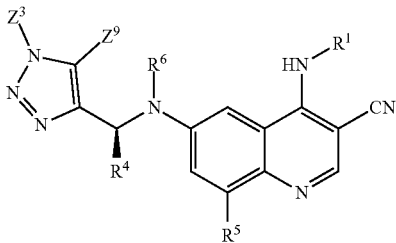

VIIIA

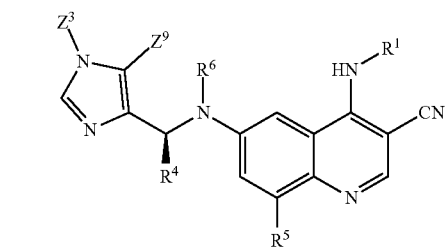

IXA wherein $Z^3$, $R^1$, $R^4$, $R^5$ and $R^6$ are as defined herein and $Z^9$ is hydrogen, halo, —CN, or —O—$R^{12}$.

In certain embodiments, the compound of Formula I is represented by Formula X or XI:

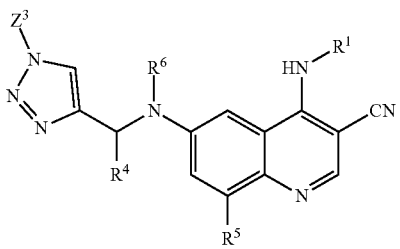

X

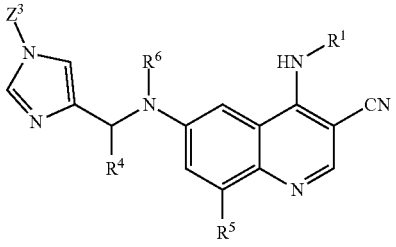

XI wherein $Z^3$, $R^1$, $R^4$, $R^5$ and $R^6$ are as defined herein.

In certain embodiments, the compound of Formula I is represented by Formula XA or XIA:

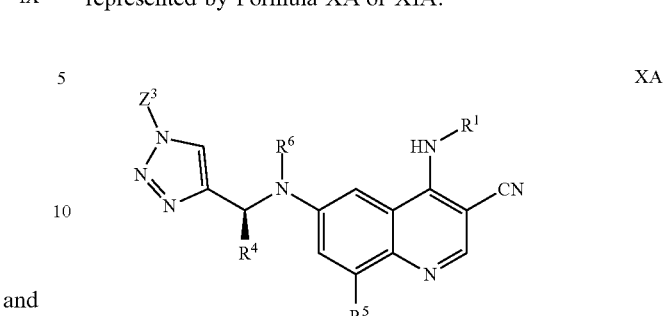

XA

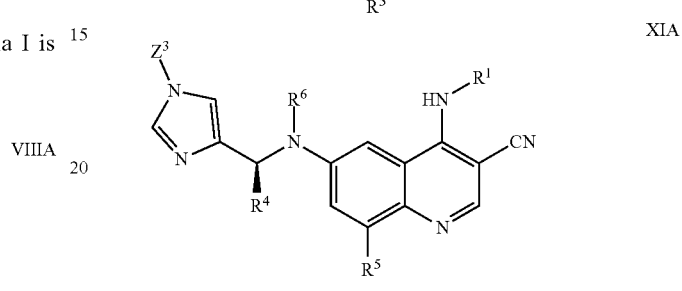

XIA wherein $Z^3$, $R^1$, $R^4$, $R^5$ and $R^6$ are as defined herein.

In certain embodiments, $R^6$ is hydrogen.

In certain embodiments, $Z^3$ is hydrogen, $C_{1-9}$ alkyl, $C_{3-15}$ cycloalkyl, heterocyclyl, aryl, or heteroaryl;
  wherein said $C_{1-9}$ alkyl, $C_{3-15}$ cycloalkyl, heterocyclyl, aryl, or heteroaryl, may be optionally substituted with one to four substituents independently selected from the group consisting of —CN, halo, —O—$R^{12}$, —C(O)—$R^{12}$, —OC(O)—$R^{12}$, —C(O)O—$R^{12}$, —C(O)—N($R^{13}$)($R^{14}$), —N($R^{13}$)($R^{14}$), —N($R^{13}$)$_2$($R^{14}$)$^+$, —S(O)$_2$—$R^{12}$, —Si($R^{12}$)$_3$, $C_{1-9}$ alkyl, $C_{3-15}$ cycloalkyl, aryl, heterocyclyl, and heteroaryl; and
  wherein said $C_{1-9}$ alkyl, $C_{3-15}$ cycloalkyl, heterocyclyl, aryl, or heteroaryl may be optionally substituted with one to three substituents independently selected from the group consisting of halo, —O($C_{1-9}$ alkyl), —C(O)N($C_{1-9}$ alkyl)$_2$, $C_{1-9}$ alkyl, and heterocyclyl.

In certain embodiments, $Z^3$ is hydrogen, $C_{1-9}$ alkyl, $C_{3-15}$ cycloalkyl, heterocyclyl, aryl, or heteroaryl;
  wherein said $C_{1-9}$ alkyl, $C_{3-15}$ cycloalkyl, aryl, or heterocyclyl, may be optionally substituted with one to four substituents independently selected from the group consisting of —CN, halo, —O—$R^{12}$, —C(O)—$R^{12}$, —OC(O)—$R^{12}$, —C(O)O—$R^{12}$, —C(O)—N($R^{13}$)($R^{14}$), —N($R^{13}$)($R^{14}$), —N($R^{13}$)$_2$($R^{14}$)$^+$, —S(O)$_2$—$R^{12}$, —Si($R^{12}$)$_3$, $C_{1-9}$ alkyl, $C_{3-15}$ cycloalkyl, aryl, heterocyclyl, and heteroaryl; and
  wherein said $C_{1-9}$ alkyl, $C_{3-15}$ cycloalkyl, heterocyclyl, or aryl may be optionally substituted with one to three substituents independently selected from the group consisting of halo, —O($C_{1-9}$ alkyl), —C(O)N($C_{1-9}$ alkyl)$_2$, $C_{1-9}$ alkyl, and heterocyclyl.

In certain embodiments, $Z^3$ is hydrogen or $C_{1-9}$ alkyl;
  wherein said $C_{1-9}$ alkyl may be optionally substituted with one to four substituents independently selected from the group consisting of —CN, halo, —O—$R^{12}$, —C(O)—$R^{12}$, —OC(O)—$R^{12}$, —C(O)O—$R^{12}$, —C(O)—N($R^{13}$)($R^{14}$), —N($R^{13}$)($R^{14}$), —N($R^{13}$)$_2$($R^{14}$)$^+$, —S(O)$_2$—$R^{12}$, —Si($R^{12}$)$_3$, $C_{1-9}$ alkyl, $C_{3-15}$ cycloalkyl, aryl, heterocyclyl, and heteroaryl; and wherein said $C_{1-9}$ alkyl, $C_{3-15}$ cycloalkyl, heterocyclyl, or aryl may be optionally substituted with one to three substituents independently selected from the group consisting of halo, —O($C_{1-9}$ alkyl), —C(O)N($C_{1-9}$ alkyl)$_2$, $C_{1-9}$ alkyl, and heterocyclyl.

In certain embodiments, $Z^3$ is hydrogen or $C_{1-9}$ alkyl optionally substituted with one to four substituents independently selected from the group consisting of —CN, halo, —O—$R^{12}$, —C(O)O—$R^{12}$, —OC(O)—$R^{12}$, —N($R^{13}$)($R^{14}$), —N($R^{13}$)$_2$($R^{14}$)$^+$, $C_{1-9}$ alkyl, heterocyclyl, and heteroaryl.

In certain embodiments, $Z^3$ is $C_{3-15}$ cycloalkyl, heterocyclyl, aryl, or heteroaryl;
  wherein said $C_{3-15}$ cycloalkyl, heterocyclyl, aryl, or heteroaryl, may be optionally substituted with one to four substituents independently selected from the group consisting of —CN, halo, —O—$R^{12}$, —C(O)—$R^{12}$, —OC(O)—$R^{12}$, —C(O)O—$R^{12}$, —C(O)—N($R^{13}$)($R^{14}$), —N($R^{13}$)($R^{14}$), —N($R^{13}$)$_2$($R^{14}$)$^+$, —S(O)$_2$—$R^{12}$, —Si($R^{12}$)$_3$, $C_{1-9}$ alkyl, $C_{3-15}$ cycloalkyl, aryl, heterocyclyl, and heteroaryl; and
    wherein said $C_{1-9}$ alkyl, $C_{3-15}$ cycloalkyl, aryl, heterocyclyl, or heteroaryl may be optionally substituted with one to three substituents independently selected from the group consisting of halo, —O($C_{1-9}$ alkyl), —C(O)N($C_{1-9}$ alkyl)$_2$, $C_{1-9}$ alkyl, and heterocyclyl.

In certain embodiments, $Z^3$ is $C_{3-15}$ cycloalkyl, heterocyclyl, aryl, or heteroaryl;
  wherein said $C_{3-15}$ cycloalkyl, heterocyclyl, or aryl may be optionally substituted with one to four substituents independently selected from the group consisting of —CN, halo, —O—$R^{12}$, —C(O)—$R^{12}$, —OC(O)—$R^{12}$, —C(O)O—$R^{12}$, —C(O)—N($R^{13}$)($R^{14}$), —N($R^{13}$)($R^{14}$), —N($R^{13}$)$_2$($R^{14}$)$^+$, —S(O)$_2$—$R^{12}$, —Si($R^{12}$)$_3$, $C_{1-9}$ alkyl, $C_{3-15}$ cycloalkyl, aryl, heterocyclyl, and heteroaryl; and
    wherein said $C_{1-9}$ alkyl, $C_{3-15}$ cycloalkyl, heterocyclyl, or aryl may be optionally substituted with one to three substituents independently selected from the group consisting of halo, —O($C_{1-9}$ alkyl), —C(O)N($C_{1-9}$ alkyl)$_2$, $C_{1-9}$ alkyl, and heterocyclyl.

In certain embodiments, $Z^3$ is hydrogen or $C_{1-9}$ alkyl optionally substituted with one to four substituents independently selected from the group consisting of —CN, halo, —O—$R^{12}$, —C(O)O—$R^{12}$, —OC(O)—$R^{12}$, —N($R^{13}$)($R^{14}$), —N($R^{13}$)$_2$($R^{14}$)$^+$, —C(O)N($R^{12}$)—S(O)$_2$$R^{12}$, $C_{1-9}$ alkyl, heterocyclyl, aryl, and heteroaryl.

In certain embodiments, $Z^3$ is hydrogen or $C_{1-9}$ alkyl optionally substituted with one to four substituents independently selected from the group consisting of —CN, halo, —O—$R^{12}$, —C(O)O—$R^{12}$, —OC(O)—$R^{12}$, —N($R^{13}$)($R^{14}$), —N($R^{13}$)$_2$($R^{14}$)$^+$, $C_{1-9}$ alkyl, heterocyclyl, and heteroaryl.

In certain embodiments, $Z^3$ is $C_{3-15}$ cycloalkyl, heterocyclyl, aryl, or heteroaryl; and said $C_{3-15}$ cycloalkyl, heterocyclyl, aryl, or heteroaryl may be optionally substituted with one to four substituents independently selected from the group consisting of —CN, halo, —O—$R^{12}$, —C(O)—$R^{12}$, —C(O)O—$R^{12}$, —OC(O)—$R^{12}$, —N($R^{13}$)($R^{14}$), —N($R^{13}$)$_2$($R^{14}$)$^+$, $C_{1-9}$ alkyl, $C_{1-8}$ haloalkyl, $C_{1-8}$ hydroxyalkyl, $C_{3-15}$ cycloalkyl, heterocyclyl, and heteroaryl.

In certain embodiments, $Z^3$ is $C_{3-15}$ cycloalkyl, heterocyclyl, aryl, or heteroaryl; and said $C_{3-15}$ cycloalkyl, heterocyclyl, aryl, or heteroaryl may be optionally substituted with one to four substituents independently selected from the group consisting of —CN, halo, —O—$R^{12}$, —C(O)O—$R^{12}$, —OC(O)—$R^{12}$, —N($R^{13}$)($R^{14}$), —N($R^{13}$)$_2$($R^{14}$)$^+$, $C_{1-9}$ alkyl, heterocyclyl, and heteroaryl.

In certain embodiments, $Z^3$ is hydrogen, $C_{1-9}$ alkyl, $C_{3-15}$ cycloalkyl, heterocyclyl, aryl, or heteroaryl;
  wherein said $C_{1-9}$ alkyl, $C_{3-15}$ cycloalkyl, or heterocyclyl may be optionally substituted with one to four substituents independently selected from the group consisting of oxo, —CN, halo, —O—$R^{12}$, —C(O)—$R^{12}$, —C(O)O—$R^{12}$, —OC(O)—$R^{12}$, —C(O)—N($R^{13}$)($R^{14}$), —N($R^{12}$)S(O)$_2$($R^{12}$), —N($R^{13}$)($R^{14}$), —N($R^{13}$)$_2$($R^{14}$)$^+$, —C(O)N($R^{12}$)—S(O)$_2$$R^{12}$, $C_{1-9}$ alkyl, $C_{1-8}$ haloalkyl, $C_{1-8}$ hydroxyalkyl, $C_{3-15}$ cycloalkyl, aryl, heterocyclyl, and heteroaryl;

$Z^9$ is hydrogen;

$R^1$ is $C_{1-9}$ alkyl, $C_{3-15}$ cycloalkyl, heterocyclyl, aryl, or heteroaryl;
  wherein said $C_{1-9}$ alkyl, heterocyclyl, aryl, or heteroaryl may be optionally substituted with one to three substituents independently selected the group consisting of halo, —CN, —O—$R^{12}$, —S(O)$_2$$R^{12}$, $C_{1-9}$ alkyl, $C_{1-9}$ haloalkyl, heterocyclyl, and aryl, wherein said $C_{3-15}$ cycloalkyl may be optionally substituted with one to four substituents independently selected the group consisting of $C_{1-9}$ alkyl, and $C_{1-9}$ haloalkyl;

$R^4$ is heterocyclyl or heteroaryl;
  wherein said heterocyclyl or heteroaryl is optionally substituted with one to three substituents independently selected from the group consisting of —CN, halo, —O—$R^{12}$, —C(O)—$R^{12}$, —N($R^{13}$)($R^{14}$), $C_{1-9}$ alkyl, $C_{1-9}$ haloalkyl, and heterocyclyl;

$R^5$ is —CN, halo, —O—$R^7$ or —S(O)$_2$$R^7$;

$R^6$ is hydrogen;

each $R^7$ is independently hydrogen or $C_{1-9}$ alkyl;
  wherein said $C_{1-9}$ alkyl may be optionally substituted with one to three substituents independently selected from the group consisting of hydroxyl, halo, —O($C_{1-9}$ alkyl) and aryl;

each $R^{12}$ is independently hydrogen, $C_{1-9}$ alkyl or heterocyclyl;
  wherein said $C_{1-9}$ alkyl may be optionally substituted with one to three substituents independently selected from the group consisting of hydroxyl, halo, —O($C_{1-9}$ alkyl) and aryl; and each $R^{13}$ and $R^{14}$ is independently hydrogen or $C_{1-9}$ alkyl;
  wherein said $C_{1-9}$ alkyl may be optionally substituted with one to three substituents independently selected from the group consisting of hydroxyl, halo, —O($C_{1-9}$ alkyl) and aryl;

or a pharmaceutically acceptable salt, tautomer, stereoisomer, mixture of stereoisomers, or deuterated analog thereof.

In certain embodiments, $Z^3$ is hydrogen, $C_{1-9}$ alkyl, $C_{3-15}$ cycloalkyl, heterocyclyl, aryl, or heteroaryl;
  wherein said $C_{1-9}$ alkyl, or heterocyclyl may be optionally substituted with one to four substituents independently selected from the group consisting of —CN, halo, —O—$R^{12}$, —C(O)O—$R^{12}$, —OC(O)—$R^{12}$, —N($R^{13}$)($R^{14}$), —N($R^{13}$)$_2$($R^{14}$)$^+$, $C_{1-9}$ alkyl, heterocyclyl, and heteroaryl;

$R^1$ is $C_{1-9}$ alkyl, $C_{3-15}$ cycloalkyl, heterocyclyl, aryl, or heteroaryl;
  wherein said $C_{1-9}$ alkyl, heterocyclyl, aryl, or heteroaryl may be optionally substituted with one to three substituents independently selected the group consisting of halo, —CN, —O—$R^{12}$, $C_{1-9}$ alkyl and aryl;

$R^4$ is heterocyclyl or heteroaryl;
  wherein said heterocyclyl or heteroaryl is optionally substituted with one to three substituents independently selected from the group consisting of —CN, halo, —O—$R^{12}$, —C(O)—$R^{12}$, $C_{1-9}$ alkyl, $C_{1-9}$ haloalkyl, and heterocyclyl;
$R^5$ is —CN, halo, or —O—$R^7$;
$R^6$ is hydrogen;
each $R^7$ is independently hydrogen or $C_{1-9}$ alkyl;
  wherein said $C_{1-9}$ alkyl may be optionally substituted with one to three substituents independently selected from the group consisting of hydroxyl, halo, —O($C_{1-9}$ alkyl) and aryl;
each $R^{12}$ is independently hydrogen or $C_{1-9}$ alkyl;
  wherein said $C_{1-9}$ alkyl may be optionally substituted with one to three substituents independently selected from the group consisting of hydroxyl, halo, —O($C_{1-9}$ alkyl) and aryl; and
each $R^{13}$ and $R^{14}$ is independently hydrogen or $C_{1-9}$ alkyl;
  wherein said $C_{1-9}$ alkyl may be optionally substituted with one to three substituents independently selected from the group consisting of hydroxyl, halo, —O($C_{1-9}$ alkyl) and aryl;
or a pharmaceutically acceptable salt, tautomer, stereoisomer, mixture of stereoisomers, prodrug, or deuterated analog thereof.

In certain embodiments, $Z^3$ is hydrogen, $C_{1-9}$ alkyl, $C_{3-15}$ cycloalkyl, heterocyclyl, aryl, or heteroaryl;
  wherein said $C_{1-9}$ alkyl, $C_{3-15}$ cycloalkyl, or heterocyclyl may be optionally substituted with one to four substituents independently selected from the group consisting of oxo, —CN, halo, —O—$R^{12}$, —C(O)—$R^{12}$, —C(O)O—$R^{12}$, —OC(O)—$R^{12}$, —C(O)—N($R^{13}$)($R^{14}$), —N($R^{12}$)S(O)$_2$($R^{12}$), —N($R^{13}$)($R^{14}$), —N($R^{13}$)$_2$($R^{14}$)$^+$, $C_{1-9}$ alkyl, $C_{3-15}$ cycloalkyl, aryl, heterocyclyl, and heteroaryl;
    wherein said $C_{1-9}$ alkyl may be optionally substituted with one to four substituents independently selected from the group consisting of halo and hydroxyl.
$R^1$ is $C_{1-9}$ alkyl, $C_{3-15}$ cycloalkyl, heterocyclyl, aryl, or heteroaryl;
  wherein said $C_{1-9}$ alkyl, heterocyclyl, aryl, or heteroaryl may be optionally substituted with one to three substituents independently selected the group consisting of halo, —CN, —O—$R^{12}$, $C_{1-9}$ alkyl and aryl;
$R^4$ is heterocyclyl or heteroaryl;
  wherein said heterocyclyl or heteroaryl is optionally substituted with one to three substituents independently selected from the group consisting of —CN, halo, —O—$R^{12}$, —C(O)—$R^{12}$, —N($R^{13}$)($R^{14}$), $C_{1-9}$ alkyl, $C_{1-9}$ haloalkyl, and heterocyclyl;
$R^5$ is —CN, halo, —O—$R^7$ or —S(O)$_2$$R^7$;
$R^6$ is hydrogen;
each $R^7$ is independently hydrogen or $C_{1-9}$ alkyl;
  wherein said $C_{1-9}$ alkyl may be optionally substituted with one to three substituents independently selected from the group consisting of hydroxyl, halo, —O($C_{1-9}$ alkyl) and aryl;
each $R^{12}$ is independently hydrogen, $C_{1-9}$ alkyl or heterocyclyl;
  wherein said $C_{1-9}$ alkyl may be optionally substituted with one to three substituents independently selected from the group consisting of hydroxyl, halo, —O($C_{1-9}$ alkyl) and aryl; and
each $R^{13}$ and $R^{14}$ is independently hydrogen or $C_{1-9}$ alkyl;
  wherein said $C_{1-9}$ alkyl may be optionally substituted with one to three substituents independently selected from the group consisting of hydroxyl, halo, —O($C_{1-9}$ alkyl) and aryl;
or a pharmaceutically acceptable salt, tautomer, stereoisomer, mixture of stereoisomers, or deuterated analog thereof.

In certain embodiments, $Z^3$ is $C_{3-15}$ cycloalkyl optionally substituted with one to four substituents independently selected from the group consisting of —CN, halo, —C(O)—$R^{12}$, —OC(O)—$R^{12}$, —C(O)N($R^{13}$)($R^{14}$), $C_{1-9}$ alkyl, $C_{1-8}$ haloalkyl, $C_{1-8}$ hydroxyalkyl, $C_{3-15}$ cycloalkyl, and heteroaryl.

In certain embodiments, $Z^3$ is heterocyclyl optionally substituted with one to four substituents independently selected from the group consisting of —O—$R^{12}$, —C(O)O—$R^{12}$, $C_{1-9}$ alkyl, $C_{1-8}$ haloalkyl, $C_{1-8}$ hydroxyalkyl, and heterocyclyl.

In certain embodiments, $R^1$ is $C_{1-9}$ alkyl, $C_{3-15}$ cycloalkyl, heterocyclyl, aryl, or heteroaryl; and said $C_{1-9}$ alkyl, $C_{3-15}$ cycloalkyl, heterocyclyl, aryl, or heteroaryl may be optionally substituted with one to four substituents independently selected the group consisting of halo, —CN, —O—$R^{12}$, $C_{1-9}$ alkyl, and aryl.

In certain embodiments, $R^1$ is —O—$R^7$, $C_{1-9}$ alkyl, $C_{3-15}$ cycloalkyl, heterocyclyl, aryl, or heteroaryl; and said $C_{1-9}$ alkyl, $C_{3-15}$ cycloalkyl, heterocyclyl, aryl, or heteroaryl may be optionally substituted with one to four substituents independently selected the group consisting of halo, —CN, —O—$R^{12}$, —S(O)$_2$$R^{12}$, $C_{1-9}$ alkyl, $C_{1-9}$ haloalkyl, $C_{3-15}$ cycloalkyl, heterocyclyl, and aryl, wherein said $C_{3-15}$ cycloalkyl may be optionally substituted with one to four substituents independently selected the group consisting of $C_{1-9}$ alkyl, and $C_{1-9}$ haloalkyl.

In certain embodiments, $R^1$ is —O—$R^7$, $C_{1-9}$ alkyl, $C_{3-15}$ cycloalkyl, heterocyclyl, aryl, or heteroaryl; and said $C_{1-9}$ alkyl, $C_{3-15}$ cycloalkyl, heterocyclyl, aryl, or heteroaryl may be optionally substituted with one to four substituents independently selected the group consisting of halo, —CN, —O—$R^{12}$, $C_{1-9}$ alkyl, $C_{3-15}$ cycloalkyl, and aryl. In certain embodiments, $R^1$ is $C_{1-9}$ alkyl, optionally substituted with one to three substituents independently selected the group consisting of halo, —CN, —O—$R^{12}$, —S(O)$_2$$R^{12}$, $C_{3-15}$ cycloalkyl, heterocyclyl, and aryl, wherein said $C_{3-15}$ cycloalkyl or heterocyclyl may be optionally substituted with one to four substituents independently selected the group consisting of $C_{1-9}$ alkyl, and $C_{1-9}$ haloalkyl.

In certain embodiments, $R^1$ is $C_{1-9}$ alkyl, optionally substituted with one to three substituents independently selected the group consisting of halo, —CN, —O—$R^{12}$, $C_{1-9}$ alkyl, and aryl.

In certain embodiments, $R^1$ is $C_{3-15}$ cycloalkyl, heterocyclyl, or heteroaryl;
  wherein said $C_{3-15}$ cycloalkyl, heterocyclyl, or heteroaryl may be optionally substituted with one to three substituents independently selected from the group consisting of —CN, halo, —O—$R^{12}$, —N($R^{13}$)($R^{14}$), —NH—C(O)O—$R^{12}$, —S(O)$_2$—$R^{12}$, —Si($R^{12}$)$_3$, $C_{1-9}$ alkyl, $C_{3-15}$ cycloalkyl, heterocyclyl, aryl, and heteroaryl; and
    wherein said $C_{1-9}$ alkyl, $C_{3-15}$ cycloalkyl, aryl, or heteroaryl may be optionally substituted with one to three substituents independently selected from the group consisting of —CN, halo, —O—$R^{12}$, —N($R^{13}$)($R^{14}$), $C_{1-9}$ alkyl, $C_{3-15}$ cycloalkyl, and aryl.

In certain embodiments, $R^1$ is $C_{3-15}$ cycloalkyl, heterocyclyl or heteroaryl, wherein said $C_{3-15}$ cycloalkyl, heterocyclyl or heteroaryl is optionally substituted with one to three substituents independently selected the group consisting of halo, —CN, —O—$R^{12}$, $C_{1-9}$ alkyl, and aryl.

In certain embodiments, $R^1$ is heterocyclyl or heteroaryl, wherein said heterocyclyl or heteroaryl is optionally substituted with one to three substituents independently selected the group consisting of halo, and $C_{1-9}$ alkyl.

In certain embodiments, $R^1$ is aryl;
wherein said aryl may be optionally substituted with one to three substituents independently selected from the group consisting of —CN, halo, —O—$R^{12}$, —N($R^{13}$)($R^{14}$), —NH—C(O)O—$R^{12}$, —S(O)$_2$—$R^{12}$, —Si($R^{12}$)$_3$, $C_{1-9}$ alkyl, $C_{3-15}$ cycloalkyl, heterocyclyl, aryl, and heteroaryl; and
wherein said $C_{1-9}$ alkyl, $C_{3-15}$ cycloalkyl, aryl, or heteroaryl may be optionally substituted with one to three substituents independently selected from the group consisting of —CN, halo, —O—$R^{12}$, —N($R^{13}$)($R^{14}$), $C_{1-9}$ alkyl, $C_{3-15}$ cycloalkyl, and aryl.

In certain embodiments, $R^1$ is aryl, optionally substituted with one to three substituents independently selected the group consisting of halo, —CN, —O—$R^7$, $C_{1-9}$ alkyl, and aryl.

In certain embodiments, $R^1$ is aryl, optionally substituted with one to three substituents independently selected the group consisting of halo, —O—$R^7$, and $C_{1-9}$ alkyl.

In one embodiment, $R^1$ is (1S,3S,5S,7S)-adamantan-2-yl, (R)-1-phenylethyl, (R)-1-phenylpropyl, (R)-1-phenylpropyl-1,2,2,3,3,3-d6, (R)-1-phenylpropyl-2,2,3,3,3-d5, (R)-2-cyano-1-phenylethyl, (R)-2-hydroxy-1-phenylethyl, (R)-2-hydroxy-2-methyl-1-phenylpropyl, (R)-2-methoxy-1-phenylethyl, (R)-3-cyano-1-phenylpropyl, (R)-3-fluoro-1-phenylpropyl, (R)-3-hydroxy-1-phenylpropyl, (S)-1-phenylpropyl-2,2,3,3,3-d5, (S)-2-cyano-1-phenylethyl, (S)-2-hydroxy-1-phenylethyl, (S)-2-hydroxy-2-methyl-1-phenylpropyl, (S)-3-cyano-1-phenylpropyl, (S)-3-hydroxy-1-phenylpropyl, 1-phenylpropyl-2,2,3,3,3-d5, 2-cyano-1-phenylethyl, 3,3-dimethyltetrahydro-2H-pyran-4-yl, 3,4-dichloro-2-fluorophenyl, 3,4-difluorophenyl, 3-chloro-2,6-difluorophenyl, 3-chloro-2-fluorophenyl, 3-chloro-2-methoxyphenyl, 3-chloro-4-fluorophenyl, 3-chloro-4-methoxyphenyl, 3-chlorophenyl, 3-cyano-1-phenylpropyl, 5,6-difluoropyridin-3-yl, 5-chloro-6-fluoropyridin-3-yl, 5-chloropyridin-3-yl, cycloheptyl, cyclohexyl, neopentyl, neopentyl-1,1-d2, (1-(difluoromethyl)cyclopropyl)methyl, (1-methylcyclobutyl)methyl, (1R,5S)-bicyclo[3.1.0]hexan-6-yl, (1R,5S,6r)-3-oxabicyclo[3.1.0]hexan-6-yl, (R)-2,2-dimethyltetrahydrofuran-3-yl, (R)-3,3-dimethylbutan-2-yl, (R)-3,3-dimethyltetrahydro-2H-pyran-4-yl, (R)-cyclopropyl(phenyl)methyl, (S)-2,2-dimethyltetrahydrofuran-3-yl, (S)-3,3-dimethyltetrahydro-2H-pyran-4-yl, 2,2-dimethylpropyl-1,1-d2, 2,2-dimethyltetrahydrofuran-3-yl, 2-cyano-2-methylpropyl, 2-methyl-2-phenylpropyl, 3-chloro-2,2-dimethylpropyl, 3-cyano-2,2-dimethylpropyl, 3-hydroxy-2,2-dimethylpropyl, tert-butoxy, or tetrahydro-2H-pyran-4-yl.

In one embodiment, $R^1$ is (1 S,3 S,5S,7S)-adamantan-2-yl, (R)-1-phenylethyl, (R)-1-phenylpropyl, (R)-1-phenylpropyl-1,2,2,3,3,3-d6, (R)-1-phenylpropyl-2,2,3,3,3-d5, (R)-2-cyano-1-phenylethyl, (R)-2-hydroxy-1-phenylethyl, (R)-2-hydroxy-2-methyl-1-phenylpropyl, (R)-2-m ethoxy-1-phenylethyl, (R)-3-cyano-1-phenylpropyl, (R)-3-fluoro-1-phenylpropyl, (R)-3-hydroxy-1-phenylpropyl, (S)-1-phenylpropyl-2,2,3,3,3-d5, (S)-2-cyano-1-phenylethyl, (S)-2-hydroxy-1-phenylethyl, (S)-2-hydroxy-2-methyl-1-phenylpropyl, (S)-3-cyano-1-phenylpropyl, (S)-3-hydroxy-1-phenylpropyl, 1-phenylpropyl-2,2,3,3,3-d5, 2-cyano-1-phenylethyl, 3,3-dimethyltetrahydro-2H-pyran-4-yl, 3,4-dichloro-2-fluorophenyl, 3,4-difluorophenyl, 3-chloro-2,6-difluorophenyl, 3-chloro-2-fluorophenyl, 3-chloro-2-methoxyphenyl, 3-chloro-4-fluorophenyl, 3-chloro-4-methoxyphenyl, 3-chlorophenyl, 3-cyano-1-phenylpropyl, 5,6-difluoropyridin-3-yl, 5-chloro-6-fluoropyridin-3-yl, 5-chloropyridin-3-y, cycloheptyl, cyclohexyl, neopentyl, neopentyl-1,1-d2, or tetrahydro-2H-pyran-4-yl.

In another embodiment, $R^1$ is (R)-1-phenylethyl, (R)-1-phenylpropyl, 3,4-dichloro-2-fluorophenyl, 3-chloro-2-fluorophenyl, 3-chloro-4-fluorophenyl, 5,6-difluoropyridin-3-yl, or neopentyl.

In one embodiment, $R^2$ is hydrogen. In one embodiment, $R^2$ is $C_{1-6}$ alkyl. In one embodiment, $R^2$ is methyl.

In one embodiment, $R^1$ and $R^2$ together with the nitrogen atom to which they are attached form a heterocyclyl or heterocyclyl. In certain embodiments, $R^1$ and $R^2$ together with the nitrogen to which they are attached to form a heterocyclyl or heteroaryl, wherein said heterocyclyl may be optionally substituted with one to three $C_{1-9}$ alkyl. In certain embodiments, $R^1$ and $R^2$ together with the nitrogen atom to which they are attached form an optionally substituted pyrazolyl. In certain embodiments, $R^1$ and together with the nitrogen atom to which they are attached form 3,3-dimethylpiperidin-1-yl.

In one embodiment, $R^3$ is heterocyclyl or heteroaryl, wherein each heterocyclyl or heteroaryl is optionally substituted with one or more substituents (i.e., $Z^3$) selected from the group consisting of (1R,5S,6r)-3-(oxetan-3-yl)-3-azabicyclo[3.1.0]hexan-6-yl, (1R,5S,6s)-3-(oxetan-3-yl)-3-azabicyclo[3.1.0]hexan-6-yl, (1R,5S,6s)-3-azabicyclo[3.1.0]hexan-6-yl, (3-hydroxyoxetan-3-yl)methyl, (R)-1,1,1-trifluoropropan-2-yl, (R)-1-ethylpyrrolidin-3-yl, (R)-pyrrolidin-3-yl, (S)-1-fluoropropan-2-yl, 1-((benzyloxy)carbonyl)piperid-4-yl, 1-((benzyloxy)carbonyl)pyrrolidin-4-yl, 1-((tert-butyloxy)carbonyl)methyl, 1-((tert-butyloxy)carbonyl)piperid-4-yl, oxetan-3-yl, 1-(oxetan-3-yl)piperidin-4-yl, 1-(tert-butyl)piperidin-4-yl, 1,1-difluoro-2-hydroxyethyl, 1-ethylpiperidin-4-yl, 1-propylpiperidin-4-yl, 2-(2-hydroxyethoxy)ethyl, 2-(2-methoxyethoxy)ethyl, 2-(diethyl(methyl)ammonio)ethyl, 2-(dimethylamino)ethyl, 2-(piperidin-1-yl)ethyl, 2,2,2-trifluoroethyl, 2,2,6,6-tetramethylpiperidin-4-yl, 2-aminoethyl, 2-fluoroethyl, 2-hydroxyethyl, 2-methoxyethyl, 2-morpholinoethyl, 3-(dimethylamino)propyl, 3-(pyrrolidin-1-yl)propyl, carboxymethyl, cyanomethyl, cyclopentyl, cyclopropyl, hydrogen, isopropyl, methyl, oxetan-3-yl, phenyl, piperidin-4-yl, pyridin-2-ylmethyl, pyridin-3-yl, (1R,2S)-2-fluorocyclopropyl, [1,1'-bi(cyclopropan)]-1-yl, 1-(difluoromethyl)cyclopropyl, 1-(fluoromethyl)cyclopropyl, 1-(hydroxymethyl)cyclopropyl, 1-(morpholine-4-carbonyl)cycloprop-1-yl, 1-(pyridin-4-yl)cyclopropyl, 1-(pyrrolidine-1-carbonyl)cycloprop-1-yl, 1-(trifluoromethyl)cyclopropyl, 1,1,1-trifluoro-2-methylpropan-2-yl, 1,1-difluoro-2-methylpropan-2-yl, 1-carbamoylcyclobut-1-yl, 1-carbamoylcycloprop-1-yl, 1-carboxycyclopropyl, 1-cyanocyclobutyl, 1-cyanocyclopropyl, 1-fluoro-2-methylpropan-2-yl, 1-methylcyclopropyl, 1-N,N-dimethylcarbamoylcycloprop-1-yl, 2-(methylsulfonamido)-2-oxoethyl, 2,2-difluoroethyl, 2,6-difluorobenzyl, 3-(hydroxymethyl)oxetan-3-yl, 3-(trifluoromethyl)oxetan-3-yl, 3,3-difluoro-1-(carboxy)cyclobut-1-yl, 3,3-difluorocyclobutyl, bicyclo[1.1.1]pentan-1-yl, chloro, cyano, fluoro, iodo, or tert-butyl.

In one embodiment, $R^3$ is heterocyclyl or heteroaryl, wherein each heterocyclyl or heteroaryl is optionally substituted with one or more substituents (i.e., $Z^3$) selected from the group consisting of (1R,5S,6r)-3-(oxetan-3-yl)-3-azabicyclo[3.1.0]hexan-6-yl, (1R,5S,6s)-3-(oxetan-3-yl)-3-azabicyclo[3.1.0]hexan-6-yl, (1R,5S,6s)-3-azabicyclo[3.1.0]hexan-6-yl, (3-hydroxyoxetan-3-yl)methyl, (R)-1,1,1-trifluoropropan-2-yl, (R)-1-ethylpyrrolidin-3-yl, (R)-pyrrolidin-3-yl, (S)-1-fluoropropan-2-yl, 1-((benzyloxy)carbonyl)piperid-4-yl, 1-((benzyloxy)carbonyl)pyrrolidin-4-yl, 1-((tert-butyloxy)carbonyl)methyl, 1-((tert-butyloxy)carbonyl)piperid-4-yl, oxetan-3-yl, 1-(oxetan-3-yl)piperidin-4-yl, 1-(tert-butyl)piperidin-4-yl, 1,1-difluoro-2-hydroxyethyl, 1-ethylpiperidin-4-yl, 1-propylpiperidin-4-yl, 2-(2-hydroxyethoxy)ethyl, 2-(2-methoxyethoxy)ethyl, 2-(diethyl(methyl)ammonio)ethyl, 2-(dimethylamino)ethyl, 2-(piperidin-1-yl)ethyl, 2,2,2-trifluoroethyl, 2,2,6,6-tetramethylpiperidin-4-yl, 2-aminoethyl, 2-fluoroethyl, 2-hydroxyethyl, 2-methoxyethyl, 2-morpholinoethyl, 3-(dimethylamino)propyl, 3-(pyrrolidin-1-yl)propyl, carboxymethyl, cyanomethyl, cyclopentyl, cyclopropyl, hydrogen, isopropyl, methyl, oxetan-3-yl, phenyl, phenyl, piperidin-4-yl, pyridin-2-ylmethyl, pyridin-3-yl, or tert-butyl.

In another embodiment, $R^3$ is heterocyclyl or heteroaryl, wherein each heterocyclyl or heteroaryl is optionally substituted with one or more substituents (i.e., $Z^3$) selected from the group consisting of hydrogen, isopropyl, methyl, oxetan-3-yl, 1-(tert-butyl)piperidin-4-yl, 1-ethylpiperidin-4-yl, cyclopropyl, 1-(trifluoromethyl)cyclopropyl, 1-(difluoromethyl)cyclopropyl, 1-(fluoromethyl)cyclopropyl, 1-cyanocyclopropyl, or piperidin-4-yl.

In another embodiment, $R^3$ is heterocyclyl or heteroaryl, wherein each heterocyclyl or heteroaryl is optionally substituted with one or more substituents (i.e., $Z^3$) selected from the group consisting of hydrogen, isopropyl, methyl, oxetan-3-yl, 1-(tert-butyl)piperidin-4-yl, 1-ethylpiperidin-4-yl, cyclopropyl, or piperidin-4-yl.

In one embodiment, $R^3$ is triazolyl, pyrazolyl, isoxazolyl, isoxazolyl, oxazolyl, pyrazinyl, pyridinyl, pyrimidinyl, imidazolyl, thiadiazolyl, tetrazolyl, or oxadiazolyl, wherein each is optionally substituted by one or more $Z^3$ groups as described herein. In one embodiment, $R^3$ is optionally substituted triazole (e.g., 1H-1,2,3-triazolyl).

In certain embodiments, $R^3$ is triazole substituted with one or more substituents selected from the group consisting of 1-(benzyloxycarbonyl)piperidin-4-yl, 1-(tert-butyl)piperidin-4-yl, 1-ethylpiperidin-4-yl, cyclopropyl, isopropyl, methyl, and piperidin-4-yl.

In one embodiment, $R^4$ is heterocyclyl or heteroaryl; and said heterocyclyl or heteroaryl is optionally substituted with one to three substituents independently selected from the group consisting of —CN, halo, —O—$R^{12}$, —C(O)—$R^{12}$, $C_{1-6}$ alkyl, $C_{1-6}$ haloalkyl, and heterocyclyl.

In certain embodiments, $R^4$ is heteroaryl optionally substituted with one to three substituents independently selected from the group consisting of —CN, halo, —O—$R^{12}$, —C(O)—$R^{12}$, $C_{1-9}$ alkyl, $C_{1-9}$ haloalkyl, and heterocyclyl.

In certain embodiments, $R^4$ is heterocyclyl optionally substituted with one to three substituents independently selected from the group consisting of —CN, halo, —O—$R^{12}$, —C(O)—$R^{12}$, $C_{1-9}$ alkyl, $C_{1-9}$ haloalkyl, and heterocyclyl.

In certain embodiments, $R^4$ is heteroaryl optionally substituted with one to three substituents independently selected from the group consisting of —CN, halo, —O—$R^{12}$, —C(O)—$R^{12}$, —N($R^{13}$)($R^{14}$), $C_{1-9}$ alkyl, $C_{1-9}$ haloalkyl, and heterocyclyl.

In certain embodiments, $R^4$ is heterocyclyl optionally substituted with one or more substituents selected from the group consisting of —CN, halo, —O—$R^{12}$, —C(O)—$R^{12}$, —N($R^{13}$)($R^{14}$), $C_{1-9}$ alkyl, $C_{1-9}$ haloalkyl, and heterocyclyl.

In certain embodiments, $R^4$ is optionally substituted bicyclic heterocyclyl or optionally substituted bicyclic heteroaryl. In certain embodiments, $R^4$ is

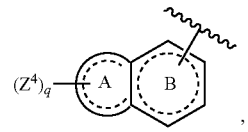

where $Z^4$ is as defined herein, q is 0, 1, 2, 3 or 4, ring A is a 5- or 6-membered cycloalkyl, heterocyclyl or heteroaryl ring, and ring B is a 6-membered cycloalkyl, heterocyclyl or heteroaryl ring, provided that at least one heteroatom is present in ring A or ring B such that $R^4$ is an optionally substituted bicyclic heterocyclyl or optionally substituted bicyclic heteroaryl. In the above, the wavy line indicates the point of attachment to the remainder of the molecule, where the attachment can through either ring (i.e., ring A or ring B) of the optionally substituted bicyclic heterocyclyl or optionally substituted bicyclic heteroaryl. In some embodiments, ring A and/or ring B comprises an oxo (=O).

In certain embodiments, $R^4$ is optionally substituted bicyclic heteroaryl. In certain embodiments, $R^4$ is an optionally substituted bicyclic heteroaryl selected from the group consisting of

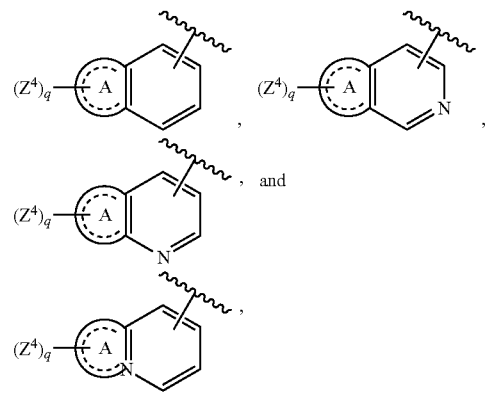

where $Z^4$ is as defined herein, q is 0, 1, 2, 3 or 4 and ring A is a 5- or 6-membered heterocyclyl or heteroaryl ring. In some embodiments, ring A comprises an oxo (=O).

$R^4$ is

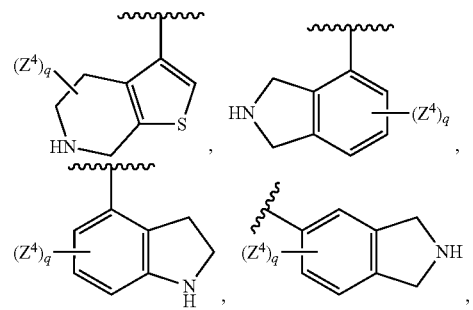

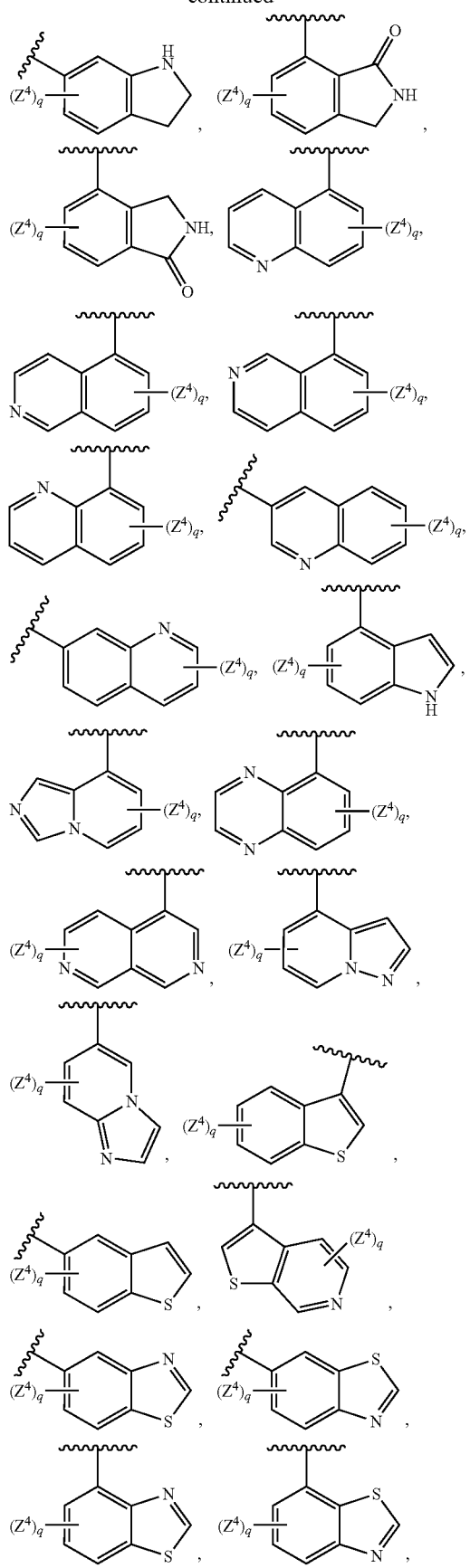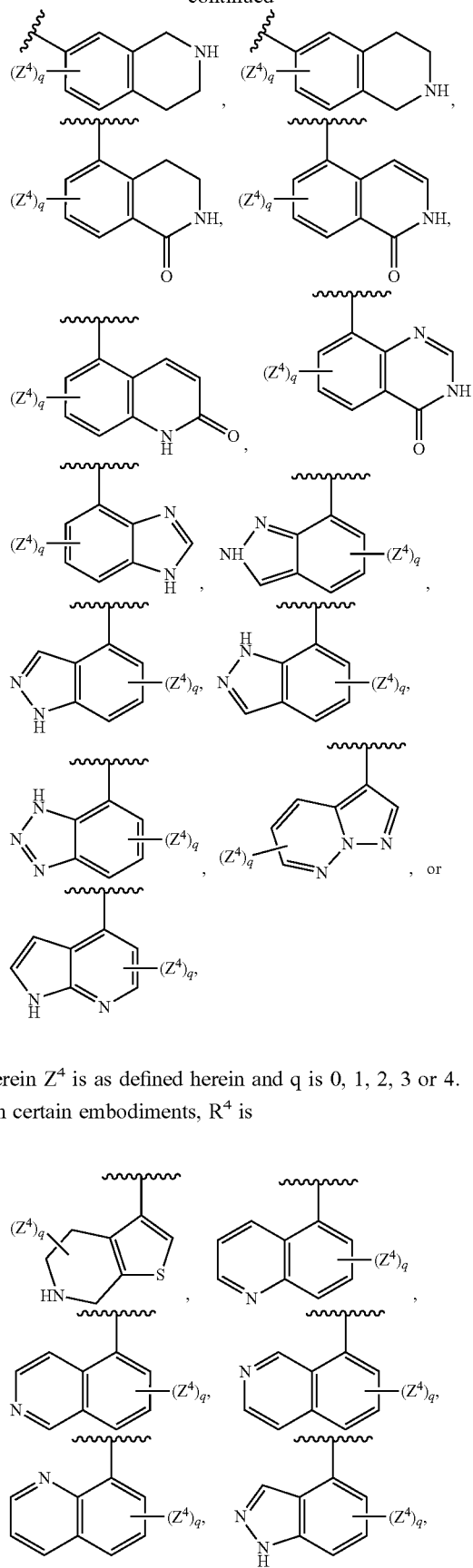
wherein $Z^4$ is as defined herein and q is 0, 1, 2, 3 or 4.
In certain embodiments, $R^4$ is
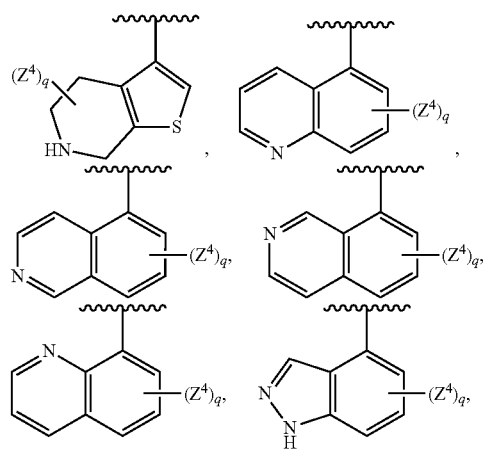

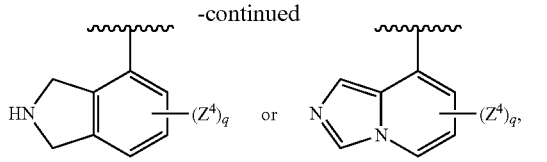

where $Z^4$ is as defined herein and q is 0, 1, 2, 3 or 4.

In certain embodiments, the compound of Formula I is represented by Formula XII:

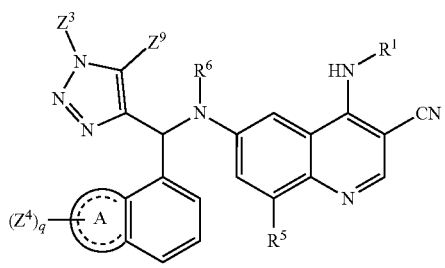

XII

Wherein q, $Z^3$, $R^1$, $Z^4$, $R^5$ and $R^6$ are as defined herein, ring A is a 5- or 6-membered heterocyclyl or heteroaryl and $Z^9$ is hydrogen, halo, —CN, or —O—$R^{12}$. In certain embodiments, the compound of Formula I is represented by Formula XIIA:

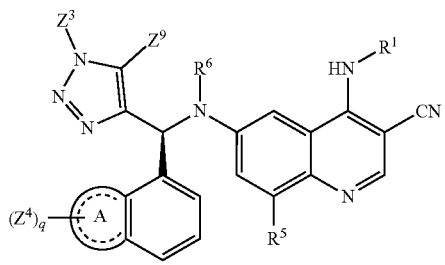

XIIA wherein q, $Z^3$, $R^1$, $Z^4$, $R^5$ and $R^6$ are as defined herein, ring A is a 5- or 6-membered heterocyclyl or heteroaryl and $Z^9$ is hydrogen, halo, —CN, or —O—$R^{12}$.

In certain embodiments, the compound of Formula I is represented by Formula XIII:

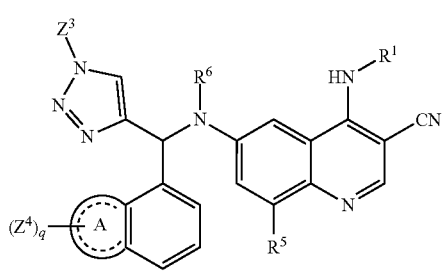

XIII wherein q, $Z^3$, $R^1$, $Z^4$, $R^5$, and $R^6$ are as defined herein and ring A is a 5- or 6-membered heterocyclyl or heteroaryl. In certain embodiments, the compound of Formula I is represented by Formula XIIIA

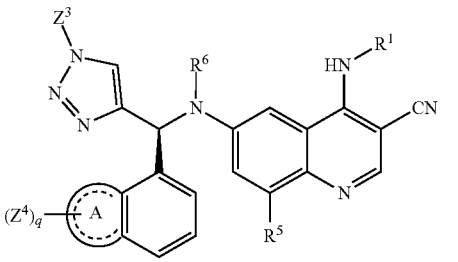

XIIIA wherein q, $Z^3$, $R^1$, $Z^4$, $R^5$, and $R^6$ are as defined herein and ring A is a 5- or 6-membered heterocyclyl or heteroaryl.

In certain embodiments, the compound of Formula I is represented by Formula XIIIB:

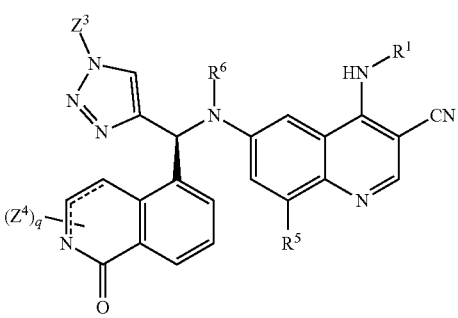

XIIIB wherein q, $Z^3$, $R^1$, $Z^4$, $R^5$, and $R^6$ are as defined herein.

In certain embodiments, the compound of Formula I is represented by Formula XIIIC:

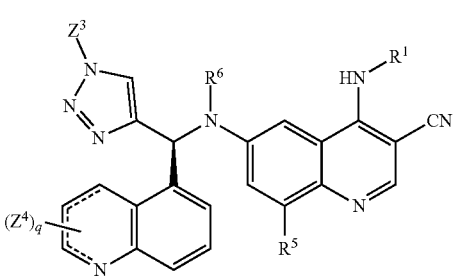

XIIIC wherein q, $Z^3$, $R^1$, $Z^4$, $R^5$, and $R^6$ are as defined herein.

In certain embodiments, the compound of Formula I is represented by Formula XIIID:

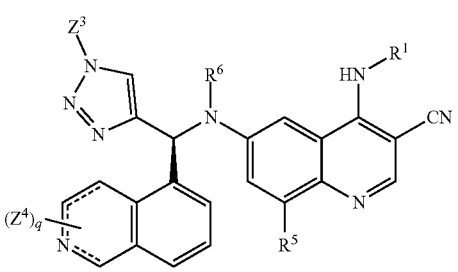

XIIID wherein q, $Z^3$, $R^1$, $Z^4$, $R^5$, and $R^6$ are as defined herein.

In certain embodiments, each $Z^4$ is independently selected from the group consisting of —CN, halo, —O—$R^{12}$, —C(O)—$R^{12}$, —N($R^{13}$)($R^{14}$), $C_{1-9}$ alkyl, $C_{1-9}$ haloalkyl, and heterocyclyl. In some embodiments, each $Z^4$ is independently selected from the group consisting of —CN, halo, —O—$R^{12}$, and $C_{1-9}$ alkyl.

In certain embodiments, $R^4$ is optionally substituted monocyclic heteroaryl. In certain embodiments, $R^4$ is

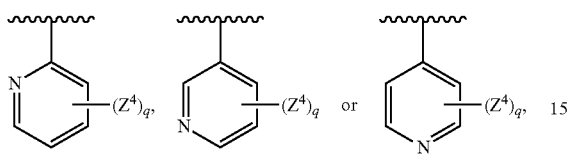

where $Z^4$ is as defined herein and q is 0, 1, 2, 3 or 4. In certain embodiments, $R^4$ is

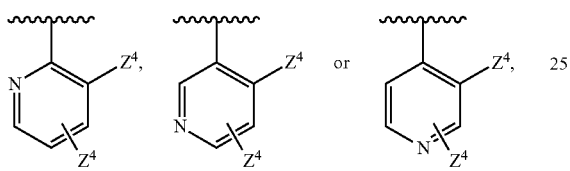

where $Z^4$ is as defined herein. In certain embodiments, the compound of Formula I is represented by Formula XIV:

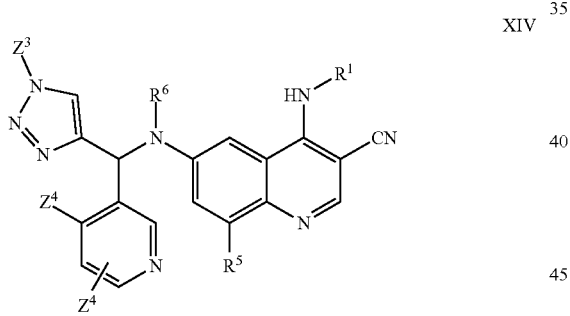

XIV wherein $Z^3$, $R^1$, $Z^4$, $R^5$ and $R^6$ are as defined herein. In certain embodiments, the compound of Formula I is represented by Formula XIVA:

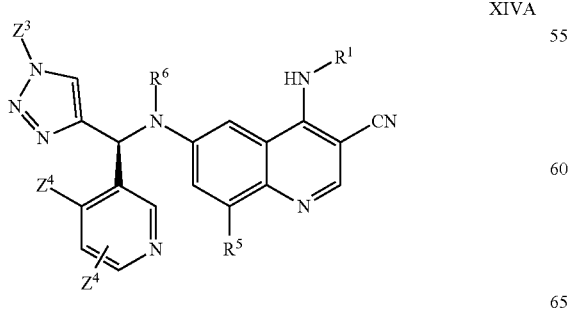

XIVA wherein $Z^3$, $R^1$, $Z^4$, $R^5$ and $R^6$ are as defined herein.

In certain embodiments, $Z^3$ is

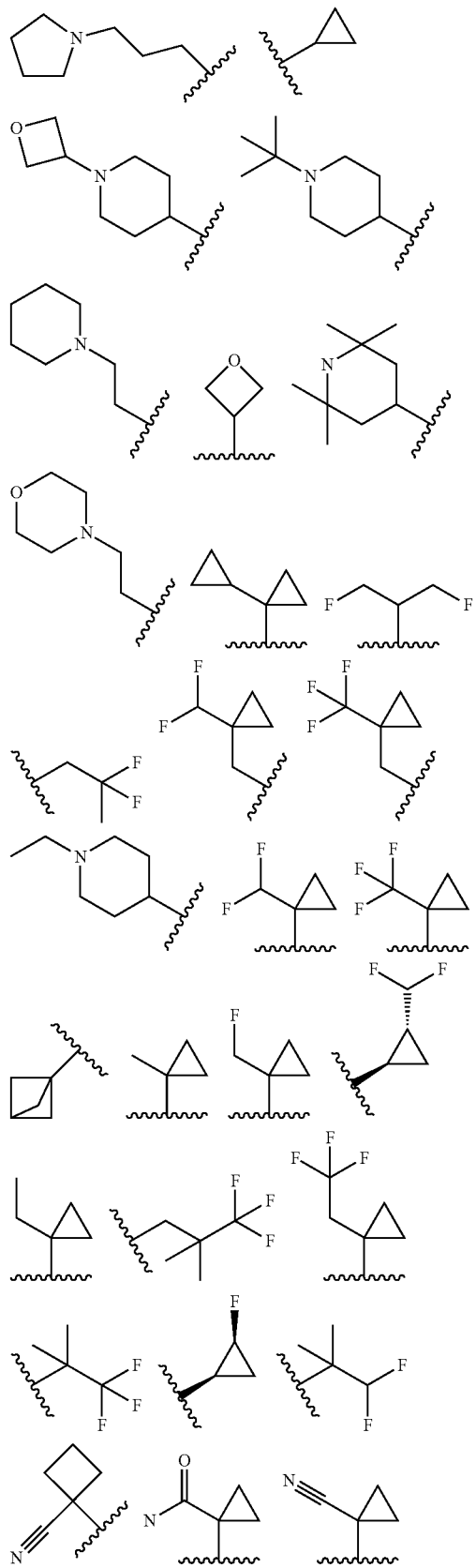

-continued

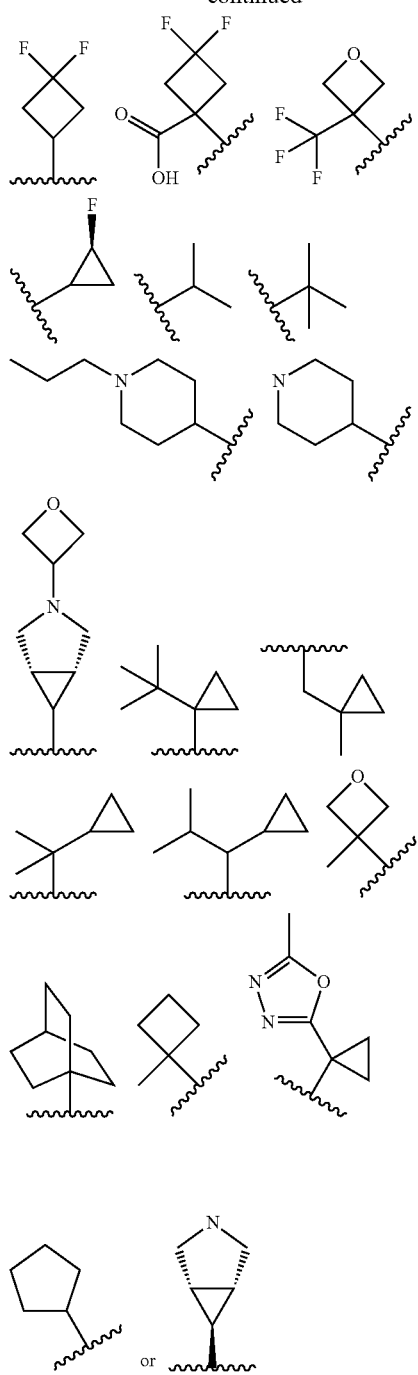

In certain embodiments, each $Z^4$ is independently selected from the group consisting of —CN, halo, —O—$R^{12}$, —C(O)—$R^{12}$, —N($R^{13}$)($R^{14}$), $C_{1-9}$ alkyl, $C_{1-9}$ haloalkyl, and heterocyclyl. In some embodiments, each $Z^4$ is independently selected from the group consisting of —CN, halo, —O—$R^{12}$, and $C_{1-9}$ alkyl. In certain embodiments of compounds of Formula IX or X, $R^1$ is $C_{1-9}$ alkyl, optionally substituted with one to three substituents independently selected the group consisting of halo, —CN, —O—$R^{12}$, $C_{1-9}$ alkyl, and aryl. In certain embodiments of compounds of Formula IX or X, $R^6$ is hydrogen. In certain embodiments of compounds of Formula IX or X, $R^5$ is halo or cyano.

In one embodiment, $R^4$ is

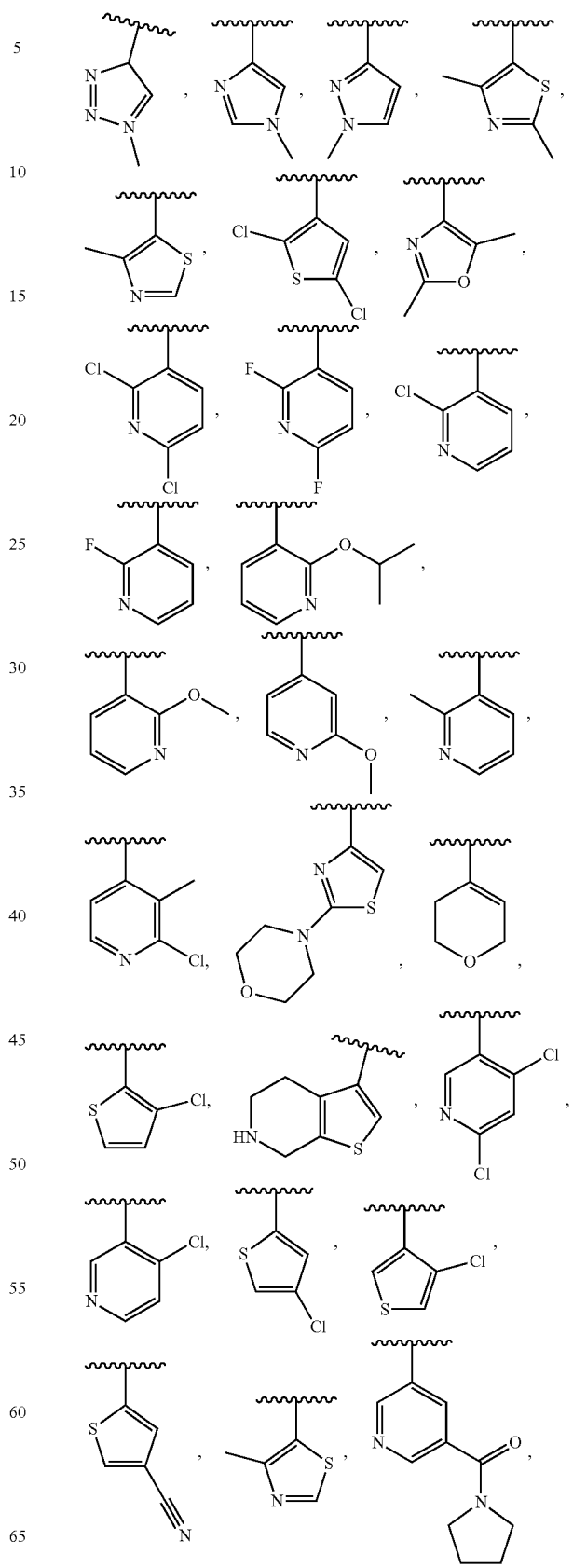

-continued
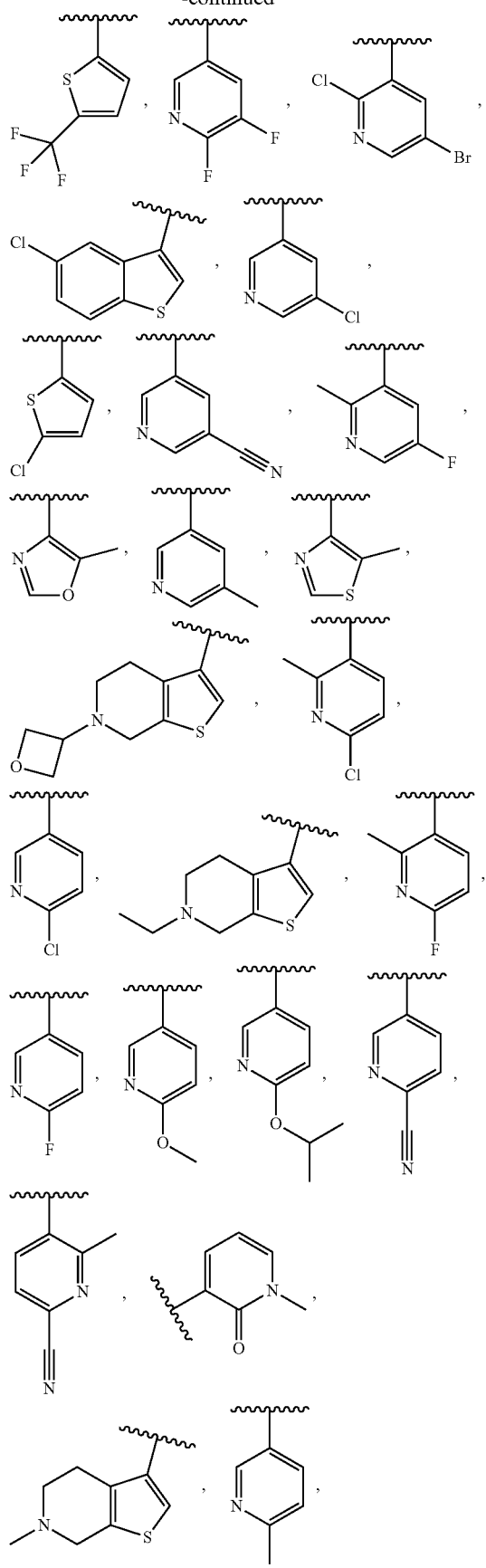
-continued
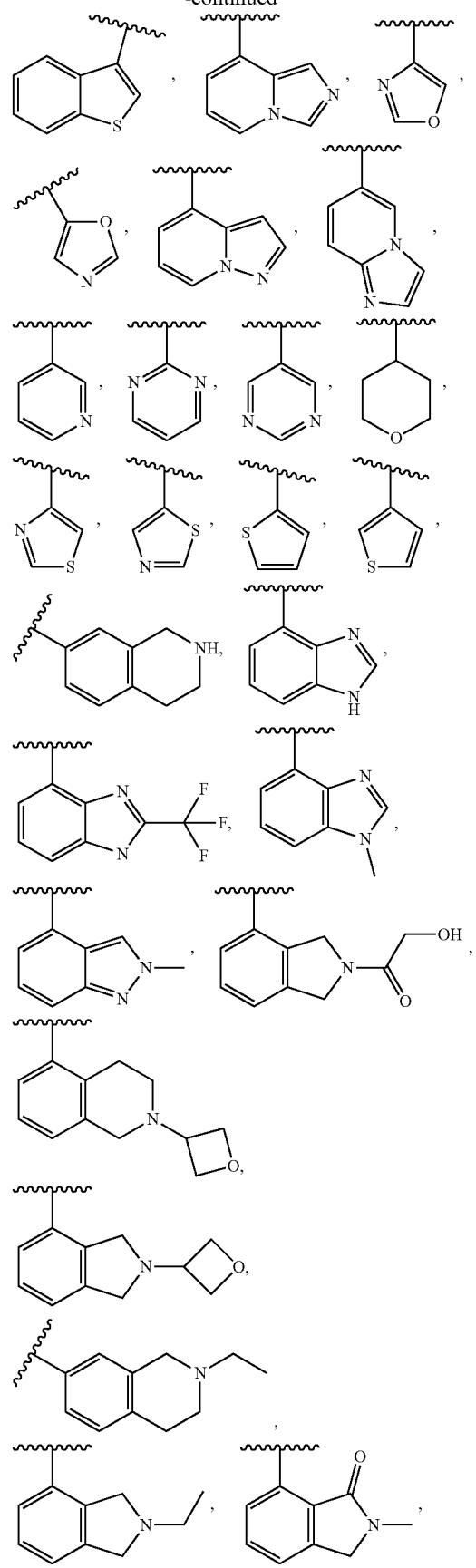

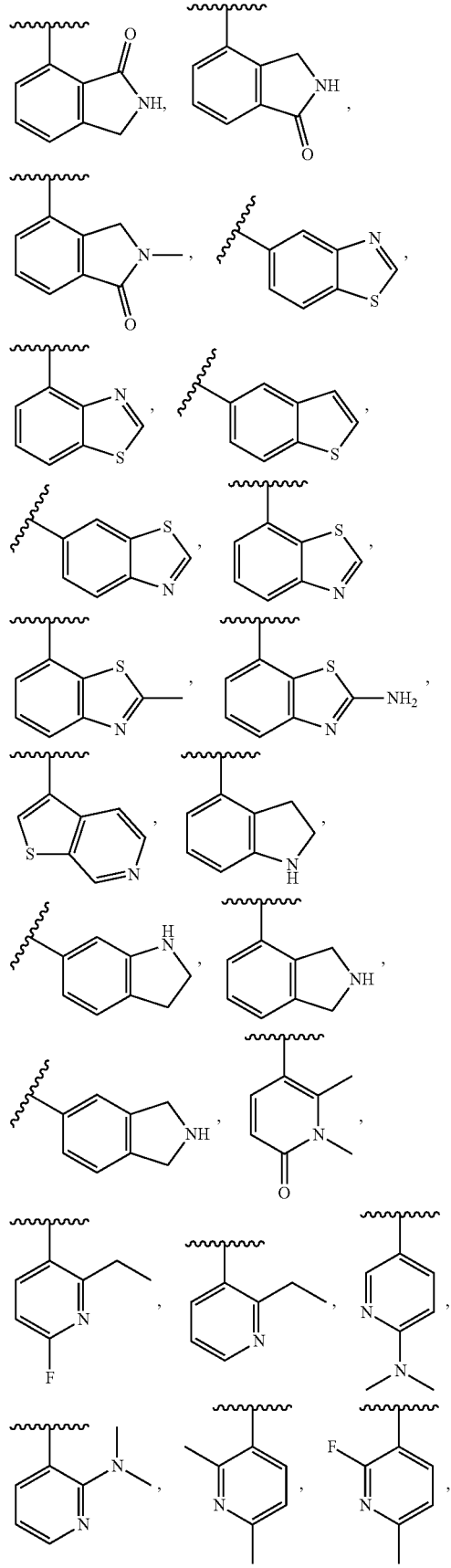
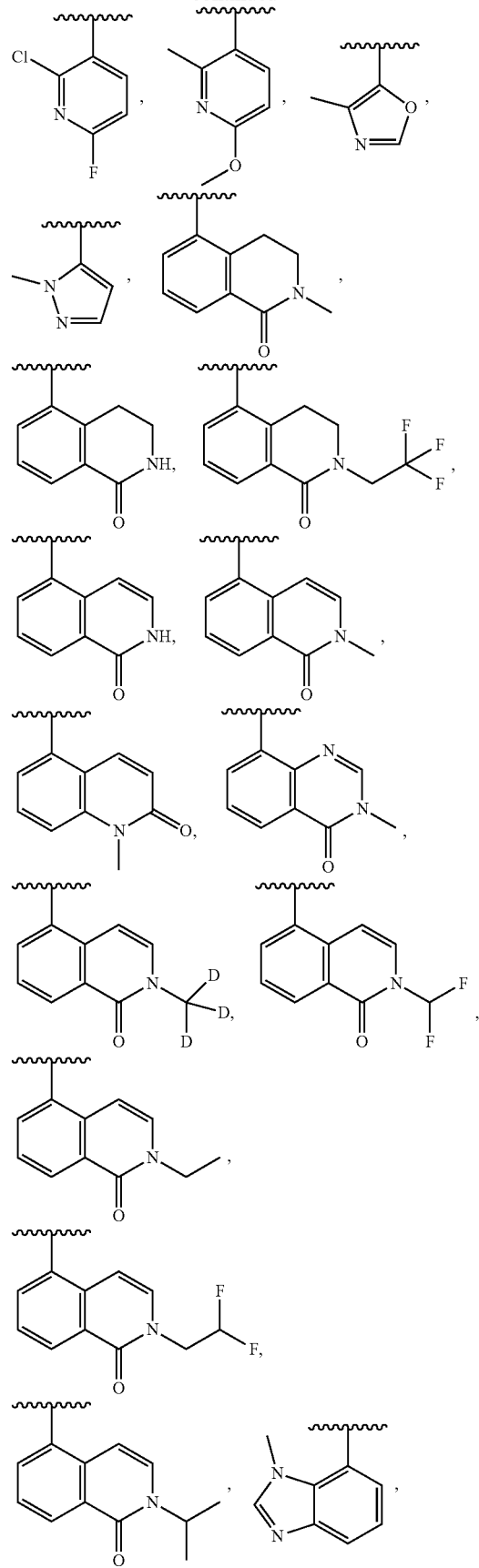

-continued
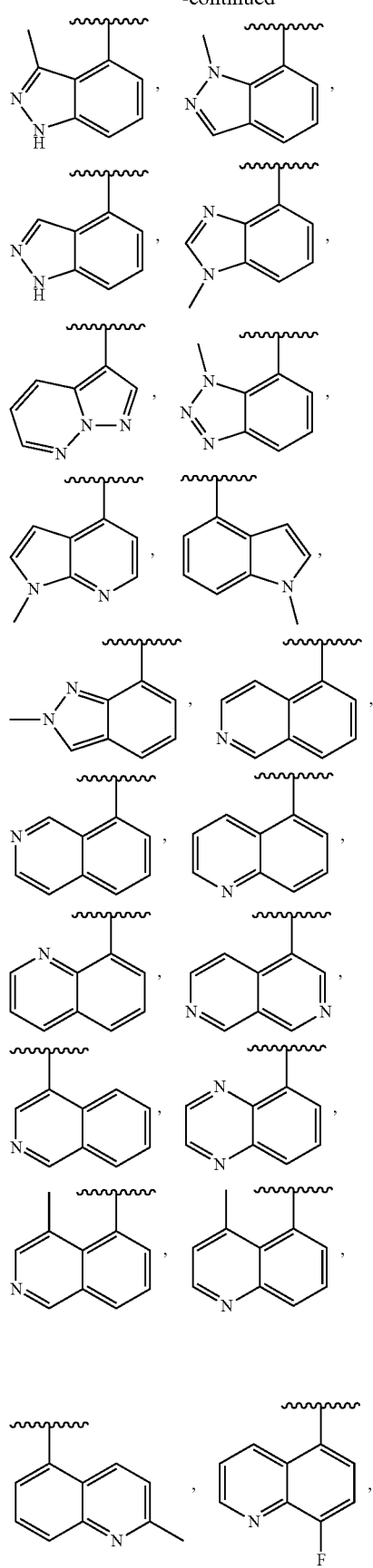
-continued
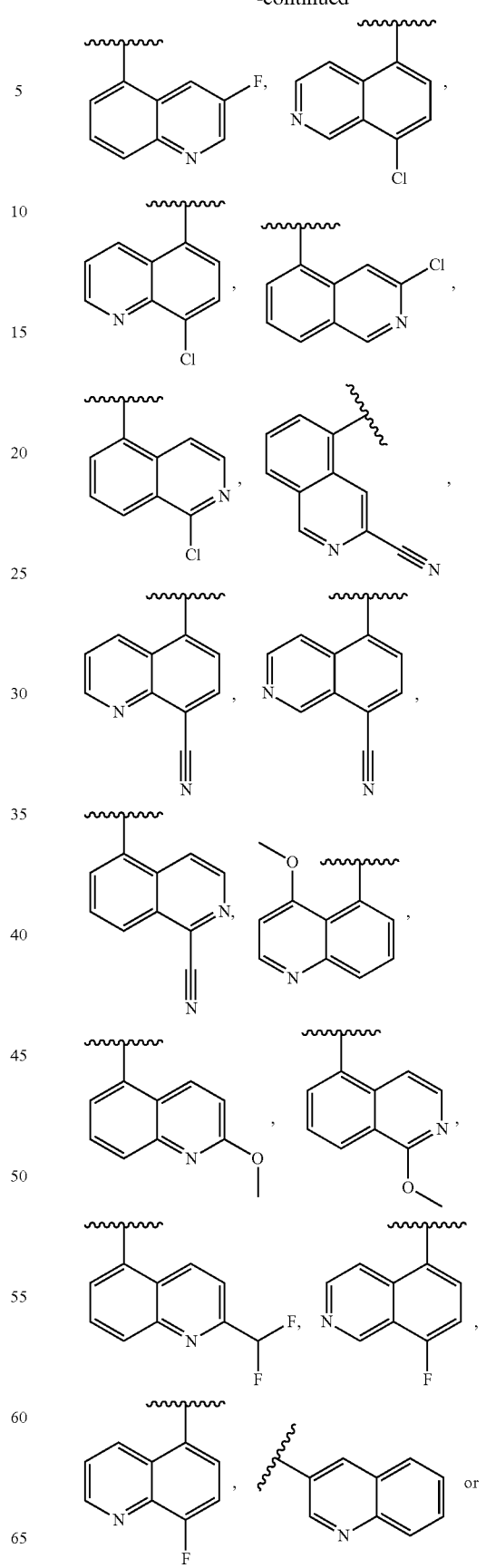

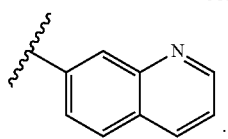
In one embodiment, R⁴ is
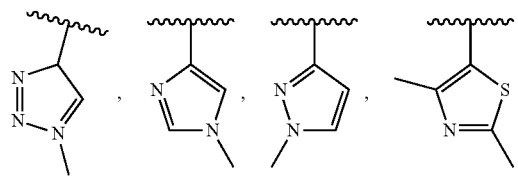
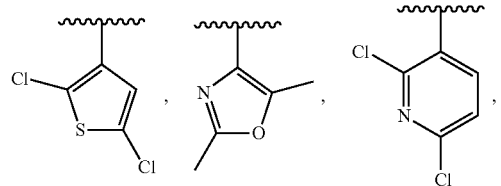
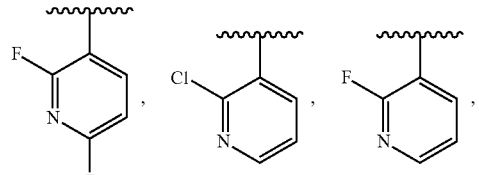
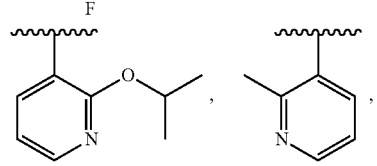
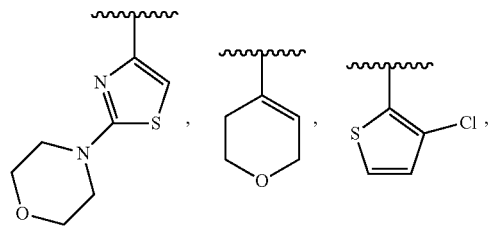
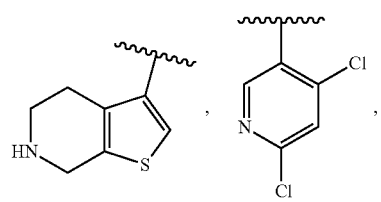
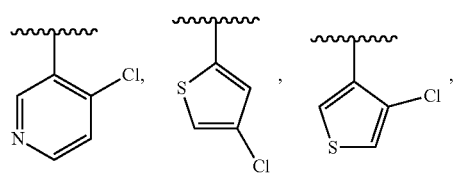
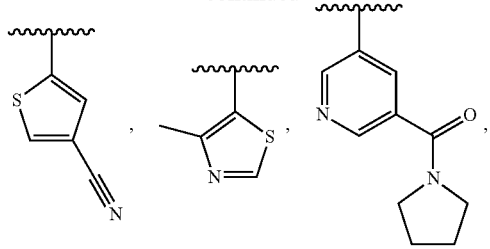
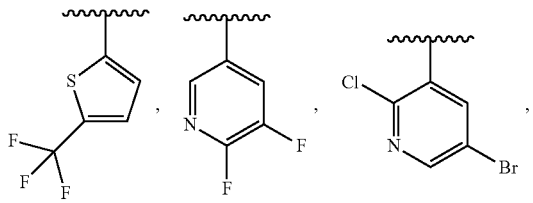
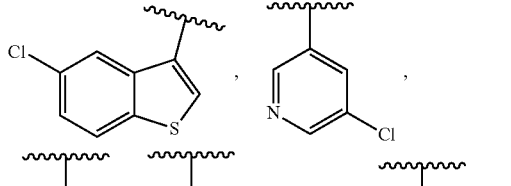
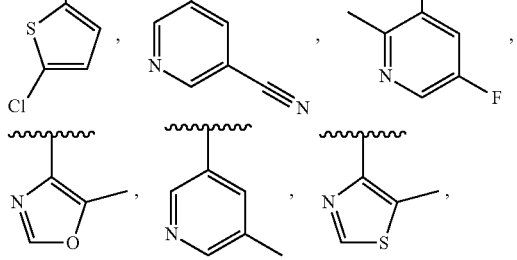
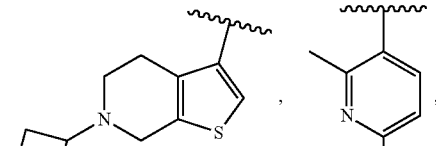
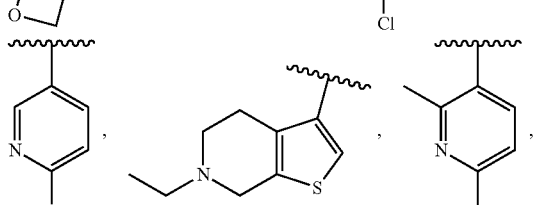
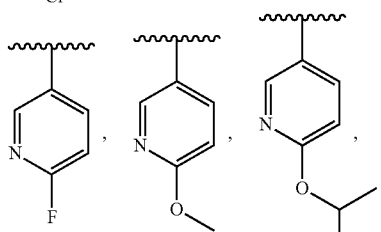
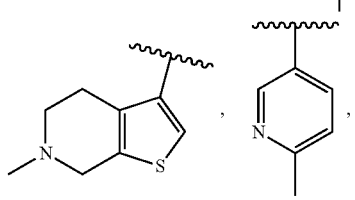

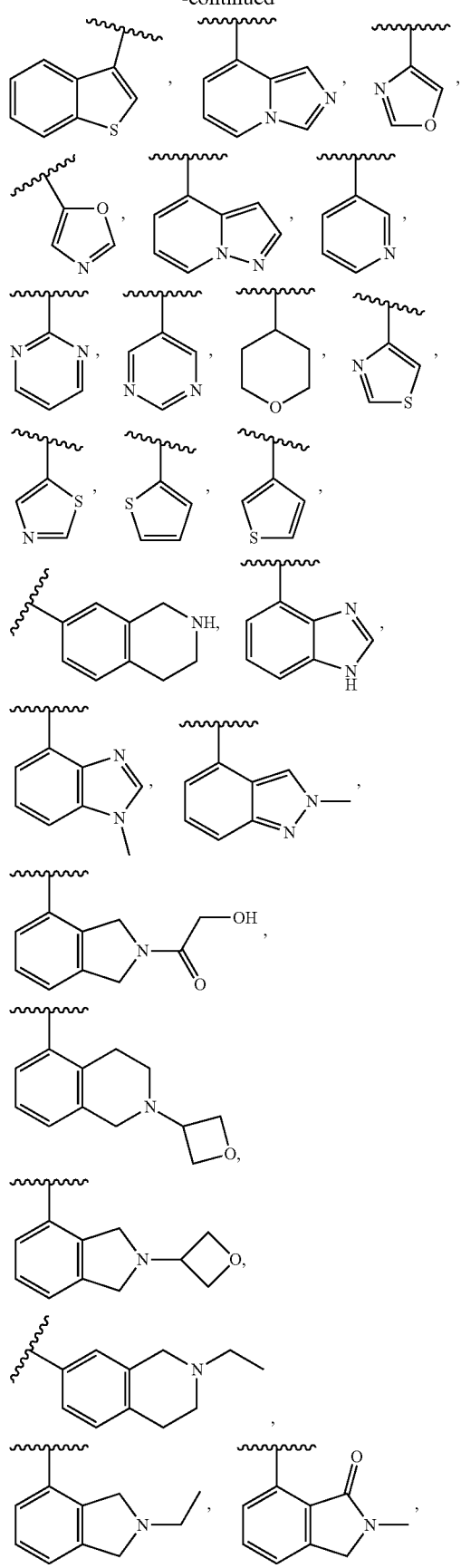
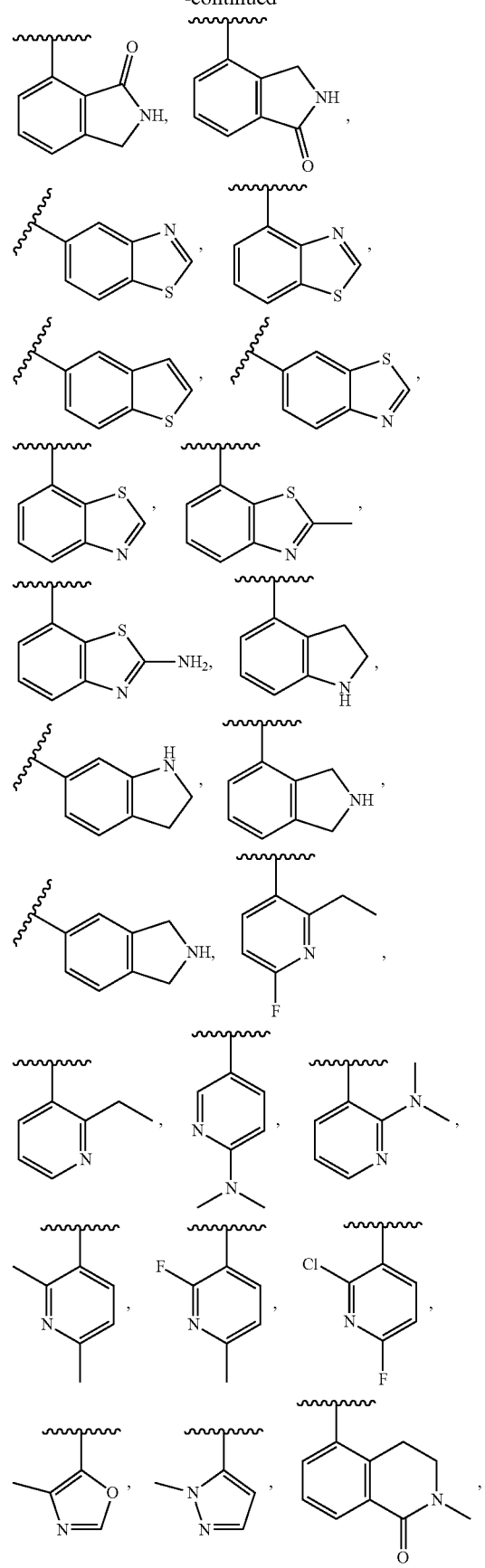

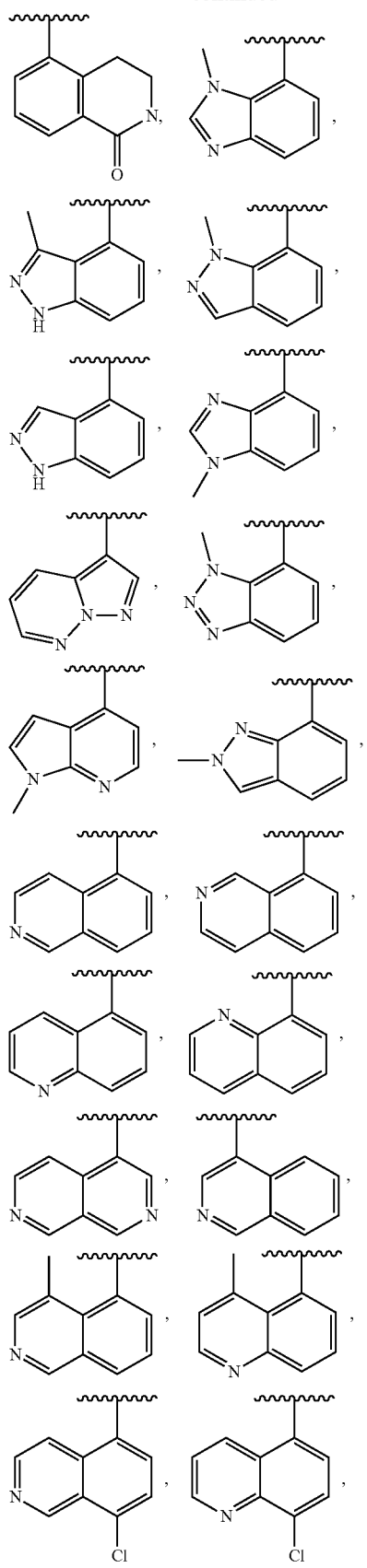
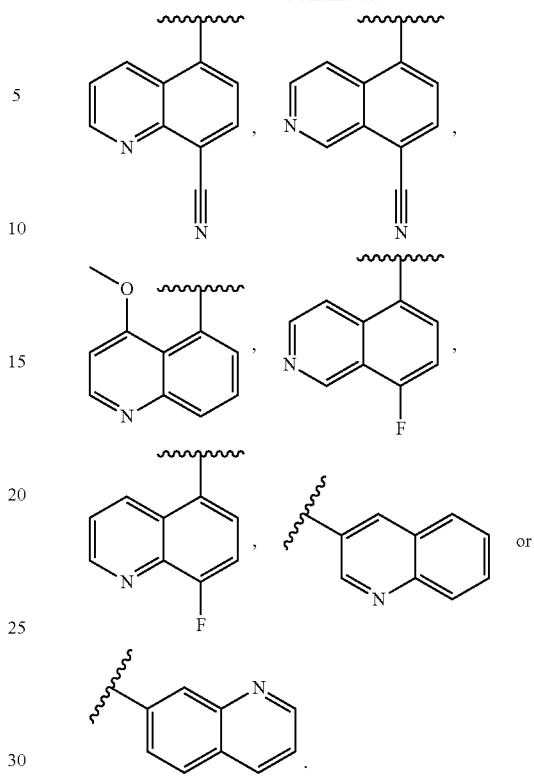
In one embodiment, R⁴ is
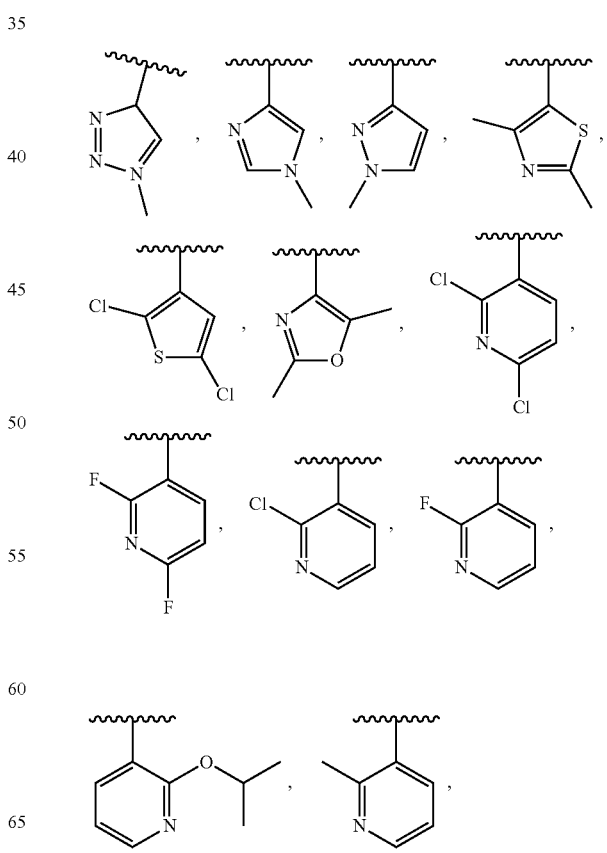

-continued
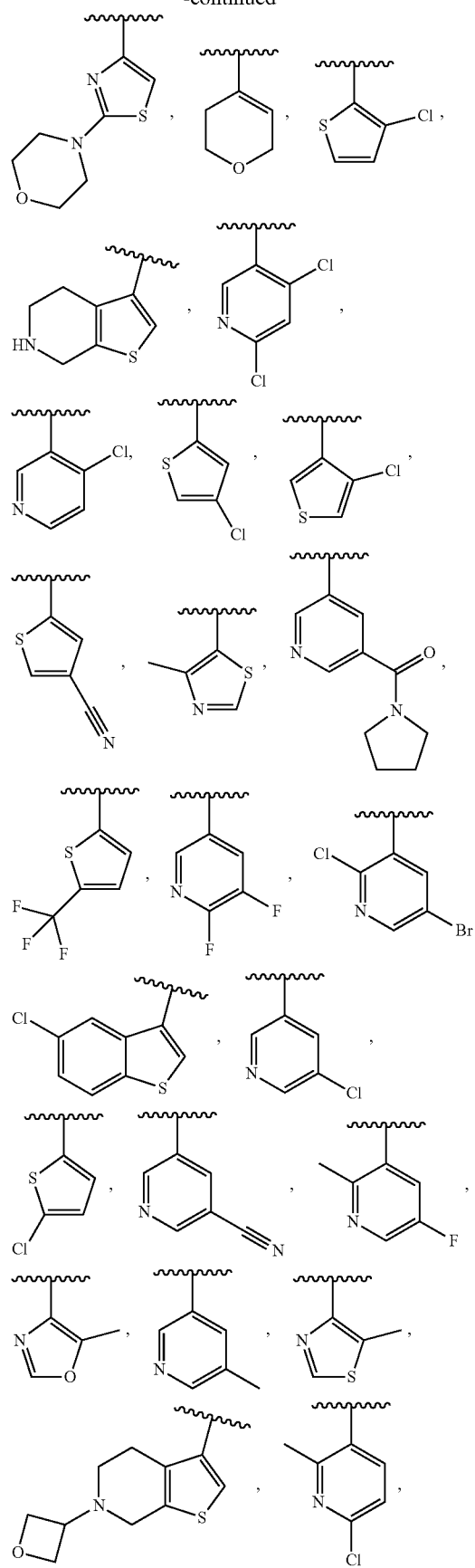
-continued
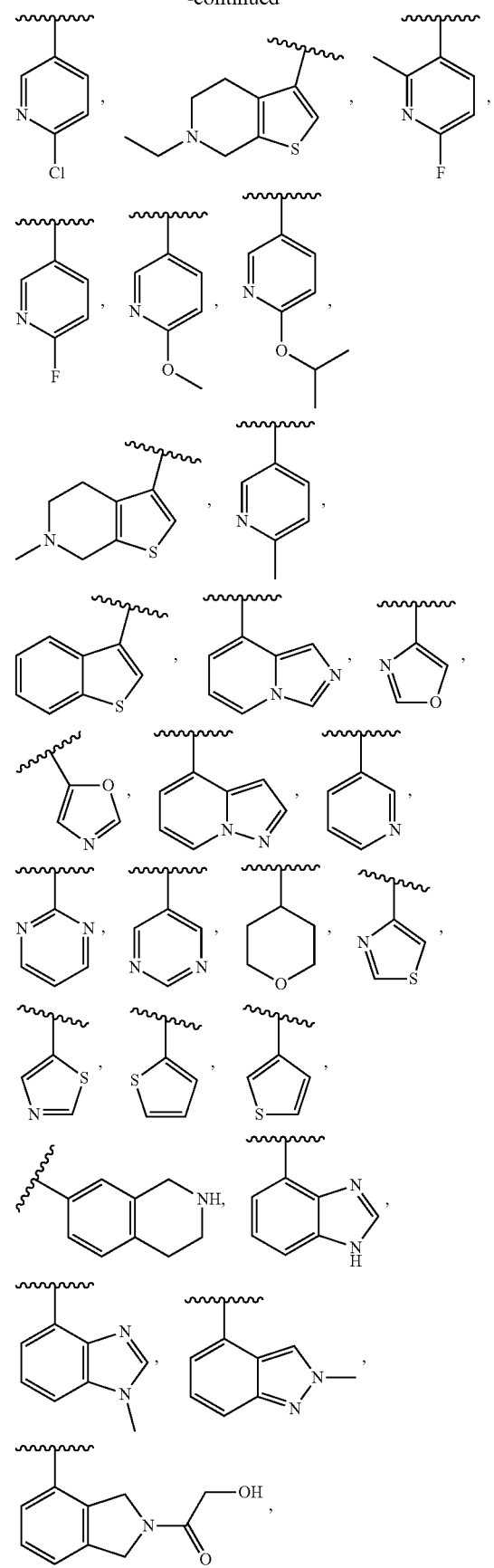

-continued
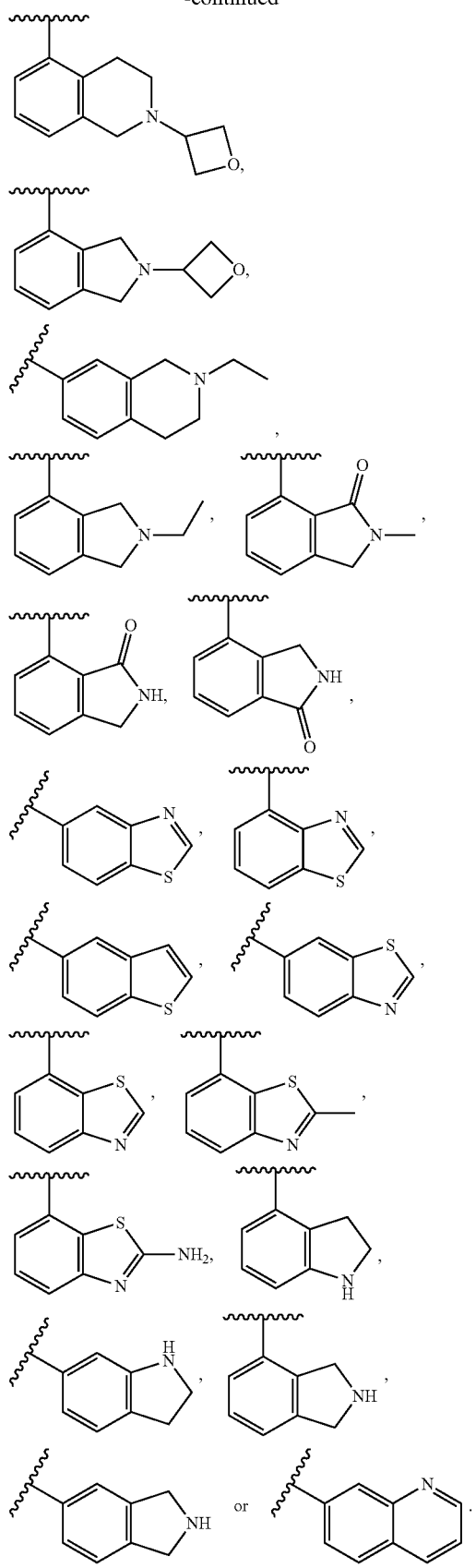
In one embodiment, $R^4$ is
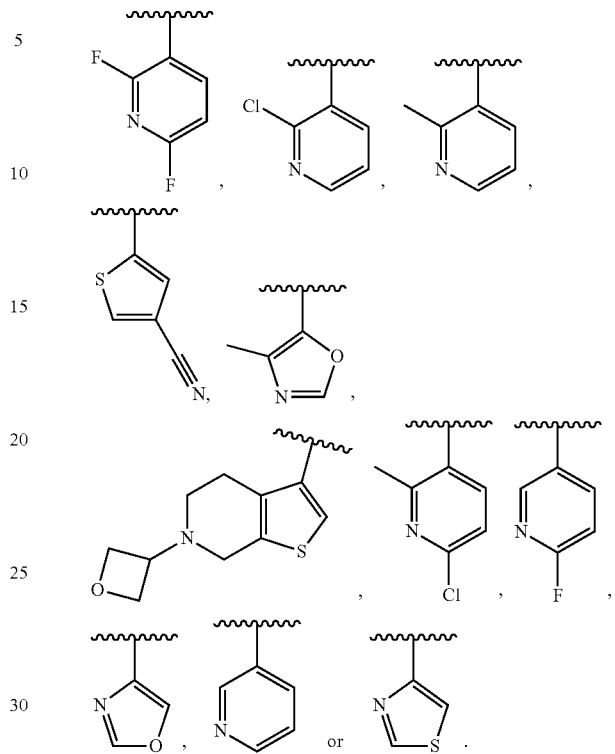
In one embodiment, $R^4$ is
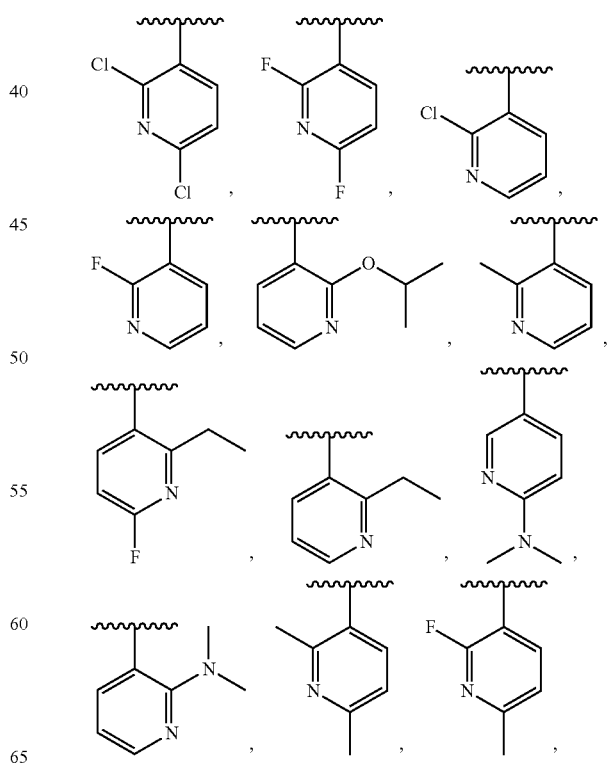

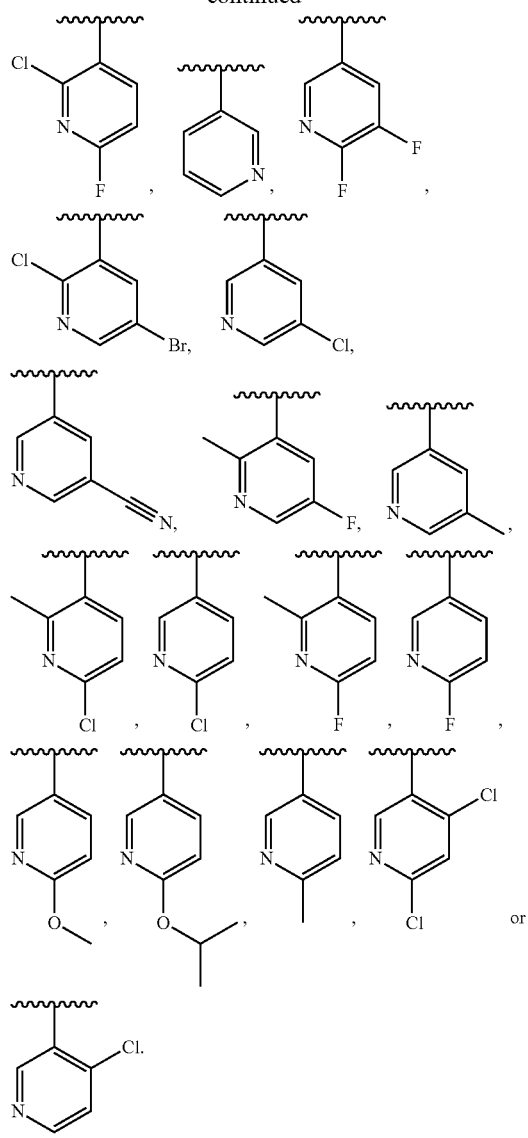
In certain embodiments, R⁴ is
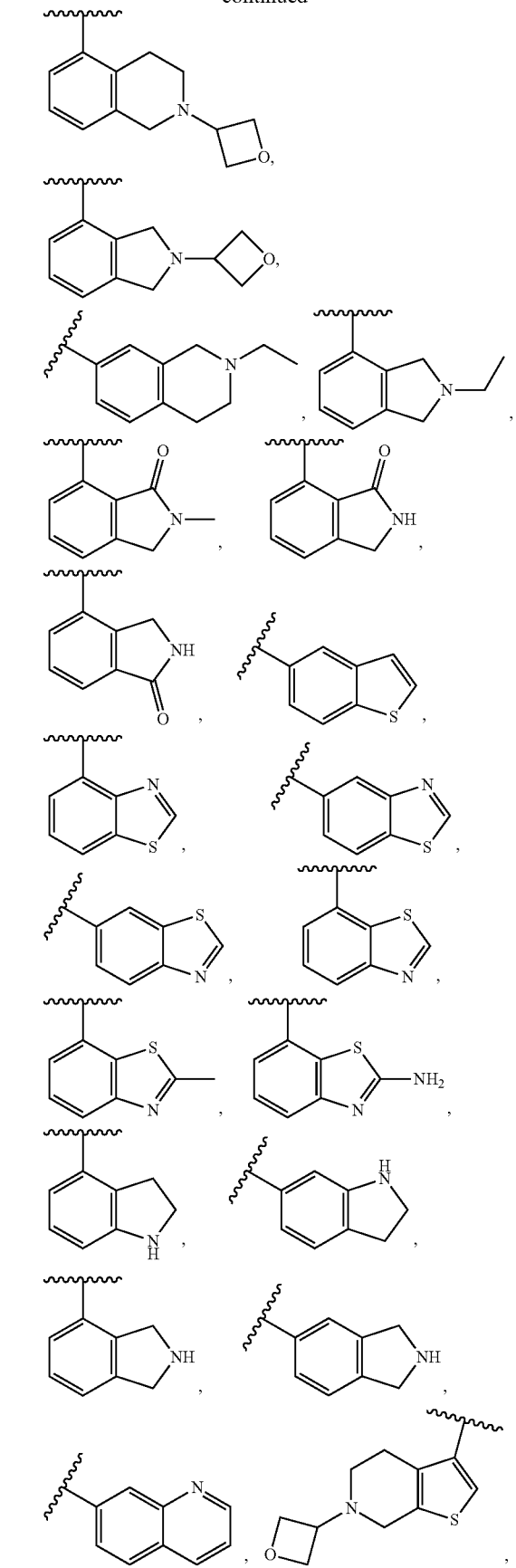

-continued

In certain embodiments, $R^5$ is hydrogen, halo, —CN, —O—$R^7$, —S(O)—$R^7$, —S(O)$_2R^7$, —S(O)$_2$N($R^7$)$_2$, —C(O)$R^7$, —C(O)N($R^7$)$_2$, $C_{1-9}$ alkyl, $C_{2-6}$ alkenyl, $C_{2-6}$ alkynyl, $C_{3-15}$ cycloalkyl, aryl, heterocyclyl, or heteroaryl; wherein each $C_{1-9}$ alkyl, $C_{2-6}$ alkenyl, $C_{2-6}$ alkynyl, $C_{3-15}$ cycloalkyl, aryl, heterocyclyl, and heteroaryl may be optionally substituted with one to four $Z^5$.

In certain embodiments, $R^5$ is hydrogen, halo, —CN, —C(O)$R^7$, or heteroaryl. In one embodiment, $R^5$ is —CN, halo or —O—$R^7$. In certain embodiments, $R^5$ is hydrogen, halo, —CN, —C(O)$R^7$, —O—$R^7$, —S(O)$_2R^7$ or heteroaryl. In one embodiment, $R^5$ is halo.

In certain embodiments, $R^5$ is 1H-pyrazol-4-yl, 1-hydroxyethyl, 1-methyl-1H-pyrazol-4-yl, 4-(acetylamino)phenyl, 6-fluoropyridin-3-yl, methyl acetyl, bromo, chloro, cyano, cyclopropyl, dimethylaminocarbonyl, ethynyl, fluoro, iodo, methoxy, methyl, hydroxyl, phenyl, pyridin-3-yl, pyridin-4-yl, pyrimidin-5-yl, acetyl, methyl sulfonyl or trifluoromethyl. In one embodiment, $R^5$ is chloro.

In one embodiment, m is 0. In another embodiment, m is 1.

In general, the specific compounds exemplified herein are named using ChemBioDraw Ultra. However, it is understood that other names may be used to identify compounds of the same structure. In particular, the compounds may also be named using other nomenclature systems and symbols that are commonly recognized in the art of chemistry including, for example, Chemical Abstract Service (CAS) and International Union of Pure and Applied Chemistry (IUPAC). Other compounds or radicals may be named with common names, or systematic or non-systematic names.

In certain embodiments, provided are optical isomers, racemates, or other mixtures thereof of the compounds described herein or pharmaceutically acceptable salts or a mixture thereof. In those situations, the single enantiomer or diastereomer, i.e., optically active form, can be obtained by asymmetric synthesis or by resolution. Resolution can be accomplished, for example, by conventional methods such as crystallization in the presence of a resolving agent, or chromatography, using for example, a chiral high pressure liquid chromatography (HPLC) column.

Compositions provided herein that include a compound described herein or pharmaceutically acceptable salts, isomer, or a mixture thereof may include racemic mixtures, or mixtures containing an enantiomeric excess of one enantiomer or single diastereomers or diastereomeric mixtures. All such isomeric forms of these compounds are expressly included herein the same as if each and every isomeric form were specifically and individually listed.

A composition comprising a mixture of enantiomers (or diastereomers) of a compound described herein or a pharmaceutically acceptable salt thereof, is also provided herein. In some embodiments, the composition comprises a single enantiomer of the compound and is substantially free of the other enantiomer. In certain embodiments, the compound of Formula I (or another Formula as described herein) contains one or more additional stereogenic atom(s) (e.g., at $R^1$ and/or $R^3$). In such instances, the composition may contain a mixture of diastereomers. In some embodiments, the composition comprises a single enantiomer of the compound and is substantially free (i.e., having less than or about 40%, 30%, 25%, 20%, 15%, 10%, 5%, 1%, 0.05%, or 0.01%) of one or more diastereomers.

Accordingly, in certain embodiments, provided is a composition comprising a mixture of Formula IA, or a pharmaceutically acceptable salt thereof, and Formula IB, or a pharmaceutically acceptable salt thereof.

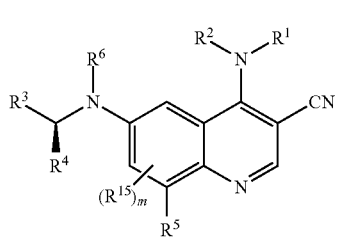

IA

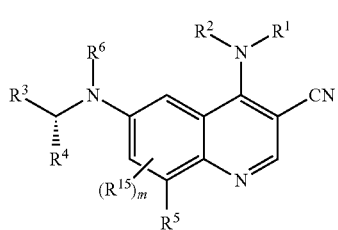

IB wherein m, $R^1$, $R^2$, $R^3$, $R^4$, $R^5$, $R^6$ and $R^{15}$ are as defined herein.

In one embodiment, the mixture is a racemic mixture. In other embodiments, the composition comprises a mixture of Formula IA, or a pharmaceutically acceptable salt thereof, and Formula IB, or a pharmaceutically acceptable salt thereof, wherein Formula IA is present in excess of over Formula IB, or a pharmaceutically acceptable salt thereof. In certain embodiments, provided is a composition substantially free of Formula IB, having less than or about 40%, 30%, 25%, 20%, 15%, 10%, 5%, 1%, 0.05%, or 0.01% of compounds of Formula IB.

In certain embodiments, provided here in is a composition comprising a mixture of stereoisomers of a compound of Formula I:

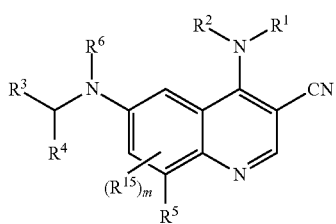

I wherein the mixture comprises compounds of Formula IA and IB in a ratio of at least about 3:1:

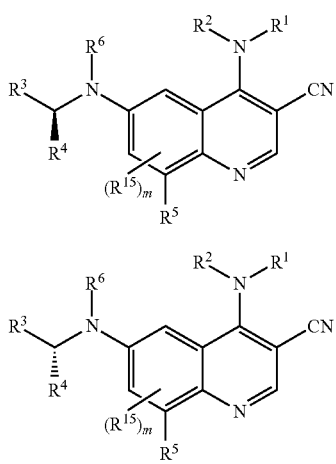

IA

IB wherein m, $R^1$, $R^2$, $R^3$, $R^4$, $R^5$, $R^6$ and $R^{15}$ are as defined herein.

The stereochemistry of the $R^4$ group depicted in Formula IA may be represented in an alternative way, provided that the configuration of the carbon atom to which it is attached is not altered. For example, compounds of Formula 1A may be depicted in any one of the equivalent representations of Formula IA shown below.

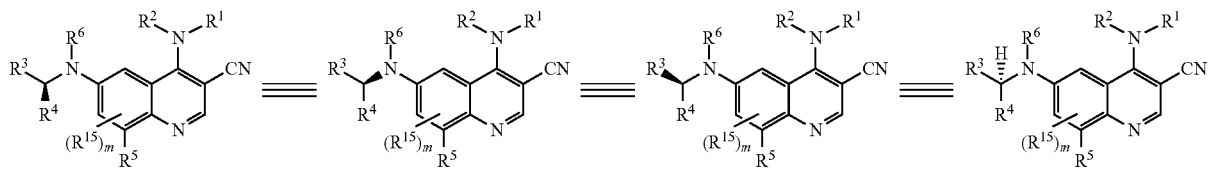

In other embodiments, the mixture comprises compounds of Formula IA and IB in a molar ratio of at least or about 3:1, at least or about 4:1, at least or about 5:1, at least or about 6:1, at least or about 7:1, at least or about 8:1, at least or about 9:1, at least or about 10:1, at least or about 11:1, at least or about 12:1, at least or about 20:1, at least or about 30:1, at least or about 40:1, at least or about 80:1, at least or about 160:1, or at least or about 320:1, respectively.

In certain embodiments, provided are also chelates, non-covalent complexes, and mixtures thereof, of the compounds described herein or a pharmaceutically acceptable salt, tautomer, stereoisomer, mixture of stereoisomers, prodrug, or deuterated analog thereof. A "chelate" is formed by the coordination of a compound to a metal ion at two (or more) points. A "non-covalent complex" is formed by the interaction of a compound and another molecule wherein a covalent bond is not formed between the compound and the molecule. For example, complexation can occur through van der Waals interactions, hydrogen bonding, and electrostatic interactions (also called ionic bonding).

In certain embodiments, provided are prodrugs of the compounds described herein. "Prodrug" refers to any compound that when administered to a biological system generates the drug substance, or active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically active compound. Non-limiting examples of prodrugs include ester moieties, quaternary ammonium moieties, glycol moieties, and the like.

In certain embodiments, provided is a compound of Formula I, IA, IB, II, IIA, III, IIIA, IV, IVA, V, VA, VI, VIA, VII, VIIA, VIII, VIIIA, IX, IXA, X, XA, XI, XIA, XII, XIIA, XIII, XIIIA, XIV, or XIVA, wherein $R^6$ is

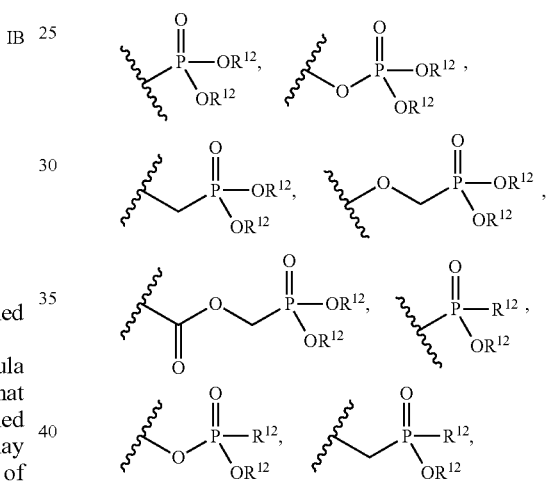

-continued

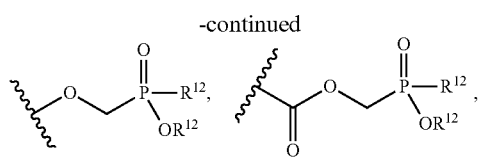

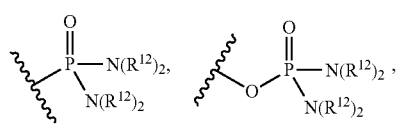

-continued where each $R^{12}$ is independently hydrogen, $C_{1-9}$ alkyl, $C_{2-6}$ alkenyl, $C_{2-6}$ alkynyl, $C_{3-15}$ cycloalkyl, aryl, heteroaryl or heterocyclyl;
    wherein any alkyl, alkenyl, alkynyl, cycloalkyl, aryl, heteroaryl or heterocyclyl is optionally substituted with one to four $Z^{1b}$ groups; and
each $Z^{1b}$ is independently oxo, thioxo, hydroxy, halo, —NO$_2$, —N$_3$, —CN, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O($C_{1-9}$ alkyl), —O($C_{2-6}$ alkenyl), —O($C_{2-6}$ alkynyl), —O($C_{3-15}$ cycloalkyl), —O($C_{1-8}$ haloalkyl), —O(aryl), —O(heteroaryl), —O(heterocyclyl), —NH$_2$, —NH($C_{1-9}$ alkyl), —NH($C_{2-6}$ alkenyl), —NH($C_{2-6}$ alkynyl), —NH($C_{3-15}$ cycloalkyl), —NH(C haloalkyl), —NH(aryl), —NH(heteroaryl), —NH(heterocyclyl), —N($C_{1-9}$ alkyl)$_2$, —N($C_{3-15}$ cycloalkyl)$_2$, —N($C_{2-6}$ alkenyl)$_2$, —N($C_{2-6}$ alkynyl)$_2$, —N($C_{3-15}$ cycloalkyl)$_2$, —N($C_{1-8}$ haloalkyl)$_2$, —N(aryl)$_2$, —N(heteroaryl)$_2$, —N(heterocyclyl)$_2$, —N($C_{1-9}$ alkyl)($C_{3-15}$ cycloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)($C_{1-8}$ haloalkyl), —N($C_{1-9}$ alkyl)(aryl), —N($C_{1-9}$ alkyl)(heteroaryl), —N($C_{1-9}$ alkyl)(heterocyclyl), —C(O)($C_{1-9}$ alkyl), —C(O)($C_{2-6}$ alkenyl), —C(O)($C_{2-6}$ alkynyl), —C(O)($C_{3-15}$ cycloalkyl), —C(O)($C_{1-8}$ haloalkyl), —C(O)(aryl), —C(O)(heteroaryl), —C(O)(heterocyclyl), —C(O)O($C_{1-9}$ alkyl), —C(O)O($C_{2-6}$ alkenyl), —C(O)O($C_{2-6}$ alkynyl), —C(O)O($C_{3-15}$ cycloalkyl), —C(O)O($C_{1-8}$ haloalkyl), —C(O)O(aryl), —C(O)O(heteroaryl), —C(O)O(heterocyclyl), —C(O)NH$_2$, —C(O)NH($C_{1-9}$ alkyl), —C(O)NH($C_{2-6}$ alkenyl), —C(O)NH($C_{2-6}$ alkynyl), —C(O)NH($C_{3-15}$ cycloalkyl), —C(O)NH($C_{1-8}$ haloalkyl), —C(O)NH(aryl), —C(O)NH(heteroaryl), —C(O)NH(heterocyclyl), —C(O)N($C_{1-9}$ alkyl)$_2$, —C(O)N($C_{3-15}$ cycloalkyl)$_2$, —C(O)N($C_{2-6}$ alkenyl)$_2$, —C(O)N($C_{2-6}$ alkynyl)$_2$, —C(O)N($C_{3-15}$ cycloalkyl)$_2$, —C(O)N($C_{2-8}$ haloalkyl)$_2$, —C(O)N(aryl)$_2$, —C(O)N(heteroaryl)$_2$, —C(O)N(heterocyclyl)$_2$, —NHC(O)($C_{1-9}$ alkyl), —NHC(O)($C_{2-6}$ alkenyl), —NHC(O)($C_{2-6}$ alkynyl), —NHC(O)($C_{3-15}$ cycloalkyl), —NHC(O)(C haloalkyl), —NHC(O)(aryl), —NHC(O)(heteroaryl), —NHC(O)(heterocyclyl), —NHC(O)O($C_{1-9}$ alkyl), —NHC(O)O($C_{2-6}$ alkenyl), —NHC(O)O($C_{2-6}$ alkynyl), —NHC(O)O($C_{3-15}$ cycloalkyl), —NHC(O)O($C_{1-8}$ haloalkyl), —NHC(O)O(aryl), —NHC(O)O(heteroaryl), —NHC(O)O(heterocyclyl), —NHC(O)NH($C_{1-9}$ alkyl), —NHC(O)NH($C_{2-6}$ alkenyl), —NHC(O)NH($C_{2-6}$ alkynyl), —NHC(O)NH($C_{3-15}$ cycloalkyl), —NHC(O)NH($C_{1-8}$ haloalkyl), —NHC(O)NH(aryl), —NHC(O)NH(heteroaryl), —NHC(O)NH(heterocyclyl), —SH, —S($C_{1-9}$ alkyl), —S($C_{2-6}$ alkenyl), —S($C_{2-6}$ alkynyl), —S($C_{3-15}$ cycloalkyl), —S($C_{1-8}$ haloalkyl), —S(aryl), —S(heteroaryl), —S(heterocyclyl), —NHS(O)($C_{1-9}$ alkyl), —N($C_{1-9}$ alkyl)(S(O)($C_{1-9}$ alkyl), —S(O)N($C_{1-9}$ alkyl)$_2$, —S(O)($C_{1-9}$ alkyl), —S(O)(NH)($C_{1-9}$ alkyl), —S(O)($C_{2-6}$ alkenyl), —S(O)($C_{2-6}$ alkynyl), —S(O)($C_{3-15}$ cycloalkyl), —S(O)($C_{1-8}$ haloalkyl), —S(O)(aryl), —S(O)(heteroaryl), —S(O)(heterocyclyl), —S(O)$_2$($C_{1-9}$ alkyl), —S(O)$_2$($C_{2-6}$ alkenyl), —S(O)$_2$($C_{2-6}$ alkynyl), —S(O)$_2$($C_{3-15}$ cycloalkyl), —S(O)$_2$($C_{1-8}$ haloalkyl), —S(O)$_2$(aryl), —S(O)$_2$(heteroaryl), —S(O)$_2$(heterocyclyl), —S(O)$_2$NH($C_{1-9}$ alkyl), or —S(O)$_2$N($C_{1-9}$ alkyl)$_2$;
    wherein any alkyl, cycloalkyl, aryl, heteroaryl, or heterocyclyl is optionally substituted with one to four halo, $C_{1-9}$ alkyl, $C_{1-8}$ haloalkyl, —OH, —NH$_2$, —NH($C_{1-9}$ alkyl), —NH($C_{3-15}$ cycloalkyl), —NH($C_{1-8}$ haloalkyl), —NH(aryl), —NH(heteroaryl), —NH(heterocyclyl), —N($C_{1-9}$ alkyl)$_2$, —N($C_{3-15}$ cycloalkyl)$_2$, —NHC(O)($C_{3-15}$ cycloalkyl), —NHC(O)($C_{1-8}$ haloalkyl), —NHC(O)(aryl), —NHC(O)(heteroaryl), —NHC(O)(heterocyclyl), —NHC(O)O($C_{1-9}$ alkyl), —NHC(O)O($C_{2-6}$ alkynyl), —NHC(O)O($C_{3-15}$ cycloalkyl), —NHC(O)O($C_{1-8}$ haloalkyl), —NHC(O)O(aryl), —NHC(O)O(heteroaryl), —NHC(O)O(heterocyclyl), —NHC(O)NH($C_{1-9}$ alkyl), —S(O)(NH)($C_{1-9}$ alkyl), S(O)$_2$($C_{1-9}$ alkyl), —S(O)$_2$($C_{3-15}$ cycloalkyl), —S(O)$_2$($C_{1-8}$ haloalkyl), —S(O)$_2$(aryl), —S(O)$_2$(heteroaryl), —S(O)$_2$(heterocyclyl), —S(O)$_2$NH($C_{1-9}$ alkyl), —S(O)$_2$N($C_{1-9}$ alkyl)$_2$, —O($C_{3-15}$ cycloalkyl), —O($C_{1-8}$ haloalkyl), —O(aryl), —O(heteroaryl), —O(heterocyclyl), or —O($C_{1-9}$ alkyl).

In certain embodiments, $R^6$ is

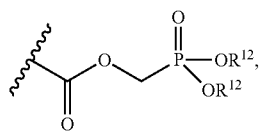

and each $R^{12}$ is independently as defined herein.

In certain embodiments, $R^6$ is

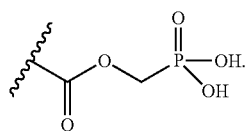 [SMILES: *C(=O)OCP(=O)(O)O]

$R^6$ also includes all individual stereoisomers, and mixtures thereof, including but not limited to, chirality at the phosphorous atom such as in the exemplary moieties shown above.

Also provided herein are the in vivo metabolic products of the compounds described herein. Such products may result, for example, from the oxidation, reduction, hydrolysis, amidation, esterification, and the like, of the administered compound, primarily due to enzymatic processes.

Therapeutic Uses of the Compounds

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy and/or veterinary applications. In some embodiments, the subject is a mammal. In one embodiment, the subject is a human.

The term "therapeutically effective amount" or "effective amount" of a compound described herein or a pharmaceutically acceptable salt, tautomer, stereoisomer, mixture of stereoisomers, prodrug, or deuterated analog thereof means an amount sufficient to effect treatment when administered to a subject, to provide a therapeutic benefit such as amelioration of symptoms or slowing of disease progression. For example, a therapeutically effective amount may be an amount sufficient to decrease a symptom of a disease or condition responsive to inhibition of Cot activity. The therapeutically effective amount may vary depending on the subject, and disease or condition being treated, the weight and age of the subject, the severity of the disease or condition, and the manner of administering, which can readily be determined by one or ordinary skill in the art.

The term "inhibition" indicates a decrease in the baseline activity of a biological activity or process. "Inhibition of activity of Cot" or variants thereof refers to a decrease in activity in Cot as a direct or indirect response to the presence of a compound of the present application relative to the activity Cot in the absence of the compound of the present application. "Inhibition of Cot" refers to a decrease in Cot activity as a direct or indirect response to the presence of a compound described herein relative to the activity of Cot in the absence of the compound described herein. In some embodiments, the inhibition of Cot activity may be compared in the same subject prior to treatment, or other subjects not receiving the treatment.

The methods described herein may be applied to cell populations in vivo or ex vivo. "In vivo" means within a living individual, as within an animal or human. In this context, the methods described herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine, and saliva. Exemplary tissue samples include tumors and biopsies thereof. In this context, the compounds and compositions described herein may be used for a variety of purposes, including therapeutic and experimental purposes. For example, the compounds and compositions described herein may be used ex vivo to determine the optimal schedule and/or dosing of administration of a Cot inhibitor for a given indication, cell type, individual, and other parameters. Information gleaned from such use may be used for experimental purposes or in the clinic to set protocols for in vivo treatment. Other ex vivo uses for which the compounds and compositions described herein may be suited are described below or will become apparent to those skilled in the art. The selected compounds may be further characterized to examine the safety or tolerance dosage in human or non-human subjects. Such properties may be examined using commonly known methods to those skilled in the art.

The compounds disclosed herein are useful for the treatment of diseases or conditions mediated by Cot. Non-limiting examples of diseases or conditions mediated by Cot include, without limitation, cancer, diabetes, and inflammatory diseases such as rheumatoid arthritis (RA), multiple sclerosis (MS), inflammatory bowel disease (IBD), sepsis, psoriasis, misregulated TNF expression and graft rejection.

In further embodiments, the methods are provided for alleviating a symptom of a disease or disorder mediated by Cot. In some embodiments, the methods include identifying a mammal having a symptom of a disease or disorder mediated by Cot, and providing to the mammal an amount of a compound as described herein effective to ameliorate (i.e., lessen the severity of) the symptom.

In some embodiments, the disease or condition mediated by Cot is a solid tumor.

In particular embodiments, the solid tumor is from pancreatic cancer, bladder cancer, colorectal cancer, breast cancer, prostate cancer, renal cancer, hepatocellular cancer, lung cancer, ovarian cancer, cervical cancer, gastric cancer, esophageal cancer, head and neck cancer, melanoma, neuroendocrine cancers, CNS cancers, brain tumors (e.g., glioma, anaplastic oligodendroglioma, adult glioblastoma multiforme, and adult anaplastic astrocytoma), bone cancer, or soft tissue sarcoma. In some embodiments, the solid tumor is from non-small cell lung cancer, small-cell lung cancer, colon cancer, CNS cancer, melanoma, ovarian cancer, renal cancer, prostate cancer, or breast cancer.

In some embodiments, the disease or condition mediated by Cot is diabetes, which includes any metabolic disorder characterized by impaired insulin production and glucose tolerance. In some embodiments, diabetes includes type 1 and type 2 diabetes, gestational diabetes, prediabetes, insulin resistance, metabolic syndrome, impaired fasting glycaemia and impaired glucose tolerance. Type 1 diabetes is also known as Insulin Dependent Diabetes Mellitus (IDDM). Type 2 is also known as Non-Insulin-Dependent Diabetes Mellitus (NIDDM).

In some embodiments, the disease or condition mediated by Cot is an inflammatory disease or LPS induced endotoxin shock. In some embodiments, the disease is an autoimmune disease. In particular embodiments, the autoimmune disease is systemic lupus erythematosus (SLE), myestenia gravis, rheumatoid arthritis (RA), acute disseminated encephalomyelitis, idiopathic thrombocytopenic purpura, multiple sclerosis (MS), inflammatory bowel disease (IBD), sepsis, psoriasis, Sjoegren's syndrome, autoimmune hemolytic anemia, asthma, or chronic obstructive pulmonary disease (COPD), ankylosing spondylitis, acute gout and ankylosing spondylitis, reactive arthritis, monoarticular arthritis, osteoarthritis, gouty arthritis, juvenile arthritis, juvenile onset rheumatoid arthritis, juvenile rheumatoid arthritis or psoriatic arthritis. In other embodiments, the disease is inflammation. In yet other embodiments, the disease is excessive or destructive immune reactions, such as asthma, rheumatoid arthritis, multiple sclerosis, chronic obstructive pulmonary disease (COPD), and lupus.

In some embodiments, the disease or condition mediated by Cot is inflammatory bowel disease (IBD). The term "inflammatory bowel disease" or "IBD" as used herein is a collective term describing inflammatory disorders of the gastrointestinal tract, the most common forms of which are ulcerative colitis and Crohn's disease. Other forms of IBD that can be treated with the presently disclosed compounds, compositions and methods include diversion colitis, ischemic colitis, infectious colitis, chemical colitis, microscopic colitis (including collagenous colitis and lymphocytic colitis), atypical colitis, pseudomembranous colitis, fulminant colitis, autistic enterocolitis, indeterminate colitis, Behçet's disease, gastroduodenal CD, jejunoileitis, ileitis, ileocolitis, Crohn's (granulomatous) colitis, irritable bowel syndrome, mucositis, radiation induced enteritis, short bowel syndrome, celiac disease, stomach ulcers, diverticulitis, pouchitis, proctitis, and chronic diarrhea.

Treating or preventing IBD also includes ameliorating or reducing one or more symptoms of IBD. As used herein, the term "symptoms of IBD" refers to detected symptoms such as abdominal pain, diarrhea, rectal bleeding, weight loss, fever, loss of appetite, and other more serious complications, such as dehydration, anemia and malnutrition. A number of such symptoms are subject to quantitative analysis (e.g. weight loss, fever, anemia, etc.). Some symptoms are readily determined from a blood test (e.g. anemia) or a test that detects the presence of blood (e.g. rectal bleeding). The term "wherein said symptoms are reduced" refers to a qualitative or quantitative reduction in detectable symptoms, including but not limited to a detectable impact on the rate of recovery from disease (e.g. rate of weight gain). The diagnosis is typically determined by way of an endoscopic observation of the mucosa, and pathologic examination of endoscopic biopsy specimens.

The course of IBD varies, and is often associated with intermittent periods of disease remission and disease exacerbation. Various methods have been described for characterizing disease activity and severity of IBD as well as response to treatment in subjects having IBD. Treatment according to the present methods are generally applicable to a subject having IBD of any level or degree of disease activity.

In some embodiments, the disease or condition treated by the administration of a compound of composition described herein includes acute gout and ankylosing spondylitis, allergic disorders, Alzheimer's disease, Amyotrophic lateral sclerosis (ALS), Amyotrophic lateral sclerosis and multiple sclerosis, atherosclerosis, bacterial infections, bone cancer pain and pain due to endometriosis, BRAF resistant melanoma, brain stem glioma or pituitary adenomas, burns, bursitis, cancer of the anal region, cancer of the endocrine system, cancer of the kidney or ureter (e.g. renal cell carcinoma carcinoma of the renal pelvis), cancer of the penis, cancer of the small intestine, cancer of the thyroid, cancer of the urethra, cancers of the blood such as acute myeloid leukemia, cancers of the tongue, carcinoma of the cervix, carcinoma of the endometrium, carcinoma of the fallopian tubes, carcinoma of the renal pelvis, carcinoma of the vagina or carcinoma of the vulva, chronic mueloid leukemia, chronic or acute leukemia, chronic pain, classic Bartter syndrome, common cold conjunctivitis, coronary heart disease, cutaneous or intraocular melanoma, dermatitis, dysmenorrhea, eczema, endometriosis, familial adenomatous polyposis, fibromyalgia, fungal infections, gout, gynecologic tumors, uterine sarcomas, carcinoma of the fallopian tubes, headache, hemophilic arthropathy, Parkinson's disease, AIDS, herpes zoster, Hodgkin's disease, Huntington's, hyperprostaglandin E syndrome, influenza, iritis, juvenile arthritis, juvenile onset rheumatoid arthritis, juvenile rheumatoid arthritis, low back and neck pain, lynphocytic lymphomas, myofascial disorders, myositis, neuralgia, neurodegenerative disorders such as Alzheimer's disease, neuroinflammatory disorders, neuropathic pain, carcinoma of the vulva, Parkinson's disease, pediatric malignancy, pulmonary fibrosis rectal cancer, rhinitis, sarcoidosis, sarcomas of soft tissues, scleritis, skin cancer, solid tumors of childhood, spinal axis tumors, sprains and strains, stomach cancer, stroke, subacute and chronic musculoskeletal pain syndromes such as bursitis, surgical or dental procedures, symptoms associated with influenza or other viral infections, synovitis, toothache, ulcers, uterine cancer, uterine sarcomas, uveitis, vasculitis, viral infections, viral infections {e.g. influenza) and wound healing.

Criteria useful for assessment of disease activity in subjects with ulcerative colitis can be found in, e.g., Truelove et al. (1955) Br Med J 2:1041-1048.) Using these criteria, disease activity can be characterized in a subject having IBD as mild disease activity or severe disease activity. Subjects who do not meet all the criteria for severe disease activity, and who exceed the criteria for mild disease activity are classified as having moderate disease activity.

The presently disclosed treatment methods can also be applied at any point in the course of the disease. In certain embodiments, the methods are applied to a subject having IBD during a time period of remission (i.e., inactive disease). In such embodiments, the present methods provide benefit by extending the time period of remission (e.g., extending the period of inactive disease) or by preventing, reducing, or delaying the onset of active disease. In other embodiments, methods may be applied to a subject having IBD during a period of active disease. Such methods provide benefit by reducing the duration of the period of active disease, reducing or ameliorating one or more symptoms of IBD, or treating IBD.

Measures for determining efficacy of treatment of IBD in clinical practice have been described and include, for example, the following: symptom control; fistula closure; extent of corticosteroid therapy required; and, improvement in quality of life. Heath-related quality of life (HRQL) can be assessed using the Inflammatory Bowel Disease Questionnaire (IBDQ), which is extensively used in clinical practice to assess quality of life in a subject with IBD. (See Guyatt et al. (1989) Gastroenterology 96:804-810.) In some embodiments, the disease or condition is immune-mediated liver injury, disease or condition. Tpl2 can mediate immune related liver diseases or conditions. (Vyrla et. al., The Journal of Immunology, 2016, 196; Perugorria et. al., Hepatology, 2013; 57:1238-1249)

In some embodiments, the disease or condition mediated by Cot is alcoholic hepatitis. Alcoholic hepatitis is a clinical syndrome characterized by jaundice and liver failure that develops in subjects with chronic and active alcohol abuse. (See Akriviadis E. et. al, Ann Gastroenterol. 2016 April-June; 29(2): 236-237). Alcoholic hepatitis can cause cirrhosis and fibrosis of the liver cells. Glucocorticoids, (e.g. prednisolone) and phosophodiesterase inhibitors (e.g. pentoxifylline) can be used to treat alcoholic hepatitis. The compounds herein can be used as stand-alone treatments or in combination with the current treatments for alcoholic hepatitis.

In some embodiments, the disease or condition mediated by Cot is systemic lupus erythematosus (SLE), lupus nephritis, lupus-related, or other autoimmune disorders or a symptom of SLE. Symptoms of systemic lupus erythematosus include joint pain, joint swelling, arthritis, fatigue, hair loss, mouth sores, swollen lymph nodes, sensitivity to sunlight, skin rash, headaches, numbness, tingling, seizures, vision problems, personality changes, abdominal pain, nausea, vomiting, abnormal heart rhythms, coughing up blood and difficulty breathing, patchy skin color and Raynaud's phenomenon.

Improvements in any of the foregoing response criteria are specifically provided by the methods of the present disclosure.

Combination Therapies

In one embodiment, the compounds disclosed herein may be used in combination with one or more additional therapeutic agent that are being used and/or developed to treat inflammatory disorders (e.g., IBD). The one or more additional therapeutic agent may be a α4β7 inhibitor, a steroid, a MMP-9 antibody, a S1P1 agonist, a TNF biologic, or any combination thereof.

In some embodiments, the one or more additional therapeutic agent may be a α4β7 integrin inhibitor, or an agent that inhibits the expression and/or activity of α4β7 integrin. The inhibitor can be small molecule or biologic. For example, the α4β7 integrin inhibitor can be natalizumab or vedolizumab.

In some embodiments, the one or more additional therapeutic agent may be a steroid, including but not limited to, corticosteroids. Corticosteroids may be administered by various routes, including intravenously (i.e., methylprednisolone, hydrocortisone), orally (i.e., prednisone, prednisolone, budesonide, dexamethasone), or topically (i.e., enema, suppository, or foam preparations).

In some embodiments, the one or more additional therapeutic agent may be an MMP9 inhibitor, or an agent that inhibits the expression and/or activity of MMP9. A representative protein sequence for MMP9 is GenBank Accession No. NP_004985. The inhibitor can be small molecule or biologic. For instance, Gu et al., *The Journal of Neuroscience*, 25(27): 6401-6408 (2005) discloses a specific MMP9 inhibitor, SB-3CT (CAS 292605-14-2). Further, siRNA, antisense RNA and antibodies have also been demonstrated to inhibit the expression or activity of MMP9 and are within the scope of the present disclosure. In one embodiment, an MMP9 inhibitor is a monoclonal anti-MMP9 antibody. In some embodiment, the one or more additional therapeutic agent includes an MMP9 inhibitor and a nucleoside analog such as gemcitabine.

In some embodiments, the one or more additional therapeutic agent may be a Sphingosine 1-Phosphate Receptor (S1P1) inhibitor, or an agent that inhibits the expression and/or activity of S1P1. The inhibitor can be small molecule or biologic. For example, the S1P1 inhibitor can be RPC1063.

In some embodiments, the one or more additional therapeutic agent may be a TNF inhibitor, or an agent that inhibits the expression and/or activity of TNF. The inhibitor can be small molecule or biologic. For example, the TNF inhibitor can be golimumab.

In some embodiments, the one or more additional therapeutic agent is being used and/or developed to treat ulcerative colitis (UC) and/or Crohn disease (CD). The agent can be a biologic or small molecule. In some embodiments, the agent is a modulator (e.g., agonist or antagonist) of S1P1, IL-6, CX3CL1, DHODH, α4, β7, JAK, TNF, CB, IL-12/IL-23, CCL20, TLR9, MAdCAM, CCR9, CXCL10, Smad7, PDE4, MC, VLA-1, GC, GATA-3, Eotaxin, FFA2, LIGHT, FMS, MMP9, CD40, Steroid, 5-ASA, Immunomod, STAT3, and/or EP4.

Non-limiting examples of agents being used and/or developed to treat ulcerative colitis (UC) include GSK3050002 (CCL20 modulator, by GSK), GS-5745 (MMP9 modulator, by Gilead), AVX-470 (TNF modulator, by Avaxia), Bertilimumab (Eotaxin modulator, by Immune Pharma), Simponi (TNF modulator, by Johnson & Johnson and Merck), RX-10001 (by Resolvyx), IBD-98 (5-ASA modulator, by Holy Stone), SP-333 (GC modulator, by Synergy), KAG-308 (EP4 modulator, by Kaken), SB012 (GATA-3 modulator, by Sterna), AJM300 (α4 modulator, by Ajinomoto), BL-7040 (TLR9 modulator, by BiolineRx), TAK-114 (SAT3 modulator, by Takeda), CyCol (by Sigmoid), GWP-42003 (CB modulator, by GW Pharma), ASP3291 (MC modulator, by Drais), GLPG0974 (FFA2 modulator, by Galapagos), Ozanimod (S1P1 modulator, by Receptos), ASP015K (JAK modulator, by Astellas), Apremilast (PDE4 modulator, by Celgene), Zoenasa (by Altheus), Kappaproct (TLR9 modulator, by InDex), Phosphatidylcholine (by Dr Falk/Lipid Tx), Tofacitinib (JAk modulator, by Pfizer), Cortment (Steroid modulator, by Ferring), Uceris (Steroid modulator, by Salix), and 5-ASA modulators such as Delzicol (by Actavis), Canasa (by Aptalis), Asacol (by Actavis), Pentasa (by Shire/Ferring), Lialda (by Shire), Mezavant (by Shire), Apriso (by Salix), Colazal (by Salix), Giazo (by Salix), and Salofalk (by Dr Falk). Non-limiting examples of agents being used and/or developed to treat Crohn disease (CD) include FFP102 (CD40 modulator, by Fast Forward), E6011 (CX3CL1 modulator, by Eisai), PF-06480605 (by Pfizer), QBECO SSI (Immunomod modulator, by Qu Biologics), PDA-001 (by Celgene), BI 655066 (IL-12/IL-23 modulator, by Boehringer), TNFα kinoid (TNF modulator, by Neovacs), AMG 139/MEDI-2070 (IL-12/IL-23 modulator, by AstraZeneca), PF-04236921 (IL-6 modulator, by Pfizer), Tysabri (β7 modulator, marketed by Biogen Idec in the U.S.), Cimzia (marketed by UCB in the U.S.), JNJ-40346527 (FMS modulator, by J&J), SGX-203 (Steroid modulator, by Solgenix), CyCron (by Sigmoid), CCX507 (CCR9 modulator, by ChemoCentryx), MT1303 (S1P1 modulator, by Mitsubishi), 6-MP (by Teva), ABT-494 (JAk modulator, by Abbvie), Tofacitinib (JAk modulator, by Pfizer), GLPG0634 (JAk modulator, by Galapagos), TRK-170 (β7 modulator, by Toray), Mongersen (Smad7 modulator, by Celgene), RHB-104 (by Redhill), Rifaxmin EIR (by Salix), Budenofalk (by Dr Falk), and Entocort (by AstraZeneca).

Non-limiting examples of agents being used and/or developed to treat ulcerative colitis (UC) and Crohn disease (CD) include PF-06410293 (by Pfizer), SAN-300 (VLA-1 modulator, by Salix), SAR252067 (LIGHT modualtor, by Sanofi), PF-00547659 (MAdCAM modualtor, by Pfizer), Eldelumab (Smad7 modulator, by BMS), AMG 181/MEDI-7183 ($\beta$7 modulator, by Amgen/AstraZeneca), Etrolizumab ($\beta$7 modulator, by Roche), Ustekinumab (IL-12/IL-23 modulator, by J&J), Remicade (TNF modulator, by J&J and Merck), Entyvio ($\beta$7 modulator, by Takeda), Humira (TNF modulator, by Abbvie), Infliximab (by Celtrion), PF-06651600 (by Pfizer), GSK2982772 (by GSK), GLPG1205 (FFA2 modulator, by Galapagos), AG014 (by Intrexon) and Vidofludimus (DHODH modulator, by 4SC).

In some embodiments, the one or more additional therapeutic agent may be a JAK inhibitor, particularly a JAK-1 selective inhibitor. The inhibitor can be small molecule or biologic. For example, the JAK inhibitor can be Filgotinib, GLPG0634 (JAK modulator, by Galapágos).

Kits

Provided herein are also kits that include a compound of Formula I, or a pharmaceutically acceptable salt, tautomer, stereoisomer, mixture of stereoisomers, prodrug, or deuterated analog thereof, and suitable packaging. In one embodiment, a kit further includes instructions for use. In one aspect, a kit includes a compound of Formula I (or any other Formula described herein), or a pharmaceutically acceptable salt, tautomer, stereoisomer, mixture of stereoisomers, prodrug, or deuterated analog thereof, and a label and/or instructions for use of the compounds in the treatment of the indications, including the diseases or conditions, described herein.

Provided herein are also articles of manufacture that include a compound described herein or a pharmaceutically acceptable salt, tautomer, stereoisomer, mixture of stereoisomers, prodrug, or deuterated analog thereof in a suitable container. The container may be a vial, jar, ampoule, preloaded syringe, and intravenous bag.

Pharmaceutical Compositions and Modes of Administration

Compounds provided herein are usually administered in the form of pharmaceutical compositions. Thus, provided herein are also pharmaceutical compositions that contain one or more of the compounds described herein or a pharmaceutically acceptable salt, tautomer, stereoisomer, mixture of stereoisomers, prodrug, or deuterated analog thereof and one or more pharmaceutically acceptable vehicles selected from carriers, adjuvants and excipients. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.).

The pharmaceutical compositions may be administered in either single or multiple doses. The pharmaceutical composition may be administered by various methods including, for example, rectal, buccal, intranasal and transdermal routes. In certain embodiments, the pharmaceutical composition may be administered by intra-arterial injection, intravenously, intraperitoneally, parenterally, intramuscularly, subcutaneously, orally, topically, or as an inhalant.

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Oral administration may be another route for administration of the compounds described herein. Administration may be via, for example, capsule or enteric coated tablets. In making the pharmaceutical compositions that include at least one compound described herein or a pharmaceutically acceptable salt, tautomer, stereoisomer, mixture of stereoisomers, prodrug, or deuterated analog thereof, the active ingredient is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include lubricating agents such as talc, magnesium stearate, and mineral oil; wetting agents; emulsifying and suspending agents; preserving agents such as methyl and propylhydroxy-benzoates; sweetening agents; and flavoring agents.

The compositions that include at least one compound described herein or a pharmaceutically acceptable salt, tautomer, stereoisomer, mixture of stereoisomers, prodrug, or deuterated analog thereof can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods disclosed herein employ transdermal delivery devices ("patches"). Such transdermal patches may be used to provide continuous or discontinuous infusion of the compounds described herein in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

For preparing solid compositions such as tablets, the principal active ingredient may be mixed with a pharmaceutical excipient to form a solid preformulation composition containing a homogeneous mixture of a compound described herein or a pharmaceutically acceptable salt, tautomer, stereoisomer, mixture of stereoisomers, prodrug, or deuterated analog thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described herein. In some embodiments, the compositions are administered by the oral or nasal respiratory route for local or systemic effect. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

Dosing

The specific dose level of a compound of the present application for any particular subject will depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of a compound described herein per kilogram of the subject's body weight (mg/kg). Dosages of between about 0.1 and 150 mg/kg may be appropriate. In some embodiments, about 0.1 and 100 mg/kg may be appropriate. In other embodiments a dosage of between 0.5 and 60 mg/kg may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

The daily dosage may also be described as a total amount of a compound described herein administered per dose or per day. Daily dosage of a compound of Formula I may be between about 1 mg and 4,000 mg, between about 2,000 to 4,000 mg/day, between about 1 to 2,000 mg/day, between about 1 to 1,000 mg/day, between about 10 to 500 mg/day, between about 20 to 500 mg/day, between about 50 to 300 mg/day, between about 75 to 200 mg/day, or between about 15 to 150 mg/day.

When administered orally, the total daily dosage for a human subject may be between 1 mg and 1,000 mg, between about 1,000-2,000 mg/day, between about 10-500 mg/day, between about 50-300 mg/day, between about 75-200 mg/day, or between about 100-150 mg/day.

The compounds of the present application or the compositions thereof may be administered once, twice, three, or four times daily, using any suitable mode described above. Also, administration or treatment with the compounds may be continued for a number of days; for example, commonly treatment would continue for at least 7 days, 14 days, or 28 days, for one cycle of treatment. Treatment cycles are well known in cancer chemotherapy, and are frequently alternated with resting periods of about 1 to 28 days, commonly about 7 days or about 14 days, between cycles. The treatment cycles, in other embodiments, may also be continuous.

In a particular embodiment, the method comprises administering to the subject an initial daily dose of about 1 to 800 mg of a compound described herein and increasing the dose by increments until clinical efficacy is achieved. Increments of about 5, 10, 25, 50, or 100 mg can be used to increase the dose. The dosage can be increased daily, every other day, twice per week, or once per week.

Synthesis of the Compounds of Formula I

The compounds may be prepared using the methods disclosed herein and routine modifications thereof, which will be apparent given the disclosure herein and methods well known in the art. Conventional and well-known synthetic methods may be used in addition to the teachings herein. The synthesis of typical compounds described herein may be accomplished as described in the following examples. If available, reagents may be purchased commercially, e.g., from Sigma Aldrich or other chemical suppliers.

General Synthesis

Typical embodiments of compounds described herein may be synthesized using the general reaction schemes described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Given a desired product for which the substituent groups are defined, the necessary starting materials generally may be determined by inspection. Starting materials are typically obtained from commercial sources or synthesized using published methods. For synthesizing compounds which are embodiments described in the present disclosure, inspection of the structure of the compound to be synthesized will provide the identity of each substituent group. The identity of the final product will generally render apparent the identity of the necessary starting materials by a simple process of inspection, given the examples herein. In general, compounds described herein are typically stable and isolatable at room temperature and pressure.

Synthetic Reaction Parameters

The compounds of this disclosure can be prepared from readily available starting materials using, for example, the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts (1999) Protecting Groups in Organic Synthesis, 3rd Edition, Wiley, New York, and references cited therein.

Furthermore, the compounds of this disclosure may contain one or more chiral centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989) organic Reactions, Volumes 1-40 (John Wiley, and Sons, 1991), March's Advanced Organic Chemistry, (John Wiley, and Sons, 5th Edition, 2001), and Larock's Comprehensive Organic Transformations (VCH Publishers Inc., 1989).

The term "solvent" generally refers to a solvent inert under the conditions of the reaction being described in conjunction therewith (including, for example, benzene, toluene, acetonitrile, tetrahydrofuran (THF), dimethylformamide (DMF), chloroform, methylene chloride (or dichloromethane), diethyl ether, methanol, and the like). Unless specified to the contrary, the solvents are inert organic solvents, and the reactions may carried out under an inert gas, preferably argon or nitrogen.

The term "q.s." means adding a quantity sufficient to achieve a stated function, e.g., to bring a solution to the desired volume (i.e., 100%).

The compounds of Formula I may prepared by first providing the substituted quinoline core, and optionally further modifying the core as desired to provide the substituents disclosed herein. Scheme 1 shows the preparation of the quinoline core to provide compounds of Formula 1-e, where m, $R^5$ and $R^{15}$ are as defined herein, or is a functional group that may be converted thereto using standard reaction conditions.

Scheme 1

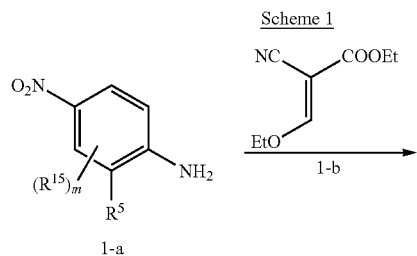

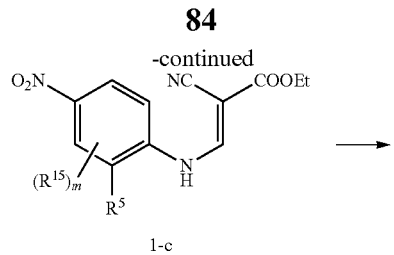

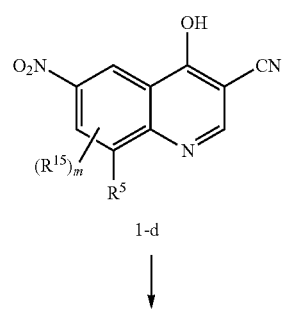

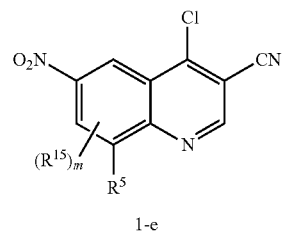

In Scheme 1, suitably substituted 1-a and 1-b are condensed in a suitable solvent (e.g., DMF, etc.) in the presence of catalyst (e.g., $Cs_2CO_3$, etc.) at an elevated temperature (e.g., about 40-50° C.) to provide 1-c. Compound 1-c is then converted to 1-d under thermal cyclization conditions (i.e., about 250° C.) or under microwave conditions. Chlorination of 1-d to provide 1-e is achieved using a suitable chlorinating agent (e.g., $POCl_3$, $SOCl_2$, etc.) at an elevated temperature (e.g., about 110-120° C.) in the presence of a base (e.g. pyridine, dimethylaniline, diethylaniline, etc.) or a catalyst (e.g., DMF, DEF, etc.) and in a suitable solvent (e.g. chlorobenzene, $CH_3CN$, etc.) or solvent-free conditions (i.e., neat).

Scheme 2 shows the synthesis of compounds of Formula 2-c and 2-d where m, $R^1$, $R^2$, $R^5$ and $R^{15}$ are as defined herein.

Scheme 2

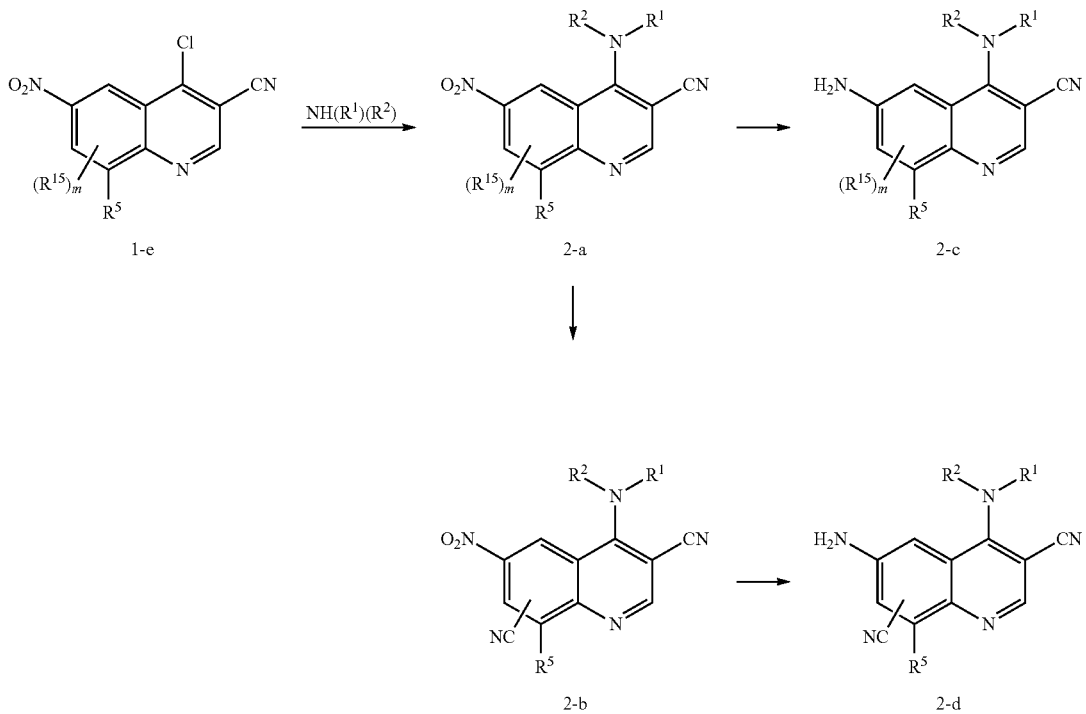

In Scheme 2, 1-e is reacted with a suitable amine under standard nucleophilic aromatic substitution conditions in the presence of a base (e.g., NEt$_3$, etc.) and at elevated temperature (e.g., 150° C.) to obtain 2-a. Compounds of Formula I where R$^5$ and/or R$^{15}$ is cyano are provided by reacting 2-a with a suitable cyanating agent (e.g., CuCN, Zn(CN)$_2$, etc.) in the presence of a catalyst (e.g., palladium, nickel, copper, etc.). Compounds 2-c and 2-d are then provided via reduction of the nitro group of compounds 2-a or 2-b, respectively (using e.g., Fe, SnCl$_2$, etc.).

Scheme 3 shows the synthesis of compounds 3-d and 3-e, where R$^4$ is as defined herein.

In Scheme 3, deuterated 3-c is provided by reducing suitably substituted aldehyde 3-a with a deuteride-containing reducing agent (e.g., NaBD$_4$), followed by oxidation of 3-b to the corresponding aldehyde 3-c under standard oxidizing conditions (e.g., MnO$_2$, Fe$_2$O$_3$, NiO, CuO, ZnO, ZrO$_2$, La$_2$O$_3$, Sm$_2$O$_3$, Eu$_2$O$_3$, Yb$_2$O$_3$, etc.). Compound 3-d is obtained in two steps by reaction of 3-c with ethynyl Grignard, followed by acylation of the resulting alcohol with acetic anhydride in the presence of a base (e.g., pyridine, TEA, etc.). Compound 3-e is provided in a similar two-step process by reacting suitably substituted aldehyde 3-a with ethynyl Grignard, followed by acylation of the resulting alcohol with acetic anhydride.

Scheme 4 shows the synthesis of suitably protected azide compounds of Formula 4-b, where Lg is a leaving group and Z$^3$ is as defined herein.

Scheme 3

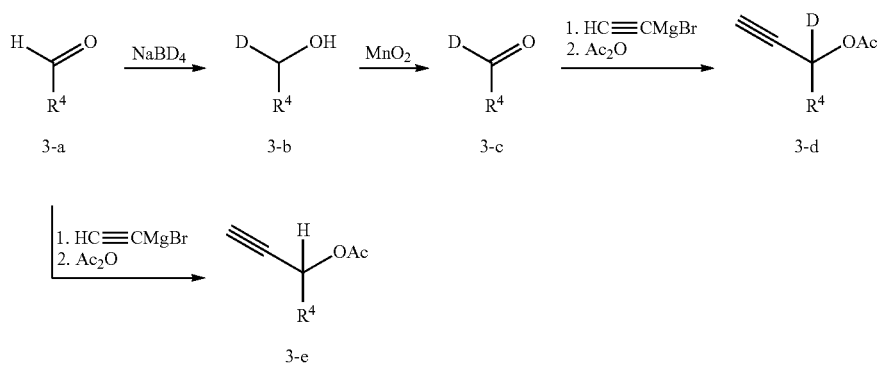

Scheme 4

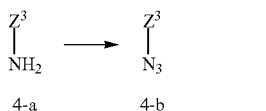

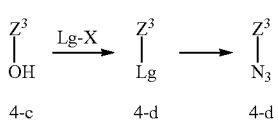

In Scheme 4, suitably substituted amine 4-a is treated with a diazo transfer agent (e.g., imidazole-1-sulfonyl azide hydrochloride) to afford corresponding 4-b. Alternatively, 4-b may be obtained in two steps from alcohol 4-c by conversion of the hydroxyl moiety to a suitable leaving group (Lg) (e.g., TsO—, MsO—, NsO—, TfO—, etc.) followed by nucleophilic displacement with azide.

Scheme 5 shows the synthesis of intermediate compounds of Formula 5-c, where $R^{50}$ is alkyl and $Z^3$ is as defined herein.

Scheme 5

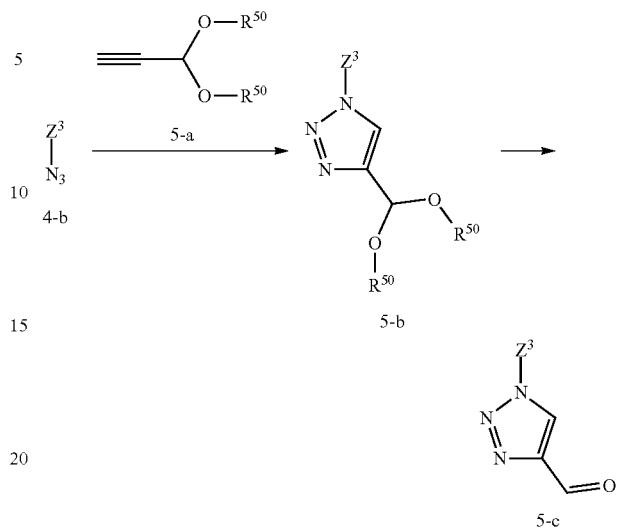

In Scheme 5, suitably substituted triazole 5-b is obtained by reaction of 4-b with 5-a using standard 1,3-dipolar cycloaddition conditions. Acetal 5-b is converted to the corresponding aldehyde 5-c under standard carbonyl deprotection conditions (e.g., aqueous acid).

Scheme 6 shows a general synthesis of exemplary compounds of Formula I, where $Z^3$, m, $R^1$, $R^2$, $R^4$, $R^5$ and $R^{15}$ and are as defined herein.

Scheme 6

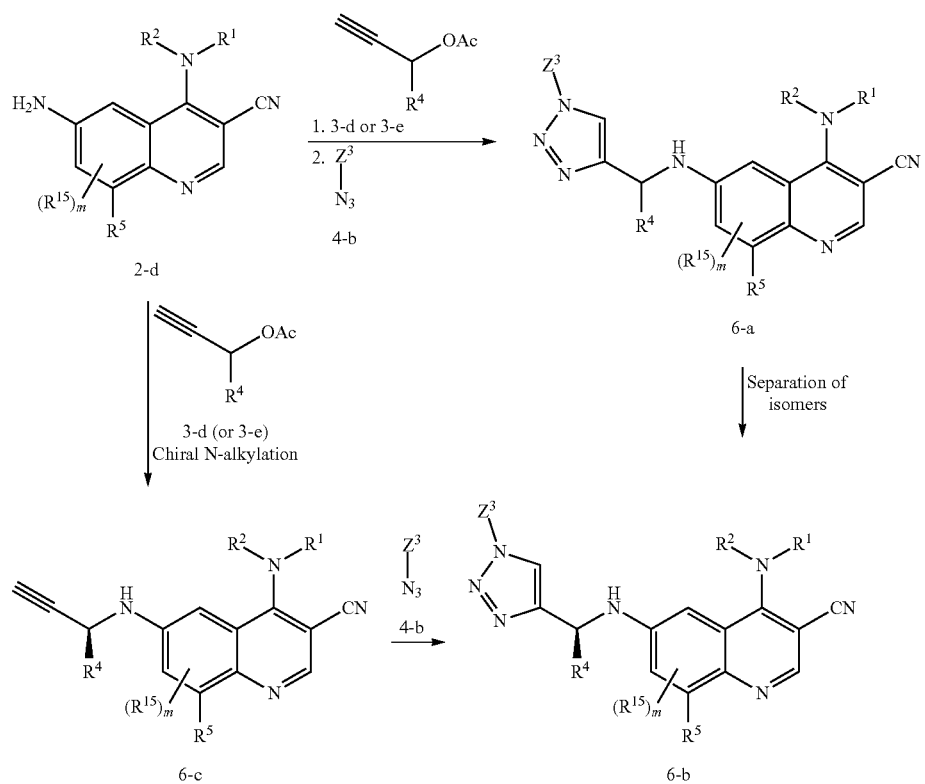

In Scheme 6, compounds of Formula 6-c can be provided via N-alkylation of amine 2-d with 3-d (or 3-e), followed by cyclization with azide 4-b under standard 1,3-dipolar cycloaddition conditions. Separation of the isomers of Formula 6-a to give compounds of Formula 6-b can be performed using standard chiral separation/resolution techniques (e.g., chiral chromatography, crystallization, etc.). Alternatively, compounds of Formula 6-b can be provided via enantioselective N-alkylation of 2-d with 3-d (or 3-e) using a chiral metal complex (e.g., [Cu(CH$_3$CN)$_4$]PF$_6$, CuOTf.benzene, Cu(OAc)$_2$, or Cu(I)I, etc., with a chiral ligand). Suitable reaction conditions and exemplary chiral ligands/complexes can be found in the literature (see, e.g., Detz, et al. Angew. Chem. Int. Ed. 2008, 47, 3777-3780). Contacting compound 6-c with azide 4-b under standard 1,3-dipolar cycloaddition conditions provide compound 6-b. 6-c may or may not be isolated prior to the addition of compound 4-b.

Scheme 7 shows an alternate synthesis of compounds of Formula I via imine formation and subsequent nucleophilic addition, where $Z^3$, m, $R^1$, $R^2$, $R^3$, $R^4$, $R^5$ and $R^{15}$ are as defined herein.

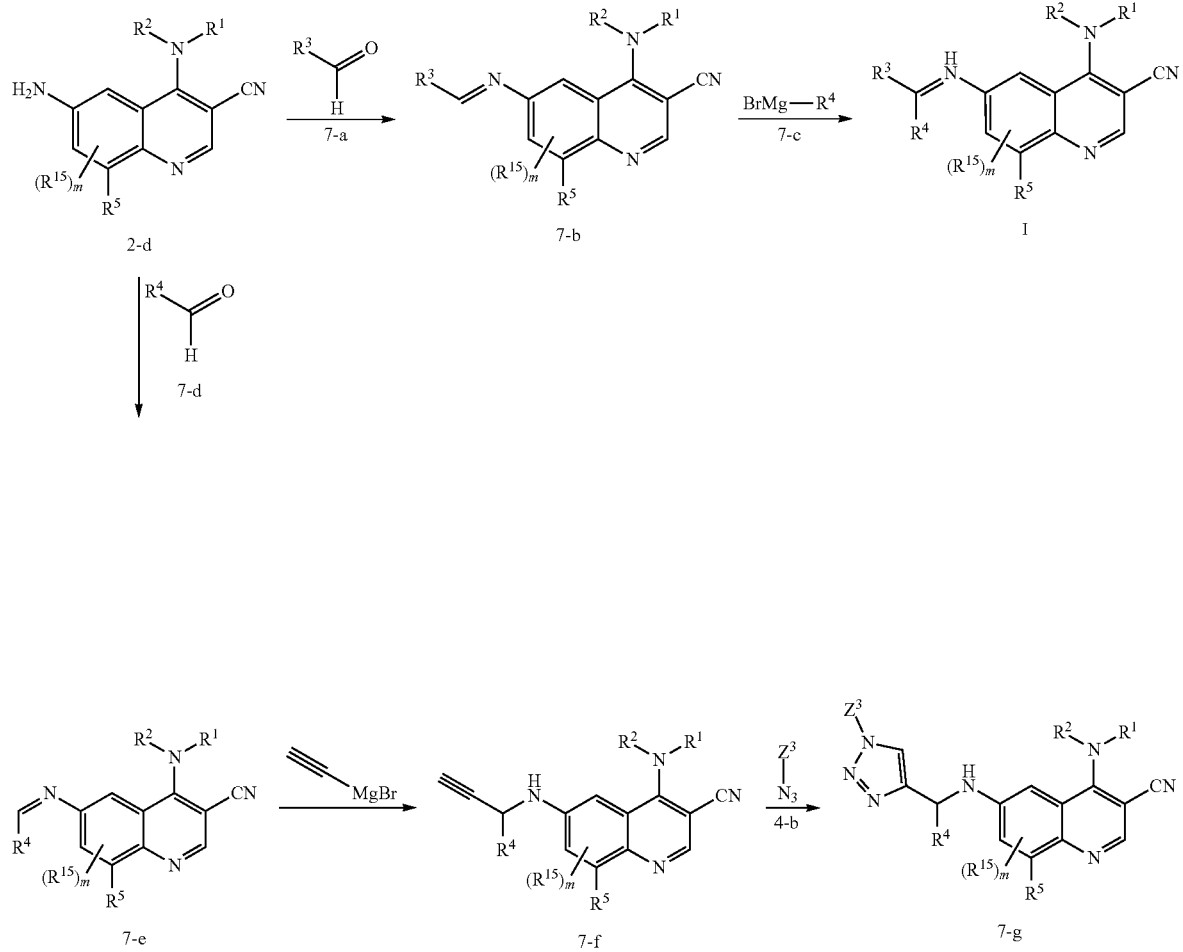

In Scheme 7, amine 2-d is reacted with aldehyde 7-a to afford the corresponding imine 7-b under standard imine-forming conditions. Compound 7-b is then reacted with Grignard reagent 7-c to provide Formula I. Alternatively, 2-d can be reacted with aldehyde 7-d to afford imine 7-e, which is then reacted with ethynyl Grignard to provide compound 7-f. Compound 7-f can then be converted to compound 7-g under standard 1,3-dipolar cycloaddition conditions with 4-b as shown in Scheme 6. Further, resolution of the isomers of Formula I or compound 7-g can be performed using standard chiral separation/resolution conditions (e.g., chiral chromatography, crystallization, etc.).

Scheme 8 shows another alternate general synthesis of compounds of Formula I, where m, $R^1$, $R^2$, $R^3$, $R^4$, $R^5$ and $R^{15}$ are as defined herein.

Scheme 8

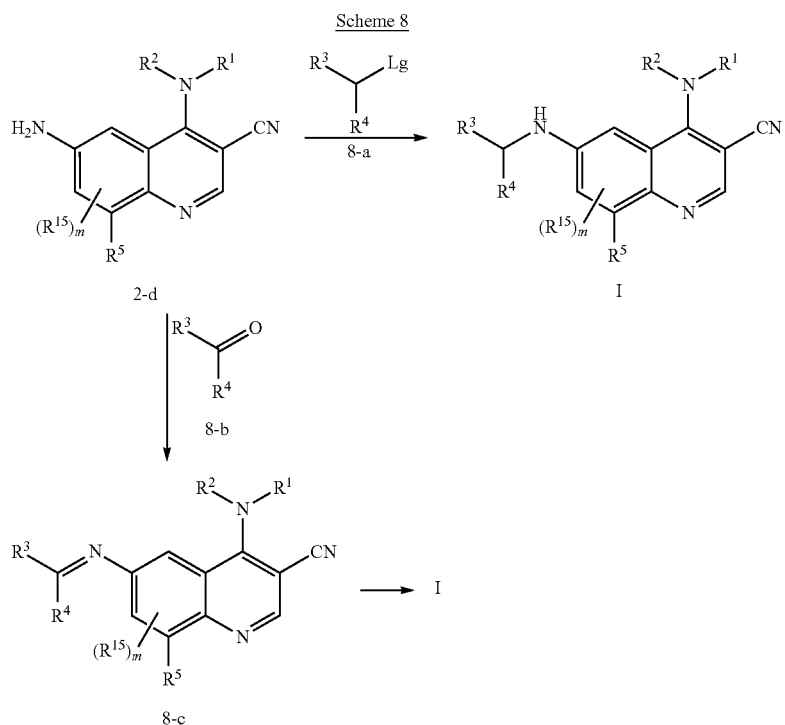

In Scheme 8, amine 2-d is reacted with appropriately substituted 8-a under nucleophilic substitution conditions, where Lg is a suitable leaving group, such as a halide (e.g., fluoro, chloro, bromo, iodo) or an activated alcohol (e.g., AcO—, TsO—, TfO—, MsO—, etc.) in the presence of a base, to provide compound of Formula I. Alternatively, amine 2-d is reacted with ketone 8-b to provide 8-c, which is subsequently reduced to provide compound of Formula I. Resolution of the isomers of Formula I can be performed using standard chiral separation/resolution conditions (e.g., chiral chromatography, crystallization, etc.).

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

LIST OF ABBREVIATIONS AND ACRONYMS

| Abbreviation | Meaning |
| --- | --- |
| °C. | Degree Celsius |
| Ac | Acetyl |
| aq. | Aqueous |
| ATP | Adenosine triphosphate |
| BOC | tert-Butoxycarbonyl |
| br | Broad |
| BSA | Bovine serum albumin |
| Cbz | Carboxybenzyl |
| COD | Cyclooctadiene |
| COPD | Chronic obstructive pulmonary disease |
| Cp | Cyclopentadienyl |
| d | Doublet |
| DABCO | 1,4-Diazabicyclo[2.2.2]octane |
| DBU | 1,8-Diazabicyclo[5.4.0]undec-7-ene |
| DCE | Dichloroethene |
| DCM | Dichloromethane |
| dd | Doublet of doublets |
| DEF | N,N-Diethylformamide |
| DMF | Dimethylformamide |
| DMSO | Dimethylsulfoxide |
| dppf | 1,1'-Bis(diphenylphosphino)ferrocene |
| dt | Doublet-triplet |
| DTT | Dithiothreitol |
| EC50 | The half maximal effective concentration |
| EGFR | Epidermal growth factor receptor |
| eq | Equivalents |
| ES/MS | Electrospray mass spectrometry |
| Et | Ethyl |
| FBS | Fetal bovine serum |
| g | Grams |
| HEPES | 2-[4-(2-hydroxyethyl)piperazin-1-yl]ethanesulfonic acid |
| HPLC | High pressure liquid chromatography |
| hrs | Hours |
| Hz | Hertz |
| IBD | Inflammatory bowel disease |
| i-pr | Isopropyl |
| J | Coupling constant (MHz) |
| Kg/kg | Kilogram |
| LCMS | Liquid chromatography-mass spectrometry |
| LPS | Lipopolysaccharide |
| M | Molar |
| m | multiplet |
| M+ | Mass peak |

-continued

| Abbreviation | Meaning |
|---|---|
| M + H+ | Mass peak plus hydrogen |
| Me | Methyl |
| mg | Milligram |
| MHz | Megahertz |
| min | Minute |
| ml/mL | Milliliter |
| mM | Millimolar |
| mmol | Millimole |
| MOPS | 3-Morpholinopropane-1-sulfonic acid |
| MS | Mass spectroscopy |
| Ms | Mesyl |
| nBu/Bu | Butyl |
| nL | Nanoliter |
| nm | Nanometer |
| NMR | Nuclear magnetic resonance |
| NP-40 | Nonyl phenoxypolyethoxylethanol |
| Ns | Nosyl |
| Pd-C/Pd/C | Palladium on Carbon |
| pg | Pictogram |
| Ph | Phenyl |
| PPTS | Pyridinium p-toluenesulfonate |
| PS | Polystyrene |
| p-TSOH/pTSA | p-Toluenesulfonic acid |
| q | Quartet |
| q.s. | Quantity sufficient to achieve a stated function |
| RBF | Round bottom flask |
| RP | Reverse phase |
| RPMI | Roswell Park Memorial Institute medium |
| rt | Room temperature |
| s | Singlet |
| sat. | Saturated |
| t | Triplet |
| TBAF | Tetra-n-butylammonium fluoride |
| TBS | tert-Butyldimethylsilyl |
| t-Bu | tert-Butyl |
| TC | Thiophene-2-carboxylate |
| TEA | Triethanolamine |
| Tf | Trifluoromethanesulfonyl |
| TFA | Trifluoroacetic acid |
| THF | Tetrahydrofuran |
| Tpl-2 | Tumor Progression Locus 2 |
| TR-FRET | Time-resolved fluorescence energy transfer |
| Ts | Tosyl |
| δ | Chemical shift (ppm) |
| μL/μl | Microliter |
| μM | Micromolar |

Intermediates:

Example Synthesis of a Cyanoquinolinecore:

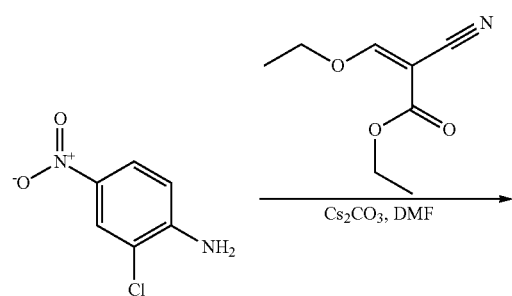

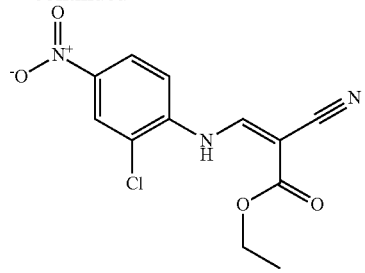

A mixture of 2-chloro-4-nitroaniline (1 eq), (Z)-ethyl 2-cyano-3-ethoxyacrylate (1.3 eq) and $Cs_2CO_3$ (1.3 eq) in DMF was heated at 45° C. overnight. After being cooled to room temperature, the mixture was poured into water. The formed solid was filtered, and washed with water and dried to give the title compound as a solid which was used for the next step without further purification. $^1$H NMR (DMSO-$d_6$, 300 MHz): δ 11.28 (d, J=12.9 Hz, 1H), 8.84 (d, J=12.9 Hz, 1H), 8.42 (d, J=2.4 Hz, 1H), 8.26-8.22 (m, 1H), 8.02 (d, J=9.3 Hz, 1H), 4.27 (q, J=7.2 Hz, 2H), 1.27 (t, J=7.2 Hz, 3H).

Synthesis of 8-Chloro-6-nitro-4-oxo-1,4-dihydroquinoline-3-carbonitrile

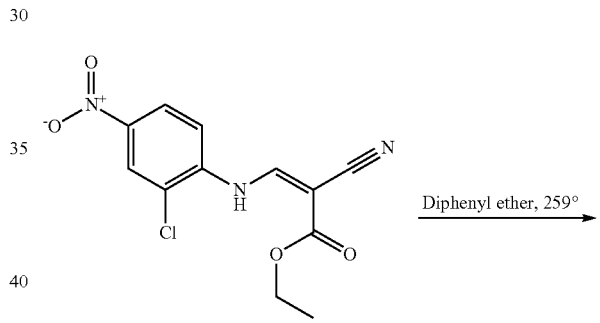

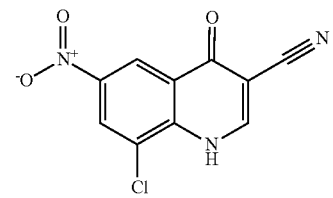

A suspension of (Z)-ethyl 3-((2-chloro-4-nitrophenyl)amino)-2-cyanoacrylate in diphenyl ether under nitrogen was heated to reflux with a sand bath in a heating mantle for 24 hours. After cooling to room temperature, the reaction mixture was poured into hexane and stirred for 2 hours. The mixture was filtered and the filter cake was washed with hexane twice to give title compound as a brown solid. $^1$H NMR (DMSO-$d_6$, 300 MHz): δ 12.86 (br s, 1H), 8.73-8.71 (m, 3H).

Synthesis of 4,8-Dichloro-6-nitroquinoline-3-carbonitrile

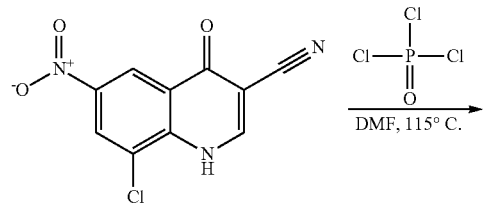

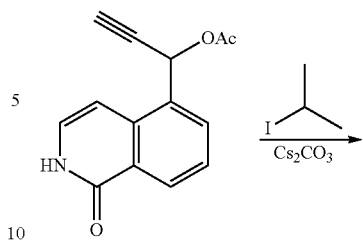

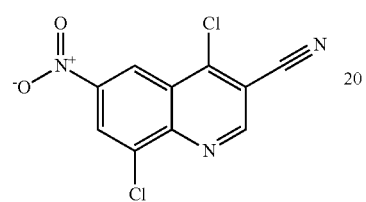

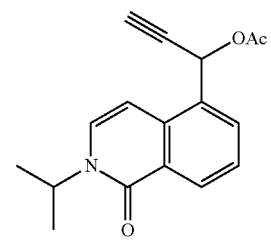

A suspension of 8-chloro-6-nitro-4-oxo-1,4-dihydroquinoline-3-carbonitrile and five drops of DMF in POCl$_3$ was heated at 115° C. overnight. The brown clear solution was cooled down to room temperature and excess of POCl$_3$ was removed. The residue was dissolved in DCM, washed with sat. NaHCO$_3$, brine and dried over Na$_2$SO$_4$. The solution was filtered and concentrated to give a crude product. The residue was triturated with hexane and EtOAc to afford the title compound as a brown solid. $^1$H NMR (DMSO-d$_6$, 300 MHz): δ 9.50 (s, 1H), 8.98 (d, J=2.4 Hz, 1H), 8.89 (d, J=2.4 Hz, 1H).

Example Alkynylacetate

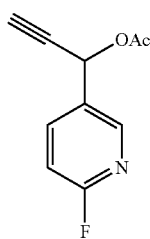

1-(6-fluoropyridin-3-yl)prop-2-yn-1-yl acetate: 6-fluoronicotinaldehyde (300 mg, 2.40 mmol) was dissolved in THF (15 mL) and brought to 0° C. Ethynylmagnesium bromide (0.5 M in THF, 5.76 mL, 2.88 mmol) was added slowly and the resulting solution allowed to stir for 30 minutes. Acetic anhydride (0.45 mL, 4.80 mmol) was then added, the cold bath removed, and the reaction mixture allowed to warm to room temperature over 2 hours. The reaction contents were quenched by the addition of saturated aqueous NH$_4$Cl (5 mL), poured into water (5 mL), and extract with EtOAc (3×15 mL). The combined organic phase was washed with brine (10 mL), dried over MgSO$_4$ and concentrated. The crude residue was purified by flash chromatography (eluent: EtOAc/hexanes) to give the desired product.

1-(1-oxo-1,2-dihydroisoquinolin-5-yl)prop-2-yn-1-yl acetate (200 mg, 0.83 mmol) was dissolved in DMF (2 mL) after which cesium carbonate (405 mg, 1.2 mmol) and 2-iodopropane (211 mg, 1.2 mmol) were added and the resulting mixture stirred at 25° C. under ambient atmosphere overnight. The reaction mixture was poured into water (3 mL) and extracted with EtOAc (3×5 mL). The organic layer was dried over MgSO$_4$, filtered, concentrated, and purified by via silica gel chromatography (eluent: EtOAc/hexanes) to give the N-alkylated product. Note: The same alkylation protocol could be performed on the preceding 1-oxo-1,2-dihydroisoquinoline-5-carbaldehyde.

Example Aldehydes for Alkynyl Acetate Synthesis

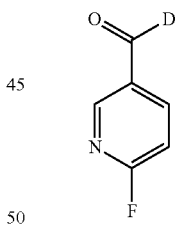

6-fluoronicotin-aldehyde-α-D: 6-fluoronicotinaldehyde (1.14 g, 9.11 mmol) was dissolved in MeOH (8 mL) at room temperature. NaBD$_4$ (458 mg, 10.9 mmol) was then added as a single portion and the reaction mixture stirred for 20 minutes. The reaction mixture was carefully quenched with water (5 mL) and extracted with EtOAc (3×15 mL). The combined organic layers were washed with brine (5 mL), dried over MgSO$_4$ and concentrated to give crude alcohol which was carried forward without further purification. The crude alcohol was re-dissolved in DCM (40 mL) and manganese(IV) oxide (19.9 g, 281 mmol) was added at room temperature. After 2 hours the reaction mixture was filtered through a pad of celite rinsing with DCM and EtOAc. The filtrate was then concentrated to give the desired product with approximately 95% deuterium incorporation.

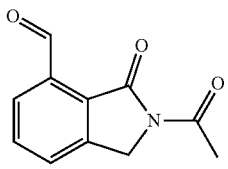

2-acetyl-3-oxoisoindoline-4-carbaldehyde: 3-oxoisoindoline-4-carbaldehyde (300 mg, 1.86 mmol) was dissolved in THF (5 mL) at room temperature. Acetic anhydride (0.53 mL, 5.59 mmol) and DMAP (45 mg, 0.37 mmol) were added and the reaction mixture stirred overnight. The reaction contents were quenched by the addition of saturated aqueous NH$_4$Cl (3 mL), poured into water (3 mL), and extracted with EtOAc (3×8 mL). The combined organic phases were washed with brine (5 mL), dried over MgSO$_4$ and concentrated. The crude residue was purified by flash chromatography (eluent: EtOAc/hexanes) to give the desired product.

tert-butyl (7-formylbenzo[d]thiazol-2-yl)carbamate

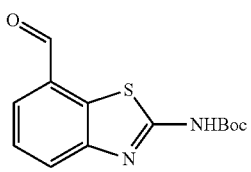 [SMILES: CC(C)(C)OC(=O)Nc1nc2cccc(C=O)c2s1]

ethyl 2-((tert-butoxycarbonyl)amino)benzo[d]thiazole-7-carboxylate: ethyl 2-aminobenzo[d]thiazole-7-carboxylate (300 mg, 1.35 mmol), di-tert-butyl dicarbonate (0.34 mL, 1.49 mmol) and DMAP (181 mg, 1.49 mmol) were dissolved in DCM (10 mL) and stirred at room temperature for 3 hours. The reaction mixture was then poured into water (10 mL) and extracted with DCM (2×20 mL). The combined organic extracts were dried over MgSO$_4$, concentrated, and purified by flash chromatography (eluent: EtOAc/hexanes) to give the desired product.

tert-butyl (7-(hydroxymethyl)benzo[d]thiazol-2-yl)carbamate: ethyl 2-((tert-butoxycarbonyl)amino)benzo[d]thiazole-7-carboxylate (204 mg, 0.63 mmol) was dissolved in THF (7 mL) and brought to 0° C. LiAlH$_4$ (72 mg, 1.90 mmol) was added portionwise and the reaction mixture allowed to stir for 90 minutes. The reaction mixture was quenched at 0° C. carefully with water (5 mL) and extracted with EtOAc (3×8 mL). The combined organic phases were washed with brine (5 mL), dried over MgSO$_4$ and concentrated to give the desired product which was used without further purification.

tert-butyl (7-formylbenzo[d]thiazol-2-yl)carbamate: tert-butyl (7-(hydroxymethyl)benzo[d]thiazol-2-yl)carbamate (177 mg, 0.63 mmol) was dissolved in DCM (5 mL) after which Dess-Martin periodinane (321 mg, 0.76 mmol) was added at room temperature. After 30 minutes the reaction contents were quenched by the addition of saturated aqueous Na$_2$SO$_3$ (3 mL) and stirred vigorously for 5 minutes. The reaction mixture was then poured into saturated aqueous NaHCO$_3$ (5 mL) and extracted with EtOAc (3×15 mL). The combined organic phase was washed with brine (5 mL), dried over MgSO$_4$ and concentrated to give the desired aldehyde which was used without further purification.

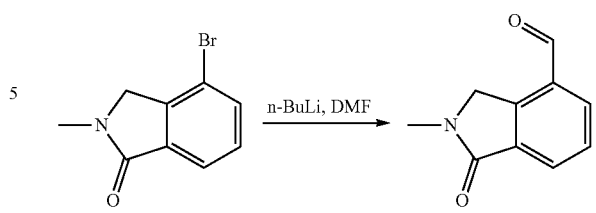

2-methyl-1-oxoisoindoline-4-carbaldehyde: To a solution of 4-bromo-2-methylisoindolin-1-one (200 mg, 0.89 mmol) in THF (3 mL), n-BuLi (0.78 mL, 1.95 mmol) was added to the solution at −78° C. After 30 minutes, DMF (0.273 mL, 3.57 mmol) was added to the solution. After 1 hour, the reaction was warmed up. Diluted with EtOAc and washed with brine. The organic layer was dried over sodium sulfate, and concentrated. The product was purified by chromatography on silica gel (eluent: EtOAc/hexanes) to yield the product after lyophilization from water/MeCN.

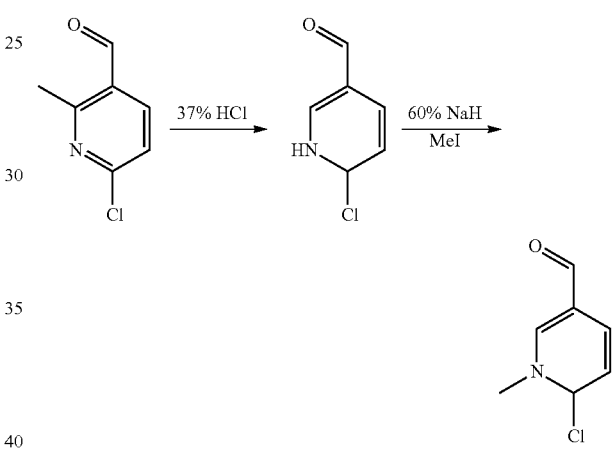

1-methyl-6-oxo-1,6-dihydropyridine-3-carbaldehyde: To a solution of 6-chloro-2-methylnicotinaldehyde (1.0 g, 6.43 mmol) in conc. HCl (3 mL), was heated to 90° C. for O.N. Cooled it down and poured it to ice water (20 mL). Filtered and dried with vacuum. Used without further purification.

To a suspension of 6-oxo-1,6-dihydropyridine-3-carbaldehyde (300 mg, 2.19 mmol) in DMF, sodium hydride (96 mg, 2.4 mmol) was added to the suspension under ice bath condition. Iodomethane (0.15 mL, 2.4 mmol) was added to the suspension. Then it was stirred for overnight. Diluted with EtOAc and washed with brine. The organic layer was dried and concentrated. Used without further purification.

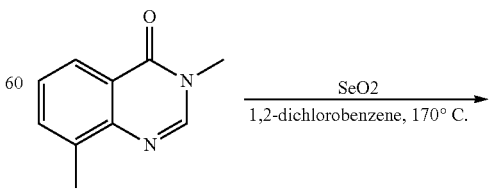

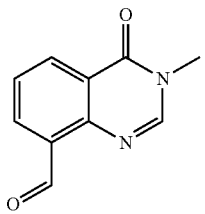

3-methyl-4-oxo-3,4-dihydroquinazoline-8-carbaldehyde: To a suspension of 3,8-dimethylquinazolin-4(3H)-one (300 mg, 2 mmol) (prepared according to Organic and Biomolecular Chemistry, 2011, vol. 9, No. 17 p. 6089-6099) and selenium dioxide (955 mg, 9 mmol) in 1,2-dichlorobenzene (1270 mg, 9 mmol) was heated to 170° C. overnight. The organic layer was dried over MgSO$_4$, filtered, concentrated, and purified by via silica gel chromatography (eluent: EtOAc/hexanes) to yield the title compound.

Example Amines

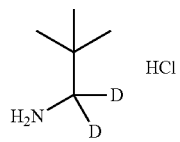

(2,2-dimethylpropyl-1,1-d2)amine HCl: LiAlD$_4$ (252 mg, 6.02 mmol) was suspended in Et$_2$O (10 mL) at room temperature. Trimethylacetonitrile (0.67 mL, 6.02 mmol) was then added slowly as a solution in Et$_2$O (6 mL) keeping the temperature below reflux. After 30 minutes the reaction mixture was quenched by careful, slow addition of water until gas evolution ceased. Saturated aqueous Rochelle's salt solution (50 mL) was then added and the resulting solution stirred vigorously for 2 hours. The phases were then separated and the aqueous extracted with Et$_2$O (3×30 mL). The combined organic phases were washed with brine (15 mL), dried over MgSO$_4$ and filtered. To the product solution in ether was added HCl (1.0M in ether, 15 mL, 15 mmol) after which the newly formed HCl salt was collected by filtration.

(R)-1-phenylpropan-1-amine-d7

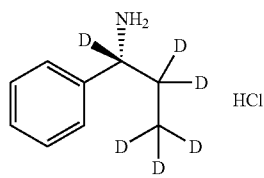 [SMILES: [2H]C([2H])([2H])C([2H])([2H])[C@@]([2H])(N)c1ccccc1 ; Cl]

Ellman auxiliary condensation: (S)-(−)-2-methyl-2-propanesulfinamide (862 mg, 7.12 mmol) was dissolved in DCM (15 mL). PPTS (81 mg, 0.32 mmol), MgSO$_4$ (3.89 g, 32.3 mmol), and benzaldehyde-d were then added and the resulting mixture allowed to stir at room temperature for 4 hours. The reaction mixture was filtered through celite rinsing with DCM, concentrated and purified by flash chromatography (eluent: EtOAc/hexanes) to give the desired product.

Grignard formation and addition to sulfinimine: Ethylbromide-d5 (1.00 g, 8.77 mmol) as a solution in dry THF (2 mL) was added to a suspension of magnesium turnings (426 mg, 17.5 mmol) in dry THF (7 mL) and stirred at room temperature for 2 hours. Heat generation and discoloration indicate successful Grignard reagent formation to give an approximately 1.0M solution of EtMgBr-d5 in THF. EtMgBr-d5 (1.0M in THF, 7.2 mL, 7.2 mmol) was added dropwise to a solution of sulfinimine (752 mg, 3.58 mmol) in DCM (10 mL) at −78° C. After stirring for 3 hours at −78° C., the reaction mixture was allowed to warm to room temperature overnight. The reaction contents were quenched by the addition of saturated aqueous NH$_4$Cl (5 mL), poured into water (5 mL) and extracted with EtOAc (3×30 mL). The combined organic phases were washed with brine (15 mL), dried over MgSO$_4$ and concentrated. The crude residue was purified by flash chromatography (eluent: EtOAc/hexanes) to give the desired product.

Auxiliary removal: Starting material (451 mg, 1.84 mmol) was dissolved in MeOH (0.9 mL) at room temperature. HCl (4.0M in dioxane, 0.92 mL, 3.69 mmol) was added and the solution stirred for 30 minutes. Reaction mixture was diluted with Et$_2$O (20 mL) and the resulting precipitate collected by filtration to give the desired product as an HCl salt.

(1R,2R)-2-((S)-amino(phenyl)methyl)cyclopropanecarbonitrile

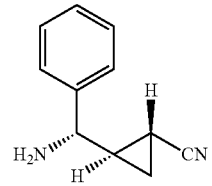

2-benzoylcyclopropanecarbonitrile: Phenacyl chloride (10.0 g, 64.7 mmol) and DABCO (7.26 g, 64.7 mmol) were dissolved in THF (200 mL) and DMSO (50 mL) at room temperature and stirred for 30 minutes. Na$_2$CO$_3$ (10.3 g, 97.0 mmol) and acrylonitrile (8.48 mL, 129.4 mmol) were then added and the resulting mixture heated to 90° C. overnight. The reaction contents were quenched by the addition of saturated aqueous NH$_4$Cl (40 mL), poured into water (20 mL) and extracted with EtOAc (3×150 mL). The combined organic phases were washed with brine (40 mL), dried over MgSO$_4$ and concentrated. The crude residue was purified by flash chromatography (eluent: EtOAc/hexanes) to give trans-2-benzoylcyclopropanecarbonitrile (5.91 g, 53%) and cis-2-benzoylcyclopropanecarbonitrile separately and both as racemic mixtures.

(R)—N-(((1S,2S)-2-cyanocyclopropyl)(phenyl)methylene)-2-methylpropane-2-sulfinamide and (R)—N-(((1R,2R)-2-cyanocyclopropyl)(phenyl)methylene)-2-methylpropane-2-sulfinamide: Racemic trans-2-benzoylcyclopropanecarbonitrile (1.00 g, 5.84 mmol), (R)-(+)-2-methyl-2-propanesulfinamide (2.12 g, 17.5 mmol) and titanium(IV) ethoxide (7.35 mL, 35.1 mmol) were combined and heated to 85° C. for 3 hours. The reaction mixture was cooled to room temperature, diluted with EtOAc (100 mL) followed by water (5 mL) and allowed to stir for 30 minutes). The white precipitate was removed via filtration and the filtrate was washed with brine and concentrated. The crude residue was purified by flash chromatography (eluent: EtOAc/hexanes) to give (R)—N-(((1R,2R)-2-cyanocyclopropyl)(phenyl)methylene)-2-methylpropane-2-sulfinamide and (R)—N-(((1S,2S)-2-cyanocyclopropyl)(phenyl)methylene)-2-methylpropane-2-sulfinamide as pure enantiomers.

(R)—N—((S)-((1R,2R)-2-cyanocyclopropyl)(phenyl)methyl)-2-methylpropane-2-sulfinamide: (R)—N-(((1R,2R)-2-cyanocyclopropyl)(phenyl)methylene)-2-methylpropane-2-sulfinamide (250 mg, 0.91 mmol) was dissolved in THF and brought to −78° C. NaBH$_4$ (70.0 mg, 1.85 mmol) was added as a single portion and the reaction mixture allowed to warm slowly to room temperature. Upon reaching room temperature the reaction contents were quenched with water (2 mL) and extracted with EtOAc (3×8 mL). The combined organic phases were washed with brine (5 mL), dried over MgSO$_4$ and concentrated. The crude residue was purified by flash chromatography (eluent: EtOAc/hexanes) to give (R)—N—((R)-((1R,2R)-2-cyanocyclopropyl)(phenyl)methyl)-2-methylpropane-2-sulfinamide (56 mg, 22%) and (R)—N—((S)-((1R,2R)-2-cyanocyclopropyl)(phenyl)methyl)-2-methylpropane-2-sulfinamide as pure enantiomers.

(1R,2R)-2-((S)-amino(phenyl)methyl)cyclopropanecarbonitrile: (R)—N—((S)-((1R,2R)-2-cyanocyclopropyl)(phenyl)methyl)-2-methylpropane-2-sulfinamide (143 mg, 0.52 mmol) was dissolved in MeOH (0.5 mL) at room temperature. HCl (4.0M in dioxane, 0.26 mL, 1.04 mmol) was added and the solution stirred for 30 minutes. Reaction mixture was diluted with Et$_2$O (20 mL) and the resulting precipitate collected by filtration to give the desired product as an HCl salt.

3-chloro-2-cyclopropoxyaniline

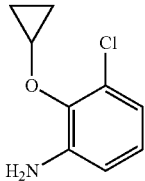

1-chloro-2-cyclopropoxy-3-nitrobenzene: To a solution of NaH (60% dispersion in mineral oil, 319 mg, 7.98 mmol) in THF (10 mL) was slowly added cyclopropyl alcohol (0.35 mL, 5.58 mmol). After 15 minutes of stirring, 1-chloro-2-fluoro-3-nitrobenzene (700 mg, 3.99 mmol) was added and the resulting solution heated to 75° C. for 1 hour. The reaction mixture was cooled to room temperature, quenched with water (5 mL) and extracted with EtOAc (3×15 mL). The combined organic phases were washed with brine (5 mL), dried over MgSO$_4$ and concentrated. The crude residue was purified by flash chromatography (eluent: EtOAc/hexanes) to give the desired product.

3-chloro-2-cyclopropoxyaniline: 1-chloro-2-cyclopropoxy-3-nitrobenzene (420 mg, 1.97 mmol) was dissolved in EtOH (8 mL) at room temperature. Iron (549 mg, 9.83 mmol), CaCl$_2$ (327 mg, 2.95 mmol) and water (1 mL) were then added and the resulting mixture heated to 75° C. for 3 hours. The solids were removed by filtration washing with MeOH and EtOAc, the filtrate concentrated, and then redissolved in EtOAc (100 mL). The organic phase was washed with saturated aqueous NaHCO$_3$ (2×20 mL), brine (20 mL), dried over MgSO$_4$ and concentrated to give the product which was used without further purification.

Diazotransfer Reaction and Generation of Azides

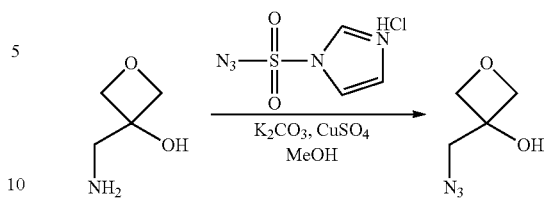

3-(Aminomethyl)oxetan-3-ol (50 mg, 0.49 mmol) was added to a suspension of 1H-imidazole-1-sulfonyl azide hydrochloride (129.5 mg, 0.62 mmol), potassium carbonate (136 mg, 0.99 mmol), and copper (II) sulfate pentahydrate (12.3 mg, 0.049 mmol) in methanol (1.0 mL). The blue mixture was stirred at room temperature for 16 hrs and was used without workup in the Click chemistry (Example 4). Reference: E. D. Goddard, et. al., Org. Lett., 2007, p. 3797.

Piperidine-Triazole Aldehyde

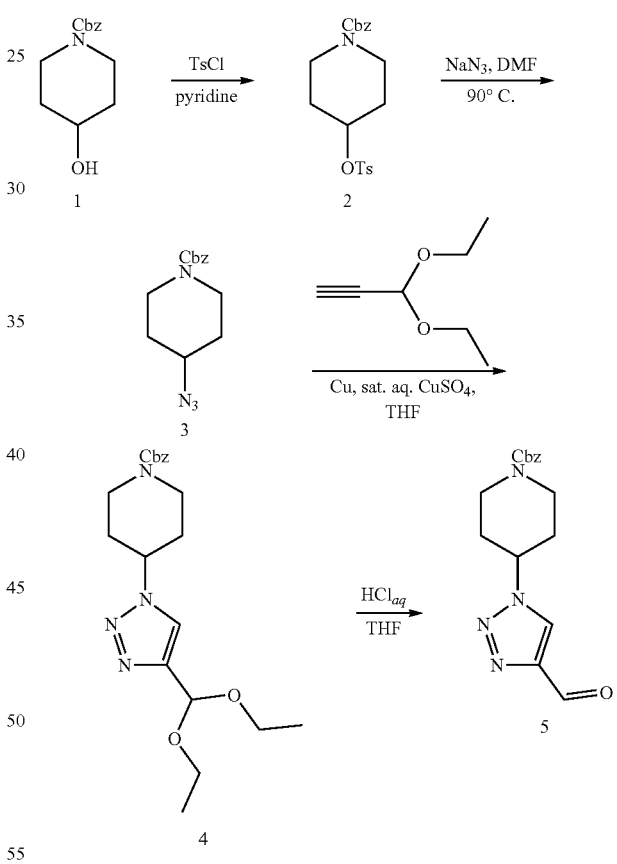

Benzyl 4-(tosyloxy)piperidine-1-carboxylate (2)

Benzyl 4-hydroxypiperidine-1-carboxylate (1) (17.2 g, 73.1 mmol) and p-toluenesulfonyl chloride (15.3 g, 80.4 mmol) were dissolved in pyridine (50 mL) and stirred at room temperature. After 23 hrs, the pyridine was removed under reduced pressure and the residue was dissolved in EtOAc (300 mL). The organic phase was washed with water (2×150 mL) and saturated ammonium chloride (100 mL), dried over sodium sulfate and the solvent was removed under reduced pressure. The residue was subjected to flash chromatography (eluent: ethyl acetate/hexanes). The fractions containing product were combined and the solvent was removed under reduced pressure, providing benzyl 4-(tosyloxy)piperidine-1-carboxylate (2).

Benzyl 4-azidopiperidine-1-carboxylate (3)

Sodium azide (2.48 g, 38.2 mmol) was added to a solution of benzyl 4-(tosyloxy)piperidine-1-carboxylate (2) (12.4 g, 31.8 mmol) in dimethylformamide (100 mL). The mixture was heated at 90° C. for 30 minutes. The mixture was cooled and diluted with ethyl acetate (250 mL) and washed with water (2×15 mL), 5% aqueous lithium chloride (10 mL) and brine (10 mL). The organic phase was dried over sodium sulfate and concentrated (NOT to dryness) providing the desired material. All material was used in the next step.

Benzyl 4-(4-(diethoxymethyl)-1H-1,2,3-triazol-1-yl)piperidine-1-carboxylate (4)

Copper powder (2.0 g, 31.5 mmol), was added to a solution of benzyl 4-azidopiperidine-1-carboxylate (3) (8.2 g, 31.5 mmol) 3,3-diethoxyprop-1-yne (4.44 g, 34.6 mmol) and saturated copper (II) sulfate (8 mL) in tetrahydrofuran (100 mL). After 17 hrs, the mixture was filtered through a pad of celite. The solvent was removed under reduced pressure and the residue was taken up in ethyl acetate (200 mL). The organic phase was washed with brine (3×100 mL), dried over sodium sulfate and concentrated. The residue was subjected to flash chromatography on silica gel (eluent: ethyl acetate/hexanes). The fractions containing product were combined and the solvent was removed under reduced pressure providing benzyl 4-(4-(diethoxymethyl)-1H-1,2,3-triazol-1-yl)piperidine-1-carboxylate (4).

Benzyl 4-(4-formyl-1H-1,2,3-triazol-1-yl)piperidine-1-carboxylate (5)

Aqueous hydrochloric acid (1 M, 2.2 mL, 2.2 mmol) was added to a solution of benzyl 4-(4-(diethoxymethyl)-1H-1,2,3-triazol-1-yl)piperidine-1-carboxylate (4) (429 mg, 1.1 mmol) in tetrahydrofuran (4 mL) and water (2 mL). The organic solvent was removed under reduced pressure. The aqueous mixture was diluted with acetonitrile (2 mL) and subjected to lyophilization.

tert-butyl 3-formyl-4,7-dihydrothieno[2,3-c]pyridine-6(5H)-carboxylate

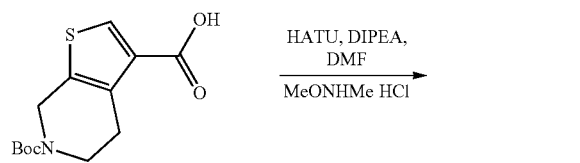

N,N-Diisopropylethylamine (1.53 mL, 8.82 mmol) was added to a solution of 6-(tert-butoxycarbonyl)-4,5,6,7-tetrahydrothieno[2,3-c]pyridine-3-carboxylic acid (1.00 g, 3.53 mmol) and N-[(Dimethylamino)-1H-1,2,3-triazolo-[4,5-b]pyridin-1-ylmethylene]-N-methylmethanaminium hexafluorophosphate N-oxide (1.62 g, 4.24 mmol) in dimethylformamide (15 mL). After 2 min N,O-Dimetylhydroxylamine hydrochloride (413 mg, 4.24 mmol) was added. After 16 h the reaction was diluted with ethyl acetate (75 mL) and washed with water (2×25 mL), saturated ammonium chloride (2×25 mL) and brine (25 mL). The organic phase was dried over sodium sulfate and the solvent was removed under reduced pressure. The residue was subjected to flash chromatography (0-100% ethyl acetate/hexanes). The fractions containing product were combined and the solvent was removed under reduced pressure, providing tert-butyl 3-(methoxy(methyl)carbamoyl)-4,7-dihydrothieno[2,3-c]pyridine-6(5H)-carboxylate.

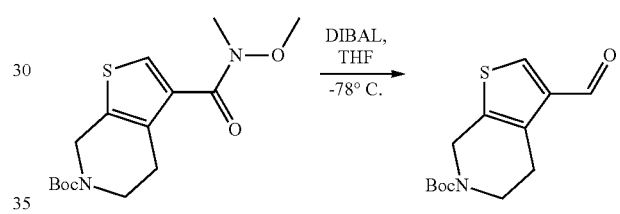

A solution of diisobutylaluminum hydride in tetrahydrofuran (4.42 mL, 1.0 M, 4.42 mmol) was added dropwise to a solution of tert-butyl 3-(methoxy(methyl)carbamoyl)-4,7-dihydrothieno[2,3-c]pyridine-6(5H)-carboxylate (1.03 g, 3.15 mmol) in tetrahydrofuran (20 mL) at −78° C. under an atmosphere of argon. After 5 h at −78° C. the reaction was 40% complete. A solution of diisobutylaluminum hydride in tetrahydrofuran (3.15 mL, 1.0 M, 3.15 mmol was added dropwise. After 30 min the reaction was quenched with saturated ammonium chloride (20 mL) at −78° C. and allowed to warm to room temperature. The organic phase was shaken with water (20 mL) and ethyl acetate (75 mL) (causing a gel to form). Hydrochloric acid (2 N, 5 mL) was added and the solid was removed by filtration through a pad of celite. The organic phase was washed with saturated sodium bicarbonate (25 mL) and brine (25 mL). The organic phase was dried over sodium sulfate and concentrated. The residue was subjected to flash chromatography (0-50% ethyl acetate/hexanes). The fractions containing product were combined and the solvent was removed under reduced pressure, providing tert-butyl 3-formyl-4,7-dihydrothieno[2,3-c]pyridine-6(5H)-carboxylate.

COMPOUND EXAMPLES

Example 1 Procedure 1

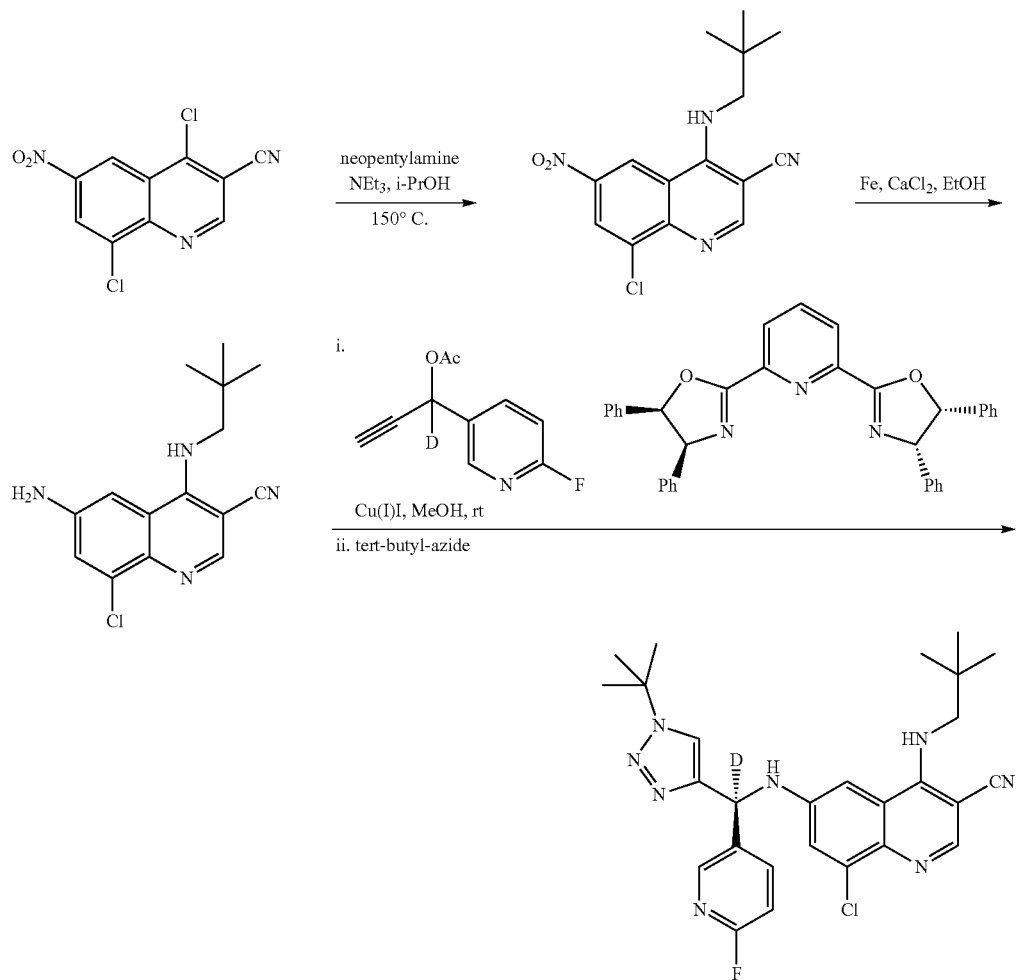

8-chloro-4-(neopentylamino)-6-nitroquinoline-3-carbonitrile: 4,8-dichloro-6-nitroquinoline-3-carbonitrile (615 mg, 2.29 mmol), neopentylamine (220 mg, 0.25 mmol) and triethylamine (278 mg, 2.75 mmol) in iso-propanol (4 mL) were heated under microwave conditions at 150° C. for 45 minutes. The reaction was cooled to room temperature. Water was added and the resulting precipitate was collected via filtration. The crude product was used in the next step without further purification.

ES/MS 319.1 (M+H$^+$).

Alternative reaction conditions for this transformation: 4,8-dichloro-6-nitroquinoline-3-carbonitrile (3000 mg, 11.2 mmol), neopentylamine (1073 mg, 12.3 mmol) and triethylamine (1246 mg, 12.3 mmol) in iso-propanol (60 mL) were heated at 80° C. for 4 hrs. The reaction was cooled to room temperature. Removed the solvents and purified the crude reaction product via chromatography on silica gel (eluent: EtOAc/hexanes) yielding the product.

ES/MS (M+H$^+$) 319.1.

6-amino-8-chloro-4-(neopentylamino)quinoline-3-carbonitrile: 8-chloro-4-(neopentylamino)-6-nitroquinoline-3-carbonitrile (699 mg, 2.2 mmol), calcium chloride (483.6 mg, 3.28 mmol), iron powder (612.3 mg, 10.96 mmol) were heated in ethanol (22 mL)/water (2.2 mL) at 60° C. for 1 hour. The reaction was cooled to room temperature and solids were removed via filtration. The solids were washed with EtOAc and the combined organic layers were washed with aqueous sodium bicarbonate solution, brine, and were dried over sodium sulfate. Filtration and evaporation of all volatiles yielded the product.

ES/MS 289.1 (M+H$^+$).

Alternative reduction conditions with tin chloride: 8-chloro-4-(neopentylamino)-6-nitroquinoline-3-carbonitrile (2,000 mg, 6.2 mmol) and tin chloride (7079 mg, 31.3 mmol) heated at 70° C. for 4 h. More tin chloride (2832 mg, 12.6 mmol) was added. After 5 hrs, the reaction was complete. The reaction was cooled to room temperature. Half of the ethanol was removed under reduced pressure. The mixture was added to NaHCO$_3$ (200 mL) and diluted with EtOAc (500 mL). The organic phase was washed with brine (200 mL) and dried over sodium sulfate. The solvent was removed under reduced pressure, providing the desired material.

1H NMR (400 MHz, DMSO-d6) δ 8.19 (s, 1H), 7.32 (d, J=2.1 Hz, 1H), 7.29 (t, J=7.3 Hz, 1H), 7.18 (d, J=2.3 Hz, 1H), 5.74 (s, 2H), 3.66 (d, J=6.6 Hz, 2H), 0.96 (s, 9H).

ES/MS 289.1 (M+H$^+$).

(S)-8-chloro-6-(((1-cyclopropyl-1H-1,2,3-triazol-4-yl)(4-fluoro-3-pyridyl)methyl-d)amino)-4-(neopentylamino)quinoline-3-carbonitrile: 6-amino-8-chloro-4-(neopentylamino)quinoline-3-carbonitrile (75 mg, 0.26 mmol), CuI (3.6 mg, 0.019 mmol) and 2,6-bis((4S,5R)-4,5-diphenyl-4,5-dihydrooxazol-2-yl)pyridine [oxazoline ligand] (9.9 mg, 0.019 mmol) were sonicated in MeOH (3.5 mL) for ~1 minute. Alkynyl acetate (44.4 mg, 0.23 mmol) and di-isopropyl ethyl amine (29.4 mg, 0.229 mmol) were added and the reaction was stirred at room temperature overnight. Tert-butyl azide (45 mg, 0.454 mmol) was added and the reaction was stirred or additional 24 hrs at room temperature. Solvents were removed in vacuo and the crude material was purified via RP-HPLC (eluent: water/MeCN*0.1% TFA) to yield the product as trifluoro acetate salt.

1H NMR (400 MHz, DMSO-d6) δ 8.37 (m, 2H), 8.17 (s, 1H), 8.05 (m, 1H), 7.79 (brs, 1H), 7.62 (d, J=2.2 Hz, 1H), 7.51 (br s, 1H), 7.15 (m, 2H), 4.03 (m, 1H), 3.44 (dd, J=13.9/5.5 Hz, 1H), 1.59 (s, 9H), 0.88 (s, 9H).

ES/MS 522.2 (M+H$^+$).

Example 2 Procedure 2

8-chloro-6-4(S)-(1-isopropyl-1H-1,2,3-triazol-4-yl)(2-methylpyridin-3-yl)methyl)amino)-4-(((R)-1-phenylpropyl)amino)quinoline-3-carbonitrile

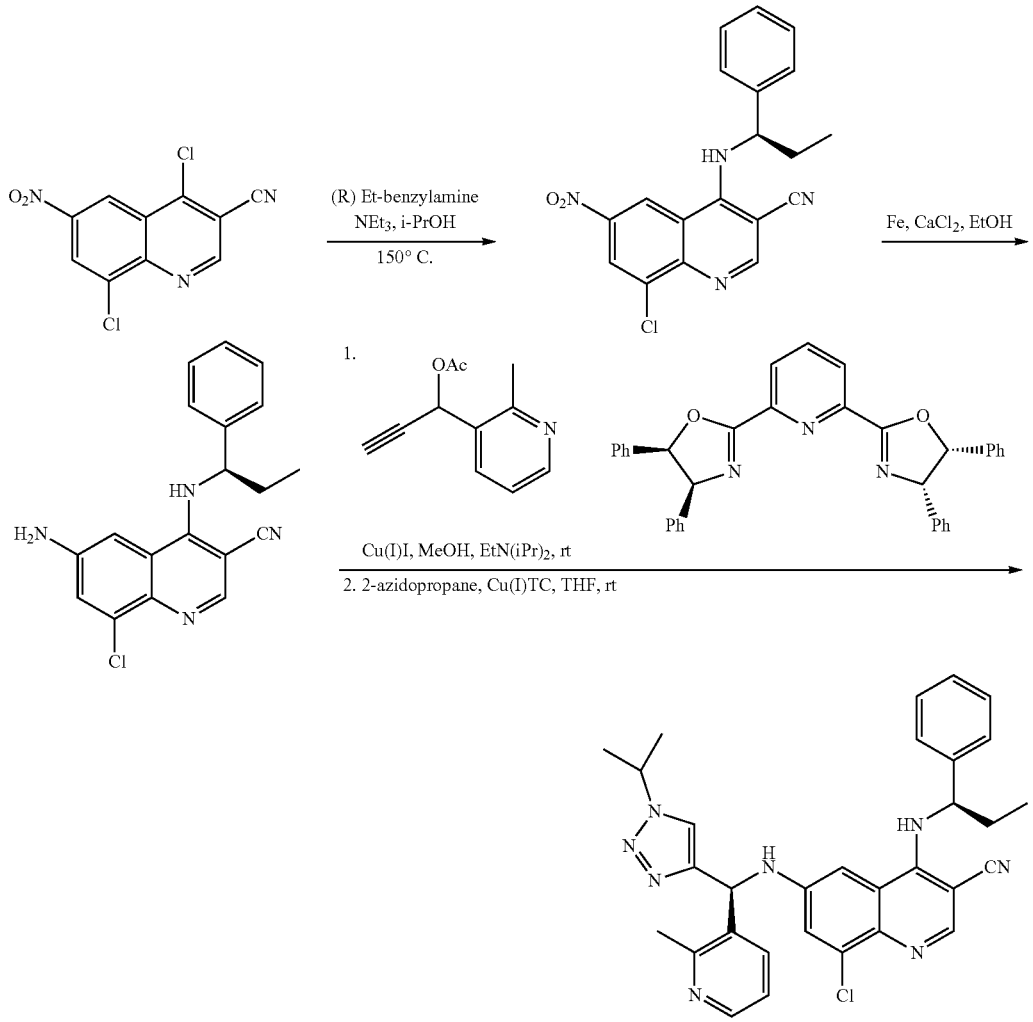

(R)-8-chloro-6-nitro-4-((1-phenylpropyl)amino)quinoline-3-carbonitrile: 4,8-dichloro-6-nitroquinoline-3-carbonitrile (200 mg, 0.75 mmol), (R)-ethyl benzylamine (121 mg, 0.895 mmol) in iso-propanol (3 mL) were heated under microwave conditions at 150° C. for 45 minutes. The reaction was cooled to room temperature. Water and EtOAc were added. The aqueous layer was extracted with EtOAc and the combined organic layers were dried over sodium sulfate. Filtration and evaporation of solvents yielded the crude product which was used in the next step without further purification.

ES/MS 367.1 (M+H$^+$).

6-amino-8-chloro-4-((1-phenylpropyl)amino)quinoline-3-carbonitrile: (R)-6-amino-8-chloro-4-((1-phenylpropyl)amino)quinoline-3-carbonitrile (287 mg, 0.78 mmol), calcium chloride (172.6 mg, 1.17 mmol), iron powder (218.5 mg, 3.91 mmol) were heated in ethanol (5 mL)/water (0.5 mL) at 60° C. for 1 hour. The reaction was cooled to room temperature and solids were removed via filtration. The solids were washed with EtOAc and the combined organic layers were washed with aqueous sodium bicarbonate solution, brine, and were dried over sodium sulfate. Filtration and evaporation of all volatiles yielded the product.

ES/MS 337.1 (M+H$^+$).

8-chloro-6-(((R)-1-(2-methylpyridin-3-yl)prop-2-yn-1-yl)amino)-4-(((R)-1-phenylethyl)amino)quinoline-3-carbonitrile: CuI (2.0 mg, 0.01 mmol) and 2,6-bis((4S,5R)-4,5-diphenyl-4,5-dihydrooxazol-2-yl)pyridine [oxazoline ligand] (6.9 mg, 0.013 mmol) were sonicated in MeOH (3.0 mL) for ~5 minutes. 1-(2-methylpyridin-3-yl)prop-2-yn-1-yl acetate (50 mg, 0.27 mmol) in MeOH (1 mL), (R)-6-amino-8-chloro-4-((1-phenylpropyl)amino)quinoline-3-carbonitrile (75 mg, 0.223 mmol), and di-isopropyl ethyl amine (34 mg, 0.27 mmol) were added and the reaction was stirred at room temperature overnight. The crude reaction product was purified by silica gel chromatography (20%-100% EtOAc in hexanes) to provide the product.

ES/MS 465.99 (M+H$^+$).

8-chloro-6-(((S)-(1-isopropyl-1H-1,2,3-triazol-4-yl)(2-methylpyridin-3-yl)methyl)amino)-4-(((R)-1-phenylpropyl)amino)quinoline-3-carbonitrile: 8-chloro-6-(((R)-1-(2-methylpyridin-3-yl)prop-2-yn-1-yl)amino)-4-(((R)-1-phenylethyl)amino)quinoline-3-carbonitrile (45 mg, 0.10 mmol) was dissolved in THF (0.5 mL) at room temperature and copper (I) thiophene carboxylate (5.7 mg, 0.030 mmol) was added. 2-azidopropane (10 mg, 0.120 mmol) was added and the reaction was stirred for 4 hours at room temperature. The reaction was partitioned between aqueous sodium bicarbonate solution and EtOAc. The aqueous layer was extracted with EtOAc and the combined layers were washed with saturated sodium bicarbonate solution and dried over sodium sulfate. Filtration and evaporation of solvents gives crude material. The crude material was purified RP-HPLC (eluent: water/MeCN*0.1% TFA) to yield the product as trifluoroacetate salt.

$^1$H NMR (400 MHz, CD$_3$OD) δ 8.61 (m, 1H), 8.37 (m, 1H), 8.29 (m, 1H), 8.05 (m, 1H), 7.73 (m, 1H), 7.60 (s, 1H), 7.32 (m, 5H), 7.14 (m, 1H), 6.46 (s, 1H), 5.64 (m, 1H), 4.88 (m, 1H), 2.83 (s, 3H), 2.17-2.02 (m, 2H), 1.56 (d, 6H), 0.97 (m, 3H).

ES/MS 551.09 (M+H$^+$).

Example 3 Procedure 3

8-chloro-6-(((S)-(1-cyclopropyl-1H-1,2,3-triazol-4-yl)(2,6-difluoropyridin-3-yl)methyl-d))amino)-4-(((R)-1-phenylpropyl)amino)quinoline-3-carbonitrile

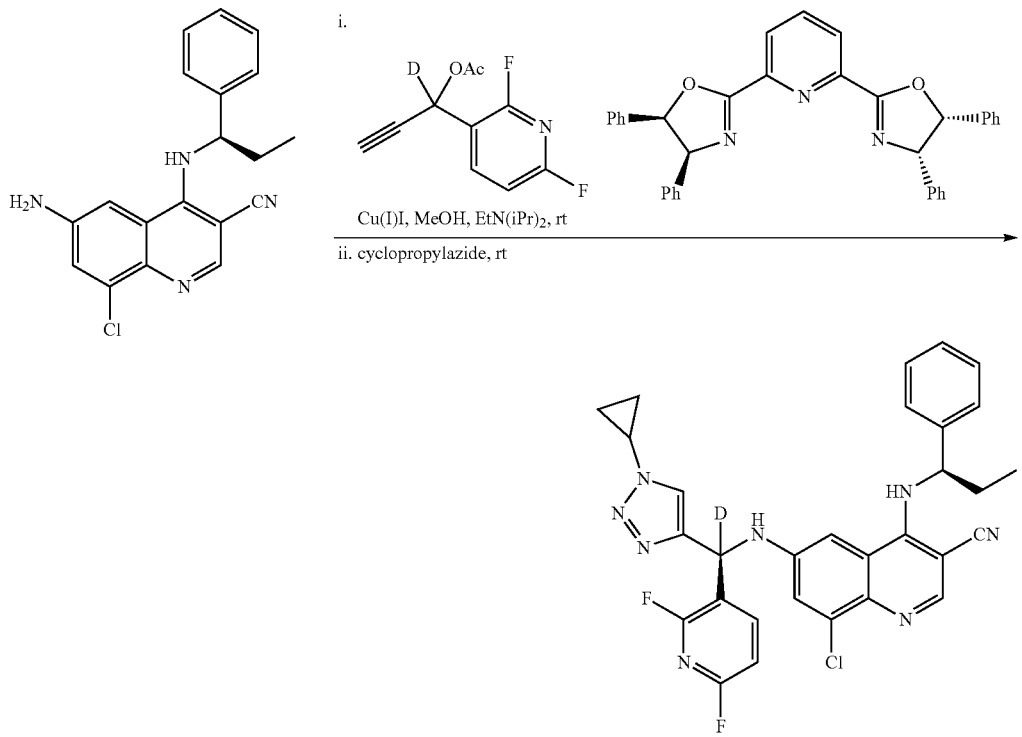

8-chloro-6-(((S)-(1-cyclopropyl-1H-1,2,3-triazol-4-yl)(2,6-difluoropyridin-3-yl)methyl-d))amino)-4-(((R)-1-phenylpropyl)amino)quinoline-3-carbonitrile: CuI (2.0 mg, 0.01 mmol) and 2,6-bis((4S,5R)-4,5-diphenyl-4,5-dihydrooxazol-2-yl)pyridine [oxazoline ligand] (4.6 mg, 0.009 mmol) were sonicated in MeOH (3.0 mL) for ~5 minutes. alkynyl acetate (79 mg, 0.37 mmol) in MeOH (1 mL), (R)-6-amino-8-chloro-4-((1-phenylpropyl)amino)quinoline-3-carbonitrile (50 mg, 0.148 mmol), and di-isopropyl ethyl amine (23 mg, 0.18 mmol) were added and the reaction was stirred at room temperature overnight. The crude reaction mixture was used directly for the next step.

ES/MS: 489.19 (M+H$^+$).

To the reaction mixture was added cyclopropylazide (16 mg, 0.192 mmol). After 1 hour at room temperature, the mixture was filtered and then purified by RP-HPLC (eluent: water/MeCN*0.1% TFA) to yield the product as trifluoroacetate salt.

¹H NMR (400 MHz, CD₃OD) δ 8.43 (m, 1H), 8.05 (m, 1H), 8.01 (m, 1H), 7.64 (m, 1H), 7.42-7.25 (m, 6H), 6.98 (m, 1H), 5.80-5.66 (m, 1H), 3.97-3.84 (m, 1H), 2.25-2.01 (m, 2H), 1.28-1.11 (m, 4H), 1.01 (m, 3H).

ES/MS: 572.24 (M+H⁻).

Example 4 Procedure 4

8-chloro-6-(((S)-(1-((3-hydroxyoxetan-3-yl)methyl)-1H-1,2,3-triazol-4-yl)(pyridin-3-yl)methyl)amino)-4-(((R)-1-phenylpropyl)amino)quinoline-3-carbonitrile: 8-chloro-4-(((R)-1-phenylpropyl)amino)-6-(((R)-1-(pyridin-3-yl)prop-2-yn-1-yl)amino)quinoline-3-carbonitrile (20 mg, 0.046 mmol), copper powder (15 mg, 0.23 mmol), acetic acid (118 uL, 1.8 mmol) and saturated aqueous copper (II) sulfate (0.1 mL) and THF (3 mL) were added to the stock solution of 3-(azidomethyl)oxetan-3-ol (0.049 mmol). After 2 hrs, the reaction was complete and volatiles were removed in vacuo. The crude was partitioned between ethyl acetate (15 mL) and water. The organic layer was washed with saturated sodium bicarbonate, brine, dried over Na₂SO₄ and concentrated after filtration. The residue was taken up in water (1 mL) and MeOH (1 mL) with 2 drops of TFA and subjected to RP-HPLC (eluent: water/MeCN*0.1% TFA). The fractions containing the desired product were combined and subjected to lyophilization, providing the desired compound.

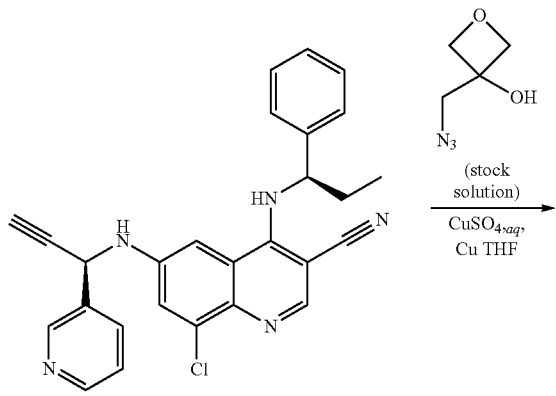

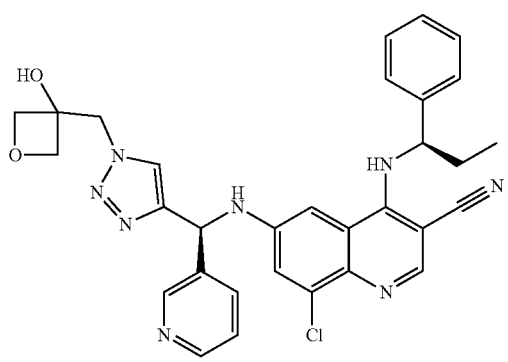

1H NMR (400 MHz, DMSO-d6) δ 8.84 (dd, J=14.0, 2.2 Hz, 1H), 8.64-8.52 (m, 1H), 8.23 (d, J=2.1 Hz, 1H), 8.14 (d, J=7.8 Hz, 1H), 8.05 (d, J=6.7 Hz, 1H), 7.65-7.54 (m, 2H), 7.46 (d, J=9.5 Hz, 1H), 7.43-7.38 (m, 1H), 7.38-7.31 (m, 2H), 7.28-7.21 (m, 2H), 7.21-7.15 (m, 3H), 6.48 (d, J=6.9 Hz, 1H), 5.48 (q, J=7.7 Hz, 1H), 4.68 (d, J=2.0 Hz, 2H), 4.50 (dd, J=6.2, 4.5 Hz, 3H), 4.41 (dd, J=6.7, 3.4 Hz, 2H), 2.12 (dt, J=14.5, 7.4 Hz, 1H), 2.04-1.78 (m, 1H), 0.94 (t, J=7.3 Hz, 3H).

ES/MS 581.2 (M+H⁺).

Example 5 Procedure 5

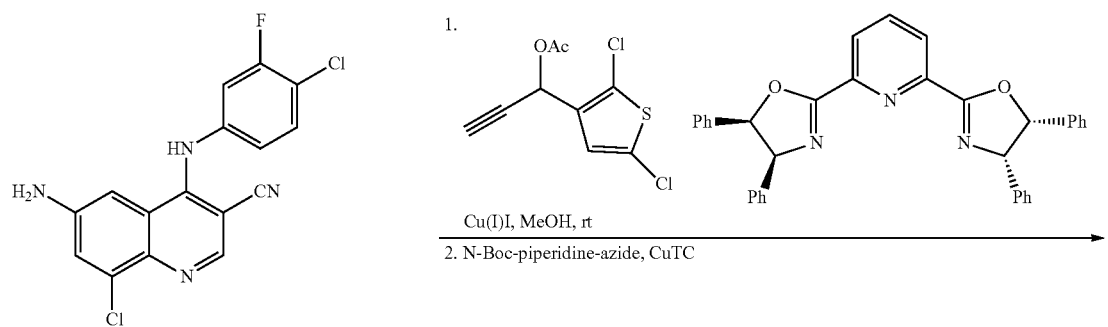

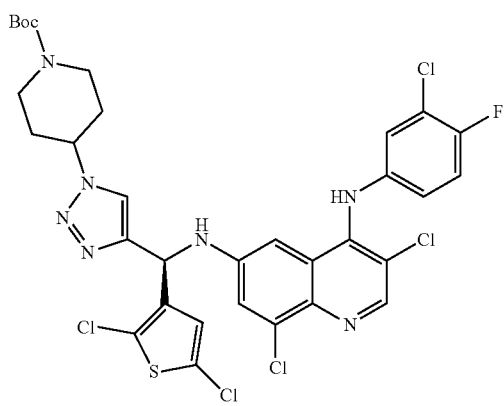

i. HCl, Dioxane
ii. Acetaldehyde

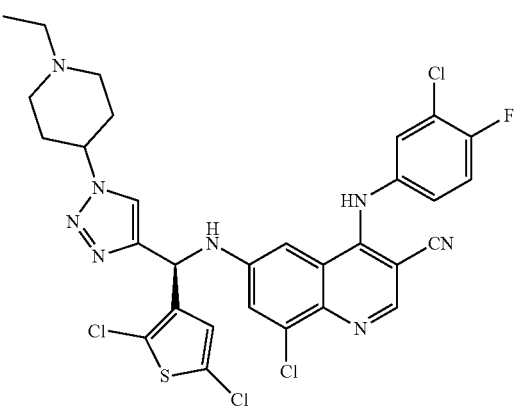

(R)-8-chloro-4-((3-chloro-4-fluorophenyl)amino)-6-((1-(2,5-dichlorothiophen-3-yl)prop-2-yn-1-yl)amino)quinoline-3-carbonitrile: CuI (4.1 mg, 0.022 mmol) and 2,6-bis((4S,5R)-4,5-diphenyl-4,5-dihydrooxazol-2-yl)pyridine [oxazoline ligand] (13.5 mg, 0.026 mmol) were sonicated in MeOH (1 mL) for ~5 minutes. Additional MeOH (4 mL) was added. Alkynyl acetate (150.7 mg, 0.61 mmol), 6-amino-8-chloro-4-((4-chloro-3-fluorophenyl)amino)quinoline-3-carbonitrile (150 mg, 0.43 mmol), and di-isopropyl ethyl amine (67 mg, 0.52 mmol) were added and the reaction was stirred at −15° C. for 4 days. The solvents were removed in vacuo. The crude reaction product was purified via silica gel chromatography (eluent: EtOAc/hexanes) to yield the product.

1H NMR (400 MHz, DMSO-d6) δ 9.51 (s, 1H), 8.45 (s, 1H), 7.54 (dd, J=6.4, 2.4 Hz, 2H), 7.43 (t, J=9.0 Hz, 1H), 7.38 (d, J=2.3 Hz, 1H), 7.30 (d, J=4.3 Hz, 1H), 7.27 (s, 1H), 7.11 (d, J=8.6 Hz, 1H), 5.54 (dd, J=8.6, 2.2 Hz, 1H), 3.51 (d, J=2.2 Hz, 1H).

ES/MS 534.9 (M+H$^+$).

(S)-tert-butyl 4-(4-(((8-chloro-4-((3-chloro-4-fluorophenyl)amino)-3-cyanoquinolin-6-yl)amino)(2,5-dichlorothiophen-3-yl)methyl)-1H-1,2,3-triazol-1-yl)piperidine-1-carboxylate: (R)-8-chloro-4-((3-chloro-4-fluorophenyl)amino)-6-((1-(2,5-dichlorothiophen-3-yl)prop-2-yn-1-yl)amino)quinoline-3-carbonitrile (174 mg, 0.324 mmol) and N-Boc piperidine 4 azide (73.4 mg, 0.324 mmol) were dissolved in THF (5 mL). Copper thiophenecarboxylate (6.2 mg, 0.032 mmol) was added and the reaction was stirred at room temperature for 16 hrs. The volatiles were removed under reduced pressure and the residue was purified by chromatography on silica gel (eluent: EtOAc/hexanes). The fractions containing product were combined and the solvent was removed under reduced pressure, providing the product.

1H NMR (400 MHz, DMSO-d6) δ 9.41 (s, 1H), 8.47 (s, 1H), 8.16 (s, 1H), 7.60 (d, J=2.2 Hz, 1H), 7.40-7.33 (m, 2H), 7.27 (d, J=8.3 Hz, 1H), 7.14 (dd, J=7.1, 2.0 Hz, 2H), 7.10 (s, 1H), 5.96 (d, J=8.2 Hz, 1H), 4.72-4.59 (m, 1H), 4.01 (q, J=9.1, 8.1 Hz, 3H), 2.86 (d, J=17.5 Hz, 2H), 1.96 (d, J=5.0 Hz, 3H), 1.77 (qd, J=12.2, 4.4 Hz, 2H), 1.39 (s, 9H).

ES/MS 762.9 (M+H$^+$).

Alternatively, the cycloaddition can be performed in a one-pot fashion using the Cu(I) present from the N-alkylation.

(S)-8-chloro-4-((3-chloro-4-fluorophenyl)amino)-6-(((2,5-dichlorothiophen-3-yl)(1-(piperidin-4-yl)-1H-1,2,3-triazol-4-yl)methyl)amino)quinoline-3-carbonitrile: (S)-tert-butyl 4-(4-(((8-chloro-4-((3-chloro-4-fluorophenyl)amino)-3-cyanoquinolin-6-yl)amino)(2,5-dichlorothiophen-3-yl)methyl)-1H-1,2,3-triazol-1-yl)piperidine-1-carboxylate (157 mg, 0.206 mmol) was suspended in DCM (0.5 mL). HCl in dioxane (5 mL; 4M) was added and the reaction was stirred at room temperature for 30 minutes. The solvents were removed under reduced pressure. The residue was subjected to flash chromatography (eluent: (20% MeOH in EtOAc)/hexanes). The fractions containing product were combined and the solvent was removed under reduced pressure. The residue was taken up in EtOAc/aqueous saturated sodium bicarbonate solution. The organic layer was isolated and dried over sodium sulfate. Filtration and evaporation of the solvent in vacuo gave the product.

1H NMR (400 MHz, DMSO-d6) δ 9.41 (s, 1H), 8.45 (s, 1H), 8.10 (s, 1H), 7.59 (d, J=2.1 Hz, 1H), 7.37 (t, J=8.9 Hz, 2H), 7.26 (d, J=8.1 Hz, 1H), 7.13 (d, J=10.0 Hz, 3H), 5.96 (d, J=8.2 Hz, 1H), 4.48 (tt, J=11.8, 4.3 Hz, 1H), 3.75-3.62 (m, 1H), 3.55 (s, 1H), 3.46 (dq, J=9.7, 5.2 Hz, 1H), 2.99 (d, J=12.2 Hz, 2H), 2.55 (td, J=12.5, 2.4 Hz, 2H), 1.92 (dd, J=11.9, 3.7 Hz, 2H), 1.75 (t, J=12.0 Hz, 3H).

ES/MS 662.1 (M+H$^+$).

(S)-8-chloro-4-((3-chloro-4-fluorophenyl)amino)-6-(((2,5-dichlorothiophen-3-yl)(1-(1-ethylpiperidin-4-yl)-1H-1,2,3-triazol-4-yl)methyl)amino)quinoline-3-carbonitrile: (S)-8-chloro-4-((3-chloro-4-fluorophenyl)amino)-6-(((2,5-dichlorothiophen-3-yl)(1-(piperidin-4-yl)-1H-1,2,3-triazol-4-yl)methyl)amino)quinoline-3-carbonitrile (138 mg, 0.208 mmol) was dissolved in THF (3 mL) and dichloro ethane (3 mL). Acetaldehyde (91.8 mg, 2.08 mmol) and sodium triacetoxy borohydride (176 mg, 0.833 mmol) were added and the reaction was stirred at room temperature for 1 hr. The reaction was diluted with EtOAc and washed with aqueous sodium bicarbonate solution, brine, and was dried over sodium sulfate. The crude material was filtered and the volatiles were removed in vacuo and the crude was purified via chromatography on silica get (eluent: MeOH (20%) in EtOAc/hexanes) to yield the product.

1H NMR (400 MHz, DMSO-d6) δ 9.41 (s, 1H), 8.47 (s, 1H), 8.14 (s, 1H), 7.60 (d, J=2.3 Hz, 1H), 7.41-7.34 (m, 2H), 7.27 (d, J=8.2 Hz, 1H), 7.15 (dd, J=9.1, 3.3 Hz, 2H), 7.12 (s, 1H), 5.96 (d, J=8.1 Hz, 1H), 4.50-4.32 (m, 1H), 3.00-2.83 (m, 2H), 2.42-2.25 (m, 2H), 2.18-1.81 (m, 6H), 0.98 (t, J=7.2 Hz, 3H).

ES/MS 689.9 (M+H$^+$).

Example 6 Procedure 6

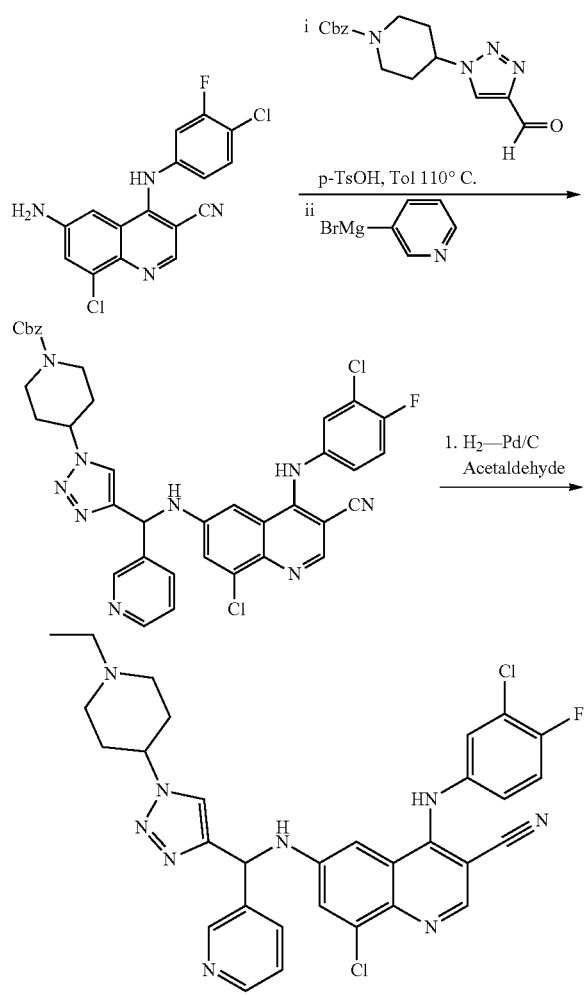

Benzyl 4-(4-(((8-chloro-4-((3-chloro-4-fluorophenyl) amino)-3-cyanoquinolin-6-yl)amino)(3-pyridyl)methyl)-1H-1,2,3-triazol-1-yl)piperidine-1-carboxylate: A suspension of the 6-amino-8-chloro-4-((4-chloro-3-fluorophenyl) amino)quinoline-3-carbonitrile (159 mg, 0.51 mmol), aldehyde (176 mg, 0.51 mmol) and pTSA (9.6 mg, 0.05 mmol) in toluene (12 mL) was heated at reflux (50 mL RBF equipped with a Hickman still). After 4 hrs, the solvent was removed under reduced pressure. The solid was dissolved in methyl-THF and 3-pyridylmagnesium bromide (2.03 mmol; 8.1 mL 0.25-M Me-THF) was added dropwise at −10 C. After 130 min, the reaction was quenched with sat NH$_4$Cl (3 mL). The layers were separated and the aqueous phase was extracted with EtOAc (15 mL). The combined organic layers were washed with brine (5 mL), dried over sodium sulfate and concentrated. The residue was subjected to flash chromatography on silica gel (eluent: EtOAc/hexanes). The fractions containing product were combined and the solvent was removed providing the product.

8-chloro-4-((3-chloro-4-fluorophenyl)amino)-6-(((1-(1-ethylpiperidin-4-yl)-1H-1,2,3-triazol-4-yl)(pyridin-3-yl) methyl)amino)quinoline-3-carbonitrile: Benzyl 4-(4-(((8-chloro-4-((3-chloro-4-fluorophenyl)amino)-3-cyanoquinolin-6-yl)amino)(pyridin-3-yl)methyl)-1H-1,2,3-triazol-1-yl)piperidine-1-carboxylate (57 mg, 0.079 mmol) Acetaldehyde (34.7 mg, 0.79 mmol) and Pd—C (25 mg, 10%) in EtOH (3 mL)/EtOAc (2 mL) were stirred under an atmosphere of hydrogen. After 43 hrs, the reaction was filtered and the volatiles were removed in vacuo and the crude was purified via RP-HPLC (eluent: water/MeCN 0.1% TFA) to yield the product as trifluoro acetate salt.

$^1$H NMR (400 MHz, DMSO-d$_6$) δ 9.41 (s, 1H), 8.74 (d, J=2.2 Hz, 1H), 8.54 (dd, J=5.0, 1.5 Hz, 1H), 8.41 (s, 1H), 8.13 (s, 1H), 8.00 (d, J=8.0 Hz, 1H), 7.67 (d, J=2.2 Hz, 1H), 7.49 (tt, J=6.8, 3.7 Hz, 3H), 7.42 (t, J=9.0 Hz, 1H), 7.26 (d, J=2.5 Hz, 1H), 7.25-7.21 (m, 1H), 6.20 (d, J=7.8 Hz, 2H), 4.79-4.69 (m, 1H), 3.61 (d, J=12.4 Hz, 2H), 3.26-2.98 (m, 4H), 2.34 (d, J=13.9 Hz, 2H), 2.15 (q, J=12.5, 11.6 Hz, 2H), 1.22 (t, J=7.3 Hz, 3H).

ES/MS: 616.1 (M+H$^+$).

Compounds of this sequence can be separated into the respective stereoisomers via appropriate means (eg. chromatography with chiral stationary phase, crystallography) after the C6 N-alkylation has been performed.

Removal of the protecting group in the absence of a reaction partner yields the corresponding un-alkylated amine derivatives.

Example 7 Procedure 7

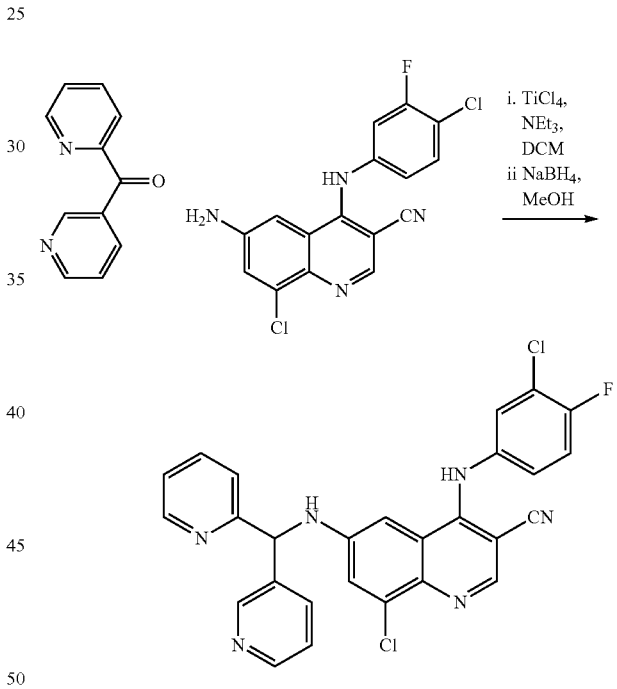

8-chloro-4-((3-chloro-4-fluorophenyl)amino)-6-((pyridin-2-yl)pyridin-3-yl)methyl)amino)quinoline-3-carbonitrile: To a suspension of the 6-amino-8-chloro-4-((4-chloro-3-fluorophenyl)amino)quinoline-3-carbonitrile (50 mg, 0.144 mmol) and pyridin-2-yl(pyridin-3-yl)methanone (27 mg, 0.144 mmol) in DCM (1 mL) was added triethylamine (35 mg, 0.346 mmol) followed by TiCl$_4$ in DCM (0.086 mmol/0.086 mL). The reaction was stirred overnight at room temperature. It was diluted with MeOH (2 mL) and sodium borohydride (16 mg, 0.432 mmol) was added. The reaction was stirred for 2 hours, then was diluted with water and treated with 1M NaOH until a pH of ~13 was reached. Solids were removed via filtration and washed with DCM. The combined organic layers were dried over sodium sulfate, filtered, and concentrated. The product was purified by chromatography on silica gel (eluent: EtOAc/hexanes) to yield the product after lyophilization from water/MeCN.

1H NMR (400 MHz, DMSO-d6) δ 9.42 (s, 1H), 8.66 (dd, J=2.4, 0.8 Hz, 1H), 8.56 (ddd, J=4.9, 1.8, 0.9 Hz, 1H), 8.47-8.39 (m, 2H), 7.87-7.75 (m, 3H), 7.61-7.19 (m, 8H), 6.08 (d, J=8.7 Hz, 1H).

ES/MS: 515.1 (M+H⁺).

Example 8 Procedure 8

(S)-8-chloro-4-((5,6-difluoropyridin-3-yl)amino)-6-(((1-isopropyl-1H-1,2,3-triazol-4-yl)(pyridin-3-yl)methyl)amino)quinoline-3-carbonitrile): Made from 6-amino-8-chloro-4-((5,6-difluoropyridin-3-yl)amino)quinoline-3-carbonitrile by step-3 of general procedure 1. ES/MS 532.1 (M+H⁺).

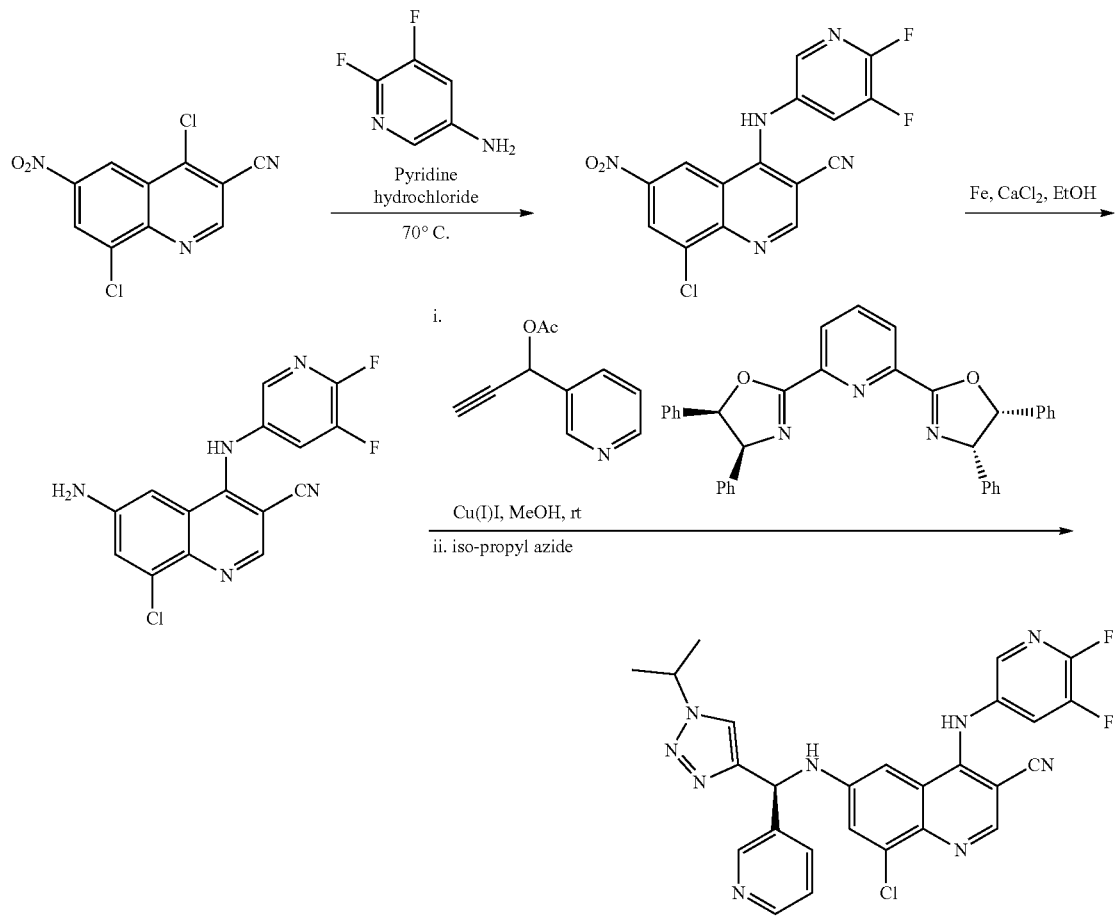

8-chloro-4-((5,6-difluoropyridin-3-yl)amino)-6-nitroquinoline-3-carbonitrile: 4,8-dichloro-6-nitroquinoline-3-carbonitrile (1.4 g, 5.22 mmol), 2,6-difluoropyridin-3-amine (755 mg, 5.74 mmol) and pyridine hydrochloride (1.8 g, 15.6 mmol) in iso-propanol (40 mL) was heated at 70° C. overnight. The reaction was cooled to room temperature. Water was added and the resulting precipitate was collected via filtration. The crude product was used in the next step without further purification. ES/MS 362.0 (M+H⁻).

6-amino-8-chloro-4-((5,6-difluoropyridin-3-yl)amino)quinoline-3-carbonitrile: Made from 8-chloro-4-((5,6-difluoropyridin-3-yl)amino)-6-nitroquinoline-3-carbonitrile via step-2 of general procedure 1. ES/MS 332.0 (M+H⁺).

Example 9 Procedure 9

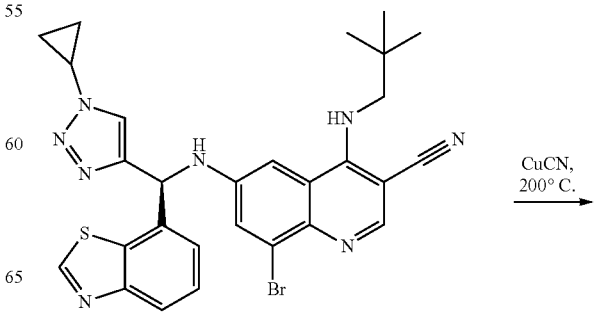

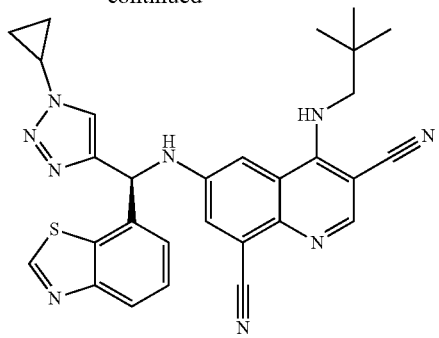

(S)-6-((benzo[d]thiazol-7-yl(1-cyclopropyl-1H-1,2,3-triazol-4-yl)methyl)amino)-4-(neopentylamino)quinoline-3,8-dicarbonitrile ( ): DMF (2 mL) was added to (S)-6-((benzo[d]thiazol-7-yl(1-cyclopropyl-1H-1,2,3-triazol-4-yl)methyl)amino)-8-bromo-4-(neopentylamino)quinoline-3-carbonitrile (38 mg, 0.064 mmol) and CuCN (41 mg, 0.46 mmol) in a microwave vial. The vial was heated to 200° C. for 15 minutes in a microwave and allowed to cool to room temperature. The reaction mixture was poured into water (4 mL) and extracted with EtOAc (3×8 mL). The combined organic phases were washed with brine (5 mL), dried over MgSO$_4$ and concentrated. The crude residue was purified by RP-HPLC (eluent: water/MeCN*0.1% TFA) to yield the product as trifluoro acetate salt. $^1$H NMR (400 MHz, Methanol-d$_4$) δ 9.20 (s, 1H), 8.34 (s, 1H), 8.05 (dd, J=7.3, 1.9 Hz, 1H), 7.86 (d, J=2.5 Hz, 1H), 7.82 (s, 1H), 7.64-7.54 (m, 2H), 7.16 (d, J=2.6 Hz, 1H), 6.34 (s, 1H), 3.97 (d, J=13.7 Hz, 1H), 3.91-3.80 (m, 1H), 3.49 (d, J=13.7 Hz, 1H), 1.23-1.07 (m, 4H), 0.81 (s, 9H). ES/MS 534.1 (M+H$^+$).

Alternative Introduction of the 8 Cyano Group

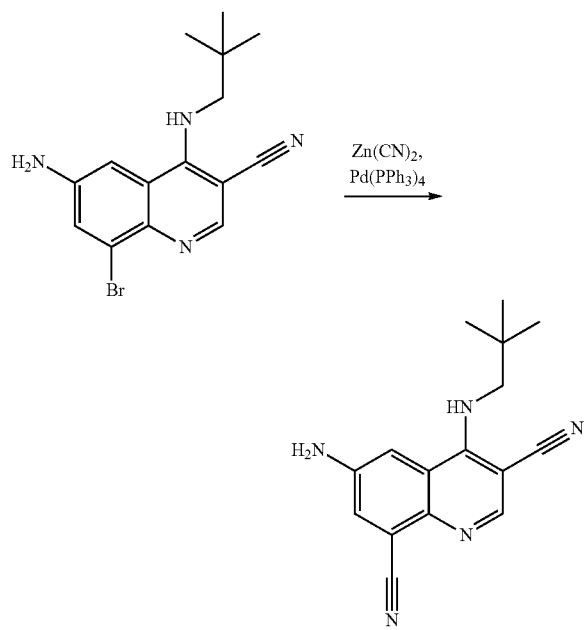

6-amino-4-(neopentylamino)quinoline-3,8-dicarbonitrile: Solid Zn(CN)$_2$ (211 mg, 1.8 mmol) and Pd(PPh)$_4$ (35 mg, 0.03 mmol) were added to a solution of 6-amino-8-bromo-4-(neopentylamino)quinoline-3-carbonitrile (500 mg, 1.5 mmol) in NMP (20 mL). The resulting mixture was degased by bubbling argon gas through for 5 min. The reaction vessel was sealed then heated to 120° C. for 16 h. The reaction mixture was cooled then loaded directly to silica column to afford the pure nitrile. ES/MS 280.3 (M+H$^+$).

Further elaboration to final compound according to procedures outlined in this document Example 10 Procedure 10

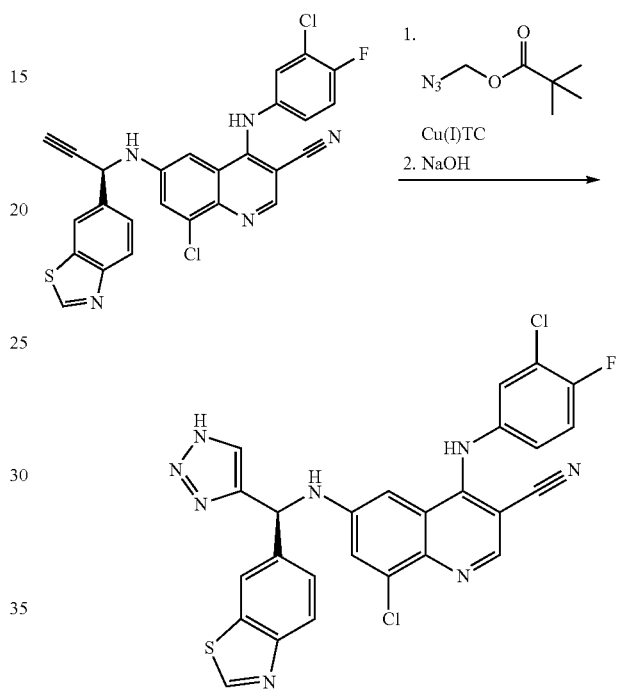

(S)-6-((benzo[d]thiazol-6-yl(1H-1,2,3-triazol-4-yl)methyl)amino)-8-chloro-4-((3-chloro-4-fluorophenyl)amino)quinoline-3-carbonitrile: (R)-6-((1-(benzo[d]thiazol-6-yl)prop-2-yn-1-yl)amino)-8-chloro-4-((3-chloro-4-fluorophenyl)amino)quinoline-3-carbonitrile (40.0 mg, 0.077 mmol) was dissolved in THF (2 mL). Cu(I)-thiophene-2-carboxylate (4.4 mg, 0.023 mmol) and azidomethyloxy pivalate (0.018 mL, 0.12 mmol) were added and the resulting solution stirred at room temperature for 30 minutes. The reaction contents were poured into saturated aqueous NaHCO$_3$ solution (5 mL) and extracted with EtOAc (3×8 mL). The combined organic layers were washed with brine (5 mL), dried over MgSO$_4$ and concentrated. The resulting crude residue was then dissolved in MeOH (2 mL). NaOH (1.0M in water, 0.17 mL, 0.17 mmol) was added and the reaction allowed to stir at room temperature for 30 min. HCl (1.0M in water, 0.17 mL, 0.17 mmol) was then added, the resulting solution poured into water (5 mL) and extracted with EtOAc (3×8 mL). The combined organic layers were washed with brine (5 mL), dried over MgSO$_4$ and concentrated. The resulting crude residue was purified by RP-HPLC (eluent: water/MeCN*0.1% TFA) to yield the product as trifluoro acetate salt.

ES/MS 561.0 (M+H$^+$).

Example 11 Procedure 11

8-chloro-6-[[(S)-(1-cyclopropyltriazol-4-yl)-deuterio-(6-fluoropyridin-3-yl)methyl]amino]-4-[[(1R)-3-fluoro-1-phenylpropyl]amino]quinoline-3-carbonitrile

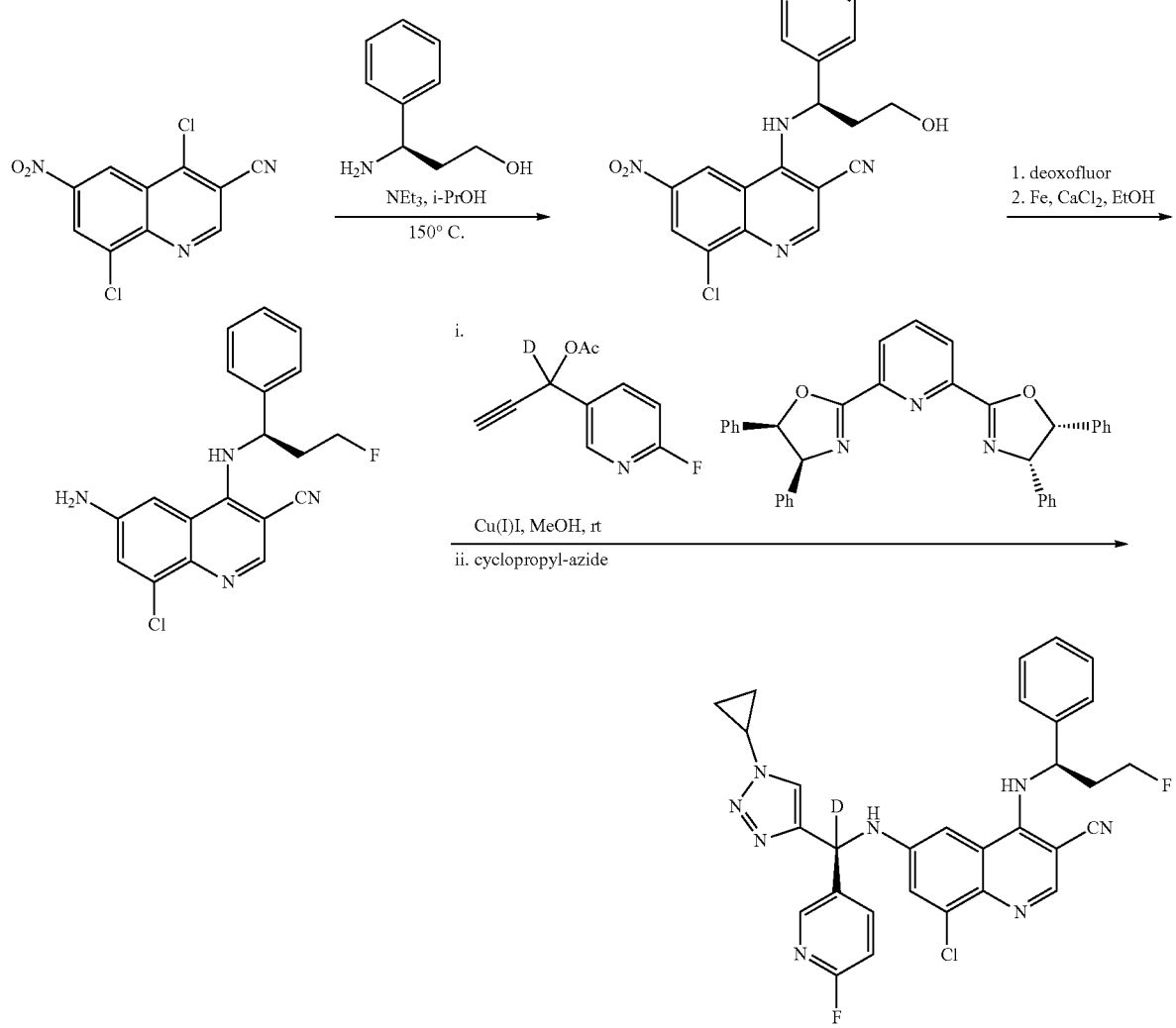

room temperature for 16 hours. The reaction mixture was cooled in an ice bath and carefully quenched with saturated sodium bicarbonate solution, then extracted with ethyl acetate. The organic phase was dried over sodium sulfate, filtered and concentrated to give the crude product (115 mg) which was used without further purification.

ES/MS 385.1 (M+H$^+$).

(R)-8-chloro-4-((3-hydroxy-1-phenylpropyl)amino)-6-nitroquinoline-3-carbonitrile: 4,8-dichloro-6-nitroquinoline-3-carbonitrile (400 mg, 1.49 mmol), (R)-3-amino-3-phenylpropan-1-ol (270.76 mg, 1.79 mmol) in iso-propanol (1.5 mL) were heated under microwave conditions at 150° C. for 45 minutes. The reaction was cooled to room temperature. Water and Et$_2$O were added. The aqueous layer was extracted with Et$_2$O and the combined organic layers were dried over sodium sulfate. Filtration and evaporation of solvents yielded the crude product which was used in the next step without further purification.

ES/MS 383.1 (M+H$^+$).

(R)-8-chloro-4-((3-fluoro-1-phenylpropyl)amino)-6-nitroquinoline-3-carbonitrile: (R)-8-chloro-4-((3-hydroxy-1-phenylpropyl)amino)-6-nitroquinoline-3-carbonitrile (100 mg, 0.26 mmol) was treated with Deoxofluor® (0.6 mL) at (R)-6-amino-8-chloro-4-((3-fluoro-1-phenylpropyl)amino)quinoline-3-carbonitrile: (R)-8-chloro-4-((3-fluoro-1-phenylpropyl)amino)-6-nitroquinoline-3-carbonitrile (115 mg, 0.3 mmol), Calcium chloride dihydrate (66 mg, 0.45 mmol), and iron powder (83 mg, 1.49 mmol) were heated in ethanol (3 mL)/water (0.3 mL) at 60° C. for 12 hours. The reaction was cooled to room temperature and solids were removed via filtration. The solids were washed with EtOAc and the combined organic layers were washed with aqueous sodium bicarbonate solution, brine, and were dried over sodium sulfate. Filtration and evaporation of all volatiles yielded the product.

ES/MS 355.0 (M+H$^+$).

8-chloro-6-(((S)-(1-cyclopropyl-1H-1,2,3-triazol-4-yl)(4-fluorophenyl)methyl)amino)-4-(((R)-3-fluoro-1-phenylpropyl)amino)quinoline-3-carbonitrile: (R)-6-amino-8-chloro- 4-((3-fluoro-1-phenylpropyl)amino)quinoline-3-carbonitrile (50 mg, 0.14 mmol), CuI (1.4 mg, 0.05 eq) and 2,6-bis((4S,5R)-4,5-diphenyl-4,5-dihydrooxazol-2-yl)pyridine [oxazoline ligand] (4.4 mg,0.06 eq) were sonicated in MeOH (2.0 mL) for ~1 minute. Alkynyl acetate (68 mg, 0.35 mmol) and di-isopropyl ethyl amine (22 mg, 0.17 mmol) were added and the reaction was stirred overnight. Cyclopropylazide (16 mg) was added and the reaction was stirred for additional 16 hrs at room temperature. Solvents were removed in vacuo and the crude material was purified by RP-HPLC (eluent: water/MeCN*0.1% TFA) to yield the product as trifluoroacetate salt.

ES/MS 572.0 (M+H$^+$).

Example 12 Procedure 12

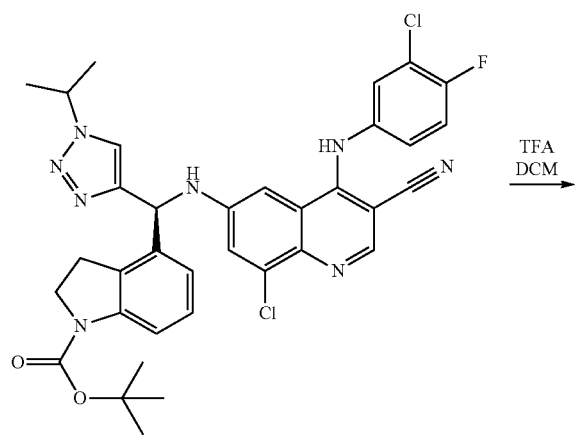

(S)-8-chloro-4-((3-chloro-4-fluorophenyl)amino)-6-((indolin-4-yl(1-isopropyl-1H-1,2,3-triazol-4-yl)methyl)amino)quinoline-3-carbonitrile: (S)-tert-butyl 4-(((8-chloro-4-((3-chloro-4-fluorophenyl)amino)-3-cyanoquinolin-6-yl)amino)(1-isopropyl-1H-1,2,3-triazol-4-yl)methyl)indoline-1-carboxylate (45 mg, 0.065 mmol) was dissolved in DCM and trifluoroacetic acid and stirred at room temperature. After 30 minutes the reaction mixture was concentrated to dryness and the residue purified by RP-HPLC (eluent: water/MeCN*0.1% TFA) to yield the product as trifluoro acetate salt.

ES/MS 586.9 (M+H$^+$).

Example 13 Procedure 13

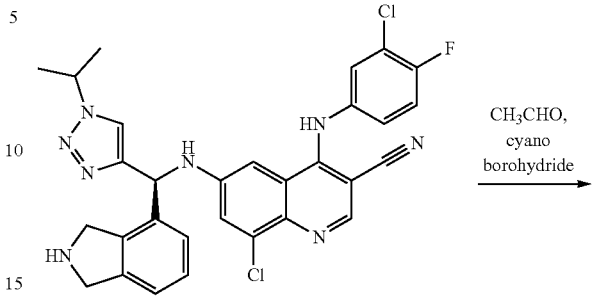

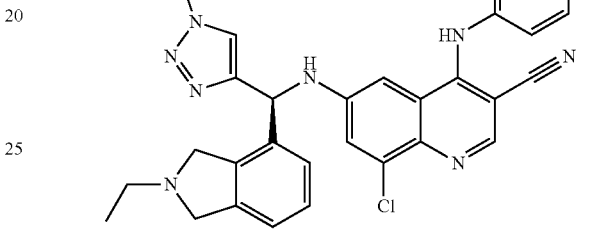

(S)-6-(((1-(1-(tert-butyl)piperidin-4-yl)-1H-1,2,3-triazol-4-yl)(2-ethylisoindolin-4-yl)methyl)amino)-8-chloro-4-((3-chloro-4-fluorophenyl)amino)quinoline-3-carbonitrile: (S)-6-(((1-(1-(tert-butyl)piperidin-4-yl)-1H-1,2,3-triazol-4-yl)(isoindolin-4-yl)methyl)amino)-8-chloro-4-((3-chloro-4-fluorophenyl)amino)quinoline-3-carbonitrile (80.0 mg, 0.12 mmol) was dissolved in MeOH (3 mL) and AcOH (1 mL) at room temperature. Acetaldehyde (0.066 mL, 1.17 mmol) and polymer bound PS—CNBH$_3$ (467 mg, 1.17 mmol) were then added and the reaction stirred at room temperature. After 1 hour additional acetaldehyde (0.066 mL, 1.17 mmol) and polymer bound PS—CNBH$_3$ (467 mg, 1.17 mmol) were added. After 1 additional hour the PS—CNBH$_3$ was removed via vacuum filtration and the filtrate concentrated to dryness. The resulting crude residue was purified by RP-HPLC (eluent: water/MeCN*0.1% TFA) to yield the product as trifluoro acetate salt.

ES/MS 712.1 (M+H$^+$).

Example 14 Procedure 14

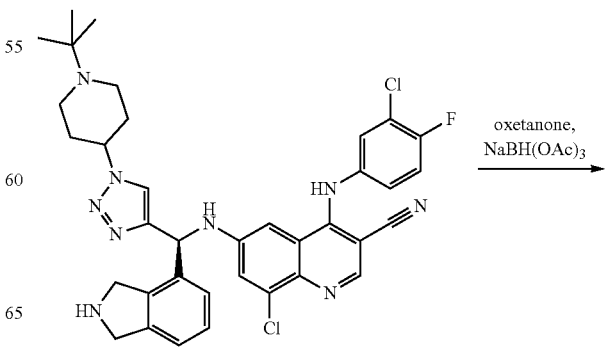

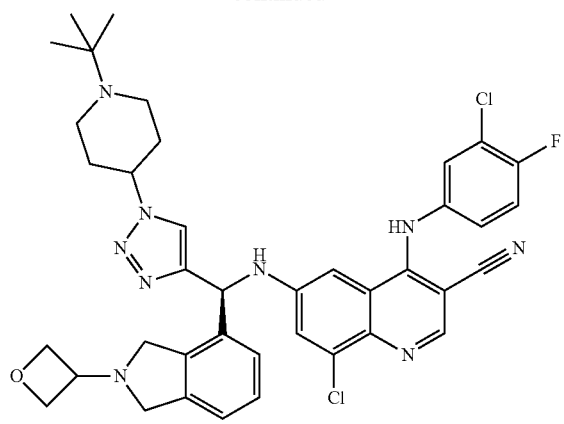

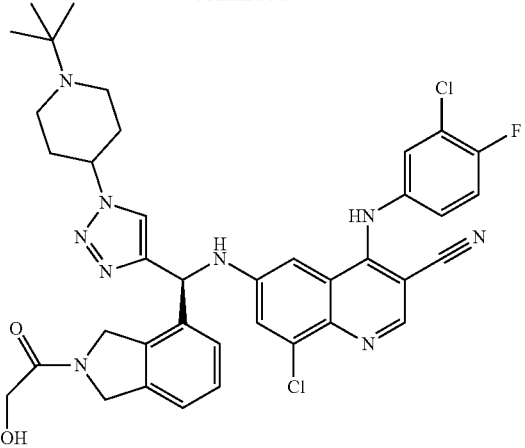

(S)-6-(((1-(1-(tert-butyl)piperidin-4-yl)-1H-1,2,3-triazol-4-yl)(2-(oxetan-3-yl)isoindolin-4-yl)methyl)amino)-8-chloro-4-((3-chloro-4-fluorophenyl)amino)quinoline-3-carbonitrile: (S)-6-(((1-(1-(tert-butyl)piperidin-4-yl)-1H-1,2,3-triazol-4-yl)(isoindolin-4-yl)methyl)amino)-8-chloro-4-((3-chloro-4-fluorophenyl)amino)quinoline-3-carbonitrile (15 mg, 0.022 mmol) was dissolved in a 1:1 mixture of THF and DCE after which oxetanone (0.007 mL, 0.11 mmol) and sodium triacetoxyborohydride (23.2 mg, 0.11 mmol) were added. After 1.5 hours the reaction mixture was poured into saturated aqueous NaHCO₃ and extracted with EtOAc. The combined organic phases were washed with brine, dried over MgSO₄ and concentrated. The crude residue was purified by RP-HPLC (eluent: water/MeCN*0.1% TFA) to yield the product as trifluoro acetate salt.

ES/MS 740.0 (M+H⁺).

Example 15 Procedure 15

(S)-6-(((1-(1-(tert-butyl)piperidin-4-yl)-1H-1,2,3-triazol-4-yl)(2-(2-hydroxyacetyl)isoindolin-4-yl)methyl)amino)-8-chloro-4-((3-chloro-4-fluorophenyl)amino)quinoline-3-carbonitrile: (S)-6-((1-(1-(tert-butyl)piperidin-4-yl)-1H-1,2,3-triazol-4-yl)(isoindolin-4-yl)methyl)amino)-8-chloro-4-((3-chloro-4-fluorophenyl)amino)quinoline-3-carbonitrile (10.0 mg, 0.015 mmol) was dissolved in DMF (1 mL) after which glycolic acid (5.6 mg, 0.073 mmol), diisopropylethylamine (0.008 mL, 0.044 mmol) and HATU (7.1 mg, 0.022 mmL) were added at room temperature. The reaction mixture was stirred for 20 minutes at which point it was poured into water (4 mL) and extracted with EtOAc (3×8 mL). The combined organic phases were washed with brine (5 mL), dried over MgSO₄ and concentrated. The crude residue was purified by RP-HPLC (eluent: water/MeCN*0.1% TFA) to yield the product as trifluoro acetate salt.

ES/MS 742.1 (M+H⁺).

Example 16 Procedure 16

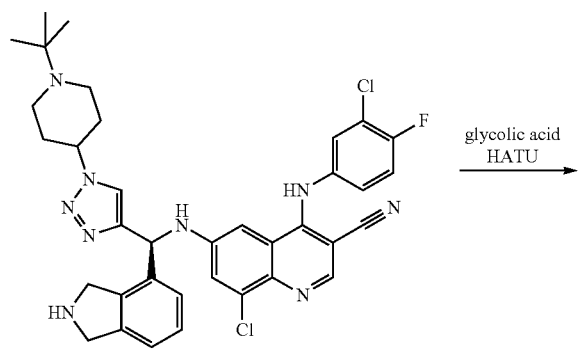

glycolic acid
HATU

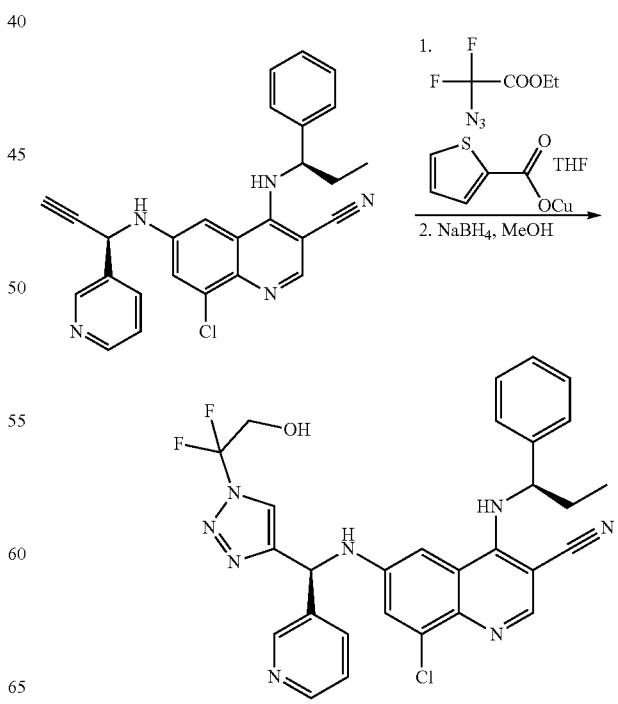

8-chloro-6-(((S)-(1-(1,1-difluoro-2-hydroxyethyl)-1H-1,2,3-triazol-4-yl)(pyridin-3-yl)methyl)amino)-4-(((R)-1-phenylpropyl)amino)quinoline-3-carbonitrile Ethyl 2-azido-2,2-difluoroacetate (47 mg, 0.29 mmol) was added to a solution of 8-chloro-4-(((R)-1-phenylpropyl)amino)-6-(((R)-1-(pyridin-3-yl)prop-2-yn-1-yl)amino)quinoline-3-carbonitrile (130 mg, 0.26 mmol) and copper(I) thiophene-2-carboxylate (4.9 mg, 0.026 mmol) in THF (2 mL). After 1 h the solvent was removed under reduced pressure. The residue was taken up in methanol (6 mL) and sodium borohydride (19.5 mg, 0.52 mmol) was added to the solution. After 1 h the reaction was quenched with water and extracted with ethyl acetate (3×10 mL). The combined organic phases were washed with brine, dried over sodium sulfate and concentrated. The residue was subjected to flash chromatography (0-100% (20% methanol in ethyl acetate) vs hexanes). The fractions containing product were combined and the solvent was removed under reduced pressure. The residue was taken up in methanol/water with two drops of trifluoroacetic acid and subjected to preparative HPLC eluted with acetonitrile/water with 0.1% trifluoroacetic acid. Fractions containing product were combined and subjected to lyophilization, providing 8-chloro-6-(((S)-(1-(1,1-difluoro-2-hydroxyethyl)-1H-1,2,3-triazol-4-yl)(pyridin-3-yl)methyl)amino)-4-(((R)-1-phenylpropyl)amino)quinoline-3-carbonitrile.

$^1$H NMR (400 MHz, DMSO-d6) δ 8.92-8.83 (m, 1H), 8.67 (d, J=9.5 Hz, 1H), 8.65-8.58 (m, 1H), 8.24 (d, J=3.3 Hz, 1H), 8.15 (d, J=7.7 Hz, 1H), 7.64-7.56 (m, 2H), 7.52 (d, J=8.3 Hz, 1H), 7.42 (d, J=8.5 Hz, 1H), 7.39-7.29 (m, 2H), 7.29-7.16 (m, 6H), 6.54 (d, J=7.8 Hz, 1H), 5.47 (q, J=7.6 Hz, 1H), 4.32 (t, J=12.0 Hz, 2H), 2.11 (m, 1H), 2.04-1.83 (m, 1H), 0.93 (t, J=7.3 Hz, 3H).

ES/MS 575.1 (M+H$^+$).

Example 17 Procedure 17

(S)-6-(((1-(1-(tert-butyl)piperidin-4-yl)-1H-1,2,3-triazol-4-yl)(6-isopropoxypyridin-3-yl)methyl)amino)-8-chloro-4-((3-chloro-4-fluorophenyl)amino)quinoline-3-carbonitrile

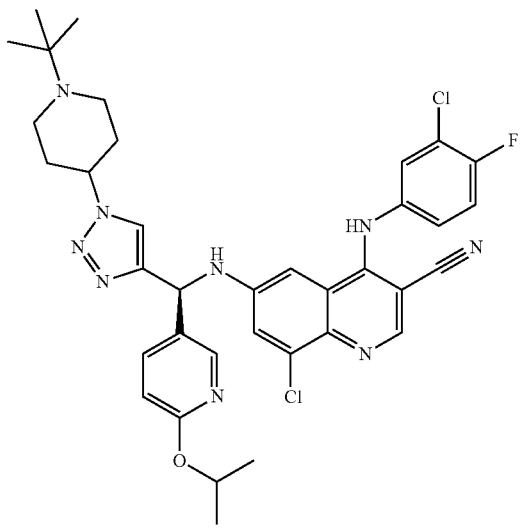

NaH (60% dispersion in mineral oil, 26.6 mg, 0.66 mmol) added to iPrOH (2 mL) at 0° C. for 20 minutes. (S)-6-(((1-(1-(tert-butyl)piperidin-4-yl)-1H-1,2,3-triazol-4-yl)(6-fluoropyridin-3-yl)methyl)amino)-8-chloro-4-((3-chloro-4-fluorophenyl)amino)quinoline-3-carbonitrile (22 mg, 0.033 mmol) in DMF (0.5 mL) then added to newly formed alkoxide. The cold bath was removed and the resulting solution heated to 70° C. for 1 hour. The reaction mixture was quenched by water (1 mL) and extracted with EtOAc (3×8 mL). The combined organic phases were then washed with brine (5 mL), dried over MgSO$_4$ and concentrated. The crude residue was purified by RP-HPLC (eluent: water/MeCN*0.1% TFA) to yield the product as trifluoro acetate salt.

Example 18 Procedure 18

(S)-6-(((1-(1-(tert-butyl)piperidin-4-yl)-1H-1,2,3-triazol-4-yl)(tetrahydro-2H-pyran-4-yl)methyl)amino)-8-chloro-4-((3-chloro-4-fluorophenyl)amino)quinoline-3-carbonitrile

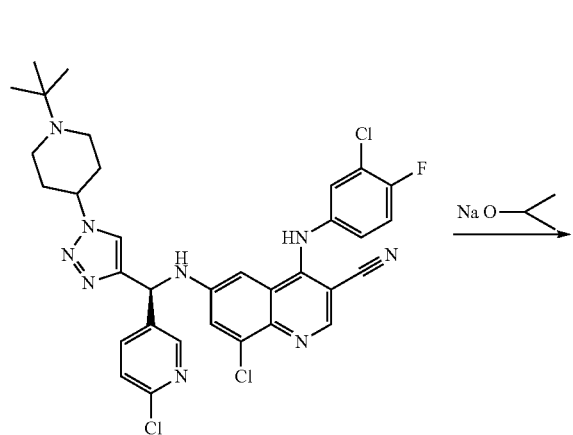

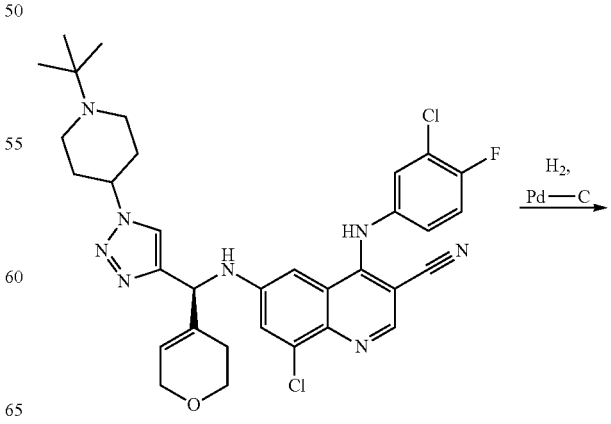

-continued

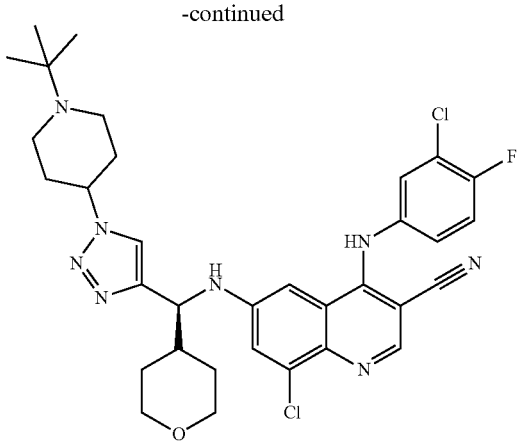

(S)-6-((1-(1-(tert-butyl)piperidin-4-yl)-1H-1,2,3-triazol-4-yl)(3,6-dihydro-2H-pyran-4-yl)methyl)amino)-8-chloro-4-((3-chloro-4-fluorophenyl)amino)quinoline-3-carbonitrile (20.0 mg, 0.023 mmol), 10% Pd/C (2.5 mg, 0.002 mmol) and EtOH (1.5 mL) were combined and H₂ was bubbled through the reaction mixture for 5 minutes. The reaction mixture was allowed to stir overnight under 1 atm of H₂ after which it was filtered through celite washing with EtOAc and EtOH. The filtrate was then concentrated and purified by RP-HPLC (eluent: water/MeCN*0.1% TFA) to yield the product as trifluoro acetate salt.

Example 19 Procedure 19

(S)-6-(((1-cyclopropyl-1H-1,2,3-triazol-4-yl)(3-oxoisoindolin-4-yl)methyl)amino)-4-(neopentylamino)quinoline-3,8-dicarbonitrile

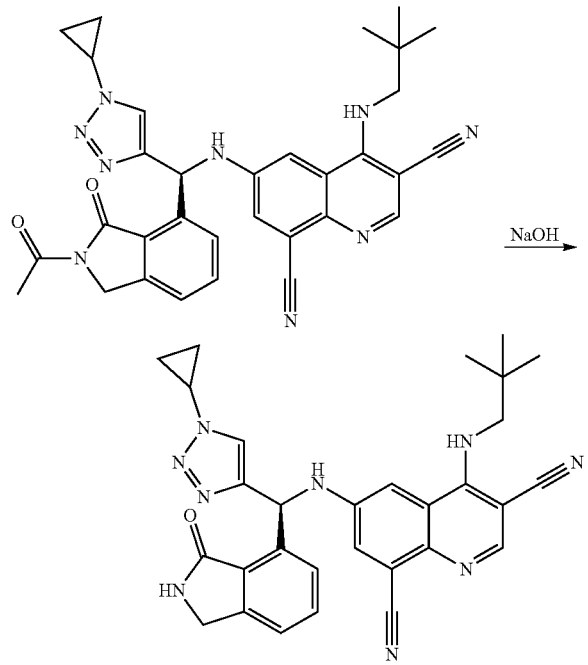

(S)-6-((2-acetyl-3-oxoisoindolin-4-yl)(1-cyclopropyl-1H-1,2,3-triazol-4-yl)methyl)amino)-4-(neopentylamino)

quinoline-3,8-dicarbonitrile (34 mg, 0.059 mmol) was dissolved in MeOH (2 mL) at room temperature. NaOH (1.0M aq, 0.30 mL, 0.30 mmol) was added and the reaction stirred for 30 minutes. HCl ((1.0M aq, 0.30 mL, 0.30 mmol) was added after which the reaction mixture was poured into water (3 mL) and extracted with EtOAc (3×8 mL). The combined organic phases were washed with brine (5 mL), dried over MgSO₄ and concentrated. The crude residue was purified by RP-HPLC (eluent: water/MeCN*0.1% TFA) to yield the product as trifluoro acetate salt.

Example 20 Procedure 20

8-chloro-4-(3-chloro-4-fluoroanilino)-6-[[(S)-[1-(1-ethylpiperidin-4-yl)triazol-4-yl]-(1,3-thiazol-4-yl)methyl]amino]quinoline-3-carbonitrile

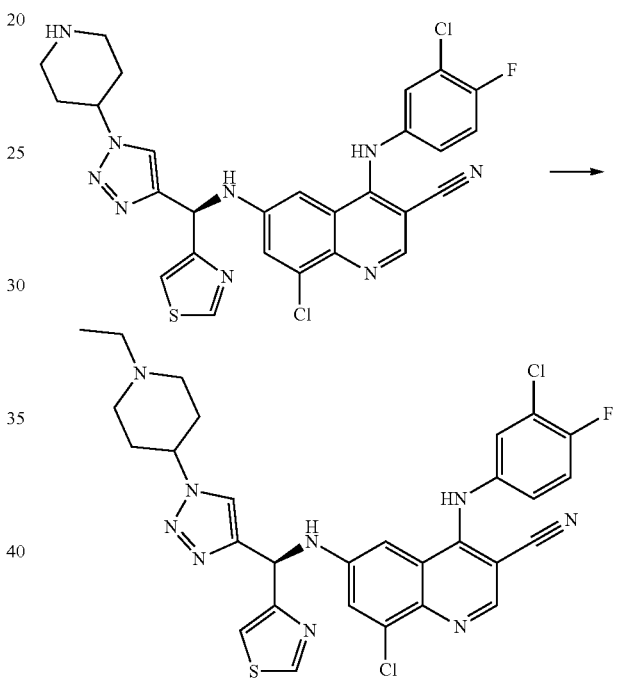

The title compound was prepared as conditions for the final step as follows: (S)-8-chloro-4-((3-chloro-4-fluorophenyl)amino)-6-(((1-(piperidin-4-yl)-1H-1,2,3-triazol-4-yl)(thiazol-4-yl)methyl)amino)quinoline-3-carbonitrile (74.31 mg, 0.13 mmol) was dissolved in 1.20 mL of 3:1 2-methyltetrahyrdofuran:acetic acid and treated with acetaldehyde (10.52 µl, 0.19 mmol) and PS—BH₃CN (polystyrene supported cyanoborohydride, 58 mg, 2.28 mmol/g). The mixture was stirred overnight. Additional acetaldehyde and 0.1 mL of methanol were added, and the reaction was complete in one hour. The resin was filtered and the resulting filtrate was concentrated, dissolved in dichloromethane, washed with saturated sodium bicarbonate, dried over sodium sulfate, filtered and concentrated. Purification using RP-HPLC (eluent: water/MeCN*0.1% TFA) provided the product as trifluoroacetate salt.

¹H NMR (400 MHz, CD₃OD) δ 9.02 (m, 1H), 8.46 (s, 1H), 8.01 (m, 1H), 7.68 (m, 1H), 7.60 (m, 1H), 7.52 (m, 1H), 7.33 (m, 4H), 6.31 (s, 1H), 3.75 (m, 2H), 3.25-3.13 (m, 3H), 2.45 (m, 2H), 2.36 (m, 2H), 2.25-2.01 (m, 2H), 1.37 (m, 3H), ES/MS 622.0 (M+H⁺)

Example 21 Procedure 21

8-chloro-4-(3-chloro-4-fluoroanilino)-6-[[(S)-(1-propan-2-yltriazol-4-yl)-[5-(pyrrolidine-1-carbonyl)pyridin-3-yl]methyl]amino]quinoline-3-carbonitrile

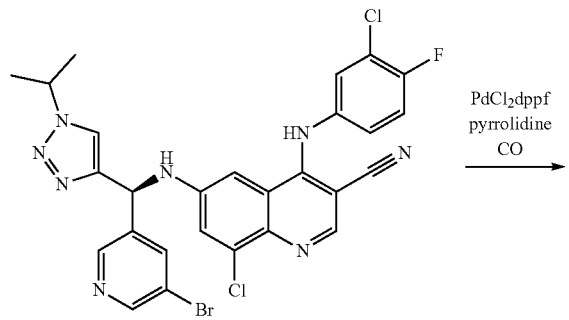

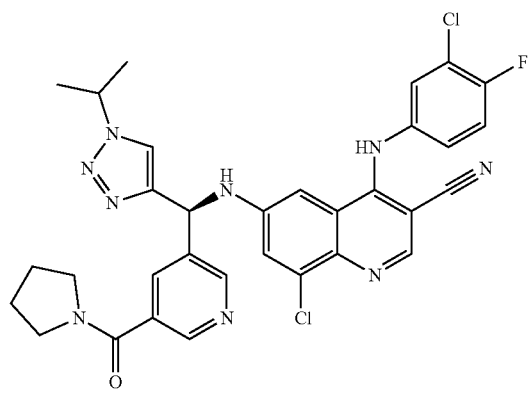

A mixture of (S)-6-(((5-bromopyridin-3-yl)(1-isopropyl-1H-1,2,3-triazol-4-yl)methyl)amino)-8-chloro-4-((3-chloro-4-fluorophenyl)amino)quinoline-3-carbonitrile (200 mg, 0.32 mmol), pyrrolidine (580.6 mg, 8.16 mmol), and Dichloro 1,1-bis(diphenylphosphino)ferrocene palladium (II) dichloromethane (269.1 mg, 0.32 mmol) in DMF (1.2 ml) was degassed and purged with carbon monoxide twice, the heated at 80° C. for 5 hours. The solution was cooled and poured into water, then extracted with ethyl acetate. The combined organic layers were dried over sodium sulfate, filtered and concentrated. The crude product was purified by RP-HPLC (eluent: water/MeCN*0.1% TFA) to yield the product as trifluoroacetate salt.

ES/MS 644.1 (M+H$^+$)

Example 22 Procedure 22

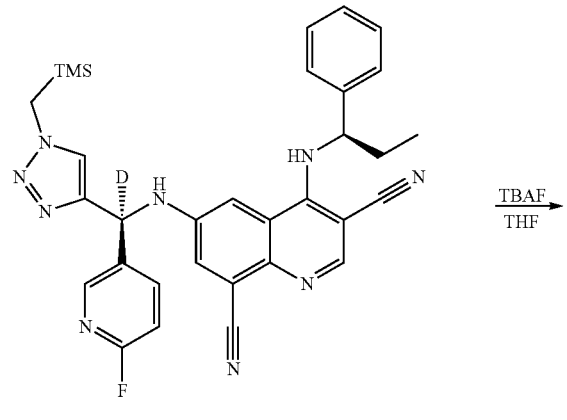

6-(((S)-(6-fluoropyridin-3-yl)(1-methyl-1H-1,2,3-triazol-4-yl)methyl-d)amino)-4-(((R)-1-phenylpropyl)amino)quinoline-3,8-dicarbonitrile: 1.0 M solution of TBAF (0.38 mL, 0.38 mmol) in THF was added to the stirring solution of 6-(((R)-(6-fluoropyridin-3-yl)(1-((trimethylsilyl)methyl)-1H-1,2,3-triazol-4-yl)deteromethyl)amino)-4-(((R)-1-phenylpropyl)amino)quinoline-3,8-dicarbonitrile (150 mg, 0.25 mmol) in THF (5 mL). The resulting solution was stirred for 2 h then concentrated to give crude material. HPLC purification afforded the title compound.

1H NMR (400 MHz, DMSO-d6) δ 8.49-8.38 (m, 1H), 8.28 (d, J=5.1 Hz, 1H), 8.13-8.02 (m, 2H), 7.84 (t, J=2.4 Hz, 1H), 7.65-7.52 (m, 2H), 7.42-7.31 (m, 1H), 7.31-7.15 (m, 4H), 5.49 (q, J=7.7 Hz, 1H), 4.04 (s, 3H), 3.20-3.11 (m, 1H), 2.20-2.05 (m, 1H), 2.05-1.85 (m, 1H), 1.63-1.50 (m, 1H), 1.37-1.20 (m, 1H), 0.99-0.83 (m, 3H).

ES/MS 519.2 (M+H$^+$).

Example 23 Procedure 23

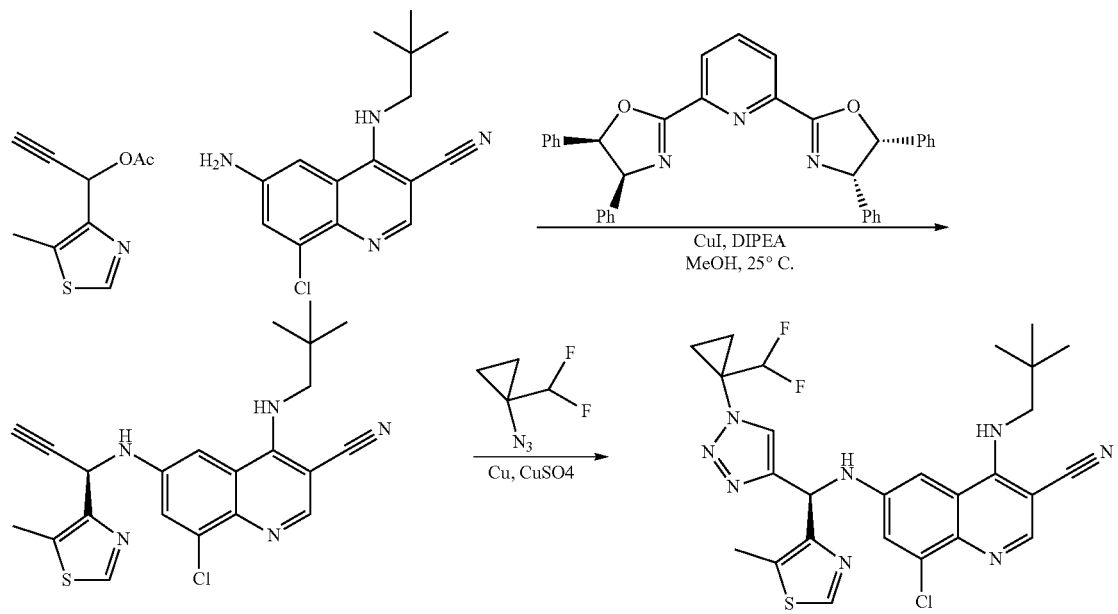

The CuI (2.6 mg, 0.014 mmol) and ligand (8.7 mg, 0.017 mmol) were suspended in MeOH (1 mL) and sonicated under argon for 5 min. The remaining MeOH was added followed by the acetate (70.3 mg, 0.36 mmol) and amine (80 mg, 0.27 mmol) and DIPEA (43 mg, 0.33 mmol) in that order at room temperature. After 14 h the N-alkylation reactions was complete. Evaporation and purification on silica get (eluent: EtOAc in hexanes) yielded 95 mg of N-alkylated product. The material was taken into THF (2 mL). Azide stock (1 mL/1 eq.), Cu and CuSO4 were added. Stirring at room temperature for 1 hr. Diluted with EtOAc, washed with NaHCO3 brine and dried over sodium sulfate. Filtration, evaporation, and purification via RP-HPLC (eluent: water/MeCN*0.1 TFA) yielded the product as the TFA salt.

$^1$H NMR (400 MHz, Methanol-d4) δ 8.79 (s, 1H), 8.49 (s, 1H), 8.00 (s, 1H), 7.69 (d, J=2.3 Hz, 1H), 7.26 (d, J=2.3 Hz, 1H), 6.31 (s, 1H), 5.91 (t, J=54.8 Hz, 1H), 4.09 (d, J=13.9 Hz, 1H), 3.93 (d, J=14.0 Hz, 1H), 2.56 (s, 3H), 1.50 (m, 4H), 1.05 (s, 9H).

Example 24 Procedure 24

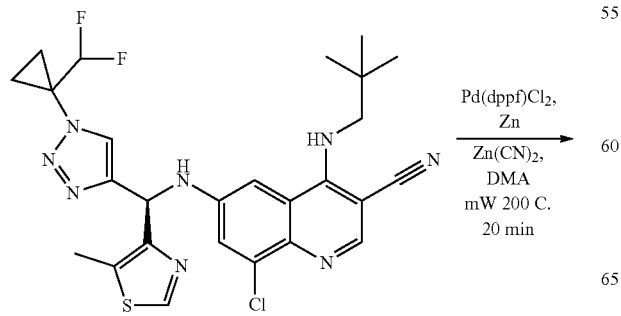

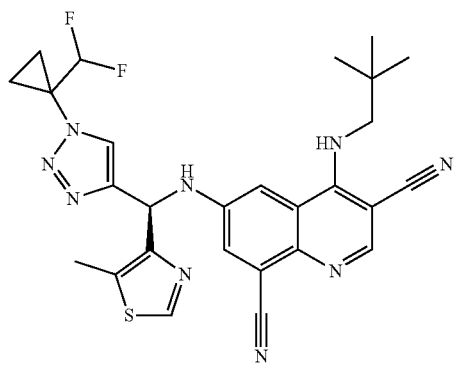

The SM (38 mg, 0.05 mmol), Zn (0.4 mg, 0.007 mmol), PddppfCl$_2$ (0.8 mg, 0.001 mmol) and Zn(CN)$_2$ (7.1 mg, 0.061 mmol) were combined in dimethylacetamide (1 mL) and degassed for 2 min. The mixture was heated in a microwave reactor at 200° C. for 20 min. The mixture was filtered and purified via RP-HPLC. The product fractions were combined and subjected to lyophilization, providing the desired compound as TFA salt.

$^1$H NMR (400 MHz, Methanol-d4) δ 8.78 (s, 1H), 8.37 (s, 1H), 8.02 (s, 1H), 7.83 (d, J=2.5 Hz, 1H), 7.44 (d, J=2.5 Hz, 1H), 6.32 (s, 1H), 5.92 (t, J=54.8 Hz, 1H), 3.96 (d, J=13.9 Hz, 1H), 3.80 (d, J=13.9 Hz, 1H), 2.56 (s, 3H), 1.50 (m, 4H), 1.02 (s, 9H).

Example 25 Procedure 25

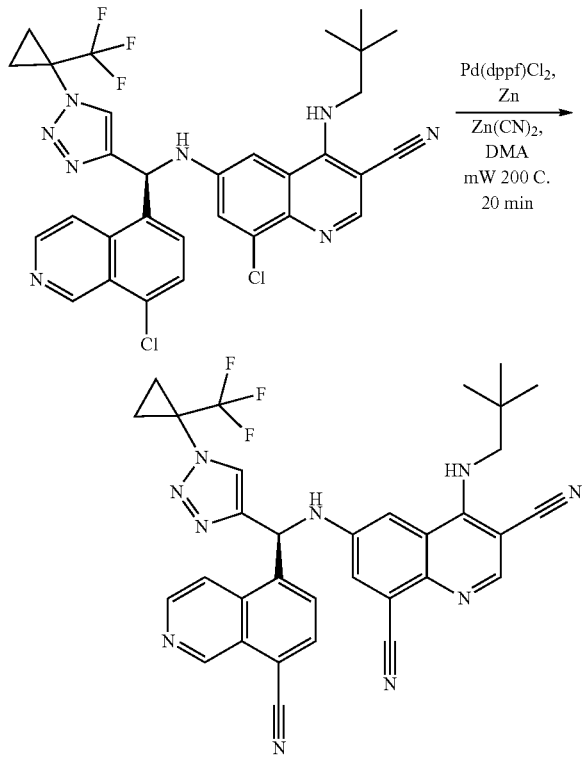

SM (0.04 g, 0.06 mmol), Zn powder (0.006 g, 0.09 mmol), Pd(dppf)Cl2 (0.009 g, 0.012 mmol) and Zn(CN)2 (0.021 g, 0.18 mmol) were combined in dimethylacetamide (0.7 mL) and degassed for 1 min. The mixture was heated in a microwave reactor at 200° C. for 15 min. The mixture was filtered and purified via RP-HPLC. The product fractions were combined and subjected to lyophilization, providing the desired compound as TFA salt.

¹H NMR (400 MHz, Methanol-d4) δ 9.61 (s, 1H), 8.69 (d, J=6.1 Hz, 1H), 8.33 (s, 1H), 8.23 (s, 1H), 8.17 (d, J=7.6 Hz, 1H), 8.16 (d, J=6.1 Hz, 1H), 8.02 (d, J=7.6 Hz, 1H), 7.83 (d, J=2.5 Hz, 1H), 7.02 (d, J=2.5 Hz, 1H), 6.91 (s, 1H), 3.82 (d, J=13.8 Hz, 1H), 3.42 (d, J=13.7 Hz, 1H), 1.79-1.55 (m, 4H), 0.62 (s, 9H).

Example 26 Procedure 26

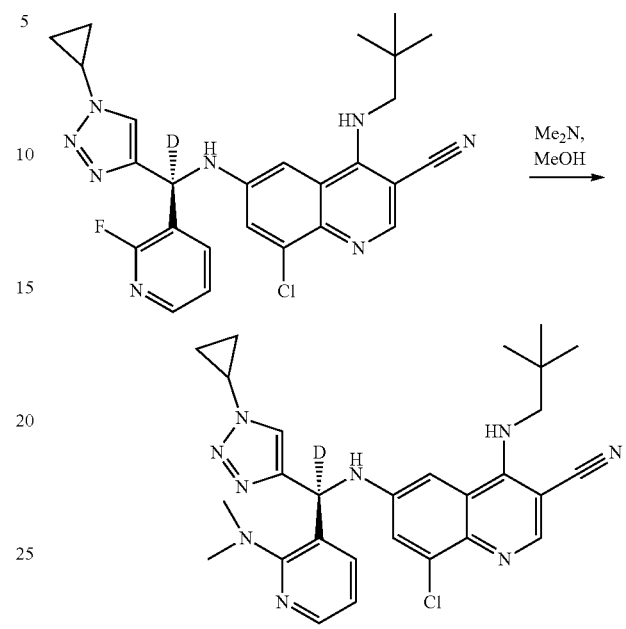

To (S)-8-chloro-6-(((1-cyclopropyl-1H-1,2,3-triazol-4-yl)(2-fluoropyridin-3-yl)methyl-d)amino)-4-(neopentylamino)quinoline-3-carbonitrile (TFA salt, 24 mg, 0.04 mmol) was added dimethylamine (2M solution in MeOH, 0.9 mL). The solution was heated to 100° C. (external temperature, µW) for 8 h. The resulting solution was concentrated, purified via preparative HPLC (Gemini column, 10-42% MeCN/H₂O/0.1% TFA) and lyophilized to provide the product as the corresponding TFA salt.

¹H NMR (400 MHz, Methanol-d4) δ 8.38 (s, 1H), 8.06 (dd, J=5.4, 1.8 Hz, 1H), 7.92 (s, 1H), 7.81 (dd, J=7.6, 1.8 Hz, 1H), 7.49 (d, J=2.3 Hz, 1H), 7.06 (d, J=2.3 Hz, 1H), 7.02 (dd, J=7.6, 5.4 Hz, 1H), 4.10 (d, J=14.0 Hz, 1H), 3.78 (ddd, J=11.4, 7.1, 4.2 Hz, 1H), 3.63 (d, J=14.0 Hz, 1H), 2.97 (s, 6H), 1.12-1.02 (m, 4H), 0.91 (s, 9H).

Example 27 Procedure 27

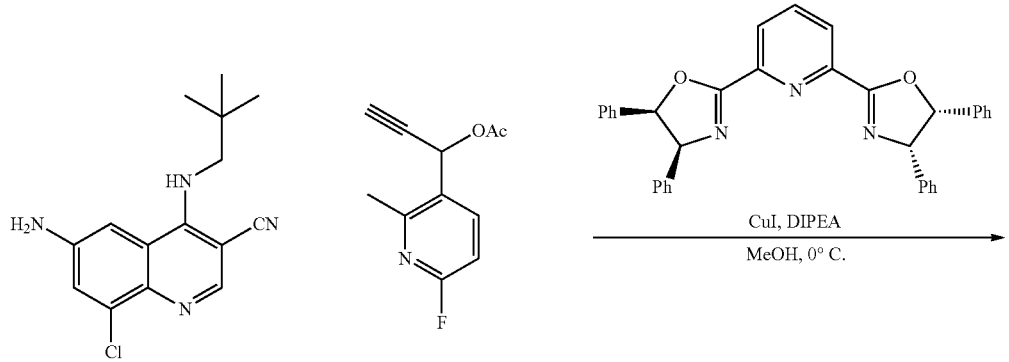

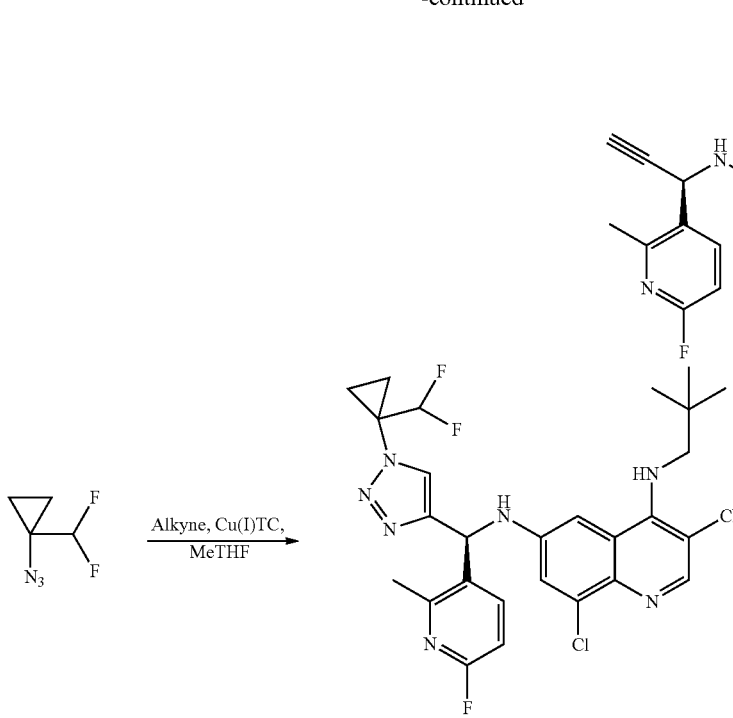

Cu(I)iodide (16.5 mg, 0.09 mmol) and bis-oxazoline ligand (54.2 mg) were sonicated in MeOH (10 mL) for 5 minutes. The mixture was cooled to 0° C. A solution of alkynyl acetate (687 mg, 3.3 mmol) in MeOH (7 mL) was added followed by quinoline (500 mg, 1.73 mmol) and di-iso-propyl ethyl amine (268.5 mg, 2.08 mmol). Stirring at 0° C. was continued. After consumption of starting material, the reaction volume was reduced and the crude material was purified via silica gel chromatography (el: EtOAc in hexanes) to yield the product.

$^1$H NMR (400 MHz, Acetonitrile-d3) δ 8.34 (s, 1H), 8.14 (t, J=8.2 Hz, 1H), 7.43 (d, J=2.3 Hz, 1H), 6.95-6.82 (m, 2H), 5.98 (t, J=6.4 Hz, 1H), 5.64 (dd, J=7.1, 2.2 Hz, 1H), 5.52 (d, J=7.2 Hz, 1H), 3.81 (dd, J=13.4, 6.7 Hz, 1H), 3.67 (dd, J=13.4, 6.0 Hz, 1H), 2.88 (d, J=2.2 Hz, 1H), 2.56 (s, 3H), 2.23 (s, 1H), 1.01 (s, 9H).

ES/MS m/z: 436.2.

The alkyne starting material (1.6 g, 3.67 mmol) was dissolved in MeTHF (16 mL) and azide solution in MTBE (0.5 M, 7.34 mL) and copper(I)thiophenecarboxylate (24 mg, 0.18 mmol) were added and stirring at room temperature was continued. After the SM was consumed, the reaction was diluted with EtOAc and was washed with aqueous sodium bicarbonate solution and dried over sodium sulfate. Filtration and evaporation of solvents gives crude material which was purified via silica gel chromatography (el. EtOAc in hexanes) to yield product.

$^1$H NMR (400 MHz, Chloroform-d) δ 8.45 (s, 1H), 7.93 (t, J=8.1 Hz, 1H), 7.41 (s, 1H), 7.35 (d, J=2.3 Hz, 1H), 6.80 (dd, J=8.4, 3.2 Hz, 1H), 6.25 (s, 1H), 5.93 (s, 1H), 5.91 (t, J=56.0 Hz, 1H), 5.27 (s, 1H), 3.57 (m, 2H), 2.58 (s, 3H), 1.55-1.50 (m, 4H), 0.94 (s, 9H).

ES/MS m/z: 569.6.

Example 28 Procedure 28

(S)-8-chloro-6-(((1-cyclopropyl-5-iodo-1H-1,2,3-triazol-4-yl)(6-fluoro-2-methylpyridin-3-yl)methyl)amino)-4-(neopentylamino)quinoline-3-carbonitrile

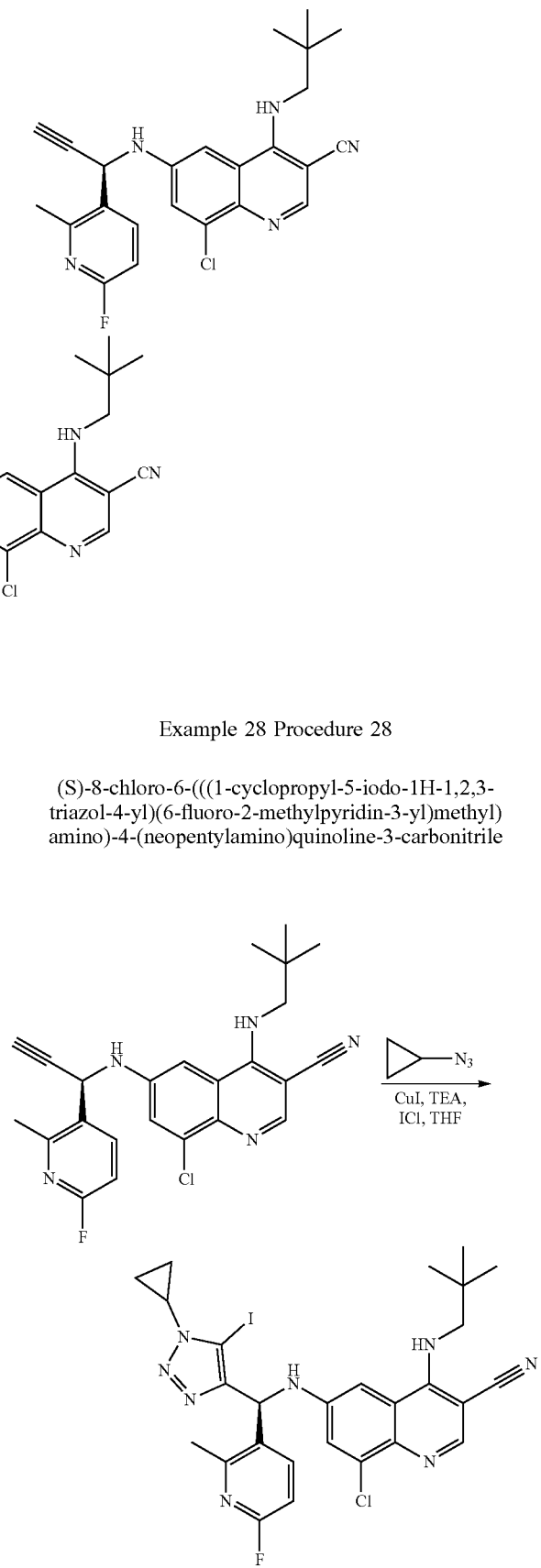

Copper (I) iodide (172.5 mg, 0.906 mmol) and iodine monochloride (147 mg, 0.906 mmol) were added to a solution of (R)-8-chloro-6-((1-(6-fluoro-2-methylpyridin-3-yl)prop-2-yn-1-yl)amino)-4-(neopentylamino)quinoline-3-carbonitrile (394 mg, 0.906 mmol), cyclopropyl azide (79.1 mg 0.906 mmol), and triethylamine (151.6 uL, 1.09 mmol) in tetrahydrofuran (15 mL). After 16 h the reaction was diluted with ethyl acetate (50 mL) and washed with water (25 mL) and brine (25 mL). The organic phase was dried over sodium sulfate and the solvent was removed under reduced pressure. The material was mixed with ethyl acetate (5 mL) and the solid was isolated by filtration providing (S)-8-chloro-6-(((1-cyclopropyl-5-iodo-1H-1,2,3-triazol-4-yl)(6-fluoro-2-methylpyridin-3-yl)methyl)amino)-4-(neopentylamino)quinoline-3-carbonitrile.

Example 29 Procedure 29

(S)-8-Chloro-6-(((1,5-dicyclopropyl-1H-1,2,3-triazol-4-yl)(6-fluoro-2-methylpyridin-3-yl)methyl)amino)-4-(neopentylamino)quinoline-3-carbonitrile

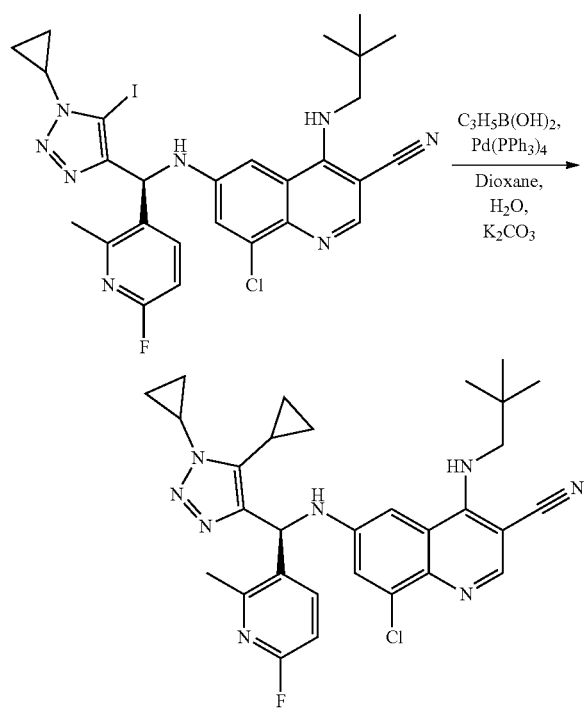

1,4-Dioxane (4.0 mL) and water (0.5 mL) were added to (S)-8-Chloro-6-(((1-cyclopropyl-5-iodo-1H-1,2,3-triazol-4-yl)(6-fluoro-2-methylpyridin-3-yl)methyl)amino)-4-(neopentylamino)quinoline-3-carbonitrile (100 mg, 0.155 mmol), cyclopropylboronic acid (20 mg, 0.223 mmol), tetrakis(triphenylphosphine)palladium(0) (35.8 mg, 0.031 mmol), and potassium carbonate (42.8 mg, 0.310 mmol) in a microwave vial. The reaction was heated in a microwave reactor for 20 minutes at 130° C. The mixture was diluted with ethyl acetate (10 mL) and washed with brine (5 mL). The organic phase was dried over sodium sulfate and the solvent was removed under reduced pressure. The residue was subjected to flash chromatography (0-100% ethyl acetate/hexanes). The fractions containing product were combined and the solvent was removed under reduced pressure. The residue was taken up in methanol (1 mL) and water (0.5 mL) with 2 drops of trifluoroacetic acid and subjected to preparative HPLC. The clean fractions were combined and subjected to lyophilization, providing (S)-8-Chloro-6-(((1,5-dicyclopropyl-1H-1,2,3-triazol-4-yl)(6-fluoro-2-methylpyridin-3-yl)methyl)amino)-4-(neopentylamino)quinoline-3-carbonitrile.

Example 30 Procedure 30

(S)-8-chloro-6-(((1-cyclopropyl-5-fluoro-1H-1,2,3-triazol-4-yl)(6-fluoro-2-methylpyridin-3-yl)methyl)amino)-4-(neopentylamino)quinoline-3-carbonitrile

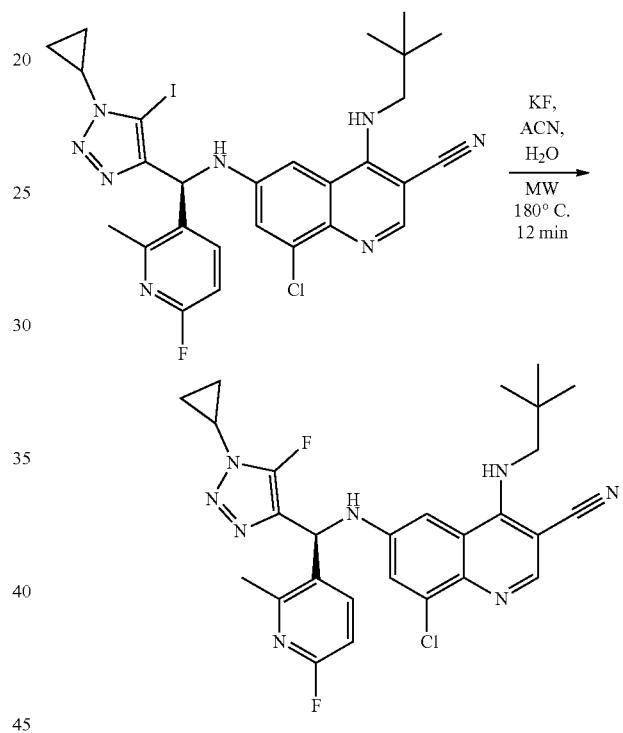

Acetonitrile (1.0 mL) and water (1.0 mL) were added to (S)-8-Chloro-6-(((1-cyclopropyl-5-iodo-1H-1,2,3-triazol-4-yl)(6-fluoro-2-methylpyridin-3-yl)methyl)amino)-4-(neopentylamino)quinoline-3-carbonitrile (50 mg, 0.078 mmol) and potassium fluoride (22.5 mg, 0.388 mmol) in a microwave vial. The vial was sealed and the reaction was heated in a microwave reactor at 180° C. for 12 minutes. The reaction was diluted with ethyl acetate (10 mL) and washed with brine (5 mL). The organic phase was dried over sodium sulfate and the solvent was removed under reduced pressure. The residue was subjected to flash chromatography (0-100% ethyl acetate/hexanes). The fractions containing product were combined and the solvent was removed under reduced pressure. The residue was taken up in methanol (1 mL) and water (0.5 mL) with 2 drops of trifluoroacetic acid and subjected to preparative HPLC. The clean fractions were combined and subjected to lyophilization, providing (S)-8-chloro-6-(((1-cyclopropyl-5-fluoro-1H-1,2,3-triazol-4-yl)(6-fluoro-2-methylpyridin-3-yl)methyl)amino)-4-(neopentylamino)quinoline-3-carbonitrile.

Example 31 Procedure 31

(S)-8-chloro-6-(((1-cyclopropyl-5-methoxy-1H-1,2,3-triazol-4-yl)(6-fluoro-2-methylpyridin-3-yl)methyl)amino)-4-(neopentylamino)quinoline-3-carbonitrile

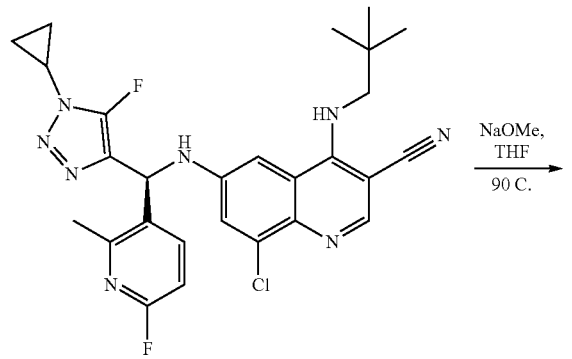

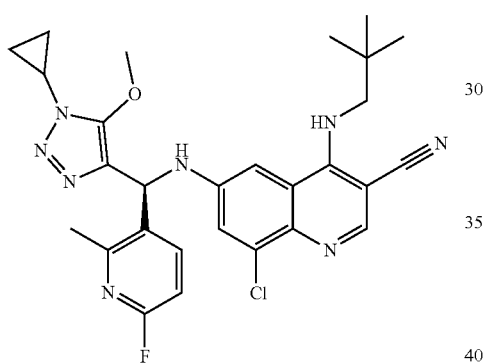

Sodium methoxide (26 uL, 0.119 mmol, 25% pure in THF) was added to a solution of (S)-8-chloro-6-(((1-cyclopropyl-5-fluoro-1H-1,2,3-triazol-4-yl)(6-fluoro-2-methylpyridin-3-yl)methyl)amino)-4-(neopentylamino)quinoline-3-carbonitrile (42.6 mg, 0.079 mmol) in tetrahydrofuran (2.0 mL). The solution was heated at 90° C. for 30 minutes and the reaction was quenched with 2 drops of acetic acid. The solution was diluted with ethyl acetate (15 mL) and washed with saturated sodium bicarbonate (5 mL) and brine (5 mL). The organic phase was dried over sodium sulfate and the solvent was removed under reduced pressure. The residue was subjected to flash chromatography (0-100% ethyl acetate/hexanes). The fractions containing product were combined and the solvent was removed under reduced pressure. The residue was taken up in methanol (1 mL) and water (0.5 mL) with 2 drops of trifluoroacetic acid and subjected to preparative HPLC. The clean fractions containing product were combined and subjected to lyophilization, providing (S)-8-chloro-6-(((1-cyclopropyl-5-methoxy-1H-1,2,3-triazol-4-yl)(6-fluoro-2-methylpyridin-3-yl)methyl)amino)-4-(neopentylamino)quinoline-3-carbonitrile.

Example 32 Procedure 32

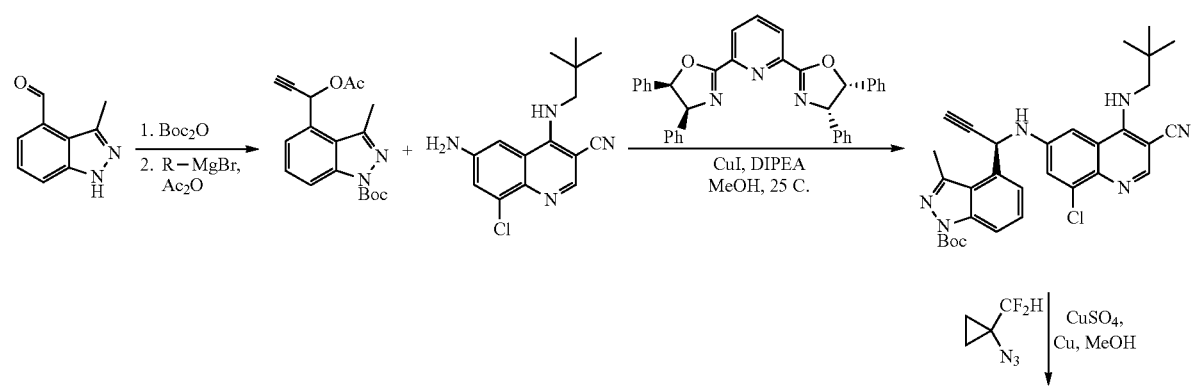

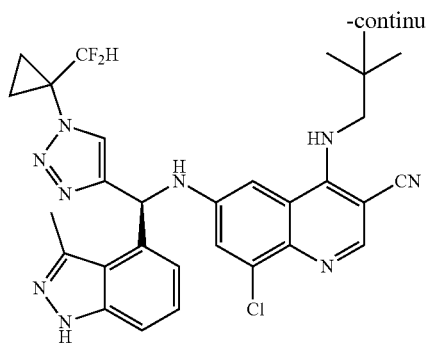
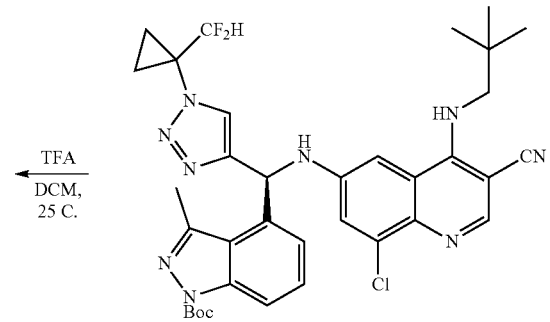

Aldehyde (223 mg, 1.4 mmol) was dissolved in acetonitrile (8 mL). Triethylamine (0.29 mL, 2.1 mmol) and DMAP (34 mg, 0.28 mmol) were added followed by Boc₂O (365 mg, 1.7 mmol) and the resulting mixture stirred for 2 minutes. Upon completion the reaction contents were concentrated directly then purified via silica gel chromatography (EtOAc in hexanes) to yield the product.

The newly formed material was taken up in THF (15 mL) and brought to 0° C. Ethynylmagnesium bromide (0.5M in THF, 3.7 mL, 1.8 mmol) was added dropwise and the resulting solution stirred for 30 minutes at which point acetic anhydride (0.29 mL, 3.1 mmol) was added and the reaction contents allowed to warm to room temperature over 1h. The reaction was quenched by the addition of saturated aqueous NH₄Cl and extracted with EtOAc. The organic layers were washed with brine, dried over magnesium sulfate, filtered and concentrated to give the crude propargyl acetate which was used without further purification.

The CuI (6.6 mg, 0.035 mmol) and ligand (22 mg, 0.042 mmol) were suspended in MeOH (5 mL) and sonicated under argon for 5 min. The acetate (136 mg, 0.42 mmol) as a solution in MeOH (2 mL), amine (100 mg, 0.35 mmol) and DIPEA (54 mg, 0.42 mmol) were added in that order at room temperature. After 2 h reaction mixture was concentrated directly and purified on silica gel (EtOAc in hexanes) to give the alkylated product.

The material was taken into THF (2 mL). Azide stock (1 mL/1 eq.), Cu and CuSO4 were added and the resulting mixture stirred at room temperature for 30 min. Diluted with EtOAc, washed with water, brine and dried over magnesium sulfate. Filtration and concentration gave the crude product which was then stirred in 1 mL of a 1:1 DCM:trifluoroacetic acid mixture for 30 min. The DCM and TFA were removed by rotary evaporation after which the crude residue was purified RP-HPLC (eluent: water/MeCN*0.1 TFA) yielded the product as TFA salt.

Example 33 Procedure 33

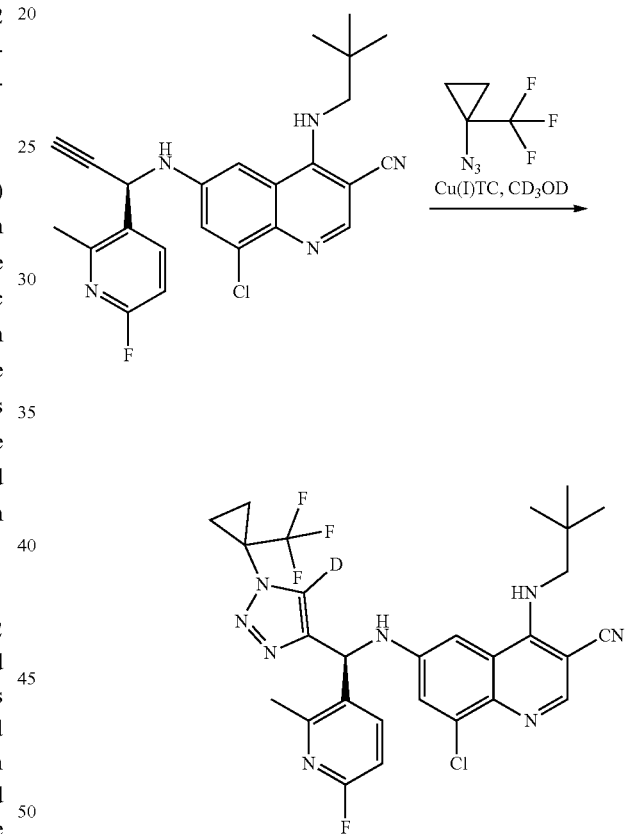

A solution of the alkyne starting material (50 mg, 0.115 mmol) in deuterated methanol (CD₃OD, 2 mL) was treated with azide solution in DCM (25% by weight, 80 mg, 0.138 mmol) and copper(I)thiophenecarboxylate (1 mg) at room temperature. After 1 hour, the reaction was diluted with EtOAc and was washed with aqueous sodium bicarbonate solution and dried over sodium sulfate. Filtration and evaporation of solvents gives crude material which was purified via reverse phase HPLC to yield clean product.

¹H NMR (400 MHz, Acetonitrile-d3) δ 8.44 (s, 1H), 7.82 (t, J=8.2 Hz, 1H), 7.49 (d, J=2.3 Hz, 1H), 6.84 (dd, J=8.4, 3.2 Hz, 1H), 6.78 (s, 1H), 6.17 (s, 1H), 3.83 (m, 2H), 1.78-1.65 (m, 2H), 1.65 (m, 2H), 0.95 (s, 9H).

ES/MS m/z: 588.31.

Example 34 Procedure 34

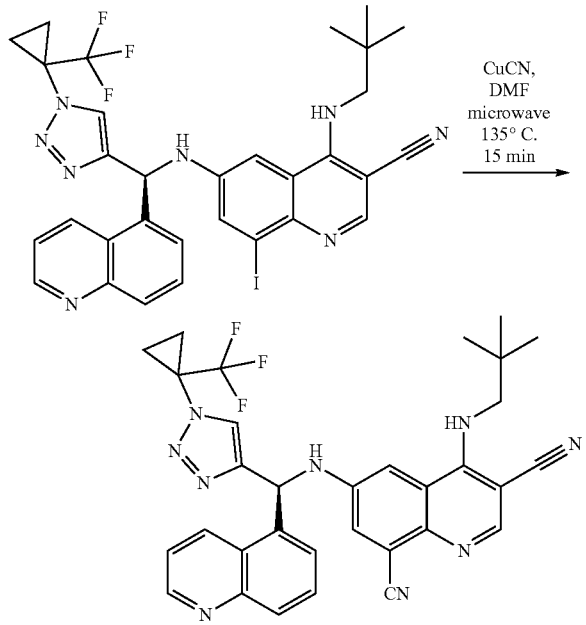

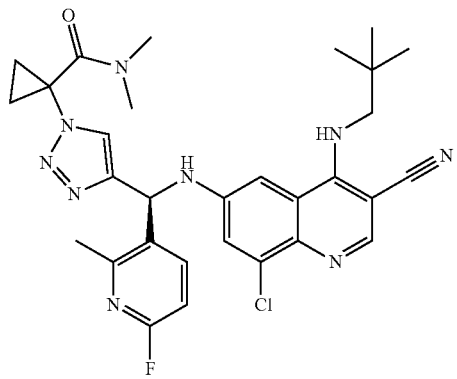

A mixture of (S)-8-iodo-4-(neopentylamino)-6-((quinolin-5-yl(1-(1-(trifluoromethyl)cyclopropyl)-1H-1,2,3-triazol-4-yl)methyl)amino)quinoline-3-carbonitrile (61 mg, 0.09 mmol) and Cuprous cyanide (23.53 mg, 0.26 mmol) in DMF (2 mL) was heated at 135° C. in the microwave for 15 minutes. The solution was treated with Si-thiol, filtered and purified by reverse phase HPLC to provide (S)-4-(neopentylamino)-6-((quinolin-5-yl(1-(1-(trifluoromethyl)cyclopropyl)-1H-1,2,3-triazol-4-yl)methyl)amino)quinoline-3,8-dicarbonitrile as the bis-trifluoroacetate salt.

¹H NMR (400 MHz, Methanol-d4) δ 9.11 (s, 1H), 9.04 (d, J=8.7 Hz, 1H), 8.30 (s, 1H), 8.21 (s, 1H), 8.18-8.10 (m, 1H), 7.99-7.90 (m, 1H), 7.90-7.82 (m, 2H), 7.80 (s, 1H), 7.14-7.08 (m, 1H), 6.94 (s, 1H), 3.79 (d, J=13.8 Hz, 1H), 3.48 (d, J=13.8 Hz, 1H), 1.75-1.56 (m, 4H), 0.66 (s, 9H).

ES/MS m/z: 596.35.

Example 35 Procedure 35

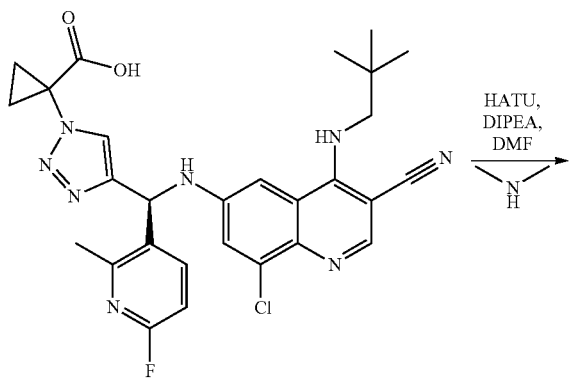

N-Ethyldiisopropylamine (15.47 µl, 0.09 mmol) was added to a mixture of (S)-1-(4-(((8-chloro-3-cyano-4-(neopentylamino)quinolin-6-yl)amino)(6-fluoro-2-methylpyridin-3-yl)methyl)-1H-1,2,3-triazol-1-yl)cyclopropane-1-carboxylic acid (25 mg, 0.044 mmol), 2-(7-Aza-1H-benzotriazole-1-yl)-1,1,3,3-tetramethyluronium hexafluorophosphate (HATU), 99% (17.27 mg, 0.05 mmol), and 2M Dimethylamine solution (44.4 µl, 0.053 mmol) in dimethylformamide (1 mL). After 3 hours half of the solvent was removed under reduced pressure. The solution was diluted with methanol (0.75 mL) water (0.5 mL) and TFA (50 uL). This solution was subjected to preperative HPLC. The cleaner fractions containing product were combined and subjected to lyophilization, providing the desired compound. The lyophilized solid was taken up in methanol (0.5 mL) and passed through a carbonate resin with methanol washing (5 mL). The solvent was removed under reduced pressure and the residue was taken up in ACN (1 mL) and water (1 mL) with TFA (0.02 mL) and subjected to lyophilization providing the (S)-1-(4-(((8-chloro-3-cyano-4-(neopentylamino)quinolin-6-yl)amino)(6-fluoro-2-methylpyridin-3-yl)methyl)-1H-1,2,3-triazol-1-yl)-N,N-dimethylcyclopropane-1-carboxamide.

Example 36 Procedure 36

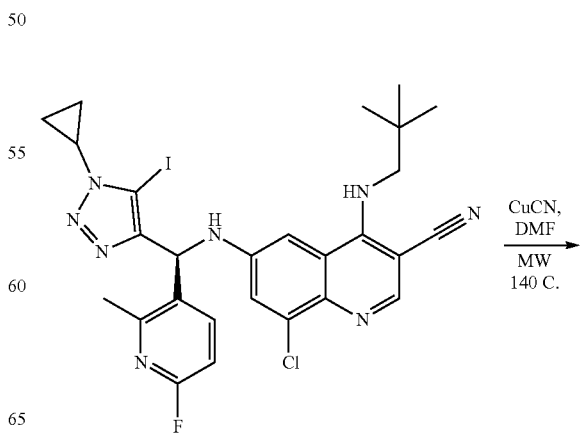

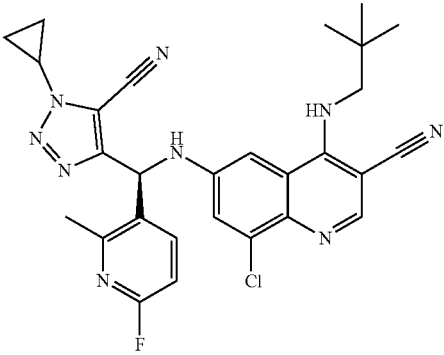

A solution of (S)-8-chloro-6-(((1-cyclopropyl-5-iodo-1H-1,2,3-triazol-4-yl)(6-fluoro-2-methylpyridin-3-yl)methyl)amino)-4-(neopentylamino)quinoline-3-carbonitrile (33 mg, 0.051 mmol), copper (I) cyanide (13.7 mg, 0.15 mmol) in dimethylformamide (1 mL) was heated in a microwave reactor at 200 C for 20 min. The mixture was diluted with ethyl acetate (10 ml) and washed with 5% lithium chloride (2×5 mL) and brine (5 mL). The organic phase was dried over sodium sulfate and the solvent was removed under reduced pressure. The residue was subjected to flash chromatography (0-100% EtOAc/hexanes). The fractions containing product were combined and the solvent was removed under reduced pressure. The residue was taken up in water (0.5 ml) and methanol (1 mL) with 2 drops of TFA and subjected to preperative HPLC. The clean fractions combined and subjected to lyophilization, providing (S)-8-chloro-6-(((5-cyano-1-cyclopropyl-1H-1,2,3-triazol-4-yl)(6-fluoro-2-methylpyridin-3-yl)methyl)amino)-4-(neopentylamino)quinoline-3-carbonitrile.

Example 37 Procedure 37 triazol-4-yl)methyl)-4,7-dihydrothieno[2,3-c]pyridine-6(5H)-carboxylate (60.3 mg, 0.082 mmol), tetrakis(triphenylphosphine)palladium(0) (7.55 mg, 0.01 mmol), and zinc cyanide (23.96 mg, 0.20 mmol) was degassed with argon for 10 minutes, The mixture was heated in a sealed vial at 100° C. After 36 h the reaction was diluted with ethyl acetate (20 ml) and washed with 5% lithium chloride (2×5 mL) and brine (5 mL). The organic phase was dried over sodium sulfate and the solvent was removed under reduced pressure. The residue was subjected to flash chromatography (0-100% (20% methanol/ethyl acetate)/hexanes). The fractions containing product were combined and the solvent was removed under reduced pressure, providing tert-butyl (S)-3-((1-cyclopropyl-1H-1,2,3-triazol-4-yl)((3,8-dicyano-4-(neopentylamino)quinolin-6-yl)amino)methyl)-4,7-dihydrothieno[2,3-c]pyridine-6(5H)-carboxylate.

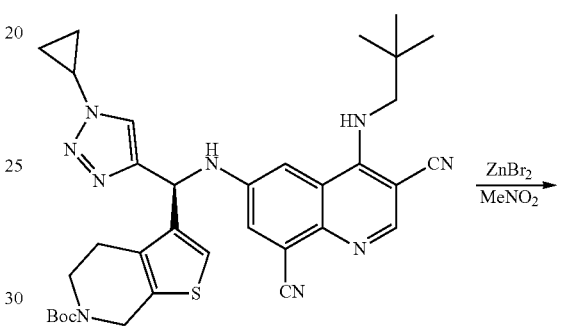

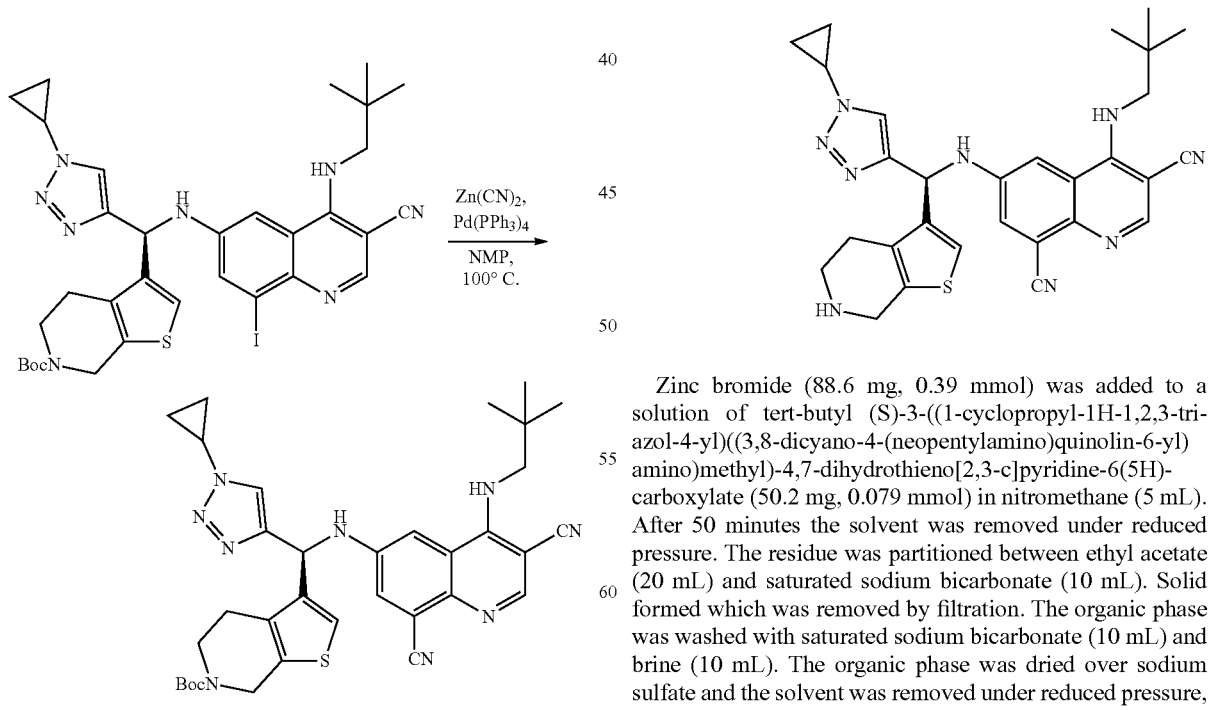

A solution of tert-Butyl (S)-3-(((3-cyano-8-iodo-4-(neopentylamino)quinolin-6-yl)amino)(1-cyclopropyl-1H-1,2,3-

Zinc bromide (88.6 mg, 0.39 mmol) was added to a solution of tert-butyl (S)-3-((1-cyclopropyl-1H-1,2,3-triazol-4-yl)((3,8-dicyano-4-(neopentylamino)quinolin-6-yl)amino)methyl)-4,7-dihydrothieno[2,3-c]pyridine-6(5H)-carboxylate (50.2 mg, 0.079 mmol) in nitromethane (5 mL). After 50 minutes the solvent was removed under reduced pressure. The residue was partitioned between ethyl acetate (20 mL) and saturated sodium bicarbonate (10 mL). Solid formed which was removed by filtration. The organic phase was washed with saturated sodium bicarbonate (10 mL) and brine (10 mL). The organic phase was dried over sodium sulfate and the solvent was removed under reduced pressure, providing (S)-6-(((1-cyclopropyl-1H-1,2,3-triazol-4-yl)(4,5,6,7-tetrahydrothieno[2,3-c]pyridin-3-yl)methyl)amino)-4-(neopentylamino)quinoline-3,8-dicarbonitrile.

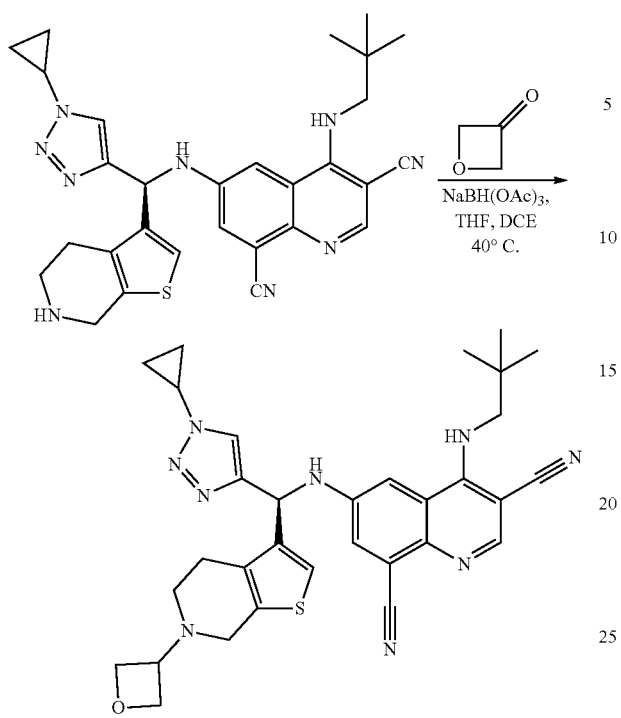

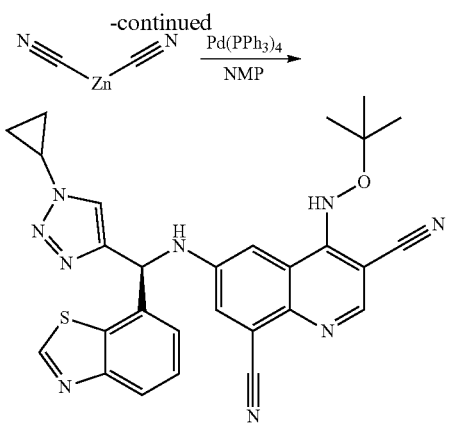

3-Oxetanone (38.75 µl, 0.6 mmol) was added to a mixture of (S)-6-(((1-cyclopropyl-1H-1,2,3-triazol-4-yl)(4,5,6,7-tetrahydrothieno[2,3-c]pyridin-3-yl)methyl)amino)-4-(neopentylamino)quinoline-3,8-dicarbonitrile (32.5 mg, 0.060 mmol) and sodium triacetoxyborohydride (128.1 mg, 0.60 mmol) in tetrahydrofuran (2 mL) dichloroethane (2 mL) and heated at 40° C. for 16 h. The mixture was diluted with ethyl acetate (10 mL) and washed with saturated sodium bicarbonate (2×5 mL) and brine (5 mL). The organic phase was dried over sodium sulfate and he solvent was removed under reduced pressure. The residue was subjected to flash chromatography (0-100% (20% methanol in ethyl acetate)/hexanes). The fractions containing product were combined and the solvent was removed under reduced pressure. The residue was taken up in methanol (0.5 mL)/water (0.5 mL) with 2 drops of TFA and subjected to preperative HPLC (eluted with 0-100% acetonitrile an water with 0.05% trifluoroacetic acid). The clean fractions were combined and subjected to lyophilization, (S)-6-(((1-cyclopropyl-1H-1,2,3-triazol-4-yl)(6-(oxetan-3-yl)-4,5,6,7-tetrahydrothieno[2,3-c]pyridin-3-yl)methyl)amino)-4-(neopentylamino)quinoline-3,8-dicarbonitrile.

Example 38 Procedure 38

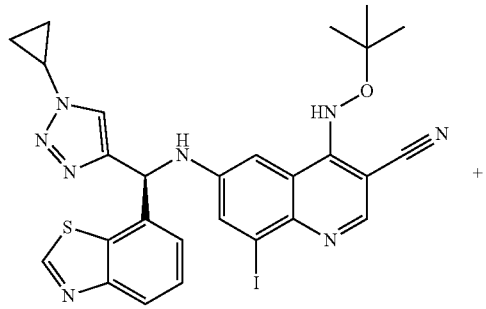

(S)-6-((benzo[d]thiazol-7-yl(1-cyclopropyl-1H-1,2,3-triazol-4-yl)methyl)amino)-4-(tert-butoxyamino)quinoline-3,8-dicarbonitrile: To (S)-6-((benzo[d]thiazol-7-yl(1-cyclopropyl-1H-1,2,3-triazol-4-yl)methyl)amino)-4-(tert-butoxyamino)-8-iodoquinoline-3-carbonitrile (59 mg, 0.093 mmol) in N-methyl-2-pyrrolidone (1 mL) was added zinc cyanide (27 mg, 0.232 mmol) and palladium tetrakis triphenylphosphine (9 mg, 0.007 mmol). The reaction mixture was degassed with nitrogen for 5 minutes, then stirred at 100° C. overnight. The reaction was then brought to room temperature and diluted with water and EtOAc. Aqueous layer was extracted once more with EtOAc. Combined organics were washed with water, brine, dried (Na₂SO₄) and concentrated to give the crude product which was purified by HPLC (eluent: water/MeCN*0.1% TFA) to yield the title product. ES/MS 536.20 (M+H⁺).

Example 39 Procedure 39

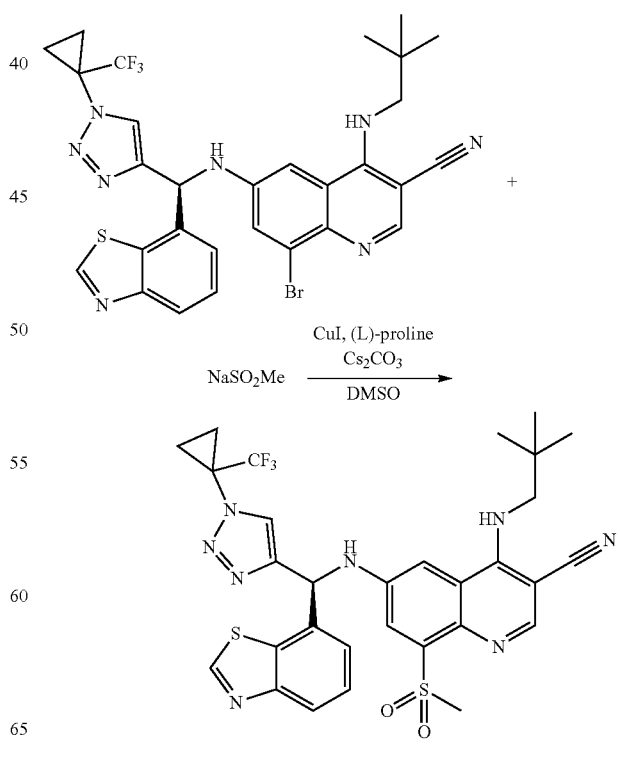

(S)-6-((benzo[d]thiazol-7-yl(1-(1-(trifluoromethyl)cyclopropyl)-1H-1,2,3-triazol-4-yl)methyl)amino)-8-(methylsulfonyl)-4-(neopentylamino)quinoline-3-carbonitrile: To (S)-6-((benzo[d]thiazol-7-yl(1-(1-(trifluoromethyl)cyclopropyl)-1H-1,2,3-triazol-4-yl)methyl)amino)-8-bromo-4-(neopentylamino)quinoline-3-carbonitrile (31 mg, 0.047 mmol), (L)-proline (1.1 mg, 0.009 mmol), Cu(I)I (1 mg, 0.005 mmol), sodium methylsulfonate (5.8 mg, 0.057 mmol), and Cs$_2$CO$_3$ (15 mg, 0.047 mmol) was added DMSO (0.8 mL). The reaction mixture was placed under an atmosphere of nitrogen stirred at 110° C. overnight. The reaction was then brought to room temperature and diluted with water and EtOAc. Aqueous layer was extracted once more with EtOAc. Combined organics were washed with water, brine, dried (Na$_2$SO$_4$) and concentrated to give the crude product which was purified by HPLC (eluent: water/MeCN*0.1% TFA) to yield the title product. ES/MS 655.7 (M+H$^+$).

Example 40 Procedure 40

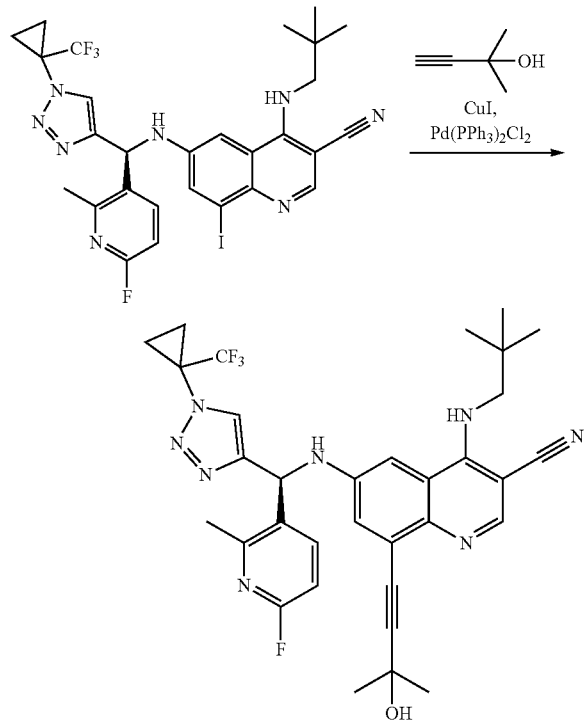

6-(((6-Fluoro-2-methylpyridin-3-yl)(1-(1-(trifluoromethyl)cyclopropyl)-1H-1,2,3-triazol-4-yl)methyl)amino)-8-(3-hydroxy-3-methylbut-1-yn-1-yl)-4-(neopentylamino)quinoline-3-carbonitrile: 6-(((6-Fluoro-2-methylpyridin-3-yl)(1-(1-(trifluoromethyl)cyclopropyl)-1H-1,2,3-triazol-4-yl)methyl)amino)-8-iodo-4-(neopentylamino)quinoline-3-carbonitrile (30 mg, 0.044 mmol), copper iodide (0.84 mg, 0.004 mmol), and 2-methyl-3-butyn-2-ol (18.6 mg, 0.22 mmol) were dissolved in Me-THF. Then Bis(triphenylphosphine)palladium(II) dichloride (3.1 mg, 0.004 mmol) was add to the mixture followed by diethylamine (0.05 ml, 0.44 mmol). The reaction was heated to 80 C for one hour, then diluted with EtOAc and brine, the organic layer was kept, dried over sodium sulfate, and concentrated. The crude residue was purified by RP-HPLC (eluent: water/MeCN*0.1% TFA) to yield the product as trifluoro acetate salt.

Example 41 Procedure 41

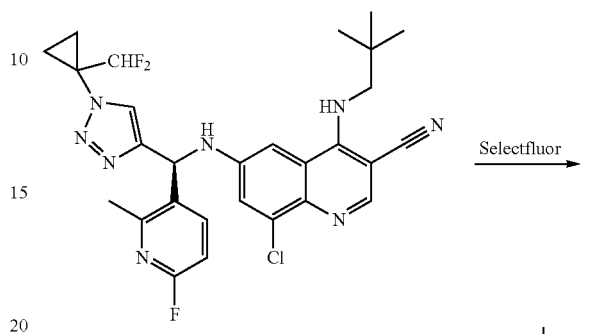

(S)-8-Chloro-6-(((1-(1-(difluoromethyl)cyclopropyl)-1H-1,2,3-triazol-4-yl)(6-fluoro-2-methylpyridin-3-yl)methyl)amino)-5-fluoro-4-(neopentylamino)quinoline-3-carbonitrile: (S)-8-Chloro-6-(((1-(1-(difluoromethyl)cyclopropyl)-1H-1,2,3-triazol-4-yl)(6-fluoro-2-methylpyridin-3-yl)methyl)amino)-4-(neopentylamino)quinoline-3-carbonitrile (100 mg, 0.18 mmol) was dissolved in ACN. Selectfluor (31.8 mg, 0.176 mmol) was added to the stirring mixture. The reaction was stopped after 20 minutes, diluted with EtOAc and water. The organic layer was dried over sodium sulfate, and concentrated. The product was purified by chromatography on silica gel (eluent: EtOAc/hexanes) to yield the product after lyophilization from water/MeCN.

Example 42 Procedure 42

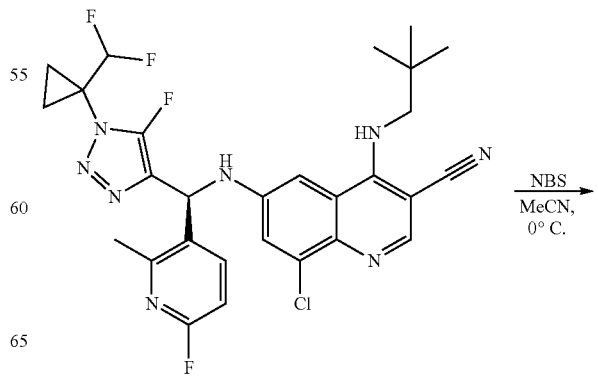

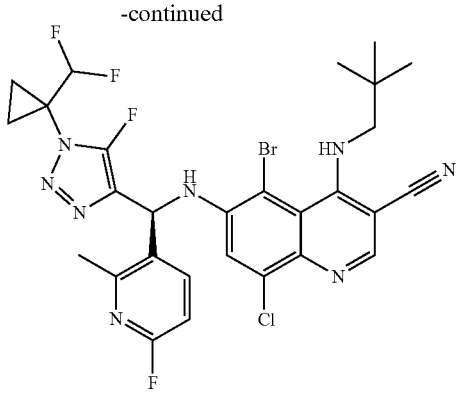

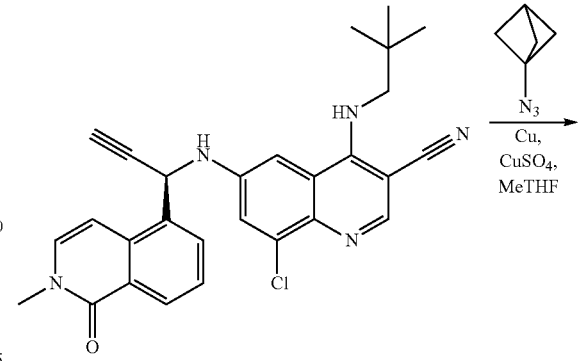

(S)-5-bromo-8-chloro-6-(((1-(1-(difluoromethyl)cyclopropyl)-5-fluoro-1H-1,2,3-triazol-4-yl)(6-fluoro-2-methylpyridin-3-yl)methyl)amino)-4-(neopentylamino)quinoline-3-carbonitrile: N-Bromosuccinimide (7.8 mg, 0.044 mmol) was added to a solution of (S)-8-chloro-6-(((1-(1-(difluoromethyl)cyclopropyl)-5-fluoro-1H-1,2,3-triazol-4-yl)(6-fluoro-2-methylpyridin-3-yl)methyl)amino)-4-(neopentylamino)quinoline-3-carbonitrile (26 mg, 0.044 mmol) in acetonitrile (1 mL) at 0° C. After 24 h at room temperature trifluoroacetic acid (4 drops) was added and the mixture was diluted with water. The yellow solution was subjected to preparative HPLC. The fractions containing product were combined and the solvent was reduced pressure, providing the (S)-5-bromo-8-chloro-6-(((1-(1-(difluoromethyl)cyclopropyl)-5-fluoro-1H-1,2,3-triazol-4-yl)(6-fluoro-2-methylpyridin-3-yl)methyl)amino)-4-(neopentylamino)quinoline-3-carbonitrile as the TFA salt.

Example 43 Procedure 43

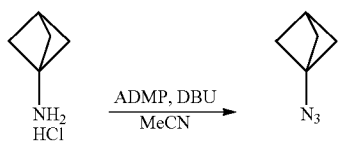

1-Azidobicyclo[1.1.1]pentane: A solution of 2-azido-1,3-dimethylimidazolinium hexafluorophosphate (429 mg, 1.5 mmol) in acetonitrile (2 mL) was added to solution of the bicyclo[1.1.1]pentan-1-amine hydrochloride (150 mg, 1.25 mmol) and 1,8-diazabicyclo[5.4.0]undec-7-ene (420 mg, 4.2 mmol) in acetonitrile (3 mL) dropwise over 1 min. After 16 h at RT the reaction was heated at 40 C for 3 h. The reaction was assumed to be complete and was added to the Click reaction as is.

(S)-6-(((1-(bicyclo[1.1.1]pentan-1-yl)-1H-1,2,3-triazol-4-yl)(2-methyl-1-oxo-1,2-dihydroisoquinolin-5-yl)methyl)amino)-8-chloro-4-(neopentylamino)quinoline-3-carbonitrile: 2-Methyltetrahydrofuran (12 mL), copper powder (394 mg, 6.2 mmol) and (R)-8-chloro-6-((1-(2-methyl-1-oxo-1,2-dihydroisoquinolin-5-yl)prop-2-yn-1-yl)amino)-4-(neopentylamino)quinoline-3-carbonitrile (500 mg, 1.03 mmol) were combined. Saturated copper (II) sulfate (0.6 mL) was added followed by acetic acid (236 uL, 4.13 mmol). A solution of 1-azidobicyclo[1.1.1]pentane (137 mg, 1.25 mmol) in acetonitrile (5 mL—reaction mixture from above) was added. After 1 h the solids were removed by filtration. The mixture was partitioned with ethyl acetate (50 mL) and saturated ammonium chloride (50 mL). An emulsion formed with a light solid. The solid was removed by filtration through celite. The organic phase was washed with saturated ammonium chloride (50 mL), saturated sodium bicarbonate (4×50 mL) and brine (50 mL). The organic phase was dried over sodium sulfate and the solvent was removed under reduced pressure. The residue was subjected to flash chromatography (0-70% ethyl acetate/hexanes). The fractions containing product were combined and the solvent was removed under reduced pressure. The residue was taken up in acetonitrile (15 mL) and water (15 mL) and subjected to lyophilization, providing (S)-6-(((1-(bicyclo[1.1.1]pentan-1-yl)-1H-1,2,3-triazol-4-yl)(2-methyl-1-oxo-1,2-dihydroisoquinolin-5-yl)methyl)amino)-8-chloro-4-(neopentylamino)quinoline-3-carbonitrile.

Example 44 Procedure 44

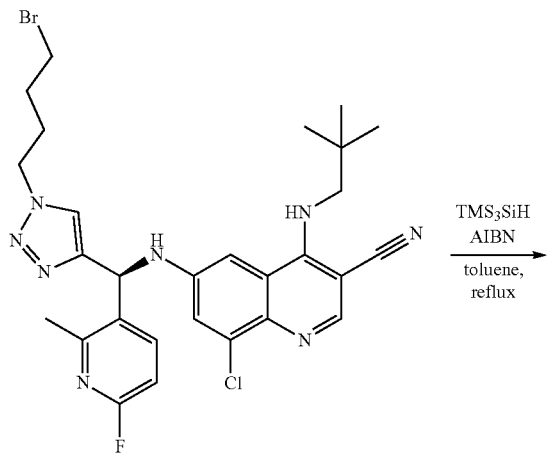

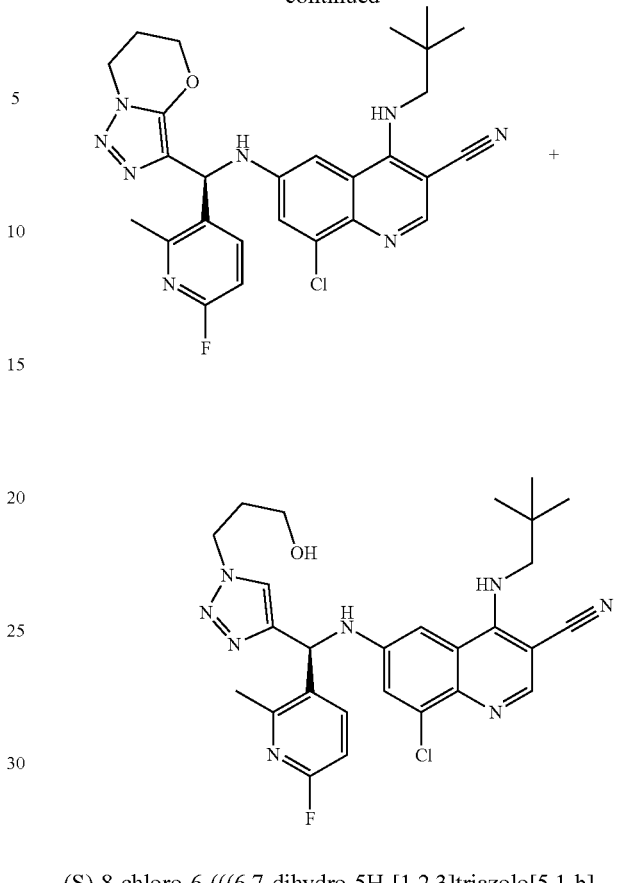

(S)-8-chloro-6-((((6-fluoro-2-methylpyridin-3-yl)(4,5,6,7-tetrahydro-[1,2,3]triazolo[1,5-a]pyridin-3-yl)methyl)amino)-4-(neopentylamino)quinoline-3-carbonitrile: A mixture of the bromoalkane (54 mg, 0.09 mmol) in 4.4 mL toluene was purged with argon for 45 minutes. It was heated to reflux and then Tris(trimethylsilyl)silane (43.74 mg, 0.18 mmol) was added, followed by dropwise addition of 2,2'-Azobisisobutyronitrile, 98% (1.44 mg, 0.01 mmol) in 0.44 mL toluene. After 16 hours heating at reflux, another portion of the silane was added and heating was continued for 4 hours more. The mixture was concentrated and purified by RP-HPLC to yield the product as the trifluoroacetate salt.

Example 45 Procedure 45

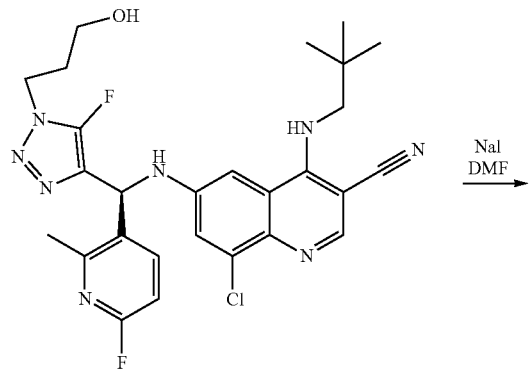

(S)-8-chloro-6-((((6,7-dihydro-5H-[1,2,3]triazolo[5,1-b][1,3]oxazin-3-yl)(6-fluoro-2-methylpyridin-3-yl)methyl)amino)-4-(neopentylamino)quinoline-3-carbonitrile and (S)-8-chloro-6-((((6-fluoro-2-methylpyridin-3-yl)(1-(3-hydroxypropyl)-1H-1,2,3-triazol-4-yl)methyl)amino)-4-(neopentylamino)quinoline-3-carbonitrile: (S)-8-chloro-6-((((5-fluoro-1-(3-hydroxypropyl)-1H-1,2,3-triazol-4-yl)(6-fluoro-2-methylpyridin-3-yl)methyl)amino)-4-(neopentylamino)quinoline-3-carbonitrile (37 mg, 0.07 mmol, prepared as for example 23) was dissolved in DMF and cooled in an ice water bath. Sodium hydride 60% dispersion in mineral oil (5.6 mg, 0.23 mmol) was added NaH and the mixture was allowed to warm to room temperature. After 1 hour, the reaction was complete by UPLC-MS and contained dehalogenated, uncyclized product as well. Purification by RP HPLC 15 minutes 10-49% gave the two products independently as the corresponding trifluoroacetate salts.

(S)-8-chloro-6-((((6,7-dihydro-5H-[1,2,3]triazolo[5,1-b][1,3]oxazin-3-yl)(6-fluoro-2-methylpyridin-3-yl)methyl)amino)-4-(neopentylamino)quinoline-3-carbonitrile: ES/MS m/z: 535.34. 1H NMR (400 MHz, Acetonitrile-d3) δ 8.42 (s, 1H), 7.92 (m, 1H), 7.48 (s, 1H), 6.79 (m, 1H), 6.70 (s, 1H), 5.97 (s, 1H), 4.35 (m, 4H), 3.90 (m, 1H), 3.68 (m, 1H), 2.50 (s, 3H), 2.23 (m, 2H), 0.94 (s, 9H).

(S)-8-chloro-6-((((6-fluoro-2-methylpyridin-3-yl)(1-(3-hydroxypropyl)-1H-1,2,3-triazol-4-yl)methyl)amino)-4-(neopentylamino)quinoline-3-carbonitrile: ES/MS m/z: 537.27. 1H NMR (400 MHz, Acetonitrile-d3) δ 8.41 (s, 1H), 7.84 (m, 1H), 7.66 (m, 1H), 7.48 (m, 1H), 6.82 (m, 1H), 6.74 (m, 1H), 6.15 (m, 1H), 4.42 (m, 2H), 3.76 (m, 2H), 3.48 (m, 2H), 2.51 (s, 3H), 1.98 (m, 2H), 0.94 (s, 9H).

Example 46 Procedure 46

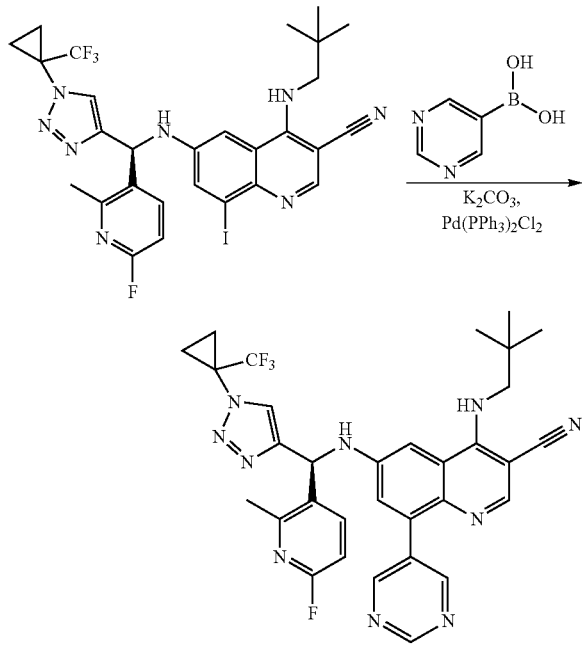

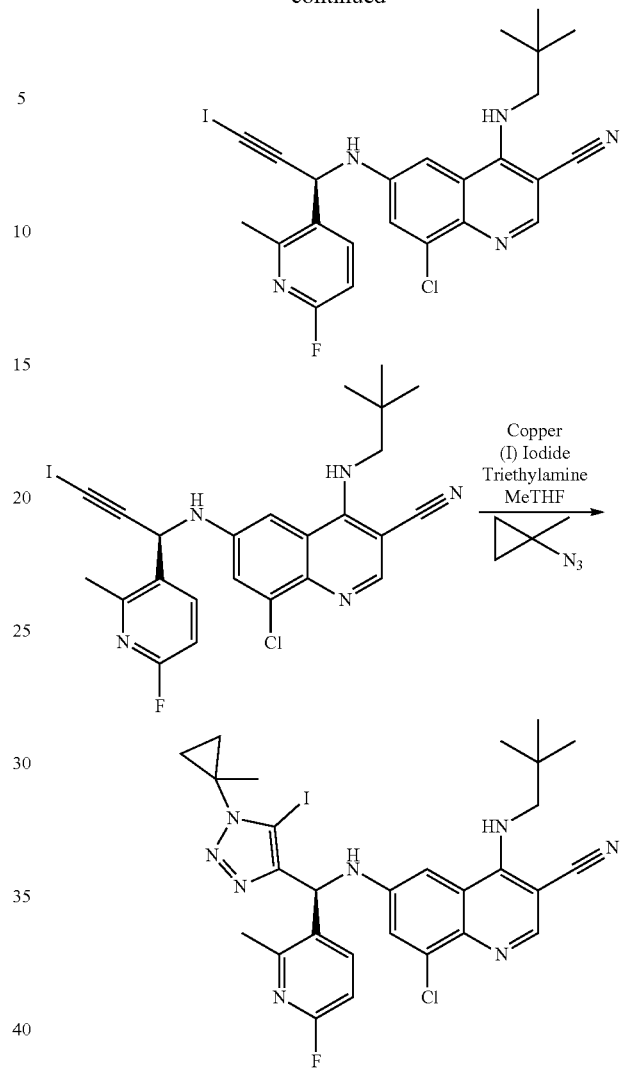

(S)-6-((((6-fluoro-2-methylpyridin-3-yl)(1-(1-(trifluoromethyl)cyclopropyl)-1H-1,2,3-triazol-4-yl)methyl)amino)-4-(neopentylamino)-8-(pyrimidin-5-yl)quinoline-3-carbonitrile: 6-(((6-fluoro-2-methylpyridin-3-yl)(1-(1-(trifluoromethyl)cyclopropyl)-1H-1,2,3-triazol-4-yl)methyl)amino)-8-iodo-4-(neopentylamino)quinoline-3-carbonitrile (20 mg, 0.03 mmol), potassium carbonate (0.03 mL, 0.06 mmol), and pyrimidin-5-ylboronic acid (5.3 mg, 0.045 mmol) were dissolved in DME. Then bis(triphenylphosphine)palladium(II) dichloride (1.0 mg, 0.002 mmol) was add to the mixture. The reaction was heated to 110° C. in microwave reactor for 5 minutes, then diluted with EtOAc and brine, the organic layer was kept, dried over sodium sulfate, and concentrated. The crude residue was purified by RP-HPLC (eluent: water/MeCN*0.1% TFA) to yield the product as trifluoro acetate salt.

Example 47 Procedure 47

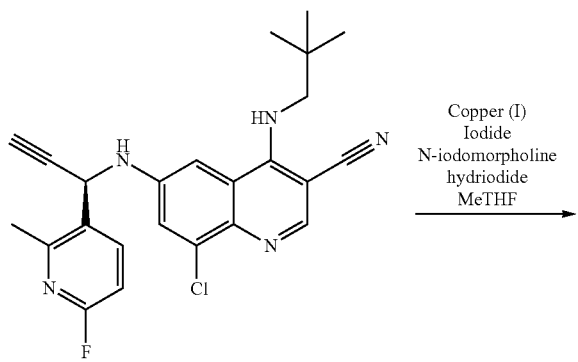

(S)-8-chloro-6-((((6-fluoro-2-methylpyridin-3-yl)(5-iodo-1-(1-methylcyclopropyl)-1H-1,2,3-triazol-4-yl)methyl)amino)-4-(neopentylamino)quinoline-3-carbonitrile: To (R)-8-chloro-6-((1-(6-fluoro-2-methylpyridin-3-yl)prop-2-yn-1-yl)amino)-4-(neopentylamino)quinoline-3-carbonitrile (100 mg, 0.23 mmol) in MeTHF (2 mL) was added Copper (i) iodide (4 mg, 0.02 mmol) and N-iodomorpholine hydriodide (95 mg, 0.28 mmol). The solution was stirred at room temperature for 5 h. The resulting solution was filtered through a carbonate resin and concentrated to give the crude (S)-8-chloro-6-((1-(6-fluoro-2-methylpyridin-3-yl)-3-iodoprop-2-yn-1-yl)amino)-4-(neopentylamino)quinoline-3-carbonitrile.

To a solution of (S)-8-chloro-6-((1-(6-fluoro-2-methylpyridin-3-yl)-3-iodoprop-2-yn-1-yl)amino)-4-(neopentylamino)quinoline-3-carbonitrile in MeTHF (2 mL) was added triethylamine (0.05 mL, 0.36 mmol), Copper (I) iodide (4 mg, 0.02 mmol), and 1-azido-1-methylcyclopropane (0.5 mL, 0.5 M in MTBE, 0.25 mmol). The resulting solution was stirred at room temperature for 3 days and then washed with aqueous bicarbonate. The aqueous layer was back-extracted with EtOAc (2×), and the combined organic layers were dried over $Na_2SO_4$ and concentrated. The crude residue was purified by reverse-phase HPLC (10-60%

MeCN/H₂O with 0.1% TFA) to provide the product as a TFA salt. The product was dissolved in EtOAc and washed with aqueous bicarbonate. The aqueous layer was back-extracted with EtOAc (2×), and the combined organic layers were dried over Na₂SO₄ and concentrated. The crude residue was purified by normal-phase chromatography (10-50% EtOAc/CH₂Cl₂) to provide the product.

1H NMR (400 MHz, Methanol-d4) δ 8.51 (d, J=1.1 Hz, 1H), 7.81 (t, J=8.1 Hz, 1H), 7.65 (d, J=2.3 Hz, 1H), 6.86 (dd, J=8.6, 2.7 Hz, 1H), 6.83 (d, J=2.3 Hz, 1H), 6.07 (s, 1H), 4.13 (d, J=13.9 Hz, 1H), 3.70 (d, J=13.9 Hz, 1H), 2.40 (s, 3H), 1.64 (s, 3H), 1.44-1.31 (m, 2H), 1.22 (t, J=2.0 Hz, 2H), 0.89 (s, 9H).

ES/MS: 659.255 (M+H+).

Example 48 Procedure 48

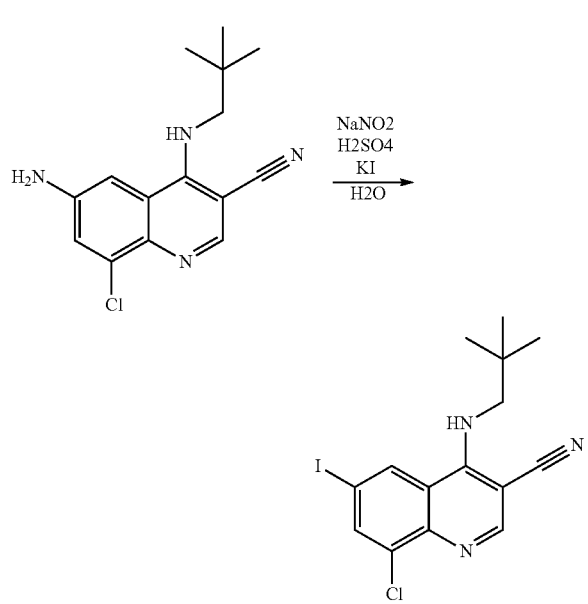

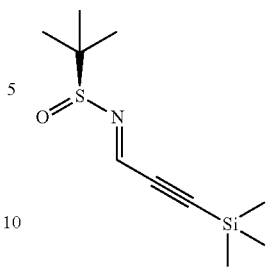

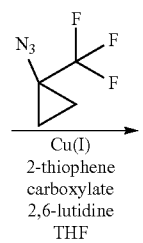

(S)-8-chloro-6-(((6-fluoro-2-methylpyridin-3-yl)(1-(1-(trifluoromethyl)cyclopropyl)-1H-1,2,3-triazol-4-yl)methyl)(methyl)amino)-4-(neopentylamino)quinoline-3-carbonitrile: To a slurry of 6-amino-8-chloro-4-(neopentylamino)quinoline-3-carbonitrile (1 g, 3.46 mmol) in H₂O (35 mL) and H2SO4 (1.8 mL) at 0° C. (external) was dropwise added 1.5M aqueous NaNO₂ (2.8 ml). The resulting solution was stirred at 0° C. for 1.5 h before potassium iodide (1.2 g, 7.23 mmol) in H₂O (15 mL) was added. The resulting slurry was vigorously stirred at room temperature for 18 h. The slurry was neutralized with NaOH (2M), filtered, and washed twice with H₂O. The resulting filtrate was dissolved in EtOAc and washed with aqueous NaCl. The aqueous layer was back-extracted with EtOAc and the combined organic layers were dried over MgSO₄ and concentrated. The crude material was purified by SiO₂ chromatography (5-25-100% EtOAc/Hex, 20% MeOH/EtOAc wash) to provide the desired product.

1H NMR (400 MHz, DMSO-d6) δ 8.82 (d, J=1.7 Hz, 1H), 8.55 (s, 1H), 8.25 (d, J=1.5 Hz, 1H), 8.19 (t, J=7.0 Hz, 1H), 3.72 (d, J=6.8 Hz, 2H), 0.96 (s, 9H).

ES/MS: 400.428 (M+H+).

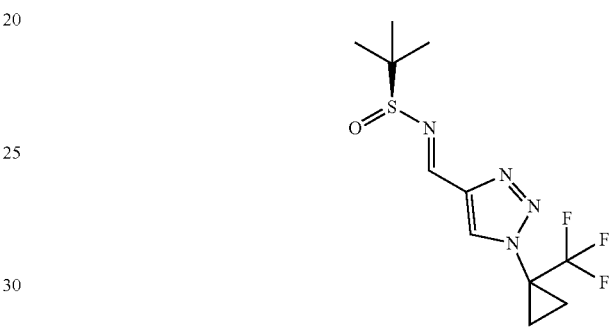

To a solution of (S,E)-2-methyl-N-(3-(trimethylsilyl)prop-2-yn-1-ylidene)propane-2-sulfinamide (0.5 g, 2.18 mmol) in THF (7.5 mL) was added Cu(I) 2-thiophene carboxylate (50 mg, 0.26 mmol), 2,6-Lutidine (1.3 ml, 11.16 mmol), and Cyclopropyl azide (17% in MTBE, 1 ml, 7.82 mmol). The resulting solution was stirred at 40° C. (external) for 18 h and then diluted with EtOAc. The solution was washed with H2O and twice with aqueous NH4Cl. The aqueous layers were back-extracted with EtOAc and the combined organic layers were dried over MgSO4 and concentrated. The crude residue was purified by SiO2 chromatography (15-50% EtOAc/CH2Cl2) to provide the desired product.

1H NMR (400 MHz, Chloroform-d) δ 8.78 (d, J=1.2 Hz, 1H), 8.26 (s, 1H), 1.82-1.75 (m, 2H), 1.72 (dt, J=8.0, 4.9 Hz, 2H), 1.26 (d, J=1.2 Hz, 9H).

ES/MS: 309.100 (M+H+).

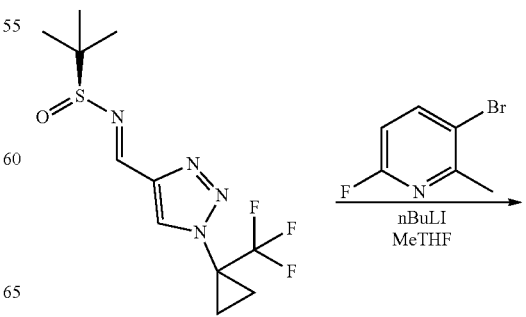

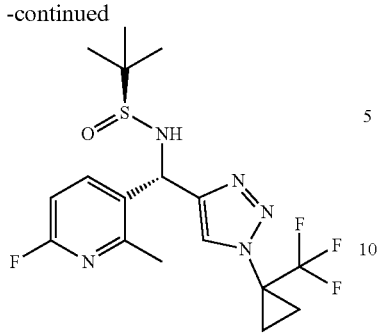

To a solution of 3-bromo-6-fluoro-2-methylpyridine (370 mg, 1.95 mmol) in MeTHF (7.5 mL) at −78° C. (external). An n-Butyllithium solution (2.5 M in hexanes, 1.25 ml) was added dropwise and the reaction was stirred at −78° C. for 1.5 h. To the yellow/orange solution was added (S,E)-2-methyl-N-((1-(1-(trifluoromethyl)cyclopropyl)-1H-1,2,3-triazol-4-yl)methylene)propane-2-sulfinamide (200 mg, 0.65 mmol) in MeTHF (2 mL), and the resulting solution was warmed to room temperature for 2 h. The reaction was diluted with 50% NH4Cl and extracted twice with EtOAc. The combined organic layers were dried over Na2SO4 and concentrated. The crude material was purified by SiO2 chromatography (25-60% EtOAc(5% MeOH)/CH2Cl2) to provide the desired product as a single isomer.

1H NMR (400 MHz, Chloroform-d) δ 7.91-7.81 (m, 1H), 7.52 (s, 1H), 6.81 (dd, J=8.5, 3.3 Hz, 1H), 5.93 (d, J=3.4 Hz, 1H), 4.41 (d, J=3.5 Hz, 1H), 2.55 (s, 3H), 1.74-1.59 (m, 1H), 1.24 (d, J=0.8 Hz, 9H).

ES/MS: 420.099 (M+H+).

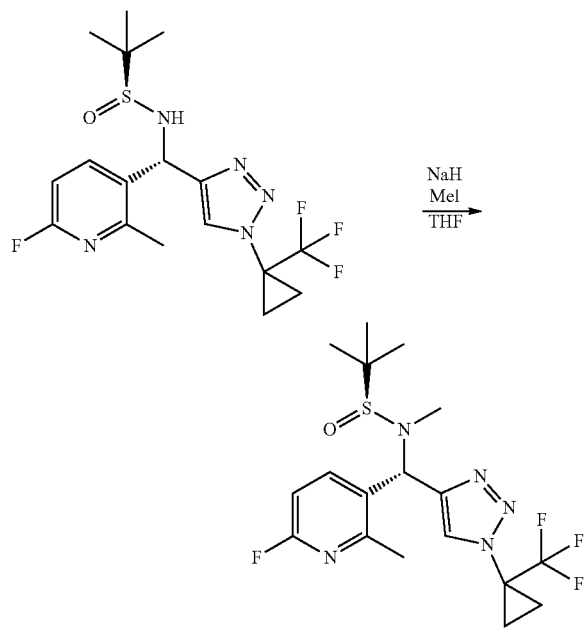

A solution of (S)—N—((S)-(6-fluoro-2-methylpyridin-3-yl)(1-(1-(trifluoromethyl)cyclopropyl)-1H-1,2,3-triazol-4-yl)methyl)-2-methylpropane-2-sulfinamide (0.1 g, 0.25 mmol) in THF (3 mL) was cooled to 0° C. Sodium hydride (60% dispersion in mineral oil, 0.01 g, 0.29 mmol) was added and stirred for 30 min before iodomethane was added (0.02 mL, 0.32 mmol). The resulting solution was stirred at room temperature for 24 h and diluted with EtOAc. The solution was washed with 50% NH4Cl and the aqueous solution was back-extracted with EtOAc. The combine organic layers were dried over Na2SO4 and concentrated. The crude residue was purified by SiO2 chromatography (20-50-60% EtOAc (5% MeOH)/CH2Cl2) to provide the desired product.

1H NMR (400 MHz, Chloroform-d) δ 7.95 (t, J=8.2 Hz, 1H), 7.78 (s, 1H), 6.83 (dd, J=8.5, 3.3 Hz, 1H), 5.99 (s, 1H), 2.58 (s, 3H), 2.46 (s, 3H), 1.63 (d, J=62.7 Hz, 4H), 1.17 (s, 9H).

ES/MS: 433.820 (M+H+).

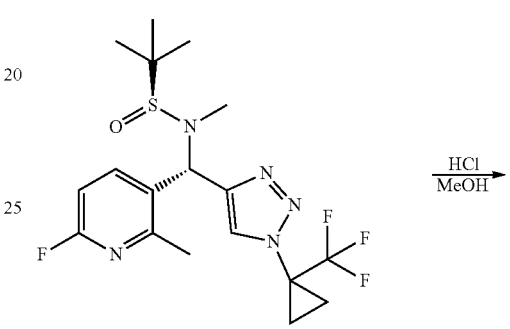

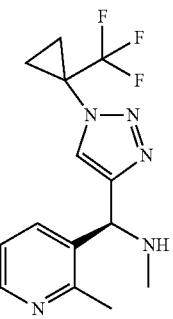

To a solution of (S)—N—((S)-(6-fluoro-2-methylpyridin-3-yl)(1-(1-(trifluoromethyl)cyclopropyl)-1H-1,2,3-triazol-4-yl)methyl)-N,2-dimethylpropane-2-sulfinamide (0.07 g, 0.17 mmol) in MeOH (1 mL) was added 4M HCl in dioxane (0.45 ml). The resulting solution was stirred at room temperature for 2 h and concentrated. The crude residue was diluted with EtOAc and washed with aqueous bicarbonate. The aqueous layer was back-extracted with EtOAc and the combine organic layers were dried over Na2SO4 and concentrated. The crude amine was dissolved in a 1:1 mixture of CH2Cl2 and toluene and concentrated to dryness to provide the desired product.

ES/MS: 329.872 (M+H+).

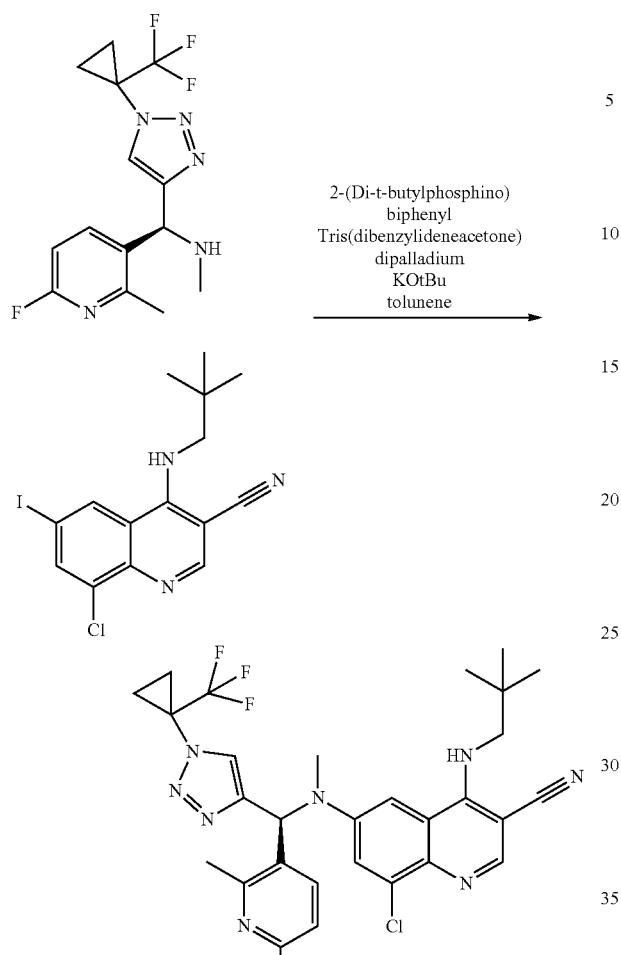

To a solution of (S)-1-(6-fluoro-2-methylpyridin-3-yl)-N-methyl-1-(1-(1-(trifluoromethyl)cyclopropyl)-1H-1,2,3-triazol-4-yl)methanamine (0.05 g, 0.17 mmol) in toluene (3.5 mL) was added 8-chloro-6-iodo-4-(neopentylamino)quinoline-3-carbonitrile (0.07 g, 0.17 mmol), 2-(di-t-butylphosphino)biphenyl (0.02 g, 0.07 mmol), and tris(dibenzylideneacetone)dipalladium (O) (0.03 g, 0.03 mmol). The slurry was degassed with argon for 5 min and potassium tert-butoxide, 95% (0.06 g, 0.5 mmol) was added. The resulting slurry was heated to 80° C. (external) for 2 h. The reaction mixture was then diluted with EtOAc and washed with aqueous bicarbonate. The aqueous layers were back-extracted and the resulting organic layers were concentrated. The crude oil was then purified by reverse-phase HPLC (10-70% MeCN/H2O with 0.1% TFA). The product was purified a second time by reverse-phase HPLC (10-65% MeCN/H2O with 0.1% TFA) to provide the desired product as a TFA salt.

1H NMR (400 MHz, Methanol-d4) δ 8.55 (d, J=1.6 Hz, 1H), 8.32 (s, 1H), 7.88 (d, J=2.6 Hz, 1H), 7.59 (t, J=8.1 Hz, 1H), 7.40 (d, J=2.6 Hz, 1H), 6.92 (dd, J=8.5, 2.8 Hz, 1H), 6.76 (s, 1H), 4.09 (d, J=14.1 Hz, 1H), 3.96 (d, J=14.1 Hz, 1H), 2.97 (s, 3H), 2.35 (s, 3H), 1.80-1.70 (m, 4H), 1.02 (d, J=3.2 Hz, 9H).

ES/MS: 601.367 (M+H+).

Example 49, Procedure 49

(S)-8-acetyl-6-(((1-(1-(difluoromethyl)cyclopropyl)-1H-1,2,3-triazol-4-yl)(6-fluoro-2-methylpyridin-3-yl)methyl)amino)-4-(neopentylamino)quinoline-3-carbonitrile

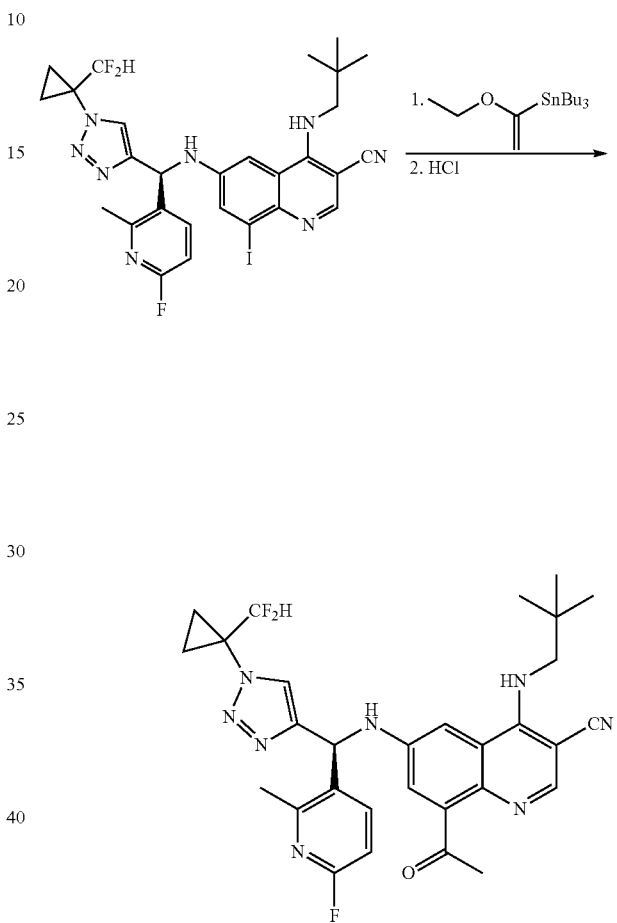

To (S)-6-(((1-(1-(difluoromethyl)cyclopropyl)-1H-1,2,3-triazol-4-yl)(6-fluoro-2-methylpyridin-3-yl)methyl)amino)-8-iodo-4-(neopentylamino)quinoline-3-carbonitrile (37 mg, 0.056 mmol) and bis(triphenylphosphine)palladium(II) dichloride (5 mg, 0.006 mmol) in toluene (1 mL) was added tributyl(2-ethoxyallyl)stannane (23 mg, 0.062 mmol). The reaction mixture was flushed with nitrogen and heated at 100° C. overnight. After cooling to room temperature, 2N HCl (1 mL) was added and the mixture stirred for 2 hours. Reaction was diluted with water and extracted thrice with EtOAc. Combined organics were washed with water and brine and dried (Na2SO4). Filtrate was concentrated to yield the crude material which was purified twice by HPLC (eluent: water/MeCN*0.1% TFA) to give the product.

The following compounds were prepared according to the Examples and

Procedures described herein (and indicated in Table 1 under Example/Procedure) using the appropriate starting material(s) and appropriate protecting group chemistry as needed.

TABLE 1

| Comp | Structure | Name | Example Procedure | ES/MS m/z |
|---|---|---|---|---|
| 1 | 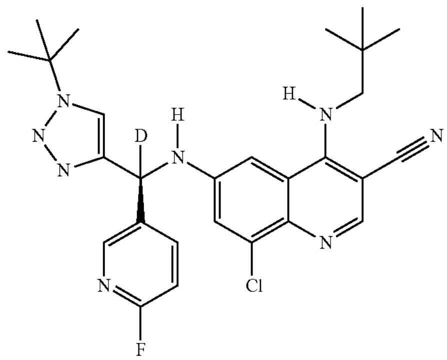 [SMILES: [2H][C@](Nc1cc(Cl)c2ncc(C#N)c(NCC(C)(C)C)c2c1)(C1=CN(C(C)(C)C)NN1)c1ccc(F)nc1] | (S)-6-(((1-(tert-butyl)-1H-1,2,3-triazol-4-yl)(6-fluoropyridin-3-yl)methyl-d)amino)-8-chloro-4-(neopentylamino)quinoline-3-carbonitrile | 1 | ES/MS 522.2 (M + H+) |
| 2 | 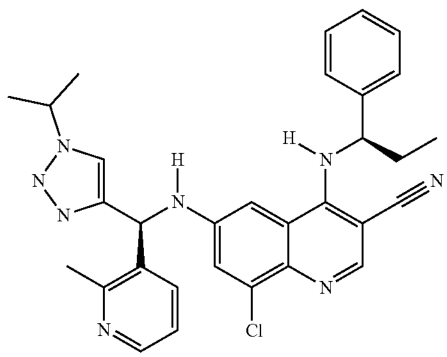 [SMILES: CC[C@@H](Nc1c(C#N)cnc2c(Cl)cc(N[C@H](C3=CN(C(C)C)NN3)c3cccnc3C)cc12)c1ccccc1] | 8-chloro-6-(((S)-(1-isopropyl-1H-1,2,3-triazol-4-yl)(2-methylpyridin-3-yl)rnethyl)amino)-4-(((R)-1-phenylpropyl)amino)quinoline-3-carbonitrile | 2 | ES/MS 551.09 (M + H+) |
| 3 | 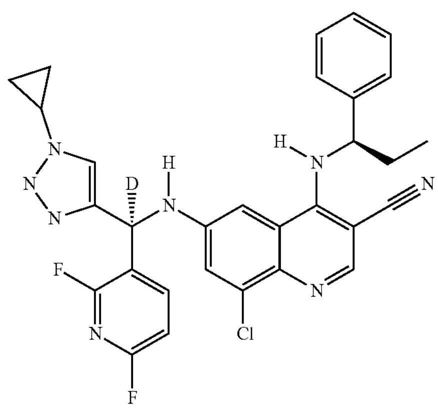 [SMILES: [2H][C@@](Nc1cc(Cl)c2ncc(C#N)c(N[C@H](CC)c3ccccc3)c2c1)(C1=CN(C2CC2)NN1)c1ccc(F)nc1F] | 8-chloro-6-(((1-cyclopropyl-1H-1,2,3-triazol-4-yl)(2,6-difluoropyridin-3-yl)methyl-d)amino)-4-(((R)-1-phenylpropyl)amino)quinoline-3-carbonitrile | 2 | ES/MS: 572.24 (M + H+) |
| 4 | 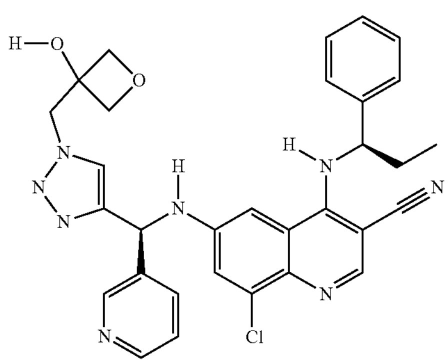 [SMILES: CC[C@@H](Nc1c(C#N)cnc2c(Cl)cc(N[C@H](C3=CN(CC4(O)COC4)NN3)c3cccnc3)cc12)c1ccccc1] | 8-chloro-6-(((S)-(1-((3-hydroxyoxetan-3-yl)methyl)-1H-1,2,3-triazol-4-yl)(pyridin-3-yl)methyl)amino)-4-(((R)-1-phenylpropyl)amino)quinoline-3-carbonitrile | 4 | ES/MS 581.1 (M + H+) |

TABLE 1-continued

| Comp | Structure | Name | Example Procedure | ES/MS m/z |
|---|---|---|---|---|
| 5 | 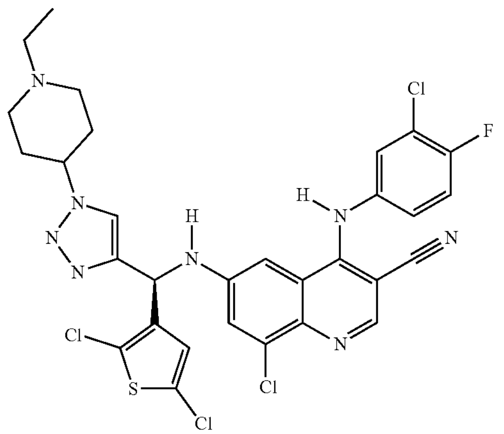 [SMILES: CCN1CCC(N2C=C([C@@H](Nc3cc(Cl)c4ncc(C#N)c(Nc5ccc(F)c(Cl)c5)c4c3)c3cc(Cl)sc3Cl)NN2)CC1] | (S)-8-chloro-4-((3-chloro-4-fluorophenyl)amino)-6-(((2,5-dichlorothiophen-3-yl)(1-(1-ethylpiperidin-4-yl)-1H-1,2,3-triazol-4-yl)methyl)amino)quinoline-3-carbonitrile | 5 | ES/MS 688.9 (M + H+) |
| 6 | 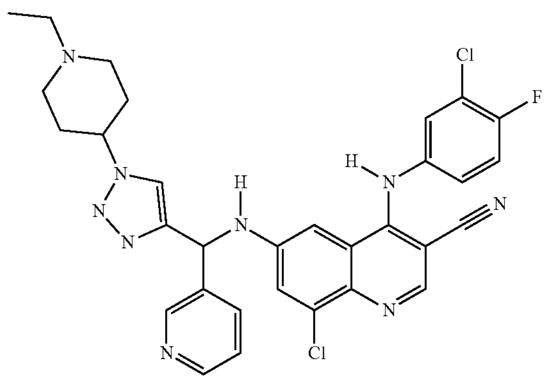 [SMILES: CCN1CCC(N2C=C(C(Nc3cc(Cl)c4ncc(C#N)c(Nc5ccc(F)c(Cl)c5)c4c3)c3cccnc3)NN2)CC1] | 8-chloro-4-((3-chloro-4-fluorophenyl)amino)-6-(((1-(1-ethylpiperidin-4-yl)-1H-1,2,3-triazol-4-yl)(pyridin-3-yl)methyl)amino)quinoline-3-carbonitrile | 6 | |
| 7 | 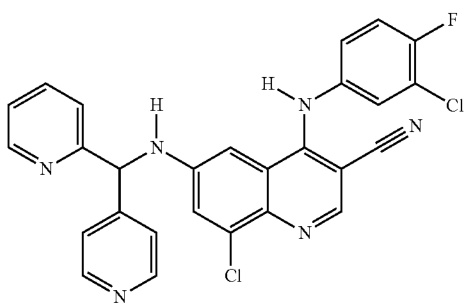 [SMILES: N#Cc1cnc2c(Cl)cc(NC(c3ccncc3)c3ccccn3)cc2c1Nc1ccc(F)c(Cl)c1] | 8-chloro-4-((3-chloro-4-fluorophenyl)amino)-6-((pyridin-2-yl(pyridin-4-yl)methyl)amino)quinoline-3-carbonitrile | 7 | ES/MS 515.0 (M + H+) |
| 8 | 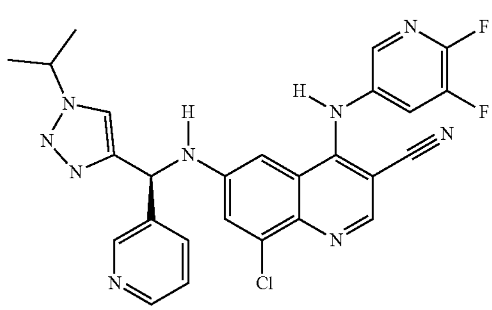 [SMILES: CC(C)N1C=C([C@@H](Nc2cc(Cl)c3ncc(C#N)c(Nc4cnc(F)c(F)c4)c3c2)c2cccnc2)NN1] | (S)-8-chloro-4-((5,6-difluoropyridin-3-yl)amino)-6-(((1-isopropyl-1H-1,2,3-triazol-4-yl)(pyridin-3-yl)methyl)amino)quinoline-3-carbonitrile | 8 | ES/MS 532.1 (M + H+) |

TABLE 1-continued

| Comp | Structure | Name | Example Procedure | ES/MS m/z |
|---|---|---|---|---|
| 9 | 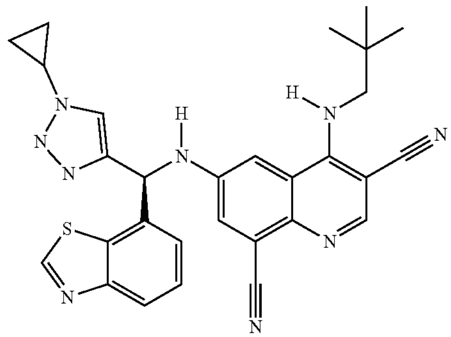 [SMILES: CC(C)(C)CNc1c(C#N)cnc2c(C#N)cc(N[C@H](C3=CN(C4CC4)NN3)c3cccc4ncsc34)cc12] | (S)-6-((benzo[d]thiazol-7-yl(1-cyclopropyl-1H-1,2,3-triazol-4-yl)methyl)amino)-4-(neopentyl-amino)quinoline-3,8-dicarbonitrile | 9a | ES/MS 534.1 (M + H+) |
| 10 | 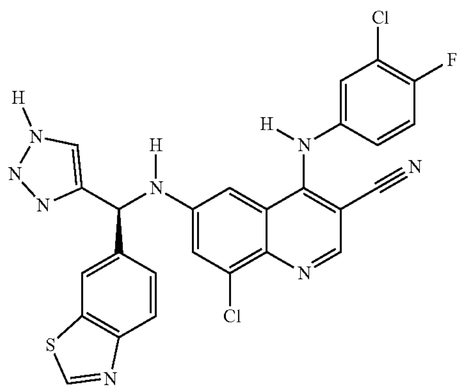 [SMILES: N#Cc1cnc2c(Cl)cc(N[C@H](C3=CNNN3)c3ccc4ncsc4c3)cc2c1Nc1ccc(F)c(Cl)c1] | (S)-6-((benzo[d]thiazol-6-yl(1H-1,2,3-triazol-4-yl)methyl)amino)-8-chloro-4-((3-chloro-4-fluorophenyl)-amino)quinoline-3-carbonitrile | 10 | ES/MS 561 0 (M + H+) |
| 11 | 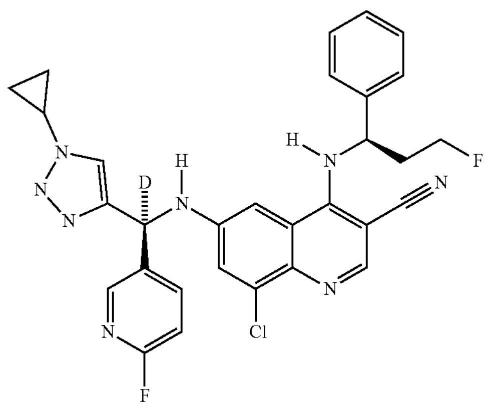 | 8-chloro-6-(((1-cyclopropyl-1H-1,2,3-triazol-4-yl)(6-fluoropyridin-3-yl)methyl-d)amino)-4-(((R)-3-fluoro-1-phenylpropyl)amino)quinoline-3-carbonitrile | 11 | 572 |
| 12 | 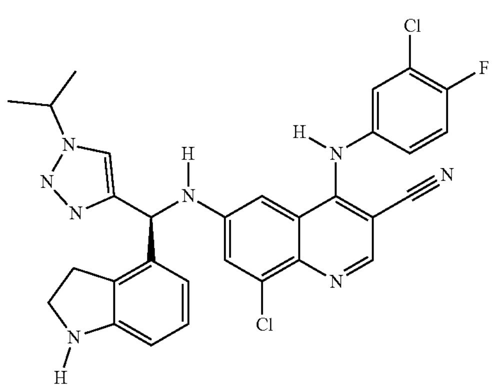 [SMILES: CC(C)N1C=C([C@@H](Nc2cc(Cl)c3ncc(C#N)c(Nc4ccc(F)c(Cl)c4)c3c2)c2cccc3c2CCN3)NN1] | (S)-8-chloro-4-t-((3-chloro-4-fluorophenyl)amino)-6-((indolin-4-yl(1-isopropyl-1H-1,2,3-triazol-4-yl)methyl)amino)quinoline-3-carbonitrile | 12 | ES/MS 586.9 (M + H+) |

TABLE 1-continued

| Comp | Structure | Name | Example Procedure | ES/MS m/z |
|---|---|---|---|---|
| 13 | 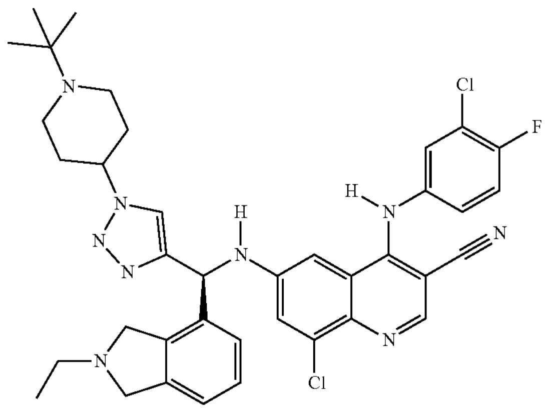 [SMILES: CCN1Cc2cccc([C@H](Nc3cc(Cl)c4ncc(C#N)c(Nc5ccc(F)c(Cl)c5)c4c3)C3=CN(C4CCN(C(C)(C)C)CC4)NN3)c2C1] | (S)-6-(((1-(1-(tert-butyl)piperidin-4-yl)-1H-1,2,3-triazol-4-yl)(2-ethylisoindolin-4-yl)methyl)amino)-8-chloro-4-((3-chloro-4-fluorophenyl)amino)-quinoline-3-carbonitrile | 13 | ES/MS 712.1 (M + H+) |
| 14 | 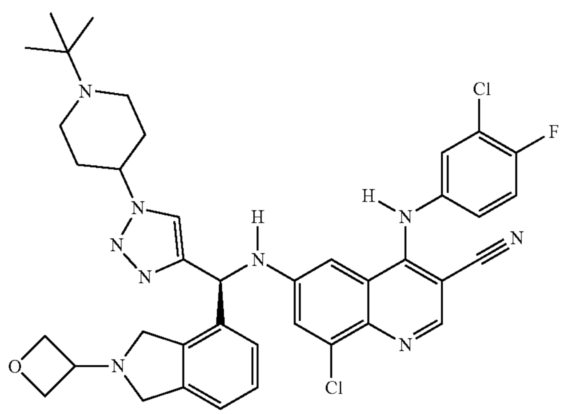 [SMILES: CC(C)(C)N1CCC(N2C=C([C@@H](Nc3cc(Cl)c4ncc(C#N)c(Nc5ccc(F)c(Cl)c5)c4c3)c3cccc4c3CN(C3COC3)C4)NN2)CC1] | (S)-6-(((1-(1-(tert-butyl)piperidin-4-yl)-1H-1,2,3-triazol-4-yl)(2-(oxetan-3-yl)isoindolin-4-yl)methyl)amino)-8-chloro-4-4-((3-chloro-4-fluorophenyl)-amino)quinoline-3-carbonitrile | 14 | ES/MS 740 0 (M + H+) |
| 15 | 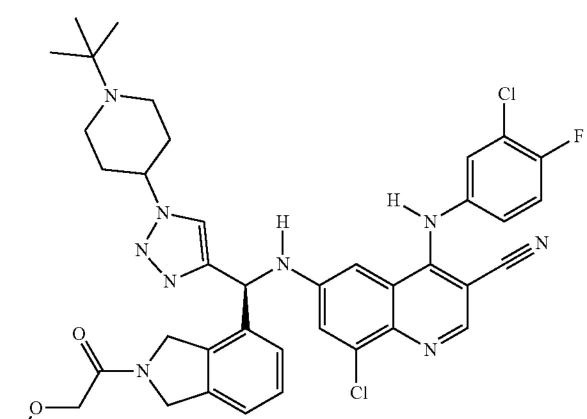 | (S)-6-(((1-(1-(tert-butyl)piperidin-4-yl)-1H-1,2,3-triazol-4-yl)(2-(2-hydroxyacetyl)isoindolin-4-yl)methyl)-amino)-8-chloro-4-((3-chloro-4-fluorophenyl)amino)quinoline-3-carbonitrile | 15 | ES/MS 742.1 (M + H+) |

TABLE 1-continued

| Comp | Structure | Name | Example Procedure | ES/MS m/z |
|---|---|---|---|---|
| 16 | 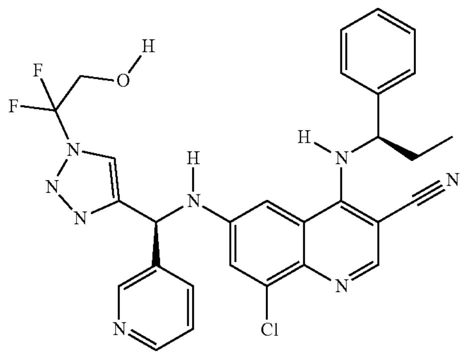 [SMILES: CC[C@@H](Nc1c(C#N)cnc2c(Cl)cc(N[C@H](C3=CN(C(F)(F)CO)NN3)c3cccnc3)cc12)c1ccccc1] | 8-chloro-6-(((S)-(1-(1,1-difluoro-2-hydroxyethyl)-1H-1,2,3-triazol-4-yl)(pyridin-3-yl)methyl)amino)-4-(((R)-1-phenylpropyl)amino)quinoline-3-carbonitrile | 16 | ES/MS 575.1 (M + H+) |
| 17 | 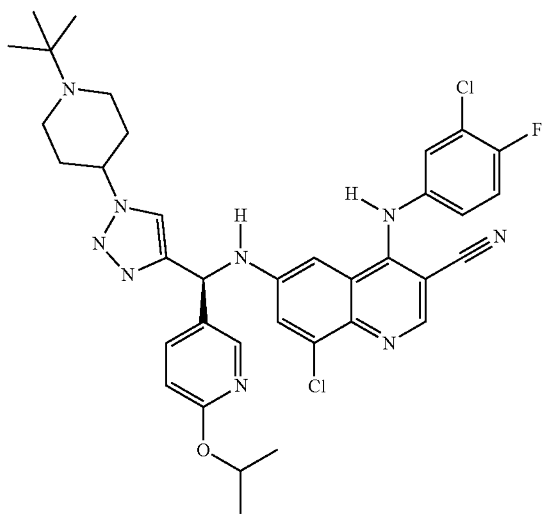 [SMILES: CC(C)Oc1ccc([C@H](Nc2cc(Cl)c3ncc(C#N)c(Nc4ccc(F)c(Cl)c4)c3c2)C2=CN(C3CCN(C(C)(C)C)CC3)NN2)cn1] | (S)-6-(((1-(1-(tert-butyl)piperidin-4-yl)-1H-1,2,3-triazol-4-yl)(6-isopropoxypyridin-3-yl)methyl)amino)-8-chloro-4-((3-chloro-4-fluorophenyl)amino)quinoline-3-carbonitrile | 17 | ES/MS 702.0 (M + H+) |
| 18 | 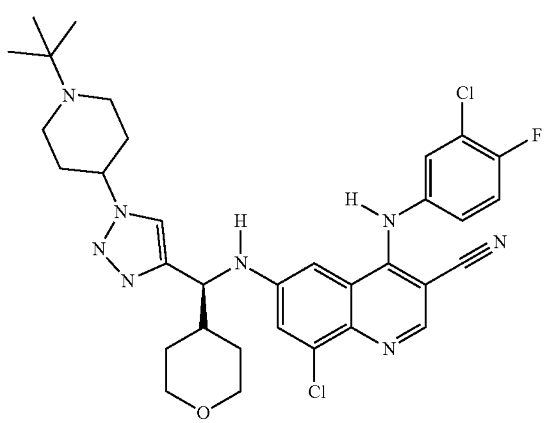 [SMILES: CC(C)(C)N1CCC(N2C=C([C@@H](Nc3cc(Cl)c4ncc(C#N)c(Nc5ccc(F)c(Cl)c5)c4c3)C3CCOCC3)NN2)CC1] | (S)-6-(((1-(1-(tert-butyl)piperidin-4-yl)-1H-1,2,3-triazol-4-yl)(tetrahydro-2H-pyran-4-yl)methyl)amino)-8-chloro-4-((3-chloro-4-fluorophenyl)amino)-quinoline-3-carbonitrile | 18 | ES/MS 651.1 (M + H+) |

TABLE 1-continued

| Comp | Structure | Name | Example Procedure | ES/MS m/z |
|---|---|---|---|---|
| 19 | 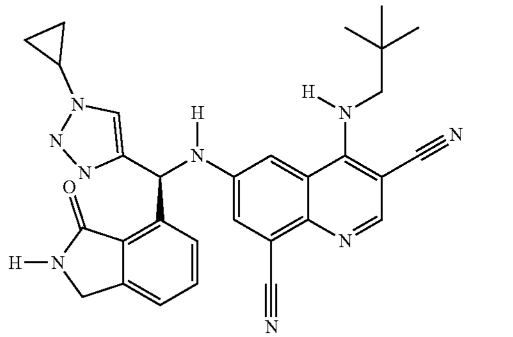 [SMILES: CC(C)(C)CNc1c(C#N)cnc2c(C#N)cc(N[C@H](C3=CN(C4CC4)NN3)c3cccc4c3C(=O)NC4)cc12] | (S)-6-(((1-cyclopropyl-1H-1,2,3-triazol-4-yl)(3-oxoisoindolin-4-yl)methyl)amino)-4-(neopentylamino)quinoline-3,8-dicarbonitrile | 19 | ES/MS 532.2 (M + H+) |
| 20 | 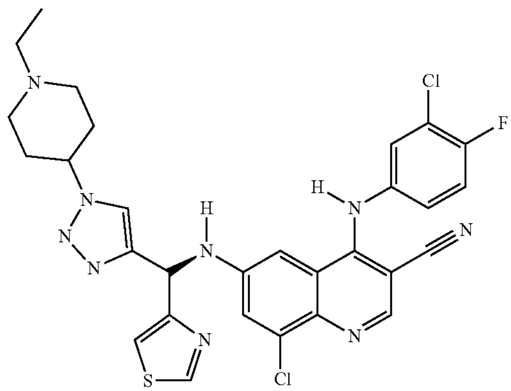 | (S)-8-chloro-4-((3-chloro-4-fluorophenyl)amino)-6-(((1-(1-ethylpiperidin-4-yl)-1H-1,2,3-triazol-4-yl)(thiazol-4-yl)methyl)amino)-quinoline-3-carbonitrile | 20 | ES/MS 622.0 (M + H+) |
| 21 | 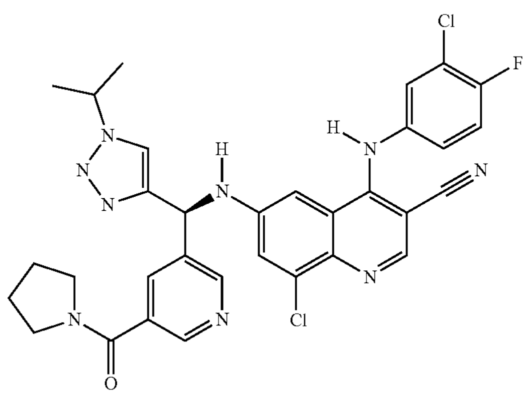 [SMILES: CC(C)N1C=C([C@@H](Nc2cc(Cl)c3ncc(C#N)c(Nc4ccc(F)c(Cl)c4)c3c2)c2cncc(C(=O)N3CCCC3)c2)NN1] | (S)-8-chloro-4-((3-chloro-4-fluorophenyl)amino)-6-(((1-isopropyl-1H-1,2,3-triazol-4-yl)(5-(pyrrolidine-1-carbonyl)pyridin-3-yl)methyl)amino)quinoline-3-carbonitrile | 21 | ES/MS 644.1 (M + H+) |
| 22 | 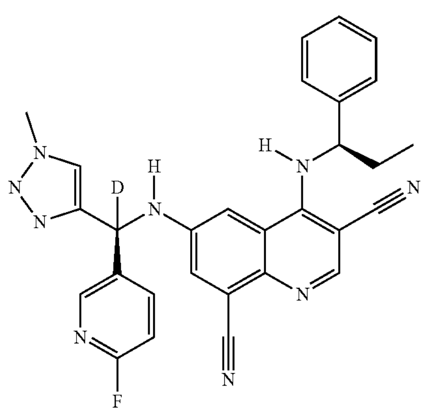 [SMILES: [2H][C@](Nc1cc(C#N)c2ncc(C#N)c(N[C@H](CC)c3ccccc3)c2c1)(C1=CN(C)NN1)c1ccc(F)nc1] | 6-(((S)-(6-fluoropyridin-3-yl)(1-methyl-1H-1,2,3-triazol-4-yl)methyl-d)amino)-4-(((R)-1-phenylpropyl)amino)quinoline-3,8-dicarbonitrile | 22 | ES/MS 519.2 (M + H+) |

TABLE 1-continued

| Comp | Structure | Name | Example Procedure | ES/MS m/z |
|---|---|---|---|---|
| 23 | 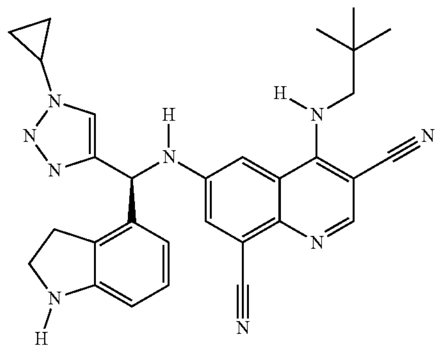 [SMILES: CC(C)(C)CNc1c(C#N)cnc2c(C#N)cc(N[C@H](C3=CN(C4CC4)NN3)c3cccc4c3CCN4)cc12] | (S)-6-(((1-cyclopropyl-1H-1,2,3-triazol-4-yl)(indolin-4-yl)methyl)amino)-4-(neopentylamino)quinoline-3,8-dicarbonitrile | 12 | ES/MS 518.2 (M + H+) |
| 24 | 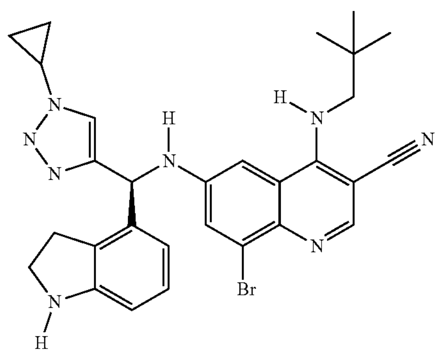 [SMILES: CC(C)(C)CNc1c(C#N)cnc2c(Br)cc(N[C@H](C3=CN(C4CC4)NN3)c3cccc4c3CCN4)cc12] | (S)-8-bromo-6-(((1-cyclopropyl-1H-1,2,3-triazol-4-yl)(indolin-4-yl)methyl)amino)-4-(neopentylamino)quinoline-3-carbonitrile | 12 | ES/MS 571.1 (M + H+) |
| 25 | 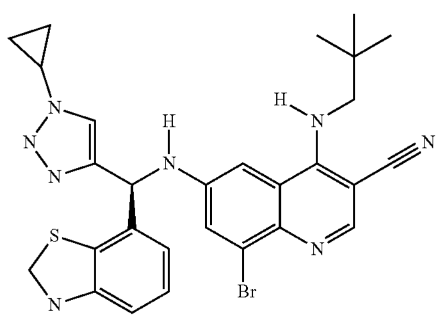 | (S)-6-((benzo[d]thiazol-7-yl(1-cyclopropyl-1H-1,2,3-triazol-4-yl)methyl)amino)-8-bromo-4-(neopentylamino)quinoline-3-carbonitrile | 2 | ES/MS 587.2 (M + H+) |
| 26 | 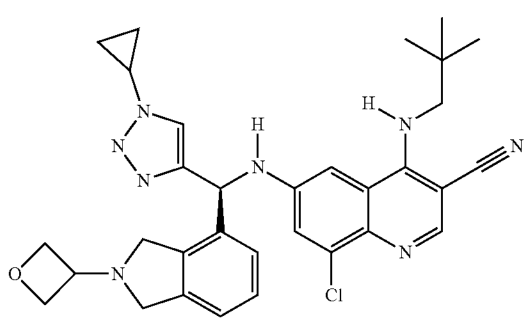 [SMILES: CC(C)(C)CNc1c(C#N)cnc2c(Cl)cc(N[C@H](C3=CN(C4CC4)NN3)c3cccc4c3CN(C3COC3)C4)cc12] | (S)-8-chloro-6-(((1-cyclopropyl-1H-1,2,3-triazol-4-yl)(2-(oxetan-3-yl)isoindolin-4-yl)methyl)amino)-4-(neopentylamino)quinoline-3-carbonitrile | 14 | ES/MS 583.1 (M + H+) |

TABLE 1-continued

| Comp | Structure | Name | Example Procedure | ES/MS m/z |
|---|---|---|---|---|
| 27 | 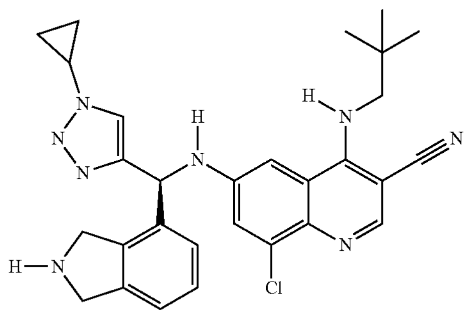 [SMILES: CC(C)(C)CNc1c(C#N)cnc2c(Cl)cc(N[C@H](C3=CN(C4CC4)NN3)c3cccc4c3CNC4)cc12] | (S)-8-chloro-6-(((1-cyclopropyl-1H-1,2,3-triazol-4-yl)(isoindolin-4-yl)methyl)amino)-4-(neopentylamino)quinoline-3-carbonitrile | 12 | ES/MS 527.0 (M + H+) |
| 28 | 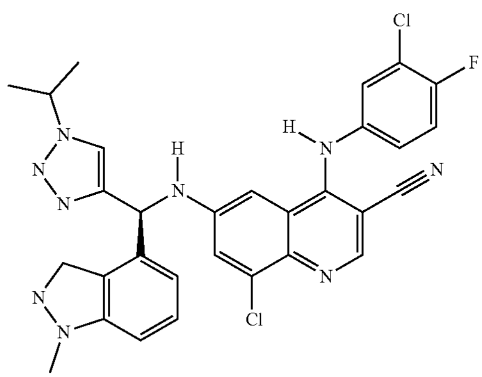 | (S)-8-chloro-4-((3-chloro-4-fluorophenyl)amino)-6-(((1-isopropyl-1H-1,2,3-triazol-4-yl)(1-methyl-1H-indazol-4-yl)methyl)amino)quinoline-3-carbonitrile | 2 | ES/MS 600.0 (M + H+) |
| 29 | 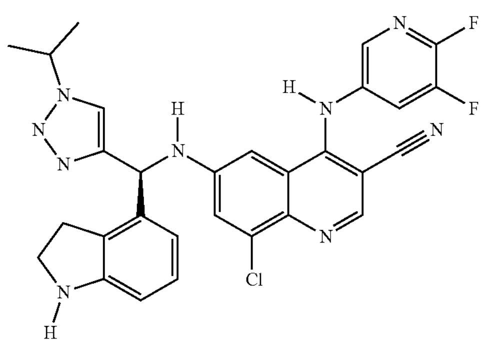 [SMILES: CC(C)N1C=C([C@@H](Nc2cc(Cl)c3ncc(C#N)c(Nc4cnc(F)c(F)c4)c3c2)c2cccc3c2CCN3)NN1] | (S)-8-chloro-4-((5,6-difluoropyridin-3-yl)amino)6-((indolin-4-yl (1-isopropyl-1H-1,2,3-triazo-4-yl)methyl)amino)-quinoline-3-carbonitrile | 12 | ES/MS 572.1 (M + H+) |
| 30 | 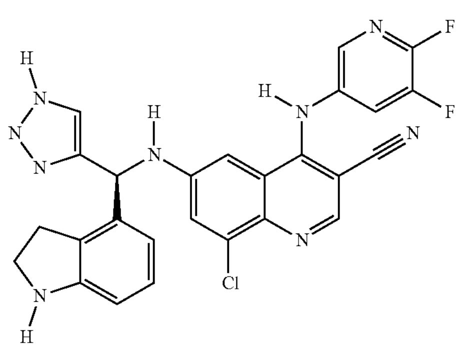 [SMILES: N#Cc1cnc2c(Cl)cc(N[C@H](C3=CNNN3)c3cccc4c3CCN4)cc2c1Nc1cnc(F)c(F)c1] | (S)-8-chloro-4-((5,6-difluoropyridin-3-yl)amino)-6-((indolin-4-yl(1H-1,2,3-triazol-4-yl)methyl)amino)quinoline-3-carbonitrile | 12 | ES/MS 530.1 (M + H+) |

TABLE 1-continued

| Comp | Structure | Name | Example Procedure | ES/MS m/z |
|---|---|---|---|---|
| 31 | 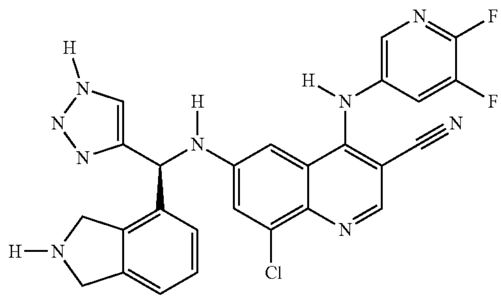 [SMILES: N#Cc1cnc2c(Cl)cc(N[C@H](C3=CNNN3)c3cccc4c3CNC4)cc2c1Nc1cnc(F)c(F)c1] | (S)-8-chloro-4-((5,6-difluoropyridin-3-yl)amino)-6-((isoindolin-4-yl(1H-1,2,3-triazol-4-yl)methyl)amino)quinoline-3-carbonitrile | 12 | ES/MS 530.0 (M + H+) |
| 32 | 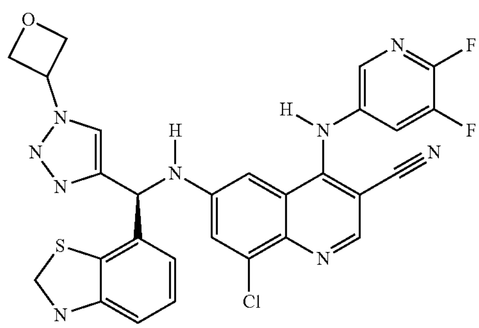 [SMILES: N#Cc1cnc2c(Cl)cc(N[C@H](C3=CN(C4COC4)NN3)c3cccc4c3SCN4)cc2c1Nc1cnc(F)c(F)c1] | (S)-6-((benzo[d]thiazol-7-yl(1-(oxetan-3-yl)-1H-1,2,3-triazol-4-yl)methyl)amino)-8-chloro-4-((5,6-difluoropyridin-3-yl)amino)quinoline-3-carbonitrile | 2 | ES/MS 601.9 (M + H+) |
| 33 | 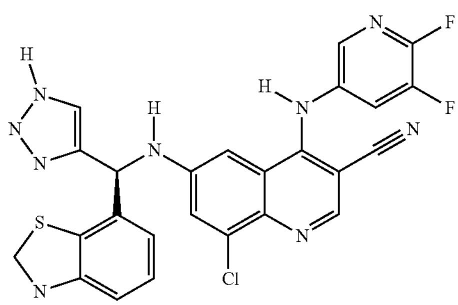 [SMILES: N#Cc1cnc2c(Cl)cc(N[C@H](C3=CNNN3)c3cccc4c3SCN4)cc2c1Nc1cnc(F)c(F)c1] | (S)-6-((benzo[d]thiazol-7-yl(1H-1,2,3-triazol-4-yl)methyl)amino)-8-chloro-4-((5,6-difluoropyridin-3-yl)amino)quinoline-3-carbonitrile | 10 | ES/MS 545.9 (M + H+) |
| 34 | 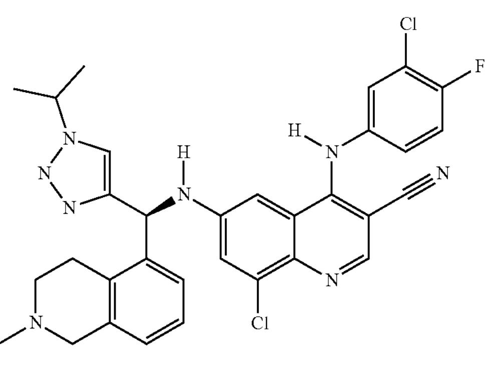 | (S)-8-chloro-4-((3-chloro-4-fluorophenyl)amino)-6-(((1-isopropyl-1H-1,2,3-triazol-4-yl)(2-(oxetan-3-yl)-1,2,3,4-tetrahydroisoquinolin-5-yl)methyl)amino)quinoline-3-carbonitrile | 13 | ES/MS 657.3 (M + H+) |

TABLE 1-continued

| Comp | Structure | Name | Example Procedure | ES/MS m/z |
|---|---|---|---|---|
| 35 | 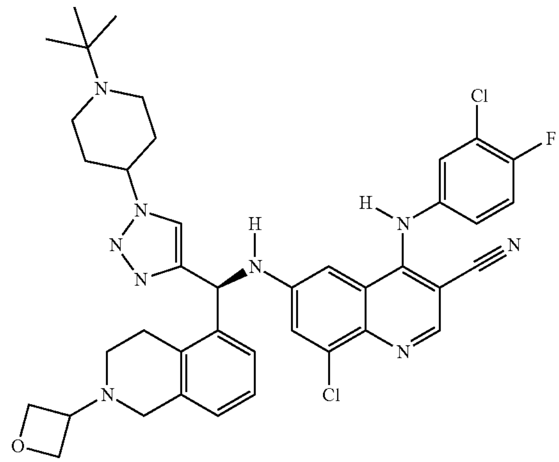 [SMILES: CC(C)(C)N1CCC(N2C=C([C@@H](Nc3cc(Cl)c4ncc(C#N)c(Nc5ccc(F)c(Cl)c5)c4c3)c3cccc4c3CCN(C3COC3)C4)NN2)CC1] | (S)-6-(((1-(1-(tert-butyl)piperidin-4-yl)-1H-1,2,3-triazol-4-yl)(2-(oxetan-3-yl)-1,2,3,4-tetrahydroisoquinolin-5-yl)methyl)amino)-8-chloro-4-4-((3-chloro-4-fluorophenyl)amino)quinoline-3-carbonitrile | 13 | ES/MS 754.2 (M + H+) |
| 36 | 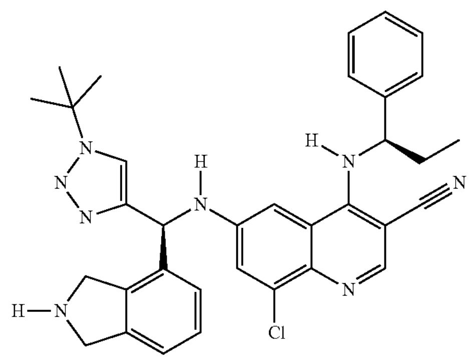 [SMILES: CC[C@@H](Nc1c(C#N)cnc2c(Cl)cc(N[C@H](C3=CN(C(C)(C)C)NN3)c3cccc4c3CNC4)cc12)c1ccccc1] | 6-(((SH 1-(tert-butyl)-1H-1,2,3-triazol-4-yl)(isoindolin-4-yl)methyl)amino)-8-chloro-4-(R)-1-phenylpropyl)amino)-quinoline-3-carbonitrile | 12 | ES/MS 591.2 (M + H+) |
| 37 | 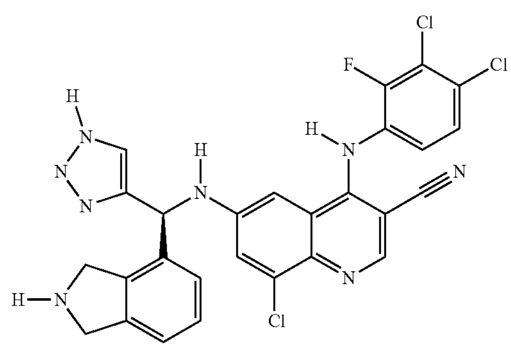 [SMILES: N#Cc1cnc2c(Cl)cc(N[C@H](C3=CNNN3)c3cccc4c3CNC4)cc2c1Nc1ccc(Cl)c(Cl)c1F] | (S)-8-chloro-4-((3,4-dichloro-2-fluorophenyl)amino)-6-((isoindolin-4-yl(1H-1,2,3-triazol-4-yl)methyl)amino)quinoline-3-carbonitrile | 12 | ES/MS 579.0 (M + H+) |
| 38 | 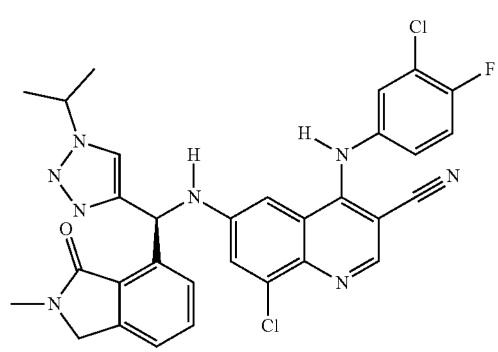 [SMILES: CC(C)N1C=C([C@@H](Nc2cc(Cl)c3ncc(C#N)c(Nc4ccc(F)c(Cl)c4)c3c2)c2cccc3c2C(=O)N(C)C3)NN1] | (S)-8-chloro-4-((3-chloro-4-fluorophenyl)amino)-6-(((1-isopropyl-1H-1,2,3-triazol-4-yl)(2-methyl-3-oxoisoindolin-4-yl)methyl)amino)quinoline-3-carbonitrile | 2 | ES/MS 614.9 (M + H+) |

TABLE 1-continued

| Comp | Structure | Name | Example Procedure | ES/MS m/z |
|---|---|---|---|---|
| 39 | 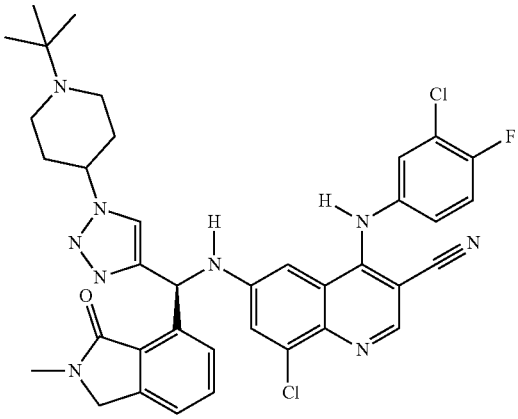 [SMILES: CN1Cc2cccc([C@H](Nc3cc(Cl)c4ncc(C#N)c(Nc5ccc(F)c(Cl)c5)c4c3)C3=CN(C4CCN(C(C)(C)C)CC4)NN3)c2C1=O] | (S)-6-(((1-(1-(tert-butyl)piperidin-4-yl)-1H-1,2,3-triazol-4-yl)(2-methyl-3-oxoisoindolin-4-yl)methyl)amino)-8-chloro))-((3-chloro-4-fluorophenyl)amino)-quinoline-3-carbonitrile | 2 | ES/MS 712.1 (M + H+) |
| 40 | 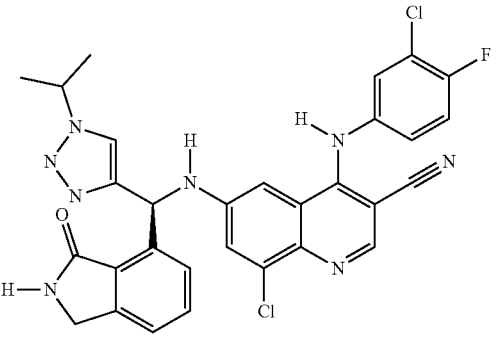 [SMILES: CC(C)N1C=C([C@@H](Nc2cc(Cl)c3ncc(C#N)c(Nc4ccc(F)c(Cl)c4)c3c2)c2cccc3c2C(=O)NC3)NN1] | (S)-8-chloro-4-((3-chloro-4-fluorophenyl)amino)-6-(((1-isopropyl-1H-1,2,3-triazol-4-yl)(3-oxoisoindolin-4-yl)methyl)amino)quinoline-3-carbonitrile | 2 | ES/MS 601.0 (M + H+) |
| 41 | 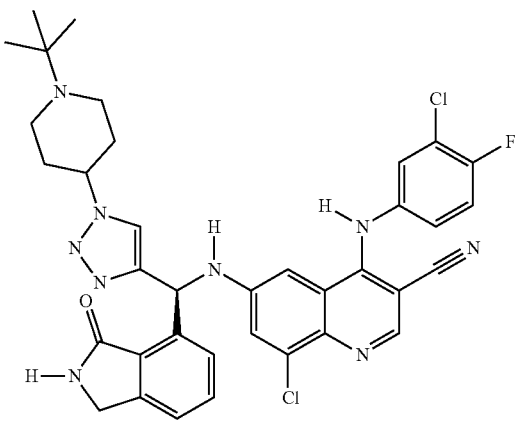 | (S)-6-(((1-(1-(ten-butyl)piperidin-4-yl)-1H-1,2,3-triazol-4-yl)(3-oxoisoindolin-4-yl)methyl)amino)-8-chloro-4-((3-chloro-4-fluorophenyl)amino)quinoline-3-carbonitrile | 2 | ES/MS 698.1 (M + H+) |

TABLE 1-continued

| Comp | Structure | Name | Example Procedure | ES/MS m/z |
|---|---|---|---|---|
| 42 | 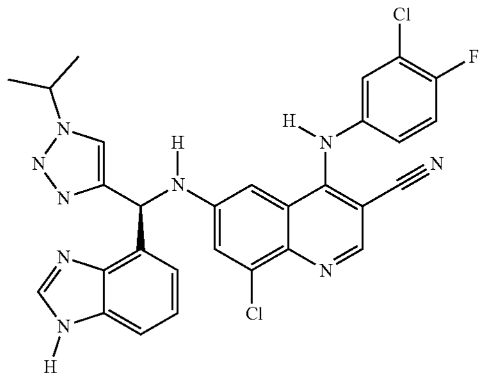 [SMILES: CC(C)N1C=C([C@@H](Nc2cc(Cl)c3ncc(C#N)c(Nc4ccc(F)c(Cl)c4)c3c2)c2cccc3[nH]cnc23)NN1] | (S)-6-(((1H-benzo[d]imidazol-4-yl)(1-isopropyl-1H-1,2,3-triazol-4-yl)methyl)amino)-8-chloro-4-((3-chloro-4-fluorophenyl)amino)-quinoline-3-carbonitrile | 2 | ES/MS 586.0 (M + H+) |
| 43 | 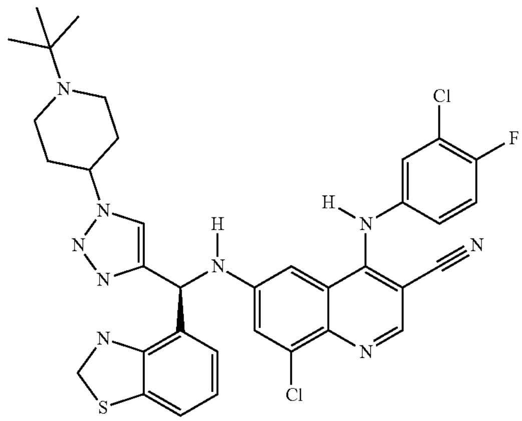 | (S)-6-((benzo[d]thiazol-4-yl(1-(1-(tert-butyl)piperidin-4-yl)-1H-1,2,3-triazol-4-yl)methyl)amino)-8-chloro-4-((3-chloro-4-fluorophenyl)amino)-quinoline-3-carbonitrile | 2 | ES/MS 700.5 (M + H+) |
| 44 | 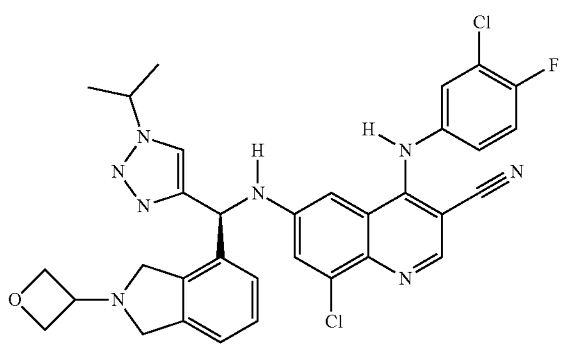 [SMILES: CC(C)N1C=C([C@@H](Nc2cc(Cl)c3ncc(C#N)c(Nc4ccc(F)c(Cl)c4)c3c2)c2cccc3c2CN(C2COC2)C3)NN1] | (S)-8-chloro-4-((3-chloro-4-fluorophenyl)amino)-6-(((1-isopropyl-1H-1,2,3-triazol-4-yl)(2-(oxetan-3-yl)isoindolin-4-yl)methyl)amino)quinoline-3-carbonitrile | 14 | ES/MS 644.0 (M + H+) |
| 45 | 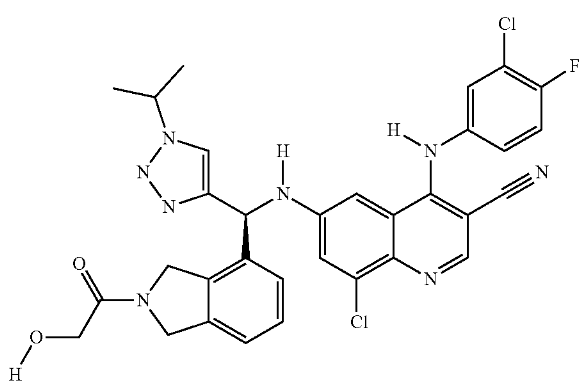 [SMILES: CC(C)N1C=C([C@@H](Nc2cc(Cl)c3ncc(C#N)c(Nc4ccc(F)c(Cl)c4)c3c2)c2cccc3c2CN(C(=O)CO)C3)NN1] | (S)-8-chloro-4-((3-chloro-4-fluorophenyl)amino)-6-(((2-(2-hydroxyacetyl)isoindolin-4-yl)(1-isopropyl-1H-1,2,3-triazol-4-yl)methyl)amino)quinoline-3-carbonitrile | 15 | ES/MS 645.3 (M + H+) |

TABLE 1-continued

| Comp | Structure | Name | Example Procedure | ES/MS m/z |
|---|---|---|---|---|
| 46 | 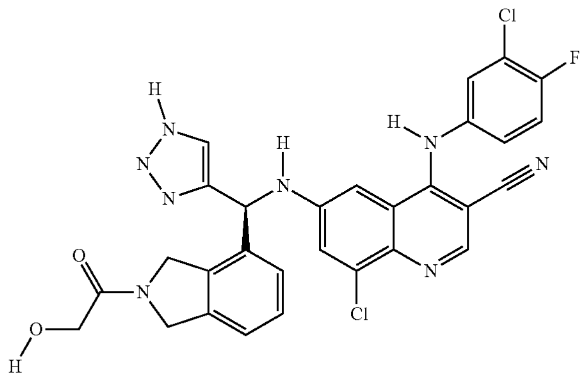 [SMILES: N#Cc1cnc2c(Cl)cc(N[C@H](C3=CNNN3)c3cccc4c3CN(C(=O)CO)C4)cc2c1Nc1ccc(F)c(Cl)c1] | (S)-8-chloro-4-((3-chloro-4-fluorophenyl)amino)-6-(((2-(2-hydroxyacetyl)isoindolin-4-yl)(1H-1,2,3-triazol-4-yl)methyl)amino)quinoline-3-carbonitrile | 15 | ES/MS 603.0 (M + H+) |
| 47 | 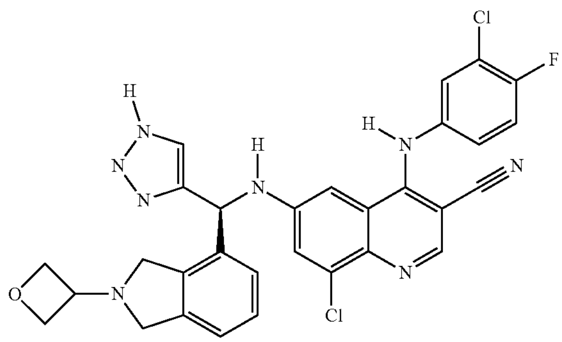 [SMILES: N#Cc1cnc2c(Cl)cc(N[C@H](C3=CNNN3)c3cccc4c3CN(C3COC3)C4)cc2c1Nc1ccc(F)c(Cl)c1] | (S)-8-chloro-4-((3-chloro-4-fluorophenyl)amino)-6-(((2-(oxetan-3-yl)isoindolin-4-yl)(1H-1,2,3-triazol-4-yl)methyl)amino)quinoline-3-carbonitrile | 14 | ES/MS 601.1 (M + H+) |
| 48 | 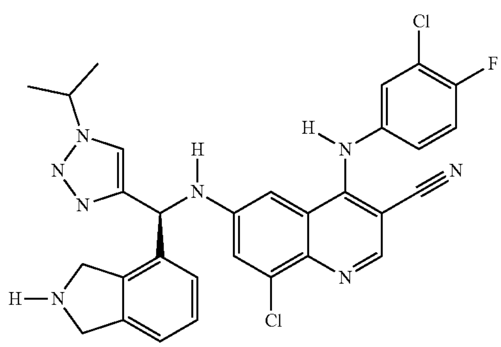 [SMILES: CC(C)N1C=C([C@@H](Nc2cc(Cl)c3ncc(C#N)c(Nc4ccc(F)c(Cl)c4)c3c2)c2cccc3c2CNC3)NN1] | (S)-8-chloro-4-((3-chloro-4-fluorophenyl)amino)-6-((isoindolin-4-yl(1-isopropyl-1H-1,2,3-triazol-4-yl)methyl)amino)quinoline-3-carbonitrile | 12 | ES/MS 587.0 (M + H+) |
| 49 | 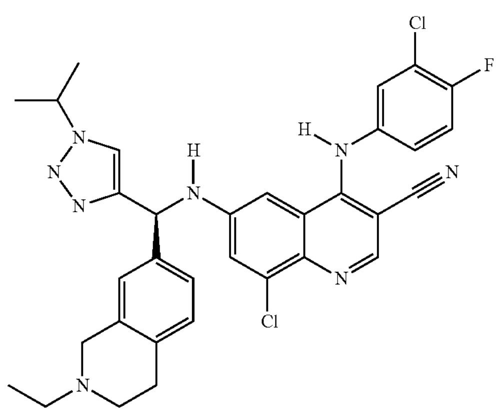 [SMILES: CCN1CCc2ccc([C@H](Nc3cc(Cl)c4ncc(C#N)c(Nc5ccc(F)c(Cl)c5)c4c3)C3=CN(C(C)C)NN3)cc2C1] | (S)-8-chloro-4-((3-chloro-4-fluorophenyl)amino)-6-(((2-ethyl-1,2,3,4-tetrahydroisoquinolin-7-yl)(1-isopropyl-1H-1,2,3-triazol-4-yl)methyl)amino)quinoline-3-carbonitrile | 13 | ES/MS 628.9 (M + H+) |

TABLE 1-continued

| Comp | Structure | Name | Example Procedure | ES/MS m/z |
|---|---|---|---|---|
| 50 | 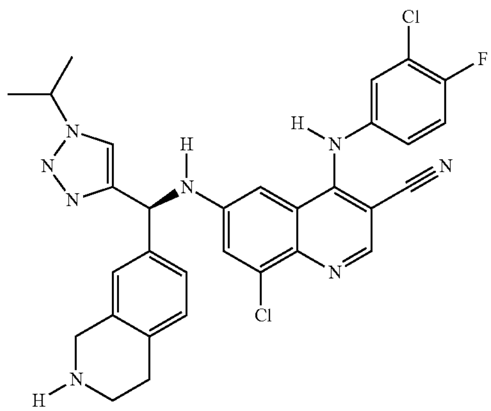 [SMILES: CC(C)N1C=C([C@@H](Nc2cc(Cl)c3ncc(C#N)c(Nc4ccc(F)c(Cl)c4)c3c2)c2ccc3c(c2)CNCC3)NN1] | (S)-8-chloro-4-((3-chloro-4-fluorophenyl)amino)-6-(((1-isopropyl-1H-1,2,3-triazol-4-yl)(1,2,3,4-tetrahydroisoquinolin-7-yl)methyl)amino)quinoline-3-carbonitrile | 12 | ES/MS 601.1 (M + H+) |
| 51 | 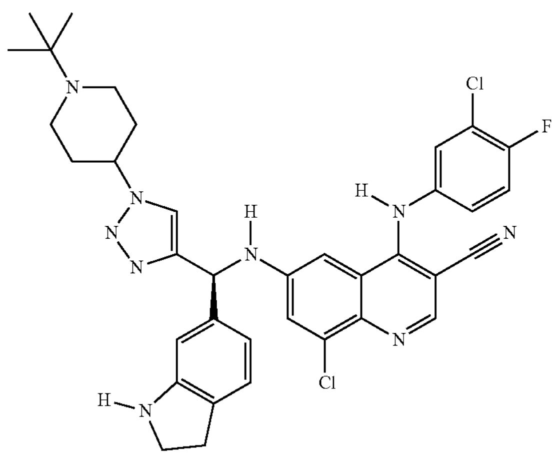 [SMILES: CC(C)(C)N1CCC(N2C=C([C@@H](Nc3cc(Cl)c4ncc(C#N)c(Nc5ccc(F)c(Cl)c5)c4c3)c3ccc4c(c3)NCC4)NN2)CC1] | (S)-6-(((1-(1-(tert-butyl)piperidin-4-yl)-1H-1,2,3-triazol-4-yl)(indolin-6-yl)methyl)amino)-8-chloro-4-((3-chloro-4-fluorophenyl)amino)quinoline-3-carbonitrile | 12 | ES/MS 684.2 (M + H+) |
| 52 | 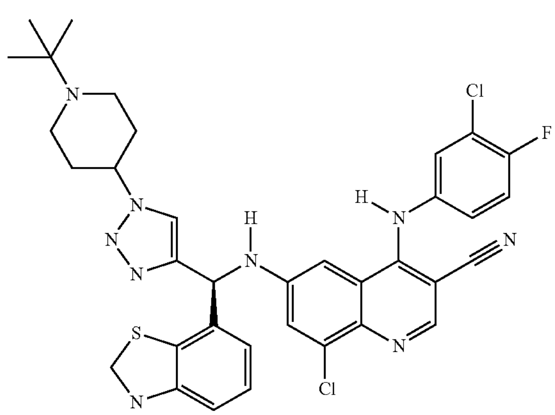 | (S)-6-((benzo[d]thiazol-7-yl(1-(1-(tert-butyl)piperidin-4-yl)-1H-1,2,3-triazol-4-yl)methyl)amino)-8-chloro-4-((3-chloro-4-fluorophenyl)amino)quinoline-3-carbonitrile | 2 | ES/MS 700.0 (M + H+) |

TABLE 1-continued

| Comp | Structure | Name | Example Procedure | ES/MS m/z |
|---|---|---|---|---|
| 53 | 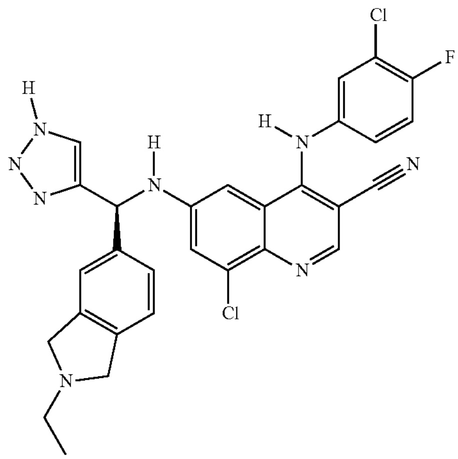 [SMILES: CCN1Cc2ccc([C@H](Nc3cc(Cl)c4ncc(C#N)c(Nc5ccc(F)c(Cl)c5)c4c3)C3=CNNN3)cc2C1] | (S)-8-chloro-4-((3-chloro-4-fluorophenyl)amino)-6-(((2-ethylisoindolin-5-yl)(1H-1,2,3-triazol-4-yl)methyl)-amino)quinoline-3-carbonitrile | 13 | ES/MS 573.1 (M + H+) |
| 54 | 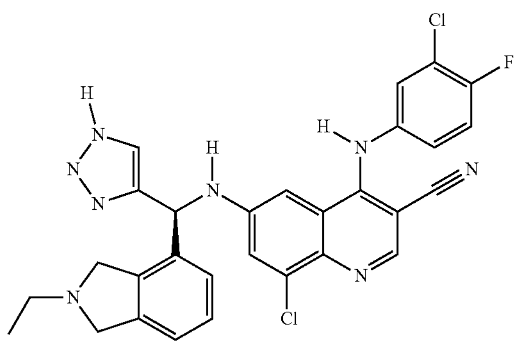 [SMILES: CCN1Cc2cccc([C@H](Nc3cc(Cl)c4ncc(C#N)c(Nc5ccc(F)c(Cl)c5)c4c3)C3=CNNN3)c2C1] | (S)-8-chloro-4-((3-chloro-4-fluorophenyl)amino)-6-(((2-ethylisoindolin-4-yl)(1H-1,2,3-triazol-4-yl)methyl)amino)quinoline-3-carbonitrile | 13 | ES/MS 573.1 (M + H+) |
| 55 | 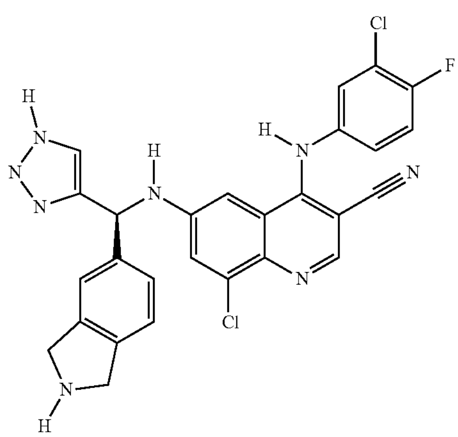 [SMILES: N#Cc1cnc2c(Cl)cc(N[C@H](C3=CNNN3)c3ccc4c(c3)CNC4)cc2c1Nc1ccc(F)c(Cl)c1] | (S)-8-chloro-4-((3-chloro-4-fluorophenyl)amino)-6-((isoindolin-5-yl(1H-1,2,3-triazol-4-yl)methyl)amino)quinoline-3-carbonitrile | 12 | ES/MS 545.0 (M + H+) |

TABLE 1-continued

| Comp | Structure | Name | Example Procedure | ES/MS m/z |
|---|---|---|---|---|
| 56 | 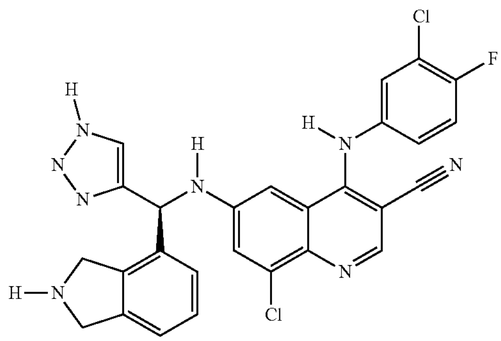 [SMILES: N#Cc1cnc2c(Cl)cc(N[C@H](C3=CNNN3)c3cccc4c3CNC4)cc2c1Nc1ccc(F)c(Cl)c1] | (S)-8-chloro-4-((3-chloro-4-fluorophenyl)amino)-6-((isoindolin-4-yl(1H-1,2,3-triazol-4-yl)methyl)amino)quinoline-3-carbonitrile | 12 | ES/MS 545.0 (M + H+) |
| 57 | 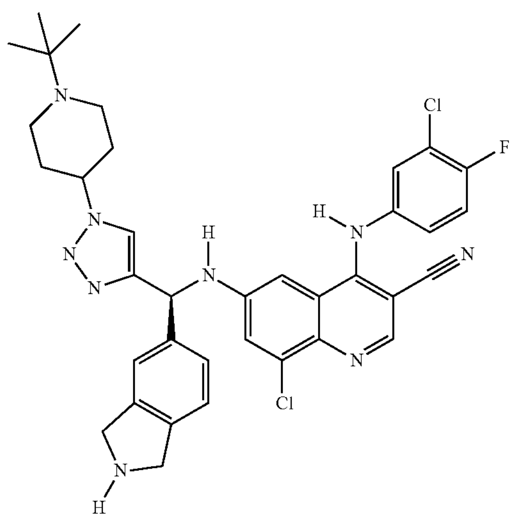 [SMILES: CC(C)(C)N1CCC(N2C=C([C@@H](Nc3cc(Cl)c4ncc(C#N)c(Nc5ccc(F)c(Cl)c5)c4c3)c3ccc4c(c3)CNC4)NN2)CC1] | (S)-6-(((1-(1-(tert-butyl)piperidin-4-yl)-1H-1,2,3-triazol-4-yl)(isoindolin-5-yl)methyl)amino)-8-chloro-4-((3-chloro-4-fluorophenyl)amino)quinoline-3-carbonitrile | 12 | ES/MS 684.2 (M + H+) |
| 58 | 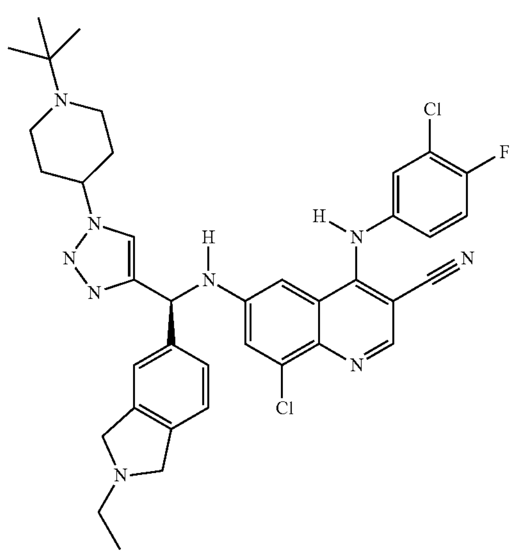 [SMILES: CCN1Cc2ccc([C@H](Nc3cc(Cl)c4ncc(C#N)c(Nc5ccc(F)c(Cl)c5)c4c3)C3=CN(C4CCN(C(C)(C)C)CC4)NN3)cc2C1] | (S)-6-(((1-(1-(tert-butyl)piperidin-4-yl)-1H-1,2,3-triazol-4-yl)(2-ethylisoindolin-5-yl)methyl)amino)-8-chloro-4-((3-chloro-4-fluorophenyl)amino)quinoline-3-carbonitrile | 13 | ES/MS 712.0 (M + H+) |

TABLE 1-continued

| Comp | Structure | Name | Example Procedure | ES/MS m/z |
|---|---|---|---|---|
| 59 | 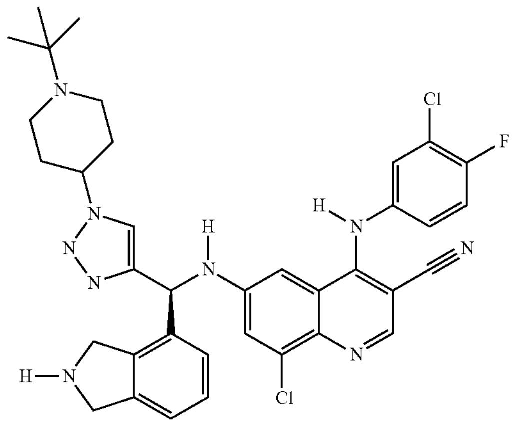 [SMILES: CC(C)(C)N1CCC(N2C=C([C@@H](Nc3cc(Cl)c4ncc(C#N)c(Nc5ccc(F)c(Cl)c5)c4c3)c3cccc4c3CNC4)NN2)CC1] | (S)-6-(((1-(1-(tert-butyl)piperidin-4-yl)-1H-1,2,3-triazol-4-yl)(isoindolin-4-yl)methyl)amino)-8-chloro-4-((3-chloro-4-fluorophenyl)amino)quinoline-3-carbonitrile | 12 | ES/MS 684.0 (M + H+) |
| 60 | 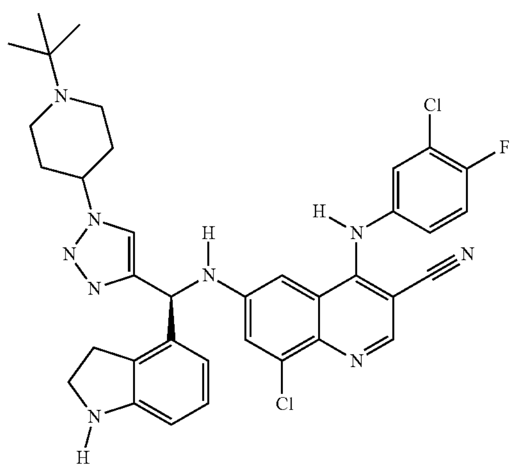 [SMILES: CC(C)(C)N1CCC(N2C=C([C@@H](Nc3cc(Cl)c4ncc(C#N)c(Nc5ccc(F)c(Cl)c5)c4c3)c3cccc4c3CCN4)NN2)CC1] | (S)-6-(((1-(1-(tert-butyl)piperidin-4-yl)-1H-1,2,3-triazol-4-yl)(indolin-4-yl)methyl)amino)-8-chloro-4-((3-chloro-4-fluorophenyl)amino)quinoline-3-carbonitrile | 12 | ES/MS 684.2 (M + H+) |
| 61 | 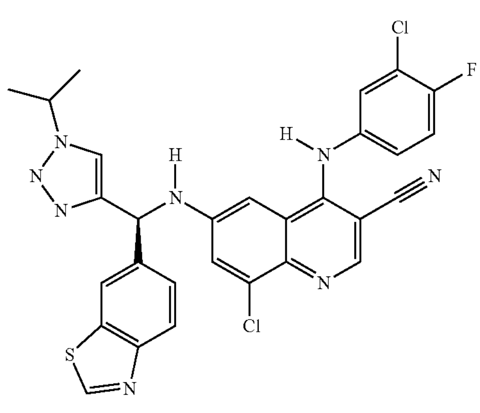 [SMILES: CC(C)N1C=C([C@@H](Nc2cc(Cl)c3ncc(C#N)c(Nc4ccc(F)c(Cl)c4)c3c2)c2ccc3ncsc3c2)NN1] | (S)-6-((benzo[d]thiazol-6-yl(1-isopropyl-1H-1,2,3-triazol-4-yl)nielhyl)amino)-8-chloro-4-((3-chloro-4-fluorophenyl)amino)quinoline-3-carbonitrile | 2 | ES/MS 603.0 (M + H+) |

TABLE 1-continued

| Comp | Structure | Name | Example Procedure | ES/MS m/z |
|---|---|---|---|---|
| 62 | 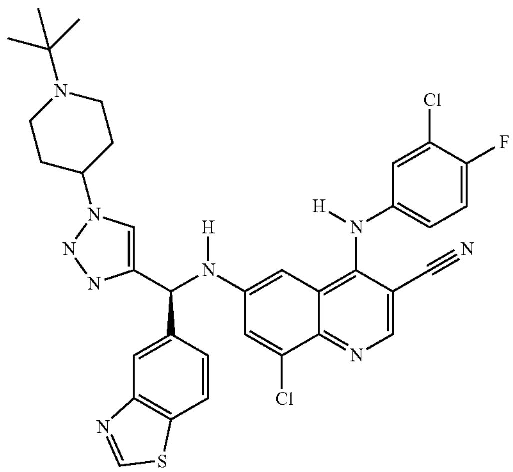 [SMILES: CC(C)(C)N1CCC(N2C=C([C@@H](Nc3cc(Cl)c4ncc(C#N)c(Nc5ccc(F)c(Cl)c5)c4c3)c3ccc4scnc4c3)NN2)CC1] | (S)-6-((benzo[d]thiazol-5-yl(1-(1-(tert-butyl)piperidin-4-yl)-1H-1,2,3-triazol-4-yl)methyl)amino)-8-chloro-4-((3-chloro-4-fluorophenyl)amino)quinoline-3-carbonitrile | 2 | ES/MS 700.0 (M + H+) |
| 63 | 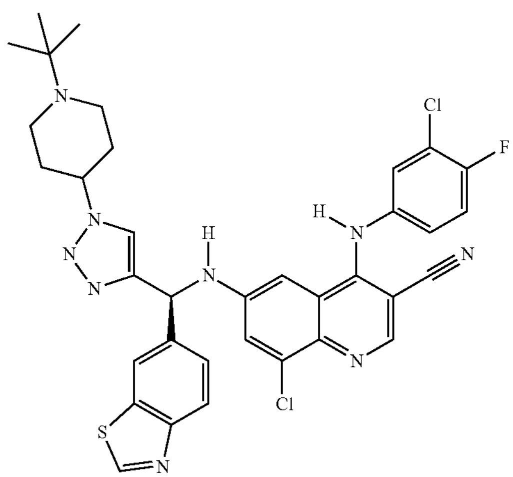 [SMILES: CC(C)(C)N1CCC(N2C=C([C@@H](Nc3cc(Cl)c4ncc(C#N)c(Nc5ccc(F)c(Cl)c5)c4c3)c3ccc4ncsc4c3)NN2)CC1] | (S)-6-((benzo[d]thiazol-6-yl(1-(1-(tert-butyl)piperidin-4-yl)-1H-1,2,3-triazol-4-yl)methyl)amino)-8-chloro-4-((3-chloro-4-fluorophenyl)amino)quinoline-3-carbonitrile | 2 | ES/MS 700.0 (M + H+) |
| 64 | 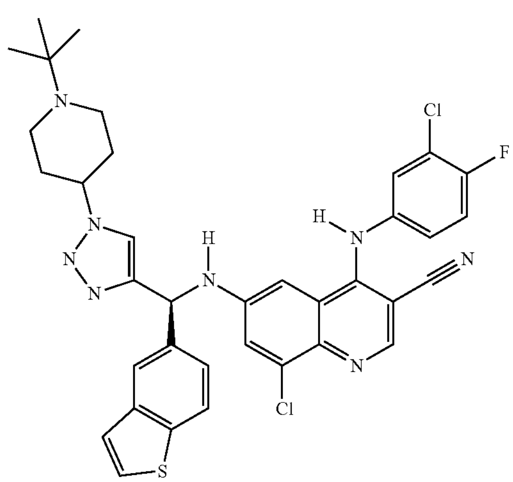 [SMILES: CC(C)(C)N1CCC(N2C=C([C@@H](Nc3cc(Cl)c4ncc(C#N)c(Nc5ccc(F)c(Cl)c5)c4c3)c3ccc4sccc4c3)NN2)CC1] | (S)-6-((benzo[b]thiophen-5-yl(1-(1-(tert-butyl)piperidin-4-yl)-1H-1,2,3-triazol-4-yl)methyl)amino)-8-chloro-4-((3-chloro-4-fluorophenyl)amino)quinoline-3-carbonitrile | 2 | ES/MS 698.9 (M + H+) |

TABLE 1-continued

| Comp | Structure | Name | Example Procedure | ES/MS m/z |
|---|---|---|---|---|
| 65 | 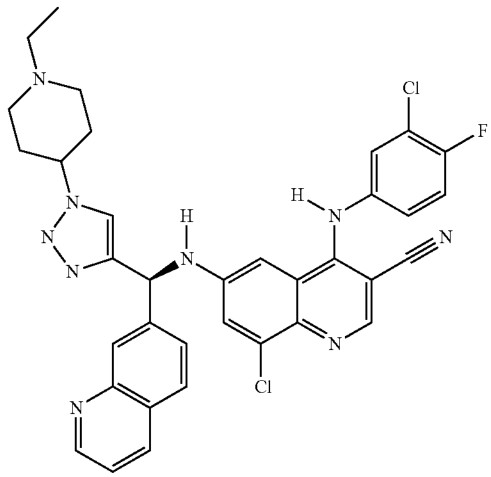 [SMILES: CCN1CCC(N2C=C([C@@H](Nc3cc(Cl)c4ncc(C#N)c(Nc5ccc(F)c(Cl)c5)c4c3)c3ccc4cccnc4c3)NN2)CC1] | (S)-8-chloro-4-((3-chloro-4-fluorophenyl)amino)-6-(((1-(1-ethylpiperidin-4-yl)-1H-1,2,3-triazol-4-yl)(quinolin-7-yl)methyl)amino)quinoline-3-carbonitrile | 5 | ES/MS 666.1 (M + H+) |
| 66 | 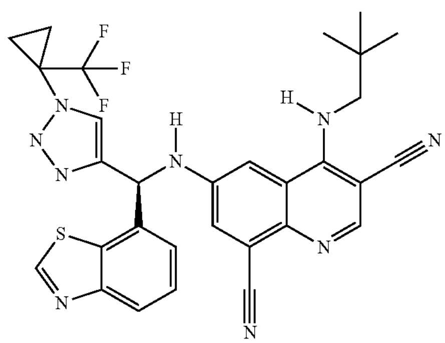 [SMILES: CC(C)(C)CNc1c(C#N)cnc2c(C#N)cc(N[C@H](C3=CN(C4(C(F)(F)F)CC4)NN3)c3cccc4ncsc34)cc12] | (S)-6-((benzo[d]thiazol-7-yl(1-(1-(trifluoromethyl)cyclopropyl)-1H-1,2,3-triazol-4-yl)methyl)amino)-4-(neopentylamino)quinoline-3,8-dicarbonitrile | 9a | ES/MS 602.2 (M + H+) |
| 67 | 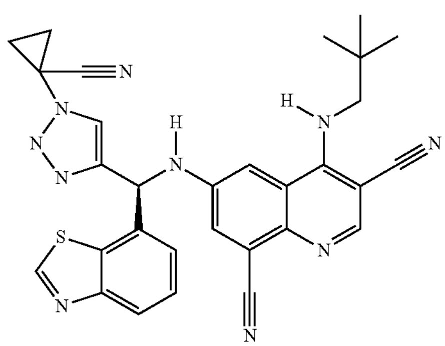 [SMILES: CC(C)(C)CNc1c(C#N)cnc2c(C#N)cc(N[C@H](C3=CN(C4(C#N)CC4)NN3)c3cccc4ncsc34)cc12] | (S)-6-((benzo[d]thiazol-7-yl(1-(1-cyanocyclopropyl)-1H-1,2,3-triazol-4-yl)methyl)amino)-4-(neopentylamino)quinoline-3,8-dicarbonitrile | 9a | ES/MS 559.1 (M + H+) |
| 68 | 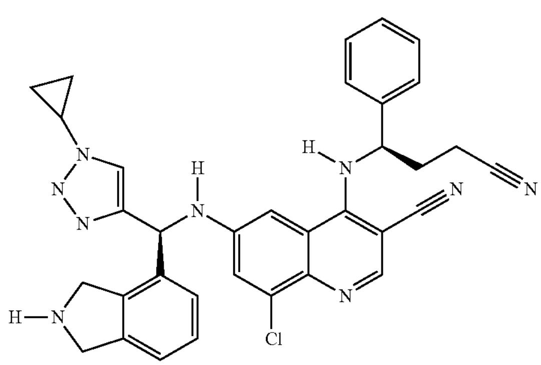 [SMILES: N#CCC[C@@H](Nc1c(C#N)cnc2c(Cl)cc(N[C@H](C3=CN(C4CC4)NN3)c3cccc4c3CNC4)cc12)c1ccccc1] | 8-chloro-4-(((R)-3-cyano-1-phenyl-propyl)amino)-6-(((S)-(1-cyclopropyl-1H-1,2,3-triazol-4-yl)(isoindolin-4-yl)methyl)amino)quinoline-3-carbonitrile | 12 | ES/MS 600.0 (M + H+) |

TABLE 1-continued

| Comp | Structure | Name | Example Procedure | ES/MS m/z |
|---|---|---|---|---|
| 69 | 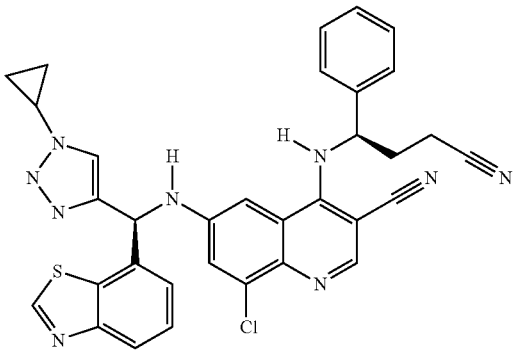 [SMILES: N#CCC[C@@H](Nc1c(C#N)cnc2c(Cl)cc(N[C@H](C3=CN(C4CC4)NN3)c3cccc4ncsc34)cc12)c1ccccc1] | 6-(((S)-benzo[d]thiazol-7-yl(1-cyclopropyl-1H-1,2,3-triazol-4-yl)methyl)amino)-8-chloro-4-(((R)-3-cyano-1-phenylpropyl)amino)quinoline-3-carbonitrile | 2 | ES/MS 616.1 (M + H+) |
| 70 | 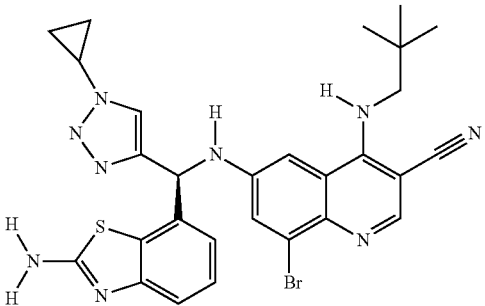 [SMILES: CC(C)(C)CNc1c(C#N)cnc2c(Br)cc(N[C@H](C3=CN(C4CC4)NN3)c3cccc4nc(N)sc34)cc12] | (S)-6-(((2-aminobenzo[d]thiazol-7-yl)(1-cyclopropyl-1H-1,2,3-triazol-4-yl)methyl)amino)-8-bromo-4-(neopentylamino)quinoline-3-carbonitrile | 12 | ES/MS 602.1 (M + H+) |
| 71 | 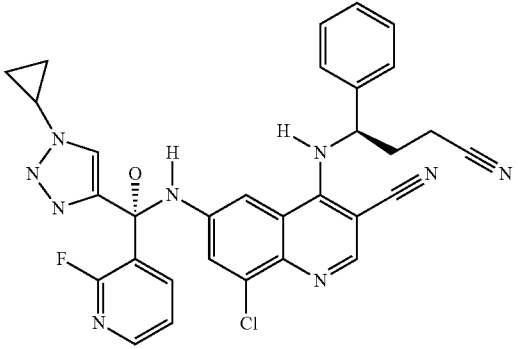 [SMILES: N#CCC[C@@H](Nc1c(C#N)cnc2c(Cl)cc(N[C@](O)(C3=CN(C4CC4)NN3)c3cccnc3F)cc12)c1ccccc1] | 8-chloro-4-(((R)-3-cyano-1-phenyl-propyl)amino)-6-(((1-cyclopropyl-1H-1,2,3-triazol-4-yl)(2-fluoropyridin-3-yl)methyl-d)amino)quinoline-3-carbonitrile | 2 | 579.1 |
| 72 | 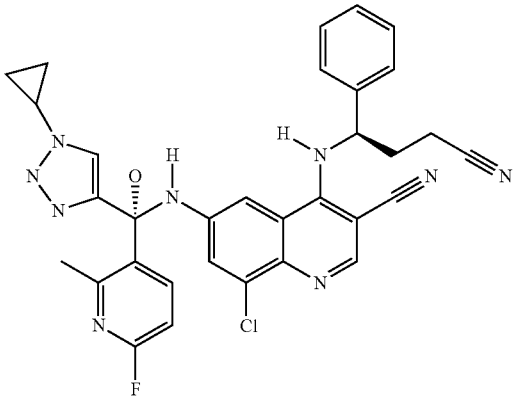 [SMILES: Cc1nc(F)ccc1[C@](O)(Nc1cc(Cl)c2ncc(C#N)c(N[C@H](CCC#N)c3ccccc3)c2c1)C1=CN(C2CC2)NN1] | 8-chloro-4-(((R)-3-cyano-1-phenyl-propyl)amino)-6-(((1-cyclopropyl-1H-1,2,3-triazol-4-yl)(6-fluoro-2-methylpyridin-3-yl)methyl-d)amino)quinoline-3-carbonitrile | 2 | 593.2 |

TABLE 1-continued

| Comp | Structure | Name | Example Procedure | ES/MS m/z |
|---|---|---|---|---|
| 73 | 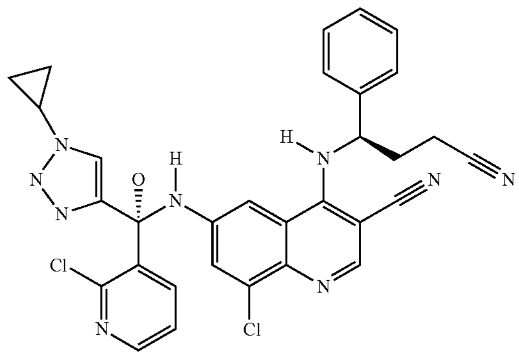 [SMILES: N#CCC[C@@H](Nc1c(C#N)cnc2c(Cl)cc(N[C@](O)(C3=CN(C4CC4)NN3)c3cccnc3Cl)cc12)c1ccccc1] | 8-chloro-6-(((2-chloropyridin-3-yl)(1-cyclopropyl-1H-1,2,3-triazol-4-yl)methyl-d)amino)-4-(((R)-3-cyano-1-phenylpropyl)amino)quinoline-3-carbonitrile | 2 | 595.1 |
| 74 | 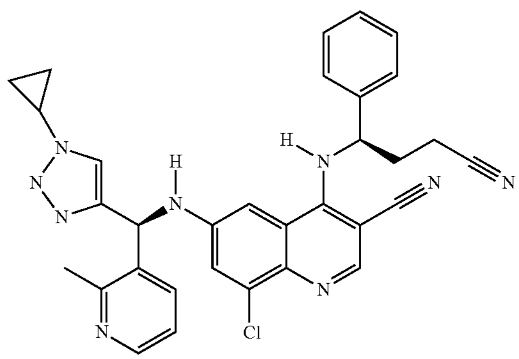 [SMILES: Cc1ncccc1[C@H](Nc1cc(Cl)c2ncc(C#N)c(N[C@H](CCC#N)c3ccccc3)c2c1)C1=CN(C2CC2)NN1] | 8-chloro-4-(((R)-3-cyano-1-phenylpropyl)amino)-6-(((S)-(1-cyclopropyl-1H-1,2,3-triazol-4-yl)(2-methylpyridin-3-yl)methyl)amino)-quinoline-3-carbonitrile | 2 | 574.1 |
| 75 | 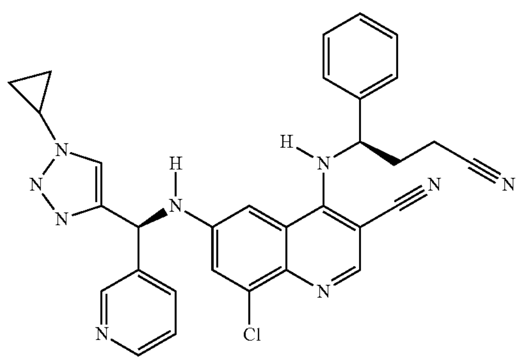 [SMILES: N#CCC[C@@H](Nc1c(C#N)cnc2c(Cl)cc(N[C@H](C3=CN(C4CC4)NN3)c3cccnc3)cc12)c1ccccc1] | 8-chloro-4-(((R)-3-cyano-1-phenylpropyl)amino)-6-(((S)-(1-cyclopropyl-1H-1,2,3-triazol-4-yl)(pyridin-3-yl)methyl)amino)quinoline-3-carbonitrile | 2 | 560.1 |
| 76 | 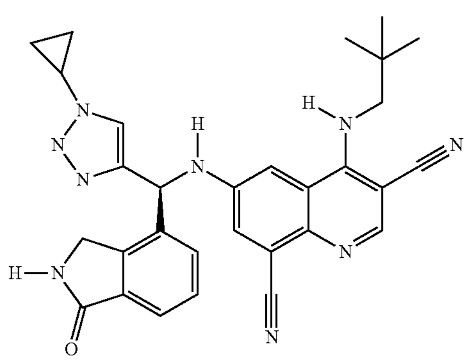 [SMILES: CC(C)(C)CNc1c(C#N)cnc2c(C#N)cc(N[C@H](C3=CN(C4CC4)NN3)c3cccc4c3CNC4=O)cc12] | (S)-6-(((1-cyclopropyl-1H-1,2,3-triazol-4-yl)(1-oxoisoindolin-4-yl)methyl)amino)-4-(neopentylamino)quinoline-3,8-dicarbonitrile | 9a | ES/MS 532.1 (M + H+) |

TABLE 1-continued

| Comp | Structure | Name | Example Procedure | ES/MS m/z |
|---|---|---|---|---|
| 77 | 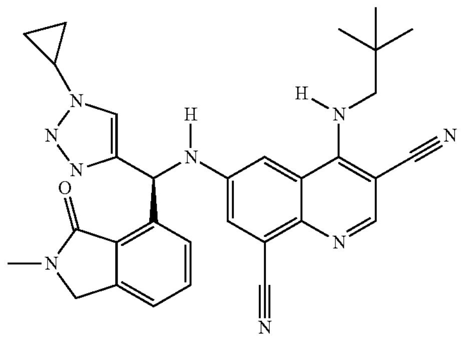 [SMILES: CN1Cc2cccc([C@H](Nc3cc(C#N)c4ncc(C#N)c(NCC(C)(C)C)c4c3)C3=CN(C4CC4)NN3)c2C1=O] | (S)-6-(((1-cyclopropyl-1H-1,2,3-triazol-4-yl)(2-methyl-3-oxoisoindolin-4-yl)methyl)amino)-4-(neopentylamino)quinoline-3,8-dicarbonitrile | 9a | ES/MS 546.2 (M + H+) |
| 78 | 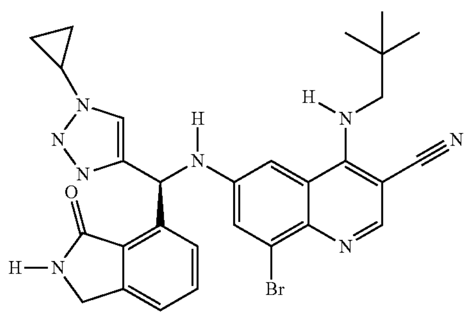 [SMILES: CC(C)(C)CNc1c(C#N)cnc2c(Br)cc(N[C@H](C3=CN(C4CC4)NN3)c3cccc4c3C(=O)NC4)cc12] | (S)-8-bromo-6-(((1-cyclopropyl-1H-1,2,3-triazol-4-yl)(3-oxoisoindolin-4-yl)methyl)amino)-4-(neopentylamino)quinoline-3-carbonitrile | 2 | ES/MS 585.1 (M + H+) |
| 79 | 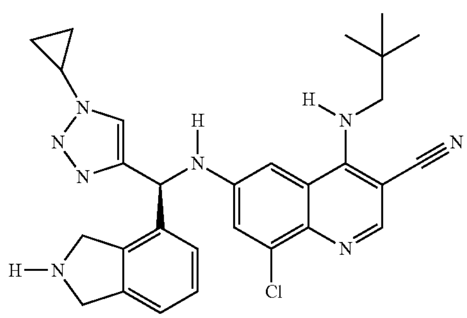 | (S)-6-(((1-cyclopropyl-1H-1,2,3-triazol-4-yl)(isoindolin-4-yl)methyl)amino)-4-(neopentylamino)quinoline-3,8-dicarbonitrile | 12 | ES/MS 518.6 (M + H+) |
| 80 | 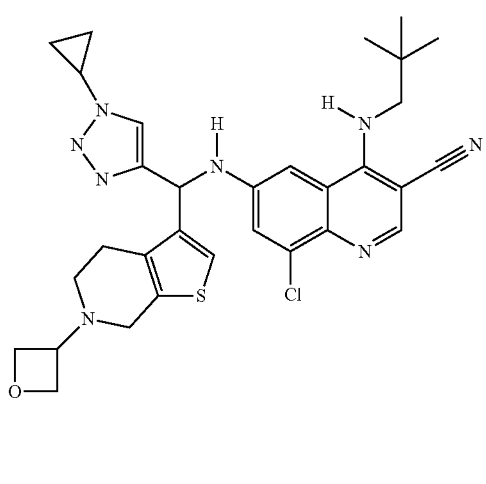 [SMILES: CC(C)(C)CNc1c(C#N)cnc2c(Cl)cc(NC(C3=CN(C4CC4)NN3)c3csc4c3CCN(C3COC3)C4)cc12] | (S)-8-chloro-6-(((1-cyclopropyl-1H-1,2,3-triazol-4-yl)(6-(oxetan-3-yl)-4,5,6,7-tetrahydrothieno[2,3-c]pyridin-3-yl)methyl)amino)-4-(neopentylamino)-quinoline-3-carbonitrile | 5 | ES/MS 603.2 (M + H+) |

TABLE 1-continued

| Comp | Structure | Name | Example Procedure | ES/MS m/z |
|---|---|---|---|---|
| 81 | 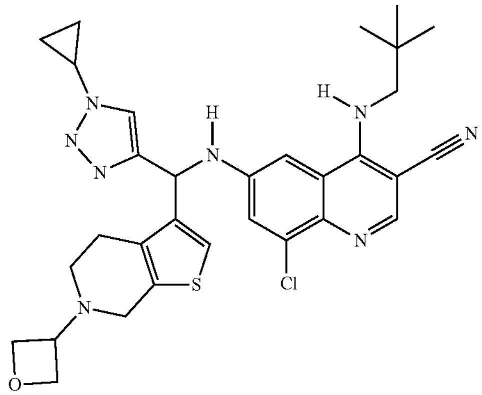 [SMILES: CC(C)(C)CNc1c(C#N)cnc2c(Cl)cc(NC(C3=CN(C4CC4)NN3)c3csc4c3CCN(C3COC3)C4)cc12] | (R)-8-chloro-6-(((1-cyclopropyl-1H-1,2,3-triazol-4-yl)(6-(oxctan-3-yl)-4,5,6,7-tetrahydrothieno[2,3-c]pyridin-3-yl)methyl)amino)-4-(neopentylamino)-quinoline-3-carbonitrile | 5 | ES/MS 603.2 (M + H+) |
| 82 | 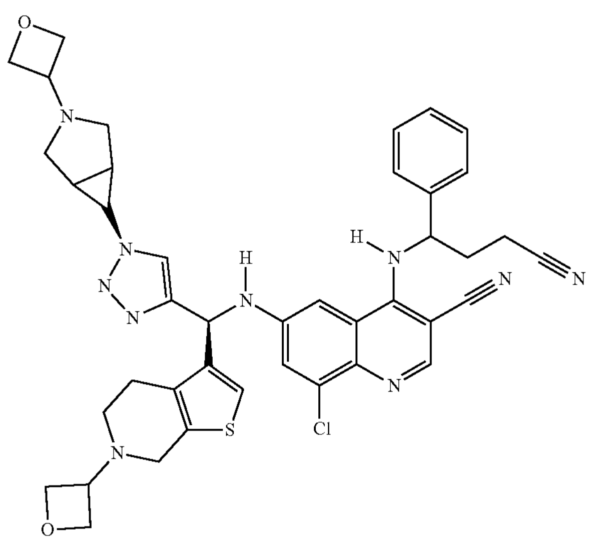 | 8-chloro-4-((3-cyano-1-phenylpropyl)amino)-6-(((S)-(1-((1R,5S,6r)-3-(oxetan-3-yl)-3-azabicyclo[3.1.0]hexan-6-yl)-1H-1,2,3-triazol-4-yl)(6-(oxetan-3-yl)-4,5,6,7-tetrahydrothieno[2,3-c]pyridin-3-yl)methyl)amino)-quinoline-3-carbonitrile | 5 | ES/MS 773.1 (M + H+) |
| 83 | 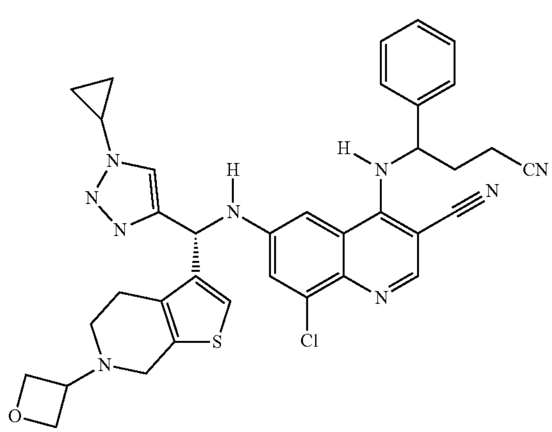 [SMILES: N#CCCC(Nc1c(C#N)cnc2c(Cl)cc(N[C@@H](C3=CN(C4CC4)NN3)c3csc4c3CCN(C3COC3)C4)cc12)c1ccccc1] | 8-chloro-4-((3-cyano-1-phenylpropyl)amino)-6-(((R)-1-cyclopropyl-1H-1,2,3-triazol-4-yl)(6-(oxetan-3-yl)-4,5,6,7-tetrahydrothieno[2,3-c]pyridin-3-yl)methyl)amino)-quinoline-3-carbonitrile | 5 | ES/MS 676.1 (M + H+) |

TABLE 1-continued

| Comp | Structure | Name | Example Procedure | ES/MS m/z |
|---|---|---|---|---|
| 84 | 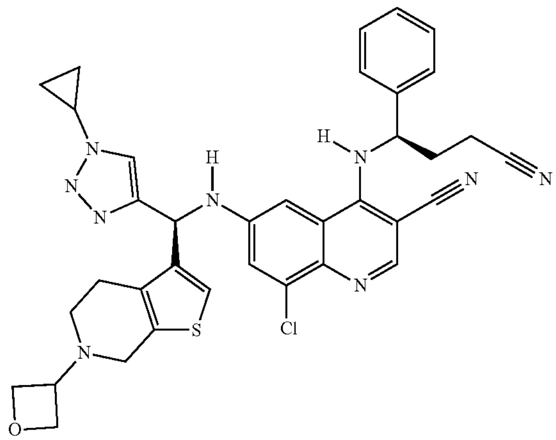 [SMILES: N#CCC[C@@H](Nc1c(C#N)cnc2c(Cl)cc(N[C@H](C3=CN(C4CC4)NN3)c3csc4c3CCN(C3COC3)C4)cc12)c1ccccc1] | 8-chloro-4-(((R)-3-cyano-1-phenylpropyl)amino)-6-(((S)-(1-cyclopropyl-1H-1,2,3-triazol-4-yl)(6-(oxetan-3-yl)-4,5,6,7-tetrahydrothieno[2,3-c]pyridin-3-yl)methyl)amino)quinoline-3-carbonitrile | 5 | ES/MS 676.1 (M + H+) |
| 85 | 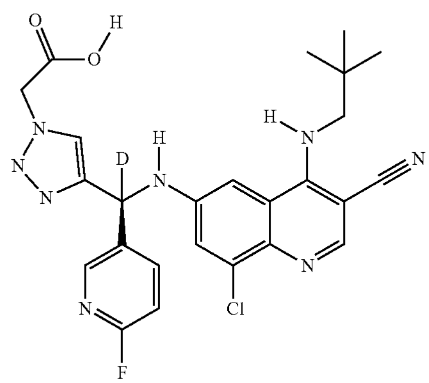 [SMILES: [2H][C@](Nc1cc(Cl)c2ncc(C#N)c(NCC(C)(C)C)c2c1)(C1=CN(CC(=O)O)NN1)c1ccc(F)nc1] | (S)-2-(4-(((8-chloro-3-cyano-4-(neopentylamino)quinolin-6-yl)amino)(6-fluoropyridin-3-yl)methyl-d)-1H-1,2,3-triazol-1-yl)acetic acid | 1 | ES/MS 524.2 (M + H+) |
| 86 | 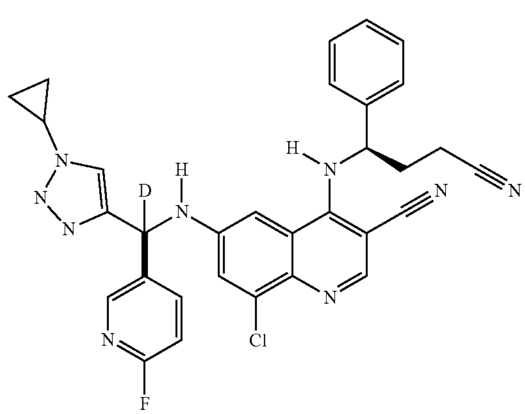 [SMILES: [2H][C@](Nc1cc(Cl)c2ncc(C#N)c(N[C@H](CCC#N)c3ccccc3)c2c1)(C1=CN(C2CC2)NN1)c1ccc(F)nc1] | 8-chloro-4-(((R)-3-cyano-1-phenylpropyl)amino)-6-(((1-cyclopropyl-1H-1,2,3-triazol-4-yl)(6-fluoropyridin-3-yl)methyl-d)amino)quinoline-3-carbonitrile | 2 | ES/MS 579.2 (M + H+) |

TABLE 1-continued

| Comp | Structure | Name | Example Procedure | ES/MS m/z |
|---|---|---|---|---|
| 87 | 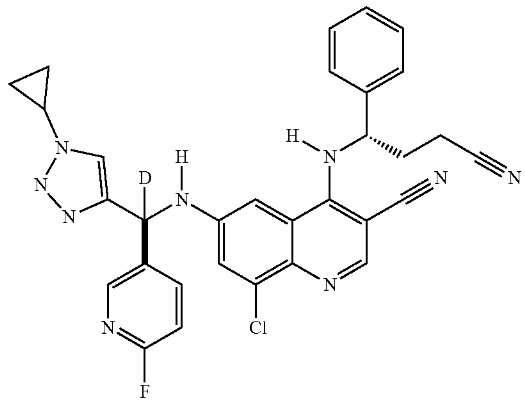 [SMILES: [2H][C@](Nc1cc(Cl)c2ncc(C#N)c(N[C@@H](CCC#N)c3ccccc3)c2c1)(C1=CN(C2CC2)NN1)c1ccc(F)nc1] | 8-chloro-4-(((S)-3-cyano-1-phenylpropyl)amino)-6-(((1-cyclopropyl-1H-1,2,3-triazol-4-yl)(6-fluoropyridin-3-yl)methyl-d)amino)quinoline-3-carbonitrile | 2 | ES/MS 579.2 (M + H+) |
| 88 | 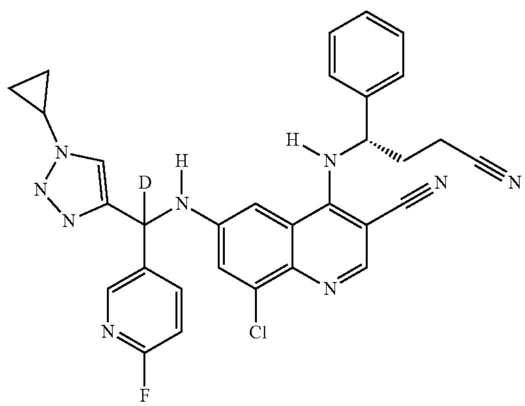 [SMILES: [2H]C(Nc1cc(Cl)c2ncc(C#N)c(N[C@@H](CCC#N)c3ccccc3)c2c1)(C1=CN(C2CC2)NN1)c1ccc(F)nc1] | 8-chloro-4-(((S)-3-cyano-1-phenylpropyl)amino)-6-(((1-cyclopropyl-1H-1,2,3-triazol-4-yl)(6-fluoropyridin-3-yl)methyl-d)amino)quinoline-3-carbonitrile | 2 | ES/MS 579.2 (M + H+) |
| 89 | 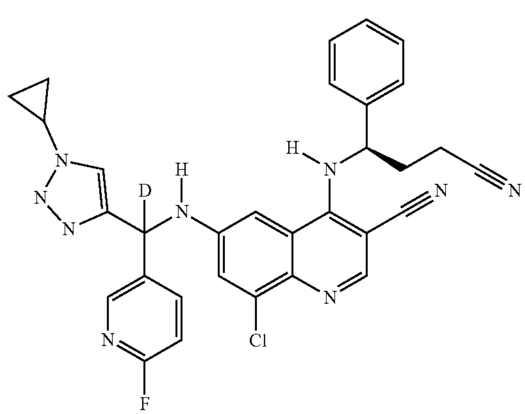 [SMILES: [2H]C(Nc1cc(Cl)c2ncc(C#N)c(N[C@H](CCC#N)c3ccccc3)c2c1)(C1=CN(C2CC2)NN1)c1ccc(F)nc1] | 8-chloro-4-(((R)-3-cyano-1-phenylpropyl)amino)-6-(((1-cyclopropyl-1H-1,2,3-triazol-4-yl)(6-fluoropyridin-3-yl)methyl-d)amino)quinoline-3-carbonitrile | 2 | ES/MS 579.2 (M + H+) |

TABLE 1-continued

| Comp | Structure | Name | Example Procedure | ES/MS m/z |
|---|---|---|---|---|
| 90 | 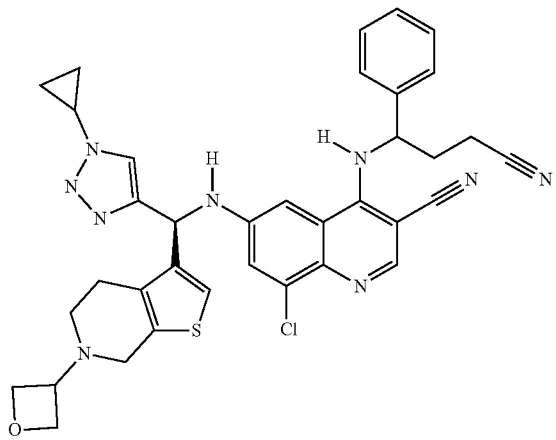 [SMILES: N#CCCC(Nc1c(C#N)cnc2c(Cl)cc(N[C@H](C3=CN(C4CC4)NN3)c3csc4c3CCN(C3COC3)C4)cc12)c1ccccc1] | 8-chloro-4-((3-cyano-1-phenyl-propyl)amino)-6-(((S)-(1-cyclopropyl-1H-1,2,3-triazol-4-yl)(6-(oxetan-3-yl)-4,5,6,7-tetrahydrothieno[2,3-c]pyridin-3-yl)methyl)amino)quinoline-3-carbonitrile | 5 | ES/MS 676.1 (M + H+) |
| 91 | 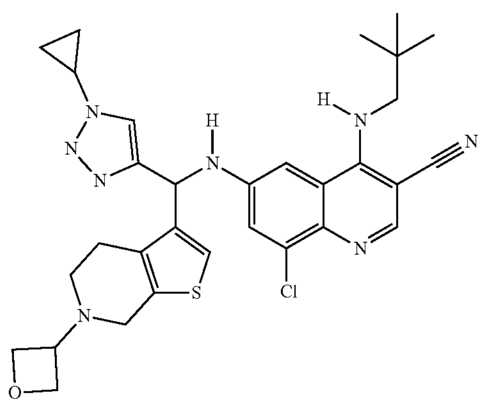 [SMILES: CC(C)(C)CNc1c(C#N)cnc2c(Cl)cc(NC(C3=CN(C4CC4)NN3)c3csc4c3CCN(C3COC3)C4)cc12] | 8-chloro-6-(((1-cyclopropyl-1H-1,2,3-triazol-4-yl)(6-(oxetan-3-yl)-4,5,6,7-tetrahydro-thieno[2,3-c]pyridin-3-yl)-methyl)amino)-4-(neopentylamino)-quinoline-3-carbonitrile | 5 | ES/MS 603.2 (M + H+) |
| 92 | 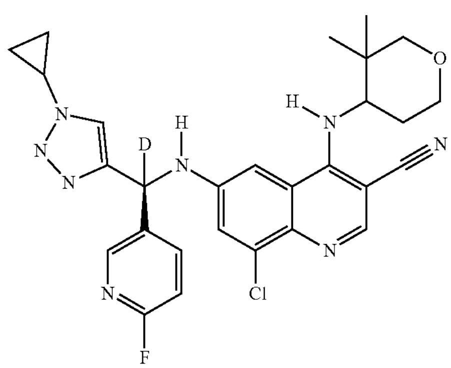 [SMILES: [2H][C@](Nc1cc(Cl)c2ncc(C#N)c(NC3CCOCC3(C)C)c2c1)(C1=CN(C2CC2)NN1)c1ccc(F)nc1] | 8-chloro-6-(((S)-(1-cyclopropyl-1H-1,2,3-triazol-4-yl)(6-fluoropyridin-3-yl)methyl-d)amino)-4-((3,3-dimethyltetrahydro-2H-pyran-4-yl)amino)quinoline-3-carbonitrile | 1 | ES/MS 548.2 (M + H+) |

TABLE 1-continued

| Comp | Structure | Name | Example Procedure | ES/MS m/z |
|---|---|---|---|---|
| 93 | 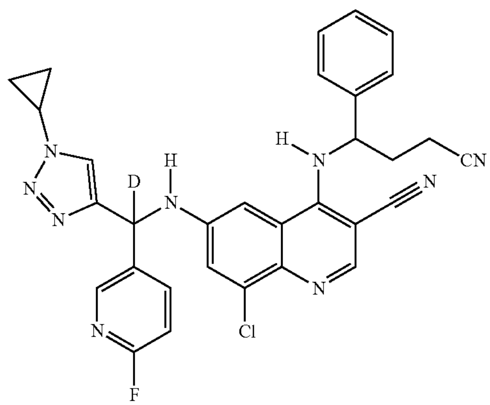 [SMILES: [2H]C(Nc1cc(Cl)c2ncc(C#N)c(NC(CCC#N)c3ccccc3)c2c1)(c1ccc(F)nc1)c1cn(C2CC2)nn1] | 8-chloro-4-((3-cyano-1-phenylpropyl)amino)-6-(((1-cyclopropyl-1H-1,2,3-triazol-4-yl)(6-fluoropyridin-3-yl)methyl-d)amino)quinoline-3-carbonitrile | 2 | ES/MS 579.2 (M + H+) |
| 94 | 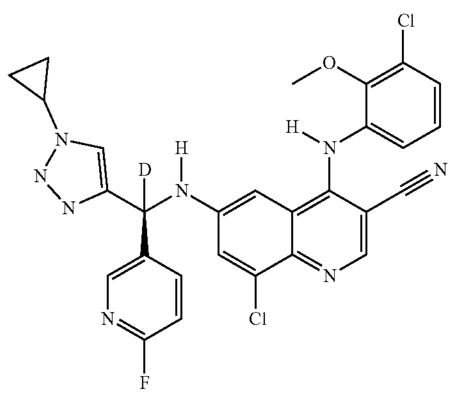 [SMILES: [2H][C@](Nc1cc(Cl)c2ncc(C#N)c(Nc3cccc(Cl)c3OC)c2c1)(C1=CN(C2CC2)NN1)c1ccc(F)nc1] | (S)-8-chloro-4-((3-chloro-2-methoxyphenyl)amino)-6-(((1-cyclopropyl-1H-1,2,3-triazol-4-yl)(6-fluoropyridin-3-yl)methyl-d)amino)quinoline-3-carbonitrile | 8 | ES/MS 576.1 (M + H+) |
| 95 | 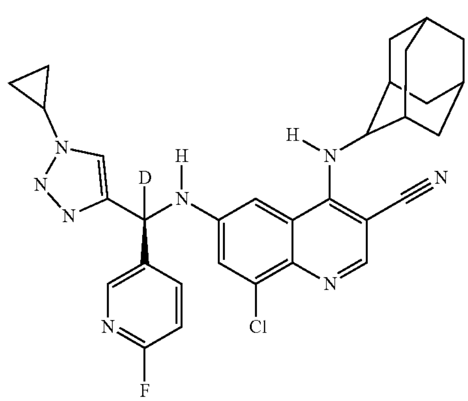 [SMILES: [2H][C@](Nc1cc(Cl)c2ncc(C#N)c(NC3C4CC5CC(C4)CC3C5)c2c1)(C1=CN(C2CC2)NN1)c1ccc(F)nc1] | 4-(((1S,3S,5S,7S)-adamantan-2-yl)amino)-8-chloro-6-(((S)-(1-cyclopropyl-1H-1,2,3-triazol-4-yl)(6-fluoropyridin-3-yl)methyl-d)amino)quinoline-3-carbonitrile | 1 | ES/MS 570.2 (M + H+) |

TABLE 1-continued

| Comp | Structure | Name | Example Procedure | ES/MS m/z |
|---|---|---|---|---|
| 96 | 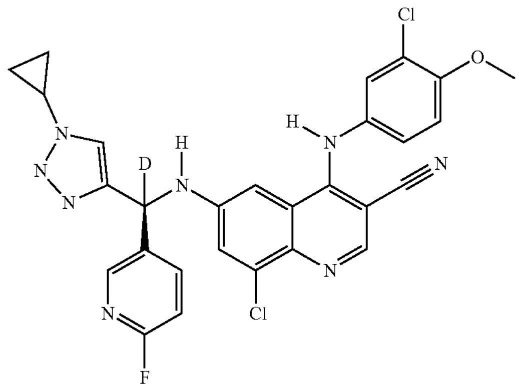 [SMILES: [2H][C@](Nc1cc(Cl)c2ncc(C#N)c(Nc3ccc(OC)c(Cl)c3)c2c1)(C1=CN(C2CC2)NN1)c1ccc(F)nc1] | (S)-8-chloro-4-((3-chloro-4-methoxyphenyl)amino)-6-(((1-cyclopropyl-1H-1,2,3-triazol-4-yl)(6-fluoropyridin-3-yl)methyl-d)amino)quinoline-3-carbonitrile | 8 | ES/MS 576.2 (M + H+) |
| 97 | 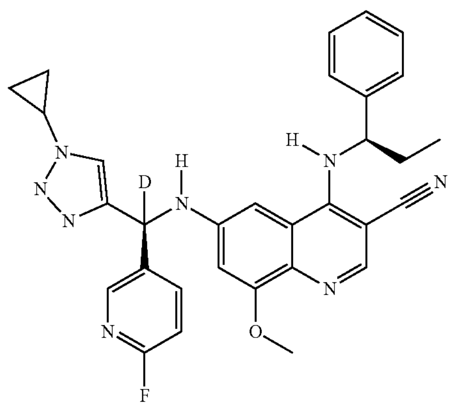 [SMILES: [2H][C@](Nc1cc(OC)c2ncc(C#N)c(N[C@H](CC)c3ccccc3)c2c1)(C1=CN(C2CC2)NN1)c1ccc(F)nc1] | 6-(((S)-(1-cyclopropyl-1H-1,2,3-triazol-4-yl)(6-fluoropyridin-3-yl)methyl-d)amino)-8-methoxy-4-(((R)-1-phenylpropyl)amino)-quinoline-3-carbonitrile | 2 | ES/MS 550.1 (M + H+) |
| 98 | 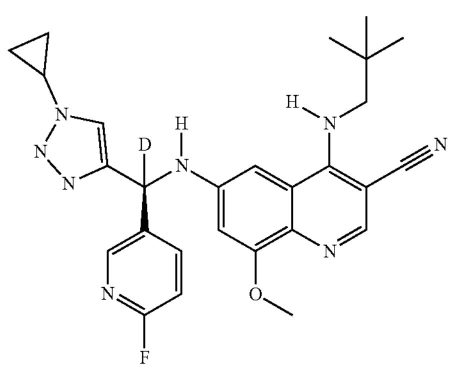 [SMILES: [2H][C@](Nc1cc(OC)c2ncc(C#N)c(NCC(C)(C)C)c2c1)(C1=CN(C2CC2)NN1)c1ccc(F)nc1] | (S)-6-(((1-cyclopropyl-1H-1,2,3-triazol-4-yl)(6-fluoropyridin-3-yl)methyl-d)amino)-8-methoxy-4-(neopentylamino)quinoline-3-carbonitrile | 2 | ES/MS 502.3 (M + H+) |
| 99 | 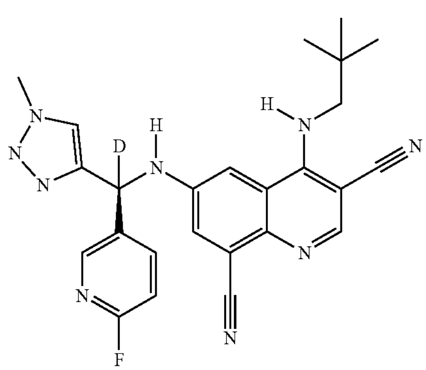 [SMILES: [2H][C@](Nc1cc(C#N)c2ncc(C#N)c(NCC(C)(C)C)c2c1)(C1=CN(C)NN1)c1ccc(F)nc1] | (S)-6-(((6-fluoropyridin-3-yl)(1-methyl-1H-1,2,3-triazol-4-yl)methyl-d)amino)-4-(neopentylamino)quinoline-3,8-dicarbonitrile | 22 | ES/MS 471.3 (M + H+) |

TABLE 1-continued

| Comp | Structure | Name | Example Procedure | ES/MS m/z |
|---|---|---|---|---|
| 100 | 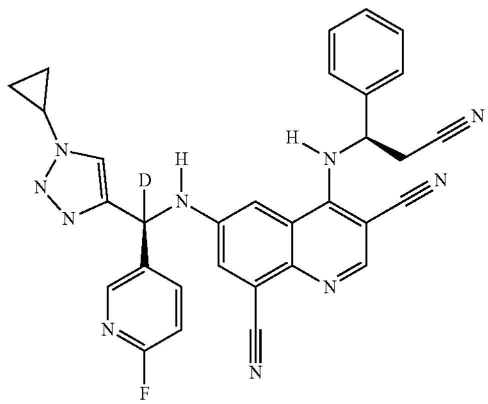 [SMILES: [2H][C@](Nc1cc(C#N)c2ncc(C#N)c(N[C@H](CC#N)c3ccccc3)c2c1)(C1=CN(C2CC2)NN1)c1ccc(F)nc1] | 4-(((R)-2-cyano-1-phenylethyl)amino)-6-(((S)-(1-cyclopropyl-1H-1,2,3-triazol-4-yl)(6-fluoropyridin-3-yl)methyl-d)amino)quinoline-3,8-dicarbonitrile | 1 | ES/MS 556.2 (M + H+) |
| 101 | 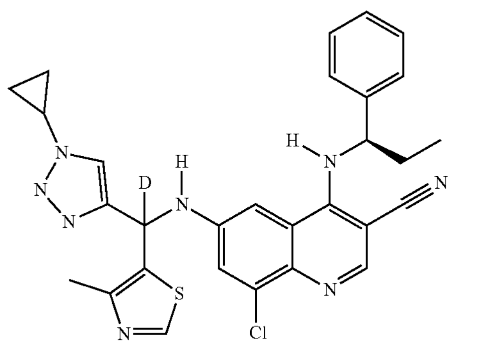 [SMILES: [2H]C(Nc1cc(Cl)c2ncc(C#N)c(N[C@H](CC)c3ccccc3)c2c1)(C1=CN(C2CC2)NN1)c1scnc1C] | 8-chloro-6-(((1-cyclopropyl-1H-1,2,3-triazol-4-yl)(4-methylthiazol-5-yl)methyl-d)amino)-4-(((R)-1-phenylpropyl)amino)quinoline-3-carbonitrile | 2 | ES/MS: 556.2 (M + H+) |
| 102 | 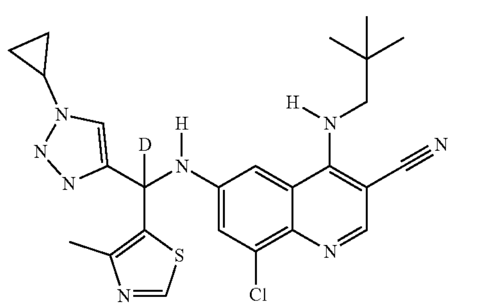 [SMILES: [2H]C(Nc1cc(Cl)c2ncc(C#N)c(NCC(C)(C)C)c2c1)(C1=CN(C2CC2)NN1)c1scnc1C] | 8-chloro-6-(((1-cyclopropyl-1H-1,2,3-triazol-4-yl)(4-methylthiazol-5-yl)methyl-d)amino)-4-(neopentylamino)quinoline-3-carbonitrile | 1 | ES/MS: 508.3 (M + H+) |
| 103 | 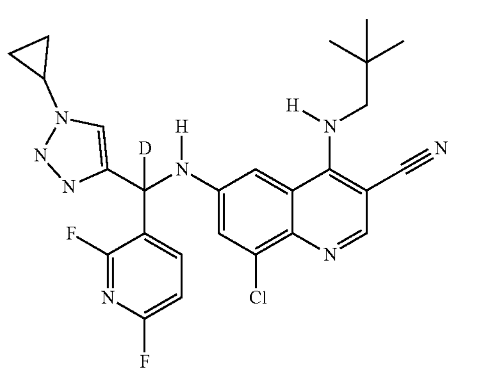 [SMILES: [2H]C(Nc1cc(Cl)c2ncc(C#N)c(NCC(C)(C)C)c2c1)(C1=CN(C2CC2)NN1)c1ccc(F)nc1F] | 8-chloro-6-(((1-cyclopropyl-1H-1,2,3-triazol-4-yl)(2,6-difluoropyridin-3-yl)methyl-d)amino)-4-(neopentylamino)quinoline-3-carbonitrile | 1 | ES/MS: 524.3 (M + H+) |

TABLE 1-continued

| Comp | Structure | Name | Example Procedure | ES/MS m/z |
|------|-----------|------|-------------------|-----------|
| 104 | 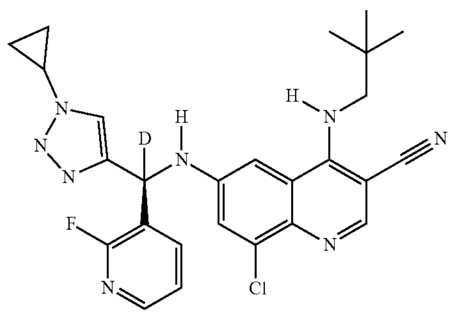 [SMILES: [2H][C@](Nc1cc(Cl)c2ncc(C#N)c(NCC(C)(C)C)c2c1)(C1=CN(C2CC2)NN1)c1cccnc1F] | (S)-8-chloro-6-(((1-cyclopropyl-1H-1,2,3-triazol-4-yl)(2-fluoropyridin-3-yl)methyl-d)amino)-4-(neopentyl-amino)quinoline-3-carbonitrile | 2 | ES/MS 506.4 (M + H+) |
| 105 | 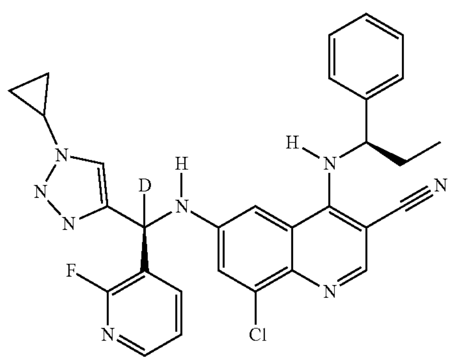 [SMILES: [2H][C@](Nc1cc(Cl)c2ncc(C#N)c(N[C@H](CC)c3ccccc3)c2c1)(C1=CN(C2CC2)NN1)c1cccnc1F] | 8-chloro-6-(((S)-(1-cyclopropyl-1H-1,2,3-triazol-4-yl)(2-fluoropyridin-3-yl)methyl-d)amino)-4-(((R)-1-phenylpropyl)amino)quinoline-3-carbonitrile | 2 | ES/MS 554.2 (M + H+) |
| 106 | 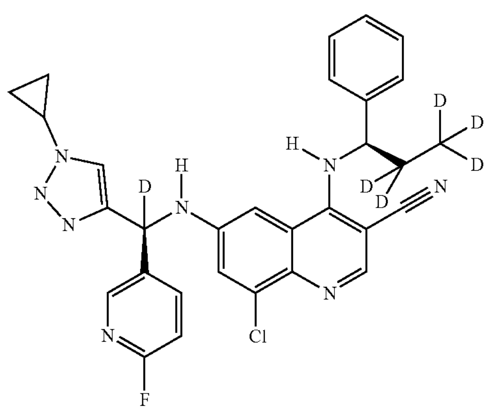 [SMILES: [2H]C([2H])([2H])C([2H])([2H])[C@@H](Nc1c(C#N)cnc2c(Cl)cc(N[C@@]([2H])(C3=CN(C4CC4)NN3)c3ccc(F)nc3)cc12)c1ccccc1] | 8-chloro-6-(((S)-(1-cyclopropyl-1H-1,2,3-triazol-4-yl)(6-fluoropyridin-3-yl)methyl-d)amino)-4-(((R)-1-phenylpropyl-2,2,3,3,3-d5)amino)-quinoline-3-carbonitrile | 2 | ES/MS 559.2 (M + H+) |
| 107 | 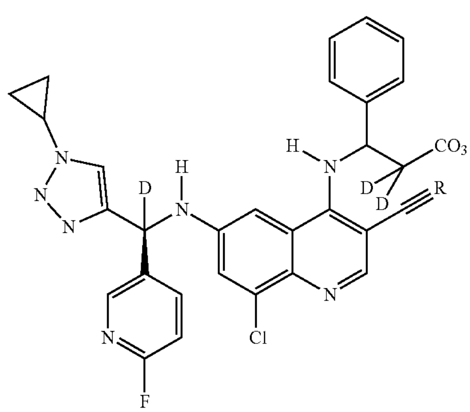 | 8-chloro-6-(((S)-(1-cyclopropyl-1H-1,2,3-triazol-4-yl)(6-fluoropyridin-3-yl)methyl-d)amino)-4-(((S)-1-phenyl-propyl-2,2,3,3,3-d5)amino)quinoline-3-carbonitrile | 2 | ES/MS 559.2 (M + H+) |

TABLE 1-continued

| Comp | Structure | Name | Example Procedure | ES/MS m/z |
|------|-----------|------|-------------------|-----------|
| 108 | 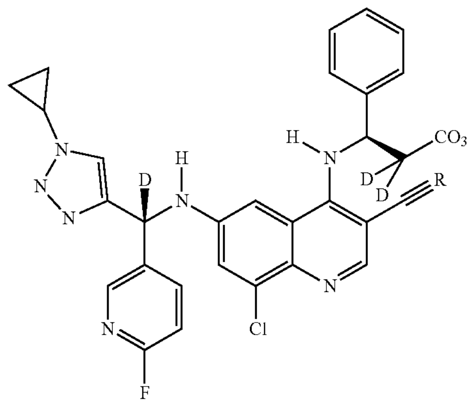 | 8-chloro-6-(((R)-(1-cyclopropyl-1H-1,2,3-triazol-4-yl)(6-fluoropyridin-3-yl)methyl-d)amino)-4-(((R)-1-phenyl-propyl-2,2,3,3,3-d5)amino)quinoline-3-carbonitrile | 2 | ES/MS 559.1 (M + H+) |
| 109 | 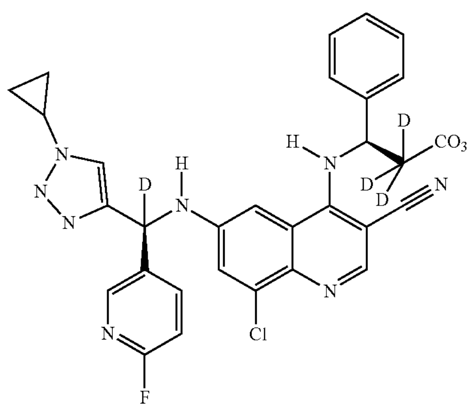 | 8-chloro-6-(((S)-(1-cyclopropyl-1H-1,2,3-triazol-4-yl)(6-fluoropyridin-3-yl)methyl-d)amino)-4-(((R)-1-phenylpropyl-1,2,2,3,3,3-d6)amino)quinoline-3-carbonitrile | 2 | ES/MS 560.2 (M + H+) |
| 110 | 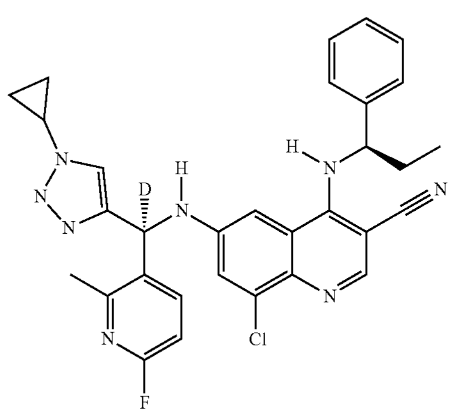 [SMILES: [2H][C@@](Nc1cc(Cl)c2ncc(C#N)c(N[C@H](CC)c3ccccc3)c2c1)(C1=CN(C2CC2)NN1)c1ccc(F)nc1C] | 8-chloro-6-(((1-cyclopropyl-1H-1,2,3-triazol-4-yl)(6-fluoro-2-methylpyridin-3-yl)methyl-d)amino)-4-(((R)-1-phenylpropyl)amino)quinoline-3-carbonitrile | 2 | ES/MS: 568.2 (M + H+) |

TABLE 1-continued

| Comp | Structure | Name | Example Procedure | ES/MS m/z |
|---|---|---|---|---|
| 111 | 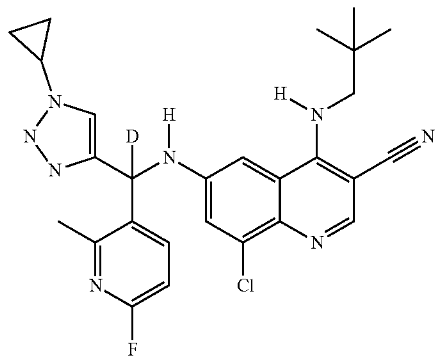 [SMILES: [2H]C(Nc1cc(Cl)c2ncc(C#N)c(NCC(C)(C)C)c2c1)(C1=CN(C2CC2)NN1)c1ccc(F)nc1C] | 8-chloro-6-(((1-cyclopropyl-1H-1,2,3-triazol-4-yl)(6-fluoro-2-methylpyridin-3-yl)methyl-d)amino)-4-(neopentylamino)quinoline-3-carbonitrile | 1 | ES/MS: 520.3 (M + H+) |
| 112 | 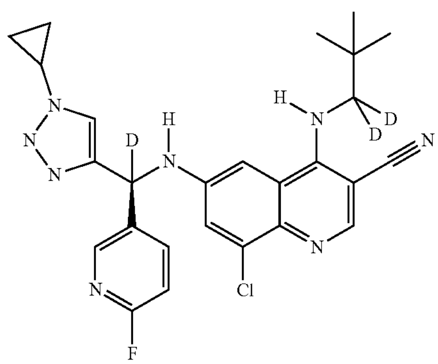 [SMILES: [2H]C([2H])(Nc1c(C#N)cnc2c(Cl)cc(N[C@@]([2H])(C3=CN(C4CC4)NN3)c3ccc(F)nc3)cc12)C(C)(C)C] | (S)-8-chloro-6-(((1-cyclopropyl-1H-1,2,3-triazol-4-yl)(6-fluoropyridin-3-yl)methyl-d)amino)-4-((2,2-dimethylpropyl-1,1-d2)amino)quinoline-3-carbonitrile | 2 | ES/MS 508.3 (M + H+) |
| 113 | 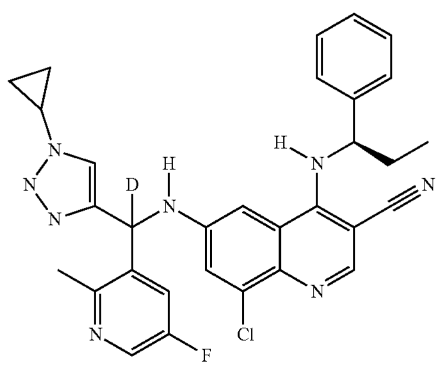 [SMILES: [2H]C(Nc1cc(Cl)c2ncc(C#N)c(N[C@H](CC)c3ccccc3)c2c1)(C1=CN(C2CC2)NN1)c1cc(F)cnc1C] | 8-chloro-6-(((1-cyclopropyl-1H-1,2,3-triazol-4-yl)(5-fluoro-2-methylpyridin-3-yl)methyl-d)amino)-4-(((R)-1-phenylpropyl)amino)quinoline-3-carbonitrile | 2 | ES/MS: 568.2 (M + H+) |
| 114 | 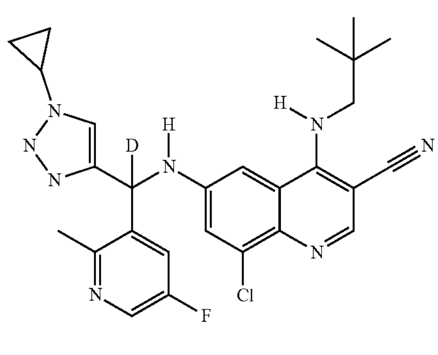 [SMILES: [2H]C(Nc1cc(Cl)c2ncc(C#N)c(NCC(C)(C)C)c2c1)(C1=CN(C2CC2)NN1)c1cc(F)cnc1C] | 8-chloro-6-(((1-cyclopropyl-1H-1,2,3-triazol-4-yl)(5-fluoro-2-methylpyridin-3-yl)methyl-d)amino)-4-(neopentylamino)quinoline-3-carbonitrile | 1 | ES/MS 520.2 (M + H+) |

TABLE 1-continued

| Comp | Structure | Name | Example Procedure | ES/MS m/z |
|---|---|---|---|---|
| 115 | 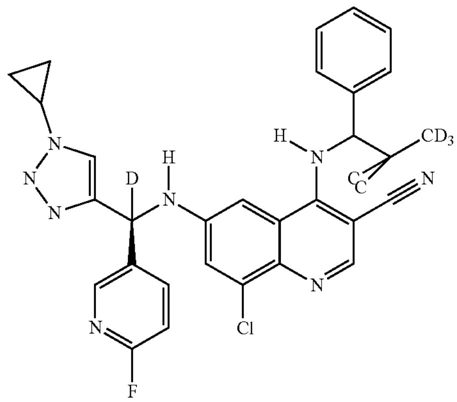 | 8-chloro-6-(((S)-(1-cyclopropyl-1H-1,2,3-triazol-4-yl)(6-fluoropyridin-3-yl)methyl-d)amino)-4-((1-phenylpropyl-2,2,3,3,3-d5)amino)quinoline-3-carbonitrile | 2 | ES/MS 559.3 (M + H+) |
| 116 | 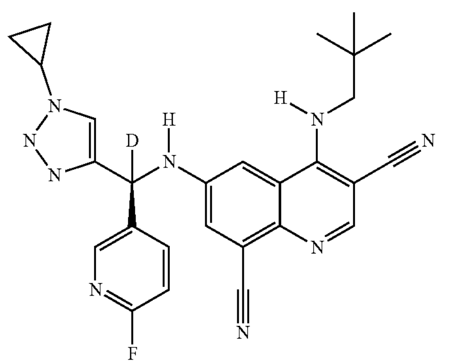 | (S)-6-(((1-cyclopropyl-1H-1,2,3-triazol-4-yl)(6-fluoropyridin-3-yl)methyl-d)amino)-4-(neopentylamino)quinoline-3,8-dicarbonitrile | 1 | ES/MS 597.2 (M + H+) |
| 117 | 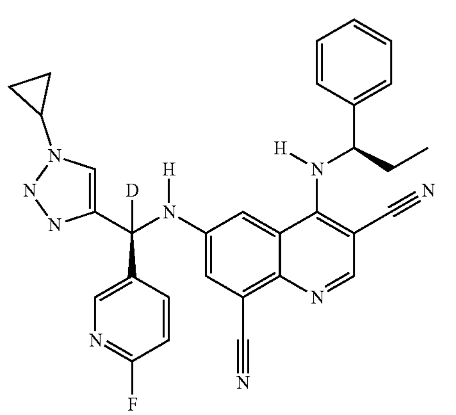 [SMILES: [2H][C@](Nc1cc(C#N)c2ncc(C#N)c(N[C@H](CC)c3ccccc3)c2c1)(C1=CN(C2CC2)NN1)c1ccc(F)nc1] | 6-(((S)-(-cyclopropyl-1H-1,2,3-triazol-4-yl)(6-fluoropyridin-3-yl)methyl-d)amino)-4-(((R)-1-phenylpropyl)amino)quinoline-3,8-dicarbonitrile | 1 | ES/MS 545.2 (M + H+) |

TABLE 1-continued

| Comp | Structure | Name | Example Procedure | ES/MS m/z |
|---|---|---|---|---|
| 118 | 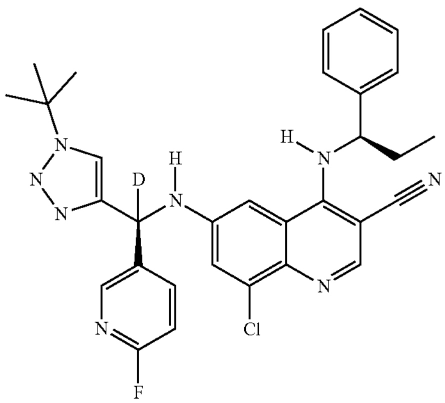 [SMILES: [2H][C@](Nc1cc(Cl)c2ncc(C#N)c(N[C@H](CC)c3ccccc3)c2c1)(C1=CN(C(C)(C)C)NN1)c1ccc(F)nc1] | 6-(((S)-(1-(tert-butyl)-1H-1,2,3-triazol-4-yl)(6-fluoropyridin-3-yl)methyl-d)amino)-8-chloro-4-(((R)-1-phenylpropyl)amino)quinoline-3-carbonitrile | 3 | ES/MS 570.3 (M + H+) |
| 119 | 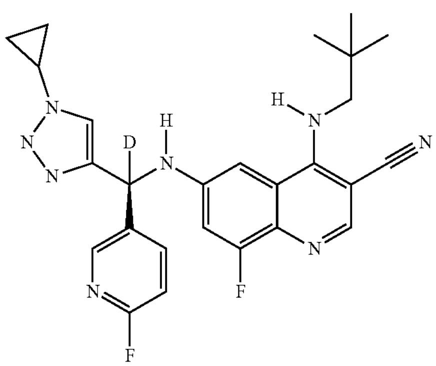 [SMILES: [2H][C@](Nc1cc(F)c2ncc(C#N)c(NCC(C)(C)C)c2c1)(C1=CN(C2CC2)NN1)c1ccc(F)nc1] | (S)-6-(((1-cyclopropyl-1H-1,2,3-triazol-4-yl)(6-fluoropyridin-3-yl)methyl-d)amino)-8-lluoro-4-(neopentylamino)quinoline-3-carbonitrile | 1 | ES/MS 490.2 (M + H+) |
| 120 | 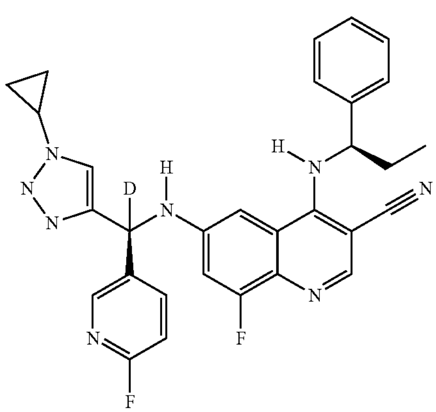 [SMILES: [2H][C@](Nc1cc(F)c2ncc(C#N)c(N[C@H](CC)c3ccccc3)c2c1)(C1=CN(C2CC2)NN1)c1ccc(F)nc1] | 6-(((S)-(-cyclopropyl-1H-1,2,3-triazol-4-yl)(6-fluoropyridin-3-yl)methyl-d)amino)-8-fluoro-4-(((R)-1-phenylpropyl)amino)quinolme-3-carbonitrile | 1 | ES/MS 538.2 (M + H+) |

TABLE 1-continued

| Comp | Structure | Name | Example Procedure | ES/MS m/z |
|---|---|---|---|---|
| 121 | 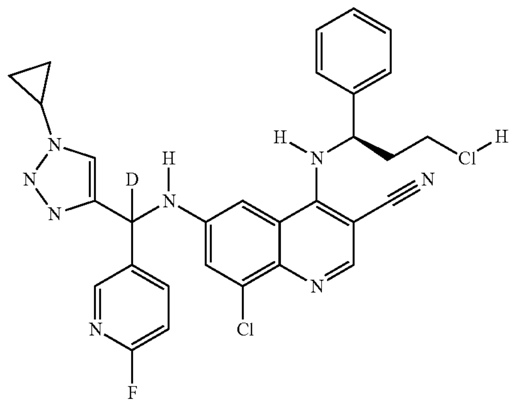 | 8-chloro-6-(((1-cyclopropyl-1H-1,2,3-triazol-4-yl)(6-fluoropyridin-3-yl)methyl-d)amino)-4-(((R)-3-hydroxy-1-phenylpropyl)amino)quinoline-3-carbonitrile | 2 | ES/MS 570.1 (M + H+) |
| 122 | 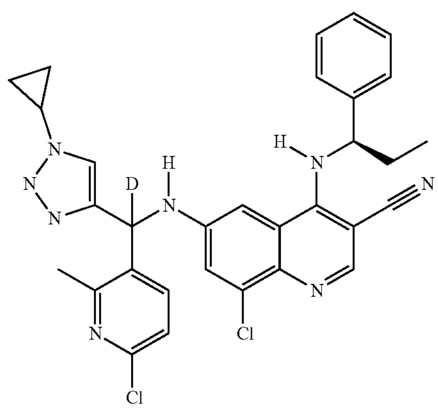 [SMILES: [2H]C(Nc1cc(Cl)c2ncc(C#N)c(N[C@H](CC)c3ccccc3)c2c1)(C1=CN(C2CC2)NN1)c1ccc(Cl)nc1C] | 8-chloro-6-(((6-chloro-2-methylpyridin-3-yl)(1-cyclopropyl-1H-1,2,3-triazol-4-yl)methyl-d)amino)-4-(((R)-1-phenylpropyl)amino)quinoline-3-carbonitrile | 2 | ES/MS: 584.3 (M + H+) |
| 123 | 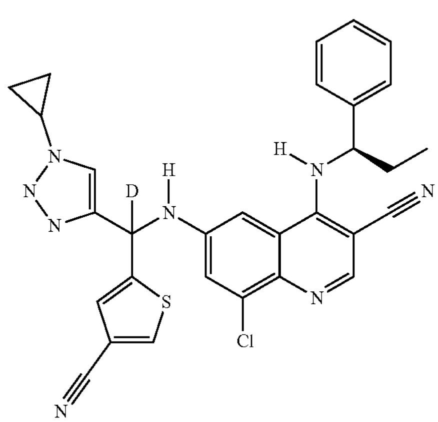 | 8-chloro-6-(((4-cyanothiophen-2-yl)(1-cyclopropyl-1H-1,2,3-triazol-4-yl)methyl-d)amino)-4-(((R)-1-phenylpropyl)amino)quinoline-3-carbonitrile | 2 | ES/MS: 5660 (M + H+) |

TABLE 1-continued

| Comp | Structure | Name | Example Procedure | ES/MS m/z |
|---|---|---|---|---|
| 124 | 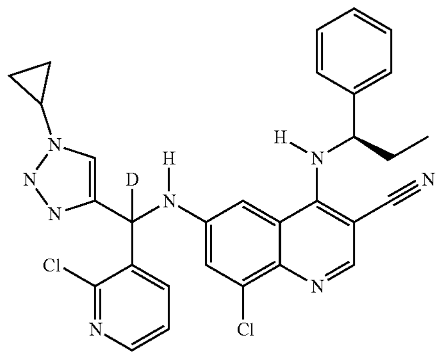 [SMILES: [2H]C(Nc1cc(Cl)c2ncc(C#N)c(N[C@H](CC)c3ccccc3)c2c1)(C1=CN(C2CC2)NN1)c1cccnc1Cl] | 8-chloro-6-(((2-chloropyridin-3-yl)(1-cyclopropyl-1H-1,2,3-triazol-4-yl)methyl-d)amino)-4-(((R)-1-phenylpropyl)amino)quinolme-3-carbonitrile | 2 | ES/MS: 570.5 (M + H+) |
| 125 | 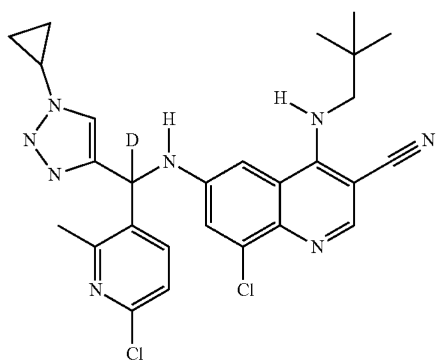 | 8-chloro-6-(((6-chloro-2-methylpyridin-3-yl)(1-cyclopropyl-1H-1,2,3-triazol-4-yl)methyl-d)amino)-4-(neopentylamino)quinoline-3-carbonitrile | 1 | ES/MS: 536.9 (M + H+) |
| 126 | 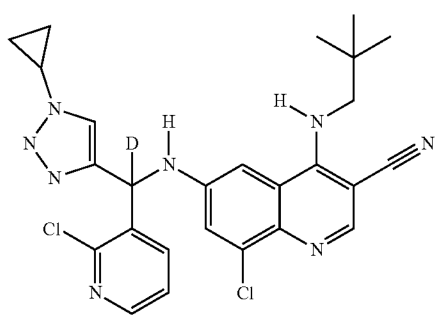 [SMILES: [2H]C(Nc1cc(Cl)c2ncc(C#N)c(NCC(C)(C)C)c2c1)(C1=CN(C2CC2)NN1)c1cccnc1Cl] | 8-chloro-6-(((2-chloropyridin-3-yl)(1-cyclopropyl-1H-1,2,3-triazol-4-yl)methyl-d)amino)-4-(neopentylamino)quinoline-3-carbonitrile | 1 | ES/MS: 522.4 (M + H+) |
| 127 | 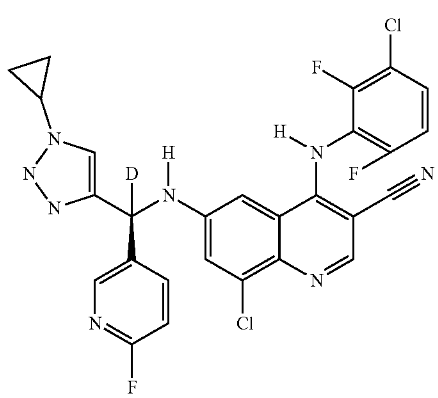 [SMILES: [2H][C@](Nc1cc(Cl)c2ncc(C#N)c(Nc3c(F)ccc(Cl)c3F)c2c1)(C1=CN(C2CC2)NN1)c1ccc(F)nc1] | (S)-8-chloro-4-((3-chloro-2,6-difluorophenyl)amino)-6-(((1-cyclopropyl-1H-1,2,3-triazol-4-yl)(6-fluoropyridin-3-yl)methyl-d)amino)quinoline-3-carbonitrile | 2 | ES/MS 582.2 (M + H+) |

TABLE 1-continued

| Comp | Structure | Name | Example Procedure | ES/MS m/z |
|---|---|---|---|---|
| 128 | 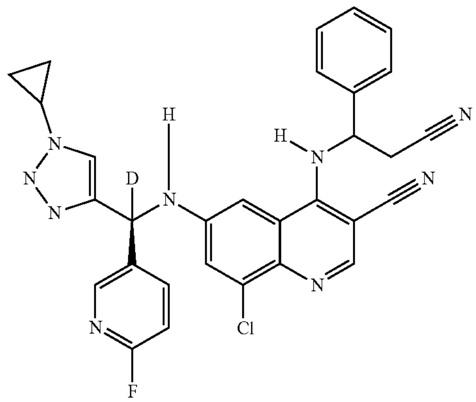 [SMILES: [2H][C@](C1=CN(C2CC2)NN1)(c1ccc(F)nc1)N(C)c1cc(Cl)c2ncc(C#N)c(NC(CC#N)c3ccccc3)c2c1] | 8-chloro-4-(((S)-2-cyano-1-phenylethyl)amino)-6-(((S)-(1-cyclopropyl-1H-1,2,3-triazol-4-yl)(6-fluoropyridin-3-yl)methyl-d)amino)quinoline-3-carbonitrile | 2 | ES/MS 565.1 (M + H+) |
| 129 | 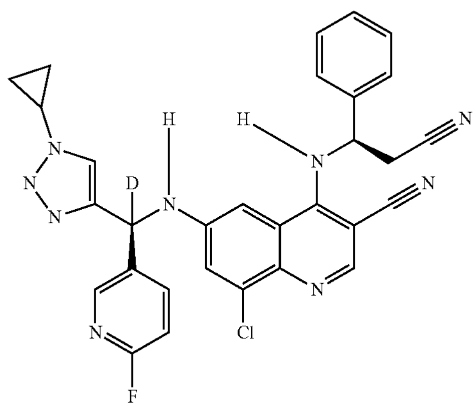 [SMILES: [2H][C@](C1=CN(C2CC2)NN1)(c1ccc(F)nc1)N(C)c1cc(Cl)c2ncc(C#N)c(N(C)[C@H](CC#N)c3ccccc3)c2c1] | 8-chloro-4-(((R)-2-cyano-1-phenylethyl)amino)-6-(((S)-(1-cyclopropyl-1H-1,2,3-triazol-4-yl)(6-fluoropyridin-3-yl)methyl-d)amino)quinoline-3-carbonitrile | 2 | ES/MS 565.1 (M + H+) |
| 130 | 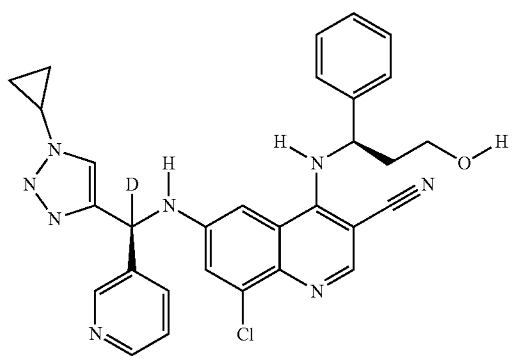 [SMILES: [2H][C@](Nc1cc(Cl)c2ncc(C#N)c(N[C@H](CCO)c3ccccc3)c2c1)(C1=CN(C2CC2)NN1)c1cccnc1] | 8-chloro-6-(((1-cyclopropyl-1H-1,2,3-triazol-4-yl)(pyridin-3-yl)methyl-d)amino)-4-(((R)-3-hydroxy-1-phenylpropyl)amino)quinoline-3-carbonitrile | 2 | ES/MS 552.1 (M + H+) |
| 131 | 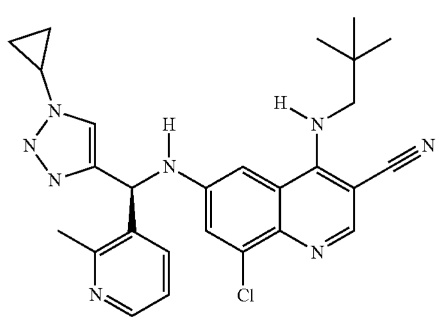 [SMILES: Cc1ncccc1[C@H](Nc1cc(Cl)c2ncc(C#N)c(NCC(C)(C)C)c2c1)C1=CN(C2CC2)NN1] | (S)-8-chloro-6-(((1-cyclopropyl-1H-1,2,3-triazol-4-yl)(2-methylpyridin-3-yl)methyl)amino)-4-(neopentyl-amino)quinoline-3-carbonitrile | 1 | ES/MS: 501.2 (M + H+) |

TABLE 1-continued

| Comp | Structure | Name | Example Procedure | ES/MS m/z |
|---|---|---|---|---|
| 132 | 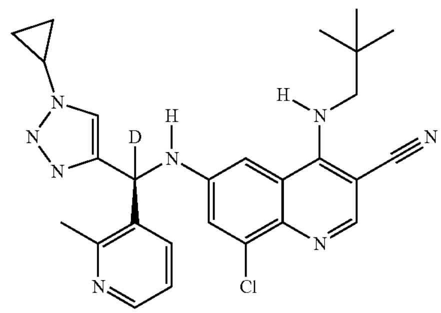 [SMILES: [2H][C@](Nc1cc(Cl)c2ncc(C#N)c(NCC(C)(C)C)c2c1)(C1=CN(C2CC2)NN1)c1cccnc1C] | 8-chloro-6-(((1-cyclopropyl-1H-1,2,3-triazol-4-yl)(2-methylpyridin-3-yl)methyl-d)amino)-4-(neopentylamino)quinoline-3-carbonitrile | 1 | ES/MS: 502.16 (M + H+) |
| 133 | 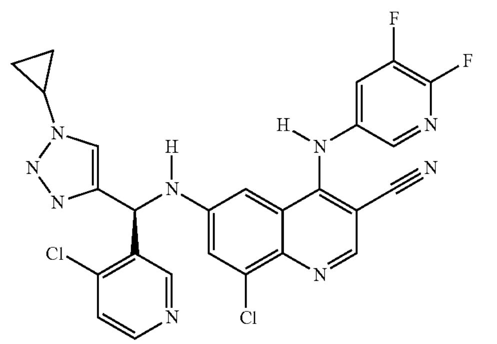 [SMILES: N#Cc1cnc2c(Cl)cc(N[C@H](C3=CN(C4CC4)NN3)c3cnccc3Cl)cc2c1Nc1cnc(F)c(F)c1] | (S)-8-chloro-6-(((4-chloropyridin-3-yl)(1-cyclopropyl-1H-1,2,3-triazol-4-yl)methyl)amino)-4-((5,6-difluoropyridin-3-yl)amino)quinoline-3-carbonitrile | 1 | ES/MS 563.9 (M + H+) |
| 134 | 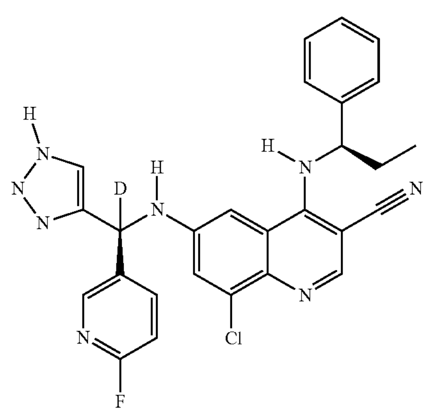 [SMILES: [2H][C@](Nc1cc(Cl)c2ncc(C#N)c(N[C@H](CC)c3ccccc3)c2c1)(C1=CNNN1)c1ccc(F)nc1] | 8-chloro-6-(((S)-(6-fluoropyridin-3-yl)(1H-1,2,3-triazol-4-yl)methyl-d)amino)-4-(((R)-1-phenylpropyl)amino)quinoline-3-carbonitrile | 10 | ES/MS 514.1 (M + H+) |
| 135 | 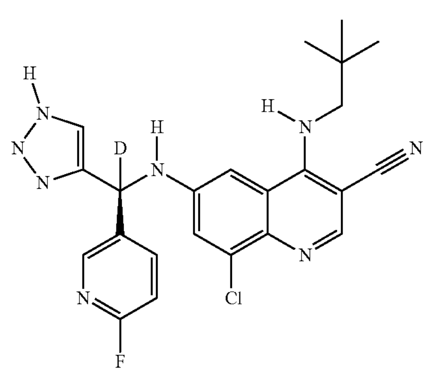 [SMILES: [2H][C@](Nc1cc(Cl)c2ncc(C#N)c(NCC(C)(C)C)c2c1)(C1=CNNN1)c1ccc(F)nc1] | (S)-8-chloro-6-(((6-fluoropyridin-3-yl)(1H-1,2,3-triazol-4-yl)methyl-d)amino)-4-(neopentylamino)quinoline-3-carbonitrile | 10 | ES/MS 466.1 (M + H+) |

TABLE 1-continued

| Comp | Structure | Name | Example Procedure | ES/MS m/z |
|---|---|---|---|---|
| 136 | 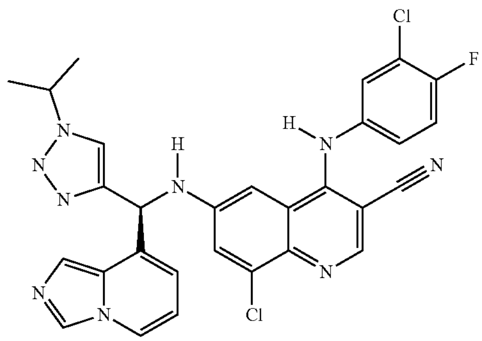 [SMILES: CC(C)N1C=C([C@@H](Nc2cc(Cl)c3ncc(C#N)c(Nc4ccc(F)c(Cl)c4)c3c2)c2cccn3cncc23)NN1] | (S)-8-chloro-4-((3-chloro-4-fluorophenyl)amino)-6-((imidazo[1,5-a]pyridin-8-yl(1-isopropyl-1H-1,2,3-triazol-4-yl)methyl)amino)quinoline-3-carbonitrile | 2 | ES/MS 586.0 (M + H+) |
| 137 | 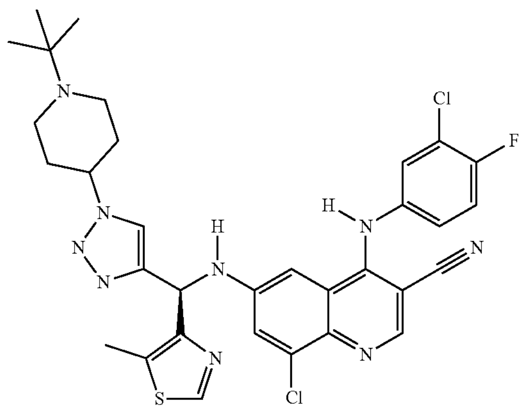 | (S)-6-(((1-(1-(tert-butyl)piperidin-4-yl)-1H-1,2,3-triazol-4-yl)(5-methylthiazol-4-yl)methyl)amino)-8-chloro-4-((3-chloro-4-fluorophenyl)amino)quinoline-3-carbonitrile | 2 | ES/MS 664.1 (M + H+) |
| 138 | 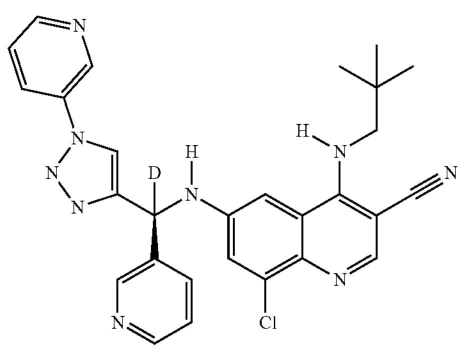 [SMILES: [2H][C@](Nc1cc(Cl)c2ncc(C#N)c(NCC(C)(C)C)c2c1)(C1=CN(c2cccnc2)NN1)c1cccnc1] | (S)-8-chloro-4-(neopentylamino)-6-((pyridin-3-yl(1-(pyridin-3-yl)-1H-1,2,3-triazol-4-yl)methyl-d)amino)quinoline-3-carbonitrile | 2 | ES/MS 525.2 (M + H+) |
| 139 | 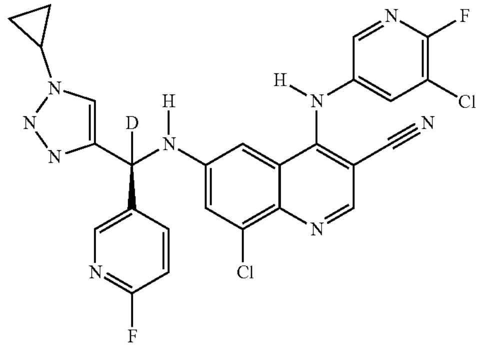 [SMILES: [2H][C@](Nc1cc(Cl)c2ncc(C#N)c(Nc3cnc(F)c(Cl)c3)c2c1)(C1=CN(C2CC2)NN1)c1ccc(F)nc1] | (S)-8-chloro-4-((5-chloro-6-fluoropyridin-3-yl)amino)-6-(((1-cyclopropyl-1H-1,2,3-triazol-4-yl)(6-fluoropyridin-3-yl)methyl-d)amino)quinoline-3-carbonitrile | 2 | ES/MS 564.9 (M + H+) |

TABLE 1-continued

| Comp | Structure | Name | Example Procedure | ES/MS m/z |
|---|---|---|---|---|
| 140 | 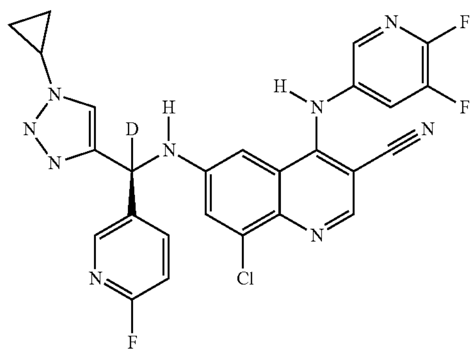 [SMILES: [2H][C@](Nc1cc(Cl)c2ncc(C#N)c(Nc3cnc(F)c(F)c3)c2c1)(C1=CN(C2CC2)NN1)c1ccc(F)nc1] | (S)-8-chloro-6-(((1-cyclopropyl-1H-1,2,3-triazol-4-yl)(6-fluoropyridin-3-yl)methyl-d)amino)-4-((5,6-difluoropyridin-3-yl)amino)quinoline-3-carbonitrile | 2 | ES/MS 549.1 (M + H+) |
| 141 | 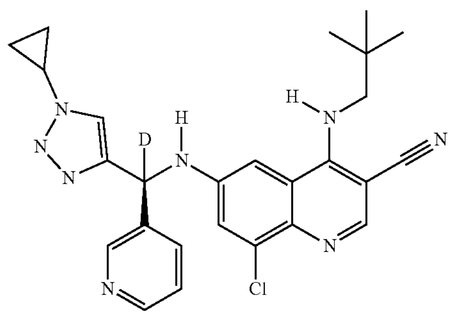 | (S)-8-chloro-6-(((1-cyclopropyl-1H-1,2,3-triazol-4-yl)(pyridin-3-yl)methyl-d)amino)-4-(neopentylamino)quinoline-3-carbonitrile | 2 | ES/MS 488.1 (M + H+) |
| 142 | 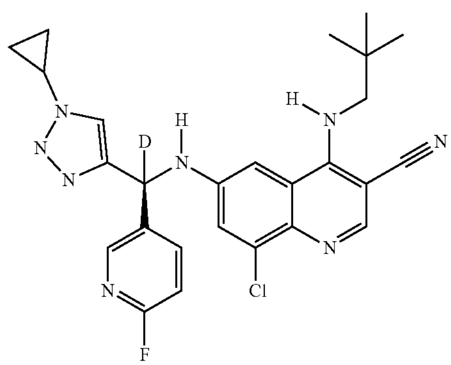 | (S)-8-chloro-6-(((1-cyclopropyl-1H-1,2,3-triazol-4-yl)(6-fluoropyridin-3-yl)methyl-d)amino)-4-(neopentylamino)quinoline-3-carbonitrile | 2 | ES/MS 506.1 (M + H+) |
| 143 | 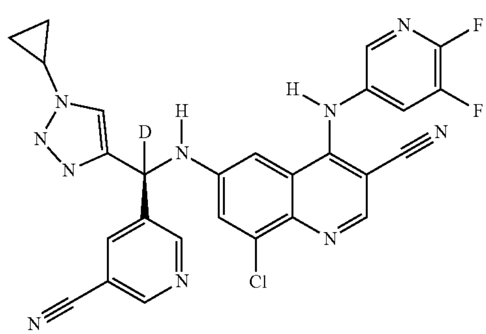 [SMILES: [2H][C@](Nc1cc(Cl)c2ncc(C#N)c(Nc3cnc(F)c(F)c3)c2c1)(C1=CN(C2CC2)NN1)c1cncc(C#N)c1] | (S)-8-chloro-6-(((5-cyanopyridin-3-yl)(1-cyclopropyl-1H-1,2,3-triazol-4-yl)methyl-d)amino)-4-((5,6-difluoropyridin-3-yl)amino)quinoline-3-carbonitrile | 2 | ES/MS 556.1 (M + H+) |

TABLE 1-continued

| Comp | Structure | Name | Example Procedure | ES/MS m/z |
|---|---|---|---|---|
| 144 | 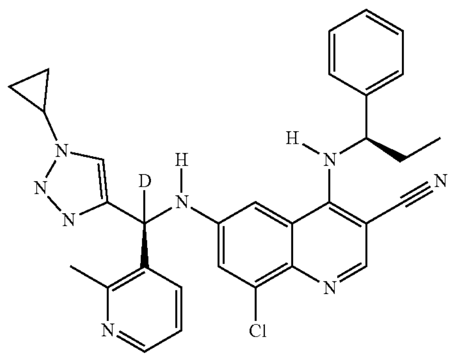 | 8-chloro-6-(((1-cyclopropyl-1H-1,2,3-triazol-4-yl)(2-methylpyridin-3-yl)methyl-d)amino)-4-(((R)-1-phenylpropyl)amino)quinoline-3-carbonitrile | 2 | ES/MS: 550.1 (M + H+) |
| 145 | 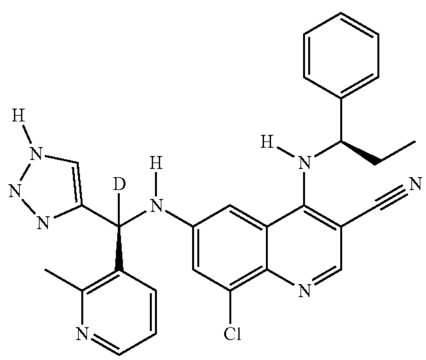 [SMILES: [2H][C@](Nc1cc(Cl)c2ncc(C#N)c(N[C@H](CC)c3ccccc3)c2c1)(C1=CNNN1)c1cccnc1C] | 8-chloro-6-(((2-methylpyridin-3-yl)(1H-1,2,3-triazol-4-yl)methyl-d)amino)-4-(((R)-1-phenyl propyl)amino)quinoline-3-carbonitrile | 10 | ES/MS 510.0 (M + H+) |
| 146 | 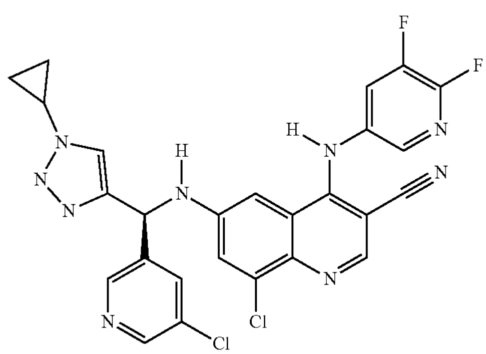 [SMILES: N#Cc1cnc2c(Cl)cc(N[C@H](C3=CN(C4CC4)NN3)c3cncc(Cl)c3)cc2c1Nc1cnc(F)c(F)c1] | (S)-8-chloro-6-(((5-chloropyridin-3-yl)(1-cyclopropyl-1H-1,2,3-triazol-4-yl)methyl)amino)-4-((5,6-difluoropyridin-3-yl)amino)-quinoline-3-carbonitrile | 1 | ES/MS 564 0 (M + H+) |
| 147 | 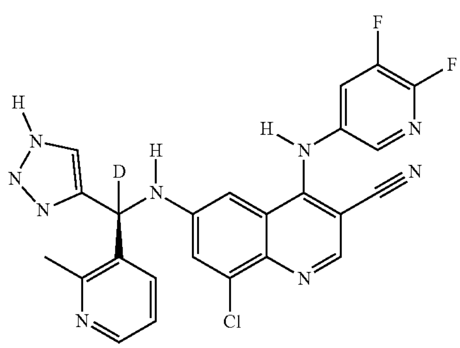 [SMILES: [2H][C@](Nc1cc(Cl)c2ncc(C#N)c(Nc3cnc(F)c(F)c3)c2c1)(C1=CNNN1)c1cccnc1C] | 8-chloro-4-((5,6-difluoropyridin-3-yl)amino)-6-(((2-methylpyridin-3-yl)(1H-1,2,3-triazol-4-yl)methyl-d)amino)quinoline-3-carbonitrile | 10 | ES/MS 505.0 (M + H+) |

TABLE 1-continued

| Comp | Structure | Name | Example Procedure | ES/MS m/z |
|---|---|---|---|---|
| 148 | 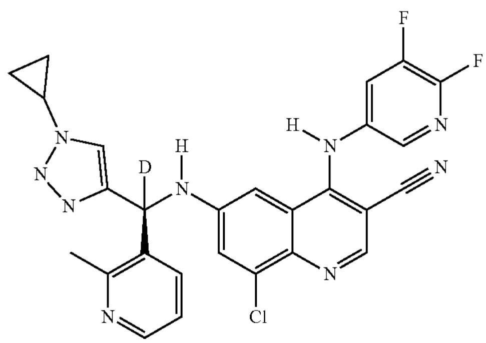 [SMILES: [2H][C@](Nc1cc(Cl)c2ncc(C#N)c(Nc3cnc(F)c(F)c3)c2c1)(C1=CN(C2CC2)NN1)c1cccnc1C] | 8-chloro-6-(((1-cyclopropyl-1H-1,2,3-triazol-4-yl)(2-methylpyridin-3-yl)methyl-d)amino)-4-((5,6-difluoropyridin-3-yl)amino)quinoline-3-carbonitrile | 1 | ES/MS 545.1 (M + H+) |
| 149 | 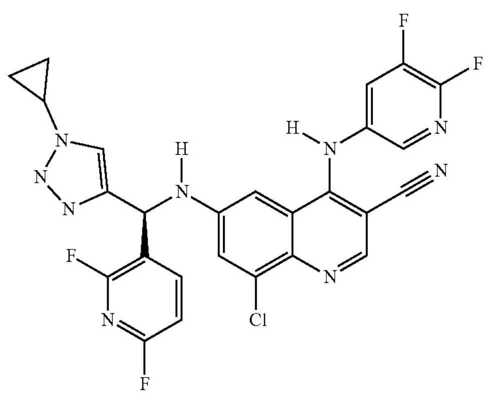 [SMILES: N#Cc1cnc2c(Cl)cc(N[C@H](C3=CN(C4CC4)NN3)c3ccc(F)nc3F)cc2c1Nc1cnc(F)c(F)c1] | (S)-8-chloro-6-(((1-cyclopropyl-1H-1,2,3-triazol-4-yl)(2,6-difluoropyridin-3-yl)methyl)amino)-4-((5,6-difluoropyridin-3-yl)amino)quinoline-3-carbonitrile | 1 | ES/MS 566.0 (M + H+) |
| 150 | 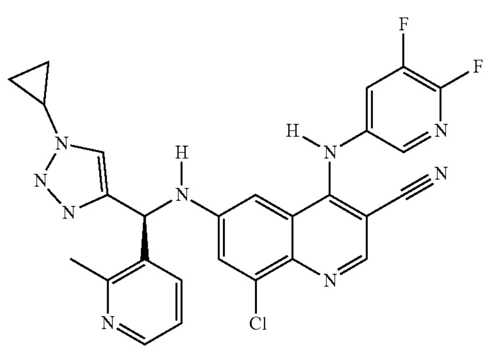 [SMILES: Cc1ncccc1[C@H](Nc1cc(Cl)c2ncc(C#N)c(Nc3cnc(F)c(F)c3)c2c1)C1=CN(C2CC2)NN1] | (S)-8-chloro-6-(((1-cyclopropyl-1H-1,2,3-triazol-4-yl)(2-methylpyridin-3-yl)methyl)amino)-4-((5,6-difluoropyridin-3-yl)amino)quinoline-3-carbonitrile | 1 | ES/MS 543.9 (M + H+) |
| 151 | 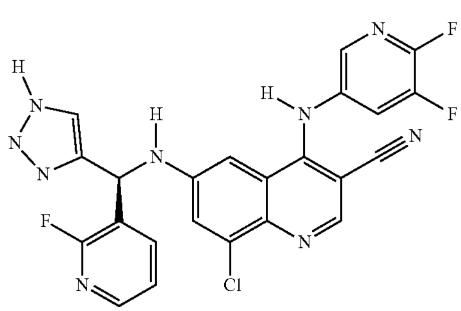 [SMILES: N#Cc1cnc2c(Cl)cc(N[C@H](C3=CNNN3)c3cccnc3F)cc2c1Nc1cnc(F)c(F)c1] | (S)-8-chloro-4-((5,6-difluoropyridin-3-yl)amino)-6-(((2-fluoropyridin-3-yl)(1H-1,2,3-triazol-4-yl)methyl)amino)quinoline-3-carbonitrile | 10 | ES/MS 508.1 (M + H+) |

TABLE 1-continued

| Comp | Structure | Name | Example Procedure | ES/MS m/z |
|---|---|---|---|---|
| 152 | 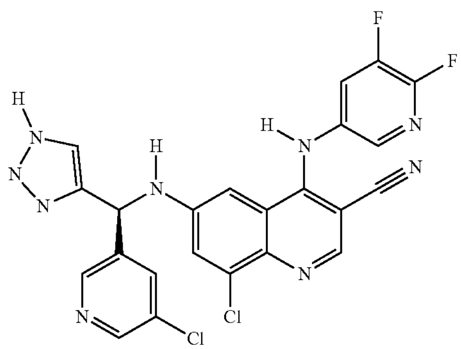 [SMILES: N#Cc1cnc2c(Cl)cc(N[C@H](C3=CNNN3)c3cncc(Cl)c3)cc2c1Nc1cnc(F)c(F)c1] | (S)-8-chloro-6-(((5-chloropyridin-3-yl)(1H-1,2,3-triazol-4-yl)methyl)amino)-4-((5,6-difluoropyridin-3-yl)amino)quinoline-3-carbonitrile | 10 | ES/MS 524 0 (M + H+) |
| 153 | 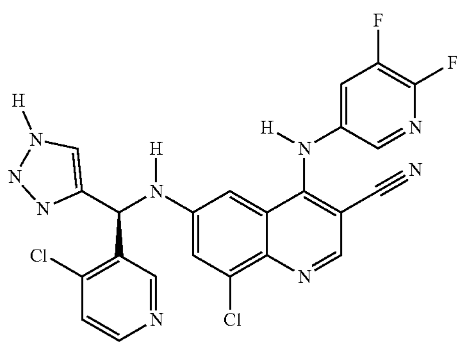 [SMILES: N#Cc1cnc2c(Cl)cc(N[C@H](C3=CNNN3)c3cnccc3Cl)cc2c1Nc1cnc(F)c(F)c1] | (S)-8-chloro-6-(((4-chloropyridin-3-yl)(1H-1,2,3-triazol-4-yl)methyl)amin o)-4-((5,6-difluoropyridin-3-yl)amino)quinoline-3-carbonitrile | 10 | ES/MS 524.0 (M + H+) |
| 154 | 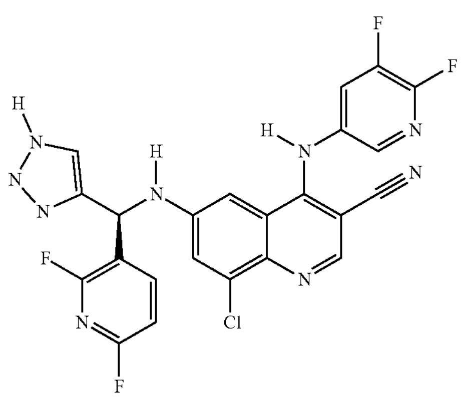 [SMILES: N#Cc1cnc2c(Cl)cc(N[C@H](C3=CNNN3)c3ccc(F)nc3F)cc2c1Nc1cnc(F)c(F)c1] | (S)-8-chloro-6-(((2,6-difluoropyridin-3-yl)(1H-1,2,3-triazol-4-yl)methyl)amino)-4-((5,6-difluoropyridin-3-yl)amino)quinoline-3-carbonitrile | 10 | ES/MS 526.0 (M + H+) |
| 155 | 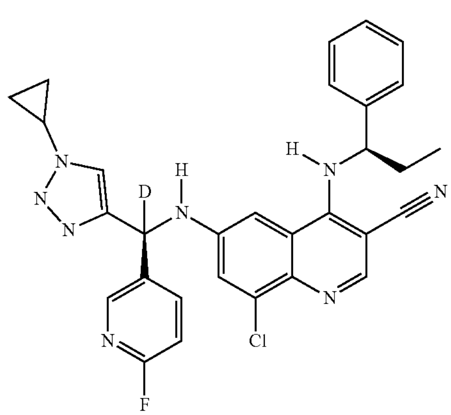 [SMILES: [2H][C@](Nc1cc(Cl)c2ncc(C#N)c(N[C@H](CC)c3ccccc3)c2c1)(C1=CN(C2CC2)NN1)c1ccc(F)nc1] | 8-chloro-6-(((S)-(1-cyclopropyl-1H-1,2,3-triazol-4-yl)(6-fluoropyridin-3-yl)methyl-d)amino)-4-(((R)-1-phenylpropyl)amino)quinoline-3-carbonitrile | 2 | ES/MS 554.1 (M + H+) |

TABLE 1-continued

| Comp | Structure | Name | Example Procedure | ES/MS m/z |
|---|---|---|---|---|
| 156 | 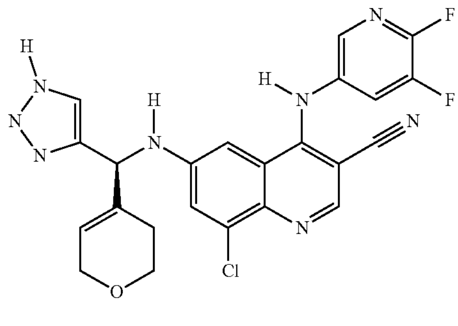 [SMILES: N#Cc1cnc2c(Cl)cc(N[C@@H](C3=CCOCC3)C3=CNNN3)cc2c1Nc1cnc(F)c(F)c1] | (S)-8-chloro-4-((5,6-difluoropyridin-3-yl)amino)-6-(((3,6-dihydro-2H-pyran-4-yl)(1H-1,2,3-triazol-4-yl)methyl)amino)quinoline-3-carbonitrile | 10 | ES/MS 495.1 (M + H+) |
| 157 | 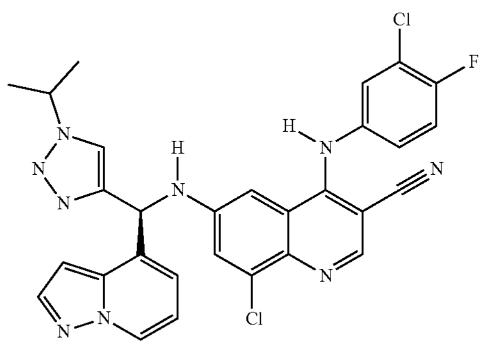 [SMILES: CC(C)N1C=C([C@@H](Nc2cc(Cl)c3ncc(C#N)c(Nc4ccc(F)c(Cl)c4)c3c2)c2cccn3nccc23)NN1] | (S)-8-chloro-4-((3-chloro-4-fluorophenyl)amino)-6-(((1-isopropyl-1H-1,2,3-triazol-4-yl)(pyrazolo[1,5-a]pyridin-4-yl)methyl)amino)-quinoline-3-carbonitrile | 2 | ES/MS 586.2 (M + H+) |
| 158 | 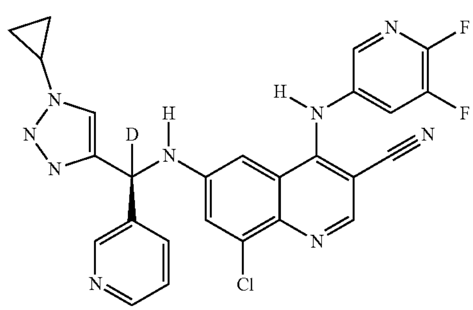 [SMILES: [2H][C@](Nc1cc(Cl)c2ncc(C#N)c(Nc3cnc(F)c(F)c3)c2c1)(C1=CN(C2CC2)NN1)c1cccnc1] | (S)-8-chloro-6-(((1-cyclopropyl-1H-1,2,3-triazol-4-yl)(pyridin-3-yl)methyl-d)amino)-4-((5,6-difluoropyridin-3-yl)amino)quinoline-3-carbonitrile | 2 | ES/MS 530.9 (M + H+) |
| 159 | 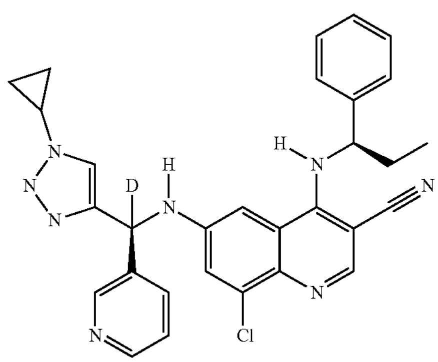 [SMILES: [2H][C@](Nc1cc(Cl)c2ncc(C#N)c(N[C@H](CC)c3ccccc3)c2c1)(C1=CN(C2CC2)NN1)c1cccnc1] | 8-chloro-6-(((S)-(1-cyclopropyl-1H-1,2,3-triazol-4-yl)(pyridin-3-yl)methyl-d)amino)-4-(((R)-1-phenyl propyl)amino)quinoline-3-carbonitrile | 2 | ES/MS 536.1 (M + H+) |

TABLE 1-continued

| Comp | Structure | Name | Example Procedure | ES/MS m/z |
|---|---|---|---|---|
| 160 | 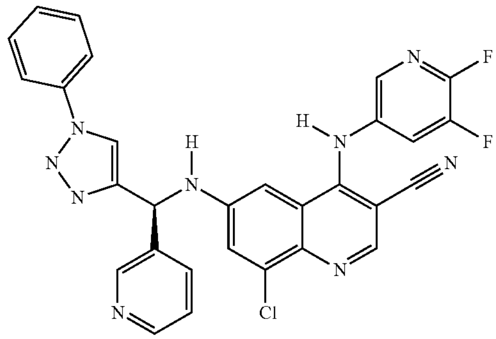 [SMILES: N#Cc1cnc2c(Cl)cc(N[C@H](C3=CN(c4ccccc4)NN3)c3cccnc3)cc2c1Nc1cnc(F)c(F)c1] | (S)-8-chloro-4-((5,6-difluoropyridin-3-yl)amino)-6-(((1-phenyl-1H-1,2,3-triazol-4-yl)(pyridin-3-yl)methyl)amino)quinoline-3-carbonitrile | 2 | ES/MS 565.9 (M + H+) |
| 161 | 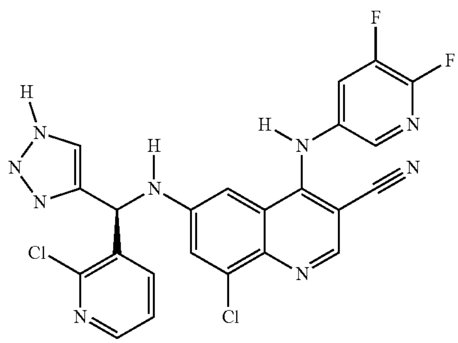 [SMILES: N#Cc1cnc2c(Cl)cc(N[C@H](C3=CNNN3)c3cccnc3Cl)cc2c1Nc1cnc(F)c(F)c1] | (S)-8-chloro-6-(((2-chloropyridin-3-yl)(1H-1,2,3-triazol-4-yl)methyl)amino)-4-((5,6-difluoropyridin-3-yl)amino)quinoline-3-carbonitrile | 10 | ES/MS 524.0 (M + H+) |
| 162 | 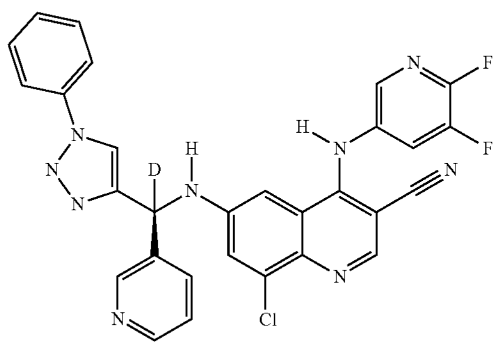 [SMILES: [2H][C@](Nc1cc(Cl)c2ncc(C#N)c(Nc3cnc(F)c(F)c3)c2c1)(C1=CN(c2ccccc2)NN1)c1cccnc1] | (S)-8-chloro-4-((5,6-difluoropyridin-3-yl)amino)-6-(((1-phenyl-1H-1,2,3-triazol-4-yl)(pyridin-3-yl)methyl-d)amino)quinoline-3-carbonitrile | 2 | ES/MS 567.1 (M + H+) |
| 163 | 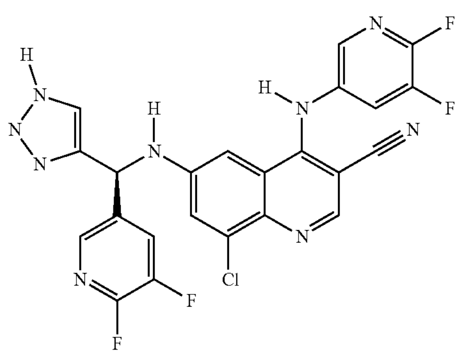 [SMILES: N#Cc1cnc2c(Cl)cc(N[C@H](C3=CNNN3)c3cnc(F)c(F)c3)cc2c1Nc1cnc(F)c(F)c1] | (S)-8-chloro-6-(((5,6-difluoropyridin-3-yl)(1H-1,2,3-triazol-4-yl)methyl)amino)-4-((5,6-difluoropyridin-3-yl)amino)quinoline-3-carbonitrile | 10 | ES/MS 526.0 (M + H+) |

TABLE 1-continued

| Comp | Structure | Name | Example Procedure | ES/MS m/z |
|---|---|---|---|---|
| 164 | 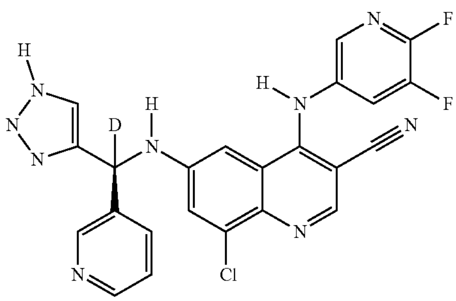 [SMILES: [2H][C@](Nc1cc(Cl)c2ncc(C#N)c(Nc3cnc(F)c(F)c3)c2c1)(C1=CNNN1)c1cccnc1] | (S)-8-chloro-4-((5,6-difluoropyridin-3-yl)amino)-6-((pyridin-3-yl(1H-1,2,3-triazol-4-yl)methyl-d)amino)quinoline-3-carbonitrile | 10 | ES/MS 491.1 (M + H+) |
| 165 | 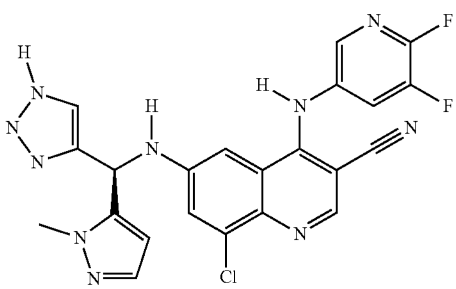 [SMILES: Cn1nccc1[C@H](Nc1cc(Cl)c2ncc(C#N)c(Nc3cnc(F)c(F)c3)c2c1)C1=CNNN1] | (S)-8-chloro-4-((5,6-difluoropyridin-3-yl)amino)-6-(((1-methyl-1H-pyrazol-5-yl)(1H-1,2,3-triazol-4-yl)methyl)amino)quinoline-3-carbonitrile | 10 | ES/MS 493.1 (M + H+) |
| 166 | 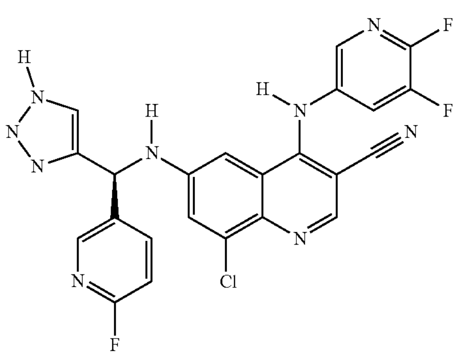 [SMILES: N#Cc1cnc2c(Cl)cc(N[C@H](C3=CNNN3)c3ccc(F)nc3)cc2c1Nc1cnc(F)c(F)c1] | (S)-8-chloro-4-((5,6-difluoropyridin-3-yl)amino)-6-(((6-fluoropyridin-3-yl)(1H-1,2,3-triazol-4-yl)methyl)amino)quinoline-3-carbonitrile | 10 | ES/MS 508.0 (M + H+) |
| 167 | 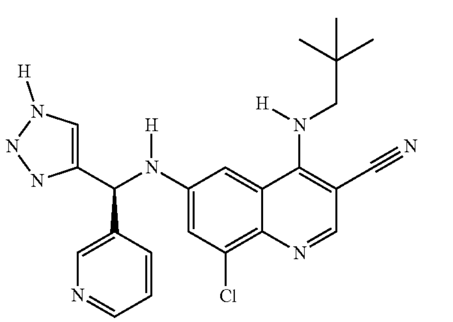 [SMILES: CC(C)(C)CNc1c(C#N)cnc2c(Cl)cc(N[C@H](C3=CNNN3)c3cccnc3)cc12] | (S)-8-chloro-4-(neopentylamino)-6-((pyridin-3-yl(1H-1,2,3-triazol-4-yl)methyl)amino)quinoline-3-carbonitrile | 10 | ES/MS 447.2 (M + H+) |

TABLE 1-continued

| Comp | Structure | Name | Example Procedure | ES/MS m/z |
|---|---|---|---|---|
| 168 | 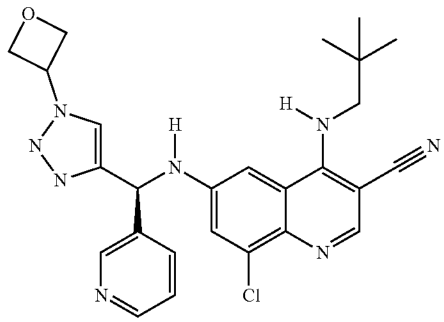 [SMILES: CC(C)(C)CNc1c(C#N)cnc2c(Cl)cc(N[C@H](C3=CN(C4COC4)NN3)c3cccnc3)cc12] | (S)-8-chloro-4-(neopentylamino)-6-(((1-(oxetan-3-yl)-1H-1,2,3-triazol-4-yl)(pyridin-3-yl)methyl)amino)quinoline-3-carbonitrile | 1 | ES/MS 503.2 (M + H+) |
| 169 | 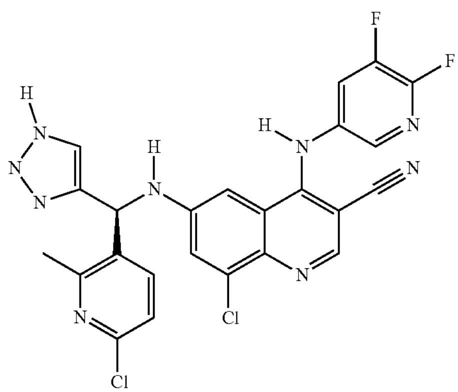 [SMILES: Cc1nc(Cl)ccc1[C@H](Nc1cc(Cl)c2ncc(C#N)c(Nc3cnc(F)c(F)c3)c2c1)C1=CNNN1] | (S)-8-chloro-6-((((6-chloro-2-methylpyridin-3-yl)(1H-1,2,3-triazol-4-yl)methyl)amino)-4-((5,6-difluoropyridin-3-yl)amino)quinoline-3-carbonitrile | 10 | ES/MS 538.1 (M + H+) |
| 170 | 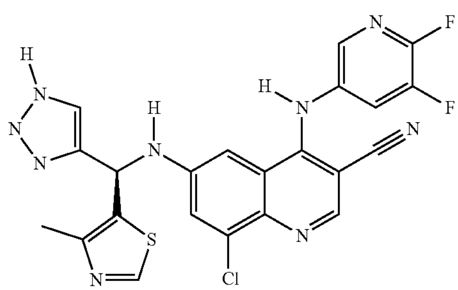 [SMILES: Cc1ncsc1[C@H](Nc1cc(Cl)c2ncc(C#N)c(Nc3cnc(F)c(F)c3)c2c1)C1=CNNN1] | (R)-8-chloro-4-((5,6-difluoropyridin-3-yl)amino)-6-(((4-methylthiazol-5-yl)(1H-1,2,3-triazol-4-yl)methyl)amino)quinoline-3-carbonitrile | 10 | ES/MS 510.0 (M + H+) |
| 171 | 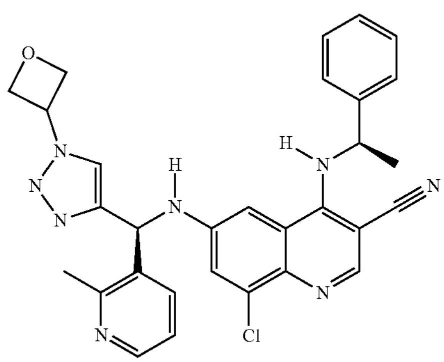 [SMILES: Cc1ncccc1[C@H](Nc1cc(Cl)c2ncc(C#N)c(N[C@H](C)c3ccccc3)c2c1)C1=CN(C2COC2)NN1] | 8-chloro-6-(((S)-(2-methylpyridin-3-yl)(1-(oxetan-3-yl)-1H-1,2,3-triazol-4-yl)methyl)amino)-4-(((R)-1-phenylethyl)amino)quinoline-3-carbonitrile | 2 | ES/MS 551.1 (M + H+) |

TABLE 1-continued

| Comp | Structure | Name | Example Procedure | ES/MS m/z |
|---|---|---|---|---|
| 172 | 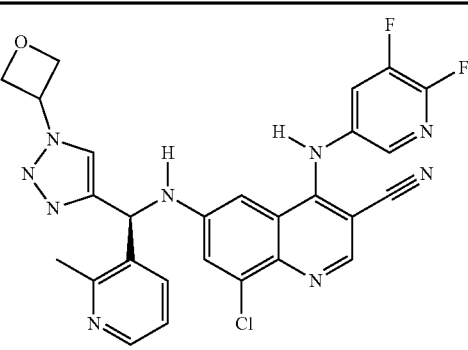 | (S)-8-chloro-4-((5,6-difluoropyridin-3-yl)amino)-6-(((2-methylpyridin-3-yl)(1-(oxetan-3-yl)-1H-1,2,3-triazol-4-yl)methyl)amino)quinoline-3-carbonitrile | 1 | ES/MS 560.0 (M + H+) |
| 173 | 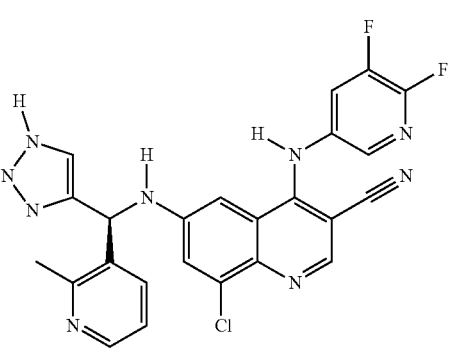 [SMILES: Cc1ncccc1[C@H](Nc1cc(Cl)c2ncc(C#N)c(Nc3cnc(F)c(F)c3)c2c1)C1=CNNN1] | (S)-8-chloro-4-((5,6-difluoropyridin-3-yl)amino)-6-(((2-methylpyridin-3-yl)(1H-1,2,3-triazol-4-yl)methyl)amino)quinoline-3-carbonitrile | 10 | ES/MS 504.0 (M + H+) |
| 174 | 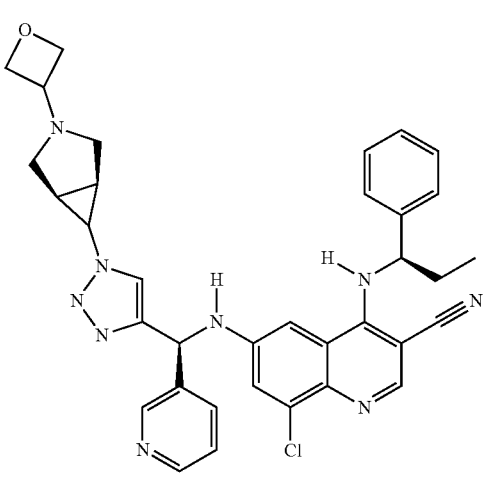 [SMILES: CC[C@@H](Nc1c(C#N)cnc2c(Cl)cc(N[C@H](C3=CN(C4[C@H]5CN(C6COC6)C[C@@H]45)NN3)c3cccnc3)cc12)c1ccccc1] | 8-chloro-6-(((S)-(1-((1R,5S,6s)-3-(oxetan-3-yl)-3-azabicyclo[3.1.0]hexan-6-yl)-1H-1,2,3-triazol-4-yl)(pyridin-3-yl)methyl)amino)-4-(((R)-1-phenylpropyl)amino)quinoline-3-carbonitrile | 4 | ES/MS 632.2 (M + H+) |
| 175 | 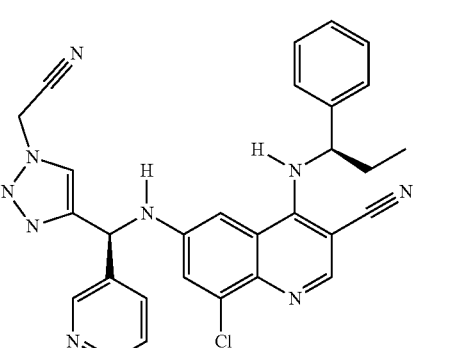 | 8-chloro-6-(((S)-(1-(cyanomethyl)-1H-1,2,3-triazol-4-yl)(pyridin-3-yl)methyl)amino)-4-(((R)-1-phenylpropyl)amino)quinoline-3-carbonitrile | 2 | ES/MS 534.1 (M + H+) |

TABLE 1-continued

| Comp | Structure | Name | Example Procedure | ES/MS m/z |
|---|---|---|---|---|
| 176 | 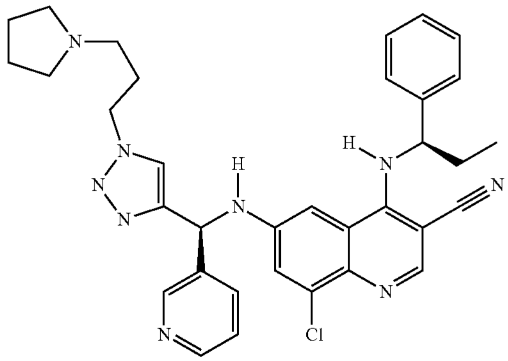 [SMILES: CC[C@@H](Nc1c(C#N)cnc2c(Cl)cc(N[C@H](C3=CN(CCCN4CCCC4)NN3)c3cccnc3)cc12)c1ccccc1] | 8-chloro-4-(((R)-1-phenylpropyl)amino)-6-(((S)-pyridin-3-yl(1-(3-(pyrrolidin-1-yl)propyl)-1H-1,2,3-triazol-4-yl)methyl)amino)quinoline-3-carbonitrile | 3 | ES/MS 606.3 (M + H+) |
| 177 | 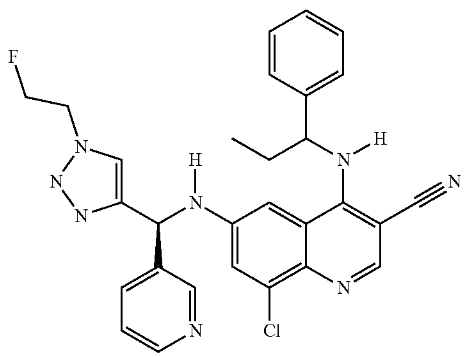 [SMILES: CCC(Nc1c(C#N)cnc2c(Cl)cc(N[C@H](C3=CN(CCF)NN3)c3cccnc3)cc12)c1ccccc1] | 8-chloro-6-(((S)-(1-(2-fluoroethyl)-1H-1,2,3-triazol-4-yl)(pyridin-3-yl)methyl)amino)-4-(((R)-1-phenylpropyl)amino)quinoline-3-carbonitrile | 1 | ES/MS 541.2 (M + H+) |
| 178 | 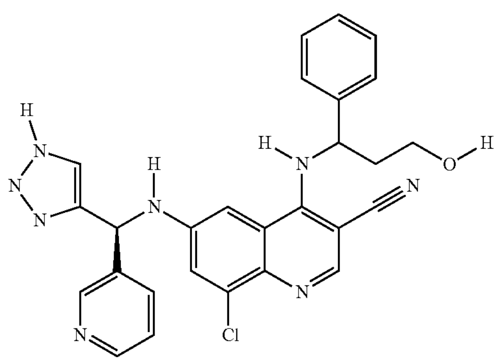 [SMILES: N#Cc1cnc2c(Cl)cc(N[C@H](C3=CNNN3)c3cccnc3)cc2c1NC(CCO)c1ccccc1] | 8-chloro-4-(((S)-3-hydroxy-1-phenyl propyl)amino)-6-(((S)-pyridin-3-yl(1H-1,2,3-triazol-4-yl)methyl)amino)quinoline-3-carbonitrile | 10 | ES/MS 511.1 (M + H+) |
| 179 | 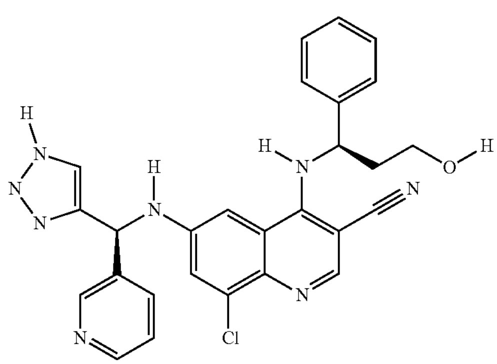 [SMILES: N#Cc1cnc2c(Cl)cc(N[C@H](C3=CNNN3)c3cccnc3)cc2c1N[C@H](CCO)c1ccccc1] | 8-chloro-4-(((R)-3-hydroxy-1-phenyl propyl)amino)-6-(((S)-pyridin-3-yl(1H-1,2,3-triazol-4-yl)methyl)amino)quinoline-3-carbonitrile | 10 | ES/MS 511.1 (M + H+) |

TABLE 1-continued

| Comp | Structure | Name | Example Procedure | ES/MS m/z |
|---|---|---|---|---|
| 180 | 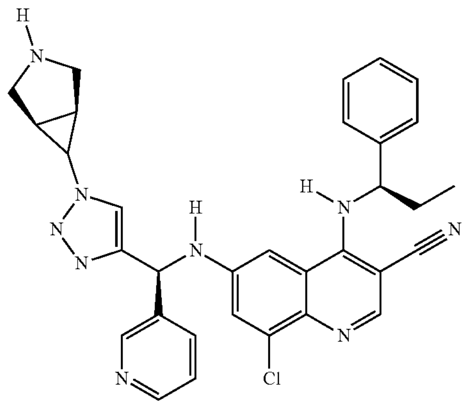 [SMILES: CC[C@@H](Nc1c(C#N)cnc2c(Cl)cc(N[C@H](C3=CN(C4[C@H]5CNC[C@@H]45)NN3)c3cccnc3)cc12)c1ccccc1] | 6-(((S)-(1-((•R,5S,6s)-3-azabicyclo[3.1.0]hexan-6-yl)-1H-1,2,3-triazol-4-yl)(pyridin-3-yl)methyl)amino)-8-chloro-4-(((R)-1-phenyl propyl)amino)-quinoline-3-carbonitrile | 4 | ES/MS 576.2 (M + H+) |
| 181 | 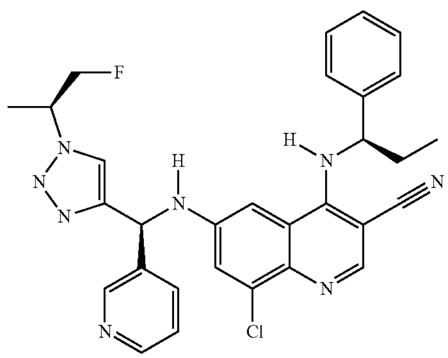 [SMILES: CC[C@@H](Nc1c(C#N)cnc2c(Cl)cc(N[C@H](C3=CN([C@@H](C)CF)NN3)c3cccnc3)cc12)c1ccccc1] | 8-chloro-6-(((S)-(1-((S)-1-fluoropropan-2-yl)-1H-1,2,3-triazol-4-yl)(pyridin-3-yl)methyl)amino)-4-(((R)-1-phenylpropyl)amino)quinoline-3-carbonitrile | 4 | ES/MS 555.1 (M + H+) |
| 182 | 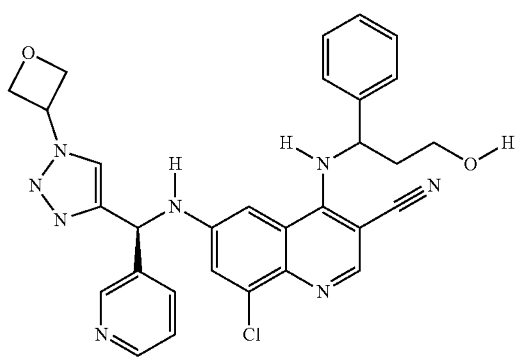 [SMILES: N#Cc1cnc2c(Cl)cc(N[C@H](C3=CN(C4COC4)NN3)c3cccnc3)cc2c1NC(CCO)c1ccccc1] | 8-chloro-4-(((S)-3-hydroxy-1-phenylpropyl)amino)-6-(((S)-(1-(oxetan-3-yl)-1H-1,2,3-triazol-4-yl)(pyridin-3-yl)methyl)amino)quinoline-3-carbonitrile | 2 | ES/MS 567.1 (M + H+) |
| 183 | 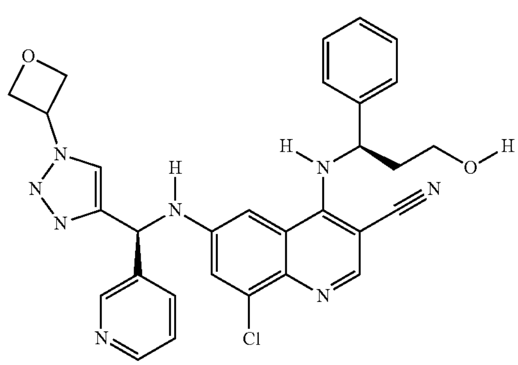 [SMILES: N#Cc1cnc2c(Cl)cc(N[C@H](C3=CN(C4COC4)NN3)c3cccnc3)cc2c1N[C@H](CCO)c1ccccc1] | 8-chloro-4-(((R)-3-hydroxy-1-phenylpropyl)amino)-6-(((S)-(1-(oxetan-3-yl)-1H-1,2,3-triazol-4-yl)(pyridin-3-l)methyl)amino)-quinoline-3-carbonitrile | 2 | ES/MS 567.1 (M + H+) |

TABLE 1-continued

| Comp | Structure | Name | Example Procedure | ES/MS m/z |
|---|---|---|---|---|
| 184 | 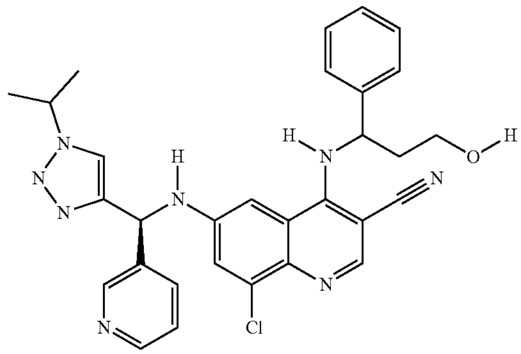 [SMILES: CC(C)N1C=C([C@@H](Nc2cc(Cl)c3ncc(C#N)c(NC(CCO)c4ccccc4)c3c2)c2cccnc2)NN1] | 8-chloro-4-(((S)-3-hydroxy-1-phenylpropyl)amino)-6-(((S)-(1-isopropyl-1H-1,2,3-triazol-4-yl)(pyridin-3-l)methyl)amino)-quinoline-3-carbonitrile | 2 | ES/MS 553.1 (M + H+) |
| 185 | 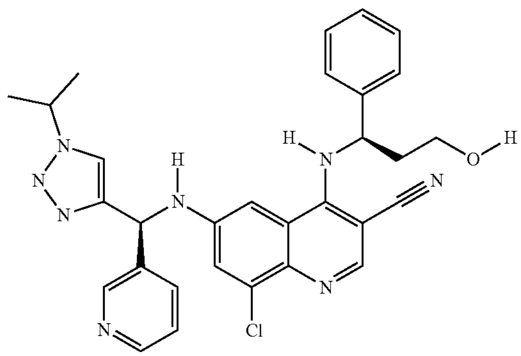 [SMILES: CC(C)N1C=C([C@@H](Nc2cc(Cl)c3ncc(C#N)c(N[C@H](CCO)c4ccccc4)c3c2)c2cccnc2)NN1] | 8-chloro-4-(((R)-3-hydroxy-1-phenylpropyl)amino)-6-(((S)-(1-isopropyl-1H-1,2,3-triazol-4-yl)(pyridin-3-yl)methyl)amino)quinoline-3-carbonitrile | 2 | ES/MS 553.1 (M + H+) |
| 186 | 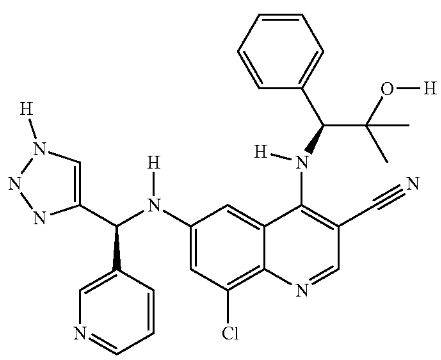 [SMILES: CC(C)(O)[C@@H](Nc1c(C#N)cnc2c(Cl)cc(N[C@H](C3=CNNN3)c3cccnc3)cc12)c1ccccc1] | 8-chloro-4-(((S)-2-hydroxy-2-methyl-1-phenylpropyl)amino)-6-(((S)-pyridin-3-yl(1H-1,2,3-triazol-4-yl)methyl)amino)quinoline-3-carbonitrile | 10 | ES/MS 525.1 (M + H+) |
| 187 | 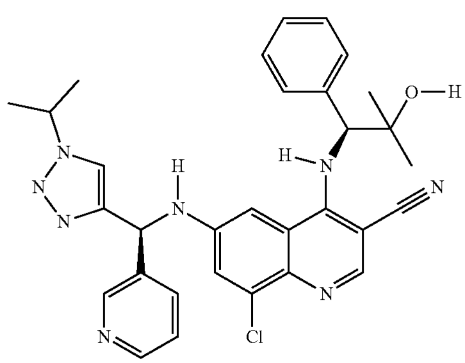 [SMILES: CC(C)N1C=C([C@@H](Nc2cc(Cl)c3ncc(C#N)c(N[C@@H](c4ccccc4)C(C)(C)O)c3c2)c2cccnc2)NN1] | 8-chloro-4-(((S)-2-hydroxy-2-methyl-1-phenylpropyl)amino)-6-(((S)-(1-isopropyl-1H-1,2,3-triazol-4-yl)(pyridin-3-yl)methyl)amino)-quinoline-3-carbonitrile | 2 | ES/MS 567.1 (M + H+) |

TABLE 1-continued

| Comp | Structure | Name | Example Procedure | ES/MS m/z |
|---|---|---|---|---|
| 188 | 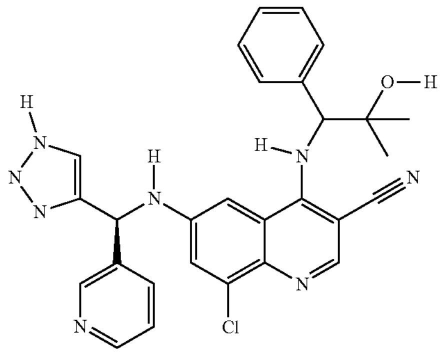 [SMILES: CC(C)(O)C(Nc1c(C#N)cnc2c(Cl)cc(N[C@H](C3=CNNN3)c3cccnc3)cc12)c1ccccc1] | 8-chloro-4-(((R)-2-hydroxy-2-methyl-1-phenylpropyl)amino)-6-(((S)-pyridin-3-yl(1H-1,2,3-triazol-4-yl)methyl)amino)quinoline-3-carbonitrile | 10 | ES/MS 525.1 (M + H+) |
| 189 | 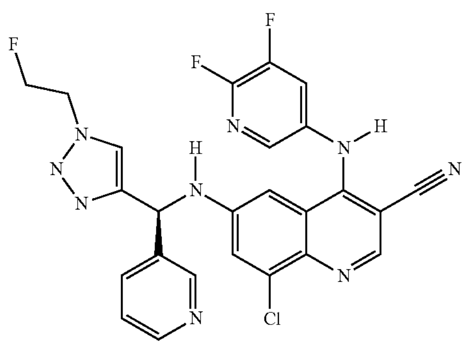 [SMILES: N#Cc1cnc2c(Cl)cc(N[C@H](C3=CN(CCF)NN3)c3cccnc3)cc2c1Nc1cnc(F)c(F)c1] | (S)-8-chloro-4-((5,6-difluoropyridin-3-yl)amino)-6-(((1-(2-fluoroethyl)-1H-1,2,3-triazol-4-yl)(pyridin-3-yl)methyl)amino)quinoline-3-carbonitrile | 1 | ES/MS 536.1 (M + H+) |
| 190 | 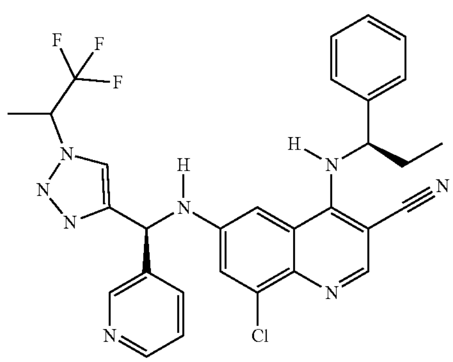 [SMILES: CC[C@@H](Nc1c(C#N)cnc2c(Cl)cc(N[C@H](C3=CN(C(C)C(F)(F)F)NN3)c3cccnc3)cc12)c1ccccc1] | 8-chloro-4-(((R)-1-phenylpropyl)amino)-6-(((S)-pyridin-3-yl (1-((R)-1,1,1-trifluoropropan-2-yl)-1H-1,2,3-triazol-4-yl)methyl)amino)quinoline-3-carbonitrile | 4 | ES/MS 591.1 (M + H+) |
| 191 | 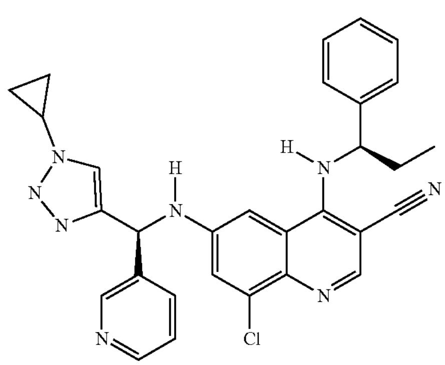 [SMILES: CC[C@@H](Nc1c(C#N)cnc2c(Cl)cc(N[C@H](C3=CN(C4CC4)NN3)c3cccnc3)cc12)c1ccccc1] | 8-chloro-6-(((S)-(1-cyclopropyl-1H-1,2,3-triazol-4-yl)(pyridin-3-yl)methyl)amino)-4-(((R)-1-phenylpropyl)amino)quinoline-3-carbonitrile | 4 | ES/MS 535.1 (M + H+) |

TABLE 1-continued

| Comp | Structure | Name | Example Procedure | ES/MS m/z |
|---|---|---|---|---|
| 192 | 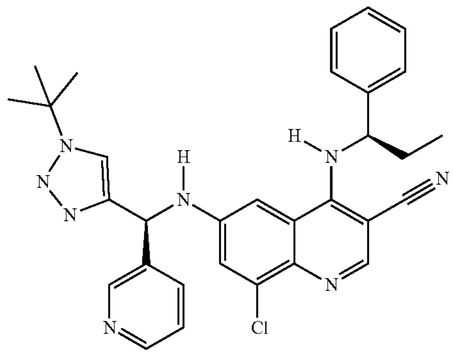 [SMILES: CC[C@@H](Nc1c(C#N)cnc2c(Cl)cc(N[C@H](C3=CN(C(C)(C)C)NN3)c3cccnc3)cc12)c1ccccc1] | 6-(((S)-(1-(tert-butyl)-1H-1,2,3-triazol-4-yl)(pyridin-3-yl)methyl)amino)-8-chloro-4-(((R)-1-phenylpropyl)arnino)quinoline-3-carbonitrile | 2 | ES/MS 551.2 (M + H+) |
| 193 | 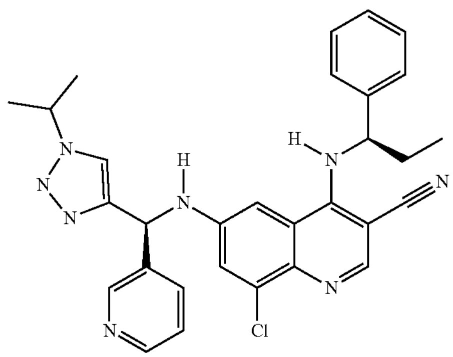 [SMILES: CC[C@@H](Nc1c(C#N)cnc2c(Cl)cc(N[C@H](C3=CN(C(C)C)NN3)c3cccnc3)cc12)c1ccccc1] | 8-chloro-6-(((S)-(1-isopropyl-1H-1,2,3-triazol-4-yl)(pyridin-3-yl)methyl)amino)-4-(((R)-1-phenyl propyl)amino)quinoline-3-carbonitrile | 2 | ES/MS 537.1 (M + H+) |
| 194 | 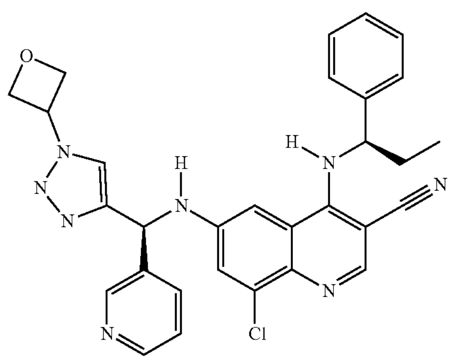 [SMILES: CC[C@@H](Nc1c(C#N)cnc2c(Cl)cc(N[C@H](C3=CN(C4COC4)NN3)c3cccnc3)cc12)c1ccccc1] | 8-chloro-6-(((S)-(1-(oxetan-3-yl)-1H-1,2,3-triazol-4-yl)(pyridin-3-yl)methyl)amino)-4-(((R)-1-phenyl propyl)amino)quinoline-3-carbonitrile | 2 | ES/MS 551.1 (M + H+) |
| 195 | 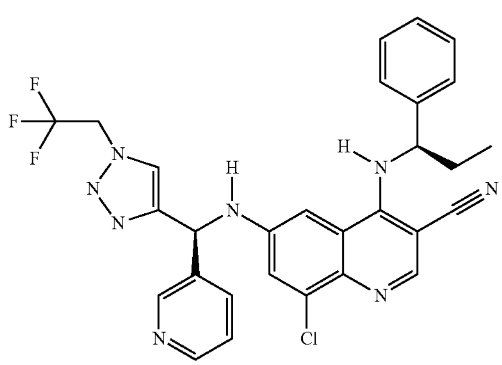 [SMILES: CC[C@@H](Nc1c(C#N)cnc2c(Cl)cc(N[C@H](C3=CN(CC(F)(F)F)NN3)c3cccnc3)cc12)c1ccccc1] | 8-chloro-4-(((R)-1-phenyl propyl)amino)-6-(((S)-pyridin-3-yl(1-(2,2,2-trifluoroethyl)-1H-1,2,3-triazol-4-yl)methyl)amino)quinoline-3-carbonitrile | 2 | ES/MS 577.1 (M + H+) |

TABLE 1-continued

| Comp | Structure | Name | Example Procedure | ES/MS m/z |
|---|---|---|---|---|
| 196 | 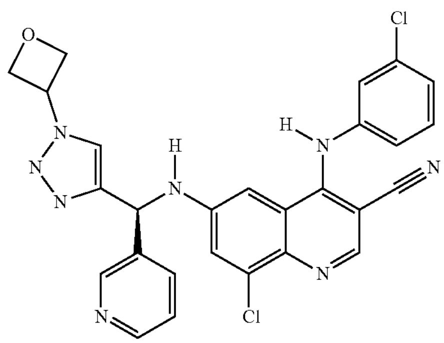 [SMILES: N#Cc1cnc2c(Cl)cc(N[C@H](C3=CN(C4COC4)NN3)c3cccnc3)cc2c1Nc1cccc(Cl)c1] | (S)-8-chloro-4-((3-chlorophenyl)amino)-6-(((1-(oxetan-3-yl)-1H-1,2,3-triazol-4-yl)(pyridin-3-yl)methyl)amino)quinoline-3-carbonitrile | 2 | ES/MS 543.1 (M + H+) |
| 197 | 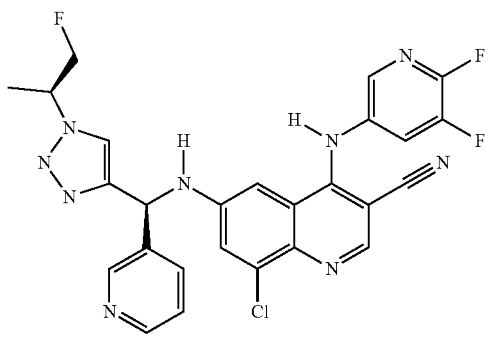 [SMILES: C[C@@H](CF)N1C=C([C@@H](Nc2cc(Cl)c3ncc(C#N)c(Nc4cnc(F)c(F)c4)c3c2)c2cccnc2)NN1] | 8-chloro-4-((5,6-difluoropyridin-3-yl)amino)-6-(((S)-(1-((S)-1-fluoropropan-2-yl)-1H-1,2,3-triazol-4-yl)(pyridin-3-yl)methyl)amino)quinoline-3-carbonitrile | 4 | ES/MS 549.9 (M + H+) |
| 198 | 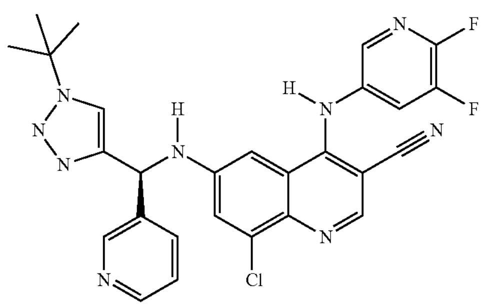 [SMILES: CC(C)(C)N1C=C([C@@H](Nc2cc(Cl)c3ncc(C#N)c(Nc4cnc(F)c(F)c4)c3c2)c2cccnc2)NN1] | (S)-6-(((1-(tert-butyl)-1H-1,2,3-triazol-4-yl)(pyridin-3-yl)methyl)amino)-8-chloro-4-((5,6-difluoropyridin-3-yl)amino)quinoline-3-carbonitrile | 8 | ES/MS 546.2 (M + H+) |
| 199 | 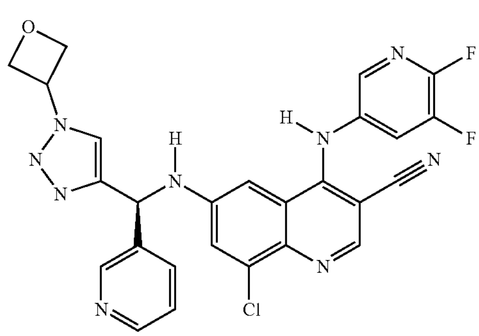 [SMILES: N#Cc1cnc2c(Cl)cc(N[C@H](C3=CN(C4COC4)NN3)c3cccnc3)cc2c1Nc1cnc(F)c(F)c1] | (S)-8-chloro-4-((5,6-difluoropyridin-3-yl)amino)-6-(((1-(oxetan-3-yl)-1H-1,2,3-triazol-4-yl)(pyridin-3-yl)methyl)amino)quinoline-3-carbonitrile | 8 | ES/MS 546.1 (M + H+) |

TABLE 1-continued

| Comp | Structure | Name | Example Procedure | ES/MS m/z |
|---|---|---|---|---|
| 200 | 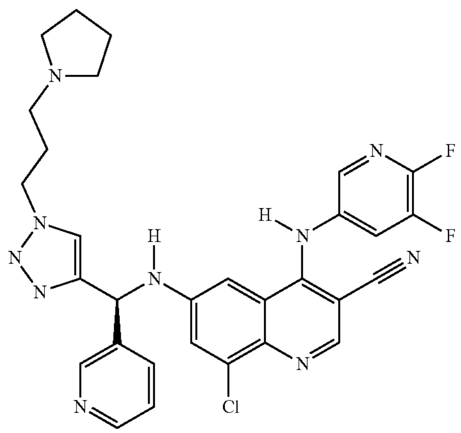 [SMILES: N#Cc1cnc2c(Cl)cc(N[C@H](C3=CN(CCCN4CCCC4)NN3)c3cccnc3)cc2c1Nc1cnc(F)c(F)c1] | (S)-8-chloro-4-((5,6-difluoropyridin-3-yl)amino)-6-((pyridin-3-yl(1-(3-(pyrrolidin-1-yl)propyl)-1H-1,2,3-triazol-4-yl)methyl)amino)quinoline-3-carbonitrile | 8 | ES/MS 601.2 (M + H+) |
| 201 | 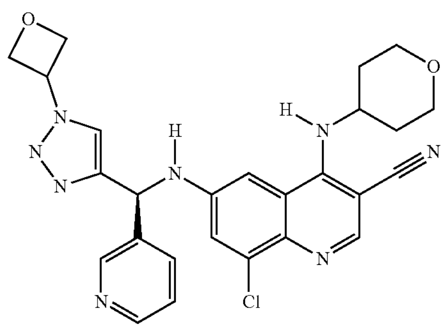 [SMILES: N#Cc1cnc2c(Cl)cc(N[C@H](C3=CN(C4COC4)NN3)c3cccnc3)cc2c1NC1CCOCC1] | (S)-8-chloro-6-(((1-(oxetan-3-yl)-1H-1,2,3-triazol-4-yl)(pyridin-3-yl)methyl)amino)-4-((tetrahydro-2H-pyran-4-yl)amino)quinoline-3-carbonitrile | 2 | ES/MS 517.1 (M + H+) |
| 202 | 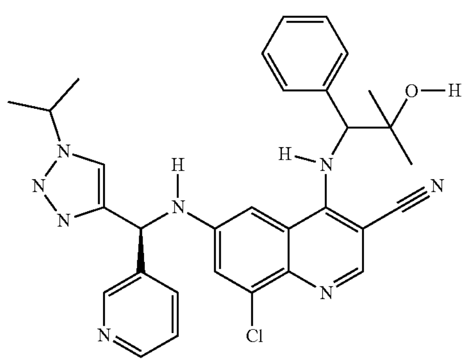 [SMILES: CC(C)N1C=C([C@@H](Nc2cc(Cl)c3ncc(C#N)c(NC(c4ccccc4)C(C)(C)O)c3c2)c2cccnc2)NN1] | 8-chloro-4-(((R)-2-hydroxy-2-methyl-1-phenylpropyl)amino)-6-(((S)-(1-isopropyl-1H-1,2,3-triazol-4-yl)(pyridin-3-yl)methyl)amino)quinoline-3-carbonitrile | 2 | ES/MS 567.2 (M + H+) |
| 203 | 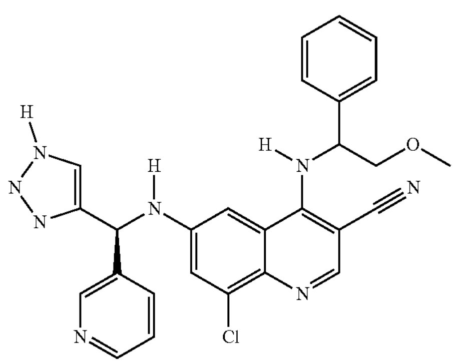 [SMILES: COCC(Nc1c(C#N)cnc2c(Cl)cc(N[C@H](C3=CNNN3)c3cccnc3)cc12)c1ccccc1] | 8-chloro-4-(((R)-2-methoxy-1-phenylethyl)amino)-6-(((S)-pyridin-3-yl(1H-1,2,3-triazol-4-yl)methyl)amino)quinoline-3-carbonitrile | 10 | ES/MS 511.0 (M + H+) |

TABLE 1-continued

| Comp | Structure | Name | Example Procedure | ES/MS m/z |
|---|---|---|---|---|
| 204 | 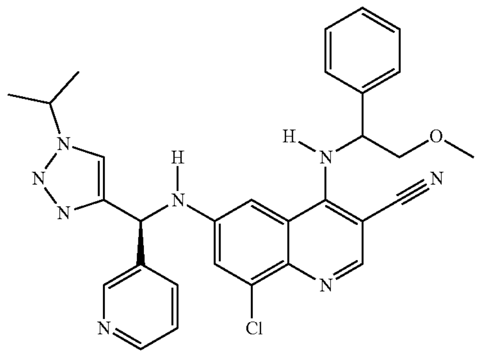 [SMILES: COCC(Nc1c(C#N)cnc2c(Cl)cc(N[C@H](C3=CN(C(C)C)NN3)c3cccnc3)cc12)c1ccccc1] | 8-chloro-6-(((S)-(1-isopropyl-1H-1,2,3-triazol-4-yl)(pyridin-3-yl)methyl)amino)-4-(((R)-2-methoxy-1-phenylethyl)amino)quinoline-3-carbonitrile | 2 | ES/MS 553.3 (M + H+) |
| 205 | 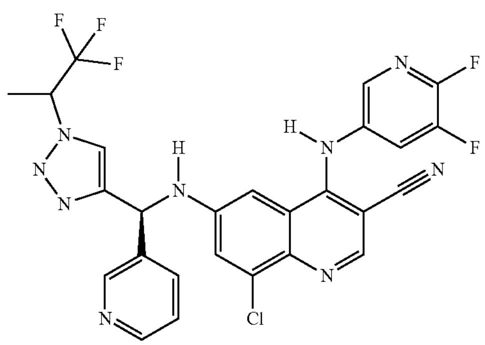 [SMILES: CC(N1C=C([C@@H](Nc2cc(Cl)c3ncc(C#N)c(Nc4cnc(F)c(F)c4)c3c2)c2cccnc2)NN1)C(F)(F)F] | 8-chloro-4-((5,6-difluoropyridin-3-yl)amino)-6-(((S)-pyridin-3-yl(1-((R)-1,1,1-trifluoropropan-2-yl)-1H-1,2,3-triazol-4-yl)methyl)amino)quinoline-3-carbonitrile | 4 | ES/MS 585.9 (M + H+) |
| 206 | 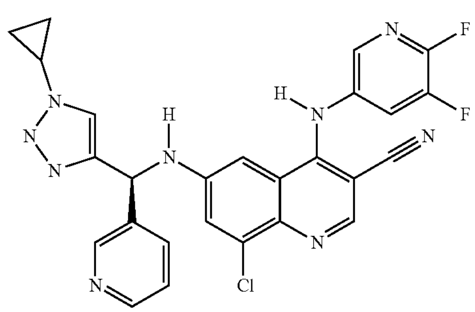 [SMILES: N#Cc1cnc2c(Cl)cc(N[C@H](C3=CN(C4CC4)NN3)c3cccnc3)cc2c1Nc1cnc(F)c(F)c1] | (S)-8-chloro-6-(((1-cyclopropyl-1H-1,2,3-triazol-4-yl)(pyridin-3-yl)methyl)amino)-4-((5,6-difluoropyridin-3-yl)amino)quinoline-3-carbonitrile | 2 | ES/MS 529.9 (M + H+) |
| 207 | 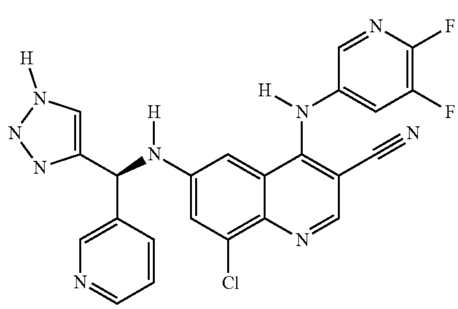 [SMILES: N#Cc1cnc2c(Cl)cc(N[C@H](C3=CNNN3)c3cccnc3)cc2c1Nc1cnc(F)c(F)c1] | (S)-8-chloro-4-((5,6-difluoropyridin-3-yl)amino)-6-((pyridin-3-yl(1H-1,2,3-triazol-4-yl)methyl)amino)quinoline-3-carbonitrile | 10 | ES/MS 490.1 (M + H+) |

TABLE 1-continued

| Comp | Structure | Name | Example Procedure | ES/MS m/z |
|---|---|---|---|---|
| 208 | 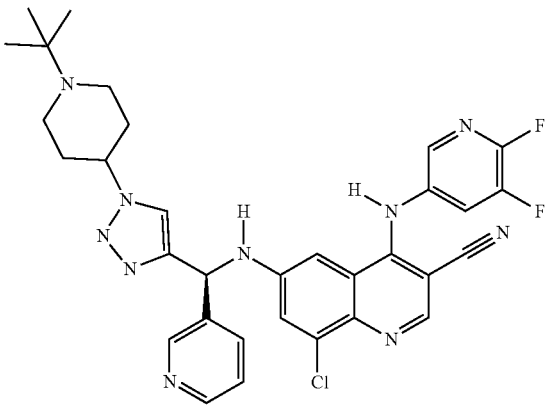 [SMILES: CC(C)(C)N1CCC(N2C=C([C@@H](Nc3cc(Cl)c4ncc(C#N)c(Nc5cnc(F)c(F)c5)c4c3)c3cccnc3)NN2)CC1] | (S)-6-(((H1-(tert-butyl)piperidin-4-yl)-1H-1,2,3-triazol-4-yl)(pyridin-3-yl)methyl)amino)-8-chloro-4-((5,6-difluoropyridin-3-yl)amino)quinoline-3-carbonitrile | 8 | ES/MS 629.3 (M + H+) |
| 209 | 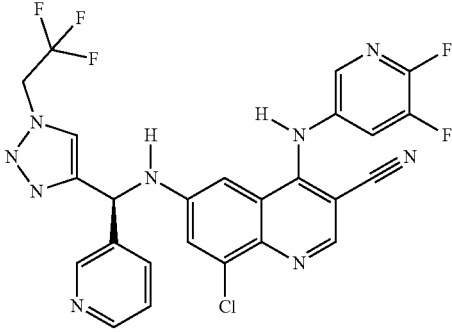 [SMILES: N#Cc1cnc2c(Cl)cc(N[C@H](C3=CN(CC(F)(F)F)NN3)c3cccnc3)cc2c1Nc1cnc(F)c(F)c1] | (S)-8-chloro-4-((5,6-difluoropyridin-3-yl)amino)-6-((pyridin-3-yl(1-(2,2,2-trifluoroethyl)-1H-1,2,3-triazol-4-yl)methyl)amino)quinoline-3-carbonitrile | 2 | ES/MS 572.0 (M + H+) |
| 210 | 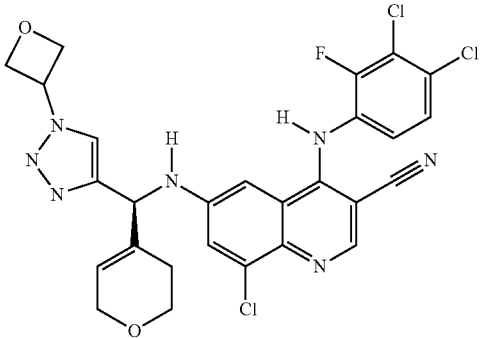 [SMILES: N#Cc1cnc2c(Cl)cc(N[C@@H](C3=CCOCC3)C3=CN(C4COC4)NN3)cc2c1Nc1ccc(Cl)c(Cl)c1F] | (S)-8-chloro-4-((3,4-dichloro-2-fluorophenyl)amino)-6-(((3,6-dihydro-2H-pyran-4-yl)(1-(oxetan-3-yl)-1H-1,2,3-triazol-4-yl)methyl)amino)quinoline-3-carbonitrile | 2 | ES/MS 599.8 (M + H+) |
| 211 | 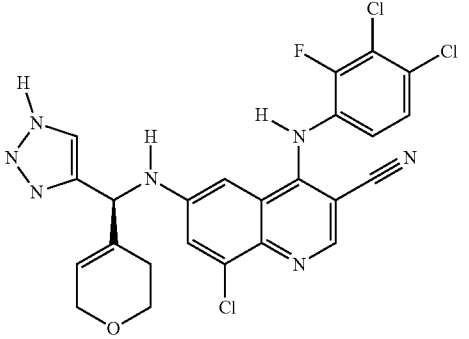 [SMILES: N#Cc1cnc2c(Cl)cc(N[C@@H](C3=CCOCC3)C3=CNNN3)cc2c1Nc1ccc(Cl)c(Cl)c1F] | (S)-8-chloro-4-((3,4-dichloro-2-fluorophenyl)amino)-6-(((3,6-dihydro-2H-pyran-4-yl)(1H-1,2,3-triazol-4-yl)methyl)amino)quinoline-3-carbonitrile | 10 | ES/MS 544.0 (M + H+) |

TABLE 1-continued

| Comp | Structure | Name | Example Procedure | ES/MS m/z |
|---|---|---|---|---|
| 212 | 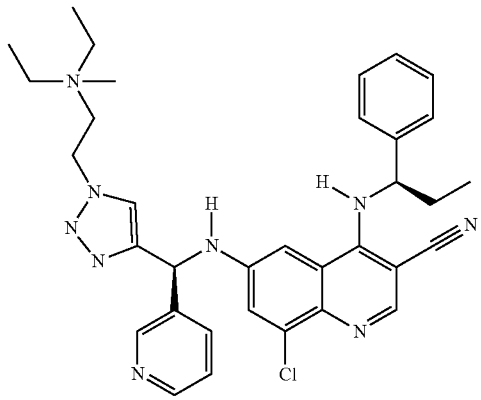 | 2-(4-((S)-((8-chloro-3-cyano-4-(((R)-1-phenylpropyl)amino)quinolin-6-yl)amino)(pyridin-3-yl)methyl)-1H-1,2,3-triazol-1-yl)-N,N-diethyl-N-methylethan-1-aminium | 1 | |
| 213 | 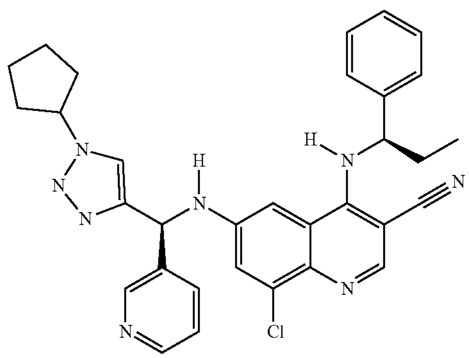 [SMILES: CC[C@@H](Nc1c(C#N)cnc2c(Cl)cc(N[C@H](C3=CN(C4CCCC4)NN3)c3cccnc3)cc12)c1ccccc1] | 8-chloro-6-(((S)-(1-cyclopentyl-1H-1,2,3-triazol-4-yl)(pyridin-3-yl)methyl)amino)-4-(((R)-1-phenylpropyl)amino)quinoline-3-carbonitrile | 1 | ES/MS 563.2 (M + H+) |
| 214 | 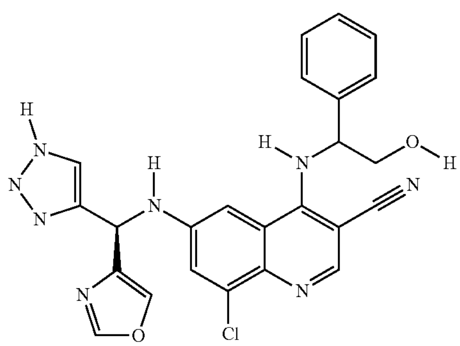 [SMILES: N#Cc1cnc2c(Cl)cc(N[C@H](C3=CNNN3)c3cocn3)cc2c1NC(CO)c1ccccc1] | 8-chloro-4-(((R)-2-hydroxy-1-phenylethyl)amino)-6-(((S)-o)(azol-4-yl(1H-1,2,3-triazol-4-yl)methyl)amino)quinoline-3-carbonitrile | 10 | ES/MS 487.1 (M + H+) |
| 215 | 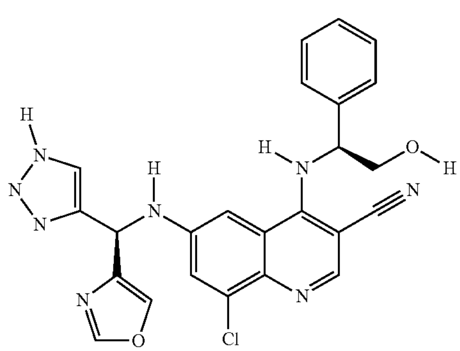 [SMILES: N#Cc1cnc2c(Cl)cc(N[C@H](C3=CNNN3)c3cocn3)cc2c1N[C@H](CO)c1ccccc1] | 8-chloro-4-(((S)-2-hydroxy-1-phenylethyl)amino)-6-(((S)-o)(azol-4-yl(1H-1,2,3-triazol-4-yl)methyl)amino)quinoline-3-carbonitrile | 10 | ES/MS 487.0 (M + H+) |

TABLE 1-continued

| Comp | Structure | Name | Example Procedure | ES/MS m/z |
|---|---|---|---|---|
| 216 | 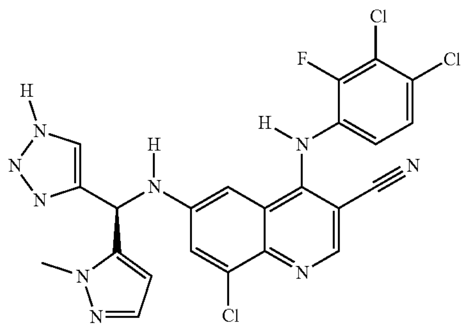 [SMILES: Cn1nccc1[C@H](Nc1cc(Cl)c2ncc(C#N)c(Nc3ccc(Cl)c(Cl)c3F)c2c1)C1=CNNN1] | (S)-8-chloro-4-((3,4-dichloro-2-fluorophenyl)amino)-6-(((1-methyl-1H-pyrazol-5-yl)(1H-1,2,3-triazol-4-yl)methyl)amino)quinoline-3-carbonitrile | 10 | ES/MS 542.0 (M + H+) |
| 217 | 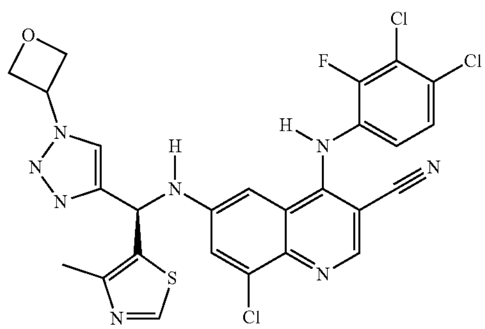 [SMILES: Cc1ncsc1[C@H](Nc1cc(Cl)c2ncc(C#N)c(Nc3ccc(Cl)c(Cl)c3F)c2c1)C1=CN(C2COC2)NN1] | (R)-8-chloro-4-((3,4-dichloro-2-fluorophenyl)amino)-6-(((4-methylthiazol-5-yl)(1-(oxetan-3-yl)-1H-1,2,3-triazol-4-yl)methyl)amino)quinoline-3-carbonitrile | 2 | ES/MS 614.8 (M + H+) |
| 218 | 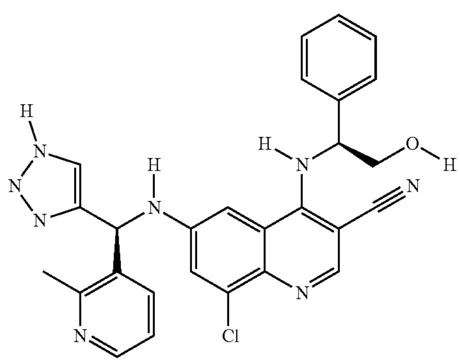 [SMILES: Cc1ncccc1[C@H](Nc1cc(Cl)c2ncc(C#N)c(N[C@H](CO)c3ccccc3)c2c1)C1=CNNN1] | 8-chloro-4-(((S)-2-hydroxy-1-phenylethyl)amino)-6-(((S)-(2-methylpyridin-3-yl)(1H-1,2,3-triazol-4-yl)methyl)amino)quinoline-3-carbonitrile | 10 | ES/MS 511.1 (M + H+) |
| 219 | 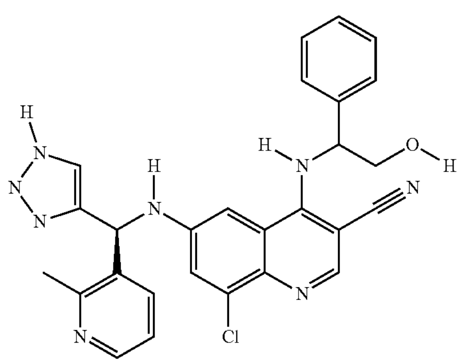 [SMILES: Cc1ncccc1[C@H](Nc1cc(Cl)c2ncc(C#N)c(NC(CO)c3ccccc3)c2c1)C1=CNNN1] | 8-chloro-4-(((R)-2-hydroxy-1-phenylethyl)amino)-6-(((S)-(2-methylpyridin-3-yl)(1H-1,2,3-triazol-4-yl)methyl)amino)quinoline-3-carbonitrile | 10 | ES/MS 511.1 (M + H+) |

TABLE 1-continued

| Comp | Structure | Name | Example Procedure | ES/MS m/z |
|---|---|---|---|---|
| 220 | 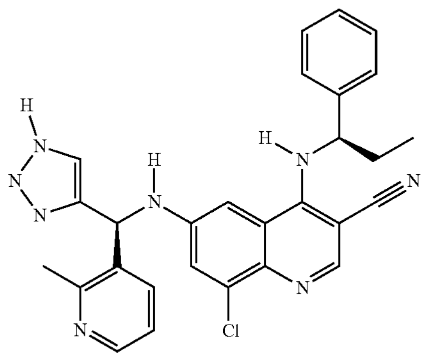 [SMILES: CC[C@@H](Nc1c(C#N)cnc2c(Cl)cc(N[C@H](C3=CNNN3)c3cccnc3C)cc12)c1ccccc1] | 8-chloro-6-(((S)-(2-methylpyridin-3-yl)(1H-1,2,3-triazol-4-yl)methyl)amino)-4-(((R)-1-phenylpropyl)amino)quinoline-3-carbonitrile | 10 | ES/MS 509.0 (M + H+) |
| 221 | 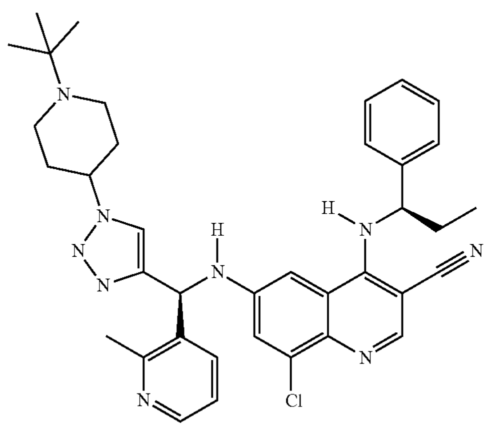 [SMILES: CC[C@@H](Nc1c(C#N)cnc2c(Cl)cc(N[C@H](C3=CN(C4CCN(C(C)(C)C)CC4)NN3)c3cccnc3C)cc12)c1ccccc1] | 6-(((S)-(1-(1-(tert-butyl)piperidin-4-yl)-1H-1,2,3-triazol-4-yl)(2-methylpyridin-3-yl)methyl)amino)-8-chloro-4-(((R)-1-phenylpropyl)amino)quinoline-3-carbonitrile | 2 | ES/MS 648.2 (M + H+) |
| 222 | 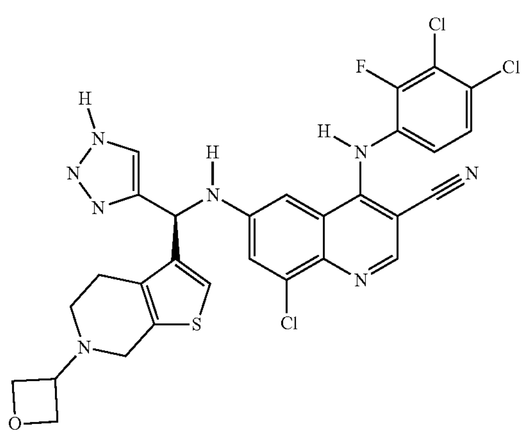 [SMILES: N#Cc1cnc2c(Cl)cc(N[C@H](C3=CNNN3)c3csc4c3CCN(C3COC3)C4)cc2c1Nc1ccc(Cl)c(Cl)c1F] | (S)-8-chloro-4-((3,4-dichloro-2-fluorophenyl)amino)-6-(((6-(oxetan-3-yl)-4,5,6,7-tetrahydrothieno[2,3-c]pyridin-3-yl)(1H-1,2,3-triazol-4-yl)methyl)amino)quinoline-3-carbonitrile | 10 | ES/MS 655.4 (M + H+) |

TABLE 1-continued

| Comp | Structure | Name | Example Procedure | ES/MS m/z |
|---|---|---|---|---|
| 223 | 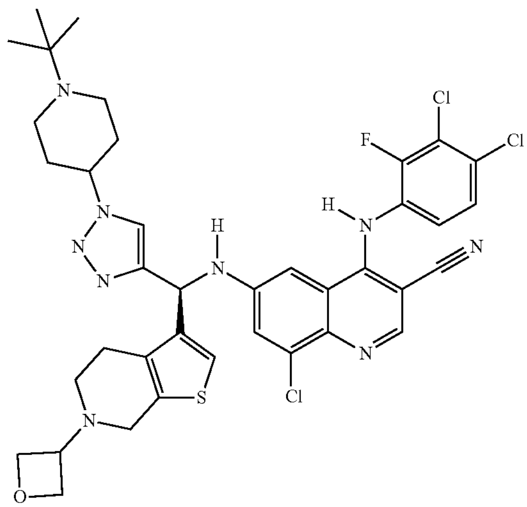 [SMILES: CC(C)(C)N1CCC(N2C=C([C@@H](Nc3cc(Cl)c4ncc(C#N)c(Nc5ccc(Cl)c(Cl)c5F)c4c3)c3csc4c3CCN(C3COC3)C4)NN2)CC1] | (S)-6-(((1-(1-(tert-butyl)piperidin-4-yl)-1H-1,2,3-triazol-4-yl)(6-(oxetan-3-yl)-4,5,6,7-tetrahydrothieno[2,3-c]pyridin-3-yl)methyl)amino)-8-chloro-4-((3,4-dichloro-2-fluorophenyl)amino)quinoline-3-carbonitrile | 5 | ES/MS 794.3 (M + H+) |
| 224 | 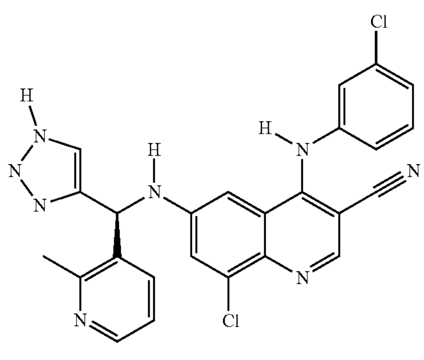 [SMILES: Cc1ncccc1[C@H](Nc1cc(Cl)c2ncc(C#N)c(Nc3cccc(Cl)c3)c2c1)C1=CNNN1] | (S)-8-chloro-4-((3-chlorophenyl)amino)-6-(((2-methylpyridin-3-yl)(1H-1,2,3-triazol-4-yl)methyl)amino)-quinoline-3-carbonitrile | 1 | ES/MS 501.0 (M + H+) |
| 225 | 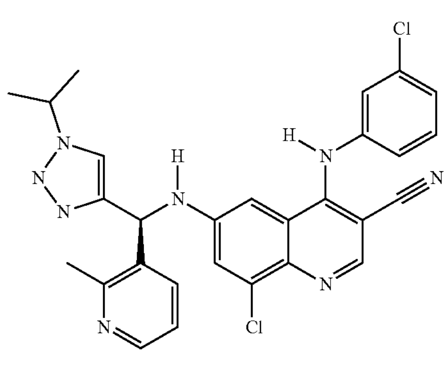 [SMILES: Cc1ncccc1[C@H](Nc1cc(Cl)c2ncc(C#N)c(Nc3cccc(Cl)c3)c2c1)C1=CN(C(C)C)NN1] | (S)-8-chloro-4-((3-chlorophenyl)amino)-6-(((1-isopropyl-1H-1,2,3-triazol-4-yl)(2-methylpyridin-3-yl)methyl)amino)quinoline-3-carbonitrile | 1 | ES/MS 543.1 (M + H+) |

TABLE 1-continued

| Comp | Structure | Name | Example Procedure | ES/MS m/z |
|---|---|---|---|---|
| 226 | 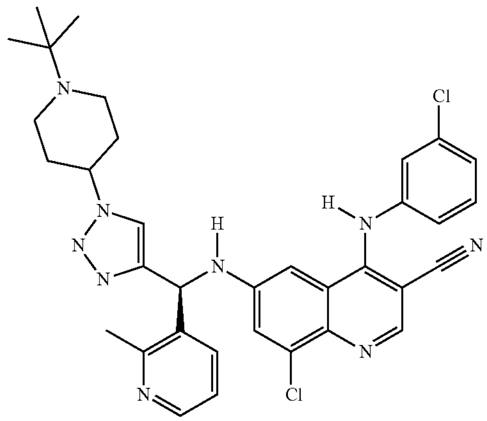 [SMILES: Cc1ncccc1[C@H](Nc1cc(Cl)c2ncc(C#N)c(Nc3cccc(Cl)c3)c2c1)C1=CN(C2CCN(C(C)(C)C)CC2)NN1] | (S)-6-(((1-(1-(tert-butyl)piperidin-4-yl)-1H-1,2,3-triazol-4-yl)(2-methylpyridin-3-yl)methyl)amino)-8-chloro-4-((3-chlorophenyl)amino)quinoline-3-carbonitrile | 1 | ES/MS 640.1 (M + H+) |
| 227 | 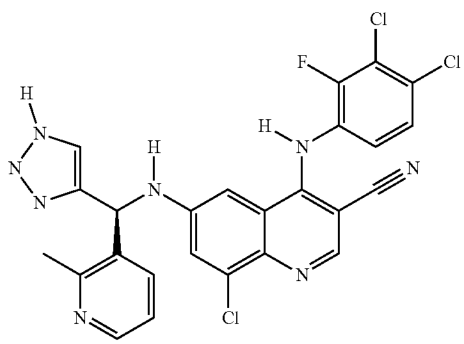 [SMILES: Cc1ncccc1[C@H](Nc1cc(Cl)c2ncc(C#N)c(Nc3ccc(Cl)c(Cl)c3F)c2c1)C1=CNNN1] | (S)-8-chloro-4-((3,4-dichloro-2-fluorophenyl)amino)-6-(((2-methylpyridin-3-yl)(1H-1,2,3-triazol-4-yl)methyl)amino)-quinoline-3-carbonitrile | 10 | ES/MS 553.0 (M + H+) |
| 228 | 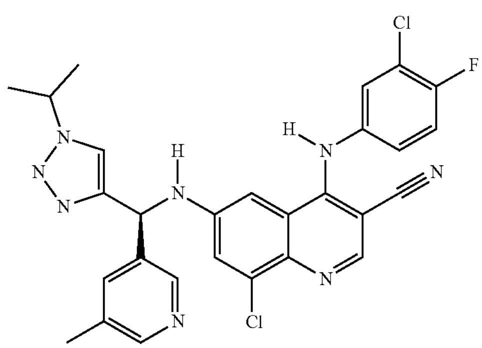 [SMILES: Cc1cncc([C@H](Nc2cc(Cl)c3ncc(C#N)c(Nc4ccc(F)c(Cl)c4)c3c2)C2=CN(C(C)C)NN2)c1] | (S)-8-chloro-4-((3-chloro-4-fluorophenyl)amino)-6-(((1-isopropyl-1H-1,2,3-triazol-4-yl)(5-methylpyridin-3-yl)methyl)amino)quinoline-3-carbonitrile | 1 | ES/MS 561.1 (M + H+) |
| 229 | 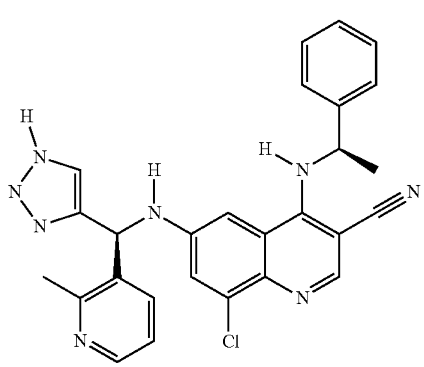 [SMILES: Cc1ncccc1[C@H](Nc1cc(Cl)c2ncc(C#N)c(N[C@H](C)c3ccccc3)c2c1)C1=CNNN1] | 8-chloro-6-(((S)-(2-methylpyridin-3-yl)(1H-1,2,3-triazol-4-yl)methyl)amino)-4-(((R)-1-phenylethyl)amino)quinoline-3-carbonitrile | 10 | ES/MS 495.0 (M + H+) |

TABLE 1-continued

| Comp | Structure | Name | Example Procedure | ES/MS m/z |
|---|---|---|---|---|
| 230 | 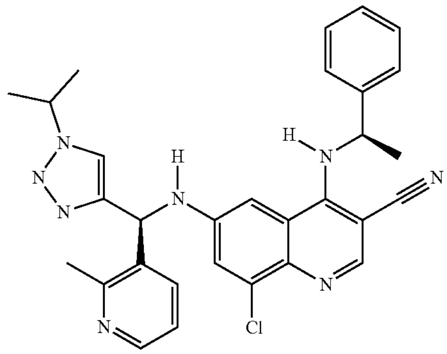 [SMILES: Cc1ncccc1[C@H](Nc1cc(Cl)c2ncc(C#N)c(N[C@H](C)c3ccccc3)c2c1)C1=CN(C(C)C)NN1] | 8-chloro-6-(((S)-(1-isopropyl-1H-1,2,3-triazol-4-yl)(2-methylpyridin-3-yl)methyl)amino)-4-(((R)-1-phenylethyl)amino)quinoline-3-carbonitrile | 2 | ES/MS 537.1 (M + H+) |
| 231 | 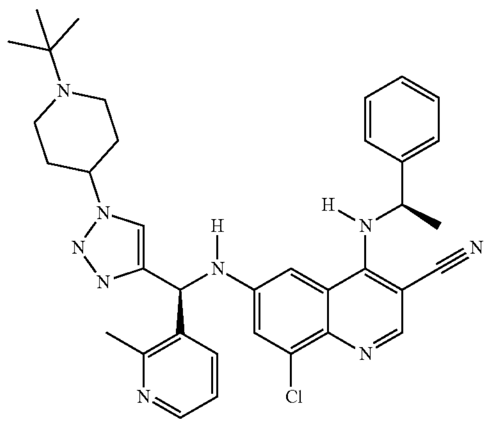 [SMILES: Cc1ncccc1[C@H](Nc1cc(Cl)c2ncc(C#N)c(N[C@H](C)c3ccccc3)c2c1)C1=CN(C2CCN(C(C)(C)C)CC2)NN1] | 6-(((S)-(1-(Mtert-butyl)piperidin-4-yl)-1H-1,2,3-triazol-4-yl)(2-methyl pyridin-3-yl)methyl)amino)-8-chloro-4-(((R)-1-phenylethyl)-amino)quinoline-3-carbonitrile | 2 | ES/MS 634.1 (M + H+) |
| 232 | 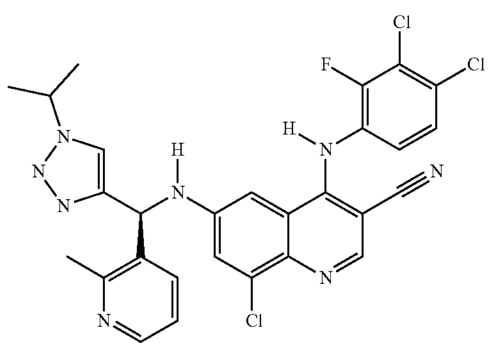 [SMILES: Cc1ncccc1[C@H](Nc1cc(Cl)c2ncc(C#N)c(Nc3ccc(Cl)c(Cl)c3F)c2c1)C1=CN(C(C)C)NN1] | (S)-8-chloro-4-((3,4-dichloro-2-fluorophenyl)amino)-6-(((1-isopropyl-1H-1,2,3-triazol-4-yl)(2-methylpyridin-3-yl)methyl)amino)quinoline-3-carbonitrile | 1 | ES/MS 595.0 (M + H+) |
| 233 | 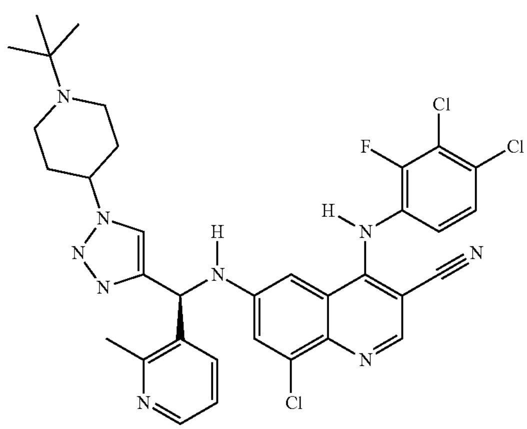 [SMILES: Cc1ncccc1[C@H](Nc1cc(Cl)c2ncc(C#N)c(Nc3ccc(Cl)c(Cl)c3F)c2c1)C1=CN(C2CCN(C(C)(C)C)CC2)NN1] | (S)-6-(((1-(1-(tert-butyl)piperidin-4-yl)-1H-1,2,3-triazol-4-yl)(2-methylpyridin-3-yl)methyl)amino)-8-chloro-4-((3,4-dichloro-2-fluorophenyl)amino)quinoline-3-carbonitrile | 1 | ES/MS 692.0 (M + H+) |

TABLE 1-continued

| Comp | Structure | Name | Example Procedure | ES/MS m/z |
|---|---|---|---|---|
| 234 | 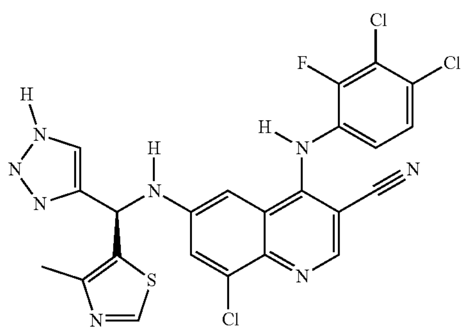 [SMILES: Cc1ncsc1[C@H](Nc1cc(Cl)c2ncc(C#N)c(Nc3ccc(Cl)c(Cl)c3F)c2c1)C1=CNNN1] | (R)-8-chloro-4-((3,4-dichloro-2-fluorophenyl)amino)-6-(((4-methylthiazol-5-yl)(1H-1,2,3-triazol-4-yl)methyl)amino)quinoline-3-carbonitrile | 10 | ES/MS 558.9 (M + H+) |
| 235 | 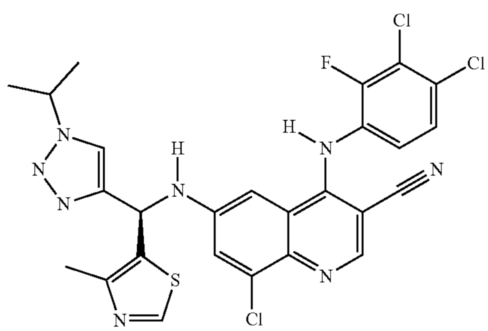 [SMILES: Cc1ncsc1[C@H](Nc1cc(Cl)c2ncc(C#N)c(Nc3ccc(Cl)c(Cl)c3F)c2c1)C1=CN(C(C)C)NN1] | (R)-8-chloro-4-((3,4-dichloro-2-fluorophenyl)amino)-6-(((1-isopropyl-1H-1,2,3-triazol-4-yl)(4-methylthiazol-5-yl)methyl)amino)quinoline-3-carbonitrile | 2 | ES/MS 600.8 (M + H+) |
| 236 | 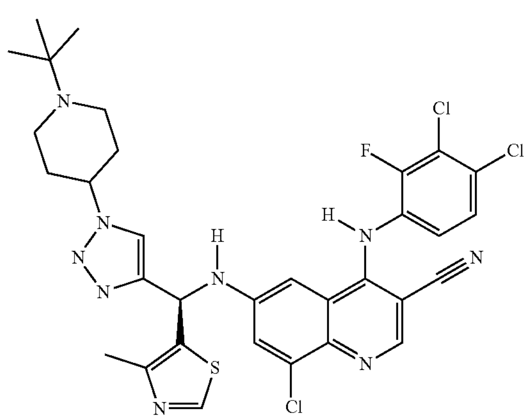 [SMILES: Cc1ncsc1[C@H](Nc1cc(Cl)c2ncc(C#N)c(Nc3ccc(Cl)c(Cl)c3F)c2c1)C1=CN(C2CCN(C(C)(C)C)CC2)NN1] | (R)-6-(((1-(1-(tert-butyl)piperidin-4-yl)-1H-1,2,3-triazol-4-yl)(4-methylthiazol-5-yl)methyl)amino)-8-chloro-4-((3,4-dichloro-2-fluorophenyl)amino)quinoline-3-carbonitrile | 2 | ES/MS 697.9 (M + H+) |

TABLE 1-continued

| Comp | Structure | Name | Example Procedure | ES/MS m/z |
|---|---|---|---|---|
| 237 | 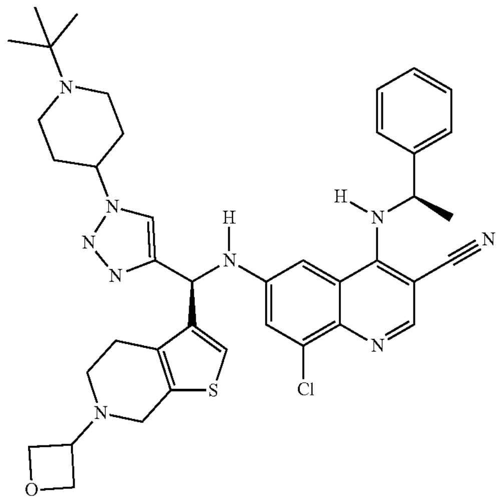 [SMILES: C[C@@H](Nc1c(C#N)cnc2c(Cl)cc(N[C@H](C3=CN(C4CCN(C(C)(C)C)CC4)NN3)c3csc4c3CCN(C3COC3)C4)cc12)c1ccccc1] | 6-(((SHHl-(tert-butyl)piperidin-4-yl)-1H-1,2,3-triazol-4-yl)(6-(oxetan-3-yl)-4,5,6,7-tetrahydrothieno[2,3-c]pyridin-3-yl)methyl)amino)-8-chloro-4-(((R)-1-phenylethyl)amino)quinoline-3-carbonitrile | 5 | ES/MS 736.2 (M + H+) |
| 238 | 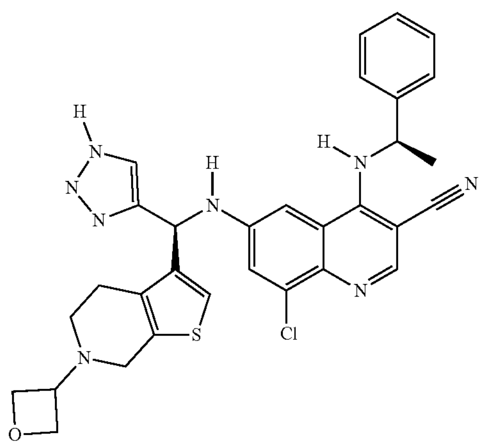 [SMILES: C[C@@H](Nc1c(C#N)cnc2c(Cl)cc(N[C@H](C3=CNNN3)c3csc4c3CCN(C3COC3)C4)cc12)c1ccccc1] | 8-chloro-6-(((S)-(6-(oxetan-3-yl)-4,5,6,7-tetrahydrothieno[2,3-c]pyridin-3-yl)(1H-1,2,3-triazol-4-yl)methyl)amino)-4-(((R)-1-phenylethyl)amino)quinoline-3-carbonitrile | 10 | ES/MS 597.1 (M + H+) |
| 239 | 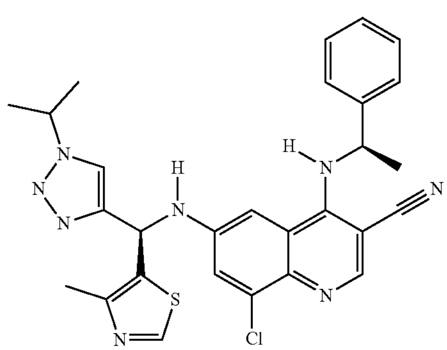 [SMILES: Cc1ncsc1[C@H](Nc1cc(Cl)c2ncc(C#N)c(N[C@H](C)c3ccccc3)c2c1)C1=CN(C(C)C)NN1] | 8-chloro-6-(((R)-(1-isopropyl-1H-1,2,3-triazol-4-yl)(4-methylthiazol-5-yl)methyl)amino)-4-(((R)-1-phenylethyl)amino)quinoline-3-carbonitrile | 2 | ES/MS 543.1 (M + H+) |

TABLE 1-continued

| Comp | Structure | Name | Example Procedure | ES/MS m/z |
|---|---|---|---|---|
| 240 | 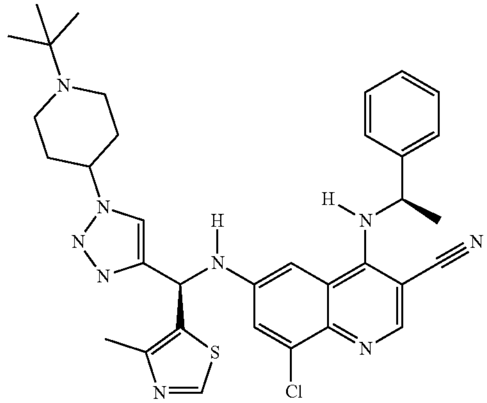 [SMILES: Cc1ncsc1[C@H](Nc1cc(Cl)c2ncc(C#N)c(N[C@H](C)c3ccccc3)c2c1)C1=CN(C2CCN(C(C)(C)C)CC2)NN1] | 6-(((R)-(1-(1-(tert-butyl)piperidin-4-yl)-1H-1,2,3-triazol-4-yl)(4-methylthiazol-5-yl)methyl)amino)-8-chloro-4-(((R)-1-phenylethyl)amino)quinoline-3-carbonitrile | 2 | ES/MS 640.1 (M + H+) |
| 241 | 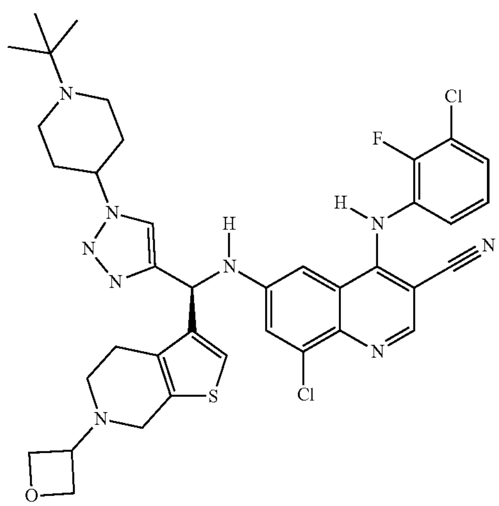 [SMILES: CC(C)(C)N1CCC(N2C=C([C@@H](Nc3cc(Cl)c4ncc(C#N)c(Nc5cccc(Cl)c5F)c4c3)c3csc4c3CCN(C3COC3)C4)NN2)CC1] | (S)-6-(((1-(1-(tert-butyl)piperidin-4-yl)-1H-1,2,3-triazol-4-yl)(6-(oxetan-3-yl)-4,5,6,7-tetrahydrothieno[2,3-c]pyridin-3-yl)methyl)amino)-8-chloro-4-((3-chloro-2-fluorophenyl)amino)-quinoline-3-carbonitrile | 5 | ES/MS 760.1 (M + H+) |
| 242 | 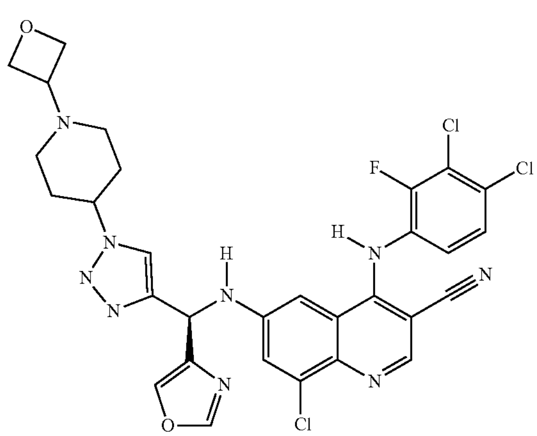 [SMILES: N#Cc1cnc2c(Cl)cc(N[C@H](C3=CN(C4CCN(C5COC5)CC4)NN3)c3cocn3)cc2c1Nc1ccc(Cl)c(Cl)c1F] | (S)-8-chloro-4-((3,4-dichloro-2-fluorophenyl)amino)-6-((o)(azol-4-yl(1-(1-(oxetan-3-yl)piperidin-4-yl)-1H-1,2,3-triazol-4-yl)methyl)amino)quinoline-3-carbonitrile | 5 | ES/MS 668.0 (M + H+) |

TABLE 1-continued

| Comp | Structure | Name | Example Procedure | ES/MS m/z |
|---|---|---|---|---|
| 243 | 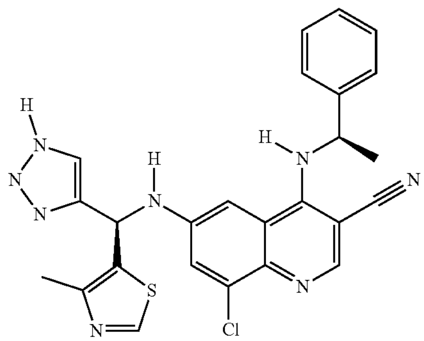 [SMILES: Cc1ncsc1[C@H](Nc1cc(Cl)c2ncc(C#N)c(N[C@H](C)c3ccccc3)c2c1)C1=CNNN1] | 8-chloro-6-(((R)-(4-methylthiazol-5-yl)(1H-1,2,3-triazol-4-yl)methyl)amino)-4-(((R)-1-phenylethyl)amino)quinoline-3-carbonitrile | 10 | ES/MS 501.0 (M + H+) |
| 244 | 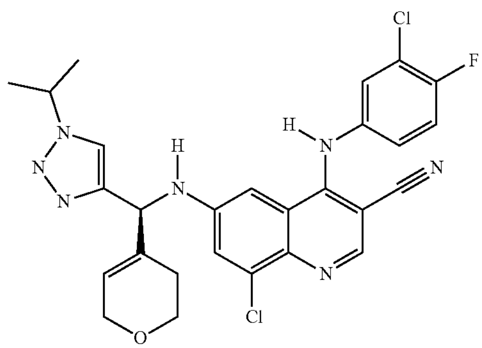 [SMILES: CC(C)N1C=C([C@@H](Nc2cc(Cl)c3ncc(C#N)c(Nc4ccc(F)c(Cl)c4)c3c2)C2=CCOCC2)NN1] | (S)-8-chloro-4-((3-chloro-4-fluorophenyl)amino)-6-(((3,6-dihydro-2H-pyran-4-yl)(1-isopropyl-1H-1,2,3-triazol-4-yl)methyl)amino)quinoline-3-carbonitrile | 2 | ES/MS 551.9 (M + H+) |
| 245 | 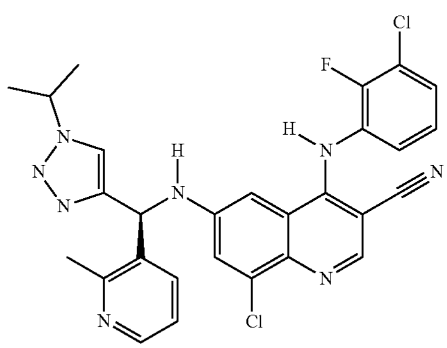 [SMILES: Cc1ncccc1[C@H](Nc1cc(Cl)c2ncc(C#N)c(Nc3cccc(Cl)c3F)c2c1)C1=CN(C(C)C)NN1] | (S)-8-chloro-4-((3-chloro-2-fluorophenyl)amino)-6-(((1-isopropyl-1H-1,2,3-triazol-4-yl)(2-methylpyridin-3-yl)methyl)amino)quinoline-3-carbonitrile | 1 | ES/MS 561.2 (M + H+) |
| 246 | 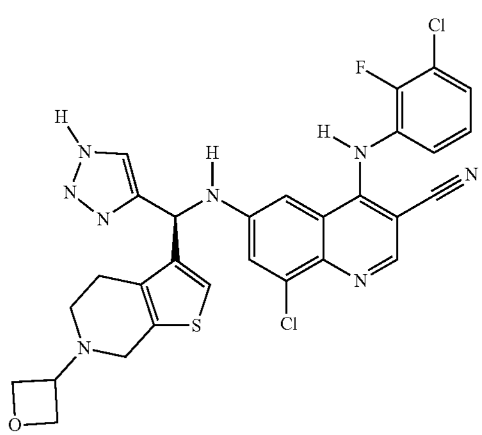 [SMILES: N#Cc1cnc2c(Cl)cc(N[C@H](C3=CNNN3)c3csc4c3CCN(C3COC3)C4)cc2c1Nc1cccc(Cl)c1F] | (S)-8-chloro-4-((3-chloro-2-fluorophenyl)amino)-6-(((6-(oxetan-3-yl)-4,5,6,7-tetrahydrothieno[2,3-c]pyridin-3-yl)(1H-1,2,3-triazol-4-yl)methyl)amino)quinoline-3-carbonitrile | 10 | ES/MS 621.5 (M + H+) |

TABLE 1-continued

| Comp | Structure | Name | Example Procedure | ES/MS m/z |
|---|---|---|---|---|
| 247 | 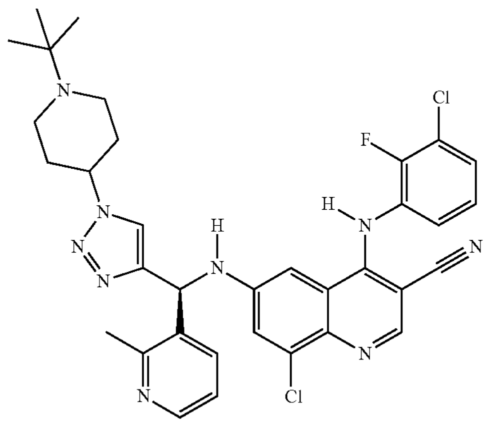 [SMILES: Cc1ncccc1[C@H](Nc1cc(Cl)c2ncc(C#N)c(Nc3cccc(Cl)c3F)c2c1)c1cn(C2CCN(C(C)(C)C)CC2)nn1] | (S)-6-(((1-(1-(tert-butyl)piperidin-4-yl)-1H-1,2,3-triazol-4-yl)(2-methylpyridin-3-yl)methyl)amino)-8-chloro-4-((3-chloro-2-fluorophenyl)amino)quinoline-3-carbonitrile | 1 | ES/MS 658.1 (M + H+) |
| 248 | 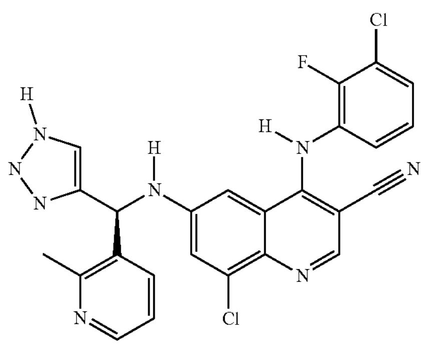 [SMILES: Cc1ncccc1[C@H](Nc1cc(Cl)c2ncc(C#N)c(Nc3cccc(Cl)c3F)c2c1)C1=CNNN1] | (S)-8-chloro-4-((3-chloro-2-fluorophenyl)amino)-6-(((2-methylpyridin-3-yl)(1H-1,2,3-triazol-4-yl)methyl)amino)-quinoline-3-carbonitrile | 10 | ES/MS 519.2 (M + H+) |
| 249 | 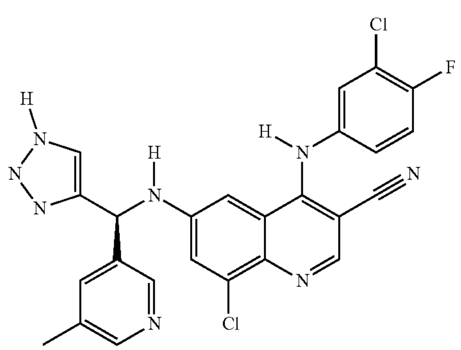 [SMILES: Cc1cncc([C@H](Nc2cc(Cl)c3ncc(C#N)c(Nc4ccc(F)c(Cl)c4)c3c2)C2=CNNN2)c1] | (S)-8-chloro-4--((3-chloro-4-fluorophenyl)amino)-6-(((5-methylpyridin-3-yl)(1H-1,2,3-triazol-4-yl)methyl)amino)quinoline-3-carbonitrile | 1 | ES/MS 519.0 (M + H+) |
| 250 | 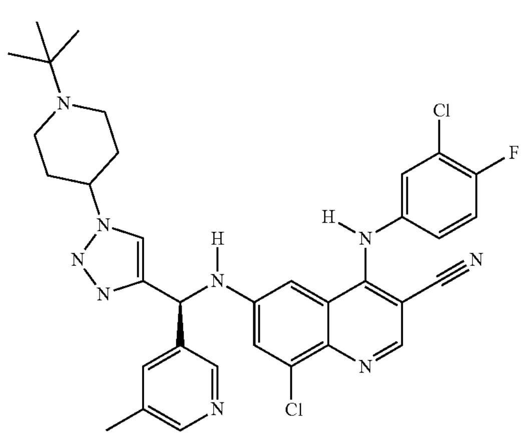 [SMILES: Cc1cncc([C@H](Nc2cc(Cl)c3ncc(C#N)c(Nc4ccc(F)c(Cl)c4)c3c2)C2=CN(C3CCN(C(C)(C)C)CC3)NN2)c1] | (S)-6-(((1-(1-(tert-butyl)piperidin-4-yl)-1H-1,2,3-triazol-4-yl)(5-methylpyridin-3-yl)methyl)amino)-8-chloro-4-((3-chloro-4-fluorophenyl)amino)quinoline-3-carbonitrile | 1 | ES/MS 658.1 (M + H+) |

TABLE 1-continued

| Comp | Structure | Name | Example Procedure | ES/MS m/z |
|---|---|---|---|---|
| 251 | 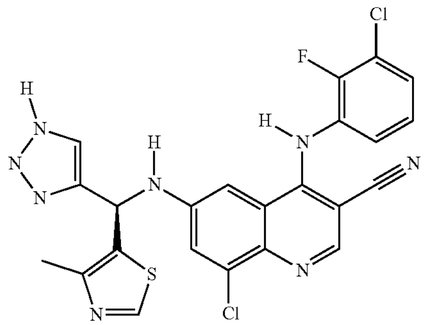 [SMILES: Cc1ncsc1[C@H](Nc1cc(Cl)c2ncc(C#N)c(Nc3cccc(Cl)c3F)c2c1)C1=CNNN1] | (R)-8-chloro-4-((3-chloro-2-fluorophenyl)amino)-6-(((4-methylthiazol-5-yl)(1H-1,2,3-triazol-4-yl)methyl)amino)quinoline-3-carbonitrile | 10 | ES/MS 525.1 (M + H+) |
| 252 | 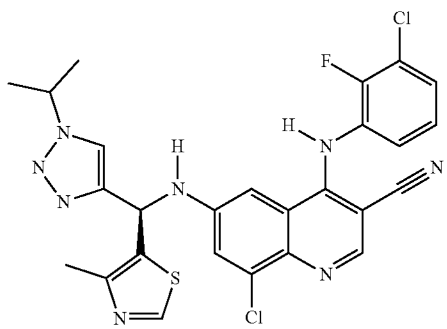 [SMILES: Cc1ncsc1[C@H](Nc1cc(Cl)c2ncc(C#N)c(Nc3cccc(Cl)c3F)c2c1)C1=CN(C(C)C)NN1] | (R)-8-chloro-4-((3-chloro-2-fluorophenyl)amino)-6-(((1-isopropyl-1H-1,2,3-triazol-4-yl)(4-methyl thiazol-5-yl)methyl)-amino)quinoline-3-carbonitrile | 2 | ES/MS 567.1 (M + H+) |
| 253 | 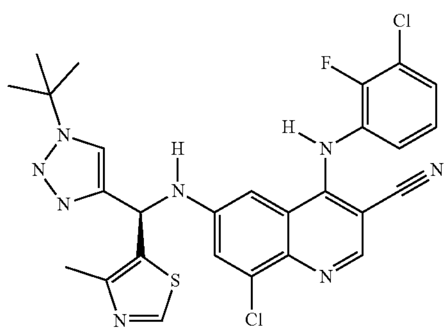 | (R)-6-(((1-(1-(tert-butyl)piperidin-4-yl)-1H-1,2,3-triazol-4-yl)(4-methylthiazol-5-yl)methyl)amino)-8-chloro-4-((3-chloro-2-fluorophenyl)amino)quinoline-3-carbonitrile | 2 | ES/MS 664.2 (M + H+) |
| 254 | 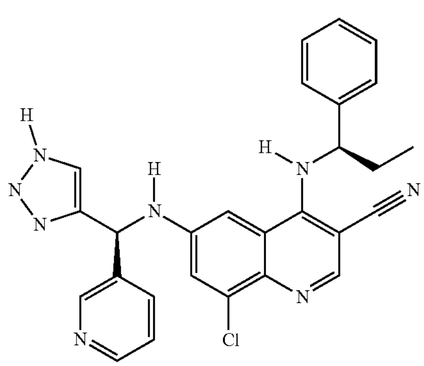 [SMILES: CC[C@@H](Nc1c(C#N)cnc2c(Cl)cc(N[C@H](C3=CNNN3)c3cccnc3)cc12)c1ccccc1] | 8-chloro-4-(((R)-1-phenylpropyl)amino)-6-(((S)-pyridin-3-yl(1H-1,2,3-triazol-4-yl)methyl)amino)quinoline-3-carbonitrile | 10 | ES/MS 495.2 (M + H+) |

TABLE 1-continued

| Comp | Structure | Name | Example Procedure | ES/MS m/z |
|---|---|---|---|---|
| 255 | 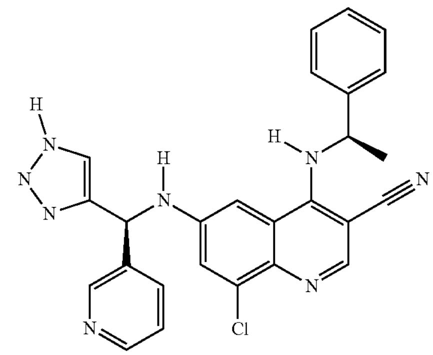 [SMILES: C[C@@H](Nc1c(C#N)cnc2c(Cl)cc(N[C@H](C3=CNNN3)c3cccnc3)cc12)c1ccccc1] | 8-chloro-4-(((R)-1-phenylethyl)amino)-6-(((S)-pyridin-3-yl(1H-1,2,3-triazol-4-yl)methyl)amino)quinoline-3-carbonitrile | 10 | ES/MS 481.2 (M + H+) |
| 256 | 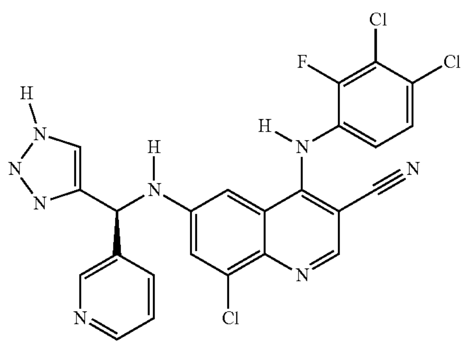 [SMILES: N#Cc1cnc2c(Cl)cc(N[C@H](C3=CNNN3)c3cccnc3)cc2c1Nc1ccc(Cl)c(Cl)c1F] | (S)-8-chloro-4-((3,4-dichloro-2-fluorophenyl)amino)-6-((pyridin-3-yl(1H-1,2,3-triazol-4-yl)methyl)-amino)quinoline-3-carbonitrile | 10 | ES/MS 539.1 (M + H+) |
| 257 | 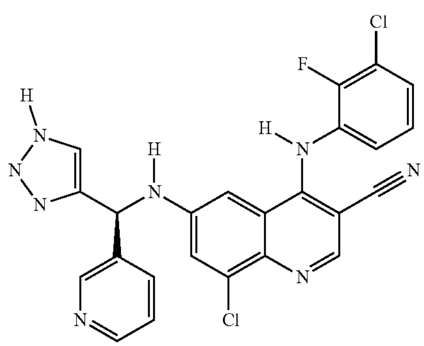 [SMILES: N#Cc1cnc2c(Cl)cc(N[C@H](C3=CNNN3)c3cccnc3)cc2c1Nc1cccc(Cl)c1F] | (S)-8-chloro-4-((3-chloro-2-fluorophenyl)amino)-6-((pyridin-3-yl(1H-1,2,3-triazol-4-yl)methyl)-amino)quinoline-3-carbonitrile | 10 | ES/MS 505.1 (M + H+) |
| 258 | 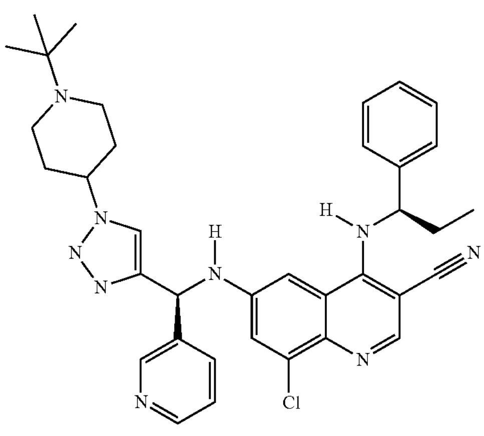 [SMILES: CC[C@@H](Nc1c(C#N)cnc2c(Cl)cc(N[C@H](C3=CN(C4CCN(C(C)(C)C)CC4)NN3)c3cccnc3)cc12)c1ccccc1] | 6-(((SMM1-(tert-butyl)piperidin-4-yl)-1H-1,2,3-triazol-4-yl)(pyridin-3-yl)methyl)amino)-8-chloro-4-(((R)-1-phenyl propyl)amino)quinoline-3-carbonitrile | 1 | ES/MS 634.3 (M + H+) |

TABLE 1-continued

| Comp | Structure | Name | Example Procedure | ES/MS m/z |
|---|---|---|---|---|
| 259 | 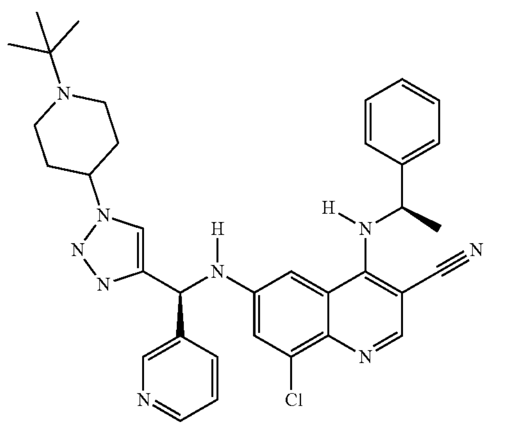 [SMILES: C[C@@H](Nc1c(C#N)cnc2c(Cl)cc(N[C@H](C3=CN(C4CCN(C(C)(C)C)CC4)NN3)c3cccnc3)cc12)c1ccccc1] | 6-(((S)-(1-(1-(tert-butyl)piperidin-4-yl)-1H-1,2,3-triazol-4-yl)(pyridin-3-yl)methyl)amino)-8-chloro-4-(((R)-1-phenylethyl)amino)quinoline-3-carbonitrile | 1 | ES/MS 620.3 (M + H+) |
| 260 | 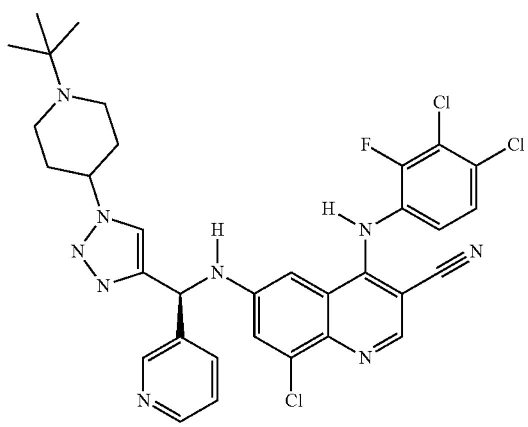 [SMILES: CC(C)(C)N1CCC(N2C=C([C@@H](Nc3cc(Cl)c4ncc(C#N)c(Nc5ccc(Cl)c(Cl)c5F)c4c3)c3cccnc3)NN2)CC1] | (S)-6-(((1-(1-(tert-butyl)piperidin-4-yl)-1H-1,2,3-triazol-4-yl )(pyridin-3-yl)methyl)amino)-8-chloro-4-((3,4-dichloro-2-fluorophenyl)amino)-quinoline-3-carbonitrile | 8 | ES/MS 678.1 (M + H+). |
| 261 | 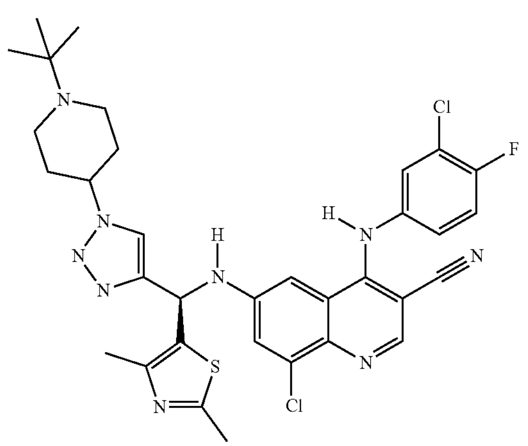 [SMILES: Cc1nc(C)c([C@H](Nc2cc(Cl)c3ncc(C#N)c(Nc4ccc(F)c(Cl)c4)c3c2)C2=CN(C3CCN(C(C)(C)C)CC3)NN2)s1] | (R)-6-(((1-(1-(tert-butyl)piperidin-4-yl)-1H-1,2,3-triazol-4-yl)(2,4-dimethyl-thiazol-5-yl)methyl)amino)-8-chloro-4-((3-chloro-4-fluorophenyl)amino)-quinoline-3-carbonitrile | 2 | ES/MS 678.0 (M + H+) |

TABLE 1-continued

| Comp | Structure | Name | Example Procedure | ES/MS m/z |
|---|---|---|---|---|
| 262 | 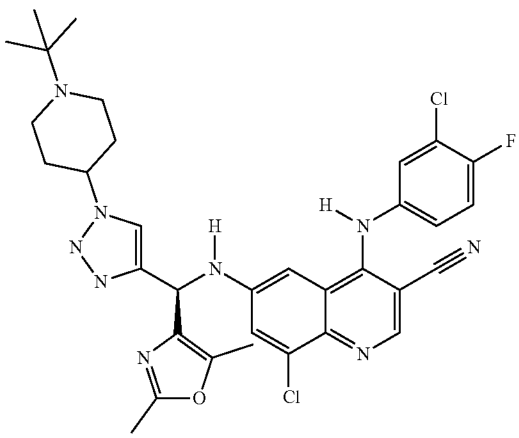 [SMILES: Cc1nc([C@H](Nc2cc(Cl)c3ncc(C#N)c(Nc4ccc(F)c(Cl)c4)c3c2)C2=CN(C3CCN(C(C)(C)C)CC3)NN2)c(C)o1] | (S)-6-(((1-(1-(tert-butyl)piperidin-4-yl)-1H-1,2,3-triazol-4-yl)(2,5-dimethyloxazol-4-yl)methyl)amino)-8-chloro-4-((3-chloro-4-fluorophenyl)amino)quinoline-3-carbonitrile | 2 | ES/MS 662.0 (M + H+) |
| 263 | 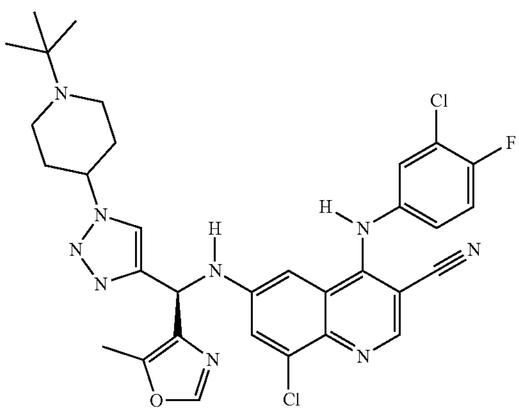 [SMILES: Cc1ocnc1[C@H](Nc1cc(Cl)c2ncc(C#N)c(Nc3ccc(F)c(Cl)c3)c2c1)C1=CN(C2CCN(C(C)(C)C)CC2)NN1] | (S)-6-(((1-(1-(tert-butyl)piperidin-4-yl)-1H-1,2,3-triazol-4-yl)(5-methyloxazol-4-yl)methyl)amino)-8-chloro-4-((3-chloro-4-fluorophenyl)amino)quinoline-3-carbonitrile | 2 | ES/MS 648.3 (M + H+) |
| 264 | 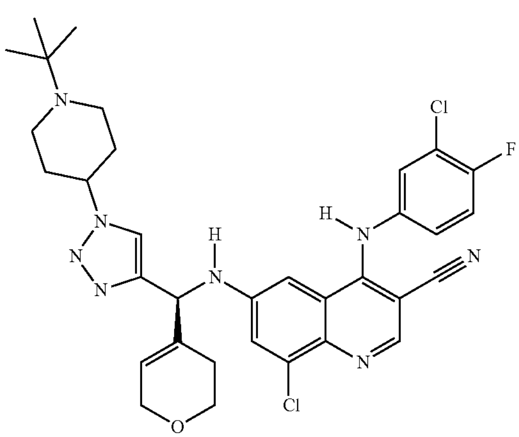 [SMILES: CC(C)(C)N1CCC(N2C=C([C@@H](Nc3cc(Cl)c4ncc(C#N)c(Nc5ccc(F)c(Cl)c5)c4c3)C3=CCOCC3)NN2)CC1] | (S)-6-(((1-(1-(tert-butyl)piperidin-4-yl)-1H-1,2,3-triazol-4-yl)(3,6-dihydro-2H-pyran-4-yl)methyl)amino)-8-chloro-4-((3-chloro-4-fluorophenyl)amino)quinoline-3-carbonitrile | 2 | ES/MS 649.1 (M + H+) |

TABLE 1-continued

| Comp | Structure | Name | Example Procedure | ES/MS m/z |
|---|---|---|---|---|
| 265 | 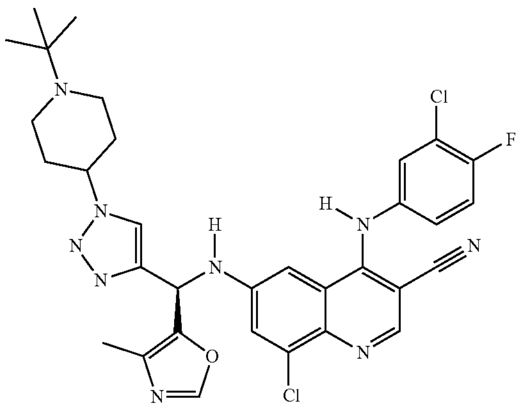 | (R)-6-(((1-(1-(tert-butyl)piperidin-4-yl)-1H-1,2,3-triazol-4-yl)(4-methyloxazol-5-yl)methyl)amino)-8-chloro-4-((3-chloro-4-fluorophenyl)amino)quinoline-3-carbonitrile | 2 | ES/MS 648.2 (M + H+) |
| 266 | 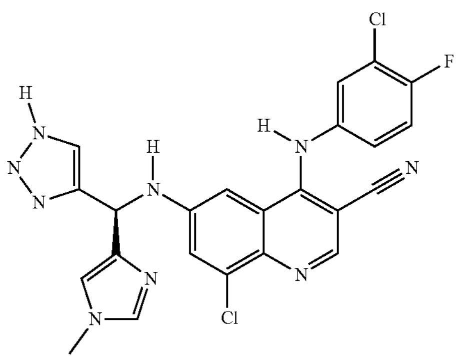 [SMILES: Cn1cnc([C@H](Nc2cc(Cl)c3ncc(C#N)c(Nc4ccc(F)c(Cl)c4)c3c2)C2=CNNN2)c1] | (S)-8-chloro-4-((3-chloro-4-fluorophenyl)amino)-6-(((1-methyl-1H-imidazol-4-yl)(1H-1,2,3-triazol-4-yl)methyl)amino)-quinoline-3-carbonitrile | 10 | ES/MS 508.1 (M + H+) |
| 267 | 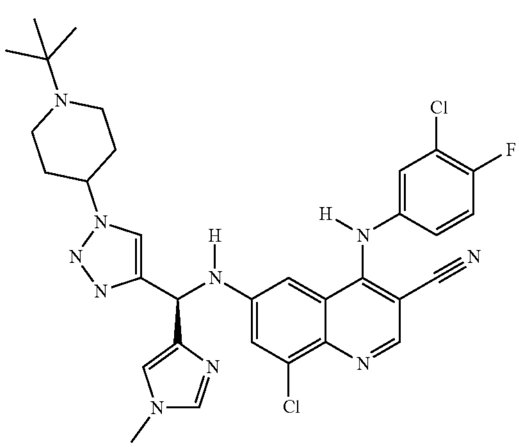 [SMILES: Cn1cnc([C@H](Nc2cc(Cl)c3ncc(C#N)c(Nc4ccc(F)c(Cl)c4)c3c2)C2=CN(C3CCN(C(C)(C)C)CC3)NN2)c1] | (S)-6-(((1-(1-(tert-butyl)piperidin-4-yl)-1H-1,2,3-triazol-4-yl)(1-methyl-1H-imidazol-4-yl)methyl)amino)-8-chloro-4-((3-chloro-4-fluorophenyl)-amino)quinoline-3-carbonitrile | 2 | ES/MS 647.1 (M + H+) |

TABLE 1-continued

| Comp | Structure | Name | Example Procedure | ES/MS m/z |
|---|---|---|---|---|
| 268 | 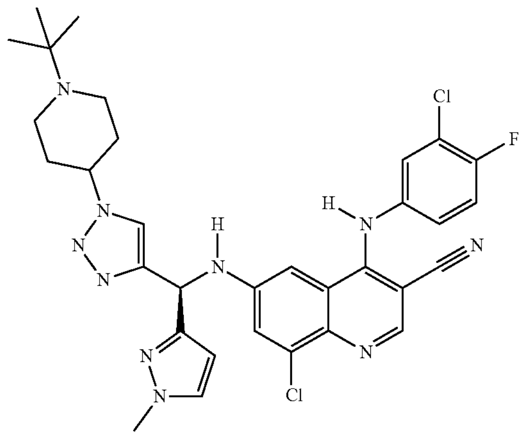 [SMILES: Cn1ccc([C@H](Nc2cc(Cl)c3ncc(C#N)c(Nc4ccc(F)c(Cl)c4)c3c2)C2=CN(C3CCN(C(C)(C)C)CC3)NN2)n1] | (R)-6-(((1-(1-(tert-butyl)piperidin-4-yl)-1H-1,2,3-triazol-4-yl)(1-methyl-1H-pyrazol-3-yl)methyl)amino)-8-chloro-4-((3-chloro-4-fluorophenyl)-amino)quinoline-3-carbonitrile | 2 | ES/MS 647.0 (M + H+) |
| 269 | 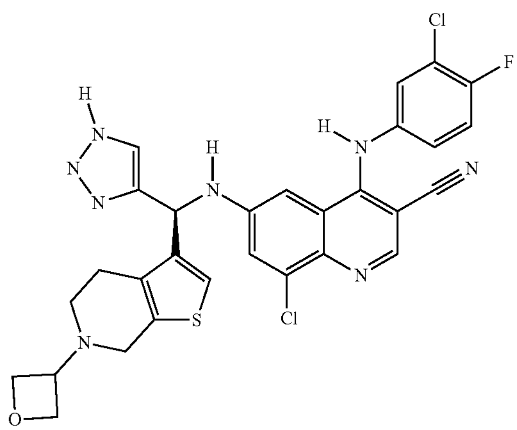 [SMILES: N#Cc1cnc2c(Cl)cc(N[C@H](C3=CNNN3)c3csc4c3CCN(C3COC3)C4)cc2c1Nc1ccc(F)c(Cl)c1] | (S)-8-chloro-4-((3-chloro-4-fluorophenyl)amino)-6-(((6-(oxetan-3-yl )-4,5,6,7-tetrahydrothieno[2,3-c]pyridin-yl)(1H-1,2,3-triazol-4-yl)methyl)amino)quinoline-3-carbonitrile | 10 | ES/MS 621.1 (M + H+) |
| 270 | 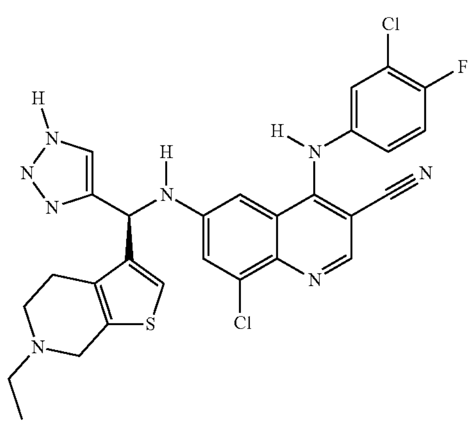 [SMILES: CCN1CCc2c([C@H](Nc3cc(Cl)c4ncc(C#N)c(Nc5ccc(F)c(Cl)c5)c4c3)C3=CNNN3)csc2C1] | (S)-8-chloro-4-((3-chloro-4-fluoro-phenyl)amino)-6-(((6-ethyl-4,5,6,7-tetrahydrothieno[2,3-c]pyridin-3-yl)(1H-1,2,3-triazol-4-yl)methyl)-amino)quinoline-3-carbonitrile | 10 | ES/MS 593.1 (M + H+) |

TABLE 1-continued

| Comp | Structure | Name | Example Procedure | ES/MS m/z |
|---|---|---|---|---|
| 271 | 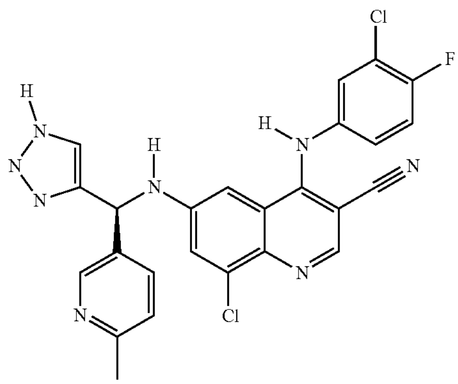 [SMILES: Cc1ccc([C@H](Nc2cc(Cl)c3ncc(C#N)c(Nc4ccc(F)c(Cl)c4)c3c2)C2=CNNN2)cn1] | (S)-8-chloro-4-((3-chloro-4-fluorophenyl)amino)-6-(((6-methylpyridin-3-yl)(1H-1,2,3-triazol-4-yl)methyl)amino)quinoline-3-carbonitrile | 10 | ES/MS 519.0 (M + H+) |
| 272 | 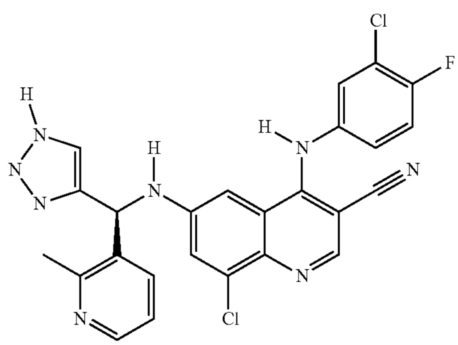 [SMILES: Cc1ncccc1[C@H](Nc1cc(Cl)c2ncc(C#N)c(Nc3ccc(F)c(Cl)c3)c2c1)C1=CNNN1] | (S)-8-chloro-4-((3-chloro-4-fluorophenyl)amino)-6-(((2-methylpyridin-3-yl)(1H-1,2,3-triazol-4-yl)methyl)amino)quinoline-3-carbonitrile | 1 | ES/MS 519.0 (M + H+) |
| 273 | 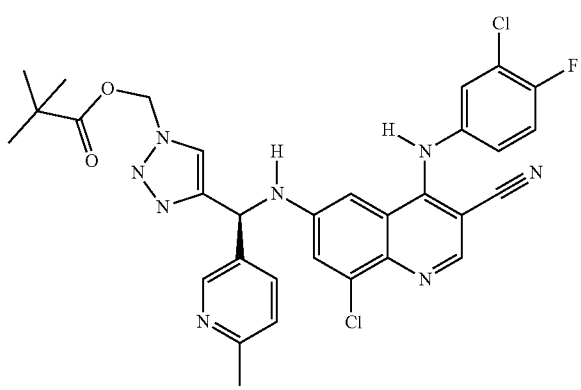 [SMILES: Cc1ccc([C@H](Nc2cc(Cl)c3ncc(C#N)c(Nc4ccc(F)c(Cl)c4)c3c2)C2=CN(COC(=O)C(C)(C)C)NN2)cn1] | (S)-(4-(((8-chloro-4-((3-chloro-4-fluorophenyl)amino)-3-cyanoquinolin-6-yl)amino)(6-methylpyridin-3-yl)methyl)-1H-1,2,3-triazol-1-yl)methyl pivalate | 10 | ES/MS 633.1 (M + H+) |
| 274 | 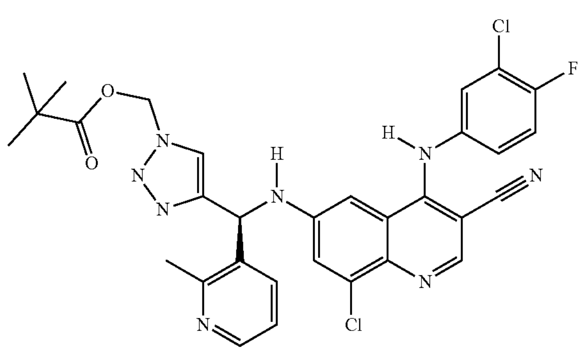 [SMILES: Cc1ncccc1[C@H](Nc1cc(Cl)c2ncc(C#N)c(Nc3ccc(F)c(Cl)c3)c2c1)C1=CN(COC(=O)C(C)(C)C)NN1] | (S)-(4-(((8-chloro-4-((3-chloro-4-fluorophenyl)amino)-3-cyanoquinolin-6-yl)amino)(2-methylpyridin-3-yl)methyl)-1H-1,2,3-triazol-1-yl)methyl pivalate | 10 | ES/MS 633.0 (M + H+) |

TABLE 1-continued

| Comp | Structure | Name | Example Procedure | ES/MS m/z |
|---|---|---|---|---|
| 275 | 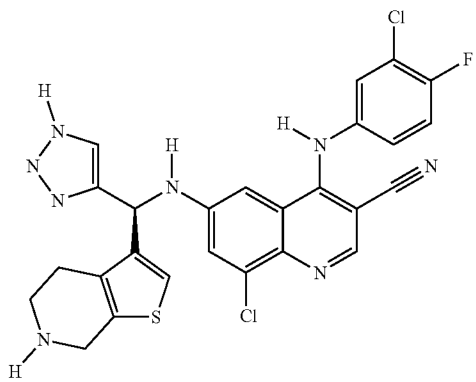 [SMILES: N#Cc1cnc2c(Cl)cc(N[C@H](C3=CNNN3)c3csc4c3CCNC4)cc2c1Nc1ccc(F)c(Cl)c1] | (S)-8-chloro-4-((3-chloro-4-fluorophenyl)amino)-6-(((4,5,6,7-tetrahydrothieno[2,3-c]pyridin-3-yl)(1H-1,2,3-triazol-4-yl)methyl)amino)quinoline-3-carbonitrile | 10 | ES/MS 565.1 (M + H+) |
| 276 | 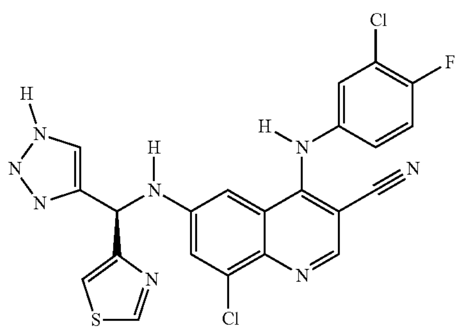 [SMILES: N#Cc1cnc2c(Cl)cc(N[C@H](C3=CNNN3)c3cscn3)cc2c1Nc1ccc(F)c(Cl)c1] | (S)-8-chloro-4-((3-chloro-4-fluorophenyl)amino)-6-((thiazol-4-yl(1H-1,2,3-triazol-4-yl)methyl)amino)quinoline-3-carbonitrile | 10 | ES/MS 511.0 (M + H+) |
| 277 | 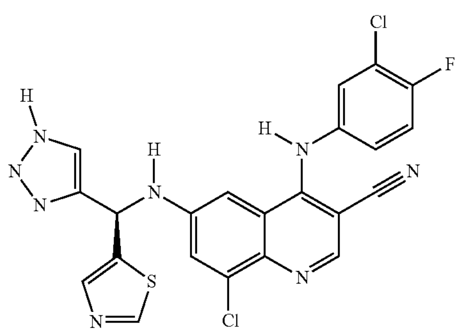 [SMILES: N#Cc1cnc2c(Cl)cc(N[C@H](C3=CNNN3)c3cncs3)cc2c1Nc1ccc(F)c(Cl)c1] | (R)-B-chloro-4-((3-chloro-4-fluorophenyl)amino)-6-((thiazol-5-yl(1H-1,2,3-triazol-4-yl)methyl)amino)quinoline-3-carbonitrile | 10 | ES/MS 511.1 (M + H+) |
| 278 | 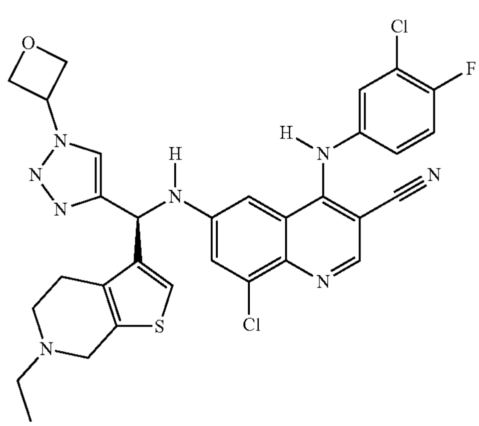 [SMILES: CCN1CCc2c([C@H](Nc3cc(Cl)c4ncc(C#N)c(Nc5ccc(F)c(Cl)c5)c4c3)C3=CN(C4COC4)NN3)csc2C1] | (S)-8-chloro-4-((3-chloro-4-fluorophenyl)amino)-6-(((6-ethyl-4,5,6,7-tetrahydro-thieno[2,3-c]pyridin-3-yl)(1-(oxetan-3-yl)-1H-1,2,3-triazol-4-yl)methyl)amino)quinoline-3-carbonitrile | 2 | ES/MS 649.1 (M + H+). |

TABLE 1-continued

| Comp | Structure | Name | Example Procedure | ES/MS m/z |
|---|---|---|---|---|
| 279 | 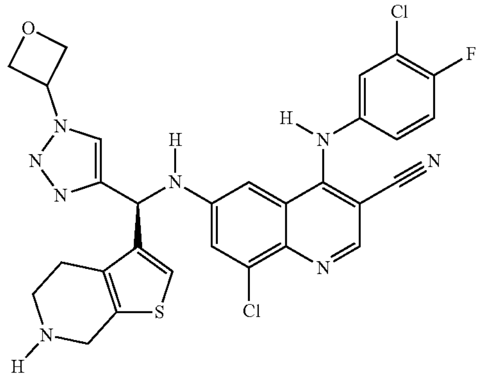 [SMILES: N#Cc1cnc2c(Cl)cc(N[C@H](C3=CN(C4COC4)NN3)c3csc4c3CCNC4)cc2c1Nc1ccc(F)c(Cl)c1] | (S)-8-chloro-4-((3-chloro-4-fluorophenyl)amino)-6-(((1-(oxetan-3-yl)-1H-1,2,3-triazol-4-yl)(4,5,6,7-tetrahydrothieno[2,3-c]pyridin-3-yl)methyl)amino)quinoline-3-carbonitrile | 5 | ES/MS 621.0 (M + H+) |
| 280 | 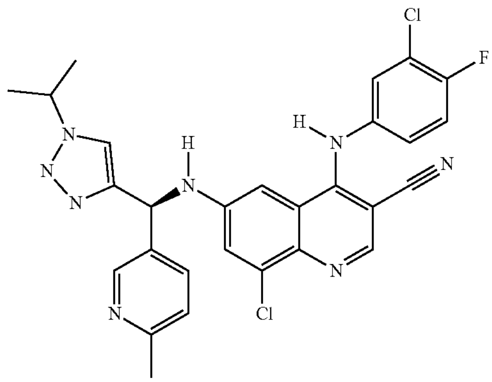 [SMILES: Cc1ccc([C@H](Nc2cc(Cl)c3ncc(C#N)c(Nc4ccc(F)c(Cl)c4)c3c2)C2=CN(C(C)C)NN2)cn1] | (S)-8-chloro-4-((3-chloro-4-fluorophenyl)amino)-6-(((1-isopropyl-1H-1,2,3-triazol-4-yl)(6-methylpyridin-3-yl)methyl)amino)quinoline-3-carbonitrile | 1 | ES/MS 561.2 (M + H+) |
| 281 | 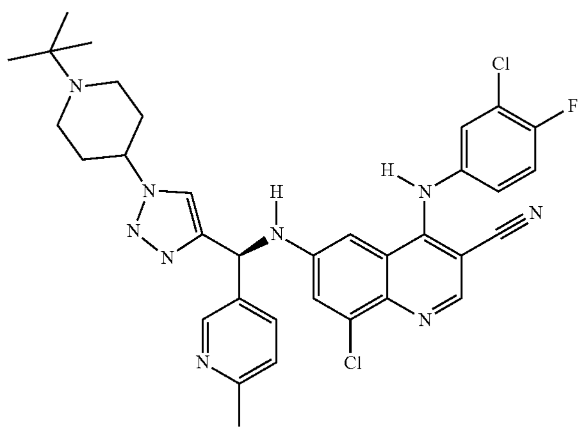 [SMILES: Cc1ccc([C@H](Nc2cc(Cl)c3ncc(C#N)c(Nc4ccc(F)c(Cl)c4)c3c2)C2=CN(C3CCN(C(C)(C)C)CC3)NN2)cn1] | (S)-6-(((1-(1-(tert-butyl)piperidin-4-yl)-1H-1,2,3-triazol-4-yl)(6-methylpyridin-3-yl)methyl)amino)-8-chloro-4-((3-chloro-4-fluorophenyl)-amino)quinoline-3-carbonitrile | 1 | ES/MS 658.1 (M + H+) |
| 282 | 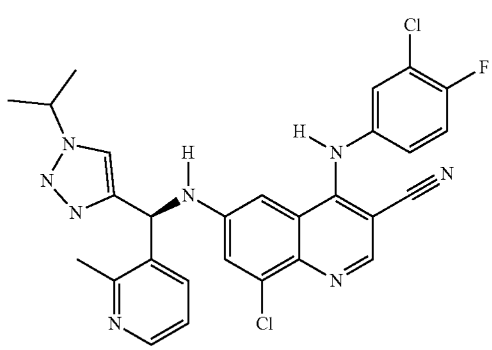 [SMILES: Cc1ncccc1[C@H](Nc1cc(Cl)c2ncc(C#N)c(Nc3ccc(F)c(Cl)c3)c2c1)C1=CN(C(C)C)NN1] | (S)-8-chloro-4-((3-chloro-4-fluorophenyl)amino)-6-(((1-isopropyl-1H-1,2,3-triazol-4-yl)(2-methylpyridin-3-yl)methyl)amino)-quinoline-3-carbonitrile | 1 | ES/MS 561.2 (M + H+) |

TABLE 1-continued

| Comp | Structure | Name | Example Procedure | ES/MS m/z |
|---|---|---|---|---|
| 283 | 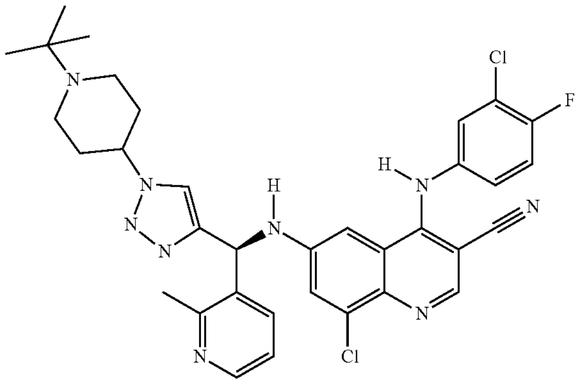 [SMILES: Cc1ncccc1[C@H](Nc1cc(Cl)c2ncc(C#N)c(Nc3ccc(F)c(Cl)c3)c2c1)C1=CN(C2CCN(C(C)(C)C)CC2)NN1] | (S)-6-(((1-0-(tert-butyl)piperidin-4-yl)-1H-1,2,3-triazol-4-yl)(2-methyl-pyridin-3-yl)methyl)amino)-8-chloro-4-((3-chloro-4-fluorophenyl)-amino)quinoline-3-carbonitrile | 1 | ES/MS 658.1 (M + H+) |
| 284 | 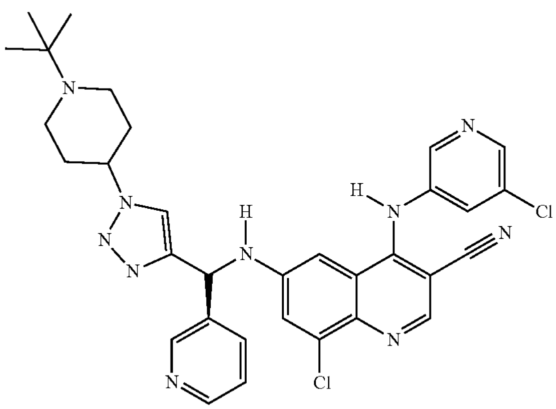 | (S)-6-(((1-(1-(tert-butyl)piperidin-4-yl)-1H-1,2,3-triazol-4-yl)(pyridin-3-yl)methyl)amino)-8-chloro-4-((5-chloropyridin-3-yl)amino)quinoline-3-carbonitrile | 8 | ES/MS 629.2 (M + H+). |
| 285 | 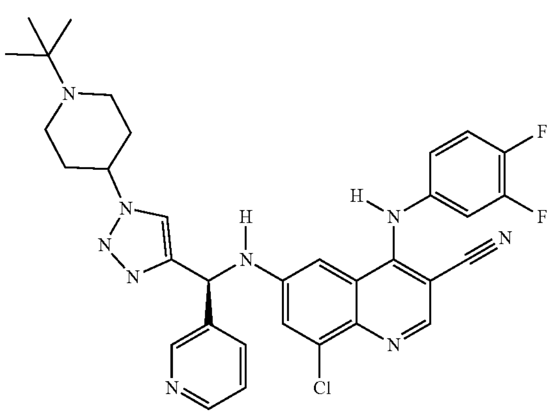 [SMILES: CC(C)(C)N1CCC(N2C=C([C@@H](Nc3cc(Cl)c4ncc(C#N)c(Nc5ccc(F)c(F)c5)c4c3)c3cccnc3)NN2)CC1] | (S)-6-(((1-(1-(tert-butyl)piperidin-4-yl)-1H-1,2,3-triazol-4-yl)(p yridin-3-yl)methyl)amino)-8-chloro-4-((3,4-difluorophenyl)amino)quinoline-3-carbonitrile | 8 | ES/MS 628.2 (M + H+) |

TABLE 1-continued

| Comp | Structure | Name | Example Procedure | ES/MS m/z |
|---|---|---|---|---|
| 286 | 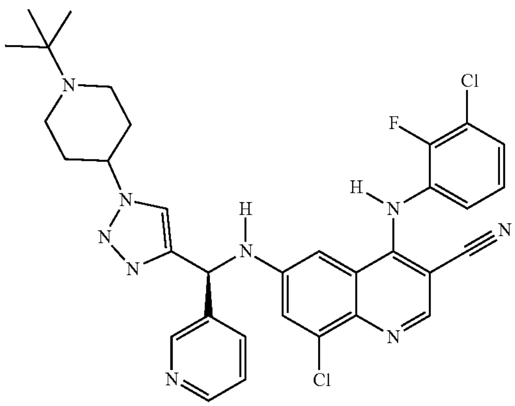 [SMILES: CC(C)(C)N1CCC(N2C=C([C@@H](Nc3cc(Cl)c4ncc(C#N)c(Nc5cccc(Cl)c5F)c4c3)c3cccnc3)NN2)CC1] | (S)-6-(((Ml-(tert-butyl)piperidin-4-yl)-1H-1,2,3-triazol-4-yl)(pyridin-3-yl)methyl)amino)-8-chloro-4-((3-chloro-2-fluorophenyl)-amino)quinoline-3-carbonitrile | 8 | ES/MS 644.2 (M + H+) |
| 287 | 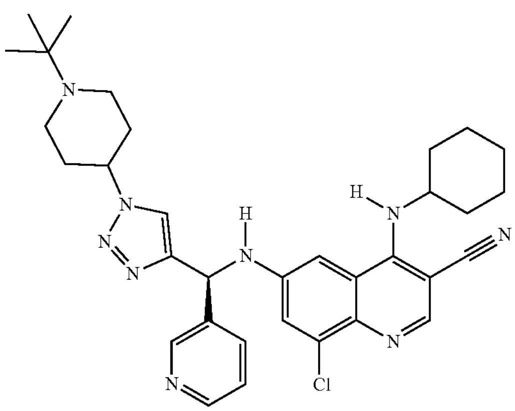 [SMILES: CC(C)(C)N1CCC(n2cc([C@@H](Nc3cc(Cl)c4ncc(C#N)c(NC5CCCCC5)c4c3)c3cccnc3)nn2)CC1] | (S)-6-(((1-(1-(tert-butyl)piperidin-4-yl)-1H-1,2,3-triazol-4-yl)(pyridin-3-yl)methyl)amino)-8-chloro-4-(cyclohexylamino)quinoline-3-carbonitrile | 1 | ES/MS 598.3 (M + H+) |
| 288 | 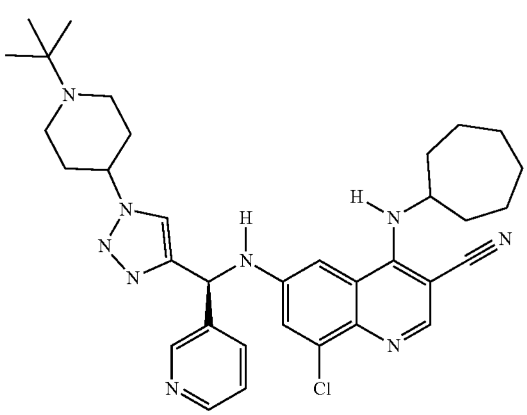 [SMILES: CC(C)(C)N1CCC(N2C=C([C@@H](Nc3cc(Cl)c4ncc(C#N)c(NC5CCCCCC5)c4c3)c3cccnc3)NN2)CC1] | (S)-6-(((1-(1-(tert-butyl)piperidin-4-yl)-1H-1,2,3-triazol-4-yl)(pyridin-3-yl)methyl)amino)-8-chloro-4-(cycloheptylamino)quinoline-3-carbonitrile | 1 | ES/MS 612.3 (M + H+) |

TABLE 1-continued

| Comp | Structure | Name | Example Procedure | ES/MS m/z |
|---|---|---|---|---|
| 289 | 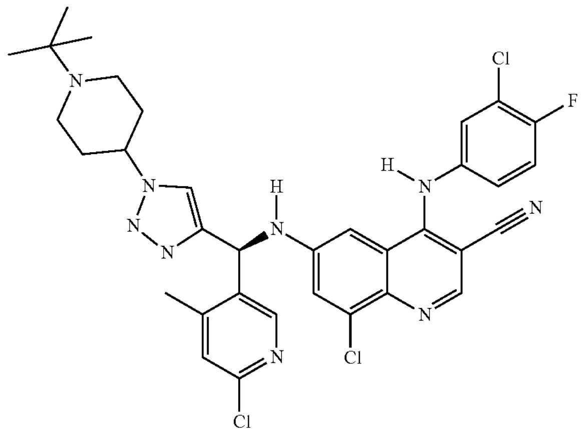 [SMILES: Cc1cc(Cl)ncc1[C@H](Nc1cc(Cl)c2ncc(C#N)c(Nc3ccc(F)c(Cl)c3)c2c1)C1=CN(C2CCN(C(C)(C)C)CC2)NN1] | (S)-6-(((H1-(tert-butyl)piperidin-4-yl)-1H-1,2,3-triazol-4-yl)(6-chloro-4-methylpyridin-3-yl)methyl)amino)-8-chloro-4-((3-chloro-4-fluorophenyl)amino)quinoline-3-carbonitrile | 1 | ES/MS 692.2 (M + H+) |
| 290 | 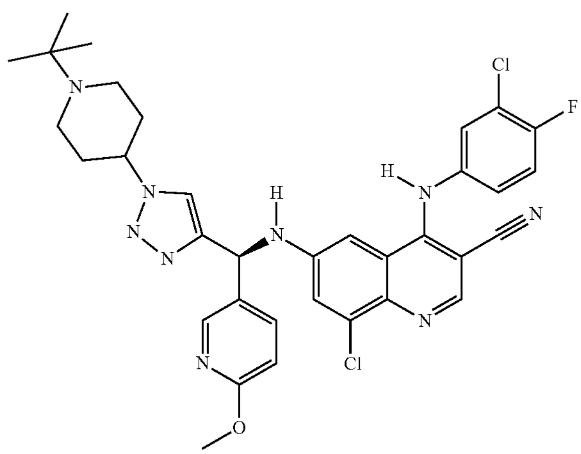 [SMILES: COc1ccc([C@H](Nc2cc(Cl)c3ncc(C#N)c(Nc4ccc(F)c(Cl)c4)c3c2)C2=CN(C3CCN(C(C)(C)C)CC3)NN2)cn1] | (S)-6-(((1-(1-(tert-butyl)piperidin-4-yl)-1H-1,2,3-triazol-4-yl)(6-methoxypyridin-3-yl)methyl)amino)-8-chloro-4-((3-chloro-4-fluorophenyl)amino)quinoline-3-carbonitrile | 1 | ES/MS 674.2 (M + H+) |
| 291 | 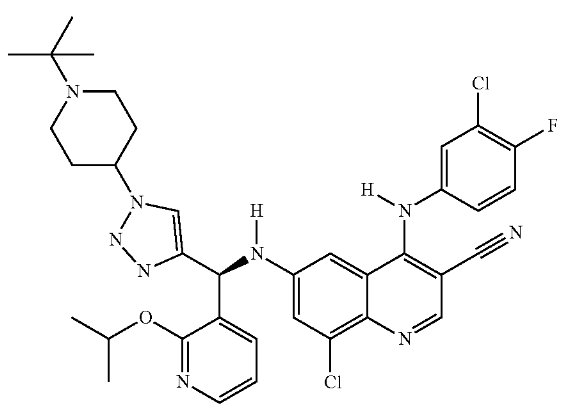 [SMILES: CC(C)Oc1ncccc1[C@H](Nc1cc(Cl)c2ncc(C#N)c(Nc3ccc(F)c(Cl)c3)c2c1)C1=CN(C2CCN(C(C)(C)C)CC2)NN1] | (S)-6-(((1-(1-(tert-butyl)piperidin-4-yl)-1H-1,2,3-triazol-4-yl)(2-isopropoxypyridin-3-yl)methyl)amino)-8-chloro-4-((3-chloro-4-fluorophenyl)amino)quinoline-3-carbonitrile | 1 | ES/MS 702.1 (M + H+) |

TABLE 1-continued

| Comp | Structure | Name | Example Procedure | ES/MS m/z |
|---|---|---|---|---|
| 292 | 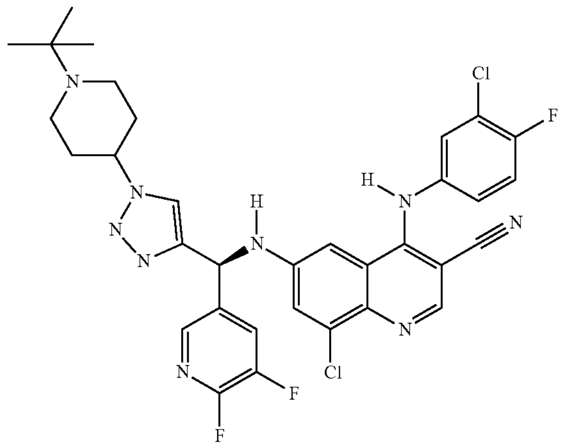 [SMILES: CC(C)(C)N1CCC(N2C=C([C@@H](Nc3cc(Cl)c4ncc(C#N)c(Nc5ccc(F)c(Cl)c5)c4c3)c3cnc(F)c(F)c3)NN2)CC1] | (S)-6-(((1-(1-(tert-butyl)piperidin-4-yl)-1H-1,2,3-triazol-4-yl)(5,6-difluoropyridin-3-yl)methyl)amino)-8-chloro-4-((3-chloro-4-fluorophenyl)amino)quinoline-3-carbonitrile | 1 | ES/MS 680.2 (M + H+) |
| 293 | 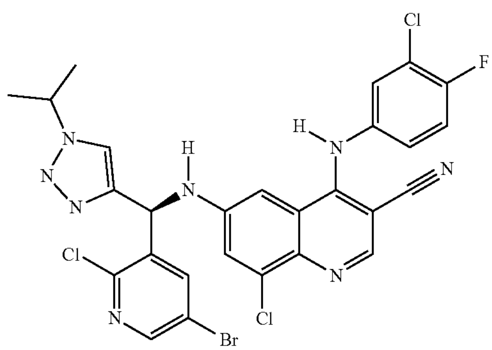 [SMILES: CC(C)N1C=C([C@@H](Nc2cc(Cl)c3ncc(C#N)c(Nc4ccc(F)c(Cl)c4)c3c2)c2cc(Br)cnc2Cl)NN1] | (S)-6-(((5-bromo-2-chloropyridin-3-yl)(1-isopropyl-1H-1,2,3-triazol-4-yl)methyl)amino)-8-chloro-4-((3-chloro-4-fluorophenyl)amino)quinoline-3-carbonitrile | 1 | ES/MS 661.2 (M + H+) |
| 294 | 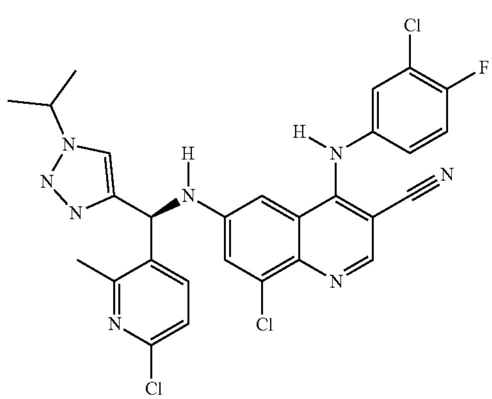 [SMILES: Cc1nc(Cl)ccc1[C@H](Nc1cc(Cl)c2ncc(C#N)c(Nc3ccc(F)c(Cl)c3)c2c1)C1=CN(C(C)C)NN1] | (S)-8-chloro-6-(((6-chloro-2-methylpyridin-3-yl)(1-isopropyl-1H-1,2,3-triazol-4-yl)methyl)amino)-4-((3-chloro-4-fluorophenyl)amino)quinoline-3-carbonitrile | 1 | ES/MS 595.6 (M + H+) |

TABLE 1-continued

| Comp | Structure | Name | Example Procedure | ES/MS m/z |
|---|---|---|---|---|
| 295 | 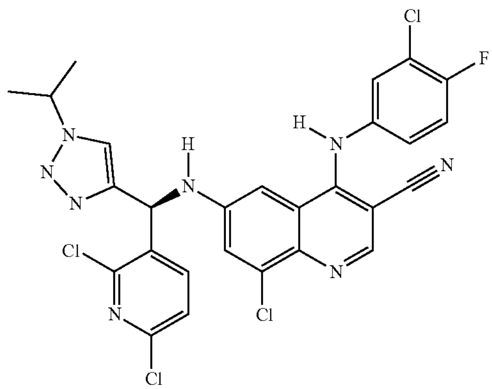 | (S)-8-chloro-4-((3-chloro-4-fluorophenyl)amino)-6-(((2,6-dichloropyridin-3-yl)(1-isopropyl-1H-1,2,3-triazol-4-yl)methyl)amino)quinoline-3-carbonitrile | 1 | ES/MS 617.1 (M + H+) |
| 296 | 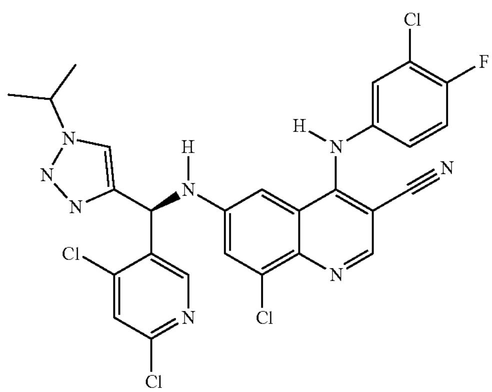 [SMILES: CC(C)N1C=C([C@@H](Nc2cc(Cl)c3ncc(C#N)c(Nc4ccc(F)c(Cl)c4)c3c2)c2cnc(Cl)cc2Cl)NN1] | (S)-8-chloro-4-((3-chloro-4-fluorophenyl)amino)-6-(((4,6-dichloropyridin-3-yl)(1-isopropyl-1H-1,2,3-triazol-4-yl)methyl)amino)quinoline-3-carbonitrile | 1 | ES/MS 617.1 (M + H+) |
| 297 | 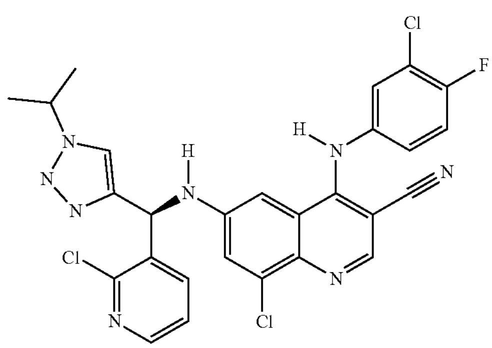 [SMILES: CC(C)N1C=C([C@@H](Nc2cc(Cl)c3ncc(C#N)c(Nc4ccc(F)c(Cl)c4)c3c2)c2cccnc2Cl)NN1] | (S)-8-chloro-4-((3-chloro-4-fluorophenyl)amino)-6-(((2-chloropyridin-3-yl)(1-isopropyl-1H-1,2,3-triazol-4-yl)methyl)amino)quinoline-3-carbonitrile | 1 | ES/MS 581.2 (M + H+) |
| 298 | 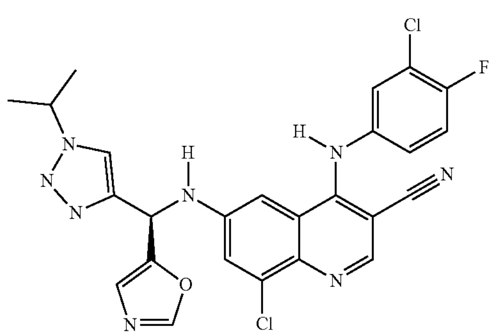 [SMILES: CC(C)N1C=C([C@@H](Nc2cc(Cl)c3ncc(C#N)c(Nc4ccc(F)c(Cl)c4)c3c2)c2cnco2)NN1] | (R)-8-chloro-4-((3-chloro-4-fluorophenyl)amino)-6-(((1-isopropyl-1H-1,2,3-triazol-4-yl)(oxazol-5-yl)methyl)amino)quinoline-3-carbonitrile | 2 | ES/MS 537.1 (M + H+) |

TABLE 1-continued

| Comp | Structure | Name | Example Procedure | ES/MS m/z |
|---|---|---|---|---|
| 299 | 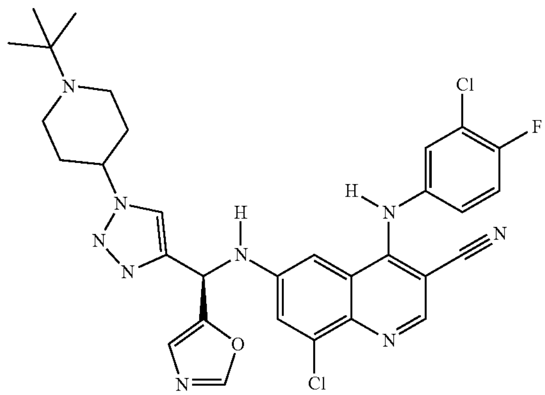 [SMILES: CC(C)(C)N1CCC(N2C=C([C@@H](Nc3cc(Cl)c4ncc(C#N)c(Nc5ccc(F)c(Cl)c5)c4c3)c3cnco3)NN2)CC1] | (R)-6-(((1-(1-(tert-butyl)piperidin-4-yl)-1H-1,2,3-triazol-4-yl)(oxazol-5-yl)methyl)amino)-8-chloro-4-((3-chloro-4-fluorophenyl)amino)quinoline-3-carbonitrile | 2 | ES/MS 634.1 (M + H+) |
| 300 | 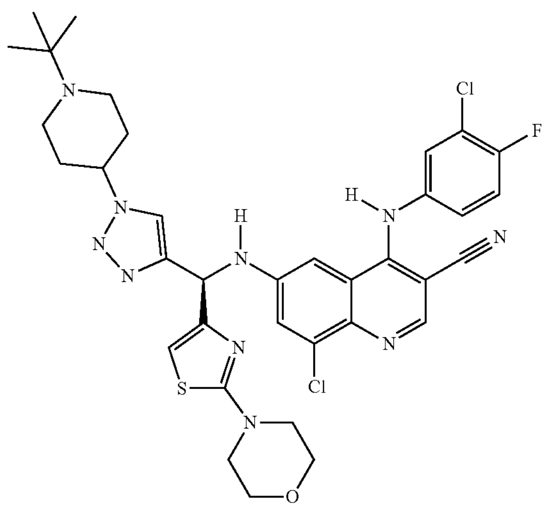 [SMILES: CC(C)(C)N1CCC(N2C=C([C@@H](Nc3cc(Cl)c4ncc(C#N)c(Nc5ccc(F)c(Cl)c5)c4c3)c3csc(N4CCOCC4)n3)NN2)CC1] | (S)-6-(((1-0-(tert-butyl)piperidin-4-yl)-1H-1,2,3-triazol-4-yl)(2-morpholino-thiazol-4-yl)methyl)amino)-8-chloro-4-((3-chloro-4-fluorophenyl)amino)quinoline-3-carbonitrile | 2 | ES/MS 735.1 (M + H+) |
| 301 | 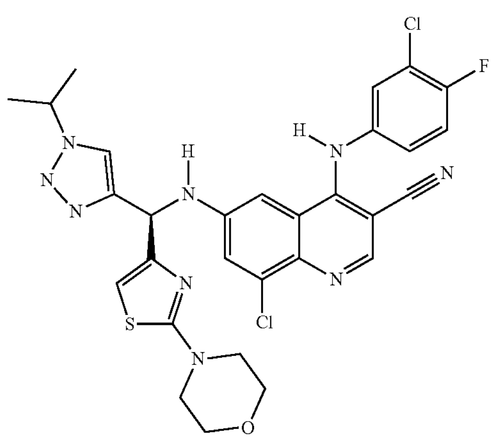 [SMILES: CC(C)N1C=C([C@@H](Nc2cc(Cl)c3ncc(C#N)c(Nc4ccc(F)c(Cl)c4)c3c2)c2csc(N3CCOCC3)n2)NN1] | (S)-8-chloro-4-((3-chloro-4-fluorophenyl)amino)-6-(((1-isopropyl-1H-1,2,3-triazol-4-yl)(2-morpholinothiazol-4-yl)methyl)amino)quinoline-3-carbonitrile | 2 | ES/MS 638.0 (M + H+) |

TABLE 1-continued

| Comp | Structure | Name | Example Procedure | ES/MS m/z |
|---|---|---|---|---|
| 302 | 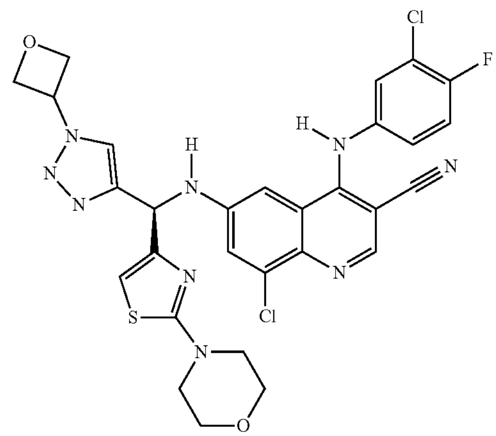 [SMILES: N#Cc1cnc2c(Cl)cc(N[C@H](C3=CN(C4COC4)NN3)c3csc(N4CCOCC4)n3)cc2c1Nc1ccc(F)c(Cl)c1] | (S)-8-chloro-4-((3-chloro-4-fluorophenyl)amino)-6-(((2-morpholinothiazol-4-yl)(1-(oxetan-3-yl)-1H-1,2,3-triazol-4-yl)methyl)amino)quinoline-3-carbonitrile | 2 | ES/MS 652.0 (M + H+) |
| 303 | 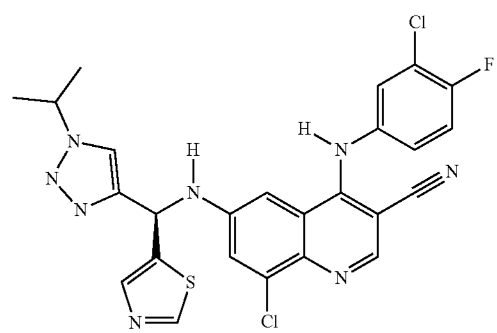 | (R)-8-chloro-4-((3-chloro-4-fluorophenyl)amino)-6-(((1-isopropyl-1H-1,2,3-triazol-4-yl)(thiazol-5-yl)methyl)amino)quinoline-3-carbonitrile | 2 | ES/MS 553.0 (M + H+) |
| 304 | 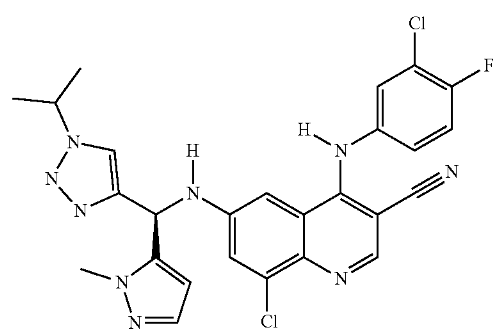 [SMILES: CC(C)N1C=C([C@@H](Nc2cc(Cl)c3ncc(C#N)c(Nc4ccc(F)c(Cl)c4)c3c2)c2ccnn2C)NN1] | (S)-8-chloro-4-((3-chloro-4-fluorophenyl)amino)-6-(((1-isopropyl-1H-1,2,3-triazol-4-yl)(1-methyl-1H-pyrazol-5-yl)methyl)amino)quinoline-3-carbonitrile | 2 | ES/MS 550.1 (M + H+) |
| 305 | 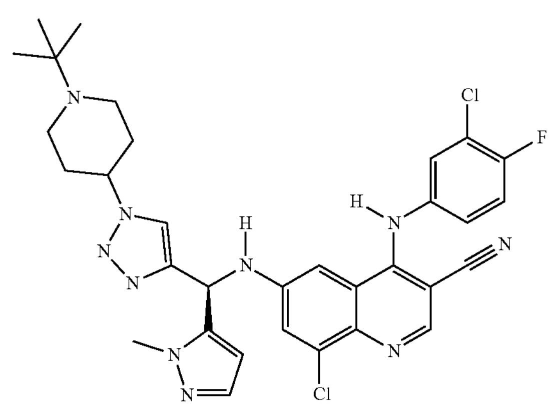 [SMILES: Cn1nccc1[C@H](Nc1cc(Cl)c2ncc(C#N)c(Nc3ccc(F)c(Cl)c3)c2c1)C1=CN(C2CCN(C(C)(C)C)CC2)NN1] | (S)-6-(((1-(1-(tert-butyl)piperidin-4-yl)-1H-1,2,3-triazol-4-yl)(1-methyl-1H-pyrazol-5-yl)methyl)amino)-8-chloro-4-((3-chloro-4-fluorophenyl)amino)quinoline-3-carbonitrile | 2 | ES/MS 647.1 (M + H+) |

TABLE 1-continued

| Comp | Structure | Name | Example Procedure | ES/MS m/z |
|---|---|---|---|---|
| 306 | 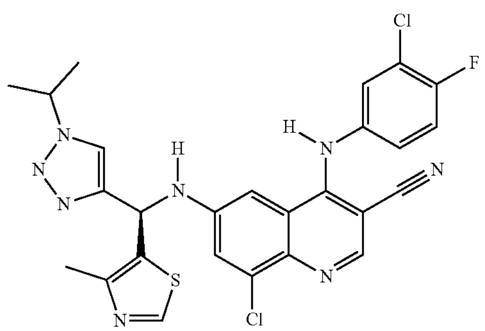 [SMILES: Cc1ncsc1[C@H](Nc1cc(Cl)c2ncc(C#N)c(Nc3ccc(F)c(Cl)c3)c2c1)C1=CN(C(C)C)NN1] | (R)-8-chloro-4-((3-chloro-4-fluorophenyl)amino)-6-(((1-isopropyl-1H-1,2,3-triazol-4-yl)(4-methylthiazol-5-yl)methyl)amino)quinoline-3-carbonitrile | 2 | ES/MS 566.9 (M + H+) |
| 307 | 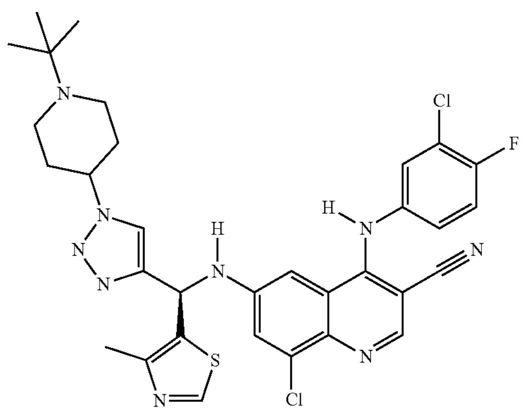 [SMILES: Cc1ncsc1[C@H](Nc1cc(Cl)c2ncc(C#N)c(Nc3ccc(F)c(Cl)c3)c2c1)C1=CN(C2CCN(C(C)(C)C)CC2)NN1] | (R)-6-(((1-(1-(tert-butyl)piperidin-4-yl)-1H-1,2,3-triazol-4-yl)(4-methyl thiazol-5-yl)methyl)amino)-8-chloro-4-((3-chloro-4-fluorophenyl)amino)quinoline-3-carbonitrile | 2 | ES/MS 664.0 (M + H+) |
| 308 | 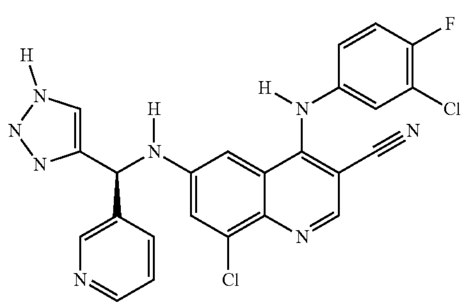 [SMILES: N#Cc1cnc2c(Cl)cc(N[C@H](C3=CNNN3)c3cccnc3)cc2c1Nc1ccc(F)c(Cl)c1] | (S)-8-chloro-4-((3-chloro-4-fluorophenyl)amino)-6-((pyridin-3-yl(1H-1,2,3-triazol-4-yl)methyl)amino)-quinoline-3-carbonitrile | 10 | ES/MS 505.1 (M + H+) |
| 309 | 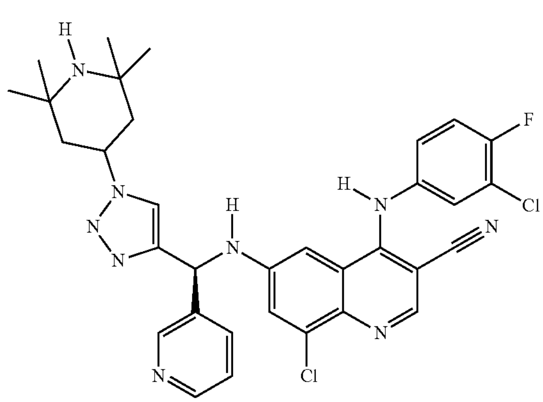 [SMILES: CC1(C)CC(N2C=C([C@@H](Nc3cc(Cl)c4ncc(C#N)c(Nc5ccc(F)c(Cl)c5)c4c3)c3cccnc3)NN2)CC(C)(C)N1] | (S)-8-chloro-4-((3-chloro-4-fluorophenyl)amino)-6-((pyridin-3-yl(1H-2,2,6,6-tetramethylpiperidin-4-yl)-1H-1,2,3-triazol-4-yl)methyl)amino)-quinoline-3-carbonitrile | 8 | ES/MS 644.2 (M + H+) |

TABLE 1-continued

| Comp | Structure | Name | Example Procedure | ES/MS m/z |
|---|---|---|---|---|
| 310 | 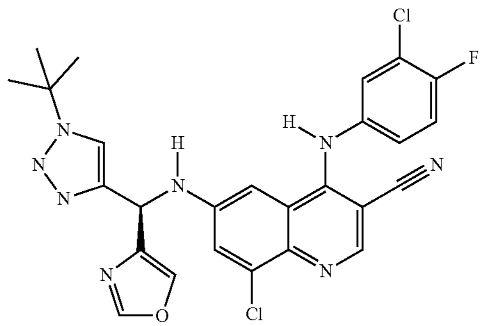 [SMILES: CC(C)(C)N1C=C([C@@H](Nc2cc(Cl)c3ncc(C#N)c(Nc4ccc(F)c(Cl)c4)c3c2)c2cocn2)NN1] | (S)-6-(((1-(tert-butyl)-1H-1,2,3-triazol-4-yl)(oxazol-4-yl)methyl)amino)-8-chloro-4-((3-chloro-4-fluorophenyl)amino)-quinoline-3-carbonitrile | 2 | ES/MS 551.1 (M + H+) |
| 311 | 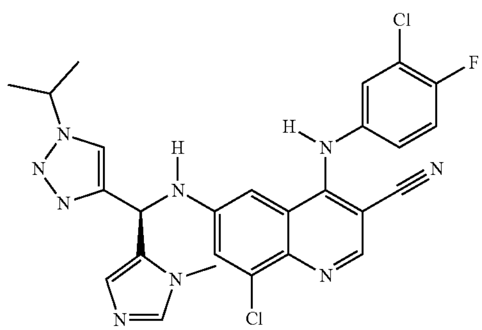 [SMILES: CC(C)N1C=C([C@@H](Nc2cc(Cl)c3ncc(C#N)c(Nc4ccc(F)c(Cl)c4)c3c2)c2cncn2C)NN1] | (S)-8-chloro-4-((3-chloro-4-fluorophenyl)amino)-6-(((1-isopropyl-1H-1,2,3-triazol-4-yl)(1-methyl-1H-imidazol-5-yl)methyl)amino)quinoline-3-carbonitrile | 2 | ES/MS 550.1 (M + H+) |
| 312 | 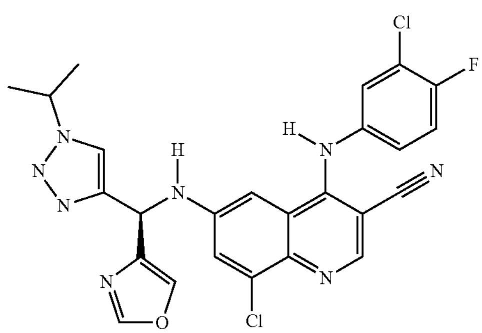 [SMILES: CC(C)N1C=C([C@@H](Nc2cc(Cl)c3ncc(C#N)c(Nc4ccc(F)c(Cl)c4)c3c2)c2cocn2)NN1] | (S)-8-chloro-4-((3-chloro-4-fluorophenyl)amino)-6-(((1-isopropyl-1H-1,2,3-triazol-4-yl)(oxazol-4-yl)methyl)amino)quinoline-3-carbonitrile | 2 | ES/MS 537.0 (M + H+) |
| 313 | 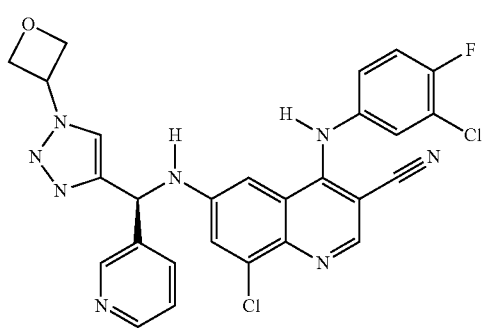 [SMILES: N#Cc1cnc2c(Cl)cc(N[C@H](C3=CN(C4COC4)NN3)c3cccnc3)cc2c1Nc1ccc(F)c(Cl)c1] | (S)-8-chloro-4-((3-chloro-4-fluorophenyl)amino)-6-(((1-(oxetan-3-yl)-1H-1,2,3-triazol-4-yl)(pyridin-3-yl)methyl)amino)quinoline-3-carbonitrile | 8 | ES/MS 505.1 (M + H+) |

TABLE 1-continued

| Comp | Structure | Name | Example Procedure | ES/MS m/z |
|---|---|---|---|---|
| 314 | 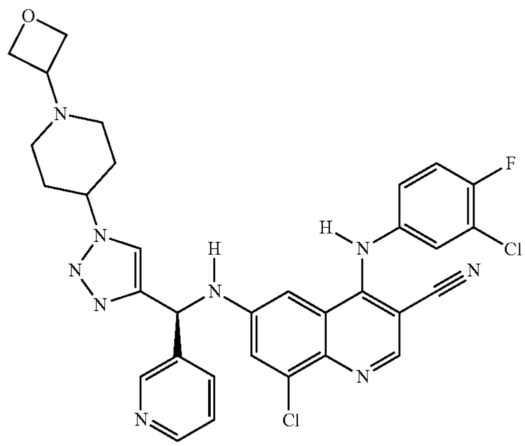 [SMILES: N#Cc1cnc2c(Cl)cc(N[C@H](C3=CN(C4CCN(C5COC5)CC4)NN3)c3cccnc3)cc2c1Nc1ccc(F)c(Cl)c1] | (S)-8-chloro-4-((3-chloro-4-fluorophenyl)amino)-6-(((1-(1-(oxetan-3-yl)piperidin-4-yl)-1H-1,2,3-triazol-4-yl)(pyridin-3-yl)methyl)amino)quinoline-3-carbonitrile | 8 | ES/MS 644.2 (M + H+) |
| 315 | 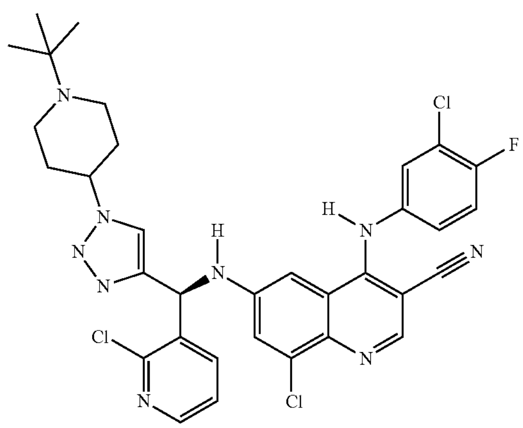 [SMILES: CC(C)(C)N1CCC(N2C=C([C@@H](Nc3cc(Cl)c4ncc(C#N)c(Nc5ccc(F)c(Cl)c5)c4c3)c3cccnc3Cl)NN2)CC1] | (S)-6-(((1-(1-(tert-butyl)piperidin-4-yl)-1H-1,2,3-triazol-4-yl)(2-chloropyridin-3-yl)methyl)arnino)-8-chloro-4-((3-chloro-4-fluorophenyl)amino)quinoline-3-carbonitrile | 1 | ES/MS 680.1 (M + H+) |
| 316 | 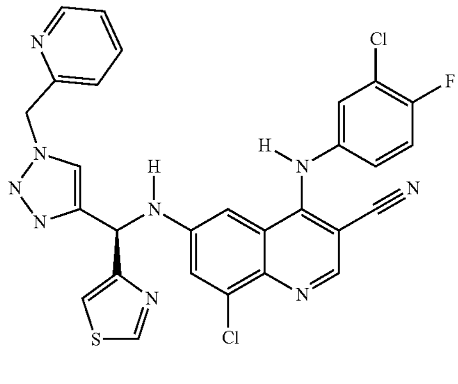 [SMILES: N#Cc1cnc2c(Cl)cc(N[C@H](C3=CN(Cc4ccccn4)NN3)c3cscn3)cc2c1Nc1ccc(F)c(Cl)c1] | (S)-8-chloro-4-((3-chloro-4-fluorophenyl)amino)-6-(((1-(pyridin-2-ylmethyl)-1H-1,2,3-triazol-4-yl)(thiazol-4-yl)methyl)amino)quinoline-3-carbonitrile | 2 | ES/MS 601.9 (M + H+) |

TABLE 1-continued

| Comp | Structure | Name | Example Procedure | ES/MS m/z |
|---|---|---|---|---|
| 317 | 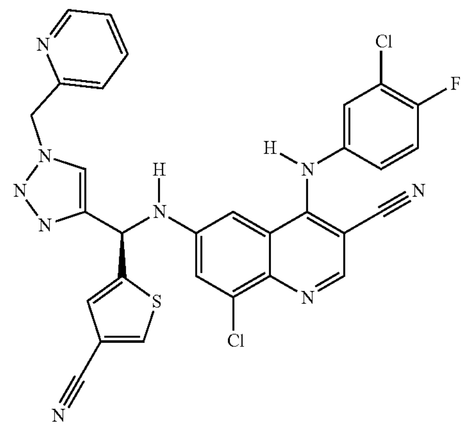 [SMILES: N#Cc1csc([C@H](Nc2cc(Cl)c3ncc(C#N)c(Nc4ccc(F)c(Cl)c4)c3c2)C2=CN(Cc3ccccn3)NN2)c1] | (R)-8-chloro-4-((3-chloro-4-fluorophenyl)amino)-6-(((4-cyanothiophen-2-yl)(1-(pyridin-2-ylmethyl)-1H-1,2,3-triazol-4-yl)methyl)amino)quinoline-3-carbonitrile | 2 | ES/MS 626.0 (M + H+) |
| 318 | 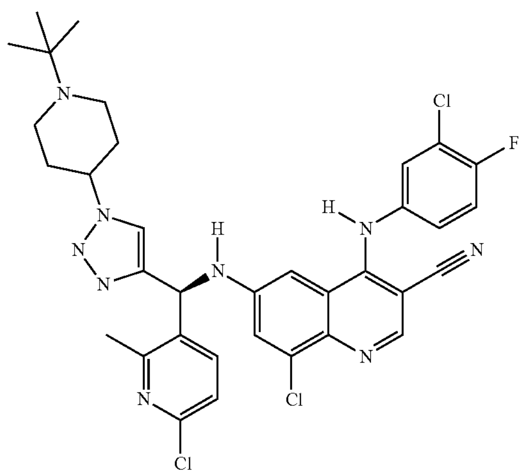 [SMILES: Cc1nc(Cl)ccc1[C@H](Nc1cc(Cl)c2ncc(C#N)c(Nc3ccc(F)c(Cl)c3)c2c1)C1=CN(C2CCN(C(C)(C)C)CC2)NN1] | (S)-6-(((Ml-(tert-butyl)piperidin-4-yl)-1H-1,2,3-triazol-4-yl)(6-chloro-2-methylpyridin-3-yl)methyl)amino)-8-chloro-4-((3-chloro-4-fluorophenyl)amino)quinoline-3-carbonitrile | 1 | ES/MS 692.2 (M + H+) |
| 319 | 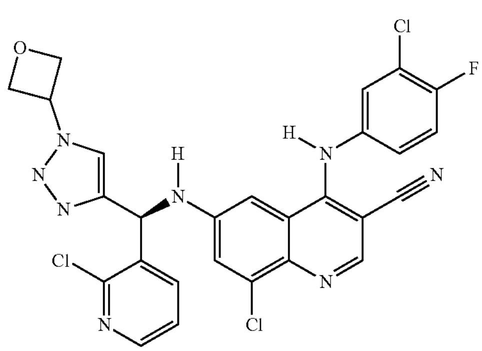 [SMILES: N#Cc1cnc2c(Cl)cc(N[C@H](C3=CN(C4COC4)NN3)c3cccnc3Cl)cc2c1Nc1ccc(F)c(Cl)c1] | (S)-8-chloro-4-((3-chloro-4-fluorophenyl)amino)-6-(((2-chloropyridin-3-yl)(1-(oxetan-3-yl)-1H-1,2,3-triazol-4-yl)methyl)amino)quinoline-3-carbonitrile | 1 | ES/MS 595.0 (M + H+) |

TABLE 1-continued

| Comp | Structure | Name | Example Procedure | ES/MS m/z |
|---|---|---|---|---|
| 320 | 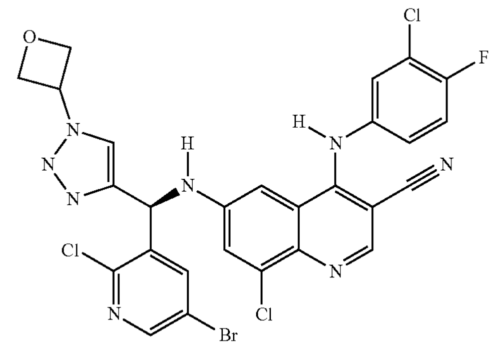 [SMILES: N#Cc1cnc2c(Cl)cc(N[C@H](C3=CN(C4COC4)NN3)c3cc(Br)cnc3Cl)cc2c1Nc1ccc(F)c(Cl)c1] | (S)-6-(((5-bromo-2-chloropyridin-3-yl)(1-(oxetan-3-yl)-1H-1,2,3-triazol-4-yl)methyl)amino)-8-chloro-4-((3-chloro-4-fluorophenyl)amino)quinoline-3-carbonitrile | 1 | ES/MS 675.0 (M + H+) |
| 321 | 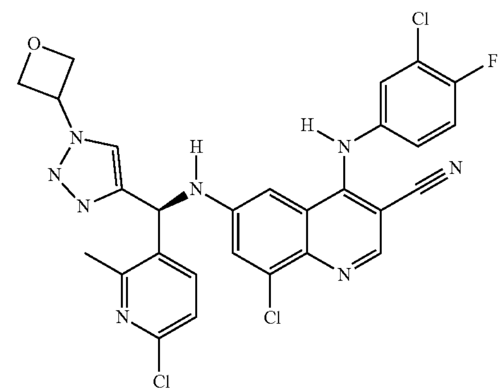 [SMILES: Cc1nc(Cl)ccc1[C@H](Nc1cc(Cl)c2ncc(C#N)c(Nc3ccc(F)c(Cl)c3)c2c1)C1=CN(C2COC2)NN1] | (S)-8-chloro-6-(((6-chloro-2-methyl-pyridin-3-yl)(1-(oxetan-3-yl)-1H-1,2,3-triazol-4-yl)methyl)amino)-4-((3-chloro-4-fluorophenyl)amino)quinoline-3-carbonitrile | 1 | ES/MS 609.1 (M + H+) |
| 322 | 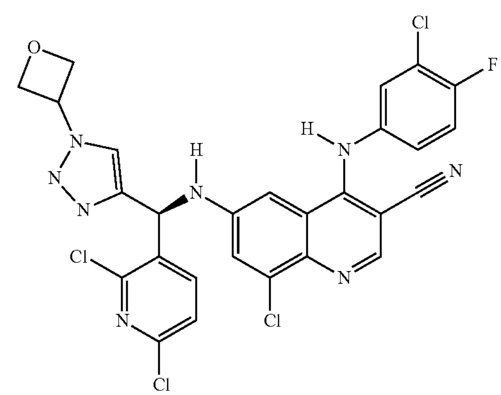 [SMILES: N#Cc1cnc2c(Cl)cc(N[C@H](C3=CN(C4COC4)NN3)c3ccc(Cl)nc3Cl)cc2c1Nc1ccc(F)c(Cl)c1] | (S)-8-chloro-4-((3-chloro-4-fluorophenyl)amino)-6-(((2,6-dichloro-pyridin-3-yl)(1-(oxetan-3-yl)-1H-1,2,3-triazol-4-yl)methyl)amino)quinoline-3-carbonitrile | 1 | ES/MS 631.0 (M + H+) |
| 323 | 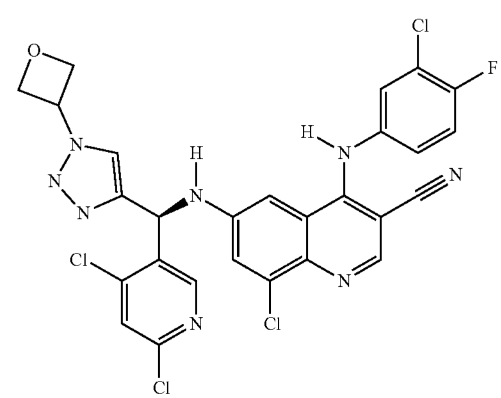 | (S)-8-chloro-4-((3-chloro-4-fluorophenyl)amino)-6-(((4,6-dichloro-pyridin-3-yl)(1-(oxetan-3-yl)-1H-1,2,3-triazol-4-yl)methyl)amino)-quinoline-3-carbonitrile | 1 | ES/MS 631.0 (M + H+) |

TABLE 1-continued

| Comp | Structure | Name | Example Procedure | ES/MS m/z |
|---|---|---|---|---|
| 324 | 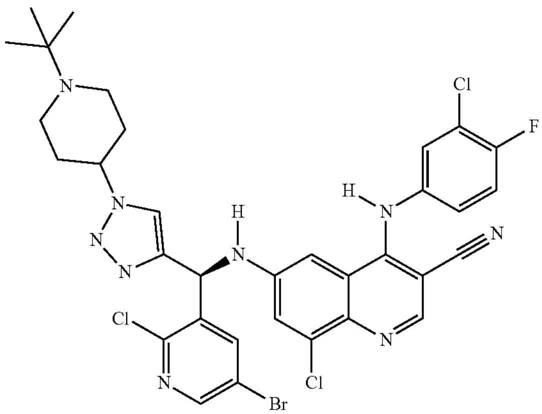 [SMILES: CC(C)(C)N1CCC(N2C=C([C@@H](Nc3cc(Cl)c4ncc(C#N)c(Nc5ccc(F)c(Cl)c5)c4c3)c3cc(Br)cnc3Cl)NN2)CC1] | (S)-6-(((5-bromo-2-chloropyridin-3-yl)(1-(1-(tert-butyl)piperidin-4-yl)-1H-1,2,3-triazol-4-yl)methyl)amino)-8-chloro-4-((3-chloro-4-fluorophenyl)-amino)quinoline-3-carbonitrile | 1 | ES/MS 758.1 (M + H+) |
| 325 | 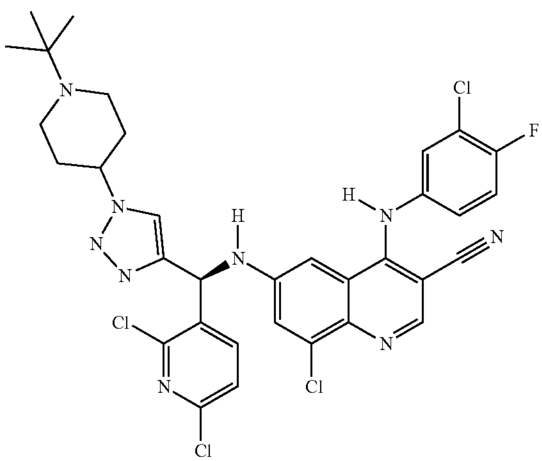 [SMILES: CC(C)(C)N1CCC(N2C=C([C@@H](Nc3cc(Cl)c4ncc(C#N)c(Nc5ccc(F)c(Cl)c5)c4c3)c3ccc(Cl)nc3Cl)NN2)CC1] | (S)-6-(((1-(1-(tert-butyl)piperidin-4-yl)-1H-1,2,3-triazol-4-yl)(2,6-dichloropyridin-3-yl)methyl)amino)-8-chloro-4-((3-chloro-4-fluorophenyl)-amino)quinoline-3-carbonitrile | 1 | ES/MS 714.2 (M + H+) |
| 326 | 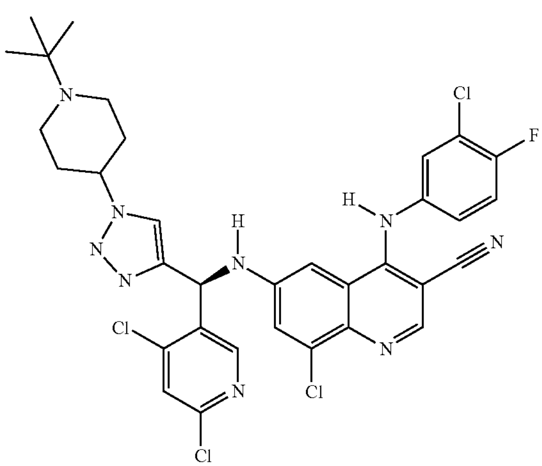 [SMILES: CC(C)(C)N1CCC(N2C=C([C@@H](Nc3cc(Cl)c4ncc(C#N)c(Nc5ccc(F)c(Cl)c5)c4c3)c3cnc(Cl)cc3Cl)NN2)CC1] | (S)-6-(((1-(1-(tert-butyl)piperidin-4-yl)-1H-1,2,3-triazol-4-yl)(4,6-dichloropyridin-3-yl)methyl)amino)-8-chloro-4-((3-chloro-4-fluorophenyl)-amino)quinoline-3-carbonitrile | 1 | ES/MS 714.1 (M + H+) |

TABLE 1-continued

| Comp | Structure | Name | Example Procedure | ES/MS m/z |
|---|---|---|---|---|
| 327 | 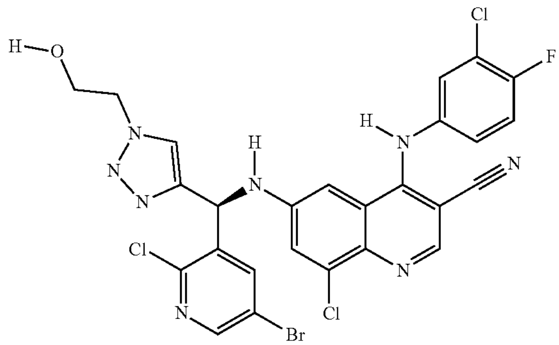 [SMILES: N#Cc1cnc2c(Cl)cc(N[C@H](C3=CN(CCO)NN3)c3cc(Br)cnc3Cl)cc2c1Nc1ccc(F)c(Cl)c1] | (S)-6-(((5-bromo-2-chloropyridin-3-yl)(1-(2-hydroxyethyl)-1H-1,2,3-triazol-4-yl)methyl)amino)-8-chloro-4-((3-chloro-4-fluorophenyl)amino)-quinoline-3-carbonitrile | 1 | ES/MS 663.0 (M + H+) |
| 328 | 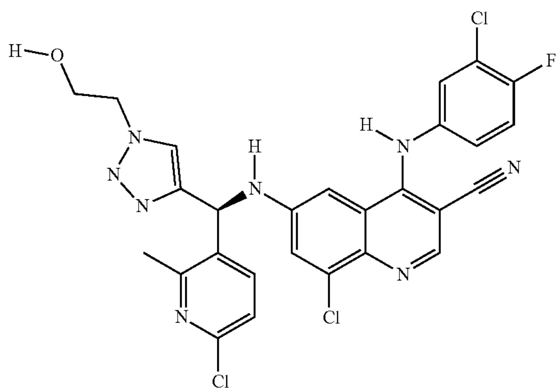 [SMILES: Cc1nc(Cl)ccc1[C@H](Nc1cc(Cl)c2ncc(C#N)c(Nc3ccc(F)c(Cl)c3)c2c1)C1=CN(CCO)NN1] | (S)-8-chloro-6-(((6-chloro-2-methylpyridin-3-yl)(1-(2-hydroxyethyl)-1H-1,2,3-triazol-4-yl)methyl)amino)-4-((3-chloro-4-fluorophenyl)amino)-quinoline-3-carbonitrile | 1 | ES/MS 597.0 (M + H+) |
| 329 | 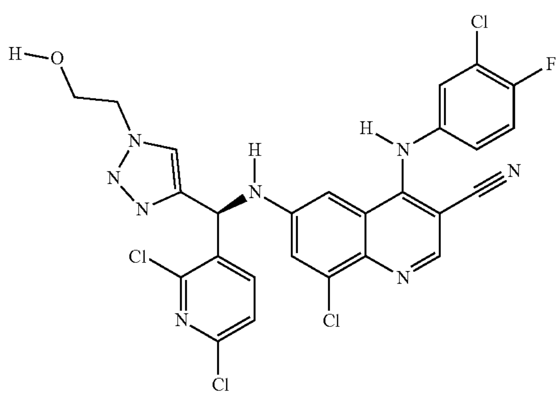 [SMILES: N#Cc1cnc2c(Cl)cc(N[C@H](C3=CN(CCO)NN3)c3ccc(Cl)nc3Cl)cc2c1Nc1ccc(F)c(Cl)c1] | (S)-8-chloro-4-4-((3-chloro-4-fluorophenyl)amino)-6-(((2,6-dichloropyridin-3-yl)(1-(2-hydroxyethyl)-1H-1,2,3-triazol-4-yl)methyl)amino)-quinoline-3-carbonitrile | 1 | ES/MS 619.0 (M + H+) |
| 330 | 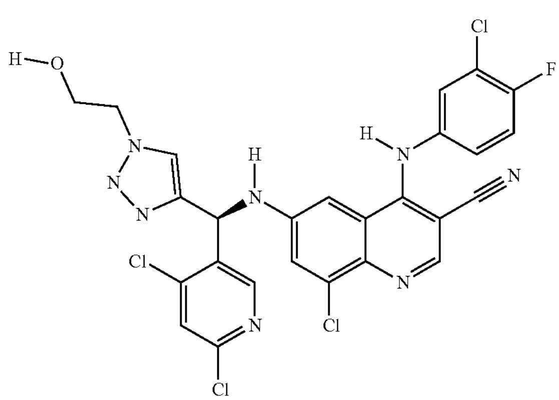 [SMILES: N#Cc1cnc2c(Cl)cc(N[C@H](C3=CN(CCO)NN3)c3cnc(Cl)cc3Cl)cc2c1Nc1ccc(F)c(Cl)c1] | (S)-8-chloro-4-((3-chloro-4-fluorophenyl)amino)-6-(((4,6-dichloropyridin-3-yl)(1-(2-hydroxyethyl)-1H-1,2,3-triazol-4-yl)methyl)-amino)quinoline-3-carbonitrile | 1 | ES/MS 619.0 (M + H+) |

TABLE 1-continued

| Comp | Structure | Name | Example Procedure | ES/MS m/z |
|---|---|---|---|---|
| 331 | 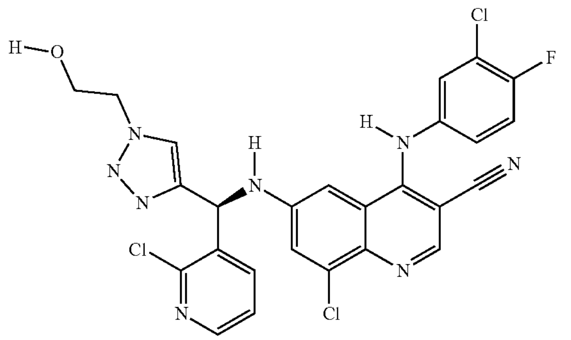 [SMILES: N#Cc1cnc2c(Cl)cc(N[C@H](C3=CN(CCO)NN3)c3cccnc3Cl)cc2c1Nc1ccc(F)c(Cl)c1] | (S)-8-chloro-4-((3-chloro-4-fluorophenyl)amino)-6-(((2-chloropyridin-3-yl)(1-(2-hydroxyethyl)-1H-1,2,3-triazol-4-yl)methyl)amino)quinoline-3-carbonitrile | 1 | ES/MS 583.1 (M + H+) |
| 332 | 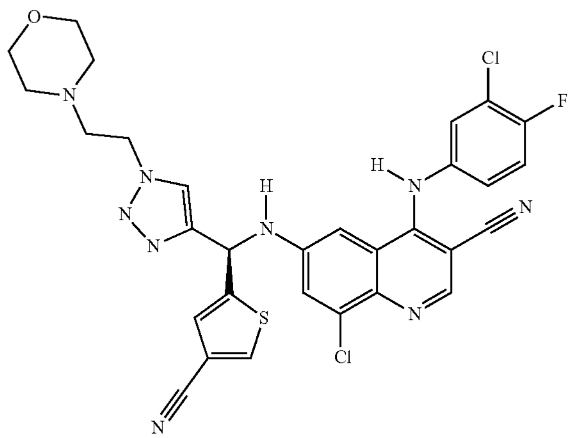 [SMILES: N#Cc1csc([C@H](Nc2cc(Cl)c3ncc(C#N)c(Nc4ccc(F)c(Cl)c4)c3c2)C2=CN(CCN3CCOCC3)NN2)c1] | (R)-8-chloro-4-((3-chloro-4-fluorophenyl)amino)-6-(((4-cyanothiophen-2-yl)(1-(2-morpholinoethyl)-1H-1,2,3-triazol-4-yl)methyl)amino)quinoline-3-carbonitrile | 2 | ES/MS 648.1 (M + H+) |
| 333 | 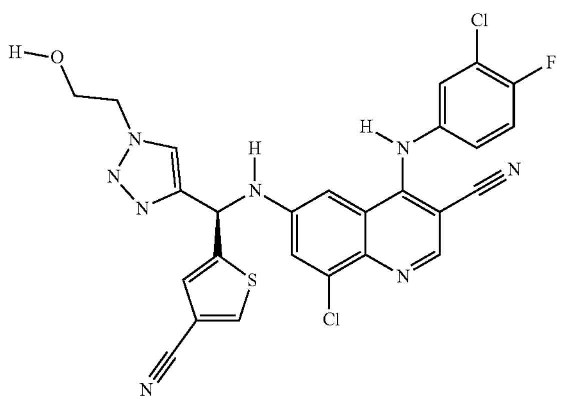 [SMILES: N#Cc1csc([C@H](Nc2cc(Cl)c3ncc(C#N)c(Nc4ccc(F)c(Cl)c4)c3c2)C2=CN(CCO)NN2)c1] | (R)-8-chloro-4-((3-chloro-4-fluorophenyl)amino)-6-(((4-cyanothiophen-2-yl)(1-(2-hydroxyethyl)-1H-1,2,3-triazol-4-yl)methyl)amino)quinoline-3-carbonitrile | 2 | ES/MS 579.0 (M + H+) |
| 334 | 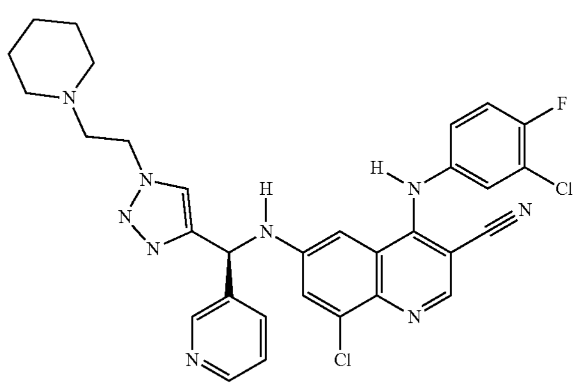 [SMILES: N#Cc1cnc2c(Cl)cc(N[C@H](C3=CN(CCN4CCCCC4)NN3)c3cccnc3)cc2c1Nc1ccc(F)c(Cl)c1] | (S)-8-chloro-4-((3-chloro-4-fluorophenyl)amino)-6-(((1-(2-(piperidin-1-yl)ethyl)-1H-1,2,3-triazol-4-yl)(pyridin-3-yl)methyl)amino)quinoline-3-carbonitrile | 8 | ES/MS 616.2 (M + H+) |

TABLE 1-continued

| Comp | Structure | Name | Example Procedure | ES/MS m/z |
|---|---|---|---|---|
| 335 | 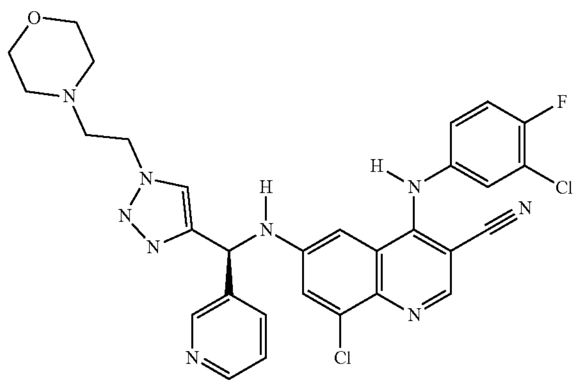 [SMILES: N#Cc1cnc2c(Cl)cc(N[C@H](C3=CN(CCN4CCOCC4)NN3)c3cccnc3)cc2c1Nc1ccc(F)c(Cl)c1] | (S)-8-chloro-4-((3-chloro-4-fluorophenyl)amino)-6-(((1-(2-morpholinoethyl)-1H-1,2,3-triazol-4-yl)(pyridin-3-yl)methyl)amino)-quinoline-3-carbonitrile | 8 | ES/MS 570.2 (M + H+) |
| 336 | 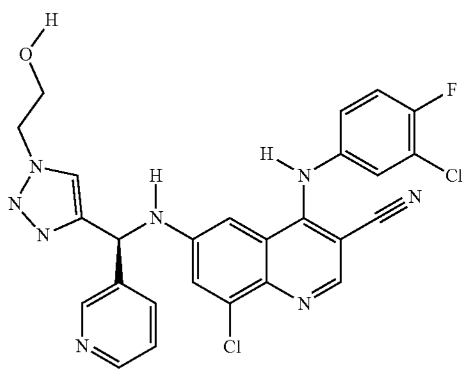 [SMILES: N#Cc1cnc2c(Cl)cc(N[C@H](C3=CN(CCO)NN3)c3cccnc3)cc2c1Nc1ccc(F)c(Cl)c1] | (S)-8-chloro-4-((3-chloro-4-fluorophenyl)amino)-6-(((1-(2-hydroxyethyl)-1H-1,2,3-triazol-4-yl)(pyridin-3-yl)methyl)amino)quinoline-3-carbonitrile | 8 | ES/MS 549.1 (M + H+) |
| 337 | 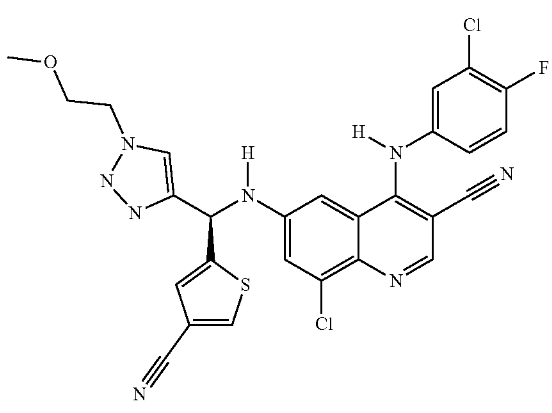 [SMILES: COCCN1C=C([C@@H](Nc2cc(Cl)c3ncc(C#N)c(Nc4ccc(F)c(Cl)c4)c3c2)c2cc(C#N)cs2)NN1] | (R)-8-chloro-4-((3-chloro-4-fluorophenyl)amino)-6-(((4-cyanothiophen-2-yl)(1-(2-methoxyethyl)-1H-1,2,3-triazol-4-yl)methyl)amino)quinoline-3-carbonitrile | 2 | ES/MS 593.0 (M + H+) |

TABLE 1-continued

| Comp | Structure | Name | Example Procedure | ES/MS m/z |
|---|---|---|---|---|
| 338 | 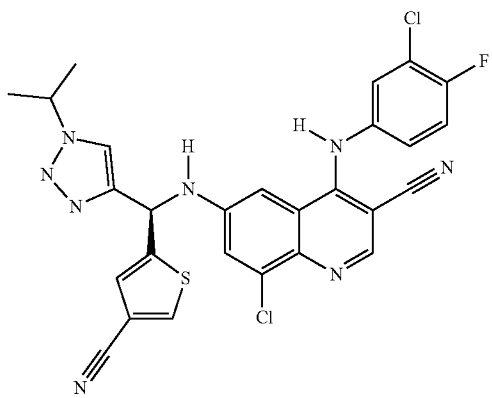 [SMILES: CC(C)N1C=C([C@@H](Nc2cc(Cl)c3ncc(C#N)c(Nc4ccc(F)c(Cl)c4)c3c2)c2cc(C#N)cs2)NN1] | (R)-8-chloro-4-((3-chloro-4-fluorophenyl)amino)-6-(((4-cyanothiophen-2-yl)(1-isopropyl-1H-1,2,3-triazol-4-yl)methyl)-amino)quinoline-3-carbonitrile | 2 | ES/MS 577.0 (M + H+) |
| 339 | 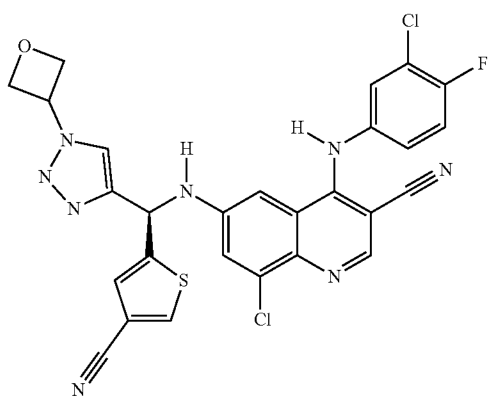 [SMILES: N#Cc1csc([C@H](Nc2cc(Cl)c3ncc(C#N)c(Nc4ccc(F)c(Cl)c4)c3c2)C2=CN(C3COC3)NN2)c1] | (R)-8-chloro-4-((3-chloro-4-fluorophenyl)amino)-6-(((4-cyanothiophen-2-yl)(1-(oxetan-3-yl)-1H-1,2,3-triazol-4-yl)methyl)amino)-quinoline-3-carbonitrile | 2 | ES/MS 591.0 (M + H+) |
| 340 | 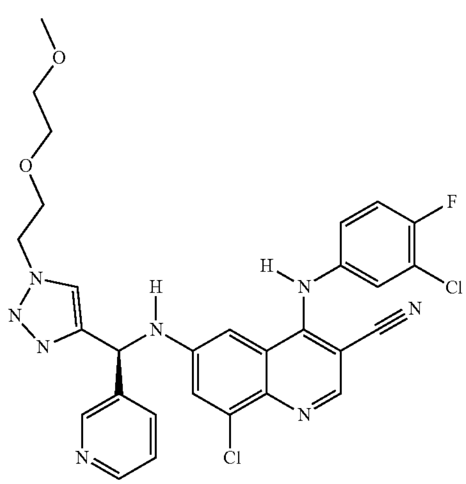 [SMILES: COCCOCCN1C=C([C@@H](Nc2cc(Cl)c3ncc(C#N)c(Nc4ccc(F)c(Cl)c4)c3c2)c2cccnc2)NN1] | (S)-8-chloro-4-((3-chloro-4-fluorophenyl)amino)-6-(((1-(2-(2-methoxyethoxy)ethyl)-1H-1,2,3-triazol-4-yl)(pyridin-3-yl)methyl)-amino)quinoline-3-carbonitrile | 8 | ES/MS 607.2 (M + H+) |

TABLE 1-continued

| Comp | Structure | Name | Example Procedure | ES/MS m/z |
|---|---|---|---|---|
| 341 | 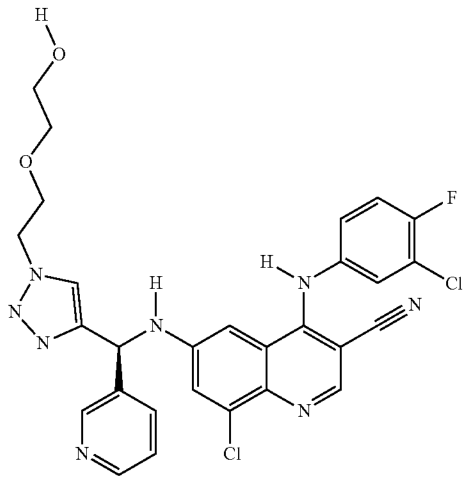 [SMILES: N#Cc1cnc2c(Cl)cc(N[C@H](C3=CN(CCOCCO)NN3)c3cccnc3)cc2c1Nc1ccc(F)c(Cl)c1] | (S)-8-chloro-4-((3-chloro-4-fluorophenyl)amino)-6-(((1-(2-(2-hydroxyethoxy)ethyl)-1H-1,2,3-triazol-4-yl)(pyridin-3-yl)methyl)amino)quinoline-3-carbonitrile | 8 | ES/MS 593.2 (M + H+) |
| 342 | 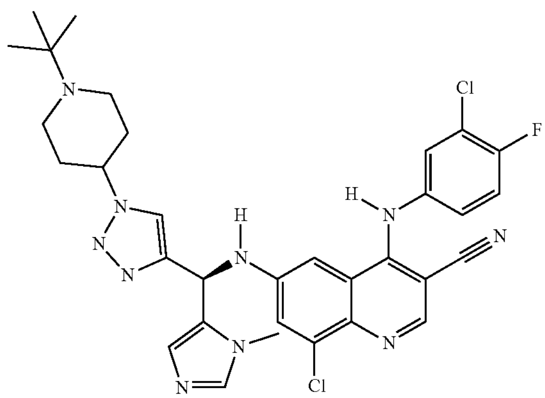 [SMILES: Cn1cncc1[C@H](Nc1cc(Cl)c2ncc(C#N)c(Nc3ccc(F)c(Cl)c3)c2c1)C1=CN(C2CCN(C(C)(C)C)CC2)NN1] | (S)-6-(((1-(1-(tert-butyl)piperidin-4-yl)-1H-1,2,3-triazol-4-yl)(1-methyl-1H-imidazol-5-yl)methyl)amino)-8-chloro-4-((3-chloro-4-fluorophenyl)amino)quinoline-3-carbonitrile | 2 | ES/MS 647.0 (M + H+) |
| 343 | 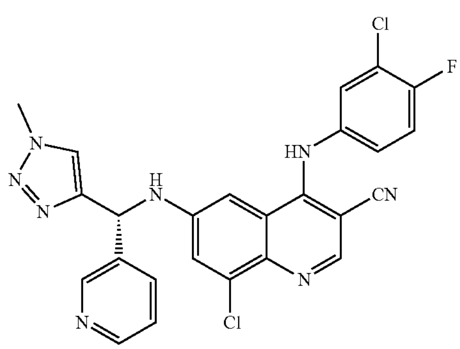 [SMILES: Cn1cc([C@H](Nc2cc(Cl)c3ncc(C#N)c(Nc4ccc(F)c(Cl)c4)c3c2)c2cccnc2)nn1] | (R)-8-chloro-4-((3-chloro-4-fluorophenyl)amino)-6-(((1-methyl-1H-1,2,3-triazol-4-yl)(pyridin-3-yl)methyl)amino)quinoline-3-carbonitrile | 6 | |

TABLE 1-continued

| Comp | Structure | Name | Example Procedure | ES/MS m/z |
|---|---|---|---|---|
| 344 | 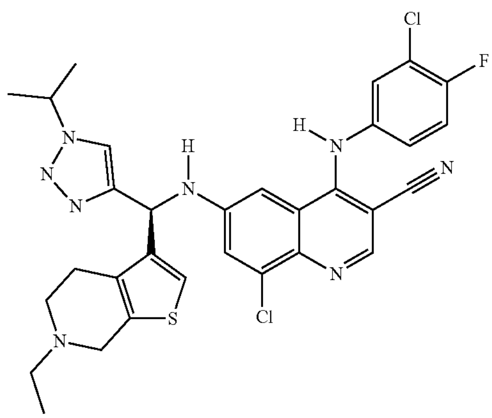 [SMILES: CCN1CCc2c([C@H](Nc3cc(Cl)c4ncc(C#N)c(Nc5ccc(F)c(Cl)c5)c4c3)C3=CN(C(C)C)NN3)csc2C1] | (S)-8-chloro-4-((3-chloro-4-fluorophenyl)amino)-6-(((6-ethyl-4,5,6,7-tetrahydrothieno[2,3-c]pyridin-3-yl)(1-isopropyl-1H-1,2,3-triazol-4-yl)methyl)amino)quinoline-3-carbonitrile | 5 | ES/MS 635.0 (M + H+) |
| 345 | 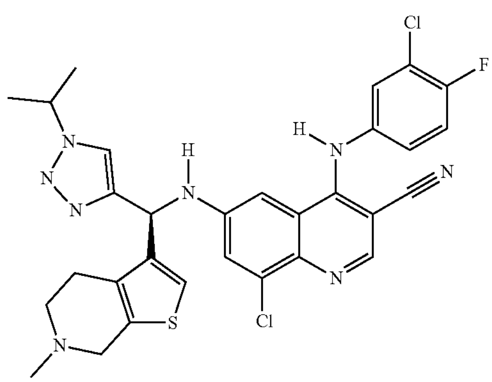 [SMILES: CC(C)N1C=C([C@@H](Nc2cc(Cl)c3ncc(C#N)c(Nc4ccc(F)c(Cl)c4)c3c2)c2csc3c2CCN(C)C3)NN1] | (S)-8-chloro-4-((3-chloro-4-fluorophenyl)amino)-6-(((1-isopropyl-1H-1,2,3-triazol-4-yl)(6-methyl-4,5,6,7-tetrahydrothieno[2,3-c]pyridin-3-yl)methyl)amino)quinoline-3-carbonitrile | 5 | ES/MS 620.9 (M + H+) |
| 346 | 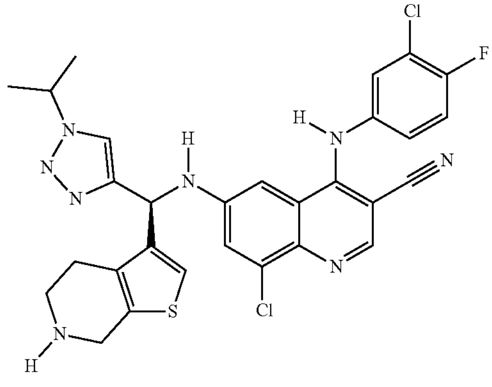 [SMILES: CC(C)N1C=C([C@@H](Nc2cc(Cl)c3ncc(C#N)c(Nc4ccc(F)c(Cl)c4)c3c2)c2csc3c2CCNC3)NN1] | (S)-8-chloro-4-((3-chloro-4-fluorophenyl)amino)-6-(((1-isopropyl-1H-1,2,3-triazol-4-yl)(4,5,6,7-tetrahydrothieno[2,3-c]pyridin-3-yl)methyl)amino)quinoline-3-carbonitrile | 5 | ES/MS 606.9 (M + H+) |

TABLE 1-continued

| Comp | Structure | Name | Example Procedure | ES/MS m/z |
|---|---|---|---|---|
| 347 | 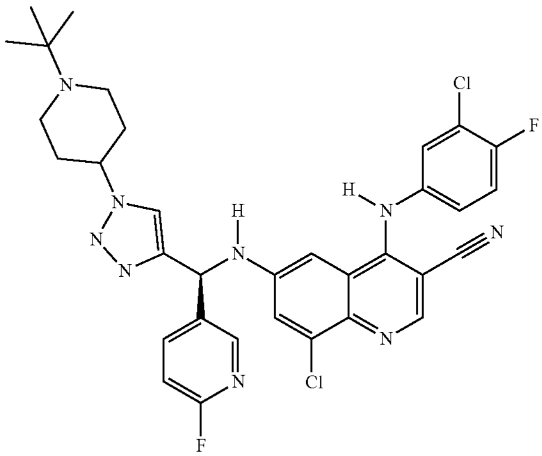 [SMILES: CC(C)(C)N1CCC(N2C=C([C@@H](Nc3cc(Cl)c4ncc(C#N)c(Nc5ccc(F)c(Cl)c5)c4c3)c3ccc(F)nc3)NN2)CC1] | (S)-6-(((1-(1-(tert-butyl)piperidin-4-yl)-1H-1,2,3-triazol-4-yl)(6-fluoropyridin-3-yl)methyl)amino)-8-chloro-4-((3-chloro-4-fluorophenyl)amino)quinoline-3-carbonitrile | 2 | ES/MS 662.1 (M + H+) |
| 348 | 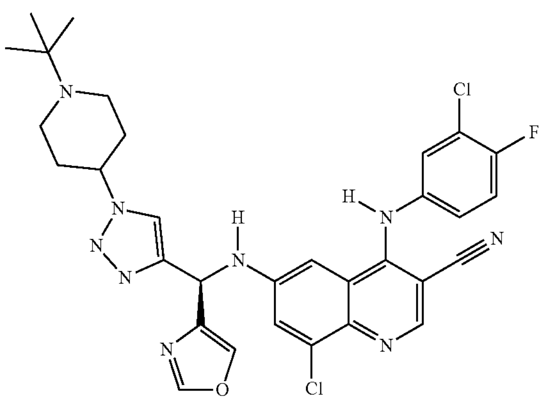 [SMILES: CC(C)(C)N1CCC(N2C=C([C@@H](Nc3cc(Cl)c4ncc(C#N)c(Nc5ccc(F)c(Cl)c5)c4c3)c3cocn3)NN2)CC1] | (S)-6-(((1-(1-(tert-butyl)piperidin-4-yl)-1H-1,2,3-triazol-4-yl)(oxazol-4-yl)methyl)amino)-8-chloro-4-((3-chloro-4-fluorophenyl)amino)-quinoline-3-carbonitrile | 2 | ES/MS 634.1 (M + H+) |
| 349 | 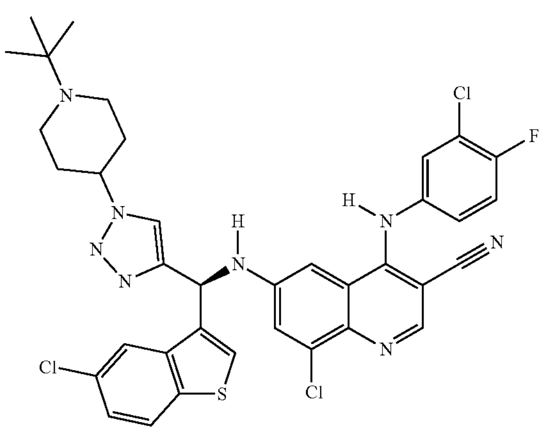 [SMILES: CC(C)(C)N1CCC(N2C=C([C@@H](Nc3cc(Cl)c4ncc(C#N)c(Nc5ccc(F)c(Cl)c5)c4c3)c3csc4ccc(Cl)cc34)NN2)CC1] | (S)-6-(((1-(1-(tert-butyl)piperidin-4-yl)-1H-1,2,3-triazol-4-yl)(5-chlorobenzo[b]-thiophen-3-yl)methyl)amino)-8-chloro-4-((3-chloro-4-fluorophenyl)amino)quinoline-3-carbonitrile | 2 | ES/MS 735.0 (M + H+) |

TABLE 1-continued

| Comp | Structure | Name | Example Procedure | ES/MS m/z |
|---|---|---|---|---|
| 350 | 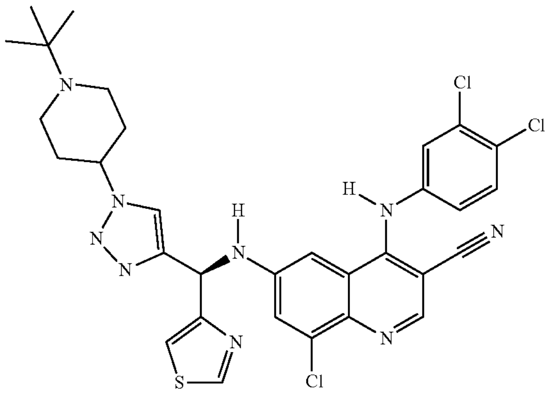 [SMILES: CC(C)(C)N1CCC(N2C=C([C@@H](Nc3cc(Cl)c4ncc(C#N)c(Nc5ccc(Cl)c(Cl)c5)c4c3)c3cscn3)NN2)CC1] | (S)-6-(((1-(1-(tert-butyl)piperidin-4-yl)-1H-1,2,3-triazol-4-yl)(thiazol-4-yl)methyl)amino)-8-chloro-4-((3,4-dichlorophenyl)amino)quinoline-3-carbonitrile | 2 | ES/MS 665.9 (M + H+) |
| 351 | 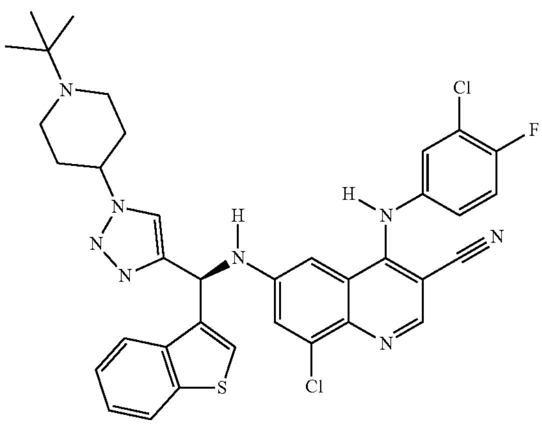 [SMILES: CC(C)(C)N1CCC(N2C=C([C@@H](Nc3cc(Cl)c4ncc(C#N)c(Nc5ccc(F)c(Cl)c5)c4c3)c3csc4ccccc34)NN2)CC1] | (S)-6-((benzo[b]thiophen-3-yl(1-(1-(tert-butyl)piperidin-4-yl)-1H-1,2,3-triazol-4-yl)methyl)amino)-8-chloro-4-((3-chloro-4-fluorophenyl)amino)-quinoline-3-carbonitrile | 2 | ES/MS 699.7 (M + H+) |
| 352 | 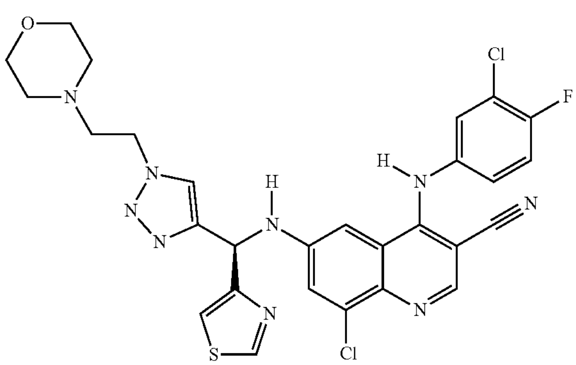 [SMILES: N#Cc1cnc2c(Cl)cc(N[C@H](C3=CN(CCN4CCOCC4)NN3)c3cscn3)cc2c1Nc1ccc(F)c(Cl)c1] | (S)-8-chloro-4-((3-chloro-4-fluorophenyl)amino)-6-(((1-(2-morpholinoethyl)-1H-1,2,3-triazol-4-yl)(thiazol-4-yl)methyl)amino)-quinoline-3-carbonitrile | 2 | ES/MS 624.1 (M + H+) |

TABLE 1-continued

| Comp | Structure | Name | Example Procedure | ES/MS m/z |
|---|---|---|---|---|
| 353 | 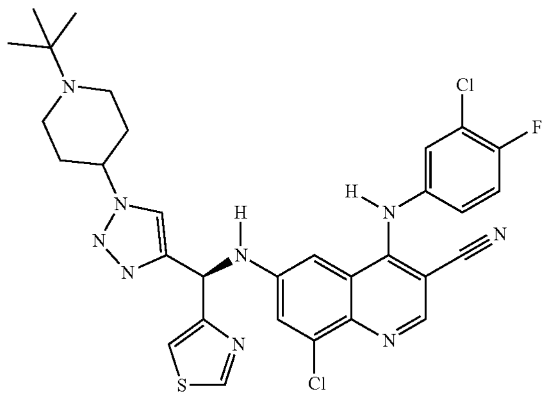 [SMILES: CC(C)(C)N1CCC(N2C=C([C@@H](Nc3cc(Cl)c4ncc(C#N)c(Nc5ccc(F)c(Cl)c5)c4c3)c3cscn3)NN2)CC1] | (S)-6-(((1-(1-(tert-butyl)piperidin-4-yl)-1H-1,2,3-triazol-4-yl)(thiazol-4-yl)methyl)amino)-8-chloro-4-((3-chloro-4-fluorophenyl)amino)-quinoline-3-carbonitrile | 2 | ES/MS 650.1 (M + H+) |
| 354 | 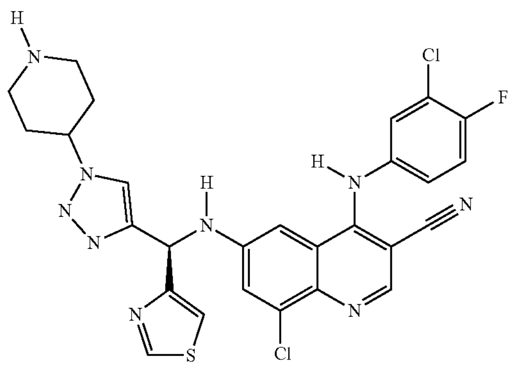 [SMILES: N#Cc1cnc2c(Cl)cc(N[C@H](C3=CN(C4CCNCC4)NN3)c3cscn3)cc2c1Nc1ccc(F)c(Cl)c1] | (S)-8-chloro-4-((3-chloro-4-fluorophenyl)amino)-6-(((1-(piperidin-4-yl)-1H-1,2,3-triazol-4-yl)(thiazol-4-yl)methyl)amino)-quinoline-3-carbonitrile | 5 | ES/MS 594.0 (M + H+) |
| 355 | 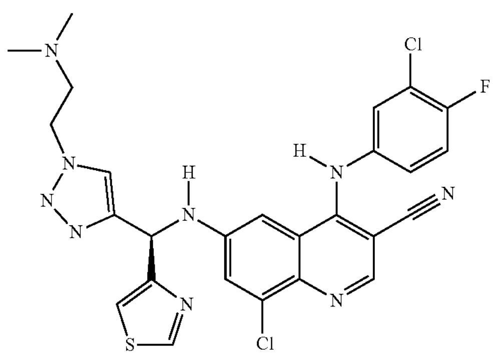 [SMILES: CN(C)CCN1C=C([C@@H](Nc2cc(Cl)c3ncc(C#N)c(Nc4ccc(F)c(Cl)c4)c3c2)c2cscn2)NN1] | (S)-8-chloro-4-((3-chloro-4-fluorophenyl)amino)-6-(((1-(2-(dimethylamino)ethyl)-1H-1,2,3-triazol-4-yl)(thiazol-4-yl)methyl)-amino)quinoline-3-carbonitrile | 2 | ES/MS 581.9 (M + H+) |
| 356 | 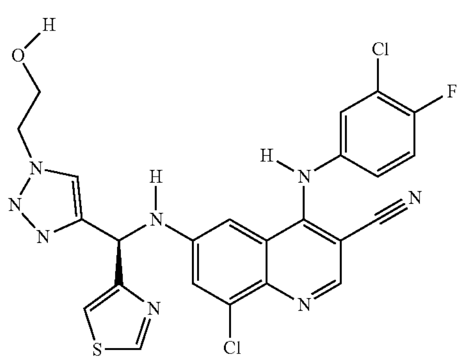 [SMILES: N#Cc1cnc2c(Cl)cc(N[C@H](C3=CN(CCO)NN3)c3cscn3)cc2c1Nc1ccc(F)c(Cl)c1] | (S)-8-chloro-4-((3-chloro-4-fluorophenyl)amino)-6-(((1-(2-hydroxyethyl)-1H-1,2,3-triazol-4-yl)(thiazol-4-yl)methyl)amino)-quinoline-3-carbonitrile | 2 | ES/MS 555.0 (M + H+) |

TABLE 1-continued

| Comp | Structure | Name | Example Procedure | ES/MS m/z |
|---|---|---|---|---|
| 357 | 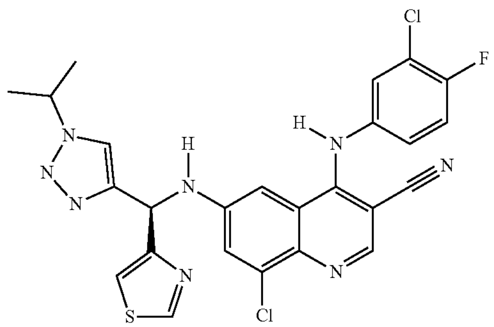 [SMILES: CC(C)N1C=C([C@@H](Nc2cc(Cl)c3ncc(C#N)c(Nc4ccc(F)c(Cl)c4)c3c2)c2cscn2)NN1] | (S)-8-chloro-4-((3-chloro-4-fluorophenyl)amino)-6-(((1-isopropyl-1H-1,2,3-triazol-4-yl)(thiazol-4-yl)methyl)amino)quinoline-3-carbonitrile | 2 | ES/MS 553.0 (M + H+) |
| 358 | 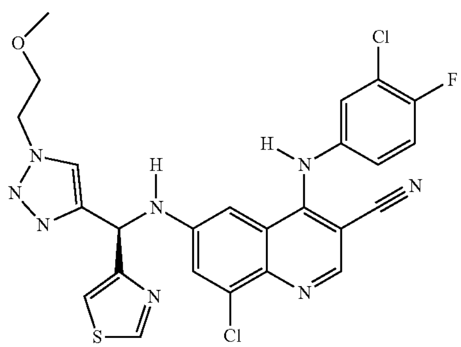 [SMILES: COCCN1C=C([C@@H](Nc2cc(Cl)c3ncc(C#N)c(Nc4ccc(F)c(Cl)c4)c3c2)c2cscn2)NN1] | (S)-8-chloro-4-((3-chloro-4-fluorophenyl)amino)-6-(((1-(2-methoxyethyl)-1H-1,2,3-triazol-4-yl)(thiazol-4-yl)methyl)amino)-quinoline-3-carbonitrile | 2 | ES/MS 569.0 (M + H+) |
| 359 | 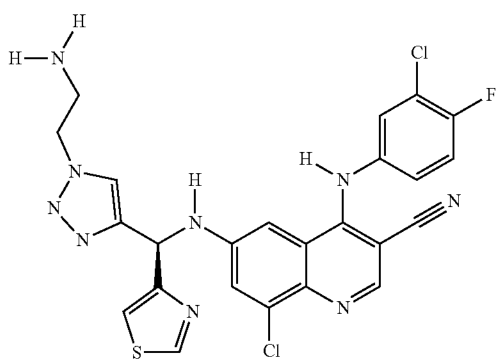 [SMILES: N#Cc1cnc2c(Cl)cc(N[C@H](C3=CN(CCN)NN3)c3cscn3)cc2c1Nc1ccc(F)c(Cl)c1] | (S)-6-(((1-(2-aminoethyl)-1H-1,2,3-triazol-4-yl)(thiazol-4-yl)methyl)-amino)-8-chloro-4-((3-chloro-4-fluorophenyl)amino)quinoline-3-carbonitrile | 2 | ES/MS 553.9 (M + H+) |
| 360 | 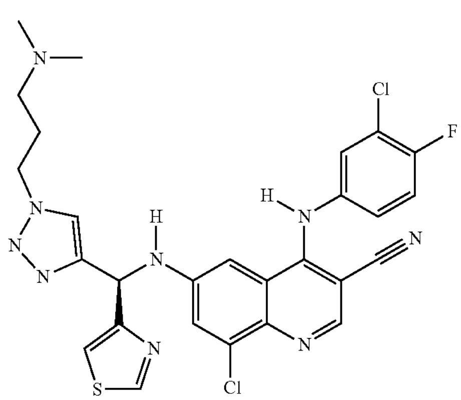 [SMILES: CN(C)CCCN1C=C([C@@H](Nc2cc(Cl)c3ncc(C#N)c(Nc4ccc(F)c(Cl)c4)c3c2)c2cscn2)NN1] | (S)-8-chloro-4-((3-chloro-4-fluorophenyl)amino)-6-(((1-(3-(dimethylamino)propyl)-1H-1,2,3-triazol-4-yl)(thiazol-4-yl)methyl)-amino)quinoline-3-carbonitrile | 2 | ES/MS 596.0 (M + H+) |

TABLE 1-continued

| Comp | Structure | Name | Example Procedure | ES/MS m/z |
|---|---|---|---|---|
| 361 | 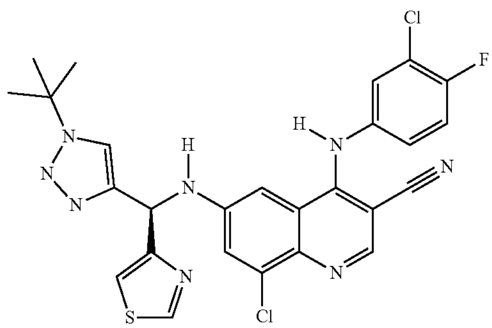 [SMILES: CC(C)(C)N1C=C([C@@H](Nc2cc(Cl)c3ncc(C#N)c(Nc4ccc(F)c(Cl)c4)c3c2)c2cscn2)NN1] | (S)-6-(((1-(tert-butyl)-1H-1,2,3-triazol-4-yl)(thiazol-4-yl)methyl)-amino)-8-chloro-4-((3-chloro-4-fluorophenyl)amino)quinoline-3-carbonitrile | 2 | ES/MS 567.0 (M + H+) |
| 362 | 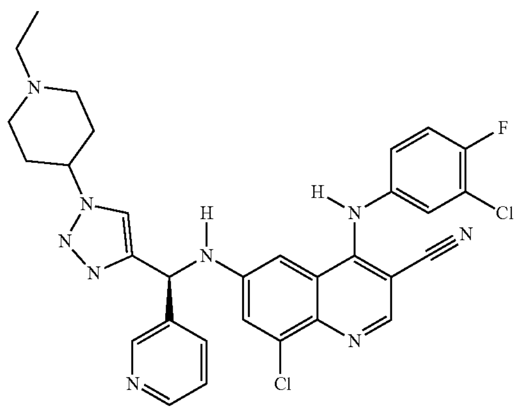 [SMILES: CCN1CCC(N2C=C([C@@H](Nc3cc(Cl)c4ncc(C#N)c(Nc5ccc(F)c(Cl)c5)c4c3)c3cccnc3)NN2)CC1] | (S)-8-chloro-4-((3-chloro-4-fluorophenyl)amino)-6-(((1-(1-ethylpiperidin-4-yl)-1H-1,2,3-triazol-4-yl)(pyridin-3-yl)methyl)amino)-quinoline-3-carbonitrile | 5 | ES/MS 616.1 (M + H+) |
| 363 | 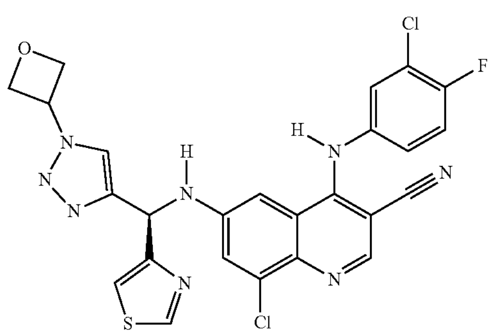 [SMILES: N#Cc1cnc2c(Cl)cc(N[C@H](C3=CN(C4COC4)NN3)c3cscn3)cc2c1Nc1ccc(F)c(Cl)c1] | (S)-8-chloro-4-((3-chloro-4-fluorophenyl)amino)-6-(((1-(oxetan-3-yl)-1H-1,2,3-triazol-4-yl)(thiazol-4-yl)methyl)amino)quinoline-3-carbonitrile | 2 | ES/MS 567.0 (M + H+) |
| 364 | 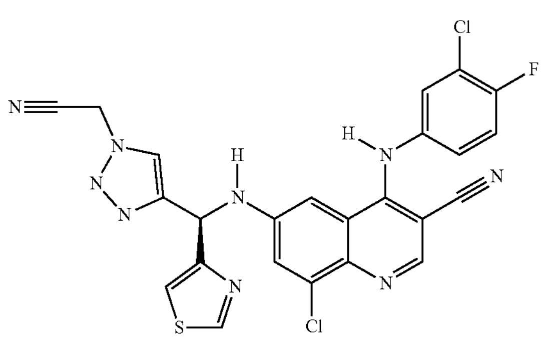 [SMILES: N#CCN1C=C([C@@H](Nc2cc(Cl)c3ncc(C#N)c(Nc4ccc(F)c(Cl)c4)c3c2)c2cscn2)NN1] | (S)-8-chloro-4-((3-chloro-4-fluorophenyl)amino)-6-(((1-(cyanomethyl)-1H-1,2,3-triazol-4-yl)(thiazol-4-yl)methyl)amino)-quinoline-3-carbonitrile | 2 | ES/MS 550.0 (M + H+) |

TABLE 1-continued

| Comp | Structure | Name | Example Procedure | ES/MS m/z |
|---|---|---|---|---|
| 365 | 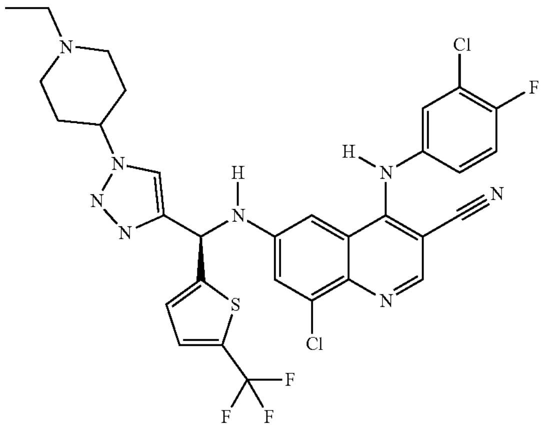 [SMILES: CCN1CCC(N2C=C([C@@H](Nc3cc(Cl)c4ncc(C#N)c(Nc5ccc(F)c(Cl)c5)c4c3)c3ccc(C(F)(F)F)s3)NN2)CC1] | (R)-8-chloro-4-((3-chloro-4-fluorophenyl)amino)-6-(((1-(1-ethylpiperidin-4-yl)-1H-1,2,3-triazol-4-yl)(5-(trifluoromethyl)thiophen-2-yl)methyl)amino)quinoline-3-carbonitrile | 5 | ES/MS 689.1 (M + H+) |
| 366 | 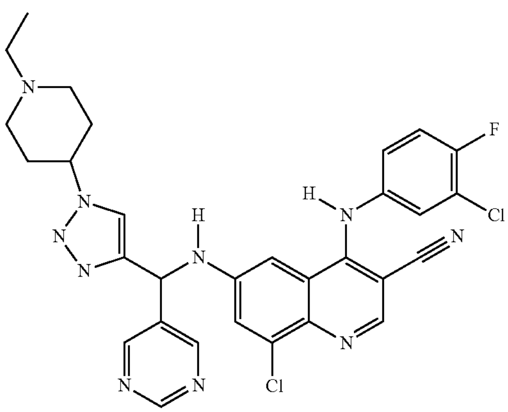 [SMILES: CCN1CCC(N2C=C(C(Nc3cc(Cl)c4ncc(C#N)c(Nc5ccc(F)c(Cl)c5)c4c3)c3cncnc3)NN2)CC1] | 8-chloro-4-((3-chloro-4-fluorophenyl)amino)-6-(((1-(1-ethylpiperidin-4-yl)-1H-1,2,3-triazol-4-yl)(pyrimidin-5-yl)methyl)amino)quinoline-3-carbonitrile | 7 | ES/MS 617.1 (M + H+). |
| 367 | 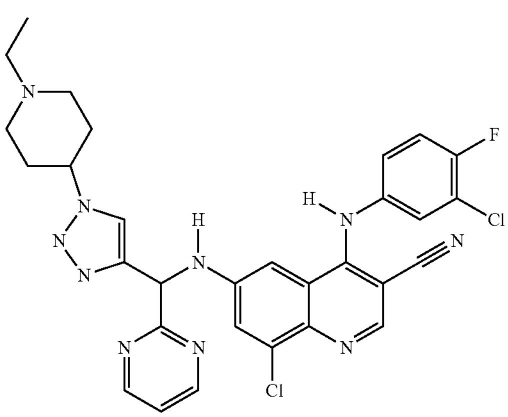 [SMILES: CCN1CCC(N2C=C(C(Nc3cc(Cl)c4ncc(C#N)c(Nc5ccc(F)c(Cl)c5)c4c3)c3ncccn3)NN2)CC1] | 8-chloro-4-((3-chloro-4-fluorophenyl)amino)-6-(((1-(1-ethylpiperidin-4-yl)-1H-1,2,3-triazol-4-yl)(pyrimidin-2-yl)methyl)amino)quinoline-3-carbonitrile | 7 | ES/MS 617.2 (M + H+) |

TABLE 1-continued

| Comp | Structure | Name | Example Procedure | ES/MS m/z |
|---|---|---|---|---|
| 368 | 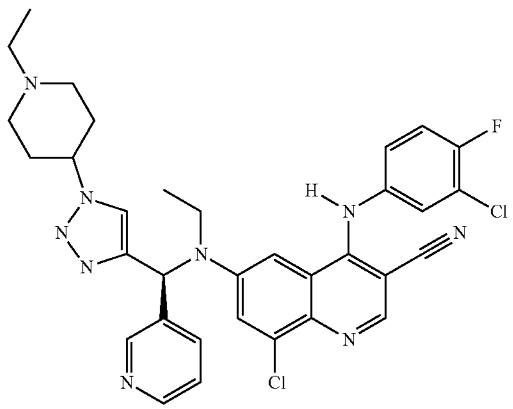 [SMILES: CCN1CCC(N2C=C([C@H](c3cccnc3)N(CC)c3cc(Cl)c4ncc(C#N)c(Nc5ccc(F)c(Cl)c5)c4c3)NN2)CC1] | (S)-8-chloro-4-((3-chloro-4-fluorophenyl)amino)-6-(ethyl((1-(1-ethylpiperidin-4-yl)-1H-1,2,3-triazol-4-yl)(pyridin-3-yl)methyl)-amino)quinoline-3-carbonitrile | 8 | ES/MS 644.2 (M + H+). |
| 369 | 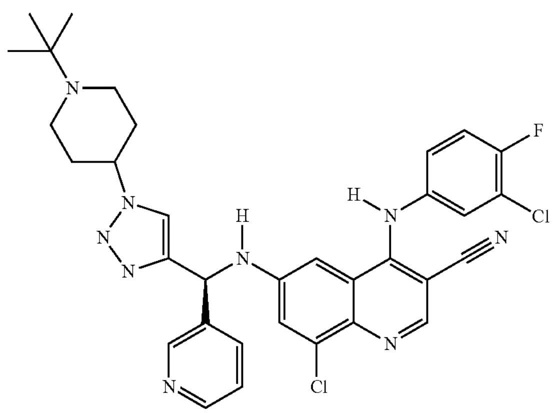 [SMILES: CC(C)(C)N1CCC(N2C=C([C@@H](Nc3cc(Cl)c4ncc(C#N)c(Nc5ccc(F)c(Cl)c5)c4c3)c3cccnc3)NN2)CC1] | (S)-6-(((1-(1-(tert-butyl)piperidin-4-yl)-1H-1,2,3-triazol-4-yl)(pyridin-3-yl)methyl)amino)-8-chloro-4-((3-chloro-4-fluorophenyl)amino)quinoline-3-carbonitrile | 8 | ES/MS 644.2 (M + H+) |
| 370 | 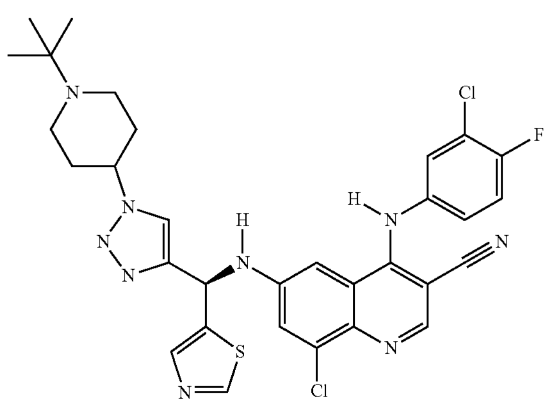 [SMILES: CC(C)(C)N1CCC(N2C=C([C@@H](Nc3cc(Cl)c4ncc(C#N)c(Nc5ccc(F)c(Cl)c5)c4c3)c3cncs3)NN2)CC1] | (R)-6-(((1-(Mtert-butyl)piperidin-4-yl)-1H-1,2,3-triazol-4-yl)(thiazol-5-yl)methyl)amino)-8-chloro-4-((3-chloro-4-fluorophenyl)amino)quinoline-3-carbonitrile | 2 | ES/MS 650.1 (M + H+) |

TABLE 1-continued

| Comp | Structure | Name | Example Procedure | ES/MS m/z |
|---|---|---|---|---|
| 371 | 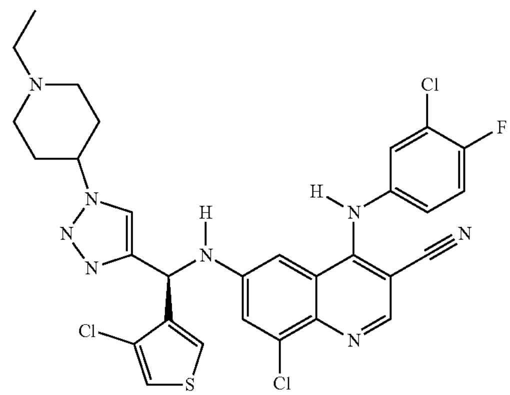 [SMILES: CCN1CCC(N2C=C([C@@H](Nc3cc(Cl)c4ncc(C#N)c(Nc5ccc(F)c(Cl)c5)c4c3)c3cscc3Cl)NN2)CC1] | (S)-8-chloro-4-((3-chloro-4-fluorophenyl)amino)-6-(((4-chlorothiophen-3-yl)(1-(1-ethylpiperidin-4-yl)-1H-1,2,3-triazol-4-yl)methyl)-amino)quinoline-3-carbonitrile | 3 | ES/MS 655.3 (M + H+). |
| 372 | 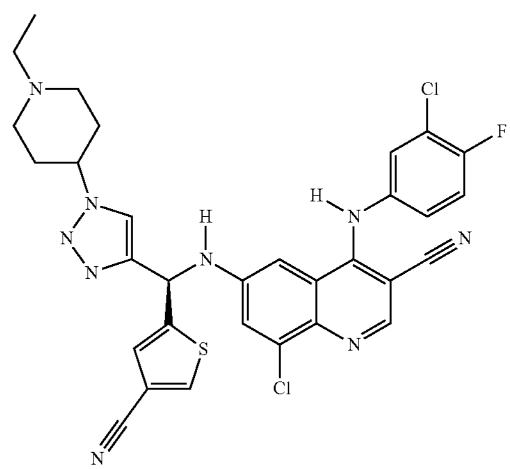 [SMILES: CCN1CCC(N2C=C([C@@H](Nc3cc(Cl)c4ncc(C#N)c(Nc5ccc(F)c(Cl)c5)c4c3)c3cc(C#N)cs3)NN2)CC1] | (R)-8-chloro-4-((3-chloro-4-fluorophenyl)amino)-6-(((4-cyanothiophen-2-yl)(1-(1-ethylpiperidin-4-yl)-1H-1,2,3-triazol-4-yl)methyl)-amino)quinoline-3-carbonitrile | 5 | ES/MS 646.2 (M + H+) |
| 373 | 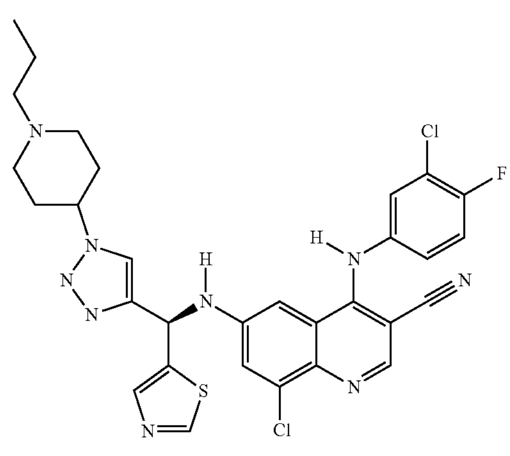 [SMILES: CCCN1CCC(N2C=C([C@@H](Nc3cc(Cl)c4ncc(C#N)c(Nc5ccc(F)c(Cl)c5)c4c3)c3cncs3)NN2)CC1] | (R)-8-chloro-4-((3-chloro-4-fluorophenyl)amino)-6-(((1-(1-propylpiperidin-4-yl)-1H-1,2,3-triazol-4-yl)(thiazol-5-yl)methyl)amino)-quinoline-3-carbonitrile | 5 | ES/MS 636.1 (M + H+) |

TABLE 1-continued

| Comp | Structure | Name | Example Procedure | ES/MS m/z |
|---|---|---|---|---|
| 374 | 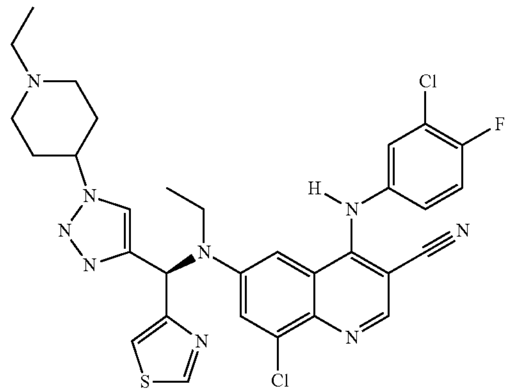 | (S)-8-chloro-4-((3-chloro-4-fluorophenyl)amino)-6-(ethyl((1-(1-ethylpiperidin-4-yl)-1H-1,2,3-triazol-4-yl)(thiazol-4-yl)methyl)amino)quinoline-3-carbonitrile | 5 | ES/MS 622.1 (M + H+) |
| 375 | 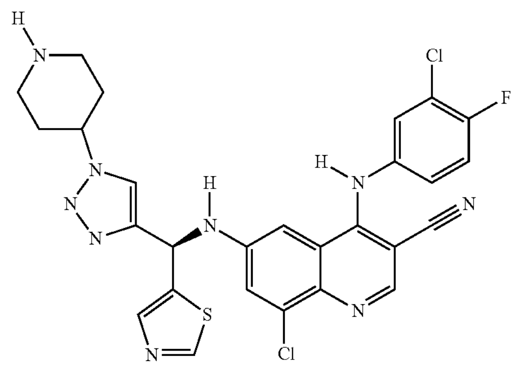 [SMILES: N#Cc1cnc2c(Cl)cc(N[C@H](C3=CN(C4CCNCC4)NN3)c3cncs3)cc2c1Nc1ccc(F)c(Cl)c1] | (R)-8-chloro-4-((3-chloro-4-fluorophenyl)amino)-6-(((1-(piperidin-4-yl)-1H-1,2,3-triazol-4-yl)(thiazol-5-yl)methyl)amino)quinoline-3-carbonitrile | 5 | ES/MS 594.1 (M + H+) |
| 376 | 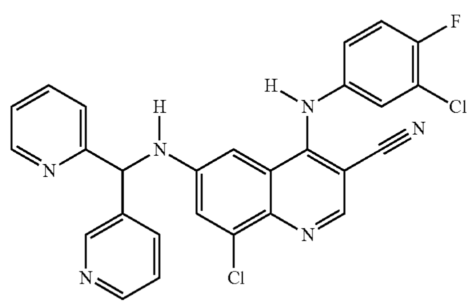 [SMILES: N#Cc1cnc2c(Cl)cc(NC(c3cccnc3)c3ccccn3)cc2c1Nc1ccc(F)c(Cl)c1] | 8-chloro-4-((3-chloro-4-fluorophenyl)amino)-6-((pyridin-2-yl(pyridin-3-yl)methyl)amino)quinoline-3-carbonitrile | 7 | ES/MS 515.1 (M + H+) |
| 377 | 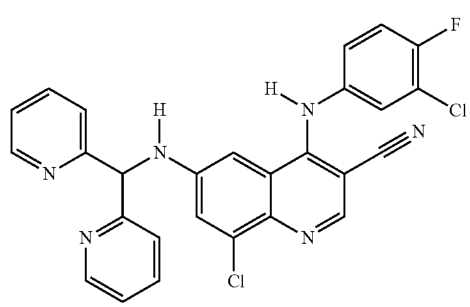 [SMILES: N#Cc1cnc2c(Cl)cc(NC(c3ccccn3)c3ccccn3)cc2c1Nc1ccc(F)c(Cl)c1] | 8-chloro-4-((3-chloro-4-fluorophenyl)amino)-6-((di(pyridin-2-yl)methyl)amino)quinoline-3-carbonitrile | 7 | ES/MS 515.1 (M + H+) |

TABLE 1-continued

| Comp | Structure | Name | Example Procedure | ES/MS m/z |
|---|---|---|---|---|
| 378 | 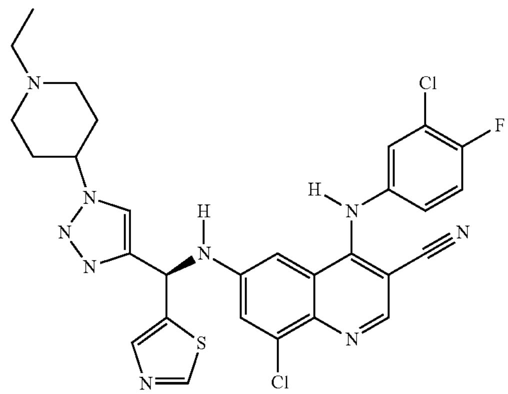 [SMILES: CCN1CCC(N2C=C([C@@H](Nc3cc(Cl)c4ncc(C#N)c(Nc5ccc(F)c(Cl)c5)c4c3)c3cncs3)NN2)CC1] | (R)-8-chloro-4-((3-chloro-4-fluorophenyl)amino)-6-(((1-(1-ethylpiperidin-4-yl)-1H-1,2,3-triazol-4-yl)(thiazol-5-yl)methyl)amino)quinoline-3-carbonitrile | 20 | ES/MS 621.9 (M + H+) |
| 379 | 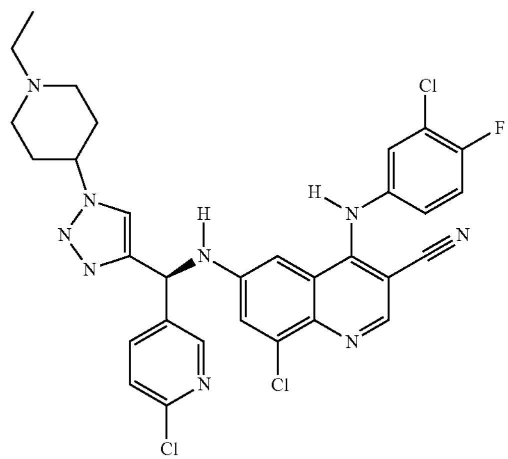 [SMILES: CCN1CCC(N2C=C([C@@H](Nc3cc(Cl)c4ncc(C#N)c(Nc5ccc(F)c(Cl)c5)c4c3)c3ccc(Cl)nc3)NN2)CC1] | (S)-8-chloro-4-((3-chloro-4-fluorophenyl)amino)-6-(((6-chloropyridin-3-yl)(1-(1-ethylpiperidin-4-yl)-1H-1,2,3-triazol-4-yl)methyl)amino)quinoline-3-carbonitrile | 20 | ES/MS 650.0 (M + H+) |
| 380 | 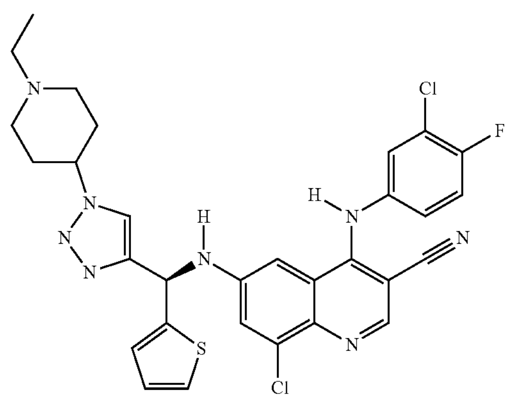 [SMILES: CCN1CCC(N2C=C([C@@H](Nc3cc(Cl)c4ncc(C#N)c(Nc5ccc(F)c(Cl)c5)c4c3)c3cccs3)NN2)CC1] | (R)-8-chloro-4-((3-chloro-4-fluorophenyl)amino)-6-(((1-(1-ethylpiperidin-4-yl)-1H-1,2,3-triazol-4-yl)(thiophen-2-yl)methyl)amino)quinoline-3-carbonitrile | 20 | ES/MS 620.9 (M + H+) |

TABLE 1-continued

| Comp | Structure | Name | Example Procedure | ES/MS m/z |
|---|---|---|---|---|
| 381 | 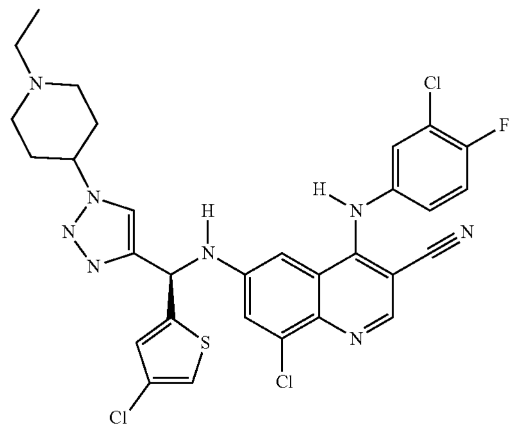 [SMILES: CCN1CCC(N2C=C([C@@H](Nc3cc(Cl)c4ncc(C#N)c(Nc5ccc(F)c(Cl)c5)c4c3)c3cc(Cl)cs3)NN2)CC1] | (R)-8-chloro-4-((3-chloro-4-fluorophenyl)amino)-6-(((4-chlorothiophen-2-yl)(1-(1-ethylpiperidin-4-yl)-1H-1,2,3-triazol-4-yl)methyl)amino)-quinoline-3-carbonitrile | 3 | ES/MS 654.9 (M + H+) |
| 382 | 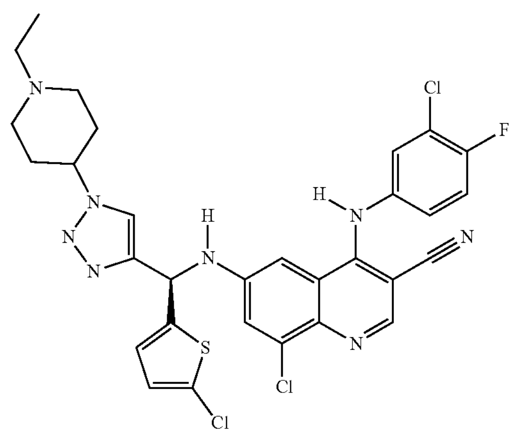 [SMILES: CCN1CCC(N2C=C([C@@H](Nc3cc(Cl)c4ncc(C#N)c(Nc5ccc(F)c(Cl)c5)c4c3)c3ccc(Cl)s3)NN2)CC1] | (R)-8-chloro-4-((3-chloro-4-fluorophenyl)amino)-6-(((5-chlorothiophen-2-yl)(1-(1-ethyl piperidin-4-yl)-1H-1,2,3-triazol-4-yl)methyl)amino)quinoline-3-carbonitrile | 3 | ES/MS 654.9 (M + H+) |
| 383 | 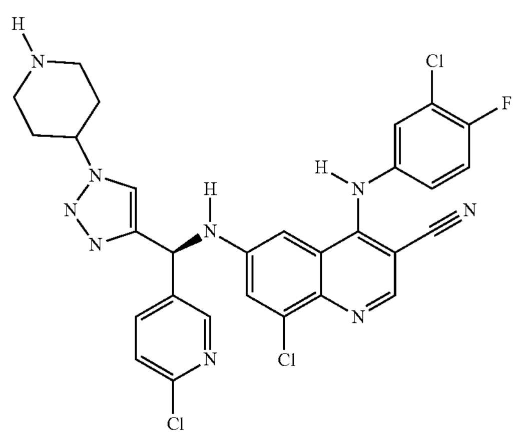 [SMILES: N#Cc1cnc2c(Cl)cc(N[C@H](C3=CN(C4CCNCC4)NN3)c3ccc(Cl)nc3)cc2c1Nc1ccc(F)c(Cl)c1] | (S)-8-chloro-4-((3-chloro-4-fluorophenyl)amino)-6-(((6-chloropyridin-3-yl)(1-(piperidin-4-yl)-1H-1,2,3-triazol-4-yl)methyl)amino)quinoline-3-carbonitrile | 5 | ES/MS 624.0 (M + H+) |

TABLE 1-continued

| Comp | Structure | Name | Example Procedure | ES/MS m/z |
|---|---|---|---|---|
| 384 | 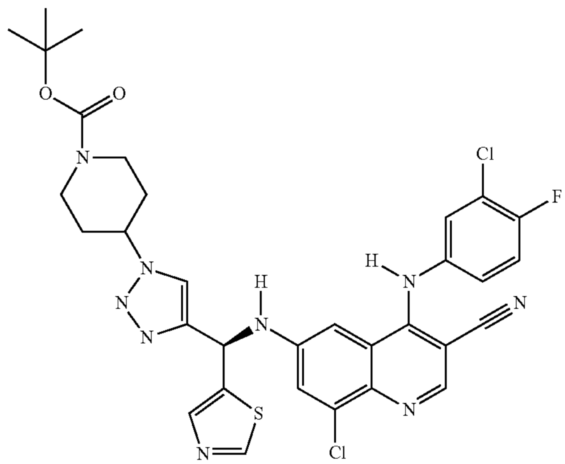 [SMILES: CC(C)(C)OC(=O)N1CCC(N2C=C([C@@H](Nc3cc(Cl)c4ncc(C#N)c(Nc5ccc(F)c(Cl)c5)c4c3)c3cncs3)NN2)CC1] | tert-butyl (R)-4-(4-(((8-chloro-4-((3-chloro-4-fluorophenyl)amino)-3-cyanoquinolin-6-yl)amino)(thiazol-5-yl)methyl)-1H-1,2,3-triazol-1-yl)piperidine-1-carboxylate | 5 | ES/MS 694.0 (M + H+) |
| 385 | 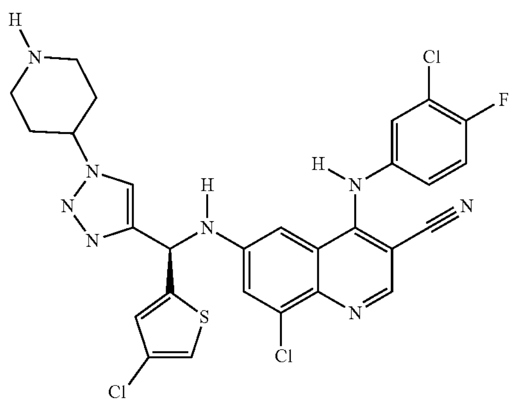 [SMILES: N#Cc1cnc2c(Cl)cc(N[C@H](C3=CN(C4CCNCC4)NN3)c3cc(Cl)cs3)cc2c1Nc1ccc(F)c(Cl)c1] | (R)-8-chloro-4-((3-chloro-4-fluorophenyl)amino)-6-(((4-chlorothiophen-2-yl)(1-(piperidin-4-yl)-1H-1,2,3-triazol-4-yl)methyl)amino)quinoline-3-carbonitrile | 3 | ES/MS 627.0 (M + H+) |
| 386 | 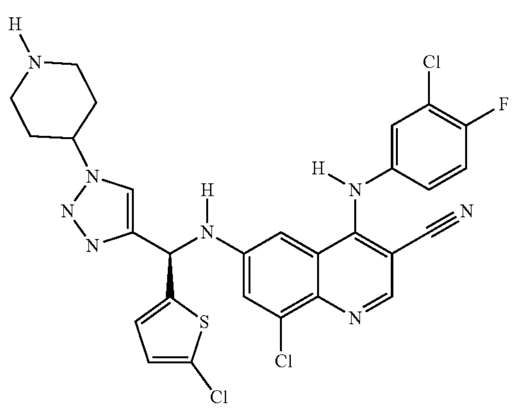 [SMILES: N#Cc1cnc2c(Cl)cc(N[C@H](C3=CN(C4CCNCC4)NN3)c3ccc(Cl)s3)cc2c1Nc1ccc(F)c(Cl)c1] | (R)-8-chloro-4-((3-chloro-4-fluorophenyl)amino)-6-(((5-chlorothiophen-2-yl)(1-(piperidin-4-yl)-1H-1,2,3-triazol-4-yl)methyl)amino)quinoline-3-carbonitrile | 3 | ES/MS 628.9 (M + H+) |

TABLE 1-continued

| Comp | Structure | Name | Example Procedure | ES/MS m/z |
|---|---|---|---|---|
| 387 | 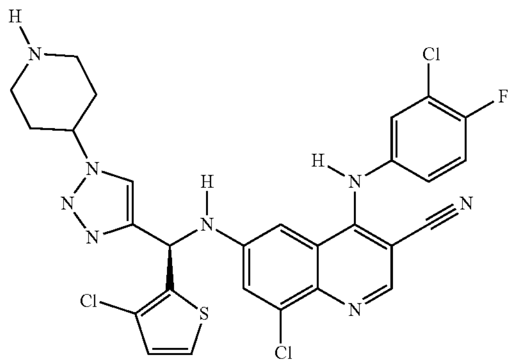 [SMILES: N#Cc1cnc2c(Cl)cc(N[C@H](C3=CN(C4CCNCC4)NN3)c3sccc3Cl)cc2c1Nc1ccc(F)c(Cl)c1] | (R)-8-chloro-4-((3-chloro-4-fluorophenyl)amino)-6-(((3-chlorothiophen-2-yl)(1-(piperidin-4-yl)-1H-1,2,3-triazol-4-yl)methyl)amino)quinoline-3-carbonitrile | 5 | ES/MS 626.9 (M + H+) |
| 388 | 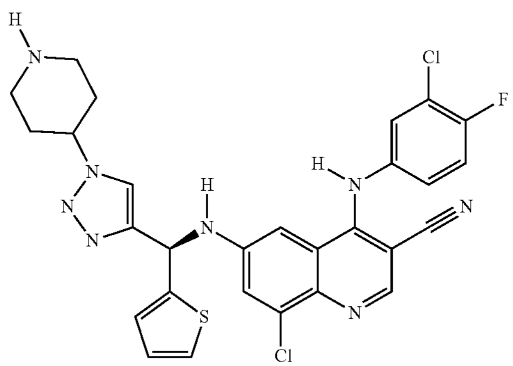 [SMILES: N#Cc1cnc2c(Cl)cc(N[C@H](C3=CN(C4CCNCC4)NN3)c3cccs3)cc2c1Nc1ccc(F)c(Cl)c1] | (R)-8-chloro-4-((3-chloro-4-fluorophenyl)amino)-6-(((1-(piperidin-4-yl)-1H-1,2,3-triazol-4-yl)(thiophen-2-yl)methyl)amino)quinoline-3-carbonitrile | 5 | ES/MS 593.0 (M + H+) |
| 389 | 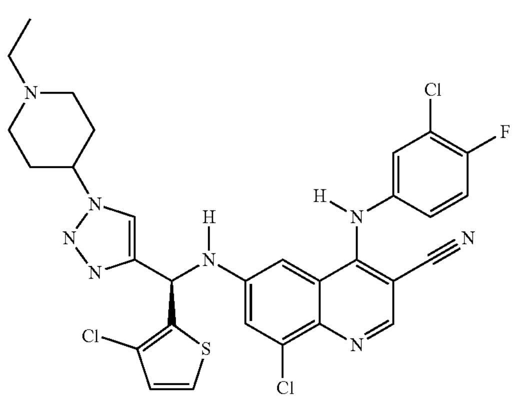 [SMILES: CCN1CCC(N2C=C([C@@H](Nc3cc(Cl)c4ncc(C#N)c(Nc5ccc(F)c(Cl)c5)c4c3)c3sccc3Cl)NN2)CC1] | (R)-8-chloro-4-((3-chloro-4-fluorophenyl)amino)-6-(((3-chlorothiophen-2-yl)(1-(1-ethylpiperidin-4-yl)-1H-1,2,3-triazol-4-yl)methyl)amino)-quinoline-3-carbonitrile | 5 | ES/MS 655.0 (M + H+) |

TABLE 1-continued

| Comp | Structure | Name | Example Procedure | ES/MS m/z |
|---|---|---|---|---|
| 390 | 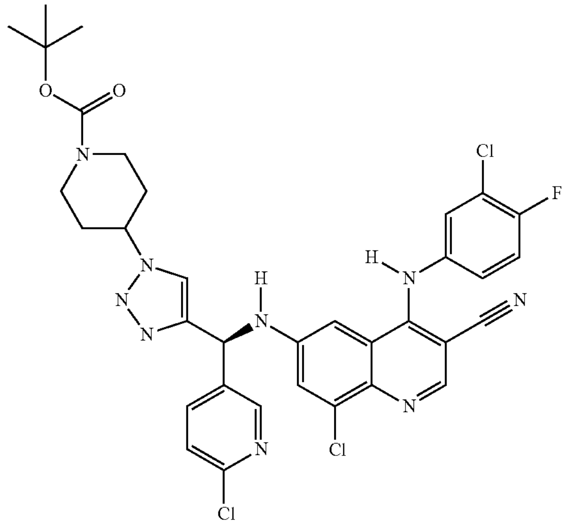 [SMILES: CC(C)(C)OC(=O)N1CCC(N2C=C([C@@H](Nc3cc(Cl)c4ncc(C#N)c(Nc5ccc(F)c(Cl)c5)c4c3)c3ccc(Cl)nc3)NN2)CC1] | tert-butyl (S)-4-(4-(((8-chloro-4-((3-chloro-4-fluorophenyl)amino)-3-cyanoquinolin-6-yl)amino)(6-chloropyridin-3-yl)methyl)-1H-1,2,3-triazol-1-yl)piperidine-1-carboxylate | 5 | ES/MS 723.2 (M + H+) |
| 391 | 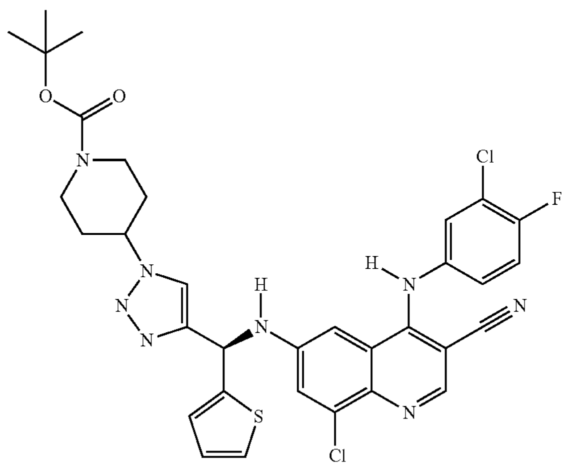 [SMILES: CC(C)(C)OC(=O)N1CCC(N2C=C([C@@H](Nc3cc(Cl)c4ncc(C#N)c(Nc5ccc(F)c(Cl)c5)c4c3)c3cccs3)NN2)CC1] | tert-butyl (R)-4-(4-(((8-chloro-4-((3-chloro-4-fluorophenyl)amino)-3-cyanoquinolin-6-yl)amino)(thiophen-2-yl)methyl)-1H-1,2,3-triazol-1-yl)piperidine-1-carboxylate | 5 | ES/MS 694.2 (M + H+) |
| 392 | 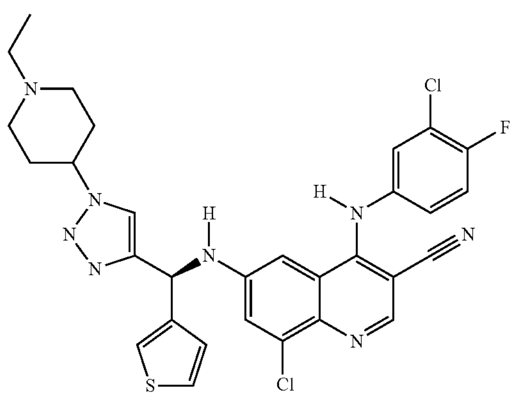 [SMILES: CCN1CCC(N2C=C([C@@H](Nc3cc(Cl)c4ncc(C#N)c(Nc5ccc(F)c(Cl)c5)c4c3)c3ccsc3)NN2)CC1] | (S)-8-chloro-4-((3-chloro-4-fluorophenyl)amino)-6-(((1-(1-ethylpiperidin-4-yl)-1H-1,2,3-triazol-4-yl)(thiophen-3-yl)methyl)amino)quinoline-3-carbonitrile | 20 | ES/MS 621.2 (M + H+) |

TABLE 1-continued

| Comp | Structure | Name | Example Procedure | ES/MS m/z |
|---|---|---|---|---|
| 393 | 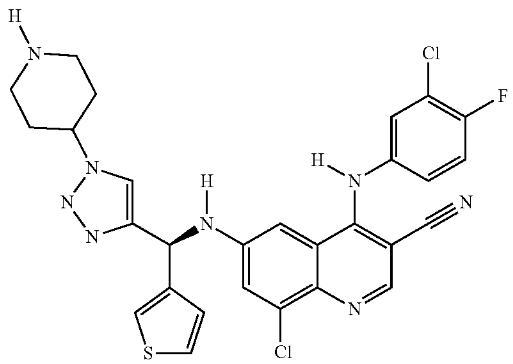 [SMILES: N#Cc1cnc2c(Cl)cc(N[C@H](C3=CN(C4CCNCC4)NN3)c3ccsc3)cc2c1Nc1ccc(F)c(Cl)c1] | (S)-8-chloro-4-t-((3-chloro-4-fluorophenyl)amino)-6-(((1-(piperidin-4-yl)-1H-1,2,3-triazol-4-yl)(thiophen-3-yl)methyl)amino)quinoline-3-carbonitrile | 5 | ES/MS 593.2 (M + H+) |
| 394 | 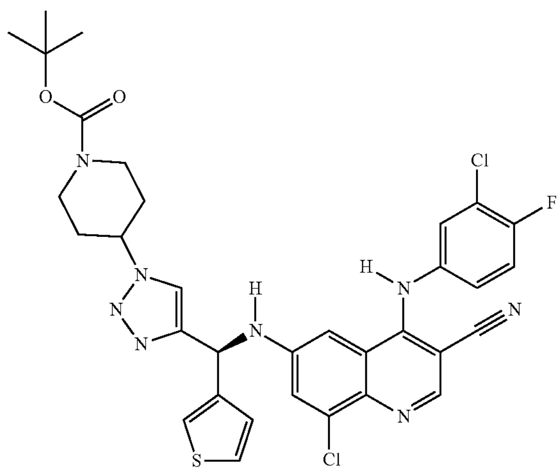 [SMILES: CC(C)(C)OC(=O)N1CCC(N2C=C([C@@H](Nc3cc(Cl)c4ncc(C#N)c(Nc5ccc(F)c(Cl)c5)c4c3)c3ccsc3)NN2)CC1] | tert-butyl (S)-4-(4-(((8-chloro-4-((3-chloro-4-fluorophenyl)amino)-3-cyanoquinolin-6-yl)amino)(thiophen-3-yl)methyl)-1H-1,2,3-triazol-1-yl)piperidine-1-carboxylate | 5 | ES/MS 694.0 (M + H+) |
| 395 | 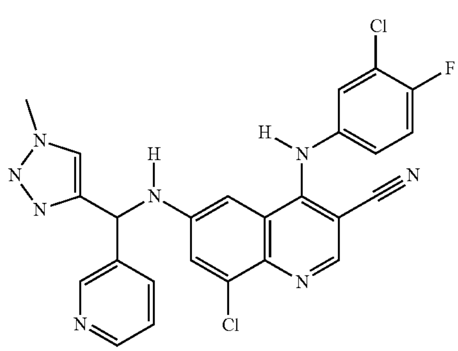 [SMILES: CN1C=C(C(Nc2cc(Cl)c3ncc(C#N)c(Nc4ccc(F)c(Cl)c4)c3c2)c2cccnc2)NN1] | 8-chloro-4-((3-chloro-4-fluorophenyl)amino)-6-(((1-methyl-1H-1,2,3-triazol-4-yl)(pyridin-3-yl)methyl)amino)quinoline-3-carbonitrile | 6 | |

TABLE 1-continued

| Comp | Structure | Name | Example Procedure | ES/MS m/z |
|---|---|---|---|---|
| 396 | 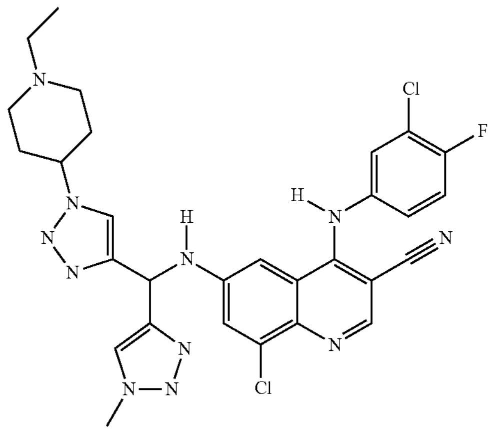 | 8-chloro-4-((3-chloro-4-fluorophenyl)amino)-6-(((1-(1-ethyl-piperidin-4-yl)-1H-1,2,3-triazol-4-yl)(1-methyl-1H-1,2,3-triazol-4-yl)methyl)amino)quinoline-3-carbonitrile | 20 | ES/MS 620.1 (M + H+) |
| 397 | 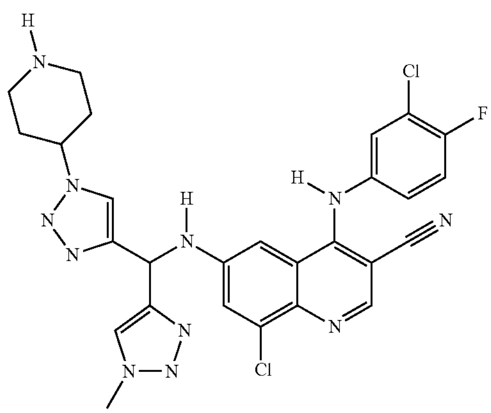 | 8-chloro-4-((3-chloro-4-fluorophenyl)amino)-6-(((1-methyl-1H-1,2,3-triazol-4-yl)(1-(piperidin-4-yl)-1H-1,2,3-triazol-4-yl)methyl)amino)-quinoline-3-carbonitrile | 6 | ES/MS 592.0 (M + H+) |
| 398 | 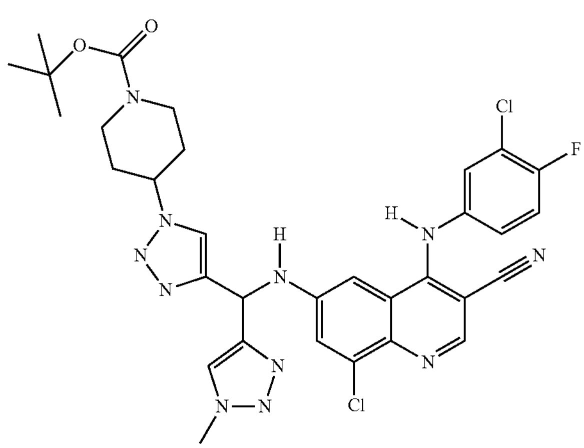 | tert-butyl 4-(4-(((8-chloro-4-((3-chloro-4-fluorophenyl)amino)-3-cyanoquinolin-6-yl)amino)(1-methyl-1H-1,2,3-triazol-4-yl)methyl)-1H-1,2,3-triazol-1-yl)piperidine-1-carboxylate | 6 | ES/MS 693.2 (M + H+) |

TABLE 1-continued

| Comp | Structure | Name | Example Procedure | ES/MS m/z |
|---|---|---|---|---|
| 399 | 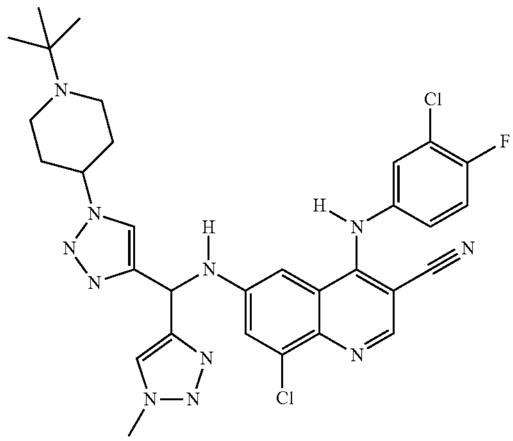 | 6-(((1-(1-(tert-butyl)piperidin-4-yl)-1H-1,2,3-triazol-4-yl)(1-methyl-1H-1,2,3-triazol-4-yl)methyl)amino)-8-chloro-4-((3-chloro-4-fluorophenyl)-amino)quinoline-3-carbonitrile | 6 | ES/MS 648.3 (M + H+) |
| 400 | 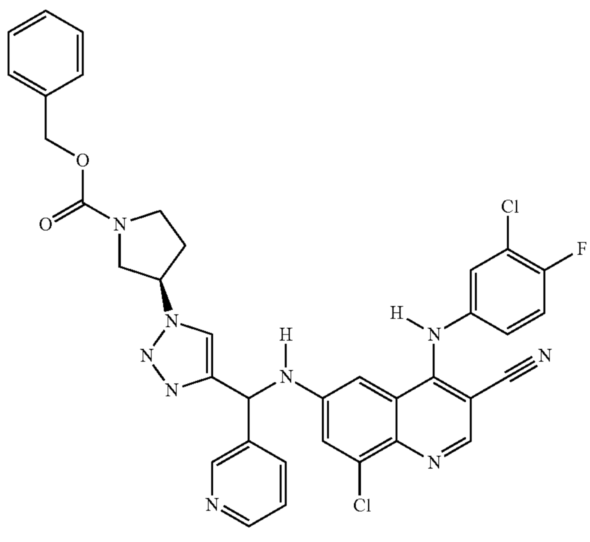 [SMILES: N#Cc1cnc2c(Cl)cc(NC(C3=CN([C@@H]4CCN(C(=O)OCc5ccccc5)C4)NN3)c3cccnc3)cc2c1Nc1ccc(F)c(Cl)c1] | benzyl (3R)-3-(4-(((8-chloro-4-((3-chloro-4-fluorophenyl)amino)-3-cyanoquinolin-6-yl)amino)(pyridin-3-yl)methyl)-1H-1,2,3-triazol-1-yl)pyrrolidine-1-carboxylate | 6 | |
| 401 | 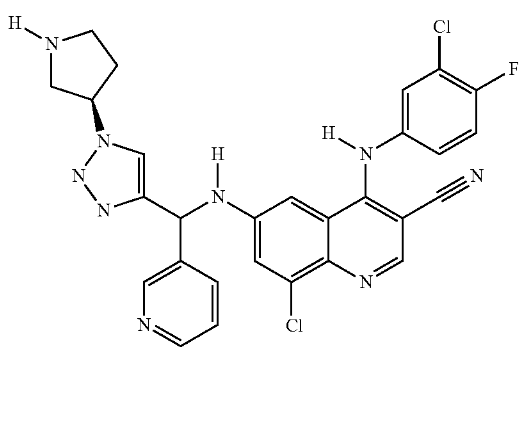 [SMILES: N#Cc1cnc2c(Cl)cc(NC(C3=CN([C@@H]4CCNC4)NN3)c3cccnc3)cc2c1Nc1ccc(F)c(Cl)c1] | 8-chloro-4-((3-chloro-4-fluorophenyl)amino)-6-((pyridin-3-yl(1-((R)-pyrrolidin-3-yl)-1H-1,2,3-triazol-4-yl)methyl)amino)quinoline-3-carbonitrile | 6 | |

TABLE 1-continued

| Comp | Structure | Name | Example Procedure | ES/MS m/z |
|---|---|---|---|---|
| 402 | 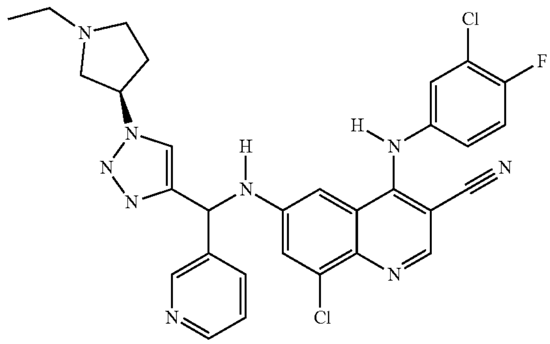 [SMILES: CCN1CC[C@@H](N2C=C(C(Nc3cc(Cl)c4ncc(C#N)c(Nc5ccc(F)c(Cl)c5)c4c3)c3cccnc3)NN2)C1] | 8-chloro-4-((3-chloro-4-fluorophenyl)amino)-6-(((1-((R)-1-ethyl pyrrolidin-3-yl)-1H-1,2,3-triazol-4-yl)(pyridin-3-yl)methyl)-amino)quinoline-3-carbonitrile | 6 | |
| 403 | 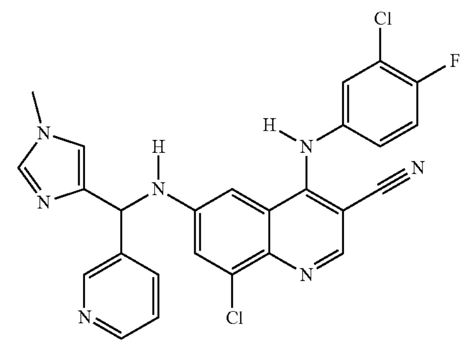 [SMILES: Cn1cnc(C(Nc2cc(Cl)c3ncc(C#N)c(Nc4ccc(F)c(Cl)c4)c3c2)c2cccnc2)c1] | 8-chloro-4-((3-chloro-4-fluorophenyl)amino)-6-(((1-methyl-1H-imidazol-4-yl)(pyridin-3-yl)methyl)-amino)quinoline-3-carbonitrile | 6 | ES/MS 518.1 (M + H+) |
| 404 | 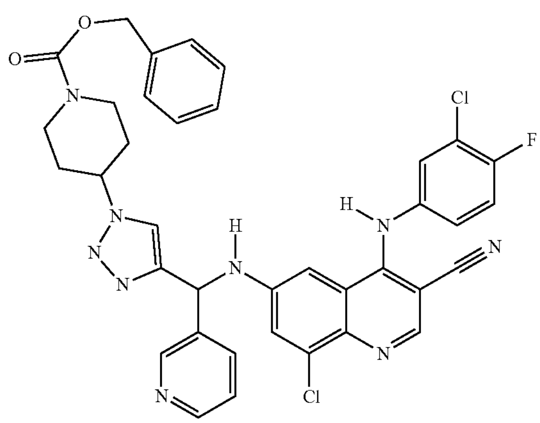 [SMILES: N#Cc1cnc2c(Cl)cc(NC(C3=CN(C4CCN(C(=O)OCc5ccccc5)CC4)NN3)c3cccnc3)cc2c1Nc1ccc(F)c(Cl)c1] | benzyl 4-(4-(((8-chloro-4-((3-chloro-4-fluorophenyl)am ino)-3-cyanoquinolin-6-yl)amino)(pyridin-3-yl)methyl)-1H-1,2,3-triazol-1-yl)piperidine-1-carboxylate | 6 | |
| 405 | 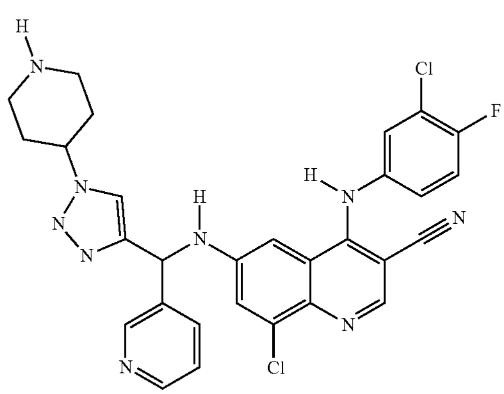 [SMILES: N#Cc1cnc2c(Cl)cc(NC(C3=CN(C4CCNCC4)NN3)c3cccnc3)cc2c1Nc1ccc(F)c(Cl)c1] | 8-chloro-4-((3-chloro-4-fluorophenyl)amino)-6-(((1-(piperidin-4-yl)-1H-1,2,3-triazol-4-yl)(pyridin-3-yl)methyl)amino)quinoline-3-carbonitrile | 6 | |

TABLE 1-continued

| Comp | Structure | Name | Example Procedure | ES/MS m/z |
|---|---|---|---|---|
| 406 | 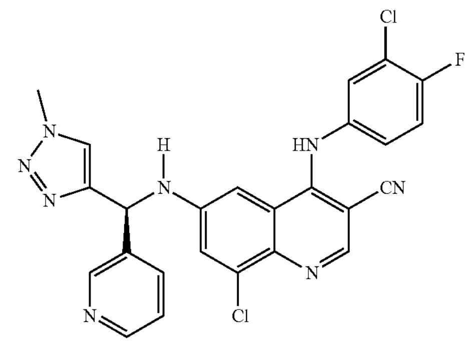 [SMILES: Cn1cc([C@@H](Nc2cc(Cl)c3ncc(C#N)c(Nc4ccc(F)c(Cl)c4)c3c2)c2cccnc2)nn1] | (S)-8-chloro-4-((3-chloro-4-fluorophenyl)amino)-6-(((1-methyl-1H-1,2,3-triazol-4-yl)(pyridin-3-yl)methyl)amino)quinoline-3-carbonitrile | 6 | |
| 407 | 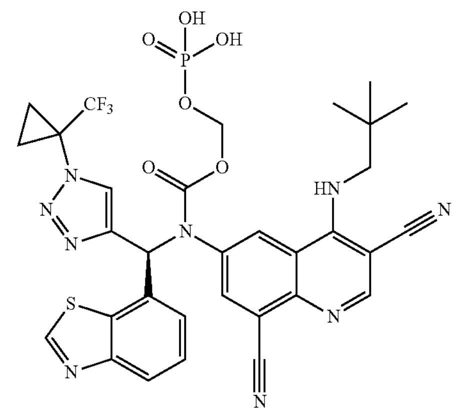 [SMILES: CC(C)(C)CNc1c(C#N)cnc2c(C#N)cc(N(C(=O)OCOP(=O)(O)O)[C@H](c3cn(C4(C(F)(F)F)CC4)nn3)c3cccc4ncsc34)cc12] | (phosphonooxy)methyl (S)-(benzo[d]thiazol-7-yl(1-(1-(trifluoromethyl)cyclopropyl)-1H-1,2,3-triazol-4-yl)methyl)(3,8-dicyano-4-(neopentylamino)quinolin-6-yl)carbamate | | |
| 408 | 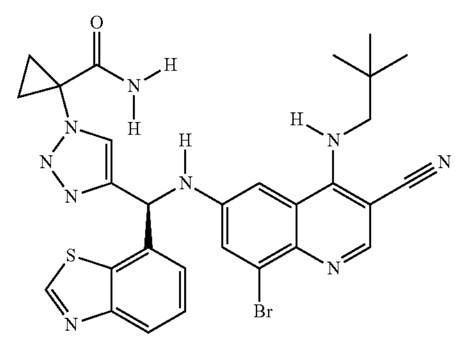 [SMILES: CC(C)(C)CNc1c(C#N)cnc2c(Br)cc(N[C@H](C3=CN(C4(C(N)=O)CC4)NN3)c3cccc4ncsc34)cc12] | (S)-1-(4-(benzo[d]thiazol-7-yl((8-bromo-3-cyano-4-(neopentylamino)-quinolin-6-yl)amino)methyl)-1H-1,2,3-triazol-1-yl)cyclopropane-1-carboxamide | 4 | 631 |
| 409 | 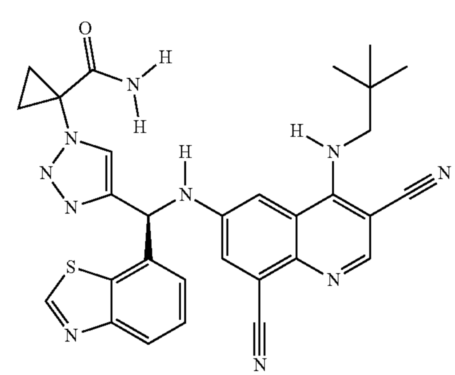 [SMILES: CC(C)(C)CNc1c(C#N)cnc2c(C#N)cc(N[C@H](C3=CN(C4(C(N)=O)CC4)NN3)c3cccc4ncsc34)cc12] | (S)-1-(4-(benzo[d]thiazol-7-yl((3,8-dicyano-4-(neopentylamino)quinolin-6-yl)amino)methyl)-1H-1,2,3-triazol-1-yl)cyclopropane-1-carboxamide | 9 | 577.10 |

TABLE 1-continued

| Comp | Structure | Name | Example Procedure | ES/MS m/z |
|---|---|---|---|---|
| 410 | 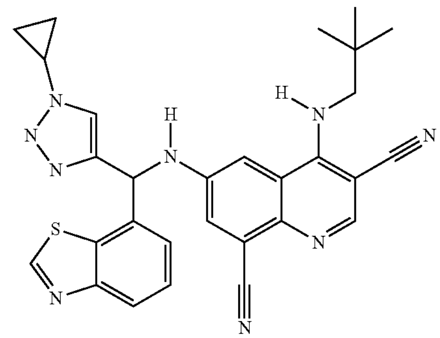 [SMILES: CC(C)(C)CNc1c(C#N)cnc2c(C#N)cc(NC(C3=CN(C4CC4)NN3)c3cccc4ncsc34)cc12] | (R)-6-((benzo[d]thiazol-7-yl(1-cyclopropyl-1H-1,2,3-triazol-4-yl)methyl)amino)-4-(neopentyl-amino)quinoline-3,8-dicarbonitrile | 9 | 534.20 |
| 411 | 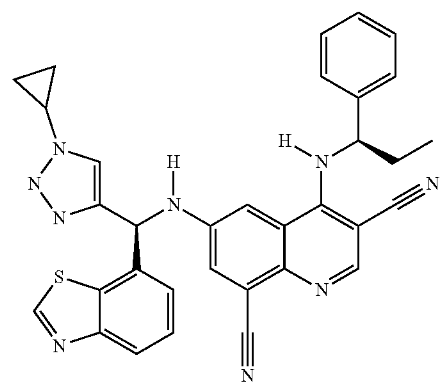 [SMILES: CC[C@@H](Nc1c(C#N)cnc2c(C#N)cc(N[C@H](C3=CN(C4CC4)NN3)c3cccc4ncsc34)cc12)c1ccccc1] | 6-(((S)-benzo[d]thiazol-7-yl(1-cyclopropyl-1H-1,2,3-triazol-4-yl)methyl)amino)-4-(((R)-1-phenylpropyl)amino)quinoline-3,8-dicarbonitrile | 9 | 582.10 |
| 412 | 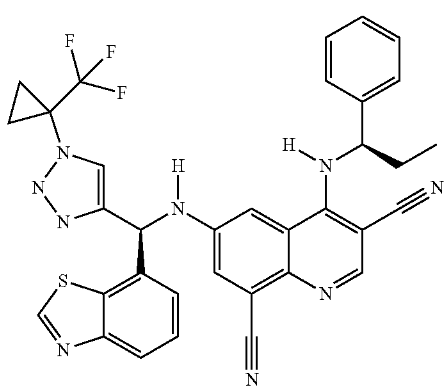 [SMILES: CC[C@@H](Nc1c(C#N)cnc2c(C#N)cc(N[C@H](C3=CN(C4(C(F)(F)F)CC4)NN3)c3cccc4ncsc34)cc12)c1ccccc1] | 6-(((S)-benzo[d]thiazol-7-yl(1-(1-(trifluoromethyl)-cyclopropyl)-1H-1,2,3-triazol-4-yl)methyl)amino)-4-(((R)-1-phenylpropyl)amino)quinoline-3,8-dicarbonitrile | 9 | 650.20 |
| 413 | 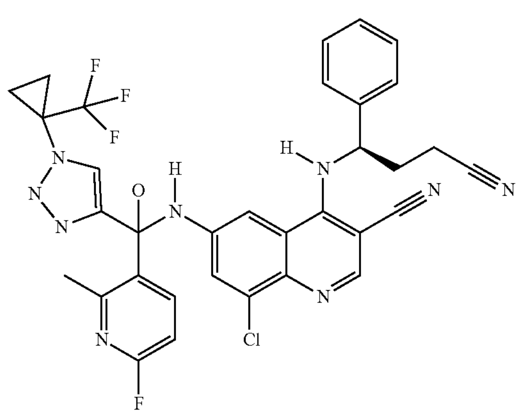 [SMILES: Cc1nc(F)ccc1C(O)(Nc1cc(Cl)c2ncc(C#N)c(N[C@H](CCC#N)c3ccccc3)c2c1)C1=CN(C2(C(F)(F)F)CC2)NN1] | 8-chloro-4-(((R)-3-cyano-1-phenyl-propyl)amino)-6-(((6-fluoro-2-methyl-pyridin-3-yl)(1-(1-(trifluoromethyl)-cyclopropyl)-1H-1,2,3-triazol-4-yl)methyl-d)amino)quinoline-3-carbonitrile | 4 | 661.26 |

TABLE 1-continued

| Comp | Structure | Name | Example Procedure | ES/MS m/z |
|---|---|---|---|---|
| 414 | 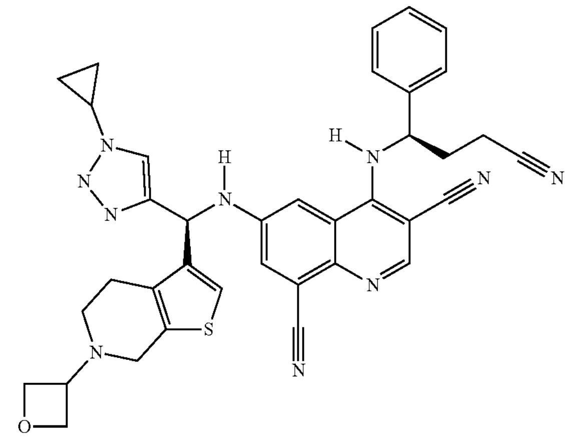 [SMILES: N#CCC[C@@H](Nc1c(C#N)cnc2c(C#N)cc(N[C@H](C3=CN(C4CC4)NN3)c3csc4c3CCN(C3COC3)C4)cc12)c1ccccc1] | 4-(((R)-3-cyano-1-phenylpropyl)amino)-6-(((S)-(1-cyclopropyl-1H-1,2,3-triazol-4-yl)(6-(oxetan-3-yl)-4,5,6,7-tetrahydrothieno[2,3-c]pyridin-3-yl)methyl)amino)-quinoline-3,8-dicarbonitrile | 37 | 667.30 |
| 415 | 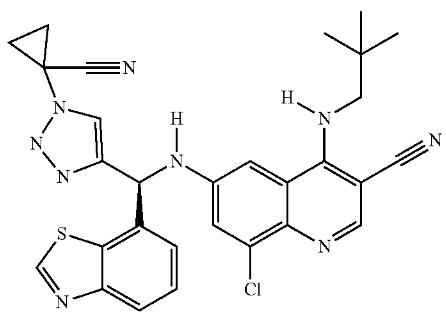 [SMILES: CC(C)(C)CNc1c(C#N)cnc2c(Cl)cc(N[C@H](C3=CN(C4(C#N)CC4)NN3)c3cccc4ncsc34)cc12] | (S)-6-((benzo[d]thiazol-7-yl(1-(1-cyanocyclopropyl)-1H-1,2,3-triazol-4-yl)methyl)amino)-8-chloro-4-(neopentylamino)quinoline-3-carbonitrile | 4 | 568.30 |
| 416 | 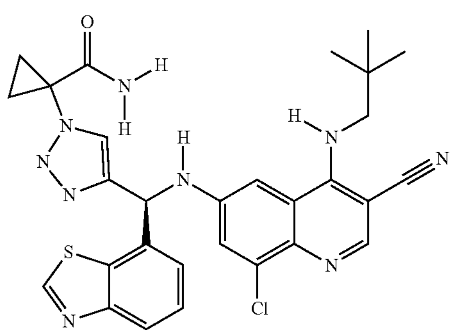 [SMILES: CC(C)(C)CNc1c(C#N)cnc2c(Cl)cc(N[C@H](C3=CN(C4(C(N)=O)CC4)NN3)c3cccc4ncsc34)cc12] | (S)-1-(4-(benzo[d]thiazol-7-yl((8-chloro-3-cyano-4-(neopentylamino)quinolin-6-yl)amino)methyl)-1H-1,2,3-triazol-1-yl)cyclopropane-1-carboxamide | 4 | 586.50 |
| 417 | 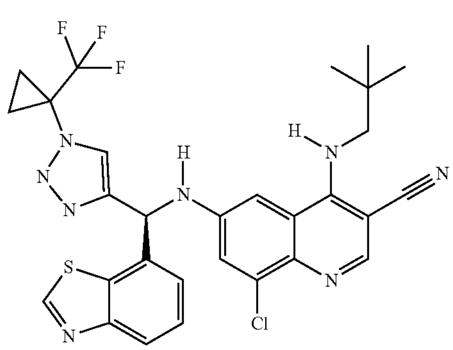 [SMILES: CC(C)(C)CNc1c(C#N)cnc2c(Cl)cc(N[C@H](C3=CN(C4(C(F)(F)F)CC4)NN3)c3cccc4ncsc34)cc12] | (S)-6-((benzo[d]thiazol-7-yl(1-(1-(trifluoromethyl)cyclopropyl)-1H-1,2,3-triazol-4-yl)methyl)amino)-8-chloro-4-(neopentylamino)quinoline-3-carbonitrile | 4 | 611.70 |

TABLE 1-continued

| Comp | Structure | Name | Example Procedure | ES/MS m/z |
|---|---|---|---|---|
| 418 | 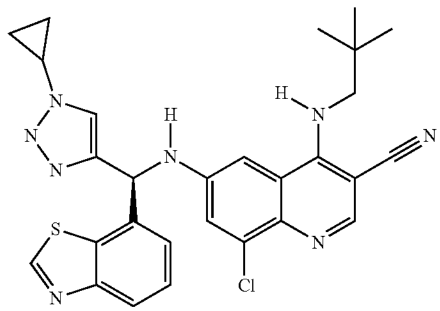 [SMILES: CC(C)(C)CNc1c(C#N)cnc2c(Cl)cc(N[C@H](C3=CN(C4CC4)NN3)c3cccc4ncsc34)cc12] | (S)-6-((benzo[d]thiazol-7-yl(1-cyclopropyl-1H-1,2,3-triazol-4-yl)methyl)amino)-8-chloro-4-(neopentylamino)quinoline-3-carbonitrile | 2 | 543.30 |
| 419 | 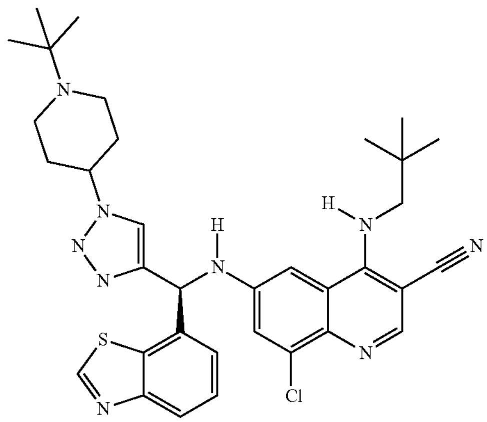 [SMILES: CC(C)(C)CNc1c(C#N)cnc2c(Cl)cc(N[C@H](C3=CN(C4CCN(C(C)(C)C)CC4)NN3)c3cccc4ncsc34)cc12] | (S)-6-((benzo[d]thiazol-7-yl(1-(1-(tert-butyl)piperidin-4-yl)-1H-1,2,3-triazol-4-yl)methyl)amino)-8-chloro-4-(neopentylamino)quinoline-3-carbonitrile | 2 | 642.30 |
| 420 | 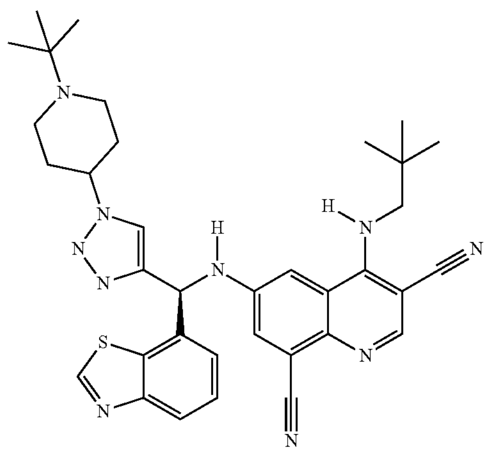 [SMILES: CC(C)(C)CNc1c(C#N)cnc2c(C#N)cc(N[C@H](C3=CN(C4CCN(C(C)(C)C)CC4)NN3)c3cccc4ncsc34)cc12] | (S)-6-((benzo[d]thiazol-7-yl(1-(1-(tert-butyl)piperidin-4-yl)-1H-1,2,3-triazol-4-yl)methyl)amino)-4-(neopentylamino)quinoline-3,8-dicarbonitrile | 9 | 633.20 |
| 421 | 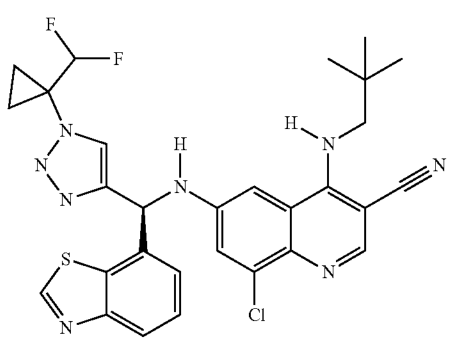 [SMILES: CC(C)(C)CNc1c(C#N)cnc2c(Cl)cc(N[C@H](C3=CN(C4(C(F)F)CC4)NN3)c3cccc4ncsc34)cc12] | (S)-6-((benzo[d]thiazol-7-yl(1-(1-(difluoromethyl)cyclopropyl)-1H-1,2,3-triazol-4-yl)methyl)amino)-8-chloro-4-(neopentylamino)quinoline-3-carbonitrile | 4 | 593.40 |

TABLE 1-continued

| Comp | Structure | Name | Example Procedure | ES/MS m/z |
|---|---|---|---|---|
| 422 | 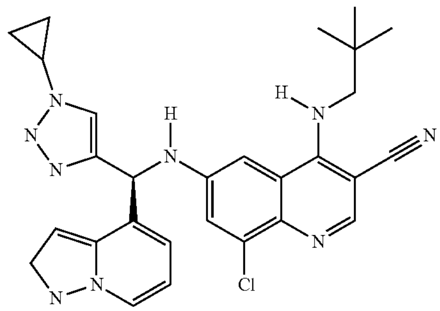 [SMILES: CC(C)(C)CNc1c(C#N)cnc2c(Cl)cc(N[C@H](C3=CN(C4CC4)NN3)C3=CC=CN4NCC=C34)cc12] | (S)-8-chloro-6-(((1-cyclopropyl-1H-1,2,3-triazol-4-yl)(pyrazolo[1,5-a]pyridin-4-yl)methyl)amino)-4-(neopentylamino)-quinoline-3-carbonitrile | 2 | 526.40 |
| 423 | 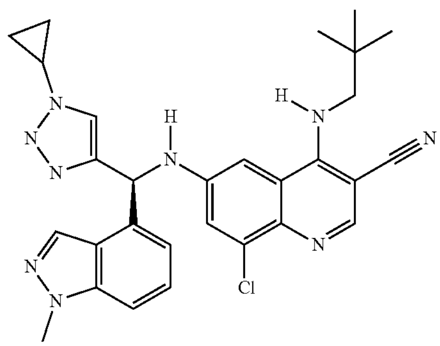 [SMILES: Cn1ncc2c([C@H](Nc3cc(Cl)c4ncc(C#N)c(NCC(C)(C)C)c4c3)C3=CN(C4CC4)NN3)cccc21] | (S)-8-chloro-6-(((1-cyclopropyl-1H-1,2,3-triazol-4-yl)(1-methyl-1H-indazol-4-yl)methyl)amino)-4-(neopentylamino)-quinoline-3-carbonitrile | 2 | 540.30 |
| 424 | 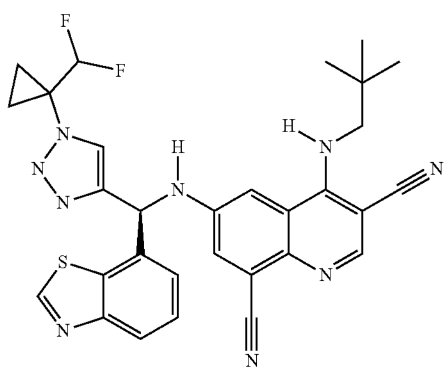 [SMILES: CC(C)(C)CNc1c(C#N)cnc2c(C#N)cc(N[C@H](C3=CN(C4(C(F)F)CC4)NN3)c3cccc4ncsc34)cc12] | (S)-6-((benzo[d]thiazol-7-yl(1-(1-(difluoromethyl)cyclopropyl)-1H-1,2,3-triazol-4-yl)methyl)amino)-4-(neopentylamino)quinoline-3,8-dicarbonitrile | 9 | 584.30 |
| 425 | 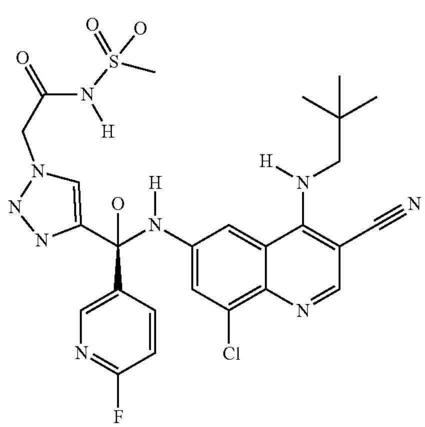 | (S)-2-(4-(((8-chloro-3-cyano-4-(neopentylamino)quinolin-6-yl)amino)(6-fluoropyridin-3-yl)methyl-d)-1H-1,2,3-triazol-1-yl)-N-(methylsulfonyl)acetamide | 1 | 600.99 |

TABLE 1-continued

| Comp | Structure | Name | Example Procedure | ES/MS m/z |
|---|---|---|---|---|
| 426 | 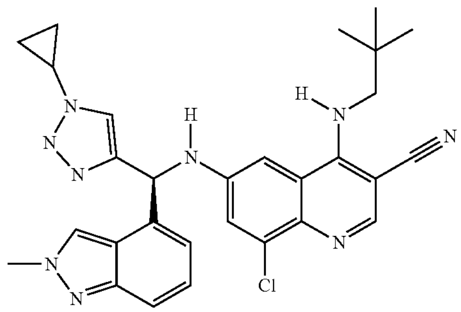 [SMILES: Cn1cc2c([C@H](Nc3cc(Cl)c4ncc(C#N)c(NCC(C)(C)C)c4c3)C3=CN(C4CC4)NN3)cccc2n1] | (S)-8-chloro-6-(((1-cyclopropyl-1H-1,2,3-triazol-4-yl)(2-methyl-2H-indazol-4-yl)methyl)amino)-4-(neopentylamino)-quinoline-3-carbonitrile | 2 | 540.30 |
| 427 | 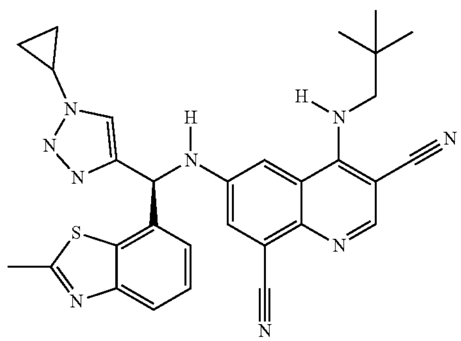 [SMILES: Cc1nc2cccc([C@H](Nc3cc(C#N)c4ncc(C#N)c(NCC(C)(C)C)c4c3)C3=CN(C4CC4)NN3)c2s1] | (S)-6-(((1-cyclopropyl-1H-1,2,3-triazol-4-yl)(2-methylbenzo[d]thiazol-7-yl)methyl)amino)-4-(neopentylamino)-quinoline-3,8-dicarbonitrile | 9 | 548.20 |
| 428 | 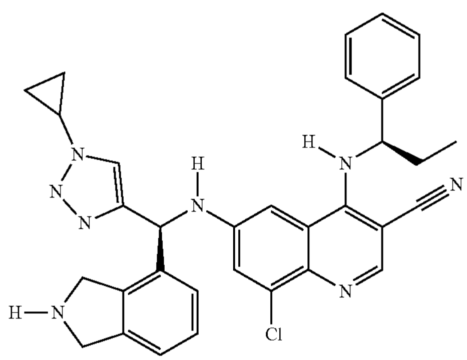 [SMILES: CC[C@@H](Nc1c(C#N)cnc2c(Cl)cc(N[C@H](C3=CN(C4CC4)NN3)c3cccc4c3CNC4)cc12)c1ccccc1] | 6-(((S)-(1-cyclopropyl-1H-1,2,3-triazol-4-yl)(isoindolin-4-yl)methyl)amino)-4-(((R)-1-phenylpropyl)amino)quinoline-3,8-dicarbonitrile | 12 | 566.20 |
| 429 | 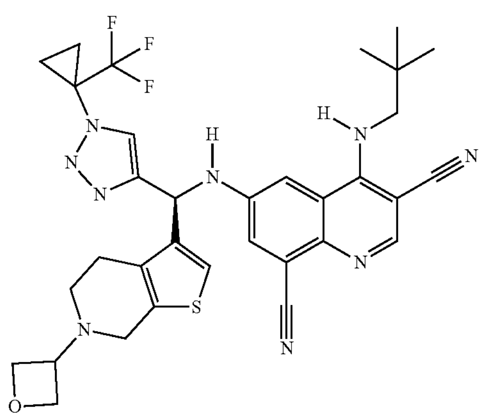 [SMILES: CC(C)(C)CNc1c(C#N)cnc2c(C#N)cc(N[C@H](C3=CN(C4(C(F)(F)F)CC4)NN3)c3csc4c3CCN(C3COC3)C4)cc12] | (S)-4-(neopentylamino)-6-(((6-(oxetan-3-yl)-4,5,6,7-tetrahydrothieno[2,3-c]pyridin-3-yl)(1-(1-(trifluoromethyl)cyclopropyl)-1H-1,2,3-triazol-4-yl)methyl)amino)-quinoline-3,8-dicarbonitrile | 37 | 662.40 |

TABLE 1-continued

| Comp | Structure | Name | Example Procedure | ES/MS m/z |
|---|---|---|---|---|
| 430 | 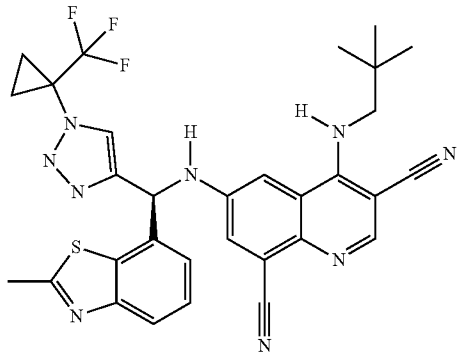 [SMILES: Cc1nc2cccc([C@H](Nc3cc(C#N)c4ncc(C#N)c(NCC(C)(C)C)c4c3)C3=CN(C4(C(F)(F)F)CC4)NN3)c2s1] | (S)-6-(((2-methylbenzo[d]thiazol-7-yl)(1-(1-(trifluoromethyl)cyclopropyl)-1H-1,2,3-triazol-4-yl)methyl)amino)-4-(neopentylamino)quinoline-3,8-dicarbonitrile | 9 | 616.30 |
| 431 | 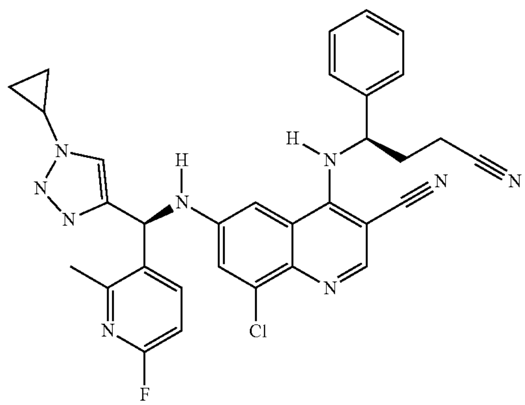 [SMILES: Cc1nc(F)ccc1[C@H](Nc1cc(Cl)c2ncc(C#N)c(N[C@H](CCC#N)c3ccccc3)c2c1)C1=CN(C2CC2)NN1] | 8-chloro-4-(((R)-3-cyano-1-phenyl-propyl)amino)-6-(((S)-(1-cyclopropyl-1H-1,2,3-triazol-4-yl)(6-fluoro-2-methylpyridin-3-yl)methyl)amino)-quinoline-3-carbonitrile | 23 | 592.12 |
| 432 | 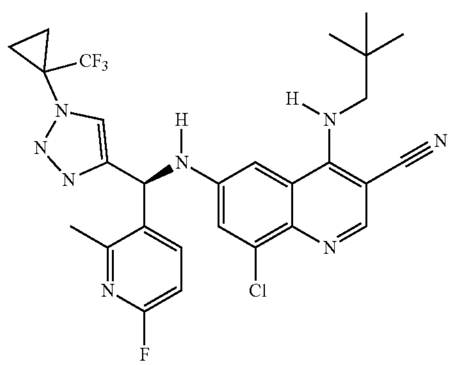 [SMILES: Cc1nc(F)ccc1[C@H](Nc1cc(Cl)c2ncc(C#N)c(NCC(C)(C)C)c2c1)C1=CN(C2(C(F)(F)F)CC2)NN1] | (S)-8-chloro-6-(((6-fluoro-2-methyl-pyridin-3-yl)(1-(1-(trifluoromethyl)-cyclopropyl)-1H-1,2,3-triazol-4-yl)methyl)amino)-4-(neopentylamino)-quinoline-3-carbonitrile | 23 | 587.27 |
| 433 | 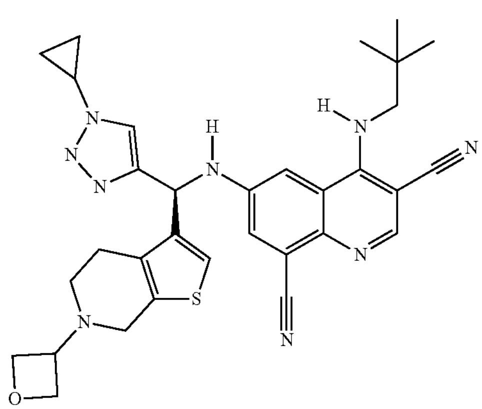 [SMILES: CC(C)(C)CNc1c(C#N)cnc2c(C#N)cc(N[C@H](C3=CN(C4CC4)NN3)c3csc4c3CCN(C3COC3)C4)cc12] | (S)-6-(((1-cyclopropyl-1H-1,2,3-triazol-4-yl)(6-(oxetan-3-yl)-4,5,6,7-tetrahydrothieno[2,3-c]pyridin-3-yl)methyl)amino)-4-(neopentylamino)-quinoline-3,8-dicarbonitrile | 37 | 594.20 |

TABLE 1-continued

| Comp | Structure | Name | Example Procedure | ES/MS m/z |
|---|---|---|---|---|
| 434 | 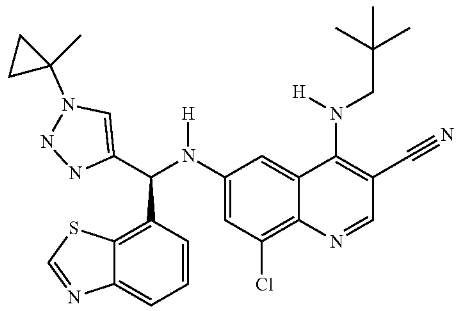 [SMILES: CC(C)(C)CNc1c(C#N)cnc2c(Cl)cc(N[C@H](C3=CN(C4(C)CC4)NN3)c3cccc4ncsc34)cc12] | (S)-6-((benzo[d]thiazol-7-yl(1-(1-methylcyclopropyl)-1H-1,2,3-triazol-4-yl)methyl)amino)-8-chloro-4-(neopentylamino)quinoline-3-carbonitrile | 4 | 557.40 |
| 435 | 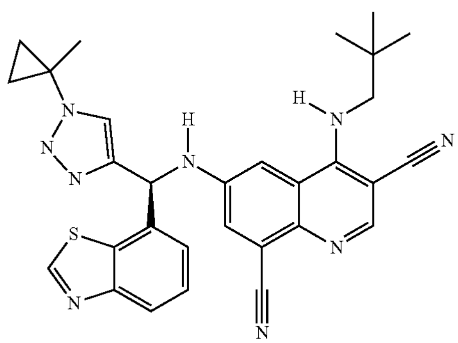 [SMILES: CC(C)(C)CNc1c(C#N)cnc2c(C#N)cc(N[C@H](C3=CN(C4(C)CC4)NN3)c3cccc4ncsc34)cc12] | (S)-6-((benzo[d]thiazol-7-yl(1-(1-methylcyclopropyl)-1H-1,2,3-triazol-4-yl)methyl)amino)-4-(neopentylamino)-quinoline-3,8-dicarbonitrile | 9 | 548.20 |
| 436 | 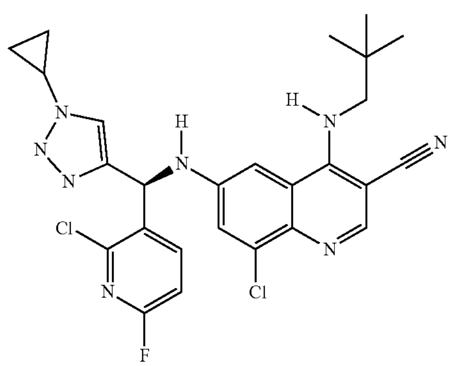 [SMILES: CC(C)(C)CNc1c(C#N)cnc2c(Cl)cc(N[C@H](C3=CN(C4CC4)NN3)c3ccc(F)nc3Cl)cc12] | (S)-8-chloro-6-(((2-chloro-6-fluoropyridin-3-yl)(1-cyclopropyl-1H-1,2,3-triazol-4-yl)methyl)amino)-4-(neopentylamino)quinoline-3-carbonitrile | 23 | 539.57 |
| 437 | 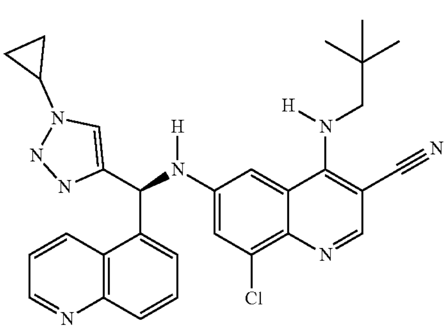 [SMILES: CC(C)(C)CNc1c(C#N)cnc2c(Cl)cc(N[C@H](C3=CN(C4CC4)NN3)c3cccc4ncccc34)cc12] | (S)-8-chloro-6-(((1-cyclopropyl-1H-1,2,3-triazol-4-yl)(quinolin-5-yl)methyl)amino)-4-(neopentylamino)quinoline-3-carbonitrile | 23 | 537.25 |

TABLE 1-continued

| Comp | Structure | Name | Example Procedure | ES/MS m/z |
|---|---|---|---|---|
| 438 | 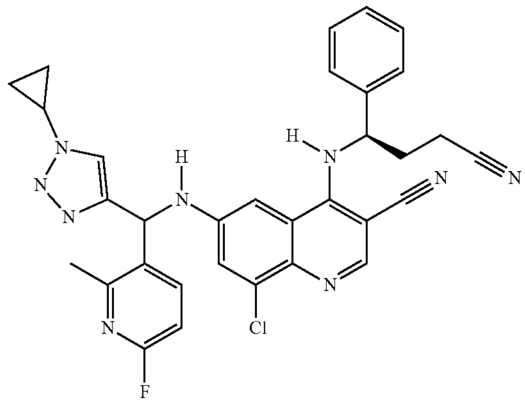 [SMILES: Cc1nc(F)ccc1C(Nc1cc(Cl)c2ncc(C#N)c(N[C@H](CCC#N)c3ccccc3)c2c1)C1=CN(C2CC2)NN1] | 8-chloro-4-(((R)-3-cyano-1-phenyl-propyl)amino)-6-(((R)-(1-cyclopropyl-1H-1,2,3-triazol-4-yl)(6-fluoro-2-methylpyridin-3-yl)methyl)amino)-quinoline-3-carbonitrile | 23 | 592.12 |
| 439 | 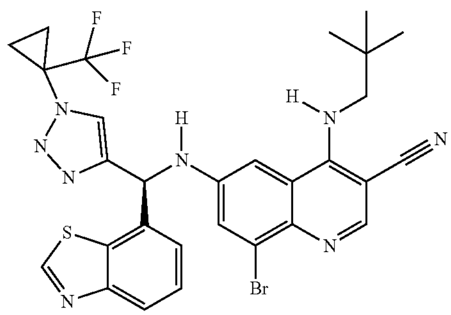 [SMILES: CC(C)(C)CNc1c(C#N)cnc2c(Br)cc(N[C@H](C3=CN(C4(C(F)(F)F)CC4)NN3)c3cccc4ncsc34)cc12] | (S)-6-((benzo[d]thiazol-7-yl(1-(1-(trifluoromethyl)cyclopropyl)-1H-1,2,3-triazol-4-yl)methyl)amino)-8-bromo-4-(neopentylamino)quinoline-3-carbonitrile | 1 | 655.05 |
| 440 | 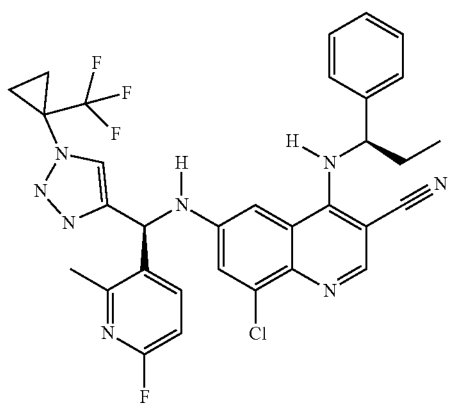 [SMILES: CC[C@@H](Nc1c(C#N)cnc2c(Cl)cc(N[C@H](C3=CN(C4(C(F)(F)F)CC4)NN3)c3ccc(F)nc3C)cc12)c1ccccc1] | 8-chloro-6-(((S)-(6-fluoro-2-methyl-pyridin-3-yl)(1-(1-(trifluoromethyl)-cyclopropyl)-1H-1,2,3-triazol-4-yl)methyl)amino)-4-(((R)-1-phenyl-propyl)amino)quinoline-3-carbonitrile | 4 | 635.45 |
| 441 | 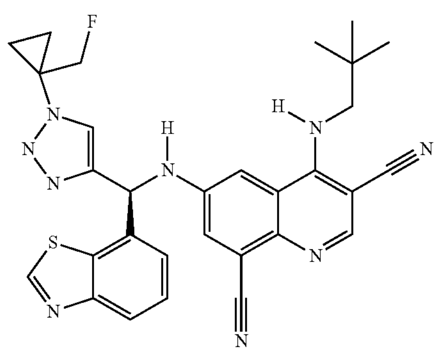 [SMILES: CC(C)(C)CNc1c(C#N)cnc2c(C#N)cc(N[C@H](C3=CN(C4(CF)CC4)NN3)c3cccc4ncsc34)cc12] | (S)-6-((benzo[d]thiazol-7-yl(1-(1-(fluoromethyl)cyclopropyl)-1H-1,2,3-triazol-4-yl)methyl)amino)-4-(neopentylamino)quinoline-3,8-dicarbonitrile | 9 | 566.30 |

TABLE 1-continued

| Comp | Structure | Name | Example Procedure | ES/MS m/z |
|---|---|---|---|---|
| 442 | 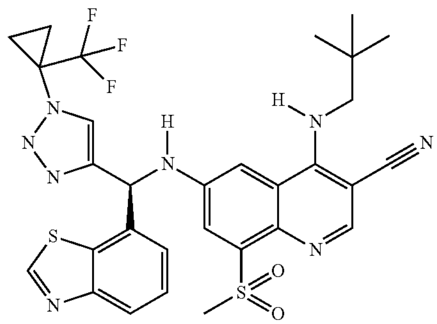 [SMILES: CC(C)(C)CNc1c(C#N)cnc2c(S(C)(=O)=O)cc(N[C@H](C3=CN(C4(C(F)(F)F)CC4)NN3)c3cccc4ncsc34)cc12] | (S)-6-((benzo[d]thiazol-7-yl(1-(1-(trifluoromethyl)cyclopropyl)-1H-1,2,3-triazol-4-yl)methyl)amino)-8-(methylsulfonyl)-4-(neopentylamino)quinoline-3-carbonitrile | 39 | 655.65 |
| 443 | 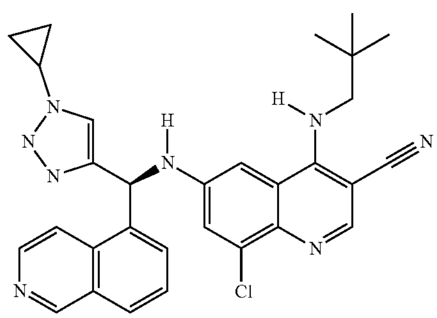 [SMILES: CC(C)(C)CNc1c(C#N)cnc2c(Cl)cc(N[C@H](C3=CN(C4CC4)NN3)c3cccc4cnccc34)cc12] | (S)-8-chloro-6-(((1-cyclopropyl-1H-1,2,3-triazol-4-yl)(isoquinolin-5-yl)methyl)amino)-4-(neopentylamino)quinoline-3-carbonitrile | 1 | 537.15 |
| 444 | 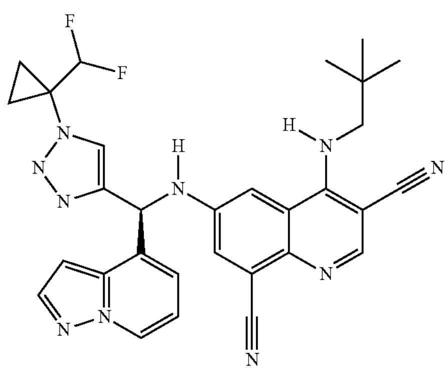 | (S)-6-(((Ml-(difluoromethyl)cyclopropyl)-1H-1,2,3-triazol-4-yl)(pyrazolo[1,5-a]pyridin-4-yl)methyl)amino)-4-(neopentylamino)quinoline-3,8-dicarbonitrile | 9 | 567.20 |
| 445 | 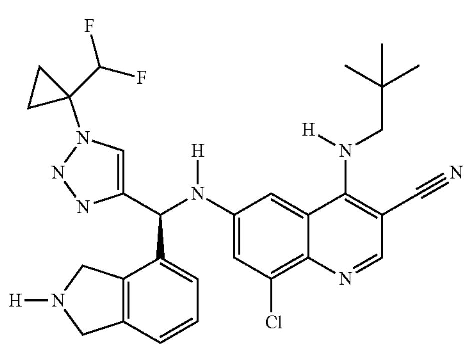 [SMILES: CC(C)(C)CNc1c(C#N)cnc2c(Cl)cc(N[C@H](C3=CN(C4(C(F)F)CC4)NN3)c3cccc4c3CNC4)cc12] | (S)-8-chloro-6-((((1-(1-(difluoromethyl)-cyclopropyl)-1H-1,2,3-triazol-4-yl)(isoindolin-4-yl)methyl)amino)-4-(neopentylamino)quinoline-3-carbonitrile | 12 | 577.20 |

TABLE 1-continued

| Comp | Structure | Name | Example Procedure | ES/MS m/z |
|---|---|---|---|---|
| 446 | 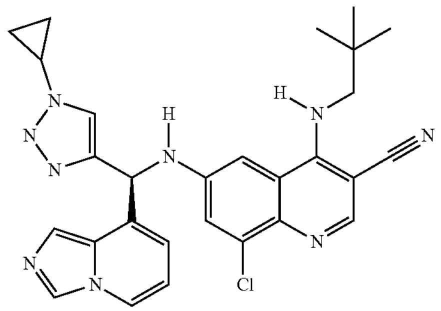 [SMILES: CC(C)(C)CNc1c(C#N)cnc2c(Cl)cc(N[C@H](C3=CN(C4CC4)NN3)c3cccn4cncc34)cc12] | (S)-8-chloro-6-(((1-cyclopropyl-1H-1,2,3-triazol-4-yl)(imidazo[1,5-a]pyridin-8-yl)methyl)amino)-4-(neopentylamino)-quinoline-3-carbonitrile | 2 | 526.30 |
| 447 | 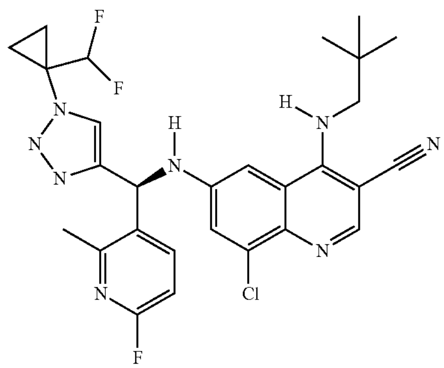 [SMILES: Cc1nc(F)ccc1[C@H](Nc1cc(Cl)c2ncc(C#N)c(NCC(C)(C)C)c2c1)C1=CN(C2(C(F)F)CC2)NN1] | (S)-8-chloro-6-((((1-(1-(difluoromethyl)-cyclopropyl)-1H-1,2,3-triazol-4-yl)(6-fluoro-2-methylpyridin-3-yl)methyl)-amino)-4-(neopentylamino)quinoline-3-carbonitrile | 27 | 569.60 |
| 448 | 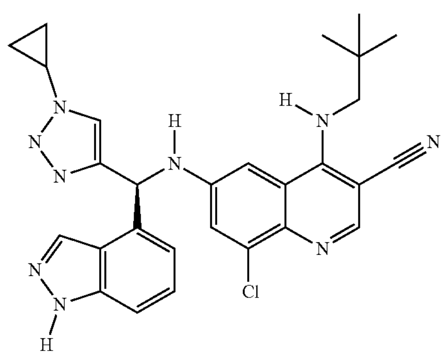 [SMILES: CC(C)(C)CNc1c(C#N)cnc2c(Cl)cc(N[C@H](C3=CN(C4CC4)NN3)c3cccc4[nH]ncc34)cc12] | (S)-8-chloro-6-(((1-cyclopropyl-1H-1,2,3-triazol-4-yl)(1H-indazol-4-yl)methyl)-amino)-4-(neopentylamino)quinoline-3-carbonitrile | 2 | 526.30 |
| 449 | 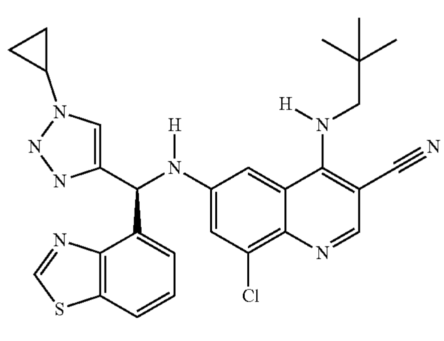 [SMILES: CC(C)(C)CNc1c(C#N)cnc2c(Cl)cc(N[C@H](C3=CN(C4CC4)NN3)c3cccc4scnc34)cc12] | (S)-6-((benzo[d]thiazol-4-yl(1-cyclopropyl-1H-1,2,3-triazol-4-yl)methyl)amino)-8-chloro-4-(neopentylamino)quinoline-3-carbonitrile | 2 | 543.30 |

TABLE 1-continued

| Comp | Structure | Name | Example Procedure | ES/MS m/z |
|---|---|---|---|---|
| 450 | 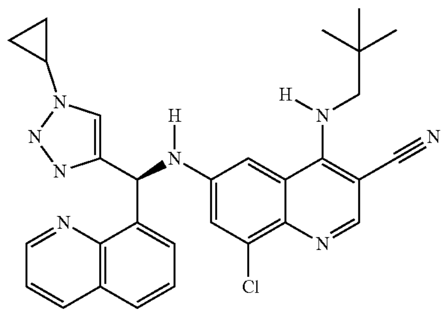 [SMILES: CC(C)(C)CNc1c(C#N)cnc2c(Cl)cc(N[C@H](C3=CN(C4CC4)NN3)c3cccc4cccnc34)cc12] | (S)-8-chloro-6-(((1-cyclopropyl-1H-1,2,3-triazol-4-yl)(quinolin-8-yl)methyl)amino)-4-(neopentylamino)quinoline-3-carbonitrile | 1 | 537.46 |
| 451 | 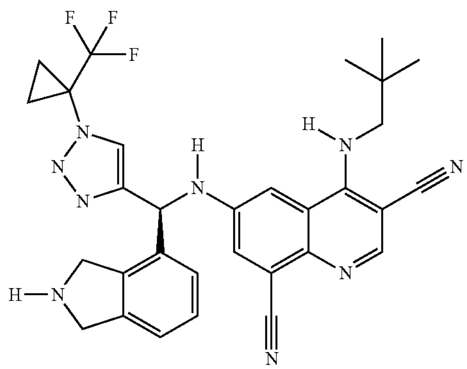 [SMILES: CC(C)(C)CNc1c(C#N)cnc2c(C#N)cc(N[C@H](C3=CN(C4(C(F)(F)F)CC4)NN3)c3cccc4c3CNC4)cc12] | (S)-6-((isoindolin-4-yl(1-(1-(trifluoromethyl)cyclopropyl)-1H-1,2,3-triazol-4-yl)methyl)amino)-4-(neopentylamino)-quinoline-3,8-dicarbonitrile | 12 | 586.10 |
| 452 | 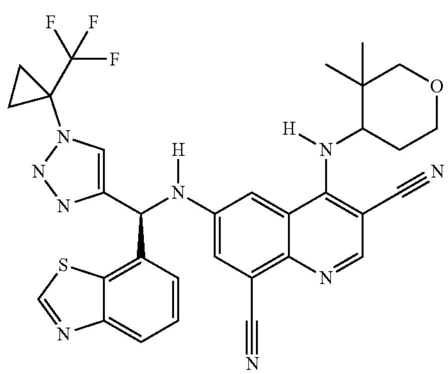 [SMILES: CC1(C)COCCC1Nc1c(C#N)cnc2c(C#N)cc(N[C@H](C3=CN(C4(C(F)(F)F)CC4)NN3)c3cccc4ncsc34)cc12] | 6-(((S)-benzo[d]thiazol-7-yl(1-(1-(trifluoromethyl)cyclopropyl)-1H-1,2,3-triazol-4-yl)methyl)amino)-4-((3,3-dimethyltetrahydro-2H-pyran-4-yl)amino)quinoline-3,8-dicarbonitrile | 34 | 644.10 |
| 453 | 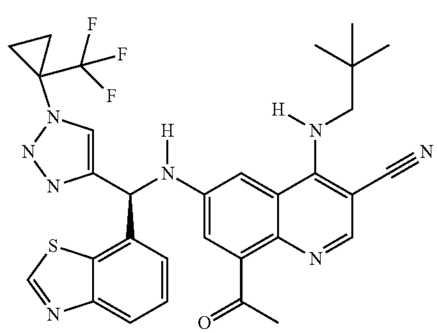 [SMILES: CC(=O)c1cc(N[C@H](C2=CN(C3(C(F)(F)F)CC3)NN2)c2cccc3ncsc23)cc2c(NCC(C)(C)C)c(C#N)cnc12] | (S)-8-acetyl-6-((benzo[d]thiazol-7-yl(1-(1-(trifluoromethyl)cyclopropyl)-1H-1,2,3-triazol-4-yl)methyl)amino)-4-(neopentylamino)quinoline-3-carbonitrile | 14 | 619.48 |

TABLE 1-continued

| Comp | Structure | Name | Example Procedure | ES/MS m/z |
|---|---|---|---|---|
| 454 | 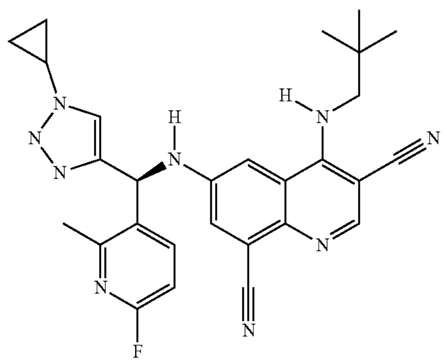 [SMILES: Cc1nc(F)ccc1[C@H](Nc1cc(C#N)c2ncc(C#N)c(NCC(C)(C)C)c2c1)C1=CN(C2CC2)NN1] | (S)-6-(((1-cyclopropyl-1H-1,2,3-triazol-4-yl)(6-fluoro-2-methylpyridin-3-yl)methyl)amino)-4-(neopentylamino)-quinoline-3,8-dicarbonitrile | 34 | 510.66 |
| 455 | 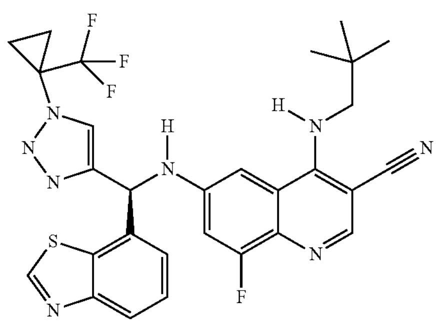 [SMILES: CC(C)(C)CNc1c(C#N)cnc2c(F)cc(N[C@H](C3=CN(C4(C(F)(F)F)CC4)NN3)c3cccc4ncsc34)cc12] | (S)-6-((benzo[d]thiazol-7-yl(1-(1-(trifluoromethyl)cyclopropyl)-1H-1,2,3-triazol-4-yl)methyl)amino)-8-fluoro-4-(neopentylamino)quinoline-3-carbonitrile | 4 | 595.2 |
| 456 | 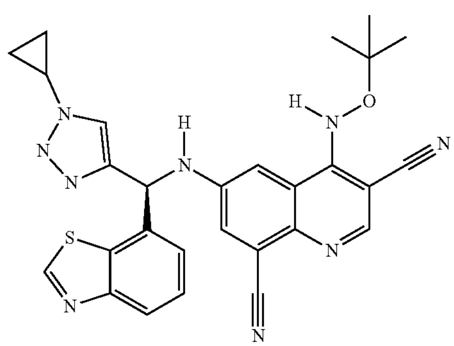 [SMILES: CC(C)(C)ONc1c(C#N)cnc2c(C#N)cc(N[C@H](C3=CN(C4CC4)NN3)c3cccc4ncsc34)cc12] | (S)-6-((benzo[d]thiazol-7-yl(1-cyclopropyl-1H-1,2,3-triazol-4-yl)methyl)amino)-4-(tert-butoxyamino)quinoline-3,8-dicarbonitrile | 38 | 536.20 |
| 457 | 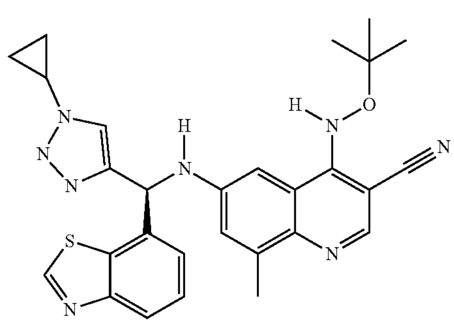 [SMILES: Cc1cc(N[C@H](C2=CN(C3CC3)NN2)c2cccc3ncsc23)cc2c(NOC(C)(C)C)c(C#N)cnc12] | (S)-6-((benzo[d]thiazol-7-yl(1-cyclopropyl-1H-1,2,3-triazol-4-yl)methyl)amino)-4-(tert-butoxyamino)-8-iodoquinoline-3-carbonitrile | 1 | 637.10 |

TABLE 1-continued

| Comp | Structure | Name | Example Procedure | ES/MS m/z |
|---|---|---|---|---|
| 458 | 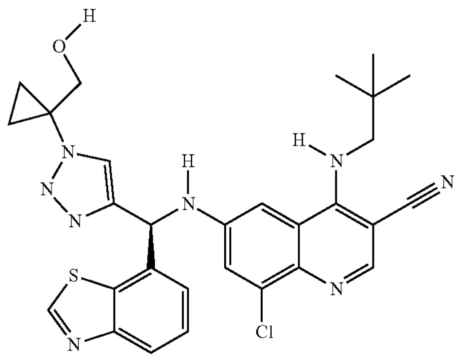 [SMILES: CC(C)(C)CNc1c(C#N)cnc2c(Cl)cc(N[C@H](C3=CN(C4(CO)CC4)NN3)c3cccc4ncsc34)cc12] | (S)-6-((benzo[d]thiazol-7-yl(1-(1-(hydroxymethyl)cyclopropyl)-1H-1,2,3-triazol-4-yl)methyl)amino)-8-chloro-4-(neopentylamino)quinoline-3-carbonitrile | 4 | 573.2 |
| 459 | 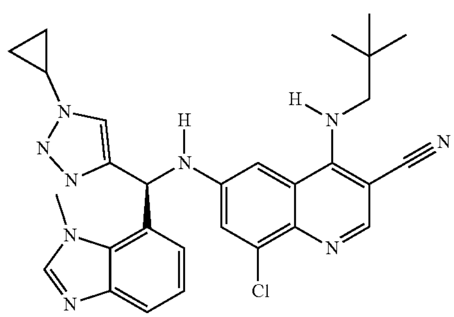 [SMILES: Cn1cnc2cccc([C@H](Nc3cc(Cl)c4ncc(C#N)c(NCC(C)(C)C)c4c3)C3=CN(C4CC4)NN3)c21] | (S)-8-chloro-6-(((1-cyclopropyl-1H-1,2,3-triazol-4-yl)(1-methyl-1H-benzo[d]imidazol-7-yl)methyl)amino)-4-(neopentylamino)quinoline-3-carbonitrile | 2 | 540.2 |
| 460 | 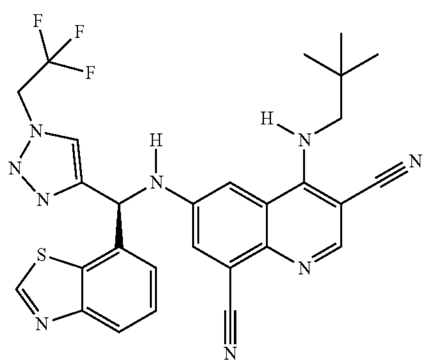 [SMILES: CC(C)(C)CNc1c(C#N)cnc2c(C#N)cc(N[C@H](C3=CN(CC(F)(F)F)NN3)c3cccc4ncsc34)cc12] | (S)-6-((benzo[d]thiazol-7-yl(1-(2,2,2-trifluoroethyl)-1H-1,2,3-triazol-4-yl)methyl)amino)-4-(neopentylamino)-quinoline-3,8-dicarbonitrile | 9 | 576.1 |
| 461 | 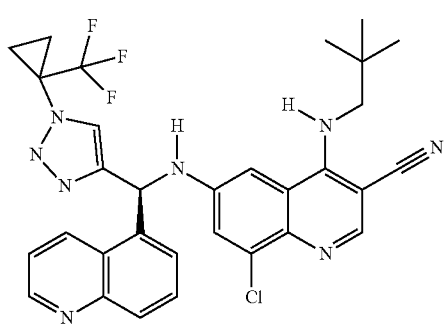 [SMILES: CC(C)(C)CNc1c(C#N)cnc2c(Cl)cc(N[C@H](C3=CN(C4(C(F)(F)F)CC4)NN3)c3cccc4ncccc34)cc12] | (S)-8-chloro-4-(neopentylamino)-6-((quinolin-5-yl(1-(1-(trifluoromethyl)-cyclopropyl)-1H-1,2,3-triazol-4-yl)methyl)amino)quinoline-3-carbonitrile | 23 | 605.10 |

TABLE 1-continued

| Comp | Structure | Name | Example Procedure | ES/MS m/z |
|---|---|---|---|---|
| 462 | 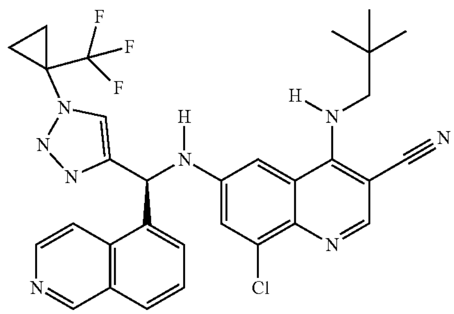 [SMILES: CC(C)(C)CNc1c(C#N)cnc2c(Cl)cc(N[C@H](C3=CN(C4(C(F)(F)F)CC4)NN3)c3cccc4cnccc34)cc12] | (S)-8-chloro-6-((isoquinolin-5-yl(1-(1-(trifluoromethyl)cyclopropyl)-1H-1,2,3-triazol-4-yl)methyl)amino)-4-(neopentylamino)quinoline-3-carbonitrile | 23 | 605.19 |
| 463 | 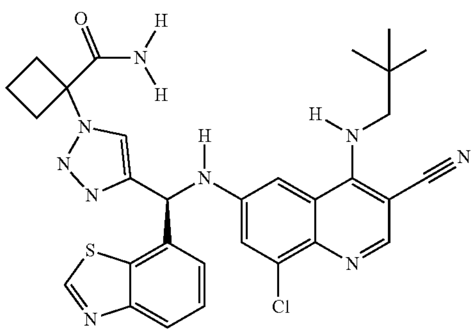 [SMILES: CC(C)(C)CNc1c(C#N)cnc2c(Cl)cc(N[C@H](C3=CN(C4(C(N)=O)CCC4)NN3)c3cccc4ncsc34)cc12] | (S)-1-(4-(benzo[d]thiazol-7-yl((8-chloro-3-cyano-4-(neopentylamino)quinolin-6-yl)amino)methyl)-1H-1,2,3-triazol-1-yl)cyclobutane-1-carboxamide | 4 | 600.2 |
| 464 | 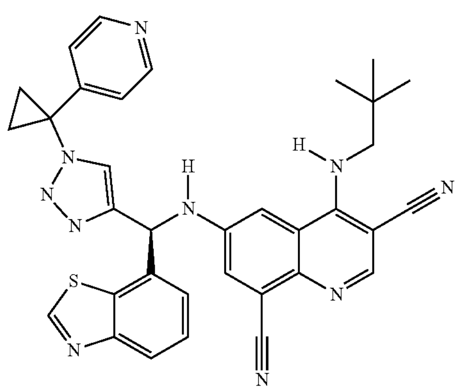 [SMILES: CC(C)(C)CNc1c(C#N)cnc2c(C#N)cc(N[C@H](C3=CN(C4(c5ccncc5)CC4)NN3)c3cccc4ncsc34)cc12] | (S)-6-((benzo[d]thiazol-7-yl(1-(1-(pyridin-4-yl)cyclopropyl)-1H-1,2,3-triazol-4-yl)methyl)amino)-4-(neopentylamino)-quinoline-3,8-dicarbonitrile | 34 | 611.1 |
| 465 | 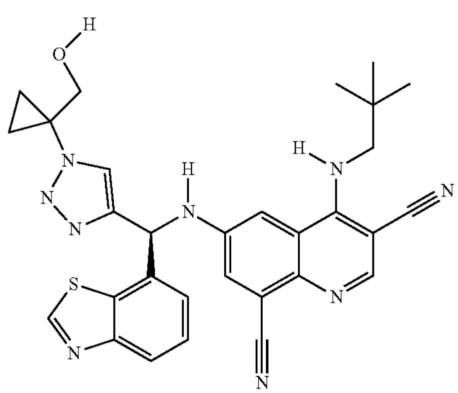 [SMILES: CC(C)(C)CNc1c(C#N)cnc2c(C#N)cc(N[C@H](C3=CN(C4(CO)CC4)NN3)c3cccc4ncsc34)cc12] | (S)-6-((benzo[d]thiazol-7-yl(1-(1-(hydroxymethyl)cyclopropyl)-1H-1,2,3-triazol-4-yl)methyl)amino)-4-(neopentylamino)quinoline-3,8-dicarbonitrile | 34 | 564.2 |

TABLE 1-continued

| Comp | Structure | Name | Example Procedure | ES/MS m/z |
|---|---|---|---|---|
| 466 | 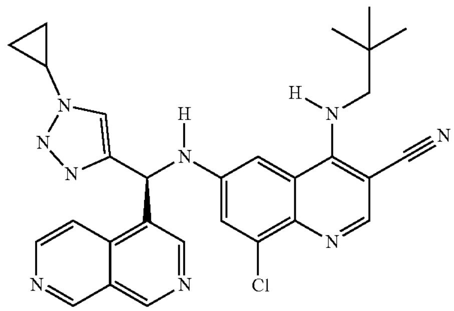 [SMILES: CC(C)(C)CNc1c(C#N)cnc2c(Cl)cc(N[C@H](C3=CN(C4CC4)NN3)c3cncc4cnccc34)cc12] | (S)-8-chloro-6-(((1-cyclopropyl-1H-1,2,3-triazol-4-yl)(2,7-naphthyridin-4-yl)methyl)amino)-4-(neopentylamino)-quinoline-3-carbonitrile | 2 | 538.3 |
| 467 | 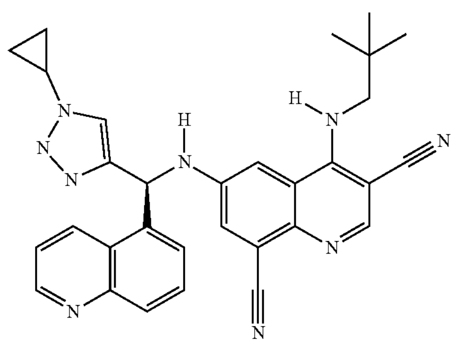 [SMILES: CC(C)(C)CNc1c(C#N)cnc2c(C#N)cc(N[C@H](C3=CN(C4CC4)NN3)c3cccc4ncccc34)cc12] | (S)-6-(((1-cyclopropyl-1H-1,2,3-triazol-4-yl)(quinolin-5-yl)methyl)amino)-4-(neopentylamino)quinoline-3,8-dicarbonitrile | 34 | 528.13 |
| 468 | 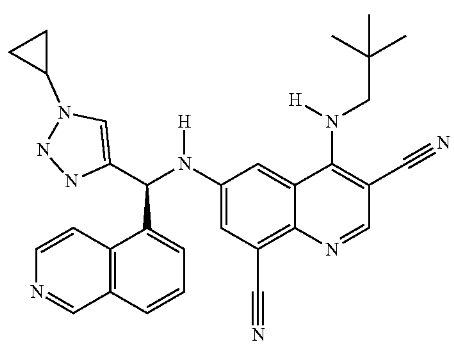 [SMILES: CC(C)(C)CNc1c(C#N)cnc2c(C#N)cc(N[C@H](C3=CN(C4CC4)NN3)c3cccc4cnccc34)cc12] | (S)-6-(((1-cyclopropyl-1H-1,2,3-triazol-4-yl)(isoquinolin-5-yl)methyl)amino)-4-(neopentylamino)quinoline-3,8-dicarbonitrile | 34 | 528.15 |
| 469 | 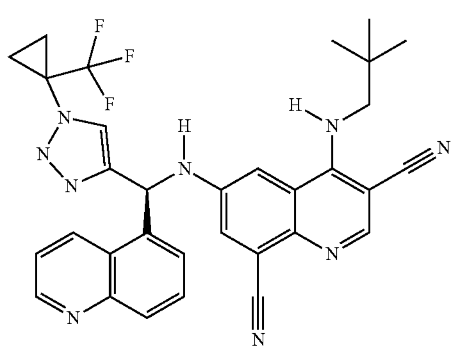 | (S)-4-(neopentylamino)-6-((quinolin-5-yl(1-(1-(trifluoromethyl)-cyclopropyl)-1H-1,2,3-triazol-4-yl)methyl)amino)quinoline-3,8-dicarbonitrile | 34 | 596.35 |

TABLE 1-continued

| Comp | Structure | Name | Example Procedure | ES/MS m/z |
|---|---|---|---|---|
| 470 | 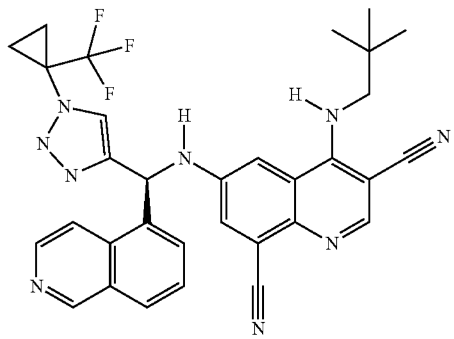 [SMILES: CC(C)(C)CNc1c(C#N)cnc2c(C#N)cc(N[C@H](C3=CN(C4(C(F)(F)F)CC4)NN3)c3cccc4cnccc34)cc12] | (S)-6-((isoquinolin-5-yl(1-(1-(trifluoromethyl)cyclopropyl)-1H-1,2,3-triazol-4-yl)methyl)amino)-4-(neopentylamino)quinoline-3,8-dicarbonitrile | 34 | 596.27 |
| 471 | 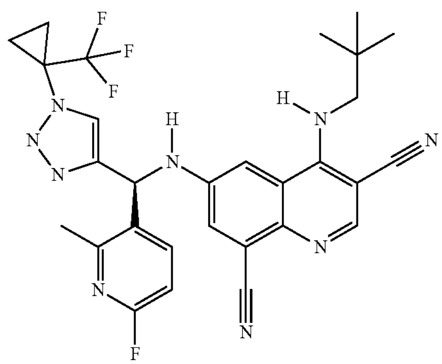 [SMILES: Cc1nc(F)ccc1[C@H](Nc1cc(C#N)c2ncc(C#N)c(NCC(C)(C)C)c2c1)C1=CN(C2(C(F)(F)F)CC2)NN1] | (S)-6-(((6-fluoro-2-methylpyridin-3-yl)(1-(1-(trifluoromethyl)cyclopropyl)-1H-1,2,3-triazol-4-yl)methyl)amino)-4-(neopentylamino)quinoline-3,8-dicarbonitrile | 34 | 578.24 |
| 472 | 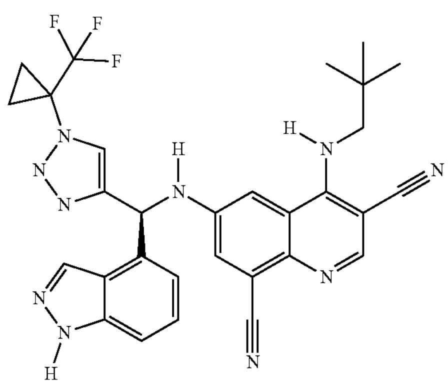 [SMILES: CC(C)(C)CNc1c(C#N)cnc2c(C#N)cc(N[C@H](C3=CN(C4(C(F)(F)F)CC4)NN3)c3cccc4[nH]ncc34)cc12] | (S)-6-(((1H-indazol-4-yl)(1-(1-(trifluoromethyl)cyclopropyl)-1H-1,2,3-triazol-4-yl)methyl)amino)-4-(neopentylamino)quinoline-3,8-dicarbonitrile | 34 | 585.2 |
| 473 | 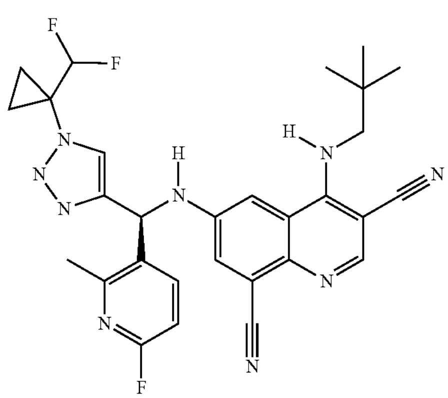 [SMILES: Cc1nc(F)ccc1[C@H](Nc1cc(C#N)c2ncc(C#N)c(NCC(C)(C)C)c2c1)C1=CN(C2(C(F)F)CC2)NN1] | (S)-6-(((1-(1-(difluoromethyl)cyclopropyl)-1H-1,2,3-triazol-4-yl)(6-fluoro-2-methylpyridin-3-yl)methyl)amino)-4-(neopentylamino)quinoline-3,8-dicarbonitrile | 34 | 560.2 |

TABLE 1-continued

| Comp | Structure | Name | Example Procedure | ES/MS m/z |
|---|---|---|---|---|
| 474 | 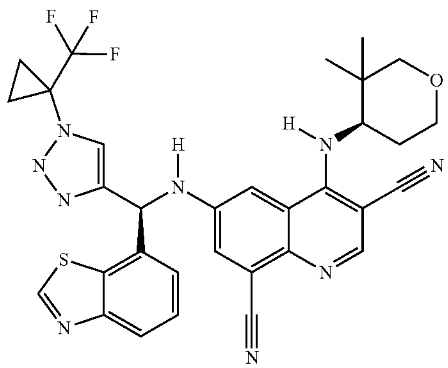 [SMILES: CC1(C)COCC[C@H]1Nc1c(C#N)cnc2c(C#N)cc(N[C@H](C3=CN(C4(C(F)(F)F)CC4)NN3)c3cccc4ncsc34)cc12] | 6-(((S)-benzo[d]thiazol-7-yl(1-(1-(trifluoromethyl)cyclopropyl)-1H-1,2,3-triazol-4-yl)methyl)amino)-4-(((R)-3,3-dimethyltetrahydro-2H-pyran-4-yl)amino)quinoline-3,8-dicarbonitrile | 34 | 644.20 |
| 475 | 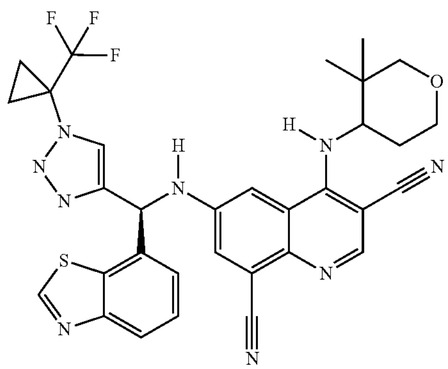 [SMILES: CC1(C)COCCC1Nc1c(C#N)cnc2c(C#N)cc(N[C@H](C3=CN(C4(C(F)(F)F)CC4)NN3)c3cccc4ncsc34)cc12] | 6-(((S)-benzo[d]thiazol-7-yl(1-(1-(trifluoromethyl)cyclopropyl)-1H-1,2,3-triazol-4-yl)methyl)amino)-4-(((S)-3,3-dimethyltetrahydro-2H-pyran-4-yl)amino)quinoline-3,8-dicarbonitrile | 34 | 644.20 |
| 476 | 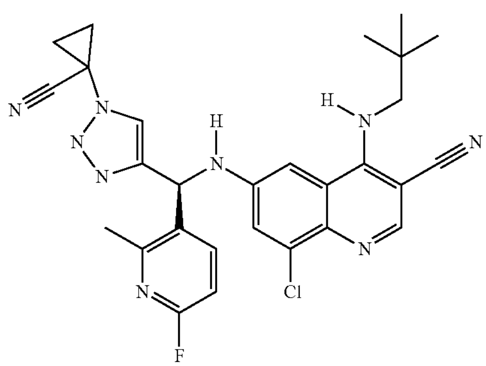 [SMILES: Cc1nc(F)ccc1[C@H](Nc1cc(Cl)c2ncc(C#N)c(NCC(C)(C)C)c2c1)C1=CN(C2(C#N)CC2)NN1] | (S)-8-chloro-6-(((1-(1-cyanocyclopropyl)-1H-1,2,3-triazol-4-yl)(6-fluoro-2-methylpyridin-3-yl)methyl)amino)-4-(neopentylamino)-quinoline-3-carbonitrile | 4 | 544.2 |
| 477 | 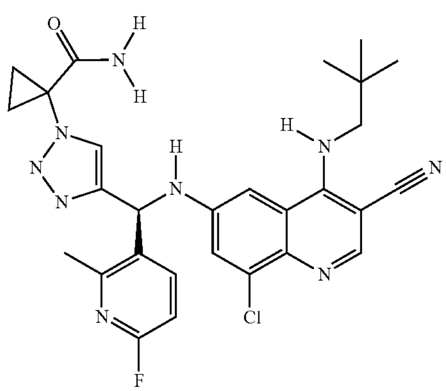 [SMILES: Cc1nc(F)ccc1[C@H](Nc1cc(Cl)c2ncc(C#N)c(NCC(C)(C)C)c2c1)C1=CN(C2(C(N)=O)CC2)NN1] | (S)-1-(4-(((8-chloro-3-cyano-4-(neopentylamino)quinolin-6-yl)amino)(6-fluoro-2-methylpyridin-3-yl)methyl)-1H-1,2,3-triazol-1-yl)cyclopropane-1-carboxamide | 4 | 562.3 |

TABLE 1-continued

| Comp | Structure | Name | Example Procedure | ES/MS m/z |
|---|---|---|---|---|
| 478 | 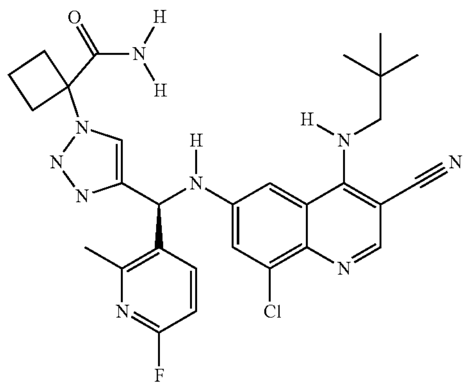 [SMILES: Cc1nc(F)ccc1[C@H](Nc1cc(Cl)c2ncc(C#N)c(NCC(C)(C)C)c2c1)C1=CN(C2(C(N)=O)CCC2)NN1] | (S)-1-(4-(((8-chloro-3-cyano-4-(neopentylamino)quinolin-6-yl)amino)(6-fluoro-2-methylpyridin-3-yl)methyl)-1H-1,2,3-triazol-1-yl)cyclobutane-1-carboxamide | 4 | 576.3 |
| 479 | 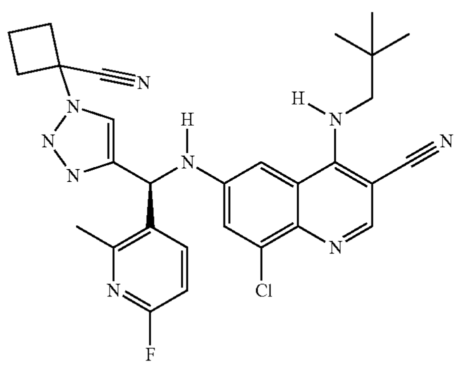 [SMILES: Cc1nc(F)ccc1[C@H](Nc1cc(Cl)c2ncc(C#N)c(NCC(C)(C)C)c2c1)C1=CN(C2(C#N)CCC2)NN1] | (S)-8-chloro-6-(((1-(1-cyanocyclobutyl)-1H-1,2,3-triazol-4-yl)(6-fluoro-2-methylpyridin-3-yl)methyl)amino)-4-(neopentylamino)quinoline-3-carbonitrile | 4 | 558.2 |
| 480 | 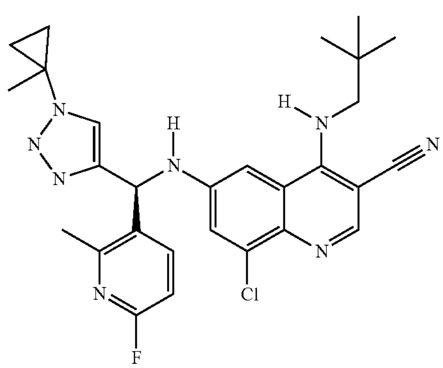 [SMILES: Cc1nc(F)ccc1[C@H](Nc1cc(Cl)c2ncc(C#N)c(NCC(C)(C)C)c2c1)C1=CN(C2(C)CC2)NN1] | (S)-8-chloro-6-(((6-fluoro-2-methylpyridin-3-yl)(1-(1-methylcyclopropyl)-1H-1,2,3-triazol-4-yl)methyl)amino)-4-(neopentylamino)-quinoline-3-carbonitrile | 4 | 533.3 |
| 481 | 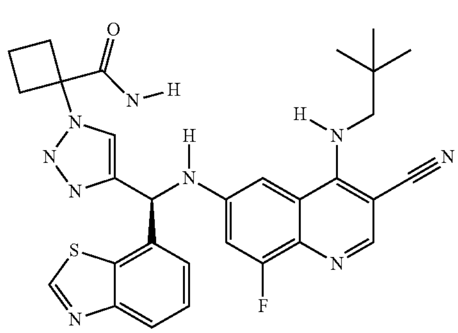 [SMILES: CC(C)(C)CNc1c(C#N)cnc2c(F)cc(N[C@H](C3=CN(C4(C(N)=O)CCC4)NN3)c3cccc4ncsc34)cc12] | (S)-1-(4-(benzo[d]thiazol-7-yl((3-cyano-8-fluoro-4-(neopentylamino)quinolin-6-yl)-amino)methyl)-1H-1,2,3-triazol-1-yl)cyclobutane-1-carboxamide | 4 | 584.20 |

TABLE 1-continued

| Comp | Structure | Name | Example Procedure | ES/MS m/z |
|---|---|---|---|---|
| 482 | 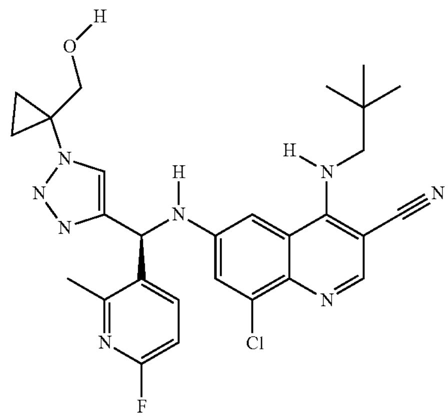 [SMILES: Cc1nc(F)ccc1[C@H](Nc1cc(Cl)c2ncc(C#N)c(NCC(C)(C)C)c2c1)C1=CN(C2(CO)CC2)NN1] | (S)-8-chloro-6-(((6-fluoro-2-methylpyridin-3-yl)(1-(1-(hydroxymethyl)cyclopropyl)-1H-1,2,3-triazol-4-yl)methyl)amino)-4-(neopentylamino)quinoline-3-carbonitrile | 23 | 549.18 |
| 483 | 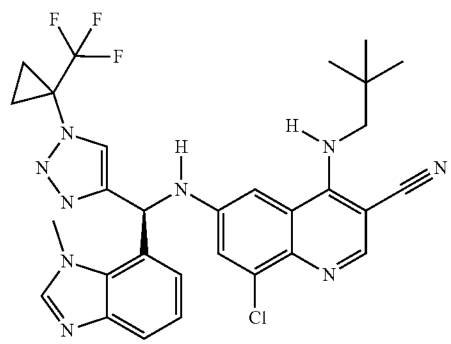 [SMILES: Cn1cnc2cccc([C@H](Nc3cc(Cl)c4ncc(C#N)c(NCC(C)(C)C)c4c3)C3=CN(C4(C(F)(F)F)CC4)NN3)c21] | (S)-8-chloro-6-(((1-methyl-1H-benzo[d]imidazol-7-yl)(1-(1-(trifluoromethyl)cyclopropyl)-1H-1,2,3-triazol-4-yl)methyl)amino)-4-(neopentylamino)quinoline-3-carbonitrile | 4 | 608.5 |
| 484 | 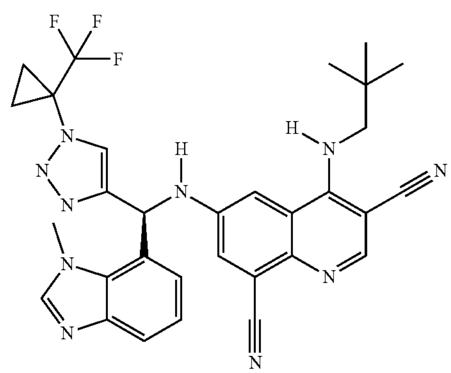 [SMILES: Cn1cnc2cccc([C@H](Nc3cc(C#N)c4ncc(C#N)c(NCC(C)(C)C)c4c3)C3=CN(C4(C(F)(F)F)CC4)NN3)c21] | (S)-6-(((1-methyl-1H-benzo[d]imidazol-7-yl)(1-(1-(trifluoromethyl)cyclopropyl)-1H-1,2,3-triazol-4-yl)methyl)amino)-4-(neopentylamino)quinoline-3,8-dicarbonitrile | 34 | 599.3 |
| 485 | 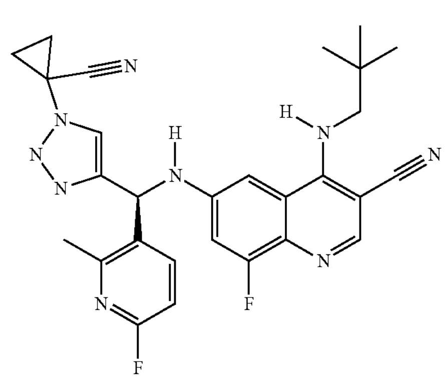 [SMILES: Cc1nc(F)ccc1[C@H](Nc1cc(F)c2ncc(C#N)c(NCC(C)(C)C)c2c1)C1=CN(C2(C#N)CC2)NN1] | (S)-6-(((1-(1-cyanocyclopropyl)-1H-1,2,3-triazol-4-yl)(6-fluoro-2-methylpyridin-3-yl)methyl)amino)-8-fluoro-4-(neopentylamino)quinoline-3-carbonitrile | 4 | 528.2 |

TABLE 1-continued

| Comp | Structure | Name | Example Procedure | ES/MS m/z |
|---|---|---|---|---|
| 486 | 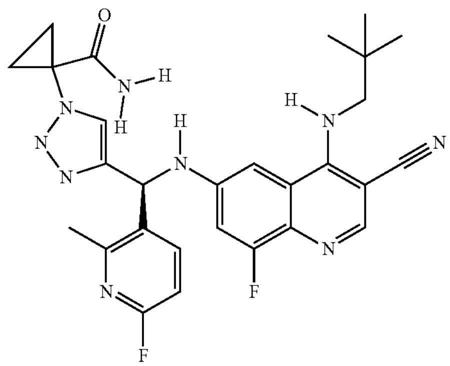 [SMILES: Cc1nc(F)ccc1[C@H](Nc1cc(F)c2ncc(C#N)c(NCC(C)(C)C)c2c1)C1=CN(C2(C(N)=O)CC2)NN1] | (S)-1-(4-(((3-cyano-8-fluoro-4-(neopentyl-amino)quinolin-6-yl)amino)(6-fluoro-2-methylpyridin-3-yl)methyl)-1H-1,2,3-triazol-1-yl)cyclopropane-1-carboxamide | 4 | 546.3 |
| 487 | 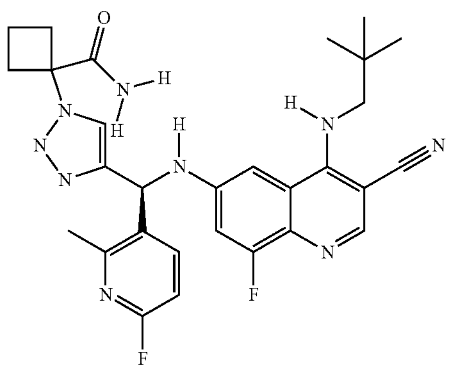 [SMILES: Cc1nc(F)ccc1[C@H](Nc1cc(F)c2ncc(C#N)c(NCC(C)(C)C)c2c1)C1=CN(C2(C(N)=O)CCC2)NN1] | (S)-1-(4-(((3-cyano-8-fluoro-4-(neopentyl-amino)quinolin-6-yl)amino)(6-fluoro-2-methylpyridin-3-yl)methyl)-1H-1,2,3-triazol-1-yl)cyclobutane-1-carboxamide | 4 | 560.3 |
| 488 | 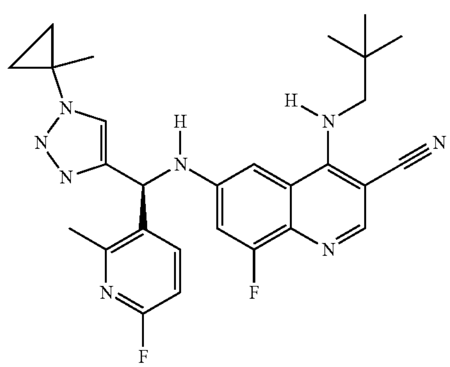 [SMILES: Cc1nc(F)ccc1[C@H](Nc1cc(F)c2ncc(C#N)c(NCC(C)(C)C)c2c1)C1=CN(C2(C)CC2)NN1] | (S)-8-fluoro-6-(((6-fluoro-2-methylpyridin-3-yl)(1-(1-methylcyclopropyl)-1H-1,2,3-triazol-4-yl)methyl)amino)-4-(neopentyl-amino)quinoline-3-carbonitrile | 4 | 517.3 |
| 489 | 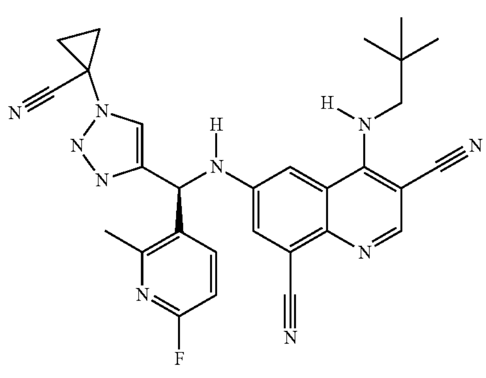 [SMILES: Cc1nc(F)ccc1[C@H](Nc1cc(C#N)c2ncc(C#N)c(NCC(C)(C)C)c2c1)C1=CN(C2(C#N)CC2)NN1] | (S)-6-(((1-(1-cyanocyclopropyl)-1H-1,2,3-triazol-4-yl)(6-fluoro-2-methylpyridin-3-yl)methyl)amino)-4-(neopentylamino)-quinoline-3,8-dicarbonitrile | 24 | 535.2 |

TABLE 1-continued

| Comp | Structure | Name | Example Procedure | ES/MS m/z |
|---|---|---|---|---|
| 490 | 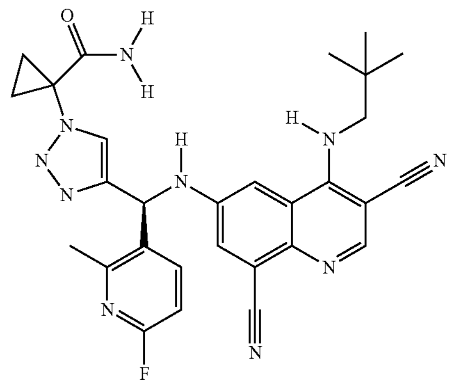 [SMILES: Cc1nc(F)ccc1[C@H](Nc1cc(C#N)c2ncc(C#N)c(NCC(C)(C)C)c2c1)C1=CN(C2(C(N)=O)CC2)NN1] | (S)-1-(4-(((3,8-dicyano-4-(neopentylamino)-quinolin-6-yl)amino)(6-fluoro-2-methylpyridin-3-yl)methyl)-1H-1,2,3-triazol-1-yl)cyclopropane-1-carboxamide | 24 | 553.3 |
| 491 | 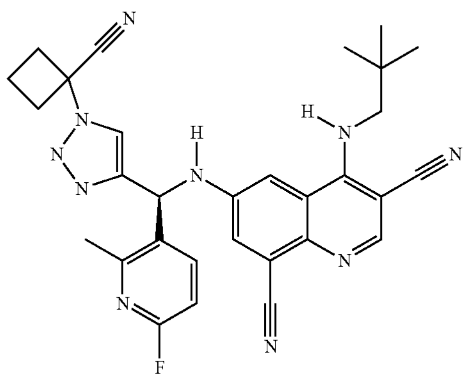 [SMILES: Cc1nc(F)ccc1[C@H](Nc1cc(C#N)c2ncc(C#N)c(NCC(C)(C)C)c2c1)C1=CN(C2(C#N)CCC2)NN1] | (S)-6-(((1-(1-cyanocyclobutyl)-1H-1,2,3-triazol-4-yl)(6-fluoro-2-methylpyridin-3-yl)methyl)amino)-4-(neopentylamino)-quinoline-3,8-dicarbonitrile | 24 | 549.3 |
| 492 | 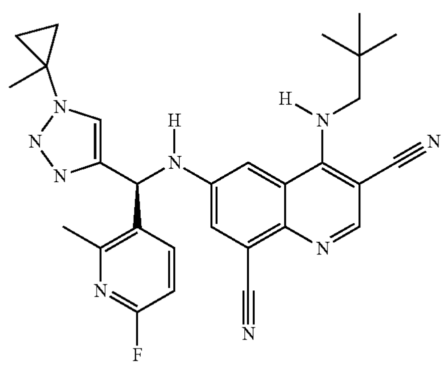 [SMILES: Cc1nc(F)ccc1[C@H](Nc1cc(C#N)c2ncc(C#N)c(NCC(C)(C)C)c2c1)C1=CN(C2(C)CC2)NN1] | (S)-6-(((6-fluoro-2-methylpyridin-3-yl)(1-(1-methylcyclopropyl)-1H-1,2,3-triazol-4-yl)methyl)amino)-4-(neopentylamino)-quinoline-3,8-dicarbonitrile | 24 | 524.2 |
| 493 | 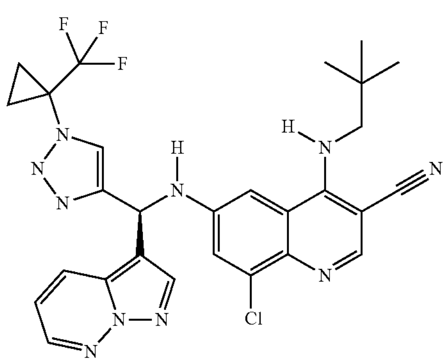 [SMILES: CC(C)(C)CNc1c(C#N)cnc2c(Cl)cc(N[C@H](C3=CN(C4(C(F)(F)F)CC4)NN3)c3cnn4ncccc34)cc12] | (S)-8-chloro-4-(neopentylamino)-6-((pyrazolo[1,5-b]pyridazin-3-yl(1-(1-(trifluoromethyl)cyclopropyl)-1H-1,2,3-triazol-4-yl)methyl)amino)quinoline-3-carbonitrile | 4 | 595.3 |

TABLE 1-continued

| Comp | Structure | Name | Example Procedure | ES/MS m/z |
|---|---|---|---|---|
| 494 | 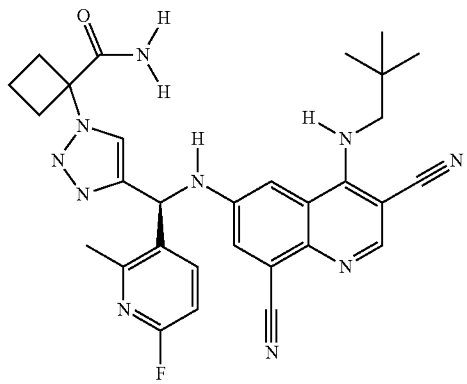 [SMILES: Cc1nc(F)ccc1[C@H](Nc1cc(C#N)c2ncc(C#N)c(NCC(C)(C)C)c2c1)C1=CN(C2(C(N)=O)CCC2)NN1] | (S)-1-(4-(((3,8-dicyano-4-(neopentyl-amino)quinolin-6-yl)amino)(6-fluoro-2-methylpyridin-3-yl)methyl)-1H-1,2,3-triazol-1-yl)cyclobutane-1-carboxamide | 24 | 567.3 |
| 495 | 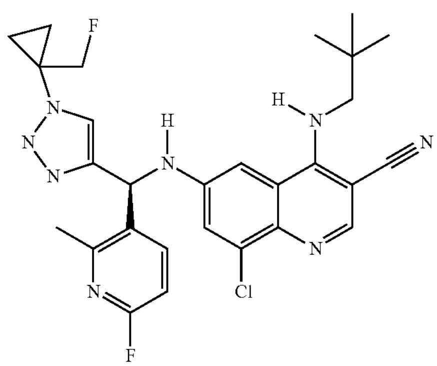 [SMILES: Cc1nc(F)ccc1[C@H](Nc1cc(Cl)c2ncc(C#N)c(NCC(C)(C)C)c2c1)C1=CN(C2(CF)CC2)NN1] | (S)-8-chloro-6-(((6-fluoro-2-methylpyridin-3-yl)(1-(1-(fluoromethyl)cyclopropyl)-1H-1,2,3-triazol-4-yl)methyl)amino)-4-(neopentylamino)quinoline-3-carbonitrile | 27 | 551.30 |
| 496 | 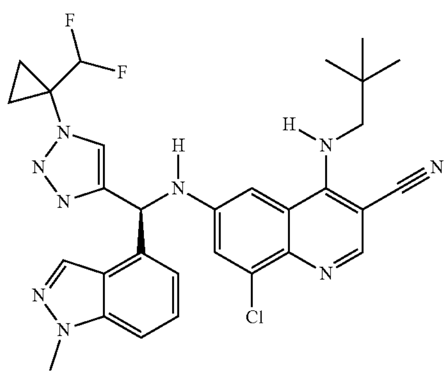 [SMILES: Cn1ncc2c([C@H](Nc3cc(Cl)c4ncc(C#N)c(NCC(C)(C)C)c4c3)C3=CN(C4(C(F)F)CC4)NN3)cccc21] | (S)-8-chloro-6-(((1-(1-(difluoromethyl)-cyclopropyl)-1H-1,2,3-triazol-4-yl)(1-methyl-1H-indazol-4-yl)methyl)amino)-4-(neopentylamino)quinoline-3-carbonitrile | 4 | 590.5 |
| 497 | 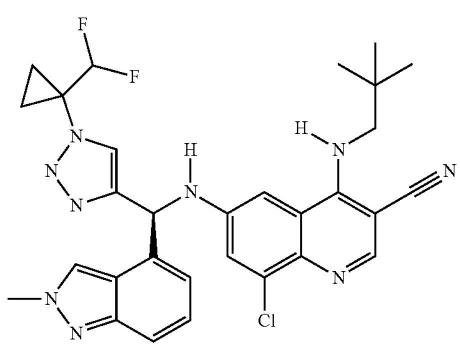 [SMILES: Cn1cc2c([C@H](Nc3cc(Cl)c4ncc(C#N)c(NCC(C)(C)C)c4c3)C3=CN(C4(C(F)F)CC4)NN3)cccc2n1] | (S)-8-chloro-6-(((1-(1-(difluoromethyl)-cyclopropyl)-1H-1,2,3-triazol-4-yl)(2-methyl-2H-indazol-4-yl)methyl)amino)-4-(neopentylamino)quinoline-3-carbonitrile | 4 | 590.4 |

TABLE 1-continued

| Comp | Structure | Name | Example Procedure | ES/MS m/z |
|---|---|---|---|---|
| 498 | 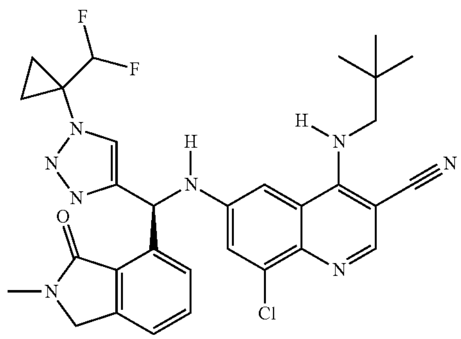 [SMILES: CN1Cc2cccc([C@H](Nc3cc(Cl)c4ncc(C#N)c(NCC(C)(C)C)c4c3)C3=CN(C4(C(F)F)CC4)NN3)c2C1=O] | (S)-8-chloro-6-(((1-(1-(difluoromethyl)-cyclopropyl)-1H-1,2,3-triazol-4-yl)(2-methyl-3-oxoisoindolin-4-yl)methyl)-amino)-4-(neopentylamino)quinoline-3-carbonitrile | 4 | 605.3 |
| 499 | 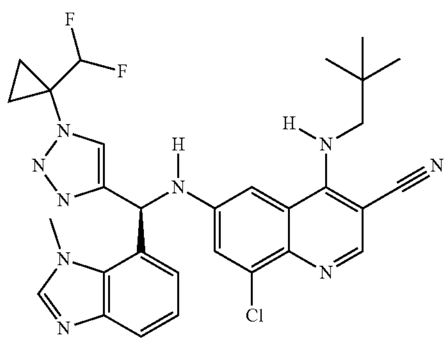 [SMILES: Cn1cnc2cccc([C@H](Nc3cc(Cl)c4ncc(C#N)c(NCC(C)(C)C)c4c3)C3=CN(C4(C(F)F)CC4)NN3)c21] | (S)-8-chloro-6-(((1-(1-(difluoromethyl)-cyclopropyl)-1H-1,2,3-triazol-4-yl)(1-methyl-1H-benzo[d]imidazol-7-yl)methyl)amino)-4-(neopentylamino)-quinoline-3-carbonitrile | 4 | 590.3 |
| 500 | 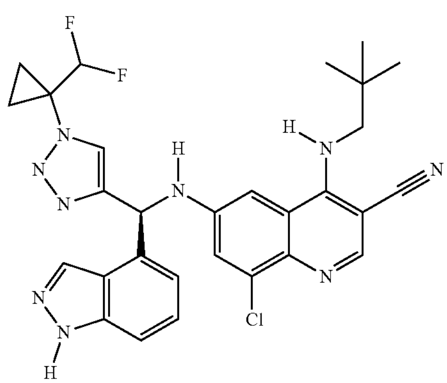 [SMILES: CC(C)(C)CNc1c(C#N)cnc2c(Cl)cc(N[C@H](C3=CN(C4(C(F)F)CC4)NN3)c3cccc4[nH]ncc34)cc12] | (S)-8-chloro-6-(((1-(1-(difluoromethyl)cyclopropyl)-1H-1,2,3-triazol-4-yl)(1H-indazol-4-yl)methyl)amino)-4-(neopentylamino)quinoline-3-carbonitrile | 32 | 576.2 |
| 501 | 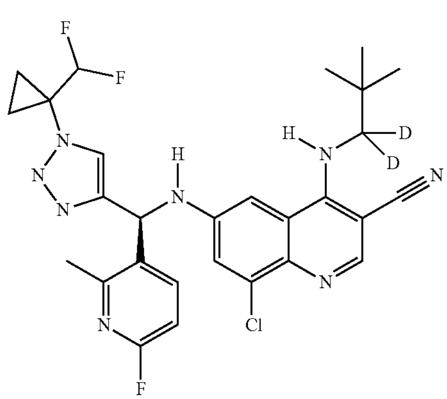 [SMILES: [2H]C([2H])(Nc1c(C#N)cnc2c(Cl)cc(N[C@H](C3=CN(C4(C(F)F)CC4)NN3)c3ccc(F)nc3C)cc12)C(C)(C)C] | (S)-8-chloro-6-(((1-(1-(difluoromethyl)-cyclopropyl)-1H-1,2,3-triazol-4-yl)(6-fluoro-2-methylpyridin-3-yl)methyl)amino)-4-((2,2-dimethylpropyl-1,1-d2)amino)-quinoline-3-carbonitrile | 4 | 571.3 |

TABLE 1-continued

| Comp | Structure | Name | Example Procedure | ES/MS m/z |
|---|---|---|---|---|
| 502 | 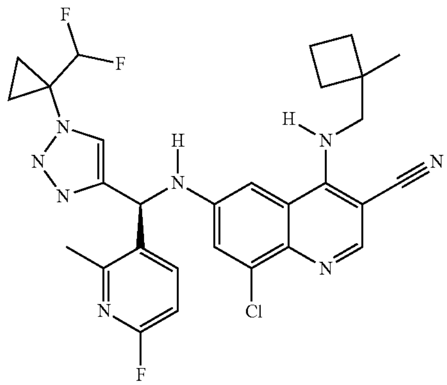 [SMILES: Cc1nc(F)ccc1[C@H](Nc1cc(Cl)c2ncc(C#N)c(NCC3(C)CCC3)c2c1)C1=CN(C2(C(F)F)CC2)NN1] | (S)-8-chloro-6-(((1-(1-(difluoromethyl)-cyclopropyl)-1H-1,2,3-triazol-4-yl)(6-fluoro-2-methylpyridin-3-yl)methyl)-amino)-4-(((1-methylcyclobutyl)methyl)-amino) quinoline-3-carbonitrile | 4 | 581.3 |
| 503 | 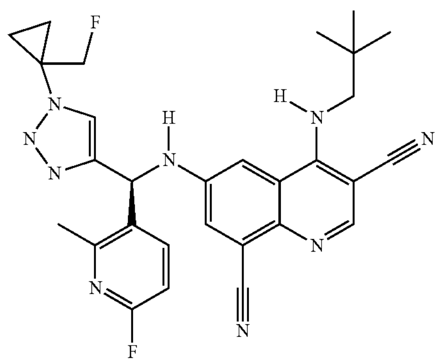 [SMILES: Cc1nc(F)ccc1[C@H](Nc1cc(C#N)c2ncc(C#N)c(NCC(C)(C)C)c2c1)C1=CN(C2(CF)CC2)NN1] | (S)-6-(((6-fluoro-2-methylpyridin-3-yl)(1-(1-(fluoromethyl)cyclopropyl)-1H-1,2,3-triazol-4-yl)methyl)amino)-4-(neopentylamino)quinoline-3,8-dicarbonitrile | 9 | 542.30 |
| 504 | 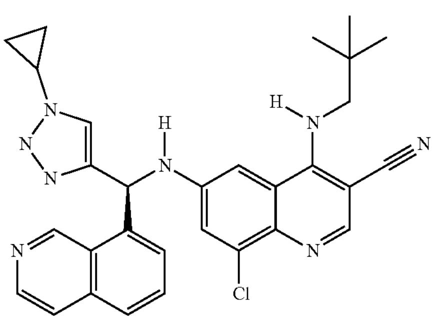 [SMILES: CC(C)(C)CNc1c(C#N)cnc2c(Cl)cc(N[C@H](C3=CN(C4CC4)NN3)c3cccc4ccncc34)cc12] | (S)-8-chloro-6-(((1-cyclopropyl-1H-1,2,3-triazol-4-yl)(isoquinolin-8-yl)methyl)amino)-4-(neopentylamino)quinoline-3-carbonitrile | 1 | 537.13 |
| 505 | 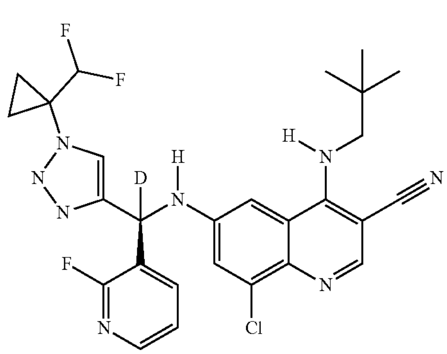 [SMILES: [2H][C@](Nc1cc(Cl)c2ncc(C#N)c(NCC(C)(C)C)c2c1)(C1=CN(C2(C(F)F)CC2)NN1)c1cccnc1F] | 8-chloro-6-(((1-(1-(difluoromethyl)-cyclopropyl)-1H-1,2,3-triazol-4-yl)(2-fluoropyridin-3-yl)methyl-d)amino)-4-(neopentylamino)quinoline-3-carbonitrile | 23 | 556.14 |

TABLE 1-continued

| Comp | Structure | Name | Example Procedure | ES/MS m/z |
|---|---|---|---|---|
| 506 | 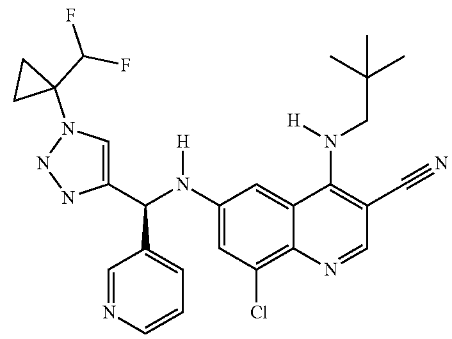 [SMILES: CC(C)(C)CNc1c(C#N)cnc2c(Cl)cc(N[C@H](C3=CN(C4(C(F)F)CC4)NN3)c3cccnc3)cc12] | (S)-8-chloro-6-(((1-(1-(difluoromethyl)-cyclopropyl)-1H-1,2,3-triazol-4-yl)(pyridin-3-yl)methyl)amino)-4-(neopentylamino)quinoline-3-carbonitrile | 23 | 537.08 |
| 507 | 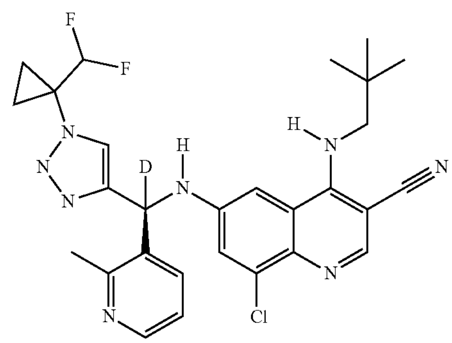 [SMILES: [2H][C@](Nc1cc(Cl)c2ncc(C#N)c(NCC(C)(C)C)c2c1)(C1=CN(C2(C(F)F)CC2)NN1)c1cccnc1C] | 8-chloro-6-(((1-(1-(difluoromethyl)cyclo-propyl)-1H-1,2,3-triazol-4-yl)(2-methyl-pyridin-3-yl)methyl-d)amino)-4-(neopentylamino)quinoline-3-carbonitrile | 23 | 552.18 |
| 508 | 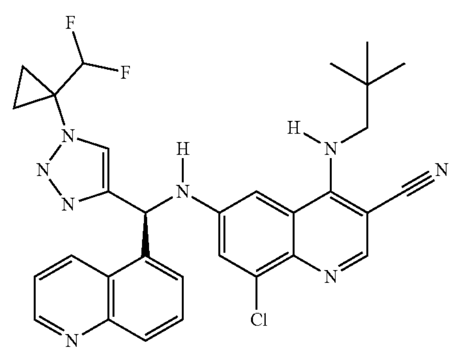 [SMILES: CC(C)(C)CNc1c(C#N)cnc2c(Cl)cc(N[C@H](C3=CN(C4(C(F)F)CC4)NN3)c3cccc4ncccc34)cc12] | (S)-8-chloro-6-(((1-(1-(difluoromethyl)-cyclopropyl)-1H-1,2,3-triazol-4-yl)(quinolin-5-yl)methyl)amino)-4-(neopentylamino)-quinoline-3-carbonitrile | 23 | 587.11 |
| 509 | 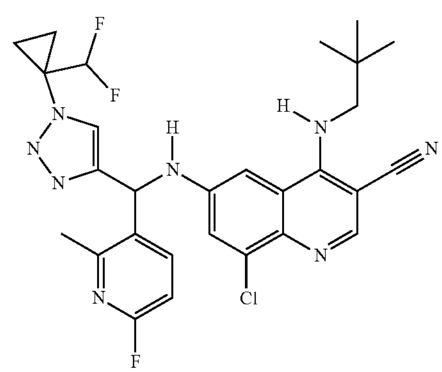 [SMILES: Cc1nc(F)ccc1C(Nc1cc(Cl)c2ncc(C#N)c(NCC(C)(C)C)c2c1)C1=CN(C2(C(F)F)CC2)NN1] | (R)-8-chloro-6-(((1-(1-(difluoromethyl)-cyclopropyl)-1H-1,2,3-triazol-4-yl)(6-fluoro-2-methylpyridin-3-yl)methyl)amino)-4-(neopentylamino)quinoline-3-carbonitrile | 23 | 569.60 |

TABLE 1-continued

| Comp | Structure | Name | Example Procedure | ES/MS m/z |
|---|---|---|---|---|
| 510 | 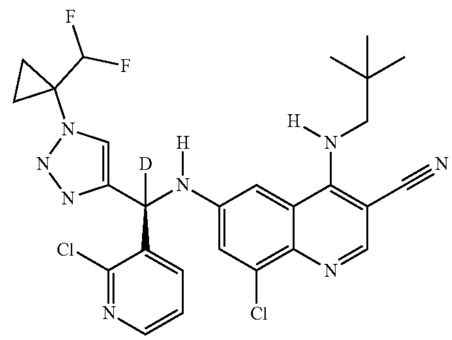 [SMILES: [2H][C@](Nc1cc(Cl)c2ncc(C#N)c(NCC(C)(C)C)c2c1)(C1=CN(C2(C(F)F)CC2)NN1)c1cccnc1Cl] | 8-chloro-6-(((2-chloropyridin-3-yl)(1-(1-(difluoromethyl)cyclopropyl)-1H-1,2,3-triazol-4-yl)methyl-d)amino)-4-(neopentyl-amino)quinoline-3-carbonitrile | 23 | 572.11 |
| 511 | 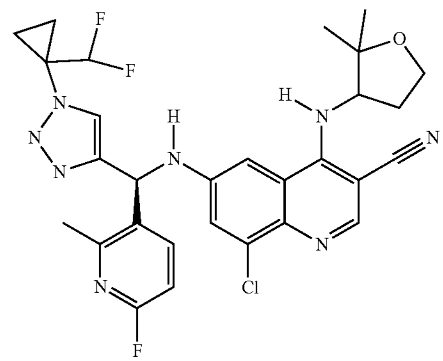 [SMILES: Cc1nc(F)ccc1[C@H](Nc1cc(Cl)c2ncc(C#N)c(NC3CCOC3(C)C)c2c1)C1=CN(C2(C(F)F)CC2)NN1] | 8-chloro-6-(((S)-(1-(1-(difluoromethyl)-cyclopropyl)-1H-1,2,3-triazol-4-yl)(6-fluoro-2-methylpyridin-3-yl)methyl)amino)-4-((2,2-dimethyltetrahydrofuran-3-yl)amino)-quinoline-3-carbonitrile | 23 | 597.25 |
| 512 | 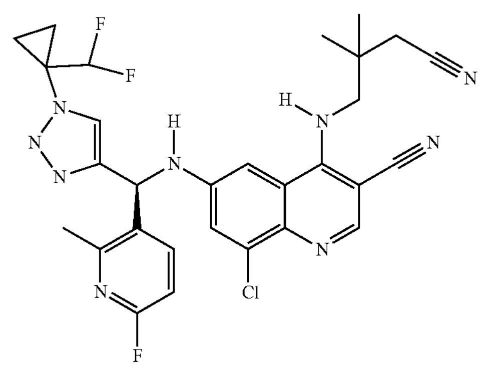 [SMILES: Cc1nc(F)ccc1[C@H](Nc1cc(Cl)c2ncc(C#N)c(NCC(C)(C)CC#N)c2c1)C1=CN(C2(C(F)F)CC2)NN1] | (S)-8-chloro-4-((3-cyano-2,2-dimethyl-propyl)amino)-6-(((1-(1-(difluoromethyl)-cyclopropyl)-1H-1,2,3-triazol-4-yl)(6-fluoro-2-methylpyridin-3-yl)methyl)amino)quinoline-3-carbonitrile | 23 | 594.19 |
| 513 | 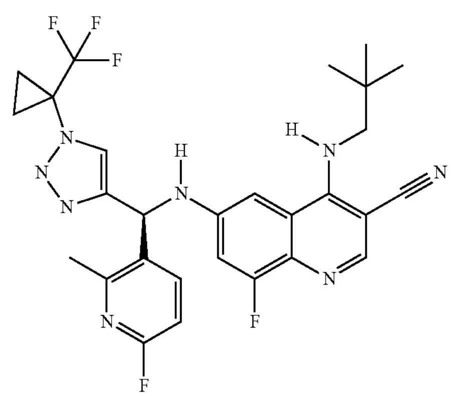 [SMILES: Cc1nc(F)ccc1[C@H](Nc1cc(F)c2ncc(C#N)c(NCC(C)(C)C)c2c1)C1=CN(C2(C(F)(F)F)CC2)NN1] | (S)-8-fluoro-6-(((6-fluoro-2-methylpyridin-3-yl)(1-(1-(trifluoromethyl)cyclopropyl)-1H-1,2,3-triazol-4-yl)methyl)amino)-4-(neopentylamino)quinoline-3-carbonitrile | 4 | 571.20 |

TABLE 1-continued

| Comp | Structure | Name | Example Procedure | ES/MS m/z |
|---|---|---|---|---|
| 514 | 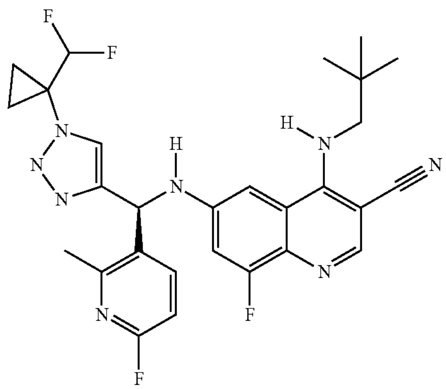 [SMILES: Cc1nc(F)ccc1[C@H](Nc1cc(F)c2ncc(C#N)c(NCC(C)(C)C)c2c1)C1=CN(C2(C(F)F)CC2)NN1] | (S)-6-(((1-(1-(difluoromethyl)cyclopropyl)-1H-1,2,3-triazol-4-yl)(6-fluoro-2-methylpyridin-3-yl)methyl)amino)-8-fluoro-4-(neopentylamino)quinoline-3-carbonitrile | 4 | 553.30 |
| 515 | 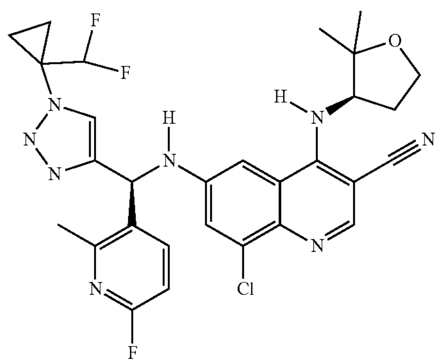 [SMILES: Cc1nc(F)ccc1[C@H](Nc1cc(Cl)c2ncc(C#N)c(N[C@@H]3CCOC3(C)C)c2c1)C1=CN(C2(C(F)F)CC2)NN1] | 8-chloro-6-(((S)-(1-(1-(difluoromethyl)-cyclopropyl)-1H-1,2,3-triazol-4-yl)(6-fluoro-2-methylpyridin-3-yl)methyl)amino)-4-(((R)-2,2-dimethyltetrahydro-furan-3-yl)amino)quinoline-3-carbonitrile | 23 | 597.24 |
| 516 | 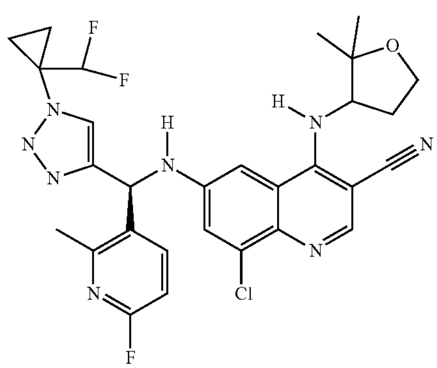 [SMILES: Cc1nc(F)ccc1[C@H](Nc1cc(Cl)c2ncc(C#N)c(NC3CCOC3(C)C)c2c1)C1=CN(C2(C(F)F)CC2)NN1] | 8-chloro-6-(((S)-(1-(1-(difluoromethyl)-cyclopropyl)-1H-1,2,3-triazol-4-yl)(6-fluoro-2-methylpyridin-3-yl)methyl)amino)-4-(((S)-2,2-dimethyltetrahydrofuran-3-yl)amino)quinoline-3-carbonitrile | 23 | 597.17 |
| 517 | 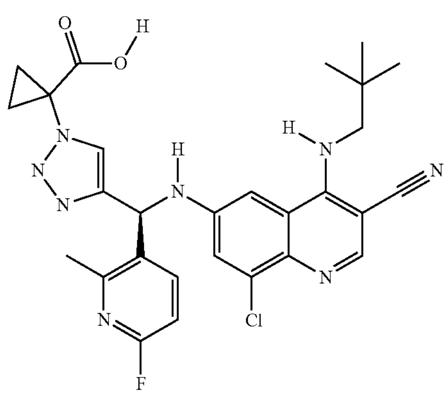 [SMILES: Cc1nc(F)ccc1[C@H](Nc1cc(Cl)c2ncc(C#N)c(NCC(C)(C)C)c2c1)C1=CN(C2(C(=O)O)CC2)NN1] | (S)-1-(4-(((8-chloro-3-cyano-4-(neopentylamino)quinolin-6-yl)amino)(6-fluoro-2-methylpyridin-3-yl)methyl)-1H-1,2,3-triazol-1-yl)cyclopropane-1-carboxylic acid | 4 | 563.1 |

TABLE 1-continued

| Comp | Structure | Name | Example Procedure | ES/MS m/z |
|---|---|---|---|---|
| 518 | 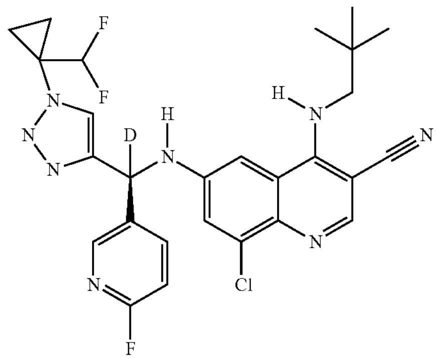 [SMILES: [2H][C@](Nc1cc(Cl)c2ncc(C#N)c(NCC(C)(C)C)c2c1)(C1=CN(C2(C(F)F)CC2)NN1)c1ccc(F)nc1] | (S)-8-chloro-6-(((1-(1-(difluoromethyl)-cyclopropyl)-1H-1,2,3-triazol-4-yl)(6-fluoropyridin-3-yl)methyl-d)amino)-4-(neopentylamino)quinoline-3-carbonitrile | 27 | 556.3 |
| 519 | 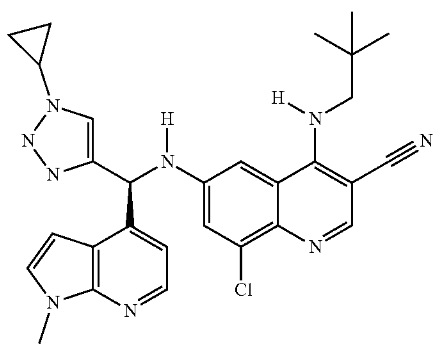 [SMILES: Cn1ccc2c([C@H](Nc3cc(Cl)c4ncc(C#N)c(NCC(C)(C)C)c4c3)C3=CN(C4CC4)NN3)ccnc21] | (S)-8-chloro-6-(((1-cyclopropyl-1H-1,2,3-triazol-4-yl)(1-methyl-1H-pyrrolo[2,3-b]pyridin-4-yl)methyl)amino)-4-(neopentylamino)quinoline-3-carbonitrile | 2 | 540.3 |
| 520 | 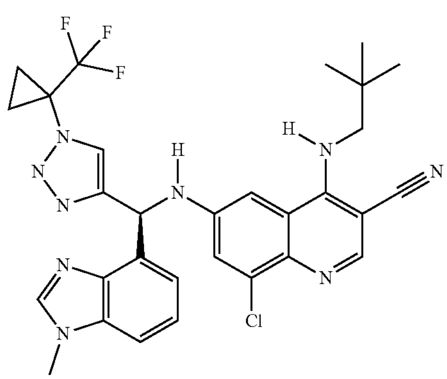 [SMILES: Cn1cnc2c([C@H](Nc3cc(Cl)c4ncc(C#N)c(NCC(C)(C)C)c4c3)C3=CN(C4(C(F)(F)F)CC4)NN3)cccc21] | (S)-8-chloro-6-(((1-methyl-1H-benzo[d]imidazol-4-yl)(1-(1-(trifluoromethyl)cyclopropyl)-1H-1,2,3-triazol-4-yl)methyl)amino)-4-(neopentylamino)quinoline-3-carbonitrile | 4 | 608.3 |
| 521 | 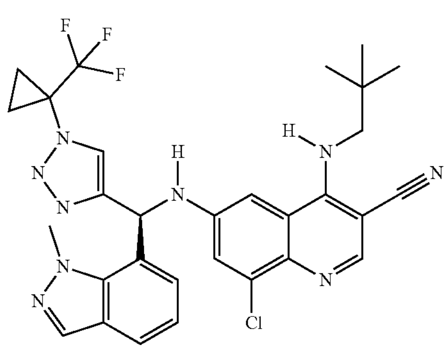 [SMILES: Cn1ncc2cccc([C@H](Nc3cc(Cl)c4ncc(C#N)c(NCC(C)(C)C)c4c3)C3=CN(C4(C(F)(F)F)CC4)NN3)c21] | (S)-8-chloro-6-(((1-methyl-1H-indazol-7-yl)(1-(1-(trifluoromethyl)-cyclopropyl)-1H-1,2,3-triazol-4-yl)methyl)amino)-4-(neopentylamino)-quinoline-3-carbonitrile | 4 | 608.3 |

TABLE 1-continued

| Comp | Structure | Name | Example Procedure | ES/MS m/z |
|---|---|---|---|---|
| 522 | 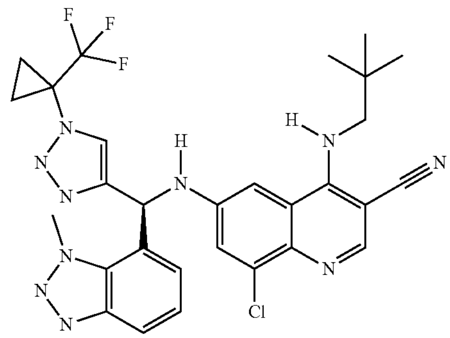 [SMILES: CN1NNc2cccc([C@H](Nc3cc(Cl)c4ncc(C#N)c(NCC(C)(C)C)c4c3)C3=CN(C4(C(F)(F)F)CC4)NN3)c21] | (S)-8-chloro-6-(((1-methyl-1H-benzo[d][1,2,3]triazol-7-yl)(1-(1-(trifluoromethyl)cyclopropyl)-1H-1,2,3-triazol-4-yl)methyl)amino)-4-(neopentylamino)quinoline-3-carbonitrile | 4 | 609.3 |
| 523 | 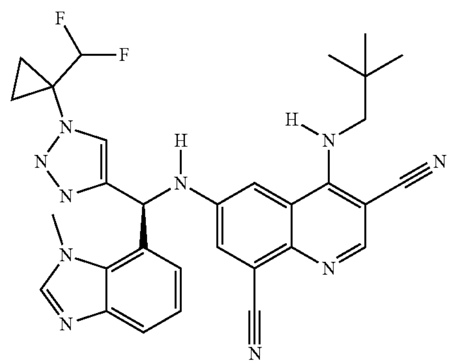 [SMILES: Cn1cnc2cccc([C@H](Nc3cc(C#N)c4ncc(C#N)c(NCC(C)(C)C)c4c3)C3=CN(C4(C(F)F)CC4)NN3)c21] | (S)-6-(((Ml-(difluoromethyl)cyclopropyl)-1H-1,2,3-triazol-4-yl)(1-methyl-1H-benzo[d]imidazol-7-yl)methyl)amino)-4-(neopentylamino)quinoline-3,8-dicarbonitrile | 34 | 581.2 |
| 524 | 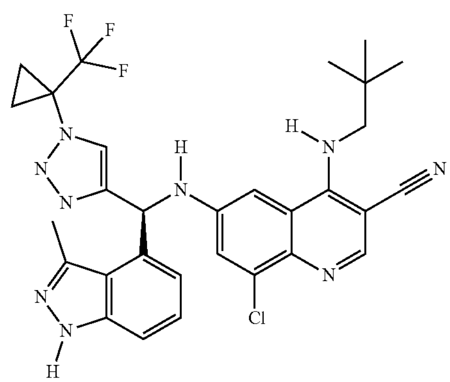 [SMILES: Cc1n[nH]c2cccc([C@H](Nc3cc(Cl)c4ncc(C#N)c(NCC(C)(C)C)c4c3)C3=CN(C4(C(F)(F)F)CC4)NN3)c12] | (S)-8-chloro-6-(((3-methyl-1H-indazol-4-yl)(1-(1-(trifluoromethyl)cyclopropyl)-1H-1,2,3-triazol-4-yl)methyl)amino)-4-(neopentylamino)quinoline-3-carbonitrile | 4 | 608.4 |
| 525 | 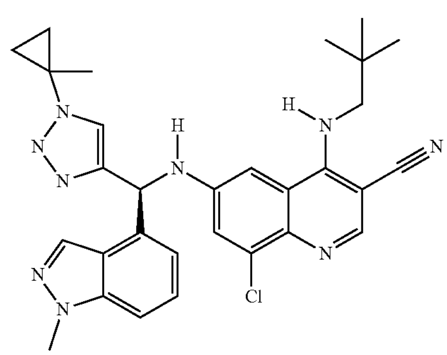 [SMILES: Cn1ncc2c([C@H](Nc3cc(Cl)c4ncc(C#N)c(NCC(C)(C)C)c4c3)C3=CN(C4(C)CC4)NN3)cccc21] | (S)-8-chloro-6-(((1-methyl-1H-indazol-4-yl)(1-(1-methylcyclopropyl)-1H-1,2,3-triazol-4-yl)methyl)amino)-4-(neopentylamino)quinoline-3-carbonitrile | 27 | 554.3 |

TABLE 1-continued

| Comp | Structure | Name | Example Procedure | ES/MS m/z |
|---|---|---|---|---|
| 526 | 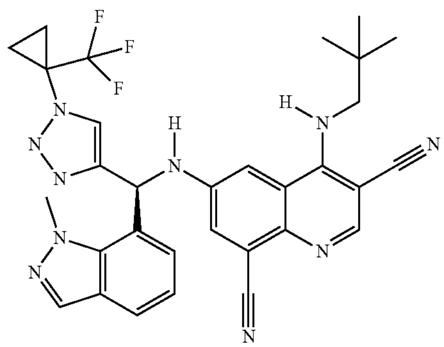 [SMILES: Cn1ncc2cccc([C@H](Nc3cc(C#N)c4ncc(C#N)c(NCC(C)(C)C)c4c3)C3=CN(C4(C(F)(F)F)CC4)NN3)c21] | (S)-6-(((1-methyl-1H-indazol-7-yl)(1-(1-(trifluoromethyl)cyclopropyl)-1H-1,2,3-triazol-4-yl)methyl)amino)-4-(neopentylamino)quinoline-3,8-dicarbonitrile | 24 | 599.5 |
| 527 | 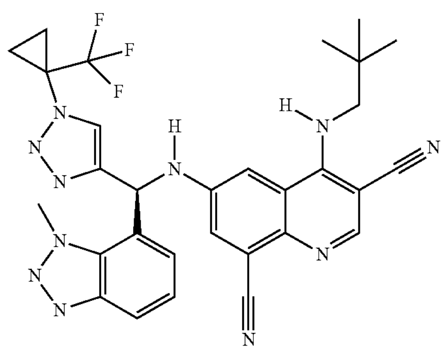 [SMILES: CN1NNc2cccc([C@H](Nc3cc(C#N)c4ncc(C#N)c(NCC(C)(C)C)c4c3)C3=CN(C4(C(F)(F)F)CC4)NN3)c21] | (S)-6-(((1-methyl-1H-benzo[d][1,2,3]triazol-7-yl)(1-(1-(trifluoromethyl)cyclopropyl)-1H-1,2,3-triazol-4-yl)methyl)amino)-4-(neopentylamino)quinoline-3,8-dicarbonitrile | 24 | 600.5 |
| 528 | 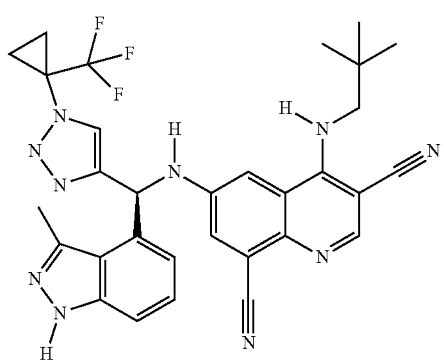 [SMILES: Cc1n[nH]c2cccc([C@H](Nc3cc(C#N)c4ncc(C#N)c(NCC(C)(C)C)c4c3)C3=CN(C4(C(F)(F)F)CC4)NN3)c12] | (S)-6-(((3-methyl-1H-indazol-4-yl)(1-(1-(trifluoromethyl)cyclopropyl)-1H-1,2,3-triazol-4-yl)methyl)amino)-4-(neopentylamino)quinoline-3,8-dicarbonitrile | 24 | 599.3 |
| 529 | 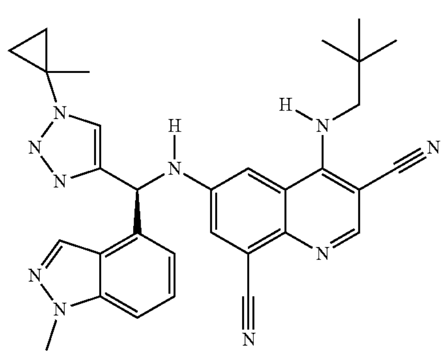 [SMILES: Cn1ncc2c([C@H](Nc3cc(C#N)c4ncc(C#N)c(NCC(C)(C)C)c4c3)C3=CN(C4(C)CC4)NN3)cccc21] | (S)-6-(((1-methyl-1H-indazol-4-yl)(1-(1-methylcyclopropyl)-1H-1,2,3-triazol-4-yl)methyl)amino)-4-(neopentylamino)quinoline-3,8-dicarbonitrile | 9 | 545.3 |

TABLE 1-continued

| Comp | Structure | Name | Example Procedure | ES/MS m/z |
|---|---|---|---|---|
| 530 | 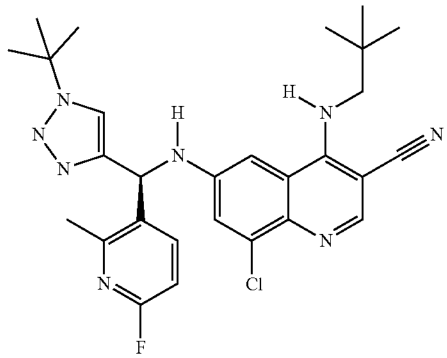 [SMILES: Cc1nc(F)ccc1[C@H](Nc1cc(Cl)c2ncc(C#N)c(NCC(C)(C)C)c2c1)C1=CN(C(C)(C)C)NN1] | (S)-6-(((1-(tert-butyl)-1H-1,2,3-triazol-4-yl)(6-fluoro-2-methylpyridin-3-yl)methyl)amino)-8-chloro-4-(neopentylamino)quinoline-3-carbonitrile | 1 | 535.4 |
| 531 | 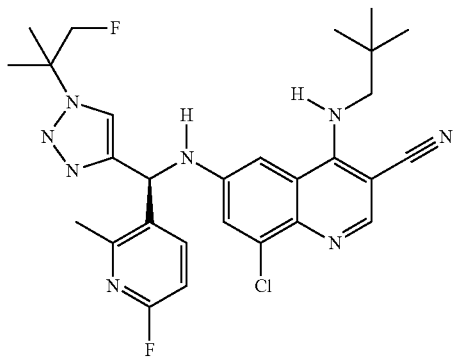 [SMILES: Cc1nc(F)ccc1[C@H](Nc1cc(Cl)c2ncc(C#N)c(NCC(C)(C)C)c2c1)C1=CN(C(C)(C)CF)NN1] | (S)-8-chloro-6-(((1-(1-fluoro-2-methylpropan-2-yl)-1H-1,2,3-triazol-4-yl)(6-fluoro-2-methylpyridin-3-yl)methyl)amino)-4-(neopentylamino)quinoline-3-carbonitrile | 4 | 553.2 |
| 532 | 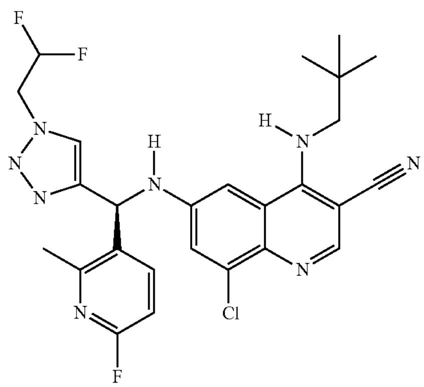 [SMILES: Cc1nc(F)ccc1[C@H](Nc1cc(Cl)c2ncc(C#N)c(NCC(C)(C)C)c2c1)C1=CN(CC(F)F)NN1] | (S)-8-chloro-6-(((1-(2,2-difluoroethyl)-1H-1,2,3-triazol-4-yl)(6-fluoro-2-methylpyridin-3-yl)methyl)amino)-4-(neopentylamino)quinoline-3-carbonitrile | 4 | 543.2 |
| 533 | 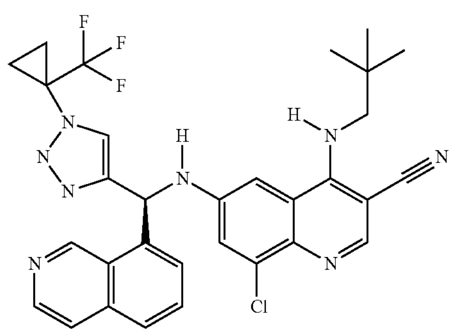 [SMILES: CC(C)(C)CNc1c(C#N)cnc2c(Cl)cc(N[C@H](C3=CN(C4(C(F)(F)F)CC4)NN3)c3cccc4ccncc34)cc12] | (S)-8-chloro-6-((isoquinolin-8-yl(1-(1-(trifluoromethyl)cyclopropyl)-1H-1,2,3-triazol-4-yl)methyl)amino)-4-(neopentylamino)quinoline-3-carbonitrile | 27 | 605.36 |

TABLE 1-continued

| Comp | Structure | Name | Example Procedure | ES/MS m/z |
|---|---|---|---|---|
| 534 | 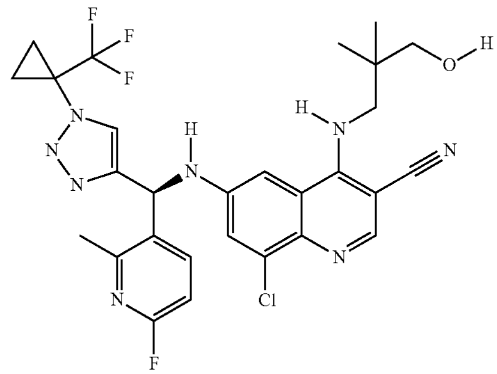 [SMILES: Cc1nc(F)ccc1[C@H](Nc1cc(Cl)c2ncc(C#N)c(NCC(C)(C)CO)c2c1)C1=CN(C2(C(F)(F)F)CC2)NN1] | (S)-8-chloro-6-(((6-fluoro-2-methylpyridin-3-yl)(1-(1-(trifluoromethyl)cyclopropyl)-1H-1,2,3-triazol-4-yl)methyl)amino)-4-((3-hydroxy-2,2-dimethylpropyl)amino)-quinoline-3-carbonitrile | 1 | 603.17 |
| 535 | 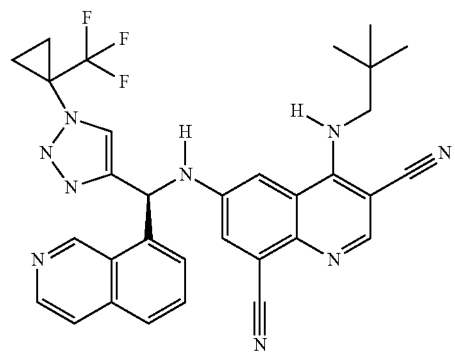 [SMILES: CC(C)(C)CNc1c(C#N)cnc2c(C#N)cc(N[C@H](C3=CN(C4(C(F)(F)F)CC4)NN3)c3cccc4ccncc34)cc12] | (S)-6-((isoquinolin-8-yl(1-(1-(trifluoromethyl)cyclopropyl)-1H-1,2,3-triazol-4-yl)methyl)amino)-4-(neopentylamino)-quinoline-3,8-dicarbonitrile | 24 | 596.14 |
| 536 | 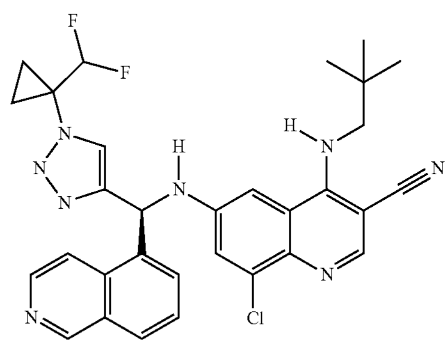 [SMILES: CC(C)(C)CNc1c(C#N)cnc2c(Cl)cc(N[C@H](C3=CN(C4(C(F)F)CC4)NN3)c3cccc4cnccc34)cc12] | (S)-8-chloro-6-(((1-(1-(difluoromethyl)-cyclopropyl)-1H-1,2,3-triazol-4-yl)(isoquinolin-5-yl)methyl)amino)-4-(neopentylamino)quinoline-3-carbonitrile | 23 | 587.23 |
| 537 | 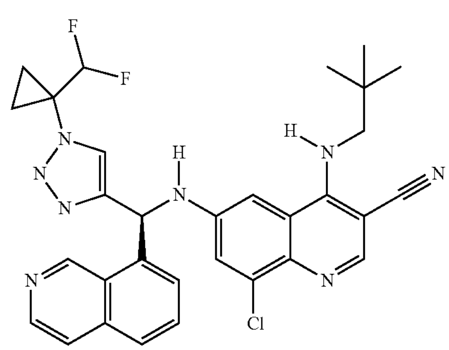 [SMILES: CC(C)(C)CNc1c(C#N)cnc2c(Cl)cc(N[C@H](C3=CN(C4(C(F)F)CC4)NN3)c3cccc4ccncc34)cc12] | (S)-8-chloro-6-(((1-(1-(difluoromethyl)-cyclopropyl)-1H-1,2,3-triazol-4-yl)(isoquinolin-8-yl)methyl)amino)-4-(neopentylamino)quinoline-3-carbonitrile | 23 | 587.21 |

TABLE 1-continued

| Comp | Structure | Name | Example Procedure | ES/MS m/z |
|---|---|---|---|---|
| 538 | 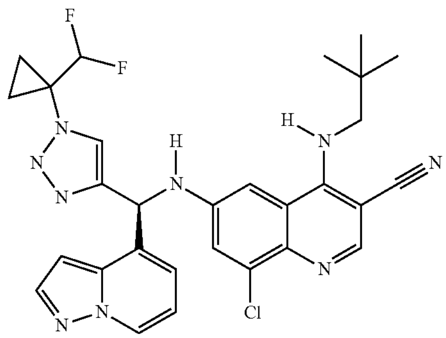 [SMILES: CC(C)(C)CNc1c(C#N)cnc2c(Cl)cc(N[C@H](C3=CN(C4(C(F)F)CC4)NN3)c3cccn4nccc34)cc12] | (S)-8-chloro-6-(((1-(1-(difluoromethyl)-cyclopropyl)-1H-1,2,3-triazol-4-yl)(pyrazolo[1,5-a]pyridin-4-yl)methyl)amino)-4-(neopentylamino)-quinoline-3-carbonitrile | 4 | 576.3 |
| 539 | 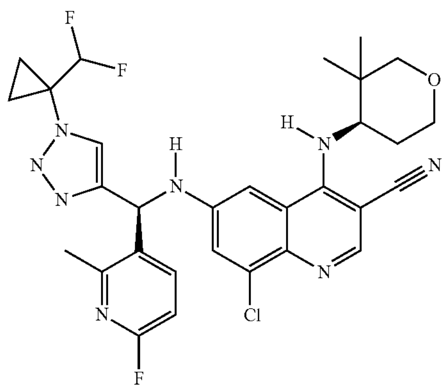 [SMILES: Cc1nc(F)ccc1[C@H](Nc1cc(Cl)c2ncc(C#N)c(N[C@@H]3CCOCC3(C)C)c2c1)C1=CN(C2(C(F)F)CC2)NN1] | 8-chloro-6-(((S)-(1-(1-(difluoromethyl)-cyclopropyl)-1H-1,2,3-triazol-4-yl)(6-fluoro-2-methylpyridin-3-yl)methyl)-amino)-4-(((R)-3,3-dimethyltetrahydro-2H-pyran-4-yl)amino)quinoline-3-carbonitrile | 4 | 611.3 |
| 540 | 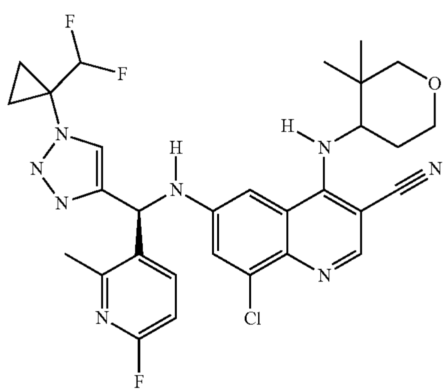 [SMILES: Cc1nc(F)ccc1[C@H](Nc1cc(Cl)c2ncc(C#N)c(NC3CCOCC3(C)C)c2c1)C1=CN(C2(C(F)F)CC2)NN1] | 8-chloro-6-(((S)-(1-(1-(difluoromethyl)-cyclopropyl)-1H-1,2,3-triazol-4-yl)(6-fluoro-2-methylpyridin-3-yl)methyl)-amino)-4-(((S)-3,3-dimethyltetrahydro-2H-pyran-4-yl)amino)quinoline-3-carbonitrile | 4 | 611.2 |
| 541 | 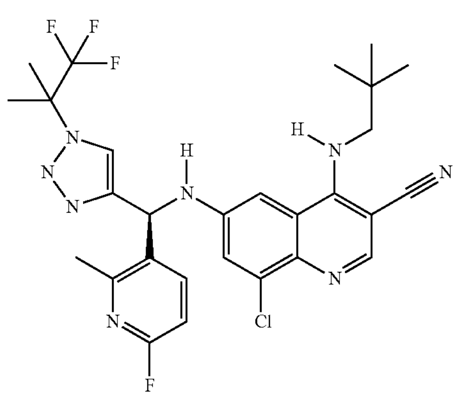 [SMILES: Cc1nc(F)ccc1[C@H](Nc1cc(Cl)c2ncc(C#N)c(NCC(C)(C)C)c2c1)C1=CN(C(C)(C)C(F)(F)F)NN1] | (S)-8-chloro-6-(((6-fluoro-2-methyl-pyridin-3-yl)(1-(1,1,1-trifluoro-2-methylpropan-2-yl)-1H-1,2,3-triazol-4-yl)methyl)amino)-4-(neopentylamino)-quinoline-3-carbonitrile | 4 | 589.3 |

TABLE 1-continued

| Comp | Structure | Name | Example Procedure | ES/MS m/z |
|---|---|---|---|---|
| 542 | 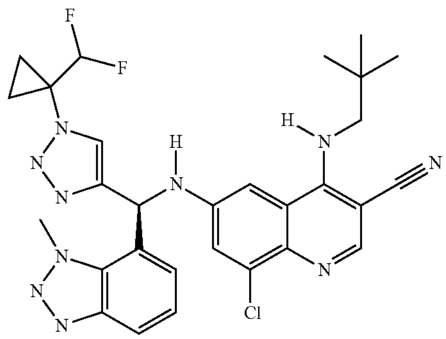 [SMILES: CN1NNc2cccc([C@H](Nc3cc(Cl)c4ncc(C#N)c(NCC(C)(C)C)c4c3)C3=CN(C4(C(F)F)CC4)NN3)c21] | (S)-8-chloro-6-(((1-(1-(difluoromethyl)-cyclopropyl)-1H-1,2,3-triazol-4-yl)(1-methyl-1H-benzo[d][1,2,3]triazol-7-yl)methyl)amino)-4-(neopentylamino)-quinoline-3-carbonitrile | 4 | 591.7 |
| 543 | 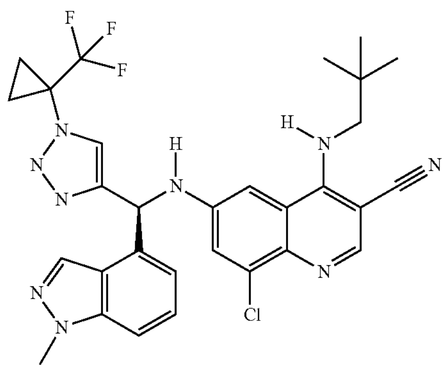 [SMILES: Cn1ncc2c([C@H](Nc3cc(Cl)c4ncc(C#N)c(NCC(C)(C)C)c4c3)C3=CN(C4(C(F)(F)F)CC4)NN3)cccc21] | (S)-8-chloro-6-(((1-methyl-1H-indazol-4-yl)(1-(1-(trifluoromethyl)cyclopropyl)-1H-1,2,3-triazol-4-yl)methyl)amino)-4-(neopentylamino)quinoline-3-carbonitrile | 4 | 608.5 |
| 544 | 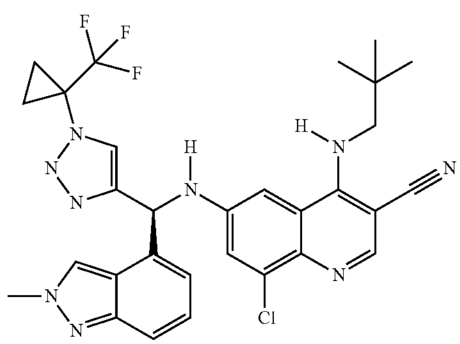 [SMILES: Cn1cc2c([C@H](Nc3cc(Cl)c4ncc(C#N)c(NCC(C)(C)C)c4c3)C3=CN(C4(C(F)(F)F)CC4)NN3)cccc2n1] | (S)-8-chloro-6-(((2-methyl-2H-indazol-4-yl)(1-(1-(trifluoromethyl)cyclopropyl)-1H-1,2,3-triazol-4-yl)methyl)amino)-4-(neopentylamino)quinoline-3-carbonitrile | 4 | 608.7 |
| 545 | 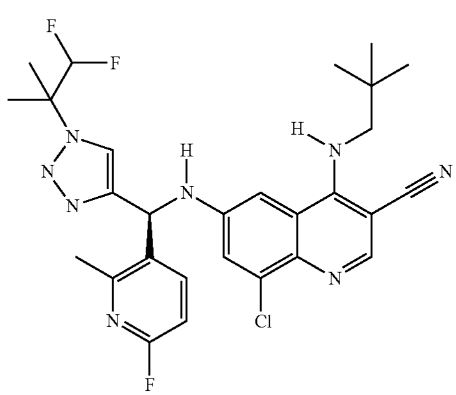 [SMILES: Cc1nc(F)ccc1[C@H](Nc1cc(Cl)c2ncc(C#N)c(NCC(C)(C)C)c2c1)C1=CN(C(C)(C)C(F)F)NN1] | (S)-8-chloro-6-(((1-(1,1-difluoro-2-methylpropan-2-yl)-1H-1,2,3-triazol-4-yl)(6-fluoro-2-methylpyridin-3-yl)methyl)-amino)-4-(neopentylamino)quinoline-3-carbonitrile | 4 | 571.3 |

TABLE 1-continued

| Comp | Structure | Name | Example Procedure | ES/MS m/z |
|---|---|---|---|---|
| 546 | 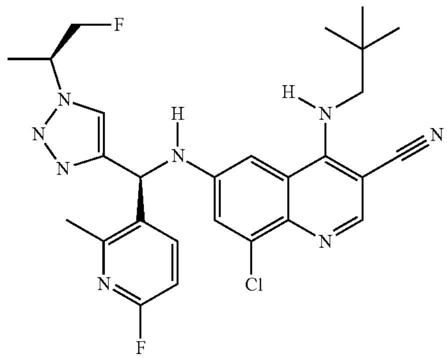 [SMILES: Cc1nc(F)ccc1[C@H](Nc1cc(Cl)c2ncc(C#N)c(NCC(C)(C)C)c2c1)C1=CN([C@@H](C)CF)NN1] | 8-chloro-6-(((S)-(6-fluoro-2-methylpyridin-3-yl)(1-((S)-1-fluoropropan-2-yl)-1H-1,2,3-triazol-4-yl)methyl)amino)-4-(neopentylamino)quinoline-3-carbonitrile | 4 | 539.4 |
| 547 | 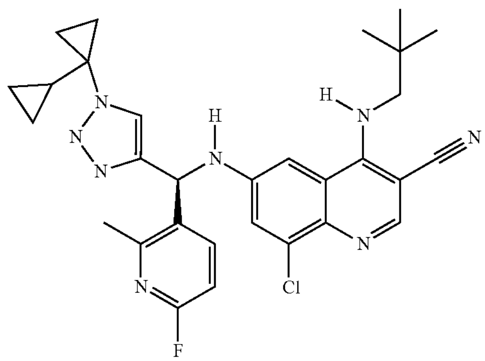 [SMILES: Cc1nc(F)ccc1[C@H](Nc1cc(Cl)c2ncc(C#N)c(NCC(C)(C)C)c2c1)C1=CN(C2(C3CC3)CC2)NN1] | (S)-6-(((M[i,r-bi(cyclopropan)]-1-yl)-1H-1,2,3-triazol-4-yl)(6-fluoro-2-methylpyridin-3-yl)methyl)amino)-8-chloro-4-(neopentylamino)quinoline-3-carbonitrile | 4 | 559.6 |
| 548 | 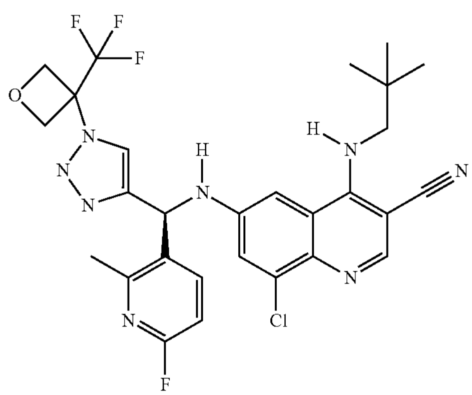 [SMILES: Cc1nc(F)ccc1[C@H](Nc1cc(Cl)c2ncc(C#N)c(NCC(C)(C)C)c2c1)C1=CN(C2(C(F)(F)F)COC2)NN1] | (S)-8-chloro-6-(((6-fluoro-2-methylpyridin-3-yl)(1-(3-(trifluoromethyl)oxetan-3-yl)-1H-1,2,3-triazol-4-yl)methyl)amino)-4-(neopentylamino)quinoline-3-carbonitrile | 4 | 603.4 |
| 549 | 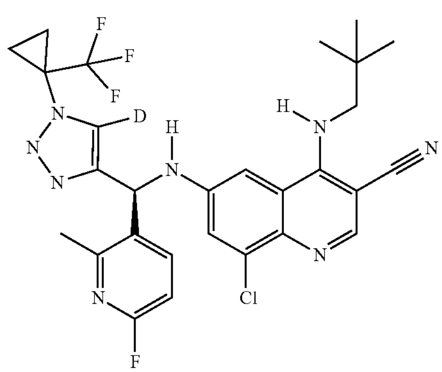 [SMILES: [2H]C1=C([C@@H](Nc2cc(Cl)c3ncc(C#N)c(NCC(C)(C)C)c3c2)c2ccc(F)nc2C)NNN1C1(C(F)(F)F)CC1] | (S)-8-chloro-6-(((6-fluoro-2-methylpyridin-3-yl)(1-(1-(trifluoromethyl)cyclopropyl)-1H-1,2,3-triazol-4-yl-5-d)methyl)amino)-4-(neopentylamino)quinoline-3-carbonitrile | 33 | 588.31 |

TABLE 1-continued

| Comp | Structure | Name | Example Procedure | ES/MS m/z |
|---|---|---|---|---|
| 550 | 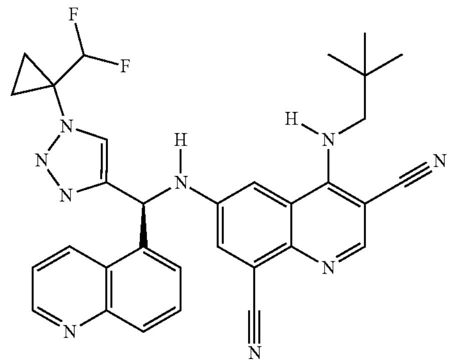 [SMILES: CC(C)(C)CNc1c(C#N)cnc2c(C#N)cc(N[C@H](C3=CN(C4(C(F)F)CC4)NN3)c3cccc4ncccc34)cc12] | (S)-6-(((1-(1-(difluoromethyl)cyclopropyl)-1H-1,2,3-triazol-4-yl)(quinolin-5-yl)methyl)amino)-4-(neopentylamino)-quinoline-3,8-dicarbonitrile | 24 | 578.28 |
| 551 | 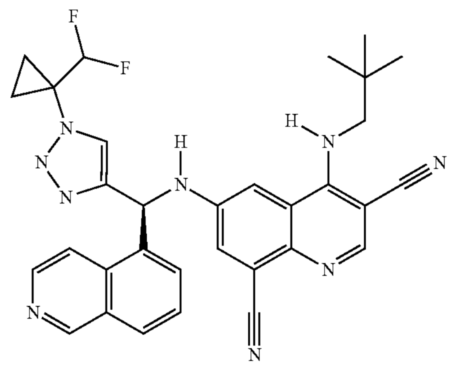 [SMILES: CC(C)(C)CNc1c(C#N)cnc2c(C#N)cc(N[C@H](C3=CN(C4(C(F)F)CC4)NN3)c3cccc4cnccc34)cc12] | (S)-6-(((4-(1-(1-(difluoromethyl)-cyclopropyl)-1H-1,2,3-triazol-4-yl)(isoquinolin-5-yl)methyl)amino)-4-(neopentylamino)-quinoline-3,8-dicarbonitrile | 24 | 578.2 |
| 552 | 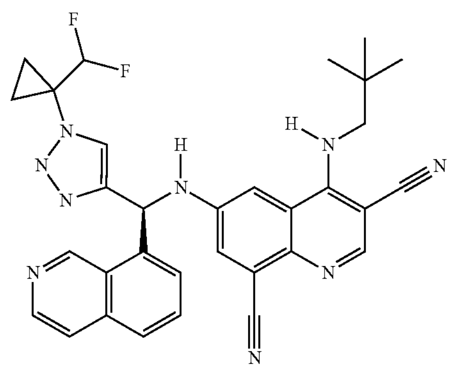 [SMILES: CC(C)(C)CNc1c(C#N)cnc2c(C#N)cc(N[C@H](C3=CN(C4(C(F)F)CC4)NN3)c3cccc4ccncc34)cc12] | (S)-6-(((1-(1-(difluoromethyl)cyclopropyl)-1H-1,2,3-triazol-4-yl)(isoquinolin-8-yl)methyl)-amino)-4-(neopentylamino)quinoline-3,8-dicarbonitrile | 24 | 578.19 |
| 553 | 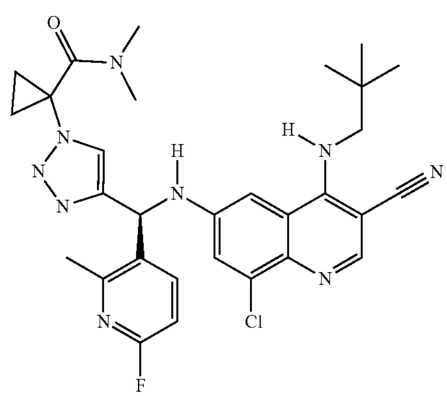 [SMILES: Cc1nc(F)ccc1[C@H](Nc1cc(Cl)c2ncc(C#N)c(NCC(C)(C)C)c2c1)C1=CN(C2(C(=O)N(C)C)CC2)NN1] | (S)-1-(4-(((8-chloro-3-cyano-4-(neopentyl-amino)quinolin-6-yl)amino)(6-fluoro-2-methylpyridin-3-yl)methyl)-1H-1,2,3-triazol-1-yl)-N,N-dimethylcyclopropane-1-carboxamide | 35 | 590.2 |

TABLE 1-continued

| Comp | Structure | Name | Example Procedure | ES/MS m/z |
|---|---|---|---|---|
| 554 | 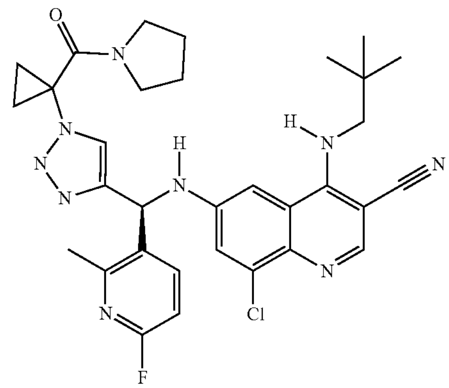 [SMILES: Cc1nc(F)ccc1[C@H](Nc1cc(Cl)c2ncc(C#N)c(NCC(C)(C)C)c2c1)C1=CN(C2(C(=O)N3CCCC3)CC2)NN1] | (S)-8-chloro-6-(((6-fluoro-2-methylpyridin-3-yl)(1-(1-(pyrrolidine-1-carbonyl)cyclopropyl)-1H-1,2,3-triazol-4-yl)methyl)amino)-4-(neopentylamino)quinoline-3-carbonitrile | 35 | 616.2 |
| 555 | 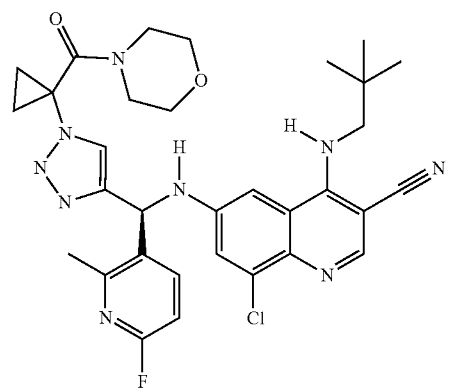 [SMILES: Cc1nc(F)ccc1[C@H](Nc1cc(Cl)c2ncc(C#N)c(NCC(C)(C)C)c2c1)C1=CN(C2(C(=O)N3CCOCC3)CC2)NN1] | (S)-8-chloro-6-(((6-fluoro-2-methylpyridin-3-yl)(1-(1-(morpholine-4-carbonyl)cyclopropyl)-1H-1,2,3-triazol-4-yl)methyl)amino)-4-(neopentylamino)quinoline-3-carbonitrile | 35 | 632.3 |
| 556 | 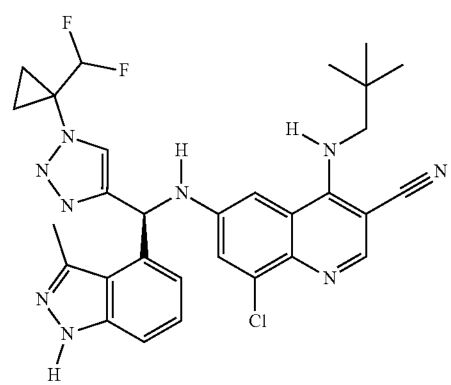 [SMILES: Cc1n[nH]c2cccc([C@H](Nc3cc(Cl)c4ncc(C#N)c(NCC(C)(C)C)c4c3)C3=CN(C4(C(F)F)CC4)NN3)c12] | (S)-8-chloro-6-(((1-(1-(difluoromethyl)cyclopropyl)-1H-1,2,3-triazol-4-yl)(3-methyl-1H-indazol-4-yl)methyl)amino)-4-(neopentylamino)quinoline-3-carbonitrile | 32 | 590.4 |
| 557 | 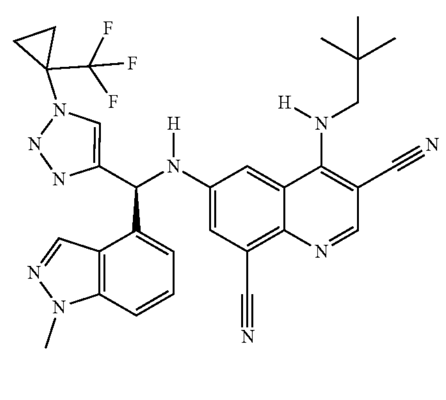 [SMILES: Cn1ncc2c([C@H](Nc3cc(C#N)c4ncc(C#N)c(NCC(C)(C)C)c4c3)C3=CN(C4(C(F)(F)F)CC4)NN3)cccc21] | (S)-6-(((1-methyl-1H-indazol-4-yl)(1-(1-(trifluoromethyl)cyclopropyl)-1H-1,2,3-triazol-4-yl)methyl)amino)-4-(neopentylamino)quinoline-3,8-dicarbonitrile | 24 | 599.3 |

TABLE 1-continued

| Comp | Structure | Name | Example Procedure | ES/MS m/z |
|---|---|---|---|---|
| 558 | 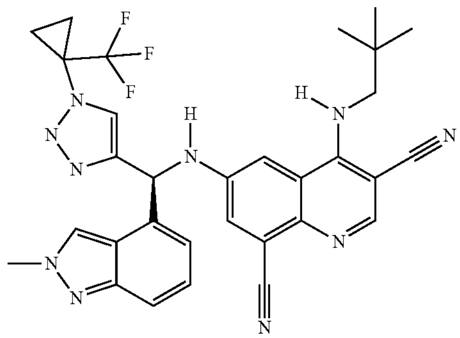 [SMILES: Cn1cc2c([C@H](Nc3cc(C#N)c4ncc(C#N)c(NCC(C)(C)C)c4c3)C3=CN(C4(C(F)(F)F)CC4)NN3)cccc2n1] | (S)-6-(((2-methyl-2H-indazol-4-yl)(1-(1-(trifluoromethyl)cyclopropyl)-1H-1,2,3-triazol-4-yl)methyl)amino)-4-(neopentylamino)quinoline-3,8-dicarbonitrile | 24 | 599.2 |
| 559 | 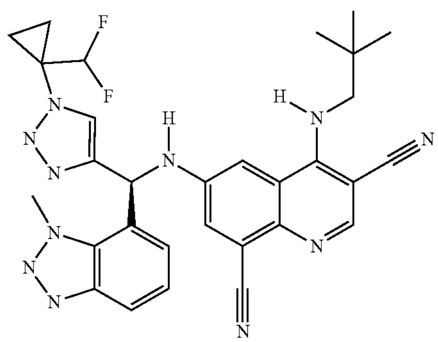 [SMILES: CN1NNc2cccc([C@H](Nc3cc(C#N)c4ncc(C#N)c(NCC(C)(C)C)c4c3)C3=CN(C4(C(F)F)CC4)NN3)c21] | (S)-6-(((4-(1-1-(difluoromethyl)cyclopropyl)-1H-1,2,3-triazol-4-yl)(1-methyl-1H-benzo[d][1,2,3]triazol-7-yl)methyl)amino)-4-(neopentylamino)quinoline-3,8-dicarbonitrile | 24 | 582.2 |
| 560 | 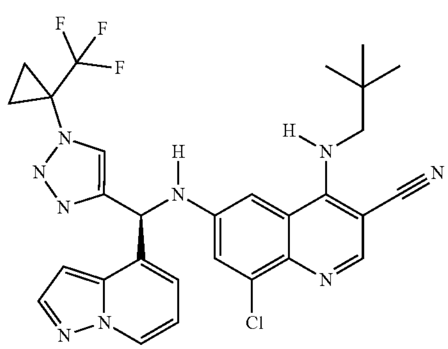 [SMILES: CC(C)(C)CNc1c(C#N)cnc2c(Cl)cc(N[C@H](C3=CN(C4(C(F)(F)F)CC4)NN3)c3cccn4nccc34)cc12] | (S)-8-chloro-4-(neopentylamino)-6-((pyrazolo[1,5-a]pyridin-4-yl(1-(1-(trifluoromethyl)cyclopropyl)-1H-1,2,3-triazol-4-yl)methyl)amino)quinoline-3-carbonitrile | 4 | 594.3 |
| 561 | 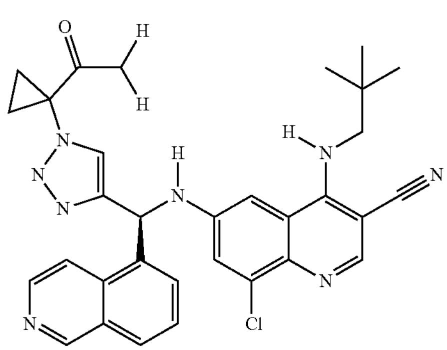 [SMILES: CC(=O)C1(N2C=C([C@@H](Nc3cc(Cl)c4ncc(C#N)c(NCC(C)(C)C)c4c3)c3cccc4cnccc34)NN2)CC1] | (S)-1-(4-(((8-chloro-3-cyano-4-(neopentylamino)quinolin-6-yl)amino)(isoquinolin-5-yl)methyl)-1H-1,2,3-triazol-1-yl)cyclopropane-1-carboxamide | 4 | 580.2 |

TABLE 1-continued

| Comp | Structure | Name | Example Procedure | ES/MS m/z |
|---|---|---|---|---|
| 562 | 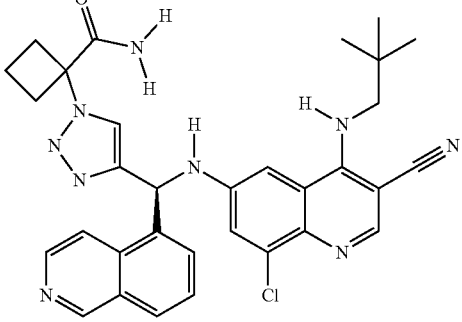 | (S)-1-(4-(((8-chloro-3-cyano-4-(neopentyl-amino)quinolin-6-yl)amino)(isoquinolin-5-yl)methyl)-1H-1,2,3-triazol-1-yl)cyclobutane-1-carboxamide | 4 | 594.2 |
| 563 | 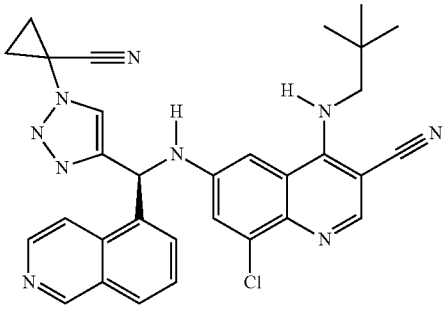 [SMILES: CC(C)(C)CNc1c(C#N)cnc2c(Cl)cc(N[C@H](C3=CN(C4(C#N)CC4)NN3)c3cccc4cnccc34)cc12] | (S)-8-chloro-6-(((1-(1-cyanocyclopropyl)-1H-1,2,3-triazol-4-yl)(isoquinolin-5-yl)methyl)amino)-4-(neopentylamino)-quinoline-3-carbonitrile | 4 | 562.1 |
| 564 | 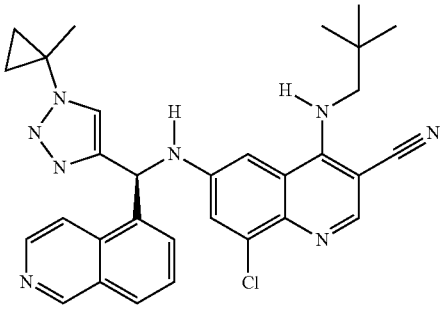 [SMILES: CC(C)(C)CNc1c(C#N)cnc2c(Cl)cc(N[C@H](C3=CN(C4(C)CC4)NN3)c3cccc4cnccc34)cc12] | (S)-8-chloro-6-((isoquinolin-5-yl(1-(1-methylcyclopropyl)-1H-1,2,3-triazol-4-yl)methyl)amino)-4-(neopentylamino)-quinoline-3-carbonitrile | 4 | 551.2 |
| 565 | 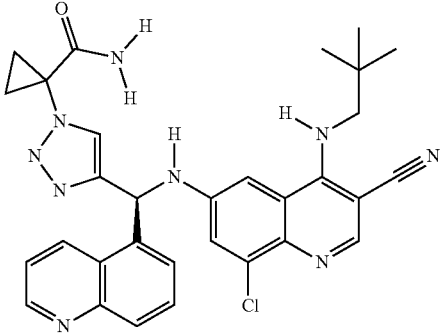 [SMILES: CC(C)(C)CNc1c(C#N)cnc2c(Cl)cc(N[C@H](C3=CN(C4(C(N)=O)CC4)NN3)c3cccc4ncccc34)cc12] | (S)-1-(4-(((8-chloro-3-cyano-4-(neopentyl-amino)quinolin-6-yl)amino)(quinolin-5-yl)methyl)-1H-1,2,3-triazol-1-yl)cyclo-propane-1-carboxamide | 23 | 580.17 |

TABLE 1-continued

| Comp | Structure | Name | Example Procedure | ES/MS m/z |
|---|---|---|---|---|
| 566 | 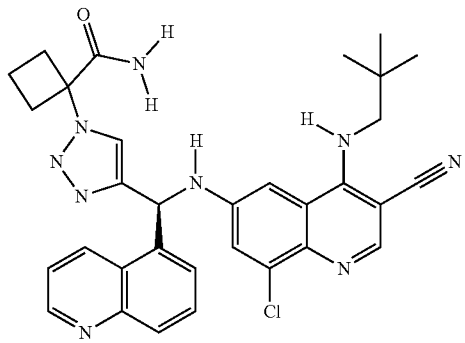 [SMILES: CC(C)(C)CNc1c(C#N)cnc2c(Cl)cc(N[C@H](C3=CN(C4(C(N)=O)CCC4)NN3)c3cccc4ncccc34)cc12] | (S)-1-(4-(((8-chloro-3-cyano-4-(neopentylamino)quinolin-6-yl)amino)(quinolin-5-yl)methyl)-1H-1,2,3-triazol-1-yl)cyclobutane-1-carboxamide | 23 | 594.21 |
| 567 | 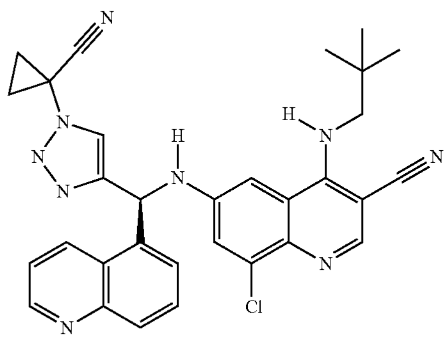 [SMILES: CC(C)(C)CNc1c(C#N)cnc2c(Cl)cc(N[C@H](C3=CN(C4(C#N)CC4)NN3)c3cccc4ncccc34)cc12] | (S)-8-chloro-6-(((1-(1-cyanocyclopropyl)-1H-1,2,3-triazol-4-yl)(quinolin-5-yl)methyl)amino)-4-(neopentylamino)-quinoline-3-carbonitrile | 23 | 562.22 |
| 568 | 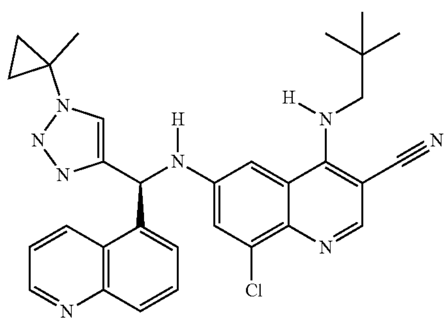 [SMILES: CC(C)(C)CNc1c(C#N)cnc2c(Cl)cc(N[C@H](C3=CN(C4(C)CC4)NN3)c3cccc4ncccc34)cc12] | (S)-8-chloro-6-(((1-(1-methylcyclopropyl)-1H-1,2,3-triazol-4-yl)(quinolin-5-yl)methyl)amino)-4-(neopentylamino)-quinoline-3-carbonitrile | 23 | 551.25 |
| 569 | 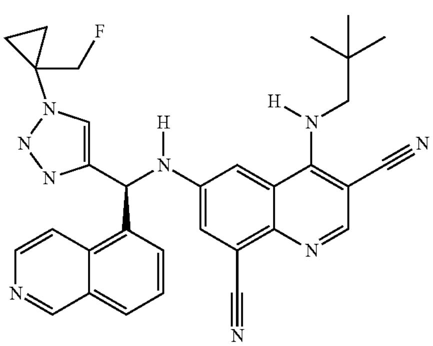 [SMILES: CC(C)(C)CNc1c(C#N)cnc2c(C#N)cc(N[C@H](C3=CN(C4(CF)CC4)NN3)c3cccc4cnccc34)cc12] | (S)-6-(((M1-(fluoromethyl)cyclopropyl)-1H-1,2,3-triazol-4-yl)(isoquinolin-5-yl)methyl)amino)-4-(neopentylamino)quinoline-3,8-dicarbonitrile | 9 | 560.3 |

TABLE 1-continued

| Comp | Structure | Name | Example Procedure | ES/MS m/z |
|---|---|---|---|---|
| 570 | 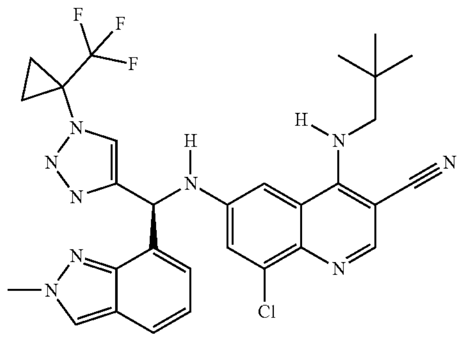 [SMILES: Cn1cc2cccc([C@H](Nc3cc(Cl)c4ncc(C#N)c(NCC(C)(C)C)c4c3)C3=CN(C4(C(F)(F)F)CC4)NN3)c2n1] | (S)-8-chloro-6-(((2-methyl-2H-indazol-7-yl)(1-(1-(trifluoromethyl)cyclopropyl)-1H-1,2,3-triazol-4-yl)methyl)amino)-4-(neopentylamino)quinoline-3-carbonitrile | 4 | 608.2 |
| 571 | 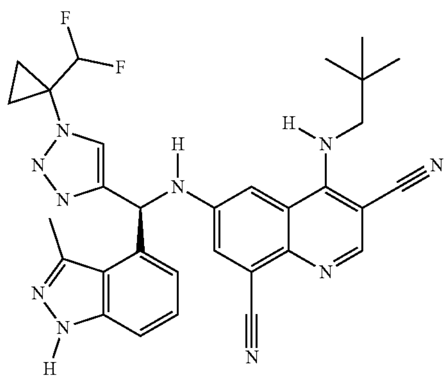 [SMILES: Cc1n[nH]c2cccc([C@H](Nc3cc(C#N)c4ncc(C#N)c(NCC(C)(C)C)c4c3)C3=CN(C4(C(F)F)CC4)NN3)c12] | (S)-6-(((H1-(difluoromethyl)cyclopropyl)-1H-1,2,3-triazol-4-yl)(3-methyl-1H-indazol-4-yl)methyl)amino)-4-(neopentylamino)quinoline-3,8-dicarbonitrile | 24 | 581.2 |
| 572 | 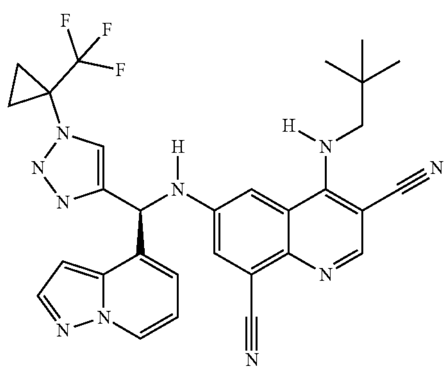 [SMILES: CC(C)(C)CNc1c(C#N)cnc2c(C#N)cc(N[C@H](C3=CN(C4(C(F)(F)F)CC4)NN3)c3cccn4nccc34)cc12] | (S)-4-(neopentylamino)-6-((pyrazolo[1,5-a]pyridin-4-yl(1-(1-(trifluoromethyl)cyclopropyl)-1H-1,2,3-triazol-4-yl)methyl)amino)quinoline-3,8-dicarbonitrile | 24 | 585.2 |
| 573 | 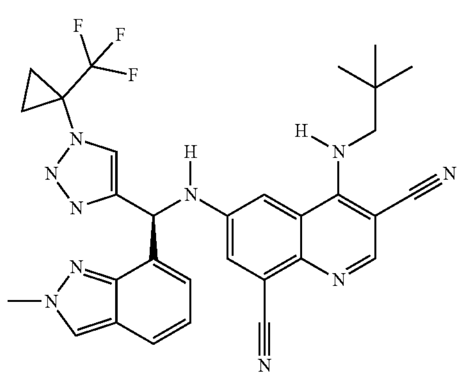 [SMILES: Cn1cc2cccc([C@H](Nc3cc(C#N)c4ncc(C#N)c(NCC(C)(C)C)c4c3)C3=CN(C4(C(F)(F)F)CC4)NN3)c2n1] | (S)-6-(((2-methyl-2H-indazol-7-yl)(1-(1-(trifluoromethyl)cyclopropyl)-1H-1,2,3-triazol-4-yl)methyl)amino)-4-(neopentylamino)quinoline-3,8-dicarbonitrile | 24 | 599.2 |

TABLE 1-continued

| Comp | Structure | Name | Example Procedure | ES/MS m/z |
|---|---|---|---|---|
| 574 | 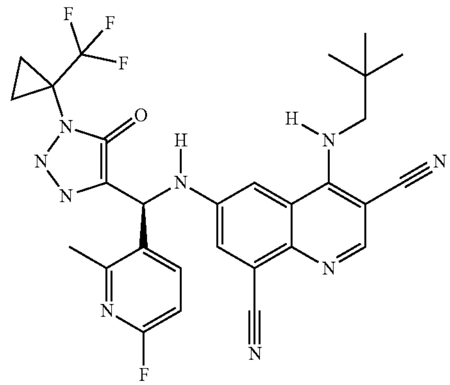 | (S)-6-(((6-fluoro-2-methylpyridin-3-yl)(1-(1-(trifluoromethyl)cyclopropyl)-1H-1,2,3-triazol-4-yl-5-d)methyl)amino)-4-(neopentylamino)quinoline-3,8-dicarbonitrile | 24 | 579.17 |
| 575 | 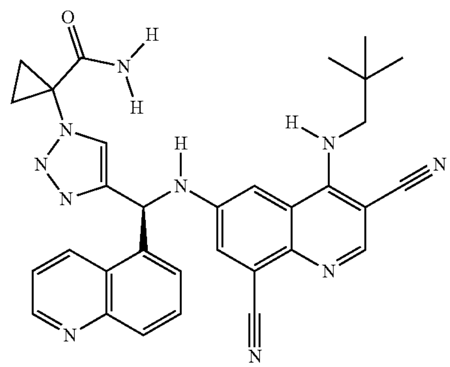 [SMILES: CC(C)(C)CNc1c(C#N)cnc2c(C#N)cc(N[C@H](C3=CN(C4(C(N)=O)CC4)NN3)c3cccc4ncccc34)cc12] | (S)-1-(4-(((3,8-dicyano-4-(neopentylamino)-quinolin-6-yl)amino)(quinolin-5-yl)methyl)-1H-1,2,3-triazol-1-yl)cyclopropane-1-carboxamide | 24 | 571.18 |
| 576 | 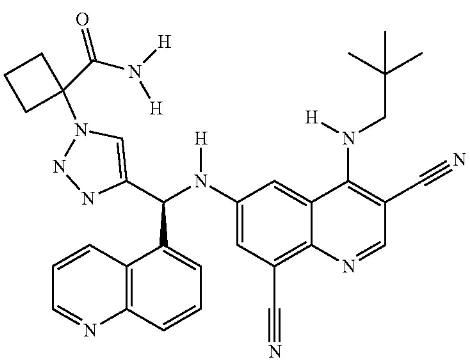 [SMILES: CC(C)(C)CNc1c(C#N)cnc2c(C#N)cc(N[C@H](C3=CN(C4(C(N)=O)CCC4)NN3)c3cccc4ncccc34)cc12] | (S)-1-(4-(((3,8-dicyano-4-(neopentyl-amino)quinolin-6-yl)amino)(quinolin-5-yl)methyl)-1H-1,2,3-triazol-1-yl)cyclobutane-1-carboxamide | 24 | 585.10 |
| 577 | 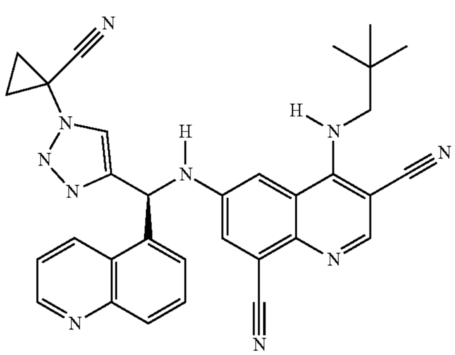 [SMILES: CC(C)(C)CNc1c(C#N)cnc2c(C#N)cc(N[C@H](C3=CN(C4(C#N)CC4)NN3)c3cccc4ncccc34)cc12] | (S)-6-(((1-(1-cyanocyclopropyl)-1H-1,2,3-triazol-4-yl)(quinolin-5-yl)methyl)amino)-4-(neopentylamino)-quinoline-3,8-dicarbonitrile | 24 | 553.12 |

TABLE 1-continued

| Comp | Structure | Name | Example Procedure | ES/MS m/z |
|---|---|---|---|---|
| 578 | 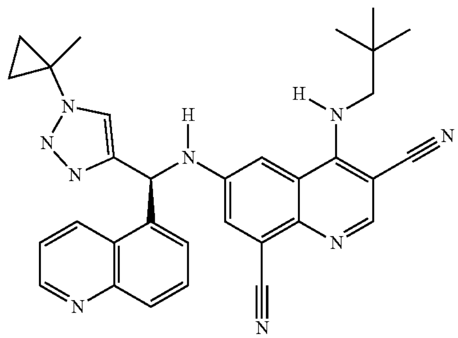 [SMILES: CC(C)(C)CNc1c(C#N)cnc2c(C#N)cc(N[C@H](C3=CN(C4(C)CC4)NN3)c3cccc4ncccc34)cc12] | (S)-6-(((1-(1-methylcyclopropyl)-1H-1,2,3-triazol-4-yl)(quinolin-5-yl)methyl)amino)-4-(neopentylamino)quinoline-3,8-dicarbonitrile | 24 | 542.17 |
| 579 | 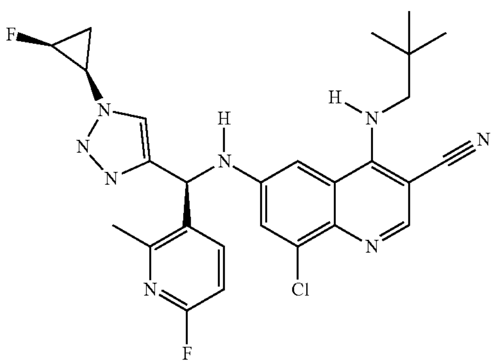 [SMILES: Cc1nc(F)ccc1[C@H](Nc1cc(Cl)c2ncc(C#N)c(NCC(C)(C)C)c2c1)C1=CN([C@@H]2C[C@@H]2F)NN1] | 8-chloro-6-(((S)-(6-fluoro-2-methylpyridin-3-yl)(1-((1R,2S)-2-fluorocyclopropyl)-1H-1,2,3-triazol-4-yl)methyl)amino)-4-(neopentylamino)quinoline-3-carbonitrile | 4 | 537.3 |
| 580 | 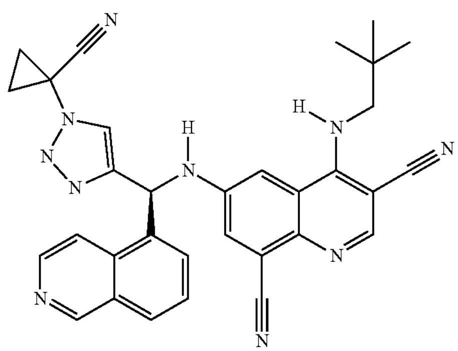 [SMILES: CC(C)(C)CNc1c(C#N)cnc2c(C#N)cc(N[C@H](C3=CN(C4(C#N)CC4)NN3)c3cccc4cnccc34)cc12] | (S)-6-(((1-(1-cyanocyclopropyl)-1H-1,2,3-triazol-4-yl)(isoquinolin-5-yl)methyl)amino)-4-(neopentylamino)-quinoline-3,8-dicarbonitrile | 24 | 553.2 |
| 581 | 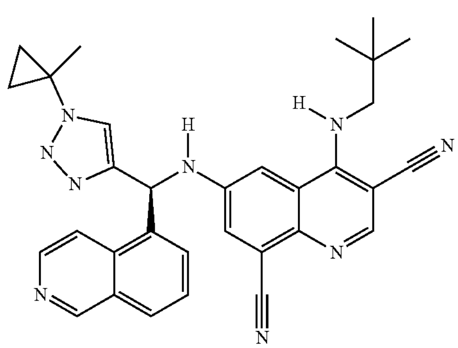 [SMILES: CC(C)(C)CNc1c(C#N)cnc2c(C#N)cc(N[C@H](C3=CN(C4(C)CC4)NN3)c3cccc4cnccc34)cc12] | (S)-6-(((isoquinolin-5-yl(1-(1-methylcyclopropyl)-1H-1,2,3-triazol-4-yl)methyl)amino)-4-(neopentylamino)quinoline-3,8-dicarbonitrile | 24 | 542.2 |

TABLE 1-continued

| Comp | Structure | Name | Example Procedure | ES/MS m/z |
|---|---|---|---|---|
| 582 | 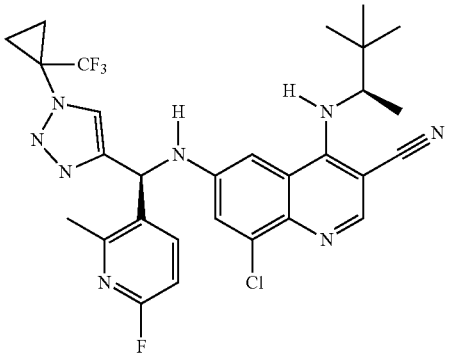 [SMILES: Cc1nc(F)ccc1[C@H](Nc1cc(Cl)c2ncc(C#N)c(N[C@H](C)C(C)(C)C)c2c1)C1=CN(C2(C(F)(F)F)CC2)NN1] | 8-chloro-4-(((R)-3,3-dimethylbutan-2-yl)amino)-6-(((S)-(6-fluoro-2-methylpyridin-3-yl)(1-(1-(trifluoromethyl)cyclopropyl)-1H-1,2,3-triazol-4-yl)methyl)amino)quinoline-3-carbonitrile | 23 | 601.25 |
| 583 | 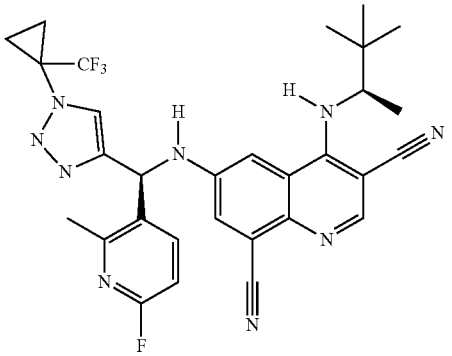 [SMILES: Cc1nc(F)ccc1[C@H](Nc1cc(C#N)c2ncc(C#N)c(N[C@H](C)C(C)(C)C)c2c1)C1=CN(C2(C(F)(F)F)CC2)NN1] | 4-(((R)-3,3-dimethylbutan-2-yl)amino)-6-(((S)-(6-fluoro-2-methylpyridin-3-yl)(1-(1-(trifluoromethyl)cyclopropyl)-1H-1,2,3-triazol-4-yl)methyl)amino)quinoline-3,8-dicarbonitrile | 25 | 592.30 |
| 584 | 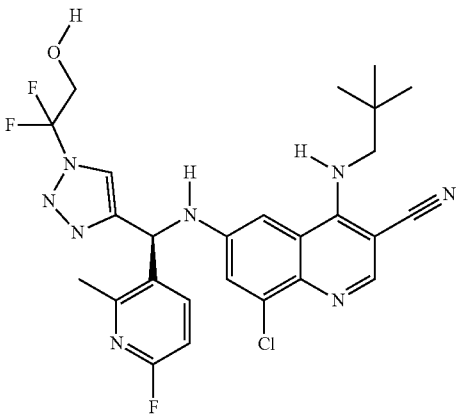 [SMILES: Cc1nc(F)ccc1[C@H](Nc1cc(Cl)c2ncc(C#N)c(NCC(C)(C)C)c2c1)C1=CN(C(F)(F)CO)NN1] | (S)-8-chloro-6-(((1-(i, 1-difluoro-2-hydroxyethyl)-1H-1,2,3-triazol-4-yl)(6-fluoro-2-methylpyridin-3-yl)methyl)amino)-4-(neopentylamino)quinoline-3-carbonitrile | 4 | 559.3 |
| 585 | 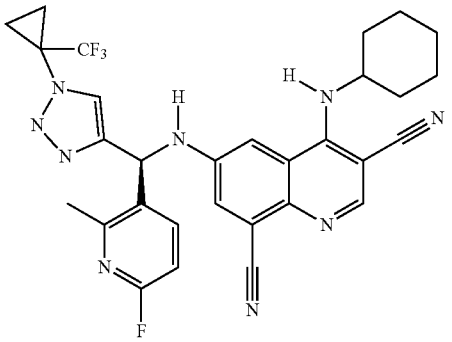 [SMILES: Cc1nc(F)ccc1[C@H](Nc1cc(C#N)c2ncc(C#N)c(NC3CCCCC3)c2c1)C1=CN(C2(C(F)(F)F)CC2)NN1] | (S)-4-(cyclohexylamino)-6-(((6-fluoro-2-methylpyridin-3-yl)(1-(1-(trifluoromethyl)-cyclopropyl)-1H-1,2,3-triazol-4-yl)methyl)amino)quinoline-3,8-dicarbonitrile | 25 | 590.30 |

TABLE 1-continued

| Comp | Structure | Name | Example Procedure | ES/MS m/z |
|---|---|---|---|---|
| 586 | 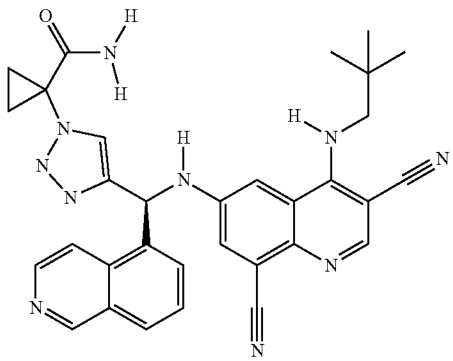 [SMILES: CC(C)(C)CNc1c(C#N)cnc2c(C#N)cc(N[C@H](C3=CN(C4(C(N)=O)CC4)NN3)c3cccc4cnccc34)cc12] | (S)-1-(4-(((3,8-dicyano-4-(neopentylamino)-quinolin-6-yl)atnino)(isoquinolin-5-yl)methyl)-1H-1,2,3-triazol-yl)cyclopropane-1-carboxamide | 24 | 571.3 |
| 587 | 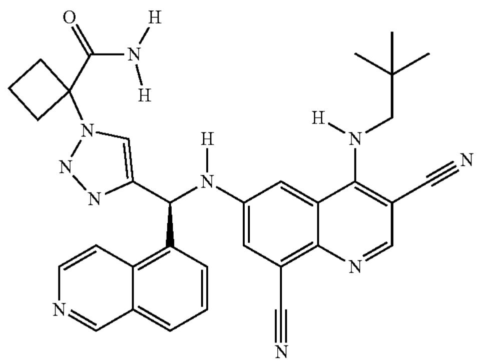 [SMILES: CC(C)(C)CNc1c(C#N)cnc2c(C#N)cc(N[C@H](C3=CN(C4(C(N)=O)CCC4)NN3)c3cccc4cnccc34)cc12] | (S)-1-(4-(((3,8-dicyano-(neopentylamino)-quinolin-6-yl)amino)(isoquinolin-5-yl)methyl)-1H-1,2,3-triazol-1-yl)cyclobutane-1-carboxamide | 24 | 585.2 |
| 588 | 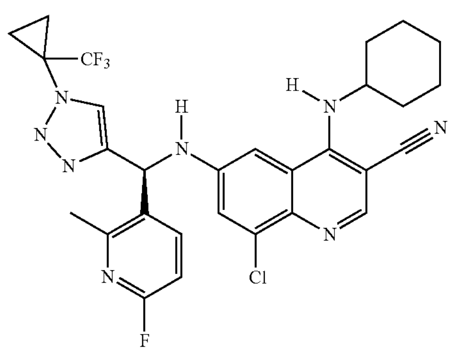 [SMILES: Cc1nc(F)ccc1[C@H](Nc1cc(Cl)c2ncc(C#N)c(NC3CCCCC3)c2c1)C1=CN(C2(C(F)(F)F)CC2)NN1] | (S)-8-chloro-4-(cyclohexylamino)-6-(((6-fluoro-2-methylpyridin-3-yl)(1-(1-(trifluoromethyl)cyclopropyl)-1H-1,2,3-triazol-4-yl)methyl)amino)quinoline-3-carbonitrile | 1 | 599.32 |
| 589 | 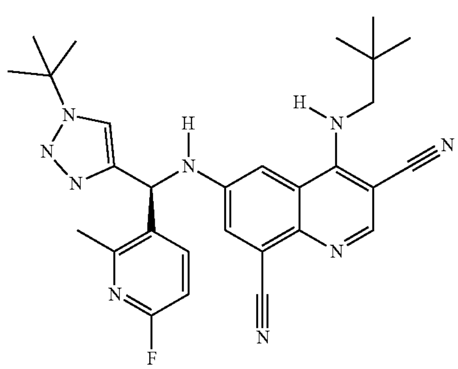 [SMILES: Cc1nc(F)ccc1[C@H](Nc1cc(C#N)c2ncc(C#N)c(NCC(C)(C)C)c2c1)C1=CN(C(C)(C)C)NN1] | (S)-6-(((1-(tert-butyl)-1H-1,2,3-triazol-4-yl)(6-fluoro-2-methylpyridin-3-yl)methyl)amino)-4-(neopentylamino)quinoline-3,8-dicarbonitrile | 24 | 526.3 |

TABLE 1-continued

| Comp | Structure | Name | Example Procedure | ES/MS m/z |
|---|---|---|---|---|
| 590 | 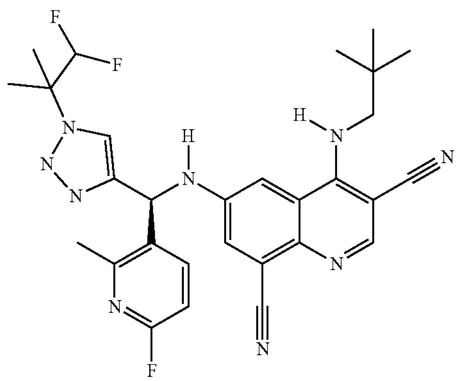 [SMILES: Cc1nc(F)ccc1[C@H](Nc1cc(C#N)c2ncc(C#N)c(NCC(C)(C)C)c2c1)C1=CN(C(C)(C)C(F)F)NN1] | (S)-6-(((1-(1,1-difluoro-2-methylpropan-2-yl)-1H-1,2,3-triazol-4-yl)(6-fluoro-2-methylpyridin-3-yl)methyl)amino)-4-(neopentylamino)-quinoline-3,8-dicarbonitrile | 24 | 562.2 |
| 591 | 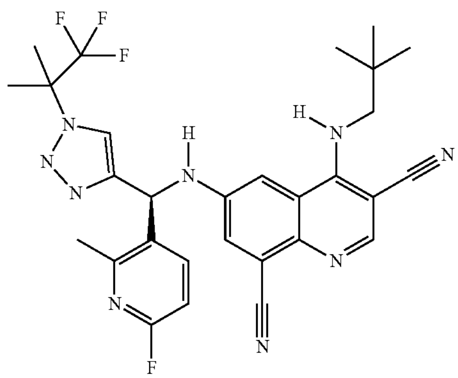 [SMILES: Cc1nc(F)ccc1[C@H](Nc1cc(C#N)c2ncc(C#N)c(NCC(C)(C)C)c2c1)C1=CN(C(C)(C)C(F)(F)F)NN1] | (S)-6-(((6-fluoro-2-methylpyridin-3-yl)(1-(1,1,1-trifluoro-2-methylpropan-2-yl)-1H-1,2,3-triazol-4-yl)methyl)amino)-4-(neopentylamino)quinoline-3,8-dicarbonitrile | 24 | 580.2 |
| 592 | 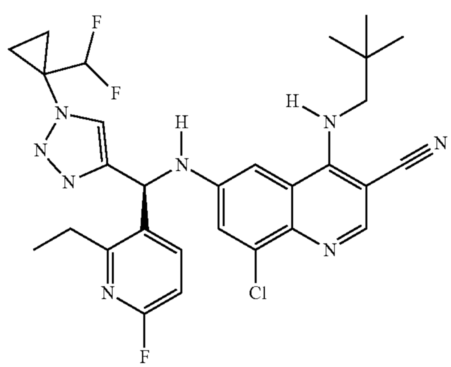 [SMILES: CCc1nc(F)ccc1[C@H](Nc1cc(Cl)c2ncc(C#N)c(NCC(C)(C)C)c2c1)C1=CN(C2(C(F)F)CC2)NN1] | (S)-8-chloro-6-(((1-(1-(difluoromethyl)cyclopropyl)-1H-1,2,3-triazol-4-yl)(2-ethyl-6-fluoropyridin-3-yl)methyl)amino)-4-(neopentylamino)quinoline-3-carbonitrile | 23 | 583.25 |
| 593 | 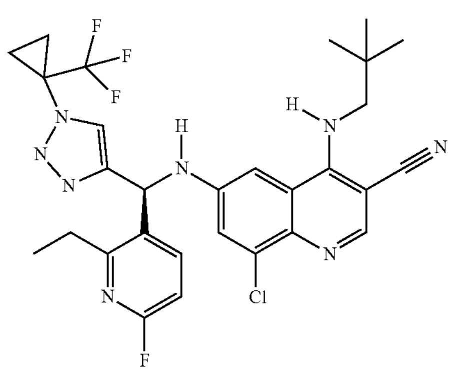 | (S)-8-chloro-6-(((2-ethyl-6-fluoropyridin-3-yl)(1-(1-(trifluoromethyl)cyclopropyl)-1H-1,2,3-triazol-4-yl)methyl)amino)-4-(neopentylamino)quinoline-3-carbonitrile | 23 | 601.42 |

TABLE 1-continued

| Comp | Structure | Name | Example Procedure | ES/MS m/z |
|---|---|---|---|---|
| 594 | 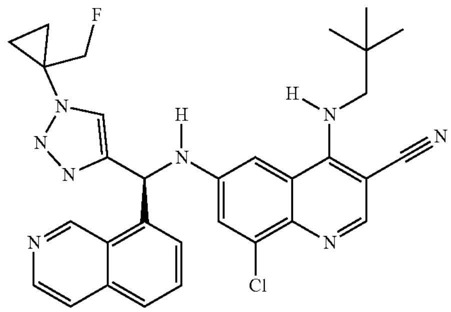 [SMILES: CC(C)(C)CNc1c(C#N)cnc2c(Cl)cc(N[C@H](C3=CN(C4(CF)CC4)NN3)c3cccc4ccncc34)cc12] | (S)-8-chloro-6-(((1-(1-(fluoromethyl)cyclopropyl)-1H-1,2,3-triazol-4-yl)(isoquinolin-8-yl)methyl)amino)-4-(neopentylamino)quinoline-3-carbonitrile | 27 | 569.3 |
| 595 | 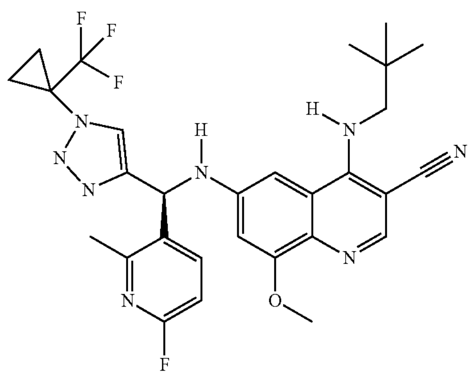 [SMILES: COc1cc(N[C@H](C2=CN(C3(C(F)(F)F)CC3)NN2)c2ccc(F)nc2C)cc2c(NCC(C)(C)C)c(C#N)cnc12] | (S)-6-(((6-fluoro-2-methylpyridin-3-yl)(1-(1-(trifluoromethyl)cyclopropyl)-1H-1,2,3-triazol-4-yl)methyl)amino)-8-methoxy-4-(neopentylamino)quinoline-3-carbonitrile | 4 | 583.20 |
| 596 | 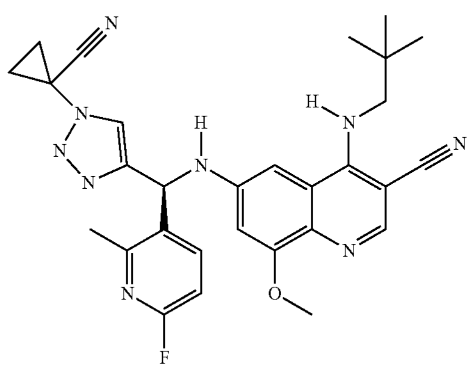 [SMILES: COc1cc(N[C@H](C2=CN(C3(C#N)CC3)NN2)c2ccc(F)nc2C)cc2c(NCC(C)(C)C)c(C#N)cnc12] | (S)-6-(((1-(1-cyanocyclopropyl)-1H-1,2,3-triazol-4-yl)(6-fluoro-2-methylpyridin-3-yl)methyl)amino)-8-methoxy-4-(neopentylamino)quinoline-3-carbonitrile | 4 | 540.2 |
| 597 | 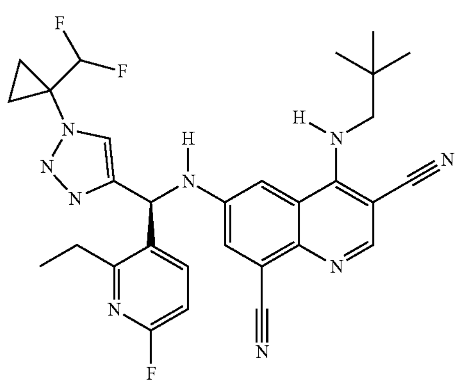 [SMILES: CCc1nc(F)ccc1[C@H](Nc1cc(C#N)c2ncc(C#N)c(NCC(C)(C)C)c2c1)C1=CN(C2(C(F)F)CC2)NN1] | (S)-6-(((1-(1-(difluoromethyl)cyclopropyl)-1H-1,2,3-triazol-4-yl)(2-ethyl-6-fluoropyridin-3-yl)methyl)amino)-4-(neopentylamino)quinoline-3,8-dicarbonitrile | 24 | 574.23 |

TABLE 1-continued

| Comp | Structure | Name | Example Procedure | ES/MS m/z |
|---|---|---|---|---|
| 598 | 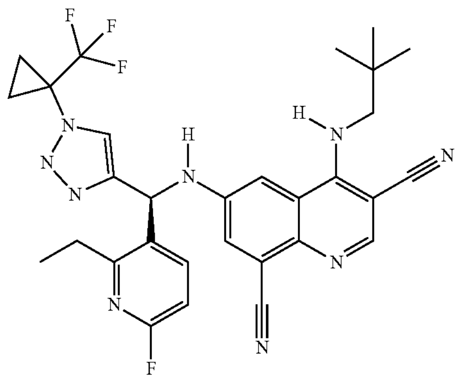 [SMILES: CCc1nc(F)ccc1[C@H](Nc1cc(C#N)c2ncc(C#N)c(NCC(C)(C)C)c2c1)C1=CN(C2(C(F)(F)F)CC2)NN1] | (S)-6-(((2-ethyl-6-fluoropyridin-3-yl)(1-(1-(trifluoromethyl)cyclopropyl)-1H-1,2,3-triazol-4-yl)methyl)amino)-4-(neopentylamino)-quinoline-3,8-dicarbonitrile | 24 | 592.39 |
| 599 | 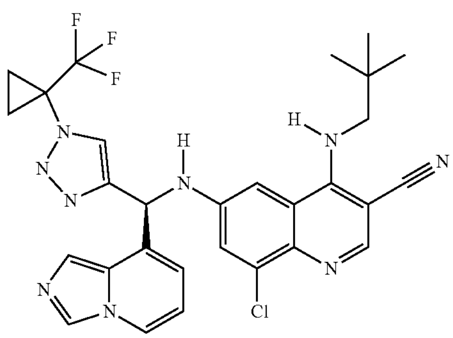 [SMILES: CC(C)(C)CNc1c(C#N)cnc2c(Cl)cc(N[C@H](C3=CN(C4(C(F)(F)F)CC4)NN3)c3cccn4cncc34)cc12] | (S)-8-chloro-6-((imidazo[1,5-a]pyridin-8-yl(1-(1-(trifluoromethyl)cyclopropyl)-1H-1,2,3-triazol-4-yl)methyl)amino)-4-(neopentylamino)quinoline-3-carbonitrile | 4 | 594.1 |
| 600 | 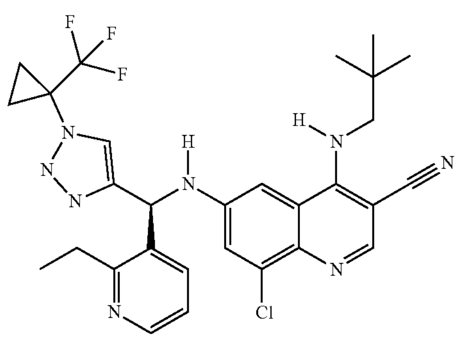 [SMILES: CCc1ncccc1[C@H](Nc1cc(Cl)c2ncc(C#N)c(NCC(C)(C)C)c2c1)C1=CN(C2(C(F)(F)F)CC2)NN1] | (S)-8-chloro-6-(((2-ethylpyridin-3-yl)(1-(1-(trifluoromethyl)cyclopropyl)-1H-1,2,3-triazol-4-yl)methyl)amino)-4-(neopentylamino)quinoline-3-carbonitrile | 4 | 583.3 |
| 601 | 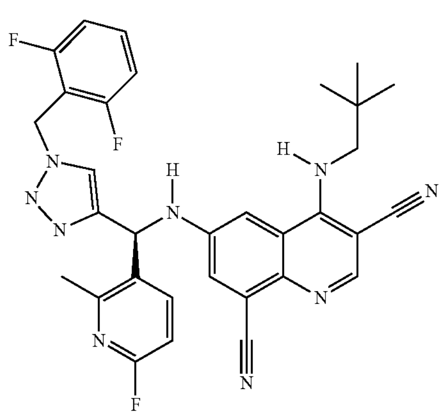 [SMILES: Cc1nc(F)ccc1[C@H](Nc1cc(C#N)c2ncc(C#N)c(NCC(C)(C)C)c2c1)C1=CN(Cc2c(F)cccc2F)NN1] | (S)-6-(((1-(2,6-difluorobenzyl)-1H-1,2,3-triazol-4-yl)(6-fluoro-2-methylpyridin-3-yl)methyl)amino)-4-(neopentylamino)quinoline-3,8-dicarbonitrile | 9 | 596.3 |

TABLE 1-continued

| Comp | Structure | Name | Example Procedure | ES/MS m/z |
|---|---|---|---|---|
| 602 | 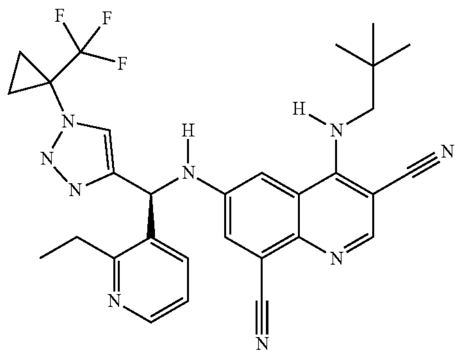 [SMILES: CCc1ncccc1[C@H](Nc1cc(C#N)c2ncc(C#N)c(NCC(C)(C)C)c2c1)C1=CN(C2(C(F)(F)F)CC2)NN1] | (S)-6-(((2-ethylpyridin-3-yl)(1-(1-(trifluoromethyl)cyclopropyl)-1H-1,2,3-triazol-4-yl)methyl)amino)-4-(neopentylamino)-quinoline-3,8-dicarbonitrile | 24 | 574.2 |
| 603 | 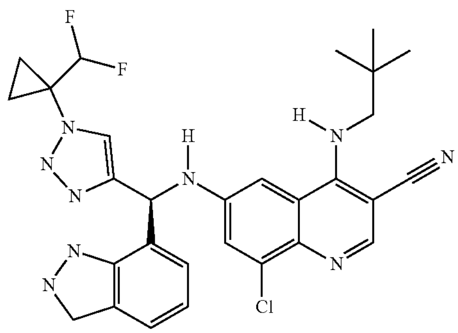 [SMILES: CC(C)(C)CNc1c(C#N)cnc2c(Cl)cc(N[C@H](C3=CN(C4(C(F)F)CC4)NN3)c3cccc4c3NNC4)cc12] | (S)-8-chloro-6-(((1-(1-(difluoromethyl)cyclopropyl)-1H-1,2,3-triazol-4-yl)(1-methyl-1H-indazol-7-yl)methyl)amino)-4-(neopentylamino)quinoline-3-carbonitrile | 4 | 590.3 |
| 604 | 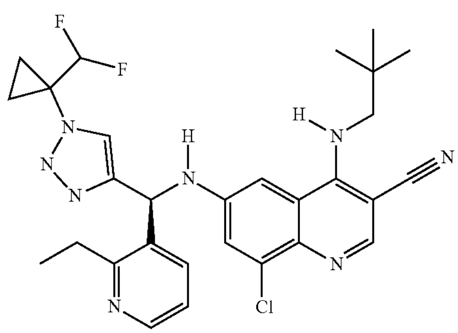 [SMILES: CCc1ncccc1[C@H](Nc1cc(Cl)c2ncc(C#N)c(NCC(C)(C)C)c2c1)C1=CN(C2(C(F)F)CC2)NN1] | (S)-8-chloro-6-(((1-(1-(difluoromethyl)cyclopropyl)-1H-1,2,3-triazol-4-yl)(2-ethylpyridin-3-yl)methyl)amino)-4-(neopentylamino)-quinoline-3-carbonitrile | 4 | 565.2 |
| 605 | 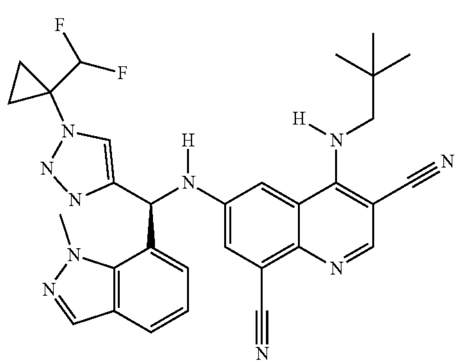 [SMILES: Cn1ncc2cccc([C@H](Nc3cc(C#N)c4ncc(C#N)c(NCC(C)(C)C)c4c3)C3=CN(C4(C(F)F)CC4)NN3)c21] | (S)-6-(((Ml-(difluoromethyl)cyclopropyl)-1H-1,2,3-triazol-4-yl)(1-methyl-1H-indazol-7-yl)methyl)amino)-4-(neopentylamino)quinoline-3,8-dicarbonitrile | 24 | 581.2 |

TABLE 1-continued

| Comp | Structure | Name | Example Procedure | ES/MS m/z |
|---|---|---|---|---|
| 606 | 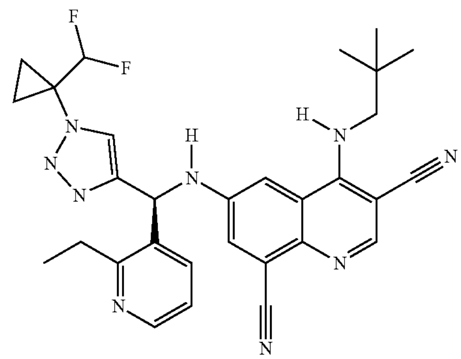 [SMILES: CCc1ncccc1[C@H](Nc1cc(C#N)c2ncc(C#N)c(NCC(C)(C)C)c2c1)C1=CN(C2(C(F)F)CC2)NN1] | (S)-6-(((1-{1-(difluoromethyl)-cyclopropyl)-1H-1,2,3-triazol-4-yl)(2-ethylpyridin-3-yl)methyl)amino)-4-(neopentylamino)quinoline-3,8-dicarbonitrile | 24 | 556.3 |
| 607 | 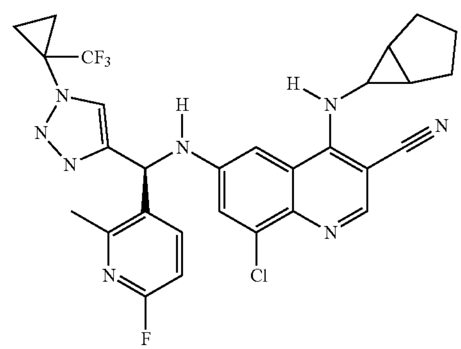 [SMILES: Cc1nc(F)ccc1[C@H](Nc1cc(Cl)c2ncc(C#N)c(NC3C4CCCC43)c2c1)C1=CN(C2(C(F)(F)F)CC2)NN1] | 4-((((1R,5S)-bicyclo[3.1.0]hexan-6-yl)amino)-8-chloro-6-(((S)-(6-fluoro-2-methylpyridin-3-yl)(1-(1-(trifluoromethyl)cyclopropyl)-1H-1,2,3-triazol-4-yl)methyl)amino)quinoline-3-carbonitrile | 1 | 597.26 |
| 608 | 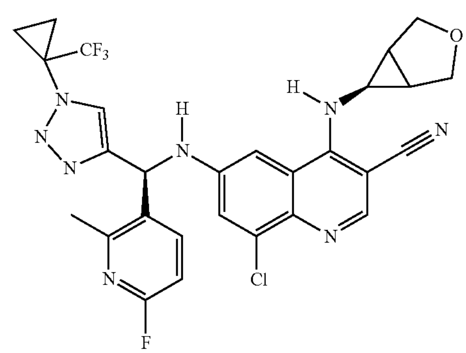 | 4-((((1R,5S,6r)-3-oxabicyclo[3.1.0]hexan-6-yl)amino)-8-chloro-6-(((S)-(6-fluoro-2-methylpyridin-3-yl)(1-(1-(trifluoromethyl)cyclo-propyl)-1H-1,2,3-triazol-4-yl)methyl)amino)-quinoline-3-carbonitrile | 1 | 599.20 |
| 609 | 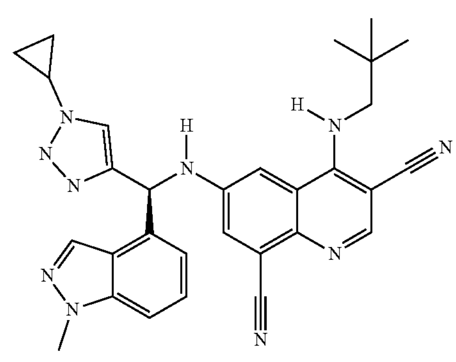 [SMILES: Cn1ncc2c([C@H](Nc3cc(C#N)c4ncc(C#N)c(NCC(C)(C)C)c4c3)C3=CN(C4CC4)NN3)cccc21] | (S)-6-(((1-cyclopropyl-1H-1,2,3-triazol-4-yl)(1-methyl-1H-indazol-4-yl)methyl)amino)-4-(neopentylamino)quinoline-3,8-dicarbonitrile | 9 | 531.4 |

TABLE 1-continued

| Comp | Structure | Name | Example Procedure | ES/MS m/z |
|---|---|---|---|---|
| 610 | 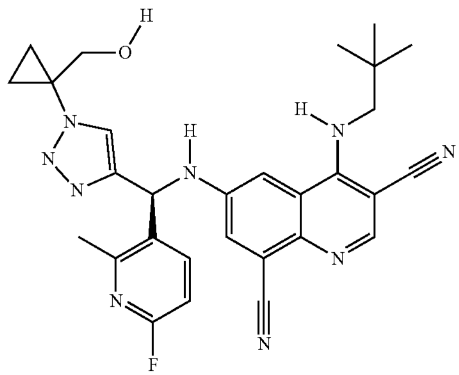 [SMILES: Cc1nc(F)ccc1[C@H](Nc1cc(C#N)c2ncc(C#N)c(NCC(C)(C)C)c2c1)C1=CN(C2(CO)CC2)NN1] | (S)-6-(((6-fluoro-2-methylpyridin-3-yl)(1-(1-(hydroxymethyl)cyclopropyl)-1H-1,2,3-triazol-4-yl)methyl)amino)-4-(neopentylamino)quinoline-3,8-dicarbonitrile | 24 | 540.3 |
| 611 | 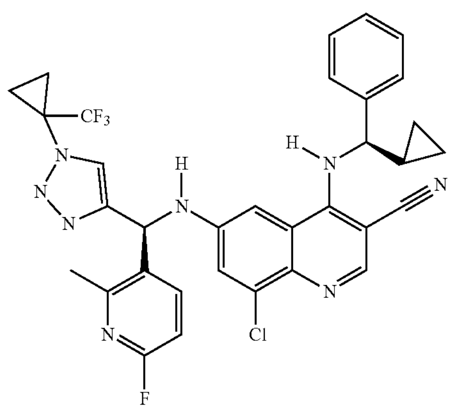 [SMILES: Cc1nc(F)ccc1[C@H](Nc1cc(Cl)c2ncc(C#N)c(N[C@@H](c3ccccc3)C3CC3)c2c1)C1=CN(C2(C(F)(F)F)CC2)NN1] | 8-chloro-4-(((R)-cyclopropyl(phenyl)methyl)-amino)-6-(((S)-(6-fluoro-2-methylpyridin-3-yl)(1-(1-(trifluoromethyl)cyclopropyl)-1H-1,2,3-triazol-4-yl)methyl)amino)quinoline-3-carbonitrile | 1 | 647.18 |
| 612 | 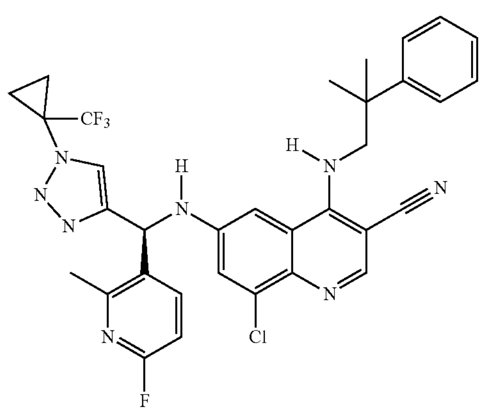 [SMILES: Cc1nc(F)ccc1[C@H](Nc1cc(Cl)c2ncc(C#N)c(NCC(C)(C)c3ccccc3)c2c1)C1=CN(C2(C(F)(F)F)CC2)NN1] | (S)-8-chloro-6-(((6-fluoro-2-methylpyridin-3-yl)(1-(1-(trifluoromethyl)cyclopropyl)-1H-1,2,3-triazol-4-yl)methyl)amino)-4-((2-methyl-2-phenylpropyl)amino)quinoline-3-carbonitrile | 1 | 649.23 |

TABLE 1-continued

| Comp | Structure | Name | Example Procedure | ES/MS m/z |
|---|---|---|---|---|
| 613 | 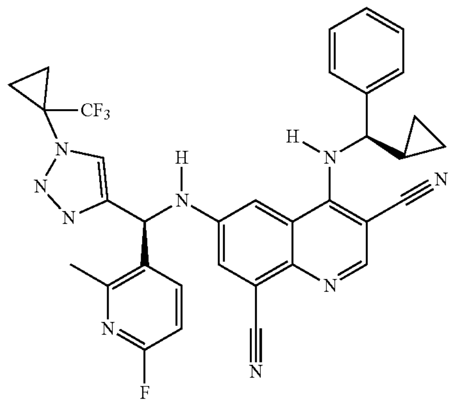 [SMILES: Cc1nc(F)ccc1[C@H](Nc1cc(C#N)c2ncc(C#N)c(N[C@@H](c3ccccc3)C3CC3)c2c1)C1=CN(C2(C(F)(F)F)CC2)NN1] | 4-(((R)-cyclopropyl(phenyl)methyl)amino)-6-(((S)-(6-fluoro-2-methylpyridin-3-yl)(1-(1-(trifluoromethyl)cyclopropyl)-1H-1,2,3-triazol-4-yl)methyl)amino)quinoline-3,8-dicarbonitrile | 25 | 638.33 |
| 614 | 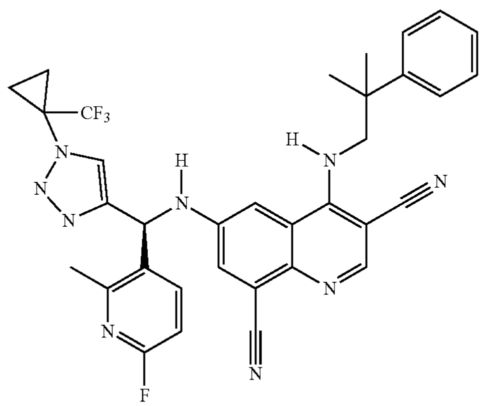 [SMILES: Cc1nc(F)ccc1[C@H](Nc1cc(C#N)c2ncc(C#N)c(NCC(C)(C)c3ccccc3)c2c1)C1=CN(C2(C(F)(F)F)CC2)NN1] | (S)-6-(((6-fluoro-2-methylpyridin-3-yl)(1-(1-(trifluoromethyl)cyclopropyl)-1H-1,2,3-triazol-4-yl)methyl)amino)-4-((2-methyl-2-phenylpropyl)amino)quinoline-3,8-dicarbonitrile | 25 | 640.30 |
| 615 | 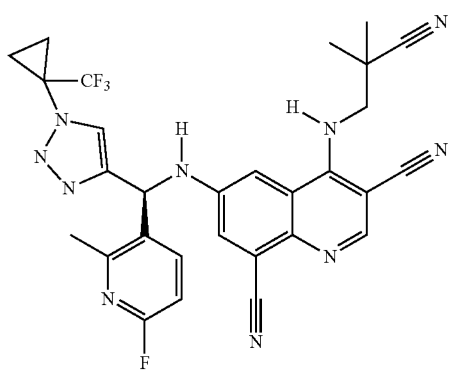 [SMILES: Cc1nc(F)ccc1[C@H](Nc1cc(C#N)c2ncc(C#N)c(NCC(C)(C)C#N)c2c1)C1=CN(C2(C(F)(F)F)CC2)NN1] | (S)-4-((2-cyano-2-methylpropyl)amino)-6-(((6-fluoro-2-methylpyridin-3-yl)(1-(1-(trifluoromethyl)cyclopropyl)-1H-1,2,3-triazol-4-yl)methyl)amino)quinoline-3,8-dicarbonitrile | 25 | 589.3 |
| 616 | 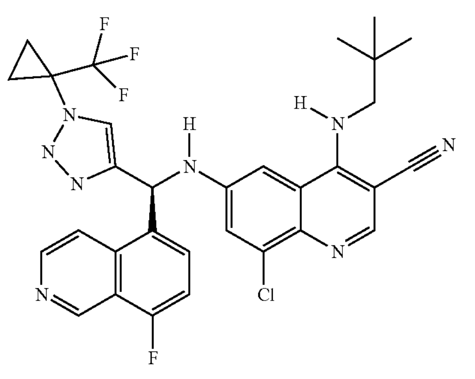 [SMILES: CC(C)(C)CNc1c(C#N)cnc2c(Cl)cc(N[C@H](C3=CN(C4(C(F)(F)F)CC4)NN3)c3ccc(F)c4cnccc34)cc12] | (S)-8-chloro-6-(((8-fluoroisoquinolin-5-yl)(1-(1-(trifluoromethyl)cyclopropyl)-1H-1,2,3-triazol-4-yl)methyl)amino)-4-(neopentylamino)quinoline-3-carbonitrile | 27 | 623.747 |

TABLE 1-continued

| Comp | Structure | Name | Example Procedure | ES/MS m/z |
|---|---|---|---|---|
| 617 | 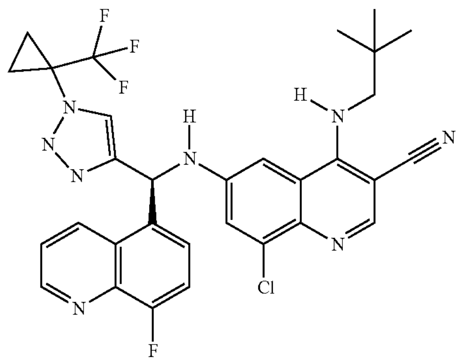 [SMILES: CC(C)(C)CNc1c(C#N)cnc2c(Cl)cc(N[C@H](C3=CN(C4(C(F)(F)F)CC4)NN3)c3ccc(F)c4ncccc34)cc12] | (S)-8-chloro-6-(((8-fluoroquinolin-5-yl)(1-(1-(trifluoromethyl)cyclopropyl)-1H-1,2,3-triazol-4-yl)methyl)amino)-4-(neopentylamino)quinoline-3-carbonitrile | 27 | 623.685 |
| 618 | 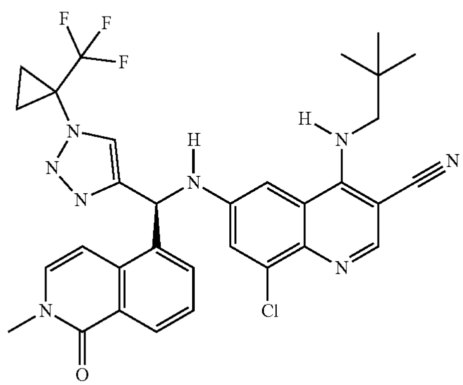 [SMILES: Cn1ccc2c([C@H](Nc3cc(Cl)c4ncc(C#N)c(NCC(C)(C)C)c4c3)C3=CN(C4(C(F)(F)F)CC4)NN3)cccc2c1=O] | (S)-8-chloro-6-(((2-methyl-1-oxo-1,2-dihydroisoquinolin-5-yl)(1-(1-(trifluoromethyl)cyclopropyl)-1H-1,2,3-triazol-4-yl)methyl)amino)-4-(neopentylamino)quinoline-3-carbonitrile | 4 | 635.4 |
| 619 | 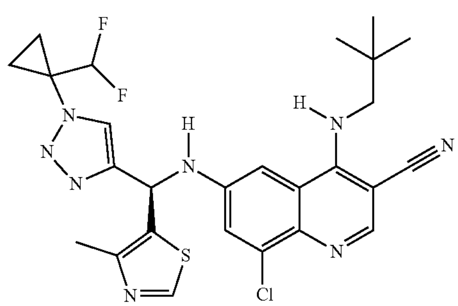 | (R)-8-chloro-6-(((1-(1-(difluoromethyl)-cyclopropyl)-1H-1,2,3-triazol-4-yl)(4-methylthiazol-5-yl)methyl)amino)-4-(neopentylamino)quinoline-3-carbonitrile | 23 | 557.4 |
| 620 | 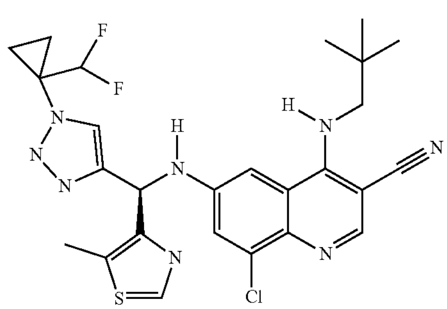 | (S)-8-chloro-6-(((1-(1-(difluoromethyl)cyclopropyl)-1H-1,2,3-triazol-4-yl)(5-methylthiazol-4-yl)methyl)amino)-4-(neopentylamino)quinoline-3-carbonitrile | 23 | 557.7 |

TABLE 1-continued

| Comp | Structure | Name | Example Procedure | ES/MS m/z |
|---|---|---|---|---|
| 621 | 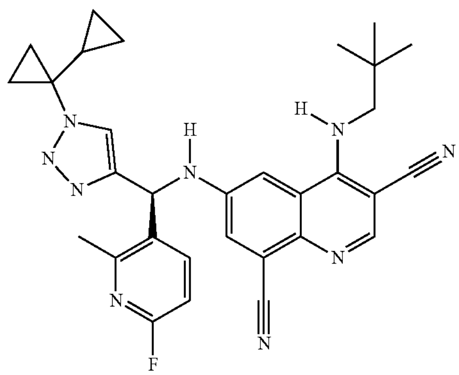 [SMILES: Cc1nc(F)ccc1[C@H](Nc1cc(C#N)c2ncc(C#N)c(NCC(C)(C)C)c2c1)C1=CN(C2(C3CC3)CC2)NN1] | (S)-6-(((1-([1,1'-bi(cyclopropan)]-1-yl)-1H-1,2,3-triazol-4-yl)(6-fluoro-2-methylpyridin-3-yl)methyl)amino)-4-(neopentylamino)quinoline-3,8-dicarbonitrile | 24 | 550.3 |
| 622 | 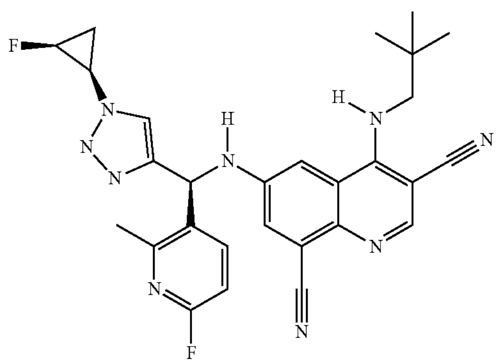 [SMILES: Cc1nc(F)ccc1[C@H](Nc1cc(C#N)c2ncc(C#N)c(NCC(C)(C)C)c2c1)C1=CN([C@@H]2C[C@@H]2F)NN1] | 6-(((S)-(6-fluoro-2-methylpyridin-3-yl)(1-((1R,2S)-2-fluorocyclopropyl)-1H-1,2,3-triazol-4-yl)methyl)amino)-4-(neopentylamino)quinoline-3,8-dicarbonitrile | 24 | 528.3 |
| 623 | 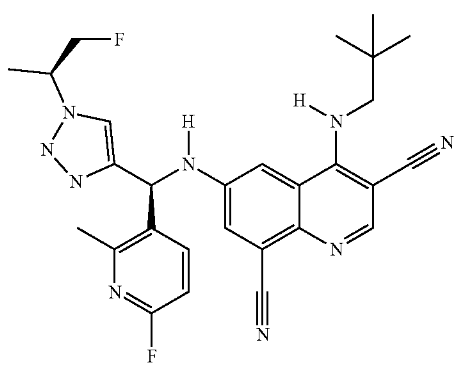 [SMILES: Cc1nc(F)ccc1[C@H](Nc1cc(C#N)c2ncc(C#N)c(NCC(C)(C)C)c2c1)C1=CN([C@@H](C)CF)NN1] | 6-(((S)-(6-fluoro-2-methylpyridin-3-yl)(1-((S)-1-fluoropropan-2-yl)-1H-1,2,3-triazol-4-yl)methyl)amino)-4-(neopentylamino)quinoline-3,8-dicarbonitrile | 24 | 530.3 |
| 624 | 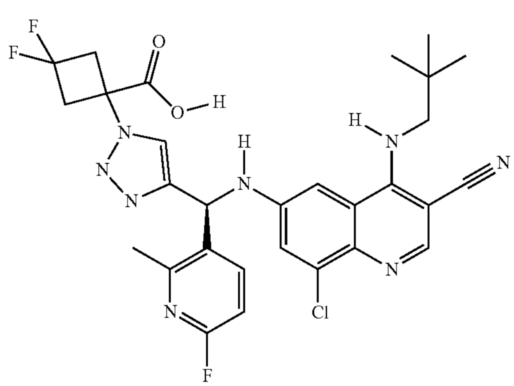 [SMILES: Cc1nc(F)ccc1[C@H](Nc1cc(Cl)c2ncc(C#N)c(NCC(C)(C)C)c2c1)C1=CN(C2(C(=O)O)CC(F)(F)C2)NN1] | (S)-1-(4-(((8-chloro-3-cyano-4-(neopentylamino)quinolin-6-yl)amino)(6-fluoro-2-methylpyridin-3-yl)methyl)-1H-1,2,3-triazol-1-yl)-3,3-difluorocyclobutane-1-carboxylic acid | 4 | 613.3 |

TABLE 1-continued

| Comp | Structure | Name | Example Procedure | ES/MS m/z |
|---|---|---|---|---|
| 625 | 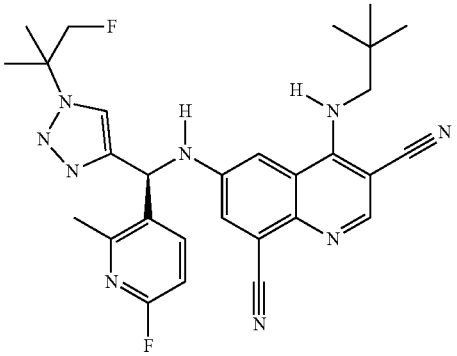 [SMILES: Cc1nc(F)ccc1[C@H](Nc1cc(C#N)c2ncc(C#N)c(NCC(C)(C)C)c2c1)C1=CN(C(C)(C)CF)NN1] | (S)-6-(((1-{1-fluoro-2-methylpropan-2-yl)-1H-1,2,3-triazol-4-yl)(6-fluoro-2-methylpyridin-3-yl)methyl)amino)-4-(neopentylamino)quinoline-3,8-dicarbonitrile | 24 | 544.5 |
| 626 | 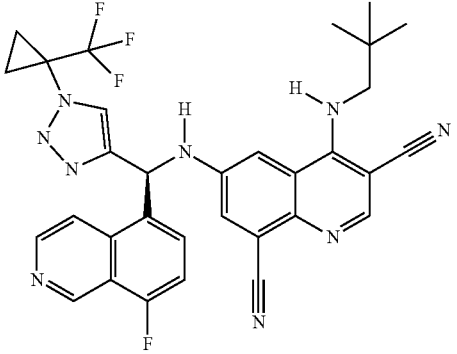 [SMILES: CC(C)(C)CNc1c(C#N)cnc2c(C#N)cc(N[C@H](C3=CN(C4(C(F)(F)F)CC4)NN3)c3ccc(F)c4cnccc34)cc12] | (S)-6-(((8-fluoroisoquinolin-5-yl)(1-(1-(trifluoromethyl)cyclopropyl)-1H-1,2,3-triazol-4-yl)methyl)amino)-4-(neopentylamino)quinoline-3,8-dicarbonitrile | 24 | 614.453 |
| 627 | 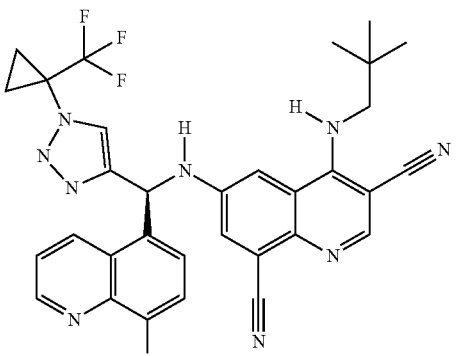 | (S)-6-(((8-fluoroquinolin-5-yl)(1-(1-(trifluoromethyl)cyclopropyl)-1H-1,2,3-triazol-4-yl)methyl)amino)-4-(neopentylamino)quinoline-3,8-dicarbonitrile | 24 | 614.444 |
| 628 | 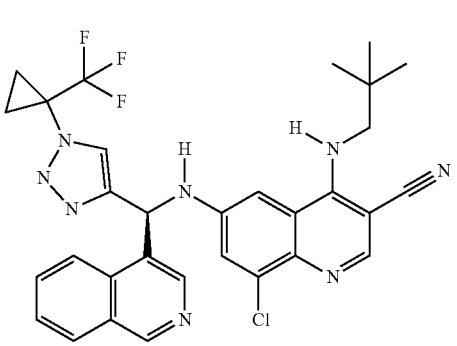 [SMILES: CC(C)(C)CNc1c(C#N)cnc2c(Cl)cc(N[C@H](C3=CN(C4(C(F)(F)F)CC4)NN3)c3cncc4ccccc34)cc12] | (S)-8-chloro-6-((isoquinolin-4-yl(1-(1-(trifluoromethyl)cyclopropyl)-1H-1,2,3-triazol-4-yl)methyl)amino)-4-(neopentylamino)quinoline-3-carbonitrile | 27 | 605.604 |

TABLE 1-continued

| Comp | Structure | Name | Example Procedure | ES/MS m/z |
|---|---|---|---|---|
| 629 | 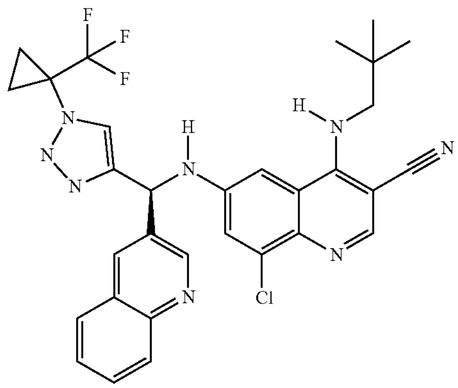 [SMILES: CC(C)(C)CNc1c(C#N)cnc2c(Cl)cc(N[C@H](C3=CN(C4(C(F)(F)F)CC4)NN3)c3cnc4ccccc4c3)cc12] | (S)-8-chloro-4-(neopentylamino)-6-((quinolin-3-yl(1-(1-(trifluoromethyl)cyclopropyl)-1H-1,2,3-triazol-4-yl)methyl)amino)quinoline-3-carbonitrile | 27 | 605.197 |
| 630 | 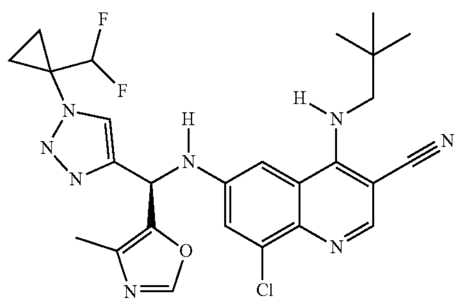 [SMILES: Cc1ncoc1[C@H](Nc1cc(Cl)c2ncc(C#N)c(NCC(C)(C)C)c2c1)C1=CN(C2(C(F)F)CC2)NN1] | (R)-8-chloro-6-(((1-(1-(difluoromethyl)cyclopropyl)-1H-1,2,3-triazol-4-yl)(4-methyloxazol-5-yl)methyl)amino)-4-(neopentylamino)quinoline-3-carbonitrile | 23 | 541.3 |
| 631 | 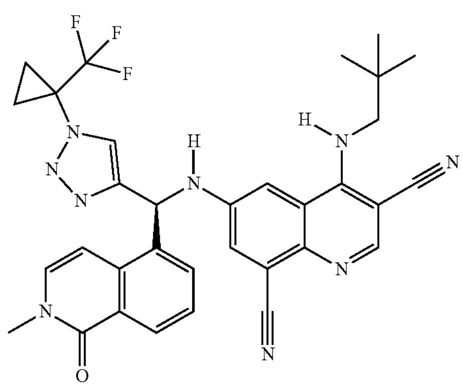 [SMILES: Cn1ccc2c([C@H](Nc3cc(C#N)c4ncc(C#N)c(NCC(C)(C)C)c4c3)C3=CN(C4(C(F)(F)F)CC4)NN3)cccc2c1=O] | (S)-6-(((2-methyl-1-oxo-1,2-dihydroisoquinolin-5-yl)(1-(1-(trifluoromethyl)cyclopropyl)-1H-1,2,3-triazol-4-yl)methyl)amino)-4-(neopentylamino)quinoline-3,8-dicarbonitrile | 24 | 626.2 |
| 632 | 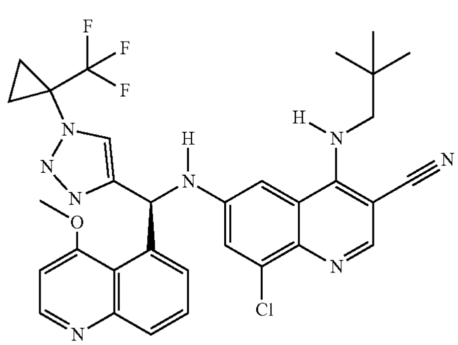 [SMILES: COc1ccnc2cccc([C@H](Nc3cc(Cl)c4ncc(C#N)c(NCC(C)(C)C)c4c3)C3=CN(C4(C(F)(F)F)CC4)NN3)c12] | (S)-8-chloro-6-(((4-methoxyquinolin-5-yl)(1-(1-(trifluoromethyl)cyclopropyl)-1H-1,2,3-triazol-4-yl)methyl)amino)-4-(neopentylamino)quinoline-3-carbonitrile | 4 | 635.3 |

TABLE 1-continued

| Comp | Structure | Name | Example Procedure | ES/MS m/z |
|---|---|---|---|---|
| 633 | 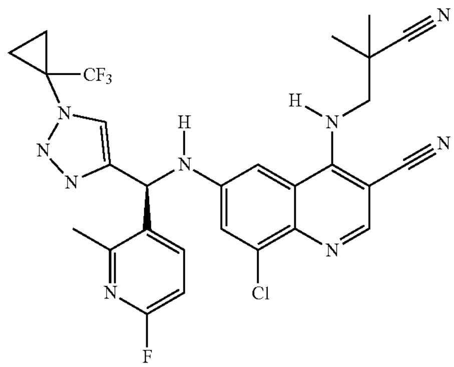 [SMILES: Cc1nc(F)ccc1[C@H](Nc1cc(Cl)c2ncc(C#N)c(NCC(C)(C)C#N)c2c1)C1=CN(C2(C(F)(F)F)CC2)NN1] | (S)-8-chloro-4-((2-cyano-2-methylpropyl)amino)-6-(((6-fluoro-2-methylpyridin-3-yl)(1-(1-(trifluoromethyl)cyclopropyl)-1H-1,2,3-triazol-4-yl)methyl)amino)quinoline-3-carbonitrile | 1 | 598.34 |
| 634 | 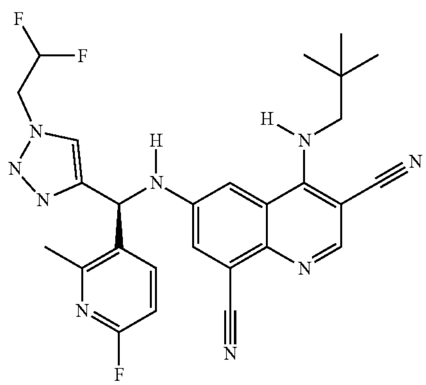 [SMILES: Cc1nc(F)ccc1[C@H](Nc1cc(C#N)c2ncc(C#N)c(NCC(C)(C)C)c2c1)C1=CN(CC(F)F)NN1] | (S)-6-(((1-(2,2-difluoroethyl)-1H-1,2,3-triazol-4-yl)(6-fluoro-2-methylpyridin-3-yl)methyl)amino)-4-(neopentylamino)quinoline-3,8-dicarbonitrile | 24 | 534.4 |
| 635 | 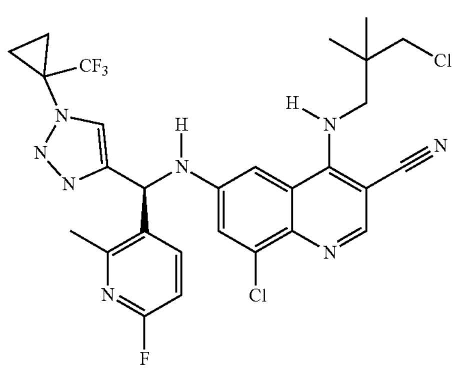 [SMILES: Cc1nc(F)ccc1[C@H](Nc1cc(Cl)c2ncc(C#N)c(NCC(C)(C)CCl)c2c1)C1=CN(C2(C(F)(F)F)CC2)NN1] | (S)-8-chloro-4-((3-chloro-2,2-dimethylpropyl)amino)-6-(((6-fluoro-2-methylpyridin-3-yl)(1-(1-(trifluoromethyl)cyclopropyl)-1H-1,2,3-triazol-4-yl)methyl)amino)quinoline-3-carbonitrile | 1 | 621.07 |
| 636 | 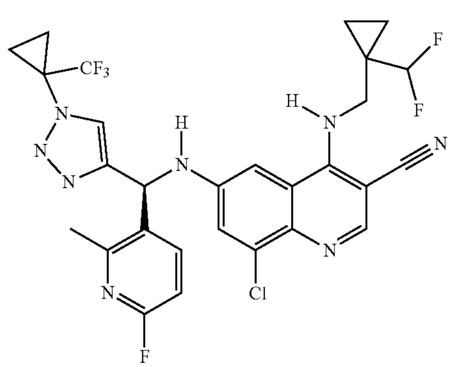 [SMILES: Cc1nc(F)ccc1[C@H](Nc1cc(Cl)c2ncc(C#N)c(NCC3(C(F)F)CC3)c2c1)C1=CN(C2(C(F)(F)F)CC2)NN1] | (S)-8-chloro-4-(((1-(difluoromethyl)cyclopropyl)methyl)amino)-6-(((6-fluoro-2-methylpyridin-3-yl)(1-(1-(trifluoromethyl)cyclopropyl)-1H-1,2,3-triazol-4-yl)methyl)amino)quinoline-3-carbonitrile | 1 | 621.06 |

TABLE 1-continued

| Comp | Structure | Name | Example Procedure | ES/MS m/z |
|---|---|---|---|---|
| 637 | 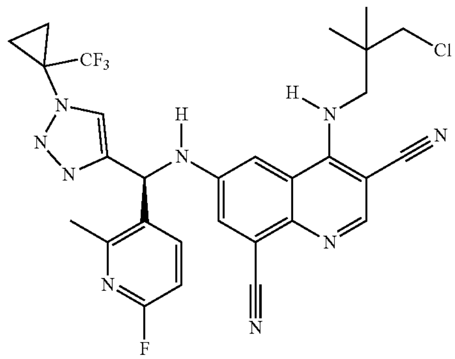 [SMILES: Cc1nc(F)ccc1[C@H](Nc1cc(C#N)c2ncc(C#N)c(NCC(C)(C)CCl)c2c1)C1=CN(C2(C(F)(F)F)CC2)NN1] | (S)-4-((3-chloro-2,2-dimethylpropyl)amino)-6-(((6-fluoro-2-methylpyridin-3-yl)(1-(1-(trifluoromethyl)-cyclopropyl)-1H-1,2,3-triazol-4-yl)methyl)amino)-quinoline-3,8-dicarbonitrile | 25 | 612.14 |
| 638 | 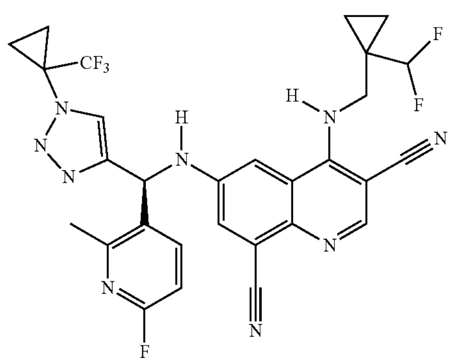 [SMILES: Cc1nc(F)ccc1[C@H](Nc1cc(C#N)c2ncc(C#N)c(NCC3(C(F)F)CC3)c2c1)C1=CN(C2(C(F)(F)F)CC2)NN1] | (S)-4-(((1-(difluoromethyl)-cyclopropyl)methyl)amino)-6-(((6-fluoro-2-methylpyridin-3-yl)(1-(1-(trifluoromethyl)cyclopropyl)-1H-1,2,3-triazol-4-yl)methyl)amino)quinoline-3,8-dicarbonitrile | 25 | 612.22 |
| 639 | 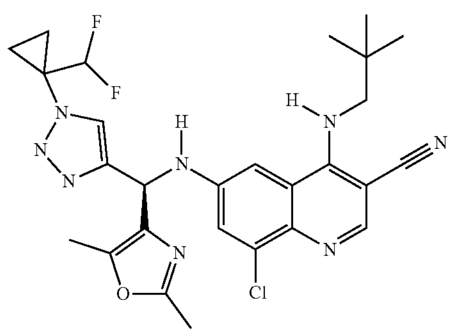 [SMILES: Cc1nc([C@H](Nc2cc(Cl)c3ncc(C#N)c(NCC(C)(C)C)c3c2)C2=CN(C3(C(F)F)CC3)NN2)c(C)o1] | (S)-8-chloro-6-(((1-(1-(difluoromethyl)cyclopropyl)-1H-1,2,3-triazol-4-yl)(2,5-dimethyloxazol-4-yl)methyl)amino)-4-(neopentylamino)quinoline-3-carbonitrile | 23 | 555.3 |
| 640 | 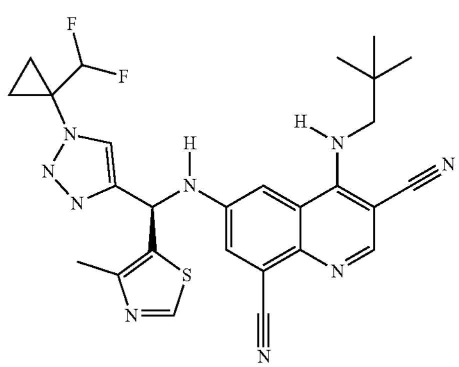 [SMILES: Cc1ncsc1[C@H](Nc1cc(C#N)c2ncc(C#N)c(NCC(C)(C)C)c2c1)C1=CN(C2(C(F)F)CC2)NN1] | (R)-6-(((1-(1-(difluoromethyl)-cyclopropyl)-1H-1,2,3-triazol-4-yl)(4-methylthiazol-5-yl)methyl)amino)-4-(neopentylamino)quinoline-3,8-dicarbonitrile | 24 | 548.4 |

TABLE 1-continued

| Comp | Structure | Name | Example Procedure | ES/MS m/z |
|---|---|---|---|---|
| 641 | 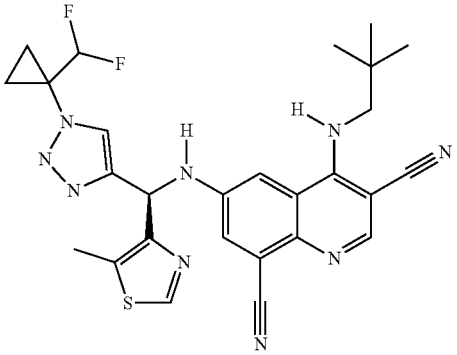 [SMILES: Cc1scnc1[C@H](Nc1cc(C#N)c2ncc(C#N)c(NCC(C)(C)C)c2c1)C1=CN(C2(C(F)F)CC2)NN1] | (S)-6-(((M1-(difluoromethyl)-cyclopropyl)-1H-1,2,3-triazol-4-yl)(5-methylthiazol-4-yl)methyl)amino)-4-(neopentylamino)quinoline-3,8-dicarbonitrile | 24 | 548.4 |
| 642 | 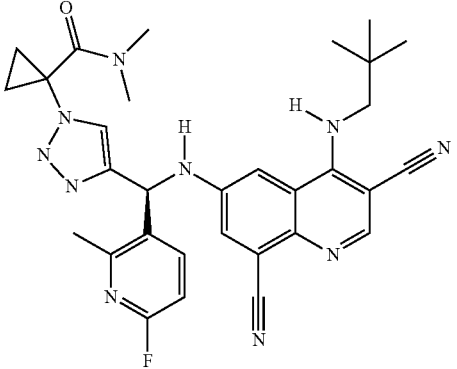 [SMILES: Cc1nc(F)ccc1[C@H](Nc1cc(C#N)c2ncc(C#N)c(NCC(C)(C)C)c2c1)C1=CN(C2(C(=O)N(C)C)CC2)NN1] | (S)-1-(4-(((3,8-dicyano-4-(neopentylamino)quinolin-6-yl)amino)(6-fluoro-2-methylpyridin-3-yl)methyl)-1H-1,2,3-triazol-1-yl)-N,N-dimethylcyclopropane-1-carboxamide | 24 | 581.2 |
| 643 | 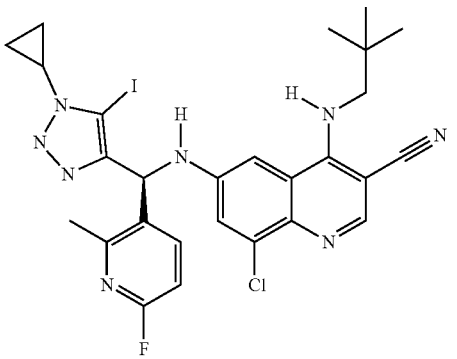 [SMILES: Cc1nc(F)ccc1[C@H](Nc1cc(Cl)c2ncc(C#N)c(NCC(C)(C)C)c2c1)C1=C(I)N(C2CC2)NN1] | (S)-8-chloro-6-(((1-cyclopropyl-5-iodo-1H-1,2,3-triazol-4-yl)(6-lluoro-2-methylpyridin-3-yl)methyl)amino)-4-(neopentylamino)quinoline-3-carbonitrile | 28 | 645.50 |
| 644 | 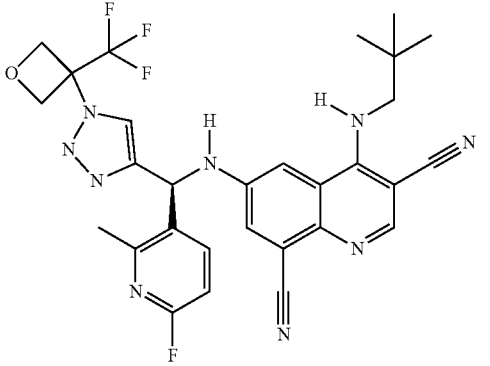 [SMILES: Cc1nc(F)ccc1[C@H](Nc1cc(C#N)c2ncc(C#N)c(NCC(C)(C)C)c2c1)C1=CN(C2(C(F)(F)F)COC2)NN1] | (S)-6-(((6-fluoro-2-methylpyridin-3-yl)(1-(3-(trifluoromethyl)oxetan-3-yl)-1H-1,2,3-triazol-4-yl)methyl)amino)-4-(neopentylamino)quinoline-3,8-dicarbonitrile | 24 | 594.4 |

TABLE 1-continued

| Comp | Structure | Name | Example Procedure | ES/MS m/z |
|---|---|---|---|---|
| 645 | 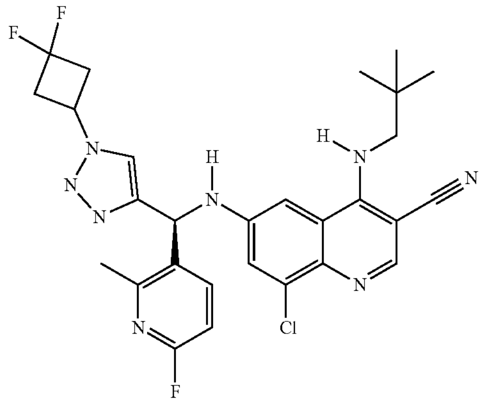 [SMILES: Cc1nc(F)ccc1[C@H](Nc1cc(Cl)c2ncc(C#N)c(NCC(C)(C)C)c2c1)C1=CN(C2CC(F)(F)C2)NN1] | (S)-8-chloro-6-(((1-(3,3-difluorocyclobutyl)-1H-1,2,3-triazol-4-yl)(6-fluoro-2-methylpyridin-3-yl)methyl)amino)-4-(neopentylamino)quinoline-3-carbonitrile | 4 | 569.4 |
| 646 | 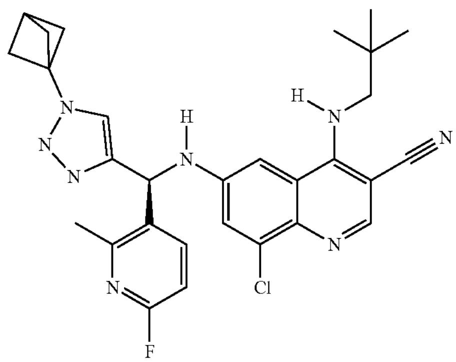 [SMILES: Cc1nc(F)ccc1[C@H](Nc1cc(Cl)c2ncc(C#N)c(NCC(C)(C)C)c2c1)C1=CN(C23CC(C2)C3)NN1] | (S)-6-(((1-(bicyclo[1.1.1]pentan-1-yl)-1H-1,2,3-triazol-4-yl)(6-fluoro-2-methylpyridin-3-yl)methyl)amino)-8-chloro-4-(neopentylamino)quinoline-3-carbonitrile | 4 | 545.7 |
| 647 | 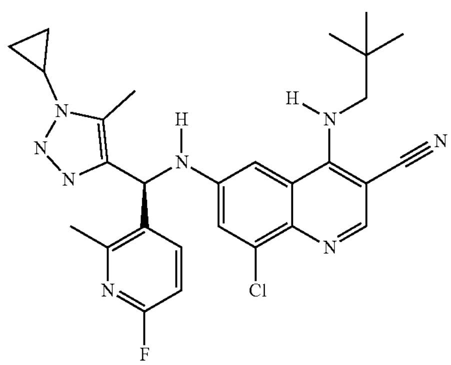 | (S)-8-chloro-6-(((1-cyclopropyl-5-methyl-1H-1,2,3-triazol-4-yl)(6-fluoro-2-methylpyridin-3-yl)methyl)amino)-4-(neopentylamino)quinoline-3-carbonitrile | 29 | 533.3 |
| 648 | 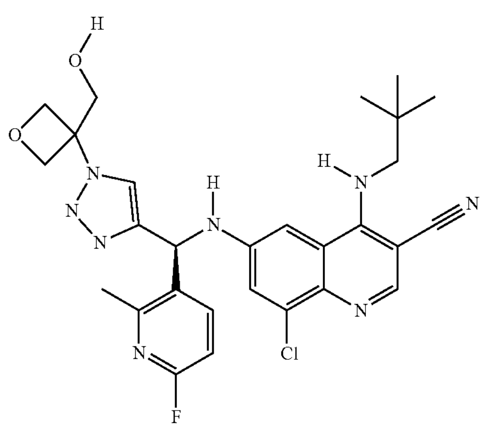 [SMILES: Cc1nc(F)ccc1[C@H](Nc1cc(Cl)c2ncc(C#N)c(NCC(C)(C)C)c2c1)C1=CN(C2(CO)COC2)NN1] | (S)-8-chloro-6-(((6-fluoro-2-methylpyridin-3-yl)(1-(3-(hydroxymethyl)oxetan-3-yl)-1H-1,2,3-triazol-4-yl)methyl)amino)-4-(neopentylamino)quinoline-3-carbonitrile | 4 | 565.4 |

TABLE 1-continued

| Comp | Structure | Name | Example Procedure | ES/MS m/z |
|---|---|---|---|---|
| 649 | 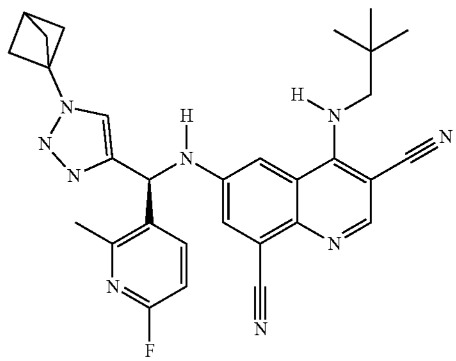 [SMILES: Cc1nc(F)ccc1[C@H](Nc1cc(C#N)c2ncc(C#N)c(NCC(C)(C)C)c2c1)C1=CN(C23CC(C2)C3)NN1] | (S)-6-(((1-(bicyclo[1.1.1]pentan-1-yl)-1H-1,2,3-triazol-4-yl)(6-fluoro-2-methylpyridin-3-yl)methyl)amino)-4-(neopentylamino)quinoline-3,8-dicarbonitrile | 24 | 536.3 |
| 650 | 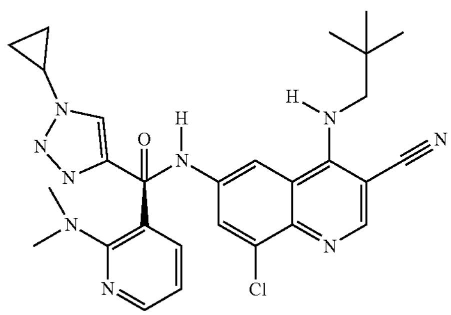 | (S)-8-chloro-6-(((1-cyclopropyl-1H-1,2,3-triazol-4-yl)(2-(dimethylamino)pyridin-3-yl)methyl-d)amino)-4-(neopentylamino)quinoline-3-carbonitrile | 26 | 531.226 |
| 651 | 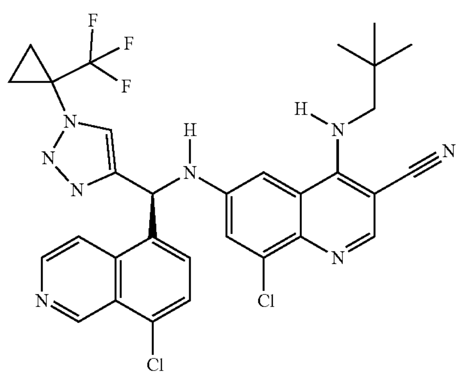 [SMILES: CC(C)(C)CNc1c(C#N)cnc2c(Cl)cc(N[C@H](C3=CN(C4(C(F)(F)F)CC4)NN3)c3ccc(Cl)c4cnccc34)cc12] | (S)-8-chloro-6-(((8-chloroisoquinolin-5-yl)(1-(1-(trifluoromethyl)cyclopropyl)-1H-1,2,3-triazol-4-yl)methyl)amino)-4-(neopentylamino)quinoline-3-carbonitrile | 27 | 639.953 |
| 652 | 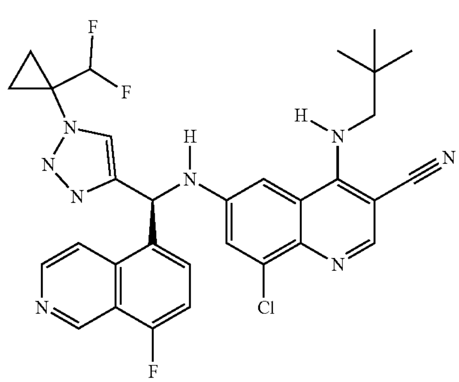 [SMILES: CC(C)(C)CNc1c(C#N)cnc2c(Cl)cc(N[C@H](C3=CN(C4(C(F)F)CC4)NN3)c3ccc(F)c4cnccc34)cc12] | (S)-8-chloro-6-(((1-(1-(difluoromethyl)cyclopropyl)-1H-1,2,3-triazol-4-yl)(8-fluoroisoquinolin-5-yl)methyl)amino)-4-(neopentylamino)quinoline-3-carbonitrile | 27 | 605.334 |

TABLE 1-continued

| Comp | Structure | Name | Example Procedure | ES/MS m/z |
|---|---|---|---|---|
| 653 | 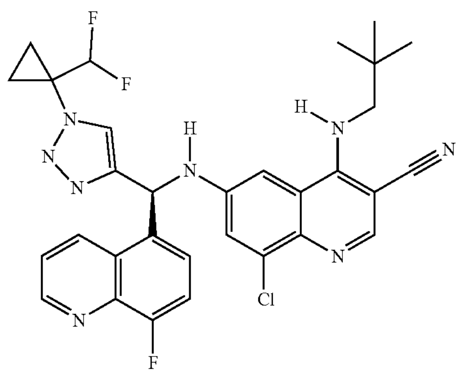 [SMILES: CC(C)(C)CNc1c(C#N)cnc2c(Cl)cc(N[C@H](C3=CN(C4(C(F)F)CC4)NN3)c3ccc(F)c4ncccc34)cc12] | (S)-8-chloro-6-(((1-(1-(difluoromethyl)cyclopropyl)-1H-1,2,3-triazol-4-yl)(8-fluoroquinolin-5-yl)methyl)amino)-4-(neopentylamino)quinoline-3-carbonitrile | 27 | 605.337 |
| 654 | 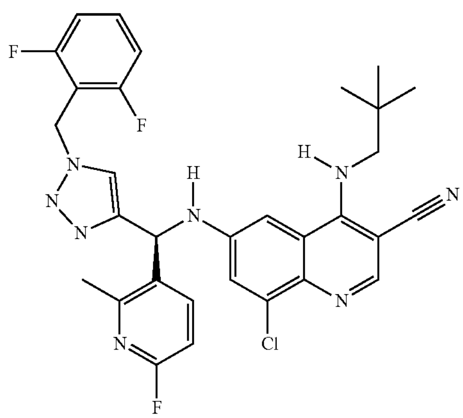 [SMILES: Cc1nc(F)ccc1[C@H](Nc1cc(Cl)c2ncc(C#N)c(NCC(C)(C)C)c2c1)C1=CN(Cc2c(F)cccc2F)NN1] | (S)-8-chloro-6-(((1-(2,6-difluorobenzyl)-1H-1,2,3-triazol-4-yl)(6-fluoro-2-methylpyridin-3-yl)methyl)amino)-4-(neopentylamino)quinoline-3-carbonitrile | 1 | 605.3 |
| 655 | 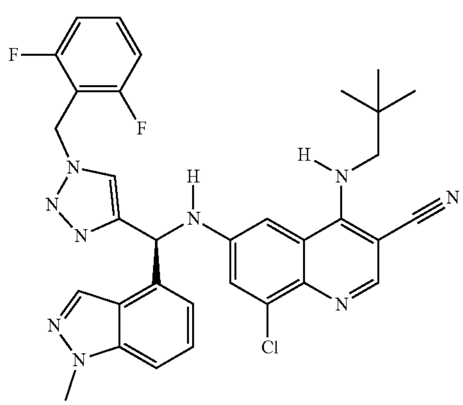 [SMILES: Cn1ncc2c([C@H](Nc3cc(Cl)c4ncc(C#N)c(NCC(C)(C)C)c4c3)C3=CN(Cc4c(F)cccc4F)NN3)cccc21] | (S)-8-chloro-6-(((1-(2,6-difluorobenzyl)-1H-1,2,3-triazol-4-yl)(1-methyl-1H-indazol-4-yl)methyl)amino)-4-(neopentylamino)quinoline-3-carbonitrile | 1 | 626.2 |

TABLE 1-continued

| Comp | Structure | Name | Example Procedure | ES/MS m/z |
|---|---|---|---|---|
| 656 | 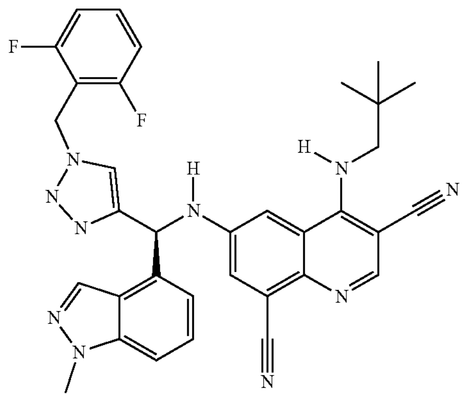 [SMILES: Cn1ncc2c([C@H](Nc3cc(C#N)c4ncc(C#N)c(NCC(C)(C)C)c4c3)C3=CN(Cc4c(F)cccc4F)NN3)cccc21] | (S)-6-(((H2,6-difluorobenzyl)-1H-1,2,3-triazol-4-yl)(1-methyl-1H-indazol-4-yl)methyl)amino)-4-(neopentylamino)quinoline-3,8-dicarbonitrile | 9 | 617.3 |
| 657 | 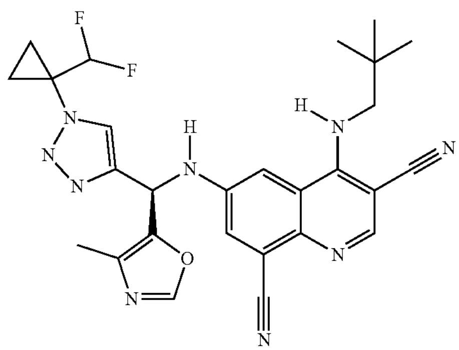 [SMILES: Cc1ncoc1[C@H](Nc1cc(C#N)c2ncc(C#N)c(NCC(C)(C)C)c2c1)C1=CN(C2(C(F)F)CC2)NN1] | (R)-6-(((1-(1-(difluoromethyl)-cyclopropyl)-1H-1,2,3-triazol-4-yl)(4-methyloxazol-5-yl)methyl)amino)-4-(neopentylamino)quinoline-3,8-dicarbonitrile | 24 | 532.4 |
| 658 | | (S)-8-chloro-6-(((1-methyl-1H-pyrrolo[2,3-b]pyridin-4-yl)(1-(1-(trifluoromethyl)-cyclopropyl)-1H-1,2,3-triazol-4-yl)methyl)amino)-4-(neopentylamino)quinoline-3-carbonitrile | 4 | 608.7 |
| 658 | | (S)-8-chloro-6-(((1-methyl-1H-pyrrolo[2,3-b]pyridin-4-yl)(1-(1-(trifluoromethyl)-cyclopropyl)-1H-1,2,3-triazol-4-yl)methyl)amino)-4-(neopentylamino)quinoline-3-carbonitrile | 4 | 608.7 |

TABLE 1-continued

| Comp | Structure | Name | Example Procedure | ES/MS m/z |
|---|---|---|---|---|
| 659 | 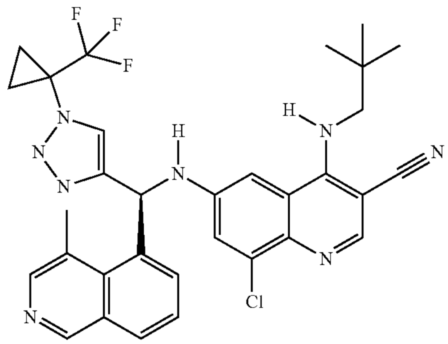 [SMILES: Cc1cncc2cccc([C@H](Nc3cc(Cl)c4ncc(C#N)c(NCC(C)(C)C)c4c3)C3=CN(C4(C(F)(F)F)CC4)NN3)c12] | (S)-8-chloro-6-(((4-methylisoquinolin-5-yl)(1-(1-(trifluoromethyl)cyclopropyl)-1H-1,2,3-triazol-4-yl)methyl)amino)-4-(neopentylamino)quinoline-3-carbonitrile | 2 | 619.51 |
| 660 | 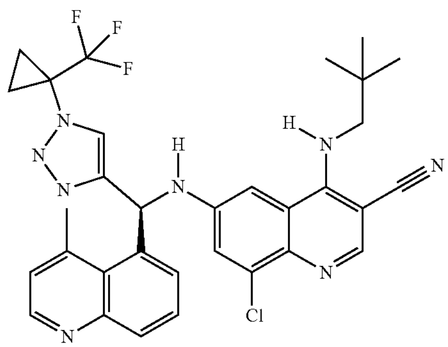 [SMILES: Cc1ccnc2cccc([C@H](Nc3cc(Cl)c4ncc(C#N)c(NCC(C)(C)C)c4c3)C3=CN(C4(C(F)(F)F)CC4)NN3)c12] | (S)-8-chloro-6-(((4-methylquinolin-5-yl)(1-(1-(trifluoromethyl)cyclopropyl)-1H-1,2,3-triazol-4-yl)methyl)amino)-4-(neopentylamino)quinoline-3-carbonitrile | 27 | 619.64 |
| 661 | 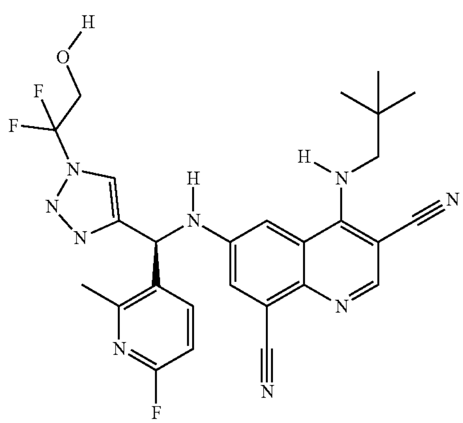 [SMILES: Cc1nc(F)ccc1[C@H](Nc1cc(C#N)c2ncc(C#N)c(NCC(C)(C)C)c2c1)C1=CN(C(F)(F)CO)NN1] | (S)-6-(((1-(1,1-difluoro-2-hydroxyethyl)-1H-1,2,3-triazol-4-yl)(6-fluoro-2-methylpyridin-3-yl)methyl)amino)-4-(neopentylamino)quinoline-3,8-dicarbonitrile | 24 | 550.2 |
| 662 | 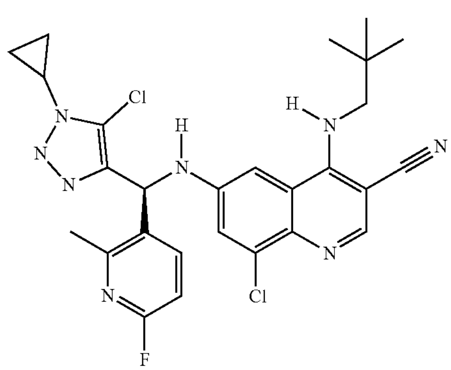 [SMILES: Cc1nc(F)ccc1[C@H](Nc1cc(Cl)c2ncc(C#N)c(NCC(C)(C)C)c2c1)C1=C(Cl)N(C2CC2)NN1] | (S)-8-chloro-6-(((5-chloro-1-cyclopropyl-1H-1,2,3-triazol-4-yl)(6-fluoro-2-methylpyridin-3-yl)methyl)amino)-4-(neopentylamino)quinoline-3-carbonitrile | 30 | 553.4 |

TABLE 1-continued

| Comp | Structure | Name | Example Procedure | ES/MS m/z |
|---|---|---|---|---|
| 663 | 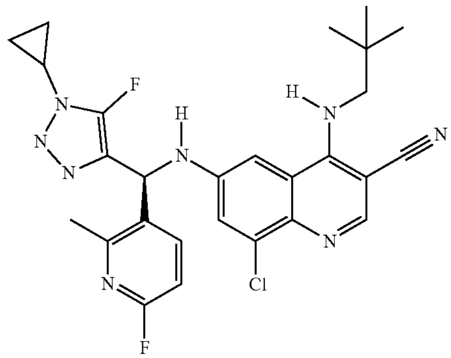 [SMILES: Cc1nc(F)ccc1[C@H](Nc1cc(Cl)c2ncc(C#N)c(NCC(C)(C)C)c2c1)C1=C(F)N(C2CC2)NN1] | (S)-8-chloro-6-(((1-cyclopropyl-5-fluoro-1H-1,2,3-triazol-4-yl)(6-fluoro-2-methylpyridin-3-yl)methyl)amino)-4-(neopentylamino)quinoline-3-carbonitrile | 30 | 537.4 |
| 664 | 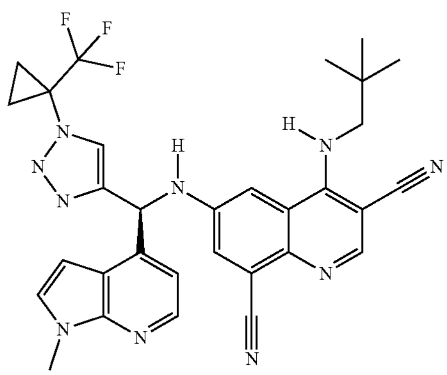 [SMILES: Cn1ccc2c([C@H](Nc3cc(C#N)c4ncc(C#N)c(NCC(C)(C)C)c4c3)C3=CN(C4(C(F)(F)F)CC4)NN3)ccnc21] | (S)-6-(((1-methyl-1H-pyrrolo[2,3-b]pyridin-4-yl)(1-(1-(trifluoromethyl)cyclopropyl)-1H-1,2,3-triazol-4-yl)methyl)amino)-4-(neopentylamino)quinoline-3,8-dicarbonitrile | 24 | 599.5 |
| 665 | 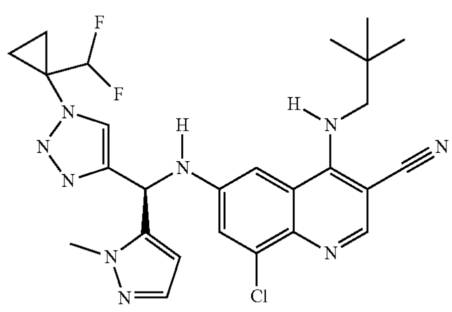 [SMILES: Cn1nccc1[C@H](Nc1cc(Cl)c2ncc(C#N)c(NCC(C)(C)C)c2c1)C1=CN(C2(C(F)F)CC2)NN1] | (S)-8-chloro-6-(((1-(1-(difluoromethyl)cyclopropyl)-1H-1,2,3-triazol-4-yl)(1-methyl-1H-pyrazol-5-yl)methyl)amino)-4-(neopentylamino)quinoline-3-carbonitrile | 23 | 540.3 |
| 666 | 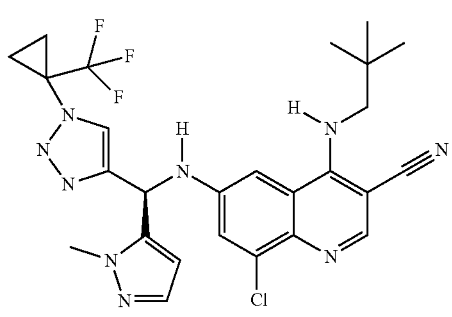 [SMILES: Cn1nccc1[C@H](Nc1cc(Cl)c2ncc(C#N)c(NCC(C)(C)C)c2c1)C1=CN(C2(C(F)(F)F)CC2)NN1] | (S)-8-chloro-6-(((1-methyl-1H-pyrazol-5-yl)(1-(1-(trifluoromethyl)cyclopropyl)-1H-1,2,3-triazol-4-yl)methyl)amino)-4-(neopentylamino)quinoline-3-carbonitrile | 23 | 558.4 |

TABLE 1-continued

| Comp | Structure | Name | Example Procedure | ES/MS m/z |
|---|---|---|---|---|
| 667 | 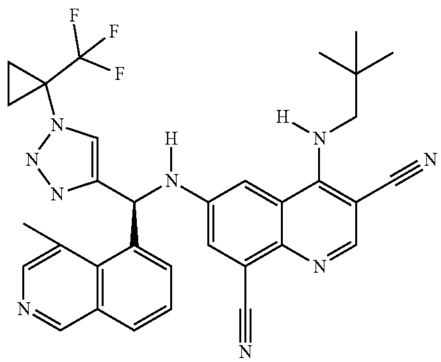 [SMILES: Cc1cncc2cccc([C@H](Nc3cc(C#N)c4ncc(C#N)c(NCC(C)(C)C)c4c3)C3=CN(C4(C(F)(F)F)CC4)NN3)c12] | (S)-6-(((4-methylisoquinolin-5-yl)(4-(1-(trifluoromethyl)cyclopropyl)-1H-1,2,3-triazol-4-yl)methyl)amino)-4-(neopentylamino)quinoline-3,8-dicarbonitrile | 24 | 610.41 |
| 668 | 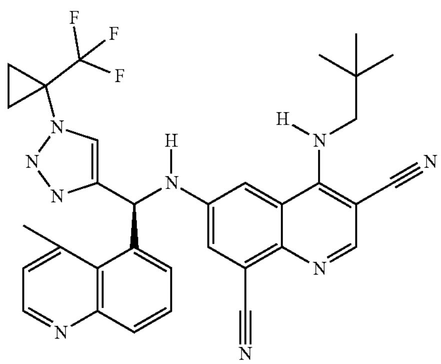 [SMILES: Cc1ccnc2cccc([C@H](Nc3cc(C#N)c4ncc(C#N)c(NCC(C)(C)C)c4c3)C3=CN(C4(C(F)(F)F)CC4)NN3)c12] | (S)-6-(((4-methylquinolin-5-yl)(4-(1-(trifluoromethyl)cyclopropyl)-1H-1,2,3-triazol-4-yl)methyl)amino)-4-(neopentylamino)quinoline-3,8-dicarbonitrile | 24 | 610.51 |
| 669 | 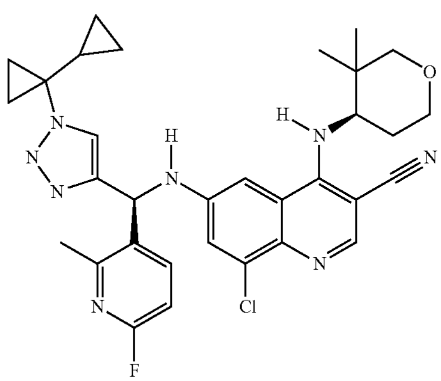 [SMILES: Cc1nc(F)ccc1[C@H](Nc1cc(Cl)c2ncc(C#N)c(N[C@@H]3CCOCC3(C)C)c2c1)C1=CN(C2(C3CC3)CC2)NN1] | bi(cyclopropan)]-1-yl)-1H-1,2,3-triazol-4-yl)(6-fluoro-2-methylpyridin-3-yl)methyl)amino)-8-chloro-4-(((R)-3,3-dimethyltetrahydro-2H-pyran-4-yl)amino)quinoline-3-carbonitrile | 4 | 601.3 |
| 670 | 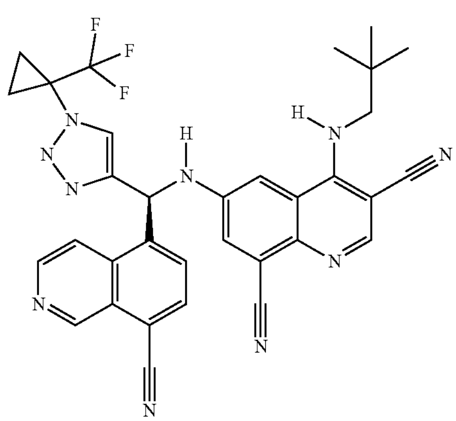 [SMILES: CC(C)(C)CNc1c(C#N)cnc2c(C#N)cc(N[C@H](C3=CN(C4(C(F)(F)F)CC4)NN3)c3ccc(C#N)c4cnccc34)cc12] | (S)-6-(((8-cyanoisoquinolin-5-yl)(1-(1-(trifluoromethyl)cyclopropyl)-1H-1,2,3-triazol-4-yl)methyl)amino)-4-(neopentylamino)quinoline-3,8-dicarbonitrile | 25 | 621.690 |

TABLE 1-continued

| Comp | Structure | Name | Example Procedure | ES/MS m/z |
|---|---|---|---|---|
| 671 | 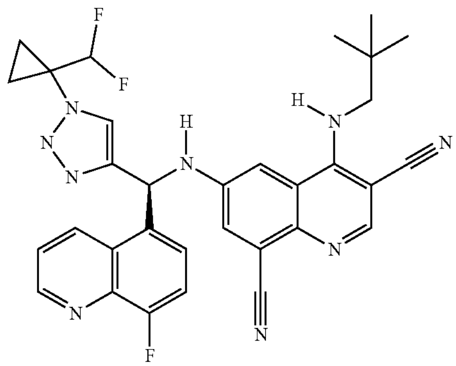 [SMILES: CC(C)(C)CNc1c(C#N)cnc2c(C#N)cc(N[C@H](C3=CN(C4(C(F)F)CC4)NN3)c3ccc(F)c4ncccc34)cc12] | (S)-6-(((1-(1-(difluoromethyl)cyciopropy])-1H-1,2,3-triazol-4-yl)(8-fluoroquinolin-5-yl)methyl)amino)-4-(neopentylamino)quinoline-3,8-dicarbonitrile | 24 | 596.477 |
| 672 | 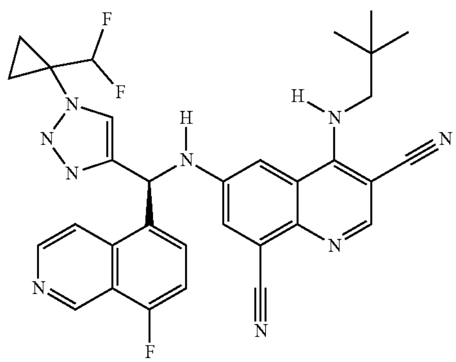 [SMILES: CC(C)(C)CNc1c(C#N)cnc2c(C#N)cc(N[C@H](C3=CN(C4(C(F)F)CC4)NN3)c3ccc(F)c4cnccc34)cc12] | (S)-6-(((H1-(difluoromethyl)cyclopropyl)-1H-1,2,3-triazol-4-yl)(8-fluoroisoquinolin-5-yl)methyl)amino)-4-(neopentylamino)quinoline-3,8-dicarbonitrile | 24 | 596.148 |
| 673 | 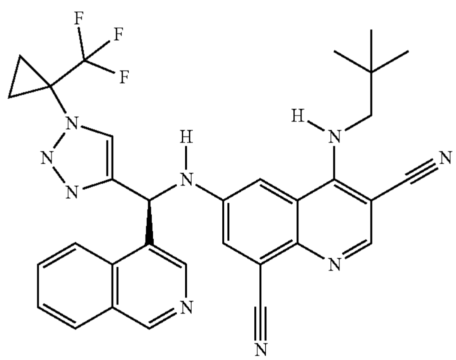 [SMILES: CC(C)(C)CNc1c(C#N)cnc2c(C#N)cc(N[C@H](C3=CN(C4(C(F)(F)F)CC4)NN3)c3cncc4ccccc34)cc12] | (S)-6-((isoquinolin-4-yl(1-(1-(trifluoromethyl)cyclopropyl)-1H-1,2,3-triazol-4-yl)methyl)amino)-4-(neopentylamino)quinoline-3,8-dicarbonitrile | 24 | 596.253 |
| 674 | 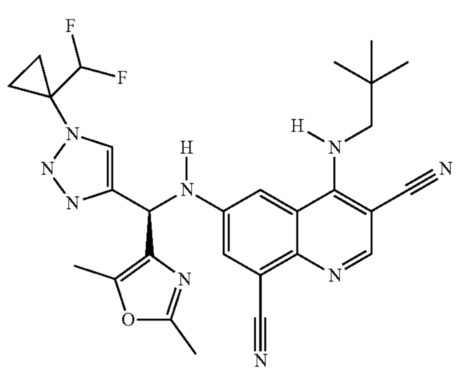 [SMILES: Cc1nc([C@H](Nc2cc(C#N)c3ncc(C#N)c(NCC(C)(C)C)c3c2)C2=CN(C3(C(F)F)CC3)NN2)c(C)o1] | (S)-6-(((1-(1-(difluoromethyl)-cyclopropyl)-1H-1,2,3-triazol-4-yl)(2,5-dimethyloxazol-4-yl)methyl)amino)-4-(neopentylamino)quinoline-3,8-dicarbonitrile | 24 | 546.4 |

TABLE 1-continued

| Comp | Structure | Name | Example Procedure | ES/MS m/z |
|---|---|---|---|---|
| 675 | 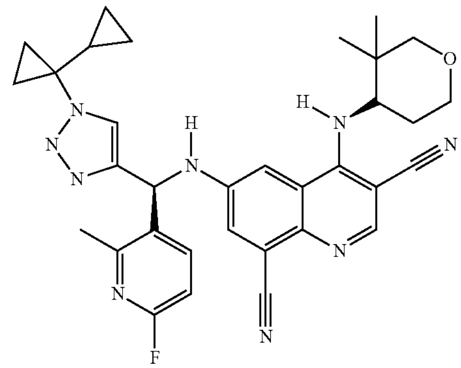 | 6-(((SMM[1,1'-bi(cyclopropan)]-1-yl)-1H-1,2,3-triazol-4-yl)(6-fluoro-2-methylpyridin-3-yl)methyl)amino)-4-(((R)-3,3-dimethyltetrahydro-2H-pyran-4-yl)amino)quinoline-3,8-dicarbonitrile | 24 | 592.4 |
| 676 | 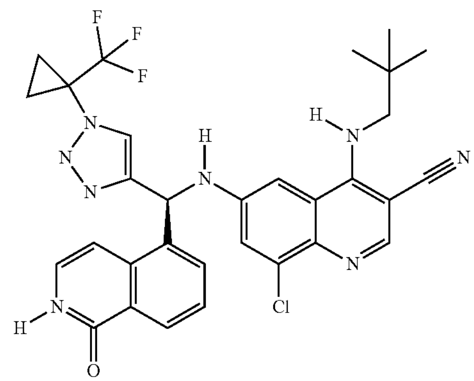 | (S)-8-chloro-4-(neopentylamino)-6-(((1-oxo-1,2-dihydroisoquinolin-5-yl)(1-(1-(trifluoromethyl)cyclopropyl)-1H-1,2,3-triazol-4-yl)methyl)amino)quinoline-3-carbonitrile | 4 | 621.3 |
| 677 | 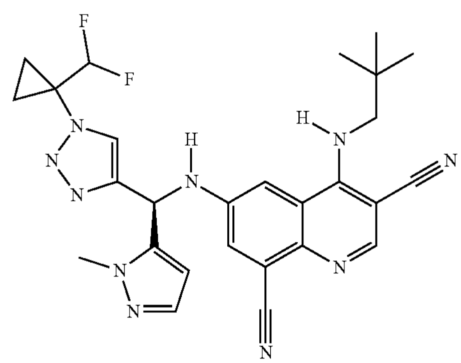 [SMILES: Cn1nccc1[C@H](Nc1cc(C#N)c2ncc(C#N)c(NCC(C)(C)C)c2c1)C1=CN(C2(C(F)F)CC2)NN1] | (S)-6-(((1-(1-(difluoromethyl)-cyclopropyl)-1H-1,2,3-triazol-4-yl)(1-methyl-1H-pyrazol-5-yl)methyl)amino)-4-(neopentylamino)quinoline-3,8-dicarbonitrile | 24 | 531.4 |
| 678 | 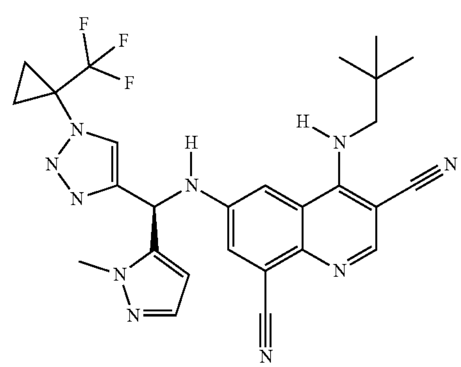 [SMILES: Cn1nccc1[C@H](Nc1cc(C#N)c2ncc(C#N)c(NCC(C)(C)C)c2c1)C1=CN(C2(C(F)(F)F)CC2)NN1] | (S)-6-(((1-methyl-1H-pyrazol-5-yl)(1-(1-(trifluoromethyl)cyclopropyl)-1H-1,2,3-triazol-4-yl)methyl)amino)-4-(neopentylamino)quinoline-3,8-dicarbonitrile | 24 | 549.2 |

TABLE 1-continued

| Comp | Structure | Name | Example Procedure | ES/MS m/z |
|---|---|---|---|---|
| 679 | 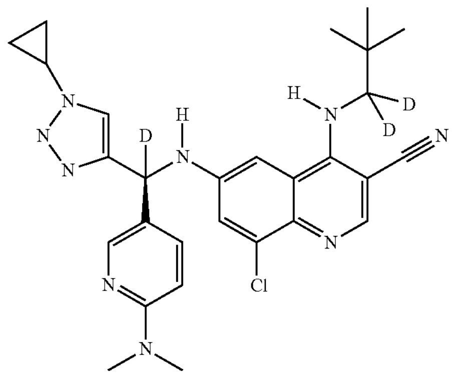 [SMILES: [2H]C([2H])(Nc1c(C#N)cnc2c(Cl)cc(N[C@@]([2H])(C3=CN(C4CC4)NN3)c3ccc(N(C)C)nc3)cc12)C(C)(C)C] | (S)-8-chloro-6-(((1-cyclopropyl-1H-1,2,3-triazol-4-yl)(6-(dimethylamino)pyridin-3-yl)methyl-d)amino)-4-((2,2-dimethylpropyl-1,1-d2)amino)quinoline-3-carbonitrile | 26 | 533.309 |
| 680 | 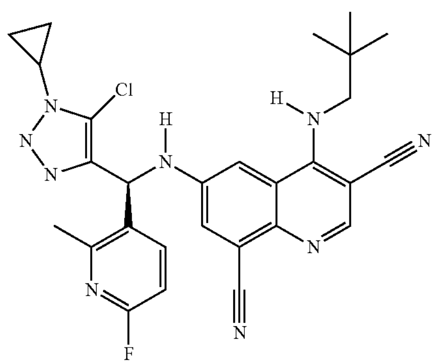 [SMILES: Cc1nc(F)ccc1[C@H](Nc1cc(C#N)c2ncc(C#N)c(NCC(C)(C)C)c2c1)C1=C(Cl)N(C2CC2)NN1] | (S)-6-(((5-chloro-1-cyclopropyl-1H-1,2,3-triazol-4-yl)(6-fluoro-2-methylpyridin-3-yl)methyl)amino)-4-(neopentylamino)quinoline-3,8-dicarbonitrile | 30 | 544.2 |
| 681 | 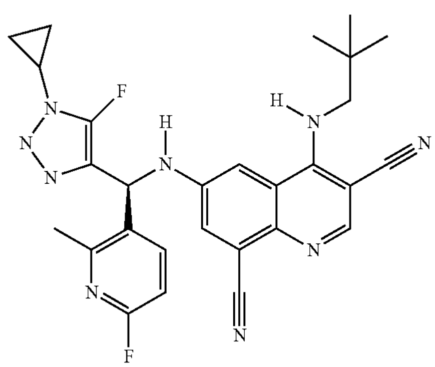 [SMILES: Cc1nc(F)ccc1[C@H](Nc1cc(C#N)c2ncc(C#N)c(NCC(C)(C)C)c2c1)C1=C(F)N(C2CC2)NN1] | (S)-6-(((1-cyclopropyl-5-fluoro-1H-1,2,3-triazol-4-yl)(6-fluoro-2-methylpyridin-3-yl)methyl)amino)-4-(neopentylamino)quinoline-3,8-dicarbonitrile | 30 | 528.1 |
| 682 | 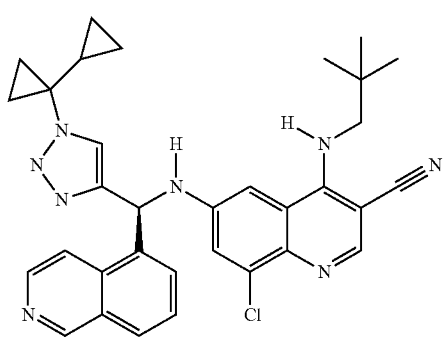 [SMILES: CC(C)(C)CNc1c(C#N)cnc2c(Cl)cc(N[C@H](C3=CN(C4(C5CC5)CC4)NN3)c3cccc4cnccc34)cc12] | (S)-6-(((4-(1-(1-bi(cyclopropan)]-1-yl)-1H-1,2,3-triazol-4-yl)(isoquinolin-5-yl)methyl)amino)-8-chloro-4-(neopentylamino)quinoline-3-carbonitrile | 4 | 577.2 |

TABLE 1-continued

| Comp | Structure | Name | Example Procedure | ES/MS m/z |
|---|---|---|---|---|
| 683 | 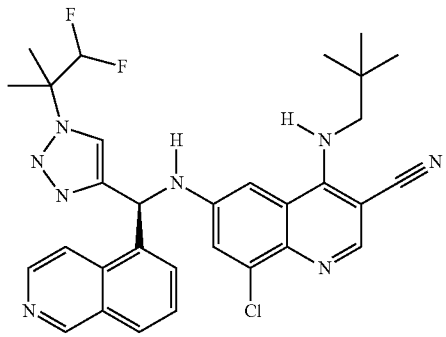 [SMILES: CC(C)(C)CNc1c(C#N)cnc2c(Cl)cc(N[C@H](C3=CN(C(C)(C)C(F)F)NN3)c3cccc4cnccc34)cc12] | (S)-8-chloro-6-(((1-(1,1-difluoro-2-methylpropan-2-yl)-1H-1,2,3-triazol-4-yl)(isoquinolin-5-yl)methyl)amino)-4-(neopentylamino)quinoline-3-carbonitrile | 4 | 589.2 |
| 684 | 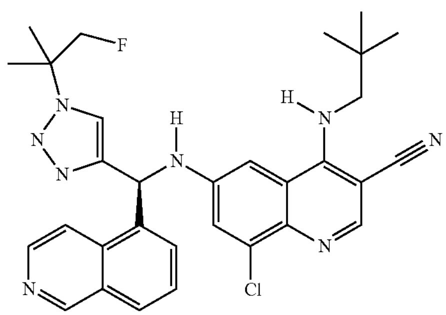 [SMILES: CC(C)(C)CNc1c(C#N)cnc2c(Cl)cc(N[C@H](C3=CN(C(C)(C)CF)NN3)c3cccc4cnccc34)cc12] | (S)-8-chloro-6-(((1-(1-fluoro-2-methylpropan-2-yl)-1H-1,2,3-triazol-4-yl)(isoquinolin-5-yl)methyl)amino)-8-chloro-4-(neopentylamino)quinoline-3-carbonitrile | 4 | 571.6 |
| 685 | 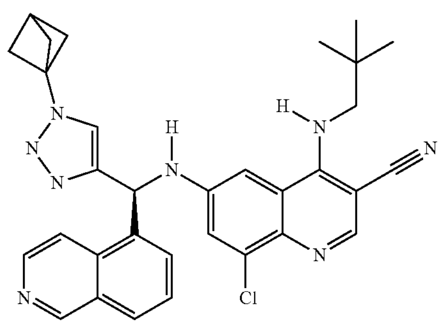 [SMILES: CC(C)(C)CNc1c(C#N)cnc2c(Cl)cc(N[C@H](C3=CN(C45CC(C4)C5)NN3)c3cccc4cnccc34)cc12] | (S)-6-(((1-(bicyclo[1.1.1]pentan-1-yl)-1H-1,2,3-triazol-4-yl)(isoquinolin-5-yl)methyl)amino)-8-chloro-4-(neopentylamino)quinoline-3-carbonitrile | 4 | 563.2 |
| 686 | 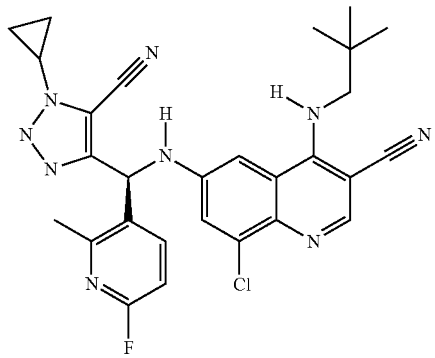 [SMILES: Cc1nc(F)ccc1[C@H](Nc1cc(Cl)c2ncc(C#N)c(NCC(C)(C)C)c2c1)C1=C(C#N)N(C2CC2)NN1] | (S)-8-chloro-6-(((5-cyano-1-cyclopropyl-1H-1,2,3-triazol-4-yl)(6-fluoro-2-methylpyridin-3-yl)methyl)amino)-4-(neopentylamino)quinoline-3-carbonitrile | 36 | 544.6 |

TABLE 1-continued

| Comp | Structure | Name | Example Procedure | ES/MS m/z |
|---|---|---|---|---|
| 687 | 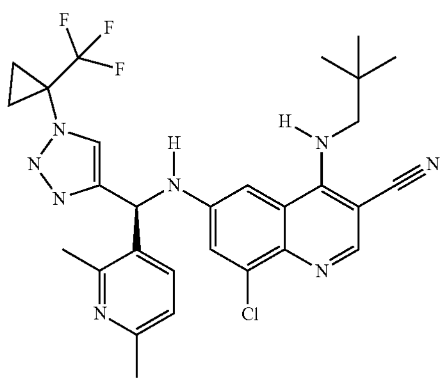 [SMILES: Cc1ccc([C@H](Nc2cc(Cl)c3ncc(C#N)c(NCC(C)(C)C)c3c2)C2=CN(C3(C(F)(F)F)CC3)NN2)c(C)n1] | (S)-8-chloro-6-(((2,6-dimethylpyridin-3-yl)(1-(1-(trifluoromethyl)cyclopropyl)-1H-1,2,3-triazol-4-yl)methyl)amino)-4-(neopentylamino)quinoline-3-carbonitrile | 23 | 583.307 |
| 688 | 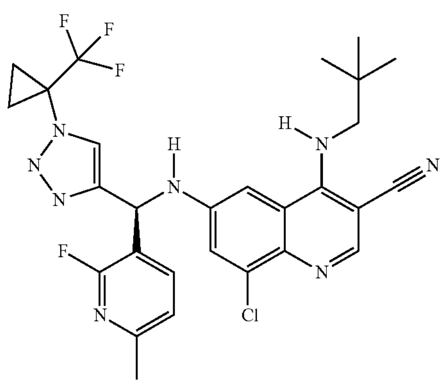 [SMILES: Cc1ccc([C@H](Nc2cc(Cl)c3ncc(C#N)c(NCC(C)(C)C)c3c2)C2=CN(C3(C(F)(F)F)CC3)NN2)c(F)n1] | (S)-8-chloro-6-(((2-fluoro-6-methylpyridin-3-yl)(1-(1-(trifluoromethyl)-cyclopropyl)-1H-1,2,3-triazol-4-yl)methyl)amino)-4-(neopentylamino)quinoline-3-carbonitrile | 23 | 587.622 |
| 689 | 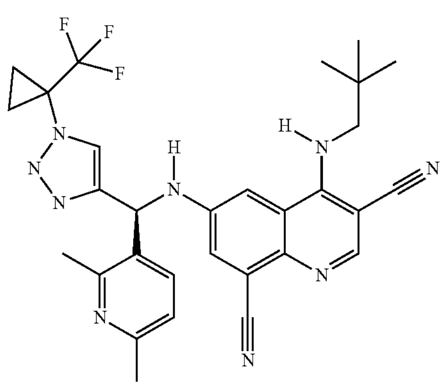 [SMILES: Cc1ccc([C@H](Nc2cc(C#N)c3ncc(C#N)c(NCC(C)(C)C)c3c2)C2=CN(C3(C(F)(F)F)CC3)NN2)c(C)n1] | (S)-6-(((2,6-dimethylpyridin-3-yl)(1-(1'-(trifluoromethyl)cyclopropyl)-1H-1,2,3-triazol-4-yl)methyl)amino)-4-(neopentylamino)quinoline-3,8-dicarbonitrile | 24 | 574.505 |
| 690 | 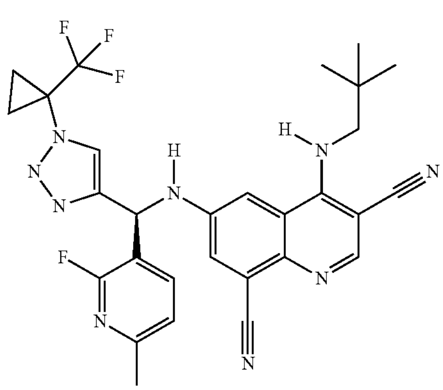 [SMILES: Cc1ccc([C@H](Nc2cc(C#N)c3ncc(C#N)c(NCC(C)(C)C)c3c2)C2=CN(C3(C(F)(F)F)CC3)NN2)c(F)n1] | (S)-6-(((2-fluoro-6-methylpyridin-3-yl)(1-(1-(trifluoromethyl)cyclopropyl)-1H-1,2,3-triazol-4-yl)methyl)amino)-4-(neopentylamino)quinoline-3,8-dicarbonitrile | 24 | 578.467 |

TABLE 1-continued

| Comp | Structure | Name | Example Procedure | ES/MS m/z |
|---|---|---|---|---|
| 691 | 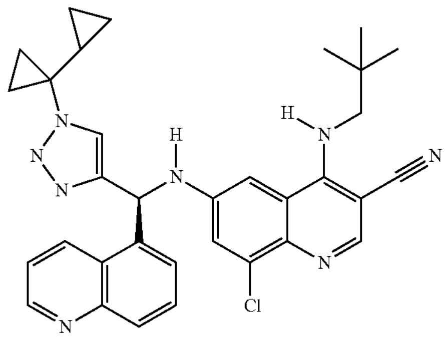 [SMILES: CC(C)(C)CNc1c(C#N)cnc2c(Cl)cc(N[C@H](C3=CN(C4(C5CC5)CC4)NN3)c3cccc4ncccc34)cc12] | (S)-6-(((1-([1,1'-bi(cyclopropan)]-1-yl)-1H-1,2,3-triazol-4-yl)(quinolin-5-yl)methyl)amino)-8-chloro-4-(neopentylamino)quinoline-3-carbonitrile | 23 | 577.37 |
| 692 | 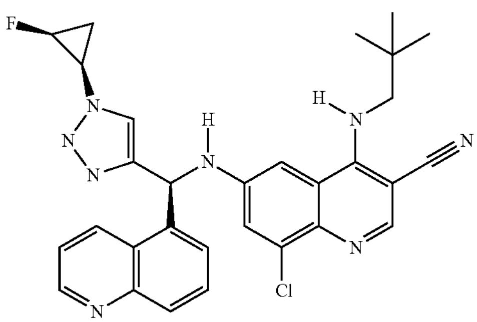 [SMILES: CC(C)(C)CNc1c(C#N)cnc2c(Cl)cc(N[C@H](C3=CN([C@@H]4C[C@@H]4F)NN3)c3cccc4ncccc34)cc12] | 8-chloro-6-(((SH 1-((1R,2S)-2-fluorocyclopropyl)-1H-1,2,3-triazol-4-yl)(quinolin-5-yl)methyl)amino)-4-(neopentylamino)quinoline-3-carbonitrile | 23 | 555.07 |
| 693 | 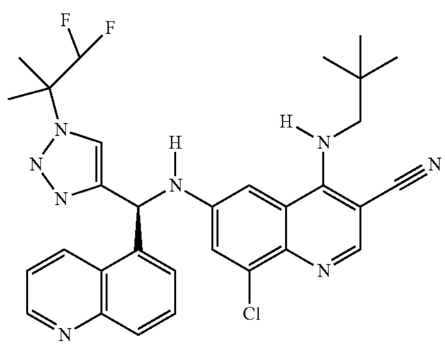 [SMILES: CC(C)(C)CNc1c(C#N)cnc2c(Cl)cc(N[C@H](C3=CN(C(C)(C)C(F)F)NN3)c3cccc4ncccc34)cc12] | (S)-8-chloro-6-(((1-(1,1-difluoro-2-methylpropan-2-yl)-1H-1,2,3-triazol-4-yl)(quinolin-5-yl)methyl)amino)-4-(neopentylamino)quinoline-3-carbonitrile | 23 | 589.14 |
| 694 | 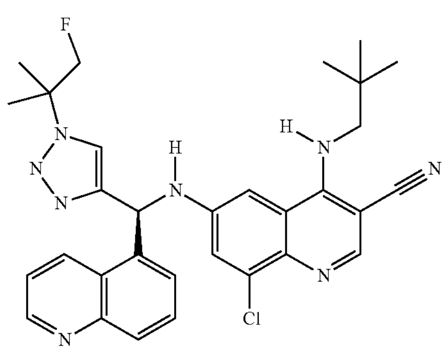 [SMILES: CC(C)(C)CNc1c(C#N)cnc2c(Cl)cc(N[C@H](C3=CN(C(C)(C)CF)NN3)c3cccc4ncccc34)cc12] | (S)-8-chloro-6-(((1-(1-fluoro-2-methylpropan-2-yl)-1H-1,2,3-triazol-4-yl)(quinolin-5-yl)methyl)amino)-4-(neopentylamino)quinoline-3-carbonitrile | 23 | 571.11 |

TABLE 1-continued

| Comp | Name | Example Procedure | ES/MS m/z |
|---|---|---|---|
| 695 | (S)-6-(((1-(bicyclo[1.1.1]pentan-1-yl)-1H-1,2,3-triazol-4-yl)(quinolin-5-yl)methyl)amino)-8-chloro-4-(neopentylamino)quinoline-3-carbonitrile | 23 | 563.36 |
| 696 | (S)-6-(((H[1,1'-bi(cyclopropan)]-1-yl)-1H-1,2,3-triazol-4-yl)(quinolin-5-yl)methyl)amino)-4-(neopentylamino)quinoline-3,8-dicarbonitrile | 24 | 568.31 |
| 697 | (S)-6-(((1-(bicyclo[1.1.1]pentan-1-yl)-1H-1,2,3-triazol-4-yl)(quinolin-5-yl)methyl)amino)-4-(neopentylamino)quinoline-3,8-dicarbonitrile | 24 | 554.30 |
| 698 | (S)-8-chloro-4-(neopentylamino)-6-((quinolin-7-yl(1-(1-(trifluoromethyl)cyclopropyl)-1H-1,2,3-triazol-4-yl)methyl)amino)quinoline-3-carbonitrile | 27 | 605.770 |

TABLE 1-continued

| Comp | Structure | Name | Example Procedure | ES/MS m/z |
|---|---|---|---|---|
| 699 | 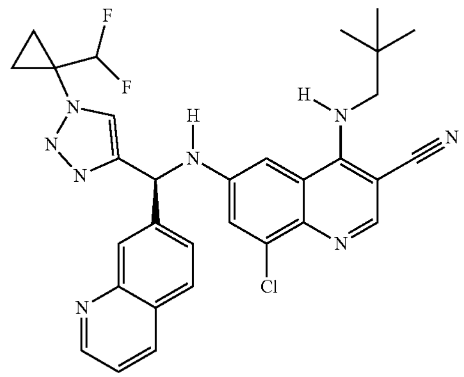 [SMILES: CC(C)(C)CNc1c(C#N)cnc2c(Cl)cc(N[C@H](C3=CN(C4(C(F)F)CC4)NN3)c3ccc4cccnc4c3)cc12] | (S)-8-chloro-6-(((1-(1-(difluoromethyl)cyclopropyl)-1H-1,2,3-triazol-4-yl)(quinolin-7-yl)methyl)amino)-4-(neopentylamino)quinoline-3-carbonitrile | 27 | 587.720 |
| 700 | 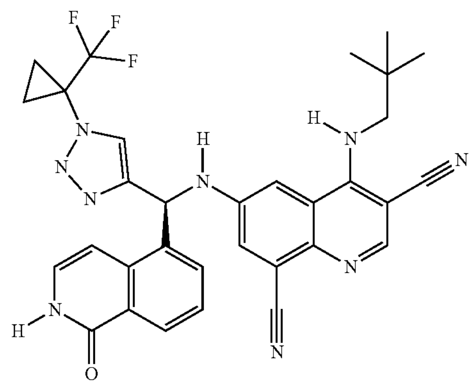 [SMILES: CC(C)(C)CNc1c(C#N)cnc2c(C#N)cc(N[C@H](C3=CN(C4(C(F)(F)F)CC4)NN3)c3cccc4c(=O)[nH]ccc34)cc12] | (S)-4-(neopentylamino)-6-(((1-oxo-1,2-dihydroisoquinolin-5-yl)(4-(1-1-(trifluoromethyl)-cyclopropyl)-1H-1,2,3-triazol-4-yl)methyl)amino)quinoline-3,8-dicarbonitrile | 24 | 612.2 |
| 701 | 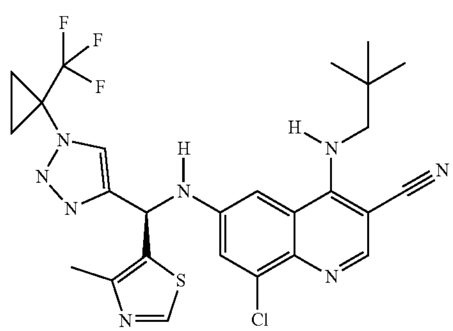 [SMILES: Cc1ncsc1[C@H](Nc1cc(Cl)c2ncc(C#N)c(NCC(C)(C)C)c2c1)C1=CN(C2(C(F)(F)F)CC2)NN1] | (R)-8-chloro-6-(((4-methylthiazol-5-yl)(1-(1-(trifluoromethyl)cyclopropyl)-1H-1,2,3-triazol-4-yl)methyl)amino)-4-(neopentylamino)quinoline-3-carbonitrile | 23 | 575.4 |
| 702 | 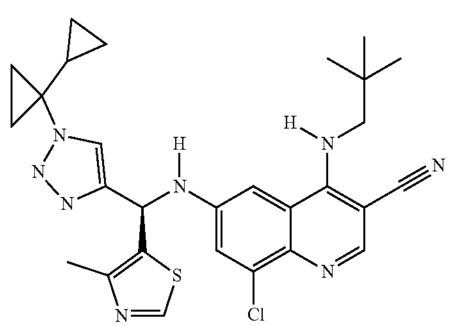 [SMILES: Cc1ncsc1[C@H](Nc1cc(Cl)c2ncc(C#N)c(NCC(C)(C)C)c2c1)C1=CN(C2(C3CC3)CC2)NN1] | (R)-6-(((1-([1,1'-bi(cyclopropan)]-1-yl)-1H-1,2,3-triazol-4-yl)(4-methylthiazol-5-yl)methyl)amino)-8-chloro-4-(neopentylamino)quinoline-3-carbonitrile | 23 | 547.6 |

TABLE 1-continued

| Comp | Structure | Name | Example Procedure | ES/MS m/z |
|---|---|---|---|---|
| 703 | 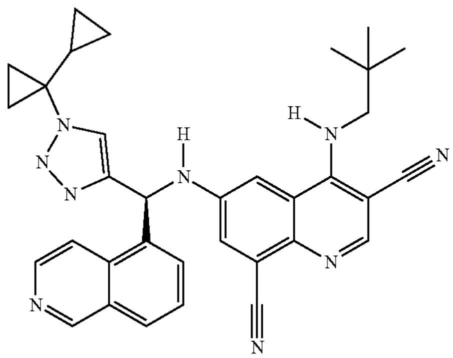 [SMILES: CC(C)(C)CNc1c(C#N)cnc2c(C#N)cc(N[C@H](C3=CN(C4(C5CC5)CC4)NN3)c3cccc4cnccc34)cc12] | (S)-6-(((1-([1,1'-bi(cyclopropan)]-1-yl)-1H-1,2,3-triazol-4-yl)(isoquinolin-5-yl)methyl)amino)-4-(neopentylamino)quinoline-3,8-dicarbonitrile | 24 | 568.2 |
| 704 | 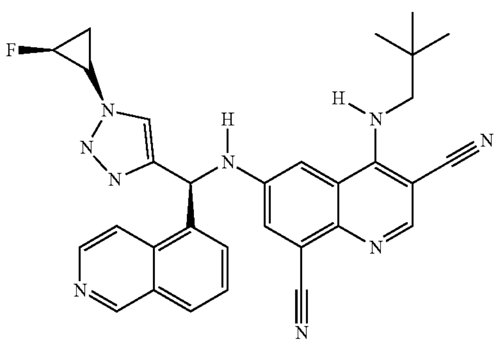 | 6-(((SHH(1S,2S)-2-fluorocyclopropyl)-1H-1,2,3-triazol-4-yl)(isoquinolin-5-yl)methyl)amino)-4-(neopentylamino)quinoline-3,8-dicarbonitrile | 24 | 546.2 |
| 705 | 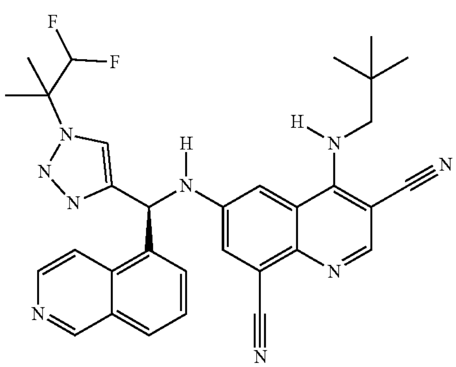 [SMILES: CC(C)(C)CNc1c(C#N)cnc2c(C#N)cc(N[C@H](C3=CN(C(C)(C)C(F)F)NN3)c3cccc4cnccc34)cc12] | (S)-6-(((1-(1,1-difluoro-2-methylpropan-2-yl)-1H-1,2,3-triazol-4-yl)(isoquinolin-5-yl)methyl)amino)-4-(neopentylamino)quinoline-3,8-dicarbonitrile | 24 | 580.2 |
| 706 | 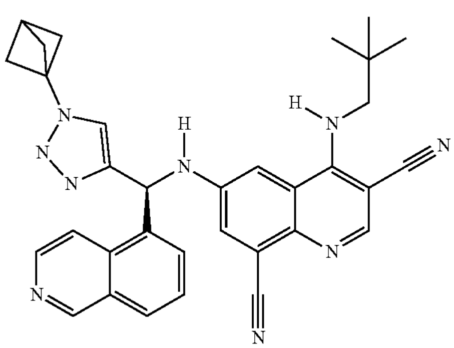 [SMILES: CC(C)(C)CNc1c(C#N)cnc2c(C#N)cc(N[C@H](C3=CN(C45CC(C4)C5)NN3)c3cccc4cnccc34)cc12] | (S)-6-(((1-(bicyclo[1.1.1]pentan-1-yl)-1H-1,2,3-triazol-4-yl)(isoquinolin-5-yl)methyl)amino)-4-(neopentylamino)quinoline-3,8-dicarbonitrile | 24 | 554.2 |

TABLE 1-continued

| Comp | Structure | Name | Example Procedure | ES/MS m/z |
|---|---|---|---|---|
| 707 | 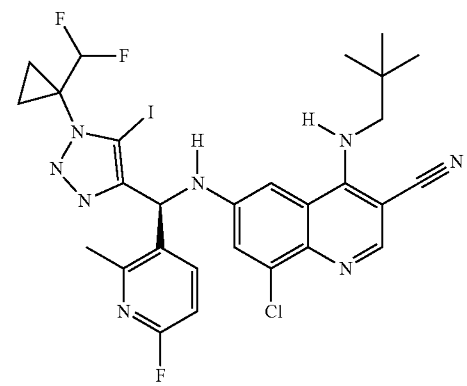 [SMILES: Cc1nc(F)ccc1[C@H](Nc1cc(Cl)c2ncc(C#N)c(NCC(C)(C)C)c2c1)C1=C(I)N(C2(C(F)F)CC2)NN1] | (S)-8-chloro-6-(((1-(1-(difluoromethyl)cyclopropyl)-5-iodo-1H-1,2,3-triazol-4-yl)(6-fluoro-2-methylpyridin-3-yl)methyl)amino)-4-(neopentylamino)quinoline-3-carbonitrile | 28 | 695.3 |
| 708 | 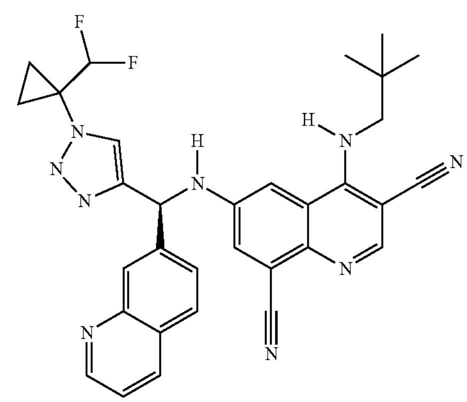 [SMILES: CC(C)(C)CNc1c(C#N)cnc2c(C#N)cc(N[C@H](C3=CN(C4(C(F)F)CC4)NN3)c3ccc4cccnc4c3)cc12] | (S)-6-(((1-(1-(difluoromethyl)cyclopropyl)-1H-1,2,3-triazol-4-yl)(quinolin-7-yl)methyl)amino)-4-(neopentylamino)quinoline-3,8-dicarbonitrile | 24 | 578.151 |
| 709 | 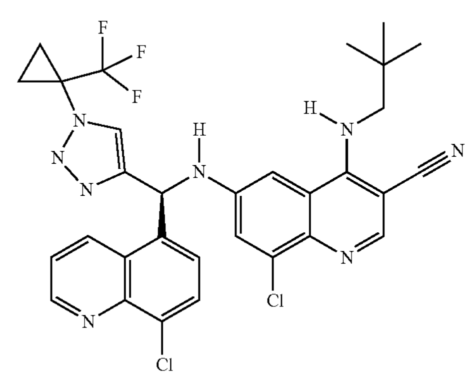 [SMILES: CC(C)(C)CNc1c(C#N)cnc2c(Cl)cc(N[C@H](C3=CN(C4(C(F)(F)F)CC4)NN3)c3ccc(Cl)c4ncccc34)cc12] | (S)-8-chloro-6-(((8-chloroquinolin-5-yl)(1-(1-(trifluoromethyl)cyclopropyl)-1H-1,2,3-triazol-4-yl)methyl)amino)-4-(neopentylamino)quinoline-3-carbonitrile | 4 | 639.263 |

TABLE 1-continued

| Comp | Structure | Name | Example Procedure | ES/MS m/z |
|---|---|---|---|---|
| 710 | 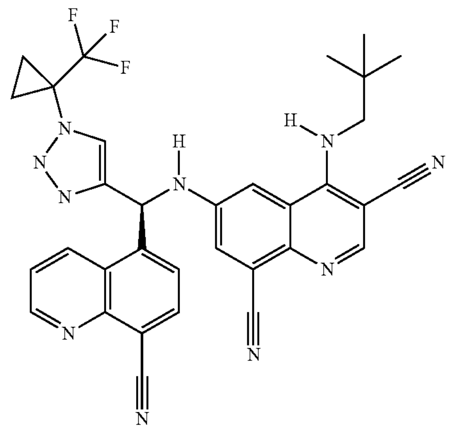 [SMILES: CC(C)(C)CNc1c(C#N)cnc2c(C#N)cc(N[C@H](C3=CN(C4(C(F)(F)F)CC4)NN3)c3ccc(C#N)c4ncccc34)cc12] | (S)-6-(((8-cyanoquinolin-5-yl)(1-(1-(trifluoromethyl)cyclopropyl)-1H-1,2,3-triazol-4-yl)methyl)amino)-4-(neopentylamino)quinoline-3,8-dicarbonitrile | 25 | 621.265 |
| 704 | 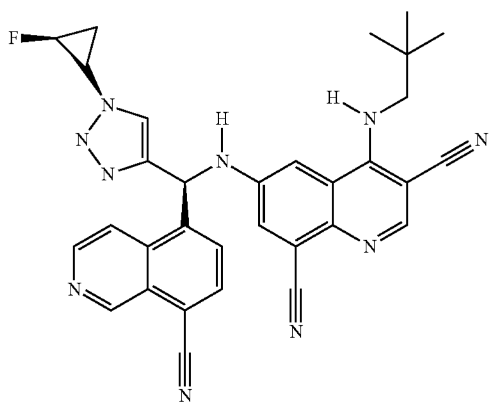 | 6-(((S)-(1-((1S,2S)-2-fluorocyclopropyl)-1H-1,2,3-triazol-4-yl)(isoquinolin-5-yl)methyl)amino)-4-(neopentylamino)quinoline-3,8-dicarbonitrile | 24 | 546.2 |
| 705 | 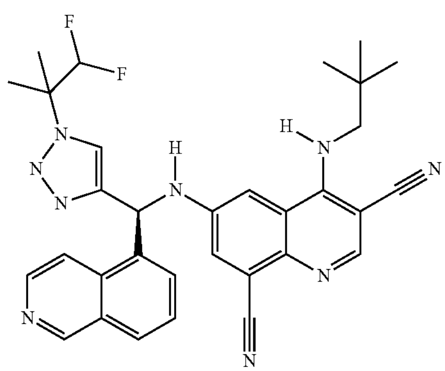 [SMILES: CC(C)(C)CNc1c(C#N)cnc2c(C#N)cc(N[C@H](C3=CN(C(C)(C)C(F)F)NN3)c3cccc4cnccc34)cc12] | (S)-6-(((1-(1,1-difluoro-2-methylpropan-2-yl)-1H-1,2,3-triazol-4-yl)(isoquinolin-5-yl)methyl)amino)-4-(neopentylamino)quinoline-3,8-dicarbonitrile | 24 | 580.2 |
| 706 | 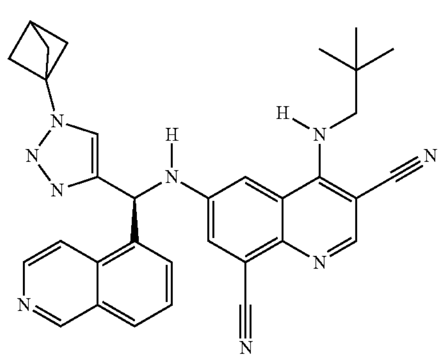 [SMILES: CC(C)(C)CNc1c(C#N)cnc2c(C#N)cc(N[C@H](C3=CN(C45CC(C4)C5)NN3)c3cccc4cnccc34)cc12] | (S)-6-(((1-(bicyclo[1.1.1]pentan-1-yl)-1H-1,2,3-triazol-4-yl)(isoquinolin-5-yl)methyl)amino)-4-(neopentylamino)quinoline-3,8-dicarbonitrile | 24 | 554.2 |

TABLE 1-continued

| Comp | Structure | Name | Example Procedure | ES/MS m/z |
|---|---|---|---|---|
| 707 | 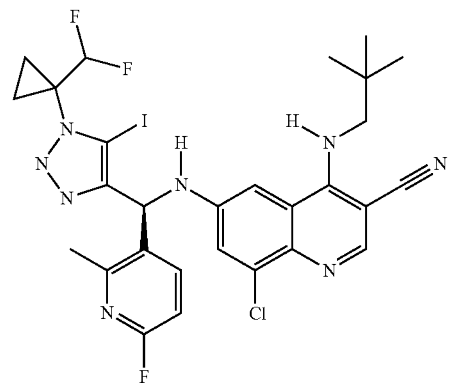 [SMILES: Cc1nc(F)ccc1[C@H](Nc1cc(Cl)c2ncc(C#N)c(NCC(C)(C)C)c2c1)C1=C(I)N(C2(C(F)F)CC2)NN1] | (S)-8-chloro-6-(((1-(1-(difluoromethyl)cyclopropyl)-5-iodo-1H-1,2,3-triazol-4-yl)(6-fluoro-2-methylpyridin-3-yl)methyl)amino)-4-neopentylamino)quinoline-3-carbonitrile | 28 | 695.3 |
| 708 | 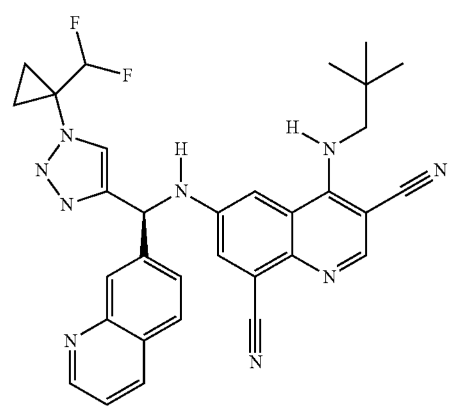 [SMILES: CC(C)(C)CNc1c(C#N)cnc2c(C#N)cc(N[C@H](C3=CN(C4(C(F)F)CC4)NN3)c3ccc4cccnc4c3)cc12] | (S)-6-(((1-(1-(difluoromethyl)cyclopropyl)-1H-1,2,3-triazol-4-yl)(quinolin-7-yl)methyl)amino)-4-(neopentylamino)quinoline-3,8-dicarbonitrile | 24 | 578.151 |
| 709 | 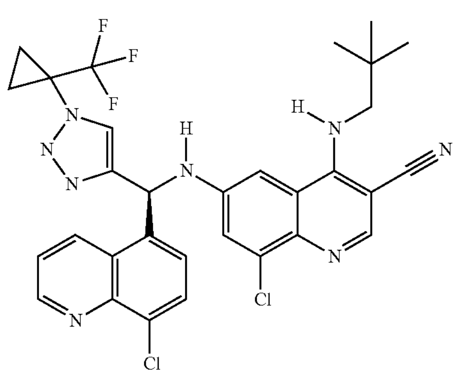 [SMILES: CC(C)(C)CNc1c(C#N)cnc2c(Cl)cc(N[C@H](C3=CN(C4(C(F)(F)F)CC4)NN3)c3ccc(Cl)c4ncccc34)cc12] | (S)-8-chloro-6-(((8-chloroquinolin-5-yl)(1-(1-(trifluoromethyl)cyclopropyl)-1H-1,2,3-triazol-4-yl)methyl)amino)-4-(neopentylamino)quinoline-3-carbonitrile | 4 | 639.263 |

TABLE 1-continued

| Comp | Structure | Name | Example Procedure | ES/MS m/z |
|---|---|---|---|---|
| 710 | 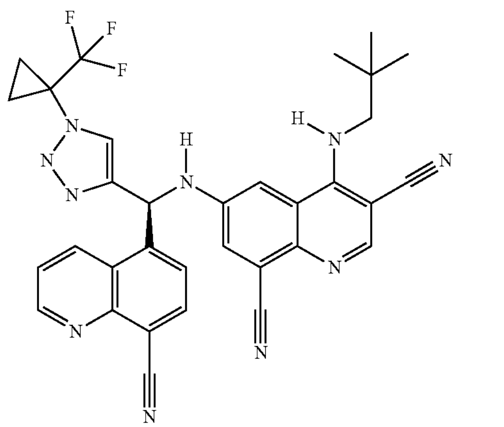 [SMILES: CC(C)(C)CNc1c(C#N)cnc2c(C#N)cc(N[C@H](C3=CN(C4(C(F)(F)F)CC4)NN3)c3ccc(C#N)c4ncccc34)cc12] | (S)-6-(((8-cyanoquinolin-5-yl)(1-(1-(trifluoromethyl)cyclopropyl)-1H-1,2,3-triazol-4-yl)methyl)amino)-4-(neopentylamino)quinoline-3,8-dicarbonitrile | 25 | 621.265 |
| 711 | 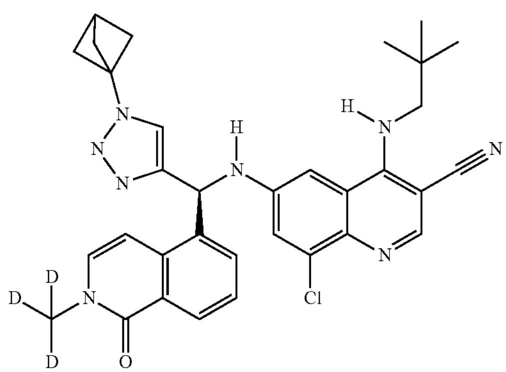 [SMILES: [2H]C([2H])([2H])n1ccc2c([C@H](Nc3cc(Cl)c4ncc(C#N)c(NCC(C)(C)C)c4c3)C3=CN(C45CC(C4)C5)NN3)cccc2c1=O] | (S)-6-(((1-(bicyclo[1.1.1]pentan-1-yl)-1H-1,2,3-triazol-4-yl)(2-(methyl-d3)-1-oxo-1,2-dihydroisoquinolin-5-yl)methyl)amino)-8-chloro-4-(neopentylamino)quinoline-3-carbonitrile | 43 | 596.32 |
| 712 | 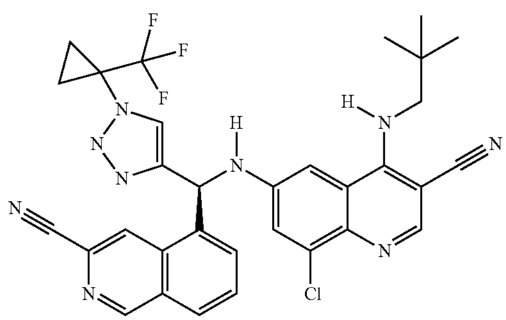 [SMILES: CC(C)(C)CNc1c(C#N)cnc2c(Cl)cc(N[C@H](C3=CN(C4(C(F)(F)F)CC4)NN3)c3cccc4cnc(C#N)cc34)cc12] | (S)-8-chloro-6-(((3-cyanoisoquinolin-5-yl)(1-(1-(trifluoromethyl)cyclopropyl)-1H-1,2,3-triazol-4-yl)methyl)amino)-4-(neopentylamino)quinoline-3-carbonitrile | 9 | 630.28 |
| 713 | 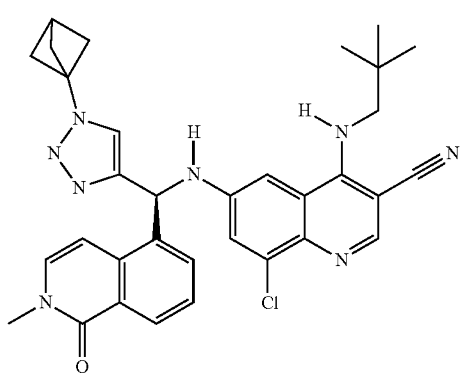 [SMILES: Cn1ccc2c([C@H](Nc3cc(Cl)c4ncc(C#N)c(NCC(C)(C)C)c4c3)C3=CN(C45CC(C4)C5)NN3)cccc2c1=O] | (S)-6-(((1-(bicyclo[1.1.1]pentan-1-yl)-1H-1,2,3-triazol-4-yl)(2-methyl-1-oxo-1,2-dihydroisoquinolin-5-yl)methyl)amino)-8-chloro-4-(neopentylamino)quinoline-3-carbonitrile | 43 | 593.40 |

TABLE 1-continued

| Comp | Name | Example Procedure | ES/MS m/z |
|---|---|---|---|
| 714 | (S)-6-(((1-(1-(tert-butyl)piperidin-4-yl)-1H-1,2,3-triazol-4-yl)(2-methyl-1-oxo-1,2-dihydroisoquinolin-5-yl)methyl)amino)-8-chloro-4-(neopentylamino)quinoline-3-carbonitrile | 1 | 666.65 |
| 715 | (S)-6-(((1-(tert-butyl)-1H-1,2,3-triazol-4-yl)(6-fluoro-2-methylpyridin-3-yl)methyl)amino)-8-chloro-4-((3,3,3-trifluoro-2,2-dimethylpropyl)amino)quinoline-3-carbonitrile | 2 | 589.34 |
| 716 | (S)-8-chloro-6-(((1-cyclopropyl-1H-1,2,3-triazol-4-yl)(6-fluoro-2-methylpyridin-3-yl)methyl)amino)-4-(neopentylamino)quinoline-3-carbonitrile | 2 | 519.25 |

TABLE 1-continued

| Comp | Structure | Name | Example Procedure | ES/MS m/z |
|---|---|---|---|---|
| 717 | 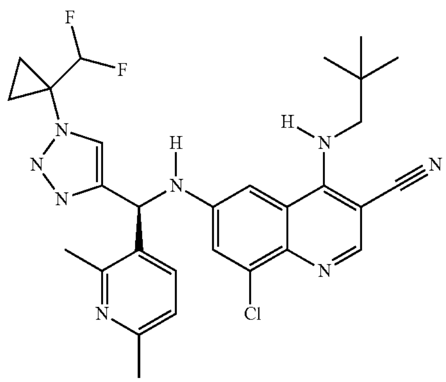 [SMILES: Cc1ccc([C@H](Nc2cc(Cl)c3ncc(C#N)c(NCC(C)(C)C)c3c2)C2=CN(C3(C(F)F)CC3)NN2)c(C)n1] | (S)-8-chloro-6-(((1-(1-(difluoromethyl)cyclopropyl)-1H-1,2,3-triazol-4-yl)(2,6-dimethylpyridin-3-yl)methyl)amino)-4-(neopentylamino)quinoline-3-carbonitrile | 2 | 564.16 |
| 718 | 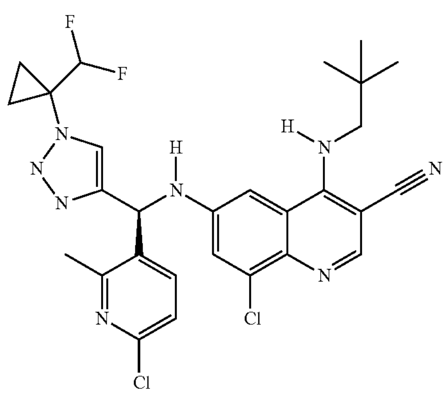 [SMILES: Cc1nc(Cl)ccc1[C@H](Nc1cc(Cl)c2ncc(C#N)c(NCC(C)(C)C)c2c1)C1=CN(C2(C(F)F)CC2)NN1] | (S)-8-chloro-6-(((6-chloro-2-methylpyridin-3-yl)(1-(1-(difluoromethyl)cyclopropyl)-1H-1,2,3-triazol-4-yl)methyl)amino)-4-(neopentylamino)quinoline-3-carbonitrile | 2 | 585.60 |
| 719 | 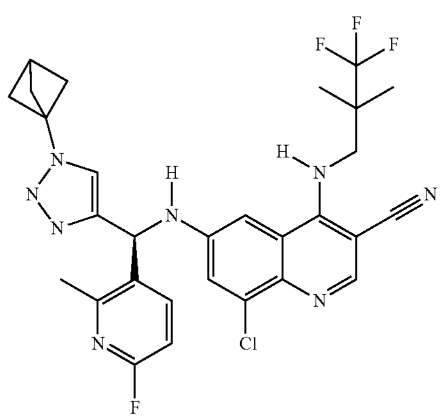 [SMILES: Cc1nc(F)ccc1[C@H](Nc1cc(Cl)c2ncc(C#N)c(NCC(C)(C)C(F)(F)F)c2c1)C1=CN(C23CC(C2)C3)NN1] | (S)-6-(((1-(bicyclo[1.1.1]pentan-1-yl)-1H-1,2,3-triazol-4-yl)(6-fluoro-2-methylpyridin-3-yl)methyl)amino)-8-chloro-4-((3,3,3-trifluoro-2,2-dimethylpropyl)amino)quinoline-3-carbonitrile | 2 | 599.17 (M + H)+ |

TABLE 1-continued

| Comp | Structure | Name | Example Procedure | ES/MS m/z |
|---|---|---|---|---|
| 720 | 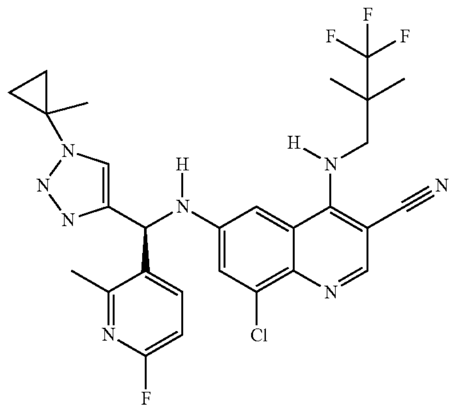 [SMILES: Cc1nc(F)ccc1[C@H](Nc1cc(Cl)c2ncc(C#N)c(NCC(C)(C)C(F)(F)F)c2c1)C1=CN(C2(C)CC2)NN1] | (S)-8-chloro-6-(((6-fluoro-2-methylpyridin-3-yl)(1-(1-methylcyclopropyl)-1H-1,2,3-triazol-4-yl)methyl)amino)-4-((3,3,3-trifluoro-2,2-dimethylpropyl)amino)-quinoline-3-carbonitrile | 2 | 587.1 (M + H)+ |
| 721 | 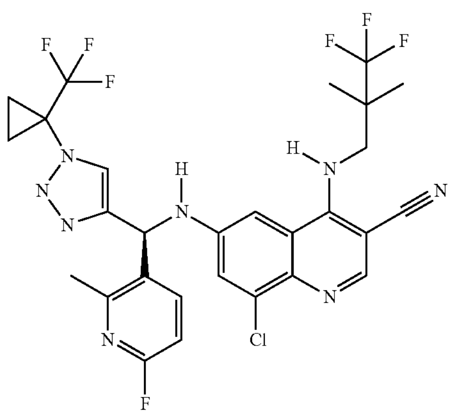 [SMILES: Cc1nc(F)ccc1[C@H](Nc1cc(Cl)c2ncc(C#N)c(NCC(C)(C)C(F)(F)F)c2c1)C1=CN(C2(C(F)(F)F)CC2)NN1] | (S)-8-chloro-6-(((6-fluoro-2-methylpyridin-3-yl)(1-(1-(trifluoromethyl)cyclopropyl)-1H-1,2,3-triazol-4-yl)methyl)amino)-4-((3,3,3-trifluoro-2,2-dimethylpropyl)amino)quinoline-3-carbonitrile | 2 | 641.1 (M + H)+ |
| 722 | 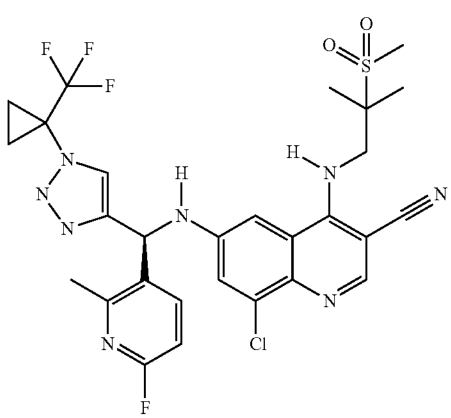 [SMILES: Cc1nc(F)ccc1[C@H](Nc1cc(Cl)c2ncc(C#N)c(NCC(C)(C)S(C)(=O)=O)c2c1)C1=CN(C2(C(F)(F)F)CC2)NN1] | (S)-8-chloro-6-(((6-fluoro-2-methylpyridin-3-yl)(1-(1-(trifluoromethyl)cyclopropyl)-1H-1,2,3-triazol-4-yl)methyl)amino)-4-((2-methyl-2-(methylsulfonyl)propyl)amino)-quinoline-3-carbonitrile | 2 | 651.22 (M + H)+ |

TABLE 1-continued

| Comp | Structure | Name | Example Procedure | ES/MS m/z |
|---|---|---|---|---|
| 723 | 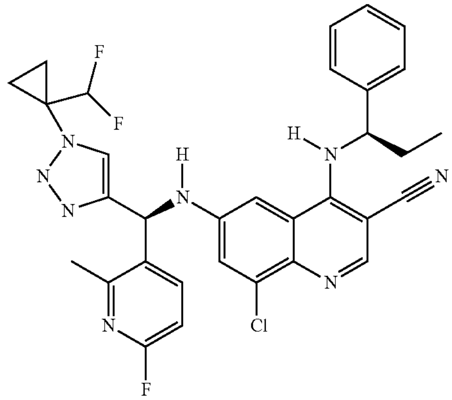 [SMILES: CC[C@@H](Nc1c(C#N)cnc2c(Cl)cc(N[C@H](C3=CN(C4(C(F)F)CC4)NN3)c3ccc(F)nc3C)cc12)c1ccccc1] | 8-chloro-6-(((S)-(1-(1-(difluoromethyl)cyclopropyl)-1H-1,2,3-triazol-4-yl)(6-fluoro-2-methylpyridin-3-yl)methyl)amino)-4-(((R)-1-phenyl-propyl)amino)quinoline-3-carbonitrile | 2 | 617.21 (M + H)+ |
| 724 | 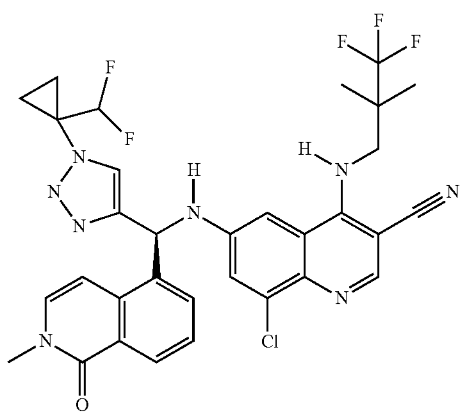 [SMILES: Cn1ccc2c([C@H](Nc3cc(Cl)c4ncc(C#N)c(NCC(C)(C)C(F)(F)F)c4c3)C3=CN(C4(C(F)F)CC4)NN3)cccc2c1=O] | (S)-8-chloro-6-(((1-(1-(difluoromethyl)cyclopropyl)-1H-1,2,3-triazol-4-yl)(2-methyl-1-oxo-1,2-dihydroisoquinolin-5-yl)methyl)amino)-4-((3,3,3-trifluoro-2,2-dimethylpropyl)amino)quinoline-3-carbonitrile | 2 | 671.2 (M + H)+ |
| 725 | 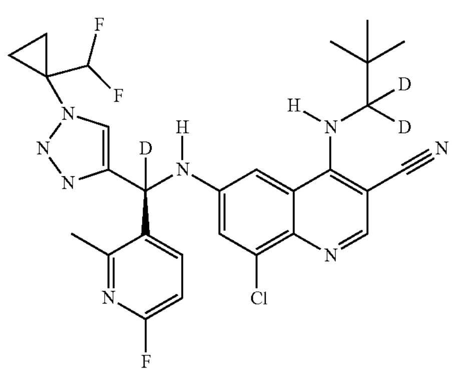 | (S)-8-chloro-6-(((1-(1-(difluoromethyl)cyclopropyl)-1H-1,2,3-triazol-4-yl)(6-fluoro-2-methylpyridin-3-yl)methyl-d)amino)-4-((2,2-dimethylpropyl-1,1-d2)amino)quinoline-3-carbonitrile | 2 | 613 (M + H)+ |

TABLE 1-continued

| Comp | Structure | Name | Example Procedure | ES/MS m/z |
|---|---|---|---|---|
| 726 | 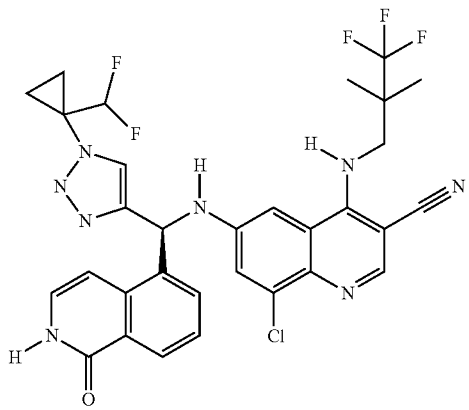 [SMILES: CC(C)(CNc1c(C#N)cnc2c(Cl)cc(N[C@H](C3=CN(C4(C(F)F)CC4)NN3)c3cccc4c(=O)[nH]ccc34)cc12)C(F)(F)F] | (S)-8-chloro-6-(((1-(1-(difluoromethyl)cyclopropyl)-1H-1,2,3-triazol-4-yl)(1-oxo-1,2-dihydroisoquinolin-5-yl)methyl)amino)-4-((3,3,3-trifluoro-2,2-dimethylpropyl)amino)quinoline-3-carbonitrile | 2 | 657.4 (M + H)+ |
| 727 | 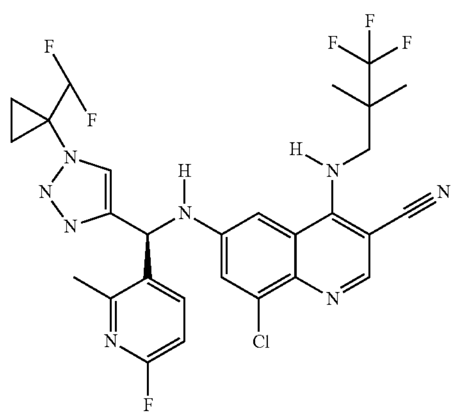 | (S)-8-chloro-6-(((1-(1-(difluoromethyl)cyclopropyl)-1H-1,2,3-triazol-4-yl)(6-fluoro-2-methylpyridin-3-yl)methyl)amino)-4-((3,3,3-trifluoro-2,2-dimethylpropyl)amino)quinoline-3-carbonitrile | 2 | 621.95 (M + H)+ |
| 728 | 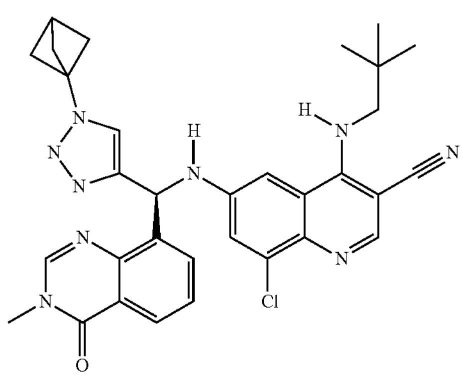 [SMILES: Cn1cnc2c([C@H](Nc3cc(Cl)c4ncc(C#N)c(NCC(C)(C)C)c4c3)C3=CN(C45CC(C4)C5)NN3)cccc2c1=O] | (S)-6-(((1-(bicyclo[1.1.1]pentan-1-yl)-1H-1,2,3-triazol-4-yl)(3-methyl-4-oxo-3,4-dihydroquinazolin-8-yl)methyl)amino)-8-chloro-4-(neopentylamino)quinoline-3-carbonitrile | 2 | 594.19 (M + H)+ |

TABLE 1-continued

| Comp | Structure | Name | Example Procedure | ES/MS m/z |
|---|---|---|---|---|
| 729 | 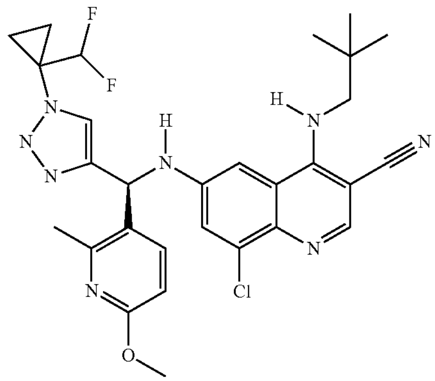 [SMILES: COc1ccc([C@H](Nc2cc(Cl)c3ncc(C#N)c(NCC(C)(C)C)c3c2)C2=CN(C3(C(F)F)CC3)NN2)c(C)n1] | (S)-8-chloro-6-(((1-(1-(difluoromethyl)cyclopropyl)-1H-1,2,3-triazol-4-yl)(6-methoxy-2-methylpyridin-3-yl)methyl)amino)-4-(neopentylamino)quinoline-3-carbonitrile | 2 | 581.44 (M + H)+ |
| 730 | 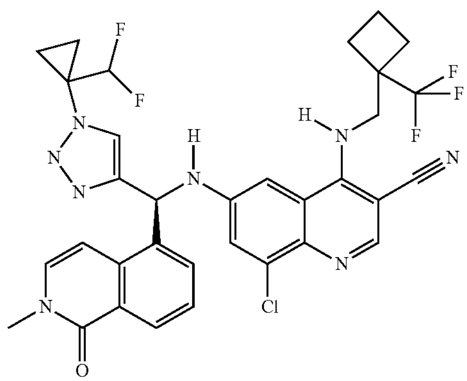 [SMILES: Cn1ccc2c([C@H](Nc3cc(Cl)c4ncc(C#N)c(NCC5(C(F)(F)F)CCC5)c4c3)C3=CN(C4(C(F)F)CC4)NN3)cccc2c1=O] | (S)-8-chloro-6-(((1-(1-(difluoromethyl)cyclopropyl)-1H-1,2,3-triazol-4-yl)(2-methyl-1-oxo-1,2-dihydroisoquinolin-5-yl)methyl)amino)-4-(((1-(trifluoromethyl)cyclobutyl)methyl)-amino)quinoline-3-carbonitrile | 2 | 683.41 (M + H)+ |
| 731 | 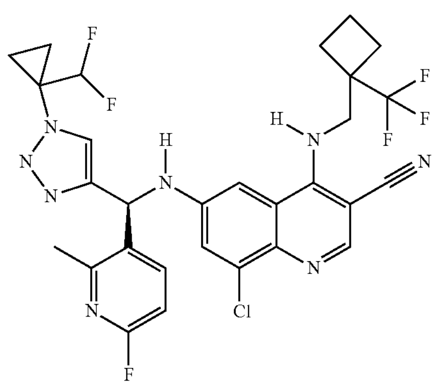 [SMILES: Cc1nc(F)ccc1[C@H](Nc1cc(Cl)c2ncc(C#N)c(NCC3(C(F)(F)F)CCC3)c2c1)C1=CN(C2(C(F)F)CC2)NN1] | (S)-8-chloro-6-(((1-(1-(difluoromethyl)cyclopropyl)-1H-1,2,3-triazol-4-yl)(6-fluoro-2-methylpyridin-3-yl)methyl)amino)-4-(((1-(trifluoromethyl)cyclobutyl)-methyl)amino)quinoline-3-carbonitrile | 2 | 635.12 (M + H)+ |
| 732 | 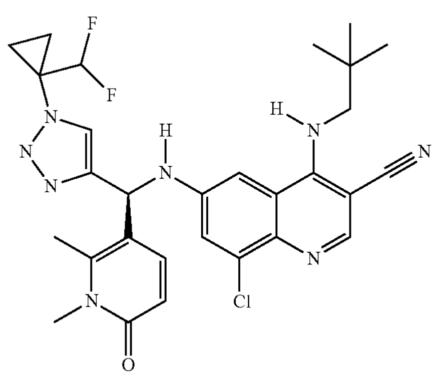 [SMILES: Cc1c([C@H](Nc2cc(Cl)c3ncc(C#N)c(NCC(C)(C)C)c3c2)C2=CN(C3(C(F)F)CC3)NN2)ccc(=O)n1C] | (S)-8-chloro-6-(((1-(1-(difluoromethyl)cyclopropyl)-1H-1,2,3-triazol-4-yl)(1,2-dimethyl-6-oxo-1,6-dihydropyridin-3-yl)methyl)amino)-4-(neopentylamino)quinoline-3-carbonitrile | 2 | 581.15 (M + H)+ |

TABLE 1-continued

| Comp | Structure | Name | Example Procedure | ES/MS m/z |
|---|---|---|---|---|
| 733 | 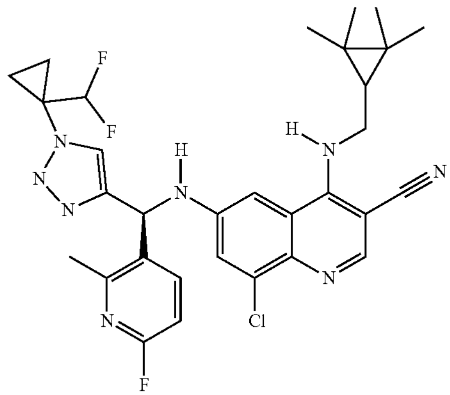 [SMILES: Cc1nc(F)ccc1[C@H](Nc1cc(Cl)c2ncc(C#N)c(NCC3C(C)(C)C3(C)C)c2c1)C1=CN(C2(C(F)F)CC2)NN1] | (S)-8-chloro-6-(((1-(1-(difluoromethyl)cyclopropyl)-1H-1,2,3-triazol-4-yl)(6-fluoro-2-methylpyridin-3-yl)methyl)amino)-4-(((2,2,3,3-tetramethylcyclopropyl)methyl)amino)quinoline-3-carbonitrile | 2 | 609.29 (M + H)+ |
| 734 | 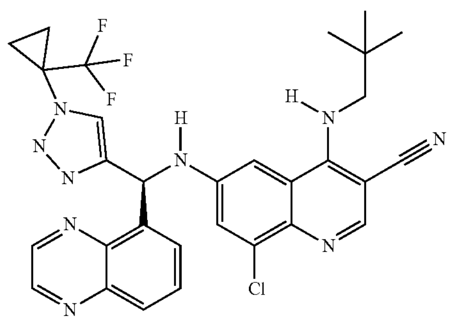 [SMILES: CC(C)(C)CNc1c(C#N)cnc2c(Cl)cc(N[C@H](C3=CN(C4(C(F)(F)F)CC4)NN3)c3cccc4nccnc34)cc12] | (S)-8-chloro-4-(neopentylamino)-6-((quinoxalin-5-yl(1-(1-(trifluoromethyl)-cyclopropyl)-1H-1,2,3-triazol-4-yl)methyl)amino)quinoline-3-carbonitrile | 2 | 606.17 (M + H)+ |
| 735 | 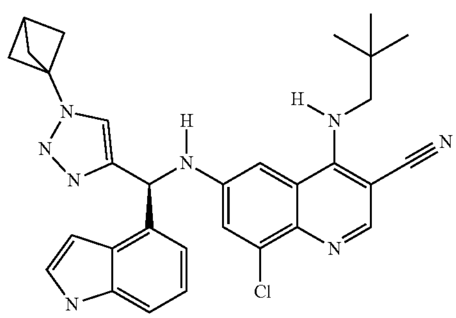 | (S)-6-(((1-(bicyclo[1.1.1]pentan-1-yl)-1H-1,2,3-triazol-4-yl)(1-methyl-1H-indol-4-yl)methyl)amino)-8-chloro-4-(neopentylamino)quinoline-3-carbonitrile | 2 | 566 (M + H)+ |
| 736 | 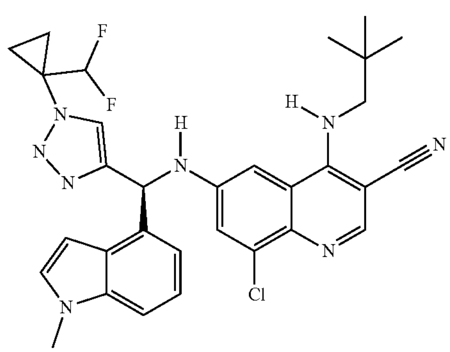 [SMILES: Cn1ccc2c([C@H](Nc3cc(Cl)c4ncc(C#N)c(NCC(C)(C)C)c4c3)C3=CN(C4(C(F)F)CC4)NN3)cccc21] | (S)-8-chloro-6-(((1-(1-(difluoromethyl)cyclopropyl)-1H-1,2,3-triazol-4-yl)(1-methyl-1H-indol-4-yl)methyl)amino)-4-(neopentylamino)quinoline-3-carbonitrile | 2 | 589.38 (M + H)+ |

TABLE 1-continued

| Comp | Structure | Name | Example Procedure | ES/MS m/z |
|---|---|---|---|---|
| 737 | 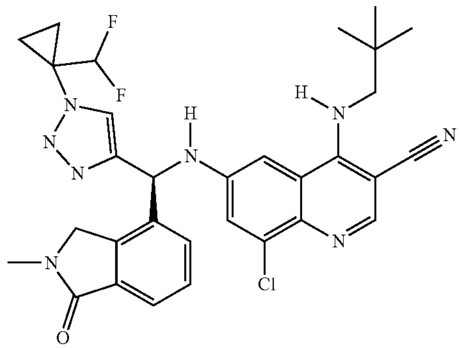 [SMILES: CN1Cc2c(cccc2[C@H](Nc2cc(Cl)c3ncc(C#N)c(NCC(C)(C)C)c3c2)C2=CN(C3(C(F)F)CC3)NN2)C1=O] | (S)-8-chloro-6-(((1-(1-(difluoromethyl)cyclopropyl)-1H-1,2,3-triazol-4-yl)(2-methyl-1-oxoisoindolin-4-yl)methyl)amino)-4-(neopentylamino)quinoline-3-carbonitrile | 2 | 605.2 (M + H)+ |
| 738 | 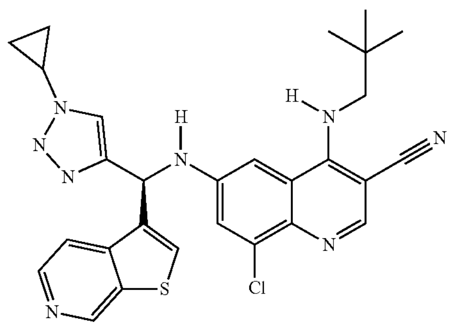 [SMILES: CC(C)(C)CNc1c(C#N)cnc2c(Cl)cc(N[C@H](C3=CN(C4CC4)NN3)c3csc4cnccc34)cc12] | (S)-8-chloro-6-(((1-cyclopropyl-1H-1,2,3-triazol-4-yl)(thieno[2,3-c]pyridin-3-yl)methyl)amino)-4-(neopentylamino)quinoline-3-carbonitrile | 2 | 543.20 |
| 739 | 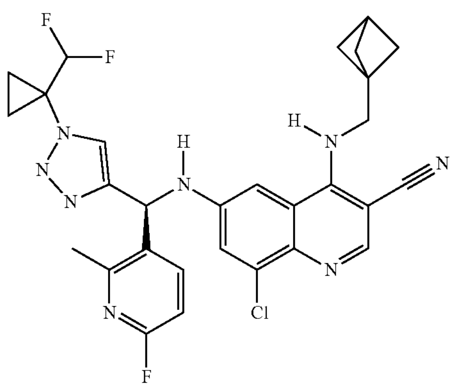 [SMILES: Cc1nc(F)ccc1[C@H](Nc1cc(Cl)c2ncc(C#N)c(NCC34CC(C3)C4)c2c1)C1=CN(C2(C(F)F)CC2)NN1] | (S)-4-((bicyclo[1.1.1]pentan-1-yl methyl)amino)-8-chloro-6-(((1-(1-(difluoromethyl)cyclopropyl)-1H-1,2,3-triazol-4-yl)(6-fluoro-2-methylpyridin-3-yl)methyl)amino)quinoline-3-carbonitrile | 2 | 579.30 |
| 740 | 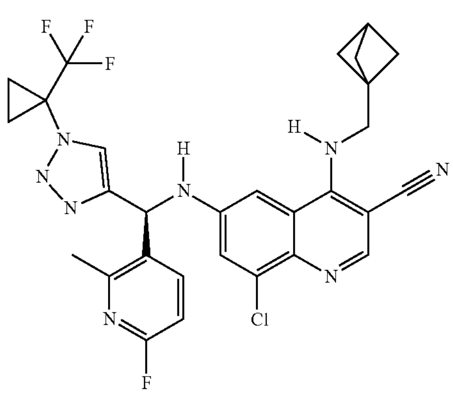 [SMILES: Cc1nc(F)ccc1[C@H](Nc1cc(Cl)c2ncc(C#N)c(NCC34CC(C3)C4)c2c1)C1=CN(C2(C(F)(F)F)CC2)NN1] | (S)-4-((bicyclo[1.1.1]pentan-1-ylmethyl)amino)-8-chloro-6-(((6-fluoro-2-methyl pyridin-3-yl)(1-(1-(trifluoromethyl)cyclopropyl)-1H-1,2,3-triazol-4-yl)methyl)amino)quinoline-3-carbonitrile | 2 | 597.30 |

TABLE 1-continued

| Comp | Structure | Name | Example Procedure | ES/MS m/z |
|---|---|---|---|---|
| 741 | 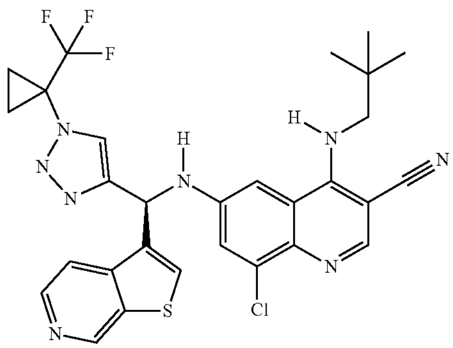 [SMILES: CC(C)(C)CNc1c(C#N)cnc2c(Cl)cc(N[C@H](C3=CN(C4(C(F)(F)F)CC4)NN3)c3csc4cnccc34)cc12] | (S)-8-chloro-4-(neopentylamino)-6-((thieno[2,3-c]pyridin-3-yl(1-(1-(trifluoromethyl)cyclopropyl)-1H-1,2,3-triazol-4-yl)methyl)amino)quinoline-3-carbonitrile | 2 | 611.20 |
| 742 | 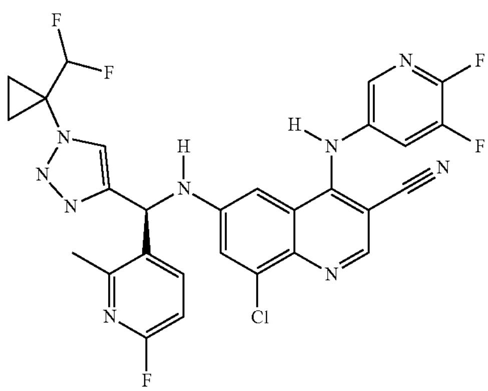 [SMILES: Cc1nc(F)ccc1[C@H](Nc1cc(Cl)c2ncc(C#N)c(Nc3cnc(F)c(F)c3)c2c1)C1=CN(C2(C(F)F)CC2)NN1] | (S)-8-chloro-6-(((1-(1-(difluoromethyl)cyclopropyl)-1H-1,2,3-triazol-4-yl)(6-fluoro-2-methylpyridin-3-yl)methyl)amino)-4-((5,6-difluoropyridin-3-yl)amino)quinoline-3-carbonitrile | 2 | 612.10 |
| 743 | 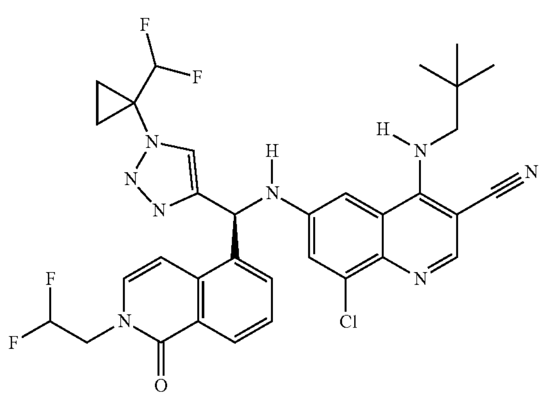 [SMILES: CC(C)(C)CNc1c(C#N)cnc2c(Cl)cc(N[C@H](C3=CN(C4(C(F)F)CC4)NN3)c3cccc4c(=O)n(CC(F)F)ccc34)cc12] | (S)-8-chloro-6-(((2-(2,2-difluoroethyl)-1-oxo-1,2-dihydroisoquinolin-5-yl)(1-(1-(difluoromethyl)cyclopropyl)-1H-1,2,3-triazol-4-yl)methyl)amino)-4-(neopentylamino)quinoline-3-carbonitrile | 2 | 667.40 |
| 744 | 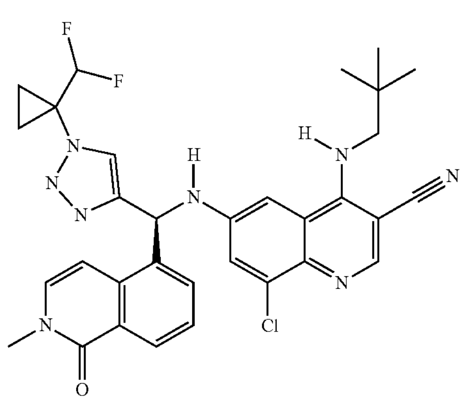 [SMILES: Cn1ccc2c([C@H](Nc3cc(Cl)c4ncc(C#N)c(NCC(C)(C)C)c4c3)C3=CN(C4(C(F)F)CC4)NN3)cccc2c1=O] | (S)-8-chloro-6-(((1-(1-(difluoromethyl)cyclopropyl)-1H-1,2,3-triazol-4-yl)(2-methyl-1-oxo-1,2-dihydroisoquinolin-5-yl)methyl)amino)-4-(neopentylamino)quinoline-3-carbonitrile | 2 | 616.20 |

TABLE 1-continued

| Comp | Structure | Name | Example Procedure | ES/MS m/z |
|---|---|---|---|---|
| 745 | 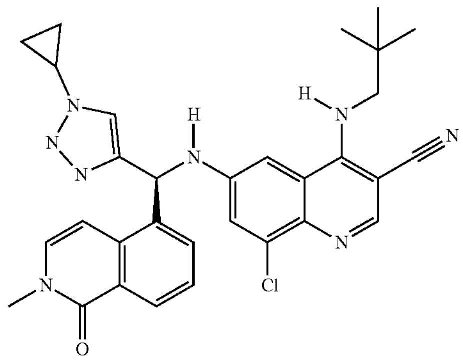 [SMILES: Cn1ccc2c([C@H](Nc3cc(Cl)c4ncc(C#N)c(NCC(C)(C)C)c4c3)C3=CN(C4CC4)NN3)cccc2c1=O] | (S)-8-chloro-6-(((1-cyclopropyl-1H-1,2,3-triazol-4-yl)(2-methyl-1-oxo-1,2-dihydroisoquinolin-5-yl)methyl)amino)-4-(neopentylamino)quinoline-3-carbonitrile | 2 | 567.40 |
| 746 | 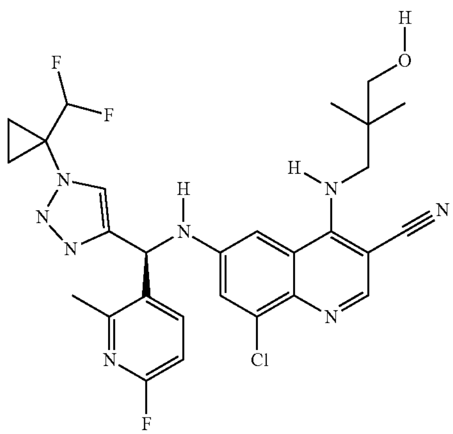 [SMILES: Cc1nc(F)ccc1[C@H](Nc1cc(Cl)c2ncc(C#N)c(NCC(C)(C)CO)c2c1)C1=CN(C2(C(F)F)CC2)NN1] | (S)-8-chloro-6-(((1-(1-(difluoromethyl)cyclopropyl)-1H-1,2,3-triazol-4-yl)(6-fluoro-2-methylpyridin-3-yl)methyl)amino)-4-((3-hydroxy-2,2-dimethylpropyl)amino)quinoline-3-carbonitrile | 2 | 585.30 |
| 747 | 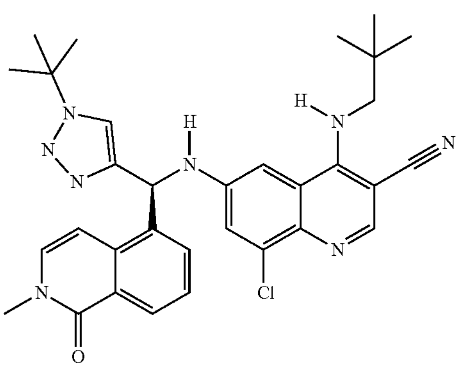 [SMILES: Cn1ccc2c([C@H](Nc3cc(Cl)c4ncc(C#N)c(NCC(C)(C)C)c4c3)C3=CN(C(C)(C)C)NN3)cccc2c1=O] | (S)-6-(((1-(tert-butyl)-1H-1,2,3-triazol-4-yl)(2-methyl-1-oxo-1,2-dihydroisoquinolin-5-yl)methyl)amino)-8-chloro-4-(neopentylamino)quinoline-3-carbonitrile | 2 | 583.50 |
| 748 | 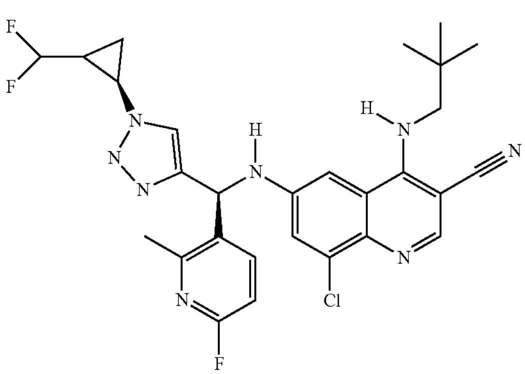 [SMILES: Cc1nc(F)ccc1[C@H](Nc1cc(Cl)c2ncc(C#N)c(NCC(C)(C)C)c2c1)C1=CN([C@@H]2CC2C(F)F)NN1] | 8-chloro-6-(((S)-(1-((1R,2R)-2-(difluoromethyl)cyclopropyl)-1H-1,2,3-triazol-4-yl)(6-fluoro-2-methylpyridin-3-yl)methyl)amino)-4-(neopentylamino)quinoline-3-carbonitrile | 4 | 548.30 |

TABLE 1-continued

| Comp | Structure | Name | Example Procedure | ES/MS m/z |
|---|---|---|---|---|
| 749 | 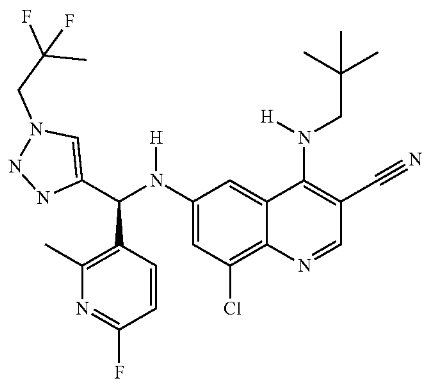 [SMILES: Cc1nc(F)ccc1[C@H](Nc1cc(Cl)c2ncc(C#N)c(NCC(C)(C)C)c2c1)C1=CN(CC(C)(F)F)NN1] | (S)-8-chloro-6-(((1-(2,2-difluoropropyl)-1H-1,2,3-triazol-4-yl)(6-fluoro-2-methylpyridin-3-yl)methyl)amino)-4-(neopentylamino)quinoline-3-carbonitrile | 4 | 557.32 (M + H)+ |
| 750 | 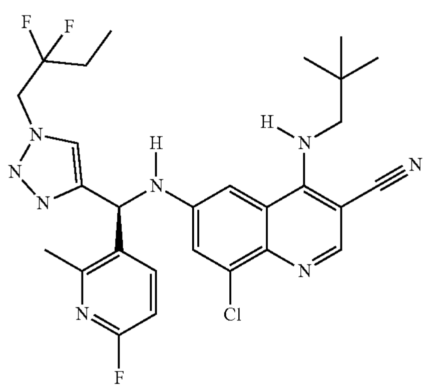 [SMILES: CCC(F)(F)CN1C=C([C@@H](Nc2cc(Cl)c3ncc(C#N)c(NCC(C)(C)C)c3c2)c2ccc(F)nc2C)NN1] | (S)-8-chloro-6-(((1-(2,2-ifluorobutyl)-1H-1,2,3-triazol-4-yl)(6-fluoro-2-methylpyridin-3-yl)methyl)amino)-4-(neopentylamino)quinoline-3-carbonitrile | 4 | 571.77 (M + H)+ |
| 751 | 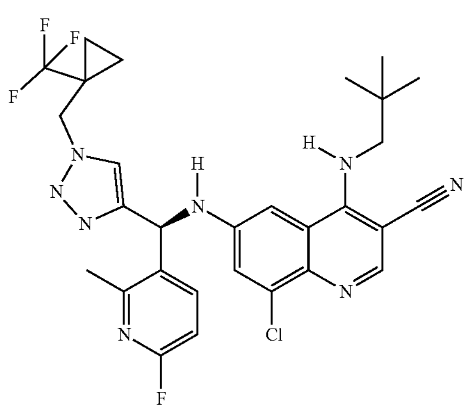 [SMILES: Cc1nc(F)ccc1[C@H](Nc1cc(Cl)c2ncc(C#N)c(NCC(C)(C)C)c2c1)C1=CN(CC2(C(F)(F)F)CC2)NN1] | (S)-8-chloro-6-(((6-fluoro-2-methylpyridin-3-yl)(1-((1-(trifluoromethyl)cyclopropyl)methyl)-1H-1,2,3-triazol-4-yl)methyl)amino)-4-(neopentylamino)quinoline-3-carbonitrile | 4 | 601.47 (M + H)+ |

TABLE 1-continued

| Comp | Structure | Name | Example Procedure | ES/MS m/z |
|---|---|---|---|---|
| 752 | 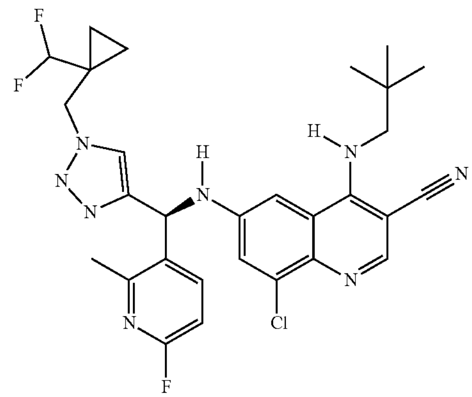 [SMILES: Cc1nc(F)ccc1[C@H](Nc1cc(Cl)c2ncc(C#N)c(NCC(C)(C)C)c2c1)C1=CN(CC2(C(F)F)CC2)NN1] | (S)-8-chloro-6-(((1-((1-(difluoromethyl)cyclopropyl)-methyl)-1H-1,2,3-triazol-4-yl)(6-fluoro-2-methylpyridin-3-yl)methyl)amino)-4-(neopentylamino)quinoline-3-carbonitrile | 4 | 583.42 (M + H)+ |
| 753 | 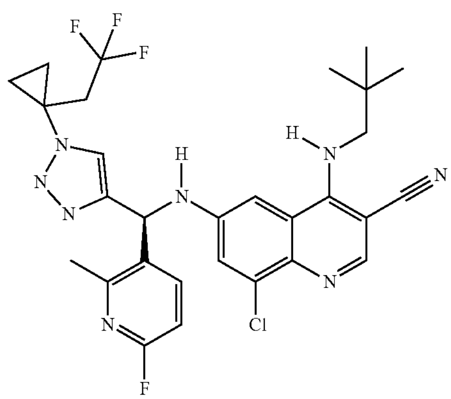 [SMILES: Cc1nc(F)ccc1[C@H](Nc1cc(Cl)c2ncc(C#N)c(NCC(C)(C)C)c2c1)C1=CN(C2(CC(F)(F)F)CC2)NN1] | (S)-8-chloro-6-(((6-fluoro-2-methylpyridin-3-yl)(1-(1-(2,2,2-trifluoroethyl)-cyclopropyl)-1H-1,2,3-triazol-4-yl)methyl)amino)-4-(neopentylamino)quinoline-3-carbonitrile | 4 | 601.39 (M + H)+ |
| 754 | 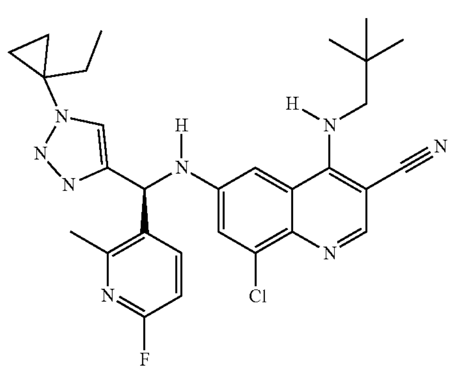 [SMILES: CCC1(N2C=C([C@@H](Nc3cc(Cl)c4ncc(C#N)c(NCC(C)(C)C)c4c3)c3ccc(F)nc3C)NN2)CC1] | (S)-8-chloro-6-(((1-(1-ethylcyclopropyl)-1H-1,2,3-triazol-4-yl)(6-fluoro-2-methylpyridin-3-yl)methyl)amino)-4-(neopentylamino)quinoline-3-carbonitrile | 4 | 547.5 (M + H)+ |

TABLE 1-continued

| Comp | Structure | Name | Example Procedure | ES/MS m/z |
|---|---|---|---|---|
| 755 | 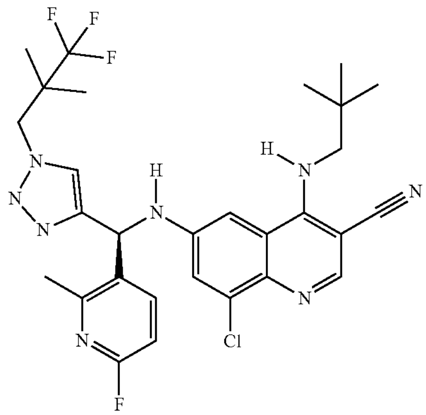 [SMILES: Cc1nc(F)ccc1[C@H](Nc1cc(Cl)c2ncc(C#N)c(NCC(C)(C)C)c2c1)C1=CN(CC(C)(C)C(F)(F)F)NN1] | (S)-8-chloro-6-(((6-fluoro-2-methylpyridin-3-yl)(1-(3,3,3-trifluoro-2,2-dimethylpropyl)-1H-1,2,3-triazol-4-yl (Methyl)amino)-4-(neopentylamino)quinoline-3-carbonitrile | 4 | 603.43 (M + H)+ |
| 756 | 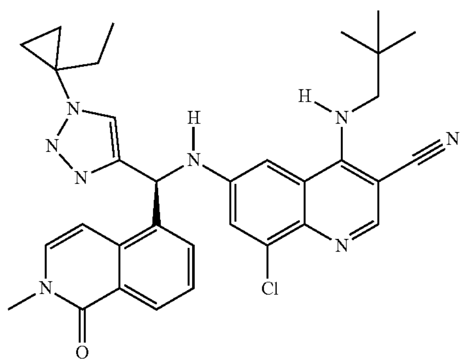 [SMILES: CCC1(N2C=C([C@@H](Nc3cc(Cl)c4ncc(C#N)c(NCC(C)(C)C)c4c3)c3cccc4c(=O)n(C)ccc34)NN2)CC1] | (S)-8-chloro-6-(((1-(1-ethylcyclopropyl)-1H-1,2,3-triazol-4-yl)(2-methyl-1-oxo-1,2-dihydroisoquinolin-5-yl)methyl)amino)-4-(neopentylamino)quinoline-3-carbonitrile | 4 | 595.1 (M + H)+ |
| 757 | 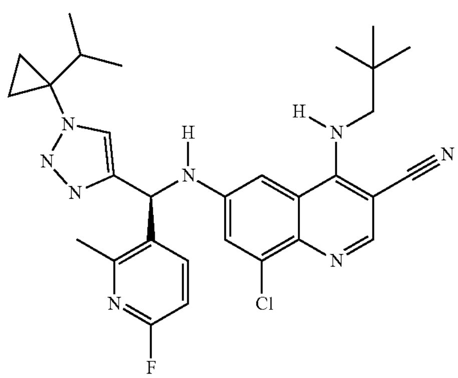 [SMILES: Cc1nc(F)ccc1[C@H](Nc1cc(Cl)c2ncc(C#N)c(NCC(C)(C)C)c2c1)C1=CN(C2(C(C)C)CC2)NN1] | (S)-8-chloro-6-(((6-fluoro-2-methylpyridin-3-yl)(1-(1-isopropylcyclopropyl)-1H-1,2,3-triazol-4-yl)methyl)amino)-4-(neopentylamino)quinoline-3-carbonitrile | 4 | 561.40 |
| 758 | 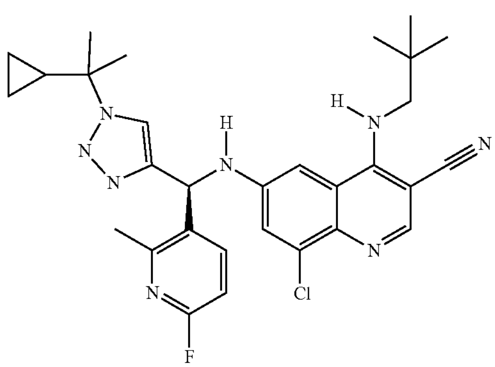 [SMILES: Cc1nc(F)ccc1[C@H](Nc1cc(Cl)c2ncc(C#N)c(NCC(C)(C)C)c2c1)C1=CN(C(C)(C)C2CC2)NN1] | (S)-8-chloro-6-(((1-(2-cyclopropylpropan-2-yl)-1H-1,2,3-triazol-4-yl)(6-fluoro-2-methylpyridin-3-yl)methyl)amino)-4-(neopentylamino)quinoline-3-carbonitrile | 4 | 561.50 |

TABLE 1-continued

| Comp | Structure | Name | Example Procedure | ES/MS m/z |
|---|---|---|---|---|
| 759 | 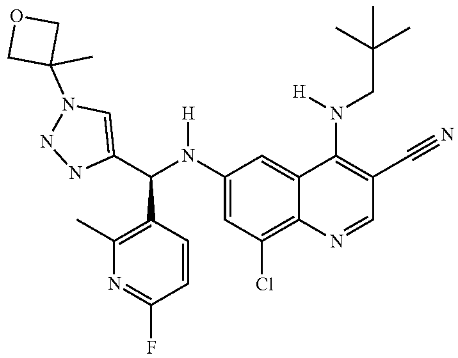 [SMILES: Cc1nc(F)ccc1[C@H](Nc1cc(Cl)c2ncc(C#N)c(NCC(C)(C)C)c2c1)C1=CN(C2(C)COC2)NN1] | (S)-8-chloro-6-(((6-fluoro-2-methylpyridin-3-yl)(1-(3-methyloxetan-3-yl)-1H-1,2,3-triazol-4-yl)methyl)amino)-4-(neopentylamino)quinoline-3-carbonitrile | 4 | 549.20 |
| 760 | 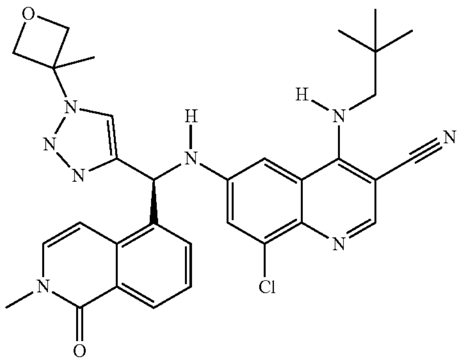 [SMILES: Cn1ccc2c([C@H](Nc3cc(Cl)c4ncc(C#N)c(NCC(C)(C)C)c4c3)C3=CN(C4(C)COC4)NN3)cccc2c1=O] | (S)-8-chloro-6-(((2-methyl-1-oxo-1,2-dihydroisoquinolin-5-yl)(1-(3-methyloxetan-3-yl)-1H-1,2,3-triazol-4-yl)methyl)amino)-4-(neopentylamino)quinoline-3-carbonitrile | 4 | 597.20 |
| 761 | 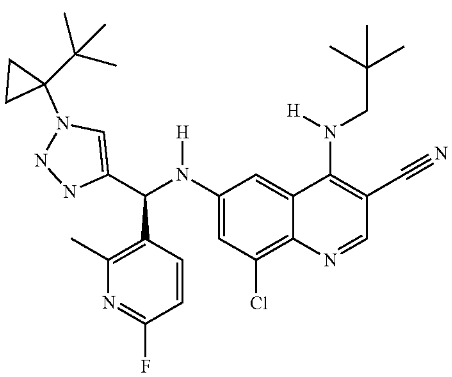 [SMILES: Cc1nc(F)ccc1[C@H](Nc1cc(Cl)c2ncc(C#N)c(NCC(C)(C)C)c2c1)C1=CN(C2(C(C)(C)C)CC2)NN1] | (S)-6-(((1-(1-(tert-butyl)cyclopropyl)-1H-1,2,3-triazol-4-yl)(6-fluoro-2-methylpyridin-3-yl)methyl)amino)-8-chloro-4-(neopentylamino)quinoline-3-carbonitrile | 4 | 575.40 |
| 762 | 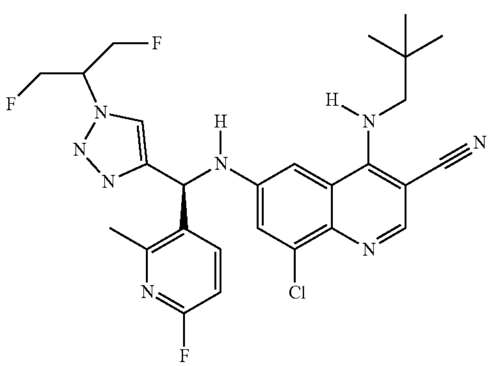 [SMILES: Cc1nc(F)ccc1[C@H](Nc1cc(Cl)c2ncc(C#N)c(NCC(C)(C)C)c2c1)C1=CN(C(CF)CF)NN1] | (S)-8-chloro-6-(((1-(1,3-difluoropropan-2-yl)-1H-1,2,3-triazol-4-yl)(6-fluoro-2-methylpyridin-3-yl)methyl)amino)-4-(neopentylamino)quinoline-3-carbonitrile | 4 | 557.37 |

TABLE 1-continued

| Comp | Structure | Name | Example Procedure | ES/MS m/z |
|---|---|---|---|---|
| 763 | 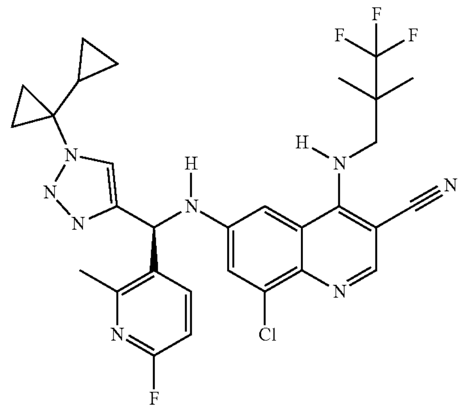 [SMILES: Cc1nc(F)ccc1[C@H](Nc1cc(Cl)c2ncc(C#N)c(NCC(C)(C)C(F)(F)F)c2c1)C1=CN(C2(C3CC3)CC2)NN1] | (S)-6-(((1-([1,1'-bi(cyclopropan)]-1-yl)-1H-1,2,3-triazol-4-yl)(6-fluoro-2-methylpyridin-3-yl)methyl)amino)-8-chloro-4-((3,3,3-trifluoro-2,2-dimethylpropyl)amino)-quinoline-3-carbonitrile | 4 | 613.30 |
| 764 | 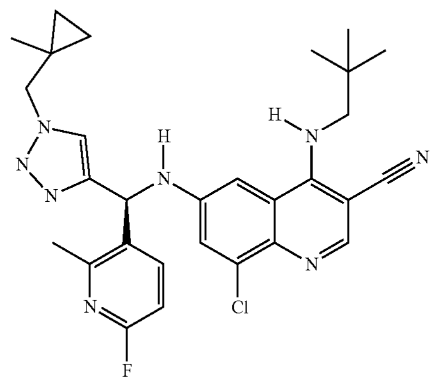 [SMILES: Cc1nc(F)ccc1[C@H](Nc1cc(Cl)c2ncc(C#N)c(NCC(C)(C)C)c2c1)C1=CN(CC2(C)CC2)NN1] | (S)-8-chloro-6-(((6-fluoro-2-methylpyridin-3-yl)(1-((1-methylcyclopropyl)-methyl)-1H-1,2,3-triazol-4-yl)methyl)amino)-4-(neopentylamino)quinoline-3-carbonitrile | 4 | 547.40 |
| 765 | 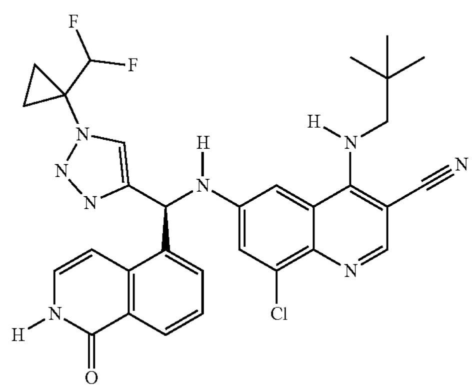 [SMILES: CC(C)(C)CNc1c(C#N)cnc2c(Cl)cc(N[C@H](C3=CN(C4(C(F)F)CC4)NN3)c3cccc4c(=O)[nH]ccc34)cc12] | (S)-8-chloro-6-(((1-(1-(difluoromethyl)cyclopropyl)-1H-1,2,3-triazol-4-yl)(1-oxo-1,2-dihydroisoquinolin-5-yl)methyl)amino)-4-(neopentylamino)quinoline-3-carbonitrile | 4 | 603.30 |
| 766 | 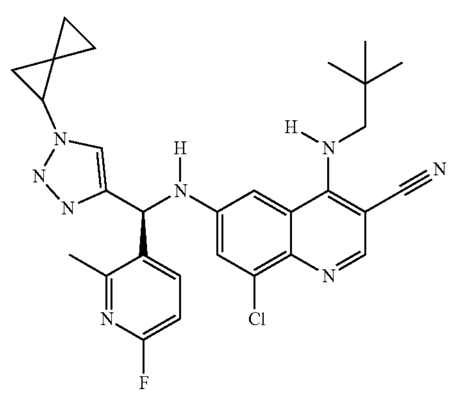 [SMILES: Cc1nc(F)ccc1[C@H](Nc1cc(Cl)c2ncc(C#N)c(NCC(C)(C)C)c2c1)C1=CN(C2CC23CC3)NN1] | 8-chloro-6-((((1S)-(6-fluoro-2-methylpyridin-3-yl)(1-(spiro[2.2]pentan-1-yl)-1H-1,2,3-triazol-4-yl)methyl)amino)-4-(neopentylamino)quinoline-3-carbonitrile | 4 | 545.30 |

TABLE 1-continued

| Comp | Structure | Name | Example Procedure | ES/MS m/z |
|---|---|---|---|---|
| 767 | 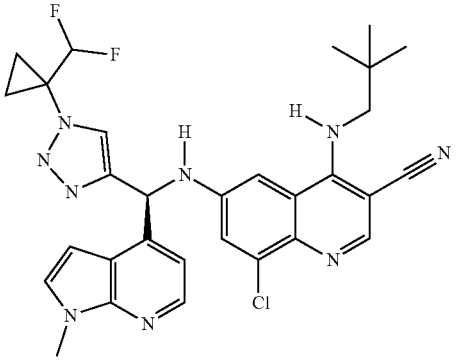 [SMILES: Cn1ccc2c([C@H](Nc3cc(Cl)c4ncc(C#N)c(NCC(C)(C)C)c4c3)C3=CN(C4(C(F)F)CC4)NN3)ccnc21] | (S)-8-chloro-6-(((1-(1-(difluoromethyl)cyclopropyl)-1H-1,2,3-triazol-4-yl)(1-methyl-1H-pyrrolo[2,3-b]pyridin-4-yl)methyl)amino)-4-(neopentylamino)quinoline-3-carbonitrile | 4 | 590.20 |
| 768 | 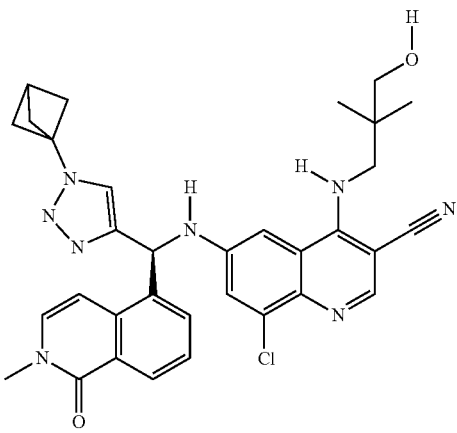 [SMILES: Cn1ccc2c([C@H](Nc3cc(Cl)c4ncc(C#N)c(NCC(C)(C)CO)c4c3)C3=CN(C45CC(C4)C5)NN3)cccc2c1=O] | (S)-6-(((1-(bicyclo[1.1.1]pentan-1-yl)-1H-1,2,3-triazol-4-yl)(2-methyl-1-oxo-1,2-dihydroisoquinolin-5-yl)methyl)amino)-8-chloro-4-((3-hydroxy-2,2-dimethylpropyl)amino)quinoline-3-carbonitrile | 4 | 609.23 |
| 769 | 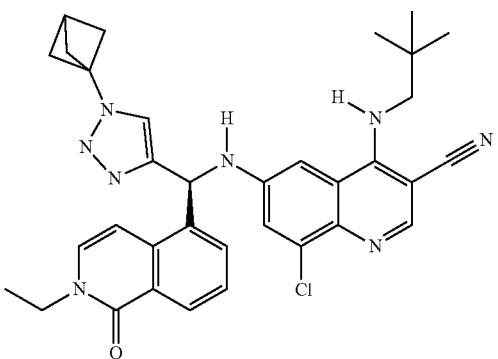 [SMILES: CCn1ccc2c([C@H](Nc3cc(Cl)c4ncc(C#N)c(NCC(C)(C)C)c4c3)C3=CN(C45CC(C4)C5)NN3)cccc2c1=O] | (S)-6-(((1-(bicyclo[1.1.1]pentan-1-yl)-1H-1,2,3-triazol-4-yl)(2-ethyl-1-oxo-1,2-dihydroisoquinolin-5-yl)methyl)amino)-8-chloro-4-(neopentylamino)quinoline-3-carbonitrile | 4 | 607.30 |
| 770 | 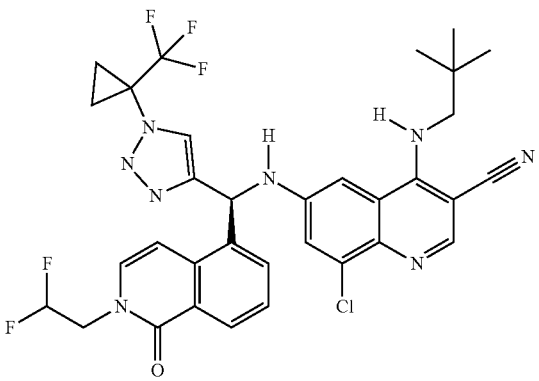 [SMILES: CC(C)(C)CNc1c(C#N)cnc2c(Cl)cc(N[C@H](C3=CN(C4(C(F)(F)F)CC4)NN3)c3cccc4c(=O)n(CC(F)F)ccc34)cc12] | (S)-8-chloro-6-(((2-(2,2-difluoroethyl)-1-oxo-1,2-dihydroisoquinolin-5-yl)(1-(1-(trifluoromethyl)cyclopropyl)-1H-1,2,3-triazol-4-yl)methyl)amino)-4-(neopentylamino)quinoline-3-carbonitrile | 4 | 684 |

TABLE 1-continued

| Comp | Structure | Name | Example Procedure | ES/MS m/z |
|---|---|---|---|---|
| 771 | 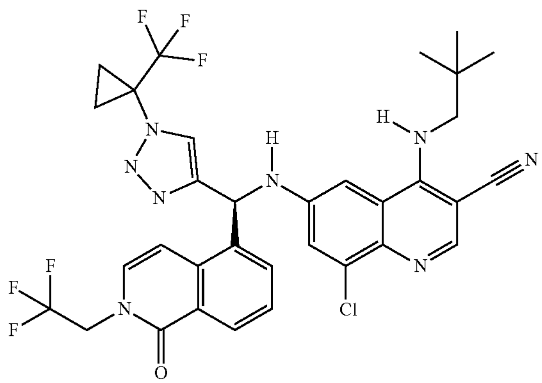 [SMILES: CC(C)(C)CNc1c(C#N)cnc2c(Cl)cc(N[C@H](C3=CN(C4(C(F)(F)F)CC4)NN3)c3cccc4c(=O)n(CC(F)(F)F)ccc34)cc12] | (S)-8-chloro-4-(neopentylamino)-6-(((1-oxo-2-(2,2,2-trifluoroethyl)-1,2-dihydroisoquinolin-5-yl)(1-(1-(trifluoromethyl)-cyclopropyl)-1H-1,2,3-triazol-4-yl)methyl)amino)quinoline-3-carbonitrile | 4 | 702.10 |
| 772 | 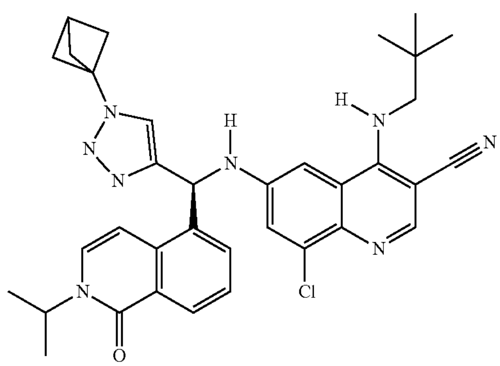 [SMILES: CC(C)n1ccc2c([C@H](Nc3cc(Cl)c4ncc(C#N)c(NCC(C)(C)C)c4c3)C3=CN(C45CC(C4)C5)NN3)cccc2c1=O] | (S)-6-(((1-(bicyclo[1.1.1]pentan-1-yl)-1H-1,2,3-triazol-4-yl)(2-isopropyl-1-oxo-1,2-dihydroisoquinolin-5-yl)methyl)amino)-8-chloro-4-(neopentylamino)quinoline-3-carbonitrile | 4 | 621.40 |
| 773 | 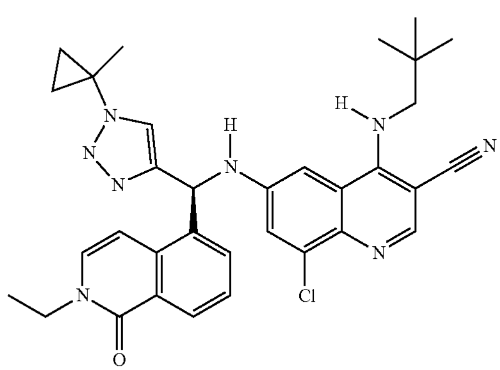 [SMILES: CCn1ccc2c([C@H](Nc3cc(Cl)c4ncc(C#N)c(NCC(C)(C)C)c4c3)C3=CN(C4(C)CC4)NN3)cccc2c1=O] | (S)-8-chloro-6-(((2-ethyl-1-oxo-1,2-dihydroisoquinolin-5-yl)(1-(1-methylcyclopropyl)-1H-1,2,3-triazol-4-yl)methyl)amino)-4-(neopentylamino)quinoline-3-carbonitrile | 4 | 595.30 |
| 774 | 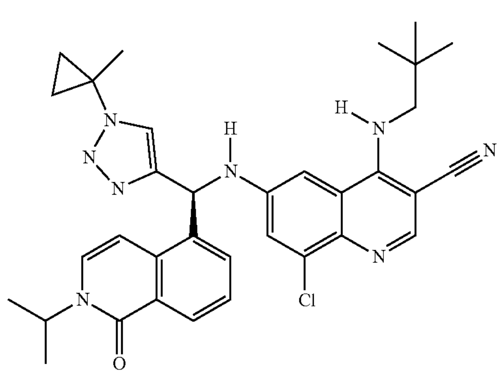 [SMILES: CC(C)n1ccc2c([C@H](Nc3cc(Cl)c4ncc(C#N)c(NCC(C)(C)C)c4c3)C3=CN(C4(C)CC4)NN3)cccc2c1=O] | (S)-8-chloro-6-(((2-isopropyl-1-oxo-1,2-dihydroisoquinolin-5-yl)(1-(1-methylcyclopropyl)-1H-1,2,3-triazol-4-yl)methyl)amino)-4-(neopentylamino)quinoline-3-carbonitrile | 4 | 609.40 |

TABLE 1-continued

| Comp | Structure | Name | Example Procedure | ES/MS m/z |
|---|---|---|---|---|
| 775 | 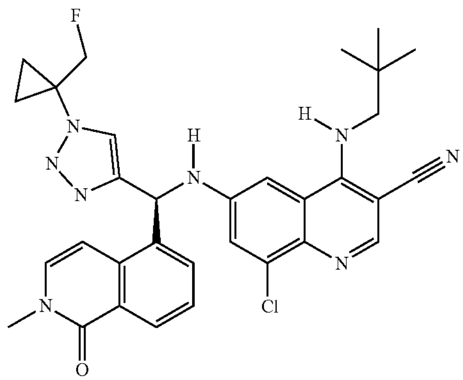 [SMILES: Cn1ccc2c([C@H](Nc3cc(Cl)c4ncc(C#N)c(NCC(C)(C)C)c4c3)C3=CN(C4(CF)CC4)NN3)cccc2c1=O] | (S)-8-chloro-6-(((1-(1-(fluoromethyl)cyclopropyl)-1H-1,2,3-triazol-4-yl)(2-methyl-1-oxo-1,2-dihydroisoquinolin-5-yl)methyl)amino)-4-(neopentylamino)quinoline-3-carbonitrile | 4 | 599.30 |
| 776 | 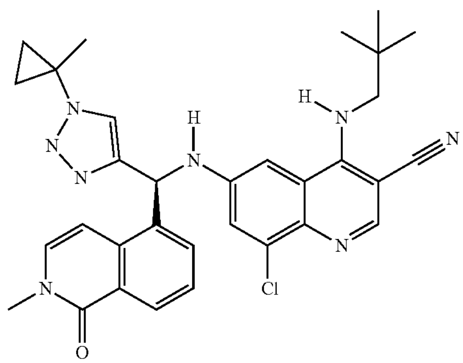 [SMILES: Cn1ccc2c([C@H](Nc3cc(Cl)c4ncc(C#N)c(NCC(C)(C)C)c4c3)C3=CN(C4(C)CC4)NN3)cccc2c1=O] | (S)-8-chloro-6-(((2-methyl-1-oxo-1,2-dihydroisoquinolin-5-yl)(1-(1-methylcyclopropyl)-1H-1,2,3-triazol-4-yl)methyl)amino)-4-(neopentylamino)quinoline-3-carbonitrile | 4 | 581.30 |
| 777 | 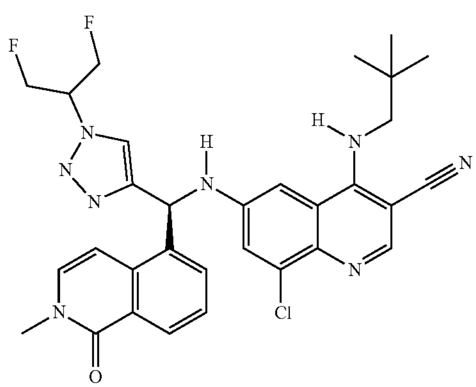 [SMILES: Cn1ccc2c([C@H](Nc3cc(Cl)c4ncc(C#N)c(NCC(C)(C)C)c4c3)C3=CN(C(CF)CF)NN3)cccc2c1=O] | (S)-8-chloro-6-(((1-(1,3-difluoropropan-2-yl)-1H-1,2,3-triazol-4-yl)(2-methyl-1-oxo-1,2-dihydroisoquinolin-5-yl)methyl)amino)-4-(neopentylamino)quinoline-3-carbonitrile | 4 | 605.30 |
| 778 | 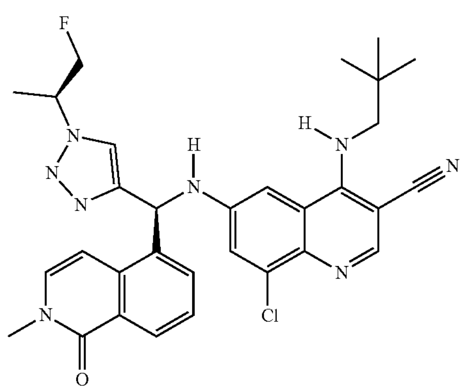 [SMILES: C[C@@H](CF)N1C=C([C@@H](Nc2cc(Cl)c3ncc(C#N)c(NCC(C)(C)C)c3c2)c2cccc3c(=O)n(C)ccc23)NN1] | 8-chloro-6-(((S)-(1-((S)-1-fluoropropan-2-yl)-1H-1,2,3-triazol-4-yl)(2-methyl-1-oxo-1,2-dihydroisoquinolin-5-yl)methyl)amino)-4-(neopentylamino)quinoline-3-carbonitrile | 4 | 587.30 |

TABLE 1-continued

| Comp | Structure | Name | Example Procedure | ES/MS m/z |
|---|---|---|---|---|
| 779 | 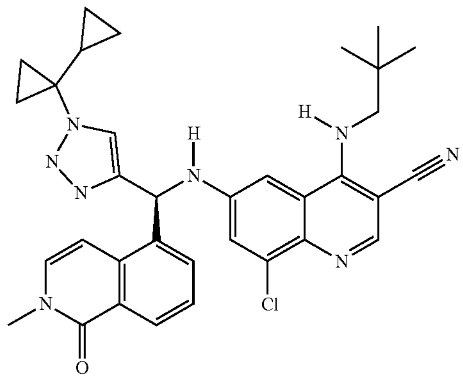 [SMILES: Cn1ccc2c([C@H](Nc3cc(Cl)c4ncc(C#N)c(NCC(C)(C)C)c4c3)C3=CN(C4(C5CC5)CC4)NN3)cccc2c1=O] | (S)-6-(((1-([1,1'-bi(cyclopropan)]-1-yl)-1H-1,2,3-triazol-4-yl)(2-methyl-1-oxo-1,2-dihydroisoquinolin-5-yl)methyl)amino)-8-chloro-4-(neopentylamino)quinoline-3-carbonitrile | 4 | 607.30 |
| 780 | 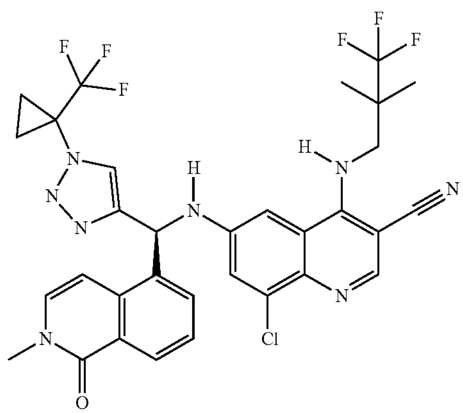 [SMILES: Cn1ccc2c([C@H](Nc3cc(Cl)c4ncc(C#N)c(NCC(C)(C)C(F)(F)F)c4c3)C3=CN(C4(C(F)(F)F)CC4)NN3)cccc2c1=O] | (S)-8-chloro-6-(((2-methyl-1-oxo-1,2-dihydroisoquinolin-5-yl)(1-(1-(trifluoromethyl)-cyclopropyl)-1H-1,2,3-triazol-4-yl)methyl)amino)-4-((3,3,3-trifluoro-2,2-dimethylpropyl)amino)-quinoline-3-carbonitrile | 4 | 689.20 |
| 781 | 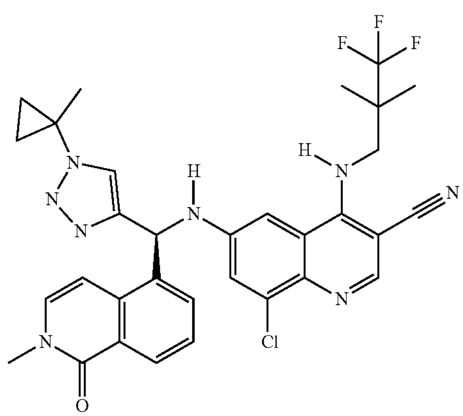 [SMILES: Cn1ccc2c([C@H](Nc3cc(Cl)c4ncc(C#N)c(NCC(C)(C)C(F)(F)F)c4c3)C3=CN(C4(C)CC4)NN3)cccc2c1=O] | (S)-8-chloro-6-(((2-methyl-1-oxo-1,2-dihydroiso-quinolin-5-yl)(1-(1-methylcyclopropyl)-1H-1,2,3-triazol-4-yl)methyl)amino)-4-((3,3,3-trifluoro-2,2-dimethylpropyl)amino)quinoline-3-carbonitrile | 4 | 635.20 |
| 782 | 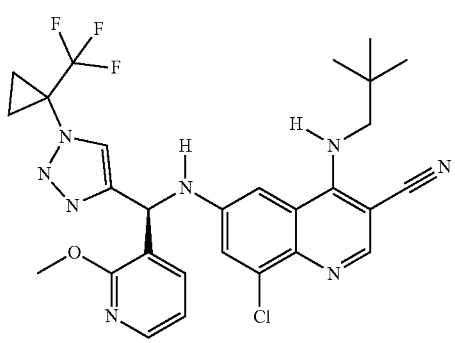 [SMILES: COc1ncccc1[C@H](Nc1cc(Cl)c2ncc(C#N)c(NCC(C)(C)C)c2c1)C1=CN(C2(C(F)(F)F)CC2)NN1] | (S)-8-chloro-6-(((2-methoxypyridin-3-yl)(1-(1-(trifluoromethyl)cyclopropyl)-1H-1,2,3-triazol-4-yl)methyl)amino)-4-(neopentylamino)quinoline-3-carbonitrile | 4 | 585.40 |

TABLE 1-continued

| Comp | Structure | Name | Example Procedure | ES/MS m/z |
|---|---|---|---|---|
| 783 | 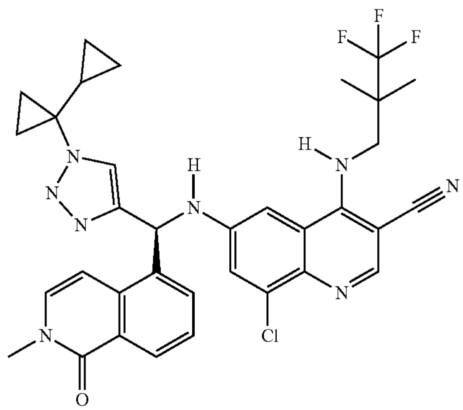 [SMILES: Cn1ccc2c([C@H](Nc3cc(Cl)c4ncc(C#N)c(NCC(C)(C)C(F)(F)F)c4c3)C3=CN(C4(C5CC5)CC4)NN3)cccc2c1=O] | (S)-6-(((1-([1,1'-bi(cyclopropan)]-1-yl)-1H-1,2,3-triazol-4-yl)(2-methyl-1-oxo-1,2-dihydroisoquinolin-5-yl)methyl)amino)-8-chloro-4-((3,3,3-trifluoro-2,2-dimethylpropyl)amino)quinoline-3-carbonitrile | 4 | 661.20 |
| 784 | 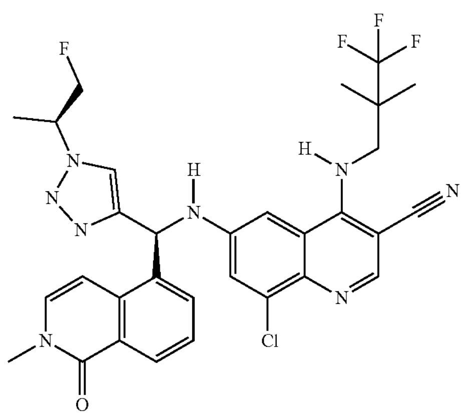 [SMILES: C[C@@H](CF)N1C=C([C@@H](Nc2cc(Cl)c3ncc(C#N)c(NCC(C)(C)C(F)(F)F)c3c2)c2cccc3c(=O)n(C)ccc23)NN1] | 8-chloro-6-(((S)-(1-((S)-1-fluoropropan-2-yl)-1H-1,2,3-triazol-4-yl)(2-methyl-1-oxo-1,2-dihydroisoquinolin-5-yl)methyl)amino)-4-((3,3,3-trifluoro-2,2-dimethylpropyl)amino)quinoline-3-carbonitrile | 4 | 641.10 |
| 785 | 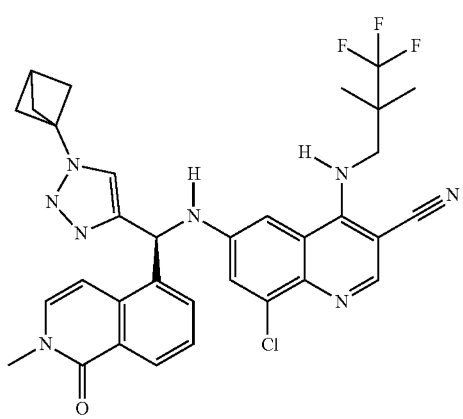 [SMILES: Cn1ccc2c([C@H](Nc3cc(Cl)c4ncc(C#N)c(NCC(C)(C)C(F)(F)F)c4c3)C3=CN(C45CC(C4)C5)NN3)cccc2c1=O] | (S)-6-(((1-(bicyclo[1.1.1]pentan-1-yl)-1H-1,2,3-triazol-4-yl)(2-methyl-1-oxo-1,2-dihydroisoquinolin-5-yl)methyl)amino)-8-chloro-4-((3,3,3-trifluoro-2,2-dimethylpropyl)amino)quinoline-3-carbonitrile | 4 | 647.20 |

TABLE 1-continued

| Comp | Structure | Name | Example Procedure | ES/MS m/z |
|---|---|---|---|---|
| 786 | 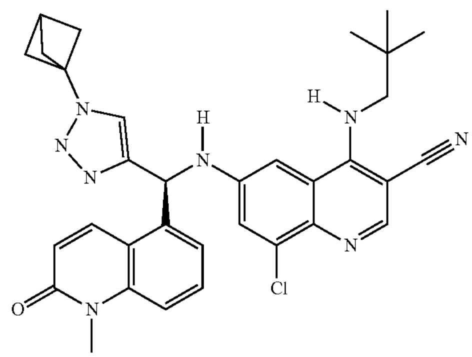 [SMILES: Cn1c(=O)ccc2c([C@H](Nc3cc(Cl)c4ncc(C#N)c(NCC(C)(C)C)c4c3)C3=CN(C45CC(C4)C5)NN3)cccc21] | (S)-6-(((1-(bicyclo[1.1.1]pentan-1-yl)-1H-1,2,3-triazol-4-yl)(1-methyl-2-oxo-1,2-dihydroquinolin-5-yl)methyl)amino)-8-chloro-4-(neopentylamino)quinoline-3-carbonitrile | 4 | 593.30 |
| 787 | 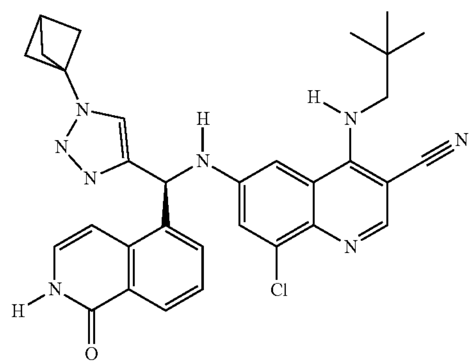 [SMILES: CC(C)(C)CNc1c(C#N)cnc2c(Cl)cc(N[C@H](C3=CN(C45CC(C4)C5)NN3)c3cccc4c(=O)[nH]ccc34)cc12] | (S)-6-(((1-(bicyclo[1.1.1]pentan-1-yl)-1H-1,2,3-triazol-4-yl)(1-oxo-1,2-dihydroisoquinolin-5-yl)methyl)amino)-8-chloro-4-(neopentylamino)quinoline-3-carbonitrile | 4 | 579.20 |
| 788 | 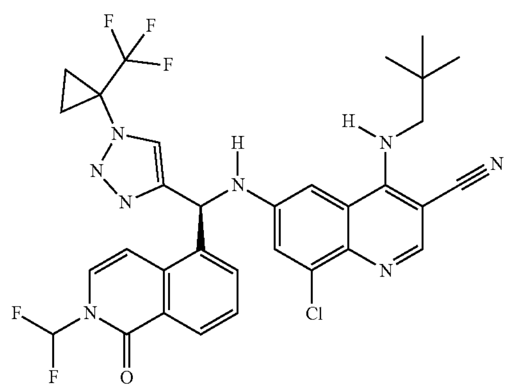 [SMILES: CC(C)(C)CNc1c(C#N)cnc2c(Cl)cc(N[C@H](C3=CN(C4(C(F)(F)F)CC4)NN3)c3cccc4c(=O)n(C(F)F)ccc34)cc12] | (S)-8-chloro-6-(((2-(difluoromethyl)-1-oxo-1,2-dihydroisoquinolin-5-yl)(1-(1-(trifluoromethyl)cyclopropyl)-1H-1,2,3-triazol-4-yl)methyl)amino)-4-(neopentylamino)quinoline-3-carbonitrile | 4 | 671.50 |
| 789 | 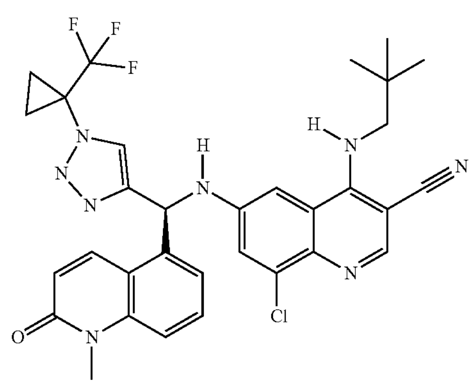 [SMILES: Cn1c(=O)ccc2c([C@H](Nc3cc(Cl)c4ncc(C#N)c(NCC(C)(C)C)c4c3)C3=CN(C4(C(F)(F)F)CC4)NN3)cccc21] | (S)-8-chloro-6-(((1-methyl-2-oxo-1,2-dihydroquinolin-5-yl)(1-(1-(trifluoromethyl)cyclopropyl)-1H-1,2,3-triazol-4-yl)methyl)amino)-4-(neopentylamino)quinoline-3-carbonitrile | 4 | 635.40 |

TABLE 1-continued

| Comp | Structure | Name | Example Procedure | ES/MS m/z |
|---|---|---|---|---|
| 790 | 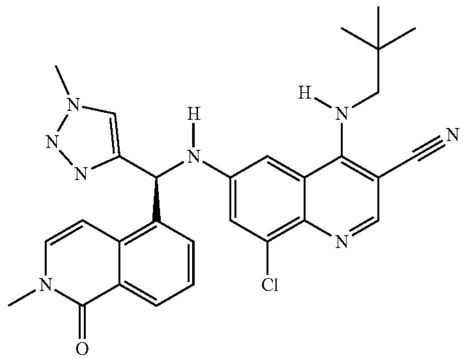 [SMILES: CN1C=C([C@@H](Nc2cc(Cl)c3ncc(C#N)c(NCC(C)(C)C)c3c2)c2cccc3c(=O)n(C)ccc23)NN1] | (S)-8-chloro-6-(((2-methyl-1-oxo-1,2-dihydroisoquinolin-5-yl)(1-methyl-1H-1,2,3-triazol-4-yl)methyl)amino)-4-(neopentylamino)quinoline-3-carbonitrile | 22 | 541.20 |
| 791 | 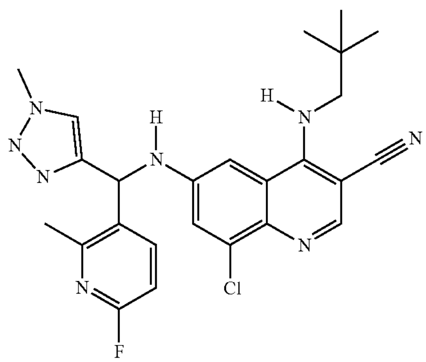 [SMILES: Cc1nc(F)ccc1C(Nc1cc(Cl)c2ncc(C#N)c(NCC(C)(C)C)c2c1)C1=CN(C)NN1] | 8-chloro-6-(((6-fluoro-2-methylpyridin-3-yl)(1-methyl-1H-1,2,3-triazol-4-yl)methyl)amino)-4-(neopentylamino)quinoline-3-carbonitrile | 22 | 493.10 |
| 792 | 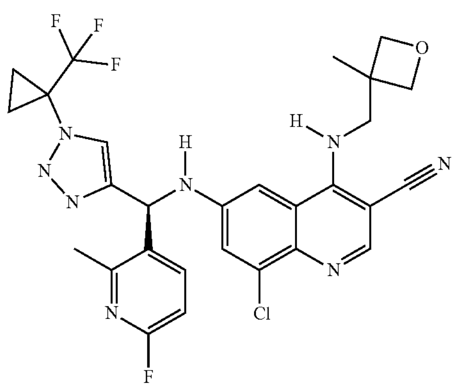 [SMILES: Cc1nc(F)ccc1[C@H](Nc1cc(Cl)c2ncc(C#N)c(NCC3(C)COC3)c2c1)C1=CN(C2(C(F)(F)F)CC2)NN1] | (S)-8-chloro-6-(((6-fluoro-2-methylpyridin-3-yl)(1-(1-(trifluoromethyl)-cyclopropyl)-1H-1,2,3-triazol-4-yl)methyl)amino)-4-(((3-methyloxetan-3-yl)methyl)amino)quinoline-3-carbonitrile | 23 | 601.34 |
| 793 | 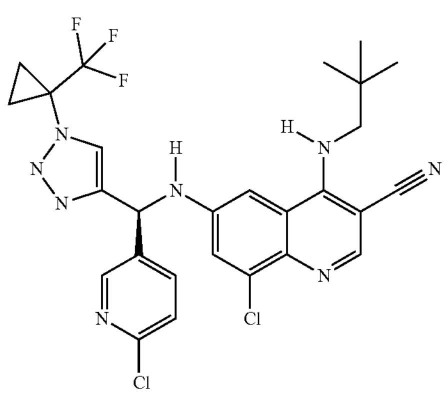 [SMILES: CC(C)(C)CNc1c(C#N)cnc2c(Cl)cc(N[C@H](C3=CN(C4(C(F)(F)F)CC4)NN3)c3ccc(Cl)nc3)cc12] | (S)-8-chloro-6-(((6-chloropyridin-3-yl)(1-(1-(trifluoromethyl)cyclopropyl)-1H-1,2,3-triazol-4-yl)methyl)amino)-4-(neopentylamino)quinoline-3-carbonitrile | 23 | 589.39 |

TABLE 1-continued

| Comp | Structure | Name | Example Procedure | ES/MS m/z |
|---|---|---|---|---|
| 794 | 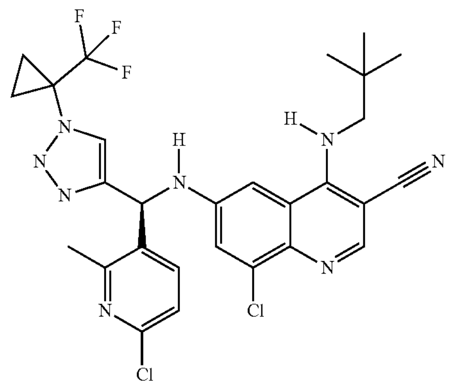 [SMILES: Cc1nc(Cl)ccc1[C@H](Nc1cc(Cl)c2ncc(C#N)c(NCC(C)(C)C)c2c1)C1=CN(C2(C(F)(F)F)CC2)NN1] | (S)-8-chloro-6-(((6-chloro-2-methylpyridin-3-yl)(1-(1-(trifluoromethyl)-cyclopropyl)-1H-1,2,3-triazol-4-yl)methyl)amino)-4-(neopentylamino)quinoline-3-carbonitrile | 23 | 602.22 |
| 795 | 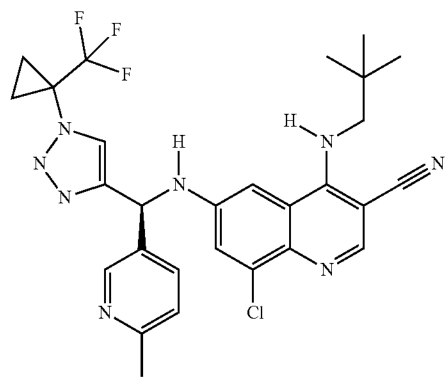 [SMILES: Cc1ccc([C@H](Nc2cc(Cl)c3ncc(C#N)c(NCC(C)(C)C)c3c2)C2=CN(C3(C(F)(F)F)CC3)NN2)cn1] | (S)-8-chloro-6-(((6-methylpyridin-3-yl)(1-(1-(trifluoromethyl)cyclopropyl)-1H-1,2,3-triazol-4-yl)methyl)amino)-4-(neopentylamino)quinoline-3-carbonitrile | 23 | 569.27 |
| 796 | 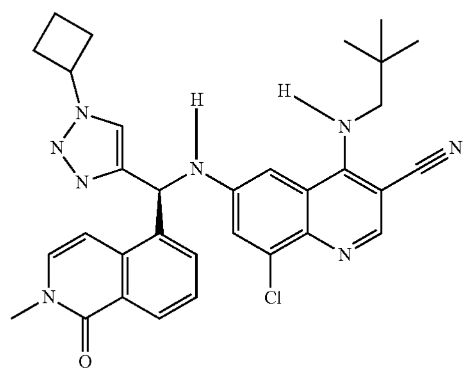 [SMILES: Cn1ccc2c([C@H](Nc3cc(Cl)c4ncc(C#N)c(NCC(C)(C)C)c4c3)C3=CN(C4CCC4)NN3)cccc2c1=O] | (S)-8-chloro-6-(((1-cyclobutyl-1H-1,2,3-triazol-4-yl)(2-methyl-1-oxo-1,2-dihydroisoquinolin-5-yl)methyl)amino)-4-(neopentylamino)quinoline-3-carbonitrile | 23 | 581.21 |
| 797 | 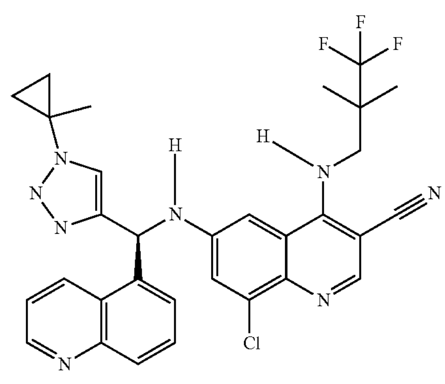 [SMILES: CC1(N2C=C([C@@H](Nc3cc(Cl)c4ncc(C#N)c(NCC(C)(C)C(F)(F)F)c4c3)c3cccc4ncccc34)NN2)CC1] | (S)-8-chloro-6-(((1-(1-methylcyclopropyl)-1H-1,2,3-triazol-4-yl)(quinolin-5-yl)methyl)amino)-4-((3,3,3-trifluoro-2,2-dimethylpropyl)amino)quinoline-3-carbonitrile | 23 | 605.14 |

TABLE 1-continued

| Comp | Structure | Name | Example Procedure | ES/MS m/z |
|---|---|---|---|---|
| 798 | 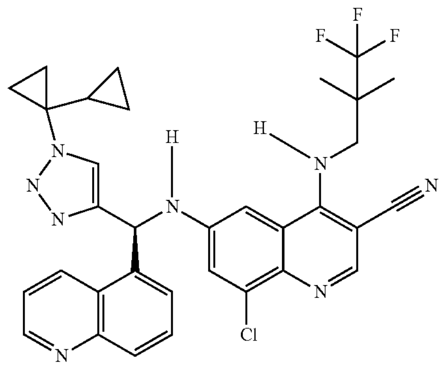 [SMILES: CC(C)(CNc1c(C#N)cnc2c(Cl)cc(N[C@H](C3=CN(C4(C5CC5)CC4)NN3)c3cccc4ncccc34)cc12)C(F)(F)F] | (S)-6-(((1-([1,1'-bi(cyclopropan)]-1-yl)-1H-1,2,3-triazol-4-yl)(quinolin-5-yl)methyl)amino)-8-chloro-4-((3,3,3-trifluoro-2,2-dimethylpropyl)amino)quinoline-3-carbonitrile | 23 | 631.09 |
| 799 | 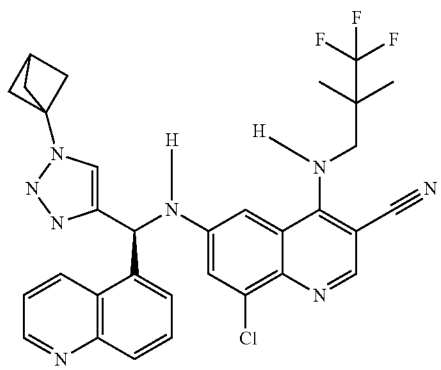 [SMILES: CC(C)(CNc1c(C#N)cnc2c(Cl)cc(N[C@H](C3=CN(C45CC(C4)C5)NN3)c3cccc4ncccc34)cc12)C(F)(F)F] | (S)-6-(((1-(bicyclo[1.1.1]pentan-1-yl)-1H-1,2,3-triazol-4-yl)(quinolin-5-yl)methyl)amino)-8-chloro-4-((3,3,3-trifluoro-2,2-dimethylpropyl)amino)quinoline-3-carbonitrile | 23 | 617.18 |
| 800 | 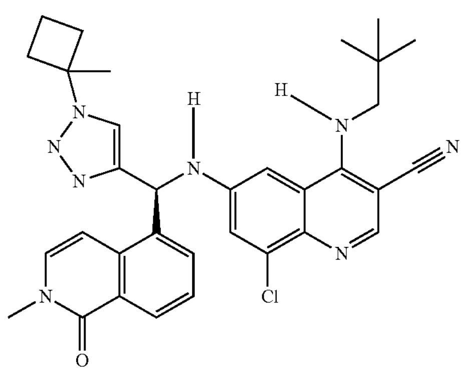 [SMILES: Cn1ccc2c([C@H](Nc3cc(Cl)c4ncc(C#N)c(NCC(C)(C)C)c4c3)C3=CN(C4(C)CCC4)NN3)cccc2c1=O] | (S)-8-chloro-6-(((2-methyl-1-oxo-1,2-dihydroisoquinolin-5-yl)(1-(1-methylcyclobutyl)-1H-1,2,3-triazol-4-yl)methyl)amino)-4-(neopentylamino)quinoline-3-carbonitrile | 23 | 595.23 |
| 801 | 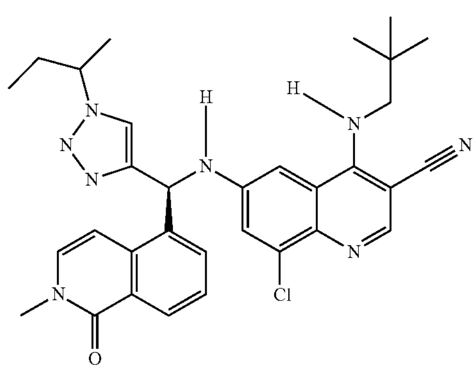 [SMILES: CCC(C)N1C=C([C@@H](Nc2cc(Cl)c3ncc(C#N)c(NCC(C)(C)C)c3c2)c2cccc3c(=O)n(C)ccc23)NN1] | 6-(((1 S)-(1-(sec-butyl)-1H-1,2,3-triazol-4-yl)(2-methyl-1-oxo-1,2-dihydroisoquinolin-5-yl)methyl)amino)-8-chloro-4-(neopentylamino)quinoline-3-carbonitrile | 23 | 583.28 |

TABLE 1-continued

| Comp | Structure | Name | Example Procedure | ES/MS m/z |
|---|---|---|---|---|
| 802 | 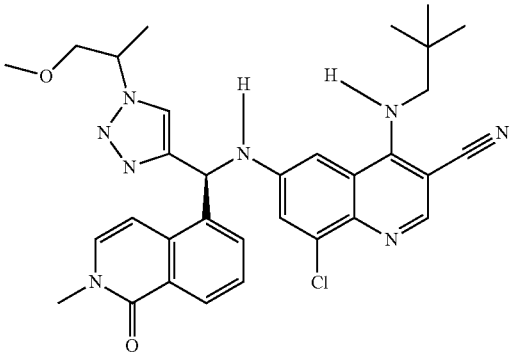 [SMILES: COCC(C)N1C=C([C@@H](Nc2cc(Cl)c3ncc(C#N)c(NCC(C)(C)C)c3c2)c2cccc3c(=O)n(C)ccc23)NN1] | 8-chloro-6-(((S)-(1-((S)-1-methoxypropan-2-yl)-1H-1,2,3-triazol-4-yl)(2-methyl-1-oxo-1,2-dihydroisoquinolin-5-yl)methyl)amino)-4-(neopentylamino)quinoline-3-carbonitrile | 23 | 599.36 |
| 803 | 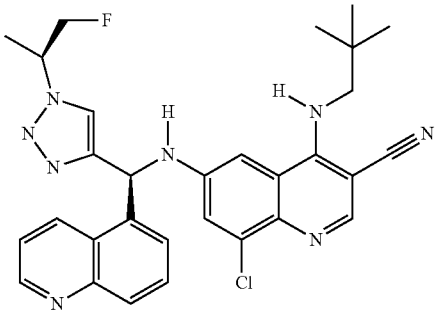 [SMILES: C[C@@H](CF)N1C=C([C@@H](Nc2cc(Cl)c3ncc(C#N)c(NCC(C)(C)C)c3c2)c2cccc3ncccc23)NN1] | 8-chloro-6-(((S)-(1-((S)-1-fluoropropan-2-yl)-1H-1,2,3-triazol-4-yl)(quinolin-5-yl)methyl)amino)-4-(neopentylamino)quinoline-3-carbonitrile | 23 | 557.28 |
| 804 | 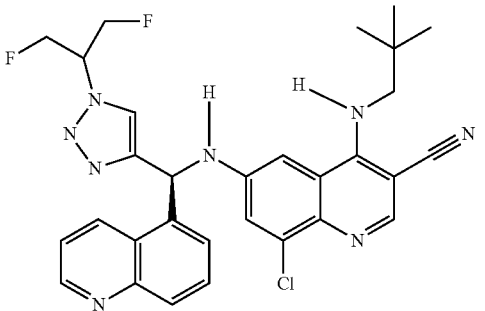 [SMILES: CC(C)(C)CNc1c(C#N)cnc2c(Cl)cc(N[C@H](C3=CN(C(CF)CF)NN3)c3cccc4ncccc34)cc12] | (S)-8-chloro-6-(((1-(1,3-difluoropropan-2-yl)-1H-1,2,3-triazol-4-yl)(quinolin-5-yl)methyl)amino)-4-(neopentylamino)quinoline-3-carbonitrile | 23 | 575.19 |
| 805 | 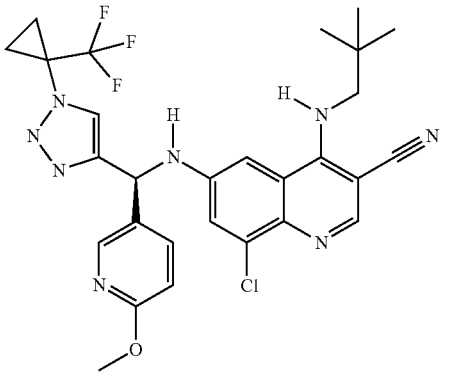 [SMILES: COc1ccc([C@H](Nc2cc(Cl)c3ncc(C#N)c(NCC(C)(C)C)c3c2)C2=CN(C3(C(F)(F)F)CC3)NN2)cn1] | (S)-8-chloro-6-(((6-methoxypyridin-3-yl)(1-(1-(trifluoromethyl)cyclopropyl)-1H-1,2,3-triazol-4-yl)methyl)amino)-4-(neopentylamino)quinoline-3-carbonitrile | 23 | 585.20 |

TABLE 1-continued

| Comp | Structure | Name | Example Procedure | ES/MS m/z |
|---|---|---|---|---|
| 806 | 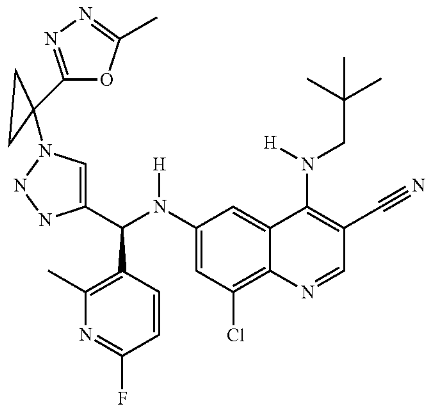 [SMILES: Cc1nnc(C2(N3C=C([C@@H](Nc4cc(Cl)c5ncc(C#N)c(NCC(C)(C)C)c5c4)c4ccc(F)nc4C)NN3)CC2)o1] | (S)-8-chloro-6-(((6-fluoro-2-methylpyridin-3-yl)(1-(1-(5-methyl-1,3,4-oxadiazol-2-yl)cyclopropyl)-1H-1,2,3-triazol-4-yl)methyl)amino)-4-(neopentylamino)quinoline-3-carbonitrile | 23 | 601.30 |
| 807 | 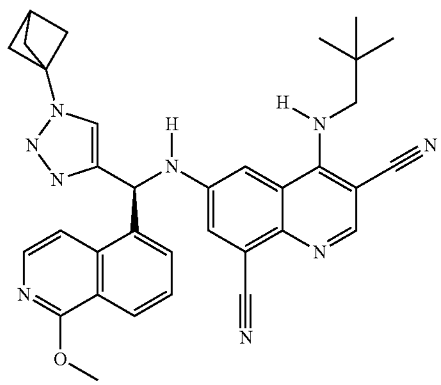 [SMILES: COc1nccc2c([C@H](Nc3cc(C#N)c4ncc(C#N)c(NCC(C)(C)C)c4c3)C3=CN(C45CC(C4)C5)NN3)cccc12] | (S)-6-(((1-(bicyclo[1.1.1]pentan-1-yl)-1H-1,2,3-triazol-4-yl)(1-methoxyisoquinolin-5-yl)methyl)amino)-4-(neopentylamino)quinoline-3,8-dicarbonitrile | 24 | 584.40 |
| 808 | 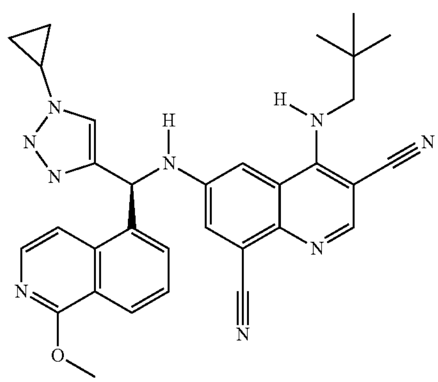 [SMILES: COc1nccc2c([C@H](Nc3cc(C#N)c4ncc(C#N)c(NCC(C)(C)C)c4c3)C3=CN(C4CC4)NN3)cccc12] | (S)-6-(((1-cyclopropyl-1H-1,2,3-triazol-4-yl)(1-methoxyisoquinolin-5-yl)methyl)airiino)-4-(neopentylamino)quinoline-3,8-dicarbonitrile | 24 | 558.32 |
| 809 | 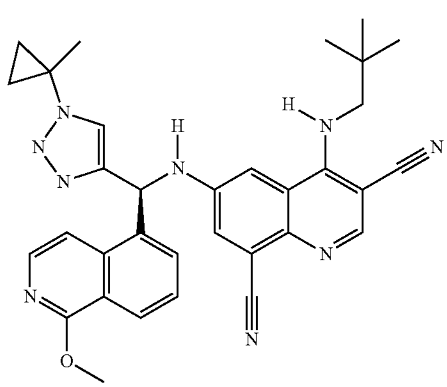 [SMILES: COc1nccc2c([C@H](Nc3cc(C#N)c4ncc(C#N)c(NCC(C)(C)C)c4c3)C3=CN(C4(C)CC4)NN3)cccc12] | (S)-6-(((1-methoxyisoquinolin-5-yl)(1-(1-methylcyclopropyl)-1H-1,2,3-triazol-4-yl)methyl)amino)-4-(neopentylamino)quinoline-3,8-dicarbonitrile | 24 | 572.32 |

TABLE 1-continued

| Comp | Structure | Name | Example Procedure | ES/MS m/z |
|---|---|---|---|---|
| 810 | 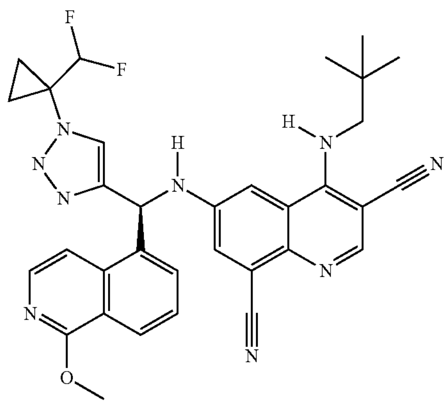 [SMILES: COc1nccc2c([C@H](Nc3cc(C#N)c4ncc(C#N)c(NCC(C)(C)C)c4c3)C3=CN(C4(C(F)F)CC4)NN3)cccc12] | (S)-6-(((1-(1-(difluoromethyl)-cyclopropyl)-1H-1,2,3-triazol-4-yl)(1-methoxylsoquinolin-5-yl)methyl)amino)-4-(neopentylamino)quinoline-3,8-dicarbonitrile | 24 | 608.43 |
| 811 | 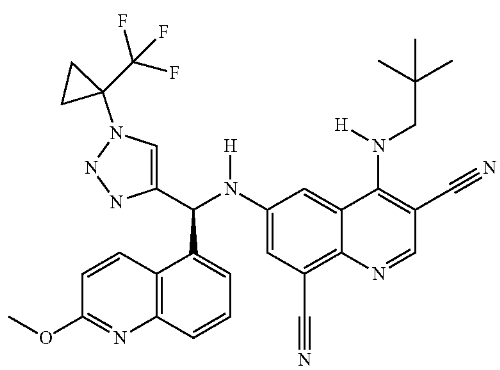 [SMILES: COc1ccc2c([C@H](Nc3cc(C#N)c4ncc(C#N)c(NCC(C)(C)C)c4c3)C3=CN(C4(C(F)(F)F)CC4)NN3)cccc2n1] | (S)-6-(((2-methoxyquinolin-5-yl)(1-(1-(trifluoromethyl)cyclopropyl)-1H-1,2,3-triazol-4-yl)methyl)amino)-4-(neopentylamino)quinoline-3,8-dicarbonitrile | 24 | 625.17 |
| 812 | 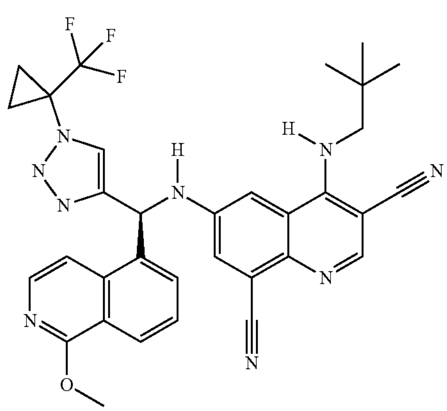 [SMILES: COc1nccc2c([C@H](Nc3cc(C#N)c4ncc(C#N)c(NCC(C)(C)C)c4c3)C3=CN(C4(C(F)(F)F)CC4)NN3)cccc12] | (S)-6-(((1-methoxylsoquinolin-5-yl)(1-(1-(trifluoromethyl)cyclopropyl)-1H-1,2,3-triazol-4-yl)methyl)amino)-4-(neopentylamino)quinoline-3,8-dicarbonitrile | 24 | 625.28 |

TABLE 1-continued

| Comp | Structure | Name | Example Procedure | ES/MS m/z |
|---|---|---|---|---|
| 813 | 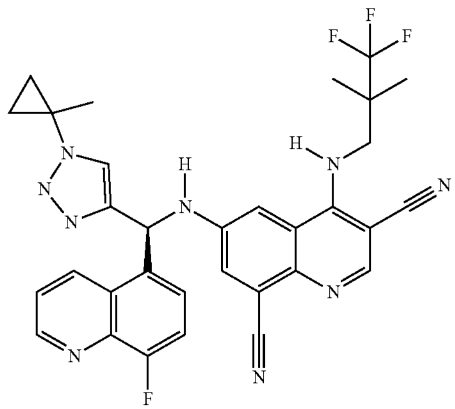 [SMILES: CC1(N2C=C([C@@H](Nc3cc(C#N)c4ncc(C#N)c(NCC(C)(C)C(F)(F)F)c4c3)c3ccc(F)c4ncccc34)NN2)CC1] | (S)-6-(((8-fluoroquinolin-5-yl)(1-(1-methylcyclopropyl)-1H-1,2,3-triazol-4-yl)methyl)amino)-4-((3,3,3-trifluoro-2,2-dimethylpropyl)amino)quinoline-3,8-dicarbonitrile | 24 | 614.13 |
| 814 | 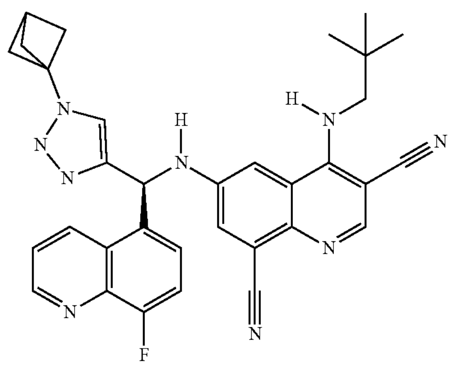 [SMILES: CC(C)(C)CNc1c(C#N)cnc2c(C#N)cc(N[C@H](C3=CN(C45CC(C4)C5)NN3)c3ccc(F)c4ncccc34)cc12] | (S)-6-(((1-(bicyclo[1.1.1]pentan-1-yl)-1H-1,2,3-triazol-4-yl)(8-fluoroquinolin-5-yl)methyl)amino)-4-(neopentylamino)quinoline-3,8-dicarbonitrile | 24 | 572.26 |
| 815 | 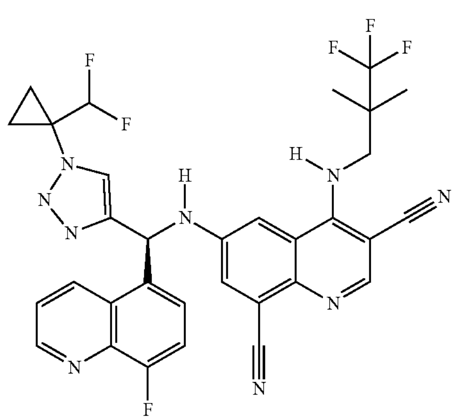 [SMILES: CC(C)(CNc1c(C#N)cnc2c(C#N)cc(N[C@H](C3=CN(C4(C(F)F)CC4)NN3)c3ccc(F)c4ncccc34)cc12)C(F)(F)F] | (S)-6-(((1-{1-(difluoromethyl)-cyclopropyl}-1H-1,2,3-triazol-4-yl)(8-fluoroquinolin-5-yl)methyl)amino)-4-((3,3,3-trifluoro-2,2-dimethylpropyl)amino)quinoline-3,8-dicarbonitrile | 24 | 650.48 |

TABLE 1-continued

| Comp | Structure | Name | Example Procedure | ES/MS m/z |
|---|---|---|---|---|
| 816 | 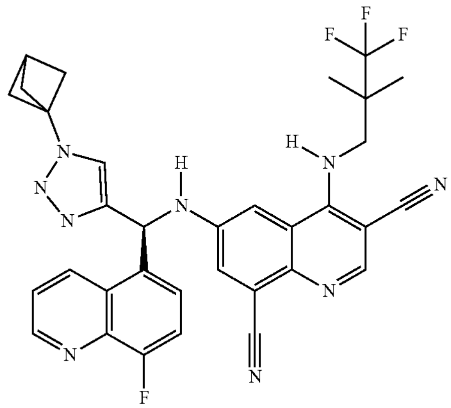 [SMILES: CC(C)(CNc1c(C#N)cnc2c(C#N)cc(N[C@H](C3=CN(C45CC(C4)C5)NN3)c3ccc(F)c4ncccc34)cc12)C(F)(F)F] | (S)-6-(((1-(bicyclo[1.1.1]pentan-1-yl)-1H-1,2,3-triazol-4-yl)(8-fluoroquinolin-5-yl)methyl)amino)-4-((3,3,3-trifluoro-2,2-dimethylpropyl)amino)quinoline-3,8-dicarbonitrile | 24 | 626.49 |
| 817 | 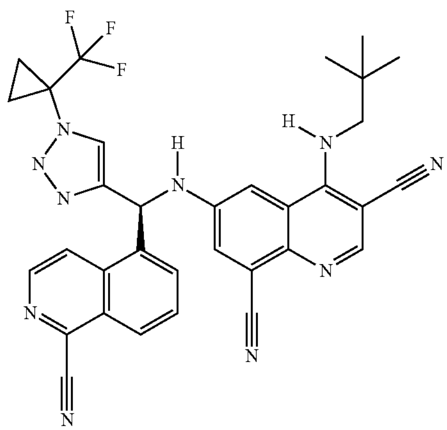 [SMILES: CC(C)(C)CNc1c(C#N)cnc2c(C#N)cc(N[C@H](C3=CN(C4(C(F)(F)F)CC4)NN3)c3cccc4c(C#N)nccc34)cc12] | (S)-6-(((1-cyanoisoquinolin-5-yl)(1-(1-(trifluoromethyl)cyclopropyl)-1H-1,2,3-triazol-4-yl)methyl)amino)-4-(neopentylamino)quinoline-3,8-dicarbonitrile | 24 | 621.60 |
| 818 | 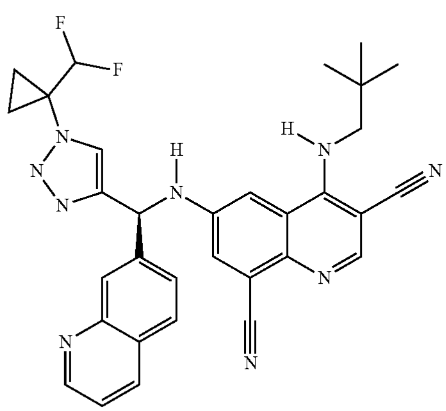 [SMILES: CC(C)(C)CNc1c(C#N)cnc2c(C#N)cc(N[C@H](C3=CN(C4(C(F)F)CC4)NN3)c3ccc4cccnc4c3)cc12] | (S)-6-(((1-(1-(difluoromethyl)-cyclopropyl)-1H-1,2,3-triazol-4-yl)(quinolin-7-yl)methyl)amino)-4-(neopentylamino)quinoline-3,8-dicarbonitrile | 24 | 578.15 |

| Comp | Structure | Name | Example Procedure | ES/MS m/z |
|---|---|---|---|---|
| 819 | 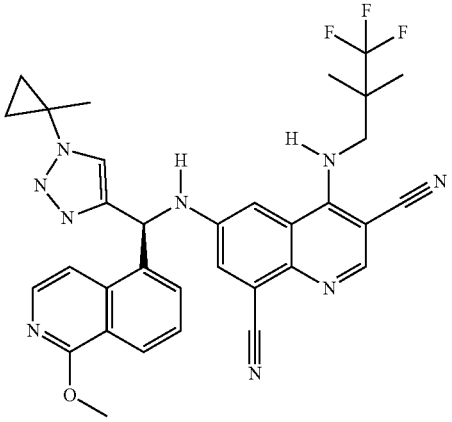 [SMILES: COc1nccc2c([C@H](Nc3cc(C#N)c4ncc(C#N)c(NCC(C)(C)C(F)(F)F)c4c3)C3=CN(C4(C)CC4)NN3)cccc12] | (S)-6-(((1-methoxylsoquinolin-5-yl)(1-(1-methylcyclopropyl)-1H-1,2,3-triazol-4-yl)methyl)amino)-4-((3,3,3-trifluoro-2,2-dimethylpropyl)amino)quinoline-3,8-dicarbonitrile | 24 | 626.22 |
| 820 | 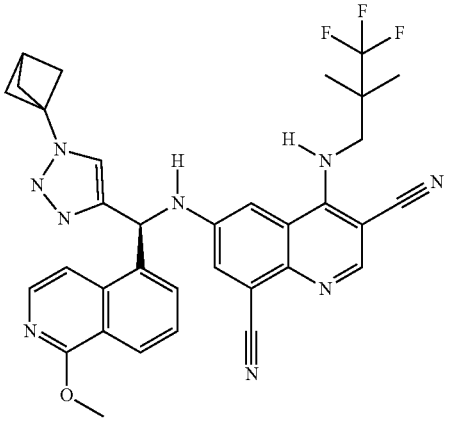 [SMILES: COc1nccc2c([C@H](Nc3cc(C#N)c4ncc(C#N)c(NCC(C)(C)C(F)(F)F)c4c3)C3=CN(C45CC(C4)C5)NN3)cccc12] | (S)-6-(((1-(bicyclo[1.1.1]pentan-1-yl)-1H-1,2,3-triazol-4-yl)(1-methoxylsoquinolin-5-yl)methyl)amino)-4-((3,3,3-trifluoro-2,2-dimethylpropyl)amino)quinoline-3,8-dicarbonitrile | 24 | 638.16 |
| 821 | 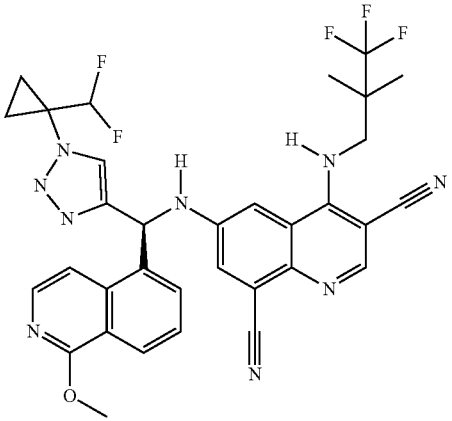 [SMILES: COc1nccc2c([C@H](Nc3cc(C#N)c4ncc(C#N)c(NCC(C)(C)C(F)(F)F)c4c3)C3=CN(C4(C(F)F)CC4)NN3)cccc12] | (S)-6-(((Ml-(difluoromethyl)cyclopropyl)-1H-1,2,3-triazol-4-yl)(1-methoxylsoquinolin-5-yl)methyl)amino)-4-((3,3,3-trifluoro-2,2-dimethylpropyl)amino)quinoline-3,8-dicarbonitrile | 24 | 662.50 |

TABLE 1-continued

| Comp | Structure | Name | Example Procedure | ES/MS m/z |
|---|---|---|---|---|
| 822 | 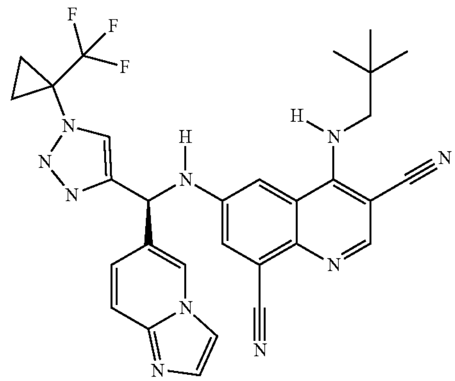 [SMILES: CC(C)(C)CNc1c(C#N)cnc2c(C#N)cc(N[C@H](C3=CN(C4(C(F)(F)F)CC4)NN3)c3ccc4nccn4c3)cc12] | (S)-6-((imidazo[1,2-a]pyridin-6-yl(1-(1-(trifluoromethyl)cyclopropyl)-1H-1,2,3-triazol-4-yl)methyl)amino)-4-(neopentylamino)quinoline-3,8-dicarbonitrile | 24 | 584.11 |
| 823 | 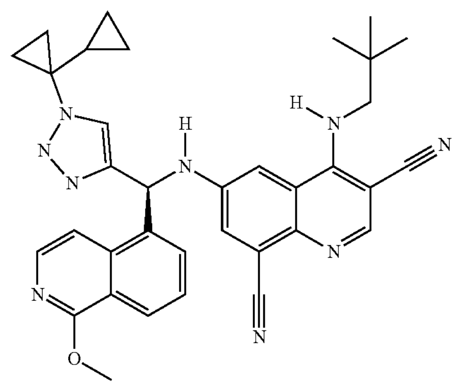 [SMILES: COc1nccc2c([C@H](Nc3cc(C#N)c4ncc(C#N)c(NCC(C)(C)C)c4c3)C3=CN(C4(C5CC5)CC4)NN3)cccc12] | (S)-6-(((1-([1,1'-bi(cyclopropan)]-1-yl)-1H-1,2,3-triazol-4-yl)(1-methoxylsoquinolin-5-yl)methyl)amino)-4-(neopentylamino)quinoline-3,8-dicarbonitrile | 24 | 598.63 |
| 824 | 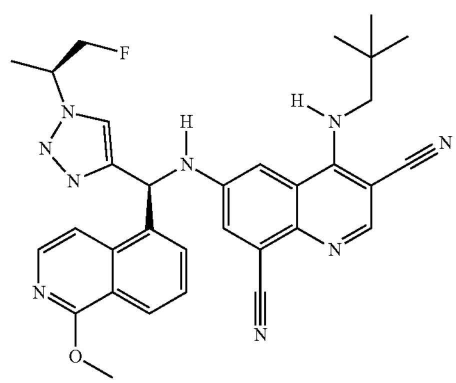 [SMILES: COc1nccc2c([C@H](Nc3cc(C#N)c4ncc(C#N)c(NCC(C)(C)C)c4c3)C3=CN([C@@H](C)CF)NN3)cccc12] | 6-(((S)-(1-((S)-1-fluoropropan-2-yl)-1H-1,2,3-triazol-4-yl)(1-methoxylsoquinolin-5-yl)methyl)amino)-4-(neopentylamino)quinoline-3,8-dicarbonitrile | 24 | 578.43 |
| 825 | 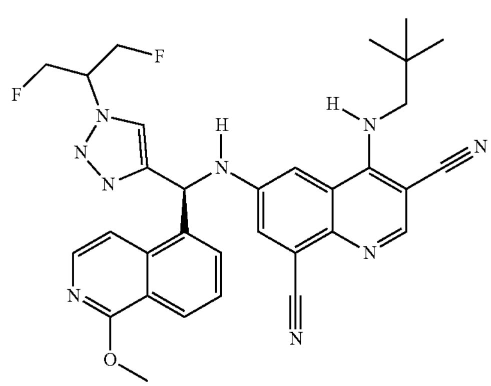 [SMILES: COc1nccc2c([C@H](Nc3cc(C#N)c4ncc(C#N)c(NCC(C)(C)C)c4c3)C3=CN(C(CF)CF)NN3)cccc12] | (S)-6-(((1-(1,3-difluoropropan-2-yl)-1H-1,2,3-triazol-4-yl)(1-methoxylsoquinolin-5-yl)methyl)amino)-4-(neopentylamino)quinoline-3,8-dicarbonitrile | 24 | 596.67 |

TABLE 1-continued

| Comp | Structure | Name | Example Procedure | ES/MS m/z |
|---|---|---|---|---|
| 826 | 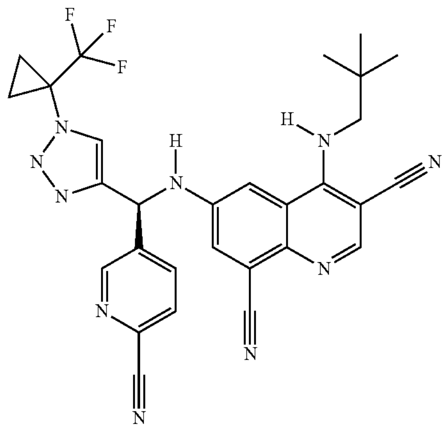 [SMILES: CC(C)(C)CNc1c(C#N)cnc2c(C#N)cc(N[C@H](C3=CN(C4(C(F)(F)F)CC4)NN3)c3ccc(C#N)nc3)cc12] | (S)-6-(((6-cyanopyridin-3-yl)(1-(1-(trifluoromethyl)cyclopropyl)-1H-1,2,3-triazol-4-yl)methyl)amino)-4-(neopentylamino)quinoline-3,8-dicarbonitrile | 24 | 571.27 |
| 827 | 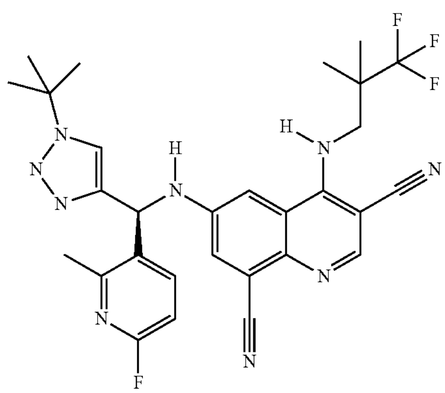 [SMILES: Cc1nc(F)ccc1[C@H](Nc1cc(C#N)c2ncc(C#N)c(NCC(C)(C)C(F)(F)F)c2c1)C1=CN(C(C)(C)C)NN1] | (S)-6-(((1-(tert-butyl)-1H-1,2,3-triazol-4-yl)(6-fluoro-2-methylpyridin-3-yl)methyl)amino)-4-((3,3,3-trifluoro-2,2-dimethylpropyl)amino)quinoline-3,8-dicarbonitrile | 24 | 580.56 |
| 828 | 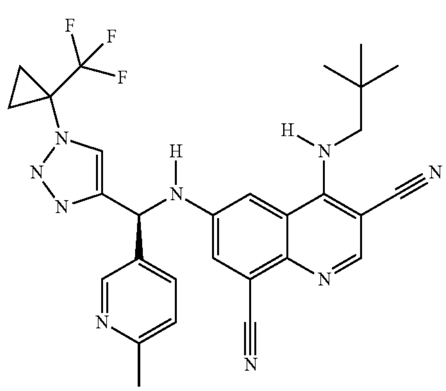 [SMILES: Cc1ccc([C@H](Nc2cc(C#N)c3ncc(C#N)c(NCC(C)(C)C)c3c2)C2=CN(C3(C(F)(F)F)CC3)NN2)cn1] | (S)-6-(((6-methylpyridin-3-yl)(1-(1-(trifluoromethyl)cyclopropyl)-1H-1,2,3-triazol-4-yl)methyl)amino)-4-(neopentylamino)quinoline-3,8-dicarbonitrile | 24 | 560.12 |

TABLE 1-continued

| Comp | Structure | Name | Example Procedure | ES/MS m/z |
|---|---|---|---|---|
| 829 | 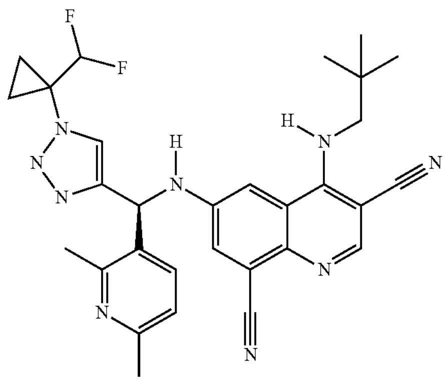 [SMILES: Cc1ccc([C@H](Nc2cc(C#N)c3ncc(C#N)c(NCC(C)(C)C)c3c2)C2=CN(C3(C(F)F)CC3)NN2)c(C)n1] | (S)-6-(((1-(1-(difluoromethyl)-cyclopropyl)-1H-1,2,3-triazol-4-yl)(2,6-dimethylpyridin-3-yl)methyl)amino)-4-(neopentylamino)quinoline-3,8-dicarbonitrile | 24 | 555.26 |
| 830 | 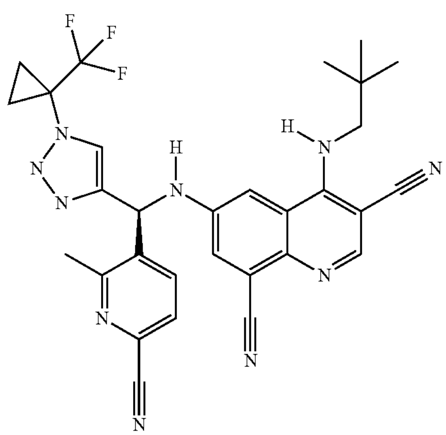 [SMILES: Cc1nc(C#N)ccc1[C@H](Nc1cc(C#N)c2ncc(C#N)c(NCC(C)(C)C)c2c1)C1=CN(C2(C(F)(F)F)CC2)NN1] | (S)-6-(((6-cyano-2-methylpyridin-3-yl)(1-(1-(trifluoromethyl)cyclopropyl)-1H-1,2,3-triazol-4-yl)methyl)amino)-4-(neopentylamino)quinoline-3,8-dicarbonitrile | 24 | 585.55 |
| 831 | 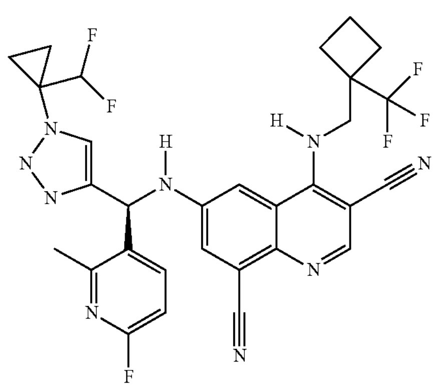 [SMILES: Cc1nc(F)ccc1[C@H](Nc1cc(C#N)c2ncc(C#N)c(NCC3(C(F)(F)F)CCC3)c2c1)C1=CN(C2(C(F)F)CC2)NN1] | (S)-6-(((1-(1-(difluoromethyl)-cyclopropyl)-1H-1,2,3-triazol-4-yl)(6-fluoro-2-methylpyridin-3-yl)methyl)amino)-4-(((1-(trifluoromethyl)cyclobutyl)methyl)-amino)quinoline-3,8-dicarbonitrile | 24 | 626.37 (M + H+) |

TABLE 1-continued

| Comp | Structure | Name | Example Procedure | ES/MS m/z |
|---|---|---|---|---|
| 832 | 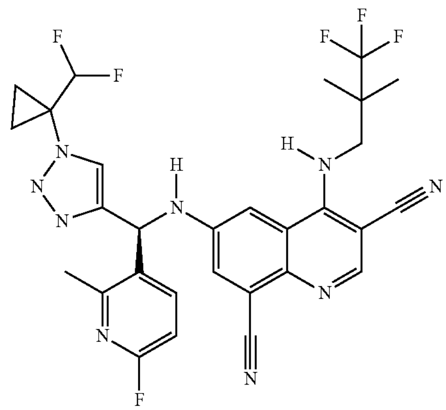 [SMILES: Cc1nc(F)ccc1[C@H](Nc1cc(C#N)c2ncc(C#N)c(NCC(C)(C)C(F)(F)F)c2c1)C1=CN(C2(C(F)F)CC2)NN1] | (S)-6-(((1-(1-(difluoromethyl)-cyclopropyl)-1H-1,2,3-triazol-4-yl)(6-fluoro-2-methylpyridin-3-yl)methyl)amino)-4-((3,3,3-trifluoro-2,2-dimethylpropyl)amino)quinoline-3,8-dicarbonitrile | 24 | 614.2 (M + H+) |
| 833 | 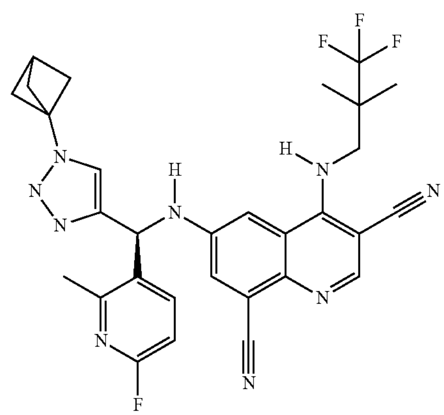 [SMILES: Cc1nc(F)ccc1[C@H](Nc1cc(C#N)c2ncc(C#N)c(NCC(C)(C)C(F)(F)F)c2c1)C1=CN(C23CC(C2)C3)NN1] | (S)-6-(((1-(bicyclo[1.1.1]pentan-1-yl)-1H-1,2,3-triazol-4-yl)(6-fluoro-2-methylpyridin-3-yl)methyl)amino)-4-((3,3,3-trifluoro-2,2-dimethylpropyl)amino)quinoline-3,8-dicarbonitrile | 24 | 590.5 (M + H+) |
| 834 | 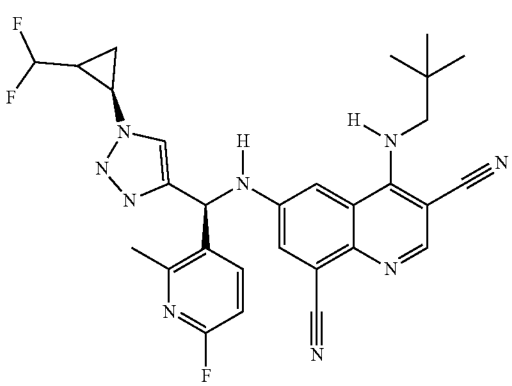 [SMILES: Cc1nc(F)ccc1[C@H](Nc1cc(C#N)c2ncc(C#N)c(NCC(C)(C)C)c2c1)C1=CN([C@@H]2CC2C(F)F)NN1] | 6-(((S)-(1-((1R,2R)-2-(difluoromethyl)cyclopropyl)-1H-1,2,3-triazol-4-yl)(6-fluoro-2-methylpyridin-3-yl)methyl)amino)-4- | 24 | 560.31 (M + H+) |

TABLE 1-continued

| Comp | Structure | Name | Example Procedure | ES/MS m/z |
|---|---|---|---|---|
| 835 | 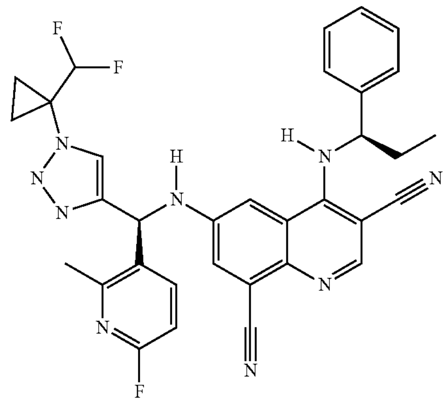 [SMILES: CC[C@@H](Nc1c(C#N)cnc2c(C#N)cc(N[C@H](C3=CN(C4(C(F)F)CC4)NN3)c3ccc(F)nc3C)cc12)c1ccccc1] | 6-(((S)-(1-(1-(difluoromethyl)cyclopropyl)-1H-1,2,3-triazol-4-yl)(6-fluoro-2-methylpyridin-3-yl)methyl)amino)-4-(((R)-1-phenylpropyl)amino)quinoline-3,8-dicarbonitrile | 24 | 548.30 |
| 836 | 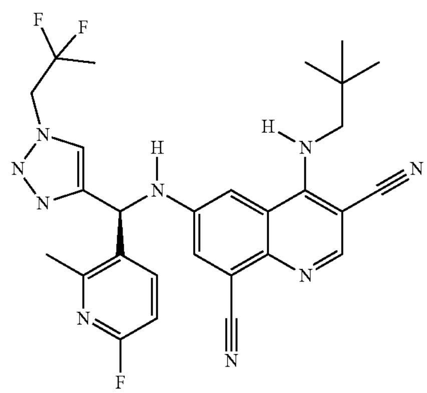 [SMILES: Cc1nc(F)ccc1[C@H](Nc1cc(C#N)c2ncc(C#N)c(NCC(C)(C)C)c2c1)C1=CN(CC(C)(F)F)NN1] | (S)-6-(((1-(2,2-difluoropropyl)-1H-1,2,3-triazol-4-yl)(6-fluoro-2-methylpyridin-3-yl)methyl)amino)-4-(neopentylamino)quinoline-3,8-dicarbonitrile | 24 | 548.30 |
| 837 | 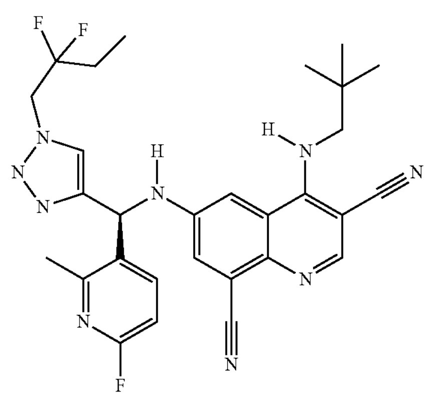 [SMILES: CCC(F)(F)CN1C=C([C@@H](Nc2cc(C#N)c3ncc(C#N)c(NCC(C)(C)C)c3c2)c2ccc(F)nc2C)NN1] | (S)-6-(((1-(2,2-difluorobutyl)-1H-1,2,3-triazol-4-yl)(6-fluoro-2-methylpyridin-3-yl)methyl)amino)-4-(neopentylamino)quinoline-3,8-dicarbonitrile | 24 | 562.35 (M + H+) |

TABLE 1-continued

| Comp | Structure | Name | Example Procedure | ES/MS m/z |
|---|---|---|---|---|
| 838 | 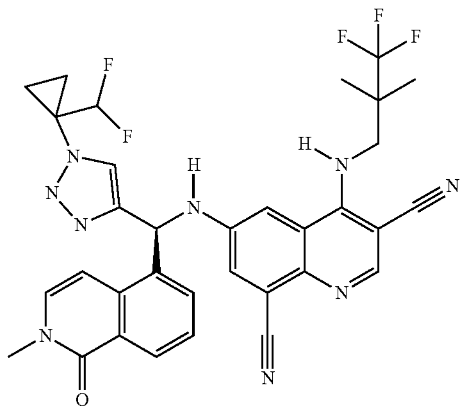 [SMILES: Cn1ccc2c([C@H](Nc3cc(C#N)c4ncc(C#N)c(NCC(C)(C)C(F)(F)F)c4c3)C3=CN(C4(C(F)F)CC4)NN3)cccc2c1=O] | (S)-6-(((1-(1-(difluoromethyl)-cyclopropyl)-1H-1,2,3-triazol-4-yl)(2-methyl-1-oxo-1,2-dihydroisoquinolin-5-yl)methyl)amino)-4-((3,3,3-trifluoro-2,2-dimethylpropyl)-amino)quinoline-3,8-dicarbonitrile | 24 | 662.5 (M + H+) |
| 839 | 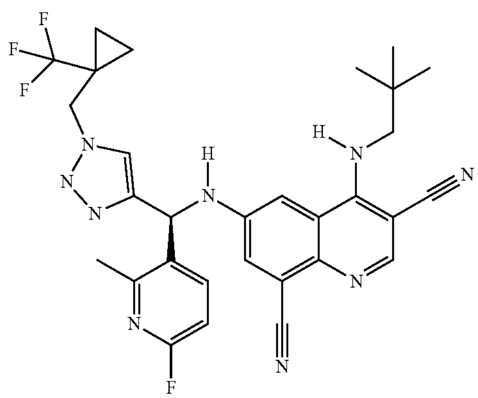 [SMILES: Cc1nc(F)ccc1[C@H](Nc1cc(C#N)c2ncc(C#N)c(NCC(C)(C)C)c2c1)C1=CN(CC2(C(F)(F)F)CC2)NN1] | (S)-6-(((6-fluoro-2-methylpyridin-3-yl)(1-((1-(trifluoromethyl)cyclo-propyl)methyl)-1H-1,2,3-triazol-4-yl)methyl)amino)-4-(neopentylamino)quinoline-3,8-dicarbonitrile | 24 | 592.3 (M + H+) |
| 840 | 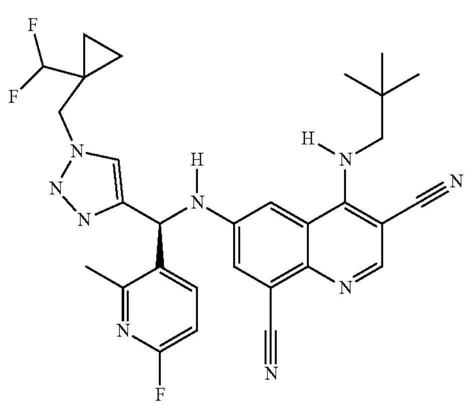 [SMILES: Cc1nc(F)ccc1[C@H](Nc1cc(C#N)c2ncc(C#N)c(NCC(C)(C)C)c2c1)C1=CN(CC2(C(F)F)CC2)NN1] | (S)-6-(((4-(1-(1-(difluoromethyl)cyclopropyl)methyl)-1H-1,2,3-triazol-4-yl)(6-fluoro-2-methylpyridin-3-yl)methyl)amino)-4-(neopentylamino)quinoline-3,8-dicarbonitrile | 24 | 574.35 (M + H+) |

TABLE 1-continued

| Comp | Structure | Name | Example Procedure | ES/MS m/z |
|---|---|---|---|---|
| 841 | 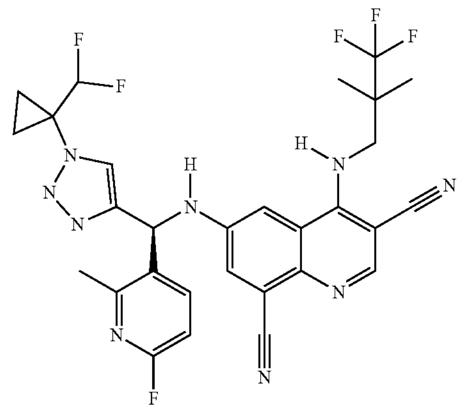 | (S)-6-(((4-(1-(difluoromethyl)-cyclopropyl)-1H-1,2,3-triazol-4-yl)(6-fluoro-2-methylpyridin-3-yl)methyl)amino)-4-((3,3,3-trifluoro-2,2-dimethylpropyl)amino)quinoline-3,8-dicarbonitrile | 24 | 613 (M + H+) |
| 842 | 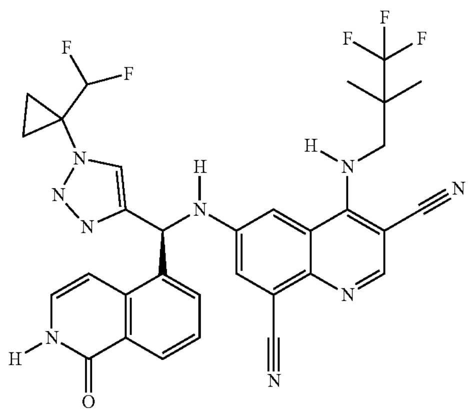 | (S)-6-(((H1-(difluoromethyl)-cyclopropyl)-1H-1,2,3-triazol-4-yl)(1-oxo-1,2-dihydroisoquinolin-5-yl)methyl)amino)-4-((3,3,3-trifluoro-2,2-dimethylpropyl)amino)quinoline-3,8-dicarbonitrile | 24 | 629.7 (M + H+) |
| 843 | 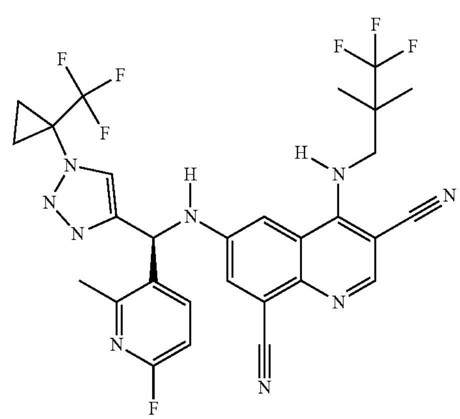 | (S)-6-(((6-fluoro-2-methylpyridin-3-yl)(1-(1-(trifluoromethyl)cyclopropyl)-1H-1,2,3-triazol-4-yl)methyl)amino)-4-((3,3,3-trifluoro-2,2-dimethylpropyl)amino)-quinoline-3,8-dicarbonitrile | 24 | 630.95 (M + H+) |

TABLE 1-continued

| Comp | Structure | Name | Example Procedure | ES/MS m/z |
|---|---|---|---|---|
| 844 | 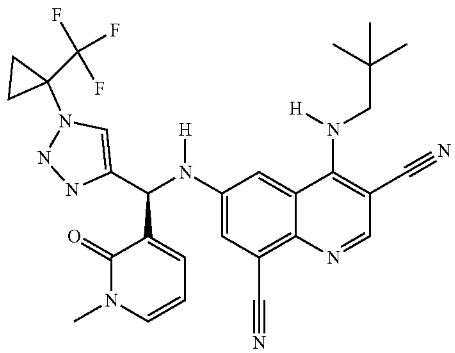 | (S)-6-(((1-methyl-2-oxo-1,2-dihydropyridin-3-yl)(1-(1-(trifluoromethyl)cyclopropyl)-1H-1,2,3-triazol-4-yl)methyl)amino)-4-(neopentylamino)quinoline-3,8-dicarbonitrile | 24 | 575.53 (M + H+) |
| 845 | 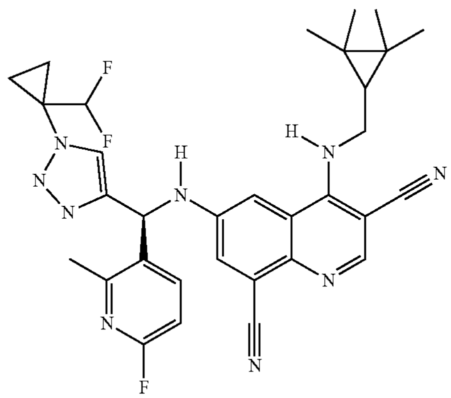 [SMILES: Cc1nc(F)ccc1[C@H](Nc1cc(C#N)c2ncc(C#N)c(NCC3C(C)(C)C3(C)C)c2c1)C1=CN(C2(C(F)F)CC2)NN1] | (S)-6-(((1-(1-(difluoromethyl)-cyclopropyl)-1H-1,2,3-triazol-4-yl)(6-fluoro-2-methylpyridin-3-yl)methyl)amino)-4-(((2,2,3,3-tetramethylcyclopropyl)methyl)-amino)quinoline-3,8-dicarbonitrile | 24 | 600.4 (M + H+) |
| 846 | 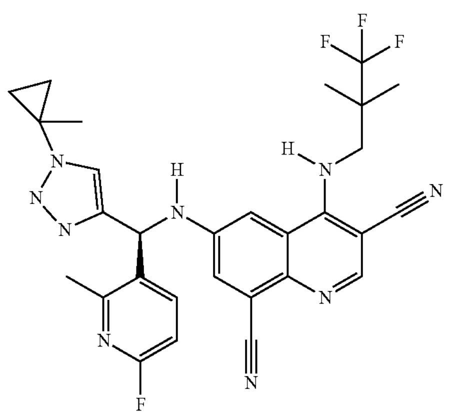 [SMILES: Cc1nc(F)ccc1[C@H](Nc1cc(C#N)c2ncc(C#N)c(NCC(C)(C)C(F)(F)F)c2c1)C1=CN(C2(C)CC2)NN1] | (S)-6-(((6-fluoro-2-methylpyridin-3-yl)(1-(1-methylcyclopropyl)-1H-1,2,3-triazol-4-yl)methyl)amino)-4-((3,3,3-trifluoro-2,2-dimethylpropyl)amino)quinoline-3,8-dicarbonitrile | 24 | 578.2 (M + H+) |
| 847 | 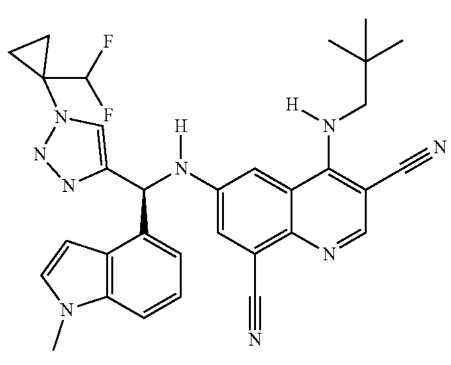 [SMILES: Cn1ccc2c([C@H](Nc3cc(C#N)c4ncc(C#N)c(NCC(C)(C)C)c4c3)C3=CN(C4(C(F)F)CC4)NN3)cccc21] | (S)-6-(((1-(1-(difluoromethyl)-cyclopropyl)-1H-1,2,3-triazol-4-yl)(1-methyl-1H-indol-4-yl)methyl)amino)-4-(neopentylamino)quinoline-3,8-dicarbonitrile | 24 | 580.12 (M + H+) |

TABLE 1-continued

| Comp | Structure | Name | Example Procedure | ES/MS m/z |
|---|---|---|---|---|
| 848 | 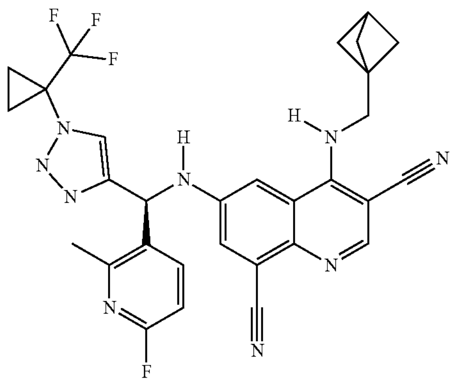 [SMILES: Cc1nc(F)ccc1[C@H](Nc1cc(C#N)c2ncc(C#N)c(NCC34CC(C3)C4)c2c1)C1=CN(C2(C(F)(F)F)CC2)NN1] | (S)-4-((bicyclo[1.1.1]pentan-1-ylmethyl)amino)-6-(((6-fluoro-2-methylpyridin-3-yl)(1-(1-(trifluoromethyl)cyclopropyl)-1H-1,2,3-triazol-4-yl)methyl)amino)quinoline-3,8-dicarbonitrile | 24 | 588.20 |
| 849 | 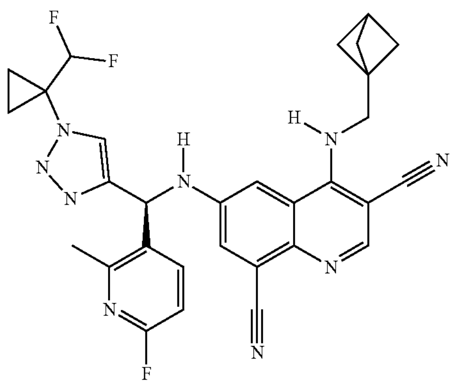 [SMILES: Cc1nc(F)ccc1[C@H](Nc1cc(C#N)c2ncc(C#N)c(NCC34CC(C3)C4)c2c1)C1=CN(C2(C(F)F)CC2)NN1] | (S)-4-((bicyclo[1.1.1]pentan-1-ylmethyl)amino)-6-(((1-(1-(difluoromethyl)-cyclopropyl)-1H-1,2,3-triazol-4-yl)(6-fluoro-2-methylpyridin-3-yl)methyl)amino)quinoline-3,8-dicarbonitrile | 24 | 570.20 |
| 850 | 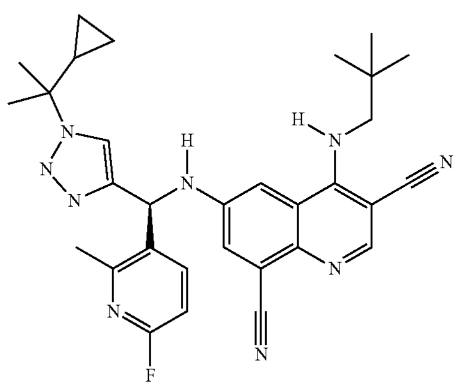 [SMILES: Cc1nc(F)ccc1[C@H](Nc1cc(C#N)c2ncc(C#N)c(NCC(C)(C)C)c2c1)C1=CN(C(C)(C)C2CC2)NN1] | (S)-6-(((1-{2-cyclopropylpropan-2-yl)-1H-1,2,3-triazol-4-yl)(6-fluoro-2-methylpyridin-3-yl)methyl)amino)-4-(neopentylamino)quinoline-3,8-dicarbonitrile | 24 | 552.50 |
| 851 | 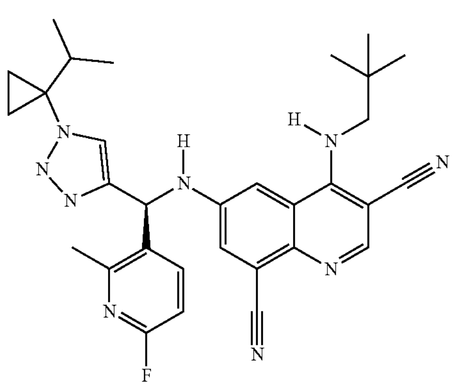 [SMILES: Cc1nc(F)ccc1[C@H](Nc1cc(C#N)c2ncc(C#N)c(NCC(C)(C)C)c2c1)C1=CN(C2(C(C)C)CC2)NN1] | (S)-6-(((6-fluoro-2-methylpyridin-3-yl)(1-(1-isopropylcyclopropyl)-1H-1,2,3-triazol-4-yl)methyl)amino)-4-(neopentylamino)quinoline-3,8-dicarbonitrile | 24 | 552.60 |

TABLE 1-continued

| Comp | Structure | Name | Example Procedure | ES/MS m/z |
|------|-----------|------|-------------------|-----------|
| 852 | 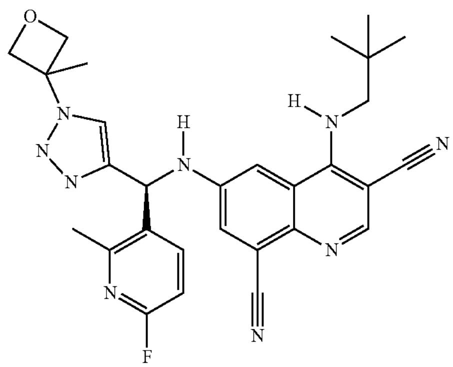 [SMILES: Cc1nc(F)ccc1[C@H](Nc1cc(C#N)c2ncc(C#N)c(NCC(C)(C)C)c2c1)C1=CN(C2(C)COC2)NN1] | (S)-6-(((6-fluoro-2-methylpyridin-3-yl)(1-(3-methyloxetan-3-yl)-1H-1,2,3-triazol-4-yl)methyl)amino)-4-(neopentylamino)quinoline-3,8-dicarbonitrile | 24 | 540.30 |
| 853 | 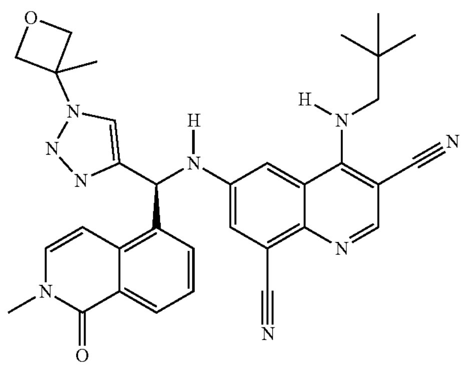 [SMILES: Cn1ccc2c([C@H](Nc3cc(C#N)c4ncc(C#N)c(NCC(C)(C)C)c4c3)C3=CN(C4(C)COC4)NN3)cccc2c1=O] | (S)-6-(((2-methyl-1-oxo-1,2-dihydroisoquinolin-5-yl)(1-(3-methyloxetan-3-yl)-1H-1,2,3-triazol-4-yl)methyl)amino)-4-(neopentylamino)quinoline-3,8-dicarbonitrile | 24 | 588.20 |
| 854 | 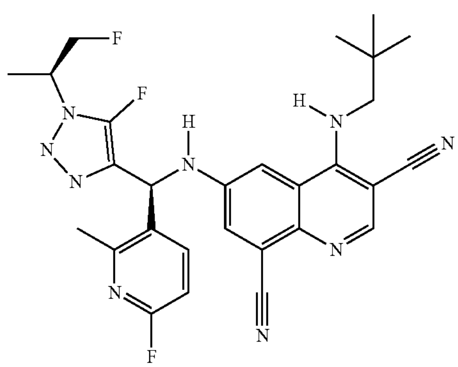 [SMILES: Cc1nc(F)ccc1[C@H](Nc1cc(C#N)c2ncc(C#N)c(NCC(C)(C)C)c2c1)C1=C(F)N([C@@H](C)CF)NN1] | 6-(((S)-(5-fluoro-1-((S)-1-fluoropropan-2-yl)-1H-1,2,3-triazol-4-yl)(6-fluoro-2-methylpyridin-3-yl)methyl)amino)-4-(neopentylamino)quinoline-3,8-dicarbonitrile | 24 | 548.20 |
| 855 | 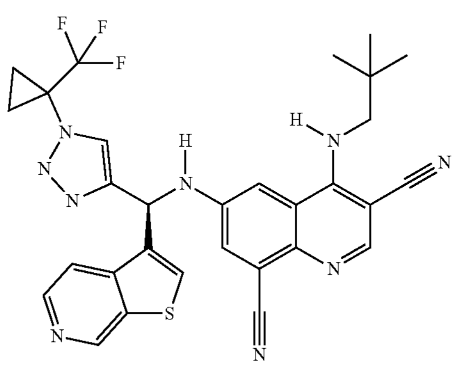 [SMILES: CC(C)(C)CNc1c(C#N)cnc2c(C#N)cc(N[C@H](C3=CN(C4(C(F)(F)F)CC4)NN3)c3csc4cnccc34)cc12] | (S)-4-(neopentylamino)-6-((thieno[2,3-c]pyridin-3-yl(1-(1-(trifluoromethyl)cyclopropyl)-1H-1,2,3-triazol-4-yl)methyl)amino)quinoline-3,8-dicarbonitrile | 24 | 602.10 |

TABLE 1-continued

| Comp | Structure | Name | Example Procedure | ES/MS m/z |
|---|---|---|---|---|
| 856 | 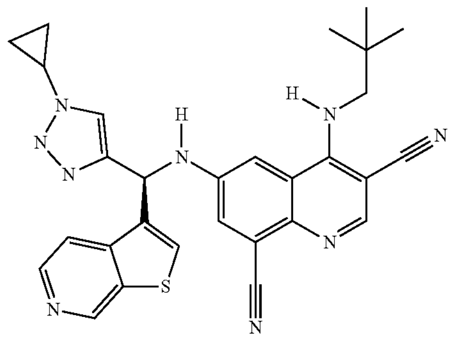 [SMILES: CC(C)(C)CNc1c(C#N)cnc2c(C#N)cc(N[C@H](C3=CN(C4CC4)NN3)c3csc4cnccc34)cc12] | (S)-6-(((1-cyclopropyl-1H-1,2,3-triazol-4-yl)(thieno[2,3-c]pyridin-3-yl)methyl)amino)-4-(neopentylamino)quinoline-3,8-dicarbonitrile | 24 | 534.30 |
| 857 | 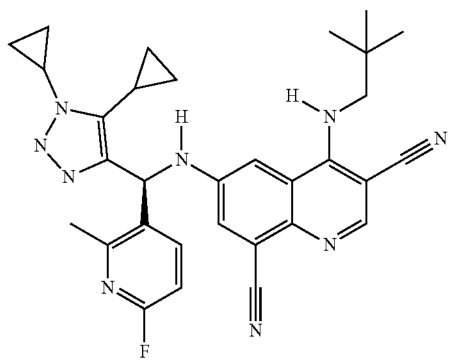 [SMILES: Cc1nc(F)ccc1[C@H](Nc1cc(C#N)c2ncc(C#N)c(NCC(C)(C)C)c2c1)C1=C(C2CC2)N(C2CC2)NN1] | (S)-6-(((1,5-dicyclopropyl-1H-1,2,3-triazol-4-yl)(6-fluoro-2-methylpyridin-3-yl)methyl)amino)-4-(neopentylamino)quinoline-3,8-dicarbonitrile | 24 | 550.29 |
| 858 | 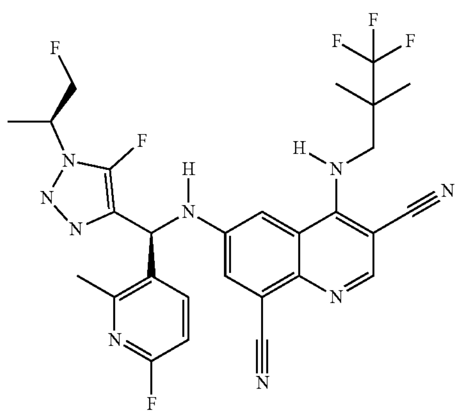 [SMILES: Cc1nc(F)ccc1[C@H](Nc1cc(C#N)c2ncc(C#N)c(NCC(C)(C)C(F)(F)F)c2c1)C1=C(F)N([C@@H](C)CF)NN1] | 6-(((S)-(5-fluoro-1-((S)-1-fluoropropan-2-yl)-1H-1,2,3-triazol-4-yl)(6-fluoro-2-methylpyridin-3-yl)methyl)amino)-4-((3,3,3-trifluoro-2,2-dimethylpropyl)amino)quinoline-3,8-dicarbonitrile | 24 | 602.10 |
| 859 | 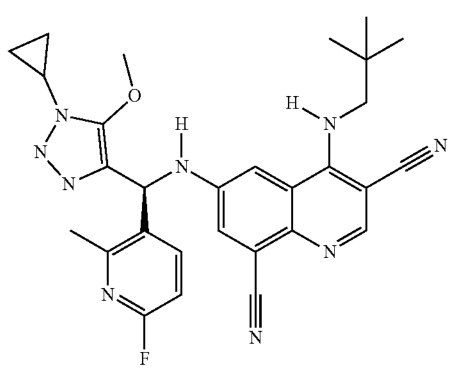 [SMILES: COC1=C([C@@H](Nc2cc(C#N)c3ncc(C#N)c(NCC(C)(C)C)c3c2)c2ccc(F)nc2C)NNN1C1CC1] | (S)-6-(((1-cyclopropyl-5-methoxy-1H-1,2,3-triazol-4-yl)(6-fluoro-2-methylpyridin-3-yl)methyl)amino)-4-(neopentylamino)quinoline-3,8-dicarbonitrile | 24 | 540.20 |

TABLE 1-continued

| Comp | Structure | Name | Example Procedure | ES/MS m/z |
|---|---|---|---|---|
| 860 | 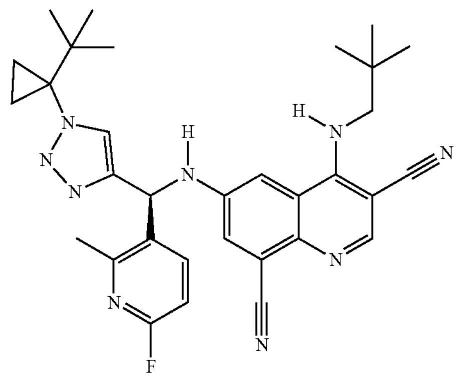 [SMILES: Cc1nc(F)ccc1[C@H](Nc1cc(C#N)c2ncc(C#N)c(NCC(C)(C)C)c2c1)C1=CN(C2(C(C)(C)C)CC2)NN1] | (S)-6-(((1-(1-(tert-butyl)cyclopropyl)-1H-1,2,3-triazol-4-yl)(6-fluoro-2-methylpyridin-3-yl)methyl)amino)-4-(neopentylamino)quinoline-3,8-dicarbonitrile | 24 | 566.40 |
| 861 | 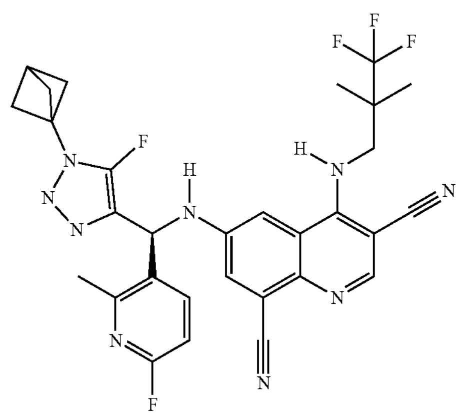 [SMILES: Cc1nc(F)ccc1[C@H](Nc1cc(C#N)c2ncc(C#N)c(NCC(C)(C)C(F)(F)F)c2c1)C1=C(F)N(C23CC(C2)C3)NN1] | (S)-6-(((1-(bicyclo[1.1.1]pentan-1-yl)-5-fluoro-1H-1,2,3-triazol-4-yl)(6-fluoro-2-methylpyridin-3-yl)methyl)amino)-4-((3,3,3-trifluoro-2,2-dimethylpropyl)amino)quinoline-3,8-dicarbonitrile | 24 | 608.30 |
| 862 | 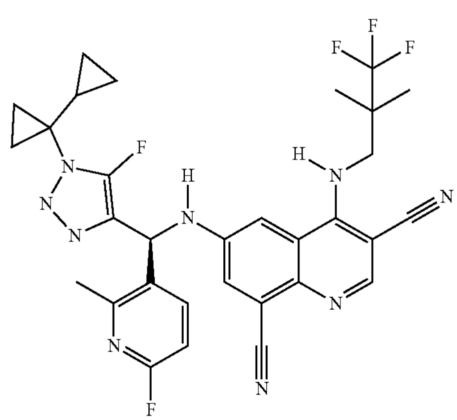 [SMILES: Cc1nc(F)ccc1[C@H](Nc1cc(C#N)c2ncc(C#N)c(NCC(C)(C)C(F)(F)F)c2c1)C1=C(F)N(C2(C3CC3)CC2)NN1] | (S)-6-(((1-([1,1'-bi(cyclopropan)]-1-yl)-5-fluoro-1H-1,2,3-triazol-4-yl)(6-fluoro-2-methylpyridin-3-yl)methyl)amino)-4-((3,3,3-trifluoro-2,2-dimethylpropyl)amino)quinoline-3,8-dicarbonitrile | 24 | 622.10 |

TABLE 1-continued

| Comp | Structure | Name | Example Procedure | ES/MS m/z |
|---|---|---|---|---|
| 863 | 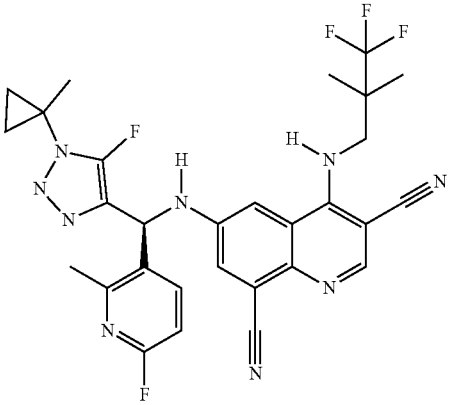 [SMILES: Cc1nc(F)ccc1[C@H](Nc1cc(C#N)c2ncc(C#N)c(NCC(C)(C)C(F)(F)F)c2c1)C1=C(F)N(C2(C)CC2)NN1] | (S)-6-(((5-fluoro-1-(1-methylcyclopropyl)-1H-1,2,3-triazol-4-yl)(6-fluoro-2-methylpyridin-3-yl)methyl)amino)-4-((3,3,3-trifluoro-2,2-dimethylpropyl)amino)-quinoline-3,8-dicarbonitrile | 24 | 596.20 |
| 864 | 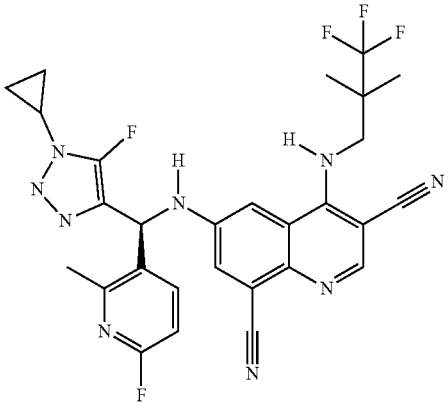 [SMILES: Cc1nc(F)ccc1[C@H](Nc1cc(C#N)c2ncc(C#N)c(NCC(C)(C)C(F)(F)F)c2c1)C1=C(F)N(C2CC2)NN1] | (S)-6-(((1-cyclopropyl-5-fluoro-1H-1,2,3-triazol-4-yl)(6-fluoro-2-methylpyridin-3-yl)methyl)amino)-4-((3,3,3-trifluoro-2,2-dimethylpropyl)amino)quinoline-3,8-dicarbonitrile | 24 | 582.10 |
| 865 | 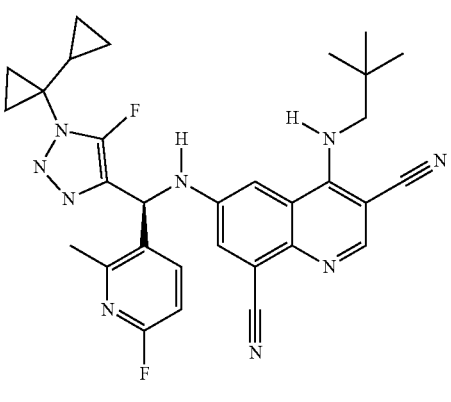 [SMILES: Cc1nc(F)ccc1[C@H](Nc1cc(C#N)c2ncc(C#N)c(NCC(C)(C)C)c2c1)C1=C(F)N(C2(C3CC3)CC2)NN1] | (S)-6-(((d-([1,1'-bi(cyclopropan)]-1-yl)-5-fluoro-1H-1,2,3-triazol-4-yl)(6-fluoro-2-methylpyridin-3-yl)methyl)amino)-4-(neopentylamino)quinoline-3,8-dicarbonitrile | 24 | 568.10 |

TABLE 1-continued

| Comp | Structure | Name | Example Procedure | ES/MS m/z |
|---|---|---|---|---|
| 866 | 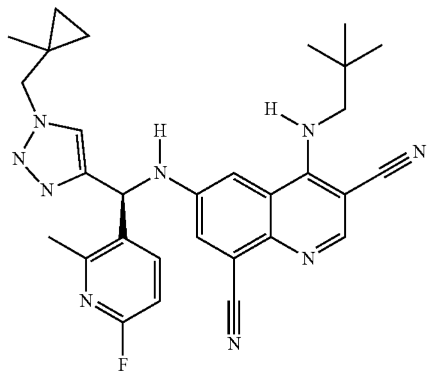 [SMILES: Cc1nc(F)ccc1[C@H](Nc1cc(C#N)c2ncc(C#N)c(NCC(C)(C)C)c2c1)C1=CN(CC2(C)CC2)NN1] | (S)-6-(((6-fluoro-2-methylpyridin-3-yl)(1-((1-methylcyclopropyl)methyl)-1H-1,2,3-triazol-4-yl)methyl)amino)-4-(neopentylamino)quinoline-3,8-dicarbonitrile | 24 | 538.30 |
| 867 | 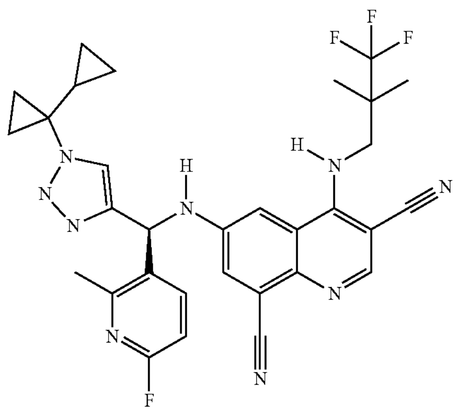 [SMILES: Cc1nc(F)ccc1[C@H](Nc1cc(C#N)c2ncc(C#N)c(NCC(C)(C)C(F)(F)F)c2c1)C1=CN(C2(C3CC3)CC2)NN1] | (S)-6-(((4-(1-(1,1-bi(cyclopropan)]-1-yl)-1H-1,2,3-triazol-4-yl)(6-fluoro-2-methylpyridin-3-yl)methyl)amino)-4-((3,3,3-trifluoro-2,2-dimethylpropyl)amino)quinoline-3,8-dicarbonitrile | 24 | 604.20 |
| 868 | 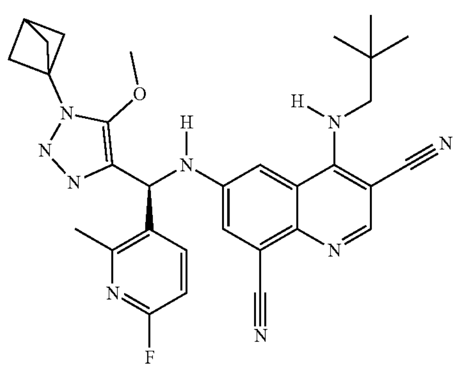 [SMILES: COC1=C([C@@H](Nc2cc(C#N)c3ncc(C#N)c(NCC(C)(C)C)c3c2)c2ccc(F)nc2C)NNN1C12CC(C1)C2] | (S)-6-(((1-(bicyclo[1.1.1]pentan-1-yl)-5-methoxy-1H-1,2,3-triazol-4-yl)(6-fluoro-2-methylpyridin-3-yl)methyl)amino)-4-(neopentylamino)quinoline-3,8-dicarbonitrile | 24 | 566.20 |
| 869 | 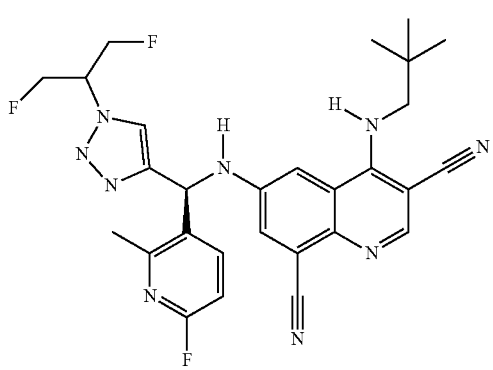 [SMILES: Cc1nc(F)ccc1[C@H](Nc1cc(C#N)c2ncc(C#N)c(NCC(C)(C)C)c2c1)C1=CN(C(CF)CF)NN1] | (S)-6-(((1-(1,3-difluoropropan-2-yl)-1H-1,2,3-triazol-4-yl)(6-fluoro-2-methylpyridin-3-yl)methyl)amino)-4-(neopentylamino)quinoline-3,8-dicarbonitrile | 24 | 548.20 |

TABLE 1-continued

| Comp | Structure | Name | Example Procedure | ES/MS m/z |
|------|-----------|------|-------------------|-----------|
| 870 | 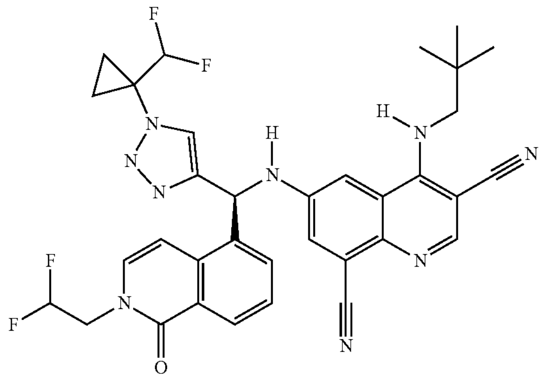 [SMILES: CC(C)(C)CNc1c(C#N)cnc2c(C#N)cc(N[C@H](C3=CN(C4(C(F)F)CC4)NN3)c3cccc4c(=O)n(CC(F)F)ccc34)cc12] | (S)-6-(((2-(2,2-difluoroethyl)-1-oxo-1,2-dihydroisoquinolin-5-yl)(1-(1-(difluoromethyl)cyclopropyl)-1H-1,2,3-triazol-4-yl)methyl)amino)-4-(neopentylamino)quinoline-3,8-dicarbonitrile | 24 | 658.30 |
| 871 | 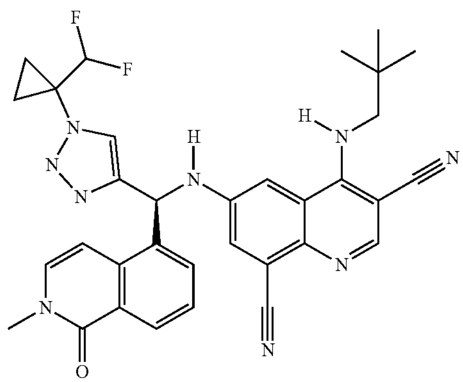 [SMILES: Cn1ccc2c([C@H](Nc3cc(C#N)c4ncc(C#N)c(NCC(C)(C)C)c4c3)C3=CN(C4(C(F)F)CC4)NN3)cccc2c1=O] | (S)-6-(((Ml-(difluoromethyl)cyclopropyl)-1H-1,2,3-triazol-4-yl)(2-methyl-1-oxo-1,2-dihydroisoquinolin-5-yl)methyl)amino)-4-(neopentylamino)quinoline-3,8-dicarbonitrile | 24 | 607.10 |
| 872 | 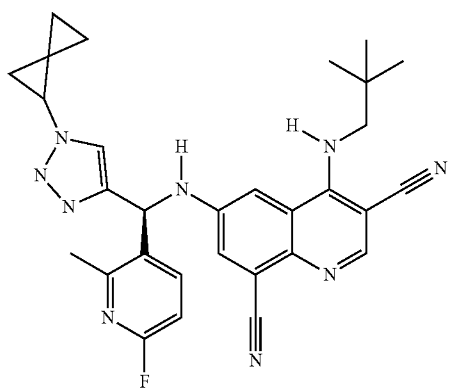 [SMILES: Cc1nc(F)ccc1[C@H](Nc1cc(C#N)c2ncc(C#N)c(NCC(C)(C)C)c2c1)C1=CN(C2CC23CC3)NN1] | 6-((((1S)-(6-fluoro-2-methylpyridin-3-yl)(1-(spiro[2.2]pentan-1-yl)-1H-1,2,3-triazol-4-yl)methyl)amino)-4-(neopentylamino)quinoline-3,8-dicarbonitrile | 24 | 535.20 |
| 873 | 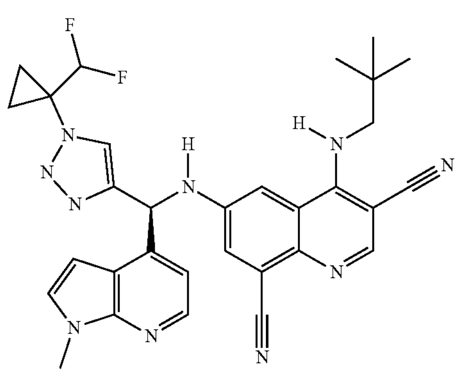 [SMILES: Cn1ccc2c([C@H](Nc3cc(C#N)c4ncc(C#N)c(NCC(C)(C)C)c4c3)C3=CN(C4(C(F)F)CC4)NN3)ccnc21] | (S)-6-(((1-(1-(difluoromethyl)cyclopropyl)-1H-1,2,3-triazol-4-yl)(1-methyl-1H-pyrrolo[2,3-b]pyridin-4-yl)methyl)amino)-4-(neopentylamino)quinoline-3,8-dicarbonitrile | 24 | 581.20 |

TABLE 1-continued

| Comp | Structure | Name | Example Procedure | ES/MS m/z |
|---|---|---|---|---|
| 874 | 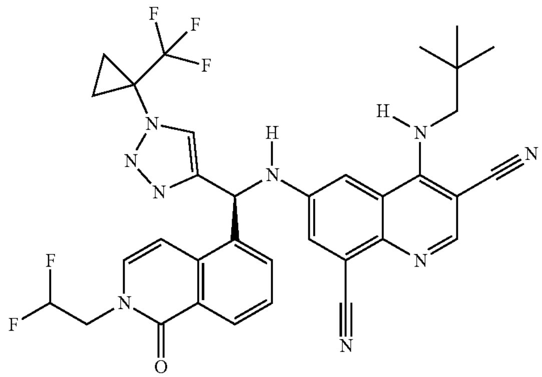 [SMILES: CC(C)(C)CNc1c(C#N)cnc2c(C#N)cc(N[C@H](C3=CN(C4(C(F)(F)F)CC4)NN3)c3cccc4c(=O)n(CC(F)F)ccc34)cc12] | (S)-6-(((2-(2,2-difluoroethyl)-1-oxo-1,2-dihydroisoquinolin-5-yl)(1-(1-(trifluoromethyl)cyclopropyl)-1H-1,2,3-triazol-4-yl)methyl)amino)-4-(neopentylamino)quinoline-3,8-dicarbonitrile | 24 | 674.90 |
| 875 | 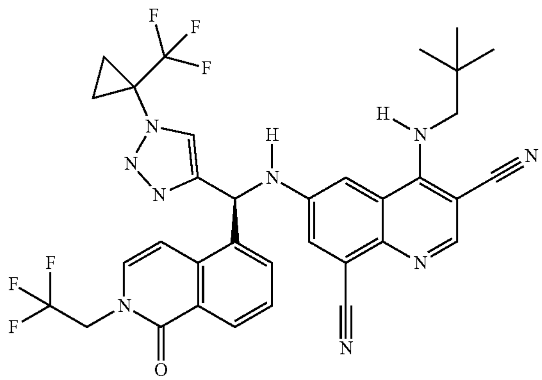 [SMILES: CC(C)(C)CNc1c(C#N)cnc2c(C#N)cc(N[C@H](C3=CN(C4(C(F)(F)F)CC4)NN3)c3cccc4c(=O)n(CC(F)(F)F)ccc34)cc12] | (S)-4-(neopentylamino)-6-(((1-oxo-2-(2,2,2-trifluoroethyl)-1,2-dihydroisoquinolin-5-yl)(1-(1-(trifluoromethyl)cyclopropyl)-1H-1,2,3-triazol-4-yl)methyl)amino)quinoline-3,8-dicarbonitrile | 24 | 692.90 |
| 876 | 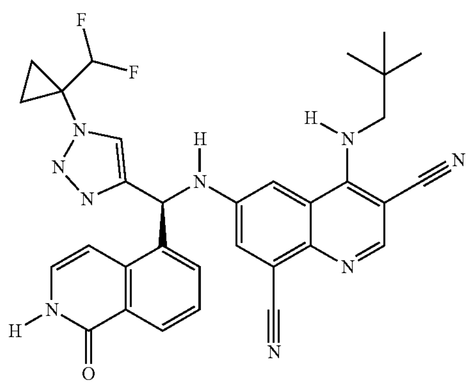 [SMILES: CC(C)(C)CNc1c(C#N)cnc2c(C#N)cc(N[C@H](C3=CN(C4(C(F)F)CC4)NN3)c3cccc4c(=O)[nH]ccc34)cc12] | (S)-6-(((1-(1-(difluoromethyl)cyclopropyl)-1H-1,2,3-triazol-4-yl)(1-oxo-1,2-dihydroisoquinolin-5-yl)methyl)amino)-4-(neopentylamino)quinoline-3,8-dicarbonitrile | 24 | 594.30 |
| 877 | 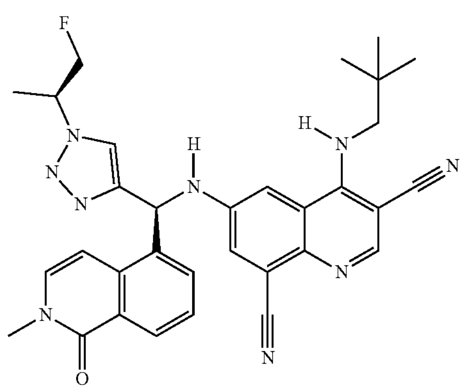 [SMILES: C[C@@H](CF)N1C=C([C@@H](Nc2cc(C#N)c3ncc(C#N)c(NCC(C)(C)C)c3c2)c2cccc3c(=O)n(C)ccc23)NN1] | 6-(((S)-(1-((S)-1-fluoropropan-2-yl)-1H-1,2,3-triazol-4-yl)(2-methyl-1-oxo-1,2-dihydroisoquinolin-5-yl)methyl)amino)-4-(neopentylamino)quinoline-3,8-dicarbonitrile | 24 | 578.30 |

TABLE 1-continued

| Comp | Structure | Name | Example Procedure | ES/MS m/z |
|------|-----------|------|-------------------|-----------|
| 878 | 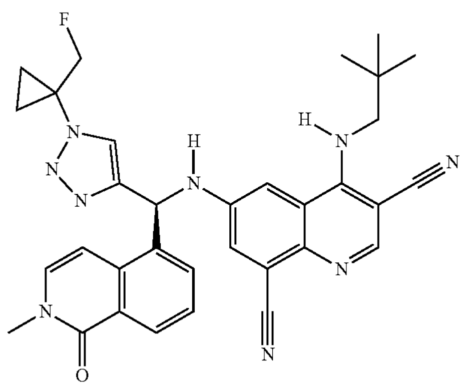 [SMILES: Cn1ccc2c([C@H](Nc3cc(C#N)c4ncc(C#N)c(NCC(C)(C)C)c4c3)C3=CN(C4(CF)CC4)NN3)cccc2c1=O] | (S)-6-(((1-(1-(fluoromethyl)cyclopropyl)-1H-1,2,3-triazol-4-yl)(2-methyl-1-oxo-1,2-dihydroisoquinolin-5-yl)methyl)amino)-4-(neopentylamino)quinoline-3,8-dicarbonitrile | 24 | 590.20 |
| 879 | 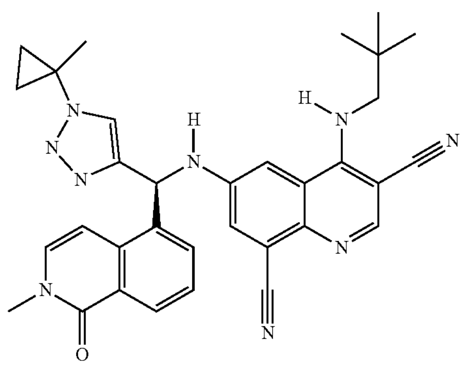 [SMILES: Cn1ccc2c([C@H](Nc3cc(C#N)c4ncc(C#N)c(NCC(C)(C)C)c4c3)C3=CN(C4(C)CC4)NN3)cccc2c1=O] | (S)-6-(((2-methyl-1-oxo-1,2-dihydroisoquinolin-5-yl)(1-(1-methylcyclopropyl)-1H-1,2,3-triazol-4-yl)methyl)amino)-4-(neopentylamino)quinoline-3,8-dicarbonitrile | 24 | 572.20 |
| 880 | 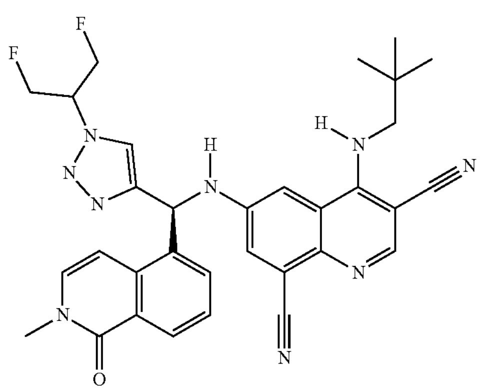 [SMILES: Cn1ccc2c([C@H](Nc3cc(C#N)c4ncc(C#N)c(NCC(C)(C)C)c4c3)C3=CN(C(CF)CF)NN3)cccc2c1=O] | (S)-6-(((1-(1,3-difluoropropan-2-yl)-1H-1,2,3-triazol-4-yl)(2-methyl-1-oxo-1,2-dihydroisoquinolin-5-yl)methyl)amino)-4-(neopentylamino)quinoline-3,8-dicarbonitrile | 24 | 596.20 |
| 881 | 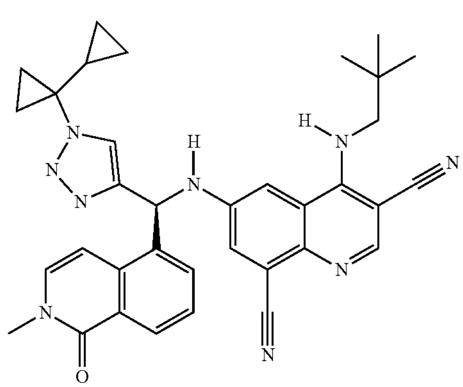 [SMILES: Cn1ccc2c([C@H](Nc3cc(C#N)c4ncc(C#N)c(NCC(C)(C)C)c4c3)C3=CN(C4(C5CC5)CC4)NN3)cccc2c1=O] | (S)-6-(((4-(1-(1-bi(cyclopropan)]-1-yl)-1H-1,2,3-triazol-4-yl)(2-methyl-1-oxo-1,2-dihydroisoquinolin-5-yl)methyl)amino)-4-(neopentylamino)quinoline-3,8-dicarbonitrile | 24 | 598.20 |

TABLE 1-continued

| Comp | Structure | Name | Example Procedure | ES/MS m/z |
|---|---|---|---|---|
| 882 | 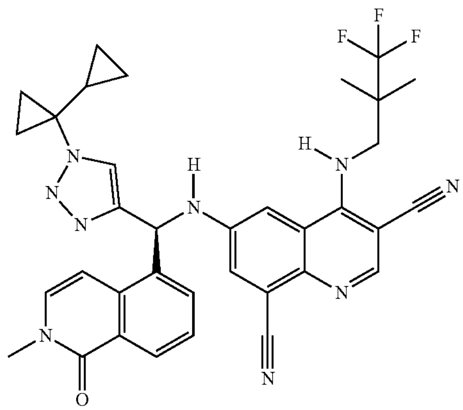 [SMILES: Cn1ccc2c([C@H](Nc3cc(C#N)c4ncc(C#N)c(NCC(C)(C)C(F)(F)F)c4c3)C3=CN(C4(C5CC5)CC4)NN3)cccc2c1=O] | (S)-6-(((1-([1,1'-bi(cyclopropan)]-1-yl)-1H-1,2,3-triazol-4-yl)(2-methyl-1-oxo-1,2-dihydroisoquinolin-5-yl)methyl)amino)-4-((3,3,3-trifluoro-2,2-dimethylpropyl)amino)quinoline-3,8-dicarbonitrile | 24 | 652.20 |
| 883 | 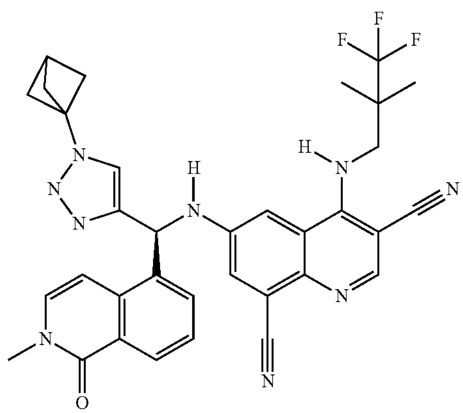 [SMILES: Cn1ccc2c([C@H](Nc3cc(C#N)c4ncc(C#N)c(NCC(C)(C)C(F)(F)F)c4c3)C3=CN(C45CC(C4)C5)NN3)cccc2c1=O] | (S)-6-(((1-(bicyclo[1.1.1]pentan-1-yl)-1H-1,2,3-triazol-4-yl)(2-methyl-1-oxo-1,2-dihydroisoquinolin-5-yl)methyl)amino)-4-((3,3,3-trifluoro-2,2-dimethylpropyl)amino)quinoline-3,8-dicarbonitrile | 24 | 638.10 |
| 884 | 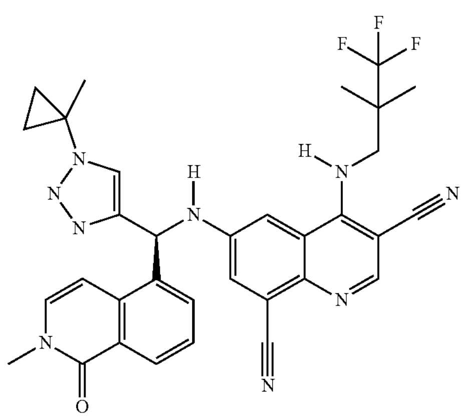 [SMILES: Cn1ccc2c([C@H](Nc3cc(C#N)c4ncc(C#N)c(NCC(C)(C)C(F)(F)F)c4c3)C3=CN(C4(C)CC4)NN3)cccc2c1=O] | (S)-6-(((2-methyl-1-oxo-1,2-dihydroisoquinolin-5-yl)(1-(1-methylcyclopropyl)-1H-1,2,3-triazol-4-yl)methyl)amino)-4-((3,3,3-trifluoro-2,2-dimethylpropyl)amino)quinoline-3,8-dicarbonitrile | 24 | 626.20 |

TABLE 1-continued

| Comp | Structure | Name | Example Procedure | ES/MS m/z |
|---|---|---|---|---|
| 885 | 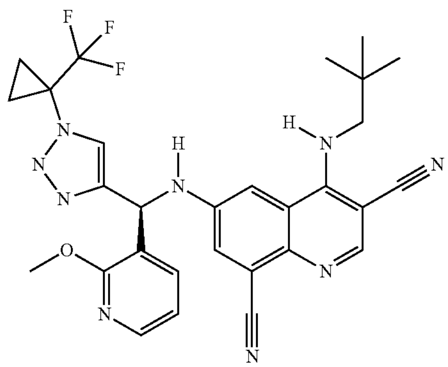 [SMILES: COc1ncccc1[C@H](Nc1cc(C#N)c2ncc(C#N)c(NCC(C)(C)C)c2c1)C1=CN(C2(C(F)(F)F)CC2)NN1] | (S)-6-(((2-methoxypyridin-3-yl)(1-(1-(trifluoromethyl)cyclopropyl)-1H-1,2,3-triazol-4-yl)methyl)amino)-4-(neopentylamino)quinoline-3,8-dicarbonitrile | 24 | 576.30 |
| 886 | 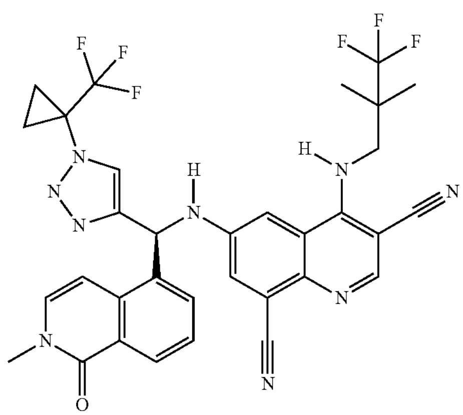 [SMILES: Cn1ccc2c([C@H](Nc3cc(C#N)c4ncc(C#N)c(NCC(C)(C)C(F)(F)F)c4c3)C3=CN(C4(C(F)(F)F)CC4)NN3)cccc2c1=O] | (S)-6-(((2-methyl-1-oxo-1,2-dihydroisoquinolin-5-yl)(1-(1-(trifluoromethyl)-cyclopropyl)-1H-1,2,3-triazol-4-yl)methyl)-amino)-4-((3,3,3-trifluoro-2,2-dimethylpropyl)-amino)quinoline-3,8-dicarbonitrile | 24 | 680.20 |
| 887 | 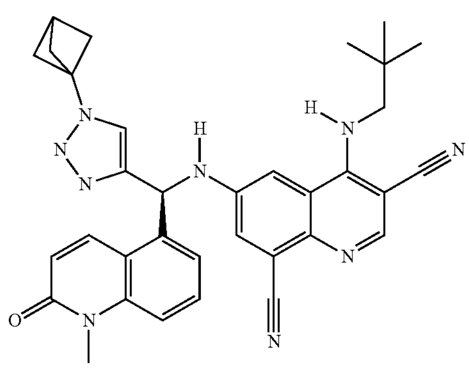 [SMILES: Cn1c(=O)ccc2c([C@H](Nc3cc(C#N)c4ncc(C#N)c(NCC(C)(C)C)c4c3)C3=CN(C45CC(C4)C5)NN3)cccc21] | (S)-6-(((1-(bicyclo[1.1.1]pentan-1-yl)-1H-1,2,3-triazol-4-yl)(1-methyl-2-oxo-1,2-dihydroquinolin-5-yl)methyl)amino)-4-(neopentylamino)quinoline-3,8-dicarbonitrile | 24 | 584.20 |
| 888 | 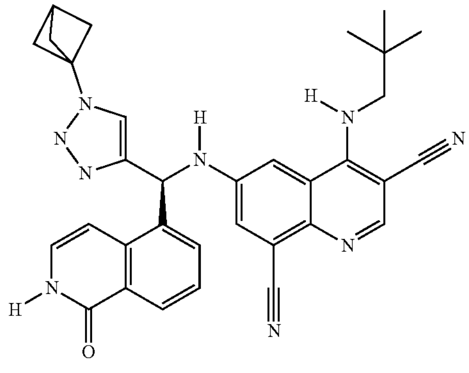 [SMILES: CC(C)(C)CNc1c(C#N)cnc2c(C#N)cc(N[C@H](C3=CN(C45CC(C4)C5)NN3)c3cccc4c(=O)[nH]ccc34)cc12] | (S)-6-(((1-(bicyclo[1.1.1]pentan-1-yl)-1H-1,2,3-triazol-4-yl)(1-oxo-1,2-dihydroisoquinolin-5-yl)methyl)amino)-4-(neopentylamino)quinoline-3,8-dicarbonitrile | 24 | 570.10 |

TABLE 1-continued

| Comp | Name | Example Procedure | ES/MS m/z |
|---|---|---|---|
| 889 | (S)-6-(((2-(difluoromethyl)-1-oxo-1,2-dihydroisoquinolin-5-yl)(1-(1-(trifluoromethyl)cyclopropyl)-1H-1,2,3-triazol-4-yl)methyl)amino)-4-(neopentylamino)quinoline-3,8-dicarbonitrile | 24 | 662.20 |
| 890 | (S)-6-(((1-methyl-2-oxo-1,2-dihydroquinolin-5-yl)(1-(1-(trifluoromethyl)cyclopropyl)-1H-1,2,3-triazol-4-yl)methyl)amino)-4-(neopentylamino)quinoline-3,8-dicarbonitrile | 24 | 626.20 |
| 891 | (S)-6-(((1-(bicyclo[1.1.1]pentan-1-yl)-1H-1,2,3-triazol-4-yl)(2-methyl-1-oxo-1,2-dihydroisoquinolin-5-yl)methyl)amino)-4-(neopentylamino)quinoline-3,8-dicarbonitrile | 24 | 584.20 |
| 892 | 6-(((S)-(1-((S)-1-fluoropropan-2-yl)-1H-1,2,3-triazol-4-yl)(quinolin-5-yl)methyl)amino)-4-(neopentylamino)quinoline-3,8-dicarbonitrile | 24 | 548.28 |

TABLE 1-continued

| Comp | Structure | Name | Example Procedure | ES/MS m/z |
|---|---|---|---|---|
| 893 | 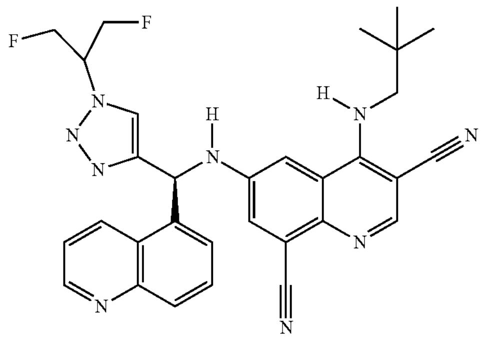 [SMILES: CC(C)(C)CNc1c(C#N)cnc2c(C#N)cc(N[C@H](C3=CN(C(CF)CF)NN3)c3cccc4ncccc34)cc12] | (S)-6-(((1-(1,3-difluoropropan-2-yl)-1H-1H-1,2,3-triazol-4-yl)(quinolin-5-yl)methyl)amino)-4-(neopentyl-amino)quinoline-3,8-dicarbonitrile | 24 | 566.30 |
| 894 | 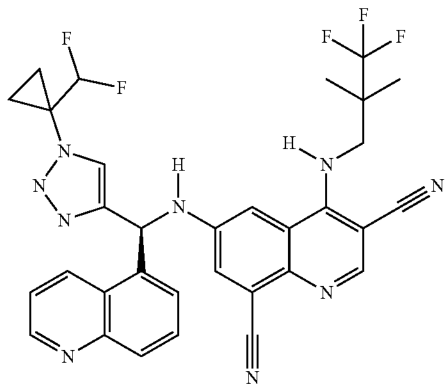 [SMILES: CC(C)(CNc1c(C#N)cnc2c(C#N)cc(N[C@H](C3=CN(C4(C(F)F)CC4)NN3)c3cccc4ncccc34)cc12)C(F)(F)F] | (S)-6-((((1-(1-(difluoromethyl)cyclopropyl)-1H-1,2,3-triazol-4-yl)(quinolin-5-yl)methyl)amino-4-((3,3,3-trifluoro-2,2-dimethylpropyl)amino)quinoline-3,8-dicarbonitrile | 24 | 632.07 |
| 895 | 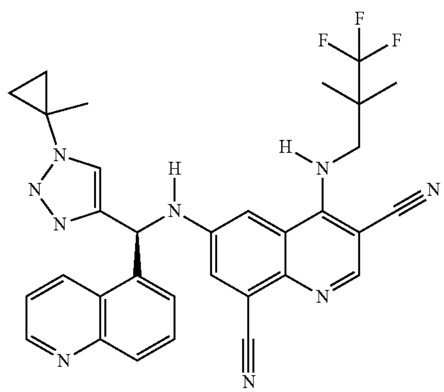 [SMILES: CC1(N2C=C([C@@H](Nc3cc(C#N)c4ncc(C#N)c(NCC(C)(C)C(F)(F)F)c4c3)c3cccc4ncccc34)NN2)CC1] | (S)-6-(((1-(1-methylcyclopropyl)-1H-1,2,3-triazol-4-yl)(quinolin-5-yl)methyl)amino)-4-((3,3,3-trifluoro-2,2-dimethylpropyl)amino)quinoline-3,8-dicarbonitrile | 24 | 596.11 |
| 896 | 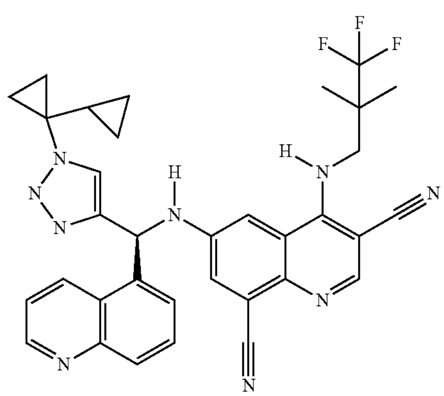 [SMILES: CC(C)(CNc1c(C#N)cnc2c(C#N)cc(N[C@H](C3=CN(C4(C5CC5)CC4)NN3)c3cccc4ncccc34)cc12)C(F)(F)F] | (S)-6-(((1-([1,1'-bi(cyclopropan)]-1-yl)-1H-1,2,3-triazol-4-yl)(quinolin-5-yl)methyl)amino)-4-((3,3,3-trifluoro-2,2-dimethylpropyl)amino)quinoline-3,8-dicarbonitrile | 24 | 622.08 |

TABLE 1-continued

| Comp | Structure | Name | Example Procedure | ES/MS m/z |
|---|---|---|---|---|
| 897 | 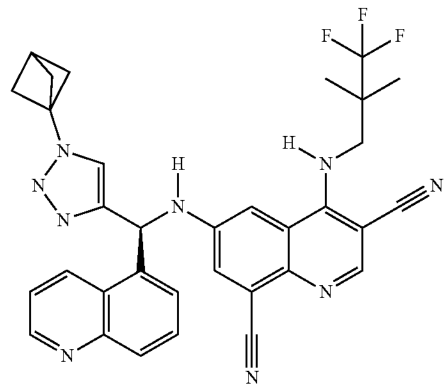 [SMILES: CC(C)(CNc1c(C#N)cnc2c(C#N)cc(N[C@H](C3=CN(C45CC(C4)C5)NN3)c3cccc4ncccc34)cc12)C(F)(F)F] | (S)-6-(((1-(bicyclo[1.1.1]pentan-1-yl)-1H-1,2,3-triazol-4-yl)(quinolin-5-yl)methyl)amino)-4-((3,3,3-trifluoro-2,2-dimethylpropyl)amino)quinoline-3,8-dicarbonitrile | 24 | 608.11 |
| 898 | 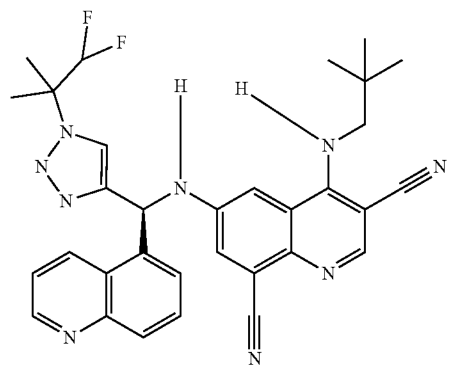 [SMILES: CC(C)(C)CNc1c(C#N)cnc2c(C#N)cc(N[C@H](C3=CN(C(C)(C)C(F)F)NN3)c3cccc4ncccc34)cc12] | (S)-6-(((1-(1,1-difluoro-2-methylpropan-2-yl)-1H-1,2,3-triazol-4-yl)(quinolin-5-yl)methyl)amino)-4-(neopentylamino)quinoline-3,8-dicarbonitrile | 24 | 580.22 |
| 899 | 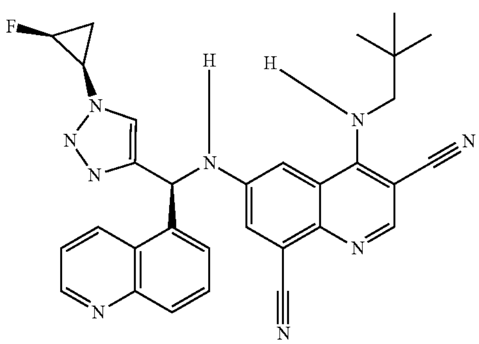 [SMILES: CC(C)(C)CNc1c(C#N)cnc2c(C#N)cc(N[C@H](C3=CN([C@@H]4C[C@@H]4F)NN3)c3cccc4ncccc34)cc12] | 6-(((S)-(1-((1R,2S)-2-fluorocyclopropyl)-1H-1,2,3-triazol-4-yl)(quinolin-5-yl)methyl)amino)-4-(neopentylamino)quinoline-3,8-dicarbonitrile | 24 | 546.22 |
| 900 | 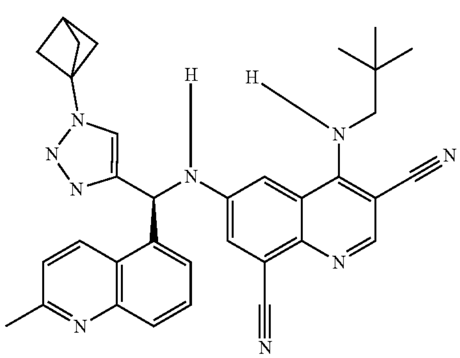 [SMILES: Cc1ccc2c([C@H](Nc3cc(C#N)c4ncc(C#N)c(NCC(C)(C)C)c4c3)C3=CN(C45CC(C4)C5)NN3)cccc2n1] | (S)-6-(((1-(bicyclo[1.1.1]pentan-1-yl)-1H-1,2,3-triazol-4-yl)(2-methylquinolin-5-yl)methyl)amino)-4-(neopentylamino)quinoline-3,8-dicarbonitrile | 24 | 568.41 |

TABLE 1-continued

| Comp | Structure | Name | Example Procedure | ES/MS m/z |
|---|---|---|---|---|
| 901 | 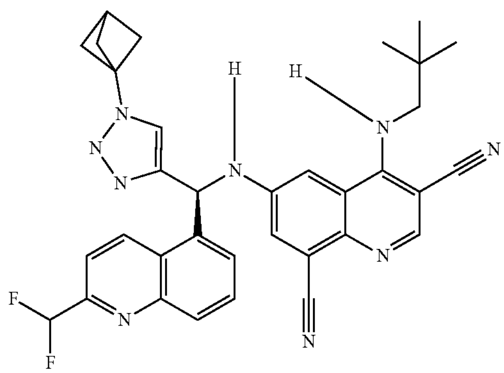 [SMILES: CC(C)(C)CNc1c(C#N)cnc2c(C#N)cc(N[C@H](C3=CN(C45CC(C4)C5)NN3)c3cccc4nc(C(F)F)ccc34)cc12] | (S)-6-(((1-(bicyclo[1.1.1]pentan-1-yl)-1H-1,2,3-triazol-4-yl)(2-(difluoromethyl)quinolin-5-yl)methyl)amino)-4-(neopentylamino)quinoline-3,8-dicarbonitrile | 24 | 604.13 |
| 902 | 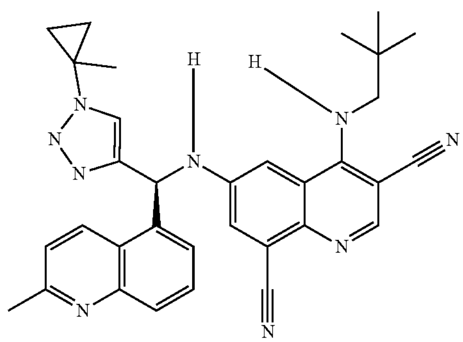 [SMILES: Cc1ccc2c([C@H](Nc3cc(C#N)c4ncc(C#N)c(NCC(C)(C)C)c4c3)C3=CN(C4(C)CC4)NN3)cccc2n1] | (S)-6-(((4-(1-(1-methylcyclopropyl)-1H-1,2,3-triazol-4-yl)(2-methylquinolin-5-yl)methyl)amino)-4-(neopentylamino)quinoline-3,8-dicarbonitrile | 24 | 556.29 |
| 903 | 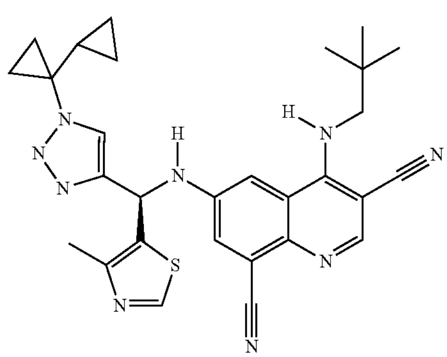 [SMILES: Cc1ncsc1[C@H](Nc1cc(C#N)c2ncc(C#N)c(NCC(C)(C)C)c2c1)C1=CN(C2(C3CC3)CC2)NN1] | (R)-6-(((1-([1,1'-bi(cyclopropan)]-1-yl)-1H-1,2,3-triazol-4-yl)(4-methyl thiazol-5-yl)methyl)amino)-4-(neopentylamino)quinoline-3,8-dicarbonitrile | 24 | 538.20 |
| 904 | 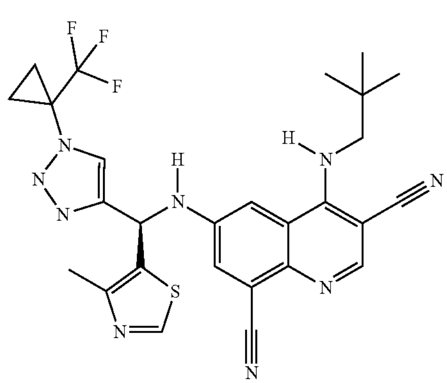 [SMILES: Cc1ncsc1[C@H](Nc1cc(C#N)c2ncc(C#N)c(NCC(C)(C)C)c2c1)C1=CN(C2(C(F)(F)F)CC2)NN1] | (R)-6-(((4-methylthiazol-5-yl)(1-(1-(trifluoromethyl)cyclopropyl)-1H-1,2,3-triazol-4-yl)methyl)amino)-4-(neopentylamino)quinoline-3,8-dicarbonitrile | 24 | 566.20 |

TABLE 1-continued

| Comp | Structure | Name | Example Procedure | ES/MS m/z |
|---|---|---|---|---|
| 905 | 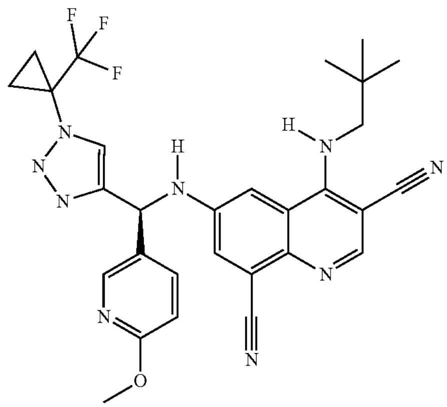 [SMILES: COc1ccc([C@H](Nc2cc(C#N)c3ncc(C#N)c(NCC(C)(C)C)c3c2)C2=CN(C3(C(F)(F)F)CC3)NN2)cn1] | (S)-6-(((6-methoxypyridin-3-yl)(1-(1-(trifluoromethyl)cyclopropyl)-1H-1,2,3-triazol-4-yl)methyl)amino)-4-(neopentylamino)quinoline-3,8-dicarbonitrile | 24 | 576.20 |
| 906 | 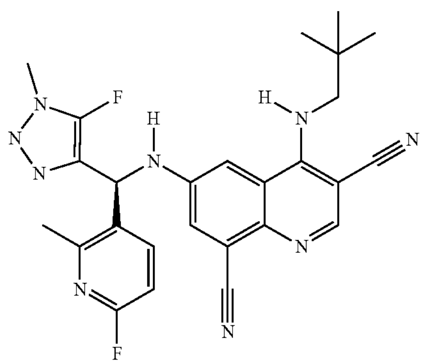 [SMILES: Cc1nc(F)ccc1[C@H](Nc1cc(C#N)c2ncc(C#N)c(NCC(C)(C)C)c2c1)C1=C(F)N(C)NN1] | (S)-6-(((5-fluoro-1-methyl-1H-1,2,3-triazol-4-yl)(6-fluoro-2-methylpyridin-3-yl)methyl)amino)-4-(neopentylamino)quinoline-3,8-dicarbonitrile | 24 | 502.20 |
| 907 | 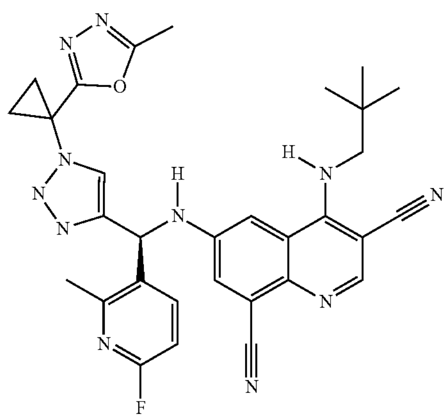 [SMILES: Cc1nnc(C2(N3C=C([C@@H](Nc4cc(C#N)c5ncc(C#N)c(NCC(C)(C)C)c5c4)c4ccc(F)nc4C)NN3)CC2)o1] | (S)-6-(((6-fluoro-2-methylpyridin-3-yl)(1-(1-(5-methyl-1,3,4-oxadiazol-2-yl)cyclopropyl)-1H-1,2,3-triazol-4-yl)methyl)amino)-4-(neopentylamino)quinoline-3,8-dicarbonitrile | 24 | 592.30 |
| 908 | 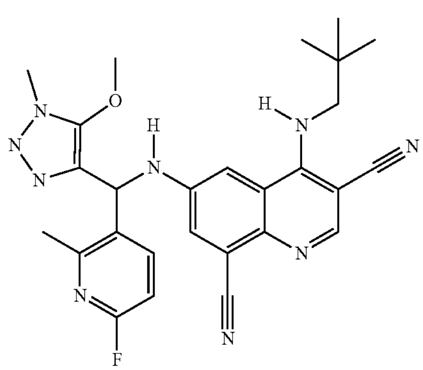 [SMILES: COC1=C(C(Nc2cc(C#N)c3ncc(C#N)c(NCC(C)(C)C)c3c2)c2ccc(F)nc2C)NNN1C] | 6-(((6-fluoro-2-methylpyridin-3-yl)(5-methoxy-1-methyl-1H-1,2,3-triazol-4-yl)methyl)amino)-4-(neopentylamino)quinoline-3,8-dicarbonitrile | 24 | 514.30 |

| Comp | Structure | Name | Example Procedure | ES/MS m/z |
|---|---|---|---|---|
| 909 | 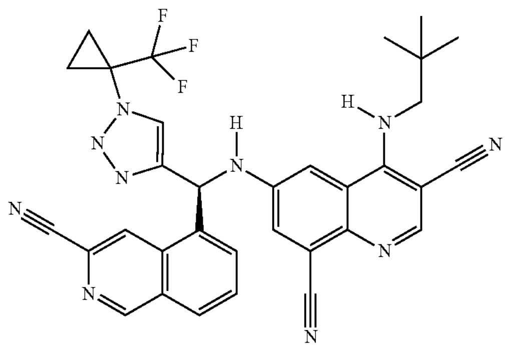 [SMILES: CC(C)(C)CNc1c(C#N)cnc2c(C#N)cc(N[C@H](C3=CN(C4(C(F)(F)F)CC4)NN3)c3cccc4cnc(C#N)cc34)cc12] | (S)-6-(((3-cyanoisoquinolin-5-yl)(1-(1-(trifluoromethyl)cyclopropyl)-1H-1,2,3-triazol-4-yl)methyl)amino)-4-(neopentylamino)quinoline-3,8-dicarbonitrile | 25 | 621.46 |
| 910 | 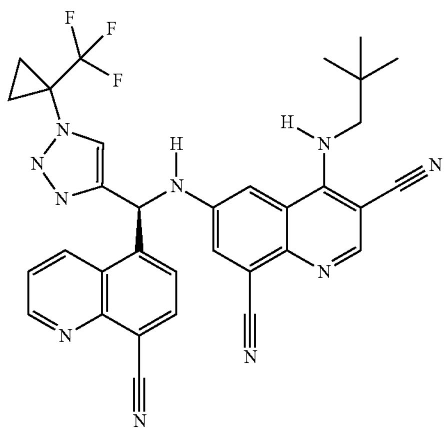 [SMILES: CC(C)(C)CNc1c(C#N)cnc2c(C#N)cc(N[C@H](C3=CN(C4(C(F)(F)F)CC4)NN3)c3ccc(C#N)c4ncccc34)cc12] | (S)-6-(((8-cyanoquinolin-5-yl)(1-(1-(trifluoromethyl)cyclopropyl)-1H-1,2,3-triazol-4-yl)methyl)amino)-4-(neopentylamino)quinoline-3,8-dicarbonitrile | 25 | 621.27 |
| 911 | 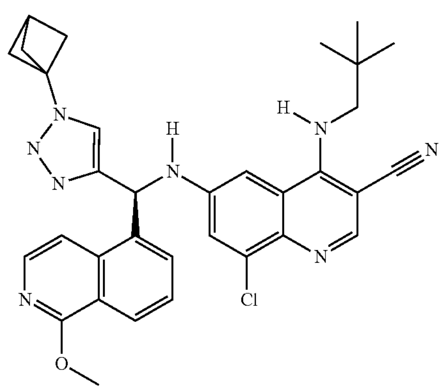 [SMILES: COc1nccc2c([C@H](Nc3cc(Cl)c4ncc(C#N)c(NCC(C)(C)C)c4c3)C3=CN(C45CC(C4)C5)NN3)cccc12] | (S)-6-(((1-(bicyclo[1.1.1]pentan-1-yl)-1H-1,2,3-triazol-4-yl)(1-methoxylsoquinolin-5-yl)methyl)amino)-8-chloro-4-(neopentylamino)quinoline-3-carbonitrile | 27 | 593.45 |
| 912 | 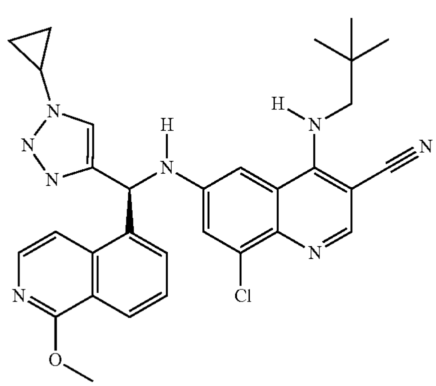 [SMILES: COc1nccc2c([C@H](Nc3cc(Cl)c4ncc(C#N)c(NCC(C)(C)C)c4c3)C3=CN(C4CC4)NN3)cccc12] | (S)-8-chloro-6-(((1-cyclopropyl-1H-1,2,3-triazol-4-yl)(1-methoxylsoquinolin-5-yl)methyl)amino)-4-(neopentylamino)quinoline-3-carbonitrile | 27 | 567.24 |

TABLE 1-continued

| Comp | Structure | Name | Example Procedure | ES/MS m/z |
|---|---|---|---|---|
| 913 | 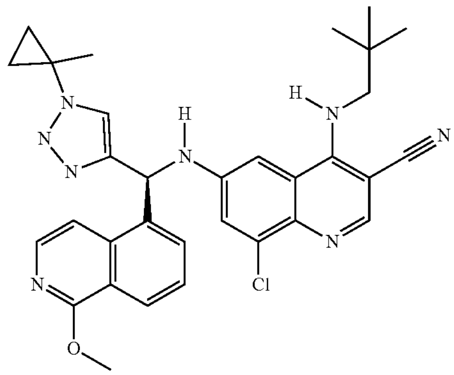 [SMILES: COc1nccc2c([C@H](Nc3cc(Cl)c4ncc(C#N)c(NCC(C)(C)C)c4c3)C3=CN(C4(C)CC4)NN3)cccc12] | (S)-8-chloro-6-(((1-methoxylsoquinolin-5-yl)(1-(1-methylcyclopropyl)-1H-1,2,3-triazol-4-yl)methyl)amino)-4-(neopentylamino)quinoline-3-carbonitrile | 27 | 581.30 |
| 914 | 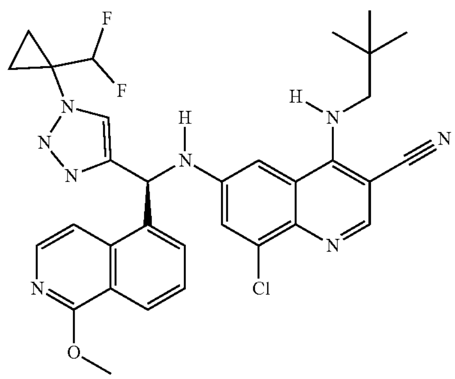 [SMILES: COc1nccc2c([C@H](Nc3cc(Cl)c4ncc(C#N)c(NCC(C)(C)C)c4c3)C3=CN(C4(C(F)F)CC4)NN3)cccc12] | (S)-8-chloro-6-(((1-(1-(difluoromethyl)cyclopropyl)-1H-1,2,3-triazol-4-yl)(1-methoxylsoquinolin-5-yl)methyl)amino)-4-(neopentylamino)quinoline-3-carbonitrile | 27 | 617.30 |
| 915 | 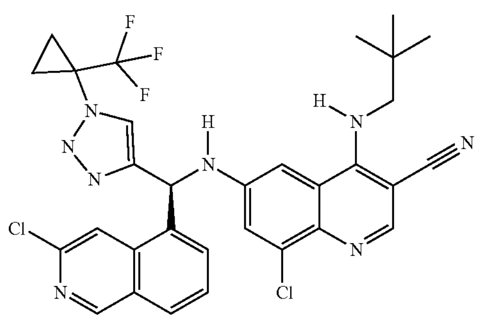 [SMILES: CC(C)(C)CNc1c(C#N)cnc2c(Cl)cc(N[C@H](C3=CN(C4(C(F)(F)F)CC4)NN3)c3cccc4cnc(Cl)cc34)cc12] | (S)-8-chloro-6-(((3-chloroisoquinolin-5-yl)(1-(1-(trifluoromethyl)cyclopropyl)-1H-1,2,3-triazol-4-yl)methyl)amino)-4-(neopentylamino)quinoline-3-carbonitrile | 27 | 639.70 |
| 916 | 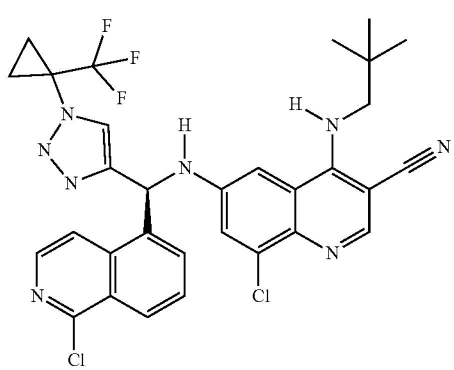 [SMILES: CC(C)(C)CNc1c(C#N)cnc2c(Cl)cc(N[C@H](C3=CN(C4(C(F)(F)F)CC4)NN3)c3cccc4c(Cl)nccc34)cc12] | (S)-8-chloro-6-(((1-chloroisoquinolin-5-yl)(1-(1-(trifluoromethyl)cyclopropyl)-1H-1,2,3-triazol-4-yl)methyl)amino)-4-(neopentylamino)quinoline-3-carbonitrile | 27 | 639.98 |

TABLE 1-continued

| Comp | Structure | Name | Example Procedure | ES/MS m/z |
|---|---|---|---|---|
| 917 | 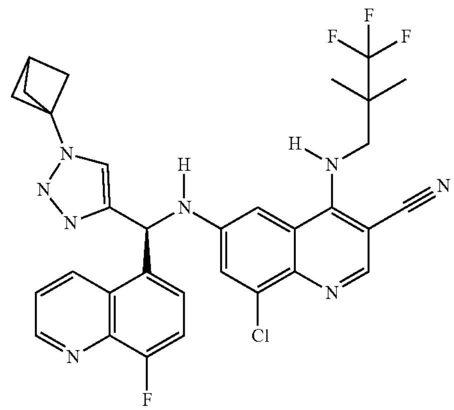 [SMILES: CC(C)(CNc1c(C#N)cnc2c(Cl)cc(N[C@H](C3=CN(C45CC(C4)C5)NN3)c3ccc(F)c4ncccc34)cc12)C(F)(F)F] | (S)-6-(((1-(bicyclo[1.1.1]pentan-1-yl)-1H-1,2,3-triazol-4-yl)(8-fluoroquinolin-5-yl)methyl)amino)-8-chloro-4-((3,3,3-trifluoro-2,2-dimethylpropyl)amino)quinoline-3-carbonitrile | 27 | 635.09 |
| 918 | 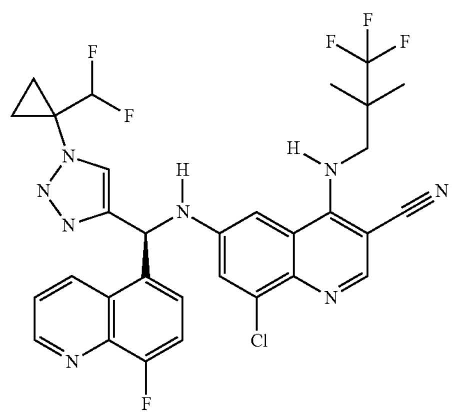 [SMILES: CC(C)(CNc1c(C#N)cnc2c(Cl)cc(N[C@H](C3=CN(C4(C(F)F)CC4)NN3)c3ccc(F)c4ncccc34)cc12)C(F)(F)F] | (S)-8-chloro-6-(((1-(1-(difluoromethyl)cyclopropyl)-1H-1,2,3-triazol-4-yl)(8-fluoroquinolin-5-yl)methyl)amino)-4-((3,3,3-trifluoro-2,2-dimethylpropyl)amino)quinoline-3-carbonitrile | 27 | 659.22 |
| 919 | 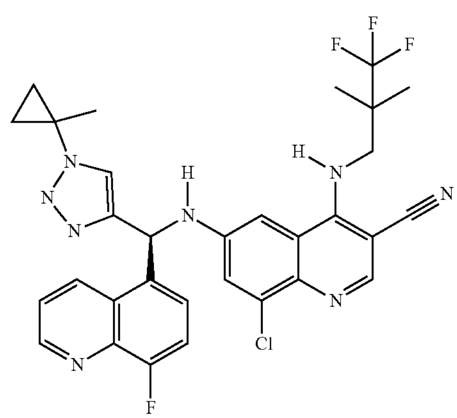 [SMILES: CC1(N2C=C([C@@H](Nc3cc(Cl)c4ncc(C#N)c(NCC(C)(C)C(F)(F)F)c4c3)c3ccc(F)c4ncccc34)NN2)CC1] | (S)-8-chloro-6-(((8-fluoroquinolin-5-yl)(1-(1-methylcyclopropyl)-1H-1,2,3-triazol-4-yl)methyl)amino)-4-((3,3,3-trifluoro-2,2-dimethylpropyl)amino)quinoline-3-carbonitrile | 27 | 623.24 |

TABLE 1-continued

| Comp | Structure | Name | Example Procedure | ES/MS m/z |
|---|---|---|---|---|
| 920 | 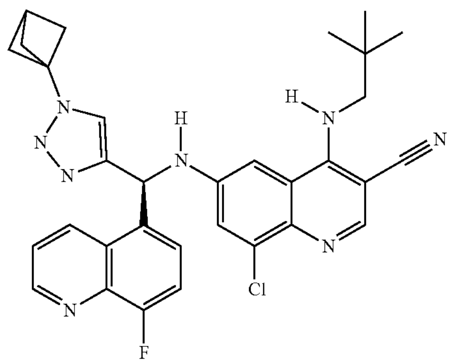 [SMILES: CC(C)(C)CNc1c(C#N)cnc2c(Cl)cc(N[C@H](C3=CN(C45CC(C4)C5)NN3)c3ccc(F)c4ncccc34)cc12] | (S)-6-(((1-(bicyclo[1.1.1]pentan-1-yl)-1H-1,2,3-triazol-4-yl)(8-fluoroquinolin-5-yl)methyl)amino)-8-chloro-4-(neopentylamino)quinoline-3-carbonitrile | 27 | 581.34 |
| 921 | 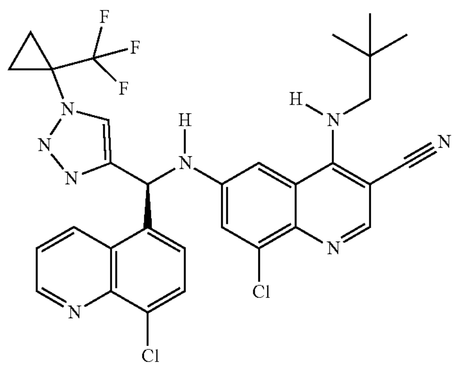 [SMILES: CC(C)(C)CNc1c(C#N)cnc2c(Cl)cc(N[C@H](C3=CN(C4(C(F)(F)F)CC4)NN3)c3ccc(Cl)c4ncccc34)cc12] | (S)-8-chloro-6-(((8-chloroquinolin-5-yl)(1-(trifluoromethyl)cyclopropyl)-1H-1,2,3-triazol-4-yl)methyl)amino)-4-(neopentylamino)quinoline-3-carbonitrile | 27 | 639.26 |
| 922 | 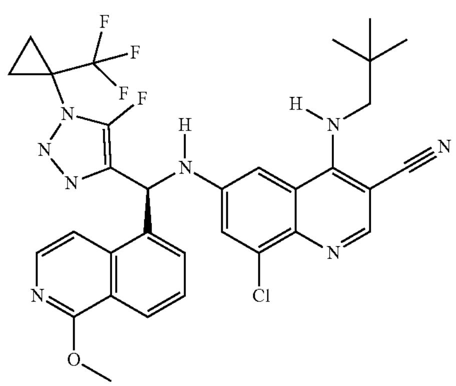 [SMILES: COc1nccc2c([C@H](Nc3cc(Cl)c4ncc(C#N)c(NCC(C)(C)C)c4c3)C3=C(I)N(C4(C(F)(F)F)CC4)NN3)cccc12] | (S)-8-chloro-6-(((5-fluoro-1-(1-(trifluoromethyl)cyclopropyl)-1H-1,2,3-triazol-4-yl)(1-methoxyisoquinolin-5-yl)methyl)amino)-4-(neopentylamino)quinoline-3-carbonitrile | 27 | 653.66 |
| 923 | 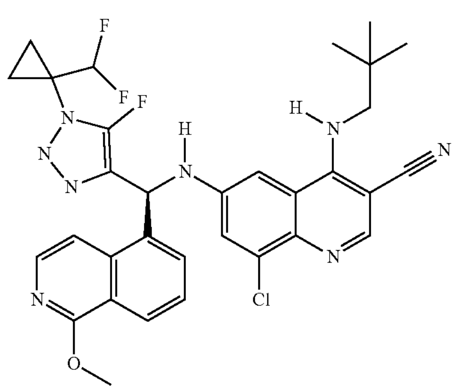 [SMILES: COc1nccc2c([C@H](Nc3cc(Cl)c4ncc(C#N)c(NCC(C)(C)C)c4c3)C3=C(I)N(C4(C(F)F)CC4)NN3)cccc12] | (S)-8-chloro-6-(((1-(1-(difluoromethyl)cyclopropyl)-5-fluoro-1H-1,2,3-triazol-4-yl)(1-methoxyisoquinolin-5-yl)methyl)amino)-4-(neopentylamino)quinoline-3-carbonitrile | 27 | 635.20 |

TABLE 1-continued

| Comp | Structure | Name | Example Procedure | ES/MS m/z |
|---|---|---|---|---|
| 924 | 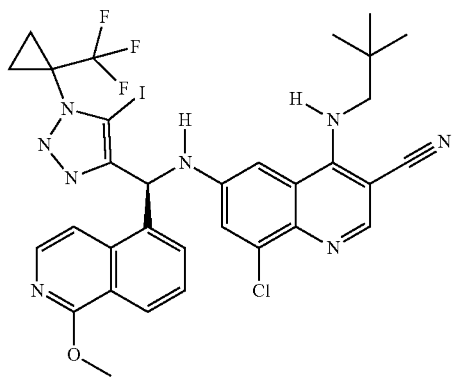 | (S)-8-chloro-6-(((5-iodo-1-(1-(trifluoromethyl)cyclopropyl)-1H-1,2,3-triazol-4-yl)(1-methoxylsoquinolin-5-yl)methyl)amino)-4-(neopentylamino)quinoline-3-carbonitrile | 27 | 761.55 |
| 925 | 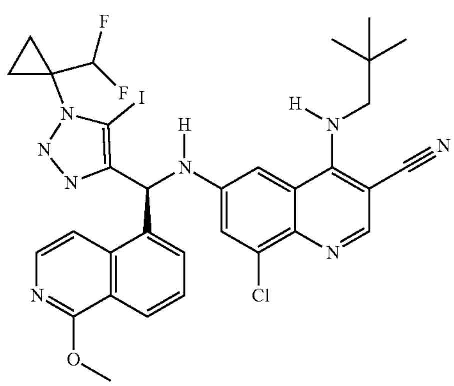 | (S)-8-chloro-6-(((1-(1-(difluoromethyl)cyclopropyl)-5-iodo-1H-1,2,3-triazol-4-yl)(1-methoxylsoquinolin-5-yl)methyl)amino)-4-(neopentylamino)quinoline-3-carbonitrile | 27 | 743.10 |
| 926 | 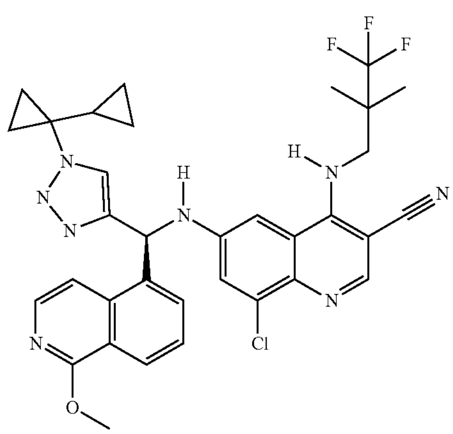 [SMILES: COc1nccc2c([C@H](Nc3cc(Cl)c4ncc(C#N)c(NCC(C)(C)C(F)(F)F)c4c3)C3=CN(C4(C5CC5)CC4)NN3)cccc12] | (S)-6-(((4-(1-(1,1-bi(cyclopropan)]-1-yl)-1H-1,2,3-triazol-4-yl)(1-methoxylsoquinolin-5-yl)methyl)amino)-8-chloro-4-((3,3,3-trifluoro-2,2-dimethylpropyl)amino)quinoline-3-carbonitrile | 27 | 661.42 |

TABLE 1-continued

| Comp | Structure | Name | Example Procedure | ES/MS m/z |
|---|---|---|---|---|
| 927 | 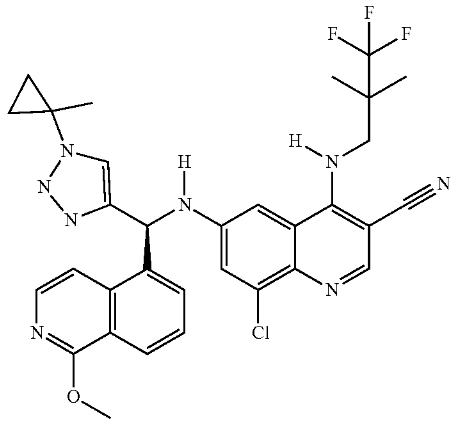 [SMILES: COc1nccc2c([C@H](Nc3cc(Cl)c4ncc(C#N)c(NCC(C)(C)C(F)(F)F)c4c3)C3=CN(C4(C)CC4)NN3)cccc12] | (S)-8-chloro-6-(((1-methoxylsoquinolin-5-yl)(1-(1-methylcyclopropyl)-1H-1,2,3-triazol-4-yl)methyl)amino)-4-((3,3,3-trifluoro-2,2-dimethylpropyl)amino)quinoline-3-carbonitrile | 27 | 635.42 |
| 928 | 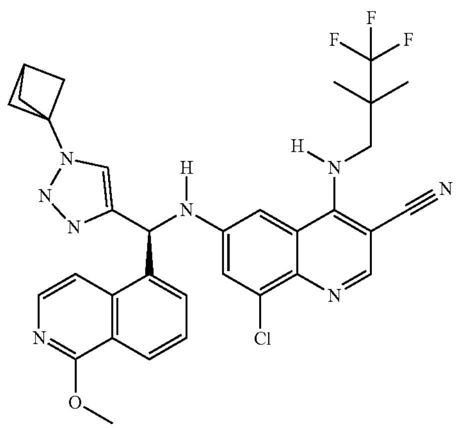 [SMILES: COc1nccc2c([C@H](Nc3cc(Cl)c4ncc(C#N)c(NCC(C)(C)C(F)(F)F)c4c3)C3=CN(C45CC(C4)C5)NN3)cccc12] | (S)-6-(((1-(bicyclo[1.1.1]pentan-1-yl)-1H-1,2,3-triazol-4-yl)(1-methoxylsoquinolin-5-yl)methyl)amino)-8-chloro-4-((3,3,3-trifluoro-2,2-dimethylpropyl)amino)quinoline-3-carbonitrile | 27 | 647.40 |
| 929 | 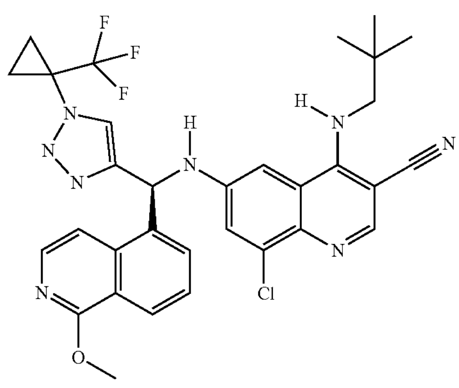 [SMILES: COc1nccc2c([C@H](Nc3cc(Cl)c4ncc(C#N)c(NCC(C)(C)C)c4c3)C3=CN(C4(C(F)(F)F)CC4)NN3)cccc12] | (S)-8-chloro-6-(((1-methoxylsoquinolin-5-yl)(1-(1-(trifluoromethyl)cyclopropyl)-1H-1,2,3-triazol-4-yl)methyl)amino)-4-(neopentylamino)quinoline-3-carbonitrile | 27 | 635.90 |
| 930 | 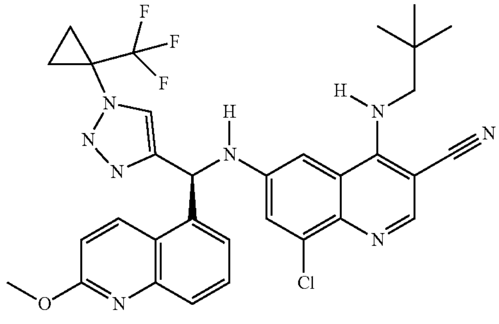 [SMILES: COc1ccc2c([C@H](Nc3cc(Cl)c4ncc(C#N)c(NCC(C)(C)C)c4c3)C3=CN(C4(C(F)(F)F)CC4)NN3)cccc2n1] | (S)-8-chloro-6-(((2-methoxyquinolin-5-yl)(1-(1-(trifluoromethyl)cyclopropyl)-1H-1,2,3-triazol-4-yl)methyl)amino)-4-(neopentylamino)quinoline-3-carbonitrile | 27 | 635.10 |

TABLE 1-continued

| Comp | Structure | Name | Example Procedure | ES/MS m/z |
|---|---|---|---|---|
| 931 | 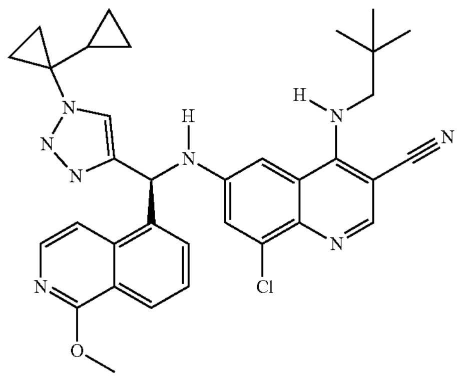 [SMILES: COc1nccc2c([C@H](Nc3cc(Cl)c4ncc(C#N)c(NCC(C)(C)C)c4c3)C3=CN(C4(C5CC5)CC4)NN3)cccc12] | (S)-6-(((1-(1,1'-bi(cyclopropan)]-1-yl)-1H-1,2,3-triazol-4-yl)(1-methoxylsoquinolin-5-yl)methyl)amino)-8-chloro-4-(neopentylamino)quinoline-3-carbonitrile | 27 | 607.63 |
| 932 | 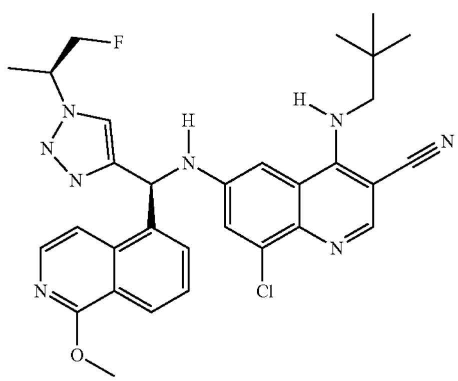 [SMILES: COc1nccc2c([C@H](Nc3cc(Cl)c4ncc(C#N)c(NCC(C)(C)C)c4c3)C3=CN([C@@H](C)CF)NN3)cccc12] | 8-chloro-6-(((S)-(1-((S)-1-fluoropropan-2-yl)-1H-1,2,3-triazol-4-yl)(1-methoxylsoquinolin-5-yl)methyl)amino)-4-(neopentylamino)quinoline-3-carbonitrile | 27 | 587.81 |
| 933 | 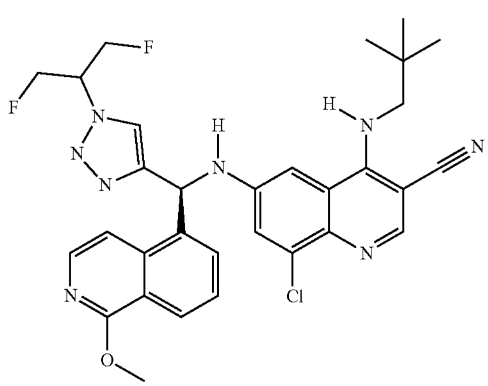 [SMILES: COc1nccc2c([C@H](Nc3cc(Cl)c4ncc(C#N)c(NCC(C)(C)C)c4c3)C3=CN(C(CF)CF)NN3)cccc12] | (S)-8-chloro-6-(((1-(1,3-difluoropropan-2-yl)-1H-1,2,3-triazol-4-yl)(1-methoxylsoquinolin-5-yl)methyl)amino)-4-(neopentylamino)quinoline-3-carbonitrile | 27 | 605.85 |

TABLE 1-continued

| Comp | Structure | Name | Example Procedure | ES/MS m/z |
|---|---|---|---|---|
| 934 | 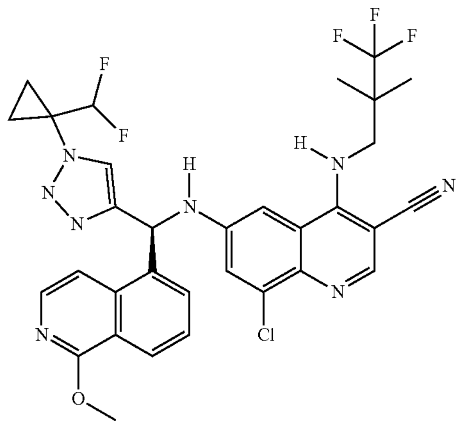 [SMILES: COc1nccc2c([C@H](Nc3cc(Cl)c4ncc(C#N)c(NCC(C)(C)C(F)(F)F)c4c3)C3=CN(C4(C(F)F)CC4)NN3)cccc12] | (S)-8-chloro-6-(((1-(1-(difluoromethyl)cyclopropyl)-1H-1,2,3-triazol-4-yl)(1-methoxyisoquinolin-5-yl)methyl)amino)-4-((3,3,3-trifluoro-2,2-dimethylpropyl)amino)quinoline-3-carbonitrile | 27 | 671.31 |
| 935 | 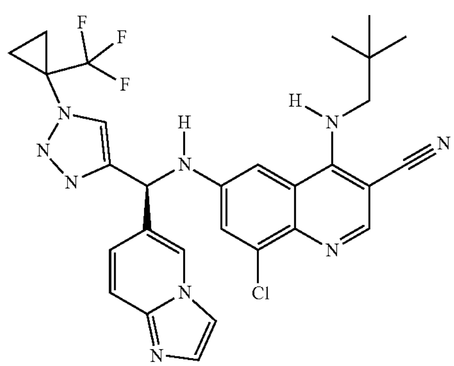 [SMILES: CC(C)(C)CNc1c(C#N)cnc2c(Cl)cc(N[C@H](C3=CN(C4(C(F)(F)F)CC4)NN3)c3ccc4nccn4c3)cc12] | (S)-8-chloro-6-((imidazo[1,2-a]pyridin-6-yl(1-(1-(trifluoromethyl)cyclopropyl)-1H-1,2,3-triazol-4-yl)methyl)amino)-4-(neopentylamino)quinoline-3-carbonitrile | 27 | 594.10 |
| 936 | 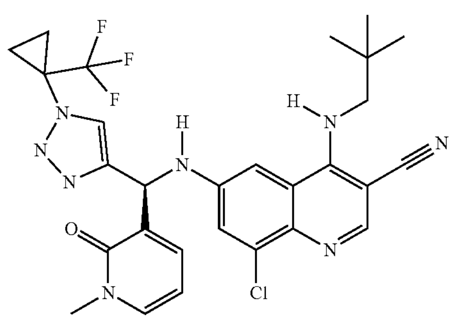 [SMILES: Cn1cccc([C@H](Nc2cc(Cl)c3ncc(C#N)c(NCC(C)(C)C)c3c2)C2=CN(C3(C(F)(F)F)CC3)NN2)c1=O] | (S)-8-chloro-6-(((1-methyl-2-oxo-1,2-dihydropyridin-3-yl)(1-(1-(trifluoromethyl)cyclopropyl)-1H-1,2,3-triazol-4-yl)methyl)amino)-4-(neopentylamino)quinoline-3-carbonitrile | 27 | 584.7 (M + H+) |
| 937 | 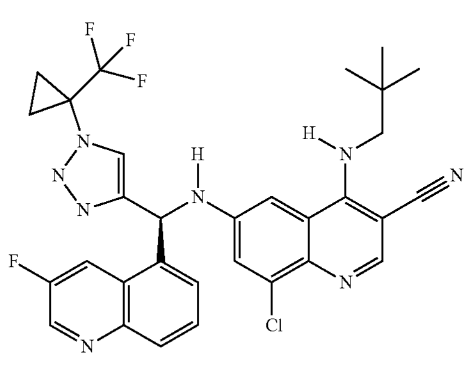 [SMILES: CC(C)(C)CNc1c(C#N)cnc2c(Cl)cc(N[C@H](C3=CN(C4(C(F)(F)F)CC4)NN3)c3cccc4ncc(F)cc34)cc12] | (S)-8-chloro-6-(((3-fluoroquinolin-5-yl)(1-(1-(trifluoromethyl)cyclopropyl)-1H-1,2,3-triazol-4-yl)methyl)amino)-4-(neopentylamino)quinoline-3-carbonitrile | 27 | 623.12 |

TABLE 1-continued

| Comp | Structure | Name | Example Procedure | ES/MS m/z |
|---|---|---|---|---|
| 938 | 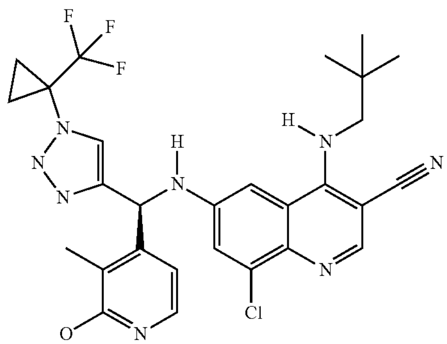 [SMILES: Cc1c([C@H](Nc2cc(Cl)c3ncc(C#N)c(NCC(C)(C)C)c3c2)C2=CN(C3(C(F)(F)F)CC3)NN2)ccnc1O] | (S)-8-chloro-6-(((2-chloro-3-methylpyridin-4-yl)(1-(1-(trifluoromethyl)cyclopropyl)-1H-1,2,3-triazol-4-yl)methyl)amino)-4-(neopentylamino)quinoline-3-carbonitrile | 27 | 603.13 |
| 939 | 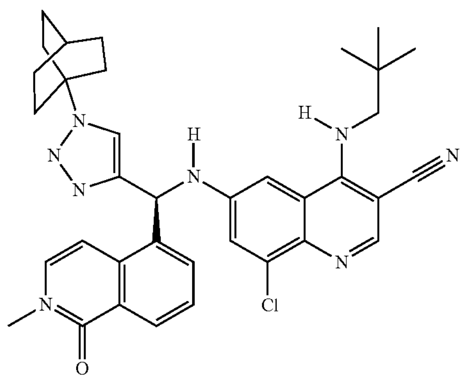 | (S)-6-(((1-(bicyclo[2.2.2]octan-1-yl)-1H-1,2,3-triazol-4-yl)(2-methyl-1-oxo-1,2-dihydroisoquinolin-5-yl)methyl)amino)-8-chloro-4-(neopentylamino)quinoline-3-carbonitrile | 27 | 635.21 |
| 940 | 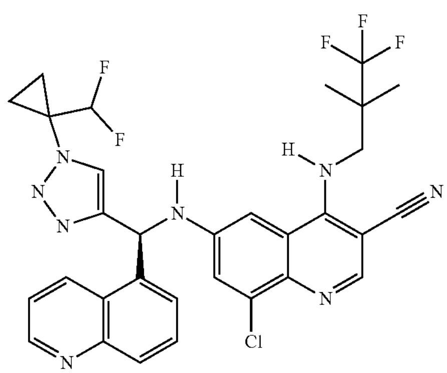 [SMILES: CC(C)(CNc1c(C#N)cnc2c(Cl)cc(N[C@H](C3=CN(C4(C(F)F)CC4)NN3)c3cccc4ncccc34)cc12)C(F)(F)F] | (S)-8-chloro-6-(((1-(1-(difluoromethyl)cyclopropyl)-1H-1,2,3-triazol-4-yl)(quinolin-5-yl)methyl)amino)-4-((3,3,3-trifluoro-2,2-dimethylpropyl)amino)quinoline-3-carbonitrile | 27 | 641.10 |
| 941 | 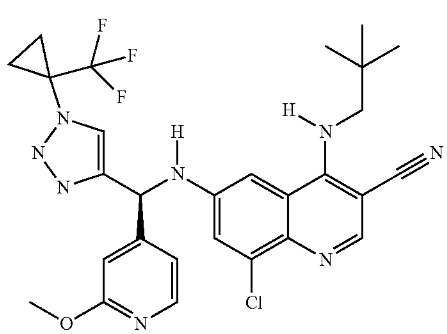 [SMILES: COc1cc([C@H](Nc2cc(Cl)c3ncc(C#N)c(NCC(C)(C)C)c3c2)C2=CN(C3(C(F)(F)F)CC3)NN2)ccn1] | (S)-8-chloro-6-(((2-methoxypyridin-4-yl)(1-(1-(trifluoromethyl)cyclopropyl)-1H-1,2,3-triazol-4-yl)methyl)amino)-4-(neopentylamino)quinoline-3-carbonitrile | 27 | 585.30 |

TABLE 1-continued

| Comp | Structure | Name | Example Procedure | ES/MS m/z |
|---|---|---|---|---|
| 942 | 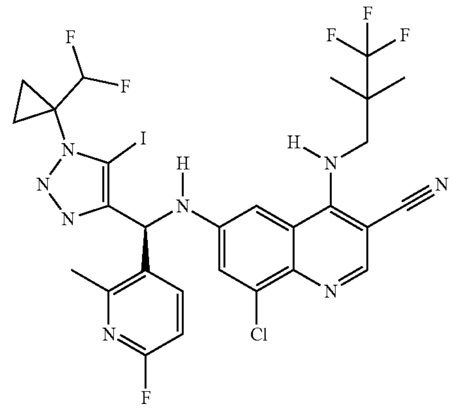 [SMILES: Cc1nc(F)ccc1[C@H](Nc1cc(Cl)c2ncc(C#N)c(NCC(C)(C)C(F)(F)F)c2c1)C1=C(I)N(C2(C(F)F)CC2)NN1] | (S)-8-chloro-6-(((1-(1-(difluoromethyl)cyclopropyl)-5-iodo-1H-1,2,3-triazol-4-yl)(6-fluoro-2-methylpyridin-3-yl)methyl)amino)-4-(((3,3,3-trifluoro-2,2-dimethylpropyl)amino)quinoline-3-carbonitrile | 28 | 749.23 (M + H+); 748.25 (M + H+) |
| 943 | 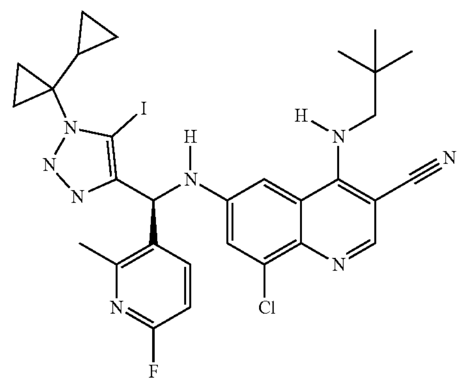 [SMILES: Cc1nc(F)ccc1[C@H](Nc1cc(Cl)c2ncc(C#N)c(NCC(C)(C)C)c2c1)C1=C(I)N(C2(C3CC3)CC2)NN1] | (S)-6-(((1-([1,1'-bi(cyclopropan)]-1-yl)-5-iodo-1H-1,2,3-triazol-4-yl)(6-fluoro-2-methylpyridin-3-yl)methyl)amino)-8-chloro-4-(neopentylamino)quinoline-3-carbonitrile | 28 | 685.20 |
| 944 | 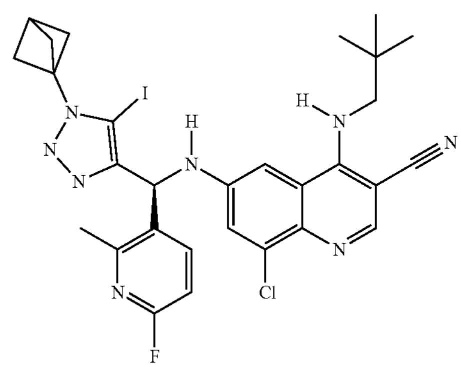 | (S)-6-(((1-(bicyclo[1.1.1]pentan-1-yl)-5-iodo-1H-1,2,3-triazol-4-yl)(6-fluoro-2-methylpyridin-3-yl)methyl)amino)-8-chloro-4-(neopentylamino)quinoline-3-carbonitrile | 28 | 671.10 |
| 945 | 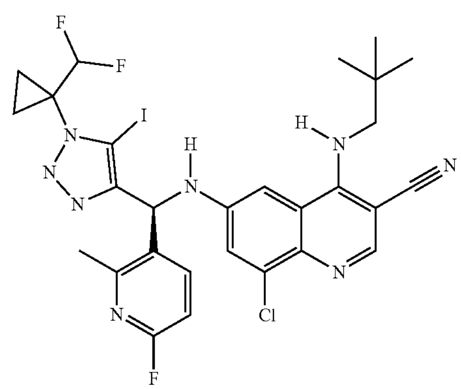 [SMILES: Cc1nc(F)ccc1[C@H](Nc1cc(Cl)c2ncc(C#N)c(NCC(C)(C)C)c2c1)C1=C(I)N(C2(C(F)F)CC2)NN1] | (S)-8-chloro-6-(((1-(1-(difluoromethyl)cyclopropyl)-5-iodo-1H-1,2,3-triazol-4-yl)(6-fluoro-2-methylpyridin-3-yl)methyl)amino)-4-(neopentylamino)quinoline-3-carbonitrile | 28 | 695.20 |

TABLE 1-continued

| Comp | Structure | Name | Example Procedure | ES/MS m/z |
|---|---|---|---|---|
| 946 | 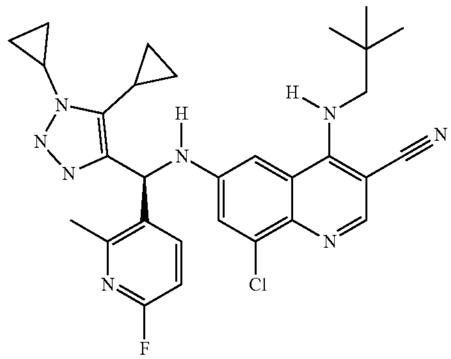 [SMILES: Cc1nc(F)ccc1[C@H](Nc1cc(Cl)c2ncc(C#N)c(NCC(C)(C)C)c2c1)C1=C(C2CC2)N(C2CC2)NN1] | (S)-8-chloro-6-(((1,5-dicyclopropyl-1H-1,2,3-triazol-4-yl)(6-fluoro-2-methylpyridin-3-yl)methyl)amino)-4-(neopentylamino)quinoline-3-carbonitrile | 29 | EXP-15-AN3588 |
| 947 | 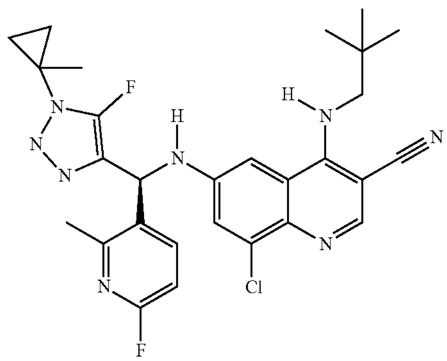 [SMILES: Cc1nc(F)ccc1[C@H](Nc1cc(Cl)c2ncc(C#N)c(NCC(C)(C)C)c2c1)C1=C(F)N(C2(C)CC2)NN1] | (S)-8-chloro-6-(((5-fluoro-1-(1-methylcyclopropyl)-1H-1,2,3-triazol-4-yl)(6-fluoro-2-methylpyridin-3-yl)methyl)amino)-4-(neopentylamino)quinoline-3-carbonitrile | 30 | 551.64 |
| 948 | 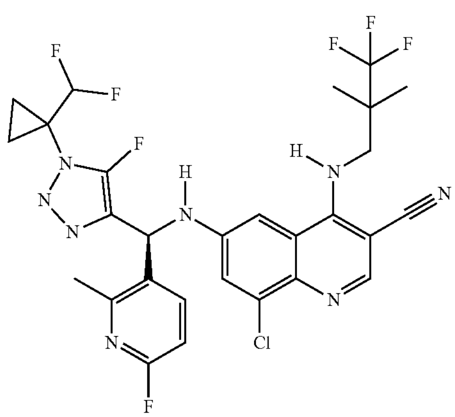 [SMILES: Cc1nc(F)ccc1[C@H](Nc1cc(Cl)c2ncc(C#N)c(NCC(C)(C)C(F)(F)F)c2c1)C1=C(F)N(C2(C(F)F)CC2)NN1] | (S)-8-chloro-6-(((1-(1-(difluoromethyl)cyclopropyl)-5-fluoro-1H-1,2,3-triazol-4-yl)(6-fluoro-2-methylpyridin-3-yl)methyl)amino)-4-((3,3,3-trifluoro-2,2-dimethylpropyl)amino)-quinoline-3-carbonitrile | 30 | 641 (M + H+) |
| 949 | 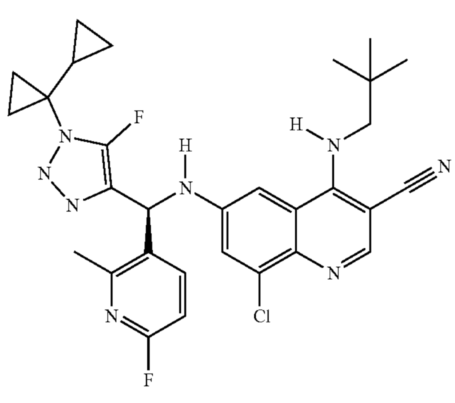 | (S)-6-(((1-([1,1'-bi(cyclopropan)]-1-yl)-5-fluoro-1H-1,2,3-triazol-4-yl)(6-fluoro-2-methylpyridin-3-yl)methyl)amino)-8-chloro-4-(neopentylamino)quinoline-3-carbonitrile | 30 | 577.10 |

TABLE 1-continued

| Comp | Structure | Name | Example Procedure | ES/MS m/z |
|---|---|---|---|---|
| 950 | 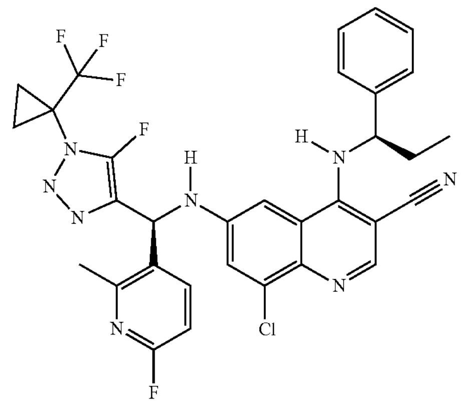 [SMILES: CC[C@@H](Nc1c(C#N)cnc2c(Cl)cc(N[C@H](C3=C(F)N(C4(C(F)(F)F)CC4)NN3)c3ccc(F)nc3C)cc12)c1ccccc1] | 8-chloro-6-(((S)-(5-fluoro-1-(1-(trifluoromethyl)cyclopropyl)-1H-1,2,3-triazol-4-yl)(6-fluoro-2-methylpyridin-3-yl)methyl)amino)-4-(((R)-1-phenylpropyl)amino)quinoline-3-carbonitrile | 30 | 653.40 |
| 951 | 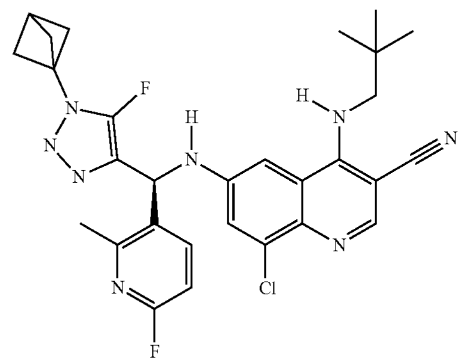 [SMILES: Cc1nc(F)ccc1[C@H](Nc1cc(Cl)c2ncc(C#N)c(NCC(C)(C)C)c2c1)C1=C(F)N(C23CC(C2)C3)NN1] | (S)-6-(((1-(bicyclo[1.1.1]pentan-1-yl)-5-fluoro-1H-1,2,3-triazol-4-yl)(6-fluoro-2-methylpyridin-3-yl)methyl)amino)-8-chloro-4-(neopentylamino)quinoline-3-carbonitrile | 30 | 563.40 |
| 952 | 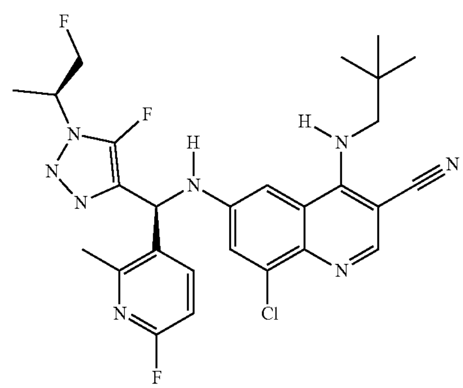 [SMILES: Cc1nc(F)ccc1[C@H](Nc1cc(Cl)c2ncc(C#N)c(NCC(C)(C)C)c2c1)C1=C(F)N([C@@H](C)CF)NN1] | 8-chloro-6-(((S)-(5-fluoro-1-((S)-1-fluoropropan-2-yl)-1H-1,2,3-triazol-4-yl)(6-fluoro-2-methylpyridin-3-yl)methyl)amino)-4-(neopentylamino)quinoline-3-carbonitrile | 30 | 557.30 |
| 953 | 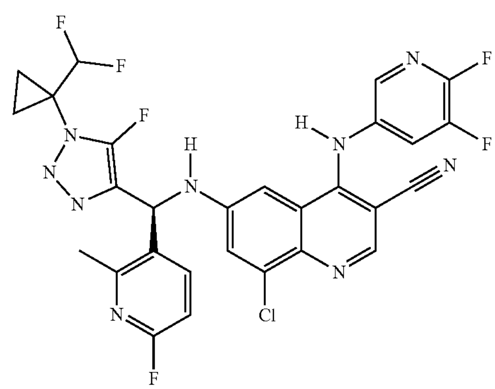 [SMILES: Cc1nc(F)ccc1[C@H](Nc1cc(Cl)c2ncc(C#N)c(Nc3cnc(F)c(F)c3)c2c1)C1=C(F)N(C2(C(F)F)CC2)NN1] | (S)-8-chloro-6-(((1-(1-(difluoromethyl)cyclopropyl)-5-fluoro-1H-1,2,3-triazol-4-yl)(6-fluoro-2-methylpyridin-3-yl)methyl)amino)-4-((5,6-difluoropyridin-3-yl)amino)quinoline-3-carbonitrile | 30 | 630.10 |

TABLE 1-continued

| Comp | Structure | Name | Example Procedure | ES/MS m/z |
|---|---|---|---|---|
| 954 | 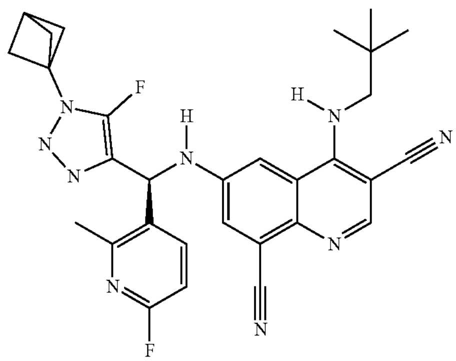 [SMILES: Cc1nc(F)ccc1[C@H](Nc1cc(C#N)c2ncc(C#N)c(NCC(C)(C)C)c2c1)C1=C(F)N(C23CC(C2)C3)NN1] | (S)-6-(((1-(bicyclo[1.1.1]pentan-1-yl)-5-fluoro-1H-1,2,3-triazol-4-yl)(6-fluoro-2-methylpyridin-3-yl)methyl)amino)-4-(neopentylamino)quinoline-3,8-dicarbonitrile | 30 | 554.40 |
| 955 | 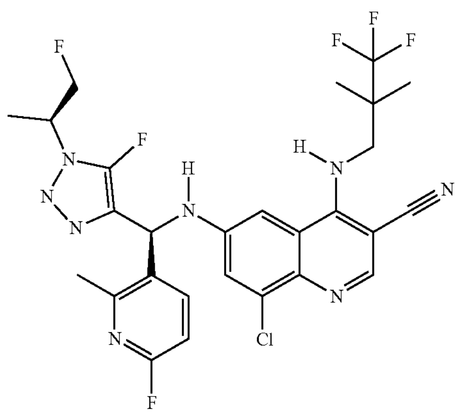 [SMILES: Cc1nc(F)ccc1[C@H](Nc1cc(Cl)c2ncc(C#N)c(NCC(C)(C)C(F)(F)F)c2c1)C1=C(F)N([C@@H](C)CF)NN1] | 8-chloro-6-(((S)-(5-fluoro-1-((S)-1-fluoropropan-2-yl)-1H-1,2,3-triazol-4-yl)(6-fluoro-2-methylpyridin-3-yl)methyl)amino)-4-((3,3,3-trifluoro-2,2-dimethylpropyl)amino)quinoline-3-carbonitrile | 30 | 611.20 |
| 956 | 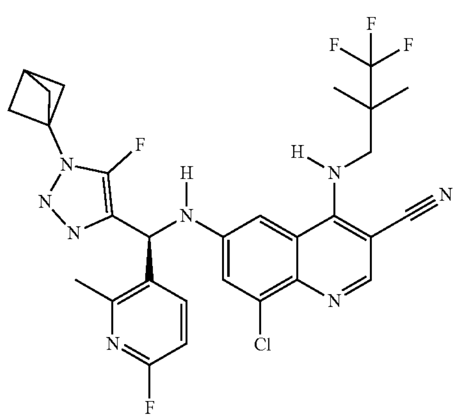 [SMILES: Cc1nc(F)ccc1[C@H](Nc1cc(Cl)c2ncc(C#N)c(NCC(C)(C)C(F)(F)F)c2c1)C1=C(F)N(C23CC(C2)C3)NN1] | (S)-6-(((1-(bicyclo[1.1.1]pentan-1-yl)-5-fluoro-1H-1,2,3-triazol-4-yl)(6-fluoro-2-methylpyridin-3-yl)methyl)amino)-8-chloro-4-((3,3,3-trifluoro-2,2-dimethylpropyl)amino)quinoline-3-carbonitrile | 30 | 617.40 |

TABLE 1-continued

| Comp | Structure | Name | Example Procedure | ES/MS m/z |
|---|---|---|---|---|
| 957 | 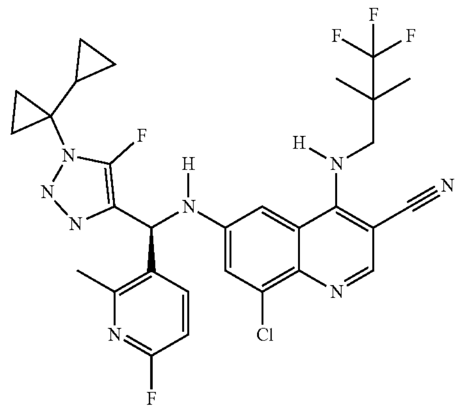 [SMILES: Cc1nc(F)ccc1[C@H](Nc1cc(Cl)c2ncc(C#N)c(NCC(C)(C)C(F)(F)F)c2c1)C1=C(F)N(C2(C3CC3)CC2)NN1] | (S)-6-(((1-([1,1'-bicyclopropan)]-1-yl)-5-fluoro-1H-1,2,3-triazol-4-yl)(6-fluoro-2-methylpyridin-3-yl)methyl)amino)-8-chloro-4-((3,3,3-trifluoro-2,2-dimethylpropyl)amino)quinoline-3-carbonitrile | 30 | 631.40 |
| 958 | 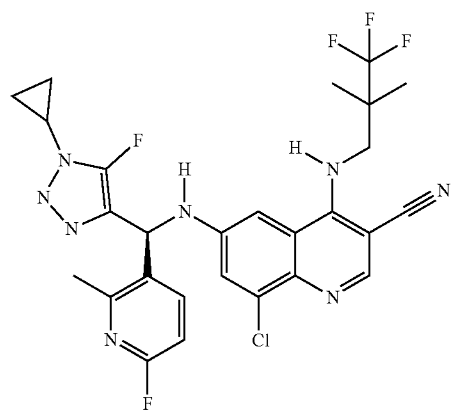 [SMILES: Cc1nc(F)ccc1[C@H](Nc1cc(Cl)c2ncc(C#N)c(NCC(C)(C)C(F)(F)F)c2c1)C1=C(F)N(C2CC2)NN1] | (S)-8-chloro-6-(((1-cyclopropyl-5-fluoro-1H-1,2,3-triazol-4-yl)(6-fluoro-2-methylpyridin-3-yl)methyl)amino)-4-((3,3,3-trifluoro-2,2-dimethylpropyl)amino)quinoline-3-carbonitrile | 30 | 591.10 |
| 959 | 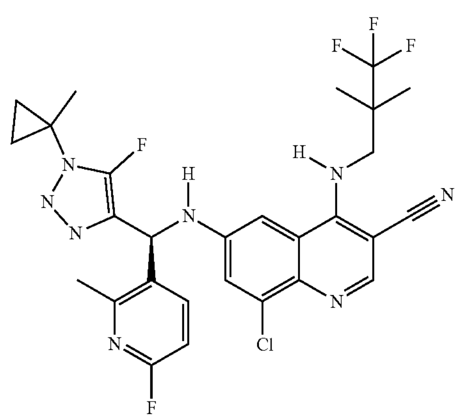 [SMILES: Cc1nc(F)ccc1[C@H](Nc1cc(Cl)c2ncc(C#N)c(NCC(C)(C)C(F)(F)F)c2c1)C1=C(F)N(C2(C)CC2)NN1] | (S)-8-chloro-6-(((5-fluoro-1-(1-methylcyclopropyl)-1H-1,2,3-triazol-4-yl)(6-fluoro-2-methylpyridin-3-yl)methyl)amino)-4-((3,3,3-trifluoro-2,2-dimethylpropyl)amino)quinoline-3-carbonitrile | 30 | 605.20 |

TABLE 1-continued

| Comp | Structure | Name | Example Procedure | ES/MS m/z |
|---|---|---|---|---|
| 960 | 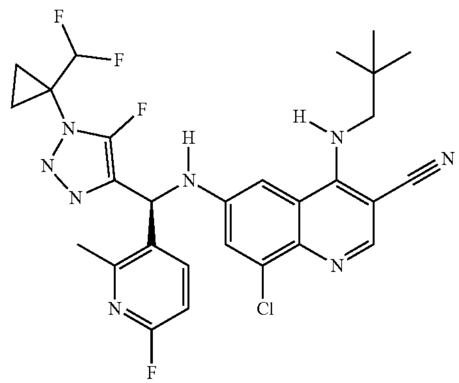 | (S)-8-chloro-6-(((1-(1-(difluoromethyl)cyclopropyl)-5-fluoro-1H-1,2,3-triazol-4-yl)(6-fluoro-2-methylpyridin-3-yl)methyl)amino)-4-(neopentylamino)quinoline-3-carbonitrile | 30 | 587.10 |
| 961 | 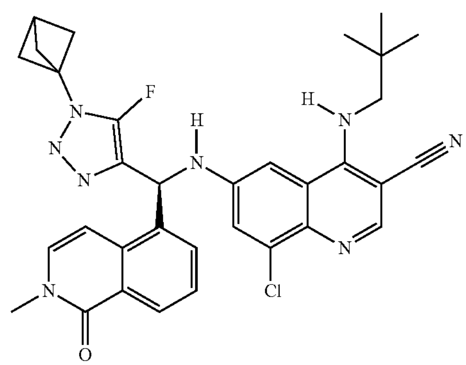 [SMILES: Cn1ccc2c([C@H](Nc3cc(Cl)c4ncc(C#N)c(NCC(C)(C)C)c4c3)C3=C(F)N(C45CC(C4)C5)NN3)cccc2c1=O] | (S)-6-(((1-(bicyclo[111]pentan-1-yl)-5-fluoro-1H-1,2,3-triazol-4-yl)(2-methyl-1-oxo-1,2-dihydroisoquinolin-5-yl)methyl)amino)-8-chloro-4-(neopentylamino)quinoline-3-carbonitrile | 30 | 611.30 |
| 962 | 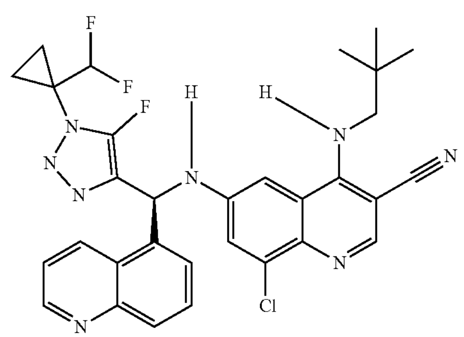 [SMILES: CN(CC(C)(C)C)c1c(C#N)cnc2c(Cl)cc(N(C)[C@H](C3=C(F)N(C4(C(F)F)CC4)NN3)c3cccc4ncccc34)cc12] | (S)-8-chloro-6-(((1-(1-(difluoromethyl)cyclopropyl)-5-fluoro-1H-1,2,3-triazol-4-yl)(quinolin-5-yl)methyl)amino)-4-(neopentylamino)quinoline-3-carbonitrile | 30 | 605.09 |
| 963 | 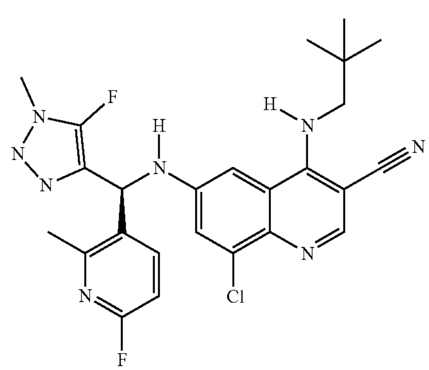 [SMILES: Cc1nc(F)ccc1[C@H](Nc1cc(Cl)c2ncc(C#N)c(NCC(C)(C)C)c2c1)C1=C(F)N(C)NN1] | (S)-8-chloro-6-(((5-fluoro-1-methyl-1H-1,2,3-triazol-4-yl)(6-fluoro-2-methylpyridin-3-yl)methyl)amino)-4-(neopentylamino)quinoline-3-carbonitrile | 30 | 511.10 |

TABLE 1-continued

| Comp | Structure | Name | Example Procedure | ES/MS m/z |
|---|---|---|---|---|
| 964 | 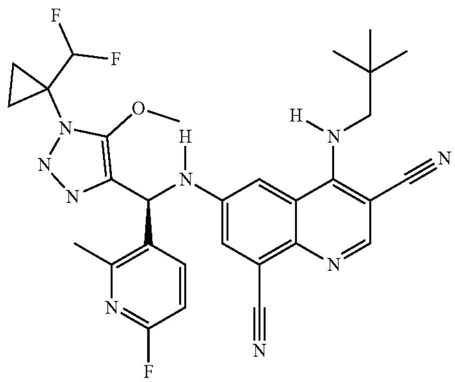 [SMILES: COC1=C([C@@H](Nc2cc(C#N)c3ncc(C#N)c(NCC(C)(C)C)c3c2)c2ccc(F)nc2C)NNN1C1(C(F)F)CC1] | (S)-6-(((1-(1-(difluoromethyl)cyclopropyl)-5-methoxy-1H-1,2,3-triazol-4-yl)(6-fluoro-2-methylpyridin-3-yl)methyl)amino)-4-(neopentylamino)quinoline-3,8-dicarbonitrile | 31 | 590.20 |
| 965 | 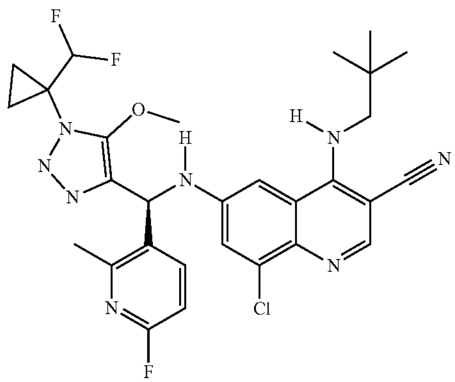 [SMILES: COC1=C([C@@H](Nc2cc(Cl)c3ncc(C#N)c(NCC(C)(C)C)c3c2)c2ccc(F)nc2C)NNN1C1(C(F)F)CC1] | (S)-8-chloro-6-(((1-(1-(difluoromethyl)cyclopropyl)-5-methoxy-1H-1,2,3-triazol-4-yl)(6-fluoro-2-methylpyridin-3-yl)methyl)amino)-4-(neopentylamino)quinoline-3-carbonitrile | 31 | 599.30 |
| 966 | 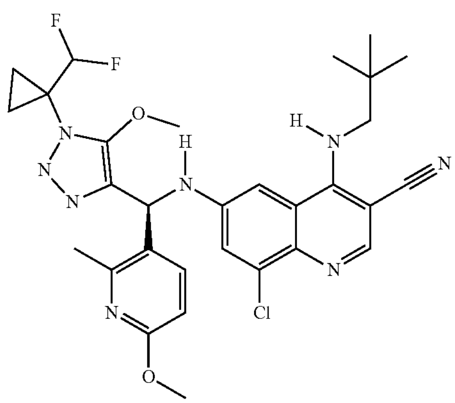 [SMILES: COC1=C([C@@H](Nc2cc(Cl)c3ncc(C#N)c(NCC(C)(C)C)c3c2)c2ccc(OC)nc2C)NNN1C1(C(F)F)CC1] | (S)-8-chloro-6-(((1-(1-(difluoromethyl)cyclopropyl)-5-methoxy-1H-1,2,3-triazol-4-yl)(6-methoxy-2-methylpyridin-3-yl)methyl)amino)-4-(neopentylamino)quinoline-3-carbonitrile | 31 | 611.20 |
| 967 | 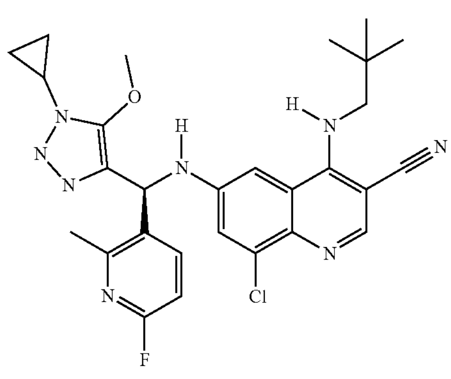 [SMILES: COC1=C([C@@H](Nc2cc(Cl)c3ncc(C#N)c(NCC(C)(C)C)c3c2)c2ccc(F)nc2C)NNN1C1CC1] | (S)-8-chloro-6-(((1-cyclopropyl-5-methoxy-1H-1,2,3-triazol-4-yl)(6-fluoro-2-methylpyridin-3-yl)methyl)amino)-4-(neopentylamino)quinoline-3-carbonitrile | 31 | 549.28 |

TABLE 1-continued

| Comp | Structure | Name | Example Procedure | ES/MS m/z |
|---|---|---|---|---|
| 968 | 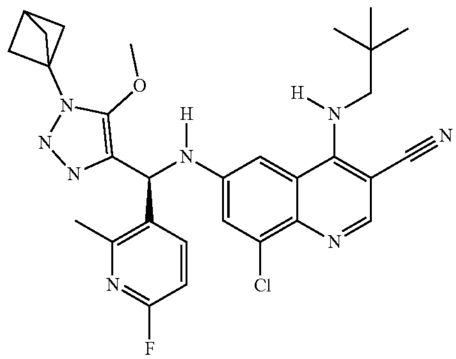 [SMILES: COC1=C([C@@H](Nc2cc(Cl)c3ncc(C#N)c(NCC(C)(C)C)c3c2)c2ccc(F)nc2C)NNN1C12CC(C1)C2] | (S)-6-((((1-(bicyclo[1.1.1]pentan-1-yl)-5-methoxy-1H-1,2,3-triazol-4-yl)(6-fluoro-2-methylpyridin-3-yl)methyl)amino)-8-chloro-4-(neopentylamino)quinoline-3-carbonitrile | 31 | 575.20 |
| 969 | 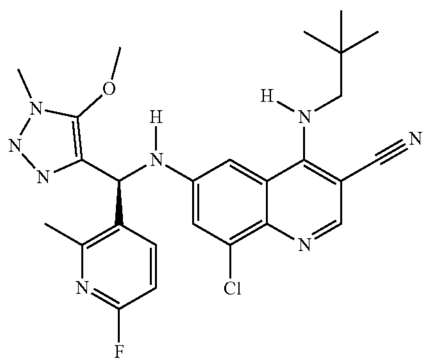 | (S)-8-chloro-6-((((6-fluoro-2-methylpyridin-3-yl)(5-methoxy-1-methyl-1H-1,2,3-triazol-4-yl)methyl)amino)-4-(neopentylamino)quinoline-3-carbonitrile | 31 | 523.20 |
| 970 | 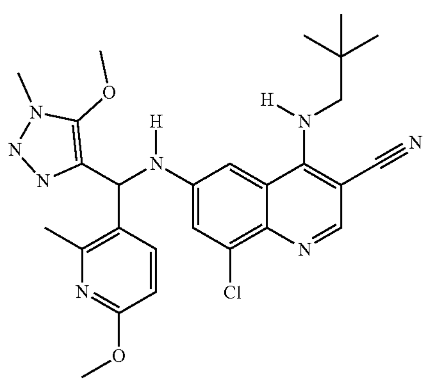 [SMILES: COC1=C(C(Nc2cc(Cl)c3ncc(C#N)c(NCC(C)(C)C)c3c2)c2ccc(OC)nc2C)NNN1C] | 8-chloro-6-(((5-methoxy-1-methyl-1H-1,2,3-triazol-4-yl)(6-methoxy-2-methylpyridin-3-yl)methyl)amino)-4-(neopentylamino)quinoline-3-carbonitrile | 31 | 535.20 |
| 971 | 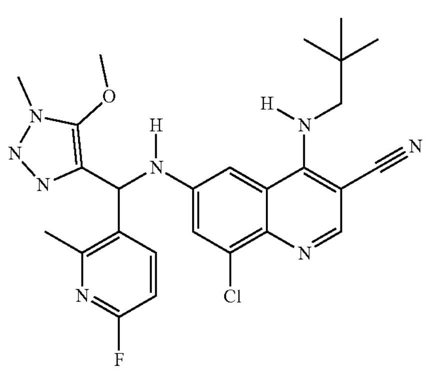 [SMILES: COC1=C(C(Nc2cc(Cl)c3ncc(C#N)c(NCC(C)(C)C)c3c2)c2ccc(F)nc2C)NNN1C] | 8-chloro-6-((((6-fluoro-2-methylpyridin-3-yl)(5-methoxy-1-methyl-1H-1,2,3-triazol-4-yl)methyl)amino)-4-(neopentylamino)quinoline-3-carbonitrile | 31 | 523.20 |

TABLE 1-continued

| Comp | Structure | Name | Example Procedure | ES/MS m/z |
|---|---|---|---|---|
| 972 | 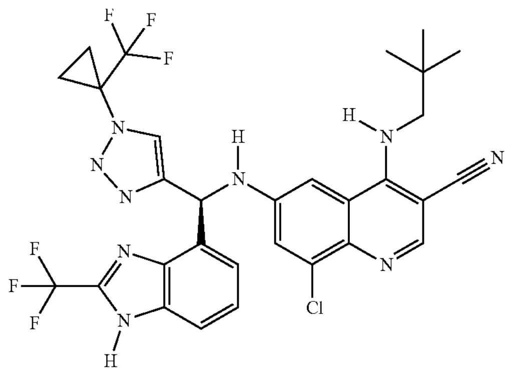 [SMILES: CC(C)(C)CNc1c(C#N)cnc2c(Cl)cc(N[C@H](C3=CN(C4(C(F)(F)F)CC4)NN3)c3cccc4[nH]c(C(F)(F)F)nc34)cc12] | (S)-8-chloro-4-(neopentylamino)-6-(((2-(trifluoromethyl)-1H-benzo[d]imidazol-4-yl)(1-(1-(trifluoromethyl)cyclopropyl)-1H-1,2,3-triazol-4-yl)methyl)amino)quinoline-3-carbonitrile | 32 | 662.14 |
| 973 | 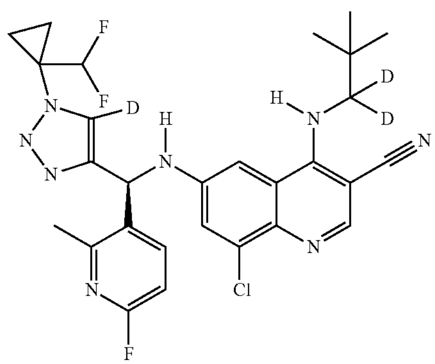 [SMILES: [2H]C1=C([C@@H](Nc2cc(Cl)c3ncc(C#N)c(NC([2H])([2H])C(C)(C)C)c3c2)c2ccc(F)nc2C)NNN1C1(C(F)F)CC1] | (S)-8-chloro-6-(((1-(1-(difluoromethyl)cyclopropyl)-1H-1,2,3-triazol-4-yl-5-d)(6-fluoro-2-methylpyridin-3-yl)methyl)amino)-4-((2,2-dimethylpropyl-1,1-d2)amino)quinoline-3-carbonitrile | 33 | 572.36 (M + H+) |
| 974 | 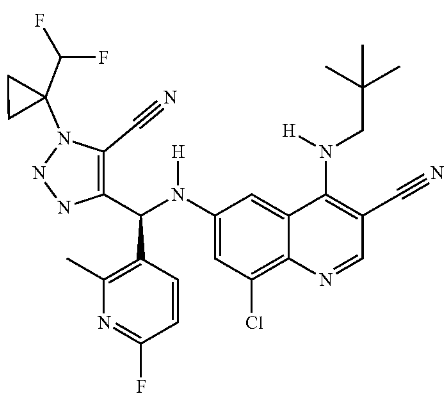 [SMILES: Cc1nc(F)ccc1[C@H](Nc1cc(Cl)c2ncc(C#N)c(NCC(C)(C)C)c2c1)C1=C(C#N)N(C2(C(F)F)CC2)NN1] | (S)-8-chloro-6-(((5-cyano-1-(1-(difluoromethyl)cyclopropyl)-1H-1,2,3-triazol-4-yl)(6-fluoro-2-methylpyridin-3-yl)methyl)amino)-4-(neopentylamino)quinoline-3-carbonitrile | 36 | 594.40 |
| 975 | 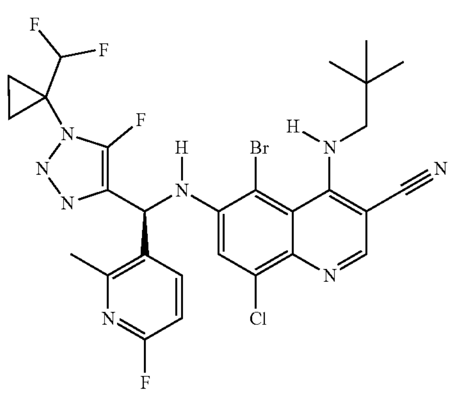 [SMILES: Cc1nc(F)ccc1[C@H](Nc1cc(Cl)c2ncc(C#N)c(NCC(C)(C)C)c2c1Br)C1=C(F)N(C2(C(F)F)CC2)NN1] | (S)-5-bromo-8-chloro-6-(((1-(1-(difluoromethyl)cyclopropyl)-5-fluoro-1H-1,2,3-triazol-4-yl)(6-fluoro-2-methylpyridin-3-yl)methyl)amino)-4-(neopentylamino)quinoline-3-carbonitrile | 42 | 665.30 |

TABLE 1-continued

| Comp | Structure | Name | Example Procedure | ES/MS m/z |
|---|---|---|---|---|
| 976 | 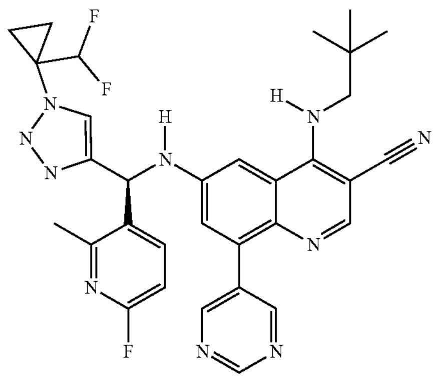 [SMILES: Cc1nc(F)ccc1[C@H](Nc1cc(-c2cncnc2)c2ncc(C#N)c(NCC(C)(C)C)c2c1)C1=CN(C2(C(F)F)CC2)NN1] | (S)-6-(((4-(1-(1-(difluoromethyl)cyclopropyl)-1H-1,2,3-triazol-4-yl)(6-fluoro-2-methylpyridin-3-yl)methyl)amino)-4-(neopentylamino)-8-(pyrimidin-5-yl)quinoline-3-carbonitrile | 46 | 613.3 (M + H+) |
| 977 | 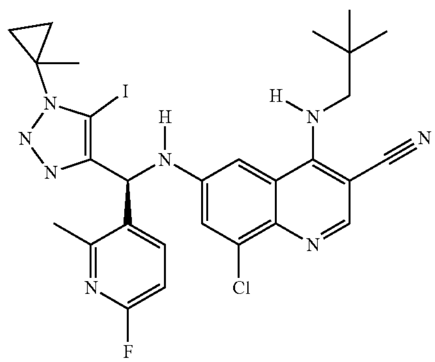 [SMILES: Cc1nc(F)ccc1[C@H](Nc1cc(Cl)c2ncc(C#N)c(NCC(C)(C)C)c2c1)C1=C(I)N(C2(C)CC2)NN1] | (S)-8-chloro-6-((((6-fluoro-2-methylpyridin-3-yl)(5-iodo-1-(1-methylcyclopropyl)-1H-1,2,3-triazol-4-yl)methyl)amino)-4-(neopentylamino)quinoline-3-carbonitrile | 47 | 659.26 |
| 978 | 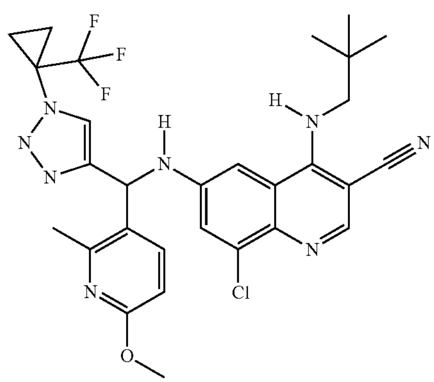 [SMILES: COc1ccc(C(Nc2cc(Cl)c3ncc(C#N)c(NCC(C)(C)C)c3c2)C2=CN(C3(C(F)(F)F)CC3)NN2)c(C)n1] | 8-chloro-6-((((6-methoxy-2-methylpyridin-3-yl)(1-(1-(trifluoromethyl)cyclopropyl)-1H-1,2,3-triazol-4-yl)methyl)amino)-4-(neopentylamino)quinoline-3-carbonitrile | 48 | 599.25 |
| 979 | 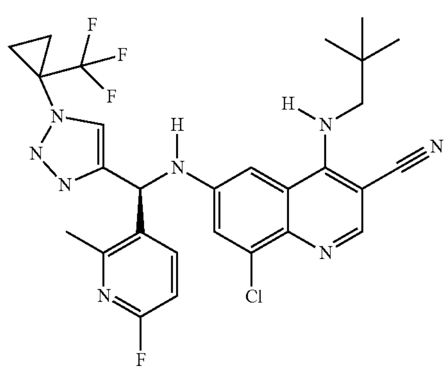 [SMILES: Cc1nc(F)ccc1[C@H](Nc1cc(Cl)c2ncc(C#N)c(NCC(C)(C)C)c2c1)C1=CN(C2(C(F)(F)F)CC2)NN1] | (S)-8-chloro-6-((((6-fluoro-2-methylpyridin-3-yl)(1-(1-(trifluoromethyl)cyclopropyl)-1H-1,2,3-triazol-4-yl)methyl)(methyl)amino)-4-(neopentylamino)quinoline-3-carbonitrile | 48 | 601.37 |

TABLE 1-continued

| Comp | Structure | Name | Example Procedure | ES/MS m/z |
|---|---|---|---|---|
| 980 | 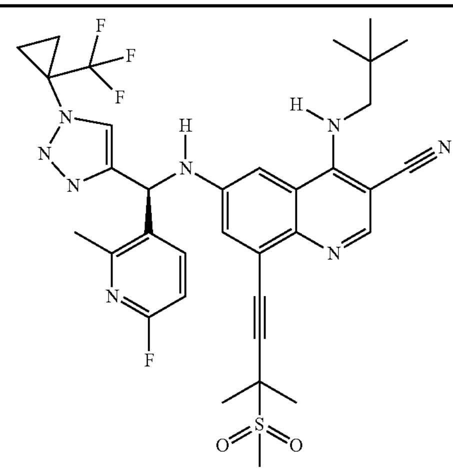 | (S)-6-(((6-fluoro-2-methylpyridin-3-yl)(1-(1-(trifluoromethyl)cyclopropyl)-1H-1,2,3-triazol-4-yl)methyl)amino)-8-(3-methyl-3-(methylsulfonyl)butyl-1-yl)-4-(neopentylamino)quinoline-3-carbonitrile | 40 | 697.29 |
| 981 | 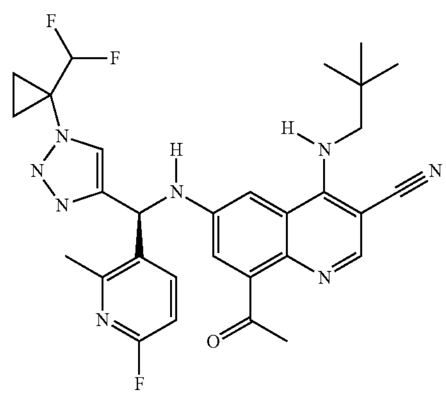 [SMILES: CC(=O)c1cc(N[C@H](C2=CN(C3(C(F)F)CC3)NN2)c2ccc(F)nc2C)cc2c(NCC(C)(C)C)c(C#N)cnc12] | (S)-8-acetyl-6-(((1-(1-(difluoromethyl)cyclopropyl)-1H-1,2,3-triazol-4-yl)(6-fluoro-2-methylpyridin-3-yl)methyl)amino)-4-(neopentylamino)quinoline-3-carbonitrile | 49 | 577.20 |
| 982 | 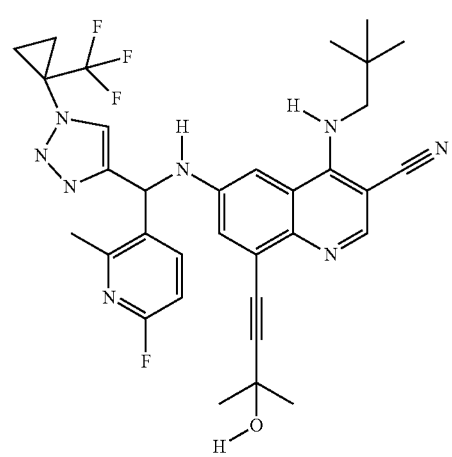 [SMILES: Cc1nc(F)ccc1C(Nc1cc(C#CC(C)(C)O)c2ncc(C#N)c(NCC(C)(C)C)c2c1)C1=CN(C2(C(F)(F)F)CC2)NN1] | 6-(((6-fluoro-2-methylpyridin-3-yl)(1-((1-(trifluoromethyl)cyclopropyl)-1H-1,2,3-triazol-4-yl)methyl)amino)-8-(3-hydroxy-3-methylbutyl-1-yl)-4-(neopentylamino)quinoline-3-carbonitrile | 40 | 635.29 |

TABLE 1-continued

| Comp | Structure | Name | Example Procedure | ES/MS m/z |
|---|---|---|---|---|
| 983 | 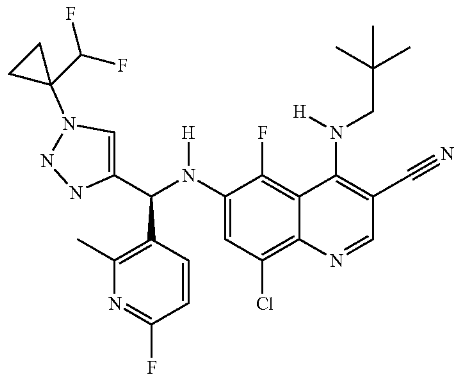 [SMILES: Cc1nc(F)ccc1[C@H](Nc1cc(Cl)c2ncc(C#N)c(NCC(C)(C)C)c2c1F)C1=CN(C2(C(F)F)CC2)NN1] | (S)-8-chloro-6-(((1-(1-(difluoromethyl)cyclopropyl)-1H-1,2,3-triazol-4-yl)(6-fluoro-2-methylpyridin-3-yl)methyl)amino)-5-fluoro-4-(neopentylamino)quinoline-3-carbonitrile | 41 | 587.45 |
| 984 | 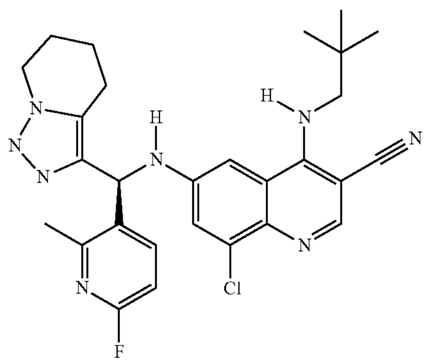 [SMILES: Cc1nc(F)ccc1[C@H](Nc1cc(Cl)c2ncc(C#N)c(NCC(C)(C)C)c2c1)C1=C2CCCCN2NN1] | (S)-8-chloro-6-(((6-fluoro-2-methylpyridin-3-yl)(4,5,6,7-tetrahydro-[1,2,3]triazolo[1,5-a]pyridin-3-yl)methyl)amino)-4-(neopentylamino)quinoline-3-carbonitrile | 44 | 534.22 |
| 985 | 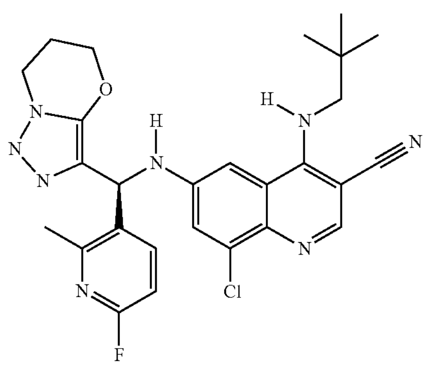 [SMILES: Cc1nc(F)ccc1[C@H](Nc1cc(Cl)c2ncc(C#N)c(NCC(C)(C)C)c2c1)C1=C2OCCCN2NN1] | (S)-8-chloro-6-(((6,7-dihydro-5H-[1,2,3]triazolo[5,1-b][1,3]oxazin-3-yl)(6-fluoro-2-methylpyridin-3-yl)methyl)amino)-4-(neopentylamino)quinoline-3-carbonitrile | 45 | 535.34 |
| 986 | 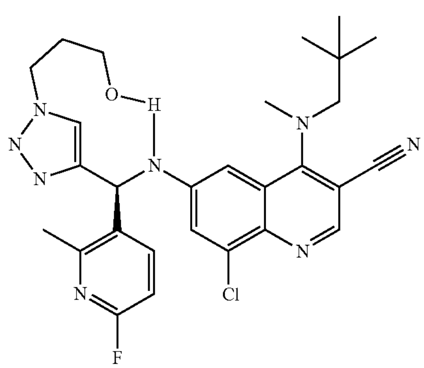 | (S)-8-chloro-6-(((6-fluoro-2-methylpyridin-3-yl)(1-(3-hydroxypropyl)-1H-1,2,3-triazol-4-yl)methyl)amino)-4-(neopentylamino)quinoline-3-carbonitrile | 46 | 537.27 |

TABLE 1-continued

| Comp | Structure | Name | Example Procedure | ES/MS m/z |
|---|---|---|---|---|
| 987 | 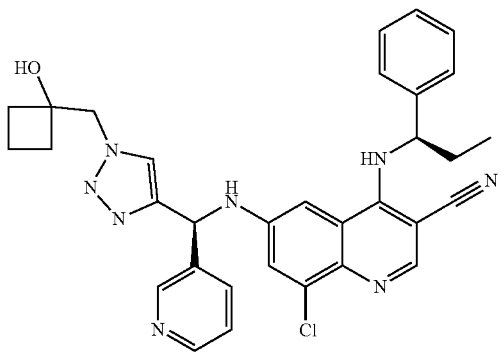 [SMILES: CC[C@@H](Nc1c(C#N)cnc2c(Cl)cc(N[C@H](C3=CN(CC4(O)CCC4)NN3)c3cccnc3)cc12)c1ccccc1] | 8-chloro-6-(((S)-(1-((1-hydroxycyclobutyl)methyl)-1H-1,2,3-triazol-4-yl)(pyridin-3-yl)methyl)amino)-4-(((R)-1-phenylpropyl)amino)quinoline-3-carbonitrile | | |

Proton NMR data for select compounds is shown below in Table 2.

TABLE 2

| Compound | $^1$H-NMR |
|---|---|
| 1 | 1H NMR (400 MHz, DMSO-d6) δ 8.37 (m, 2H), 8.17 (s, 1H), 8.05 (m, 1H), 7.79 (brs, 1H), 7.62 (d, J = 2.2 Hz, 1H), 7.51 (br s, 1H), 7.15 (m, 2H), 4.03 (m, 1H), 3.44 (dd, J = 13.9/5.5 Hz, 1H), 1.59 (s, 9H), 0.88 (s, 9H). |
| 2 | 1H NMR (400 MHz, CD30D) δ 8.61 (m, 1H), 8.37 (m, 1H), 8.29 (m, 1H), 8.05 (m, 1H), 7.73 (m, 1H), 7.60 (s, 1H), 7.32 (m, 5H), 7.14 (m, 1H), 6.46 (s, 1H), 5.64 (m, 1H), 4.88 (m, 1H), 2.83 (s, 3H), 2.17-2.02 (m, 2H), 1.56 (d, 6H), 0.97 (m, 3H). |
| 3 | 1H NMR (400 MHz, CD30D) δ 8.43 (m, 1H), 8.05 (m, 1H), 8.01 (m, 1H), 7.64 (m, 1H), 7.42-7.25 (m, 6H), 6.98 (m, 1H), 5.80-5.66 (m, 1H), 3.97-3.84 (m, 1H), 2.25-2.01 (m, 2H), 1.28-1.11 (m, 4H), 1.01 (m, 3H). |
| 4 | 1H NMR (400 MHz, DMSO-d6) δ 8.84 (dd, J = 14.0, 2.2 Hz, 1H), 8.64-8.52 (m, 1H), 8.23 (d, J = 2.1 Hz, 1H), 8.14 (d, J = 7.8 Hz, 1H), 8.05 (d, J = 6.7 Hz, 1H), 7.65-7.54 (m, 2H), 7.46 (d, J = 9.5 Hz, 1H), 7.43-7.38 (m, 2H), 7.28-7.21 (m, 2H), 7.21-7.15 (m, 3H), 6.48 (d, J = 6.9 Hz, 1H), 5.48 (q, J = 7.7 Hz, 1H), 5.35 (s, OH), 4.68 (d, J = 2.0 Hz, 2H), 4.50 (dd, J = 6.2, 4.5 Hz, 3H), 4.41 (dd, J = 6.7, 3.4 Hz, 2H), 2.12 (dt, J = 14.5, 7.4 Hz, 1H), 2.04-1.78 (m, 1H), 0.94 (t, J = 7.3 Hz, 3H), 0.85 (t, J = 7.2 Hz, 1H). |
| 5 | 1H NMR (400 MHz, DMSO-d6) δ 9.41 (s, 1H), 8.47 (s, 1H), 8.14 (s, 1H), 7.60 (d, J = 2.3 Hz, 1H), 7.41-7.34 (m, 2H), 7.27 (d, J = 8.2 Hz, 1H), 7.15 (dd, J = 9.1, 3.3 Hz, 2H), 7.12 (s, 1H), 5.96 (d, J = 8.1 Hz, 1H), 4.50-4.32 (m, 1H), 3.00-2.83 (m, 2H), 2.42-2.25 (m, 2H), 2.18-1.81 (m, 6H), 0.98 (t, J = 7.2 Hz, 3H). |
| 6 | 1H NMR (400 MHz, DMSO-d6) δ 9.41 (s, 1H), 8.74 (d, J = 2.2 Hz, 1H), 8.54 (dd, J = 5.0, 1.5 Hz, 1H), 8.41 (s, 1H), 8.13 (s, 1H), 8.00 (d, J = 8.0 Hz, 1H), 7.67 (d, J = 2.2 Hz, 1H), 7.59-7.36 (m, 3H), 7.33-7.17 (m, 2H), 6.20 (d, J = 8.0 Hz, 1H), 4.83-4.67 (m, 1H), 3.61 (d, J = 12.4 Hz, 2H), 3.28-2.97 (m, 2H), 2.34 (d, J = 13.8 Hz, 2H), 2.17 (m, 2H), 1.22 (t, J = 7.3 Hz, 2H). |
| 9 | 1H NMR (400 MHz, Methanol-d4) δ 9.20 (s, 1H), 8.34 (s, 1H), 8.05 (dd, J = 7.3, 1.9 Hz, 1H), 7.86 (d, J = 2.5 Hz, 1H), 7.82 (s, 1H), 7.64-7.54 (m, 2H), 7.16 (d, J = 2.6 Hz, 1H), 6.34 (s, 1H), 3.97 (d, J = 13.7 Hz, 1H), 3.91-3.80 (m, 1H), 3.49 (d, J = 13.7 Hz, 1H), 1.23-1.07 (m, 4H), 0.81 (s, 9H) |
| 16 | 1H NMR (400 MHz, DMSO-d6) δ 8.92-8.83 (m, 1H), 8.67 (d, J = 9.5 Hz, 1H), 8.65-8.58 (m, 1H), 8.24 (d, J = 3.3 Hz, 1H), 8.15 (d, J = 7.7 Hz, 1H), 7.64-7.56 (m, 2H), 7.52 (d, J = 8.3 Hz, 1H), 7.42 (d, J = 8.5 Hz, 1H), 7.39-7.29 (m, 2H), 7.29-7.16 (m, 6H), 6.54 (d, J = 7.8 Hz, 1H), 5.47 (q, J = 7.6 Hz, 1H), 4.32 (t, J = 12.0 Hz, 2H), 2.11 (m, 1H), 2.04-1.83 (m, 1H), 0.93 (t, J = 7.3 Hz, 3H). |
| 20 | 1H NMR (400 MHz, CD30D) δ 9.02 (m, 1H), 8.46 (s, 1H), 8.01 (m, 1H), 7.68 (m, 1H), 7.60 (m, 1H), 7.52 (m, 1H), 7.33 (m, 4H), 6.31 (s, 1H), 3.75 (m, 2H), 3.25-3.13 (m, 3H), 2.45 (m, 2H), 2.36 (m, 2H), 2.25-2.01 (m, 2H), 1.37 (m, 3H), |
| 22 | 1H NMR (400 MHz, DMSO-d6) δ 8.49-8.38 (m, 1H), 8.28 (d, J = 5.1 Hz, 1H), 8.13-8.02 (m, 2H), 7.84 (t, J = 2.4 Hz, 1H), 7.65-7.52 (m, 2H), 7.42-7.31 (m, 1H), 7.31-7.15 (m, 4H), 5.49 (q, J = 7.7 Hz, 1H), 4.04 (s, 3H), 3.20-3.11 (m, 1H), 2.20-2.05 (m, 1H), 2.05-1.85 (m, 1H), 1.63-1.50 (m, 1H), 1.37-1.20 (m, 1H), 0.99-0.83 (m, 3H) |
| 23 | 1H NMR (400 MHz, Methanol-d4) δ 8.19 (s, 1H), 7.86 (s, 1H), 7.62 (d, J = 2.5 Hz, 1H), 7.43-7.24 (m, 3H), 7.13 (d, J = 2.6 Hz, 1H), 6.05 (s, 1H), 3.86-3.63 (m, 4H), 3.56 (d, J = 13.9 Hz, 1H), 3.39-3.29 (m, 1H), 3.15-3.04 (m, 1H), 1.13-1.04 (m, 4H), 0.83 (s, 9H) |

TABLE 2-continued

| Compound | ¹H-NMR |
|---|---|
| 25 | 1H NMR (400 MHz, Chloroform-d) δ 8.97 (s, 1H), 8.41 (s, 1H), 8.14 (d, J = 8.1 Hz, 1H), 7.75 (s, 1H), 7.69 (d, J = 2.2 Hz, 1H), 7.58 (t, J = 7.7 Hz, 1H), 7.15 (s, 1H), 6.50 (br s, 1H), 6.09 (br s, 1H), 3.67 (m, 1H), 3.59 (br s, 2H), 3.53-3.45 (m, 1H), 1.23-1.17 (m, 2H), 1.17-1.08 (m, 2H), 0.84 (s, 9H) |
| 27 | 1H NMR (400 MHz, Methanol-d4) δ 8.45 (s, 1H), 7.95 (s, 1H), 7.62 (d, J = 2.3 Hz, 1H), 7.48 (dd, J = 7.1, 1.7 Hz, 1H), 7.45-7.37 (m, 2H), 7.05 (d, J = 2.3 Hz, 1H), 6.08 (s, 1H), 4.86 (d, J = 14.7 Hz, 1H), 4.57 (d, J = 1.7 Hz, 2H), 4.51 (d, J = 14.7 Hz, 1H), 4.12 (d, J = 13.9 Hz, 1H), 3.94-3.84 (m, 1H), 3.73 (d, J = 13.9 Hz, 1H), 1.25-1.13 (m, 4H), 0.95 (s, 9H) |
| 36 | 1H NMR (400 MHz, Methanol-d4) δ 8.35 (s, 1H), 8.08 (s, 1H), 7.62 (d, J = 2.2 Hz, 1H), 7.58-7.50 (m, 1H), 7.43-7.34 (m, 2H), 7.37-7.22 (m, 6H), 6.27 (s, 1H), 5.68 (t, J = 7.3 Hz, 1H), 4.92 (d, J = 14.4 Hz, 1H), 4.61-4.49 (m, 3H), 2.27-2.19 (m, 1H), 2.12-2.02 (m, 1H), 1.67 (s, 9H), 1.01 (t, J = 7.4 Hz, 2H) |
| 61 | 1H NMR (400 MHz, Methanol-d4) δ 9.24 (s, 1H), 8.49 (s, 1H), 8.18 (d, J = 1.7 Hz, 1H), 8.06 (d, J = 8.5 Hz, 1H), 7.78 (s, 1H), 7.73 (d, J = 2.3 Hz, 1H), 7.64 (dd, J = 8.4, 1.8 Hz, 1H), 7.58-7.51 (m, 1H), 7.39-7.30 (m, 2H), 7.26 (d, J = 2.4 Hz, 1H), 6.22 (s, 1H), 4.79 (m, 1H), 1.52 (dd, J = 6.7, 2.3 Hz, 6H) |
| 62 | 1H NMR (400 MHz, Methanol-d4) δ 9.26 (s, 1H), 8.45 (s, 1H), 8.15 (s, 1H), 8.08 (d, J = 8.2 Hz, 1H), 7.84 (s, 1H), 7.71 (d, J = 2.4 Hz, 1H), 7.64-7.56 (m, 1H), 7.47 (dd, J = 6.5, 2.4 Hz, 1H), 7.35-7.21 (m, 3H), 6.24 (s, 1H), 4.89-4.71 (m, 1H), 3.79 (d, J = 12.7 Hz, 2H), 3.20 (dd, J = 13.7, 10.8 Hz, 2H), 2.42 (m, 4H), 1.45 (s, 9H) |
| 63 | 1H NMR (400 MHz, Methanol-d4) δ 9.25 (s, 1H), 8.46 (s, 1H), 8.18 (d, J = 1.8 Hz, 1H), 8.06 (d, J = 8.6 Hz, 1H), 7.85 (s, 1H), 7.71 (d, J = 2.4 Hz, 1H), 7.64 (dd, J = 8.6, 1.8 Hz, 1H), 7.47 (dd, J = 6.4, 2.5 Hz, 1H), 7.35-7.20 (m, 3H), 6.21 (s, 1H), 4.83-4.73 (m, 1H), 3.79 (d, J = 12.6 Hz, 2H), 3.26-3.15 (m, 2H), 2.48-2.35 (m, 4H), 1.45 (s, 9H) |
| 64 | 1H NMR (400 MHz, Methanol-d4) δ 8.44 (s, 1H), 7.95-7.84 (m, 2H), 7.77 (s, 1H), 7.69 (d, J = 2.4 Hz, 1H), 7.59 (d, J = 5.5 Hz, 1H), 7.50-7.39 (m, 2H), 7.35-7.19 (m, 4H), 6.14 (s, 1H), 4.83-4.68 (m, 1H), 3.78 (d, J = 12.5 Hz, 2H), 3.20 (t, J = 12.6 Hz, 2H), 2.52-2.30 (m, 4H), 1.45 (s, 9H) |
| 71 | 1H NMR (400 MHz, Methanol-d4) δ 8.33 (s, 1H), 8.13-8.07 (m, 1H), 7.95-7.85 (m, 2H), 7.55 (m, 1H), 7.36-7.18 (m, 7H), 5.91-5.79 (m, 1H), 3.82 m, 1H), 2.59-2.46 (m, 2H), 2.50-2.22 (m, 2H), 1.20-1.02 (m, 4H). |
| 72 | 1H NMR (400 MHz, Methanol-d4) δ 8.43 (s, 1H), 7.92 (m, 1H), 7.85-7.72 (m, 1H), 7.60 (m, 1H), 7.49-7.28 (m, 5H), 7.27-7.14 (m, 1H), 6.88 (m, 1H), 5.92 (m, 1H), 3.90 (m, 1H), 2.66-2.50 (m, 5H), 2.43 (m, 2H), 1.28-1.10 (m, 4H). |
| 73 | 1H NMR (400 MHz, Methanol-d4) δ 8.45-8.33 (m, 2H), 8.01-7.87 (m, 2H), 7.60 (m, 1H), 7.46-7.27 (m, 6H), 7.25 (m, 1H), 5.98-5.86 (m, 1H), 3.92 (m, 1H), 2.67-2.33 (m, 4H), 1.29-1.12 (m, 4H). |
| 74 | 1H NMR (400 MHz, Methanol-d4) δ 8.64 (m, 1H), 8.39 (m, 1H), 8.07 (s, 1H), 7.79 (m, 1H), 7.60 (m, 1H), 7.41-7.29 (m, 6H), 6.46 (s, 1H), 5.86 (m, 1H), 3.93 (m, 1H), 2.63 (m, 2H), 2.43 (m, 2H), 1.29-1.13 (m, 4H). |
| 75 | 1H NMR (400 MHz, Methanol-d4) δ 8.83 (s, 1H), 8.70 (s, 1H), 8.43 (m, 1H), 8.38-8.28 (m, 1H), 8.03 (m, 1H), 7.78 (m, 1H), 7.70-7.62 (m, 1H), 7.49-7.29 (m, 5H), 6.43 (m, 1H), 6.00-5.89 (m, 1H), 2.66-1.98 (m, 4H), 1.25-1.13 (m, 4H). |
| 90 | 1H NMR (400 MHz, DMSO-d6) δ 8.21 (m, 1H), 8.09 (m, 1H), 7.60 (m, 1H), 7.55-7.48 (m, 1H), 7.41-7.33 (m, 3H), 7.31 (d, J = 5.0 Hz, 2H), 7.29-7.22 (m, 1H), 6.27 (d, J = 3.4 Hz, 1H), 5.66 (dd, J = 8.9, 5.5 Hz, 1H), 4.82-4.64 (m, 4H), 4.56-4.41 (m, 1H), 3.96 (qd, J = 7.2, 4.2 Hz, 1H), 3.00 (m, 1H), 2.82 (m, 1H), 2.62 (dd, J = 14.7, 7.5 Hz, 2H), 2.40 (dt, J = 15.1, 7.4 Hz, OH), 2.31 (d, J = 5.7 Hz, OH), 2.29-2.17 (m, 1H), 1.16-1.11 (m, 4H), 1.11 (s, 1H). |
| 91 | 1H NMR (400 MHz, DMSO-d6) δ 8.30 (s, 1H), 8.05 (s, 1H), 7.59 (d, J = 2.2 Hz, 1H), 7.43 (s, 1H), 7.13 (s, 1H), 6.11 (s, 1H), 4.73 (dt, J = 8.0, 4.4 Hz, 4H), 4.59-4.45 (m, 1H), 3.93 (tt, J = 7.6, 4.4 Hz, 1H), 3.00 (s, 1H), 2.77 (d, J = 15.6 Hz, 1H), 1.11 (td, J = 2.8, 1.7 Hz, 3H), 1.09 (t, J = 2.0 Hz, 1H), 0.89 (s, 9H). |
| 92 | 1H NMR (400 MHz, DMSO-d6) δ 8.35 (m, 1H), 8.29 (m, 1H), 8.06 (m, 1H), 7.98 (m, 1H), 7.58 (m, 1H), 7.34 (m, 1H), 7.16 (m, 1H), 7.01 (m, 1H), 6.61 (m, 1H), 4.32 (tt, m, 1H), 3.93 (m, 2H), 3.40 (m, 2H), 3.06 (m, 1H), 2.02-1.67 (m, 1H), 1.20-1.02 (m, 4H), 0.91 m, 3H), 0.54 (m, 3H) |
| 99 | 1H NMR (400 MHz, DMSO-d6) δ 8.38-8.30 (m, 2H), 8.08-7.98 (m, 2H), 7.82 (d, J = 2.4 Hz, 1H), 7.55 (t, J = 6.9 Hz, 2H), 7.41 (d, J = 2.5 Hz, 1H), 7.16 (dd, J = 8.5, 2.7 Hz, 1H), 4.02 (s, 4H), 3.42 (dd, J = 14.0, 5.5 Hz, 1H), 0.85 (s, 9H) |
| 100 | 1H NMR (400 MHz, DMSO-d6) δ 8.45 (dd, J = 2.3, 1.1 Hz, 1H), 8.42-8.34 (m, 1H), 8.20-8.05 (m, 2H), 7.97-7.84 (m, 2H), 7.68-7.58 (m, 2H), 7.50-7.25 (m, 5H), 7.23-7.12 (m, 1H), 6.05-5.90 (m, 1H), 4.03-3.92 (m, 1H), 3.42-3.17 (m, 2H), 1.23-1.05 (m, 4H) |
| 101 | 1H NMR (400 MHz, Methanol-d4) δ 8.87 (d, J = 5.4 Hz, 1H), 8.47 (d, J = 4.4 Hz, 1H), 7.97 (d, J = 6.1 Hz, 1H), 7.62 (d, J = 2.3 Hz, 1H), 7.50-7.27 (m, 6H), 5.78 (t, J = 7.2 Hz, 1H), 3.96-3.84 (m, 1H), 2.43 (s, 3H), 2.28-2.04 (m, 2H), 1.27-1.11 (m, 4H), 1.02 (t, J = 7.3 Hz, 3H). |
| 102 | 1H NMR (400 MHz, Methanol-d4) δ 8.86 (s, 1H), 8.52 (s, 1H), 7.96 (s, 1H), 7.62 (m, 1H), 7.12 (m, 1H), 4.03 (m 1H), 3.95-3.85 (m, 2H), 2.45 (s, 3H), 1.26-1.07 (m, 4H), 0.99 (s, 9H). |
| 103 | 1H NMR (400 MHz, Methanol-d4) δ 8.50 (m, 1H), 8.11-7.98 (m, 2H), 7.65 (m, 1H), 7.11-7.04 (m, 1H), 6.98 (m, 1H), 4.08 (m, 1H), 3.96-3.78 (m, 2H), 1.27-1.11 (m, 4H), 0.97 (s, 9H). |

TABLE 2-continued

| Compound | ¹H-NMR |
|---|---|
| 106 | 1H NMR (400 MHz, Methanol-d4) δ 8.40 (s, 1H), 8.33 (d, J = 2.6 Hz, 1H), 8.01 (ddd, J = 8.5, 7.5, 2.6 Hz, 1H), 7.93 (s, 1H), 7.63 (d, J = 2.3 Hz, 1H), 7.39-7.23 (m, 6H), 7.11-7.03 (m, 1H), 5.73 (s, 1H), 3.95-3.85 (m, 1H), 1.28-1.11 (m, 4H) |
| 109 | 1H NMR (400 MHz, Methanol-d4) δ 8.42 (s, 1H), 8.33 (d, J = 2.6 Hz, 1H), 8.00 (ddd, J = 8.5, 7.5, 2.6 Hz, 1H), 7.93 (s, 1H), 7.64 (t, J = 2.1 Hz, 1H), 7.42-7.25 (m, 6H), 7.07 (dd, J = 8.5, 2.6 Hz, 1H), 3.90 (m, 1H), 1.26-1.11 (m, 4H) |
| 110 | 1H NMR (400 MHz, Methanol-d4) δ 8.45 (m, 1H), 7.92 (m, 1H), 7.79 (m, 1H), 7.62 (m, 1H), 7.43-7.26 (m, 5H), 7.21-7.11 (m, 1H), 6.87 (m, 1H), 5.73 (m, 1H), 3.89 (m, 1H), 2.54 (s, 3H), 2.25-2.10 (m, 1H), 2.08 (m, 1H), 1.27-1.09 (m, 4H), 0.98 (m, 3H). |
| 111 | 1H NMR (400 MHz, Methanol-d4) δ 8.51 (s, 1H), 7.93 (s, 1H), 7.78 (t, J = 8.1 Hz, 1H), 7.63 (d, J = 2.3 Hz, 1H), 6.95 (d, J = 2.3 Hz, 1H), 6.87 (dd, J = 8.6, 2.7 Hz, 1H), 4.02 (m, 1H), 3.94-3.83 (m, 2H), 2.51 (s, 3H), 1.25-1.10 (m, 4H), 0.94 (s, 9H). |
| 112 | 1H NMR (400 MHz, Methanol-d4) δ 8.48 (s, 1H), 8.30 (dt, J = 2.6, 0.8 Hz, 1H), 8.00 (ddd, J = 8.5, 7.5, 2.6 Hz, 1H), 7.92 (s, 1H), 7.65 (d, J = 2.3 Hz, 1H), 7.12-7.04 (m, 2H), 3.89 (m, 1H), 1.25-1.10 (m, 4H), 0.97 (s, 9H) |
| 116 | 1H NMR (400 MHz, DMSO-d6) δ 8.37-8.30 (m, 2H), 8.13 (s, 1H), 8.03 (td, J = 8.2, 2.6 Hz, 1H), 7.82 (d, J = 2.3 Hz, 1H), 7.61-7.50 (m, 2H), 7.38 (d, J = 2.5 Hz, 1H), 7.19-7.11 (m, 1H), 4.01-3.91 (m, 2H), 3.42 (dd, J = 14.0, 5.5 Hz, 1H), 1.19-1.04 (m, 4H), 0.85 (s, 9H) |
| 117 | 1H NMR (400 MHz, DMSO-d6) δ 8.53-8.38 (m, 1H), 8.28 (d, J = 5.7 Hz, 1H), 8.20-8.03 (m, 2H), 7.83 (t, J = 2.5 Hz, 1H), 7.63-7.52 (m, 3H), 7.42-7.14 (m, 6H), 5.54-5.44 (m, 1H), 4.03-3.93 (m, 1H), 2.21-2.04 (m, 1H), 2.05-1.84 (m, 1H), 1.25-1.05 (m, 4H), 1.04-0.80 (m, 3H) |
| 119 | 1H NMR (400 MHz, DMSO-d6) δ 8.54 (s, 1H), 8.44-8.29 (m, 2H), 8.14 (s, 1H), 8.04 (td, J = 8.2, 2.6 Hz, 1H), 7.72 (s, 1H), 7.43-7.26 (m, 2H), 7.21-7.12 (m, 1H), 7.08 (d, J = 2.2 Hz, 1H), 4.10 (dd, J = 14.0, 8.0 Hz, 1H), 4.01-3.90 (m, 1H), 3.59-3.49 (m, 1H), 1.19-1.04 (m, 4H), 0.89 (s, 9H) |
| 120 | 1H NMR (400 MHz, DMSO-d6) δ 8.48-8.38 (m, 1H), 8.37-8.30 (m, 1H), 8.18-8.03 (m, 2H), 7.76 (d, J = 8.7 Hz, 1H), 7.55 (s, 1H), 7.43-7.14 (m, 8H), 5.56 (q, J = 8.1 Hz, 1H), 4.03-3.92 (m, 1H), 2.23-2.05 (m, 1H), 1.98 (ddt, J = 20.7, 13.7, 7.0 Hz, 1H), 1.21-1.05 (m, 4H), 1.00-0.83 (m, 3H) |
| 125 | 1H NMR (400 MHz, Methanol-d4) δ 8.48 (s, 1H), 7.91 (s, 1H), 7.69-7.59 (m, 2H), 7.26 (m, 1H), 6.85 (m, 1H), 4.03 (d, J = 13.9 Hz, 1H), 3.95-3.84 (m, 1H), 3.78 (d, J = 13.9 Hz, 1H), 2.52 (s, 3H), 1.26-1.10 (m, 4H), 0.92 (s, 9H). |
| 126 | 1H NMR (400 MHz, Methanol-d4) δ 8.48 (s, 1H), 8.35 (dd, J = 4.8, 1.9 Hz, 1H), 7.96 (s, 1H), 7.88 (dd, J = 7.7, 1.9 Hz, 1H), 7.61 (d, J = 2.3 Hz, 1H), 7.39 (m, 1H), 6.96 (d, J = 2.3 Hz, 1H), 4.02 (m, 1H), 3.96-3.78 (m, 2H), 1.27-1.07 (m, 4H), 0.96 (s, 9H). |
| 131 | 1H NMR (400 MHz, Methanol-d4) δ 8.61 (m, 1H), 8.47 (s, 1H), 8.26 (m, 1H), 8.04 (s, 1H), 7.71 (m, 1H), 7.62 (m, 1H), 6.96 (m, 1H), 6.33 (s, 1H), 4.03-3.83 (m, 3H), 2.73 (s, 3H), 1.27-1.12 (m, 4H), 0.93 (s, 9H). |
| 132 | 1H NMR (400 MHz, Methanol-d4) δ 8.62 (m, 1H), 8.48 (s, 1H), 8.28 (m, 1H), 8.05 (s, 1H), 7.73 (m, 1H), 7.63 (d, J = 2.4 Hz, 1H), 6.99 (d, J = 2.4 Hz, 1H), 4.03-3.80 (m, 3H), 2.74 (s, 3H), 1.27-1.12 (m, 4H), 0.94 (s, 9H). |
| 142 | 1H NMR (400 MHz, Methanol-d4) δ 8.51 (s, 1H), 8.30 (d, J = 2.5 Hz, 1H), 8.00 (ddd, J = 8.5, 7.5, 2.6 Hz, 1H), 7.92 (s, 1H), 7.66 (d, J = 2.3 Hz, 1H), 7.09 (d, J = 2.4 Hz, 1H), 7.08 (dd, J = 8.4, 2.4 Hz, 1H), 4.13 (d, J = 14.0 Hz, 1H), 3.89 (m, 1H), 3.82 (d, J = 14.0 Hz, 1H), 1.25-1.10 (m, 4H), 0.98 (s, 9H) |
| 143 | 1H NMR (400 MHz, DMSO-d6) δ 9.52 (s, 1H), 8.93 (d, J = 2.1 Hz, 1H), 8.91 (d, J = 1.9 Hz, 1H), 8.48 (s, 1H), 8.33 (t, J = 2.1 Hz, 1H), 8.14 (s, 1H), 7.99 (d, J = 12.5 Hz, 2H), 7.67 (d, J = 2.3 Hz, 1H), 7.49 (s, 1H), 7.17 (d, J = 2.4 Hz, 1H), 4.00-3.89 (m, 1H), 1.16-1.10(m, 2H), 1.10-1.04 (m, 2H). |
| 144 | 1H NMR (400 MHz, Methanol-d4) δ 8.61 (m, 1H), 8.38 (m, 1H), 8.29 (m, 1H), 8.04 (m, 1H), 7.71 (m, 1H), 7.59 (m, 1H), 7.38-7.27 (m, 5H), 7.18 (m, 1H), 5.66 (m, 1H), 3.92 (m, 1H), 2.77 (s, 3H), 2.28-1.95 (m, 2H), 1.25-1.07 (m, 4H), 1.03-0.92 (m, 3H). |
| 155 | 1H NMR (400 MHz, Methanol-d4) δ 8.43 (d, J = 1.0 Hz, 1H), 8.33 (d, J = 2.5 Hz, 1H), 8.00 (ddd, J = 8.5, 7.6, 2.6 Hz, 1H), 7.94 (s, 1H), 7.65 (d, J = 2.3 Hz, 1H), 7.41-7.25 (m, 6H), 7.07 (ddd, J = 8.5, 2.7, 0.7 Hz, 1H), 5.77 (t, J = 7.2 Hz, 1H), 3.95-3.83 (m, 1H), 2.26-2.03 (m, 2H), 1.26-1.11 (m, 4H), 1.03 (t, J = 7.3 Hz, 3H) |
| 174 | 1H NMR (400 MHz, DMSO-d6) δ 8.86-8.82 (m, 1H), 8.59 (dd, J = 5.0, 1.6 Hz, 1H), 8.22 (d, J = 2.3 Hz, 1H), 8.18 (d, J = 5.4 Hz, 1H), 8.06 (d, J = 2.0 Hz, 1H), 8.04 (d, J = 2.3 Hz, 1H), 7.58 (d, J = 2.2 Hz, 1H), 7.52 (dd, J = 8.0, 4.9 Hz, 1H), 7.37 (dt, J = 9.7, 3.8 Hz, 3H), 7.35-7.28 (m, 1H), 7.27-7.21 (m, 2H), 7.21-7.15 (m, 3H), 6.41 (t, J = 8.6 Hz, 1H), 5.46 (q, J = 7.7 Hz, 1H), 4.72 (t, J = 7.4 Hz, 2H), 4.58 (dd, J = 7.8, 5.1 Hz, 2H), 4.42-4.29 (m, 1H), 4.17 (s, 1H), 3.77 (3, 1H), 3.25 (m, 1H), 2.70-2.55 (m, 2H), 2.18-2.03 (m, 1H), 2.03-1.82 (m, 1H), 0.93 (t, J = 7.3 Hz, 3H). |
| 175 | 1H NMR (400 MHz, DMSO-d6) δ 8.87-8.79 (m, 1H), 8.64-8.54 (m, 1H), 8.23 (s, 2H), 8.08 (d, J = 7.8 Hz, 1H), 7.58 (d, J = 2.4 Hz, 1H), 7.57-7.53 (m, 1H), 7.47 (d, J = 8.4 Hz, 1H), 7.40 (d, J = 8.6 Hz, 1H), 7.37-7.31 (m, 2H), 7.29-7.21 (m, 2H), 7.19 (dt, J = 4.5, 3.3 Hz, 2H), 6.49 (d, J = 7.8 Hz, 1H), 5.79 (d, J = 2.0 Hz, 2H), 5.46 (q, J = 7.5 Hz, 1H), 5.35 (s, OH), 2.23-2.06 (m, 1H), 2.02-1.84 (m, 1H), 0.93 (t, J = 7.2 Hz, 3H). |

TABLE 2-continued

| Compound | ¹H-NMR |
|---|---|
| 176 | 1H NMR (400 MHz, DMSO-d6) δ 9.83 (s, 1H), 8.90 (s, 1H), 8.65 (s, 1H), 8.25 (s, 1H), 8.23-8.09 (m, 2H), 7.62 (dd, J = 3.7, 2.1 Hz, 2H), 7.47 (d, J = 8.6 Hz, 1H), 7.42-7.33 (m, 2H), 7.30-7.16 (m, 4H), 6.50 (d, J = 6.5 Hz, 1H), 5.49 (q, J = 7.7 Hz, 1H), 5.43-5.32 (m, 1H), 4.46 (t, J = 7.0 Hz, 2H), 3.55 (m, 2H), 3.22-3.09 (m, 2H), 3.03-2.90 (m, 2H), 2.27-2.07 (m, 3H), 2.07-1.77 (m, 5H), 0.95 (t, J = 7.3 Hz, 3H) |
| 177 | 1H NMR (400 MHz, DMSO-d6) δ 8.90 (s, 1H), 8.67 (s, 1H), 8.28-8.13 (m, 3H), 7.68 (s, 1H), 7.60 (dd, J = 4.8, 2.1 Hz, 1H), 7.56-7.43 (m, 2H), 7.40-7.28 (m, 2H), 7.28-7.12 (m, 5H), 6.50 (d, J = 5.9 Hz, 1H), 5.47 (q, J = 7.7 Hz, 1H), 4.86 (dd, J = 5.2, 4.1 Hz, 1H), 4.78-4.63 (m, 3H), 2.11 (dt, J = 13.6, 7.5 Hz, 1H), 1.91 (ddp, J = 20.8, 14.0, 7.3 Hz, 1H), 0.97-0.77 (m, 3H) |
| 181 | 1H NMR (400 MHz, DMSO-d6) δ 8.88 (dd, J = 10.1, 2.1 Hz, 1H), 8.64 (ddd, J = 15.1, 5.2, 1.5 Hz, 1H), 8.25 (s, 1H), 8.24 (d, J = 2.0 Hz, 1H), 8.22 (s, 2H), 8.20 (s, 1H), 7.66 (dd, J = 8.1, 5.2 Hz, 1H), 7.60 (dd, J = 4.5, 2.1 Hz, 1H), 7.49 (s, 1H), 7.43 (d, J = 8.9 Hz, 1H), 7.40-7.34 (m, 1H), 7.33 (s, 1H), 7.28-7.20 (m, 3H), 7.18 (dt, J = 8.0, 1.8 Hz, 2H), 6.50 (d, J = 5.7 Hz, 1H), 5.48 (q, J = 7.6 Hz, 1H), 5.05 (dtd, J = 18.1, 7.0, 4.2 Hz, 1H), 4.83-4.72 (m, 1H), 4.72-4.59 (m, 1H), 2.21-2.06 (m, 1H), 2.04-1.85 (m, 1H), 1.49 (d, J = 8.0 Hz, 2H), 0.94 (t, J = 7.3 Hz, 3H). |
| 189 | 1H NMR (400 MHz, DMSO-d6) δ 9.61 (s, 1H), 8.80 (s, 3H), 8.49 (s, 1H), 8.30 (d, J = 7.9 Hz, 1H), 8.17 (s, 1H), 8.09-7.98 (m, 2H), 7.81 (s, 1H), 7.72 (d, J = 2.2 Hz, 1H), 7.65 (d, J = 8.5 Hz, 1H), 7.28 (d, J = 2.4 Hz, 1H), 6.33 (d, J = 6.4 Hz, 1H), 4.87 (dd, J = 5.2, 4.0 Hz, 1H), 4.79-4.63 (m, 3H) |
| 190 | 1H NMR (400 MHz, DMSO-d6) δ 8.84 (dd, J = 14.0, 2.2 Hz, 1H), 8.64-8.52 (m, 1H), 8.23 (d, J = 2.1 Hz, 1H), 8.14 (d, J = 7.8 Hz, 1H), 8.05 (d, J = 6.7 Hz, 1H), 7.65-7.54 (m, 2H), 7.46 (d, J = 9.5 Hz, 1H), 7.43-7.38 (m, 1H), 7.38-7.31 (m, 2H), 7.28-7.21 (m, 2H), 7.21-7.15 (m, 3H), 6.48 (d, J = 6.9 Hz, 1H), 5.48 (q, J = 7.7 Hz, 1H), 5.35 (s, OH), 4.68 (d, J = 2.0 Hz, 2H), 4.50 (dd, J = 6.2, 4.5 Hz, 3H), 4.41 (dd, J = 6.7, 3.4 Hz, 2H), 2.12 (dt, J = 14.5, 7.4 Hz, 1H), 2.04-1.78 (m, 1H), 0.94 (t, J = 7.3 Hz, 3H), 0.85 (t, J = 7.2 Hz, 1H). |
| 191 | 1H NMR (400 MHz, DMSO-d6) δ 8.88 (s, 1H), 8.67 (s, 1H), 8.24 (d, J = 1.9 Hz, 1H), 8.20 (d, J = 7.8 Hz, 1H), 8.17 (d, J = 6.2 Hz, 1H), 7.67 (dt, J = 7.5, 3.2 Hz, 1H), 7.59 (dd, J = 4.1, 2.1 Hz, 1H), 7.44 (t, J = 8.1 Hz, 2H), 7.40-7.30 (m, 1H), 7.29 (d, J = 2.3 Hz, 1H), 7.26-7.20 (m, 2H), 7.20-7.13 (m, 3H), 6.45 (d, J = 4.9 Hz, 1H), 5.47 (q, J = 7.6 Hz, 1H), 4.03-3.92 (m, 1H), 2.18-2.02 (m, 1H), 2.02-1.82 (m, 1H), 1.18-1.13 (m, 2H), 1.13-1.10 (m, 2H), 0.93 (t, J = 7.3 Hz, 3H). |
| 192 | 1H NMR (400 MHz, DMSO-d6) δ 8.89 (dd, J = 10.6, 2.1 Hz, 1H), 8.65 (ddd, J = 15.0, 5.2, 1.5 Hz, 1H), 8.24 (dd, J = 6.1, 3.6 Hz, 3H), 7.72-7.65 (m, 1H), 7.60 (dd, J = 4.3, 2.1 Hz, 1H), 7.52-7.38 (m, 2H), 7.30 (d, J = 2.3 Hz, 1H), 7.28-7.19 (m, 3H), 7.16 (dq, J = 5.6, 1.6 Hz, 2H), 6.47 (m, 1H), 5.49 (q, J = 7.6 Hz, 1H), 5.35 (q, J = 7.5 Hz, OH), 2.11 (dq, J = 15.3, 7.6 Hz, 1H), 1.92 (ddq, J = 21.0, 14.1, 7.2 Hz, 1H), 1.59 (d, J = 1.0 Hz, 9H), 0.94 (t, J = 7.3 Hz, 3H). |
| 193 | 1H NMR (400 MHz, DMSO-d6) δ 8.87 (d, J = 11.9 Hz, 1H), 8.64 (d, J = 5.1 Hz, 1H), 8.23 (d, J = 2.6 Hz, 1H), 8.21-8.13 (m, 2H), 7.63 (dd, J = 8.0, 5.1 Hz, 1H), 7.60 (dd, J = 4.0, 2.2 Hz, 1H), 7.41 (dd, J = 15.7, 7.3 Hz, 2H), 7.38-7.33 (m, 1H), 7.33-7.27 (m, 1H), 7.27-7.20 (m, 2H), 7.20-7.14 (m, 2H), 6.48 (s, 1H), 5.48 (q, J = 7.6 Hz, 1H), 4.80 (h, J = 6.7 Hz, 1H), 2.11 (dq, J = 14.8, 7.3 Hz, 1H), 2.00-1.85 (m, 1H), 1.47 (d, J = 8.0 Hz, 6H), 0.94 (t, J = 7.3 Hz, 3H). |
| 194 | 1H NMR (400 MHz, DMSO-d6) δ 8.93-8.83 (m, 1H), 8.64 (ddd, J = 14.7, 5.1, 1.5 Hz, 1H), 8.36 (d, J = 7.0 Hz, 1H), 8.25 (d, J = 1.5 Hz, 1H), 8.23-8.16 (m, 1H), 7.65 (dd, J = 8.0, 5.1 Hz, 1H), 7.60 (dd, J = 4.0, 2.2 Hz, 1H), 7.44 (d, J = 8.8 Hz, 1H), 7.41-7.33 (m, 1H), 7.32 (d, J = 2.3 Hz, 1H), 7.29-7.20 (m, 2H), 7.20-7.14 (m, 2H), 6.51 (d, J = 5.6 Hz, 1H), 5.83 (tt, J = 7.6, 6.0 Hz, 1H), 5.52-5.44 (m, 1H), 4.99 (ddd, J = 7.7, 6.8, 0.8 Hz, 2H), 4.88 (m, 2H), 2.18-2.04 (m, 1H), 2.04-1.84 (m, 1H), 0.93 (t, J = 7.2 Hz, 2H). |
| 195 | 1H NMR (400 MHz, DMSO-d6) δ 8.86-8.83 (m, 1H), 8.60 (dd, J = 5.0, 1.6 Hz, 1H), 8.26-8.21 (m, 1H), 8.20 (s, 1H), 8.10-8.04 (m, 1H), 7.59 (d, J = 2.3 Hz, 1H), 7.56 (dd, J = 8.0, 5.0 Hz, 1H), 7.48 (d, J = 8.7 Hz, 1H), 7.45-7.37 (m, 1H), 7.37-7.31 (m, 2H), 7.26-7.16 (m, 6H), 6.55-6.44 (m, 2H), 5.60-5.43 (m, 4H), 2.18-2.03 (m, 1H), 2.03-1.83 (m, 1H), 0.89 (t, J = 7.3 Hz, 3H). |
| 212 | 1H NMR (400 MHz, DMSO-d6) δ 8.46 (d, J = 27.8 Hz, 2H), 8.28 (d, J = 7.1 Hz, 2H), 7.78-7.08 (m, 6H), 6.79 (s, 4H), 5.59-5.33 (m, 1H), 4.92 (t, J = 6.8 Hz, 2H), 3.79 (t, J = 6.9 Hz, 2H), 3.68-3.56 (m, 1H), 3.49-3.27 (m, 4H), 3.22-3.06 (m, 1H), 2.99 (d, J = 2.4 Hz, 3H), 2.22-2.06 (m, 1H), 2.06-1.82 (m, 1H), 1.29-1.23 (m, 3H), 1.17 (t, J = 7.1 Hz, 3H), 0.99-0.80 (m, 3H). |
| 213 | 1H NMR (400 MHz, DMSO-d6) δ 8.31-8.16 (m, 3H), 7.72 (s, 1H), 7.61 (dd, J = 4.6, 2.1 Hz, 1H), 7.53-7.43 (m, 2H), 7.43-7.13 (m, 7H), 6.55-6.44 (m, 1H), 5.49 (q, J = 7.6 Hz, 1H), 5.04-4.92 (m, 1H), 2.24-2.05 (m, 3H), 2.05-1.60 (m, 8H), 1.29-1.20 (m, 1H), 0.95 (t, J = 7.3 Hz, 3H) |
| 221 | 1H NMR (400 MHz, Methanol-d4) δ 8.47 (s, 1H), 8.20 (m, 1H), 7.90 (s, 1H), 7.74 (m, 1H), 7.66 (m, 1H), 7.52 (m, 1H), 7.45-7.32 (m, 2H), 7.32 (m, 1H), 7.27-7.20 (m, 2H), 6.82 (d, J = 8.7 Hz, 1H), 6.05 (s, 1H), 4.91-4.77 (m, 1H), 3.89 (s, 3H), 3.80 (m, 3H), 3.22 (m, 3H), 2.50-2.37 (m, 4H), 1.46 (s, 9H), 1.43 (m, 3H). |
| 223 | 1H NMR (400 MHz, DMSO-d6) δ 9.52 (s, 1H), 9.18 (s, 1H), 8.44 (s, 1H), 8.07 (s, 1H), 7.68 (d, J = 3.0 Hz, 1H), 7.62-7.50 (m, 1H), 7.47-7.19 (m, 3H), 6.10 (d, J = 8.1 Hz, 1H), 4.75 (m, 5H), 3.62 (m, 8H), 3.21-3.03 (m, 2H), 2.77 (m, 1H), 2.44-2.13 (m, 4H), 1.46-1.15 (m, 9H). |

TABLE 2-continued

| Compound | ¹H-NMR |
|---|---|
| 237 | 1H NMR (400 MHz, DMSO-d6) δ 9.21 (s, 1H), 8.21 (d, J = 2.0 Hz, 1H), 8.14 (s, 1H), 7.60 (d, J = 2.0 Hz, 1H), 7.47 (d, J = 8.2 Hz, 2H), 7.40 (s, 2H), 7.38-7.11 (m, 4H), 6.36 (d, J = 7.8 Hz, 1H), 5.81-5.70 (m, 1H), 4.90-4.78 (m, 1H), 4.70 (m, 4H), 3.68 (d, J = 12.3 Hz, 3H), 3.14 (d, J = 12.0 Hz, 3H), 2.44-2.24 (m, 5H), 1.68 (d, J = 6.7 Hz, 3H), 1.36 (s, 9H). |
| 238 | 1H NMR (400 MHz, DMSO-d6) δ 8.23 (d, J = 2.3 Hz, 1H), 7.84 (d, J = 8.0 Hz, 1H), 7.63 (dd, J = 5.4, 2.1 Hz, 1H), 7.58 (d, J = 8.3 Hz, 1H), 7.55 (s, 1H), 7.41 (s, 1H), 7.34-7.26 (m, 4H), 7.23 (ddd, J = 8.6, 5.2, 2.3 Hz, 2H), 6.38 (d, J = 6.3 Hz, 1H), 5.76 (q, J = 7.1 Hz, 1H), 4.79-4.65 (m, 4H), 4.54-4.40 (m, 1H), 3.07-2.70 (m, 3H), 1.69 (d, J = 6.6 Hz, 3H). |
| 241 | 1H NMR (400 MHz, DMSO-d6) δ 9.44 (d, J = 4.9 Hz, 1H), 9.16 (s, 1H), 8.41 (s, 1H), 8.08 (s, 1H), 7.67 (s, 1H), 7.51 (t, J = 7.5 Hz, 1H), 7.44-7.30 (m, 3H), 7.30-7.22 (m, 2H), 6.12 (d, J = 8.3 Hz, 1H), 4.92 (s, OH), 4.88-4.76 (m, 1H), 4.71 (s, 3H), 3.65 (d, J = 12.0 Hz, 2H), 3.23-3.06 (m, 2H), 2.82 (s, 1H), 2.43-2.30 (m, 2H), 2.25 (d, J = 13.8 Hz, 2H), 1.35 (s, 9H). |
| 253 | 1H NMR (400 MHz, Methanol-d4) δ 8.87 (s, 1H), 8.49 (s, 1H), 8.00 (s, 1H), 7.63 (d, J = 2.4 Hz, 1H), 7.47 (t, J = 6.7 Hz, 1H), 7.35-7.18 (m, 3H), 6.34 (s, 1H), 4.84-4.76 (m, 1H), 3.80 (d, J = 12.4 Hz, 2H), 3.27-3.16 (m, 2H), 2.53-2.36 (m, 4H), 2.42 (s, 3H), 1.46 (s, 9H). |
| 258 | 1H NMR (400 MHz, DMSO-d6) δ 9.17 (s, 1H), 8.88 (d, J = 11.8 Hz, 1H), 8.63 (d, J = 15.9 Hz, 1H), 8.37-8.05 (m, 3H), 7.68-7.10 (m, 10H), 6.49 (d, J = 7.0 Hz, 1H), 5.53-5.30 (m, 1H), 4.95-4.74 (m, 1H), 3.69 (d, J = 11.8 Hz, 2H), 3.15 (q, J = 11.6 Hz, 2H), 2.46-2.20 (m, 4H), 2.14 (dt, J = 14.4, 7.4 Hz, 1H), 1.94 (tt, J = 13.8, 7.5 Hz, 1H), 1.37 (s, 9H), 1.10-0.76 (m, 3H). |
| 264 | 1H NMR (400 MHz, Methanol-d4) δ 8.47 (s, 1H), 8.03 (s, 1H), 7.64 (d, J = 2.4 Hz, 1H), 7.59-7.53 (m, 1H), 7.37-7.34 (m, 2H), 7.23 (d, J = 2.4 Hz, 1H), 5.85 (s, 1H), 5.37 (s, 1H), 4.84-4.74 (m, 1H), 4.14 (s, 2H), 3.81 (d, J = 12.4 Hz, 2H), 3.77 (t, J = 5.6 Hz, 2H), 3.42 (s, 1H), 3.30-3.16 (m, 2H), 2.50-2.35 (m, 4H), 2.18 (d, J = 17.4 Hz, 1H), 2.06 (d, J = 17.5 Hz, 1H), 1.47 (s, 9H). |
| 275 | 1H NMR (400 MHz, DMSO-d6) δ 9.40 (s, 1H), 9.02 (d, J = 15.9 Hz, 2H), 8.40 (s, 1H), 7.67 (d, J = 2.2 Hz, 1H), 7.50 (dd, J = 6.6, 2.7 Hz, 1H), 7.43 (t, J = 9.0 Hz, 1H), 7.31 (s, 1H), 7.29 (d, J = 2.3 Hz, 1H), 7.28-7.20 (m, 2H), 6.11 (d, J = 8.6 Hz, 1H), 4.31 (d, J = 5.2 Hz, 2H), 3.33 (s, 2H), 2.88-2.72 (m, 1H), 2.72-2.56 (m, 1H). |
| 279 | 1H NMR (400 MHz, DMSO-d6) δ 9.41 (s, 1H), 9.03 (s, 2H), 8.40 (s, 1H), 8.21 (s, 1H), 7.66 (d, J = 2.2 Hz, 1H), 7.50 (dd, J = 6.5, 2.7 Hz, 1H), 7.44 (t, J = 9.0 Hz, 1H), 7.32 (s, 1H), 7.30 (t, J = 1.4 Hz, 1H), 7.29-7.24 (m, 1H), 7.22 (d, J = 9.6 Hz, 2H), 6.11 (d, J = 8.6 Hz, 1H), 5.81 (tt, J = 7.6, 6.0 Hz, 1H), 5.04-4.95 (m, 2H), 4.86 (ddd, J = 6.8, 6.0, 0.7 Hz, 2H), 4.32 (m, 2H), 3.34 (m, 2H), 2.89-2.68 (m, 3H). |
| 282 | 1H NMR (400 MHz, Methanol-d4) δ 8.66 (m, 1H), 8.49 (m, 2H), 8.09 (s, 1H), 7.87 (m, 1H), 7.68 (m, 1H), 7.40 (m, 1H), 7.29-7.19 (m, 2H), 7.06 (m, 1H), 6.31 (s, 1H), 4.97-4.86 (m, 1H), 2.69 (s, 3H), 1.56 (m, 6H). |
| 283 | 1H NMR (400 MHz, Methanol-d4) δ 8.66 (m, 1H), 8.45 (m, 2H), 8.17 (s, 1H), 7.84(m, 1H), 7.67(m, 1H), 7.39(m, 1H), 7.38-7.19 (m, 2H), 7.09(m, 1H), 6.34 (m, 1H), 4.97-4.86 (m, 1H), 3.80 (m, 2H), 3.23 (m, 2H), 2.70 (s, 3H), 2.48-2.41 (m, 4H), 1.46 (s, 9H). |
| 301 | 1H NMR (400 MHz, DMSO-d6) δ 9.65 (s, 1H), 8.46 (s, 1H), 8.05 (s, 1H), 7.74 (d, J = 2.2 Hz, 1H), 7.59 (dd, J = 6.6, 2.6 Hz, 1H), 7.50 (t, J = 9.0 Hz, 1H), 7.42 (d, J = 2.4 Hz, 1H), 7.34 (ddd, J = 8.8, 4.2, 2.6 Hz, 1H), 7.20 (d, J = 22.3 Hz, 1H), 6.78 (s, 1H), 6.07 (s, 1H), 4.83 (p, J = 6.7 Hz, 1H), 3.70 (t, J = 4.7 Hz, 4H), 3.35 (dd, J = 6.1, 3.7 Hz, 4H), 1.49 (d, J = 8.0 Hz, 65H). |
| 302 | 1H NMR (400 MHz, DMSO-d6) δ 9.68 (s, 1H), 8.47 (s, 1H), 8.23 (s, 1H), 7.74 (d, J = 2.2 Hz, 1H), 7.60 (dd, J = 6.6, 2.6 Hz, 1H), 7.51 (t, J = 9.0 Hz, 1H), 7.44 (d, J = 2.4 Hz, 1H), 7.35 (ddd, J = 8.6, 4.3, 2.6 Hz, 1H), 6.80 (s, 1H), 6.12 (s, 1H), 5.94-5.83 (m, 1H), 5.02 (t, J = 7.3 Hz, 2H), 4.92 (dt, J = 9.8, 6.6 Hz, 2H), 3.70 (t, J = 4.7 Hz, 4H), 3.35 (dd, J = 6.0, 3.7 Hz, 4H). |
| 306 | 1H NMR (400 MHz, Methanol-d4) δ 8.89 (s, 1H), 8.54 (s, 1H), 7.96 (s, 1H), 7.67 (d, J = 2.4 Hz, 1H), 7.63-7.55 (m, 1H), 7.40-7.30 (m, 3H), 6.35 (s, 1H), 4.83 (m, 1H), 2.40 (s, 3H), 1.54 (dd, J = 6.7, 0.7 Hz, 6H) |
| 307 | 1H NMR (400 MHz, Methanol-d4) δ 8.85 (s, 1H), 8.49 (s, 1H), 7.99 (s, 1H), 7.63 (d, J = 2.4 Hz, 1H), 7.47 (dd, J = 6.4, 2.5 Hz, 1H), 7.35-7.24 (m, 2H), 7.23 (d, J = 2.4 Hz, 1H), 6.32 (s, 1H), 4.82-4.75 (m, 1H), 3.81 (d, J = 12.7 Hz, 2H), 3.32-3.17 (m, 2H), 2.51-2.38 (m, 4h), 2.40 (s, 3H), 1.46 (s, 9H) |
| 308 | 1H NMR (400 MHz, DMSO-d6) δ 9.48 (s, 1H), 8.93-8.80 (m, 1H), 8.67 (dd, J = 5.2, 1.5 Hz, 1H), 8.44 (s, 1H), 8.24 (d, J = 8.1 Hz, 1H), 7.94 (s, 1H), 7.82-7.65 (m, 2H), 7.58 (d, J = 8.8 Hz, 1H), 7.53 (dd, J = 6.6, 2.6 Hz, 1H), 7.45 (t, J = 9.0 Hz, 1H), 7.34-7.24 (m, 2H), 6.32 (d, J = 7.4 Hz, 1H) |
| 310 | 1H NMR (400 MHz, Methanol-d4) δ 8.52 (s, 1H), 8.23 (s, 1H), 8.03 (s, 1H), 7.90 (s, 1H), 7.69 (d, J = 2.3 Hz, 1H), 7.63 (dd, J = 6.6, 2.4 Hz, 1H), 7.46-7.34 (m, 3H), 6.11 (s, 1H), 1.65 (s, 9H) |
| 311 | 1H NMR (400 MHz, Methanol-d4) δ 8.96 (s, 1H), 8.44 (s, 1H), 8.16 (s, 1H), 7.63 (d, J = 2.4 Hz, 1H), 7.45 (d, J = 6.7 Hz, 1H), 7.41 (s, 1H), 7.35-7.18 (m, 3H), 6.33 (s, 1H), 4.89-4.80 (m, 1H), 3.84 (s, 3H), 1.56 (d, J = 6.7 Hz, 6H) |
| 312 | 1H NMR (400 MHz, Methanol-d4) δ 8.51 (s, 1H), 8.23 (s, 1H), 7.98 (s, 1H), 7.90 (s, 1H), 7.69 (d, J = 2.4 Hz, 1H), 7.62 (dd, J = 6.4, 2.4 Hz, 1H), 7.43-7.33 (m, 3H), 6.11 (s, 1H), 4.86-4.77 (m, 1H), 1.55 (d, J = 6.8 Hz, 6H) |
| 316 | 1H NMR (400 MHz, DMSO-d6) δ 9.61 (s, 1H), 9.11 (d, J = 1.9 Hz, 1H), 8.59-8.55 (m, 1H), 8.45 (s, 1H), 8.14 (s, 1H), 7.83 (td, J = 7.6, 1.8 Hz, 1H), 7.74 (d, |

TABLE 2-continued

| Compound | ¹H-NMR |
|---|---|
| | J = 2.1 Hz, 1H), 7.70 (d, J = 2.0 Hz, 1H), 7.65-7.59 (m, 1H), 7.57-7.44 (m, 2H), 7.43-7.32 (m, 2H), 7.30 (d, J = 7.8 Hz, 1H), 6.43 (s, 1H), 5.74 (s, 2H). |
| 317 | 1H NMR (400 MHz, DMSO-d6) δ 9.53 (s, 1H), 8.56 (d, J = 5.0 Hz, 1H), 8.51 (d, J = 1.5 Hz, 1H), 8.49 (d, J = 2.0 Hz, 1H), 8.27 (d, J = 1.7 Hz, 1H), 7.85 (td, J = 7.8, 2.0 Hz, 1H), 7.71 (d, J = 2.3 Hz, 1H), 7.67-7.56 (m, 2H), 7.54-7.43 (m, 3H), 7.43-7.29 (m, 3H), 6.50 (d, J = 8.0 Hz, 1H), 5.77 (d, J = 1.9 Hz, 2H). |
| 331 | 1H NMR (400 MHz, Methanol-d4) δ 8.55 (m, 1H), 8.35 (m, 1H), 7.92 (s, 1H), 7.89 (m, 1H), 7.68 (m, 1H), 7.57 (m, 1H), 7.41 (m, 1H), 7.36 (m, 2H), 7.26 (m, 1H), 6.32 (s, 1H), 4.48 (m, 2H), 3.92 (m, 2H). |
| 332 | 1H NMR (400 MHz, DMSO-d6) δ 8.50 (s, 1H), 8.48 (d, J = 1.1 Hz, 1H), 8.22 (d, J = 1.5 Hz, 1H), 7.72 (d, J = 2.3 Hz, 1H), 7.57 (dd, J = 6.5, 2.7 Hz, 1H), 7.53-7.43 (m, 2H), 7.41 (d, J = 1.3 Hz, 1H), 7.33 (dt, J = 7.6, 3.4 Hz, 1H), 6.49 (s, 1H), 4.84 (t, J = 6.7 Hz, 2H), 3.83 (s, 4H), 3.70 (t, J = 6.7 Hz, 2H), 3.24 (d, J = 37.5 Hz, 4H). |
| 333 | 1H NMR (400 MHz, DMSO-d6) δ 9.51 (s, 1H), 8.50 (d, J = 1.4 Hz, 1H), 8.48 (s, 1H), 8.14 (s, 1H), 7.72 (d, J = 2.2 Hz, 1H), 7.60 (dd, J = 6.8, 2.8 Hz, 2H), 7.56-7.46 (m, 2H), 7.41 (s, 1H), 7.40-7.32 (m, 1H), 6.48 (d, J = 8.4 Hz, 1H), 4.45 (t, J = 5.3 Hz, 2H), 3.81 (t, J = 5.3 Hz, 2H). |
| 334 | 1H NMR (400 MHz, DMSO-d6) δ 9.43 (s, 1H), 8.67 (s, 1H), 8.48 (d, J = 4.7 Hz, 1H), 8.40 (s, 1H), 7.98 (d, J = 0.5 Hz, 1H), 7.86-7.80 (m, 1H), 7.68 (d, J = 2.2 Hz, 1H), 7.51 (dd, J = 6.6, 2.6 Hz, 1H), 7.48-7.42 (m, 2H), 7.41-7.36 (m, 1H), 7.32 (d, J = 2.4 Hz, 1H), 7.26 (ddd, J = 8.8, 4.2, 2.7 Hz, 1H), 6.29-6.07 (m, 1H), 4.42 (t, J = 6.3 Hz, 2H), 2.62 (t, J = 6.4 Hz, 2H), 2.29 (s, 4H), 1.48-1.21 (m, 6H) |
| 336 | 1H NMR (400 MHz, DMSO-d6) δ 9.42 (s, 1H), 8.69 (d, J = 2.3 Hz, 1H), 8.46 (dd, J = 4.8, 1.6 Hz, 1H), 8.40 (s, 1H), 8.02 (s, 1H), 7.88-7.80 (m, 1H), 7.68 (d, J = 2.2 Hz, 1H), 7.53 (dd, J = 6.6, 2.7 Hz, 1H), 7.49 (d, J = 9.1 Hz, 1H), 7.44 (t, J = 9.0 Hz, 1H), 7.37 (ddd, J = 7.9, 4.8, 0.8 Hz, 1H), 7.32 (d, J = 2.4 Hz, 1H), 7.28 (dd, J = 7.9, 4.4 Hz, 1H), 6.19 (d, J = 9.0 Hz, 1H), 5.09-4.99 (m, 1H), 4.38 (t, J = 5.3 Hz, 2H), 3.82-3.68 (m, 2H) |
| 337 | 1H NMR (400 MHz, DMSO-d6) δ 9.51 (s, 1H), 8.50 (d, J = 1.5 Hz, 1H), 8.48 (s, 1H), 8.13 (s, 1H), 7.72 (d, J = 2.2 Hz, 1H), 7.65-7.58 (m, 2H), 7.53-7.45 (m, 2H), 7.43 (d, J = 1.4 Hz, 1H), 7.34 (dt, J = 8.6, 3.4 Hz, 1H), 6.48 (d, J = 8.3 Hz, 1H), 4.57 (t, J = 5.1 Hz, 2H), 3.76 (t, J = 5.1 Hz, 2H), 3.24 (s, 2H). |
| 338 | 1H NMR (400 MHz, DMSO-d6) δ 9.59 (s, 1H), 8.50 (d, J = 2.2 Hz, 2H), 8.22 (d, J = 1.6 Hz, 1H), 7.72 (d, J = 2.2 Hz, 1H), 7.61 (dt, J = 6.5, 3.9 Hz, 2H), 7.50 (dd, J = 9.8, 8.2 Hz, 1H), 7.46 (dd, J = 4.2, 2.1 Hz, 2H), 7.35 (ddd, J = 8.6, 4.3, 2.5 Hz, 1H), 6.46 (q, J = 2.4 Hz, 1H), 4.86 (p, J = 6.7 Hz, 1H), 1.52 (d, J = 8.0 Hz, 6H). |
| 339 | 1H NMR (400 MHz, DMSO-d6) δ 9.53 (s, 1H), 8.50 (d, J = 1.4 Hz, 1H), 8.48 (s, 1H), 8.39 (s, 1H), 7.71 (d, J = 2.2 Hz, 1H), 7.66-7.55 (m, 2H), 7.54-7.42 (m, 3H), 7.34 (ddd, J = 8.6, 4.1, 2.4 Hz, 1H), 6.49 (d, J = 7.9 Hz, 1H), 5.88 (tt, J = 7.3, 6.1 Hz, 1H), 5.03 (t, J = 7.3 Hz, 2H), 4.93 (q, J = 6.3 Hz, 2H). |
| 340 | 1H NMR (400 MHz, DMSO-d6) δ 9.42 (s, 1H), 8.71-8.64 (m, 1H), 8.47 (dd, J = 4.8, 1.6 Hz, 1H), 8.40 (s, 1H), 7.99 (d, J = 0.5 Hz, 1H), 7.84 (dt, J = 7.9, 1.9 Hz, 1H), 7.68 (d, J = 2.2 Hz, 1H), 7.52 (dd, J = 6.6, 2.6 Hz, 1H), 7.50-7.41 (m, 2H), 7.38 (ddd, J = 7.9, 4.8, 0.8 Hz, 1H), 7.31 (d, J = 2.4 Hz, 1H), 7.27 (ddd, J = 8.9, 4.2, 2.7 Hz, 1H), 6.18 (d, J = 8.9 Hz, 1H), 4.50 (t, J = 5.2 Hz, 2H), 3.77 (dd, J = 5.6, 4.8 Hz, 2H), 3.53-3.41 (m, 2H), 3.36-3.24 (m, 2H), 3.13 (s, 3H) |
| 342 | 1H NMR (400 MHz, Methanol-d4) δ 8.97 (s, 1H), 8.45 (s, 1H), 8.26 (s, 1H), 7.64 (d, J = 2.4 Hz, 1H), 7.51-7.39 (m, 2H), 7.39-7.25 (m, 3H), 6.36 (s, 1H), 4.92-4.85 (m, 1H), 3.88 (s, 3H), 3.80 (d, J = 12.6 Hz, 2H), 3.29-3.18 (m, 2H), 2.47 (m, 4H), 1.46 (s, 9H) |
| 345 | 1H NMR (400 MHz, DMSO-d6) δ 9.92 (s, 1H), 9.40 (d, J = 8.6 Hz, 1H), 8.40 (d, J = 3.4 Hz, 1H), 8.04 (d, J = 11.0 Hz, 1H), 7.66 (dd, J = 10.6, 2.2 Hz, 1H), 7.54-7.39 (m, 2H), 7.34 (s, 1H), 7.31-7.18 (m, 3H), 6.08 (dd, J = 29.6, 8.6 Hz, 1H), 4.78 (p, J = 6.7 Hz, 1H), 4.57 (d, J = 15.6 Hz, 1H), 4.27 (s, 1H), 3.62 (s, 1H), 3.27 (d, J = 12.0 Hz, 1H), 2.93 (s, 1H), 2.86 (d, J = 4.4 Hz, 3H), 2.80 (s, 1H), 1.45 (d, J = 8.0 Hz, 6H). |
| 346 | 1H NMR (400 MHz, DMSO-d6) δ 8.39 (s, 1H), 8.01 (s, 1H), 7.65 (d, J = 2.4 Hz, 1H), 7.49 (dd, J = 6.6, 2.7 Hz, 1H), 7.43 (t, J = 9.0 Hz, 1H), 7.31 (s, 1H), 7.28-7.21 (m, 2H), 6.05 (s, 1H), 4.76 (p, J = 6.7 Hz, 1H), 4.29 (s, 2H), 3.31 (dq, J = 22.6, 6.6 Hz, 2H), 2.87-2.74 (m, 1H), 2.75-2.62 (m, 1H), 1.43 (d, J = 8.0 Hz, 6H). |
| 347 | 1H NMR (400 MHz, Methanol-d4) δ 8.45 (s, 1H), 8.28 (s, 1H), 8.02 (s, 1H), 7.96 (s, 1H), 7.66 (d, J = 2.3 Hz, 1H), 7.47 (dd, J = 6.4, 2.5 Hz, 1H), 7.43-7.24 (m, 2H), 7.20 (d, J = 2.3 Hz, 1H), 7.09 (dd, J = 8.6, 2.4 Hz, 1H), 6.15 (s, 1H), 4.79 (d, J = 11.9 Hz, 1H), 3.80 (d, J = 12.6 Hz, 2H), 3.22 (t, J = 12.5 Hz, 2H), 2.55-2.32 (m, 4H), 1.46 (s, 9H) |
| 348 | 1H NMR (400 MHz, Methanol-d4) δ 8.43 (s, 1H), 8.25-8.20 (m, 1H), 8.03 (s, 1H), 7.92 (s, 1H), 7.63 (d, J = 2.3 Hz, 1H), 7.53-7.46 (m, 1H), 7.38-7.28 (m, 3H), 6.11 (s, 1H), 4.84-4.73 (m, 1H), 3.81 (d, J = 12.1 Hz, 2H), 3.23 (t, J = 13.2 Hz, 2H), 2.51-2.35 (m, 4H), 1.46 (s, 9H) |
| 349 | 1H NMR (400 MHz, Methanol-d4) δ 8.44 (s, 1H), 7.95-7.85 (m, 2H), 7.72 (d, J = 2.0 Hz, 1H), 7.66 (d, J = 2.3 Hz, 1H), 7.59 (s, 1H), 7.43 (dd, J = 6.7, 2.3 Hz, 1H), 7.35 (dd, J = 8.6, 2.0 Hz, 1H), 7.31-7.18 (m, 3H), 6.38 (s, 1H), 4.82-4.69 (m, 1H), 3.79 (d, J = 12.6 Hz, 2H), 3.20 (t, J = 12.5 Hz, 2H), 2.57-2.29 (m, 5H), 1.45 (s, 9H) |

TABLE 2-continued

| Compound | ¹H-NMR |
|---|---|
| 350 | 1H NMR (400 MHz, Methanol-d4) δ 9.01 (d, J = 1.9 Hz, 1H), 8.49 (s, 1H), 7.95 (s, 1H), 7.68 (d, J = 2.3 Hz, 1H), 7.62-7.52 (m, 2H), 7.50-7.39 (m, 1H), 7.31-7.17 (m, 2H), 6.27 (s, 1H), 4.83-4.74 (m, 1H), 3.80 (d, J = 12.5 Hz, 2H), 3.22 (t, J = 12.7 Hz, 2H), 2.74-2.14 (m, 4H), 1.46 (s, 9H) |
| 351 | 1H NMR (400 MHz, Methanol-d4) δ 8.48 (s, 1H), 7.95-7.86 (m, 2H), 7.75-7.65 (m, 2H), 7.55-7.46 (m, 2H), 7.40-7.26 (m, 5H), 6.45 (s, 1H), 4.79 (m, 1H), 3.78 (d, J = 12.6 Hz, 2H), 3.25-3.14 (m, 2H), 2.47-2.31 (m, 4H), 1.45 (s, 9H) |
| 352 | 1H NMR (400 MHz, DMSO-d6) δ 9.06 (q, J = 1.8 Hz, 1H), 8.39 (s, 1H), 8.08 (s, 1H), 7.69 (dd, J = 2.5, 1.2 Hz, 1H), 7.65 (d, J = 2.0 Hz, 1H), 7.56-7.51 (m, 1H), 7.44 (t, J = 9.0 Hz, 1H), 7.39 (t, J = 1.9 Hz, 1H), 7.28 (m, 1H), 6.36 (s, 1H), 4.76 (t, J = 6.8 Hz, 2H), 3.76 (m, 4H), 3.63 (t, J = 6.7 Hz, 2H), 3.17 (m, 4H). |
| 353 | 1H NMR (400 MHz, Methanol-d4) δ 9.02 (d, J = 2.0 Hz, 1H), 8.46 (s, 1H), 7.98 (s, 1H), 7.68 (d, J = 2.3 Hz, 1H), 7.65-7.50 (m, 2H), 7.38-7.30 (m, 3H), 6.32 (s, 1H), 4.79 (m, 1H), 3.80 (d, J = 12.6 Hz, 2H), 3.28-3.17 (m, 2H), 2.49 (d, J = 13.0 Hz, 2H), 2.40 (d, J = 12.4 Hz, 2H), 1.46 (s, 9H) |
| 354 | 1H NMR (400 MHz, Methanol-d4) δ 9.03 (d, J = 1.9 Hz, 1H), 8.46 (s, 1H), 7.97 (s, 1H), 7.68 (d, J = 2.4 Hz, 1H), 7.60 (d, J = 1.9 Hz, 1H), 7.53 (dd, J = 5.7, 1.9 Hz, 1H), 7.37-7.30 (m, 3H), 6.31 (s, 1H), 4.86-4.80 (m, 1H), 3.60-3.50 (m, 2H), 3.22 (t, J = 11.0 Hz, 2H), 2.40 (d, J = 14.4 Hz, 2H), 2.34-2.24 (m, 2H) |
| 355 | 1H NMR (400 MHz, DMSO-d6) δ 10.02 (s, 1H), 9.68 (s, 1H), 9.08 (s, 1H), 8.40 (s, 1H), 8.11 (s, 1H), 7.75-7.65 (m, 2H), 7.55 (dd, J = 6.6, 2.6 Hz, 1H), 7.51-7.39 (m, 2H), 7.30 (ddd, J = 8.8, 4.2, 2.6 Hz, 1H), 6.39 (s, 1H), 4.78 (t, J = 6.6 Hz, 2H), 3.59 (dd, J = 7.9, 5.3 Hz, 2H), 2.77 (s, 7H). |
| 356 | 1H NMR (400 MHz, DMSO-d6) δ 9.52 (s, 1H), 9.05 (d, J = 1.9 Hz, 1H), 8.38 (s, 1H), 7.96 (s, 1H), 7.69 (d, J = 2.2 Hz, 1H), 7.62 (d, J = 2.0 Hz, 1H), 7.55 (dd, J = 6.6, 2.6 Hz, 1H), 7.44 (t, J = 9.0 Hz, 1H), 7.29 (ddd, J = 8.8, 4.3, 2.7 Hz, 1H), 6.40-6.33 (m, 1H), 4.36 (t, J = 5.4 Hz, 3H), 3.73 (t, J = 5.4 Hz, 3H). |
| 357 | 1H NMR (400 MHz, DMSO-d6) δ 9.54 (d, J = 2.1 Hz, 1H), 9.05 (d, J = 1.9 Hz, 1H), 8.39 (s, 1H), 8.01 (s, 1H), 7.68 (d, J = 2.2 Hz, 1H), 7.62 (d, J = 1.9 Hz, 1H), 7.53 (dd, J = 6.6, 2.6 Hz, 1H), 7.44 (t, J = 9.0 Hz, 1H), 7.39 (d, J = 2.3 Hz, 1H), 7.28 (ddd, J = 8.9, 4.2, 2.7 Hz, 1H), 6.33 (s, 1H), 4.77 (p, J = 6.7 Hz, 1H), 1.44 (d, J = 1.9 Hz, 3H), 1.43 (d, J = 1.9 Hz, 3H). |
| 358 | 1H NMR (400 MHz, DMSO-d6) δ 9.52 (s, 1H), 9.05 (d, J = 1.9 Hz, 1H), 8.38 (s, 1H), 7.95 (s, 1H), 7.69 (d, J = 2.2 Hz, 1H), 7.63 (d, J = 2.0 Hz, 1H), 7.54 (dd, J = 6.6, 2.6 Hz, 1H), 7.44 (t, J = 9.0 Hz, 1H), 7.41 (d, J = 2.3 Hz, 1H), 7.29 (ddd, J = 8.9, 4.3, 2.7 Hz, 1H), 6.35 (s, 1H), 4.49 (t, J = 5.1 Hz, 2H), 3.68 (t, J = 5.2 Hz, 2H), 3.18 (s, 4H). |
| 359 | 1H NMR (400 MHz, DMSO-d6) δ 9.48 (s, 1H), 9.07 (d, J = 2.0 Hz, 1H), 8.38 (s, 1H), 8.08 (s, 1H), 7.93 (s, 3H), 7.69 (d, J = 2.2 Hz, 1H), 7.64 (d, J = 2.0 Hz, 1H), 7.53 (dd, J = 6.6, 2.6 Hz, 1H), 7.44 (t, J = 9.0 Hz, 1H), 7.41 (d, J = 2.4 Hz, 1H), 7.28 (ddd, J = 8.9, 4.3, 2.7 Hz, 2H), 6.37 (s, 1H), 4.56 (t, J = 6.3 Hz, 2H), 3.39-3.25 (m, 2H). |
| 360 | 1H NMR (400 MHz, DMSO-d6) δ 9.47 (s, 1H), 9.37 (d, J = 10.0 Hz, 1H), 9.06 (d, J = 1.9 Hz, 1H), 8.38 (s, 1H), 8.03 (s, 1H), 7.69 (d, J = 2.2 Hz, 1H), 7.63 (d, J = 2.0 Hz, 1H), 7.52 (dd, J = 6.6, 2.6 Hz, 1H), 7.44 (t, J = 9.0 Hz, 1H), 7.39 (d, J = 2.3 Hz, 1H), 7.37-7.25 (m, 2H), 6.35 (d, J = 7.3 Hz, 1H), 4.40 (t, J = 7.1 Hz, 2H), 3.14-2.97 (m, 2H), 2.75 (s, 3H), 2.74 (s, 3H), 2.15 (p, J = 7.3 Hz, 2H). |
| 361 | 1H NMR (400 MHz, DMSO-d6) δ 9.59 (s, 1H), 9.04 (d, J = 1.9 Hz, 1H), 8.40 (s, 1H), 8.07 (s, 1H), 7.68 (d, J = 2.2 Hz, 1H), 7.63 (dd, J = 2.1, 0.6 Hz, 1H), 7.55 (dd, J = 6.6, 2.6 Hz, 1H), 7.45 (t, J = 9.0 Hz, 1H), 7.39 (d, J = 2.4 Hz, 1H), 7.29 (m, 1H), 6.33 (s, 1H), 1.55 (s, 9H). |
| 362 | 1H NMR (400 MHz, DMSO-d6) δ 9.44-9.36 (m, 1H), 8.75-8.65 (m, 1H), 8.46 (dd, J = 4.8, 1.6 Hz, 1H), 8.40 (s, 1H), 8.13 (s, 1H), 7.92-7.80 (m, 1H), 7.68 (d, J = 2.3 Hz, 1H), 7.50 (dd, J = 6.6, 2.6 Hz, 1H), 7.49-7.40 (m, 2H), 7.37 (ddd, J = 7.9, 4.8, 0.8 Hz, 1H), 7.29-7.23 (m, 2H), 6.13 (d, J = 8.5 Hz, 1H), 4.53-4.37 (m, 1H), 2.92 (d, J = 10.6 Hz, 2H), 2.33 (t, J = 7.1 Hz, 2H), 2.09-1.86 (m, 6H), 1.00 (t, J = 7.2 Hz, 3H). |
| 363 | 1H NMR (400 MHz, DMSO-d6) δ 9.51 (s, 1H), 9.06 (d, J = 2.0 Hz, 1H), 8.38 (s, 1H), 8.20 (s, 1H), 7.68 (d, J = 2.2 Hz, 1H), 7.64 (d, J = 1.9 Hz, 1H), 7.54 (dd, J = 6.6, 2.6 Hz, 1H), 7.44 (t, J = 9.0 Hz, 1H), 7.40 (d, J = 2.3 Hz, 1H), 7.28 (ddd, J = 8.9, 4.3, 2.7 Hz, 1H), 6.37 (s, 1H), 5.81 (tt, J = 7.6, 6.1 Hz, 1H), 4.96 (t, J = 7.3 Hz, 2H), 4.85 (q, J = 6.6 Hz, 2H). |
| 364 | 1H NMR (400 MHz, DMSO-d6) δ 9.50 (s, 1H), 9.08 (d, J = 2.0 Hz, 1H), 8.38 (s, 1H), 8.16 (s, 1H), 7.68 (dd, J = 3.9, 2.1 Hz, 2H), 7.55 (dd, J = 6.7, 2.7 Hz, 1H), 7.49-7.40 (m, 2H), 7.29 (ddd, J = 8.6, 4.3, 2.7 Hz, 1H), 6.39 (s, 1H), 5.77 (s, 2H). |
| 365 | 1H NMR (400 MHz, DMSO-d6) δ 9.38 (s, 1H), 8.42 (s, 1H), 8.19 (s, 1H), 7.66 (d, J = 2.2 Hz, 1H), 7.57-7.49 (m, 3H), 7.45-7.37 (m, 2H), 7.26 (ddd, J = 8.8, 4.2, 2.6 Hz, 1H), 7.16 (dt, J = 3.8, 1.1 Hz, 1H), 6.43 (d, J = 8.6 Hz, 1H), 4.53-4.39 (m, 1H), 2.91 (d, J = 10.8 Hz, 2H), 2.33 (q, J = 6.9 Hz, 2H), 2.13-1.98 (m, 4H), 1.93 (dq, J = 11.7, 4.0, 3.5 Hz, 2H), 0.98 (t, J = 7.2 Hz, 3H). |
| 369 | 1H NMR (400 MHz, DMSO-d6) δ 9.40 (s, 1H), 8.70 (s, 1H), 8.56-8.30 (m, 2H), 8.14 (s, 1H), 7.87 (dt, J = 8.0, 1.9 Hz, 1H), 7.68 (d, J = 2.2 Hz, 1H), 7.61-7.31 (m, 4H), 7.25 (qd, J = 4.1, 2.6 Hz, 2H), 6.12 (d, J = 8.4 Hz, 1H), 4.60-4.28 (m, 1H), 3.05 (d, J = 10.9 Hz, 2H), 2.27-1.75 (m, 6H), 1.02 (s, 9H) |
| 370 | 1H NMR (400 MHz, DMSO-d6) δ 9.46 (s, 1H), 9.03 (d, J = 0.8 Hz, 1H), 8.95 (s, 1H), 8.44 (s, 1H), 8.16 (s, 1H), 7.87 (t, J = 0.8 Hz, 1H), 7.66 (d, J = 2.3 Hz, 1H), |

TABLE 2-continued

| Compound | ¹H-NMR |
|---|---|
|  | 7.60-7.41 (m, 4H), 7.31 (dt, J = 8.8, 3.7 Hz, 1H), 6.51 (d, J = 8.7 Hz, 1H), 4.88-4.77 (m, 1H), 3.67 (d, J = 12.1 Hz, 2H), 3.20-3.09 (m, 2H), 2.39 (d, J = 13.8 Hz, 2H), 2.25 (t, J = 12.8 Hz, 2H), 1.36 (s, 9H), 1.30 (s, 1H) |
| 371 | 1H NMR (400 MHz, DMSO-d6) δ 9.45 (s, 1H), 9.26 (s, 1H), 8.42 (s, 1H), 8.03 (s, 1H), 7.64 (d, J = 2.2 Hz, 1H), 7.61 (d, J = 3.4 Hz, 1H), 7.48-7.42 (m, 2H), 7.39 (t, J = 9.0 Hz, 1H), 7.26-7.14 (m, 3H), 6.01 (d, J = 7.2 Hz, 1H), 4.72 (ddt, J = 11.8, 8.1, 4.3 Hz, 1H), 3.59 (d, J = 12.3 Hz, 2H), 3.24-2.97 (m, 4H), 2.35-2.28 (m, 2H), 2.26-2.06 (m, 2H), 1.22 (t, J = 7.3 Hz, 3H). |
| 372 | 1H NMR (400 MHz, DMSO-d6) δ 9.47 (s, 2H), 8.44 (d, J = 1.4 Hz, 1H), 8.43 (s, 1H), 8.17 (s, 1H), 7.66 (d, J = 2.2 Hz, 1H), 7.58-7.47 (m, 2H), 7.47-7.37 (m, 4H), 7.27 (ddd, J = 8.9, 4.2, 2.7 Hz, 1H), 6.42 (d, J = 7.4 Hz, 1H), 4.77 (tt, J = 11.8, 4.1 Hz, 1H), 3.73-3.57 (m, 2H), 3.12 (tdd, J = 23.8, 18.1, 9.9 Hz, 4H), 2.42-2.28 (m, 2H), 2.28-2.12 (m, 2H), 1.23 (t, J = 7.2 Hz, 3H). |
| 373 | 1H NMR (400 MHz, DMSO-d6) δ 9.53 (s, 3H), 9.03 (dd, J = 3.0, 0.8 Hz, 1H), 8.43 (s, 1H), 8.20 (s, 2H), 7.88 (t, J = 0.8 Hz, 2H), 7.66 (d, J = 2.1 Hz, 2H), 7.61-7.42 (m, 8H), 7.32 (ddd, J = 8.9, 5.6, 3.0 Hz, 2H), 6.54 (d, J = 8.4 Hz, 2H), 4.84-4.72 (m, 2H), 3.63 (d, J = 12.3 Hz, 4H), 3.43 (s, 1H), 3.17-3.00 (m, 8H), 2.36 (d, J = 14.6 Hz, 4H), 2.23 (q, J = 12.8 Hz, 5H), 1.67 (ddt, J = 15.8, 11.1, 7.5 Hz, 4H), 0.92 (td, J = 7.3, 5.5 Hz, 6H). |
| 375 | 1H NMR (400 MHz, DMSO-d6) δ 9.46 (s, 1H), 9.02 (d, J = 0.8 Hz, 1H), 8.65 (s, 1H), 8.43 (s, 1H), 8.18 (s, 1H), 7.87 (t, J = 0.8 Hz, 1H), 7.66 (d, J = 2.2 Hz, 1H), 7.57 (dd, J = 6.6, 2.6 Hz, 1H), 7.52-7.40 (m, 3H), 7.35-7.26 (m, 1H), 6.51 (d, J = 8.6 Hz, 1H), 4.86-4.76 (m, 1H), 3.41 (d, J = 13.0 Hz, 2H), 3.12-3.02 (m, 2H), 2.28 (d, J = 13.5 Hz, 2H), 2.12 (d, J = 12.5 Hz, 2H). |
| 381 | 1H NMR (400 MHz, DMSO-d6) δ 9.43 (s, 1H), 9.29 (s, 1H), 8.42 (s, 1H), 8.13 (s, 1H), 7.66 (d, J = 2.2 Hz, 1H), 7.52 (dd, J = 6.6, 2.6 Hz, 1H), 7.46 (t, J = 1.5 Hz, 1H), 7.43 (t, J = 9.0 Hz, 2H), 7.39 (d, J = 2.4 Hz, 1H), 7.27 (ddd, J = 8.8, 4.2, 2.7 Hz, 1H), 7.04-6.97 (m, 1H), 6.35 (d, J = 8.3 Hz, 1H), 4.76 (tt, J = 11.9, 4.1 Hz, 1H), 3.62 (d, J = 12.4 Hz, 2H), 3.26-2.99 (m, 4H), 2.44-2.29 (m, 2H), 2.18 (ddt, J = 22.1, 13.3, 7.4 Hz, 2H), 1.23 (t, J = 7.3 Hz, 3H). |
| 382 | 1H NMR (400 MHz, DMSO-d6) δ 9.41 (s, 1H), 9.20 (s, 1H), 8.42 (s, 1H), 8.26 (s, OH), 8.13 (s, 1H), 7.65 (d, J = 2.2 Hz, 1H), 7.51 (dd, J = 6.6, 2.6 Hz, 1H), 7.48-7.37 (m, 4H), 7.26 (ddd, J = 8.8, 4.2, 2.7 Hz, 1H), 6.95 (d, J = 3.8 Hz, 1H), 6.90 (dd, J = 3.9, 0.9 Hz, 1H), 6.31 (d, J = 8.4 Hz, 1H), 4.84-4.66 (m, 1H), 3.62 (d, J = 12.7 Hz, 2H), 3.24-2.98 (m, 4H), 2.36 (d, J = 13.3 Hz, 2H), 2.17 (dd, J = 14.6, 11.1 Hz, 2H), 1.23 (t, J = 7.3 Hz, 3H). |
| 385 | 1H NMR (400 MHz, DMSO-d6) δ 9.42 (s, 1H), 8.64 (s, 1H), 8.42 (s, 2H), 8.12 (s, 1H), 7.65 (d, J = 2.2 Hz, 1H), 7.51 (dd, J = 6.6, 2.6 Hz, 1H), 7.47-7.40 (m, 3H), 7.39 (d, J = 2.4 Hz, 1H), 7.26 (ddd, J = 8.8, 4.2, 2.7 Hz, 1H), 7.00 (dd, J = 1.6, 0.9 Hz, 1H), 6.35 (d, J = 8.4 Hz, 1H), 4.79 (tt, J = 11.0, 4.0 Hz, 1H), 3.39 (d, J = 13.0 Hz, 2H), 3.06 (q, J = 11.9 Hz, 2H), 2.26 (d, J = 13.2 Hz, 2H), 2.19-2.01 (m, 2H). |
| 386 | 1H NMR (400 MHz, DMSO-d6) δ 9.43 (s, 1H), 8.65 (s, 1H), 8.42 (s, 2H), 8.12 (s, 1H), 7.65 (d, J = 2.2 Hz, 1H), 7.52 (dd, J = 6.6, 2.6 Hz, 1H), 7.47-7.40 (m, 2H), 7.38 (d, J = 2.4 Hz, 1H), 7.26 (ddd, J = 8.8, 4.2, 2.7 Hz, 1H), 6.95 (d, J = 3.8 Hz, 1H), 6.90 (dd, J = 3.8, 0.9 Hz, 1H), 6.31 (d, J = 8.1 Hz, 1H), 4.78 (ddt, J = 11.0, 8.1, 4.1 Hz, 1H), 3.39 (d, J = 12.7 Hz, 2H), 3.07 (q, J = 11.8 Hz, 2H), 2.26 (d, J = 13.4 Hz, 2H), 2.20-2.02 (m, 2H). |
| 387 | 1H NMR (400 MHz, DMSO-d6) δ 9.43 (s, 1H), 8.61 (s, 1H), 8.47 (s, 1H), 8.37 (d, J = 18.2 Hz, 1H), 8.07 (s, 1H), 7.64 (d, J = 2.2 Hz, 1H), 7.56 (d, J = 5.4 Hz, 1H), 7.44-7.32 (m, 4H), 7.19-7.08 (m, 3H), 6.99 (d, J = 5.4 Hz, 1H), 6.22 (d, J = 7.2 Hz, 1H), 4.76 (td, J = 11.2, 5.4 Hz, 1H), 3.37 (d, J = 13.4 Hz, 2H), 3.06 (t, J = 11.6 Hz, 2H), 2.22 (d, J = 13.7 Hz, 2H), 2.09 (t, J = 12.2 Hz, 2H). |
| 389 | 1H NMR (400 MHz, DMSO-d6) δ 9.46 (s, 1H), 9.33 (s, 1H), 8.47 (s, 1H), 8.09 (s, 1H), 7.65 (d, J = 2.2 Hz, 1H), 7.56 (dd, J = 5.3, 2.1 Hz, 1H), 7.42-7.33 (m, 4H), 7.13 (ddd, J = 8.7, 3.7, 2.3 Hz, 3H), 7.01-6.96 (m, 1H), 6.22 (d, J = 6.6 Hz, 1H), 4.74 (ddt, J = 11.8, 8.2, 4.1 Hz, 1H), 3.60 (d, J = 12.3 Hz, 2H), 3.15 (qt, J = 11.5, 5.3 Hz, 3H), 3.04 (dd, J = 13.2, 10.0 Hz, 2H), 2.41-2.28 (m, 3H), 2.24-2.09 (m, 3H), 1.22 (t, J = 7.3 Hz, 3H). |
| 400 | 1H NMR (400 MHz, DMSO-d6) δ 9.41 (s, 1H), 8.80 (s, 1H), 8.60 (d, J = 5.1 Hz, 1H), 8.41 (s, 1H), 8.25-8.06 (m, 2H), 7.74-7.57 (m, 2H), 7.56-7.14 (m, 8H), 6.86 (d, J = 6.5 Hz, 1H), 6.23 (d, J = 6.9 Hz, 1H), 5.25 (s, 1H), 5.04 (t, J = 9.8 Hz, 2H), 3.96-3.76 (m, 1H), 3.67 (d, J = 10.2 Hz, 1H), 3.59-3.37 (m, 2H), 2.47-2.21 (m, 2H). |
| 401 | 1H NMR (400 MHz, DMSO-d6) δ 9.44 (s, 1H), 9.12 (brs, 2H), 8.74 (d, J = 2.2 Hz, 1H), 8.53 (dd, J = 4.9, 1.6 Hz, 1H), 8.41 (s, 1H), 8.21 (d, J = 6.3 Hz, 1H), 7.98 (d, J = 7.9 Hz, 1H), 7.66 (dd, J = 2.4, 1.3 Hz, 1H), 7.56-7.36 (m, 4H), 7.35-7.18 (m, 2H), 6.24 (d, J = 8.2 Hz, 1H), 5.49-5.31 (m, 1H), 3.75-3.56 (m, 2H), 3.36 (t, J = 6.9 Hz, 2H), 2.48 (m, 1H), 2.36-2.19 (m, 1H). |
| 402 | 1H NMR (400 MHz, DMSO-d6) δ 10.01 (brs, 1H), 9.40 (s, 1H), 8.71 (d, J = 2.2 Hz, 1H), 8.51 (dd, J = 5.0, 1.5 Hz, 1H), 8.41 (s, 1H), 8.21 (dd, J = 14.2, 7.1 Hz, 1H), 7.93 (d, J = 8.0 Hz, 1H), 7.66 (t, J = 2.1 Hz, 1H), 7.57-7.36 (m, 4H), 7.34-7.18 (m, 2H), 6.21 (d, J = 8.0 Hz, 1H), 5.58-5.32 (m, 1H), 3.95-3.49 (m, 3H), 3.38-3.14 (m, 3H), 2.80-2.62 (m, 1H), 2.42-2.19 (m, 1H), 1.21 (t, J = 7.2 Hz, 3H). |
| 403 | 1H NMR (400 MHz, DMSO-d6) δ 9.44 (s, 1H), 8.94 (s, 1H), 8.74 (dd, J = 2.3, 0.8 Hz, 1H), 8.62 (dd, J = 4.9, 1.6 Hz, 1H), 8.44 (s, 1H), 7.97 (dt, J = 8.0, 1.9 Hz, 1H), 7.63 (d, J = 2.3 Hz, 1H), 7.56 (ddd, J = 8.0, 4.9, 0.8 Hz, 1H), 7.47 (dd, J = |

TABLE 2-continued

| Compound | ¹H-NMR |
|---|---|
| | 6.6, 2.7 Hz, 2H), 7.44-7.38 (m, 2H), 7.26 (d, J = 2.4 Hz, 1H), 7.23 (ddd, J = 8.8, 4.2, 2.7 Hz, 1H), 6.13 (d, J = 7.9 Hz, 1H), 3.76 (s, 3H). |
| 404 | 1H NMR (400 MHz, DMSO-d6) δ 9.40 (s, 1H), 8.76 (s, 1H), 8.63-8.48 (m, 1H), 8.40 (s, 1H), 8.16 (s, 1H), 8.05 (d, J = 8.0 Hz, 1H), 7.66 (d, J = 2.2 Hz, 1H), 7.61-7.13 (m, 10H), 6.87 (s, 2H), 6.19 (d, J = 7.7 Hz, 1H), 5.07 (s, 2H), 4.71 (m, 1H), 4.07 (d, J = 13.1 Hz, 2H), 3.00 (m, 2H), 2.02 (d, J = 12.5 Hz, 2H), 1.92-1.66 (m, 2H). |
| 405 | 1H NMR (400 MHz, DMSO-d6) δ 9.46 (s, 1H), 8.81-8.64 (m, 2H), 8.54 (dd, J = 5.0, 1.6 Hz, 1H), 8.41 (s, 2H), 8.14 (s, 1H), 8.02 (d, J = 8.1 Hz, 1H), 7.67 (d, J = 2.2 Hz, 1H), 7.58-7.36 (m, 4H), 7.32-7.16 (m, 2H), 6.22 (d, J = 7.9 Hz, 1H), 4.87-4.66 (m, 1H), 3.38 (d, J = 12.9 Hz, 2H), 3.06 (q, J = 12.0 Hz, 2H), 2.33-2.18 (m, 2H), 2.18-1.98 (m, 2H). |
| 408 | 1H NMR (400 MHz, Methanol-d4) δ 9.20 (s, 1H), 8.43 (s, 1H), 8.09-8.02 (m, 1H), 7.98 (s, 1H), 7.89 (d, J = 2.3 Hz, 1H), 7.67 (d, J = 7.2 Hz, 1H), 7.59 (t, J = 7.8 Hz, 1H), 7.01 (d, J = 2.4 Hz, 1H), 6.38 (s, 1H), 4.21 (d, J = 13.9 Hz, 1H), 3.53 (d, J = 13.9 Hz, 1H), 1.87-1.74 (m, 2H), 1.65-1.50 (m, 2H), 0.85 (s, 9H). |
| 409 | 1H NMR (400 MHz, Methanol-d4) δ 9.20 (s, 1H), 8.33 (s, 1H), 8.04 (d, J = 7.9 Hz, 1H), 8.00 (s, 1H), 7.84 (d, J = 2.5 Hz, 1H), 7.68 (d, J = 7.3 Hz, 1H), 7.59 (t, J = 7.8 Hz, 1H), 7.15 (d, J = 2.5 Hz, 1H), 6.37 (s, 1H), 4.00 (d, J = 13.7 Hz, 1H), 3.42 (d, J = 13.7 Hz, 1H), 1.87-1.74 (m, 2H), 1.62-1.52 (m, 2H), 0.80 (s, 9H). |
| 410 | 1H NMR (400 MHz, Methanol-d4) δ 9.20 (s, 1H), 8.35 (s, 1H), 8.04 (dd, J = 7.4, 1.8 Hz, 1H), 7.87 (d, J = 2.5 Hz, 1H), 7.82 (s, 1H), 7.64-7.53 (m, 2H), 7.17 (d, J = 2.5 Hz, 1H), 6.34 (s, 1H), 3.98 (d, J = 13.7 Hz, 1H), 3.97-3.80 (m, 1H), 3.50 (d, J = 13.7 Hz, 1H), 1.23-1.07 (m, 4H), 0.81 (s, 9H). |
| 411 | 1H NMR (400 MHz, Methanol-d4) δ 9.20 (s, 1H), 8.23 (s, 1H), 8.10-8.03 (m, 1H), 7.86 (d, J = 2.5 Hz, 1H), 7.83 (s, 1H), 7.69 (d, J = 7.3 Hz, 1H), 7.65-7.54 (m, 1H), 7.36-7.29 (m, 1H), 7.21-7.11 (m, 2H), 6.92 (d, J = 6.8 Hz, 2H), 6.46 (s, 1H), 5.48 (t, J = 7.1 Hz, 1H), 3.90-3.84 (m, 1H), 2.05 (dt, J = 14.4, 7.2 Hz, 1H), 1.84 (dt, J = 13.9, 7.1 Hz, 1H), 1.22-1.10 (m, 4H), 0.94 (t, J = 7.3 Hz, 3H). |
| 412 | 1H NMR (400 MHz, Methanol-d4) δ 9.20 (s, 1H), 8.24 (s, 1H), 8.12 (s, 1H), 8.07 (dd, J = 8.1, 1.1 Hz, 1H), 7.88 (d, J = 2.6 Hz, 1H), 7.71 (d, J = 7.3 Hz, 1H), 7.62-7.55 (m, 1H), 7.38-7.30 (m, 2H), 7.23-7.10 (m, 2H), 6.96-6.89 (m, 2H), 6.53 (s, 1H), 5.49 (t, J = 7.0 Hz, 1H), 2.06 (dt, J = 14.1, 7.1 Hz, 1H), 1.85 (dt, J = 14.1, 7.3 Hz, 1H), 1.75-1.62 (m, 4H), 0.95 (t, J = 7.3 Hz, 3H). |
| 413 | 1H NMR (400 MHz, Methanol-d4) δ 8.44 (s, 1H), 8.21 (s, 1H), 8.05 (m, 1H), 7.81 (t, J = 8.1 Hz, 2H), 7.62 (d, J = 2.4 Hz, 1H), 7.44-7.29 (m, 5H), 7.24 (m, 1H), 6.97-6.85 (m, 2H), 5.95 (m, 1H), 3.47 (m, 1H), 2.67-2.41 (m, 7H), 1.80 (m, 4H). |
| 414 | 1H NMR (400 MHz, Methanol-d4) δ 8.26 (s, 1H), 7.99 (s, 1H), 7.73 (m, 1H), 7.57 (m, 1H), 7.42 (s, 1H), 7.40-7.27 (m, 5H) , 6.19 (s, 1H), 5.76 (dd, J = 8.6, 5.5 Hz, 1H), 4.90 (td, J = 7.6, 3.1 Hz, 2H), 4.78 (m, 2H), 4.55-4.35 (m, 5H), 3.92 (m, 1H), 2.91 (m, 1H), 2.63 (m, 2H), 2.44 (m, 1H), 2.36 (m, 1H), 1.22 (m, 2H), 1.17 (m, 2H). |
| 415 | 1H NMR (400 MHz, Methanol-d4) δ 9.21 (s, 1H), 8.47 (s, 1H), 8.14 (d, J = 0.6 Hz, 1H), 8.06 (dd, J = 7.4, 1.8 Hz, 1H), 7.73 (d, J = 2.3 Hz, 1H), 7.65-7.55 (m, 2H), 7.01 (d, J = 2.3 Hz, 1H), 6.40 (s, 1H), 4.17 (d, J = 13.9 Hz, 1H), 3.60 (d, J = 13.8 Hz, 1H), 2.02-1.83 (m, 4H), 0.86 (s, 9H). |
| 416 | 1H NMR (400 MHz, Methanol-d4) δ 9.20 (s, 1H), 8.49 (s, 1H), 8.05 (dd, J = 8.0, 1.1 Hz, 1H), 7.98 (s, 1H), 7.72 (d, J = 2.3 Hz, 1H), 7.67 (d, J = 7.1 Hz, 1H), 7.59 (dd, J = 8.1, 7.4 Hz, 1H), 7.01 (d, J = 2.3 Hz, 1H), 6.39 (s, 1H), 4.24 (d, J = 13.9 Hz, 1H), 3.55 (d, J = 13.9 Hz, 1H), 1.88-1.74 (m, 2H), 1.65-1.50 (m, 2H), 0.86 (s, 9H). |
| 417 | 1H NMR (400 MHz, Methanol-d4) δ 9.21 (s, 1H), 8.47 (s, 1H), 8.10 (s, 1H), 8.06 (dd, J = 7.3, 1.9 Hz, 1H), 7.74 (d, J = 2.3 Hz, 1H), 7.65-7.54 (m, 2H), 7.02 (d, J = 2.3 Hz, 1H), 6.41 (s, 1H), 4.18 (d, J = 13.8 Hz, 1H), 3.60 (d, J = 13.8 Hz, 1H), 1.79-1.59 (m, 4H), 0.86 (s, 9H). |
| 418 | 1H NMR (400 MHz, Methanol-d4) δ 9.21 (s, 1H), 8.47 (s, 1H), 8.05 (dd, J = 6.7, 2.5 Hz, 1H), 7.80 (s, 1H), 7.72 (d, J = 2.3 Hz, 1H), 7.63-7.54 (m, 2H), 6.99 (d, J = 2.4 Hz, 1H), 6.35 (s, 1H), 4.17 (d, J = 13.9 Hz, 1H), 3.86 (ddd, J = 11.4, 7.3, 4.0 Hz, 1H), 3.60 (d, J = 13.8 Hz, 1H), 1.23-1.08 (m, 4H), 0.85 (s, 9H). |
| 419 | 1H NMR (400 MHz, Methanol-d4) δ 9.21 (s, 1H), 8.45 (s, 1H), 8.09-8.02 (m, 1H), 7.83 (s, 1H), 7.72 (d, J = 2.3 Hz, 1H), 7.64 (d, J = 7.4 Hz, 1H), 7.62-7.55 (m, 1H), 7.00 (d, J = 2.4 Hz, 1H), 6.39 (s, 1H), 4.77 (td, J = 11.4, 5.5 Hz, 1H), 4.18 (d, J = 13.8 Hz, 1H), 3.79 (d, J = 12.6 Hz, 2H), 3.55 (d, J = 13.8 Hz, 1H), 3.20 (t, J = 12.0 Hz, 2H), 2.47-2.37 (m, 4H), 1.45 (s, 9H), 0.84 (s, 9H). |
| 420 | 1H NMR (400 MHz, Methanol-d4) δ 9.21 (s, 1H), 8.28 (s, 1H), 8.06 (dd, J = 7.7, 1.5 Hz, 1H), 7.82 (d, J = 2.2 Hz, 2H), 7.67-7.55 (m, 2H), 7.15 (d, J = 2.5 Hz, 1H), 6.39 (d, J = 4.6 Hz, 1H), 4.79-4.71 (m, 1H), 3.90 (d, J = 13.7 Hz, 1H), 3.80 (d, J = 12.5 Hz, 2H), 3.43 (d, J = 13.7 Hz, 1H), 3.24-3.15 (m, 2H), 2.51-2.34 (m, 4H), 1.45 (s, 9H), 0.79 (s, 9H). |
| 421 | 1H NMR (400 MHz, Methanol-d4) δ 9.21 (s, 1H), 8.47 (s, 1H), 8.06 (dd, J = 7.5, 1.8 Hz, 1H), 7.96 (s, 1H), 7.74 (d, J = 2.2 Hz, 1H), 7.65-7.54 (m, 2H), 7.02 (d, J = 2.3 Hz, 1H), 6.40 (s, 1H), 5.92 (t, J = 54.7 Hz, 1H), 4.18 (d, J = 13.9 Hz, 1H), 3.60 (d, J = 13.9 Hz, 1H), 1.54-1.46 (m, 4H), 0.86 (s, 9H). |
| 422 | 1H NMR (400 MHz, Methanol-d4) δ 8.51 (d, J = 5.8 Hz, 2H), 7.95 (d, J = 2.4 Hz, 1H), 7.90 (s, 1H), 7.68 (d, J = 2.3 Hz, 1H), 7.27 (dd, J = 7.0, 1.0 Hz, 1H), 7.00 (d, J = 2.3 Hz, 1H), 6.86 (t, J = 7.0 Hz, 1H), 6.61 (dd, J = 2.4, 0.9 Hz, 1H), |

TABLE 2-continued

| Compound | ¹H-NMR |
|---|---|
| | 6.33 (s, 1H), 4.10 (d, J = 13.9 Hz, 1H), 3.87 (tt, J = 7.5, 4.1 Hz, 1H), 3.68 (d, J = 13.8 Hz, 1H), 1.24-1.08 (m, 4H), 0.83 (s, 9H). |
| 423 | 1H NMR (400 MHz, Methanol-d4) δ 8.47 (s, 1H), 8.09 (d, J = 0.9 Hz, 1H), 7.75 (s, 1H), 7.69 (d, J = 2.2 Hz, 1H), 7.53 (d, J = 8.5 Hz, 1H), 7.39 (dd, J = 8.5, 7.1 Hz, 1H), 7.26 (d, J = 7.0 Hz, 1H), 7.01 (d, J = 2.3 Hz, 1H), 6.43 (s, 1H), 4.15 (d, J = 13.9 Hz, 1H), 4.05 (s, 3H), 3.90-3.79 (m, 1H), 3.64 (d, J = 13.9 Hz, 1H), 1.22-1.06 (m, 4H), 0.84 (s, 9H). |
| 424 | 1H NMR (400 MHz, Methanol-d4) δ 9.21 (s, 1H), 8.35 (s, 1H), 8.05 (dd, J = 7.7, 1.6 Hz, 1H), 7.97 (s, 1H), 7.88 (d, J = 2.5 Hz, 1H), 7.66-7.54 (m, 2H), 7.19 (d, J = 2.5 Hz, 1H), 6.39 (s, 1H), 5.93 (t, J = 54.7 Hz, 1H), 3.99 (d, J = 13.7 Hz, 1H), 3.49 (d, J = 13.8 Hz, 1H), 1.51-1.48 (m, 4H), 0.82 (s, 9H). |
| 425 | 1H NMR (400 MHz, DMSO-d6) δ 8.40-8.35 (m, 2H), 8.08 (d, J = 0.8 Hz, 1H), 8.05 (dd, J = 8.2, 2.6 Hz, 1H), 7.85 (s, 1H), 7.66-7.62 (m, 1H), 7.58 (s, 1H), 7.23-7.17 (m, 2H), 5.32 (s, 2H), 4.04 (dd, J = 14.1, 8.0 Hz, 1H), 3.48 (dd, J = 14.1, 5.6 Hz, 1H), 3.27 (d, J = 0.7 Hz, 3H), 0.88 (s, 9H). |
| 426 | 1H NMR (400 MHz, Methanol-d4) δ 8.47 (s, 1H), 8.25 (s, 1H), 7.76 (s, 1H), 7.69 (d, J = 2.2 Hz, 1H), 7.54 (dt, J = 8.6, 0.9 Hz, 1H), 7.25 (dd, J = 8.6, 6.9 Hz, 1H), 7.18 (d, J = 6.8 Hz, 1H), 7.00 (d, J = 2.3 Hz, 1H), 6.32 (s, 1H), 4.17 (s, 3H), 4.15 (d, J = 14.7 Hz, 1H), 3.89-3.79 (m, 1H), 3.63 (d, J = 13.8 Hz, 1H), 1.21-1.05 (m, 4H), 0.84 (s, 9H). |
| 427 | 1H NMR (400 MHz, Methanol-d4) δ 8.33 (s, 1H), 7.85 (dd, J = 6.2, 2.8 Hz, 2H), 7.80 (s, 1H), 7.56-7.44 (m, 2H), 7.14 (d, J = 2.5 Hz, 1H), 6.26 (s, 1H), 3.98 (d, J = 13.7 Hz, 1H), 3.91-3.81 (m, 1H), 3.47 (d, J = 13.7 Hz, 1H), 2.78 (s, 3H), 1.26-1.06 (m, 4H), 0.82 (s, 9H). |
| 428 | 1H NMR (400 MHz, Methanol-d4) δ 8.22 (s, 1H), 7.99 (s, 1H), 7.75 (d, J = 2.5 Hz, 1H), 7.63-7.56 (m, 1H), 7.44-7.39 (m, 2H), 7.37 (d, J = 2.5 Hz, 1H), 7.34 (d, J = 4.4 Hz, 1H), 7.31-7.21 (m, 2H), 7.15 (dd, J = 7.2, 2.5 Hz, 2H), 6.20 (s, 1H), 5.51 (t, J = 7.0 Hz, 1H), 4.62-4.48 (m, 4H), 3.94-3.88 (m, 1H), 2.20-1.89 (m, 2H), 1.23-1.17 (m, 4H), 0.99 (t, J = 7.4 Hz, 3H). |
| 429 | 1H NMR (400 MHz, Methanol-d4) δ 8.30 (s, 1H), 8.25 (s, 1H), 7.72 (d, J = 2.5 Hz, 1H), 7.39 (s, 1H), 7.35 (d, J = 2.5 Hz, 1H), 6.15 (s, 1H), 4.91 (m, 2H), 4.80 (m, 2H), 4.62-4.46 (m, 2H), 4.39 (m, 1H), 3.86 (d, J = 13.9 Hz, 1H), 3.75 (d, J = 13.9 Hz, 1H), 3.52 (s, 1H), 3.48-3.36 (m, 1H), 3.23-3.11 (m, 1H), 3.00-2.94 (m, 1H), 1.78 (m, 2H), 1.68 (3, 2H), 0.98 (s, 9H). |
| 430 | 1H NMR (400 MHz, Methanol-d4) δ 8.34 (s, 1H), 8.09 (s, 1H), 7.86 (td, J = 3.3, 2.2 Hz, 2H), 7.58-7.46 (m, 2H), 7.17 (d, J = 2.5 Hz, 1H), 6.33 (s, 1H), 3.99 (d, J = 13.8 Hz, 1H), 3.47 (d, J = 13.7 Hz, 1H), 2.77 (s, 3H), 1.79-1.57 (m, 4H), 0.83 (s, 9H). |
| 431 | 1H NMR (400 MHz, Chloroform-d) δ 8.42 (s, 1H), 7.88 (m, 1H), 7.48-7.28 (m, 6H), 6.81 (m, 1H), 6.76 (s, 1H), 5.97 (s, 1H), 5.67 (m, 1H), 5.30 (s, 2H), 3.73 (m, 1H), 2.57 (s, 3H), 2.57-2.47 (m, 1H), 2.33 (m, 1H), 1.57 (s, 2H), 0.92-0.81 (m, 4H). |
| 432 | 1H NMR (400 MHz, Methanol-d4) δ 8.44 (s, 1H), 8.20 (s, 1H), 7.79 (m, 1H), 7.61 (m, 1H), 6.88 (m, 2H), 6.24 (s, 1H), 3.88 (m, 2H), 3.62 (m, 2H), 2.51 (s, 3H), 1.86-1.56 (m, 4H), 0.92 (s, 9H). |
| 433 | 1H NMR (400 MHz, Methanol-d4) δ 8.30 (s, 1H), 7.96 (s, 1H), 7.71 (d, J = 2.5 Hz, 1H), 7.38 (s, 1H), 7.31 (d, J = 2.5 Hz, 1H), 6.07 (s, 1H), 4.92 (m, 2H), 4.82-4.78 (m, 2H), 4.64-4.47 (m, 2H), 4.40 (m, 1H), 3.90 (m, 1H), 3.85 (d, J = 14.1 Hz, 1H), 3.76 (d, J = 13.9 Hz, 1H), 3.52 (m, 1H), 3.42 (m, 1H), 3.16-3.13 (m, 1H), 3.02-2.88 (m, 1H), 1.24-1.13 (m, 4H), 0.98 (s, 9H). |
| 434 | 1H NMR (400 MHz, Methanol-d4) δ 9.21 (s, 1H), 8.46 (s, 1H), 8.05 (dd, J = 7.0, 2.2 Hz, 1H), 7.87 (s, 1H), 7.72 (d, J = 2.3 Hz, 1H), 7.64-7.54 (m, 2H), 6.98 (d, J = 2.3 Hz, 1H), 6.35 (s, 1H), 4.17 (d, J = 13.8 Hz, 1H), 3.58 (d, J = 13.8 Hz, 1H), 1.63 (s, 3H), 1.32-1.25 (m, 2H), 1.08-1.00 (m, 2H), 0.84 (s, 9H). |
| 435 | 1H NMR (400 MHz, Methanol-d4) δ 9.21 (s, 1H), 8.35 (s, 1H), 8.05 (dd, J = 7.5, 1.7 Hz, 1H), 7.89 (s, 1H), 7.87 (d, J = 2.5 Hz, 1H), 7.65-7.54 (m, 2H), 7.16 (d, J = 2.5 Hz, 1H), 6.35 (s, 1H), 4.00 (d, J = 13.7 Hz, 1H), 3.49 (d, J = 13.8 Hz, 1H), 1.63 (s, 3H), 1.31-1.25 (m, 2H), 1.08-0.99 (m, 2H), 0.81 (s, 9H). |
| 436 | 1H NMR (400 MHz, Methanol-d4) δ 8.50 (s, 1H), 8.02-7.93 (m, 2H), 7.62 (m, 1H), 7.07 (m, 1H), 6.96 (m, 1H), 6.31 (s, 1H), 4.12-3.98 (m, 1H), 3.95-3.80 (m, 1H), 3.39 (m, 1H), 1.29-1.10 (m, 2H), 1.03 (s, 2H), 0.97 (s, 9H). 4.94-4.85 (m, 4H), 4.87 (s, 21H), |
| 437 | 1H NMR (400 MHz, Methanol-d4) δ 9.01 (m, 1H), 8.83 (d, J = 8.6 Hz, 1H), 8.49 (s, 1H), 8.10 (d, J = 8.6 Hz, 1H), 7.90-7.81 (m, 2H), 7.81-7.65 (m, 4H), 6.92 (d, J = 2.3 Hz, 1H), 6.84 (s, 1H), 4.01 (d, J = 13.9 Hz, 1H), 3.86 (m, 1H), 3.62 (d, J = 13.9 Hz, 1H), 1.22-1.07 (m, 4H), 0.70 (s, 9H). |
| 438 | 1H NMR (400 MHz, Chloroform-d) δ 8.40 (s, 1H), 7.90 (m, 1H), 7.43-7.26 (m, 5H), 7.22 (m, 2H), 6.78 (m, 1H), 6.61 (s, 1H), 6.00 (s, 1H), 5.69 (m, 1H), 5.30 (s, 2H), 3.75 (m, 3.8 Hz, 1H), 2.65 (s, 3H), 2.64-2.49 (m, 1H) 2.44 (s, 2H), 2.33 (s, 1H), 0.92-0.81 (m, 4H). |
| 440 | 1H NMR (400 MHz, Methanol-d4) δ 8.45 (m, 1H), 8.21 (s, 1H), 7.82 (m, 1H), 7.64 (m, 1H), 7.40-7.25 (m, 5H), 7.13 (m, 1H), 6.93-6.83 (m, 2H), 6.37 (m, 1H), 5.79-5.64 (m, 1H), 2.53 (m, 3H), 2.23-2.09 (m, 1H), 2.07 (m, 1H), 1.81-1.64 (m, 4H), 1.04-0.91 (m, 3H) |
| 441 | 1H NMR (400 MHz, DMSO-d6) δ 9.32 (s, 1H), 8.30 (d, J = 1.5 Hz, 1H), 8.16 (s, 1H), 8.00 (dd, J = 8.1, 1.2 Hz, 1H), 7.92 (d, J = 2.3 Hz, 1H), 7.69-7.57 (m, 2H), 7.50 (td, J = 7.8, 1.5 Hz, 1H), 7.43-7.30 (m, 2H), 6.46 (d, J = 5.8 Hz, 1H), 4.72 |

TABLE 2-continued

| Compound | ¹H-NMR |
|---|---|
| | (s, 1H), 4.60 (s, 1H), 3.87 (dd, J = 13.8, 8.1 Hz, 1H), 3.34 (dd, J = 13.8, 5.0 Hz, 1H), 1.41-1.27 (m, 4H), 0.75 (s, 9H). |
| 443 | 1H NMR (400 MHz, Methanol-d4) δ 9.75 (s, 1H), 8.59 (m, 1H), 8.46 (s, 1H), 8.26 m, 1H), 8.13 (m, 1H), 8.01-7.86 (m, 3H), 7.68 (m, 1H), 6.96 (m, 2H), 4.05-3.96 (m, 1H), 3.87 (m, 1H), 3.63 (m, 1H), 1.37 (m, 1H), 1.21-1.07 (m, 4H), 0.72 (s, 9H). |
| 444 | 1H NMR (400 MHz, Methanol-d4) δ 8.50 (d, J = 7.0 Hz, 1H), 8.37 (s, 1H), 8.06 (s, 1H), 7.95 (d, J = 2.4 Hz, 1H), 7.83 (d, J = 2.5 Hz, 1H), 7.29 (dt, J = 7.0, 1.0 Hz, 1H), 7.18 (d, J = 2.5 Hz, 1H), 6.87 (t, J = 7.0 Hz, 1H), 6.64 (dd, J = 2.4, 0.9 Hz, 1H), 6.38 (s, 1H), 5.93 (t, J = 54.8 Hz, 1H), 3.93 (d, J = 13.8 Hz, 1H), 3.54 (d, J = 13.7 Hz, 1H), 1.52-1.48 (m, 4H), 0.78 (s, 9H). |
| 445 | 1H NMR (400 MHz, Methanol-d4) δ 8.43 (s, 1H), 8.13 (s, 1H), 7.62 (d, J = 2.3 Hz, 1H), 7.50 (d, J = 7.1 Hz, 1H), 7.48-7.36 (m, 2H), 7.04 (d, J = 2.3 Hz, 1H), 6.12 (s, 1H), 5.94 (t, J = 54.6 Hz, 1H), 4.92 (d, J = 14.6 Hz, 1H), 4.56 (s, 2H), 4.55 (d, J = 14.7 Hz, 1H), 4.12 (d, J = 13.9 Hz, 1H), 3.69 (d, J = 13.9 Hz, 1H), 1.58-1.50 (m, 4H), 0.96 (s, 9H). |
| 446 | 1H NMR (400 MHz, Methanol-d4) δ 9.13 (s, 1H), 8.46 (s, 1H), 8.39 (d, J = 7.1 Hz, 1H), 8.04 (s, 1H), 7.80 (s, 1H), 7.65 (d, J = 2.3 Hz, 1H), 7.20 (d, J = 6.9 Hz, 1H), 7.04 (d, J = 2.3 Hz, 1H), 6.98 (t, J = 7.0 Hz, 1H), 6.32 (s, 1H), 4.08 (d, J = 13.9 Hz, 1H), 3.89 (ddd, J = 11.5, 7.4, 4.1 Hz, 1H), 3.68 (d, J = 13.9 Hz, 1H), 1.25-1.10 (m, 4H), 0.87 (s, 9H). |
| 447 | 1H NMR (400 MHz, Chloroform-d) δ 8.45 (s, 1H), 7.93 (t, J = 8.1 Hz, 1H), 7.41 (s, 1H), 7.35 (d, J = 2.3 Hz, 1H), 6.80 (dd, J = 8.4, 3.2 Hz, 1H), 6.25 (s, 1H), 5.93 (s, 1H), 5.91 (t, J = 56.0 Hz, 1H), 5.27 (s, 1H), 3.57 (m, 2H), 2.58 (s, 3H), 1.55-1.50 (m, 4H), 0.94 (s, 9H). |
| 448 | 1H NMR (400 MHz, Methanol-d4) δ 8.47 (s, 1H), 8.13 (s, 1H), 7.74 (s, 1H), 7.69 (d, J = 2.3 Hz, 1H), 7.51 (d, J = 8.5 Hz, 1H), 7.35 (dd, J = 8.6, 7.0 Hz, 1H), 7.23 (d, J = 7.0 Hz, 1H), 7.02 (d, J = 2.3 Hz, 1H), 6.44 (s, 1H), 4.13 (d, J = 13.9 Hz, 1H), 3.90-3.79 (m, 1H), 3.69-3.60 (m, 1H), 1.22-1.06 (m, 4H), 0.84 (s, 9H). |
| 449 | 1H NMR (400 MHz, Methanol-d4) δ 9.29 (s, 1H), 8.44 (s, 1H), 8.06 (d, J = 8.1 Hz, 1H), 7.89 (s, 1H), 7.69 (s, 1H), 7.62 (d, J = 7.5 Hz, 1H), 7.47 (t, J = 7.6 Hz, 1H), 7.11 (s, 1H), 6.93 (s, 1H), 4.04 (d, J = 13.8 Hz, 1H), 3.91-3.77 (m, 1H), 3.73 (d, J = 13.8 Hz, 1H), 1.24-1.00 (m, 4H), 0.87 (s, 8H). |
| 450 | 1H NMR (400 MHz, Methanol-d4) δ 8.94 (dd, J = 4.3, 1.8 Hz, 1H), 8.47 (s, 1H), 8.37 (dd, J = 8.3, 1.8 Hz, 1H), 7.93 (dd, J = 8.1, 1.4 Hz, 1H), 7.86 (dd, J = 7.2, 1.3 Hz, 1H), 7.76 (s, 1H), 7.69 (d, J = 2.2 Hz, 1H), 7.62-7.53 (m, 2H), 7.27 (s, 1H), 7.10 (d, J = 2.2 Hz, 1H), 4.02 (d, J = 13.9 Hz, 1H), 3.86-3.70 (m, 2H), 1.19-1.04 (m, 4H), 0.80 (s, 9H). |
| 451 | 1H NMR (400 MHz, Methanol-d4) δ 8.28 (s, 2H), 7.74 (d, J = 2.5 Hz, 1H), 7.53 (d, J = 7.4 Hz, 1H), 7.44 (t, J = 7.5 Hz, 1H), 7.40 (d, J = 7.3 Hz, 1H), 7.21 (d, J = 2.5 Hz, 1H), 6.13 (s, 1H), 4.99 (d, J = 14.6 Hz, 1H), 4.59 (d, J = 14.8 Hz, 1H), 4.56 (s, 2H), 3.97 (d, J = 13.8 Hz, 1H), 3.55 (d, J = 13.8 Hz, 1H), 1.85-1.74 (m, 2H), 1.70-1.61 (m, 2H), 0.93 (s, 9H). |
| 452 | 1H NMR (400 MHz, Methanol-d4) δ 8.86 (d, J = 15.0 Hz, 2H), 8.01 (d, J = 11.5 Hz, 2H), 7.85 (s, 1H), 7.77-7.64 (m, 3H), 7.56 (d, J = 2.5 Hz, 1H), 7.50-7.41 (m, 1H), 7.34-7.19 (m, 3H), 7.12 (d, J = 7.4 Hz, 1H), 6.94 (d, J = 2.5 Hz, 1H), 6.70 (d, J = 2.5 Hz, 1H), 6.12 (s, 1H), 6.07 (s, 1H), 4.58-4.42 (m, 3H), 4.20 (dd, J = 10.0, 5.8 Hz, 1H), 4.02 (dd, J = 11.4, 4.5 Hz, 1H), 3.62 (dt, J = 15.5, 7.9 Hz, 2H), 3.20-3.07 (m, 2H), 3.02 (d, J = 11.6 Hz, 1H), 2.94 (p, J = 1.7 Hz, 14H), 2.89-2.81 (m, 1H), 2.75 (d, J = 11.6 Hz, 1H), 1.66-1.22 (m, 11H), 0.66 (s, 3H), 0.43 (s, 3H), 0.29 (s, 3H), -0.00 (s, 3H). |
| 453 | 1H NMR (400 MHz, DMSO-d6) δ 9.36 (d, J = 1.3 Hz, 1H), 8.42 (s, 2H), 8.04 (dd, J = 8.0, 1.2 Hz, 1H), 7.80 (s, 1H), 7.62 (d, J = 7.4 Hz, 1H), 7.53 (t, J = 7.6 Hz, 1H), 7.29 (s, 1H), 6.49 (d, J = 6.2 Hz, 1H), 3.97 (m, 2H), 2.69 (d, J = 1.3 Hz, 3H), 1.71 (d, J = 35.6 Hz, 4H), 0.79 (d, J = 1.3 Hz, 9H). |
| 454 | 1H NMR (400 MHz, Methanol-d4) δ 8.37 (s, 1H), 7.92 (s, 1H), 7.84-7.70 (m, 2H), 7.09 (m, 1H), 6.87 (m, 1H), 6.19 (s, 1H), 3.96-3.80 (m, 2H), 3.72 (m, 1H), 2.51 (s, 3H), 1.34-0.94 (m, 4H), 0.89 (s, 9H). |
| 455 | 1H NMR (400 MHz, DMSO-d6) δ 9.32 (s, 1H), 8.35 (m, 2H), 8.00 (d, J = 8.0 Hz, 1H), 7.67-7.54 (m, 2H), 7.49 (t, J = 7.7 Hz, 1H), 7.35 (d, J = 12.8 Hz, 1H), 6.94 (s, 1H), 6.44 (d, J = 6.1 Hz, 1H), 3.89 (dd, J = 13.7, 7.8 Hz, 1H), 3.43 (dd, J = 13.7, 5.4 Hz, 1H), 1.72 (m, 2H), 1.64 (m, 2H), 0.77 (s, 9H). |
| 456 | 1H NMR (400 MHz, DMSO-d6) δ 11.05 (s, 1H), 9.34 (d, J = 1.4 Hz, 1H), 8.07 (s, 1H), 8.01 (d, J = 8.2 Hz, 1H), 7.61 (s, 2H), 7.58-7.52 (m, 1H), 7.36 (s, 3H), 7.25 (s, 1H), 6.01 (d, J = 13.4 Hz, 1H), 3.94 (s, 1H), 1.13 (s, 13H). |
| 458 | 1H NMR (400 MHz, Methanol-d4) δ 9.21 (s, 1H), 8.48 (s, 1H), 8.05 (dd, J = 7.9, 1.4 Hz, 1H), 7.86 (s, 1H), 7.73 (d, J = 2.3 Hz, 1H), 7.60 (dt, J = 15.3, 7.3 Hz, 2H), 7.01 (d, J = 2.3 Hz, 1H), 6.37 (s, 1H), 4.21 (d, J = 13.9 Hz, 1H), 3.74 (d, J = 1.8 Hz, 2H), 3.57 (d, J = 13.9 Hz, 1H), 1.34-1.25 (m, 2H), 1.21-1.13 (m, 2H), 0.86 (s, 9H). |
| 459 | 1H NMR (400 MHz, Methanol-d4) δ 9.18 (s, 1H), 8.48 (s, 1H), 7.96 (s, 1H), 7.82 (d, J = 8.3 Hz, 1H), 7.65 (d, J = 2.2 Hz, 1H), 7.53 (t, J = 7.9 Hz, 1H), 7.42 (d, J = 7.6 Hz, 1H), 7.01 (d, J = 2.3 Hz, 1H), 6.84 (s, 1H), 4.22 (s, 3H), 3.95-3.85 (m, 1H), 3.89 (s, 2H), 1.27-1.10 (m, 4H), 0.84 (s, 9H). |
| 460 | 1H NMR (400 MHz, Methanol-d4) δ 9.21 (s, 1H), 8.33 (s, 1H), 8.06 (dd, J = 7.6, 1.5 Hz, 1H), 7.90 (s, 1H), 7.88 (d, J = 2.5 Hz, 1H), 7.67-7.55 (m, 2H), 7.19 (d, J = 2.5 Hz, 1H), 6.42 (s, 1H), 5.26 (qd, J = 8.7, 2.5 Hz, 2H), 3.99 (d, J = 13.7 Hz, 1H), 3.46 (d, J = 13.7 Hz, 1H), 0.80 (s, 9H). |

TABLE 2-continued

| Compound | ¹H-NMR |
|---|---|
| 461 | 1H NMR (400 MHz, Methanol-d4) δ 8.99 (s, 1H), 8.77 (m, 1H), 8.47 (s, 1H), 8.16-8.05 (m, 2H), 7.87-7.78 (m, 1H), 7.78-7.66 (m, 3H), 6.97-6.88 (m, 2H), 4.00 (d, J = 13.9 Hz, 1H), 3.62 (d, J = 13.9 Hz, 1H), 1.76-1.58 (m, 4H), 0.70 (s, 9H). |
| 462 | 1H NMR (400 MHz, Methanol-d4) δ 8.48 m, 3H), 8.23 (m, 1H), 8.11 (m, 1H), 7.96 m, 1H), 7.63 (m, 1H), 7.50 (m, 1H), 7.43 (s, 1H), 7.27 m, 1H), 6.45 (s, 1H), 4.08 (d, J = 14.0 Hz, 1H), 3.83 (d, J = 14.0 Hz, 1H), 1.31-1.08 (m, 4H), 0.98 (s, 9H). |
| 463 | 1H NMR (400 MHz, Methanol-d4) δ 9.21 (s, 1H), 8.49 (s, 1H), 8.06 (dd, J = 8.0, 1.3 Hz, 1H), 7.87 (s, 1H), 7.73 (d, J = 2.3 Hz, 1H), 7.67-7.54 (m, 2H), 7.02 (d, J = 2.3 Hz, 1H), 6.41 (s, 1H), 4.22 (d, J = 13.9 Hz, 1H), 3.59 (d, J = 13.9 Hz, 1H), 2.98-2.86 (m, 2H), 2.86-2.73 (m, 2H), 2.13-1.96 (m, 2H), 0.86 (s, 9H). |
| 464 | 1H NMR (400 MHz, Methanol-d4) δ 9.22 (s, 1H), 8.59 (d, J = 6.0 Hz, 2H), 8.30 (s, 1H), 8.12 (s, 1H), 8.06 (dd, J = 8.1, 1.1 Hz, 1H), 7.85 (d, J = 2.5 Hz, 1H), 7.69 (d, J = 7.4 Hz, 1H), 7.61 (dd, J = 8.1, 7.5 Hz, 1H), 7.18 (d, J = 2.5 Hz, 1H), 7.14 (d, J = 6.1 Hz, 2H), 6.45 (s, 1H), 3.94 (d, J = 13.7 Hz, 1H), 3.41 (d, J = 13.7 Hz, 1H), 2.17-1.94 (m, 4H), 0.79 (s, 9H). |
| 465 | 1H NMR (400 MHz, Methanol-d4) δ 9.21 (s, 1H), 8.34 (s, 1H), 8.08-8.01 (m, 1H), 7.88 (s, 1H), 7.87 (d, J = 2.4 Hz, 1H), 7.67-7.62 (m, 1H), 7.62-7.55 (m, 1H), 7.18 (d, J = 2.5 Hz, 1H), 6.37 (s, 1H), 4.01 (d, J = 13.7 Hz, 2H), 3.74 (d, J = 1.9 Hz, 2H), 3.46 (d, J = 13.8 Hz, 1H), 1.32-1.27 (m, 2H), 1.22-1.14 (m, 2H), 0.81 (s, 9H). |
| 466 | 1H NMR (400 MHz, Methanol-d4) δ 9.60 (s, 1H), 9.53 (s, 1H), 8.76 (d, J = 6.1 Hz, 1H), 8.72 (s, 1H), 8.51 (s, 1H), 8.01 (d, J = 6.2 Hz, 1H), 7.96 (s, 1H), 7.70 (d, J = 2.3 Hz, 1H), 7.01 (d, J = 2.3 Hz, 1H), 6.76 (s, 1H), 4.02 (d, J = 13.9 Hz, 1H), 3.96-3.76 (m, 1H), 3.70 (d, J = 13.9 Hz, 1H), 1.24-1.11 (m, 4H), 0.76 (s, 9H). |
| 467 | 1H NMR (400 MHz, Acetonitrile-d3) δ 9.08 (d, J = 4.6 Hz, 1H), 8.97 (d, J = 8.6 Hz, 1H), 8.36 (s, 1H), 8.24 (d, J = 8.2 Hz, 1H), 7.87 (s, 1H), 7.83-7.70 (m, 2H), 7.65 (s, 1H), 6.90 (d, J = 2.5 Hz, 1H), 6.77 (s, 1H), 5.74 (s, 1H), 3.65 (dd, J = 13.3, 6.8 Hz, 1H), 3.48 (dd, J = 13.5, 5.3 Hz, 1H), 1.29 (s, 1H), 1.10 (m, 4H), 0.68 (s, 9H). |
| 468 | 1H NMR (400 MHz, Acetonitrile-d3) δ 8.35 (s, 1H), 8.10 (s, 2H), 7.96 (s, 1H), 7.88 (s, 1H), 7.76 (s, 1H), 6.94 (s, 1H), 6.88 (s, 1H), 5.93 (s, 1H), 3.84-3.71 (m, 2H), 3.39 (d, J = 13.9 Hz, 1H), 1.21-0.98 (m, 4H), 0.65 (s, 9H). |
| 469 | 1H NMR (400 MHz, Methanol-d4) δ 9.11 (s, 1H), 9.04 (d, J = 8.7 Hz, 1H), 8.30 (s, 1H), 8.21 (s, 1H), 8.18-8.10 (m, 1H), 7.99-7.90 (m, 1H), 7.90-7.82 (m, 2H), 7.80 (s, 1H), 7.14-7.08 (m, 1H), 6.94 (s, 1H), 3.79 (d, J = 13.8 Hz, 1H), 3.48 (d, J = 13.8 Hz, 1H), 1.75-1.56 (m, 4H), 0.66 (s, 9H). |
| 470 | 1H NMR (400 MHz, Methanol-d4) δ 8.30 (d, J = 7.5 Hz, 2H), 8.19 (d, J = 8.0 Hz, 1H), 8.06 (t, J = 7.7 Hz, 1H), 8.00 (d, J = 7.3 Hz, 1H), 7.81 (d, J = 2.4 Hz, 1H), 7.15 (s, 1H), 7.00 (s, 1H), 3.82 (d, J = 13.7 Hz, 1H), 3.48 (d, J = 13.8 Hz, 1H), 1.82-1.53 (m, 4H), 0.68 (s, 9H). |
| 471 | 1H NMR (400 MHz, Methanol-d4) δ 8.33 (s, 1H), 8.20 (s, 1H), 7.84-7.74 (m, 3H), 7.11-7.06 (m, 1H), 6.91-6.84 (m, 1H), 6.25 (s, 1H), 3.85 (d, J = 13.8 Hz, 1H), 3.66 (d, J = 13.8 Hz, 1H), 2.51 (s, 3H), 1.80-1.65 (m, 4H), 0.88 (s, 9H). |
| 472 | 1H NMR (400 MHz, Methanol-d4) δ 8.30 (s, 1H), 8.16 (s, 1H), 8.04 (s, 1H), 7.82 (d, J = 2.5 Hz, 1H), 7.51 (d, J = 8.4 Hz, 1H), 7.40-7.31 (m, 1H), 7.26 (d, J = 7.1 Hz, 1H), 7.18 (d, J = 2.5 Hz, 1H), 6.50 (s, 1H), 3.88 (d, J = 13.6 Hz, 1H), 3.51 (d, J = 13.7 Hz, 1H), 1.79-1.54 (m, 4H), 0.79 (s, 9H). |
| 473 | 1H NMR (400 MHz, Methanol-d4) δ 8.36 (s, 1H), 8.05 (s, 1H), 7.84-7.75 (m, 2H), 7.10 (d, J = 2.5 Hz, 1H), 6.87 (dd, J = 8.4, 2.7 Hz, 1H), 6.24 (s, 1H), 5.94 (t, J = 54.7 Hz, 1H), 3.88 (d, J = 13.8 Hz, 1H), 3.68 (d, J = 13.8 Hz, 1H), 2.51 (s, 3H), 1.53 (s, 4H), 0.89 (s, 9H). |
| 474 | 1H NMR (400 MHz, Methanol-d4) δ 8.86 (s, 1H), 7.96 (s, 1H), 7.72 (s, 1H), 7.70 (d, 1H), 7.55 (d, J = 2.6 Hz, 1H), 7.33 (d, J = 7.3 Hz, 1H), 7.25 (t, J = 7.7 Hz, 1H), 6.69 (d, J = 2.6 Hz, 1H), 6.09 (s, 1H), 3.96 (dd, J = 11.1, 4.9 Hz, 1H), 3.68-3.60 (m, 1H), 3.23-3.12 (m, 1H), 3.03 (d, J = 11.5 Hz, 1H), 2.96 (p, J = 1.7 Hz, 21H), 2.77 (d, J = 11.5 Hz, 1H), 1.64-1.47 (m, 2H), 1.40-1.21 (m, 4H), 0.29 (s, 3H), 0.00 (s, 3H). |
| 475 | 1H NMR (400 MHz, Methanol-d4) δ 9.24 (s, 1H), 8.36 (s, 1H), 8.21 (s, 1H), 8.10 (d, J = 8.3 Hz, 1H), 7.79 (d, J = 2.5 Hz, 1H), 7.63 (t, J = 7.8 Hz, 1H), 7.49 (d, J = 7.4 Hz, 1H), 7.26 (d, J = 2.6 Hz, 1H), 6.48 (s, 1H), 4.56-4.47 (m, 1H), 3.95 (d, J = 11.4 Hz, 1H), 3.50 (d, J = 11.5 Hz, 2H), 3.22 (d, J = 11.7 Hz, 1H), 1.86-1.77 (m, 2H), 1.76-1.59 (m, 4H), 1.01 (s, 3H), 0.78 (s, 3H). |
| 476 | 1H NMR (400 MHz, Methanol-d4) δ 8.51 (s, 1H), 8.23 (s, 1H), 7.78 (t, J = 8.1 Hz, 1H), 7.64 (d, J = 2.2 Hz, 1H), 6.93 (d, J = 2.3 Hz, 1H), 6.88 (dd, J = 8.3, 2.8 Hz, 1H), 6.24 (s, 1H), 4.01 (d, J = 13.9 Hz, 1H), 3.85 (d, J = 13.9 Hz, 1H), 2.52 (s, 3H), 2.04-1.97 (m, 2H), 1.97-1.91 (m, 2H), 0.94 (s, 9H). |
| 477 | 1H NMR (400 MHz, Methanol-d4) δ 8.51 (s, 1H), 8.05 (s, 1H), 7.87 (t, J = 8.1 Hz, 1H), 7.61 (d, J = 2.2 Hz, 1H), 6.89 (d, J = 2.4 Hz, 1H), 6.86 (d, J = 2.7 Hz, 1H), 6.20 (s, 1H), 4.11 (d, J = 13.9 Hz, 1H), 3.76 (d, J = 13.9 Hz, 1H), 2.52 (s, 3H), 1.89-1.80 (m, 2H), 1.66-1.59 (m, 2H), 0.94 (s, 9H). |
| 478 | 1H NMR (400 MHz, Methanol-d4) δ 8.52 (s, 1H), 7.95 (s, 1H), 7.81 (t, J = 8.1 Hz, 1H), 7.64 (d, J = 2.2 Hz, 1H), 6.92 (d, J = 2.3 Hz, 1H), 6.87 (dd, J = 8.6, 2.7 Hz, 1H), 6.23 (s, 1H), 4.08 (d, J = 13.9 Hz, 1H), 3.82 (d, J = 13.9 Hz, 1H), 3.00-2.90 (m, 1H), 2.90-2.80 (m, 1H), 2.51 (s, 3H), 2.16-1.98 (m, 1H), 0.94 (s, 9H). |

TABLE 2-continued

| Compound | ¹H-NMR |
|---|---|
| 479 | 1H NMR (400 MHz, Methanol-d4) δ 8.52 (s, 1H), 8.22 (s, 1H), 7.80 (t, J = 8.1 Hz, 1H), 7.65 (d, J = 2.3 Hz, 1H), 6.95 (d, J = 2.3 Hz, 1H), 6.89 (dd, J = 8.4, 2.8 Hz, 1H), 6.27 (s, 1H), 4.02 (d, J = 13.9 Hz, 1H), 3.87 (d, J = 13.9 Hz, 1H), 3.09-2.95 (m, 3H), 2.53 (s, 3H), 2.33 (m, 1H), 2.24-2.10 (m, 1H), 0.94 (s, 9H). |
| 480 | 1H NMR (400 MHz, Methanol-d4) δ 8.49 (s, 1H), 7.96 (s, 1H), 7.77 (t, J = 8.1 Hz, 1H), 7.62 (d, J = 2.2 Hz, 1H), 6.88 (d, J = 2.3 Hz, 2H), 6.86 (d, J = 2.8 Hz, 1H), 6.18 (s, 1H), 4.01 (d, J = 13.9 Hz, 1H), 3.83 (d, J = 13.9 Hz, 1H), 2.50 (s, 3H), 1.66 (s, 3H), 1.35-1.29 (m, 2H), 1.09-1.03 (m, 2H), 0.93 (s, 9H). |
| 481 | 1H NMR (400 MHz, DMSO-d6) δ 9.31 (s, 1H), 8.38 (s, 1H), 8.11-7.92 (m, 2H), 7.78 (s, 1H), 7.64 (dd, J = 12.6, 6.8 Hz, 2H), 7.55-7.28 (m, 4H), 6.95 (s, 1H), 6.43 (d, J = 5.8 Hz, 1H), 3.97 (dd, J = 13.4, 8.5 Hz, 1H), 3.38 (d, J = 13.7, 5.2 Hz, 1H), 2.90-2.71 (m, 2H), 2.73-2.57 (m, 2H), 1.87 (q, J = 8.3 Hz, 2H), 0.78 (s, 9H). |
| 482 | 1H NMR (400 MHz, Acetonitrile-d3) δ 8.45 (s, 1H), 7.85 (t, J = 8.2 Hz, 1H), 7.79 (s, 1H), 7.50 (d, J = 2.3 Hz, 1H), 6.87-6.80 (m, 2H), 6.15 (s, 1H), 3.90 (dd, J = 13.5, 6.2 Hz, 1H), 3.81 (dd, J = 13.5, 5.6 Hz, 1H), 3.72 (s, 2H), 2.52 (s, 3H), 1.29 (s, 1H), 1.19-1.13 (m, 2H), 0.96 (s, 9H). |
| 483 | 1H NMR (400 MHz, Methanol-d4) δ 9.13 (s, 1H), 8.49 (s, 1H), 8.25 (s, 1H), 7.82 (d, J = 8.1 Hz, 1H), 7.67 (d, J = 2.3 Hz, 1H), 7.52 (t, J = 7.9 Hz, 1H), 7.40 (d, J = 7.7 Hz, 1H), 7.02 (d, J = 2.3 Hz, 1H), 6.89 (s, 1H), 4.22 (s, 3H), 3.89 (d, J = 2.5 Hz, 2H), 1.82-1.66 (m, 4H), 0.85 (s, 9H). |
| 484 | 1H NMR (400 MHz, Methanol-d4) δ 9.29 (s, 1H), 8.31 (d, J = 0.6 Hz, 1H), 8.28 (s, 1H), 7.83 (d, J = 8.2 Hz, 1H), 7.78 (d, J = 2.4 Hz, 1H), 7.57 (t, J = 7.9 Hz, 1H), 7.44 (d, J = 7.8 Hz, 1H), 7.20 (d, J = 2.5 Hz, 1H), 6.89 (s, 1H), 4.27 (s, 3H), 3.72 (q, J = 13.9 Hz, 2H), 1.81-1.65 (m, 4H), 0.81 (s, 9H). |
| 485 | 1H NMR (400 MHz, Methanol-d4) δ 8.56 (s, 1H), 8.23 (s, 1H), 7.79 (t, J = 8.1 Hz, 1H), 7.32 (dd, J = 12.3, 2.2 Hz, 1H), 6.95-6.75 (m, 2H), 6.24 (s, 1H), 4.02 (d, J = 13.9 Hz, 1H), 3.87 (d, J = 13.9 Hz, 1H), 2.51 (s, 3H), 2.04-1.88 (m, 4H), 0.95 (s, 9H). |
| 486 | 1H NMR (400 MHz, Methanol-d4) δ 8.54 (s, 1H), 8.05 (s, 1H), 7.87 (t, J = 8.1 Hz, 1H), 7.29 (dd, J = 12.5, 2.1 Hz, 1H), 6.92-6.82 (m, 1H), 6.78 (d, J = 2.1 Hz, 1H), 6.20 (s, 1H), 4.10 (d, J = 13.9 Hz, 1H), 3.76 (d, J = 13.9 Hz, 1H), 2.52 (s, 3H), 1.88-1.77 (m, 2H), 1.62 (td, J = 4.2, 1.9 Hz, 2H), 0.94 (s, 9H). |
| 487 | 1H NMR (400 MHz, DMSO-d6) δ 8.39 (s, 1H), 8.01 (s, 1H), 7.81 (m, 2H), 7.50-7.22 (m, 4H), 6.92 (dd, J = 8.5, 3.0 Hz, 1H), 6.82 (d, J = 2.1 Hz, 1H), 6.22 (d, J = 6.1 Hz, 1H), 3.94 (dd, J = 13.8, 8.0 Hz, 1H), 3.43 (dd, J = 13.7, 5.1 Hz, 1H), 2.88-2.74 (m, 1H), 2.68 (dd, J = 18.4, 8.4 Hz, 2H), 2.46 (s, 3H), 1.99-1.76 (m, 2H), 0.81 (s, 9H). |
| 488 | 1H NMR (400 MHz, DMSO-d6) δ 8.35 (s, 1H), 8.06 (s, 1H), 7.77 (t, J = 8.3 Hz, 1H), 7.65 (s, 1H), 7.38 (d, J = 7.1 Hz, 1H), 7.25 (d, J = 12.3 Hz, 1H), 6.91 (dd, J = 8.5, 3.0 Hz, 1H), 6.83-6.71 (m, 1H), 6.17 (d, J = 6.0 Hz, 1H), 3.95-3.82 (m, 1H), 3.45 (dd, J = 13.8, 5.2 Hz, 1H), 2.42 (s, 3H), 1.60 (s, 3H), 1.32-1.18 (m, 2H), 1.06-0.94 (m, 2H), 0.80 (s, 9H). |
| 489 | 1H NMR (400 MHz, Methanol-d4) δ 8.37 (s, 1H), 8.23 (s, 1H), 7.83-7.75 (m, 2H), 7.10 (d, J = 2.6 Hz, 1H), 6.87 (dd, J = 8.5, 2.8 Hz, 1H), 6.24 (s, 1H), 3.87 (d, J = 13.8 Hz, 1H), 3.71 (d, J = 13.8 Hz, 1H), 2.52 (s, 3H), 2.04-1.96 (m, 2H), 1.94 (m, 2H), 0.90 (s, 9H). |
| 490 | 1H NMR (400 MHz, Methanol-d4) δ 8.35 (s, 1H), 8.07 (s, 1H), 7.89 (t, J = 8.1 Hz, 1H), 7.75 (d, J = 2.5 Hz, 1H), 7.04 (d, J = 2.5 Hz, 1H), 6.85 (m, 1H), 6.20 (s, 1H), 3.94 (d, J = 13.8 Hz, 1H), 3.59 (d, J = 13.8 Hz, 1H), 2.53 (s, 3H), 1.83 (m, 2H), 1.62 (m, 2H), 0.89 (s, 9H). |
| 491 | 1H NMR (400 MHz, Methanol-d4) δ 8.37 (s, 1H), 8.23 (s, 1H), 7.86-7.76 (m, 2H), 7.11 (d, J = 2.5 Hz, 1H), 6.88 (dd, J = 8.5, 2.8 Hz, 1H), 6.27 (s, 1H), 3.86 (d, J = 13.8 Hz, 1H), 3.72 (d, J = 13.8 Hz, 1H), 3.10-2.91 (m, 3H), 2.54 (s, 3H), 2.33 (m, 1H), 2.21-2.12 (m, 1H), 0.90 (s, 9H). |
| 492 | 1H NMR (400 MHz, Methanol-d4) δ 8.37 (s, 1H), 7.97 (s, 1H), 7.83-7.74 (m, 2H), 7.08 (d, J = 2.5 Hz, 1H), 6.87 (dd, J = 8.6, 2.8 Hz, 1H), 6.19 (s, 1H), 3.87 (d, J = 13.9 Hz, 1H), 3.71 (d, J = 13.8 Hz, 1H), 2.50 (s, 3H), 1.66 (s, 3H), 1.35-1.28 (m, 2H), 1.10-1.01 (m, 2H), 0.89 (s, 9H). |
| 493 | 1H NMR (400 MHz, Methanol-d4) δ 8.37 (dd, J = 4.5, 1.9 Hz, 1H), 8.21 (s, 1H), 8.20 (s, 1H), 8.17 (dd, J = 9.1, 1.9 Hz, 1H), 7.99 (s, 1H), 7.53 (d, J = 2.4 Hz, 1H), 7.14 (dd, J = 9.1, 4.4 Hz, 1H), 7.01 (d, J = 2.4 Hz, 1H), 6.45 (s, 1H), 3.77 (d, J = 13.8 Hz, 1H), 3.66 (d, J = 13.8 Hz, 1H), 1.78-1.61 (m, 4H), 0.87 (s, 9H). |
| 494 | 1H NMR (400 MHz, Methanol-d4) δ 8.38 (s, 1H), 7.96 (s, 1H), 7.83 (t, J = 8.1 Hz, 1H), 7.78 (d, J = 2.0 Hz, 1H), 7.10 (s, 1H), 6.91-6.81 (m, 1H), 6.23 (s, 1H), 3.93 (d, J = 13.8 Hz, 1H), 3.67 (d, J = 13.8 Hz, 1H), 2.94 (m, 2H), 2.90-2.78 (m, 1H), 2.52 (s, 3H), 2.17-1.99 (m, 2H), 0.90 (s, 9H). |
| 495 | 1H NMR (400 MHz, DMSO-d6) δ 8.49 (s, 1H), 8.22 (s, 1H), 8.14 (s, 1H), 7.80 (t, J = 8.3 Hz, 1H), 7.67 (d, J = 2.1 Hz, 1H), 7.57 (s, 1H), 7.07-6.90 (m, 2H), 6.25 (s, 1H), 4.75 (s, 1H), 4.62 (s, 1H), 3.99 (dd, J = 13.8, 7.9 Hz, 1H), 3.51 (dd, J = 13.8, 5.3 Hz, 1H), 2.45 (s, 3H), 1.42 (dd, J = 8.2, 4.5 Hz, 2H), 1.33 (s, 2H), 0.82 (s, 9H).; 1H NMR (400 MHz, DMSO-d6) δ 8.33 (s, 1H), 8.13 (s, 1H), 7.80 (t, J = 8.3 Hz, 1H), 7.61 (d, J = 2.2 Hz, 1H), 7.47 (s, 1H), 7.36 (d, J = 7.4 Hz, 1H), 6.94 (dd, J = 8.5, 3.0 Hz, 1H), 6.91 (s, 1H), 6.23 (d, J = 6.7 Hz, 1H), 4.75 (s, 1H), 4.63 (s, 1H), 3.88 (dd, J = 13.8, 8.1 Hz, 1H), 3.40 (dd, J = 14.0, 4.8 Hz, 1H), 2.44 (s, 3H), 1.42 (s, 2H), 1.33 (s, 2H), 0.79 (d, J = 1.1 Hz, 9H). |
| 496 | 1H NMR (400 MHz, Methanol-d4) δ 8.47 (s, 1H), 8.09 (d, J = 1.0 Hz, 1H), 7.89 (s, 1H), 7.70 (d, J = 2.2 Hz, 1H), 7.56-7.49 (m, 1H), 7.39 (dd, J = 8.5, 7.1 Hz, |

TABLE 2-continued

| Compound | ¹H-NMR |
|---|---|
| | 1H), 7.28 (d, J = 7.1 Hz, 1H), 7.06 (d, J = 2.3 Hz, 1H), 6.48 (s, 1H), 5.91 (t, J = 54.7 Hz, 1H), 4.15 (d, J = 13.9 Hz, 1H), 4.05 (s, 3H), 3.64 (d, J = 13.9 Hz, 1H), 1.48 (d, J = 9.0 Hz, 4H), 0.85 (s, 9H). |
| 497 | 1H NMR (400 MHz, Methanol-d4) δ 8.47 (s, 1H), 8.25 (s, 1H), 7.91 (s, 1H), 7.69 (d, J = 2.3 Hz, 1H), 7.58-7.51 (m, 1H), 7.25 (dd, J = 8.5, 6.9 Hz, 1H), 7.20 (d, J = 6.6 Hz, 1H), 7.04 (d, J = 2.3 Hz, 1H), 6.37 (s, 1H), 5.92 (t, J = 54.7 Hz, 1H), 4.17 (s, 3H), 4.16 (d, J = 13.8 Hz, 1H), 3.63 (d, J = 13.8 Hz, 1H), 1.52-1.45 (m, 4H), 0.85 (s, 9H). |
| 498 | 1H NMR (400 MHz, Methanol-d4) δ 8.47 (s, 1H), 7.96 (s, 1H), 7.66 (d, J = 2.2 Hz, 1H), 7.64-7.59 (m, 1H), 7.56 (t, J = 7.5 Hz, 1H), 7.53-7.48 (m, 1H), 7.34 (d, J = 2.3 Hz, 1H), 7.22 (s, 1H), 5.93 (t, J = 54.8 Hz, 1H), 4.49 (d, J = 3.6 Hz, 2H), 4.05 (d, J = 14.0 Hz, 1H), 3.93 (d, J = 14.0 Hz, 1H), 3.20 (s, 3H), 1.51 (s, 4H), 1.01 (s, 9H). |
| 499 | 1H NMR (400 MHz, Methanol-d4) δ 9.05 (s, 1H), 8.46 (s, 1H), 8.08 (s, 1H), 7.80 (d, J = 7.9 Hz, 1H), 7.65 (d, J = 2.3 Hz, 1H), 7.50 (t, J = 7.9 Hz, 1H), 7.39 (d, J = 7.6 Hz, 1H), 6.99 (d, J = 2.3 Hz, 1H), 6.86 (s, 1H), 5.93 (t, J = 54.6 Hz, 1H), 4.20 (s, 3H), 3.86 (d, J = 1.7 Hz, 2H), 1.54 (s, 4H), 0.84 (s, 9H). |
| 500 | 1H NMR (400 MHz, Methanol-d4) δ 8.47 (s, 1H), 8.13 (d, J = 1.0 Hz, 1H), 7.88 (s, 1H), 7.71 (d, J = 2.3 Hz, 1H), 7.52 (d, J = 8.4 Hz, 1H), 7.35 (dd, J = 8.4, 7.0 Hz, 1H), 7.25 (d, J = 7.0 Hz, 1H), 7.06 (d, J = 2.3 Hz, 1H), 6.49 (s, 1H), 5.91 (t, J = 54.7 Hz, 1H), 4.15 (d, J = 13.9 Hz, 1H), 3.66 (d, J = 13.8 Hz, 1H), 1.61-1.37 (m, 4H), 0.86 (s, 9H). |
| 501 | 1H NMR (400 MHz, Methanol-d4) δ 8.50 (s, 1H), 8.05 (s, 1H), 7.78 (t, J = 8.1 Hz, 1H), 7.64 (d, J = 2.3 Hz, 1H), 6.93 (d, J = 2.3 Hz, 1H), 6.87 (dd, J = 8.4, 2.7 Hz, 1H), 6.23 (s, 1H), 5.94 (t, J = 54.7 Hz, 1H), 2.50 (s, 3H), 1.53 (s, 4H), 0.93 (s, 9H). |
| 502 | 1H NMR (400 MHz, Methanol-d4) δ 8.50 (s, 1H), 8.05 (s, 1H), 7.79 (t, J = 8.1 Hz, 1H), 7.64 (d, J = 2.3 Hz, 1H), 6.98 (d, J = 2.3 Hz, 1H), 6.87 (dd, J = 8.4, 2.8 Hz, 1H), 6.25 (s, 1H), 5.94 (t, J = 54.7 Hz, 1H), 4.12 (d, J = 14.2 Hz, 1H), 3.90 (d, J = 14.3 Hz, 1H), 2.50 (s, 3H), 2.03-1.90 (m, 1H), 1.76-1.66 (m, 3H), 1.54 (s, 4H), 1.19 (s, 3H). |
| 503 | 1H NMR (400 MHz, DMSO-d6) δ 8.33 (s, 1H), 8.14 (s, 1H), 7.87-7.74 (m, 2H), 7.49-7.38 (m, 2H), 7.20 (d, J = 2.5 Hz, 1H), 6.93 (dd, J = 8.3, 3.1 Hz, 1H), 6.24 (d, J = 7.2 Hz, 1H), 4.74 (s, 1H), 4.62 (s, 1H), 3.85 (dd, J = 13.8, 8.1 Hz, 1H), 3.40 (dd, J = 13.8, 5.1 Hz, 1H), 2.44 (s, 3H), 1.42 (s, 2H), 1.33 (s, 2H), 0.79 (s, 9H). |
| 504 | 1H NMR (400 MHz, Acetonitrile-d3) δ 10.01 (s, 1H), 8.60 (d, J = 6.3 Hz, 1H), 8.41 (s, 1H), 8.30 (d, J = 6.3 Hz, 1H), 8.13 (d, J = 7.9 Hz, 1H), 8.07-7.96 (m, 2H), 7.83 (s, 1H), 7.58 (d, J = 2.2 Hz, 1H), 6.89 (s, 1H), 6.81 (d, J = 2.3 Hz, 1H), 3.95-3.75 (m, 2H), 3.51 (d, J = 13.3 Hz, 1H), 1.17-1.07 (m, 4H), 0.69 (s, 9H). |
| 505 | 1H NMR (400 MHz, Acetonitrile-d3) δ 8.46 (s, 1H), 8.18 (m, 1H), 8.04-7.96 (m, 1H), 7.97 (s, 1H), 7.57 (d, J = 2.3 Hz, 1H), 7.33-7.22 (m, 2H), 6.96 (d, J = 2.3 Hz, 1H), 6.29 (s, 1H), 5.89 (t, J = 54.6 Hz, 1H), 3.98 (dd, J = 13.9, 6.3 Hz, 1H), 3.78 (dd, J = 13.8, 5.3 Hz, 1H), 1.52 (d, J = 1.2 Hz, 4H), 0.97 (s, 9H). |
| 506 | 1H NMR (400 MHz, Acetonitrile-d3) δ 8.88 (s, 1H), 8.64 (d, J = 5.2 Hz, 1H), 8.42 (s, 1H), 8.25 (d, J = 8.2 Hz, 1H), 7.97 (s, 1H), 7.70-7.62 (m, 1H), 7.55 (d, J = 2.3 Hz, 1H), 6.98 (d, J = 2.3 Hz, 1H), 6.28 (s, 1H), 6.04-5.74 (m, 1H), 3.93 (m, 1H), 3.71 m, 1H), 1.52 (s, 4H), 0.96 (s, 9H). |
| 507 | 1H NMR (400 MHz, Acetonitrile-d3) δ 8.68 (dd, J = 5.8, 1.5 Hz, 1H), 8.46 (s, 1H), 8.41 (dd, J = 8.1, 1.5 Hz, 1H), 7.97 (s, 1H), 7.74 (dd, J = 8.1, 5.8 Hz, 1H), 7.51 (d, J = 2.3 Hz, 1H), 7.38 (s, 1H), 7.00 (d, J = 2.4 Hz, 1H), 6.40 (s, 1H), 5.89 (t, J = 54.6 Hz, 1H), 3.95-3.79 (m, 2H), 2.79 (s, 3H), 1.53 (d, J = 2.8 Hz, 4H), 0.96 (s, 9H). |
| 508 | 1H NMR (400 MHz, Acetonitrile-d3) δ 9.07 (d, J = 4.8 Hz, 1H), 8.94 (d, J = 8.6 Hz, 1H), 8.44 (m, 1H), 8.27-8.20 (m, 1H), 7.92-7.81 (m, 3H), 7.76 (m, 1H), 7.56 (m, 1H), 6.85-6.76 (m, 2H), 6.67 (s, 1H), 5.85 (t, J = 54.6 Hz, 1H), 3.81 (m, 1H), 3.60 (m, 1H), 1.48 (m, 4H), 0.72 (s, 9H). |
| 509 | 1H NMR (400 MHz, Chloroform-d) δ 8.42 (s, 1H), 7.93 (t, J = 8.1 Hz, 1H), 7.42-7.35 (m, 2H), 6.78 (m, 1H), 6.16 (s, 1H), 5.92 (d, J = 3.1 Hz, 1H), 5.90 (t, J = 55.9 Hz, 1H), 5.51 (d, J = 3.1 Hz, 1H), 5.29 (s, 2H), 4.99 (s, 1H), 3.55 (m, 2H), 2.57 (s, 3H), 1.53-1.50 (m, 4H), 0.92 (s, 9H). |
| 510 | 1H NMR (400 MHz, Acetonitrile-d3) δ 8.43 (s, 1H), 8.36 (m, 1H), 7.94 (s, 1H), 7.97-7.90 (m, 1H), 7.51 (m, 1H), 7.36 (m, 1H), 6.80 (m, 1H), 3.82 (m, 1H), 1.52 (s, 4H), 0.98 (s, 9H). |
| 511 | 1H NMR (400 MHz, DMSO-d6) δ 8.35 (d, J = 1.2 Hz, 1H), 8.19-8.13 (m, 1H), 7.82 (dt, J = 15.9, 8.2 Hz, 1H), 7.61 (dd, J = 26.8, 2.1 Hz, 1H), 7.43-7.28 (m, 1H), 7.09 (s, 1H), 7.02-6.87 (m, 2H), 6.34 (dd, J = 25.4, 7.3 Hz, 1H), 6.29-5.98 (m, 1H), 4.68 (d, J = 18.2 Hz, 1H), 3.92 (s, 1H), 3.78 (d, J = 6.9 Hz, 1H), 2.45 (s, 3H), 2.50 (m, 2H), 1.50 (d, J = 4.5 Hz, 4H), 1.22 (d, J = 1.2 Hz, 3H), 1.14 (d, J = 1.2 Hz, 3H), 1.09-1.06 (m, 3H), 0.80 (s, 3H). |
| 512 | 1H NMR (400 MHz, DMSO-d6) δ 8.36 (s, 1H), 8.18 (s, 1H), 7.82 (t, J = 8.2 Hz, 1H), 7.63 (dd, J = 2.3, 1.0 Hz, 1H), 7.50-7.34 (m, 2H), 7.00-6.90 (m, 2H), 6.29-5.97 (m, 2H), 3.92 (dd, J = 14.0, 7.9 Hz, 1H), 3.59 (d, J = 14.0, 4.9 Hz, 1H), 2.47 (s, 2H), 2.45 (s, 3H), 1.51 (s, 4H), 0.90 (d, J = 8.0 Hz, 6H). |
| 513 | 1H NMR (400 MHz, Methanol-d4) δ 8.56 (d, J = 1.9 Hz, 1H), 8.20 (d, J = 1.7 Hz, 1H), 7.79 (t, J = 8.1 Hz, 1H), 7.34 (ddd, J = 12.3, 2.3, 1.2 Hz, 1H), 6.95-6.77 (m, 2H), 6.25 (s, 1H), 4.04 (dd, J = 13.9, 1.3 Hz, 1H), 3.87 (dd, J = 13.9, 2.1 Hz, 1H), 2.50 (s, 3H), 1.83-1.60 (m, 4H), 0.95 (d, J = 1.0 Hz, 9H). |

TABLE 2-continued

| Compound | ¹H-NMR |
|---|---|
| 514 | 1H NMR (400 MHz, Methanol-d4) δ 8.53 (s, 1H), 8.05 (s, 1H), 7.79 (t, J = 8.1 Hz, 1H), 7.32 (dd, J = 12.4, 2.2 Hz, 1H), 6.94-6.75 (m, 2H), 6.23 (s, 1H), 5.94 (t, J = 54.6 Hz, 1H), 4.02 (d, J = 13.9 Hz, 1H), 3.84 (d, J = 13.9 Hz, 1H), 2.50 (s, 3H), 1.54 (s, 4H), 0.94 (s, 9H). |
| 517 | 1H NMR (400 MHz, Methanol-d4) δ 8.50 (s, 1H), 8.03 (s, 1H), 7.80 (t, J = 8.1 Hz, 1H), 7.63 (d, J = 2.3 Hz, 1H), 6.89-6.84 (m, 1H), 6.21 (s, 1H), 4.05 (d, J = 14.0 Hz, 1H), 3.81 (d, J = 13.9 Hz, 1H), 2.51 (s, 3H), 1.90 (m, 2H), 1.77-1.68 (m, 2H), 0.94 (s, 9H). |
| 518 | 1H NMR (400 MHz, DMSO-d6) δ 8.39-8.30 (m, 2H), 8.26 (d, J = 1.1 Hz, 1H), 8.05 (td, J = 8.3, 2.5 Hz, 1H), 7.66-7.57 (m, 2H), 7.47 (s, 1H), 7.20-7.12 (m, 2H), 6.29-5.94 (m, 1H), 4.00 (dd, J = 13.9, 8.0 Hz, 1H), 3.45 (dd, J = 13.8, 5.4 Hz, 1H), 1.51 (s, 4H), 0.87 (d, J = 1.1 Hz, 9H). |
| 519 | 1H NMR (400 MHz, Methanol-d4) δ 8.47 (s, 1H), 8.22 (d, J = 5.0 Hz, 1H), 7.78 (s, 1H), 7.68 (d, J = 2.3 Hz, 1H), 7.39 (d, J = 3.6 Hz, 1H), 7.23 (d, J = 5.1 Hz, 1H), 6.95 (d, J = 2.3 Hz, 1H), 6.60 (d, J = 3.5 Hz, 1H), 6.44 (s, 1H), 4.12 (d, J = 13.8 Hz, 1H), 3.86 (s, 3H), 3.60 (d, J = 13.8 Hz, 1H), 1.24-1.05 (m, 4H), 0.81 (s, 9H). |
| 520 | 1H NMR (400 MHz, Methanol-d4) δ 8.88 (s, 1H), 8.47 (s, 1H), 8.12 (s, 1H), 7.75 (d, J = 8.0 Hz, 1H), 7.68 (d, J = 2.2 Hz, 1H), 7.61-7.47 (m, 2H), 7.15 (d, J = 2.3 Hz, 1H), 6.65 (s, 1H), 4.15 (d, J = 13.9 Hz, 1H), 4.04 (s, 3H), 3.69 (d, J = 14.0 Hz, 1H), 1.79-1.56 (m, 4H), 0.88 (s, 9H). |
| 521 | 1H NMR (400 MHz, Methanol-d4) δ 8.47 (s, 1H), 8.25 (s, 1H), 7.98 (s, 1H), 7.70 (d, J = 2.3 Hz, 1H), 7.69-7.63 (m, 1H), 7.37 (d, J = 6.9 Hz, 1H), 7.10 (d, J = 2.3 Hz, 1H), 7.05 (dd, J = 8.4, 6.9 Hz, 1H), 6.64 (s, 1H), 4.22 (s, 3H), 4.15 (d, J = 13.9 Hz, 1H), 3.68 (d, J = 13.9 Hz, 1H), 1.76-1.52 (m, 4H), 0.83 (s, 9H). |
| 522 | 1H NMR (400 MHz, Methanol-d4) δ 8.49 (s, 1H), 8.17 (s, 1H), 7.98 (dd, J = 5.3, 4.0 Hz, 1H), 7.69 (d, J = 2.3 Hz, 1H), 7.39-7.31 (m, 2H), 6.97 (d, J = 2.4 Hz, 1H), 6.82 (s, 1H), 4.39 (s, 3H), 3.93 (d, J = 13.9 Hz, 1H), 3.78 (d, J = 13.9 Hz, 1H), 1.79-1.63 (m, 4H), 0.78 (s, 9H). |
| 523 | 1H NMR (400 MHz, Methanol-d4) δ 9.25 (s, 1H), 8.31 (s, 1H), 8.12 (s, 1H), 7.82 (d, J = 8.2 Hz, 1H), 7.77 (d, J = 2.5 Hz, 1H), 7.57 (t, J = 8.0 Hz, 1H), 7.46 (d, J = 7.6 Hz, 1H), 7.18 (d, J = 2.5 Hz, 1H), 6.87 (s, 1H), 5.94 (t, J = 54.6 Hz, 1H), 4.26 (s, 3H), 3.71 (d, J = 1.2 Hz, 2H), 1.54 (s, 4H), 0.81 (s, 9H). |
| 524 | 1H NMR (400 MHz, Methanol-d4) δ 8.48 (s, 1H), 7.95 (s, 1H), 7.67 (d, J = 2.2 Hz, 1H), 7.46 (d, J = 8.3 Hz, 1H), 7.28 (dd, J = 8.4, 7.2 Hz, 1H), 6.97 (d, J = 7.1 Hz, 1H), 6.89 (d, J = 2.3 Hz, 1H), 6.70 (s, 1H), 3.96 (d, J = 13.8 Hz, 1H), 3.72 (d, J = 13.8 Hz, 1H), 2.52 (s, 3H), 1.84-1.56 (m, 4H), 0.77 (s, 9H). |
| 525 | 1H NMR (400 MHz, DMSO-d6) δ 8.35 (d, J = 1.4 Hz, 1H), 8.25 (d, J = 1.0 Hz, 1H), 8.07 (s, 1H), 7.80 (s, 1H), 7.68 (d, J = 2.1 Hz, 1H), 7.59 (s, 1H), 7.50 (dt, J = 7.7, 1.2 Hz, 1H), 7.34-7.23 (m, 2H), 7.14 (d, J = 2.2 Hz, 1H), 6.46 (s, 1H), 5.19 (s, 1H), 3.98 (s, 3H), 3.40 (dd, J = 13.8, 5.3 Hz, 1H), 1.59 (s, 3H), 1.26-1.18 (m, 2H), 1.04-0.96 (m, 2H), 0.81 (s, 9H). |
| 526 | 1H NMR (400 MHz, Methanol-d4) δ 8.33 (s, 1H), 8.24 (s, 1H), 8.00 (s, 1H), 7.84 (d, J = 2.5 Hz, 1H), 7.70-7.63 (m, 1H), 7.38 (d, J = 6.9 Hz, 1H), 7.24 (d, J = 2.5 Hz, 1H), 7.05 (dd, J = 8.4, 7.0 Hz, 1H), 6.62 (s, 1H), 4.22 (s, 3H), 3.94 (d, J = 13.8 Hz, 1H), 3.55 (d, J = 13.7 Hz, 1H), 1.72-1.58 (m, 4H), 0.78 (s, 9H). |
| 527 | 1H NMR (400 MHz, Methanol-d4) δ 8.35 (s, 1H), 8.17 (s, 1H), 7.97 (t, 1H), 7.82 (d, J = 2.5 Hz, 1H), 7.36 (d, J = 4.8 Hz, 2H), 7.16 (d, J = 2.6 Hz, 1H), 6.83 (s, 1H), 4.41 (s, 3H), 3.76 (d, J = 13.9 Hz, 1H), 3.66 (d, J = 13.8 Hz, 1H), 1.78-1.62 (m, 4H), 0.74 (s, 9H). |
| 528 | 1H NMR (400 MHz, Methanol-d4) δ 8.33 (s, 1H), 7.95 (s, 1H), 7.80 (d, J = 2.5 Hz, 1H), 7.45 (d, J = 8.3 Hz, 1H), 7.29 (dd, J = 8.4, 7.2 Hz, 1H), 7.04 (d, J = 2.5 Hz, 1H), 7.01 (d, J = 7.2 Hz, 1H), 6.70 (s, 1H), 3.76 (d, J = 13.6 Hz, 1H), 3.57 (d, J = 13.5 Hz, 1H), 2.54 (s, 3H), 1.78-1.56 (m, 4H), 0.72 (s, 9H). |
| 529 | 1H NMR (400 MHz, DMSO-d6) δ 8.30-8.22 (m, 2H), 8.08 (d, J = 0.4 Hz, 1H), 7.88 (d, J = 2.3 Hz, 1H), 7.57 (s, 1H), 7.50 (ddd, J = 7.4, 1.9, 1.0 Hz, 1H), 7.43-7.34 (m, 2H), 7.34-7.23 (m, 2H), 6.48 (s, 1H), 3.98 (s, 3H), 3.91 (dd, J = 13.8, 8.0 Hz, 1H), 3.35 (dd, J = 13.8, 5.2 Hz, 1H), 1.59 (s, 3H), 1.27-1.18 (m, 2H), 1.05-0.96 (m, 2H), 0.79 (s, 9H). |
| 530 | 1H NMR (400 MHz, Methanol-d4) δ 8.51 (s, 1H), 7.95 (s, 1H), 7.78 (t, J = 8.1 Hz, 1H), 7.64 (d, J = 2.3 Hz, 1H), 6.91 (d, J = 2.3 Hz, 1H), 6.87 (dd, J = 8.4, 2.8 Hz, 1H), 6.20 (s, 1H), 4.04 (d, J = 13.9 Hz, 1H), 3.85 (d, J = 13.9 Hz, 1H), 2.49 (s, 3H), 1.64 (s, 9H), 0.93 (s, 9H). |
| 531 | 1H NMR (400 MHz, Methanol-d4) δ 8.50 (s, 1H), 7.98 (s, 1H), 7.77 (t, J = 8.1 Hz, 1H), 7.64 (d, J = 2.3 Hz, 1H), 6.90 (d, J = 2.3 Hz, 1H), 6.87 (dd, J = 8.5, 2.8 Hz, 1H), 6.22 (s, 1H), 4.63 (d, J = 47.1 Hz, 2H), 4.03 (d, J = 13.9 Hz, 1H), 3.84 (d, J = 13.9 Hz, 1H), 2.49 (s, 3H), 1.67 (s, 6H), 0.93 (s, 9H). |
| 532 | 1H NMR (400 MHz, Methanol-d4) δ 8.51 (s, 1H), 7.92 (s, 1H), 7.78 (t, J = 8.1 Hz, 1H), 7.65 (d, J = 2.3 Hz, 1H), 6.94 (d, J = 2.3 Hz, 1H), 6.88 (dd, J = 8.5, 2.7 Hz, 1H), 6.27 (tt, J = 56 Hz, J = 3.3 Hz, 1H), 6.25 (s, 1H), 4.95-4.86 (m, 2H), 4.04 (d, J = 13.9 Hz, 1H), 3.83 (d, J = 14.0 Hz, 1H), 2.50 (s, 3H), 0.94 (s, 9H). |
| 533 | 1H NMR (400 MHz, Acetonitrile-d3) δ 9.88 (s, 1H), 8.51 (s, 1H), 8.22 (m, 1H), 8.12 (s, 1H), 8.03-7.92 (m, 1H), 7.87 (m, 3H), 7.46 (m, 1H), 6.95 (s, 1H), 6.62 (s, 1H), 6.22 (s, 1H), 3.71 (s, 2H), 3.35 (m, 1H), 1.57-1.45 (m, 4H), 0.50 (s, 9H). |
| 534 | 1H NMR (400 MHz, Acetonitrile-d3) δ 8.43 (s, 1H), 8.31 (s, 1H), 7.97 (s, 1H), 7.84 (m, 1H), 7.44 (m, 1H), 6.88-6.75 (m, 2H), 6.09 (s, 1H), 3.89 (m, 2H), 3.62-3.51 (m, 2H), 2.51 (s, 3H), 1.73 (s, 1H), 1.78-1.65 (m, 1H), 1.65 (s, 2H), 0.98 (s, 9H). |

TABLE 2-continued

| Compound | ¹H-NMR |
|---|---|
| 535 | 1H NMR (400 MHz, Acetonitrile-d3) δ 10.37 (s, 1H), 8.56 (d, J = 6.5 Hz, 1H), 8.38 (d, J = 6.6 Hz, 1H), 8.18-8.06 (m, 1H), 8.08-7.97 (m, 3H), 7.92 (m, 1H), 7.74 (d, J = 2.4 Hz, 1H), 7.53 (s, 1H), 7.09 (d, J = 2.5 Hz, 1H), 6.29 (s, 1H), 3.85-3.73 (m, 1H), 3.27 (m, 1H), 1.77-1.60 (m, 3H), 1.56-1.47 (m, 1H), 0.42 (s, 9H). |
| 536 | 1H NMR (400 MHz, Acetonitrile-d3) δ 9.50 (s, 1H), 8.83-8.59 (m, 2H), 8.48 (d, J = 6.7 Hz, 1H), 8.31-8.08 (m, 3H), 7.87-7.66 (m, 2H), 7.50 (d, J = 2.1 Hz, 1H), 7.26 (s, 1H), 7.08 (d, J = 2.3 Hz, 1H), 6.69 (s, 1H), 5.73 (t, J = 54.5 Hz, 1H), 3.95 (dd, J = 13.8, 8.1 Hz, 1H), 3.55 (dd, J = 13.8, 5.1 Hz, 1H), 1.48-1.17 (m, 4H), 0.50 (s, 9H). |
| 537 | 1H NMR (400 MHz, Acetonitrile-d3) δ 9.07 (d, J = 4.8 Hz, 1H), 8.94 (d, J = 8.6 Hz, 1H), 8.44 (m, 1H), 8.27-8.20 (m, 1H), 7.92-7.81 (m, 3H), 7.76 (m, 1H), 7.56 (m, 1H), 6.85-6.76 (m, 2H), 6.67 (s, 1H), 5.85 (t, J = 54.6 Hz, 1H), 3.81 (m, 1H), 3.60 (m, 1H), 1.48 (m, 4H), 0.72 (s, 9H). |
| 538 | 1H NMR (400 MHz, Methanol-d4) δ 8.51 (d, J = 7.0 Hz, 1H), 8.49 (s, 1H), 8.05 (s, 1H), 7.95 (d, J = 2.4 Hz, 1H), 7.68 (d, J = 2.3 Hz, 1H), 7.27 (d, J = 7.0 Hz, 1H), 7.02 (d, J = 2.3 Hz, 1H), 6.86 (t, J = 7.0 Hz, 1H), 6.62 (dd, J = 2.5, 1.0 Hz, 1H), 6.38 (s, 1H), 4.09 (d, J = 13.9 Hz, 1H), 3.67 (d, J = 13.9 Hz, 1H), 1.58-1.44 (m, 4H), 0.84 (s, 9H). |
| 539 | 1H NMR (400 MHz, Methanol-d4) δ 8.51 (s, 1H), 8.03 (s, 1H), 7.89 (t, J = 8.1 Hz, 1H), 7.68 (d, J = 2.3 Hz, 1H), 6.89-6.82 (m, 1H), 6.75 (d, J = 2.2 Hz, 1H), 6.23 (s, 1H), 5.96 (t, J = 54.7 Hz, 1H), 4.59 (dd, J = 11.5, 4.3 Hz, 1H), 4.09-4.01 (m, 1H), 3.58-3.46 (m, 2H), 3.21 (d, J = 11.7 Hz, 1H), 2.43 (s, 3H), 2.21-1.99 (m, 1H), 1.94 (d, J = 13.1 Hz, 1H), 1.55 (s, 4H), 0.90 (s, 3H), 0.55 (s, 3H). |
| 540 | 1H NMR (400 MHz, Methanol-d4) δ 8.53 (s, 1H), 8.09 (s, 1H), 7.66-7.58 (m, 2H), 7.09 (d, J = 2.3 Hz, 1H), 6.94-6.86 (m, 1H), 6.34 (s, 1H), 5.92 (t, J = 54.7 Hz, 1H), 4.76 (dd, J = 11.7, 4.4 Hz, 1H), 4.06 (d, J = 11.8, 4.7 Hz, 1H), 3.60-3.49 (m, 2H), 3.25 (d, J = 11.7 Hz, 1H), 2.59 (s, 3H), 2.18-2.05 (m, 1H), 1.92 (d, J = 12.6 Hz, 1H), 1.58-1.48 (m, 4H), 1.05 (s, 3H), 0.74 (s, 3H). |
| 541 | 1H NMR (400 MHz, Methanol-d4) δ 8.21 (s, 1H), 8.19 (s, 1H), 7.81 (t, J = 8.1 Hz, 1H), 7.50 (d, J = 2.4 Hz, 1H), 6.87 (dd, J = 8.5, 2.7 Hz, 1H), 6.73 (d, J = 2.4 Hz, 1H), 6.22 (s, 1H), 3.81 (d, J = 13.7 Hz, 1H), 3.59 (d, J = 13.8 Hz, 1H), 2.50 (s, 3H), 1.97-1.90 (m, 6H), 0.87 (s, 9H). |
| 542 | 1H NMR (400 MHz, Methanol-d4) δ 8.49 (s, 1H), 8.01 (s, 1H), 8.00-7.91 (m, 1H), 7.69 (d, J = 2.3 Hz, 1H), 7.45-7.28 (m, 2H), 6.95 (d, J = 2.3 Hz, 1H), 6.80 (s, 1H), 5.93 (t, J = 54.6 Hz, 1H), 4.38 (s, 3H), 3.95 (d, J = 13.9 Hz, 1H), 3.77 (d, J = 13.9 Hz, 1H), 1.61-1.42 (m, 4H), 0.77 (s, 9H). |
| 543 | 1H NMR (400 MHz, Methanol-d4) δ 8.46 (s, 1H), 8.09 (d, J = 1.0 Hz, 1H), 8.01 (s, 1H), 7.70 (d, J = 2.3 Hz, 1H), 7.53 (d, J = 8.4 Hz, 1H), 7.39 (dd, J = 8.5, 7.1 Hz, 1H), 7.27 (d, J = 7.0 Hz, 1H), 7.04 (d, J = 2.3 Hz, 1H), 6.49 (s, 1H), 4.14 (d, J = 13.8 Hz, 1H), 4.05 (s, 3H), 3.64 (d, J = 13.9 Hz, 1H), 1.77-1.55 (m, 4H), 0.85 (s, 9H). |
| 544 | 1H NMR (400 MHz, Methanol-d4) δ 8.46 (s, 1H), 8.25 (s, 1H), 8.03 (s, 1H), 7.70 (d, J = 2.3 Hz, 1H), 7.55 (d, J = 8.5 Hz, 1H), 7.25 (dd, J = 8.6, 6.9 Hz, 1H), 7.19 (d, J = 6.8 Hz, 1H), 7.02 (d, J = 2.2 Hz, 1H), 6.37 (s, 1H), 4.17 (s, 3H), 4.14 (d, J = 13.8 Hz, 1H), 3.63 (d, J = 13.9 Hz, 1H), 1.74-1.59 (m, 4H), 0.84 (s, 9H). |
| 545 | 1H NMR (400 MHz, Methanol-d4) δ 8.51 (s, 1H), 8.05 (s, 1H), 7.77 (t, J = 8.1 Hz, 1H), 7.64 (d, J = 2.2 Hz, 1H), 6.92 (d, J = 2.3 Hz, 1H), 6.88 (d, J = 8.4, 2.7 Hz, 1H), 6.24 (s, 1H), 6.12 (t, J = 56.0 Hz, 1H), 4.03 (d, J = 13.9 Hz, 1H), 3.84 (d, J = 13.9 Hz, 1H), 2.49 (s, 3H), 1.76 (s, 6H), 0.94 (s, 9H). |
| 546 | 1H NMR (400 MHz, Methanol-d4) δ 8.52 (s, 1H), 7.94 (s, 1H), 7.77 (t, J = 8.1 Hz, 1H), 7.65 (d, J = 2.3 Hz, 1H), 6.94 (d, J = 2.3 Hz, 1H), 6.88 (d, J = 8.5, 2.8 Hz, 1H), 6.23 (s, 1H), 5.10-4.93 (m, 1H), 4.77-4.72 (m, 1H), 4.64-4.60 (m, 1H), 4.05 (d, J = 14.0 Hz, 1H), 3.85 (d, J = 14.0 Hz, 1H), 2.50 (s, 3H), 1.57 (d, J = 7.1, 3H), 0.94 (s, 9H). |
| 547 | 1H NMR (400 MHz, Methanol-d4) δ 8.52 (s, 1H), 8.02 (s, 1H), 7.78 (t, J = 8.1 Hz, 1H), 7.65 (d, J = 2.2 Hz, 1H), 6.93 (d, J = 2.3 Hz, 1H), 6.87 (dd, J = 8.5, 2.8 Hz, 1H), 6.20 (s, 1H), 4.06 (d, J = 13.9 Hz, 1H), 3.84 (d, J = 13.9 Hz, 1H), 2.49 (s, 3H), 1.55 (m, 1H), 1.27-1.20 (m, 2H), 1.03 (m, 2H), 0.94 (s, 9H), 0.57-0.48 (m, 2H), 0.37-0.30 (m, 2H). |
| 548 | 1H NMR (400 MHz, Methanol-d4) δ 8.52 (s, 1H), 8.27 (s, 1H), 7.79 (t, J = 8.1 Hz, 1H), 7.66 (d, J = 2.3 Hz, 1H), 6.97 (d, J = 2.3 Hz, 1H), 6.90 (dd, J = 8.5, 2.8 Hz, 1H), 6.30 (s, 1H), 5.28-5.21 (m, 2H), 5.18 (d, J = 8.3 Hz, 2H), 4.03 (d, J = 14.0 Hz, 1H), 3.87 (d, J = 14.0 Hz, 1H), 2.52 (s, 3H), 0.94 (s, 9H). |
| 549 | 1H NMR (400 MHz, Acetonitrile-d3) δ 8.44 (s, 1H), 7.82 (t, J = 8.2 Hz, 1H), 7.49 (d, J = 2.3 Hz, 1H), 6.84 (dd, J = 8.4, 3.2 Hz, 1H), 6.78 (s, 1H), 6.17 (s, 1H), 3.83 (m, 2H), 1.78-1.65 (m, 2H), 1.65 (m, 2H), 0.95 (s, 9H). |
| 550 | 1H NMR (400 MHz, Acetonitrile-d3) δ 9.14-9.06 (m, 2H), 8.37 (s, 1H), 8.32-8.25 (m, 1H), 8.00-7.81 (m, 4H), 7.74 (d, J = 2.5 Hz, 1H), 6.91 (d, J = 2.5 Hz, 1H), 6.82 (s, 1H), 5.85 (t, J = 54.6 Hz, 1H), 5.80 (s, 1H), 3.68 m, 1H), 3.48 (m, 1H), 1.53-1.43 (m, 4H), 0.69 (s, 9H). |
| 551 | 1H NMR (400 MHz, Acetonitrile-d3) δ 9.65 (m, 1H), 9.12-9.01 (m, 2H), 8.46 (s, 1H), 8.42 (m, 1H), 8.31 (s, 1H), 8.06-7.96 (m, 2H), 7.94 (m, 1H), 7.86 (s, 1H), 7.64 (m, 1H), 7.50 (s, 1H), 7.23 (m, 1H), 6.88 (s, 1H), 5.83 (t, J = 54.6 Hz, 1H), 4.09 (m, 1H), 3.64 (m, 1H), 1.53-1.32 (m, 4H), 0.58 (s, 9H). |
| 552 | 1H NMR (400 MHz, Acetonitrile-d3) δ 9.98 (s, 1H), 8.60 (d, J = 6.3 Hz, 1H), 8.38-8.29 (m, 2H), 8.15 (d, J = 8.0 Hz, 1H), 8.09-7.98 (m, 3H), 7.76 (d, J = |

TABLE 2-continued

| Compound | ¹H-NMR |
|---|---|
| | 2.5 Hz, 1H), 6.95-6.88 (m, 2H), 6.30 (s, 1H), 5.88 (t, J = 54.6 Hz, 1H), 3.76 (m, 1H), 3.39 (m, 1H), 1.56-1.42 (m, 4H), 0.65 (m, 9H). |
| 553 | 1H NMR (400 MHz, Methanol-d4) δ 8.20 (s, 1H), 8.00 (s, 1H), 7.82 (t, J = 8.1 Hz, 1H), 7.47 (d, J = 2.4 Hz, 1H), 6.86 (dd, J = 8.5, 2.7 Hz, 1H), 6.73 (d, J = 2.4 Hz, 1H), 6.19 (s, 1H), 3.82 (d, J = 13.7 Hz, 1H), 3.57 (d, J = 13.8 Hz, 1H), 2.93 (s, 6H), 2.51 (s, 3H), 1.74-1.62 (m, 4H), 0.88 (s, 9H). |
| 554 | 1H NMR (400 MHz, Methanol-d4) δ 8.52 (s, 1H), 8.07 (s, 1H), 7.81 (t, J = 8.1 Hz, 1H), 7.64 (d, J = 2.3 Hz, 1H), 6.95 (d, J = 2.3 Hz, 1H), 6.88 (dd, J = 8.5, 2.7 Hz, 1H), 6.23 (s, 1H), 4.09 (d, J = 13.9 Hz, 1H), 3.81 (d, J = 14.0 Hz, 1H), 3.39 (m, 2H), 3.08 (m, 2H), 2.50 (s, 3H), 1.74 (m, 6H), 1.63 (m, 2H), 0.95 (s, 9H). |
| 555 | 1H NMR (400 MHz, Methanol-d4) δ 8.20 (s, 1H), 8.02 (s, 1H), 7.82 (t, J = 8.1 Hz, 1H), 7.48 (d, J = 2.4 Hz, 1H), 6.87 (dd, J = 8.5, 2.7 Hz, 1H), 6.77 (d, J = 2.4 Hz, 1H), 6.21 (s, 1H), 3.84 (d, J = 13.7 Hz, 1H), 3.62-3.52 (m, 5H), 3.40 (m, 4H), 2.53 (s, 3H), 1.77-1.67 (m, 2H), 1.65 (m, 2H), 0.89 (s, 9H). |
| 556 | 1H NMR (400 MHz, Methanol-d4) δ 8.50 (s, 1H), 7.81 (s, 1H), 7.67 (d, J = 2.3 Hz, 1H), 7.49-7.42 (m, 1H), 7.28 (dd, J = 8.4, 7.2 Hz, 1H), 6.97 (d, J = 7.2 Hz, 1H), 6.90 (d, J = 2.3 Hz, 1H), 6.70 (s, 1H), 5.91 (t, J = 54.7 Hz, 1H), 3.99 (d, J = 13.8 Hz, 1H), 3.73 (d, J = 13.8 Hz, 1H), 2.52 (s, 3H), 1.50 (s, 4H), 0.77 (s, 9H). |
| 557 | 1H NMR (400 MHz, Methanol-d4) δ 8.32 (s, 1H), 8.11 (d, J = 1.0 Hz, 1H), 8.04 (s, 1H), 7.83 (d, J = 2.5 Hz, 1H), 7.52 (d, J = 8.4 Hz, 1H), 7.39 (dd, J = 8.5, 7.1 Hz, 1H), 7.29 (d, J = 7.1 Hz, 1H), 7.18 (d, J = 2.5 Hz, 1H), 6.49 (s, 1H), 4.05 (s, 3H), 3.94 (d, J = 13.7 Hz, 1H), 3.50 (d, J = 13.7 Hz, 1H), 1.76-1.58 (m, 4H), 0.79 (s, 9H). |
| 558 | 1H NMR (400 MHz, Methanol-d4) δ 8.36 (d, J = 0.6 Hz, 1H), 8.29 (s, 1H), 8.06 (s, 1H), 7.85 (d, J = 2.4 Hz, 1H), 7.58-7.51 (m, 1H), 7.26 (dd, J = 8.6, 6.9 Hz, 1H), 7.23-7.18 (m, 2H), 6.37 (s, 1H), 4.17 (s, 3H), 3.99 (d, J = 13.7 Hz, 1H), 3.53 (d, J = 13.7 Hz, 1H), 1.77-1.59 (m, 4H), 0.80 (s, 9H). |
| 559 | 1H NMR (400 MHz, Methanol-d4) δ 8.35 (s, 1H), 8.02 (s, 1H), 7.99-7.94 (m, 1H), 7.83 (d, J = 2.5 Hz, 1H), 7.40-7.33 (m, 2H), 7.14 (d, J = 2.5 Hz, 1H), 6.81 (s, 1H), 5.93 (t, J = 54.7 Hz, 1H), 4.40 (s, 3H), 3.77 (d, J = 13.9 Hz, 1H), 3.63 (d, J = 13.8 Hz, 1H), 1.55-1.49 (m, 4H), 0.72 (s, 9H). |
| 560 | 1H NMR (400 MHz, Methanol-d4) δ 8.52 (d, J = 7.0 Hz, 1H), 8.50 (s, 1H), 8.19 (s, 1H), 7.96 (d, J = 2.5 Hz, 1H), 7.69 (d, J = 2.3 Hz, 1H), 7.28 (dt, J = 7.0, 0.9 Hz, 1H), 7.03 (d, J = 2.4 Hz, 1H), 6.87 (t, J = 7.0 Hz, 1H), 6.61 (dd, J = 2.4, 0.9 Hz, 1H), 6.39 (s, 1H), 4.10 (d, J = 13.9 Hz, 1H), 3.67 (d, J = 13.9 Hz, 1H), 1.79-1.57 (m, 4H), 0.83 (s, 9H). |
| 561 | 1H NMR (400 MHz, Methanol-d4) δ 9.64 (s, 1H), 8.56 (d, J = 6.6 Hz, 1H), 8.48 (s, 1H), 8.41 (d, J = 6.6 Hz, 1H), 8.36 (d, J = 8.3 Hz, 1H), 8.18 (d, J = 7.3 Hz, 1H), 8.07 (s, 1H), 7.88 (dd, J = 8.3, 7.4 Hz, 1H), 7.66 (d, J = 2.2 Hz, 1H), 6.95 (d, J = 2.3 Hz, 1H), 6.87 (s, 1H), 4.05 (d, J = 13.9 Hz, 1H), 3.59 (d, J = 13.9 Hz, 1H), 1.88-1.75 (m, 2H), 1.64-1.52 (m, 2H), 0.72 (s, 9H). |
| 562 | 1H NMR (400 MHz, Methanol-d4) δ 9.59 (s, 1H), 8.55 (d, J = 6.5 Hz, 1H), 8.46 (s, 1H), 8.38-8.29 (m, 2H), 8.09 (d, J = 7.3 Hz, 1H), 7.96 (s, 1H), 7.85 (t, J = 7.8 Hz, 1H), 7.66 (d, J = 2.3 Hz, 1H), 6.94 (d, J = 2.3 Hz, 1H), 6.87 (s, 1H), 4.00 (d, J = 13.9 Hz, 1H), 3.62 (d, J = 13.9 Hz, 1H), 2.99-2.86 (m, 1H), 2.81 (m, 1H), 2.59 (m, 1H), 2.40-2.24 (m, 1H), 2.18-1.95 (m, 2H), 0.72 (s, 9H). |
| 563 | 1H NMR (400 MHz, Methanol-d4) δ 9.59 (s, 1H), 8.56 (d, J = 6.5 Hz, 1H), 8.47 (s, 1H), 8.37-8.29 (m, 2H), 8.23 (s, 1H), 8.06 (d, J = 7.3 Hz, 1H), 7.85 (t, J = 7.8 Hz, 1H), 7.67 (d, J = 2.3 Hz, 1H), 6.97 (d, J = 2.3 Hz, 1H), 6.89 (s, 1H), 3.98 (d, J = 13.9 Hz, 1H), 3.67 (d, J = 13.9 Hz, 1H), 2.01-1.94 (m, 2H), 1.94-1.83 (m, 2H), 0.73 (s, 9H). |
| 564 | 1H NMR (400 MHz, Methanol-d4) δ 9.55 (s, 1H), 8.54 (d, J = 6.5 Hz, 1H), 8.45 (s, 1H), 8.28 (m, 2H), 8.03 (d, J = 7.3 Hz, 1H), 7.95 (s, 1H), 7.82 (t, J = 7.8 Hz, 1H), 7.66 (d, J = 2.3 Hz, 1H), 6.90 (d, J = 2.4 Hz, 1H), 6.82 (s, 1H), 3.97 (d, J = 13.8 Hz, 1H), 3.63 (d, J = 13.9 Hz, 1H), 1.63 (s, 3H), 1.29 (m, 2H), 1.08-1.01 (m, 2H), 0.71 (s, 9H). |
| 565 | 1H NMR (400 MHz, Acetonitrile-d3) δ 9.13-8.99 (m, 2H), 8.43 (s, 1H), 8.31-8.24 (m, 1H), 7.97-7.87 (m, 2H), 7.86-7.77 (m, 2H), 7.56 (m, 1H), 7.01 (s, 1H), 6.91-6.81 (m, 2H), 5.97 (s, 1H), 5.66 (s, 1H), 3.88 (m, 1H), 3.60 (m, 1H), 1.94 (m, 1H) 1.73 (m, 1H), 1.56-1.41 (m, 2H), 0.73 (s, 9H). |
| 566 | 1H NMR (400 MHz, Acetonitrile-d3) δ 9.14-9.05 (m, 2H), 8.44 (s, 1H), 8.29 (m, 1H), 7.98-7.76 (m, 4H), 7.56 (m, 1H), 7.13 (s, 1H), 6.91-6.83 (m, 2H), 6.58 (s, 1H), 5.96 (s, 1H), 3.90 (m, 1H), 3.61 (m, 1H), 2.93-2.80 (m, 2H), 2.79-2.64 (m, 2H), 2.12-1.96 (m, 2H), 0.73 (s, 9H). |
| 567 | 1H NMR (400 MHz, Acetonitrile-d3) δ 9.09 (dd, J = 4.8, 1.5 Hz, 1H), 8.96 (d, J = 8.5 Hz, 1H), 8.43 (s, 1H), 8.27 (d, J = 8.2 Hz, 1H), 7.95-7.83 (m, 3H), 7.80 (dd, J = 8.7, 4.8 Hz, 1H), 7.55 (d, J = 2.3 Hz, 1H), 6.93 (s, 1H), 6.87-6.79 (m, 2H), 6.42 (s, 1H), 3.85 (dd, J = 13.7, 6.6 Hz, 1H), 3.63 (dd, J = 13.4, 5.1 Hz, 1H), 1.97-1.76 (m, 4H), 0.73 (s, 9H). |
| 568 | 1H NMR (400 MHz, Acetonitrile-d3) δ 9.09 (dd, J = 4.8, 1.5 Hz, 1H), 9.01 (d, J = 8.8 Hz, 1H), 8.43 (s, 1H), 8.30-8.22 (m, 2H), 7.93-7.86 (m, 2H), 7.90-7.76 (m, 1H), 7.73 (s, 1H), 7.55 (d, J = 2.2 Hz, 1H), 6.89 (m, 1H), 6.80 (s, 1H), 3.84 (dd, J = 13.6, 6.7 Hz, 1H), 3.61 (dd, J = 13.6, 5.0 Hz, 1H), 1.60 (s, 3H), 1.28-1.19 (m, 2H), 1.05-0.98 (m, 2H), 0.72 (s, 9H). |
| 569 | 1H NMR (400 MHz, DMSO-d6) δ 9.44 (s, 1H), 8.57 (d, J = 6.0 Hz, 1H), 8.31 (s, 1H), 8.13 (d, J = 5.7 Hz, 3H), 7.89-7.83 (m, 2H), 7.69 (t, J = 7.7 Hz, 1H), 7.61 (d, J = 7.5 Hz, 1H), 7.31-7.19 (m, 2H), 6.90 (d, J = 7.3 Hz, 1H), 4.71 (s, 1H), |

TABLE 2-continued

| Compound | ¹H-NMR |
| --- | --- |
| | 4.59 (s, 1H), 3.70 (dd, J = 13.7, 7.6 Hz, 1H), 3.42-3.33 (m, 1H), 1.41-1.27 (m, 4H), 0.58 (s, 9H). |
| 570 | 1H NMR (400 MHz, Methanol-d4) δ 8.45 (s, 1H), 8.25 (s, 1H), 7.98 (s, 1H), 7.72-7.64 (m, 2H), 7.37 (d, J = 6.9 Hz, 1H), 7.11-7.01 (m, 2H), 6.63 (s, 1H), 4.22 (s, 3H), 4.12 (d, J = 13.9 Hz, 1H), 3.67 (d, J = 13.9 Hz, 1H), 1.80-1.50 (m, 2H), 1.28 (s, 2H), 0.82 (s, 9H). |
| 571 | 1H NMR (400 MHz, Methanol-d4) δ 8.36 (s, 1H), 7.82 (d, J = 2.5 Hz, 1H), 7.81 (s, 1H), 7.48-7.41 (m, 1H), 7.29 (dd, J = 8.5, 7.1 Hz, 1H), 7.05 (d, J = 2.5 Hz, 1H), 7.00 (d, J = 7.1 Hz, 1H), 6.69 (s, 1H), 3.80 (d, J = 13.6 Hz, 1H), 3.58 (d, J = 13.6 Hz, 1H), 2.54 (s, 3H), 1.50 (d, J = 2.3 Hz, 4H), 0.72 (s, 9H). |
| 572 | 1H NMR (400 MHz, Methanol-d4) δ 8.51 (d, J = 7.0 Hz, 1H), 8.37 (s, 1H), 8.20 (s, 1H), 7.96 (d, J = 2.4 Hz, 1H), 7.83 (d, J = 2.5 Hz, 1H), 7.29 (d, J = 7.1 Hz, 1H), 7.18 (d, J = 2.5 Hz, 1H), 6.87 (t, J = 7.0 Hz, 1H), 6.63 (dd, J = 2.5, 1.0 Hz, 1H), 6.39 (s, 1H), 3.92 (d, J = 13.8 Hz, 1H), 3.53 (d, J = 13.7 Hz, 1H), 1.79-1.57 (m, 4H), 0.78 (s, 9H). |
| 573 | 1H NMR (400 MHz, Methanol-d4) δ 8.35 (s, 1H), 8.25 (s, 1H), 8.00 (s, 1H), 7.85 (d, J = 2.5 Hz, 1H), 7.67 (d, J = 8.0 Hz, 1H), 7.38 (d, J = 7.0 Hz, 1H), 7.26 (d, J = 2.5 Hz, 1H), 7.05 (dd, J = 8.4, 7.0 Hz, 1H), 6.63 (s, 1H), 4.23 (s, 3H), 3.98 (d, J = 13.8 Hz, 1H), 3.57 (d, J = 13.8 Hz, 1H), 1.73-1.58 (m, 4H), 0.79 (s, 9H). |
| 574 | 1H NMR (400 MHz, Acetonitrile-d3) δ 8.41 (s, 1H), 7.81 (t, J = 8.2 Hz, 1H), 7.68 (d, J = 2.4 Hz, 1H), 6.97 (d, J = 2.4 Hz, 1H), 6.84 (dd, J = 8.4, 3.1 Hz, 1H), 6.41 (s, 1H), 6.17 (s, 1H), 3.84-3.69 (m, 2H), 2.50 (s, 3H), 1.79-1.61 (m, 4H), 0.94 (s, 9H). |
| 575 | 1H NMR (400 MHz, Acetonitrile-d3) δ 9.27-9.20 (m, 1H), 9.17-9.10 (m, 1H), 8.40-8.29 (m, 2H), 8.05-7.92 (m, 3H), 7.85 (s, 1H), 7.75 (d, J = 2.5 Hz, 1H), 6.93 (d, J = 2.5 Hz, 1H), 6.83 (s, 1H), 5.92 (s, 1H), 5.62 (s, 1H), 3.78-3.68 (m, 1H), 3.52-3.42 (m, 1H), 1.76-1.71 (m, 2H), 1.57-1.37 (m, 2H), 0.69 (s, 9H). |
| 576 | 1H NMR (400 MHz, Chloroform-d) δ 8.91 (m, 1H), 8.55 (m, 1H), 8.33 (s, 1H), 8.08 (m, 1H), 7.70 (m, 2H), 7.56-7.44 (m, 2H), 7.31 (s, 1H), 7.22 (s, 2H), 6.60 (m, 1H), 6.50 (m, 1H), 3.45 (m, 2H), 2.87-2.67 (m, 2H), 2.15-1.81 (m, 2H), 0.57 (s, 9H). |
| 577 | 1H NMR (400 MHz, Acetonitrile-d3) δ 9.14-9.03 (m, 2H), 8.37 (s, 1H), 8.30 (d, J = 8.3 Hz, 1H), 8.00-7.84 (m, 4H), 7.73 (d, J = 2.4 Hz, 1H), 6.91 (d, J = 2.5 Hz, 1H), 6.82 (s, 1H), 5.82 (s, 1H), 3.68 (dd, J = 13.3, 6.7 Hz, 1H), 3.49 (dd, J = 13.4, 5.2 Hz, 1H), 1.97-1.79 (m, 4H), 0.69 (s, 9H). |
| 578 | 1H NMR (400 MHz, Acetonitrile-d3) δ 9.18-9.08 (m, 2H), 8.33 (d, J = 22.8 Hz, 2H), 8.01-7.86 (m, 3H), 7.73 (t, J = 1.2 Hz, 2H), 6.90 (d, J = 2.5 Hz, 1H), 6.79 (s, 1H), 6.21 (s, 1H), 5.83 (s, 1H), 3.68 (dd, J = 13.3, 6.8 Hz, 1H), 3.48 (dd, J = 13.4, 5.0 Hz, 1H), 1.60 (s, 3H), 1.25 (s, 2H), 1.05-0.98 (m, 2H), 0.68 (s, 9H). |
| 579 | 1H NMR (400 MHz, Methanol-d4) δ 8.51 (s, 1H), 7.94 (s, 1H), 7.76 (t, J = 8.1 Hz, 1H), 7.64 (d, J = 2.3 Hz, 1H), 6.91 (d, J = 2.4 Hz, 1H), 6.88 (dd, J = 8.5, 2.7 Hz, 1H), 6.22 (s, 1H), 5.98-4.79 (m, 1H), 4.00 (d, J = 13.9 Hz, 1H), 3.95-3.81 (m, 2H), 2.50 (s, 3H), 2.02-1.89 (m, 1H), 1.67-1.55 (m, 1H), 0.93 (s, 9H). |
| 580 | 1H NMR (400 MHz, Methanol-d4) δ 9.74 (s, 1H), 8.60 (d, J = 6.5 Hz, 1H), 8.53 (d, J = 6.8 Hz, 1H), 8.43 (d, J = 8.3 Hz, 1H), 8.31 (s, 1H), 8.29 (s, 1H), 8.20 (d, J = 7.4 Hz, 1H), 7.95 (dd, J = 8.3, 7.4 Hz, 1H), 7.78 (d, J = 2.5 Hz, 1H), 7.14 (d, J = 2.5 Hz, 1H), 6.91 (s, 1H), 3.79 (d, J = 13.8 Hz, 1H), 3.51 (d, J = 13.8 Hz, 1H), 2.05-1.94 (m, 2H), 1.94-1.86 (m, 2H), 0.69 (s, 9H). |
| 581 | 1H NMR (400 MHz, Methanol-d4) δ 9.73 (s, 1H), 8.59 (d, J = 6.7 Hz, 1H), 8.53 (d, J = 6.7 Hz, 1H), 8.42 (d, J = 8.3 Hz, 1H), 8.30 (s, 1H), 8.19 (d, J = 7.3 Hz, 1H), 8.04 (s, 1H), 7.95 (dd, J = 8.3, 7.4 Hz, 1H), 7.77 (d, J = 2.5 Hz, 1H), 7.10 (d, J = 2.5 Hz, 1H), 6.86 (s, 1H), 3.78 (d, J = 13.8 Hz, 1H), 3.50 (d, J = 13.8 Hz, 1H), 1.64 (s, 3H), 1.34-1.25 (m, 2H), 1.09-1.00 (m, 2H), 0.68 (s, 9H). |
| 582 | 1H NMR (400 MHz, DMSO-d6) δ 8.40-8.34 (m, 2H), 7.81 (t, J = 8.3 Hz, 1H), 7.68-7.62 (m, 1H), 7.43 (d, J = 7.0 Hz, 1H), 6.90 (dd, J = 8.4, 3.1 Hz, 1H), 6.77 (d, J = 2.4 Hz, 1H), 6.30 (dd, J = 21.8, 6.2 Hz, 1H), 4.48-4.20 (m, 1H), 2.39 (s, 3H), 1.83-1.59 (m, 4H), 1.26 (dd, J = 19.5, 6.6 Hz, 4H), 0.85 (s, 3H), 0.67 (s, 9H) |
| 583 | 1H NMR (400 MHz, DMSO-d6) δ 8.37 (dd, J = 14.4, 8.7 Hz, 2H), 7.89 (d, J = 2.3 Hz, 1H), 7.84-7.76 (m, 1H), 7.52 (d, J = 7.0 Hz, 1H), 7.35-7.29 (m, 1H), 7.05 (d, J = 2.5 Hz, 1H), 6.93-6.83 (m, 2H), 6.70 (d, J = 10.5 Hz, OH), 6.28 (d, J = 6.5 Hz, 1H), 4.24 (dd, J = 10.5, 6.6 Hz, 1H), 2.39 (s, 3H), 1.81-1.60 (m, 4H), 1.26 (dd, J = 17.3, 6.6 Hz, 4H), 0.85 (s, 3H), 0.67 (s, 9H). |
| 584 | 1H NMR (400 MHz, Methanol-d4) δ 8.53 (s, 1H), 8.33 (s, 1H), 7.78 (t, J = 8.1 Hz, 1H), 7.66 (d, J = 2.3 Hz, 1H), 6.99 (d, J = 2.3 Hz, 1H), 6.89 (dd, J = 8.5, 2.8 Hz, 1H), 6.31 (s, 1H), 4.38 (ddd, J = 11.7, 10.7, 1.5 Hz, 2H), 4.00 (d, J = 14.0 Hz, 1H), 3.91 (d, J = 14.0 Hz, 1H), 2.53 (s, 3H), 0.95 (s, 9H). |
| 585 | 1H NMR (400 MHz, DMSO-d6) δ 8.35 (d, J = 9.9 Hz, 2H), 7.86 (t, J = 8.2 Hz, 1H), 7.80 (d, J = 2.3 Hz, 1H), 7.49-7.32 (m, 2H), 7.24 (d, J = 8.5 Hz, 1H), 7.01-6.94 (m, 1H), 6.35 (d, J = 7.8 Hz, 1H), 4.17 (s, 1H), 2.06 (s, 1H), 1.89 (d, J = 12.0 Hz, 1H), 1.82-1.58 (m, 8H), 1.54-1.12 (m, 6H). |
| 586 | 1H NMR (400 MHz, Methanol-d4) δ 9.76 (s, 1H), 8.63-8.55 (m, 2H), 8.44 (d, J = 8.2 Hz, 1H), 8.29 (m, 2H), 8.13 (s, 1H), 7.96 (dd, J = 8.3, 7.4 Hz, 1H), 7.77 (d, J = 2.5 Hz, 1H), 7.10 (d, J = 2.5 Hz, 1H), 6.89 (s, 1H), 3.84 (d, J = 13.8 Hz, 1H), 3.44 (d, J = 13.8 Hz, 1H), 1.86-1.77 (m, 2H), 1.63-1.52 (m, 2H), 0.67 (s, 9H). |
| 587 | 1H NMR (400 MHz, Methanol-d4) δ 9.74 (s, 1H), 8.63-8.57 (m, 1H), 8.55 (m, 1H), 8.42 (d, J = 8.3 Hz, 1H), 8.30 (s, 1H), 8.23 (d, J = 7.3 Hz, 1H), 8.03 (s, 1H), 7.95 (dd, J = 8.3, 7.4 Hz, 1H), 7.78 (d, J = 2.5 Hz, 1H), 7.13 (d, J = 2.5 Hz, 1H), |

TABLE 2-continued

| Compound | ¹H-NMR |
|---|---|
| | 6.90 (s, 1H), 3.82 (d, J = 13.8 Hz, 1H), 3.48 (d, J = 13.8 Hz, 1H), 2.93 (m, 2H), 2.81 (m, 2H), 2.16-1.95 (m, 2H), 0.69 (s, 9H). |
| 588 | 1H NMR (400 MHz, DMSO-d6) δ 8.37 (s, 1H), 8.36 (s, 1H), 7.87 (t, J = 8.3 Hz, 1H), 7.58 (d, J = 2.2 Hz, 1H), 7.48-7.37 (m, 2H), 7.08 (d, J = 2.3 Hz, 1H), 6.98 (dd, J = 8.4, 3.0 Hz, 1H), 6.34 (d, J = 7.2 Hz, 1H), 4.20 (s, OH), 2.52 (s, 3H), 2.07 (d, J = 10.4 Hz, 1H), 1.89 (d, J = 12.1 Hz, 1H), 1.84-1.60 (m, 8H), 1.54-1.27 (m, 4H), 1.27-1.14 (m, 1H). |
| 589 | 1H NMR (400 MHz, Methanol-d4) δ 8.38 (s, 1H), 7.95 (s, 1H), 7.84-7.76 (m, 2H), 7.08 (d, J = 2.5 Hz, 1H), 6.87 (dd, J = 8.5, 2.7 Hz, 1H), 6.20 (s, 1H), 3.89 (d, J = 13.9 Hz, 1H), 3.71 (d, J = 13.8 Hz, 1H), 2.50 (s, 3H), 1.64 (s, 9H), 0.90 (s, 9H). |
| 590 | 1H NMR (400 MHz, Methanol-d4) δ 8.39 (s, 1H), 8.05 (s, 1H), 7.83-7.75 (m, 2H), 7.11 (d, J = 2.5 Hz, 1H), 6.87 (dd, J = 8.5, 2.7 Hz, 1H), 6.24 (s, 1H), 6.12 (t, J = 55.5 Hz, 1H), 3.90 (d, J = 13.8 Hz, 1H), 3.72 (d, J = 13.8 Hz, 1H), 2.50 (s, 3H), 1.76 (d, J = 1.6 Hz, 6H), 0.90 (s, 9H). |
| 591 | 1H NMR (400 MHz, Methanol-d4) δ 8.39 (s, 1H), 8.21 (s, 1H), 7.83-7.75 (m, 2H), 7.11 (d, J = 2.5 Hz, 1H), 6.88 (dd, J = 8.4, 2.7 Hz, 1H), 6.25 (s, 1H), 3.89 (d, J = 13.9 Hz, 1H), 3.71 (d, J = 13.9 Hz, 1H), 2.50 (s, 3H), 1.94 (s, 6H), 0.90 (s, 9H). |
| 592 | 1H NMR (400 MHz, Methanol-d4) δ 8.48 (s, 1H), 8.05 (s, 1H), 7.76 (m, 1H), 7.60 (d, J = 2.2 Hz, 1H), 6.96 (d, J = 2.3 Hz, 1H), 6.86 (m, 1H), 6.30 (s, 1H), 5.92 (t, J = 54.6 Hz, 1H), 3.92 (m, 2H), 2.85 (dt, J = 15.3, 7.5 Hz, 2H), 1.53 (s, 4H), 1.15 (t, J = 7.5 Hz, 3H), 0.94 (s, 9H). |
| 593 | 1H NMR (400 MHz, Methanol-d4) δ 8.49 (s, 1H), 8.21 (s, 1H), 7.76 (s, OH), 7.61 (d, J = 2.3 Hz, 1H), 6.98 (d, J = 2.3 Hz, 1H), 6.86 (m, 1H), 6.31 (s, 1H), 3.93 (m, 2H), 2.94-2.70 (m, 2H), 1.84-1.54 (m, 4H), 1.15 (t, J = 7.5 Hz, 3H), 0.94 (s, 9H). |
| 594 | 1H NMR (400 MHz, DMSO-d6) δ 9.76 (s, 1H), 8.61 (d, J = 6.0 Hz, 1H), 8.28 (s, 1H), 8.21 (s, 1H), 8.12 (s, 1H), 8.03 (d, J = 7.8 Hz, 1H), 7.91-7.79 (m, 2H), 7.67 (d, J = 2.2 Hz, 1H), 7.58 (d, J = 7.3 Hz, 1H), 7.14 (s, 1H), 7.04 (d, J = 6.8 Hz, 1H), 6.95 (s, 1H), 4.72 (s, 1H), 4.60 (s, 1H), 3.83-3.70 (m, 1H), 3.26 (dd, J = 13.7, 4.9 Hz, 1H), 1.42-1.27 (m, 4H), 0.99 (s, 1H), 0.51 (s, 9H). |
| 595 | 1H NMR (400 MHz, Methanol-d4) δ 8.42 (s, 1H), 8.19 (s, 1H), 7.80 (t, J = 8.1 Hz, 1H), 7.06 (d, J = 1.9 Hz, 1H), 6.87 (dd, J = 8.4, 2.7 Hz, 1H), 6.56 (d, J = 1.9 Hz, 1H), 6.26 (s, 1H), 4.04 (m, 4H), 3.83 (d, J = 14.0 Hz, 1H), 2.51 (s, 3H), 1.83-1.60 (m, 4H), 0.93 (s, 9H). |
| 596 | 1H NMR (400 MHz, Methanol-d4) δ 8.42 (s, 1H), 8.22 (s, 1H), 7.80 (t, J = 8.1 Hz, 1H), 7.05 (d, J = 1.9 Hz, 1H), 6.95-6.80 (m, 1H), 6.55 (d, J = 1.9 Hz, 1H), 6.25 (s, 1H), 4.04 (m, 4H), 3.84 (d, J = 14.0 Hz, 1H), 2.52 (s, 3H), 2.08-1.84 (m, 4H), 0.93 (s, 9H). |
| 597 | 1H NMR (400 MHz, Methanol-d4) δ 8.35 (s, 1H), 8.06 (s, 1H), 7.84-7.67 (m, 2H), 7.14 (d, J = 2.5 Hz, 1H), 6.86 (m, 1H), 6.30 (s, 1H), 5.93 (t, J = 54.7 Hz, 1H), 3.90-3.68 (m, 2H), 2.96-2.76 (m, 2H), 1.58-1.44 (m, 4H), 1.15 (t, J = 7.5 Hz, 3H), 0.90 (s, 9H). |
| 598 | 1H NMR (400 MHz, Methanol-d4) δ 8.35 (s, 1H), 8.21 (s, 1H), 7.85-7.74 (m, 2H), 7.14 (d, J = 2.6 Hz, 1H), 6.86 (m, 1H), 6.31 (s, 1H), 3.78 (d, J = 2.6 Hz, 2H), 2.86 (m, 2H), 1.84-1.54 (m, 4H), 1.15 (t, J = 7.5 Hz, 3H), 0.90 (s, 9H). |
| 599 | 1H NMR (400 MHz, Methanol-d4) δ 8.37 (s, 1H), 8.28-8.13 (m, 3H), 7.53 (d, J = 2.3 Hz, 1H), 7.44 (s, 1H), 6.97 (d, J = 6.7 Hz, 1H), 6.81 (d, J = 2.4 Hz, 1H), 6.67 (t, J = 6.9 Hz, 1H), 6.29 (s, 1H), 3.81 (d, J = 13.6 Hz, 1H), 3.46 (d, J = 13.6 Hz, 1H), 1.78-1.58 (m, 4H), 0.77 (s, 9H). |
| 600 | 1H NMR (400 MHz, Methanol-d4) δ 8.69 (dd, J = 5.6, 1.6 Hz, 1H), 8.51 (s, 1H), 8.38 (s, 1H), 8.34 (dd, J = 8.0, 1.5 Hz, 1H), 7.77 (dd, J = 8.1, 5.6 Hz, 1H), 7.64 (d, J = 2.3 Hz, 1H), 7.15 (d, J = 2.3 Hz, 1H), 6.50 (s, 1H), 3.96 (d, J = 1.8 Hz, 2H), 3.14 (q, J = 7.6 Hz, 2H), 1.82-1.60 (m, 4H), 1.21 (t, J = 7.6 Hz, 3H), 0.97 (s, 9H). |
| 601 | 1H NMR (400 MHz, DMSO-d6) δ 8.33 (s, 1H), 8.04 (s, 1H), 7.84-7.73 (m, 2H), 7.57-7.35 (m, 3H), 7.25-7.07 (m, 3H), 6.93 (dd, J = 8.4, 3.0 Hz, 1H), 6.25 (d, J = 7.0 Hz, 1H), 5.64 (s, 2H), 3.84 (dd, J = 13.8, 8.0 Hz, 1H), 3.40 (dd, J = 13.8, 5.3 Hz, 1H), 2.44 (s, 3H), 0.79 (s, 9H). |
| 602 | 1H NMR (400 MHz, Methanol-d4) δ 8.70 (dd, J = 5.7, 1.5 Hz, 1H), 8.42 (d, J = 8.5 Hz, 1H), 8.39 (s, 1H), 8.32 (s, 1H), 7.82 (dd, J = 8.1, 5.7 Hz, 1H), 7.73 (d, J = 2.5 Hz, 1H), 7.24 (d, J = 2.5 Hz, 1H), 6.48 (s, 1H), 3.77 (s, 2H), 3.17 (q, J = 7.6 Hz, 2H), 1.82-1.64 (m, 4H), 1.22 (t, J = 7.6 Hz, 3H), 0.92 (s, 9H). |
| 603 | 1H NMR (400 MHz, Methanol-d4) δ 8.48 (s, 1H), 8.04 (s, 1H), 7.93 (s, 1H), 7.75 (dd, J = 8.1, 1.1 Hz, 1H), 7.66 (d, J = 2.3 Hz, 1H), 7.19 (d, J = 7.2 Hz, 1H), 7.13-7.04 (m, 1H), 6.97 (d, J = 2.3 Hz, 1H), 6.84 (s, 1H), 5.92 (t, J = 54.6 Hz, 1H), 4.17 (s, 3H), 3.87 (d, J = 2.9 Hz, 2H), 1.52 (s, 4H), 0.80 (s, 9H). |
| 604 | 1H NMR (400 MHz, Methanol-d4) δ 8.63 (dd, J = 5.5, 1.5 Hz, 1H), 8.48 (s, 1H), 8.21 (d, J = 5.4 Hz, 2H), 7.66 (dd, J = 8.0, 5.4 Hz, 1H), 7.61 (d, J = 2.3 Hz, 1H), 7.04 (d, J = 2.4 Hz, 1H), 6.44 (s, 1H), 5.93 (t, J = 54.4 Hz, 1H), 3.92 (d, J = 2.5 Hz, 2H), 3.09 (q, J = 7.6 Hz, 2H), 1.57-1.51 (m, 4H), 1.19 (t, J = 7.6 Hz, 3H), 0.95 (s, 9H). |
| 605 | 1H NMR (400 MHz, Methanol-d4) δ 8.37 (s, 1H), 8.04 (s, 1H), 7.92 (s, 1H), 7.82 (d, J = 2.5 Hz, 1H), 7.75 (dd, J = 7.9, 1.0 Hz, 1H), 7.20 (d, J = 7.2 Hz, 1H), 7.17 (d, J = 2.6 Hz, 1H), 7.08 (t, J = 7.6 Hz, 1H), 6.84 (s, 1H), 5.92 (t, J = 54.8 Hz, 1H), 4.19 (s, 3H), 3.73 (s, 1H), 1.51 (s, 4H), 0.78 (s, 9H). |

TABLE 2-continued

| Compound | ¹H-NMR |
|---|---|
| 606 | 1H NMR (400 MHz, Methanol-d4) δ 8.69 (dd, J = 5.7, 1.5 Hz, 1H), 8.47-8.40 (m, 1H), 8.32 (s, 1H), 8.25 (s, 1H), 7.82 (dd, J = 8.1, 5.7 Hz, 1H), 7.72 (d, J = 2.5 Hz, 1H), 7.23 (d, J = 2.5 Hz, 1H), 6.47 (s, 1H), 5.94 (t, J = 54.5 Hz, 1H), 3.84-3.70 (m, 2H), 3.16 (q, J = 7.6 Hz, 2H), 1.61-1.51 (m, 4H), 1.22 (t, J = 7.6 Hz, 3H), 0.92 (s, 9H). |
| 607 | 1H NMR (400 MHz, DMSO-d6) δ 8.39 (s, 1H), 8.34 (s, 1H), 8.04 (s, 1H), 7.86-7.79 (m, 1H), 7.56 (d, J = 2.2 Hz, 1H), 7.23 (d, J = 8.5 Hz, 1H), 7.12 (d, J = 2.4 Hz, 1H), 7.00 (dd, J = 8.4, 3.1 Hz, 1H), 6.29 (d, J = 7.8 Hz, 1H), 2.82 (s, 1H), 2.49 (s, 3H), 2.10 (dt, J = 12.5, 7.7 Hz, 2H), 1.79-1.65 (m, 5H), 1.64-1.54 (m, 1H), 1.50 (d, J = 2.4 Hz, 2H), 1.05 (m, J = 11.7 Hz, 1H). |
| 608 | 1H NMR (400 MHz, DMSO-d6) δ 8.38 (d, J = 4.0 Hz, 1H), 8.34 (d, J = 0.6 Hz, 1H), 8.07 (s, 1H), 7.84 (t, J = 8.3 Hz, 1H), 7.57 (d, J = 2.2 Hz, 1H), 7.42-7.16 (m, 1H), 7.12 (d, J = 2.4 Hz, 1H), 7.01 (dd, J = 8.4, 3.1 Hz, 1H), 6.28 (d, J = 7.9 Hz, 1H), 4.11 (t, J = 8.2 Hz, 2H), 3.68 (td, J = 8.7, 2.9 Hz, 2H), 2.89-2.82 (m, 1H), 2.48 (s, 3H), 2.03-1.92 (m, 2H), 1.80-1.65 (m, 4H). |
| 609 | 1H NMR (400 MHz, DMSO-d6) δ 8.31-8.22 (m, 2H), 8.01 (s, 1H), 7.87 (d, J = 2.4 Hz, 1H), 7.58 (d, J = 7.6 Hz, 1H), 7.51 (ddd, J = 7.0, 2.4, 1.0 Hz, 1H), 7.41-7.32 (m, 2H), 7.33-7.23 (m, 2H), 6.48 (d, J = 6.9 Hz, 1H), 3.98 (s, 3H), 3.98-3.86 (m, 2H), 3.34 (dd, J = 13.8, 5.2 Hz, 1H), 1.18-1.01 (m, 4H), 0.79 (s, 9H). |
| 610 | 1H NMR (400 MHz, Methanol-d4) δ 8.33 (s, 1H), 7.93 (s, 1H), 7.82 (t, J = 8.1 Hz, 1H), 7.75 (d, J = 2.5 Hz, 1H), 7.06 (d, J = 2.5 Hz, 1H), 6.94-6.77 (m, 1H), 6.19 (s, 1H), 3.87 (d, J = 13.8 Hz, 1H), 3.77 (d, J = 4.5 Hz, 2H), 3.63 (d, J = 13.8 Hz, 1H), 2.51 (s, 3H), 1.32 (m, 2H), 1.20 (s, 2H), 0.88 (s, 9H). |
| 611 | 1H NMR (400 MHz, DMSO-d6) δ 8.45-8.37 (m, 1H), 8.26 (d, J = 10.1 Hz, 1H), 8.02-7.83 (m, 2H), 7.64 (t, J = 1.9 Hz, 1H), 7.50-7.41 (m, 1H), 7.39-7.32 (m, 1H), 7.31-7.16 (m, 3H), 7.10 (dd, J = 6.8, 2.9 Hz, 1H), 7.00 (dd, J = 8.4, 3.0 Hz, 1H), 6.47 (d, J = 7.3 Hz, 1H), 5.02-4.70 (m, 1H), 2.56 (d, J = 8.3 Hz, 3H), 1.81-1.65 (m, 5H), 1.39 (dt, J = 8.7, 4.7 Hz, 1H), 0.72-0.57 (m, 2H), 0.57-0.29 (m, 2H). |
| 612 | 1H NMR (400 MHz, DMSO-d6) δ 8.41 (s, 1H), 8.20 (s, 1H), 7.83 (t, J = 8.3 Hz, 1H), 7.62 (d, J = 2.2 Hz, 1H), 7.55 (s, 1H), 7.40 (t, J = 7.6 Hz, 1H), 7.18-6.99 (m, 6H), 6.89 (d, J = 2.3 Hz, 1H), 6.26 (d, J = 7.1 Hz, 1H), 4.29 (dd, J = 13.9, 8.3 Hz, 1H), 3.64 (dd, J = 13.9, 5.1 Hz, 1H), 2.47 (s, 3H), 1.85-1.60 (m, 4H), 1.19 (d, J = 41.4 Hz, 6H). |
| 613 | 1H NMR (400 MHz, DMSO-d6) δ 8.43-8.38 (m, 1H), 8.27 (d, J = 0.9 Hz, 1H), 7.96-7.79 (m, 3H), 7.59-7.52 (m, 2H), 7.48-7.24 (m, 1H), 7.24-7.18 (m, 2H), 7.10 (dd, J = 6.7, 3.0 Hz, 1H), 7.00 (dd, J = 8.4, 3.2 Hz, 1H), 6.47 (d, J = 7.9 Hz, 1H), 4.92 (t, J = 8.1 Hz, 1H), 4.75 (t, J = 8.6 Hz, OH), 2.55 (d, J = 8.7 Hz, 3H), 1.83-1.65 (m, 5H), 1.37 (td, J = 8.6, 8.2, 4.5 Hz, 1H), 0.76-0.28 (m, 3H). |
| 614 | 1H NMR (400 MHz, DMSO-d6) δ 8.42 (s, 1H), 8.19 (s, 1H), 7.88-7.79 (m, 2H), 7.49 (t, J = 7.0 Hz, 2H), 7.19 (d, J = 2.5 Hz, 1H), 7.17-6.97 (m, 6H), 6.29 (d, J = 6.6 Hz, 1H), 4.27 (dd, J = 14.0, 8.3 Hz, 1H), 3.63 (dd, J = 13.9, 5.1 Hz, 1H), 2.47 (s, 3H), 1.83-1.63 (m, 4H), 1.19 (d, J = 42.4 Hz, 6H). |
| 615 | 1H NMR (400 MHz, DMSO-d6) δ 8.40 (d, J = 2.4 Hz, 2H), 7.99 (t, J = 7.1 Hz, 1H), 7.86 (d, J = 2.3 Hz, 1H), 7.80 (t, J = 8.3 Hz, 1H), 7.50 (d, J = 7.7 Hz, 1H), 7.34 (d, J = 2.5 Hz, 1H), 6.98 (dd, J = 8.4, 3.0 Hz, 1H), 6.27 (d, J = 7.5 Hz, 1H), 4.19 (dd, J = 14.7, 7.6 Hz, 1H), 3.85 (dd, J = 14.7, 6.4 Hz, 1H), 2.46 (s, 3H), 1.81-1.63 (m, 4H), 1.29 (d, J = 18.6 Hz, 6H). |
| 616 | 1H NMR (400 MHz, Methanol-d4) δ 9.56 (s, 1H), 8.59 (d, J = 6.2 Hz, 1H), 8.48 (s, 1H), 8.14 (s, 1H), 8.04 (d, J = 6.3 Hz, 1H), 7.84 (dd, J = 8.3, 5.4 Hz, 1H), 7.68 (d, J = 2.3 Hz, 1H), 7.44-7.35 (m, 1H), 6.93 (d, J = 2.3 Hz, 1H), 6.80 (s, 1H), 3.98 (d, J = 13.9 Hz, 1H), 3.67 (d, J = 14.0 Hz, 1H), 1.77-1.55 (m, 3H), 0.73 (s, 10H). |
| 617 | 1H NMR (400 MHz, Methanol-d4) δ 8.94 (d, J = 4.3 Hz, 1H), 8.59 (d, J = 8.8 Hz, 1H), 8.48 (s, 1H), 8.10 (s, 1H), 7.69 (d, J = 2.2 Hz, 1H), 7.64 (ddd, J = 16.5, 8.5, 4.6 Hz, 2H), 6.91 (d, J = 2.4 Hz, 1H), 6.81 (s, 1H), 4.00 (d, J = 13.9 Hz, 1H), 3.63 (d, J = 13.9 Hz, 1H), 1.76-1.52 (m, 3H), 0.70 (s, 11H). |
| 618 | 1H NMR (400 MHz, Methanol-d4) δ 8.47 (s, 1H), 8.38-8.31 (m, 1H), 8.06 (s, 1H), 7.73 (dd, J = 8.0, 1.0 Hz, 1H), 7.66 (d, J = 2.3 Hz, 1H), 7.53-7.44 (m, 1H), 7.41 (d, J = 7.7 Hz, 1H), 6.86 (d, J = 2.3 Hz, 1H), 6.82 (d, J = 7.6 Hz, 1H), 6.60 (s, 1H), 4.02 (d, J = 13.8 Hz, 1H), 3.66 (d, J = 13.8 Hz, 1H), 3.61 (s, 3H), 1.79-1.59 (m, 4H), 0.78 (s, 9H). |
| 619 | 1H NMR (400 MHz, Methanol-d4) δ 8.87 (s, 1H), 8.54 (s, 1H), 8.08 (s, 1H), 7.64 (d, J = 2.3 Hz, 1H), 7.17 (d, J = 2.3 Hz, 1H), 6.42 (s, 1H), 5.94 (t, J = 54.6 Hz, 1H), 4.07 (d, J = 13.9 Hz, 1H), 3.91 (d, J = 14.0 Hz, 1H), 2.44 (s, 3H), 1.54 (m, 4H), 1.00 (s, 9H). |
| 620 | 1H NMR (400 MHz, Methanol-d4) δ 8.79 (s, 1H), 8.49 (s, 1H), 8.00 (s, 1H), 7.69 (d, J = 2.3 Hz, 1H), 7.26 (d, J = 2.3 Hz, 1H), 6.31 (s, 1H), 5.91 (t, J = 54.8 Hz, 1H), 4.09 (d, J = 13.9 Hz, 1H), 3.93 (d, J = 14.0 Hz, 1H), 2.56 (s, 3H), 1.50 (m, 4H), 1.05 (s, 9H). |
| 621 | 1H NMR (400 MHz, Methanol-d4) δ 8.35 (s, 1H), 8.01 (s, 1H), 7.80 (t, J = 8.3 Hz, 1H), 7.77 (d, J = 2.5 Hz, 1H), 7.07 (d, J = 2.5 Hz, 1H), 6.87 (dd, J = 8.4, 2.7 Hz, 1H), 6.20 (s, 1H), 3.87 (d, J = 13.8 Hz, 1H), 3.68 (d, J = 13.8 Hz, 1H), 2.51 (s, 3H), 1.54 (m, 1H), 1.28-1.19 (m, 2H), 1.09-0.98 (m, 2H), 0.89 (s, 9H), 0.58-0.46 (m, 2H), 0.38-0.29 (m, 2H). |
| 622 | 1H NMR (400 MHz, Methanol-d4) δ 8.39 (s, 1H), 7.93 (s, 1H), 7.81-7.74 (m, 2H), 7.67-7.60 (m, 1H), 7.56 (dd, J = 7.1, 3.3 Hz, 1H), 7.10 (d, J = 2.6 Hz, 1H), 6.87 (dd, J = 8.5, 2.7 Hz, 1H), 6.22 (s, 1H), 4.98-4.78 (m, 1H), 3.92-3.83 (m, |

TABLE 2-continued

| Compound | ¹H-NMR |
|---|---|
| | 2H), 3.74 (d, J = 13.9 Hz, 1H), 2.51 (s, 3H), 2.01-1.88 (m, 1H), 1.60 (m, 1H), 0.90 (s, 9H). |
| 623 | 1H NMR (400 MHz, Methanol-d4) δ 8.39 (s, 1H), 7.94 (s, 1H), 7.82-7.75 (m, 2H), 7.11 (d, J = 2.5 Hz, 1H), 6.87 (dd, J = 8.6, 2.8 Hz, 1H), 6.23 (s, 1H), 5.01 (m, 1H), 4.76-4.71 (m, 1H), 4.66-4.60 (m, 1H), 3.90 (d, J = 13.9 Hz, 1H), 3.72 (d, J = 13.9 Hz, 1H), 2.51 (s, 3H), 1.57 (d, J = 7.1 Hz, 3H), 0.90 (s, 9H). |
| 625 | 1H NMR (400 MHz, Methanol-d4) δ 8.37 (s, 1H), 7.98 (s, 1H), 7.83-7.76 (m, 2H), 7.08 (d, J = 2.5 Hz, 1H), 6.87 (dd, J = 8.6, 2.7 Hz, 1H), 6.22 (s, 1H), 4.62 (d, J = 47.1 Hz, 2H), 3.88 (d, J = 13.8 Hz, 1H), 3.70 (d, J = 13.8 Hz, 1H), 2.50 (s, 3H), 1.67 (s, 6H), 0.89 (s, 9H). |
| 626 | 1H NMR (400 MHz, Methanol-d4) δ 9.66 (s, 1H), 8.62 (d, J = 6.4 Hz, 1H), 8.32 (s, 1H), 8.24 (d, J = 6.4 Hz, 1H), 8.19 (s, 1H), 7.96 (dd, J = 8.2, 5.2 Hz, 1H), 7.80 (d, J = 2.5 Hz, 1H), 7.47 (dd, J = 9.8, 8.3 Hz, 1H), 7.11 (d, J = 2.5 Hz, 1H), 6.83 (s, 1H), 3.78 (d, J = 13.7 Hz, 1H), 3.53 (d, J = 13.7 Hz, 1H), 1.79-1.68 (m, 2H), 1.64 (t, J = 9.7 Hz, 2H), 0.69 (s, 10H). |
| 627 | 1H NMR (400 MHz, Methanol-d4) δ 8.95 (dd, J = 4.4, 1.4 Hz, 1H), 8.70-8.61 (m, 1H), 8.32 (s, 1H), 8.12 (s, 1H), 7.81 (d, J = 2.5 Hz, 1H), 7.66 (ddd, J = 13.4, 8.4, 4.5 Hz, 2H), 7.48 (dd, J = 10.3, 8.2 Hz, 1H), 7.07 (d, J = 2.5 Hz, 1H), 6.82 (s, 1H), 3.78 (d, J = 13.7 Hz, 1H), 3.48 (d, J = 13.7 Hz, 1H), 1.78-1.54 (m, 4H), 0.64 (s, 10H). |
| 628 | 1H NMR (400 MHz, Methanol-d4) δ 9.49 (s, 1H), 8.51 (s, 1H), 8.47 (s, 1H), 8.37 (d, J = 8.1 Hz, 1H), 8.26 (s, 1H), 8.24 (d, J = 8.6 Hz, 1H), 8.02 (ddd, J = 8.5, 7.0, 1.3 Hz, 1H), 7.90 (ddd, J = 8.1, 7.0, 1.0 Hz, 1H), 7.68 (d, J = 2.3 Hz, 1H), 7.02 (d, J = 2.3 Hz, 1H), 6.94 (s, 1H), 3.93 (d, J = 13.9 Hz, 1H), 3.68 (d, J = 13.9 Hz, 1H), 1.78-1.58 (m, 4H), 0.73 (s, 9H). |
| 629 | 1H NMR (400 MHz, Methanol-d4) δ 9.36 (d, J = 2.2 Hz, 1H), 9.06-9.02 (m, 1H), 8.48 (d, J = 2.1 Hz, 2H), 8.15-8.09 (m, 2H), 7.94 (ddd, J = 8.4, 6.9, 1.4 Hz, 2H), 7.77-7.71 (m, 2H), 7.52 (d, J = 2.3 Hz, 1H), 7.27 (d, J = 2.3 Hz, 1H), 4.05 (s, 2H), 3.80 (t, J = 6.3 Hz, 2H), 3.60 (t, J = 6.3 Hz, 2H), 1.78-1.63 (m, 1H), 1.10 (d, J = 2.1 Hz, 9H). |
| 630 | 1H NMR (400 MHz, Methanol-d4) δ 8.52 (s, 1H), 8.13 (m, 2H), 7.65 (d, J = 2.3 Hz, 1H), 7.30 (d, J = 2.3 Hz, 1H), 6.36 (s, 1H), 5.93 (t, J = 54.6 Hz, 1H), 4.11-3.89 (m, 2H), 2.15 (s, 3H), 1.53 (s, 4H), 1.04 (s, 9H). |
| 631 | 1H NMR (400 MHz, Methanol-d4) δ 8.34 (d, J = 7.9 Hz, 1H), 8.34 (s, 1H), 8.08 (s, 1H), 7.80 (d, J = 2.5 Hz, 1H), 7.77-7.69 (m, 1H), 7.48 (t, J = 7.8 Hz, 1H), 7.42 (d, J = 7.7 Hz, 1H), 7.02 (d, J = 2.5 Hz, 1H), 6.89-6.81 (m, 1H), 6.60 (s, 1H), 3.83 (d, J = 13.6 Hz, 1H), 3.61 (s, 3H), 3.54 (d, J = 13.7 Hz, 1H), 1.78-1.59 (m, 4H), 0.73 (s, 9H). |
| 632 | 1H NMR (400 MHz, Methanol-d4) δ 9.03 (d, J = 6.7 Hz, 1H), 8.46 (s, 1H), 8.15 (s, 1H), 8.13-7.98 (m, 3H), 7.65 (d, J = 2.2 Hz, 1H), 7.50 (d, J = 6.7 Hz, 1H), 7.12 (s, 1H), 6.77 (s, 1H), 4.09 (s, 3H), 4.06 (d, J = 14.0 Hz, 1H), 3.51 (d, J = 14.0 Hz, 1H), 1.84-1.55 (m, 4H), 0.69 (s, 9H). |
| 633 | 1H NMR (400 MHz, DMSO-d6) δ 8.35 (d, J = 6.9 Hz, 2H), 7.92 (t, J = 7.0 Hz, 1H), 7.79 (t, J = 8.3 Hz, 1H), 7.60 (d, J = 2.2 Hz, 1H), 7.36 (t, J = 7.8 Hz, 1H), 7.02 (d, J = 2.3 Hz, 1H), 6.99-6.92 (m, 1H), 6.24 (d, J = 7.0 Hz, 1H), 4.20 (dd, J = 14.7, 7.6 Hz, 1H), 3.81 (dd, J = 14.7, 6.3 Hz, 1H), 2.44 (s, 3H), 1.77-1.62 (m, 4H), 1.29 (s, 3H), 1.23 (s, 3H). |
| 634 | 1H NMR (400 MHz, Methanol-d4) δ 8.38 (s, 1H), 7.92 (s, 1H), 7.84-7.75 (m, 2H), 7.13 (d, J = 2.5 Hz, 1H), 6.87 (dd, J = 8.5, 2.7 Hz, 1H), 6.43-6.09 (m, 2H), 4.88 (ddd, J = 14.9, 3.4, 1.1 Hz, 2H), 3.89 (d, J = 13.8 Hz, 1H), 3.70 (d, J = 13.8 Hz, 1H), 2.51 (s, 3H), 0.90 (s, 9H). |
| 635 | 1H NMR (400 MHz, DMSO-d6) δ 8.38 (d, J = 3.9 Hz, 2H), 7.80 (t, J = 8.3 Hz, 1H), 7.64 (d, J = 2.2 Hz, 1H), 7.40 (t, J = 8.2 Hz, 1H), 6.99-6.87 (m, 2H), 6.24 (d, J = 6.5 Hz, 1H), 3.97 (dd, J = 13.9, 8.1 Hz, 1H), 3.61 (dd, J = 13.9, 4.8 Hz, 1H), 3.52-3.33 (m, 2H), 2.44 (s, 3H), 1.81-1.64 (m, 3H), 0.85 (d, J = 3.2 Hz, 6H). |
| 636 | 1H NMR (400 MHz, DMSO-d6) δ 8.37 (d, J = 2.2 Hz, 2H), 7.81 (t, J = 8.3 Hz, 1H), 7.61 (d, J = 2.2 Hz, 1H), 7.49-7.35 (m, 2H), 7.02-6.90 (m, 2H), 6.26 (d, J = 7.0 Hz, 1H), 5.73 (t, J = 56.1 Hz, 1H), 4.30 (dd, J = 14.6, 7.1 Hz, 1H), 3.85 (dd, J = 14.6, 4.9 Hz, 1H), 2.48 (s, 3H), 1.80-1.62 (m, 3H), 0.81-0.62 (m, 4H). |
| 637 | 1H NMR (400 MHz, DMSO-d6) δ 8.39 (d, J = 7.2 Hz, 2H), 7.86 (d, J = 2.4 Hz, 1H), 7.80 (t, J = 8.2 Hz, 1H), 7.50 (d, J = 7.3 Hz, 1H), 7.19 (s, 1H), 6.99-6.90 (m, 1H), 6.25 (d, J = 7.3 Hz, 1H), 4.00-3.86 (m, 1H), 3.47 (d, J = 11.0 Hz, 3H), 2.44 (s, 3H), 1.84-1.60 (m, 3H), 0.85 (d, J = 3.5 Hz, 6H). |
| 638 | 1H NMR (400 MHz, DMSO-d6) δ 8.38 (s, 2H), 7.87-7.77 (m, 2H), 7.48 (d, J = 7.8 Hz, 1H), 7.38 (t, J = 6.2 Hz, 1H), 7.25 (d, J = 2.5 Hz, 1H), 6.97 (dd, J = 8.5, 3.0 Hz, 1H), 6.28 (d, J = 7.3 Hz, 1H), 5.73 (t, J = 56.1 Hz, 1H), 4.31-4.22 (m, 1H), 3.84 (dd, J = 14.6, 4.9 Hz, 1H), 2.48 (s, 3H), 1.83-1.59 (m, 4H), 0.80-0.62 (m, 4H). |
| 639 | 1H NMR (400 MHz, Methanol-d4) δ 8.50 (s, 1H), 8.05 (s, 1H), 7.65 (d, J = 2.2 Hz, 1H), 7.22 (s, 1H), 6.11-5.74 (m, 2H), 4.05 (d, J = 14.0 Hz, 1H), 3.95 (d, J = 14.1 Hz, 1H), 2.38 (s, 3H), 2.26 (s, 3H), 1.52 (s, 4H), 1.04 (s, 9H). |
| 640 | 1H NMR (400 MHz, Methanol-d4) δ 8.92 (s, 1H), 8.41 (s, 1H), 8.11 (s, 1H), 7.79 (d, J = 2.5 Hz, 1H), 7.35 (d, J = 2.5 Hz, 1H), 6.43 (s, 1H), 5.94 (t, J = 54.7 Hz, 1H), 3.93 (d, J = 13.9 Hz, 1H), 3.77 (d, J = 13.9 Hz, 1H), 2.45 (s, 3H), 1.53 (m, 4H), 0.97 (s, 9H). |
| 641 | 1H NMR (400 MHz, Methanol-d4) δ 8.78 (s, 1H), 8.37 (s, 1H), 8.02 (s, 1H), 7.83 (d, J = 2.5 Hz, 1H), 7.44 (d, J = 2.5 Hz, 1H), 6.32 (s, 1H), 5.92 (t, J = 54.8 Hz, |

TABLE 2-continued

| Compound | ¹H-NMR |
|---|---|
| | 1H), 3.96 (d, J = 13.9 Hz, 1H), 3.80 (d, J = 13.9 Hz, 1H), 2.56 (s, 3H), 1.50 (m, 4H), 1.02 (s, 9H). |
| 642 | 1H NMR (400 MHz, Methanol-d4) δ 8.38 (s, 1H), 8.01 (s, 1H), 7.85-7.74 (m, 2H), 7.11 (d, J = 2.5 Hz, 1H), 6.87 (dd, J = 8.5, 2.8 Hz, 1H), 6.23 (s, 1H), 3.92 (d, J = 13.8 Hz, 1H), 3.68 (d, J = 13.9 Hz, 1H), 2.95 (s, 6H), 2.50 (s, 3H), 1.68 (m, 2H), 1.66 (m, 2H), 0.91 (s, 9H). |
| 643 | 1H NMR (400 MHz, Methanol-d4) δ 8.48 (s, 1H), 7.79 (t, J = 8.0 Hz, 1H), 7.63 (d, J = 2.3 Hz, 1H), 6.90-6.83 (m, 1H), 6.81 (d, J = 2.3 Hz, 1H), 6.08 (s, 1H), 4.05 (d, J = 13.9 Hz, 1H), 3.78-3.68 (m, 2H), 2.43 (s, 3H), 1.33-1.23 (m, 4H), 0.90 (s, 9H). |
| 644 | 1H NMR (400 MHz, Methanol-d4) δ 8.36 (s, 1H), 8.26 (s, 1H), 7.85-7.76 (m, 2H), 7.12 (d, J = 2.5 Hz, 1H), 6.89 (dd, J = 8.6, 2.7 Hz, 1H), 6.30 (s, 1H), 5.24 (m, 2H), 5.18 (m, 2H), 3.85 (d, J = 13.9 Hz, 1H), 3.70 (d, J = 13.8 Hz, 1H), 2.53 (s, 3H), 0.89 (s, 9H). |
| 645 | 1H NMR (400 MHz, Methanol-d4) δ 8.49 (s, 1H), 7.97 (s, 1H), 7.79 (t, J = 8.1 Hz, 1H), 7.62 (d, J = 2.3 Hz, 1H), 6.90 (d, J = 2.3 Hz, 1H), 6.90-6.85 (m, 1H), 6.22 (s, 1H), 5.08 (q, J = 6.7, 6.1 Hz, 1H), 4.02 (d, J = 13.9 Hz, 1H), 3.82 (d, J = 13.9 Hz, 1H), 3.29-3.16 (m, 4H), 2.51 (s, 3H), 0.93 (s, 9H). |
| 646 | 1H NMR (400 MHz, Methanol-d4) δ 8.48 (s, 1H), 7.91 (s, 1H), 7.76 (t, J = 8.1 Hz, 1H), 7.62 (d, J = 2.3 Hz, 1H), 6.89 (d, J = 2.2 Hz, 2H), 6.86 (d, J = 2.8 Hz, 1H), 6.20 (s, 1H), 3.99 (d, J = 13.9 Hz, 1H), 3.84 (d, J = 13.9 Hz, 1H), 2.69 (s, 1H), 2.51 (s, 3H), 2.37 (s, 6H), 0.92 (s, 9H). |
| 647 | 1H NMR (400 MHz, Methanol-d4) δ 8.47 (s, 1H), 7.78 (t, J = 8.1 Hz, 1H), 7.61 (d, J = 2.2 Hz, 1H), 6.85 (dd, J = 8.6, 2.7 Hz, 1H), 6.80 (d, J = 2.3 Hz, 1H), 6.11 (s, 1H), 4.05 (d, J = 13.8 Hz, 1H), 3.72 (d, J = 13.9 Hz, 1H), 3.69-3.58 (m, 1H), 2.42 (s, 3H), 2.34 (s, 3H), 1.29-1.15 (m, 4H), 0.90 (s, 9H). |
| 648 | 1H NMR (400 MHz, Methanol-d4) δ 8.51 (s, 1H), 7.99 (s, 1H), 7.81 (t, J = 8.1 Hz, 1H), 7.64 (d, J = 2.3 Hz, 1H), 6.92 (d, J = 2.3 Hz, 1H), 6.87 (dd, J = 8.5, 2.7 Hz, 1H), 6.24 (s, 1H), 5.08 (d, J = 7.1 Hz, 1H), 5.03 (d, J = 7.1 Hz, 1H), 4.84-4.82 (m, 12), 4.14 (s, 2H), 4.04 (d, J = 13.9 Hz, 1H), 3.83 (d, J = 13.9 Hz, 1H), 2.52 (s, 3H), 0.94 (s, 9H). |
| 649 | 1H NMR (400 MHz, Methanol-d4) δ 8.37 (s, 1H), 7.91 (s, 1H), 7.83-7.72 (m, 2H), 7.08 (d, J = 2.5 Hz, 1H), 6.87 (dd, J = 8.4, 2.8 Hz, 1H), 6.21 (s, 1H), 3.85 (d, J = 13.8 Hz, 1H), 3.72 (d, J = 13.8 Hz, 1H), 2.69 (s, 1H), 2.52 (s, 3H), 2.37 (s, 6H), 0.89 (s, 9H). |
| 650 | 1H NMR (400 MHz, Methanol-d4) δ 8.38 (s, 1H), 8.06 (dd, J = 5.4, 1.8 Hz, 1H), 7.92 (s, 1H), 7.81 (dd, J = 7.6, 1.8 Hz, 1H), 7.49 (d, J = 2.3 Hz, 1H), 7.06 (d, J = 2.3 Hz, 1H), 7.02 (dd, J = 7.6, 5.4 Hz, 1H), 4.10 (d, J = 14.0 Hz, 1H), 3.78 (ddd, J = 11.4, 7.1, 4.2 Hz, 1H), 3.63 (d, J = 14.0 Hz, 1H), 2.97 (s, 6H), 1.12-1.02 (m, 4H), 0.91 (s, 9H). |
| 651 | 1H NMR (400 MHz, Methanol-d4) δ 9.72 (s, 1H), 8.61 (d, J = 6.1 Hz, 1H), 8.50 (s, 1H), 8.18 (s, 1H), 8.09 (d, J = 6.1 Hz, 1H), 7.88-7.75 (m, 2H), 7.70 (dd, J = 7.9, 2.3 Hz, 1H), 6.91 (d, J = 2.3 Hz, 1H), 6.83 (s, 1H), 4.02 (d, J = 13.9 Hz, 1H), 3.62 (d, J = 13.9 Hz, 1H), 1.78-1.54 (m, 4H), 0.70 (s, 9H). |
| 652 | 1H NMR (400 MHz, Methanol-d4) δ 9.56 (s, 1H), 8.59 (d, J = 6.2 Hz, 1H), 8.48 (s, 1H), 8.05 (d, J = 6.2 Hz, 1H), 8.01 (s, 1H), 7.84 (dd, J = 8.2, 5.1 Hz, 1H), 7.68 (d, J = 2.3 Hz, 1H), 7.39 (dd, J = 9.9, 8.2 Hz, 1H), 6.93 (d, J = 2.3 Hz, 1H), 6.79 (s, 1H), 5.91 (t, J = 54.6 Hz, 1H), 4.00 (d, J = 13.9 Hz, 1H), 3.66 (d, J = 13.8 Hz, 1H), 1.50 (d, J = 4.1 Hz, 4H), 0.72 (s, 9H). |
| 653 | 1H NMR (400 MHz, Methanol-d4) δ 8.94 (dd, J = 4.3, 1.4 Hz, 1H), 8.60 (dt, J = 8.9, 1.5 Hz, 1H), 8.49 (s, 1H), 7.97 (s, 1H), 7.69 (d, J = 2.3 Hz, 1H), 7.64 (ddd, J = 18.1, 8.4, 4.5 Hz, 2H), 7.47 (dd, J = 10.3, 8.2 Hz, 1H), 6.91 (d, J = 2.3 Hz, 1H), 6.80 (s, 1H), 5.90 (t, J = 54.7 Hz, 1H), 4.01 (d, J = 13.9 Hz, 1H), 3.62 (d, J = 13.9 Hz, 1H), 1.55-1.42 (m, 4H), 0.70 (s, 9H). |
| 654 | 1H NMR (400 MHz, DMSO-d6) δ 8.32 (s, 1H), 8.03 (s, 1H), 7.78 (t, J = 8.3 Hz, 1H), 7.61-7.40 (m, 2H), 7.34 (d, J = 7.4 Hz, 2H), 7.23-7.13 (m, 2H), 6.98-6.89 (m, 1H), 6.24 (d, J = 6.8 Hz, 1H), 5.63 (s, 2H), 4.11 (s, 1H), 3.88 (dd, J = 13.8, 8.0 Hz, 1H), 3.40 (dd, J = 13.7, 5.2 Hz, 1H), 2.43 (s, 3H), 0.78 (s, 9H). |
| 655 | 1H NMR (400 MHz, DMSO-d6) δ 8.31-8.21 (m, 2H), 7.99 (s, 1H), 7.62 (d, J = 2.1 Hz, 1H), 7.55-7.46 (m, 2H), 7.34-7.23 (m, 3H), 7.22-7.11 (m, 3H), 6.49 (d, J = 6.8 Hz, 1H), 5.62 (s, 2H), 4.15 (s, 1H), 4.04-3.93 (m, 4H), 3.34 (dd, J = 13.8, 5.1 Hz, 1H), 0.80 (s, 9H). |
| 656 | 1H NMR (400 MHz, DMSO-d6) δ 8.30-8.20 (m, 2H), 8.00 (s, 1H), 7.85 (d, J = 2.3 Hz, 1H), 7.61 (d, J = 7.7 Hz, 1H), 7.56-7.35 (m, 4H), 7.34-7.23 (m, 2H), 7.22-7.11 (m, 1H), 6.51 (d, J = 7.0 Hz, 1H), 5.62 (s, 2H), 4.13 (s, 1H), 3.98 (s, 3H), 3.99-3.88 (m, 1H), 3.32 (dd, J = 13.8, 5.1 Hz, 1H), 0.79 (s, 9H). |
| 657 | 1H NMR (400 MHz, Methanol-d4) δ 8.37 (s, 1H), 8.13 (m, 2H), 7.78 (d, J = 2.5 Hz, 1H), 7.46 (d, J = 2.5 Hz, 1H), 6.36 (s, 1H), 5.94 (t, J = 54.7 Hz, 1H), 3.86 (m, 2H), 2.16 (s, 3H), 1.52 (m, 4H), 1.01 (s, 9H). |
| 658 | 1H NMR (400 MHz, Methanol-d4) δ 8.47 (s, 1H), 8.22 (d, J = 5.1 Hz, 1H), 8.05 (s, 1H), 7.70 (d, J = 2.3 Hz, 1H), 7.40 (d, J = 3.6 Hz, 1H), 7.23 (d, J = 5.1 Hz, 1H), 6.98 (d, J = 2.3 Hz, 1H), 6.59 (d, J = 3.6 Hz, 1H), 6.50 (s, 1H), 4.13 (d, J = 13.9 Hz, 1H), 3.86 (s, 3H), 3.60 (d, J = 13.9 Hz, 1H), 1.75-1.57 (m, 4H), 0.82 (s, 9H). |
| 659 | 1H NMR (400 MHz, Methanol-d4) δ 9.54 (s, 1H), 8.48 (s, 1H), 8.41 (d, J = 8.3 Hz, 2H), 8.18 (s, 1H), 8.05 (d, J = 7.2 Hz, 1H), 7.87 (t, J = 7.8 Hz, 1H), 7.63 (d, J = 2.2 Hz, 1H), 7.16 (s, 1H), 6.98 (d, J = 2.3 Hz, 1H), 5.13-4.50 (m, 21H), 3.93 |

TABLE 2-continued

| Compound | ¹H-NMR |
|---|---|
| | (d, J = 14.0 Hz, 1H), 3.83 (d, J = 13.9 Hz, 1H), 3.01 (s, 3H), 1.79-1.64 (m, 4H), 0.82 (s, 9H). |
| 660 | 1H NMR (400 MHz, Methanol-d4) δ 8.97 (d, J = 5.4 Hz, 1H), 8.48 (d, J = 8.4 Hz, 2H), 8.28 (s, 1H), 8.19 (d, J = 1.2 Hz, 2H), 7.85 (dd, J = 5.4, 1.0 Hz, 1H), 7.73 (d, J = 2.3 Hz, 1H), 7.17 (d, J = 2.3 Hz, 1H), 6.47 (s, 1H), 4.95-4.81 (m, 3H), 4.11 (d, J = 14.0 Hz, 1H), 3.72 (d, J = 14.0 Hz, 1H), 2.92 (d, J = 0.9 Hz, 3H), 1.81-1.64 (m, 4H), 0.84 (s, 9H). |
| 661 | 1H NMR (400 MHz, Methanol-d4) δ 8.39 (s, 1H), 8.34 (s, 1H), 7.84-7.75 (m, 2H), 7.15 (d, J = 2.5 Hz, 1H), 6.88 (dd, J = 8.5, 2.8 Hz, 1H), 6.31 (s, 1H), 4.38 (t, J = 10.8, 2H), 3.86 (d, J = 13.9 Hz, 1H), 3.75 (d, J = 13.9 Hz, 1H), 2.54 (s, 3H), 0.90 (s, 9H). |
| 662 | 1H NMR (400 MHz, Methanol-d4) δ 8.49 (s, 1H), 7.82 (t, J = 8.1 Hz, 1H), 7.64 (d, J = 2.3 Hz, 1H), 6.87 (m, 2H), 6.17 (s, 1H), 4.03 (d, J = 13.8 Hz, 1H), 3.79 (d, J = 13.9 Hz, 1H), 3.72 (m, 1H), 2.47 (s, 3H), 1.34-1.18 (m, 3H), 0.92 (s, 9H). |
| 663 | 1H NMR (400 MHz, Methanol-d4) δ 8.48 (s, 1H), 7.86 (t, J = 8.1 Hz, 1H), 7.62 (d, J = 2.3 Hz, 1H), 6.94-6.83 (m, 2H), 6.17 (s, 1H), 4.03 (d, J = 13.9 Hz, 1H), 3.79 (d, J = 13.9 Hz, 1H), 3.71-3.63 (m, 1H), 2.51 (s, 3H), 1.32-1.17 (m, 4H), 0.93 (s, 9H). |
| 664 | 1H NMR (400 MHz, Methanol-d4) δ 8.34 (s, 1H), 8.27 (d, J = 5.2 Hz, 1H), 8.14 (s, 1H), 7.83 (d, J = 2.5 Hz, 1H), 7.46 (d, J = 3.6 Hz, 1H), 7.34 (d, J = 5.3 Hz, 1H), 7.15 (d, J = 2.5 Hz, 1H), 6.70 (d, J = 3.6 Hz, 1H), 6.54 (s, 1H), 3.95 (d, J = 13.8 Hz, 1H), 3.89 (s, 3H), 3.47 (d, J = 13.7 Hz, 1H), 1.78-1.52 (m, 4H), 0.77 (s, 9H). |
| 665 | 1H NMR (400 MHz, Methanol-d4) δ 8.51 (s, 1H), 8.08 (s, 1H), 7.65 (d, J = 2.3 Hz, 1H), 7.41 (d, J = 2.0 Hz, 1H), 7.18 (d, J = 2.3 Hz, 1H), 6.29 (s, 1H), 6.16 (d, J = 2.0 Hz, 1H), 5.93 (t, J = 54.7 Hz, 1H), 4.08-3.90 (m, 2H), 3.85 (s, 3H), 1.54 (s, 4H), 1.02 (s, 9H). |
| 666 | 1H NMR (400 MHz, Methanol-d4) δ 8.49 (s, 1H), 8.23 (s, 1H), 7.64 (d, J = 2.3 Hz, 1H), 7.41 (d, J = 2.0 Hz, 1H), 7.17 (d, J = 2.3 Hz, 1H), 6.31 (s, 1H), 6.15 (d, J = 2.0 Hz, 1H), 3.97 (q, J = 14.0 Hz, 2H), 3.85 (s, 3H), 1.84-1.60 (m, 4H), 1.01 (s, 9H). |
| 667 | 1H NMR (400 MHz, Methanol-d4) δ 9.61 (s, 1H), 8.44 (d, J = 6.7 Hz, 2H), 8.30 (s, 1H), 8.20 (s, 1H), 8.13 (d, J = 6.5 Hz, 1H), 7.96-7.87 (m, 1H), 7.74 (d, J = 2.5 Hz, 1H), 7.16 (s, 1H), 7.11 (d, J = 2.5 Hz, 1H), 3.74 (d, J = 13.8 Hz, 1H), 3.63 (d, J = 13.8 Hz, 1H), 3.04 (s, 3H), 1.74 (s, 2H), 1.66 (s, 2H), 0.76 (s, 9H). |
| 668 | 1H NMR (400 MHz, Methanol-d4) δ 8.99 (d, J = 5.5 Hz, 1H), 8.53 (s, 1H), 8.35-8.15 (m, 4H), 7.90 (d, J = 5.6 Hz, 1H), 7.83 (d, J = 2.5 Hz, 1H), 7.27 (d, J = 2.5 Hz, 1H), 6.45 (s, 1H), 3.90 (t, J = 13.5 Hz, 1H), 3.52 (d, J = 13.9 Hz, 1H), 2.95 (s, 3H), 1.76 (s, 2H), 1.67 (s, 2H), 0.78 (s, 9H). |
| 669 | 1H NMR (400 MHz, Methanol-d4) δ 8.15 (s, 1H), 7.66 (s, 1H), 7.55 (t, J = 8.1 Hz, 1H), 7.32 (d, J = 2.3 Hz, 1H), 6.52 (dd, J = 8.5, 2.7 Hz, 1H), 6.36 (d, J = 2.4 Hz, 1H), 5.85 (s, 1H), 4.20 (dd, J = 11.6, 4.3 Hz, 1H), 3.71 (dd, J = 11.8, 4.7 Hz, 1H), 3.26-3.14 (m, 1H), 3.15 (d, J = 11.5 Hz, 1H), 2.86 (d, J = 11.7 Hz, 1H), 2.09 (s, 3H), 1.82-1.66 (m, 1H), 1.59 (d, J = 13.2 Hz, 1H), 1.23 (ddd, J = 13.2, 8.2, 5.0 Hz, 1H), 1.05-0.79 (m, 2H), 0.79-0.61 (m, 2H), 0.53 (s, 3H), 0.25-0.18 (m, 2H), 0.18 (s, 3H), 0.10--0.05 (m, 2H). |
| 670 | 1H NMR (400 MHz, Methanol-d4) δ 9.61 (s, 1H), 8.69 (d, J = 6.1 Hz, 1H), 8.33 (s, 1H), 8.23 (s, 1H), 8.17 (d, J = 7.6 Hz, 1H), 8.16 (d, J = 6.1 Hz, 1H), 8.02 (d, J = 7.6 Hz, 1H), 7.83 (d, J = 2.5 Hz, 1H), 7.02 (d, J = 2.5 Hz, 1H), 6.91 (s, 1H), 3.82 (d, J = 13.8 Hz, 1H), 3.42 (d, J = 13.7 Hz, 1H), 1.79-1.55 (m, 4H), 0.62 (s, 9H). |
| 671 | 1H NMR (400 MHz, Methanol-d4) δ 8.95 (dd, J = 4.3, 1.4 Hz, 1H), 8.70-8.63 (m, 1H), 8.35 (s, 1H), 7.99 (s, 1H), 7.83 (d, J = 2.5 Hz, 1H), 7.67 (ddd, J = 15.5, 8.4, 4.6 Hz, 2H), 7.48 (dd, J = 10.3, 8.2 Hz, 1H), 7.08 (d, J = 2.5 Hz, 1H), 6.81 (s, 1H), 5.91 (t, J = 54.7 Hz, 1H), 3.82 (d, J = 13.7 Hz, 1H), 3.49 (d, J = 13.7 Hz, 1H), 1.55-1.42 (m, 4H), 0.65 (s, 9H). |
| 672 | 1H NMR (400 MHz, Methanol-d4) δ 9.56 (s, 1H), 8.59 (d, J = 6.2 Hz, 1H), 8.29 (s, 1H), 8.11 (d, J = 6.2 Hz, 1H), 8.02 (s, 1H), 7.87 (dd, J = 8.2, 5.2 Hz, 1H), 7.78 (d, J = 2.5 Hz, 1H), 7.39 (dd, J = 10.0, 8.2 Hz, 1H), 7.05 (d, J = 2.5 Hz, 1H), 6.79 (s, 1H), 5.92 (t, J = 54.8 Hz, 1H), 3.76 (d, J = 13.7 Hz, 1H), 3.44 (s, 1H), 1.50 (d, J = 3.2 Hz, 3H), 1.31 (t, J = 7.4 Hz, 1H), 0.65 (s, 9H). |
| 673 | 1H NMR (400 MHz, Methanol-d4) δ 9.64 (s, 1H), 8.58 (s, 1H), 8.49 (d, J = 8.1 Hz, 1H), 8.38-8.27 (m, 3H), 8.01 (d, J = 7.7 Hz, 1H), 7.81 (d, J = 2.5 Hz, 1H), 7.15 (d, J = 2.5 Hz, 1H), 6.98 (s, 1H), 3.74 (d, J = 13.7 Hz, 1H), 3.50 (d, J = 13.9 Hz, 1H), 1.80-1.59 (m, 4H), 0.66 (s, 10H). |
| 674 | 1H NMR (400 MHz, Methanol-d4) δ 8.39 (s, 1H), 8.06 (s, 1H), 7.80 (d, J = 2.5 Hz, 1H), 7.42 (d, J = 2.5 Hz, 1H), 6.14-5.73 (m, 2H), 3.93 (d, J = 13.9 Hz, 1H), 3.84 (d, J = 13.9 Hz, 1H), 2.37 (s, 3H), 2.26 (s, 3H), 1.51 (m, 4H), 1.01 (s, 9H). |
| 675 | 1H NMR (400 MHz, Methanol-d4) δ 8.36 (s, 1H), 7.99 (s, 1H), 7.90 (t, J = 8.1 Hz, 1H), 7.80 (d, J = 2.5 Hz, 1H), 6.90 (d, J = 2.5 Hz, 1H), 6.85 (dd, J = 8.4, 2.7 Hz, 1H), 6.19 (s, 1H), 4.35 (dd, J = 11.1, 4.9 Hz, 1H), 4.11-3.95 (m, 1H), 3.53 (td, J = 11.6, 3.3 Hz, 1H), 3.49-3.42 (m, 1H), 3.18 (d, J = 11.6 Hz, 1H), 2.44 (s, 3H), 2.04-1.84 (m, 2H), 1.57 (ddd, J = 13.2, 8.4, 5.0 Hz, 2H), 1.33-1.17 (m, 2H), 1.12-0.97 (m, 2H), 0.86 (s, 3H), 0.62-0.51 (m, 2H), 0.49 (s, 3H), 0.36 (dt, J = 6.4, 4.8 Hz, 2H). |
| 676 | 1H NMR (400 MHz, Methanol-d4) δ 8.50 (s, 1H), 8.37-8.29 (m, 1H), 8.06 (s, 1H), 7.75 (dd, J = 7.6, 1.3 Hz, 1H), 7.68 (d, J = 2.3 Hz, 1H), 7.48 (t, J = 7.8 Hz, 1H), 7.22 (d, J = 7.5 Hz, 1H), 6.89 (d, J = 2.3 Hz, 1H), 6.80 (d, J = 7.5 Hz, 1H), |

TABLE 2-continued

| Compound | ¹H-NMR |
|---|---|
| | 6.61 (s, 1H), 4.05 (d, J = 13.8 Hz, 1H), 3.68 (d, J = 13.8 Hz, 1H), 1.79-1.55 (m, 4H), 0.80 (s, 9H). |
| 677 | 1H NMR (400 MHz, Methanol-d4) δ 8.40 (s, 1H), 8.09 (s, 1H), 7.80 (d, J = 2.4 Hz, 1H), 7.39 (m, 2H), 6.31 (s, 1H), 6.15 (d, J = 2.0 Hz, 1H), 5.94 (t, J = 54.7 Hz, 1H), 3.86 (d, J = 3.9 Hz, 4H), 1.53 (s, 4H), 0.98 (s, 9H). |
| 678 | 1H NMR (400 MHz, Methanol-d4) δ 8.35 (s, 1H), 8.22 (s, 1H), 7.78 (d, J = 2.5 Hz, 1H), 7.38 (m, 2H), 6.32 (s, 1H), 6.14 (d, J = 2.0 Hz, 1H), 3.92-3.73 (m, 5H), 1.81-1.60 (m, 4H), 0.97 (s, 9H). |
| 679 | 1H NMR (400 MHz, Methanol-d4) δ 8.17 (s, 1H), 8.09 (dd, J = 2.5, 0.7 Hz, 1H), 7.83 (s, 1H), 7.57 (dd, J = 8.9, 2.5 Hz, 1H), 7.47 (d, J = 2.4 Hz, 1H), 6.86 (d, J = 2.4 Hz, 1H), 6.65 (dd, J = 8.9, 0.8 Hz, 1H), 3.93-3.81 (m, 1H), 3.04 (s, 6H), 2.03 (s, 1H), 1.21-1.10 (m, 4H), 0.91 (s, 9H). |
| 680 | 1H NMR (400 MHz, Methanol-d4) δ 8.36 (s, 1H), 7.85 (t, J = 8.1 Hz, 1H), 7.78 (d, J = 2.5 Hz, 1H), 7.06 (d, J = 2.5 Hz, 1H), 6.91-6.83 (m, 1H), 6.18 (s, 1H), 3.89 (d, J = 13.8 Hz, 1H), 3.77-3.68 (m, 1H), 3.63 (d, J = 13.8 Hz, 1H), 2.47 (s, 3H), 1.31-1.21 (m, 4H), 0.88 (s, 9H). |
| 681 | 1H NMR (400 MHz, Methanol-d4) δ 8.37 (s, 1H), 7.87 (t, J = 8.1 Hz, 1H), 7.77 (d, J = 2.5 Hz, 1H), 7.09 (d, J = 2.5 Hz, 1H), 6.87 (dd, J = 8.5, 2.8 Hz, 1H), 6.18 (s, 1H), 3.90 (d, J = 13.8 Hz, 1H), 3.66 (d, J = 13.8 Hz, 1H), 2.51 (s, 3H), 1.32-1.15 (m, 4H), 0.90 (s, 9H). |
| 682 | 1H NMR (400 MHz, Methanol-d4) δ 9.01 (dd, J = 4.6, 1.4 Hz, 1H), 8.85 (d, J = 8.7 Hz, 1H), 8.48 (s, 1H), 8.10 (d, J = 8.5 Hz, 1H), 7.96 (s, 1H), 7.90-7.82 (m, 1H), 7.81-7.73 (m, 2H), 7.69 (d, J = 2.3 Hz, 1H), 6.92 (d, J = 2.3 Hz, 1H), 6.86 (s, 1H), 4.03 (d, J = 13.9 Hz, 1H), 3.61 (d, J = 13.9 Hz, 1H), 1.56-1.44 (m, 1H), 1.24-1.13 (m, 2H), 0.99 (m, 2H), 0.70 (s, 9H), 0.53-0.42 (m, 2H), 0.29 (m, 2H). |
| 683 | 1H NMR (400 MHz, Methanol-d4) δ 8.99 (d, J = 4.4 Hz, 1H), 8.80 (d, J = 8.7 Hz, 1H), 8.48 (s, 1H), 8.09 (d, J = 8.5 Hz, 1H), 7.99 (s, 1H), 7.88-7.81 (m, 1H), 7.78-7.70 (m, 2H), 7.69 (d, J = 2.3 Hz, 1H), 6.93 (d, J = 2.3 Hz, 1H), 6.89 (s, 1H), 6.09 (t, J = 55.6 Hz, 1H), 4.00 (d, J = 13.9 Hz, 1H), 3.64 (d, J = 13.9 Hz, 1H), 1.77-1.67 (m, 6H), 0.71 (s, 9H). |
| 684 | 1H NMR (400 MHz, Methanol-d4) δ 9.03 (dd, J = 4.7, 1.5 Hz, 1H), 8.88 (d, J = 8.7 Hz, 1H), 8.49 (s, 1H), 8.11 (d, J = 8.6 Hz, 1H), 7.95 (s, 1H), 7.88 (dd, J = 8.5, 7.3 Hz, 1H), 7.82-7.75 (m, 2H), 7.69 (d, J = 2.3 Hz, 1H), 6.94 (d, J = 2.3 Hz, 1H), 6.89 (s, 1H), 4.60 (d, J = 47.1 Hz, 2H), 4.02 (d, J = 13.9 Hz, 1H), 3.64 (d, J = 13.9 Hz, 1H), 1.64 (s, 6H), 0.71 (s, 9H). |
| 685 | 1H NMR (400 MHz, Methanol-d4) δ 9.00 (dd, J = 4.6, 1.4 Hz, 1H), 8.81 (d, J = 8.7 Hz, 1H), 8.48 (s, 1H), 8.09 (d, J = 8.5 Hz, 1H), 7.89-7.81 (m, 2H), 7.78-7.70 (m, 2H), 7.68 (d, J = 2.3 Hz, 1H), 6.91 (d, J = 2.3 Hz, 1H), 6.86 (s, 1H), 4.01 (d, J = 13.9 Hz, 1H), 3.62 (d, J = 13.9 Hz, 1H), 2.67 (s, 1H), 2.34 (s, 6H), 0.69 (s, 9H). |
| 686 | 1H NMR (400 MHz, Methanol-d4) δ 8.51 (s, 1H), 7.77 (t, J = 8.1 Hz, 1H), 7.65 (d, J = 2.3 Hz, 1H), 6.98 (d, J = 2.3 Hz, 1H), 6.94-6.85 (m, 1H), 6.36 (s, 1H), 4.00-3.92 (m, 2H), 3.89 (d, J = 14.0 Hz, 1H), 2.54 (s, 3H), 1.47-1.23 (m, 4H), 0.94 (s, 9H). |
| 687 | 1H NMR (400 MHz, Methanol-d4) δ 8.42 (s, 1H), 8.37 (s, 1H), 8.27 (d, J = 8.2 Hz, 1H), 7.66 (d, J = 8.3 Hz, 1H), 7.60 (d, J = 2.3 Hz, 1H), 6.99 (d, J = 2.3 Hz, 1H), 6.38 (s, 1H), 3.96 (d, J = 14.0 Hz, 1H), 3.81 (d, J = 14.0 Hz, 1H), 2.75 (s, 3H), 2.72 (s, 3H), 1.84-1.74 (m, 2H), 1.70 (d, J = 13.9 Hz, 2H), 0.94 (s, 9H). |
| 688 | 1H NMR (400 MHz, Methanol-d4) δ 8.48 (s, 1H), 8.26 (s, 1H), 7.82 (dd, J = 10.0, 7.6 Hz, 1H), 7.66 (d, J = 2.3 Hz, 1H), 7.17 (dd, J = 7.7, 1.5 Hz, 1H), 7.07 (d, J = 2.3 Hz, 1H), 6.30 (s, 1H), 4.10 (d, J = 14.0 Hz, 1H), 3.78 (d, J = 14.0 Hz, 1H), 2.45 (s, 3H), 1.81-1.71 (m, 2H), 1.72-1.62 (m, 2H), 0.96 (s, 9H). |
| 689 | 1H NMR (400 MHz, Methanol-d4) δ 8.40 (s, 1H), 8.36 (d, J = 8.3 Hz, 1H), 8.31 (s, 1H), 7.77-7.66 (m, 2H), 7.20 (d, J = 2.5 Hz, 1H), 6.39 (s, 1H), 3.85 (d, J = 13.9 Hz, 1H), 3.69 (d, J = 14.0 Hz, 1H), 2.78 (s, 3H), 2.74 (s, 3H), 1.83-1.74 (m, 2H), 1.71 (d, J = 14.7 Hz, 2H), 0.92 (s, 9H). |
| 690 | 1H NMR (400 MHz, Methanol-d4) δ 8.37 (s, 1H), 8.27 (s, 1H), 7.87-7.76 (m, 2H), 7.26 (dd, J = 2.5, 0.6 Hz, 1H), 7.16 (dd, J = 7.7, 1.5 Hz, 1H), 6.31 (s, 1H), 3.98 (d, J = 13.9 Hz, 1H), 3.65 (d, J = 13.9 Hz, 1H), 2.45 (s, 3H), 1.80-1.71 (m, 2H), 1.71-1.62 (m, 2H), 0.92 (s, 9H). |
| 691 | 1H NMR (400 MHz, Methanol-d4) δ 9.37 (s, 1H), 8.28 (m, 1H), 8.20 (s, 1H), 8.14-8.05 (m, 2H), 7.87-7.75 (m, 2H), 7.60 (m, 1H), 7.40 (m, 1H), 6.69 (m, 1H), 6.58 (s, 1H), 3.73 (m, 1H), 3.36 (m, 1H), 3.07 (s, 1H), 2.93 (s, 1H), 1.23 (m, 1H), 0.90 (m, 2H), 0.74-0.67 (m, 2H), 0.44 (s, 9H), 0.20 (m, 2H), 0.02 (m, 2H). |
| 692 | 1H NMR (400 MHz, Methanol-d4) δ 9.59 (s, 1H), 8.56 (m, 1H), 8.48 (s, 1H), 8.32 (m, 2H), 8.05 (d, J = 7.3 Hz, 1H), 7.96 (d, J = 2.4 Hz, 1H), 7.85 (t, J = 7.8 Hz, 1H), 7.69 (d, J = 2.3 Hz, 1H), 6.97 (m, 1H), 6.88 (s, 1H), 3.98 (m, 1H), 3.94-3.76 (m, 1H), 3.68 (m, 1H), 2.01-1.88 (m, 1H), 1.61 (m, 1H), 0.74 (s, 9H). |
| 693 | 1H NMR (400 MHz, Methanol-d4) δ 9.54 (s, 1H), 8.54 (m, 1H), 8.46 (m, 1H), 8.28 (m, 2H), 8.08-7.98 (m, 2H), 7.86-7.78 (m, 1H), 7.67 (d, J = 2.3 Hz, 1H), 6.93 (d, J = 2.3 Hz, 1H), 6.88 (s, 1H), 6.10 (t, J = 55.6 Hz, 2H), 4.04-3.92 (m, 2H), 3.64 (m, 1H), 1.73 (s, 6H), 0.71 (s, 9H). |
| 694 | 1H NMR (400 MHz, Methanol-d4) δ 8.43 (s, 1H), 8.27 M, 1H), 8.00 (M, 2H), 7.80 (s, OH), 7.68 (s, 1H), 6.89 (M, 2H), 4.98-4.78 (m, 26H), 4.73-4.63 (m, 2H), 4.57 (s, 1H), 3.96 (d, J = 13.7 Hz, 1H), 3.62 (d, J = 13.7 Hz, 1H), 1.67 (s, 6H), 0.71 (s, 9H). |

TABLE 2-continued

| Compound | ¹H-NMR |
|---|---|
| 695 | 1H NMR (400 MHz, Methanol-d4) δ 9.63 (s, 1H), 8.58 (d, J = 6.5 Hz, 1H), 8.49 (s, 1H), 8.36 (d, J = 6.7 Hz, 2H), 8.09 (m, 1H), 7.96 (s, 1H), 7.92-7.83 (m, 1H), 7.68 (d, J = 2.3 Hz, 1H), 6.96 (d, J = 2.3 Hz, 1H), 6.88 (s, 1H), 4.06-3.96 (m, 1H), 3.67 (m, 1H), 3.36 (s, 1H), 2.70 (s, 1H), 2.36 (s, 6H), 1.12 (s, 1H), 0.73 (s, 9H). |
| 696 | 1H NMR (400 MHz, Methanol-d4) δ 9.66 (s, 1H), 8.57 (d, J = 6.7 Hz, 1H), 8.45 (d, J = 6.7 Hz, 1H), 8.36 (m, 1H), 8.28 (s, 1H), 8.14 (m, 1H), 8.07 (s, 1H), 7.90 (m, 1H), 7.78 (d, J = 2.5 Hz, 1H), 7.09 (d, J = 2.5 Hz, 1H), 6.86 (s, 1H), 3.78 (d, J = 13.8 Hz, 1H), 3.48 (d, J = 13.8 Hz, 1H), 1.20 (s, 2H), 1.00 (s, 2H), 0.67 (s, 9H), 0.53-0.46 (m, 2H), 0.30 (d, J = 5.2 Hz, 2H). |
| 697 | 1H NMR (400 MHz, Methanol-d4) δ 9.66 (s, 1H), 8.57 (d, J = 6.6 Hz, 1H), 8.45 (d, J = 6.6 Hz, 1H), 8.37 (m, 1H), 8.28 (s, 1H), 8.13 (m, 1H), 7.99-7.86 (m, 2H), 7.77 (d, J = 2.5 Hz, 1H), 7.09 (d, J = 2.5 Hz, 1H), 6.87 (s, 1H), 3.76 (d, J = 13.7 Hz, 1H), 3.49 (d, J = 13.7 Hz, 1H), 2.68 (s, 1H), 2.35 (s, 6H), 0.66 (s, 9H). |
| 698 | 1H NMR (400 MHz, Methanol-d4) δ 8.90 (dd, J = 4.6, 1.6 Hz, 1H), 8.53 (d, J = 8.3 Hz, 1H), 8.45 (s, 1H), 8.16 (s, 1H), 8.15-8.13 (m, 1H), 8.06 (d, J = 8.6 Hz, 1H), 7.81-7.76 (m, 1H), 7.74 (d, J = 2.3 Hz, 1H), 7.65 (dd, J = 8.3, 4.5 Hz, 1H), 7.07 (d, J = 2.3 Hz, 1H), 6.38 (s, 1H), 4.10 (d, J = 14.0 Hz, 1H), 3.63 (d, J = 14.0 Hz, 1H), 1.78-1.69 (m, 2H), 1.66 (s, 2H), 0.77 (s, 9H). |
| 699 | 1H NMR (400 MHz, Methanol-d4) δ 8.92 (dd, J = 4.7, 1.6 Hz, 1H), 8.61-8.56 (m, 1H), 8.46 (s, 1H), 8.15 (s, 1H), 8.08 (d, J = 8.5 Hz, 1H), 8.03 (s, 1H), 7.81 (dd, J = 8.5, 1.7 Hz, 1H), 7.74 (d, J = 2.3 Hz, 1H), 7.69 (dd, J = 8.4, 4.6 Hz, 1H), 7.08 (d, J = 2.3 Hz, 1H), 6.38 (s, 1H), 5.94 (t, J = 54.7 Hz, 1H), 4.11 (d, J = 14.0 Hz, 1H), 3.64 (d, J = 14.0 Hz, 1H), 1.52 (d, J = 2.4 Hz, 4H), 0.78 (s, 9H). |
| 700 | 1H NMR (400 MHz, Methanol-d4) δ 8.32 (d, J = 7.6 Hz, 1H), 8.32 (s, 1H), 8.07 (s, 1H), 7.80 (d, J = 2.5 Hz, 1H), 7.76 (dd, J = 7.6, 1.2 Hz, 1H), 7.48 (t, J = 7.8 Hz, 1H), 7.22 (d, J = 7.5 Hz, 1H), 7.01 (d, J = 2.5 Hz, 1H), 6.84 (d, J = 7.5 Hz, 1H), 6.61 (s, 1H), 3.81 (d, J = 13.6 Hz, 1H), 3.53 (d, J = 13.6 Hz, 1H), 1.80-1.54 (m, 4H), 0.74 (s, 9H). |
| 701 | 1H NMR (400 MHz, Methanol-d4) δ 8.86 (s, 1H), 8.51 (s, 1H), 8.24 (s, 1H), 7.63 (d, J = 2.3 Hz, 1H), 7.14 (d, J = 2.4 Hz, 1H), 6.42 (s, 1H), 4.05 (d, J = 14.0 Hz, 1H), 3.87 (d, J = 13.9 Hz, 1H), 2.44 (s, 3H), 1.87-1.57 (m, 4H), 0.99 (s, 9H). |
| 702 | 1H NMR (400 MHz, Methanol-d4) δ 8.85 (s, 1H), 8.50 (s, 1H), 8.06 (s, 1H), 7.61 (d, J = 2.3 Hz, 1H), 7.11 (d, J = 2.3 Hz, 1H), 6.37 (s, 1H), 4.03 (d, J = 14.0 Hz, 1H), 3.87 (d, J = 13.9 Hz, 1H), 2.44 (s, 3H), 1.61-1.47 (m, 1H), 1.23 (d, J = 2.7 Hz, 2H), 0.99 (m, 11H), 0.53 (dd, J = 8.1, 1.8 Hz, 2H), 0.40-0.27 (m, 2H). |
| 703 | 1H NMR (400 MHz, Methanol-d4) δ 9.11-9.02 (m, 2H), 8.30 (s, 1H), 8.13 (d, J = 8.5 Hz, 1H), 8.04 (s, 1H), 8.00-7.92 (m, 1H), 7.87 (m, 2H), 7.80 (d, J = 2.5 Hz, 1H), 7.08 (d, J = 2.5 Hz, 1H), 6.88 (s, 1H), 3.80 (d, J = 13.7 Hz, 1H), 3.46 (d, J = 13.8 Hz, 1H), 1.51 (m, 1H), 1.20 (m, 2H), 1.05-0.93 (m, 2H), 0.65 (s, 9H), 0.56-0.43 (m, 2H), 0.30 (m, 2H). |
| 704 | 1H NMR (400 MHz, Methanol-d4) δ 9.07 (d, J = 4.8 Hz, 1H), 9.01 (d, J = 8.7 Hz, 1H), 8.30 (s, 1H), 8.12 (d, J = 8.5 Hz, 1H), 8.00-7.90 (m, 2H), 7.90-7.82 (m, 2H), 7.79 (d, J = 2.5 Hz, 1H), 7.10 (d, J = 2.7 Hz, 1H), 6.90 (s, 1H), 4.95-4.79 (m, 1H), 3.86 (m, 1H), 3.78 (d, J = 13.7 Hz, 1H), 3.54-3.45 (m, 1H), 2.05-1.84 (m, 1H), 1.68-1.51 (m, 1H), 0.66 (m, 9H) |
| 705 | 1H NMR (400 MHz, Methanol-d4) δ 9.06 (d, J = 4.7 Hz, 1H), 8.99 (d, J = 8.6 Hz, 1H), 8.29 (s, 1H), 8.11 (d, J = 8.5 Hz, 1H), 8.06 (s, 1H), 7.98-7.87 (m, 1H), 7.87-7.73 (m, 3H), 7.09 (d, J = 2.6 Hz, 1H), 6.91 (s, 1H), 6.09 (t, J = 55.5 Hz, 1H), 3.78 (d, J = 13.8 Hz, 1H), 3.47 (d, J = 13.8 Hz, 1H), 1.73 (s, 6H), 0.65 (s, 9H). |
| 706 | 1H NMR (400 MHz, Methanol-d4) δ 9.07 (d, J = 4.7 Hz, 1H), 9.03 (d, J = 8.9 Hz, 1H), 8.30 (s, 1H), 8.12 (d, J = 8.5 Hz, 1H), 7.98-7.91 (m, 2H), 7.84 (m, 2H), 7.79 (d, J = 2.5 Hz, 1H), 7.08 (d, J = 2.5 Hz, 1H), 6.89 (s, 1H), 3.78 (d, J = 13.8 Hz, 1H), 3.46 (d, J = 13.7 Hz, 1H), 2.67 (s, 1H), 2.35 (s, 6H), 0.64 (s, 9H). |
| 707 | 1H NMR (400 MHz, Methanol-d4) δ 8.49 (s, 1H), 7.83 (t, J = 8.1 Hz, 1H), 7.65 (d, J = 2.3 Hz, 1H), 6.90-6.81 (m, 2H), 6.14-5.81 (m, 2H), 4.12 (d, J = 13.9 Hz, 1H), 3.69 (d, J = 13.9 Hz, 1H), 2.41 (s, 3H), 1.70 (m, 2H), 1.62 (m, 2H), 0.90 (s, 9H). |
| 708 | 1H NMR (400 MHz, Methanol-d4) δ 9.02 (dd, J = 5.0, 1.6 Hz, 1H), 8.84 (d, J = 8.3 Hz, 1H), 8.29 (s, 1H), 8.22 (s, 1H), 8.19 (s, 1H), 8.12 (s, 1H), 7.93 (dd, J = 8.7, 1.7 Hz, 1H), 7.89-7.81 (m, 2H), 7.22 (d, J = 2.5 Hz, 1H), 6.41 (s, 1H), 5.95 (t, J = 54.6 Hz, 1H), 3.91 (d, J = 13.9 Hz, 1H), 3.47 (d, J = 13.9 Hz, 1H), 1.54 (s, 4H), 0.72 (s, 9H). |
| 709 | 1H NMR (400 MHz, Methanol-d4) δ 8.99 (dd, J = 4.3, 1.5 Hz, 1H), 8.60 (dd, J = 8.7, 1.5 Hz, 1H), 8.50 (s, 1H), 8.12 (s, 1H), 7.87 (d, J = 7.9 Hz, 1H), 7.70 (d, J = 2.3 Hz, 1H), 7.66 (dd, J = 8.7, 4.3 Hz, 1H), 7.61 (d, J = 7.9 Hz, 1H), 6.89 (d, J = 2.3 Hz, 1H), 6.83 (s, 1H), 4.03 (d, J = 13.8 Hz, 1H), 3.58 (d, J = 13.9 Hz, 1H), 1.76-1.55 (m, 4H), 0.67 (s, 9H). |
| 710 | 1H NMR (400 MHz, Methanol-d4) δ 9.05 (dd, J = 4.2, 1.5 Hz, 1H), 8.67 (dd, J = 8.8, 1.6 Hz, 1H), 8.31 (s, 1H), 8.21 (d, J = 7.5 Hz, 2H), 7.84-7.79 (m, 2H), 7.69 (dd, J = 8.7, 4.2 Hz, 1H), 6.99 (d, J = 2.5 Hz, 1H), 6.92 (s, 1H), 3.81 (d, J = 13.7 Hz, 1H), 3.37 (d, J = 13.7 Hz, 1H), 1.77-1.55 (m, 4H), 0.58 (s, 10H). |
| 711 | 1H NMR (400 MHz, Methanol-d4) δ 8.48 (d, J = 3.3 Hz, 1H), 8.35 (d, J = 7.9 Hz, 1H), 7.75 (t, J = 4.3 Hz, 2H), 7.65 (d, J = 3.3 Hz, 1H), 7.54-7.45 (m, 1H), 7.40 (m, 1H), 6.83 (m, 2H), 6.56 (d, J = 3.2 Hz, 1H), 4.01 (m, 1H), 3.75-3.66 (m, 1H), 2.69 (d, J = 3.3 Hz, 1H), 2.36 (d, J = 3.3 Hz, 6H), 0.80 (s, 9H). |

TABLE 2-continued

| Compound | ¹H-NMR |
|---|---|
| 712 | 1H NMR (400 MHz, Methanol-d4) δ 9.17 (s, 1H), 8.26 (s, 1H), 8.14 (s, 1H), 8.12 (d, J = 8.3 Hz, 1H), 8.09 (s, 1H), 7.88 (d, J = 7.2 Hz, 1H), 7.79 (d, J = 2.5 Hz, 1H), 7.68-7.62 (m, 1H), 7.02 (d, J = 2.5 Hz, 1H), 6.78 (s, 1H), 3.73 (d, J = 13.6 Hz, 1H), 3.54-3.44 (m, 3H), 1.76-1.58 (m, 3H), 0.64 (s, 9H). |
| 713 | 1H NMR (400 MHz, Methanol-d4) δ 8.48 (d, J = 1.1 Hz, 1H), 8.33 (d, J = 8.1 Hz, 1H), 7.78 (s, 1H), 7.72 (d, J = 7.5 Hz, 1H), 7.65 (d, J = 2.2 Hz, 1H), 7.48 (t, J = 7.8 Hz, 1H), 7.41 (d, J = 7.6 Hz, 1H), 6.81 (d, J = 7.3 Hz, 2H), 6.56 (s, 1H), 4.04 (d, J = 13.8 Hz, 1H), 3.64 (d, J = 13.8 Hz, 1H), 3.61 (s, 3H), 2.67 (s, 1H), 2.35 (s, 6H), 0.76 (s, 9H). |
| 714 | 1H NMR (400 MHz, Acetonitrile-d3) δ 8.40 (s, 1H), 8.30 (d, J = 8.1 Hz, 1H), 7.82-7.75 (m, 2H), 7.53 (d, J = 2.2 Hz, 1H), 7.44 (t, J = 7.8 Hz, 1H), 7.31 (d, J = 7.7 Hz, 1H), 6.81 (d, J = 7.6 Hz, 1H), 6.60 (s, 1H), 6.48 (s, 1H), 6.24 (s, 2H), 3.77-3.56 (m, 5H), 3.54 (s, 3H), 3.04 (m, 2H), 2.35 (s, 2H), 1.42 (s, 9H), 0.80 (s, 9H). |
| 715 | 1H NMR (400 MHz, Methanol-d4) δ 8.45 (s, 1H), 7.93 (s, 1H), 7.76 (t, J = 8.1 Hz, 1H), 7.60 (d, J = 2.3 Hz, 1H), 6.86 (dd, J = 8.5, 2.8 Hz, 1H), 6.80 (d, J = 2.3 Hz, 1H), 6.17 (s, 1H), 4.30 (d, J = 15.0 Hz, 1H), 4.14 (d, J = 15.0 Hz, 1H), 2.49 (s, 3H), 1.64 (s, 9H), 1.12 (d, J = 2.2 Hz, 6H). |
| 716 | 1H NMR (400 MHz, Methanol-d4) δ 8.51 (d, J = 0.7 Hz, 1H), 7.91 (s, 1H), 7.77 (t, J = 8.1 Hz, 1H), 7.63 (d, J = 2.3 Hz, 1H), 6.94-6.84 (m, 2H), 6.18 (s, 1H), 4.02 (d, J = 13.9 Hz, 1H), 3.94-3.79 (m, 2H), 2.50 (s, 3H), 1.27-1.10 (m, 4H), 0.93 (s, 9H). |
| 717 | 1H NMR (400 MHz, Methanol-d4) δ 8.46 (d, J = 1.0 Hz, 1H), 8.31 (d, J = 8.3 Hz, 1H), 8.25 (s, 1H), 7.68 (d, J = 8.3 Hz, 1H), 7.62 (d, J = 2.3 Hz, 1H), 7.03 (d, J = 2.3 Hz, 1H), 6.38 (s, 1H), 5.94 (t, J = 54.5 Hz, 1H), 3.99 (d, J = 14.0 Hz, 1H), 3.84 (d, J = 14.0 Hz, 1H), 2.75 (d, J = 7.7 Hz, 6H), 1.56 (s, 4H), 0.95 (d, J = 1.1 Hz, 9H). |
| 718 | 1H NMR (400 MHz, Methanol-d4) δ 8.47 (s, 1H), 8.06 (s, 1H), 7.71-7.58 (m, 2H), 7.26 (d, J = 8.2 Hz, 1H), 6.87 (d, J = 2.3 Hz, 1H), 6.20 (s, 1H), 5.94 (t, J = 54.7 Hz, 1H), 4.04 (d, J = 13.9 Hz, 1H), 3.76 (d, J = 13.9 Hz, 1H), 2.51 (s, 3H), 1.54 (d, J = 1.1 Hz, 4H), 0.92 (s, 9H). |
| 719 | 1H NMR (400 MHz, Methanol-d4) δ 8.50 (s, 1H), 7.90 (s, 1H), 7.74 (t, J = 8.1 Hz, 1H), 7.62 (d, J = 2.3 Hz, 1H), 6.91-6.78 (m, 2H), 6.18 (s, 1H), 4.41-4.14 (m, 2H), 2.69 (s, 1H), 2.51 (s, 3H), 2.37 (s, 6H), 1.14 (d, J = 3.3 Hz, 6H). |
| 720 | 1H NMR (400 MHz, Methanol-d4) δ 8.53 (s, 1H), 7.95 (s, 1H), 7.74 (t, J = 8.1 Hz, 1H), 7.63 (d, J = 2.3 Hz, 1H), 6.94-6.80 (m, 2H), 6.17 (s, 1H), 4.34 (d, J = 15.0 Hz, 1H), 4.20 (d, J = 15.0 Hz, 1H), 2.49 (s, 3H), 1.65 (s, 3H), 1.31 (d, J = 5.2 Hz, 2H), 1.15 (d, J = 2.2 Hz, 6H), 1.09-1.00 (m, 2H). |
| 721 | 1H NMR (400 MHz, Methanol-d4) δ 8.44 (s, 1H), 8.18 (s, 1H), 7.76 (t, J = 8.2 Hz, 1H), 7.61 (d, J = 2.3 Hz, 1H), 6.95-6.74 (m, 2H), 6.22 (s, 1H), 4.29 (t, J = 14.9 Hz, 1H), 4.13 (d, J = 14.9 Hz, 1H), 2.50 (s, 3H), 1.84-1.59 (m, 4H), 1.13 (d, J = 2.1 Hz, 6H). |
| 722 | 1H NMR (400 MHz, Methanol-d4) δ 8.51 (s, 1H), 8.20 (s, 1H), 7.84 (t, J = 8.1 Hz, 1H), 7.65 (d, J = 2.3 Hz, 1H), 6.93-6.77 (m, 1H), 6.62 (d, J = 2.3 Hz, 1H), 6.11 (s, 1H), 4.53-4.20 (m, 2H), 3.04 (s, 3H), 2.46 (s, 3H), 1.87-1.57 (m, 4H), 1.48 (s, 3H), 1.38 (s, 3H). |
| 723 | 1H NMR (400 MHz, Methanol-d4) δ 8.43 (d, J = 3.3 Hz, 1H), 8.05 (d, J = 3.6 Hz, 1H), 7.81 (q, J = 8.0 Hz, 1H), 7.62 (d, J = 2.3 Hz, 1H), 7.46-7.21 (m, 5H), 7.14 (dd, J = 25.5, 2.3 Hz, 1H), 6.97-6.77 (m, 1H), 6.35 (d, J = 5.8 Hz, 1H), 5.94 (td, J = 54.7, 8.7 Hz, 1H), 5.70 (dt, J = 20.5, 7.2 Hz, 1H), 2.53 (d, J = 5.7 Hz, 3H), 2.12 (dh, J = 29.2, 7.2 Hz, 2H), 1.53 (d, J = 6.7 Hz, 4H), 0.97 (dt, J = 14.5, 7.3 Hz, 3H). |
| 724 | 1H NMR (400 MHz, Methanol-d4) δ 8.50 (s, 1H), 8.35 (d, J = 8.1 Hz, 1H), 7.91 (s, 1H), 7.74-7.61 (m, 2H), 7.48 (t, J = 7.8 Hz, 1H), 7.41 (d, J = 7.7 Hz, 1H), 6.94-6.74 (m, 2H), 6.57 (s, 1H), 5.92 (t, J = 54.7 Hz, 1H), 4.33 (d, J = 14.8 Hz, 1H), 4.06 (d, J = 14.8 Hz, 1H), 1.58-1.40 (m, 4H), 1.01 (d, J = 17.0 Hz, 6H). |
| 725 | 1H NMR (400 MHz, Methanol-d4) δ 8.37 (s, 1H), 8.04 (s, 1H), 7.85-7.70 (m, 2H), 7.04 (d, J = 2.5 Hz, 1H), 6.87 (dd, J = 8.4, 2.7 Hz, 1H), 6.21 (s, 1H), 5.94 (t, J = 54.7 Hz, 1H), 4.21 (d, J = 14.9 Hz, 1H), 4.05 (d, J = 14.9 Hz, 1H), 2.51 (s, 3H), 1.53 (t, J = 2.3 Hz, 4H), 1.10 (d, J = 2.4 Hz, 6H). |
| 726 | 1H NMR (400 MHz, Methanol-d4) δ 8.52 (d, J = 1.3 Hz, 1H), 8.33 (d, J = 8.1 Hz, 1H), 7.92 (s, 1H), 7.79-7.63 (m, 2H), 7.48 (t, J = 7.8 Hz, 1H), 7.23 (d, J = 7.5 Hz, 1H), 6.85 (d, J = 2.2 Hz, 1H), 6.79 (d, J = 7.6 Hz, 1H), 6.58 (s, 1H), 5.92 (t, J = 54.7 Hz, 1H), 4.36 (d, J = 14.8 Hz, 1H), 4.05 (d, J = 14.8 Hz, 1H), 1.50 (d, J = 5.1 Hz, 4H), 1.01 (d, J = 10.6 Hz, 6H). |
| 727 | 1H NMR (400 MHz, Methanol-d4) δ 8.25 (s, 1H), 8.02 (s, 1H), 7.78 (t, J = 8.1 Hz, 1H), 7.51 (d, J = 2.4 Hz, 1H), 6.86 (dd, J = 8.5, 2.7 Hz, 1H), 6.71 (d, J = 2.4 Hz, 1H), 6.19 (s, 1H), 5.95 (t, J = 54.8 Hz, 1H), 4.19 (d, J = 14.8 Hz, 1H), 3.99 (d, J = 14.8 Hz, 1H), 2.50 (s, 3H), 1.53 (q, J = 2.1 Hz, 4H), 1.07 (d, J = 2.3 Hz, 6H). |
| 728 | 1H NMR (400 MHz, Methanol-d4) δ 8.45 (s, 1H), 8.31 (s, 1H), 8.23 (dd, J = 7.9, 1.5 Hz, 1H), 7.92-7.86 (m, 1H), 7.77 (s, 1H), 7.66 (d, J = 2.2 Hz, 1H), 7.52 (t, J = 7.8 Hz, 1H), 6.98 (d, J = 2.4 Hz, 2H), 4.03 (d, J = 13.8 Hz, 1H), 3.73 (d, J = 13.9 Hz, 1H), 3.59 (s, 3H), 2.66 (s, 1H), 2.34 (s, 6H), 0.86 (s, 9H). |
| 729 | 1H NMR (400 MHz, Methanol-d4) δ 8.49 (s, 1H), 7.96 (s, 1H), 7.62 (d, J = 2.3 Hz, 1H), 7.51 (d, J = 8.6 Hz, 1H), 6.93 (d, J = 2.3 Hz, 1H), 6.61 (d, J = 8.6 Hz, 1H), 6.17 (s, 1H), 5.93 (t, J = 54.7 Hz, 1H), 4.00 (d, J = 13.9 Hz, 1H), 3.89 (s, 4H), 2.48 (s, 3H), 1.52 (s, 4H), 0.94 (s, 9H). |

TABLE 2-continued

| Compound | ¹H-NMR |
|---|---|
| 730 | 1H NMR (400 MHz, Methanol-d4) δ 8.47 (s, 1H), 8.33 (d, J = 8.1 Hz, 1H), 7.89 (s, 1H), 7.72 (dd, J = 7.2, 1.2 Hz, 1H), 7.65 (d, J = 2.3 Hz, 1H), 7.47 (t, J = 7.8 Hz, 1H), 7.41 (d, J = 7.6 Hz, 1H), 6.89-6.71 (m, 2H), 6.56 (s, 1H), 5.92 (t, J = 54.7 Hz, 1H), 4.52 (d, J = 14.9 Hz, 1H), 4.09 (d, J = 14.8 Hz, 1H), 3.61 (s, 3H), 2.20-2.04 (m, 2H), 2.04-1.76 (m, 3H), 1.68 (d, J = 8.8 Hz, 1H), 1.50 (t, J = 3.8 Hz, 4H). |
| 731 | 1H NMR (400 MHz, Methanol-d4) δ 8.51 (s, 1H), 8.03 (s, 1H), 7.77 (t, J = 8.1 Hz, 1H), 7.64 (d, J = 2.3 Hz, 1H), 6.94-6.74 (m, 2H), 6.21 (s, 1H), 5.94 (t, J = 54.7 Hz, 1H), 4.55 (d, J = 15.0 Hz, 1H), 4.28 (d, J = 15.0 Hz, 1H), 2.49 (s, 3H), 2.32 (ddd, J = 12.5, 9.3, 6.6 Hz, 2H), 2.19-1.77 (m, 4H), 1.64-1.46 (m, 4H). |
| 732 | 1H NMR (400 MHz, Methanol-d4) δ 8.21 (d, J = 12.2 Hz, 1H), 8.05 (s, 1H), 7.51-7.34 (m, 2H), 6.79 (d, J = 2.4 Hz, 1H), 6.43 (dd, J = 15.8, 9.5 Hz, 1H), 6.08 (d, J = 9.5 Hz, 1H), 3.80 (d, J = 13.8 Hz, 1H), 3.70-3.54 (m, 4H), 2.48 (s, 3H), 1.52 (s, 4H), 0.90 (d, J = 2.4 Hz, 9H). |
| 733 | 1H NMR (400 MHz, Methanol-d4) δ 8.52 (s, 1H), 8.05 (s, 1H), 7.76 (t, J = 8.1 Hz, 1H), 7.61 (d, J = 2.2 Hz, 1H), 7.05 (d, J = 2.3 Hz, 1H), 6.88 (dd, J = 8.5, 2.8 Hz, 1H), 6.26 (s, 1H), 5.94 (t, J = 54.6 Hz, 1H), 4.10 (dd, J = 14.6, 7.1 Hz, 1H), 3.97 (dd, J = 14.6, 7.3 Hz, 1H), 2.50 (s, 3H), 1.54 (s, 4H), 1.11 (d, J = 3.7 Hz, 6H), 1.02 (d, J = 3.4 Hz, 6H), 0.79 (t, J = 7.2 Hz, 1H). |
| 734 | 1H NMR (400 MHz, Methanol-d4) δ 8.92 (s, 2H), 8.45 (s, 1H), 8.21-8.02 (m, 2H), 7.97-7.88 (m, 1H), 7.83 (dd, J = 8.4, 7.3 Hz, 1H), 7.69 (d, J = 2.3 Hz, 1H), 7.31 (s, 1H), 7.06 (d, J = 2.3 Hz, 1H), 3.99 (d, J = 13.8 Hz, 1H), 3.69 (d, J = 13.9 Hz, 1H), 1.79-1.48 (m, 4H), 0.78 (s, 9H). |
| 735 | 1H NMR (400 MHz, Methanol-d4) δ 8.12 (s, 1H), 7.60 (d, J = 3.1 Hz, 1H), 7.47 (dd, J = 7.2, 2.3 Hz, 1H), 7.29 (dt, J = 7.9, 1.0 Hz, 1H), 7.22-7.03 (m, 3H), 6.65-6.49 (m, 2H), 6.28 (s, 1H), 3.76 (s, 3H), 3.67-3.57 (m, 1H), 3.53-3.41 (m, 1H), 2.60 (s, 1H), 2.29 (s, 6H), 0.73 (d, J = 1.4 Hz, 9H). |
| 736 | 1H NMR (400 MHz, Methanol-d4) δ 8.43 (s, 1H), 7.80-7.60 (m, 2H), 7.36 (p, J = 3.8 Hz, 1H), 7.24-7.08 (m, 3H), 6.96 (d, J = 2.2 Hz, 1H), 6.54 (dd, J = 3.2, 0.9 Hz, 1H), 6.39 (s, 1H), 5.90 (t, J = 54.8 Hz, 1H), 4.05 (d, J = 13.7 Hz, 1H), 3.80 (s, 3H), 3.65 (d, J = 13.8 Hz, 1H), 1.58-1.35 (m, 4H), 0.84 (s, 9H). |
| 737 | 1H NMR (400 MHz, Methanol-d4) δ 8.44 (s, 1H), 8.04 (s, 1H), 7.80-7.57 (m, 3H), 7.50 (t, J = 7.6 Hz, 1H), 7.43-7.20 (m, 1H), 6.89 (d, J = 2.3 Hz, 1H), 6.21 (s, 1H), 5.94 (t, J = 54.7 Hz, 1H), 4.69 (d, J = 18.0 Hz, 1H), 4.33 (d, J = 18.0 Hz, 1H), 4.13 (d, J = 13.8 Hz, 1H), 3.70-3.56 (m, 1H), 3.15 (s, 3H), 1.53 (d, J = 3.2 Hz, 4H), 0.85 (s, 9H). |
| 738 | 1H NMR (400 MHz, Methanol-d4) δ 9.57 (s, 1H), 8.58 (d, J = 6.4 Hz, 1H), 8.50 (s, 1H), 8.44 (d, J = 0.9 Hz, 1H), 8.24 (d, J = 6.4 Hz, 1H), 8.06 (s, 1H), 7.68 (d, J = 2.3 Hz, 1H), 7.18 (d, J = 2.3 Hz, 1H), 6.61 (s, 1H), 4.01 (d, J = 14.0 Hz, 1H), 3.90 (tt, J = 7.4, 4.0 Hz, 1H), 3.82 (d, J = 14.0 Hz, 1H), 1.24-1.13 (m, 4H), 0.88 (s, 9H). |
| 739 | 1H NMR (400 MHz, Methanol-d4) δ 8.49 (s, 1H), 8.06 (s, 1H), 7.76 (t, J = 8.1 Hz, 1H), 7.62 (d, J = 2.3 Hz, 1H), 7.06 (d, J = 2.3 Hz, 1H), 6.89 (dd, J = 8.4, 2.8 Hz, 1H), 6.25 (s, 1H), 5.93 (t, J = 54.6 Hz, 1H), 4.12 (m, 2H), 2.52 (s, 1H), 2.51 (s, 3H), 1.80 (s, 6H), 1.54 (s, 4H). |
| 740 | 1H NMR (400 MHz, Methanol-d4) δ 8.49 (s, 1H), 8.20 (s, 1H), 7.76 (t, J = 8.1 Hz, 1H), 7.62 (d, J = 2.3 Hz, 1H), 7.06 (d, J = 2.3 Hz, 1H), 6.89 (dd, J = 8.5, 2.8 Hz, 1H), 6.26 (s, 1H), 4.12 (s, 2H), 2.52 (s, 1H), 2.51 (s, 3H), 1.80 (s, 6H), 1.78-1.72 (m, 2H), 1.72-1.65 (m, 2H). |
| 741 | 1H NMR (400 MHz, Methanol-d4) δ 9.52 (s, 1H), 8.56 (d, J = 6.3 Hz, 1H), 8.48 (s, 1H), 8.38 (d, J = 1.0 Hz, 1H), 8.32 (s, 1H), 8.20 (d, J = 6.3 Hz, 1H), 7.68 (d, J = 2.3 Hz, 1H), 7.17 (d, J = 2.3 Hz, 1H), 6.65 (s, 1H), 4.00 (d, J = 14.0 Hz, 1H), 3.80 (d, J = 14.0 Hz, 1H), 1.81-1.71 (m, 2H), 1.69 (m, 2H), 0.87 (s, 9H). |
| 742 | 1H NMR (400 MHz, Methanol-d4) δ 8.53 (s, 1H), 8.04 (s, 1H), 7.98 (t, J = 2.1 Hz, 1H), 7.87-7.75 (m, 2H), 7.67 (d, J = 2.3 Hz, 1H), 7.10 (d, J = 2.4 Hz, 1H), 6.88 (dd, J = 8.4, 2.7 Hz, 1H), 6.17 (s, 1H), 5.93 (t, J = 54.7 Hz, 1H), 2.45 (s, 3H), 1.53 (s, 4H). |
| 743 | 1H NMR (400 MHz, Methanol-d4) δ 8.48 (s, 1H), 8.35 (d, J = 8.4 Hz, 1H), 7.93 (s, 1H), 7.76 (d, J = 7.3 Hz, 1H), 7.67 (d, J = 1.9 Hz, 1H), 7.50 (t, J = 7.8 Hz, 1H), 7.40 (d, J = 7.7 Hz, 1H), 6.86 (d, J = 2.2 Hz, 1H), 6.83 (d, J = 7.9 Hz, 1H), 6.60 (s, 1H), 6.23 (tt, J = 56.0, 4.1 Hz, 1H), 5.92 (t, J = 54.6 Hz, 1H), 4.56-4.43 (m, 1H), 4.44-4.28 (m, 1H), 4.04 (d, J = 13.8 Hz, 1H), 3.64 (d, J = 13.8 Hz, 1H), 1.62-1.38 (m, 4H), 0.78 (s, 9H). |
| 744 | 1H NMR (400 MHz, Methanol-d4) δ 8.47 (s, 1H), 8.34 (d, J = 8.1 Hz, 1H), 7.91 (s, 1H), 7.73 (d, J = 7.5 Hz, 1H), 7.66 (d, J = 2.3 Hz, 1H), 7.48 (t, J = 7.8 Hz, 1H), 7.41 (d, J = 7.7 Hz, 1H), 6.84 (d, J = 2.3 Hz, 1H), 6.82 (d, J = 7.8 Hz, 1H), 6.58 (s, 1H), 5.92 (t, J = 54.7 Hz, 1H), 4.02 (d, J = 13.8 Hz, 1H), 3.65 (d, J = 13.8 Hz, 1H), 3.61 (s, 3H), 1.57-1.42 (m, 4H), 0.78 (s, 9H). |
| 745 | 1H NMR (400 MHz, Methanol-d4) δ 8.49 (s, 1H), 8.33 (d, J = 8.1 Hz, 1H), 7.77 (s, 1H), 7.73 (d, J = 7.5 Hz, 1H), 7.66 (d, J = 2.3 Hz, 1H), 7.48 (t, J = 7.8 Hz, 1H), 7.41 (d, J = 7.6 Hz, 1H), 6.84 (d, J = 2.3 Hz, 1H), 6.81 (d, J = 7.7 Hz, 1H), 6.54 (s, 1H), 4.04 (d, J = 13.8 Hz, 1H), 3.91-3.81 (m, 1H), 3.66 (d, J = 13.8 Hz, 1H), 3.61 (s, 3H), 1.22-1.08 (m, 4H), 0.78 (s, 9H). |
| 746 | 1H NMR (400 MHz, Methanol-d4) δ 8.51 (s, 1H), 8.06 (s, 1H), 7.79 (t, J = 8.1 Hz, 1H), 7.63 (d, J = 2.3 Hz, 1H), 6.87 (dd, J = 8.3, 2.8 Hz, 1H), 6.72 (d, J = 2.2 Hz, 1H), 6.09 (s, 1H), 5.95 (t, J = 54.6 Hz, 1H), 4.09-3.95 (m, 2H), 3.65-3.53 (m, 2H), 2.49 (s, 3H), 1.54 (s, 4H), 1.01 (s, 3H), 0.98 (s, 3H). |

TABLE 2-continued

| Compound | ¹H-NMR |
|---|---|
| 747 | 1H NMR (400 MHz, Methanol-d4) δ 8.47 (s, 1H), 8.39-8.28 (m, 1H), 7.80 (s, 1H), 7.73 (dd, J = 7.5, 1.3 Hz, 1H), 7.65 (d, J = 2.2 Hz, 1H), 7.47 (t, J = 7.8 Hz, 1H), 7.41 (d, J = 7.7 Hz, 1H), 6.89-6.73 (m, 2H), 6.55 (s, 1H), 4.03 (d, J = 13.8 Hz, 1H), 3.63 (m, 4H), 1.61 (s, 9H), 0.77 (s, 9H). |
| 748 | 1H NMR (400 MHz, Methanol-d4) δ 8.34 (s, 1H), 7.90 (s, 1H), 7.83-7.73 (m, 2H), 7.10 (d, J = 2.5 Hz, 1H), 6.88 (dd, J = 8.5, 2.7 Hz, 1H), 6.25 (s, 1H), 3.88 (d, J = 13.8 Hz, 1H), 3.65 (d, J = 13.8 Hz, 1H), 2.50 (s, 3H), 1.65 (t, J = 18.7 Hz, 3H), 0.89 (s, 9H). |
| 749 | 1H NMR (400 MHz, Methanol-d4) δ 8.49 (d, J = 1.3 Hz, 1H), 7.90 (s, 1H), 7.78 (t, J = 8.1 Hz, 1H), 7.64 (d, J = 2.3 Hz, 1H), 6.93 (d, J = 2.1 Hz, 1H), 6.88 (dd, J = 8.5, 2.7 Hz, 1H), 6.25 (s, 1H), 4.94-4.82 (m, 1H), 4.03 (d, J = 14.2 Hz, 1H), 3.81 (d, J = 14.0 Hz, 1H), 2.50 (s, 3H), 1.66 (t, J = 18.7 Hz, 3H), 0.93 (s, 9H). |
| 750 | 1H NMR (400 MHz, Methanol-d4) δ 8.48 (s, 1H), 7.89 (s, 1H), 7.79 (t, J = 8.1 Hz, 1H), 7.63 (d, J = 2.3 Hz, 1H), 6.93 (d, J = 2.3 Hz, 1H), 6.88 (dd, J = 8.5, 2.7 Hz, 1H), 6.25 (s, 1H), 4.90 (dd, J = 13.7, 2.8 Hz, 2H), 4.02 (d, J = 13.9 Hz, 1H), 3.81 (d, J = 13.9 Hz, 1H), 2.50 (s, 3H), 1.92 (td, J = 16.9, 8.3 Hz, 2H), 1.05 (t, J = 7.5 Hz, 3H), 0.93 (s, 9H). |
| 751 | 1H NMR (400 MHz, Methanol-d4) δ 8.50 (s, 1H), 7.92 (s, 1H), 7.74 (t, J = 8.1 Hz, 1H), 7.64 (d, J = 2.3 Hz, 1H), 6.96 (d, J = 2.3 Hz, 1H), 6.88 (dd, J = 8.5, 2.7 Hz, 1H), 6.24 (s, 1H), 4.64 (d, J = 1.3 Hz, 2H), 4.01 (d, J = 13.9 Hz, 1H), 3.87 (d, J = 13.9 Hz, 1H), 2.50 (s, 3H), 1.14 (s, 4H), 0.94 (s, 9H). |
| 752 | 1H NMR (400 MHz, Methanol-d4) δ 8.51 (s, 1H), 7.88 (s, 1H), 7.75 (t, J = 8.1 Hz, 1H), 7.64 (d, J = 2.3 Hz, 1H), 6.95 (d, J = 2.3 Hz, 1H), 6.87 (dd, J = 8.4, 2.8 Hz, 1H), 6.22 (s, 1H), 5.59 (t, J = 56.0 Hz, 1H), 4.55 (s, 2H), 4.02 (d, J = 13.9 Hz, 1H), 3.86 (d, J = 13.9 Hz, 1H), 2.50 (s, 3H), 0.94 (s, 14H). |
| 753 | 1H NMR (400 MHz, Methanol-d4) δ 8.49 (s, 1H), 8.01 (s, 1H), 7.72 (t, J = 8.1 Hz, 1H), 7.62 (d, J = 2.3 Hz, 1H), 6.92 (d, J = 2.3 Hz, 1H), 6.86 (dd, J = 8.4, 2.8 Hz, 1H), 6.20 (s, 1H), 3.99 (d, J = 14.0 Hz, 1H), 3.86 (d, J = 14.0 Hz, 1H), 2.86 (q, J = 10.3 Hz, 2H), 2.48 (s, 3H), 1.52-1.23 (m, 4H), 0.93 (s, 9H). |
| 754 | 1H NMR (400 MHz, Methanol-d4) δ 8.48 (s, 1H), 7.95 (s, 1H), 7.76 (t, J = 8.1 Hz, 1H), 7.62 (d, J = 2.3 Hz, 1H), 7.00-6.78 (m, 2H), 6.19 (s, 1H), 4.00 (d, J = 13.9 Hz, 1H), 3.83 (d, J = 14.0 Hz, 1H), 2.49 (s, 3H), 1.92-1.74 (m, 2H), 1.31-1.17 (m, 2H), 1.06 (d, J = 1.8 Hz, 2H), 0.93 (s, 9H), 0.82 (t, J = 7.4 Hz, 3H). |
| 755 | 1H NMR (400 MHz, Methanol-d4) δ 8.49 (s, 1H), 7.88 (s, 1H), 7.76 (t, J = 8.1 Hz, 1H), 7.64 (d, J = 2.3 Hz, 1H), 6.94 (d, J = 2.3 Hz, 1H), 6.88 (dd, J = 8.4, 2.8 Hz, 1H), 6.23 (s, 1H), 4.55 (s, 2H), 4.01 (d, J = 13.9 Hz, 1H), 3.84 (d, J = 13.9 Hz, 1H), 2.49 (s, 3H), 1.17 (d, J = 6.7 Hz, 6H), 0.94 (s, 9H). |
| 756 | 1H NMR (400 MHz, Methanol-d4) δ 8.46 (s, 1H), 8.33 (d, J = 8.3 Hz, 1H), 7.80 (s, 1H), 7.76-7.68 (m, 1H), 7.65 (d, J = 2.3 Hz, 1H), 7.47 (t, J = 7.8 Hz, 1H), 7.40 (d, J = 7.7 Hz, 1H), 6.88-6.75 (m, 2H), 6.54 (s, 1H), 4.01 (d, J = 13.8 Hz, 1H), 3.65 (d, J = 13.8 Hz, 1H), 3.60 (s, 3H), 1.83 (q, J = 7.4 Hz, 2H), 1.21 (d, J = 5.5 Hz, 2H), 1.13-0.97 (m, 2H), 0.78 (d, J = 7.6 Hz, 12H). |
| 757 | 1H NMR (400 MHz, Methanol-d4) δ 8.51 (s, 1H), 7.91 (s, 1H), 7.76 (t, J = 8.1 Hz, 1H), 7.64 (d, J = 2.3 Hz, 1H), 6.93 (d, J = 2.3 Hz, 1H), 6.87 (dd, J = 8.5, 2.8 Hz, 1H), 6.21 (s, 1H), 4.03 (d, J = 13.9 Hz, 1H), 3.85 (d, J = 13.9 Hz, 1H), 2.49 (s, 3H), 1.65 (p, J = 6.8 Hz, 1H), 1.24-1.15 (m, 2H), 1.15-1.08 (m, 2H), 0.94 (s, 9H), 0.93-0.87 (m, 6H). |
| 758 | 1H NMR (400 MHz, Methanol-d4) δ 8.47 (s, 1H), 7.97 (s, 1H), 7.78 (t, J = 8.1 Hz, 1H), 7.63 (d, J = 2.3 Hz, 1H), 6.90-6.87 (m, 1H), 6.87-6.85 (m, 1H), 6.20 (s, 1H), 4.02 (d, J = 13.9 Hz, 1H), 3.81 (d, J = 13.9 Hz, 1H), 2.49 (s, 3H), 1.57 (s, 3H), 1.56 (s, 3H), 1.39-1.31 (m, 1H), 0.93 (s, 9H), 0.56-0.49 (m, 2H), 0.46-0.38 (m, 2H). |
| 759 | 1H NMR (400 MHz, Methanol-d4) δ 8.50 (s, 1H), 8.07 (s, 1H), 7.80 (t, J = 8.1 Hz, 1H), 7.63 (d, J = 2.3 Hz, 1H), 6.95-6.84 (m, 2H), 6.24 (s, 1H), 5.09 (t, J = 6.3 Hz, 2H), 4.75 (dd, J = 6.8, 2.3 Hz, 2H), 4.02 (d, J = 13.9 Hz, 1H), 3.84 (d, J = 13.9 Hz, 1H), 2.51 (s, 3H), 1.92 (s, 3H), 0.93 (s, 9H). |
| 760 | 1H NMR (400 MHz, Methanol-d4) δ 8.46 (s, 1H), 8.34 (d, J = 8.0 Hz, 1H), 7.92 (s, 1H), 7.75 (dd, J = 7.5, 1.0 Hz, 1H), 7.66 (d, J = 2.3 Hz, 1H), 7.48 (t, J = 7.8 Hz, 1H), 7.41 (d, J = 7.7 Hz, 1H), 6.87-6.80 (m, 2H), 6.58 (s, 1H), 5.06 (dd, J = 6.8, 4.2 Hz, 2H), 4.76-4.69 (m, 2H), 4.02 (d, J = 13.8 Hz, 1H), 3.64 (d, J = 13.8 Hz, 1H), 3.61 (s, 3H), 1.88 (s, 3H), 0.77 (s, 9H). |
| 761 | 1H NMR (400 MHz, Methanol-d4) δ 8.49 (s, 1H), 7.90 (s, 1H), 7.76 (t, J = 8.1 Hz, 1H), 7.63 (d, J = 2.3 Hz, 1H), 6.92 (d, J = 2.3 Hz, 1H), 6.87 (dd, J = 8.6, 2.8 Hz, 1H), 6.20 (s, 1H), 4.01 (d, J = 13.9 Hz, 1H), 3.85 (d, J = 13.9 Hz, 1H), 2.49 (s, 3H), 1.28 (m, 2H), 1.08 (m, 2H), 0.94 (s, 9H), 0.88 (s, 9H). |
| 762 | 1H NMR (400 MHz, Methanol-d4) δ 8.48 (s, 1H), 8.02 (s, 1H), 7.79 (t, J = 8.1 Hz, 1H), 7.64 (d, J = 2.3 Hz, 1H), 6.92 (d, J = 2.3 Hz, 1H), 6.88 (dd, J = 8.5, 2.8 Hz, 1H), 6.25 (s, 1H), 5.39-5.21 (m, 1H), 5.05-4.91 (m, 2H), 4.84 (s, 2H), 4.02 (d, J = 13.9 Hz, 1H), 3.81 (d, J = 13.9 Hz, 1H), 2.50 (s, 3H), 0.93 (s, 9H). |
| 763 | 1H NMR (400 MHz, Methanol-d4) δ 8.54 (s, 1H), 8.00 (s, 1H), 7.76 (t, J = 8.1 Hz, 1H), 7.65 (d, J = 2.3 Hz, 1H), 6.88 (d, J = 2.8 Hz, 1H), 6.86 (d, J = 2.2 Hz, 2H), 6.18 (s, 1H), 4.37 (d, J = 15.0 Hz, 1H), 4.18 (d, J = 15.0 Hz, 1H), 2.49 (s, 3H), 1.59-1.49 (m, 1H), 1.30-1.19 (m, 2H), 1.15 (s, 3H), 1.15 (s, 3H), 1.08-0.96 (m, 2H), 0.57-0.48 (m, 2H), 0.37-0.27 (m, 2H). |
| 764 | 1H NMR (400 MHz, Methanol-d4) δ 8.49 (s, 1H), 7.87 (s, 1H), 7.79 (t, J = 8.1 Hz, 1H), 7.64 (d, J = 2.3 Hz, 1H), 6.92 (d, J = 2.3 Hz, 1H), 6.88 (dd, J = 8.5, 2.8 Hz, 1H), 6.22 (s, 1H), 4.23 (d, J = 3.1 Hz, 2H), 4.04 (d, J = 13.9 Hz, 1H), 3.81 (d, J = 13.9 Hz, 1H), 2.50 (s, 3H), 0.96 (s, 3H), 0.93 (s, 9H), 0.71-0.66 (m, 2H), 0.43 (m, 2H). |

TABLE 2-continued

| Compound | ¹H-NMR |
|---|---|
| 765 | 1H NMR (400 MHz, Methanol-d4) δ 8.47 (s, 1H), 8.33 (d, J = 7.9 Hz, 1H), 7.90 (s, 1H), 7.75 (d, J = 7.6 Hz, 1H), 7.67 (d, J = 2.3 Hz, 1H), 7.48 (t, J = 7.7 Hz, 1H), 7.22 (d, J = 7.5 Hz, 1H), 6.84 (d, J = 2.2 Hz, 1H), 6.81 (d, J = 7.5 Hz, 1H), 6.59 (s, 1H), 5.92 (t, J = 54.7 Hz, 1H), 4.02 (d, J = 13.8 Hz, 1H), 3.65 (d, J = 13.8 Hz, 1H), 1.51 (s, 4H), 0.79 (s, 9H). |
| 766 | 1H NMR (400 MHz, Methanol-d4) δ 8.50 (s, 1H), 7.84 (s, 1H), 7.77 (t, J = 8.0 Hz, 1H), 7.63 (d, J = 2.3 Hz, 1H), 6.90 (d, J = 2.2 Hz, 1H), 6.87 (d, J = 8.3 Hz, 1H), 6.19 (s, 1H), 4.21-4.14 (m, 1H), 4.02 (d, J = 14.0 Hz, 1H), 3.83 (d, J = 13.9 Hz, 1H), 2.49 (s, 3H), 1.75-1.67 (m, 2H), 1.17-1.12 (m, 1H), 1.06-0.95 (m, 1H), 0.95-0.91 (m, 1H), 0.93 (s, 9H), 0.90-0.74 (m, 1H). |
| 767 | 1H NMR (400 MHz, Methanol-d4) δ 8.47 (s, 1H), 8.22 (d, J = 5.0 Hz, 1H), 7.94 (s, 1H), 7.70 (d, J = 2.3 Hz, 1H), 7.40 (d, J = 3.5 Hz, 1H), 7.25 (d, J = 5.2 Hz, 1H), 6.99 (d, J = 2.3 Hz, 1H), 6.62 (d, J = 3.6 Hz, 1H), 6.50 (s, 1H), 5.91 (t, J = 54.7 Hz, 1H), 4.14 (d, J = 13.8 Hz, 1H), 3.86 (s, 3H), 3.60 (d, J = 13.8 Hz, 1H), 1.56-1.39 (m, 4H), 0.82 (s, 9H). |
| 768 | 1H NMR (400 MHz, Methanol-d4) δ 8.49 (s, 1H), 8.34 (d, J = 8.2 Hz, 1H), 7.79 (s, 1H), 7.74-7.67 (m, 1H), 7.63 (d, J = 2.3 Hz, 1H), 7.48 (t, J = 7.8 Hz, 1H), 7.40 (d, J = 7.6 Hz, 1H), 6.78 (d, J = 7.6 Hz, 1H), 6.70 (d, J = 2.3 Hz, 1H), 6.42 (s, 1H), 4.01 (d, J = 13.3 Hz, 1H), 3.90 (d, J = 13.4 Hz, 1H), 3.61 (s, 3H), 3.48 (d, J = 10.5 Hz, 1H), 3.40 (d, J = 10.5 Hz, 1H), 2.68 (s, 1H), 2.35 (s, 6H), 0.91 (s, 3H), 0.81 (s, 3H). |
| 769 | 1H NMR (400 MHz, Methanol-d4) δ 8.44 (s, 1H), 8.33 (d, J = 8.2 Hz, 1H), 7.75 (s, 1H), 7.73 (d, J = 7.5 Hz, 1H), 7.64 (d, J = 2.3 Hz, 1H), 7.47 (t, J = 7.8 Hz, 1H), 7.42 (d, J = 7.6 Hz, 1H), 6.83 (d, J = 7.8 Hz, 1H), 6.80-6.75 (m, 1H), 6.55 (s, 1H), 4.15-4.03 (m, 2H), 4.00 (d, J = 13.8 Hz, 1H), 3.59 (d, J = 13.7 Hz, 1H), 2.67 (s, 1H), 2.34 (s, 6H), 1.36 (t, J = 7.1 Hz, 3H), 0.74 (s, 9H). |
| 770 | 1H NMR (400 MHz, Methanol-d4) δ 8.49 (s, 1H), 8.39-8.32 (m, 1H), 8.06 (s, 1H), 7.80-7.73 (m, 1H), 7.68 (d, J = 2.2 Hz, 1H), 7.51 (t, J = 7.8 Hz, 1H), 7.39 (d, J = 7.8 Hz, 1H), 6.88 (d, J = 2.3 Hz, 1H), 6.82 (d, J = 7.8 Hz, 1H), 6.61 (s, 1H), 6.39-6.05 (m, 1H), 4.55-4.32 (m, 2H), 4.04 (d, J = 13.8 Hz, 1H), 3.66 (d, J = 13.8 Hz, 1H), 1.75-1.56 (m, 4H), 0.78 (s, 9H). |
| 771 | 1H NMR (400 MHz, Methanol-d4) δ 8.49 (s, 1H), 8.36 (d, J = 8.1 Hz, 1H), 8.07 (s, 1H), 7.81-7.73 (m, 1H), 7.68 (d, J = 2.3 Hz, 1H), 7.52 (t, J = 7.8 Hz, 1H), 7.40 (d, J = 7.7 Hz, 1H), 6.88 (d, J = 2.3 Hz, 1H), 6.83 (d, J = 7.8 Hz, 1H), 6.61 (s, 1H), 5.03-4.84 (m, 1H), 4.81-4.66 (m, 1H), 4.06 (d, J = 13.8 Hz, 1H), 3.65 (d, J = 13.9 Hz, 1H), 1.84-1.53 (m, 4H), 0.78 (s, 9H). |
| 772 | 1H NMR (400 MHz, Methanol-d4) δ 8.46 (s, 1H), 8.34 (d, J = 8.1 Hz, 1H), 7.75 (s, 1H), 7.73 (d, J = 7.4 Hz, 1H), 7.65 (d, J = 2.2 Hz, 1H), 7.48 (d, J = 7.9 Hz, 1H), 7.46 (t, J = 7.8 Hz, 1H), 6.87 (d, J = 7.9 Hz, 1H), 6.79 (d, J = 2.3 Hz, 1H), 6.56 (s, 1H), 5.29 (p, J = 6.8 Hz, 1H), 4.04 (d, J = 13.7 Hz, 1H), 3.58 (d, J = 13.8 Hz, 1H), 2.67 (s, 1H), 2.34 (s, 6H), 1.42 (d, J = 6.8 Hz, 3H), 1.40 (d, J = 6.8 Hz, 3H), 0.73 (s, 9H). |
| 773 | 1H NMR (400 MHz, Methanol-d4) δ 8.46 (s, 1H), 8.37-8.30 (m, 1H), 7.82 (s, 1H), 7.73 (d, J = 7.5 Hz, 1H), 7.65 (d, J = 2.3 Hz, 1H), 7.47 (t, J = 7.8 Hz, 1H), 7.42 (d, J = 7.6 Hz, 1H), 6.83 (d, J = 7.8 Hz, 1H), 6.80 (d, J = 2.3 Hz, 1H), 6.54 (s, 1H), 4.17-3.98 (m, 2H), 4.03 (d, J = 13.8 Hz, 1H), 3.61 (d, J = 13.8 Hz, 1H), 1.62 (s, 3H), 1.36 (t, J = 7.1 Hz, 3H), 1.32-1.22 (m, 2H), 1.06-1.00 (m, 2H), 0.75 (s, 9H). |
| 774 | 1H NMR (400 MHz, Methanol-d4) δ 8.43 (s, 1H), 8.38-8.30 (m, 1H), 7.81 (s, 1H), 7.73 (d, J = 7.3 Hz, 1H), 7.63 (d, J = 2.3 Hz, 1H), 7.48 (d, J = 7.9 Hz, 1H), 7.47 (t, J = 7.8 Hz, 1H), 6.88 (d, J = 7.8 Hz, 1H), 6.76 (d, J = 2.3 Hz, 1H), 6.54 (s, 1H), 5.36-5.22 (m, 1H), 4.01 (d, J = 13.8 Hz, 1H), 3.57 (d, J = 13.8 Hz, 1H), 1.62 (s, 3H), 1.42 (d, J = 6.9 Hz, 3H), 1.40 (d, J = 6.9 Hz, 3H), 1.32-1.25 (m, 2H), 1.07-0.99 (m, 2H), 0.73 (s, 9H). |
| 775 | 1H NMR (400 MHz, Methanol-d4) δ 8.48 (d, J = 1.2 Hz, 1H), 8.34 (d, J = 8.1 Hz, 1H), 7.88 (s, 1H), 7.73 (d, J = 7.4 Hz, 1H), 7.66 (d, J = 2.2 Hz, 1H), 7.48 (t, J = 7.8 Hz, 1H), 7.41 (d, J = 7.7 Hz, 1H), 6.87-6.79 (m, 2H), 6.57 (s, 1H), 4.59 (d, J = 48.4 Hz, 2H), 4.05 (d, J = 13.8 Hz, 1H), 3.65 (d, J = 13.8 Hz, 1H), 3.61 (s, 3H), 1.46-1.29 (m, 4H), 0.77 (s, 9H). |
| 776 | 1H NMR (400 MHz, Methanol-d4) δ 8.50 (s, 1H), 8.33 (d, J = 8.1 Hz, 1H), 7.83 (s, 1H), 7.72 (d, J = 7.4 Hz, 1H), 7.66 (d, J = 2.2 Hz, 1H), 7.48 (t, J = 7.8 Hz, 1H), 7.41 (d, J = 7.7 Hz, 1H), 6.85-6.77 (m, 2H), 6.54 (s, 1H), 4.06 (d, J = 13.9 Hz, 1H), 3.64 (d, J = 13.6 Hz, 1H), 3.61 (s, 3H), 1.62 (s, 3H), 1.30-1.26 (m, 2H), 1.07-1.01 (m, 2H), 0.76 (s, 9H). |
| 777 | 1H NMR (400 MHz, Methanol-d4) δ 8.48 (s, 1H), 8.34 (d, J = 8.2 Hz, 1H), 7.88 (s, 1H), 7.77-7.70 (m, 1H), 7.67 (d, J = 2.2 Hz, 1H), 7.48 (t, J = 7.8 Hz, 1H), 7.42 (d, J = 7.7 Hz, 1H), 6.85 (d, J = 2.2 Hz, 1H), 6.82 (d, J = 7.6 Hz, 1H), 6.61 (s, 1H), 5.24 (t, J = 19.1 Hz, 1H), 5.02-4.91 (m, 2H), 4.87-4.69 (m, 2H), 4.05 (d, J = 13.8 Hz, 1H), 3.64 (d, J = 13.7 Hz, 1H), 3.61 (s, 3H), 0.77 (s, 9H). |
| 778 | 1H NMR (400 MHz, Methanol-d4) δ 8.49 (s, 1H), 8.34 (d, J = 8.2 Hz, 1H), 7.81 (s, 1H), 7.73 (d, J = 7.5 Hz, 1H), 7.67 (d, J = 2.2 Hz, 1H), 7.48 (t, J = 7.8 Hz, 1H), 7.41 (d, J = 7.7 Hz, 1H), 6.85 (d, J = 2.3 Hz, 1H), 6.81 (d, J = 7.7 Hz, 1H), 6.58 (s, 1H), 5.05-4.91 (m, 1H), 4.67 (d, J = 46.9 Hz, 1H), 4.66 (d, J = 47.0 Hz, 1H), 4.06 (d, J = 13.8 Hz, 1H), 3.65 (d, J = 13.8 Hz, 1H), 3.61 (s, 3H), 1.53 (dd, J = 7.1, 1.2 Hz, 3H), 0.77 (s, 9H). |
| 779 | 1H NMR (400 MHz, Methanol-d4) δ 8.18 (s, 1H), 8.04 (d, J = 8.0 Hz, 1H), 7.58 (s, 1H), 7.44 (d, J = 7.3 Hz, 1H), 7.36 (d, J = 2.1 Hz, 1H), 7.18 (t, J = 7.8 Hz, 1H), 7.12 (d, J = 7.7 Hz, 1H), 6.55-6.48 (m, 2H), 6.25 (s, 1H), 3.76 (d, J = 13.6 |

TABLE 2-continued

| Compound | ¹H-NMR |
|---|---|
| | Hz, 1H), 3.33 (d, J = 14.0 Hz, 1H), 3.31 (s, 3H), 1.26-1.17 (m, 1H), 0.98-0.81 (m, 2H), 0.79-0.62 (m, 2H), 0.47 (s, 9H), 0.27-0.13 (m, 2H), 0.12--0.09 (m, 2H). |
| 780 | 1H NMR (400 MHz, Methanol-d4) δ 8.51 (s, 1H), 8.35 (d, J = 8.3 Hz, 1H), 8.07 (s, 1H), 7.72-7.68 (m, 1H), 7.67 (d, J = 2.3 Hz, 1H), 7.48 (t, J = 7.8 Hz, 1H), 7.42 (d, J = 7.7 Hz, 1H), 6.85 (d, J = 2.3 Hz, 1H), 6.80 (d, J = 7.6 Hz, 1H), 6.59 (s, 1H), 4.34 (d, J = 14.9 Hz, 1H), 4.07 (d, J = 14.9 Hz, 1H), 3.61 (s, 3H), 1.85-1.55 (m, 4H), 1.02 (d, J = 16.4 Hz, 6H). |
| 781 | 1H NMR (400 MHz, Methanol-d4) δ 8.52 (s, 1H), 8.34 (d, J = 8.3 Hz, 1H), 7.84 (s, 1H), 7.72-7.67 (m, 1H), 7.66 (d, J = 2.3 Hz, 1H), 7.47 (t, J = 7.8 Hz, 1H), 7.41 (d, J = 7.7 Hz, 1H), 6.82 (d, J = 2.3 Hz, 1H), 6.80 (d, J = 7.5 Hz, 1H), 6.53 (s, 1H), 4.35 (d, J = 14.9 Hz, 1H), 4.07 (d, J = 14.9 Hz, 1H), 3.61 (s, 3H), 1.63 (s, 3H), 1.32-1.25 (m, 2H), 1.06-1.01 (m, 5H), 0.99 (s, 3H). |
| 782 | 1H NMR (400 MHz, Methanol-d4) δ 8.49 (s, 1H), 8.14 (s, 1H), 8.12 (dd, J = 5.0, 1.9 Hz, 1H), 7.68 (dd, J = 7.3, 1.9 Hz, 1H), 7.65 (d, J = 2.3 Hz, 1H), 7.06 (d, J = 2.3 Hz, 1H), 6.95 (dd, J = 7.4, 5.0 Hz, 1H), 6.29 (s, 1H), 4.05 (d, J = 13.9 Hz, 1H), 3.94 (s, 3H), 3.85 (d, J = 13.9 Hz, 1H), 1.82-1.59 (m, 4H), 0.97 (s, 9H). |
| 783 | 1H NMR (400 MHz, Methanol-d4) δ 8.18 (s, 1H), 8.08-8.00 (m, 1H), 7.57 (s, 1H), 7.46-7.38 (m, 1H), 7.35 (d, J = 2.3 Hz, 1H), 7.18 (t, J = 7.8 Hz, 1H), 7.12 (d, J = 7.6 Hz, 1H), 6.54-6.46 (m, 2H), 6.23 (s, 1H), 4.03 (d, J = 14.8 Hz, 1H), 3.71 (d, J = 14.9 Hz, 1H), 3.31 (s, 3H), 1.21 (ddd, J = 13.1, 8.1, 4.9 Hz, 1H), 0.97-0.79 (m, 2H), 0.69 (d, J = 18.4 Hz, 6H), 0.71-0.68 (m, 2H), 0.25-0.15 (m, 2H), 0.01 (t, J = 5.0 Hz, 2H). |
| 784 | 1H NMR (400 MHz, Methanol-d4) δ 9.85 (s, 1H), 9.71 (d, J = 7.9 Hz, 1H), 9.17 (s, 1H), 9.07 (d, J = 7.5 Hz, 1H), 9.02 (s, 1H), 8.85 (t, J = 8.0 Hz, 1H), 8.78 (d, J = 7.6 Hz, 1H), 8.18 (s, 2H), 7.93 (s, 1H), 6.46-6.27 (m, 1H), 6.03 (dd, J = 46.9, 5.4 Hz, 2H), 5.70 (d, J = 14.8 Hz, 1H), 5.40 (d, J = 14.8 Hz, 1H), 4.98 (s, 3H), 2.90 (d, J = 7.0 Hz, 3H), 2.36 (d, J = 17.8 Hz, 6H). |
| 785 | 1H NMR (400 MHz, Methanol-d4) δ 9.84 (s, 1H), 9.70 (d, J = 8.3 Hz, 1H), 9.14 (s, 1H), 9.05 (d, J = 7.5 Hz, 1H), 9.00 (d, J = 2.2 Hz, 1H), 8.84 (t, J = 7.8 Hz, 1H), 8.78 (d, J = 7.6 Hz, 1H), 8.28-8.05 (m, 2H), 7.90 (s, 1H), 5.66 (d, J = 14.9 Hz, 1H), 5.41 (d, J = 14.8 Hz, 1H), 4.97 (s, 3H), 4.03 (s, 1H), 3.71 (s, 6H), 2.36 (d, J = 18.1 Hz, 6H). |
| 786 | 1H NMR (400 MHz, Methanol-d4) δ 8.48 (s, 1H), 8.17 (d, J = 9.9 Hz, 1H), 7.78 (s, 1H), 7.66 (d, J = 2.3 Hz, 1H), 7.64-7.59 (m, 2H), 7.40-7.33 (m, 1H), 6.83 (d, J = 2.3 Hz, 1H), 6.71 (d, J = 9.9 Hz, 1H), 6.65 (s, 1H), 4.07 (d, J = 13.9 Hz, 1H), 3.77 (s, 3H), 3.61 (d, J = 13.9 Hz, 1H), 2.67 (s, 1H), 2.35 (s, 6H), 0.77 (s, 9H). |
| 787 | 1H NMR (400 MHz, Methanol-d4) δ 8.46 (s, 1H), 8.32 (d, J = 8.1 Hz, 1H), 7.77-7.72 (m, 2H), 7.65 (d, J = 2.3 Hz, 1H), 7.47 (t, J = 7.8 Hz, 1H), 7.22 (d, J = 7.5 Hz, 1H), 6.81 (dd, J = 5.0, 2.6 Hz, 2H), 6.56 (s, 1H), 4.01 (d, J = 13.8 Hz, 1H), 3.63 (d, J = 13.8 Hz, 1H), 2.67 (s, 1H), 2.35 (s, 6H), 0.77 (s, 9H). |
| 788 | 1H NMR (400 MHz, Methanol-d4) δ 8.49 (s, 1H), 8.36 (d, J = 8.0 Hz, 1H), 8.11 (s, 1H), 7.91 (t, J = 60.1 Hz, 1H), 7.83-7.79 (m, 1H), 7.69 (d, J = 2.3 Hz, 1H), 7.54 (t, J = 7.8 Hz, 1H), 7.49 (d, J = 8.0 Hz, 1H), 6.92 (d, J = 8.1 Hz, 1H), 6.86 (d, J = 2.3 Hz, 1H), 6.62 (s, 1H), 4.07 (d, J = 13.8 Hz, 1H), 3.64 (d, J = 13.8 Hz, 1H), 1.85-1.51 (m, 4H), 0.79 (s, 9H). |
| 789 | 1H NMR (400 MHz, Methanol-d4) δ 8.48 (s, 1H), 8.17 (d, J = 9.8 Hz, 1H), 8.08 (s, 1H), 7.68 (d, J = 2.3 Hz, 1H), 7.64 (s, 1H), 7.63 (d, J = 2.4 Hz, 1H), 7.37 (dd, J = 5.5, 3.1 Hz, 1H), 6.87 (d, J = 2.3 Hz, 1H), 6.72 (d, J = 9.8 Hz, 1H), 6.70 (s, 1H), 4.08 (d, J = 13.9 Hz, 1H), 3.78 (s, 3H), 3.61 (d, J = 13.8 Hz, 1H), 1.77-1.59 (m, 4H), 0.77 (s, 9H). |
| 790 | 1H NMR (400 MHz, Methanol-d4) δ 8.48 (s, 1H), 8.40-8.26 (m, 1H), 7.74 (dd, J = 7.6, 1.2 Hz, 1H), 7.66 (d, J = 2.0 Hz, 2H), 7.47 (t, J = 7.8 Hz, 1H), 7.40 (d, J = 7.6 Hz, 1H), 6.88-6.75 (m, 2H), 6.54 (s, 1H), 4.03 (m, 4H), 3.71-3.55 (m, 4H), 0.77 (s, 9H). |
| 791 | 1H NMR (400 MHz, Methanol-d4) δ 8.20 (s, 1H), 7.89-7.70 (m, 2H), 7.48 (d, J = 2.4 Hz, 1H), 6.86 (dd, J = 8.4, 2.7 Hz, 1H), 6.73 (d, J = 2.4 Hz, 1H), 6.16 (s, 1H), 4.07 (s, 3H), 3.79 (d, J = 13.7 Hz, 1H), 3.59 (d, J = 13.8 Hz, 1H), 2.51 (s, 3H), 0.86 (s, 9H). |
| 792 | 1H NMR (400 MHz, Methanol-d4) δ 8.50 (d, J = 1.0 Hz, 1H), 8.19 (s, 1H), 7.78 (t, J = 8.1 Hz, 1H), 7.62 (d, J = 2.3 Hz, 1H), 7.02 (d, J = 2.4 Hz, 1H), 6.88 (dd, J = 8.5, 2.7 Hz, 1H), 6.24 (s, 1H), 4.53 (dd, J = 12.1, 6.4 Hz, 2H), 4.43 (t, J = 6.1 Hz, 2H), 4.12 (s, 2H), 2.50 (s, 3H), 1.81-1.56 (m, 4H), 1.39 (s, 3H). |
| 793 | 1H NMR (400 MHz, Methanol-d4) δ 8.47 (d, J = 3.1 Hz, 2H), 8.23 (s, 1H), 7.89 (dd, J = 8.3, 2.6 Hz, 1H), 7.66 (d, J = 2.3 Hz, 1H), 7.47 (d, J = 8.3 Hz, 1H), 7.05 (d, J = 2.3 Hz, 1H), 6.20 (s, 1H), 4.15 (d, J = 14.0 Hz, 1H), 3.73 (d, J = 14.0 Hz, 1H), 1.80-1.72 (m, 2H), 1.69 (d, J = 9.1 Hz, 2H), 0.96 (s, 9H). |
| 794 | 1H NMR (400 MHz, Methanol-d4) δ 8.49 (s, 1H), 8.21 (s, 1H), 7.70-7.60 (m, 2H), 7.27 (d, J = 8.2 Hz, 1H), 6.89 (d, J = 2.3 Hz, 1H), 6.22 (s, 1H), 4.05 (d, J = 13.9 Hz, 1H), 3.77 (d, J = 13.9 Hz, 1H), 2.51 (s, 3H), 1.81-1.61 (m, 4H), 0.92 (s, 9H). |
| 795 | 1H NMR (400 MHz, Methanol-d4) δ 8.71 (d, J = 2.2 Hz, 1H), 8.48 (s, 1H), 8.31 (s, 1H), 8.28 (dd, J = 8.3, 2.3 Hz, 1H), 7.71 (d, J = 8.3 Hz, 1H), 7.67 (d, J = 2.3 Hz, 1H), 7.16 (d, J = 2.3 Hz, 1H), 6.33 (s, 1H), 4.09 (d, J = 14.0 Hz, 1H), 3.81 (d, J = 14.0 Hz, 1H), 2.69 (s, 3H), 1.80-1.73 (m, 2H), 1.72-1.62 (m, 2H), 0.97 (s, 9H). |

TABLE 2-continued

| Compound | ¹H-NMR |
|---|---|
| 796 | 1H NMR (400 MHz, Acetonitrile-d3) δ 8.39 (s, 1H), 8.31 (d, J = 8.0 Hz, 1H), 7.79 (d, J = 7.2 Hz, 1H), 7.66 (s, 1H), 7.53 (d, J = 2.3 Hz, 1H), 7.45 (t, J = 7.8 Hz, 1H), 7.31 (d, J = 7.7 Hz, 1H), 6.80 (d, J = 7.7 Hz, 1H), 6.60 (s, 1H), 6.46 (s, 1H), 5.07-4.98 (m, 1H), 3.77-3.69 (m, 1H), 3.62 (m, 1H), 3.54 (s, 3H), 2.54-2.44 (m, 4H), 1.89 (m, 2H), 0.79 (s, 9H). |
| 797 | 1H NMR (400 MHz, Methanol-d4) δ 9.03 (d, J = 4.5 Hz, 1H), 8.87 (d, J = 8.6 Hz, 1H), 8.45 (s, 1H), 8.10 (d, J = 8.5 Hz, 1H), 7.95-7.83 (m, 2H), 7.82-7.73 (m, 2H), 7.66 (d, J = 2.3 Hz, 1H), 6.85-6.79 (m, 2H), 4.30 (d, J = 14.9 Hz, 1H), 3.93 (d, J = 14.9 Hz, 1H), 1.62 (s, 3H), 1.30 (d, J = 13.3 Hz, 2H), 1.03 (s, 2H), 0.94 (s, 3H), 0.88 (s, 3H). |
| 798 | 1H NMR (400 MHz, Methanol-d4) δ 9.02 (d, J = 4.9 Hz, 1H), 8.85 (d, J = 8.4 Hz, 1H), 8.44 (s, 1H), 8.09 (d, J = 8.6 Hz, 1H), 7.96 (s, 1H), 7.87 (t, J = 7.9 Hz, 1H), 7.81-7.72 (m, 2H), 7.67 (d, J = 2.3 Hz, 1H), 6.86-6.79 (m, 2H), 4.31 (d, J = 14.8 Hz, 1H), 3.91 (d, J = 14.9 Hz, 1H), 1.18 (s, 2H), 0.99 (s, 2H), 0.94 (s, 3H), 0.88 (s, 3H), 0.49 (d, J = 7.5 Hz, 2H), 0.29 (d, J = 5.1 Hz, 2H). |
| 799 | 1H NMR (400 MHz, Methanol-d4) δ 9.05 (d, J = 4.6 Hz, 1H), 8.92 (d, J = 8.7 Hz, 1H), 8.48 (s, 1H), 8.12 (d, J = 8.6 Hz, 1H), 7.94-7.85 (m, 2H), 7.85-7.76 (m, 2H), 7.67 (d, J = 2.3 Hz, 1H), 6.88-6.81 (m, 2H), 4.31 (d, J = 14.9 Hz, 1H), 3.96 (d, J = 14.9 Hz, 1H), 2.67 (s, 1H), 2.34 (s, 6H), 0.95 (s, 3H), 0.90 (s, 3H). |
| 800 | (1H NMR (400 MHz, Acetonitrile-d3) δ 8.38 (s, 1H), 8.30 (d, J = 8.0 Hz, 1H), 7.80 (d, J = 7.5 Hz, 1H), 7.65 (s, 1H), 7.52 (d, J = 2.2 Hz, 1H), 7.45 (t, J = 7.7 Hz, 1H), 7.31 (d, J = 7.7 Hz, 1H), 6.82 (d, J = 7.7 Hz, 1H), 6.58 (s, 1H), 6.46 (s, 1H), 3.77-3.67 (m, 1H), 3.61 (m, 1H), 3.54 (s, 3H), 2.68 (d, J = 10.2 Hz, 2H), 2.5, (m, 2H), 2.27 (s, 2H), 1.69 (s, 3H), 0.78 (s, 9H). |
| 801 | 1H NMR (400 MHz, Acetonitrile-d3) δ 8.40 (s, 1H), 8.31 (d, J = 7.9 Hz, 1H), 7.78 (d, J = 7.5 Hz, 1H), 7.56 (dd, J = 21.4, 1.8 Hz, 2H), 7.45 (t, J = 7.8 Hz, 1H), 7.30 (d, J = 7.7 Hz, 1H), 6.81-6.74 (m, 1H), 6.61 (s, 1H), 6.47 (s, 1H), 3.84-3.68 (m, 1H), 3.63 (m, 1H), 3.54 (s, 3H), 1.86-1.78 (m, 2H), 1.46 (dd, J = 6.8, 3.3 Hz, 3H), 0.79 (d, J = 1.1 Hz, 9H), 0.78-0.69 (m, 3H). |
| 802 | 1H NMR (400 MHz, Acetonitrile-d3) δ 8.39 (s, 1H), 8.31 (d, J = 8.0 Hz, 1H), 7.83-7.76 (m, 1H), 7.63 (s, 1H), 7.54 (d, J = 2.3 Hz, 1H), 7.45 (t, J = 7.8 Hz, 1H), 7.31 (d, J = 7.7 Hz, 1H), 6.81 (d, J = 7.8 Hz, 1H), 6.61 (s, 1H), 6.47 (s, 1H), 6.24 (s, 1H), 4.79 (m, 1H), 3.76 (m, 1H), 3.71-3.53 (m, 3H), 3.54 (s, 3H), 3.20 (s, 3H), 1.45 (d, J = 6.9 Hz, 3H), 0.80 (s, 9H). |
| 803 | 1H NMR (400 MHz, Methanol-d4) δ 8.98 (d, J = 4.6 Hz, 1H), 8.78 (d, J = 8.6 Hz, 1H), 8.46 (s, 1H), 8.08 (d, J = 8.4 Hz, 1H), 7.89-7.79 (m, 2H), 7.79-7.65 (m, 3H), 6.95-6.85 (m, 2H), 4.96 (dd, J = 12.2, 5.9 Hz, 1H), 4.71 (d, J = 5.4 Hz, 1H), 4.60 (d, J = 5.4 Hz, 1H), 4.00 (d, J = 13.8 Hz, 1H), 3.61 (d, J = 13.9 Hz, 1H), 1.52 (dd, J = 7.1, 1.3 Hz, 3H), 0.69 (s, 9H). |
| 804 | 1H NMR (400 MHz, Methanol-d4) δ 8.98 (d, J = 4.5 Hz, 1H), 8.78 (d, J = 8.7 Hz, 1H), 8.46 (s, 1H), 8.09 (d, J = 8.5 Hz, 1H), 7.94 (s, 1H), 7.88-7.79 (m, 1H), 7.79-7.66 (m, 3H), 6.96-6.88 (m, 2H), 5.22 (s, 1H), 4.99-4.84 (m, 3H), 4.84-4.73 (m, 1H), 4.00 (d, J = 13.9 Hz, 1H), 3.61 (d, J = 13.8 Hz, 1H), 0.69 (s, 9H). |
| 805 | 1H NMR (400 MHz, Methanol-d4) δ 8.47 (s, 1H), 8.22 (s, 1H), 8.13 (s, 1H), 7.74 (dd, J = 8.7, 2.5 Hz, 1H), 7.65 (d, J = 2.1 Hz, 1H), 7.10 (s, 1H), 6.81 (d, J = 8.7 Hz, 1H), 6.10 (s, 1H), 4.12 (d, J = 14.0 Hz, 1H), 3.89 (s, 3H), 3.79 (d, J = 14.0 Hz, 1H), 1.83-1.56 (m, 4H), 0.98 (s, 9H). |
| 806 | 1H NMR (400 MHz, Methanol-d4) δ 8.54 (s, 1H), 8.20 (s, 1H), 7.84 (t, J = 8.1 Hz, 1H), 7.64 (d, J = 2.3 Hz, 1H), 6.96 (d, J = 2.3 Hz, 1H), 6.88 (dd, J = 8.7, 2.8 Hz, 1H), 6.25 (s, 1H), 4.12 (d, J = 13.9 Hz, 1H), 3.81 (d, J = 13.9 Hz, 1H), 2.52 (s, 3H), 2.46 (s, 3H), 2.06-1.93 (m, 4H), 0.94 (s, 9H). |
| 807 | 1H NMR (400 MHz, Methanol-d4) δ 8.27 (s, 1H), 8.23 (d, J = 8.3 Hz, 1H), 7.95 (d, J = 6.2 Hz, 1H), 7.75 (d, J = 2.5 Hz, 1H), 7.72 (s, 2H), 7.51 (d, J = 7.8 Hz, 1H), 7.49-7.42 (m, 2H), 6.93 (d, J = 2.5 Hz, 1H), 6.66 (s, 1H), 4.09 (s, 3H), 3.71 (d, J = 13.5 Hz, 1H), 3.44 (d, J = 13.6 Hz, 1H), 2.30 (s, 6H), 0.61 (s, 9H). |
| 808 | 1H NMR (400 MHz, Methanol-d4) δ 8.28 (s, 1H), 8.22 (d, J = 8.2 Hz, 1H), 7.95 (dd, J = 6.3, 1.4 Hz, 1H), 7.77-7.70 (m, 4H), 7.53-7.44 (m, 2H), 6.94 (d, J = 2.4 Hz, 1H), 6.64 (s, 1H), 4.09 (d, J = 1.4 Hz, 3H), 3.85-3.77 (m, OH), 3.72 (d, J = 13.4 Hz, 1H), 3.45 (d, J = 13.2 Hz, 1H), 1.16-1.04 (m, 4H), 0.62 (d, J = 1.4 Hz, 9H). |
| 809 | 1H NMR (400 MHz, Methanol-d4) δ 8.26 (s, 1H), 8.22 (d, J = 8.4 Hz, 1H), 7.95 (d, J = 6.3 Hz, 1H), 7.79 (s, 1H), 7.75 (d, J = 2.3 Hz, 1H), 7.73 (s, 1H), 7.54-7.43 (m, 2H), 6.92 (d, J = 2.5 Hz, 1H), 6.64 (s, 1H), 4.09 (d, J = 1.0 Hz, 3H), 3.71 (d, J = 13.4 Hz, 1H), 3.44 (d, J = 13.8 Hz, 1H), 1.58 (s, 3H), 1.24 (s, 3H), 1.01-0.96 (m, 2H), 0.61 (d, J = 1.0 Hz, 8H). |
| 810 | 1H NMR (400 MHz, Methanol-d4) δ 8.29 (d, J = 1.4 Hz, 1H), 8.23 (d, J = 8.3 Hz, 1H), 7.98-7.93 (m, 1H), 7.87 (s, 1H), 7.79-7.76 (m, 1H), 7.74 (d, J = 7.3 Hz, 1H), 7.54-7.44 (m, 3H), 6.98 (d, J = 2.5 Hz, 1H), 6.69 (s, 1H), 5.88 (t, J = 55.0 Hz, 1H), 4.09 (d, J = 1.2 Hz, 3H), 3.75 (d, J = 13.6 Hz, 1H), 3.47 (d, J = 13.5 Hz, 1H), 1.46 (d, J = 1.2 Hz, 2H), 0.63 (d, J = 1.1 Hz, 10H). |
| 811 | 1H NMR (400 MHz, Methanol-d4) δ 8.39 (d, J = 9.2 Hz, 1H), 8.36 (s, 1H), 8.04 (s, 1H), 7.82 (s, 1H), 7.82 (d, J = 10.3 Hz, 1H), 7.59 (t, J = 8.5, 7.4 Hz, 1H), 7.43 (d, J = 7.3 Hz, 1H), 7.09 (d, J = 2.5 Hz, 1H), 7.00 (d, J = 9.2 Hz, 1H), 6.78 (s, 1H), 4.06 (d, J = 0.6 Hz, 3H), 3.83 (d, J = 13.7 Hz, 1H), 3.55 (d, J = 13.7 Hz, 1H), 1.76-1.56 (m, 5H), 0.69 (s, 9H). |
| 812 | 1H NMR (400 MHz, Methanol-d4) δ 8.35 (s, 1H), 8.27 (d, J = 8.3 Hz, 1H), 8.07 (s, 1H), 7.99 (d, J = 6.2 Hz, 1H), 7.83 (d, J = 2.5 Hz, 1H), 7.77 (d, J = 7.2 Hz, 1H), 7.58-7.51 (m, 1H), 7.49 (d, J = 6.4 Hz, 1H), 7.04 (d, J = 2.5 Hz, 1H), 6.75 |

TABLE 2-continued

| Compound | ¹H-NMR |
|---|---|
| | (s, 1H), 4.13 (s, 3H), 3.82 (d, J = 13.7 Hz, 1H), 3.52 (d, J = 13.7 Hz, 1H), 1.77-1.55 (m, 4H), 0.66 (s, 9H). |
| 814 | 1H NMR (400 MHz, Methanol-d4) δ 8.95 (dd, J = 4.4, 1.4 Hz, 1H), 8.67 (d, J = 8.8 Hz, 1H), 8.35 (s, 1H), 7.86 (s, 1H), 7.81 (d, J = 2.4 Hz, 1H), 7.69 (dd, J = 8.7, 4.3 Hz, 1H), 7.64 (dd, J = 8.2, 4.8 Hz, 1H), 7.48 (dd, J = 10.3, 8.2 Hz, 1H), 7.06 (d, J = 2.5 Hz, 1H), 6.78 (s, 1H), 3.82 (d, J = 13.7 Hz, 1H), 3.49 (d, J = 13.8 Hz, 1H), 2.66 (s, 1H), 2.34 (s, 6H), 0.64 (s, 9H). |
| 815 | 1H NMR (400 MHz, Methanol-d4) δ 8.96 (d, J = 4.3 Hz, 1H), 8.68 (d, J = 8.8 Hz, 1H), 8.35 (s, 1H), 7.99 (s, 1H), 7.81 (d, J = 2.5 Hz, 1H), 7.71 (dd, J = 8.7, 4.4 Hz, 1H), 7.63 (dd, J = 8.2, 4.8 Hz, 1H), 7.50 (dd, J = 10.0, 8.5 Hz, 1H), 7.04 (d, J = 2.5 Hz, 1H), 6.78 (s, 1H), 5.91 (t, J = 54.7 Hz, 1H), 4.16 (d, J = 14.8 Hz, 1H), 3.86 (d, J = 14.8 Hz, 1H), 1.49 (d, J = 5.4 Hz, 4H), 0.90 (s, 3H), 0.85 (s, 3H). |
| 816 | 1H NMR (400 MHz, Methanol-d4) δ 8.95 (d, J = 4.3 Hz, 1H), 8.66 (d, J = 8.7 Hz, 1H), 8.34 (s, 1H), 7.84 (s, 1H), 7.79 (d, J = 2.4 Hz, 1H), 7.69 (dd, J = 8.8, 4.3 Hz, 1H), 7.61 (dd, J = 8.2, 4.8 Hz, 1H), 7.52-7.44 (m, 1H), 7.01 (d, J = 2.4 Hz, 1H), 6.75 (s, 1H), 4.14 (d, J = 14.8 Hz, 1H), 3.85 (d, J = 14.8 Hz, 1H), 2.66 (s, 1H), 2.34 (s, 6H), 2.02 (s, 1H), 0.88 (s, 3H), 0.83 (s, 3H). |
| 817 | 1H NMR (400 MHz, Methanol-d4) δ 8.67 (d, J = 5.9 Hz, 1H), 8.34 (d, J = 8.5 Hz, 1H), 8.30 (s, 1H), 8.29 (s, 1H), 8.16 (s, 1H), 7.98 (d, J = 7.2 Hz, 1H), 7.89-7.83 (m, 1H), 7.82 (d, J = 2.5 Hz, 1H), 7.02 (d, J = 2.5 Hz, 1H), 6.88 (s, 1H), 3.80 (d, J = 13.7 Hz, 1H), 3.43 (d, J = 13.7 Hz, 1H), 1.76-1.56 (m, 4H), 0.62 (s, 9H). |
| 818 | 1H NMR (400 MHz, Methanol-d4) δ 9.02 (dd, J = 5.0, 1.6 Hz, 1H), 8.84 (d, J = 8.3 Hz, 1H), 8.29 (s, 1H), 8.22 (s, 1H), 8.19 (s, 1H), 8.12 (s, 1H), 7.93 (dd, J = 8.7, 1.7 Hz, 1H), 7.89-7.81 (m, 2H), 7.22 (d, J = 2.5 Hz, 1H), 6.41 (s, 1H), 5.95 (t, J = 54.6 Hz, 1H), 3.91 (d, J = 13.9 Hz, 1H), 3.47 (d, J = 13.9 Hz, 1H), 1.54 (s, 4H), 0.72 (s, 9H). |
| 819 | 1H NMR (400 MHz, Methanol-d4) δ 8.32 (s, 1H), 8.26 (d, J = 8.3 Hz, 1H), 7.98 (d, J = 6.2 Hz, 1H), 7.83 (s, 1H), 7.78 (d, J = 2.4 Hz, 1H), 7.73 (d, J = 7.2 Hz, 1H), 7.53 (t, J = 7.9 Hz, 1H), 7.48 (d, J = 6.3 Hz, 1H), 6.96 (d, J = 2.5 Hz, 1H), 6.66 (s, 1H), 4.12 (d, J = 14.8 Hz, 1H), 4.12 (s, 3H), 3.85 (d, J = 14.7 Hz, 1H), 1.62 (s, 3H), 1.27 (d, J = 5.6 Hz, 2H), 1.07-0.99 (m, 2H), 0.84 (d, J = 13.7 Hz, 6H). |
| 820 | 1H NMR (400 MHz, Methanol-d4) δ 8.32 (s, 1H), 8.26 (d, J = 8.3 Hz, 1H), 7.99 (d, J = 6.2 Hz, 1H), 7.78 (d, J = 2.4 Hz, 1H), 7.76 (s, 1H), 7.72 (d, J = 7.3 Hz, 1H), 7.53 (t, J = 7.8 Hz, 1H), 7.48 (d, J = 6.2 Hz, 1H), 6.96 (d, J = 2.5 Hz, 1H), 6.67 (s, 1H), 4.10 (d, J = 12.8 Hz, 4H), 3.86 (d, J = 14.6 Hz, 1H), 2.66 (s, 1H), 2.34 (s, 6H), 0.84 (d, J = 14.2 Hz, 6H). |
| 821 | 1H NMR (400 MHz, Methanol-d4) δ 8.35 (s, 1H), 8.27 (d, J = 8.3 Hz, 1H), 7.99 (d, J = 6.3 Hz, 1H), 7.91 (s, 1H), 7.81 (d, J = 2.5 Hz, 1H), 7.73 (dd, J = 7.4, 1.2 Hz, 1H), 7.58-7.51 (m, 1H), 7.48 (d, J = 6.3 Hz, 1H), 7.01 (d, J = 2.5 Hz, 1H), 6.71 (s, 1H), 5.92 (t, J = 54.8 Hz, 1H), 4.13 (s, 4H), 3.89 (d, J = 14.7 Hz, 1H), 1.49 (d, J = 3.5 Hz, 4H), 0.87 (d, J = 12.6 Hz, 6H). |
| 822 | 1H NMR (400 MHz, Methanol-d4) δ 8.91 (s, 1H), 8.38 (s, 1H), 8.30 (s, 1H), 8.18 (d, J = 1.8 Hz, 1H), 8.05 (d, J = 2.1 Hz, 1H), 8.02 (d, J = 2.0 Hz, OH), 7.96 (s, 1H), 7.96-7.91 (m, 1H), 7.80 (d, J = 2.6 Hz, 1H), 7.28 (d, J = 2.5 Hz, 1H), 6.31 (s, 1H), 3.90 (d, J = 14.0 Hz, 1H), 3.57 (d, J = 14.0 Hz, 1H), 1.78 (s, 2H), 1.68 (s, 2H), 0.83 (s, 10H). |
| 823 | 1H NMR (400 MHz, Methanol-d4) δ 8.35 (s, 1H), 8.26 (d, J = 8.4 Hz, 1H), 7.99 (d, J = 6.2 Hz, 1H), 7.86 (s, 1H), 7.82 (d, J = 2.4 Hz, 1H), 7.78 (d, J = 7.4 Hz, 1H), 7.54 (t, J = 7.8 Hz, 1H), 7.49 (d, J = 6.3 Hz, 1H), 7.01 (d, J = 2.5 Hz, 1H), 6.69 (s, 1H), 4.12 (s, 3H), 3.81 (d, J = 13.7 Hz, 1H), 3.50 (d, J = 13.7 Hz, 1H), 1.49 (ddd, J = 13.2, 8.4, 5.0 Hz, 1H), 1.25-1.14 (m, 2H), 1.02-0.94 (m, 2H), 0.66 (s, 9H), 0.52-0.42 (m, 2H), 0.28 (q, J = 5.3 Hz, 2H). |
| 824 | 1H NMR (400 MHz, Methanol-d4) δ 8.35 (s, 1H), 8.27 (d, J = 8.3 Hz, 1H), 7.98 (d, J = 6.2 Hz, 1H), 7.82 (d, J = 2.4 Hz, 1H), 7.79 (s, 1H), 7.77 (d, J = 7.3 Hz, 1H), 7.54 (t, J = 7.8 Hz, 1H), 7.49 (d, J = 6.3 Hz, 1H), 7.02 (d, J = 2.4 Hz, 1H), 6.72 (s, 1H), 5.03-4.90 (m, 1H), 4.71 (d, J = 5.4 Hz, 1H), 4.59 (d, J = 5.4 Hz, 1H), 4.12 (s, 3H), 3.81 (d, J = 13.7 Hz, 1H), 3.51 (d, J = 13.7 Hz, 1H), 1.51 (dd, J = 7.0, 1.3 Hz, 3H), 0.66 (s, 9H), 0.09 (s, 1H). |
| 825 | 1H NMR (400 MHz, Methanol-d4) δ 8.35 (s, 1H), 8.27 (d, J = 8.3 Hz, 1H), 7.99 (d, J = 6.3 Hz, 1H), 7.87 (s, 1H), 7.83 (d, J = 2.4 Hz, 1H), 7.78 (d, J = 7.3 Hz, 1H), 7.58 (d, J = 7.1 Hz, OH), 7.54 (dd, J = 8.3, 7.3 Hz, 1H), 7.50 (d, J = 6.3 Hz, 1H), 7.03 (d, J = 2.5 Hz, 1H), 6.75 (s, 1H), 5.29-5.14 (m, 1H), 4.98-4.86 (m, 2H), 4.83-4.74 (m, 1H), 4.68 (s, OH), 4.30 (s, OH), 4.12 (s, 3H), 3.81 (d, J = 13.6 Hz, 1H), 3.51 (d, J = 13.7 Hz, 1H), 0.66 (s, 9H). |
| 826 | 1H NMR (400 MHz, Methanol-d4) δ 8.83 (d, J = 2.2 Hz, 1H), 8.33 (s, 1H), 8.29 (s, 1H), 8.07 (dd, J = 8.1, 2.3 Hz, 1H), 7.88 (d, J = 8.1 Hz, 1H), 7.81 (d, J = 2.5 Hz, 1H), 7.21 (d, J = 2.6 Hz, 1H), 6.29 (s, 1H), 4.00 (d, J = 14.0 Hz, 1H), 3.57 (d, J = 14.0 Hz, 1H), 1.80-1.72 (m, 2H), 1.69 (d, J = 9.2 Hz, 2H), 0.90 (s, 9H). |
| 827 | 1H NMR (400 MHz, Methanol-d4) δ 8.41 (s, 1H), 7.96 (s, 1H), 7.82-7.71 (m, 2H), 7.04 (d, J = 2.5 Hz, 1H), 6.87 (dd, J = 8.5, 2.7 Hz, 1H), 6.19 (s, 1H), 4.25 (d, J = 15.0 Hz, 1H), 4.08 (d, J = 14.9 Hz, 1H), 2.50 (s, 3H), 1.64 (s, 9H), 1.10 (d, J = 1.9 Hz, 6H). |
| 828 | 1H NMR (400 MHz, Methanol-d4) δ 8.79 (d, J = 2.1 Hz, 1H), 8.48 (dd, J = 8.4, 2.2 Hz, 1H), 8.37 (s, 1H), 8.31 (s, 1H), 7.86 (d, J = 8.4 Hz, 1H), 7.76 (dd, J = 2.6, |

TABLE 2-continued

| Compound | ¹H-NMR |
|---|---|
| | 1.2 Hz, 1H), 7.32 (d, J = 2.5 Hz, 1H), 6.37 (s, 1H), 3.96-3.81 (m, 1H), 3.66 (d, J = 13.9 Hz, 1H), 2.75 (s, 3H), 1.82-1.74 (m, 2H), 1.69 (d, J = 5.5 Hz, 2H), 1.07 (s, 2H), 0.94 (s, 9H). |
| 829 | 1H NMR (400 MHz, Methanol-d4) δ 8.37 (d, J = 8.3 Hz, 1H), 8.29 (d, J = 15.4 Hz, 2H), 7.76-7.64 (m, 2H), 7.20 (d, J = 2.5 Hz, 1H), 6.37 (s, 1H), 5.95 (t, J = 54.5 Hz, 1H), 3.85 (d, J = 13.9 Hz, 1H), 3.68 (d, J = 13.9 Hz, 1H), 2.76 (d, J = 12.5 Hz, 6H), 1.56 (d, J = 2.5 Hz, 4H), 0.92 (s, 9H). |
| 830 | 1H NMR (400 MHz, Methanol-d4) δ 8.32 (s, 1H), 8.26 (s, 1H), 7.88 (d, J = 7.9 Hz, 1H), 7.77 (d, J = 2.5 Hz, 1H), 7.70 (d, J = 8.0 Hz, 1H), 7.01 (d, J = 2.5 Hz, 1H), 6.29 (s, 1H), 3.89 (d, J = 13.8 Hz, 1H), 3.57 (d, J = 13.8 Hz, 1H), 2.59 (s, 3H), 1.80-1.63 (m, 4H), 0.86 (s, 9H). |
| 831 | 1H NMR (400 MHz, Methanol-d4) δ 8.37 (s, 1H), 8.04 (s, 1H), 7.82-7.70 (m, 2H), 7.01 (d, J = 2.5 Hz, 1H), 6.86 (dd, J = 8.5, 2.7 Hz, 1H), 6.20 (s, 1H), 5.95 (t, J = 54.8 Hz, 1H), 4.42 (d, J = 14.9 Hz, 1H), 4.15 (d, J = 14.9 Hz, 1H), 2.49 (s, 3H), 2.41-2.20 (m, 2H), 2.15-1.79 (m, 3H), 1.53 (s, 5H). |
| 832 | 1H NMR (400 MHz, Methanol-d4) δ 8.37 (s, 1H), 8.05 (s, 1H), 7.85-7.68 (m, 2H), 7.05 (d, J = 2.5 Hz, 1H), 6.86 (dd, J = 8.5, 2.7 Hz, 1H), 6.22 (s, 1H), 5.94 (t, J = 54.7 Hz, 1H), 5.48 (s, 1H), 4.22 (d, J = 14.9 Hz, 1H), 4.06 (d, J = 14.9 Hz, 1H), 2.50 (s, 3H), 1.52 (t, J = 1.7 Hz, 4H), 1.10 (d, J = 2.5 Hz, 6H). |
| 833 | 1H NMR (400 MHz, Methanol-d4) δ 8.37 (s, 1H), 7.90 (s, 1H), 7.82-7.68 (m, 2H), 7.02 (d, J = 2.5 Hz, 1H), 6.86 (dd, J = 8.6, 2.7 Hz, 1H), 6.18 (s, 1H), 4.25-4.00 (m, 2H), 2.68 (s, 1H), 2.51 (s, 3H), 2.37 (s, 6H), 1.09 (d, J = 3.3 Hz, 6H). |
| 834 | 1H NMR (400 MHz, Methanol-d4) δ 8.35 (s, 1H), 7.97 (s, 1H), 7.84-7.68 (m, 2H), 7.07 (d, J = 2.5 Hz, 1H), 6.87 (dd, J = 8.5, 2.7 Hz, 1H), 6.20 (s, 1H), 5.98 (tt, J = 56.8, 3.4 Hz, 1H), 4.17 (dt, J = 8.2, 4.0 Hz, 1H), 3.85 (d, J = 13.7 Hz, 1H), 3.69 (d, J = 13.8 Hz, 1H), 2.52 (s, 3H), 2.26 (ddq, J = 10.8, 7.4, 3.8 Hz, 1H), 1.66 (q, J = 10.4, 8.7 Hz, 1H), 1.52-1.43 (m, 1H), 0.89 (s, 9H). |
| 835 | 1H NMR (400 MHz, Methanol-d4) δ 8.34 (s, 1H), 7.90 (s, 1H), 7.83-7.73 (m, 2H), 7.10 (d, J = 2.5 Hz, 1H), 6.88 (dd, J = 8.5, 2.7 Hz, 1H), 6.25 (s, 1H), 3.88 (d, J = 13.8 Hz, 1H), 3.65 (d, J = 13.8 Hz, 1H), 2.50 (s, 3H), 1.65 (t, J = 18.7 Hz, 3H), 0.89 (s, 9H). |
| 836 | 1H NMR (400 MHz, Methanol-d4) δ 8.34 (s, 1H), 7.90 (s, 1H), 7.83-7.73 (m, 2H), 7.10 (d, J = 2.5 Hz, 1H), 6.88 (dd, J = 8.5, 2.7 Hz, 1H), 6.25 (s, 1H), 3.88 (d, J = 13.8 Hz, 1H), 3.65 (d, J = 13.8 Hz, 1H), 2.50 (s, 3H), 1.65 (t, J = 18.7 Hz, 3H), 0.89 (s, 9H). |
| 837 | 1H NMR (400 MHz, Methanol-d4) δ 8.37 (s, 1H), 7.90 (s, 1H), 7.84-7.75 (m, 2H), 7.18-7.08 (m, 1H), 6.88 (dd, J = 8.4, 2.8 Hz, 1H), 6.25 (s, 1H), 3.90 (d, J = 13.8 Hz, 1H), 3.68 (d, J = 13.9 Hz, 1H), 2.50 (s, 3H), 2.01-1.77 (m, 2H), 1.05 (t, J = 7.5 Hz, 3H), 0.89 (s, 9H). |
| 838 | 1H NMR (400 MHz, DMSO-d6) δ 8.35 (s, 1H), 8.18 (d, J = 7.9 Hz, 1H), 8.09 (s, 1H), 7.84 (d, J = 2.3 Hz, 1H), 7.69-7.58 (m, 1H), 7.58-7.37 (m, 4H), 7.24 (s, 1H), 6.72 (d, J = 7.7 Hz, 1H), 6.60 (d, J = 7.4 Hz, 1H), 6.08 (t, J = 54.1 Hz, 1H), 4.07 (dd, J = 14.7, 7.6 Hz, 1H), 3.86 (dd, J = 14.6, 6.1 Hz, 1H), 3.48 (s, 3H), 1.45 (t, J = 4.4 Hz, 4H), 0.88 (s, J = 18.4 Hz, 6H). |
| 839 | 1H NMR (400 MHz, Methanol-d4) δ 8.37 (s, 1H), 7.92 (s, 1H), 7.86-7.67 (m, 2H), 7.13 (d, J = 2.5 Hz, 1H), 6.87 (dd, J = 8.4, 2.7 Hz, 1H), 6.24 (s, 1H), 4.64 (d, J = 1.1 Hz, 2H), 3.86 (d, J = 13.8 Hz, 1H), 3.72 (d, J = 13.8 Hz, 1H), 2.51 (s, 3H), 1.13 (s, 4H), 0.90 (s, 9H). |
| 840 | 1H NMR (400 MHz, Methanol-d4) δ 8.36 (s, 1H), 7.88 (s, 1H), 7.82-7.68 (m, 2H), 7.11 (d, J = 2.5 Hz, 1H), 6.87 (dd, J = 8.5, 2.7 Hz, 1H), 6.22 (s, 1H), 5.59 (t, J = 56.0 Hz, 1H), 4.55 (s, 2H), 3.86 (d, J = 13.8 Hz, 1H), 3.71 (d, J = 13.8 Hz, 1H), 2.51 (s, 3H), 0.90 (s, 14H). |
| 841 | 1H NMR (400 MHz, Methanol-d4) δ 8.37 (s, 1H), 8.04 (s, 1H), 7.85-7.70 (m, 2H), 7.04 (d, J = 2.5 Hz, 1H), 6.87 (dd, J = 8.4, 2.7 Hz, 1H), 6.21 (s, 1H), 5.94 (t, J = 54.7 Hz, 1H), 4.21 (d, J = 14.9 Hz, 1H), 4.05 (d, J = 14.9 Hz, 1H), 2.51 (s, 3H), 1.53 (t, J = 2.3 Hz, 4H), 1.10 (d, J = 2.4 Hz, 6H). |
| 842 | 1H NMR (400 MHz, Methanol-d4) δ 8.33 (d, J = 6.9 Hz, 2H), 7.94 (s, 1H), 7.85-7.64 (m, 2H), 7.49 (t, J = 7.8 Hz, 1H), 7.23 (d, J = 7.5 Hz, 1H), 7.00 (d, J = 2.4 Hz, 1H), 6.83 (d, J = 7.5 Hz, 1H), 6.58 (s, 1H), 5.93 (t, J = 54.7 Hz, 1H), 4.15 (d, J = 14.7 Hz, 1H), 3.91 (d, J = 14.8 Hz, 1H), 1.50 (s, 4H), 0.94 (d, J = 11.1 Hz, 6H). |
| 843 | 1H NMR (400 MHz, Methanol-d4) δ 8.35 (s, 1H), 8.19 (s, 1H), 7.87-7.66 (m, 2H), 7.04 (d, J = 2.5 Hz, 1H), 6.87 (dd, J = 8.5, 2.7 Hz, 1H), 6.23 (s, 1H), 4.19 (d, J = 14.9 Hz, 1H), 4.04 (d, J = 14.9 Hz, 1H), 2.51 (s, 3H), 1.81-1.59 (m, 4H), 1.09 (d, J = 1.9 Hz, 6H). |
| 844 | 1H NMR (400 MHz, Methanol-d4) δ 8.35 (s, 1H), 8.21 (s, 1H), 7.79 (d, J = 2.5 Hz, 1H), 7.66 (dt, J = 6.5, 2.1 Hz, 2H), 7.25 (d, J = 2.5 Hz, 1H), 6.38 (t, J = 6.9 Hz, 1H), 6.18 (s, 1H), 4.04 (d, J = 13.9 Hz, 1H), 3.64 (d, J = 13.9 Hz, 1H), 3.59 (s, 3H), 1.81-1.54 (m, 4H), 0.96 (s, 9H). |
| 845 | 1H NMR (400 MHz, Methanol-d4) δ 8.41 (s, 1H), 8.06 (s, 1H), 7.84-7.66 (m, 2H), 7.23 (d, J = 2.5 Hz, 1H), 6.88 (dd, J = 8.5, 2.8 Hz, 1H), 6.27 (s, 1H), 5.94 (t, J = 54.7 Hz, 1H), 3.99 (dd, J = 14.4, 7.2 Hz, 1H), 3.86 (dd, J = 14.4, 7.4 Hz, 1H), 2.50 (s, 3H), 1.53 (s, 4H), 1.09 (d, J = 3.9 Hz, 6H), 1.00 (d, J = 1.7 Hz, 6H), 0.73 (d, J = 7.3 Hz, 1H). |
| 846 | 1H NMR (400 MHz, Methanol-d4) δ 8.37 (s, 1H), 7.96 (s, 1H), 7.83-7.65 (m, 2H), 7.01 (d, J = 2.5 Hz, 1H), 6.86 (dd, J = 8.4, 2.8 Hz, 1H), 6.16 (s, 1H), 4.20 (d, J = 14.9 Hz, 1H), 4.07 (d, J = 14.9 Hz, 1H), 2.50 (s, 3H), 1.65 (s, 3H), 1.41-1.24 (m, 2H), 1.07 (dd, J = 17.4, 1.8 Hz, 8H). |

TABLE 2-continued

| Compound | ¹H-NMR |
|---|---|
| 847 | 1H NMR (400 MHz, Methanol-d4) δ 8.30 (s, 1H), 7.88-7.64 (m, 2H), 7.35 (dt, J = 7.5, 3.7 Hz, 1H), 7.27-6.97 (m, 4H), 6.57 (dd, J = 3.2, 0.9 Hz, 1H), 6.38 (s, 1H), 5.90 (t, J = 54.8 Hz, 1H), 5.48 (s, 1H), 3.96-3.69 (m, 4H), 3.53 (d, J = 13.5 Hz, 1H), 1.61-1.32 (m, 4H), 0.79 (s, 9H). |
| 848 | 1H NMR (400 MHz, Methanol-d4) δ 8.36 (s, 1H), 8.20 (s, 1H), 7.81-7.72 (m, 2H), 7.22 (d, J = 2.5 Hz, 1H), 6.89 (dd, J = 8.5, 2.8 Hz, 1H), 6.26 (s, 1H), 4.04-3.91 (m, 2H), 2.52 (s, 3H), 2.49 (s, 1H), 1.74 (m, 8H), 1.69 (d, J = 8.0 Hz, 2H). |
| 849 | 1H NMR (400 MHz, Methanol-d4) δ 8.35 (s, 1H), 8.06 (s, 1H), 7.83-7.71 (m, 2H), 7.22 (d, J = 2.5 Hz, 1H), 6.88 (dd, J = 8.5, 2.8 Hz, 1H), 6.25 (s, 1H), 5.94 (t, J = 54.7 Hz, 1H), 3.97 (m, 2H), 2.52 (s, 3H), 2.49 (s, 1H), 1.74 (s, 6H), 1.53 (s, 4H). |
| 850 | 1H NMR (400 MHz, Methanol-d4) δ 8.38 (d, J = 0.8 Hz, 1H), 8.00 (s, 1H), 7.85-7.77 (m, 2H), 7.10 (d, J = 2.5 Hz, 1H), 6.89 (dd, J = 8.4, 2.7 Hz, 1H), 6.22 (s, 1H), 3.90 (d, J = 13.8 Hz, 1H), 3.71 (d, J = 13.9 Hz, 1H), 2.52 (s, 3H), 1.58 (s, 3H), 1.57 (s, 3H), 1.43-1.31 (m, 1H), 0.91 (s, 9H), 0.58-0.48 (m, 2H), 0.47-0.37 (m, 2H). |
| 851 | 1H NMR (400 MHz, Methanol-d4) δ 8.38 (s, 1H), 7.91 (s, 1H), 7.83-7.75 (m, 2H), 7.11 (d, J = 2.5 Hz, 1H), 6.89 (dd, J = 8.5, 2.8 Hz, 1H), 6.22 (s, 1H), 3.88 (d, J = 13.9 Hz, 1H), 3.73 (d, J = 13.9 Hz, 1H), 2.52 (s, 3H), 1.66 (p, J = 6.9 Hz, 1H), 1.28-1.16 (m, 2H), 1.17-1.04 (m, 2H), 0.97-0.85 (m, 15H). |
| 852 | 1H NMR (400 MHz, Methanol-d4) δ 8.36 (s, 1H), 8.07 (s, 1H), 7.85-7.75 (m, 2H), 7.12-7.06 (m, 1H), 6.87 (dd, J = 8.5, 2.7 Hz, 1H), 6.24 (s, 1H), 5.10 (t, J = 6.5 Hz, 2H), 4.75 (dd, J = 6.9, 2.0 Hz, 2H), 3.86 (d, J = 13.8 Hz, 1H), 3.70 (d, J = 13.8 Hz, 1H), 2.52 (s, 3H), 1.92 (s, 3H), 0.89 (s, 9H). |
| 853 | 1H NMR (400 MHz, Methanol-d4) δ 8.37-8.29 (m, 2H), 7.95 (s, 1H), 7.81-7.73 (m, 2H), 7.53-7.38 (m, 2H), 6.99 (d, J = 2.5 Hz, 1H), 6.87 (d, J = 7.5 Hz, 1H), 6.58 (s, 1H), 5.07 (dd, J = 6.9, 3.0 Hz, 2H), 4.72 (d, J = 6.9 Hz, 2H), 3.80 (d, J = 13.6 Hz, 1H), 3.61 (s, 3H), 3.52 (d, J = 13.6 Hz, 1H), 1.89 (s, 3H), 0.72 (s, 9H). |
| 854 | 1H NMR (400 MHz, Methanol-d4) δ 8.36 (d, J = 1.4 Hz, 1H), 7.86 (t, J = 8.1 Hz, 1H), 7.79 (d, J = 2.4 Hz, 1H), 7.10 (d, J = 2.4 Hz, 1H), 6.92-6.85 (m, 1H), 6.22 (s, 1H), 4.81-4.55 (m, 3H), 3.92 (d, J = 13.9 Hz, 1H), 3.63 (d, J = 13.8 Hz, 1H), 2.50 (s, 3H), 1.58 (d, 3H), 0.89 (s, 9H). |
| 855 | 1H NMR (400 MHz, Methanol-d4) δ 9.59 (s, 1H), 8.59 (d, J = 6.4 Hz, 1H), 8.47 (s, 1H), 8.34 (s, 1H), 8.33-8.30 (m, 2H), 7.79 (d, J = 2.5 Hz, 1H), 7.30 (d, J = 2.5 Hz, 1H), 6.66 (s, 1H), 3.83 (d, J = 13.9 Hz, 1H), 3.61 (d, J = 13.9 Hz, 1H), 1.81-1.72 (m, 2H), 1.72-1.61 (m, 2H), 0.82 (s, 9H). |
| 856 | 1H NMR (400 MHz, Methanol-d4) δ 9.59 (s, 1H), 8.58 (d, J = 6.4 Hz, 1H), 8.46 (s, 1H), 8.33-8.27 (m, 2H), 8.06 (s, 1H), 7.77 (d, J = 2.5 Hz, 1H), 7.27 (d, J = 2.6 Hz, 1H), 6.59 (d, J = 1.0 Hz, 1H), 3.97-3.87 (m, 1H), 3.82 (d, J = 13.8 Hz, 1H), 3.62 (d, J = 13.9 Hz, 1H), 1.29-1.12 (m, 4H), 0.81 (s, 9H). |
| 857 | 1H NMR (400 MHz, Methanol-d4) δ 8.39 (s, 1H), 7.82 (t, J = 8.1 Hz, 1H), 7.78 (d, J = 2.5 Hz, 1H), 6.96 (d, J = 2.5 Hz, 1H), 6.83 (dd, J = 8.5, 2.6 Hz, 1H), 6.09 (s, 1H), 4.03 (d, J = 13.8 Hz, 1H), 3.84 (tt, J = 7.4, 3.9 Hz, 1H), 3.51 (d, J = 13.8 Hz, 1H), 2.38 (s, 3H), 1.87 (tt, J = 8.5, 5.4 Hz, 1H), 1.34-1.26 (m, 2H), 1.26-1.19 (m, 2H), 1.07 (ddd, J = 8.5, 3.4, 1.6 Hz, 2H), 0.98-0.90 (m, 2H), 0.85 (s, 9H), 0.83-0.76 (m, 1H). |
| 858 | 1H NMR (400 MHz, Methanol-d4) δ 8.37 (s, 1H), 7.84 (t, J = 8.1 Hz, 1H), 7.78 (d, J = 2.5 Hz, 1H), 7.05 (d, J = 2.6 Hz, 1H), 6.88 (dd, J = 8.5, 2.7 Hz, 1H), 6.19 (s, 1H), 4.89 (s, 1H), 4.80-4.69 (m, 1H), 4.69-4.56 (m, 1H), 4.25 (d, J = 14.8 Hz, 1H), 3.99 (d, J = 14.9 Hz, 1H), 2.50 (s, 3H), 1.61-1.54 (m, 3H), 1.10 (s, 3H), 1.09 (s, 3H). |
| 859 | 1H NMR (400 MHz, Methanol-d4) δ 8.35 (s, 1H), 7.88 (t, J = 8.1 Hz, 1H), 7.78 (d, J = 2.5 Hz, 1H), 7.00 (d, J = 2.5 Hz, 1H), 6.86 (dd, J = 8.5, 2.7 Hz, 1H), 6.13 (s, 1H), 3.97 (d, J = 13.8 Hz, 1H), 3.93 (s, 3H), 3.68-3.61 (m, 1H), 3.53 (d, J = 13.8 Hz, 1H), 2.45 (s, 3H), 1.29-1.21 (m, 2H), 1.21-1.13 (m, 2H), 0.87 (s, 9H). |
| 860 | 1H NMR (400 MHz, Methanol-d4) δ 8.36 (s, 1H), 7.90 (s, 1H), 7.83-7.70 (m, 2H), 7.10 (d, J = 2.5 Hz, 1H), 6.87 (dd, J = 8.5, 2.7 Hz, 1H), 6.21 (s, 1H), 3.85 (d, J = 13.9 Hz, 1H), 3.71 (d, J = 13.9 Hz, 1H), 2.50 (s, 3H), 1.32-1.22 (m, 2H), 1.12-1.02 (m, 2H), 0.90 (s, 9H), 0.88 (s, 9H). |
| 861 | 1H NMR (400 MHz, Methanol-d4) δ 8.38 (s, 1H), 7.84 (t, J = 8.1 Hz, 1H), 7.77 (d, J = 2.5 Hz, 1H), 7.04 (d, J = 2.5 Hz, 1H), 6.87 (dd, J = 8.5, 2.7 Hz, 1H), 6.16 (s, 1H), 4.23 (d, J = 14.9 Hz, 1H), 4.03 (d, J = 14.9 Hz, 1H), 2.72 (s, 1H), 2.51 (s, 3H), 2.43 (s, 6H), 1.11 (s, 3H), 1.10 (s, 3H). |
| 862 | 1H NMR (400 MHz, Methanol-d4) δ 8.37 (s, 1H), 7.86 (t, J = 8.1 Hz, 1H), 7.78 (d, J = 2.5 Hz, 1H), 7.03 (d, J = 2.5 Hz, 1H), 6.87 (dd, J = 8.5, 2.7 Hz, 1H), 6.16 (s, 1H), 4.28 (d, J = 14.9 Hz, 1H), 3.97 (d, J = 14.9 Hz, 1H), 2.49 (s, 3H), 1.54-1.44 (m, 1H), 1.28-1.18 (m, 2H), 1.10 (s, 4H), 1.10-1.05 (m, 5H), 0.57-0.45 (m, 2H), 0.36-0.25 (m, 2H). |
| 863 | 1H NMR (400 MHz, Methanol-d4) δ 8.36 (s, 1H), 7.85 (t, J = 8.1 Hz, 1H), 7.76 (d, J = 2.5 Hz, 1H), 7.01 (d, J = 2.5 Hz, 1H), 6.87 (dd, J = 8.3, 2.7 Hz, 1H), 6.15 (s, 1H), 4.26 (d, J = 14.9 Hz, 1H), 3.97 (d, J = 14.9 Hz, 1H), 2.49 (s, 3H), 1.60 (s, 3H), 1.41-1.28 (m, 2H), 1.14-1.05 (m, 6H). |
| 864 | 1H NMR (400 MHz, Methanol-d4) δ 8.36 (s, 1H), 7.85 (t, J = 8.1 Hz, 1H), 7.76 (d, J = 2.5 Hz, 1H), 7.02 (d, J = 2.5 Hz, 1H), 6.87 (dd, J = 8.5, 2.7 Hz, 1H), 6.15 (s, 1H), 4.23 (d, J = 14.8 Hz, 1H), 4.00 (d, J = 14.9 Hz, 1H), 3.72-3.58 (m, 1H), 2.51 (s, 3H), 1.31-1.15 (m, 3H), 1.10 (s, 3H), 1.09 (s, 3H). |
| 865 | 1H NMR (400 MHz, Methanol-d4) δ 8.34 (s, 1H), 7.88 (t, J = 8.1 Hz, 1H), 7.77 (d, J = 2.5 Hz, 1H), 7.08 (d, J = 2.6 Hz, 1H), 6.87 (dd, J = 8.5, 2.7 Hz, 1H), 6.19 |

TABLE 2-continued

| Compound | ¹H-NMR |
|---|---|
| | (s, 1H), 3.90 (d, J = 13.8 Hz, 1H), 3.61 (d, J = 13.9 Hz, 1H), 2.50 (s, 3H), 1.54-1.42 (m, 1H), 1.27-1.22 (m, 2H), 1.10-1.05 (m, 2H), 0.89 (s, 9H), 0.52-0.47 (m, 2H), 0.34-0.28 (m, 2H). |
| 866 | 1H NMR (400 MHz, Methanol-d4) δ 8.36 (s, 1H), 7.87 (s, 1H), 7.84-7.76 (m, 2H), 7.10 (d, J = 2.5 Hz, 1H), 6.88 (dd, J = 8.5, 2.8 Hz, 1H), 6.23 (s, 1H), 4.23 (m, 2H), 3.86 (s, 1H), 3.68 (d, J = 13.8 Hz, 1H), 2.51 (s, 3H), 0.96 (s, 3H), 0.90 (s, 9H), 0.68 (s, 2H), 0.43 (s, 2H). |
| 867 | 1H NMR (400 MHz, Methanol-d4) δ 8.37 (s, 1H), 8.00 (s, 1H), 7.83-7.72 (m, 2H), 7.02 (d, J = 2.5 Hz, 1H), 6.87 (dd, J = 8.4, 2.7 Hz, 1H), 6.18 (s, 1H), 4.22 (d, J = 14.9 Hz, 1H), 4.03 (d, J = 14.9 Hz, 1H), 2.50 (s, 3H), 1.62-1.47 (m, 1H), 1.32-1.17 (m, 2H), 1.10 (s, 3H), 1.09 (s, 3H), 1.06-0.97 (m, 2H), 0.58-0.46 (m, 2H), 0.38-0.28 (m, 2H). |
| 868 | 1H NMR (400 MHz, Methanol-d4) δ 8.34 (s, 1H), 7.87 (t, J = 8.1 Hz, 1H), 7.77 (d, J = 2.5 Hz, 1H), 6.99 (d, J = 2.5 Hz, 1H), 6.86 (dd, J = 8.4, 2.7 Hz, 1H), 6.14 (s, 1H), 3.96 (d, J = 13.8 Hz, 1H), 3.91 (s, 3H), 3.51 (d, J = 13.8 Hz, 1H), 2.69 (s, 1H), 2.44 (s, 3H), 2.43 (s, 6H), 0.86 (s, 9H). |
| 869 | 1H NMR (400 MHz, Methanol-d4) δ 8.37 (s, 1H), 8.02 (s, 1H), 7.85-7.74 (m, 2H), 7.11 (d, J = 2.5 Hz, 1H), 6.88 (dd, J = 8.5, 2.8 Hz, 1H), 6.26 (s, 1H), 5.37-5.17 (m, 1H), 5.05-4.90 (m, 2H), 4.84 (m, 2H), 3.89 (d, J = 13.8 Hz, 1H), 3.69 (d, J = 13.8 Hz, 1H), 2.51 (s, 3H), 0.89 (s, 9H). |
| 870 | 1H NMR (400 MHz, Methanol-d4) δ 8.34 (s, 1H), 8.34 (d, 1H), 7.94 (s, 1H), 7.81 (d, J = 2.5 Hz, 1H), 7.77 (d, J = 7.5 Hz, 1H), 7.50 (t, J = 7.8 Hz, 1H), 7.40 (d, J = 7.7 Hz, 1H), 7.03 (d, J = 2.5 Hz, 1H), 6.86 (d, J = 7.8 Hz, 1H), 6.60 (s, 1H), 6.25 (tt, J = 56.0, 4.1 Hz, 1H), 5.92 (t, J = 54.7 Hz, 1H), 4.58-4.30 (m, 2H), 3.85 (d, J = 13.7 Hz, 1H), 3.52 (d, J = 13.7 Hz, 1H), 1.53-1.47 (m, 4H), 0.73 (s, 9H). |
| 871 | 1H NMR (400 MHz, Methanol-d4) δ 8.34 (d, J = 8.2 Hz, 1H), 8.30 (s, 1H), 7.92 (s, 1H), 7.78 (d, J = 2.5 Hz, 1H), 7.75 (d, J = 7.5 Hz, 1H), 7.48 (t, J = 7.8 Hz, 1H), 7.41 (d, J = 7.7 Hz, 1H), 6.98 (d, J = 2.5 Hz, 1H), 6.87 (d, J = 7.6 Hz, 1H), 6.58 (s, 1H), 5.92 (t, J = 54.8 Hz, 1H), 3.79 (d, J = 13.6 Hz, 1H), 3.61 (s, 3H), 3.50 (d, J = 13.6 Hz, 1H), 1.50 (s, 4H), 0.72 (s, 9H). |
| 872 | 1H NMR (400 MHz, Methanol-d4) δ 8.34 (s, 1H), 7.84 (s, 1H), 7.78 (t, J = 8.0 Hz, 1H), 7.76 (d, J = 2.3 Hz, 1H), 7.06 (d, J = 2.5 Hz, 1H), 6.87 (dd, J = 8.6, 2.7 Hz, 1H), 6.19 (s, 1H), 4.17 (dd, J = 7.0, 3.4 Hz, 1H), 3.84 (d, J = 14.0 Hz, 1H), 3.68 (d, J = 14.0 Hz, 1H), 2.51 (s, 3H), 1.70 (q, J = 6.0 Hz, 2H), 1.20-1.09 (m, 1H), 1.06-0.90 (m, 2H), 0.88 (s, 9H), 0.87-0.76 (m, 1H). |
| 873 | 1H NMR (400 MHz, Methanol-d4) δ 8.31 (s, 1H), 8.25 (d, J = 5.2 Hz, 1H), 7.98 (s, 1H), 7.81 (d, J = 2.5 Hz, 1H), 7.43 (d, J = 3.6 Hz, 1H), 7.31 (d, J = 5.2 Hz, 1H), 7.12 (d, J = 2.5 Hz, 1H), 6.68 (d, J = 3.6 Hz, 1H), 6.51 (s, 1H), 5.92 (t, J = 54.7 Hz, 1H), 3.90 (d, J = 13.7 Hz, 1H), 3.88 (s, 3H), 3.45 (d, J = 13.7 Hz, 1H), 1.50 (br s, 4H), 0.76 (s, 9H). |
| 874 | 1H NMR (400 MHz, Methanol-d4) δ 8.34 (d, J = 8.0 Hz, 1H), 8.34 (s, 1H), 8.09 (s, 1H), 7.81 (d, J = 2.5 Hz, 1H), 7.77 (d, J = 7.6 Hz, 1H), 7.51 (t, J = 7.8 Hz, 1H), 7.40 (d, J = 7.7 Hz, 1H), 7.04 (d, J = 2.6 Hz, 1H), 6.85 (d, J = 7.9 Hz, 1H), 6.62 (s, 1H), 6.42-6.06 (m, 1H), 4.55-4.33 (m, 2H), 3.85 (d, J = 13.7 Hz, 1H), 3.53 (d, J = 13.6 Hz, 1H), 1.75-1.59 (m, 4H), 0.73 (s, 9H). |
| 875 | 1H NMR (400 MHz, Methanol-d4) δ 8.35 (d, J = 8.0 Hz, 1H), 8.33 (s, 1H), 8.09 (s, 1H), 7.81 (d, J = 2.5 Hz, 1H), 7.78 (d, J = 7.5 Hz, 1H), 7.52 (t, J = 7.8 Hz, 1H), 7.41 (d, J = 7.8 Hz, 1H), 7.03 (d, J = 2.5 Hz, 1H), 6.86 (d, J = 7.8 Hz, 1H), 6.62 (s, 1H), 5.02-4.91 (m, 1H), 4.81-4.65 (m, 1H), 3.85 (d, J = 13.7 Hz, 1H), 3.50 (d, J = 13.8 Hz, 1H), 1.78-1.61 (m, 4H), 0.71 (s, 9H). |
| 876 | 1H NMR (400 MHz, Methanol-d4) δ 8.32 (d, J = 7.8 Hz, 1H), 8.32 (s, 1H), 7.92 (s, 1H), 7.80 (d, J = 2.4 Hz, 1H), 7.77 (d, J = 7.5 Hz, 1H), 7.48 (t, J = 7.8 Hz, 1H), 7.22 (d, J = 7.5 Hz, 1H), 6.99 (d, J = 2.5 Hz, 1H), 6.85 (d, J = 7.6 Hz, 1H), 6.59 (s, 1H), 5.93 (t, J = 54.7 Hz, 1H), 3.81 (d, J = 13.6 Hz, 1H), 3.51 (d, J = 13.6 Hz, 1H), 1.50 (s, 4H), 0.73 (s, 9H). |
| 877 | 1H NMR (400 MHz, Methanol-d4) δ 8.34 (d, J = 8.1 Hz, 1H), 8.31 (s, 1H), 7.82 (s, 1H), 7.79 (d, J = 2.5 Hz, 1H), 7.74 (d, J = 7.5 Hz, 1H), 7.49 (t, J = 7.8 Hz, 1H), 7.42 (d, J = 7.6 Hz, 1H), 6.99 (d, J = 2.4 Hz, 1H), 6.86 (d, J = 7.8 Hz, 1H), 6.58 (s, 1H), 5.05-4.91 (m, 1H), 4.67 (d, J = 46.9 Hz, 1H), 4.66 (d, J = 46.9 Hz, 1H), 3.82 (d, J = 13.6 Hz, 1H), 3.61 (s, 3H), 3.50 (d, J = 13.6 Hz, 1H), 1.56-1.49 (m, 3H), 0.71 (s, 9H). |
| 878 | 1H NMR (400 MHz, Methanol-d4) δ 8.36-8.30 (m, 2H), 7.89 (s, 1H), 7.80 (d, J = 2.4 Hz, 1H), 7.75 (d, J = 7.5 Hz, 1H), 7.48 (t, J = 7.8 Hz, 1H), 7.42 (d, J = 7.7 Hz, 1H), 6.99 (s, 1H), 6.86 (d, J = 7.6 Hz, 1H), 6.57 (s, 1H), 4.59 (d, J = 48.6 Hz, 2H), 3.84 (d, J = 13.6 Hz, 1H), 3.61 (s, 3H), 3.52 (d, J = 13.6 Hz, 1H), 1.53-1.26 (m, 4H), 0.72 (s, 9H). |
| 879 | 1H NMR (400 MHz, Methanol-d4) δ 8.36-8.29 (m, 2H), 7.85 (s, 1H), 7.78 (d, J = 2.4 Hz, 1H), 7.74 (d, J = 7.6 Hz, 1H), 7.48 (t, J = 7.8 Hz, 1H), 7.42 (d, J = 7.6 Hz, 1H), 6.96 (d, J = 2.4 Hz, 1H), 6.85 (d, J = 7.6 Hz, 1H), 6.54 (s, 1H), 3.81 (d, J = 13.7 Hz, 1H), 3.61 (d, J = 1.2 Hz, 3H), 3.51 (d, J = 13.7 Hz, 1H), 1.63 (s, 3H), 1.36-1.22 (m, 2H), 1.09-0.96 (m, 2H), 0.71 (s, 9H). |
| 880 | 1H NMR (400 MHz, Methanol-d4) δ 8.37-8.30 (m, 2H), 7.89 (s, 1H), 7.82 (d, J = 2.4 Hz, 1H), 7.75 (d, J = 7.4 Hz, 1H), 7.49 (t, J = 7.8 Hz, 1H), 7.42 (d, J = 7.6 Hz, 1H), 7.02 (d, J = 2.4 Hz, 1H), 6.86 (d, J = 7.7 Hz, 1H), 6.61 (s, 1H), 5.26-5.21 (m, 1H), 5.03-4.92 (m, 2H), 4.86-4.76 (m, 2H), 3.86 (d, J = 13.6 Hz, 1H), 3.61 (s, 3H), 3.52 (d, J = 13.7 Hz, 1H), 0.72 (s, 9H). |

TABLE 2-continued

| Compound | ¹H-NMR |
|---|---|
| 881 | 1H NMR (400 MHz, Methanol-d4) δ 8.07-8.00 (m, 2H), 7.60 (s, 1H), 7.51 (d, J = 2.4 Hz, 1H), 7.45 (d, J = 7.5 Hz, 1H), 7.18 (t, J = 7.8 Hz, 1H), 7.12 (d, J = 7.6 Hz, 1H), 6.70 (s, 1H), 6.56 (d, J = 7.8 Hz, 1H), 6.26 (s, 1H), 3.56 (d, J = 13.5 Hz, 1H), 3.31 (d, J = 1.3 Hz, 3H), 3.23 (d, J = 13.6 Hz, 1H), 1.25-1.16 (m, 1H), 0.95-0.83 (m, 2H), 0.75-0.65 (m, 2H), 0.43 (s, 9H), 0.24-0.14 (m, 2H), 0.05-0.06 (m, 2H). |
| 882 | 1H NMR (400 MHz, Methanol-d4) δ 8.05 (d, J = 8.1 Hz, 2H), 7.61 (s, 1H), 7.51 (d, J = 2.4 Hz, 1H), 7.47-7.40 (m, 1H), 7.20 (t, J = 7.8 Hz, 1H), 7.13 (d, J = 7.7 Hz, 1H), 6.69 (d, J = 2.5 Hz, 1H), 6.56 (d, J = 7.6 Hz, 1H), 6.25 (s, 1H), 3.89 (d, J = 14.7 Hz, 1H), 3.64 (d, J = 14.7 Hz, 1H), 3.33 (s, 3H), 1.30-1.16 (m, 1H), 0.96-0.88 (m, 2H), 0.75-0.68 (m, 2H), 0.69 (s, 3H), 0.64 (s, 3H), 0.21 (ddd, J = 8.2, 6.1, 4.5 Hz, 2H), 0.08--0.02 (m, 2H). |
| 883 | 1H NMR (400 MHz, Methanol-d4) δ 8.34 (s, 1H), 8.34 (d, J = 8.2 Hz, 1H), 7.79 (s, 1H), 7.78 (d, J = 2.5 Hz, 1H), 7.69 (d, J = 7.1 Hz, 1H), 7.48 (t, J = 7.8 Hz, 1H), 7.42 (d, J = 7.7 Hz, 1H), 6.97 (d, J = 2.5 Hz, 1H), 6.84 (d, J = 7.5 Hz, 1H), 6.54 (s, 1H), 4.13 (d, J = 14.8 Hz, 1H), 3.94 (d, J = 14.8 Hz, 1H), 3.61 (s, 3H), 2.67 (s, 1H), 2.35 (s, 6H), 0.94 (d, J = 19.8 Hz, 6H). |
| 884 | 1H NMR (400 MHz, Methanol-d4) δ 8.34 (s, 1H), 8.34 (d, J = 8.0 Hz, 1H), 7.85 (s, 1H), 7.78 (d, J = 2.5 Hz, 1H), 7.70 (d, J = 6.8 Hz, 1H), 7.48 (t, J = 7.8 Hz, 1H), 7.41 (d, J = 7.7 Hz, 1H), 6.96 (d, J = 2.5 Hz, 1H), 6.83 (d, J = 7.4 Hz, 1H), 6.52 (s, 1H), 4.15 (d, J = 14.7 Hz, 1H), 3.93 (d, J = 14.7 Hz, 1H), 3.61 (s, 3H), 1.63 (s, 3H), 1.36-1.24 (m, 2H), 1.07-1.01 (m, 2H), 0.94 (d, J = 19.6 Hz, 6H). |
| 885 | 1H NMR (400 MHz, Methanol-d4) δ 8.40 (s, 1H), 8.14 (s, 1H), 8.11 (dd, J = 5.1, 1.9 Hz, 1H), 7.82 (d, J = 2.4 Hz, 1H), 7.69 (dd, J = 7.3, 1.8 Hz, 1H), 7.25 (d, J = 2.5 Hz, 1H), 6.95 (dd, J = 7.4, 5.0 Hz, 1H), 6.29 (s, 1H), 3.94 (d, J = 13.9 Hz, 1H), 3.94 (s, 3H), 3.74 (d, J = 13.9 Hz, 1H), 1.83-1.57 (m, 4H), 0.94 (s, 9H). |
| 886 | 1H NMR (400 MHz, Methanol-d4) δ 8.25 (d, J = 7.3 Hz, 2H), 7.98 (s, 1H), 7.69 (d, J = 2.5 Hz, 1H), 7.64-7.57 (m, 1H), 7.39 (t, J = 7.8 Hz, 1H), 7.32 (d, J = 7.6 Hz, 1H), 6.91 (d, J = 2.5 Hz, 1H), 6.74 (d, J = 7.7 Hz, 1H), 6.49 (s, 1H), 4.05 (d, J = 14.7 Hz, 1H), 3.85 (d, J = 14.7 Hz, 1H), 3.52 (s, 3H), 1.73-1.49 (m, 4H), 0.88 (s, 3H), 0.84 (s, 3H). |
| 887 | 1H NMR (400 MHz, Methanol-d4) δ 8.23 (s, 1H), 8.12 (d, J = 9.9 Hz, 1H), 7.71 (s, 1H), 7.70 (d, J = 2.5 Hz, 1H), 7.55-7.49 (m, 2H), 7.30 (q, J = 4.8 Hz, 1H), 6.89 (d, J = 2.5 Hz, 1H), 6.62 (d, J = 9.9 Hz, 1H), 6.57 (s, 1H), 3.79 (d, J = 13.7 Hz, 1H), 3.68 (s, 3H), 3.37 (d, J = 13.7 Hz, 1H), 2.58 (s, 1H), 2.26 (s, 6H), 0.61 (s, 9H). |
| 888 | 1H NMR (400 MHz, Methanol-d4) δ 8.23 (s, 1H), 8.22 (d, J = 8.0 Hz, 1H), 7.71-7.68 (m, 2H), 7.66 (d, J = 7.4 Hz, 1H), 7.39 (t, J = 7.8 Hz, 1H), 7.13 (d, J = 7.5 Hz, 1H), 6.87 (d, J = 2.5 Hz, 1H), 6.75 (d, J = 7.6 Hz, 1H), 6.47 (s, 1H), 3.72 (d, J = 13.6 Hz, 1H), 3.41 (d, J = 13.6 Hz, 1H), 2.58 (s, 1H), 2.26 (s, 6H), 0.63 (s, 9H). |
| 889 | 1H NMR (400 MHz, Methanol-d4) δ 8.39-8.33 (m, 1H), 8.33 (s, 1H), 8.12 (s, 1H), 7.91 (t, J = 60.0 Hz, 1H), 7.87-7.79 (m, 2H), 7.54 (t, J = 7.8 Hz, 1H), 7.49 (d, J = 8.0 Hz, 1H), 7.00 (d, J = 2.5 Hz, 1H), 6.96 (d, J = 8.1 Hz, 1H), 6.62 (s, 1H), 3.86 (d, J = 13.7 Hz, 1H), 3.50 (d, J = 13.7 Hz, 1H), 1.85-1.55 (m, 4H), 0.73 (s, 9H). |
| 890 | 1H NMR (400 MHz, Methanol-d4) δ 8.22 (s, 1H), 8.12 (d, J = 9.9 Hz, 1H), 8.00 (s, 1H), 7.72 (d, J = 2.5 Hz, 1H), 7.53 (d, J = 4.4 Hz, 2H), 7.30 (t, J = 4.3 Hz, 1H), 6.92 (d, J = 2.5 Hz, 1H), 6.63 (d, J = 10.1 Hz, 1H), 6.61 (s, 1H), 3.79 (d, J = 13.7 Hz, 1H), 3.68 (s, 3H), 3.37 (d, J = 13.7 Hz, 1H), 1.74-1.45 (m, 4H), 0.62 (s, 9H). |
| 891 | 1H NMR (400 MHz, Methanol-d4) δ 8.37-8.30 (m, 2H), 7.79 (d, J = 1.9 Hz, 2H), 7.76-7.67 (m, 1H), 7.48 (t, J = 7.8 Hz, 1H), 7.42 (d, J = 7.7 Hz, 1H), 6.97 (d, J = 2.5 Hz, 1H), 6.85 (d, J = 7.6 Hz, 1H), 6.56 (s, 1H), 3.82 (d, J = 13.6 Hz, 1H), 3.61 (s, 3H), 3.52 (d, J = 13.7 Hz, 1H), 2.67 (s, 1H), 2.35 (d, J = 1.1 Hz, 6H), 0.71 (s, 9H). |
| 892 | 1H NMR (400 MHz, Methanol-d4) δ 9.09-8.97 (m, 2H), 8.29 (s, 1H), 8.12 (d, J = 8.5 Hz, 1H), 7.97-7.88 (m, 2H), 7.88-7.76 (m, 3H), 7.09 (d, J = 2.4 Hz, 1H), 6.90 (s, 1H), 4.72 (d, J = 5.5 Hz, 1H), 4.60 (d, J = 5.8 Hz, 1H), 3.78 (d, J = 13.8 Hz, 1H), 3.46 (d, J = 13.8 Hz, 1H), 1.53 (d, J = 7.4 Hz, 3H), 0.65 (s, 9H). |
| 893 | 1H NMR (400 MHz, Methanol-d4) δ 9.12-9.04 (m, 2H), 8.29 (s, 1H), 8.14 (d, J = 8.5 Hz, 1H), 8.03 (s, 1H), 8.00-7.91 (m, 1H), 7.87 (m, 2H), 7.80 (d, J = 2.5 Hz, 1H), 7.11 (d, J = 2.5 Hz, 1H), 6.94 (s, 1H), 5.00-4.74 (m, 4H), 3.80 (d, J = 13.8 Hz, 1H), 3.47 (d, J = 13.8 Hz, 1H), 0.66 (s, 9H). |
| 894 | 1H NMR (400 MHz, Acetonitrile-d3) δ 9.15-9.07 (m, 2H), 8.41 (s, 1H), 8.30 (d, J = 8.2 Hz, 1H), 8.02-7.81 (m, 4H), 7.76 (d, J = 2.4 Hz, 1H), 6.88 (d, J = 2.3 Hz, 1H), 6.81 (s, 1H), 6.25 (s, 1H), 5.90 (s, 2H), 5.85 (t, J = 54.6 Hz, 1H), 4.09 (dd, J = 14.7, 7.4 Hz, 1H), 3.86 (dd, J = 14.7, 5.8 Hz, 1H), 1.51-1.43 (m, 4H), 0.94 (d, J = 21.8 Hz, 6H). |
| 895 | 1H NMR (400 MHz, Acetonitrile-d3) δ 9.13 (t, J = 7.7 Hz, 2H), 8.41 (s, 1H), 8.30 (d, J = 8.1 Hz, 1H), 8.02-7.87 (m, 3H), 7.78-7.70 (m, 2H), 6.85 (s, 1H), 6.77 (s, 1H), 5.88 (s, 1H), 4.10 (dd, J = 14.5, 7.2 Hz, 1H), 3.91-3.81 (m, 1H), 1.60 (s, 3H), 1.25 (s, 2H), 1.01 (d, J = 1.9 Hz, 4H), 0.93 (d, J = 22.7 Hz, 6H). |
| 896 | 1H NMR (400 MHz, Acetonitrile-d3) δ 9.11 (s, 1H), 9.01 (d, J = 8.6 Hz, 1H), 8.39 (s, 1H), 8.26 (d, J = 8.0 Hz, 1H), 7.89 (s, 1H), 7.82 (d, J = 9.0 Hz, 2H), 7.74 (s, 1H), 6.85 (s, 1H), 5.88 (s, 1H), 4.09 (dd, J = 14.6, 7.3 Hz, 1H), 3.85 (dd, J = 14.6, 5.7 Hz, 1H), 3.01 (s, 1H), 2.87 (s, 1H), 2.01 (s, 1H), 1.16 (d, J = 4.5 Hz, 2H), 0.95 (s, 5H), 0.90 (s, 3H), 0.47 (dd, J = 7.4, 5.7 Hz, 2H), 0.26 (d, J = 5.4 Hz, 2H). |

TABLE 2-continued

| Compound | ¹H-NMR |
|---|---|
| 897 | 1H NMR (400 MHz, Acetonitrile-d3) δ 9.09 (dd, J = 14.8, 6.8 Hz, 2H), 8.40 (s, 1H), 8.29 (d, J = 8.2 Hz, 1H), 7.99-7.83 (m, 3H), 7.75 (d, J = 2.4 Hz, 1H), 7.65 (s, 1H), 6.87 (s, 1H), 6.78 (s, 1H), 5.89 (s, 1H), 4.08 (dd, J = 14.7, 7.2 Hz, 1H), 3.87 (dd, J = 14.7, 5.8 Hz, 1H), 2.66 (s, 1H), 2.32 (s, 6H), 0.93 (d, J = 21.2 Hz, 6H). |
| 898 | 1H NMR (400 MHz, Acetonitrile-d3) δ 9.61 (s, 1H), 8.60 (d, J = 6.7 Hz, 1H), 8.49 (d, J = 6.7 Hz, 1H), 8.38-8.33 (m, 2H), 8.19 (d, J = 7.3 Hz, 1H), 7.92-7.86 (m, 1H), 7.86 (s, 1H), 7.74 (d, J = 2.4 Hz, 1H), 6.90 (d, J = 2.4 Hz, 1H), 6.81 (s, 1H), 6.06 (t, J = 55.5 Hz, 1H), 5.80 (s, 1H), 3.68 (m, 1H), 3.47 (m, 1H), 1.70 (m, 6H), 0.68 (s, 9H). |
| 899 | 1H NMR (400 MHz, Acetonitrile-d3) δ 9.13-9.06 (m, 2H), 8.37 (s, 1H), 8.28 (d, J = 8.3 Hz, 1H), 8.00-7.89 (m, 2H), 7.87 (dd, J = 8.7, 5.1 Hz, 1H), 7.74 (d, J = 2.4 Hz, 2H), 6.91 (d, J = 2.5 Hz, 1H), 6.82 (s, 1H), 5.79 (s, 1H), 4.86 (ddd, J = 64.1, 8.9, 5.4 Hz, 1H), 3.78 (dt, J = 10.2, 5.4 Hz, 1H), 3.68 (dd, J = 13.4, 6.6 Hz, 1H), 3.48 (dd, J = 13.4, 5.0 Hz, 1H), 1.94-1.79 (m, 1H), 1.64-1.49 (m, 1H), 0.69 (s, 9H). |
| 900 | 1H NMR (400 MHz, Acetonitrile-d3) δ 9.16 (d, J = 8.9 Hz, 1H), 8.35 (d, J = 7.5 Hz, 2H), 8.03-7.90 (m, 2H), 7.82 (d, J = 8.9 Hz, 1H), 7.75-7.69 (m, 2H), 6.98 (d, J = 2.4 Hz, 1H), 6.81 (s, 1H), 6.26 (s, 1H), 6.00 (s, 1H), 3.70 (dd, J = 13.5, 6.1 Hz, 1H), 3.52 (dd, J = 13.7, 4.6 Hz, 1H), 3.00 (s, 4H), 2.67 (s, 1H), 2.33 (s, 6H), 0.72 (s, 9H). |
| 901 | 1H NMR (400 MHz, Acetonitrile-d3) δ 9.06 (d, J = 4.8 Hz, 1H), 8.94 (d, J = 8.9 Hz, 1H), 8.42 (s, 1H), 8.30-8.16 (m, 1H), 7.89-7.83 (m, 2H), 7.77 (dd, J = 8.7, 4.7 Hz, 2H), 7.68-7.60 (m, 1H), 7.59 (s, 1H), 7.38 (t, J = 52.2 Hz, 1H), 6.96 (s, 1H), 6.94-6.87 (m, 1H), 6.23 (s, 1H), 5.74 (s, 1H), 3.80-3.27 (m, 2H), 2.31 (d, J = 6.4 Hz, 6H), 1.03 (s, 1H), 0.56 (s, 9H). |
| 902 | 1H NMR (400 MHz, Acetonitrile-d3) δ 9.14-9.07 (m, 1H), 8.37 (s, 1H), 8.32 (d, J = 8.4 Hz, 1H), 8.00-7.90 (m, 2H), 7.80 (d, J = 8.9 Hz, 1H), 7.76 (s, 1H), 7.72 (d, J = 2.5 Hz, 1H), 6.92 (d, J = 2.5 Hz, 1H), 6.76 (s, 1H), 6.20 (s, 1H), 5.83 (s, 1H), 3.70 (dd, J = 13.3, 7.0 Hz, 1H), 3.50 (dd, J = 13.4, 5.3 Hz, 1H), 2.99 (s, 3H), 1.61 (s, 3H), 1.25 (s, 2H), 1.06-0.99 (m, 2H), 0.72 (s, 9H). |
| 903 | 1H NMR (400 MHz, Methanol-d4) δ 8.89 (s, 1H), 8.37 (s, 1H), 8.07 (s, 1H), 7.76 (d, J = 2.5 Hz, 1H), 7.31 (d, J = 2.5 Hz, 1H), 6.38 (s, 1H), 3.89 (d, J = 13.8 Hz, 1H), 3.75 (d, J = 13.9 Hz, 1H), 2.46 (s, 3H), 1.62-1.48 (m, 1H), 1.23 (m, 2H), 1.03 (m, 2H), 0.96 (s, 9H), 0.53 (dd, J = 8.3, 1.8 Hz, 2H), 0.40-0.27 (m, 2H). |
| 904 | 1H NMR (400 MHz, Methanol-d4) δ 8.91 (s, 1H), 8.41 (s, 1H), 8.25 (s, 1H), 7.79 (d, J = 2.5 Hz, 1H), 7.35 (d, J = 2.5 Hz, 1H), 6.44 (s, 1H), 3.92 (d, J = 13.9 Hz, 1H), 3.77 (d, J = 13.9 Hz, 1H), 2.46 (s, 3H), 1.82-1.63 (m, 4H), 0.96 (s, 9H). |
| 905 | 1H NMR (400 MHz, Methanol-d4) δ 8.30 (s, 1H), 8.23 (d, J = 2.5 Hz, 1H), 8.14 (s, 1H), 7.75 (m, 2H), 7.24 (d, J = 2.5 Hz, 1H), 6.81 (d, J = 8.6 Hz, 1H), 6.10 (s, 1H), 4.01-3.84 (m, 4H), 3.64 (d, J = 13.9 Hz, 1H), 1.79-1.59 (m, 4H), 0.93 (s, 9H). |
| 906 | 1H NMR (400 MHz, Methanol-d4) δ 8.27 (s, 1H), 7.88 (t, J = 8.1 Hz, 1H), 7.73 (d, J = 2.5 Hz, 1H), 7.05 (d, J = 2.5 Hz, 1H), 6.87 (dd, J = 8.5, 2.7 Hz, 1H), 6.18 (s, 1H), 3.95 (d, J = 1.2 Hz, 3H), 3.84 (d, J = 13.8 Hz, 1H), 3.58 (d, J = 13.7 Hz, 1H), 2.52 (s, 3H), 0.87 (s, 9H). |
| 907 | 1H NMR (400 MHz, Methanol-d4) δ 8.35 (s, 1H), 8.20 (s, 1H), 7.85 (t, J = 8.1 Hz, 1H), 7.76 (d, J = 2.5 Hz, 1H), 7.10 (d, J = 2.5 Hz, 1H), 6.88 (dd, J = 8.5, 2.7 Hz, 1H), 6.24 (s, 1H), 3.92 (d, J = 13.8 Hz, 1H), 3.63 (d, J = 13.8 Hz, 1H), 2.53 (s, 3H), 2.45 (s, 3H), 2.00 (d, J = 3.8 Hz, 4H), 0.89 (s, 9H). |
| 908 | 1H NMR (400 MHz, Methanol-d4) δ 8.32 (s, 1H), 7.88 (t, J = 8.1 Hz, 1H), 7.77 (d, J = 2.5 Hz, 1H), 7.00 (d, J = 2.5 Hz, 1H), 6.86 (dd, J = 8.6, 2.6 Hz, 1H), 6.15 (s, 1H), 4.04-3.83 (m, 7H), 3.50 (d, J = 13.8 Hz, 1H), 2.45 (s, 3H), 0.86 (s, 9H). |
| 909 | 1H NMR (400 MHz, Methanol-d4) δ 9.40 (d, J = 0.9 Hz, 1H), 8.59 (s, 1H), 8.30 (s, 1H), 8.21 (d, J = 8.7 Hz, 1H), 8.20 (s, 1H), 8.02 (d, J = 7.3 Hz, 1H), 7.85 (t, J = 7.8 Hz, 1H), 7.82 (d, J = 2.5 Hz, 1H), 7.04 (d, J = 2.5 Hz, 1H), 6.86 (s, 1H), 3.79 (d, J = 13.7 Hz, 1H), 3.51-3.44 (m, 1H), 3.34 (s, 2H), 1.77-1.59 (m, 4H), 0.65 (s, 9H). |
| 910 | 1H NMR (400 MHz, Methanol-d4) δ 9.05 (dd, J = 4.2, 1.5 Hz, 1H), 8.67 (dd, J = 8.8, 1.6 Hz, 1H), 8.31 (s, 1H), 8.21 (d, J = 7.5 Hz, 2H), 7.84-7.79 (m, 2H), 7.69 (dd, J = 8.7, 4.2 Hz, 1H), 6.99 (d, J = 2.5 Hz, 1H), 6.92 (s, 1H), 3.81 (d, J = 13.7 Hz, 1H), 3.37 (d, J = 13.7 Hz, 1H), 1.77-1.55 (m, 4H), 0.58 (s, 10H). |
| 911 | 1H NMR (400 MHz, Methanol-d4) δ 8.43 (s, 1H), 8.23 (s, 1H), 7.95 (s, 1H), 7.70 (s, 2H), 7.62 (s, 1H), 7.49 (s, 1H), 7.42 (s, 1H), 6.80 (s, 1H), 6.66 (s, 1H), 4.08 (d, J = 5.0 Hz, 4H), 2.62 (s, 1H), 2.30 (s, 8H), 0.67 (s, 9H). |
| 912 | 1H NMR (400 MHz, Methanol-d4) δ 8.39 (d, J = 1.4 Hz, 1H), 8.23 (d, J = 8.3 Hz, 1H), 7.95 (d, J = 6.2 Hz, 1H), 7.71 (d, J = 5.7 Hz, 2H), 7.60 (s, 1H), 7.50 (t, J = 7.9 Hz, 1H), 7.43 (d, J = 6.3 Hz, 1H), 6.77 (s, 1H), 6.63 (s, 1H), 4.08 (t, J = 0.9 Hz, 3H), 3.90 (d, J = 13.9 Hz, 1H), 3.57 (d, J = 13.8 Hz, 1H), 1.18-0.99 (m, 5H), 0.66 (d, J = 1.0 Hz, 10H). |
| 913 | 1H NMR (400 MHz, Methanol-d4) δ 8.39 (d, J = 1.2 Hz, 1H), 8.23 (d, J = 8.3 Hz, 1H), 7.95 (dd, J = 6.2, 1.0 Hz, 1H), 7.77 (d, J = 0.9 Hz, 1H), 7.71 (d, J = 7.3 Hz, 1H), 7.62-7.59 (m, 1H), 7.50 (t, J = 7.8 Hz, 1H), 7.43 (d, J = 6.3 Hz, 1H), 6.76 (d, J = 2.3 Hz, 1H), 6.64 (s, 1H), 4.08 (d, J = 1.1 Hz, 3H), 3.90 (d, J = 13.5 Hz, 1H), 3.57 (d, J = 13.8 Hz, 1H), 1.58 (d, J = 0.7 Hz, 3H), 1.28-1.19 (m, 2H), 1.03-0.93 (m, 2H), 0.66 (d, J = 1.1 Hz, 9H). |
| 914 | 1H NMR (400 MHz, Methanol-d4) δ 8.41 (d, J = 1.9 Hz, 1H), 8.27-8.20 (m, 1H), 7.96 (dd, J = 6.2, 1.8 Hz, 1H), 7.85 (s, 1H), 7.71 (d, J = 7.3 Hz, 1H), 7.62 |

TABLE 2-continued

| Compound | ¹H-NMR |
|---|---|
| | (dd, J = 2.6, 1.6 Hz, 1H), 7.54-7.46 (m, 1H), 7.43 (d, J = 6.3 Hz, 1H), 6.82 (d, J = 2.2 Hz, 1H), 6.69 (s, 1H), 5.87 (t, J = 54.7 Hz, 1H), 4.09 (d, J = 1.9 Hz, 3H), 3.92 (d, J = 14.2 Hz, 1H), 3.60 (d, J = 13.4 Hz, 1H), 1.46 (s, 3H), 0.68 (d, J = 1.7 Hz, 10H). |
| 915 | 1H NMR (400 MHz, Methanol-d4) δ 9.18 (s, 1H), 8.45 (s, 1H), 8.15 (s, 1H), 8.12 (s, 1H), 8.03 (s, 1H), 7.84 (d, J = 7.2 Hz, 1H), 7.68 (d, J = 2.3 Hz, 1H), 7.70-7.61 (m, 2H), 6.90 (d, J = 2.3 Hz, 1H), 6.77 (s, 1H), 3.95 (d, J = 13.8 Hz, 1H), 3.68 (d, J = 13.8 Hz, 1H), 1.78-1.56 (m, 4H), 0.73 (s, 9H). |
| 916 | 1H NMR (400 MHz, Methanol-d4) δ 8.45 (s, 1H), 8.41 (d, J = 8.5 Hz, 1H), 8.27 (d, J = 6.0 Hz, 1H), 8.11 (s, 1H), 7.96 (d, J = 6.1 Hz, 1H), 7.94-7.88 (m, 1H), 7.74 (dd, J = 8.5, 7.3 Hz, 1H), 7.68 (d, J = 2.2 Hz, 1H), 6.83 (d, J = 2.9 Hz, 2H), 3.99 (d, J = 13.8 Hz, 1H), 3.56 (d, J = 13.8 Hz, 1H), 3.34 (s, 1H), 1.77-1.54 (m, 4H), 0.67 (s, 10H). |
| 918 | 1H NMR (400 MHz, Methanol-d4) δ 8.94 (d, J = 4.4 Hz, 1H), 8.59 (d, J = 8.7 Hz, 1H), 8.51 (s, 1H), 7.97 (s, 1H), 7.68 (d, J = 2.2 Hz, 1H), 7.68-7.64 (m, 1H), 7.59 (dd, J = 8.2, 4.9 Hz, 1H), 7.51-7.42 (m, 1H), 6.87 (d, J = 2.3 Hz, 1H), 6.77 (s, 1H), 5.91 (t, J = 54.7 Hz, 1H), 4.32 (d, J = 14.9 Hz, 1H), 3.99 (d, J = 14.9 Hz, 1H), 1.49 (s, 3H), 0.95 (s, 3H), 0.92 (s, 3H). |
| 919 | 1H NMR (400 MHz, Methanol-d4) δ 8.94 (d, J = 4.2 Hz, 1H), 8.59 (d, J = 8.8 Hz, 1H), 8.49 (s, 1H), 7.88 (s, 1H), 7.69-7.63 (m, 2H), 7.59 (dd, J = 8.2, 4.9 Hz, 1H), 7.49-7.42 (m, 1H), 6.82 (d, J = 2.3 Hz, 1H), 6.72 (s, 1H), 4.32 (d, J = 14.9 Hz, 1H), 3.97 (d, J = 14.9 Hz, 1H), 1.61 (s, 3H), 1.32-1.23 (m, 2H), 1.03 (s, 2H), 0.93 (s, 3H), 0.90 (s, 3H). |
| 920 | 1H NMR (400 MHz, Methanol-d4) δ 8.94 (d, J = 4.2 Hz, 1H), 8.59 (d, J = 8.8 Hz, 1H), 8.49 (s, 1H), 7.82 (s, 1H), 7.67 (d, J = 2.5 Hz, 1H), 7.65 (d, J = 4.4 Hz, 1H), 7.61 (dd, J = 8.2, 4.9 Hz, 1H), 7.52-7.40 (m, 1H), 6.87 (s, 1H), 6.76 (s, 1H), 4.01 (d, J = 13.9 Hz, 1H), 3.61 (d, J = 13.9 Hz, 1H), 2.66 (s, 1H), 2.33 (s, 6H), 0.68 (s, 9H). |
| 921 | 1H NMR (400 MHz, Methanol-d4) δ 8.99 (dd, J = 4.3, 1.5 Hz, 1H), 8.60 (dd, J = 8.7, 1.5 Hz, 1H), 8.50 (s, 1H), 8.12 (s, 1H), 7.87 (d, J = 7.9 Hz, 1H), 7.70 (d, J = 2.3 Hz, 1H), 7.66 (dd, J = 8.7, 4.3 Hz, 1H), 7.61 (d, J = 7.9 Hz, 1H), 6.89 (d, J = 2.3 Hz, 1H), 6.83 (s, 1H), 4.03 (d, J = 13.8 Hz, 1H), 3.58 (d, J = 13.9 Hz, 1H), 1.76-1.55 (m, 4H), 0.67 (s, 9H). |
| 922 | 1H NMR (400 MHz, Methanol-d4) δ 8.47 (s, 1H), 8.28 (d, J = 8.3 Hz, 1H), 8.01 (d, J = 6.2 Hz, 1H), 7.81 (d, J = 7.3 Hz, 1H), 7.67 (d, J = 2.3 Hz, 1H), 7.54 (dd, J = 8.3, 7.4 Hz, 1H), 7.45 (d, J = 6.2 Hz, 1H), 6.91 (d, J = 2.3 Hz, 1H), 6.75 (s, 1H), 4.12 (s, 3H), 3.97 (d, J = 13.8 Hz, 1H), 3.65 (d, J = 13.8 Hz, 1H), 1.83-1.62 (m, 5H), 0.72 (s, 10H). |
| 923 | 1H NMR (400 MHz, Methanol-d4) δ 8.47 (s, 1H), 8.28 (d, J = 8.3 Hz, 1H), 8.01 (d, J = 6.2 Hz, 1H), 7.80 (d, J = 7.1 Hz, 1H), 7.68 (d, J = 2.3 Hz, 1H), 7.54 (t, J = 7.8 Hz, 1H), 7.45 (d, J = 6.3 Hz, 1H), 6.91 (d, J = 2.3 Hz, 1H), 6.73 (s, 1H), 5.85 (t, J = 54.2 Hz, 1H), 4.12 (s, 3H), 3.98 (d, J = 13.8 Hz, 1H), 3.65 (d, J = 13.8 Hz, 1H), 1.61-1.47 (m, 4H), 0.73 (s, 8H), 0.70 (s, 1H). |
| 924 | 1H NMR (400 MHz, Methanol-d4) δ 8.25 (d, J = 8.4 Hz, 1H), 8.18 (s, 1H), 7.96 (d, J = 6.3 Hz, 1H), 7.85 (d, J = 7.3 Hz, 1H), 7.56 (s, OH), 7.53 (q, J = 2.8 Hz, 2H), 7.38 (d, J = 6.3 Hz, 1H), 6.63 (s, 1H), 6.58 (s, 1H), 4.11 (s, 3H), 3.70 (d, J = 13.5 Hz, 1H), 3.38 (d, J = 13.5 Hz, 1H), 2.98 (s, 1H), 2.85 (d, J = 0.8 Hz, 1H), 1.89 (s, 2H), 1.74 (s, 2H), 1.28 (s, 1H), 0.96-0.84 (m, OH), 0.61 (s, 9H). |
| 925 | 1H NMR (400 MHz, Methanol-d4) δ 8.25 (d, J = 8.3 Hz, 1H), 8.19 (s, 1H), 7.96 (d, J = 6.2 Hz, 1H), 7.85 (d, J = 7.5 Hz, 1H), 7.58-7.48 (m, 2H), 7.39 (d, J = 6.2 Hz, 1H), 6.62 (s, 1H), 6.57 (s, 1H), 5.99 (t, J = 55.0 Hz, 1H), 4.11 (s, 3H), 3.71 (d, J = 13.4 Hz, 1H), 3.38 (d, J = 13.4 Hz, 1H), 1.68 (s, 2H), 1.58 (s, 2H), 1.28 (s, 1H), 0.62 (s, 9H). |
| 926 | 1H NMR (400 MHz, Methanol-d4) δ 8.29 (s, 1H), 8.01 (d, J = 8.3 Hz, 1H), 7.72 (d, J = 6.2 Hz, 1H), 7.60 (s, 1H), 7.45 (d, J = 7.3 Hz, 1H), 7.42 (d, J = 2.2 Hz, 1H), 7.30-7.24 (m, 1H), 7.17 (d, J = 6.3 Hz, 1H), 6.60 (d, J = 2.3 Hz, 1H), 6.42 (s, 1H), 4.12 (d, J = 14.8 Hz, 1H), 3.85 (s, 3H), 3.75 (d, J = 14.9 Hz, 1H), 1.23 (ddd, J = 13.2, 8.3, 5.0 Hz, 1H), 0.96-0.87 (m, 2H), 0.75-0.70 (m, 2H), 0.67 (d, J = 8.3 Hz, 6H), 0.25-0.17 (m, 2H), 0.02 (dt, J = 5.7, 4.5 Hz, 2H). |
| 927 | 1H NMR (400 MHz, Methanol-d4) δ 8.50 (s, 1H), 8.27 (d, J = 8.3 Hz, 1H), 7.99 (d, J = 6.2 Hz, 1H), 7.81 (s, 1H), 7.71 (dd, J = 7.3, 1.2 Hz, 1H), 7.66 (d, J = 2.3 Hz, 1H), 7.56-7.50 (m, 1H), 7.44 (d, J = 6.3 Hz, 1H), 6.82 (d, J = 2.3 Hz, 1H), 6.66 (s, 1H), 4.32 (d, J = 14.8 Hz, 1H), 4.12 (s, 3H), 4.01 (d, J = 14.8 Hz, 1H), 1.61 (s, 3H), 1.27 (d, J = 4.9 Hz, 2H), 1.05-1.00 (m, 2H), 0.93 (d, J = 9.1 Hz, 6H). |
| 928 | 1H NMR (400 MHz, Methanol-d4) δ 8.50 (s, 1H), 8.27 (d, J = 8.3 Hz, 1H), 7.99 (d, J = 6.3 Hz, 1H), 7.75 (s, 1H), 7.70 (d, J = 7.4 Hz, 1H), 7.66 (d, J = 2.3 Hz, 1H), 7.56-7.49 (m, 1H), 7.44 (dd, J = 6.3, 0.9 Hz, 1H), 6.82 (d, J = 2.3 Hz, 1H), 6.68 (s, 1H), 4.30 (d, J = 14.8 Hz, 1H), 4.12 (s, 3H), 4.02 (d, J = 14.8 Hz, 1H), 2.66 (s, 1H), 2.34 (s, 6H), 0.93 (d, J = 10.0 Hz, 6H). |
| 929 | 1H NMR (400 MHz, Methanol-d4) δ 8.47 (s, 1H), 8.28 (d, J = 8.3 Hz, 1H), 8.04 (s, 1H), 7.99 (d, J = 6.2 Hz, 1H), 7.78-7.72 (m, 1H), 7.67 (d, J = 2.3 Hz, 1H), 7.54 (dd, J = 8.2, 7.4 Hz, 1H), 7.49-7.42 (m, 1H), 6.89 (d, J = 2.3 Hz, 1H), 6.75 (s, 1H), 4.12 (s, 3H), 3.98 (d, J = 13.8 Hz, 1H), 3.66 (d, J = 13.8 Hz, 1H), 1.76-1.54 (m, 4H), 0.72 (s, 9H). |
| 930 | 1H NMR (400 MHz, Methanol-d4) δ 8.48 (s, 1H), 8.39-8.32 (m, 1H), 8.01 (s, 1H), 7.82 (d, J = 8.4 Hz, 1H), 7.68 (d, J = 2.3 Hz, 1H), 7.62-7.55 (m, 1H), 7.42 (d, J = 7.3 Hz, 1H), 6.98 (d, J = 9.2 Hz, 1H), 6.92 (d, J = 2.3 Hz, 1H), 6.77 (s, |

TABLE 2-continued

| Compound | ¹H-NMR |
|---|---|
| | 1H), 4.05 (s, 3H), 4.00 (d, J = 13.9 Hz, 1H), 3.67 (d, J = 13.8 Hz, 1H), 1.77-1.55 (m, 4H), 0.74 (s, 9H). |
| 931 | 1H NMR (400 MHz, Methanol-d4) δ 8.48 (s, 1H), 8.27 (d, J = 8.4 Hz, 1H), 7.99 (d, J = 6.2 Hz, 1H), 7.84 (s, 1H), 7.75 (dd, J = 7.3, 1.1 Hz, 1H), 7.67 (d, J = 2.3 Hz, 1H), 7.53 (dd, J = 8.3, 7.4 Hz, 1H), 7.45 (d, J = 6.2 Hz, 1H), 6.86 (d, J = 2.3 Hz, 1H), 6.69 (s, 1H), 4.12 (s, 3H), 4.01 (d, J = 13.8 Hz, 1H), 3.63 (d, J = 13.8 Hz, 1H), 1.49 (ddd, J = 13.2, 8.3, 5.0 Hz, 1H), 1.23-1.13 (m, 2H), 1.03-0.94 (m, 2H), 0.71 (s, 9H), 0.52-0.44 (m, 2H), 0.32-0.25 (m, 2H). |
| 932 | 1H NMR (400 MHz, Methanol-d4) δ 8.49 (s, 1H), 8.27 (d, J = 8.3 Hz, 1H), 7.99 (d, J = 6.2 Hz, 1H), 7.78 (s, 1H), 7.76-7.72 (m, 1H), 7.68 (d, J = 2.2 Hz, 1H), 7.53 (dd, J = 8.4, 7.3 Hz, 1H), 7.45 (dd, J = 6.3, 0.9 Hz, 1H), 6.88 (d, J = 2.3 Hz, 1H), 6.72 (s, 1H), 5.03-4.90 (m, 1H), 4.71 (d, J = 5.4 Hz, 1H), 4.62-4.56 (m, 1H), 4.12 (s, 3H), 4.01 (d, J = 13.8 Hz, 1H), 3.65 (d, J = 13.8 Hz, 1H), 1.51 (dd, J = 7.1, 1.3 Hz, 3H), 0.72 (s, 9H). |
| 933 | 1H NMR (400 MHz, Methanol-d4) δ 8.49 (s, 1H), 8.28 (d, J = 8.1 Hz, 1H), 7.99 (d, J = 6.2 Hz, 1H), 7.85 (s, 1H), 7.75 (d, J = 7.2 Hz, 1H), 7.68 (d, J = 2.3 Hz, 1H), 7.54 (dd, J = 8.4, 7.3 Hz, 1H), 7.46 (dd, J = 6.3, 0.9 Hz, 1H), 6.90 (d, J = 2.3 Hz, 1H), 6.75 (s, 1H), 5.31-5.12 (m, 1H), 4.99-4.86 (m, 2H), 4.83-4.71 (m, 2H), 4.01 (d, J = 13.8 Hz, 1H), 3.65 (d, J = 13.8 Hz, 1H), 0.72 (s, 11H). |
| 934 | 1H NMR (400 MHz, Methanol-d4) δ 8.46 (s, 1H), 8.27 (d, J = 8.3 Hz, 1H), 7.99 (d, J = 6.2 Hz, 1H), 7.89 (s, 1H), 7.71 (dd, J = 7.3, 1.1 Hz, 1H), 7.65 (d, J = 2.3 Hz, 1H), 7.53 (dd, J = 8.3, 7.4 Hz, 1H), 7.45 (d, J = 6.3 Hz, 1H), 6.82 (d, J = 2.3 Hz, 1H), 6.71 (s, 1H), 5.91 (t, J = 54.8 Hz, 1H), 4.28 (d, J = 14.7 Hz, 1H), 4.12 (s, 3H), 4.00 (d, J = 14.7 Hz, 1H), 2.02 (s, 1H), 1.49 (d, J = 4.5 Hz, 4H), 0.92 (d, J = 10.6 Hz, 6H). |
| 935 | 1H NMR (400 MHz, Methanol-d4) δ 8.91 (s, 1H), 8.39 (s, 1H), 8.36 (s, 1H), 8.18 (d, J = 2.1 Hz, 1H), 8.04 (t, J = 2.2 Hz, 1H), 8.02 (d, J = 1.6 Hz, 1H), 7.94 (d, J = 9.4 Hz, 1H), 7.66 (d, J = 2.3 Hz, 1H), 7.10 (d, J = 2.3 Hz, 1H), 6.33 (s, 1H), 4.01 (d, J = 14.0 Hz, 1H), 3.75-3.61 (m, 1H), 2.03 (s, 1H), 1.82-1.73 (m, 2H), 1.68 (s, 2H), 1.10 (s, OH), 0.87 (s, 9H). |
| 936 | 1H NMR (400 MHz, Methanol-d4) δ 8.48 (s, 1H), 8.20 (s, 1H), 7.79-7.58 (m, 3H), 7.08 (d, J = 2.3 Hz, 1H), 6.39 (t, J = 6.9 Hz, 1H), 6.19 (s, 1H), 4.17 (d, J = 14.0 Hz, 1H), 3.77 (d, J = 14.0 Hz, 1H), 3.59 (s, 3H), 1.81-1.57 (m, 4H), 0.99 (s, 9H). |
| 937 | 1H NMR (400 MHz, Methanol-d4) δ 8.88 (d, 1H), 8.45 (d, 1H), 8.25 (dd, 1H), 8.11 (s, 1H), 8.10-8.02 (m, 1H), 7.73-7.66 (m, 3H), 6.90 (d, 1H), 6.76 (s, 1H), 4.02-3.93 (m, 1H), 3.63 (d, 1H), 1.77-1.56 (m, 4H), 0.71 (s, 9H). |
| 938 | 1H NMR (400 MHz, Chloroform-d) δ 8.99-8.81 (m, 1H), 8.23 (d, 1H), 8.14 (s, 1H), 7.66-7.58 (m, 1H), 7.43 (d, 1H), 7.39-7.28 (m, 2H), 6.34 (s, 1H), 6.08 (s, 1H), 4.00 (d, 1H), 3.64 (d, 1H), 2.47 (d, 3H), 1.80-1.61 (m, 4H), 0.91 (d, 9H). |
| 939 | 1H NMR (400 MHz, Acetonitrile-d3) δ 8.44 (s, 1H), 8.30 (d, J = 7.9 Hz, 1H), 7.76 (d, J = 7.5 Hz, 1H), 7.63 (s, 1H), 7.54 (s, 1H), 7.44 (t, J = 7.8 Hz, 1H), 7.30 (d, J = 7.6 Hz, 1H), 6.78 (d, J = 7.7 Hz, 2H), 6.66 (s, 1H), 6.46 (s, 1H), 3.84 (dd, J = 13.5, 5.9 Hz, 1H), 3.68 (dd, J = 13.2, 4.7 Hz, 1H), 3.54 (s, 3H), 2.08-1.99 (m, 6H), 1.79 (m, 6H), 1.72 (m, 1H), 0.81 (s, 9H). |
| 940 | 1H NMR (400 MHz, Methanol-d4) δ 9.06 (d, J = 4.7 Hz, 1H), 8.93 (d, J = 8.7 Hz, 1H), 8.48 (s, 1H), 8.16-8.08 (m, 1H), 8.02 (s, 1H), 7.95-7.86 (m, 1H), 7.81 (t, J = 7.3 Hz, 2H), 7.68 (d, J = 2.3 Hz, 1H), 6.91-6.84 (m, 2H), 5.91 (t, J = 54.7 Hz, 1H), 4.32 (d, J = 15.0 Hz, 1H), 3.96 (d, J = 14.9 Hz, 1H), 1.50 (s, 4H), 0.96 (s, 3H), 0.91 (s, 3H). |
| 941 | 1H NMR (400 MHz, Methanol-d4) δ 8.48 (s, 1H), 8.13 (m, 2H), 7.68 (d, J = 2.1 Hz, 1H), 7.05 (s, 2H), 6.91 (s, 1H), 6.10 (s, 1H), 4.22 (d, J = 13.9 Hz, 1H), 3.88 s, 3H), 3.68 (d, J = 13.9 Hz, 1H), 1.72 (d, J = 31.5 Hz, 4H), 0.97 (d, J = 1.0 Hz, 9H). |
| 942 | 1H NMR (400 MHz, Methanol-d4) δ 8.49 (d, J = 1.3 Hz, 1H), 7.82 (t, J = 8.1 Hz, 1H), 7.64 (dd, J = 2.3, 1.1 Hz, 1H), 6.97-6.82 (m, 1H), 6.77 (d, J = 2.3 Hz, 1H), 6.17-5.79 (m, 2H), 4.44 (d, J = 15.0 Hz, 1H), 4.01 (d, J = 14.9 Hz, 1H), 2.40 (s, 3H), 1.78-1.56 (m, 4H), 1.10 (d, J = 3.3 Hz, 6H). |
| 943 | 1H NMR (400 MHz, Methanol-d4) δ 8.50 (s, 1H), 7.82 (t, J = 8.1 Hz, 1H), 7.65 (d, J = 2.3 Hz, 1H), 6.86 (dd, J = 12.6, 2.6 Hz, 2H), 6.08 (s, 1H), 4.12 (d, J = 13.9 Hz, 1H), 3.69 (d, J = 13.9 Hz, 1H), 2.40 (s, 3H), 1.66-1.55 (m, 1H), 1.35-1.25 (m, 2H), 1.22-1.13 (m, 2H), 0.90 (s, 9H), 0.55-0.46 (m, 2H), 0.43-0.32 (m, 2H). |
| 944 | 1H NMR (400 MHz, Methanol-d4) δ 8.23 (s, 1H), 7.87 (t, J = 8.1 Hz, 1H), 7.51 (d, J = 2.4 Hz, 1H), 6.93-6.82 (m, 1H), 6.67 (d, J = 2.4 Hz, 1H), 6.03 (s, 1H), 3.88 (d, J = 13.7 Hz, 1H), 3.50 (d, J = 13.6 Hz, 1H), 2.73 (s, 1H), 2.61 (s, 6H), 2.42 (s, 3H), 0.85 (s, 9H). |
| 945 | 1H NMR (400 MHz, Methanol-d4) δ 8.26 (s, 1H), 7.89 (t, J = 8.1 Hz, 1H), 7.53 (d, J = 2.4 Hz, 1H), 6.86 (dd, J = 8.5, 2.6 Hz, 1H), 6.71 (s, 1H), 6.17-5.81 (m, 2H), 3.95 (d, J = 13.8 Hz, 1H), 3.49 (d, J = 13.7 Hz, 1H), 2.39 (s, 3H), 1.69 (m, 2H), 1.65-1.56 (m, 2H), 0.85 (s, 9H). |
| 946 | 1H NMR (400 MHz, Methanol-d4) δ 8.47 (s, 1H), 7.81 (t, J = 8.1 Hz, 1H), 7.61 (d, J = 2.3 Hz, 1H), 6.83 (d, J = 6.3 Hz, 1H), 6.74 (d, J = 2.3 Hz, 1H), 6.08 (s, 1H), 4.14 (d, J = 13.8 Hz, 1H), 3.89-3.80 (m, 1H), 3.60 (d, J = 13.8 Hz, 1H), 2.37 (s, 3H), 1.91-1.83 (m, 1H), 1.35-1.26 (m, 2H), 1.27-1.19 (m, 2H), 1.07 (dd, J = 8.7, 2.9 Hz, 2H), 0.91 (s, 1H), 0.87 (s, 9H), 0.84-0.77 (m, 1H). |
| 947 | 1H NMR (400 MHz, Methanol-d4) δ 8.47 (s, 1H), 7.86 (t, J = 8.1 Hz, 1H), 7.62 (d, J = 2.2 Hz, 1H), 6.88 (q, J = 3.1 Hz, 2H), 6.17 (s, 1H), 4.05 (d, J = 13.9 Hz, |

TABLE 2-continued

| Compound | ¹H-NMR |
|---|---|
| | 1H), 3.75 (d, J = 13.9 Hz, 1H), 2.49 (s, 3H), 1.60 (s, 3H), 1.36-1.30 (m, 2H), 1.15-1.07 (m, 2H), 0.92 (s, 9H). |
| 948 | 1H NMR (400 MHz, Methanol-d4) δ 8.23 (d, J = 1.2 Hz, 1H), 7.88 (t, J = 8.1 Hz, 1H), 7.51 (d, J = 2.3 Hz, 1H), 6.86 (dd, J = 8.5, 2.7 Hz, 1H), 6.70 (d, J = 2.4 Hz, 1H), 6.17 (s, 1H), 5.90 (t, J = 54.3 Hz, 1H), 4.23 (d, J = 14.8 Hz, 1H), 3.92 (d, J = 14.8 Hz, 1H), 2.49 (s, 3H), 1.66-1.43 (m, 4H), 1.07 (d, J = 5.3 Hz, 6H). |
| 949 | 1H NMR (400 MHz, Methanol-d4) δ 8.46 (s, 1H), 7.86 (t, J = 8.1 Hz, 1H), 7.62 (d, J = 2.3 Hz, 1H), 6.88 (dd, J = 8.1, 2.5 Hz, 2H), 6.18 (s, 1H), 4.04 (d, J = 13.9 Hz, 1H), 3.74 (d, J = 13.9 Hz, 1H), 2.49 (s, 3H), 1.55-1.42 (m, 1H), 1.28-1.20 (m, 2H), 1.11-1.03 (m, 2H), 0.92 (s, 10H), 0.57-0.46 (m, 2H), 0.35-0.28 (m, 2H). |
| 950 | 1H NMR (400 MHz, Methanol-d4) δ 8.49 (s, 1H), 7.89 (t, J = 8.1 Hz, 1H), 7.65 (d, J = 2.3 Hz, 1H), 7.42-7.26 (m, 5H), 7.16 (d, J = 2.3 Hz, 1H), 6.87 (dd, J = 8.4, 2.8 Hz, 1H), 6.36 (s, 1H), 5.78 (t, J = 7.2 Hz, 1H), 2.52 (s, 3H), 2.14 (m, 2H), 1.81 (m, 2H), 1.74 (m, 2H), 1.02 (t, J = 7.3 Hz, 3H). |
| 951 | 1H NMR (400 MHz, Methanol-d4) δ 8.52 (d, J = 0.8 Hz, 1H), 7.87 (t, J = 8.1 Hz, 1H), 7.65 (dd, J = 2.3, 0.8 Hz, 1H), 6.94 (d, J = 2.3 Hz, 1H), 6.90 (dd, J = 8.4, 2.8 Hz, 1H), 6.19 (s, 1H), 4.06 (d, J = 13.9 Hz, 1H), 3.83 (d, J = 13.9 Hz, 1H), 2.75 (s, 1H), 2.52 (s, 3H), 2.45 (s, 6H), 0.96 (s, 9H). |
| 952 | 1H NMR (400 MHz, Methanol-d4) δ 8.51 (d, J = 0.9 Hz, 1H), 7.86 (t, J = 8.1 Hz, 1H), 7.66 (dd, J = 2.3, 0.9 Hz, 1H), 6.95 (d, J = 2.3 Hz, 1H), 6.90 (dd, J = 8.6, 2.8 Hz, 1H), 6.23 (s, 1H), 4.98-4.87 (m, OH), 4.82-4.58 (m, 2H), 4.14-4.02 (m, 1H), 3.81 (d, J = 13.9 Hz, 1H), 2.51 (s, 3H), 1.66-1.55 (m, 3H), 0.95 (d, J = 0.9 Hz, 9H). |
| 953 | 1H NMR (400 MHz, Methanol-d4) δ 8.52 (s, 1H), 7.92 (s, 1H), 7.89 (t, J = 8.1 Hz, 1H), 7.78-7.72 (m, 1H), 7.65 (d, J = 2.3 Hz, 1H), 7.03 (d, J = 2.4 Hz, 1H), 6.89 (dd, J = 8.5, 2.8 Hz, 1H), 6.12 (s, 1H), 5.88 (t, J = 54.2 Hz, 1H), 2.45 (s, 3H), 1.56 (m, 4H). |
| 954 | 1H NMR (400 MHz, Methanol-d4) δ 8.37 (d, J = 1.5 Hz, 1H), 7.87 (t, J = 8.1 Hz, 1H), 7.77 (d, J = 2.3 Hz, 1H), 7.09 (d, J = 2.4 Hz, 1H), 6.92-6.84 (m, 1H), 6.18 (s, 1H), 3.90 (d, J = 13.9 Hz, 1H), 3.65 (d, J = 13.8 Hz, 1H), 2.73 (s, 1H), 2.51 (s, 3H), 2.43 (s, 6H), 0.89 (s, 9H). |
| 955 | 1H NMR (400 MHz, Methanol-d4) δ 8.50 (s, 1H), 7.83 (t, J = 8.1 Hz, 1H), 7.64 (d, J = 2.3 Hz, 1H), 6.88 (dd, J = 9.0, 2.6 Hz, 2H), 6.19 (s, 1H), 4.99-4.88 (m, OH), 4.80-4.68 (m, 1H), 4.68-4.52 (m, 1H), 4.37 (d, J = 14.9 Hz, 1H), 4.13 (d, J = 15.0 Hz, 1H), 2.49 (s, 3H), 1.59 (d, J = 1.4 Hz, 2H), 1.57 (d, J = 1.4 Hz, 1H), 1.15 (s, 3H), 1.14 (s, 3H). |
| 956 | 1H NMR (400 MHz, Methanol-d4) δ 8.51 (s, 1H), 7.83 (t, J = 8.1 Hz, 1H), 7.62 (d, J = 2.3 Hz, 1H), 6.87 (dd, J = 8.5, 2.8 Hz, 1H), 6.85 (d, J = 2.3 Hz, 1H), 6.15 (s, 1H), 4.34 (d, J = 15.0 Hz, 1H), 4.16 (d, J = 15.0 Hz, 1H), 2.72 (s, 1H), 2.51 (s, 3H), 2.43 (s, 6H), 1.15 (s, 3H), 1.15 (s, 3H). |
| 957 | 1H NMR (400 MHz, Methanol-d4) δ 8.53 (s, 1H), 7.84 (t, J = 8.1 Hz, 1H), 7.65 (d, J = 2.3 Hz, 1H), 6.89 (d, J = 2.8 Hz, 1H), 6.86 (d, J = 2.2 Hz, 2H), 6.17 (s, 1H), 4.41 (d, J = 15.0 Hz, 1H), 4.12 (d, J = 15.0 Hz, 1H), 2.49 (s, 3H), 1.55-1.44 (m, 1H), 1.30-1.19 (m, 2H), 1.16 (s, 3H), 1.15 (s, 3H), 1.08 (m, 2H), 0.58-0.45 (m, 2H), 0.38-0.28 (m, 2H). |
| 958 | 1H NMR (400 MHz, Methanol-d4) δ 8.48 (s, 1H), 7.84 (t, J = 8.1 Hz, 1H), 7.61 (d, J = 2.3 Hz, 1H), 6.87 (dd, J = 8.4, 2.8 Hz, 1H), 6.83 (d, J = 2.3 Hz, 1H), 6.15 (s, 1H), 4.34 (d, J = 15.0 Hz, 1H), 4.13 (d, J = 15.0 Hz, 1H), 3.71-3.60 (m, 1H), 2.50 (s, 3H), 1.31-1.16 (m, 3H), 1.15 (s, 4H), 1.14 (s, 3H). |
| 959 | 1H NMR (400 MHz, Methanol-d4) δ 8.51 (s, 1H), 7.84 (t, J = 8.1 Hz, 1H), 7.63 (d, J = 2.3 Hz, 1H), 6.87 (dd, J = 8.5, 2.8 Hz, 1H), 6.84 (d, J = 2.3 Hz, 1H), 6.15 (s, 1H), 4.39 (d, J = 15.0 Hz, 1H), 4.12 (d, J = 15.0 Hz, 1H), 2.49 (s, 3H), 1.60 (s, 3H), 1.40-1.29 (m, 2H), 1.15 (s, 3H), 1.14 (s, 3H), 1.12-1.06 (m, 2H). |
| 960 | 1H NMR (400 MHz, Methanol-d4) δ 8.49 (s, 1H), 7.87 (t, J = 8.1 Hz, 1H), 7.64 (d, J = 2.3 Hz, 1H), 6.94 (d, J = 2.3 Hz, 1H), 6.88 (dd, J = 8.4, 2.8 Hz, 1H), 6.22 (s, 1H), 5.88 (t, J = 54.2 Hz, 1H), 4.04 (d, J = 13.9 Hz, 1H), 3.79 (d, J = 14.0 Hz, 1H), 2.50 (s, 3H), 1.58 (m, 4H), 0.94 (s, 9H). |
| 961 | 1H NMR (400 MHz, Methanol-d4) δ 8.46 (s, 1H), 8.34 (dd, J = 8.1, 1.2 Hz, 1H), 7.81-7.74 (m, 1H), 7.64 (d, J = 2.3 Hz, 1H), 7.48 (t, J = 7.8 Hz, 1H), 7.43 (d, J = 7.7 Hz, 1H), 6.83 (m, 1H), 6.82 (d, J = 4.5 Hz, 1H), 6.54 (m, 1H), 4.01 (d, J = 13.8 Hz, 1H), 3.62 (d, J = 13.8 Hz, 1H), 3.61 (s, 3H), 2.71 (s, 1H), 2.41 (s, 6H), 0.76 (s, 9H). |
| 962 | 1H NMR (400 MHz, Acetonitrile-d3) δ 8.99-8.93 (m, 1H), 8.80 (d, J = 8.7 Hz, 1H), 8.31 (s, 1H), 8.12 (d, J = 7.5 Hz, 1H), 7.83-7.72 (m, 2H), 7.66 (dd, J = 8.7, 4.7 Hz, 1H), 7.44 (d, J = 2.2 Hz, 1H), 6.69 (d, J = 3.0 Hz, 2H), 6.60 (s, 1H), 6.30 (s, 1H), 5.69 (t, J = 54.1 Hz, 1H), 3.71 (dd, J = 13.5, 6.6 Hz, 1H), 3.47 (dd, J = 13.5, 4.7 Hz, 1H), 1.88-1.82 (m, 3H), 1.43 (m, 4H), 0.60 (s, 9H). |
| 963 | 1H NMR (400 MHz, Methanol-d4) δ 8.22 (s, 1H), 7.89 (t, J = 8.1 Hz, 1H), 7.49 (d, J = 2.3 Hz, 1H), 6.86 (dd, J = 8.5, 2.7 Hz, 1H), 6.74 (d, J = 2.4 Hz, 1H), 6.15 (s, 1H), 3.94 (d, J = 1.2 Hz, 3H), 3.84 (d, J = 13.7 Hz, 1H), 3.56 (d, J = 13.7 Hz, 1H), 2.51 (s, 3H), 0.87 (s, 9H). |
| 964 | 1H NMR (400 MHz, Methanol-d4) δ 8.33 (s, 1H), 7.89 (t, J = 8.2 Hz, 1H), 7.78 (d, J = 2.5 Hz, 1H), 6.98 (d, J = 2.5 Hz, 1H), 6.91-6.81 (m, 1H), 6.18 (s, 1H), 5.96 (t, J = 55.1 Hz, 1H), 4.06 (s, 3H), 3.99 (d, J = 13.7 Hz, 1H), 3.45 (d, J = 13.8 Hz, 1H), 2.42 (s, 3H), 1.54 (m, 2H), 1.50 (m, 2H), 0.85 (s, 9H). |
| 965 | 1H NMR (400 MHz, Methanol-d4) δ 8.50 (s, 1H), 7.86 (t, J = 8.1 Hz, 1H), 7.66 (d, J = 2.3 Hz, 1H), 6.85 (m, 2H), 6.18 (s, 1H), 5.95 (t, J = 55.0 Hz, 1H), 4.17 (d, |

TABLE 2-continued

| Compound | ¹H-NMR |
|---|---|
|  | J = 13.9 Hz, 1H), 4.03 (s, 3H), 3.64 (d, J = 13.9 Hz, 1H), 2.43 (s, 3H), 1.60-1.53 (m, 2H), 1.53-1.44 (m, 2H), 0.91 (s, 9H). |
| 966 | 1H NMR (400 MHz, Methanol-d4) δ 8.50 (s, 1H), 7.64 (d, J = 2.3 Hz, 1H), 7.62 (d, J = 8.6 Hz, 1H), 6.89 (d, J = 2.3 Hz, 1H), 6.63 (d, J = 8.6 Hz, 1H), 6.14 (s, 1H), 5.94 (t, J = 55.0 Hz, 1H), 4.13 (d, J = 13.9 Hz, 1H), 3.97 (s, 3H), 3.90 (s, 3H), 3.73 (d, J = 13.9 Hz, 1H), 2.43 (s, 3H), 1.61-1.52 (m, 2H), 1.52-1.42 (m, 2H), 0.93 (s, 9H). |
| 967 | 1H NMR (400 MHz, Methanol-d4) δ 8.48 (s, 1H), 7.86 (t, J = 8.1 Hz, 1H), 7.63 (d, J = 2.3 Hz, 1H), 6.86 (dd, J = 8.4, 2.7 Hz, 1H), 6.82 (d, J = 2.3 Hz, 1H), 6.12 (s, 1H), 4.11 (d, J = 13.9 Hz, 1H), 3.91 (s, 3H), 3.69 (d, J = 13.9 Hz, 1H), 3.66-3.61 (m, 1H), 2.45 (s, 3H), 1.31-1.20 (m, 1H), 1.20-1.12 (m, 2H), 0.91 (s, 9H). |
| 968 | 1H NMR (400 MHz, Methanol-d4) δ 8.49 (s, 1H), 7.85 (t, J = 8.1 Hz, 1H), 7.63 (d, J = 2.3 Hz, 1H), 6.86 (dd, J = 8.5, 2.8 Hz, 1H), 6.82 (d, J = 2.3 Hz, 1H), 6.13 (s, 1H), 4.11 (d, J = 13.8 Hz, 1H), 3.88 (s, 3H), 3.69 (d, J = 13.9 Hz, 1H), 2.70 (s, 1H), 2.44 (s, 3H), 2.43 (s, 6H), 0.91 (s, 9H). |
| 969 | 1H NMR (400 MHz, Methanol-d4) δ 8.20 (s, 1H), 7.90 (t, J = 8.1 Hz, 1H), 7.50 (d, J = 2.3 Hz, 1H), 6.85 (dd, J = 8.4, 3.0 Hz, 1H), 6.65 (d, J = 2.4 Hz, 1H), 6.12 (s, 1H), 3.97-3.84 (m, 7H), 3.43 (d, J = 13.7 Hz, 1H), 2.44 (s, 3H), 0.84 (s, 9H). |
| 970 | 1H NMR (400 MHz, Methanol-d4) δ 8.50 (s, 1H), 7.71-7.53 (m, 2H), 6.86 (d, J = 2.3 Hz, 1H), 6.62 (d, J = 8.5 Hz, 1H), 4.07 (d, J = 13.8 Hz, 1H), 3.88 (m, 7H), 3.81 (s, 3H), 2.45 (s, 3H), 0.93 (s, 9H). |
| 971 | 1H NMR (400 MHz, Methanol-d4) δ 8.46 (s, 1H), 7.86 (t, J = 8.1 Hz, 1H), 7.63 (d, J = 2.3 Hz, 1H), 6.86 (dd, J = 8.5, 2.8 Hz, 1H), 6.81 (d, J = 2.3 Hz, 1H), 6.14 (s, 1H), 4.10 (d, J = 13.9 Hz, 1H), 3.88 (m, 6H), 3.66 (d, J = 13.8 Hz, 1H), 2.45 (s, 3H), 0.90 (s, 9H). |
| 972 | 1H NMR (400 MHz, Methanol-d4) δ 8.42 (s, 1H), 8.03 (s, 1H), 7.69 (d, 1H), 7.61 (d, 1H), 7.49-7.38 (m, 2H), 7.07 (s, 1H), 6.75 (s, 1H), 4.06 (d, 1H), 3.67 (d, 1H), 2.85-2.74 (m, 1H), 1.74-1.57 (m, 4H), 0.83 (s, 9H). |
| 973 | 1H NMR (400 MHz, DMSO-d6) δ 8.23 (s, 1H), 7.78 (t, J = 8.3 Hz, 1H), 7.57 (d, J = 2.4 Hz, 1H), 6.98-6.75 (m, 2H), 6.27-5.84 (m, 2H), 2.42 (s, 3H), 1.47 (d, J = 3.4 Hz, 4H), 0.76 (s, 9H). |
| 974 | 1H NMR (400 MHz, Methanol-d4) δ 8.53 (s, 1H), 7.77 (t, J = 8.1 Hz, 1H), 7.68 (d, J = 2.3 Hz, 1H), 7.04 (d, J = 2.3 Hz, 1H), 6.91 (dd, J = 8.5, 2.8 Hz, 1H), 6.43 (s, 1H), 5.92 (t, J = 53.7 Hz, 1H), 3.95 (s, 2H), 2.54 (s, 3H), 1.81-1.62 (m, 4H), 0.95 (s, 9H). |
| 975 | 1H NMR (400 MHz, DMSO-d6) δ 8.41 (s, 1H), 7.91 (t, J = 8.3 Hz, 1H), 7.73 (t, J = 5.5 Hz, 1H), 7.49 (s, 1H), 7.00 (dd, J = 8.5, 3.1 Hz, 1H), 6.47 (s, 2H), 6.06 (t, J = 53.4 Hz, 1H), 3.61 (d, J = 5.5 Hz, 2H), 2.50 (s, 3H), 1.56 (m, 4H), 1.05 (s, 9H). |
| 976 | 1H NMR (400 MHz, Methanol-d4) δ 9.31 (s, 1H), 8.94 (s, 2H), 8.38 (s, 1H), 8.06 (s, 1H), 7.82 (t, J = 8.1 Hz, 1H), 7.46 (d, J = 2.4 Hz, 1H), 7.08 (d, J = 2.4 Hz, 1H), 6.87 (dd, J = 8.5, 2.7 Hz, 1H), 6.29 (s, 1H), 5.93 (t, J = 54.6 Hz, 1H), 4.04 (d, J = 13.9 Hz, 1H), 3.84 (d, J = 13.9 Hz, 1H), 2.51 (s, 3H), 1.53 (s, 4H), 0.95 (s, 9H). |
| 977 | 1H NMR (400 MHz, Methanol-d4) δ 8.51 (d, J = 1.1 Hz, 1H), 7.81 (t, J = 8.1 Hz, 1H), 7.65 (d, J = 2.3 Hz, 1H), 6.86 (dd, J = 8.6, 2.7 Hz, 1H), 6.83 (d, J = 2.3 Hz, 1H), 6.07 (s, 1H), 4.13 (d, J = 13.9 Hz, 1H), 3.70 (d, J = 13.9 Hz, 1H), 2.40 (s, 3H), 1.64 (s, 3H), 1.44-1.31 (m, 2H), 1.22 (t, J = 2.0 Hz, 2H), 0.89 (s, 9H). |
| 978 | 1H NMR (400 MHz, Methanol-d4) δ 8.47 (s, 1H), 8.11 (s, 1H), 7.62 (d, J = 2.3 Hz, 1H), 7.51 (d, J = 8.5 Hz, 1H), 6.96-6.89 (m, 1H), 6.60 (d, J = 8.6 Hz, 1H), 6.19 (s, 1H), 3.98 (d, J = 13.9 Hz, 1H), 3.88 (d, J = 6.4 Hz, 4H), 2.48 (s, 3H), 1.73 (d, J = 5.6 Hz, 2H), 1.66 (s, 2H), 0.94 (s, 9H). |
| 979 | 1H NMR (400 MHz, Methanol-d4) δ 8.55 (d, J = 1.6 Hz, 1H), 8.32 (s, 1H), 7.88 (d, J = 2.6 Hz, 1H), 7.59 (t, J = 8.1 Hz, 1H), 7.40 (d, J = 2.6 Hz, 1H), 6.92 (dd, J = 8.5, 2.8 Hz, 1H), 6.76 (s, 1H), 4.09 (d, J = 14.1 Hz, 1H), 3.96 (d, J = 14.1 Hz, 1H), 2.97 (s, 3H), 2.35 (s, 3H), 1.80-1.70 (m, 4H), 1.02 (d, J = 3.2 Hz, 9H). |
| 980 | 1H NMR (400 MHz, Chloroform-d) δ 8.36 (s, 1H), 7.91 (t, 1H), 7.48 (s, 1H), 7.33 (d, 1H), 6.79 (dd, 1H), 6.40 (s, 1H), 5.94 (s, 1H), 5.20 (s, 1H), 3.56 (t, 2H), 3.33 (s, 3H), 2.59 (s, 3H), 1.79 (d, 6H), 1.77-1.70 (m, 1H), 1.68-1.50 (m, 4H) 0.94 (s, 9H). |
| 981 | 1H NMR (400 MHz, Methanol-d4) δ 8.56 (s, 1H), 8.29 (d, J = 2.4 Hz, 1H), 8.08 (s, 1H), 7.81 (t, J = 8.1 Hz, 1H), 7.18 (d, J = 2.3 Hz, 1H), 6.88 (dd, J = 8.5, 2.7 Hz, 1H), 6.29 (s, 1H), 5.93 (t, J = 54.6 Hz, 1H), 4.05 (d, J = 14.0 Hz, 1H), 3.87 (d, J = 14.0 Hz, 1H), 2.77 (s, 3H), 2.52 (s, 3H), 1.54 (s, 4H), 0.94 (s, 9H). |
| 982 | 1H NMR (400 MHz, Chloroform-d) δ 10.32 (s, 1H), 9.20 (s, 1H), 8.30-8.20 (m, 1H), 8.13 (s, 1H), 7.90 (t, 1H), 7.19 (s, 1H), 6.82-6.65 (m, 2H), 6.24 (s, 1H), 4.17-4.02 (m, 2H), 2.64 (s, 3H), 1.78 (s, 3H), 1.77 (s, 3H), 1.72-1.63 (m, 4H), 1.09 (s, 9H). |
| 983 | 1H NMR (400 MHz, DMSO-d6) δ 8.73 (s, 1H), 8.17 (t, 1H), 8.01 (s, 1H), 7.98-7.93 (m, 1H); 7.06 (dd, 1H), 6.70 (s, 1H), 6.52-6.43 (m, 1H), 6.09 (t, 1H), 3.67 (qd, 2H), 2.43 (s, 3H), 1.52-1.40 (m, 4H), 0.95 (s, 9H). |
| 984 | 1H NMR (400 MHz, Methanol-d4) δ 8.47 (s, 1H), 7.85 (s, 1H), 7.77 (m, 1H), 7.62 (s, 1H), 6.87 (m, 2H), 6.20 (s, 1H), 4.38 (t, J = 7.4 Hz, 2H), 4.01 (d, J = 13.9 Hz, 1H), 3.80 (d, J = 13.7 Hz, 1H), 2.50 (s, 5H), 1.89-1.80 (m, 2H), 1.29 (m, 2H), 0.92 (s, 11H). |
| 985 | 1H NMR (400 MHz, Acetonitrile-d3) δ 8.41 (s, 1H), 7.84 (m, 1H), 7.66 (m, 1H), 7.48 (m, 1H), 6.82 (m, 1H), 6.74 (m, 1H), 6.15 (m, 1H), 4.42 (m, 2H), 3.76 (m, 2H), 3.48 (m, 2H), 2.51 (s, 3H), 1.98 (m, 2H), 0.94 (s, 9H). |

TABLE 2-continued

| Compound | ¹H-NMR |
|---|---|
| 986 | 1H NMR (400 MHz, Acetonitrile-d3) δ 8.42 (s, 1H), 7.92 (m, 1H), 7.48 (s, 1H), 6.79 (m, 1H), 6.70 (s, 1H), 5.97 (s, 1H), 4.35 (m, 4H), 3.90 (m, 1H), 3.68 (m, 1H), 2.50 (s, 3H), 2.23 (m, 2H), 0.94 (s, 9H). |

Biological Assays

The following examples, from Examples 40 to 42, describe biological assays for measuring certain test compounds' activity against TNFα, Cot (also known as Tpl2), and EGFR. As summarized in Table 3, the test compounds are effective inhibitors of Cot.

Example 40: Cot Monocyte TNFα Cell Based Assay

Cryopreserved human monocytes (Stem Cell Technologies) were thawed, diluted in RPMI with Glutamax (10 mM HEPES, 1× Pen-Strep, 55 µM ß-mercaptoethanol, 1 mM Sodium pyruvate) media containing 10% FBS to 0.125× 10^6 cells/ml and recovered at 37° C. for 2 hours. The cell suspension was then plated at a density of 5,000 cells/well onto black 384 well Greiner clear bottom plates. Plates were pre-spotted with test compounds and serially diluted in DMSO where 200 nL/well were delivered using the Echo 550 acoustic liquid dispenser (Labcyte®) for a final DMSO concentration of 0.5%. Plated cells were treated with compound for 1 hour at 37° C. Cells were then stimulated with 50 pg/ml of LPS (Sigma) excluding outside columns of plate used for unstimulated cell control wells. Cells were incubated for an additional 4 hours at 37° C. Cells were then spun out of the media and 5 µl of sample were taken and analyzed for total TNFα content using the TR-FRET Human TNFα detection system (CisBio). This system utilizes two labeled antibodies (cryptate and XL665) that bind to two different epitopes of the TNFα molecule and produce FRET signal proportional to the concentration of TNFα in the sample. Detection antibodies are mixed 50:50 and 5 were dispensed into each well. Plates were covered with clear seals and incubated at room temp overnight. The following morning plates were read using an Envision 2103 Multilabeled reader (PerkinElmer) with excitation/emission/FRET emission at 340 nm/615 nm/665 nm, respectively. Fluorescence intensities at 615 nm and 665 nm emission wavelengths were expressed as a ratio (665 nm/615 nm). Percent of control was calculated as follows:

% Control=100×(Ratio$_{Sample}$−Ratio$_{0\% \ Stimulation}$)/(Ratio$_{100\% \ Stimulation}$−Ratio$_{0\% \ Stimulation}$)

where unstimulated cells (0% stimulation) were the negative control and stimulated cells (100% stimulation) were used as the positive control.

Example 41: High Throughput Cot Biochemical Assay

Human Cot enzyme activity was measured using KinEASE (Cisbio), a time-resolved fluorescence resonance energy transfer (TR-FRET) immunoassay. In this assay, Cot-catalyzes the phosporylation of a XL665-labeled peptide substrate. Europium conjugated phospho-tyrosine specific antibody binds the resulting phosphorylated peptide. Formation of phosphorylated peptide is quantified by TR-FRET with Europium as the donor and XL665 the acceptor in a 2-step endpoint assay. Purified recombinant human Cot catalytic domain (30-397 amino acids) was purchased from Carna Biosciences. In brief, test compounds serially diluted in DMSO were delivered into Proxy white, low volume, 384 well plates using the Echo 550 acoustic liquid dispenser (Labcyte®). Cot enzyme and substrates were dispensed into assay plates using a Multi-Flo (Bio-Tek Instruments). The standard 5 µL reaction mixture contained 400 µM ATP, 1 µM STK3 peptide, 5 nM of Cot in reaction buffer (10 mM MOPS, pH 7.0, 0.02% NaN₃, 0.5 mg/mL BSA, 10 mM MgOAc, 1 mM DTT, 0.025% NP-40, 1.5% glycerol) and 0.1% DMSO. After 2.5 hrs of incubation at room temperature, 5 µL of Stop and Detect Solution (1:200 Europium Cryptate labeled anti-phosphorylated peptide antibody solution and 125 nM strepavidin-XL665 Tracer in a 50 mM Hepes pH 7.0 detection buffer containing sufficient EDTA) was added. The plate was then further incubated for 120 minutes at room temperature and read using an Envision 2103 Multilabeled reader (PerkinElmer) with excitation/emission/FRET emission at 340 nm/615 nm/665 nm, respectively. Fluorescence intensities at 615 nm and 665 nm emission wavelengths were expressed as a ratio (665 nm/615 nm). Percent inhibition was calculated as follows:

% Inhibition=100×(Ratio$_{Sample}$−Ratio$_{0\% \ Inhibition}$)/(Ratio$_{100\% \ Inhibition}$−Ratio$_{0\% \ Inhibition}$)

where 0.1% DMSO (0% inhibition) was the negative control and 100 µM Comparative Example 1 (100% inhibition) was used as the positive control.

Example 42: High Throughput EGFR Biochemical Assay

EGFR activity was measured using KinEASE (Cisbio), a time-resolved fluorescence resonance energy transfer (TR-FRET) immunoassay. In this assay, EGFR-catalyzes the phosphorylation of a universal Tyrosine kinase peptide substrate labeled with XL665. Europium conjugated phosphor-tyrosine specific antibody binds the resulting phosphorylated peptide. Formation of phosphorylated peptide is quantified by TR-FRET with Europium as the donor and XL665 the acceptor. The assay was performed in two main steps. The first step is the kinase reaction step and the second step is the detection step with TR-FRET reagents. In brief, test compounds 1:3 serially diluted in DMSO were delivered into Corning white, low volume, non-binding 384 well plates using the Echo 550 acoustic liquid dispenser (Labcyte®). EGFR enzyme (Human EGFR, cytoplasmic domain [669-1210] from Carna Biosciences Cat. No. 08-115) and substrates TK substrate-biotin (included in Cisbio HTRF KinEASE-TK kit Cat. No. 62TK0PEJ) were dispensed into assay plates using a Multi-Flo (Bio-Tek Instruments). The standard 10 µL reaction mixture contained 6 µM ATP (1×Km) or 12 µM ATP (2×Km), 1 µM biotinylated peptide, 0.3 nM EGFR (for 1×Km ATP) or 0.1 nM EGFR (for 2×Km ATP) in reaction buffer (10 mM MOPs, pH 7.0, 1.5% Glycerol, 0.5 mg/ml BSA, 10 mM Mg-Acetate, 1 mM DTT, 0.025% NP-40). After 60 min of incubation at room temperature, 10 µL of Stop and Detect Solution (1:400 Europium Cryptate labeled anti-phosphorylated peptide antibody solution and 125 nM strepavidin-XL665 Tracer in a 50 mM Hepes pH 7.0 detection buffer containing sufficient EDTA) was added. The plate was then further incubated for over 60 minutes at room temperature and read using an Envision 2103 Multilabeled reader (PerkinElmer) with excitation/emission/FRET emission at 340 nm/615 nm/665 nm, respectively. Fluorescence intensities at 615 nm and 665 nm emission wavelengths were expressed as a ratio (665 nm/615 nm). Percent inhibition was calculated as follows:

% Inhibition=100×(Ratio$_{Sample}$−Ratio$_{0\% \, Inhibition}$)/(Ratio$_{100\% \, Inhibition}$−Ratio$_{0\% \, Inhibition}$)

where 0.05% DMSO (0% inhibition) was the negative control and 100 μM Staurosporine and Gefitinib (100% inhibition) was used as the positive control.

As shown in Table 3, the compounds of Formula I are inhibitors of Cot (cancer Osaka thyroid).

TABLE 3

| Cmpd | IC$_{50}$ HTRF (nM) | EC$_{50}$ TNF (nM) |
| --- | --- | --- |
| 1 | 8 | 218 |
| 2 | 2 | 89 |
| 3 | 8 | 314 |
| 4 | 2 | 497 |
| 5 | 9 | 258 |
| 7 | 380 | >1000 |
| 8 | 7 | 302 |
| 9 | 1 | 20 |
| 10 | 21 | 283 |
| 11 | 4 | 154 |
| 12 | 27 | 214 |
| 13 | 11 | 765 |
| 14 | 7 | 196 |
| 15 | 2 | 545 |
| 16 | 2 | 115 |
| 17 | 53 | 1388 |
| 18 | 28 | 399 |
| 19 | 2 | 156 |
| 20 | 2 | 69 |
| 21 | 14 | 2035 |
| 22 | 2 | 89 |
| 23 | 4 | 69 |
| 24 | 12 | 185 |
| 25 | 2 | 57 |
| 26 | 6 | 113 |
| 27 | 2 | 62 |
| 28 | 12 | 195 |
| 29 | 17 | 498 |
| 30 | 34 | 1322 |
| 31 | 5 | 5069 |
| 32 | 7 | 546 |
| 33 | 11 | 630 |
| 34 | 8 | 112 |
| 35 | 9 | 166 |
| 36 | 3 | 67 |
| 37 | 16 | 2638 |
| 38 | 25 | 952 |
| 39 | 11 | 295 |
| 40 | 6 | 249 |
| 41 | 8 | 137 |
| 42 | 135 | 1926 |
| 43 | 33 | 915 |
| 44 | 9 | 129 |
| 45 | 2 | 178 |
| 46 | 3 | 1102 |
| 47 | 25 | 1068 |
| 48 | 2 | 87 |
| 49 | 118 | 16684 |
| 50 | 70 | 3534 |
| 51 | 55 | 1556 |
| 52 | 4 | 88 |
| 53 | 81 | 4018 |
| 54 | 11 | 652 |
| 55 | 58 | 10816 |
| 56 | 6 | 2521 |
| 57 | 60 | 5990 |
| 58 | 72 | 2982 |
| 59 | 2 | 892 |
| 60 | 12 | 131 |
| 61 | 11 | 238 |
| 62 | 10 | 216 |
| 63 | 5 | 257 |
| 64 | 42 | 2652 |
| 65 | 6 | 538 |
| 66 | 3 | 53 |
| 67 | 1 | 32 |
| 68 | 1 | 51 |
| 69 | 2 | 33 |
| 70 | 19 | 804 |
| 71 | 2 | 36 |
| 72 | 1 | 11 |
| 73 | 2 | 33 |
| 74 | 1 | 14 |
| 75 | 2 | 79 |
| 76 | 1 | 981 |
| 77 | 3 | 154 |
| 78 | 3 | 332 |
| 79 | 1 | 203 |
| 80 | 1 | 23 |
| 81 | 400 | >1000 |
| 82 | 2 | 151 |
| 83 | 942 | 1000 |
| 84 | 1 | 10 |
| 85 | 4 | >1000 |
| 86 | 2 | 37 |
| 87 | 25 | 590 |
| 88 | 1161 | >1000 |
| 89 | 520 | >1000 |
| 90 | 1 | 18 |
| 91 | 2 | 52 |
| 92 | 6 | 65 |
| 93 | 7 | 74 |
| 94 | 2 | 130 |
| 95 | 10 | 445 |
| 96 | 11 | 173 |
| 97 | 20 | 358 |
| 98 | 49 | 821 |
| 99 | 3 | 143 |
| 100 | 3 | 142 |
| 101 | 5 | 348 |
| 102 | 3 | 461 |
| 103 | 3 | 133 |
| 104 | 1 | 99 |
| 105 | 3 | 144 |
| 106 | 2 | 76 |
| 107 | 182 | >10000 |
| 108 | 913 | >10000 |
| 109 | 2 | 54 |
| 110 | 2 | 56 |
| 111 | 2 | 77 |
| 112 | 2 | 61 |
| 113 | 13 | 253 |
| 114 | 10 | 233 |
| 115 | 5 | 119 |
| 116 | 3 | 144 |
| 117 | 3 | 94 |
| 118 | 6 | 150 |
| 119 | 4 | 99 |
| 120 | 5 | 137 |
| 121 | 7 | 171 |
| 122 | 6 | 240 |
| 123 | 6 | 193 |
| 124 | 8 | 376 |
| 125 | 3 | 78 |
| 126 | 3 | 146 |
| 127 | 16 | 194 |
| 128 | 698 | >10000 |
| 129 | 2 | 81 |
| 130 | 6 | 147 |
| 131 | 2 | 49 |
| 132 | 4 | 97 |

TABLE 3-continued

| Cmpd | IC$_{50}$ HTRF (nM) | EC$_{50}$ TNF (nM) |
|---|---|---|
| 133 | 25 | 978 |
| 134 | 6 | 197 |
| 135 | 23 | 660 |
| 136 | 10 | 291 |
| 137 | 15 | 235 |
| 138 | 3 | 141 |
| 139 | 2 | 92 |
| 140 | 3 | 183 |
| 141 | 2 | 121 |
| 142 | 2 | 66 |
| 143 | 16 | 898 |
| 144 | 2 | 77 |
| 145 | 4 | 221 |
| 146 | 10 | 370 |
| 147 | 12 | 1139 |
| 148 | 5 | 174 |
| 149 | 8 | 381 |
| 150 | 4 | 154 |
| 151 | 8 | 1305 |
| 152 | 10 | 904 |
| 153 | 44 | 3759 |
| 154 | 26 | 1667 |
| 155 | 2 | 79 |
| 156 | 8 | 1191 |
| 157 | 5 | 127 |
| 159 | 2 | 95 |
| 160 | 11 | 484 |
| 161 | 12 | 1668 |
| 162 | 7 | 429 |
| 163 | 67 | 4142 |
| 164 | 5 | 1802 |
| 165 | 9 | 2368 |
| 166 | 6 | 1425 |
| 167 | 4 | 506 |
| 168 | 6 | 394 |
| 169 | 14 | 1217 |
| 170 | 6 | 1262 |
| 171 | 10 | 320 |
| 172 | 10 | 832 |
| 173 | 7 | 1112 |
| 174 | 2 | 54 |
| 175 | 3 | 73 |
| 176 | 2 | 31 |
| 177 | 2 | 79 |
| 178 | 7 | 931 |
| 179 | 265 | >10000 |
| 180 | 1 | 104 |
| 181 | 2 | 92 |
| 182 | 13 | 1041 |
| 183 | 357 | >10000 |
| 184 | 8 | 387 |
| 185 | 305 | 9745 |
| 186 | 118 | 6618 |
| 187 | 67 | 2114 |
| 188 | >10000 | >10000 |
| 189 | 8 | 1061 |
| 190 | 9 | 238 |
| 191 | 2 | 104 |
| 192 | 3 | 186 |
| 193 | 2 | 107 |
| 194 | 2 | 111 |
| 195 | 4 | 132 |
| 196 | 6 | 668 |
| 197 | 9 | 599 |
| 198 | 17 | 982 |
| 199 | 9 | 2522 |
| 200 | 7 | 558 |
| 201 | 56 | 5595 |
| 202 | >10000 | >10000 |
| 203 | 6923 | 9089 |
| 204 | 8513 | >10000 |
| 205 | 72 | 2048 |
| 206 | 3 | 211 |
| 207 | 5 | 931 |
| 208 | 12 | 465 |
| 209 | 23 | 941 |
| 210 | 10 | 424 |

TABLE 3-continued

| Cmpd | IC$_{50}$ HTRF (nM) | EC$_{50}$ TNF (nM) |
|---|---|---|
| 211 | 16 | 544 |
| 212 | 44 | 9151 |
| 213 | 3 | 103 |
| 214 | >10000 | >10000 |
| 215 | 258 | >10000 |
| 216 | 38 | 1187 |
| 217 | 12 | 264 |
| 218 | 26 | 2711 |
| 219 | 4449 | >10000 |
| 220 | 4 | 348 |
| 221 | 2 | 28 |
| 222 | 19 | 739 |
| 223 | 7 | 94 |
| 224 | 12 | 2628 |
| 225 | 10 | 1488 |
| 226 | 8 | 880 |
| 227 | 44 | 6419 |
| 228 | 18 | 2307 |
| 229 | 12 | 1467 |
| 230 | 9 | 252 |
| 231 | 8 | 230 |
| 232 | 15 | 346 |
| 233 | 8 | 114 |
| 234 | 21 | 504 |
| 235 | 17 | 370 |
| 236 | 9 | 172 |
| 237 | 1 | 29 |
| 238 | 3 | 901 |
| 239 | 16 | 928 |
| 240 | 16 | 631 |
| 241 | 2 | 32 |
| 242 | 143 | 5801 |
| 243 | 41 | 9492 |
| 244 | 4 | 328 |
| 245 | 2 | 125 |
| 246 | 6 | 652 |
| 247 | 2 | 102 |
| 248 | 4 | 398 |
| 249 | 12 | 332 |
| 250 | 5 | 127 |
| 251 | 5 | 347 |
| 252 | 6 | 119 |
| 253 | 4 | 66 |
| 254 | 3 | 230 |
| 255 | 10 | 766 |
| 256 | 16 | 341 |
| 257 | 6 | 212 |
| 258 | 2 | 33 |
| 259 | 6 | 158 |
| 260 | 6 | 126 |
| 261 | 14 | 344 |
| 262 | 11 | 130 |
| 263 | 13 | 242 |
| 264 | 2 | 70 |
| 265 | 14 | 426 |
| 266 | 37 | 28752 |
| 267 | 30 | 5120 |
| 268 | 12 | 234 |
| 269 | 6 | 326 |
| 270 | 4 | 666 |
| 271 | 9 | 826 |
| 272 | 5 | 297 |
| 273 | 51 | 1564 |
| 274 | 12 | 370 |
| 275 | 7 | 2334 |
| 276 | 6 | 789 |
| 277 | 7 | 923 |
| 278 | 3 | 269 |
| 279 | 3 | 457 |
| 280 | 16 | 811 |
| 281 | 13 | 575 |
| 282 | 3 | 87 |
| 283 | 3 | 50 |
| 284 | 14 | 1305 |
| 285 | 8 | 219 |
| 286 | 4 | 121 |
| 287 | 20 | 373 |

TABLE 3-continued

| Cmpd | IC$_{50}$ HTRF (nM) | EC$_{50}$ TNF (nM) |
|---|---|---|
| 288 | 26 | 1058 |
| 289 | 37 | 837 |
| 290 | 12 | 185 |
| 291 | 35 | 478 |
| 292 | 17 | 327 |
| 294 | 9 | 166 |
| 295 | 23 | 565 |
| 296 | 80 | 1104 |
| 297 | 9 | 200 |
| 298 | 39 | 1503 |
| 299 | 18 | 739 |
| 300 | 7 | 165 |
| 301 | 14 | 414 |
| 302 | 10 | 472 |
| 303 | 14 | 868 |
| 304 | 6 | 234 |
| 305 | 3 | 84 |
| 306 | 6 | 202 |
| 307 | 4 | 60 |
| 308 | 4 | 286 |
| 309 | 8 | 181 |
| 310 | 40 | 2342 |
| 312 | 13 | 1235 |
| 313 | 5 | 373 |
| 314 | 15 | 302 |
| 315 | 4 | 132 |
| 316 | 6 | 298 |
| 317 | 16 | 251 |
| 318 | 8 | 271 |
| 319 | 5 | 165 |
| 321 | 10 | 212 |
| 322 | 33 | 369 |
| 323 | 86 | 666 |
| 325 | 20 | 650 |
| 326 | 34 | 3753 |
| 328 | 4 | 272 |
| 331 | 3 | 173 |
| 334 | 4 | 82 |
| 335 | 10 | 405 |
| 339 | 13 | 1010 |
| 340 | 8 | 328 |
| 341 | 6 | 843 |
| 342 | 38 | 6094 |
| 344 | 3 | 151 |
| 345 | 3 | 73 |
| 346 | 3 | 208 |
| 347 | 4 | 278 |
| 348 | 13 | 444 |
| 349 | 41 | 718 |
| 350 | 26 | 4511 |
| 351 | 10 | 744 |
| 352 | 12 | 565 |
| 353 | 4 | 184 |
| 354 | 3 | 983 |
| 355 | 5 | 194 |
| 357 | 5 | 235 |
| 358 | 3 | 130 |
| 359 | 3 | 729 |
| 360 | 4 | 151 |
| 361 | 13 | 746 |
| 362 | 1 | 46 |
| 363 | 4 | 257 |
| 364 | 7 | 241 |
| 366 | 5 | 336 |
| 367 | 13 | 338 |
| 368 | 649 | 6296 |
| 369 | 3 | 89 |
| 370 | 8 | 232 |
| 371 | 2 | 173 |
| 372 | 2 | 81 |
| 373 | 3 | 81 |
| 374 | 37 | 480 |
| 375 | 4 | 1511 |
| 376 | 182 | >1000 |
| 377 | 398 | >1000 |
| 378 | 2 | 168 |
| 379 | 6 | 179 |
| 380 | 14 | 609 |
| 381 | 7 | 303 |
| 382 | 14 | 768 |
| 389 | 11 | 328 |
| 395 | 4 | |
| 403 | 9 | 290 |
| 405 | 2 | 1044 |
| 406 | 3 | 102 |
| 6 | 2 | |
| 293 | 32 | |
| 311 | 30 | |
| 320 | 60 | |
| 324 | 10 | |
| 327 | 15 | |
| 329 | 14 | |
| 330 | 59 | |
| 332 | 65 | |
| 333 | 3 | |
| 336 | 2 | |
| 337 | 16 | |
| 338 | 13 | |
| 343 | 504 | |
| 356 | 2 | |
| 365 | 38 | |
| 384 | 153 | |
| 385 | 14 | |
| 386 | 36 | |
| 387 | 18 | |
| 388 | 10 | |
| 390 | 343 | |
| 391 | 282 | |
| 392 | 3 | |
| 393 | 5 | |
| 394 | 147 | |
| 396 | 43 | |
| 397 | 46 | |
| 398 | 435 | |
| 399 | 58 | |
| 400 | 119 | |
| 401 | 10 | |
| 402 | 19 | |
| 404 | 232 | |
| 408 | 1 | 88 |
| 409 | 1 | 559 |
| 410 | 113 | 1000 |
| 411 | 5 | 76 |
| 412 | 7 | 157 |
| 413 | 4 | 44 |
| 414 | 1 | 35 |
| 415 | 3 | 67 |
| 416 | 2 | 124 |
| 417 | 9 | 218 |
| 418 | 2 | 45 |
| 419 | 3 | 49 |
| 420 | 2 | 25 |
| 421 | 4 | 100 |
| 422 | 2 | 57 |
| 423 | 3 | 71 |
| 424 | 2 | 37 |
| 425 | 7 | 1000 |
| 426 | 2 | 95 |
| 427 | 2 | 41 |
| 428 | 1 | 69 |
| 429 | 2 | 56 |
| 430 | 5 | 214 |
| 431 | 1 | 21 |
| 432 | 6 | 89 |
| 433 | 1 | 65 |
| 434 | 2 | 61 |
| 435 | 1 | 24 |
| 436 | 5 | 289 |
| 437 | 2 | 82 |
| 438 | 473 | 1000 |
| 439 | 13 | 299 |
| 440 | 7 | 171 |
| 441 | 2 | 26 |
| 442 | 56 | 2686 |

TABLE 3-continued

| Cmpd | IC$_{50}$ HTRF (nM) | EC$_{50}$ TNF (nM) |
|---|---|---|
| 443 | 1 | 19 |
| 444 | 2 | 33 |
| 445 | 2 | 71 |
| 446 | 3 | 156 |
| 447 | 2 | 40 |
| 448 | 2 | 44 |
| 449 | 19 | 407 |
| 450 | 20 | 356 |
| 451 | 3 | 138 |
| 452 | 4 | 73 |
| 453 | 9 | 184 |
| 454 | 2 | 32 |
| 455 | 29 | 222 |
| 456 | 51 | 1000 |
| 457 | 315 | 1000 |
| 458 | 4 | 87 |
| 459 | 3 | 50 |
| 460 | 5 | 156 |
| 461 | 17 | 154 |
| 462 | 162 | 8766 |
| 463 | 2 | 63 |
| 464 | 1 | 16 |
| 465 | 2 | 155 |
| 466 | 28 | 926 |
| 467 | 2 | 47 |
| 468 | 1 | 18 |
| 469 | 4 | 69 |
| 470 | 2 | 46 |
| 471 | 3 | 45 |
| 472 | 4 | 78 |
| 473 | 2 | 26 |
| 474 | 2 | 26 |
| 475 | 20 | 258 |
| 476 | 3 | 71 |
| 477 | 2 | 185 |
| 478 | 1 | 77 |
| 479 | 5 | 78 |
| 480 | 2 | 60 |
| 481 | 6 | 391 |
| 482 | 3 | 86 |
| 483 | 7 | 108 |
| 484 | 3 | 73 |
| 485 | 3 | 29 |
| 486 | 3 | 991 |
| 487 | 1 | 245 |
| 488 | 3 | 79 |
| 489 | 2 | 129 |
| 490 | 1 | 1000 |
| 491 | 3 | 40 |
| 492 | 2 | 21 |
| 493 | 31 | 1000 |
| 494 | 1 | 444 |
| 495 | 3 | 50 |
| 496 | 6 | 467 |
| 497 | 6 | 379 |
| 498 | 19 | 689 |
| 499 | 3 | 97 |
| 500 | 8 | 321 |
| 501 | 3 | 55 |
| 502 | 6 | 206 |
| 503 | 2 | 45 |
| 504 | 1 | 38 |
| 505 | 5 | 277 |
| 506 | 8 | 528 |
| 507 | 2 | 87 |
| 508 | 4 | 96 |
| 509 | 267 | 1000 |
| 510 | 5 | 222 |
| 511 | 6 | 133 |
| 512 | 10 | 418 |
| 513 | 9 | 154 |
| 514 | 4 | 77 |
| 515 | 199 | 1000 |
| 516 | 2 | 34 |
| 517 | 3 | 1000 |
| 518 | 7 | 207 |
| 519 | 3 | 158 |
| 520 | 123 | 926 |
| 521 | 27 | 256 |
| 522 | 5 | 52 |
| 523 | 2 | 63 |
| 524 | 12 | 77 |
| 525 | 4 | 164 |
| 526 | 5 | 73 |
| 527 | 3 | 78 |
| 528 | 3 | 60 |
| 529 | 2 | 50 |
| 530 | 3 | 70 |
| 531 | 3 | 70 |
| 532 | 3 | 78 |
| 533 | 3 | 96 |
| 534 | 20 | 394 |
| 535 | 2 | 47 |
| 536 | 3 | 51 |
| 537 | 2 | 75 |
| 538 | 5 | 109 |
| 539 | 1 | 12 |
| 540 | 50 | 760 |
| 541 | 6 | 180 |
| 542 | 2 | 40 |
| 543 | 13 | 422 |
| 544 | 8 | 210 |
| 545 | 4 | 108 |
| 546 | 2 | 42 |
| 547 | 2 | 33 |
| 548 | 8 | 124 |
| 549 | 4 | 68 |
| 550 | 2 | 29 |
| 551 | 2 | 27 |
| 552 | 2 | 26 |
| 553 | 3 | 64 |
| 554 | 5 | 151 |
| 555 | 7 | 208 |
| 556 | 8 | 120 |
| 557 | 5 | 117 |
| 558 | 3 | 72 |
| 559 | 2 | 42 |
| 560 | 11 | 287 |
| 561 | 2 | 433 |
| 562 | 2 | 231 |
| 563 | 2 | 63 |
| 564 | 3 | 69 |
| 565 | 2 | 306 |
| 566 | 2 | 190 |
| 567 | 2 | 66 |
| 568 | 5 | 170 |
| 569 | 7 | 171 |
| 570 | 184 | 1000 |
| 571 | 2 | 77 |
| 572 | 4 | 79 |
| 573 | 66 | 751 |
| 574 | 4 | 86 |
| 575 | 1 | 974 |
| 576 | 1 | 433 |
| 577 | 1 | 49 |
| 578 | 2 | 32 |
| 579 | 2 | 24 |
| 580 | 2 | 84 |
| 581 | 2 | 32 |
| 582 | 14 | 184 |
| 583 | 4 | 121 |
| 584 | 2 | 53 |
| 585 | 37 | 838 |
| 586 | 2 | 1000 |
| 587 | 1 | 489 |
| 588 | 55 | 629 |
| 589 | 2 | 34 |
| 590 | 3 | 57 |
| 591 | 5 | 106 |
| 592 | 5 | 78 |
| 593 | 8 | 298 |
| 594 | 2 | 33 |
| 595 | 209 | 1000 |
| 596 | 79 | 826 |

TABLE 3-continued

| Cmpd | IC$_{50}$ HTRF (nM) | EC$_{50}$ TNF (nM) |
|---|---|---|
| 597 | 3 | 150 |
| 598 | 5 | 198 |
| 599 | 13 | 316 |
| 600 | 5 | 113 |
| 601 | 4 | 32 |
| 602 | 3 | 69 |
| 603 | 7 | 107 |
| 604 | 3 | 71 |
| 605 | 3 | 30 |
| 606 | 2 | 27 |
| 607 | 21 | 225 |
| 608 | 42 | 314 |
| 609 | 2 | 46 |
| 610 | 2 | 199 |
| 611 | 20 | 229 |
| 612 | 11 | 171 |
| 613 | 13 | 144 |
| 614 | 9 | 154 |
| 615 | 33 | 588 |
| 616 | 12 | 104 |
| 617 | 9 | 77 |
| 618 | 3 | 37 |
| 619 | 7 | 189 |
| 620 | 102 | 1000 |
| 621 | 1 | 12 |
| 622 | 1 | 24 |
| 623 | 1 | 27 |
| 624 | 11 | 1000 |
| 625 | 2 | 26 |
| 626 | 5 | 35 |
| 627 | 4 | 46 |
| 628 | 450 | 1000 |
| 629 | 181 | 1000 |
| 630 | 68 | 1000 |
| 631 | 2 | 32 |
| 632 | 380 | 1000 |
| 633 | 28 | 267 |
| 634 | 2 | 43 |
| 635 | 3 | 60 |
| 636 | 69 | 720 |
| 637 | 3 | 85 |
| 638 | 58 | 858 |
| 639 | 58 | 806 |
| 640 | 3 | 65 |
| 641 | 55 | 811 |
| 642 | 5 | 182 |
| 643 | 5 | 1000 |
| 644 | 7 | 88 |
| 645 | 11 | 66 |
| 646 | 3 | 40 |
| 647 | 3 | 133 |
| 648 | 3 | 114 |
| 649 | 2 | 14 |
| 650 | 179 | 1000 |
| 651 | 14 | 135 |
| 652 | 4 | 40 |
| 653 | 4 | 37 |
| 654 | 3 | 36 |
| 655 | 12 | 104 |
| 656 | 4 | 86 |
| 657 | 37 | 806 |
| 658 | 29 | 374 |
| 659 | 41 | 279 |
| 660 | 43 | 839 |
| 661 | 2 | 103 |
| 662 | 6 | 335 |
| 663 | 3 | 62 |
| 664 | 12 | 154 |
| 665 | 6 | 198 |
| 666 | 13 | 246 |
| 667 | 10 | 71 |
| 668 | 13 | 408 |
| 669 | 1 | 7 |
| 670 | 5 | 102 |
| 671 | 2 | 32 |
| 672 | 2 | 22 |
| 673 | 142 | 808 |
| 674 | 22 | 301 |
| 675 | 1 | 7 |
| 676 | 6 | 112 |
| 677 | 4 | 133 |
| 678 | 5 | 131 |
| 679 | 13 | 710 |
| 680 | 3 | 98 |
| 681 | 2 | 26 |
| 682 | 7 | 66 |
| 683 | 35 | 283 |
| 684 | 14 | 101 |
| 685 | 4 | 39 |
| 686 | 4 | 77 |
| 687 | 15 | 178 |
| 688 | 30 | 437 |
| 689 | 9 | 81 |
| 690 | 21 | 250 |
| 691 | 6 | 66 |
| 692 | 3 | 38 |
| 693 | 15 | 141 |
| 694 | 7 | 84 |
| 695 | 3 | 39 |
| 696 | 2 | 14 |
| 697 | 1 | 11 |
| 698 | 27 | 684 |
| 699 | 12 | 386 |
| 700 | 2 | 179 |
| 701 | 10 | 147 |
| 702 | 4 | 188 |
| 703 | 2 | 22 |
| 704 | 1 | 23 |
| 705 | 6 | 61 |
| 706 | 2 | 14 |
| 707 | 16 | 230 |
| 708 | 6 | 176 |
| 709 | 17 | 187 |
| 710 | 5 | 148 |
| 711 | 2 | 32 |
| 713 | 2 | 21 |
| 714 | 6 | 57 |
| 715 | 3 | 91 |
| 716 | 2 | 54 |
| 717 | 8 | 100 |
| 718 | 9 | 112 |
| 719 | 2 | 24 |
| 720 | 2 | 35 |
| 721 | 6 | 109 |
| 722 | 43 | 403 |
| 723 | 4 | 84 |
| 724 | 3 | 44 |
| 725 | 3 | 56 |
| 726 | 4 | 127 |
| 727 | 3 | 48 |
| 728 | 7 | 154 |
| 729 | 5 | 108 |
| 730 | 10 | 89 |
| 731 | 11 | 179 |
| 732 | 11 | 779 |
| 733 | 42 | 835 |
| 734 | 41 | 313 |
| 735 | 47 | 478 |
| 736 | 117 | 645 |
| 737 | 3 | 91 |
| 738 | 2 | 40 |
| 739 | 21 | 254 |
| 740 | 45 | 311 |
| 741 | 6 | 120 |
| 742 | 17 | 199 |
| 743 | 5 | 116 |
| 744 | 3 | 33 |
| 745 | 2 | 28 |
| 746 | 13 | 178 |
| 747 | 4 | 36 |
| 748 | 5 | 47 |
| 749 | 6 | 66 |
| 750 | 11 | 194 |
| 751 | 15 | 230 |

TABLE 3-continued

| Cmpd | IC$_{50}$ HTRF (nM) | EC$_{50}$ TNF (nM) |
|---|---|---|
| 752 | 5 | 57 |
| 753 | 5 | 59 |
| 754 | 3 | 31 |
| 755 | 25 | 365 |
| 756 | 3 | 26 |
| 757 | 5 | 60 |
| 758 | 4 | 50 |
| 759 | 2 | 42 |
| 760 | 2 | 58 |
| 761 | 6 | 69 |
| 762 | 3 | 50 |
| 763 | 3 | 40 |
| 764 | 4 | 46 |
| 765 | 4 | 131 |
| 766 | 2 | 30 |
| 767 | 18 | 209 |
| 768 | 6 | 86 |
| 769 | 2 | 28 |
| 770 | 4 | 108 |
| 771 | 4 | 293 |
| 772 | 2 | 33 |
| 773 | 2 | 35 |
| 774 | 2 | 40 |
| 775 | 3 | 27 |
| 776 | 2 | 24 |
| 777 | 5 | 46 |
| 778 | 4 | 30 |
| 779 | 3 | 26 |
| 780 | 5 | 52 |
| 781 | 2 | 22 |
| 782 | 23 | 177 |
| 783 | 2 | 23 |
| 784 | 3 | 51 |
| 785 | 2 | 23 |
| 786 | 5 | 47 |
| 787 | 2 | 65 |
| 788 | 23 | 208 |
| 789 | 13 | 156 |
| 790 | 5 | 82 |
| 791 | 22 | 242 |
| 792 | 89 | 843 |
| 793 | 35 | 782 |
| 794 | 15 | 130 |
| 795 | 34 | 530 |
| 796 | 2 | 31 |
| 797 | 3 | 77 |
| 798 | 7 | 90 |
| 799 | 4 | 46 |
| 800 | 2 | 25 |
| 801 | 3 | 31 |
| 802 | 4 | 36 |
| 803 | 7 | 97 |
| 804 | 9 | 137 |
| 805 | 28 | 778 |
| 806 | 3 | 28 |
| 807 | 3 | 31 |
| 808 | 3 | 29 |
| 809 | 3 | 32 |
| 810 | 4 | 54 |
| 811 | 11 | 333 |
| 812 | 5 | 68 |
| 813 | 2 | 24 |
| 814 | 2 | 16 |
| 815 | 3 | 39 |
| 816 | 1 | 23 |
| 817 | 10 | 116 |
| 818 | 6 | 176 |
| 819 | 2 | 28 |
| 820 | 3 | 33 |
| 821 | 3 | 60 |
| 822 | 10 | 687 |
| 823 | 4 | 53 |
| 824 | 5 | 59 |
| 825 | 7 | 113 |
| 826 | 51 | 1000 |
| 827 | 2 | 38 |
| 828 | 22 | 253 |
| 829 | 4 | 66 |
| 830 | 16 | 384 |
| 831 | 8 | 202 |
| 832 | 2 | 44 |
| 833 | 2 | 22 |
| 834 | 5 | 68 |
| 835 | 4 | 53 |
| 836 | 4 | 52 |
| 837 | 7 | 121 |
| 838 | 3 | 84 |
| 839 | 6 | 94 |
| 840 | 4 | 52 |
| 841 | 2 | 41 |
| 842 | 3 | 563 |
| 843 | 4 | 104 |
| 844 | 13 | 417 |
| 845 | 20 | 1000 |
| 846 | 2 | 17 |
| 847 | 31 | 296 |
| 848 | 31 | 247 |
| 849 | 16 | 261 |
| 850 | 6 | 65 |
| 851 | 3 | 21 |
| 852 | 2 | 58 |
| 853 | 1 | 98 |
| 854 | 4 | 17 |
| 855 | 2 | 53 |
| 856 | 1 | 29 |
| 857 | 4 | 180 |
| 858 | 7 | 44 |
| 859 | 2 | 53 |
| 860 | 3 | 31 |
| 861 | 7 | 40 |
| 862 | 8 | 49 |
| 863 | 2 | 35 |
| 864 | 2 | 37 |
| 865 | 4 | 23 |
| 866 | 2 | 18 |
| 867 | 3 | 27 |
| 868 | 2 | 70 |
| 869 | 2 | 37 |
| 870 | 2 | 169 |
| 871 | 1 | 32 |
| 872 | 1 | 15 |
| 873 | 5 | 97 |
| 874 | 3 | 73 |
| 875 | 2 | 166 |
| 876 | 2 | 385 |
| 877 | 2 | 34 |
| 878 | 2 | 31 |
| 879 | 1 | 13 |
| 880 | 3 | 80 |
| 881 | 2 | 13 |
| 882 | 2 | 18 |
| 883 | 1 | 13 |
| 884 | 1 | 19 |
| 885 | 10 | 132 |
| 886 | 3 | 30 |
| 887 | 3 | 33 |
| 888 | 2 | 165 |
| 889 | 9 | 104 |
| 890 | 6 | 68 |
| 891 | 1 | 12 |
| 892 | 2 | 44 |
| 893 | 4 | 99 |
| 894 | 3 | 54 |
| 895 | 3 | 41 |
| 896 | 3 | 30 |
| 897 | 2 | 18 |
| 898 | 5 | 56 |
| 899 | 2 | 29 |
| 900 | 3 | 30 |
| 901 | 484 | 1000 |
| 902 | 3 | 36 |
| 903 | 3 | 36 |
| 904 | 5 | 78 |
| 905 | 15 | 212 |

TABLE 3-continued

| Cmpd | IC$_{50}$ HTRF (nM) | EC$_{50}$ TNF (nM) |
|---|---|---|
| 906 | 4 | 39 |
| 907 | 4 | 51 |
| 908 | 12 | 238 |
| 909 | 8 | 116 |
| 910 | 5 | 148 |
| 911 | 7 | 85 |
| 912 | 6 | 78 |
| 913 | 6 | 86 |
| 914 | 9 | 116 |
| 915 | 44 | 324 |
| 916 | 13 | 269 |
| 917 | 3 | 31 |
| 918 | 3 | 42 |
| 919 | 2 | 49 |
| 920 | 3 | 28 |
| 921 | 17 | 187 |
| 922 | 11 | 225 |
| 923 | 16 | 258 |
| 926 | 13 | 174 |
| 927 | 6 | 124 |
| 928 | 6 | 99 |
| 929 | 11 | 157 |
| 930 | 33 | 504 |
| 931 | 10 | 134 |
| 932 | 14 | 205 |
| 933 | 29 | 247 |
| 934 | 7 | 81 |
| 935 | 24 | 424 |
| 936 | 18 | 287 |
| 937 | 23 | 277 |
| 938 | 26 | 223 |
| 939 | 18 | 104 |
| 940 | 7 | 86 |
| 941 | 64 | 804 |
| 945 | 17 | 142 |
| 946 | 5 | 153 |
| 947 | 3 | 39 |
| 948 | 5 | 99 |
| 949 | 4 | 34 |
| 950 | 17 | 260 |
| 951 | 9 | 61 |
| 952 | 4 | 36 |
| 953 | 36 | 353 |
| 954 | 7 | 16 |
| 955 | 6 | 50 |
| 956 | 7 | 44 |
| 957 | 5 | 54 |
| 958 | 2 | 56 |
| 959 | 3 | 41 |
| 960 | 7 | 55 |
| 961 | 3 | 48 |
| 962 | 13 | 135 |
| 963 | 4 | 51 |
| 964 | 3 | 105 |
| 965 | 4 | 78 |
| 966 | 15 | 191 |
| 967 | 2 | 94 |
| 968 | 2 | 94 |
| 969 | 8 | 258 |
| 970 | 34 | 722 |
| 971 | 11 | 301 |
| 972 | 1817 | 1000 |
| 973 | 3 | 34 |
| 974 | 11 | 60 |
| 975 | 1231 | 1000 |
| 976 | 21 | 276 |
| 978 | 9 | 303 |
| 979 | 244 | 1000 |
| 980 | 1000 | 1000 |
| 981 | 4 | 20 |
| 982 | 1000 | 1000 |
| 983 | 9644 | 1000 |
| 984 | 10 | 169 |
| 985 | 13 | 126 |
| 986 | 5 | 141 |

The data in Table 4 and Table 5 shows that the compounds disclosed herein are effective inhibitors of cancer Osaka thyroid (Cot). In addition, the claimed compounds are not significant EGFR ligands.

TABLE 4

| Compound | Compound Structure | IC$_{50}$/EC$_{50}$ [nM] | EGFR (IC$_{50}$) [nM] |
|---|---|---|---|
| Comparative Example 1 | 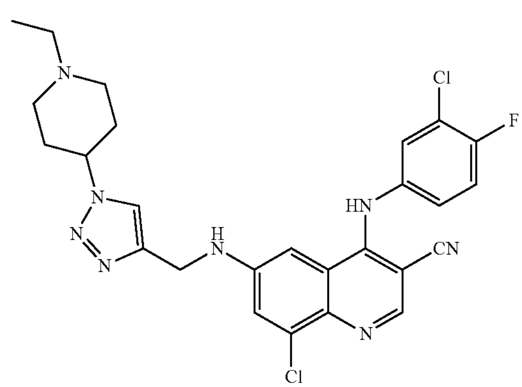 [SMILES: CCN1CCC(n2cc(CNc3cc(Cl)c4ncc(C#N)c(Nc5ccc(F)c(Cl)c5)c4c3)nn2)CC1] | 4/310 | 357 |

TABLE 4-continued

| Compound | Compound Structure | IC$_{50}$/EC$_{50}$ [nM] | EGFR (IC$_{50}$) [nM] |
|---|---|---|---|
| Comparative Example 2 | 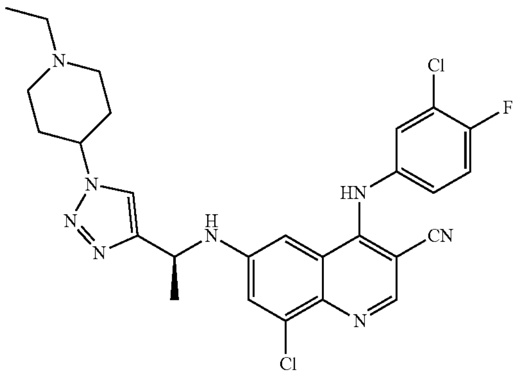 [SMILES: CCN1CCC(n2cc([C@H](C)Nc3cc(Cl)c4ncc(C#N)c(Nc5ccc(F)c(Cl)c5)c4c3)nn2)CC1] | 62/NA | NA |
| 362 | 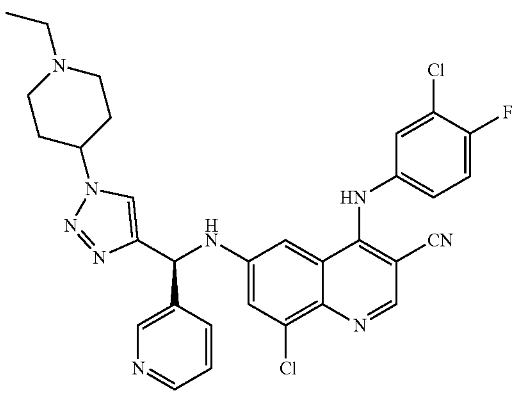 [SMILES: CCN1CCC(n2cc([C@@H](Nc3cc(Cl)c4ncc(C#N)c(Nc5ccc(F)c(Cl)c5)c4c3)c3cccnc3)nn2)CC1] | 1/46 | 3984 |

TABLE 5

| Compound | Compound Structure | IC$_{50}$/EC50 [nM] | EGFR (IC$_{50}$) [nM] |
|---|---|---|---|
| Comparative Example 3 | 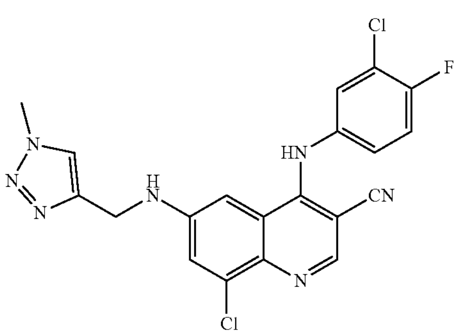 [SMILES: Cn1cc(CNc2cc(Cl)c3ncc(C#N)c(Nc4ccc(F)c(Cl)c4)c3c2)nn1] | 67/>10000 | >10000 |

TABLE 5-continued

| Compound | Compound Structure | IC$_{50}$/EC50 [nM] | EGFR (IC$_{50}$) [nM] |
|---|---|---|---|
| Comparative Example 4 | 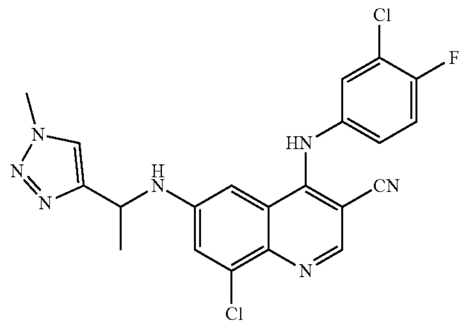 [SMILES: CC(Nc1cc(Cl)c2ncc(C#N)c(Nc3ccc(F)c(Cl)c3)c2c1)c1cn(C)nn1] | >10000/Na | >10000 |
| 395 | 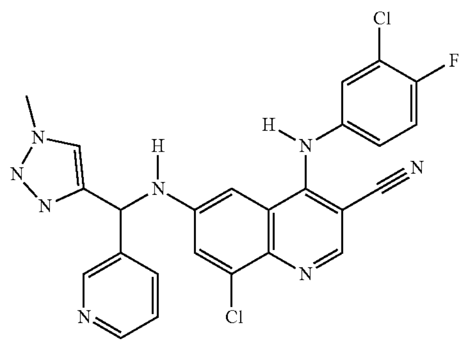 [SMILES: CN1C=C(C(Nc2cc(Cl)c3ncc(C#N)c(Nc4ccc(F)c(Cl)c4)c3c2)c2cccnc2)NN1] | 4/NA | NA |
| 406 | 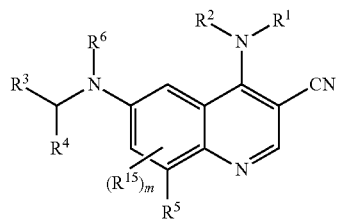 | 3/102 | >10000 |

The invention claimed is:

1. A method of treating an inflammatory disease in a subject in need thereof, comprising administering to the subject an effective amount of a compound of Formula I:

I wherein $R^1$ is hydrogen, —O—$R^7$, —N($R^8$)($R^9$), —C(O)—$R^7$, —S(O)$_2$—$R^7$, —C$_{1-9}$ alkyl, C$_{2-6}$ alkenyl, C$_{2-6}$ alkynyl, C$_{3-15}$ cycloalkyl, heterocyclyl, aryl, or heteroaryl;

wherein each C$_{1-9}$ alkyl, C$_{2-6}$ alkenyl, C$_{2-6}$ alkynyl, C$_{3-15}$ cycloalkyl, heterocyclyl, aryl, and heteroaryl may be optionally substituted with one to four $Z^1$;

$R^2$ is hydrogen, —C(O)—$R^7$, —C(O)O—$R^7$, —C(O)N($R^7$)$_2$, C$_{1-9}$ alkyl, C$_{2-6}$ alkenyl, C$_{2-6}$ alkynyl, C$_{1-6}$ haloalkyl, C$_{3-15}$ cycloalkyl, aryl, heterocyclyl, or heteroaryl;

wherein each C$_{1-9}$ alkyl, C$_{2-6}$ alkenyl, C$_{2-6}$ alkynyl, C$_{1-6}$ haloalkyl, C$_{3-15}$ cycloalkyl, aryl, heterocyclyl, and heteroaryl may be optionally substituted with one to four $Z^2$;

or $R^1$ and $R^2$ together with the nitrogen to which they are attached to form a heterocyclyl or heteroaryl, wherein each heterocyclyl or heteroaryl is optionally substituted with one to four $Z^2$;

$R^3$ is heterocyclyl or heteroaryl, wherein each heterocyclyl or heteroaryl is optionally substituted with one to four $Z^3$;

$R^4$ is heterocyclyl or heteroaryl, wherein each heterocyclyl or heteroaryl is optionally substituted with one to four $Z^4$;

$R^5$ is hydrogen, halo, —CN, —NO$_2$, —O—R$^7$, —N(R$^8$)(R$^9$), —S(O)—R$^7$, —S(O)$_2$R$^7$, —S(O)$_2$N(R$^7$)$_2$, —C(O)R$^7$, —OC(O)—R$^7$, —C(O)O—R$^7$, —OC(O)O—R$^7$, —OC(O)N(R$^{10}$)(R$^{11}$), —C(O)N(R$^7$)$_2$, —N(R$^7$)C(O)(R$^7$), C$_{1-9}$ alkyl, C$_{2-6}$ alkenyl, C$_{2-6}$ alkynyl, C$_{1-9}$ alkylthio, C$_{1-6}$ haloalkyl, C$_{3-15}$ cycloalkyl, aryl, heterocyclyl, or heteroaryl;
  wherein each C$_{1-9}$ alkyl, C$_{2-6}$ alkenyl, C$_{2-6}$ alkynyl, C$_{1-9}$ alkylthio, C$_{1-6}$ haloalkyl, C$_{3-15}$ cycloalkyl, aryl, heterocyclyl, and heteroaryl may be optionally substituted with one to four Z$^5$;

$R^6$ is hydrogen, —C(O)—R$^7$, —C(O)O—R$^7$, —C(O)N(R$^7$)$_2$, C$_{1-9}$ alkyl, C$_{2-6}$ alkenyl, C$_{2-6}$ alkynyl, C$_{1-6}$ haloalkyl, C$_{3-15}$ cycloalkyl, aryl, heterocyclyl, or heteroaryl;
  wherein each C$_{1-9}$ alkyl, C$_{2-6}$ alkenyl, C$_{2-6}$ alkynyl, C$_{1-6}$ haloalkyl, C$_{3-15}$ cycloalkyl, aryl, heterocyclyl, and heteroaryl may be optionally substituted with one to four Z$^6$;

each $R^7$ is independently hydrogen, C$_{1-9}$ alkyl, C$_{2-6}$ alkenyl, C$_{2-6}$ alkynyl, C$_{1-6}$ haloalkyl, C$_{3-15}$ cycloalkyl, aryl, heterocyclyl, or heteroaryl;
  wherein each C$_{1-9}$ alkyl, C$_{2-6}$ alkenyl, C$_{2-6}$ alkynyl, C$_{1-6}$ haloalkyl, C$_{3-15}$ cycloalkyl, aryl, heterocyclyl, and heteroaryl may be optionally substituted with one to four Z$^7$;

$R^8$ and $R^9$ at each occurrence are independently hydrogen, —S(O)$_2$R$^{10}$, —C(O)—R$^{10}$, —C(O)O—R$^{10}$, —C(O)N(R$^{10}$)(R$^{11}$), C$_{1-9}$ alkyl, C$_{2-6}$ alkenyl, C$_{2-6}$ alkynyl, C$_{1-6}$ haloalkyl, C$_{3-15}$ cycloalkyl, aryl, heterocyclyl, or heteroaryl;
  wherein each C$_{1-9}$ alkyl, C$_{2-6}$ alkenyl, C$_{2-6}$ alkynyl, C$_{1-6}$ haloalkyl, C$_{3-15}$ cycloalkyl, aryl, heterocyclyl, or heteroaryl may be optionally substituted with one to four Z$^8$;

$R^{10}$ and $R^{11}$ at each occurrence are independently hydrogen, C$_{1-9}$ alkyl, C$_{2-6}$ alkenyl, C$_{2-6}$ alkynyl, C$_{1-6}$ haloalkyl, C$_{3-15}$ cycloalkyl, aryl, heterocyclyl, or heteroaryl;
  wherein each C$_{1-9}$ alkyl, C$_{2-6}$ alkenyl, C$_{2-6}$ alkynyl, C$_{1-6}$ haloalkyl, C$_{3-15}$ cycloalkyl, aryl, heterocyclyl, and heteroaryl optionally is substituted with one to four Z$^{1b}$;

each $Z^1$, $Z^2$, $Z^3$, $Z^4$, $Z^5$, $Z^6$, $Z^7$, and $Z^8$ is independently hydrogen, oxo, halo, —NO$_2$, —N$_3$, —CN, thioxo, C$_{1-9}$ alkyl, C$_{2-6}$ alkenyl, C$_{2-6}$ alkynyl, C$_{3-15}$ cycloalkyl, C$_{1-8}$ haloalkyl, aryl, heteroaryl, heterocyclyl, —O—R$^{12}$, —C(O)—R$^{12}$, —C(O)O—R$^{12}$, —C(O)—N(R$^{13}$)(R$^{14}$), —N(R$^{13}$)(R$^{14}$), —N(R$^{13}$)$_2$(R$^{14}$)$^+$, —N(R$^{12}$)C(O)—R$^{12}$, —N(R$^{12}$)C(O)O—R$^{12}$, —N(R$^{12}$)C(O)N(R$^{13}$)(R$^{14}$), —N(R$^{12}$)S(O)$_2$(R$^{12}$), —NR$^{12}$S(O)$_2$N(R$^{13}$)(R$^{14}$), —NR$^{12}$S(O)$_2$O(R$^{12}$), —OC(O)R$^{12}$, —OC(O)—N(R$^{13}$)(R$^{14}$), —P(O)$_2$(OR$^{12}$)$_2$, —OP(O)(OR$^{12}$)$_2$, —CH$_2$P(O)(OR$^{12}$)$_2$, —OCH$_2$P(O)(OR$^{12}$)$_2$, —C(O)OCH$_2$P(O)(OR$^{12}$)$_2$, —P(O)(R$^{12}$)(OR$^{12}$), —OP(O)(R$^{12}$)(OR$^{12}$), —CH$_2$P(O)(R$^2$)(OR$^{12}$), —OCH$_2$P(O)(R$^{12}$)(OR$^{12}$), —C(O)OCH$_2$P(O)(R$^{12}$)(OR$^{12}$), —P(O)(N(R$^{12}$)$_2$)$_2$, —OP(O)(N(R$^{12}$)$_2$)$_2$, —CH$_2$P(O)(N(R$^{12}$)$_2$)$_2$, —OCH$_2$P(O)(N(R$^2$)$_2$)$_2$, —C(O))OCH$_2$P(O)(N(R$^{12}$)$_2$)$_2$, —P(O)(N(R$^{12}$)$_2$)(OR$^{12}$), —OP(O)(N(R$^{12}$)$_2$)(OR$^{12}$), —CH$_2$P(O)(N(R$^{12}$)$_2$)(OR$^{12}$), —OCH$_2$P(O)(N(R$^{12}$)$_2$)(OR$^{12}$), —C(O)OCH$_2$P(O)(N(R$^{12}$)$_2$)(OR$^{12}$), —P(O)(R$^{12}$)(N(R$^{12}$)$_2$), —OP(O)(R$^{12}$)(N(R$^{12}$)$_2$), —CH$_2$P(O)(R$^{12}$)(N(R$^{12}$)$_2$), —C(O)OCH$_2$P(O)(R$^{12}$)(N(R$^{12}$)$_2$), —Si(R$^{12}$)$_3$, —S—R$^{12}$, —S(O)R$^{12}$, —S(O)(NH)R$^{12}$, —S(O)$_2$R$^{12}$ or —S(O)$_2$N(R$^{13}$)(R$^{14}$);
  wherein any alkyl, alkenyl, alkynyl, cycloalkyl, haloalkyl, aryl, heteroaryl or heterocyclyl is optionally substituted with one to four Z$^{1a}$ groups;

each $Z^{1a}$ is independently oxo, halo, thioxo, —NO$_2$, —CN, —N$_3$, C$_{1-9}$ alkyl, C$_{2-6}$ alkenyl, C$_{2-6}$ alkynyl, C$_{3-15}$ cycloalkyl, C$_{1-8}$ haloalkyl, aryl, heteroaryl, heterocyclyl, —O—R$^{12}$, —C(O)R$^{12}$, —C(O)O—R$^{12}$, —C(O)N(R$^{13}$)(R$^{14}$), —N(R$^{13}$)(R$^{14}$), —N(R$^{13}$)$_2$(R$^{14}$)$^+$, —N(R$^{12}$)—C(O)R$^{12}$, —N(R$^{12}$)C(O)O(R$^{12}$), —N(R$^{12}$)C(O)N(R$^{13}$)(R$^{14}$), —N(R$^{12}$)S(O)$_2$(R$^{12}$), —N(R$^{12}$)S(O)$_2$—N(R$^{13}$)(R$^{14}$), —N(R$^{12}$)S(O)$_2$O(R$^{12}$), —OC(O)R$^{12}$, —OC(O)OR$^{12}$, —OC(O)—N(R$^{13}$)(R$^{14}$), —Si(R$^{12}$)$_3$, —S—R$^{12}$, —S(O)R$^{12}$, —S(O)(NH)R$^{12}$, —S(O)$_2$R$^{12}$ or —S(O)$_2$N(R$^{13}$)(R$^{14}$);
  wherein any alkyl, alkenyl, alkynyl, cycloalkyl, aryl, heteroaryl or heterocyclyl is optionally substituted with one to four Z$^{1b}$ groups;

each $R^{12}$ is independently hydrogen, C$_{1-9}$ alkyl, C$_{2-6}$ alkenyl, C$_{2-6}$ alkynyl, C$_{3-15}$ cycloalkyl, aryl, heteroaryl or heterocyclyl,
  wherein any alkyl, alkenyl, alkynyl, cycloalkyl, aryl, heteroaryl or heterocyclyl is optionally substituted with one to four Z$^{1b}$ groups;

$R^{13}$ and $R^{14}$ at each occurrence are each independently hydrogen, C$_{1-9}$ alkyl, C$_{2-6}$ alkenyl, C$_{2-6}$ alkynyl, C$_{3-15}$ cycloalkyl, aryl, heteroaryl or heterocyclyl;
  wherein any alkyl, alkenyl, alkynyl, cycloalkyl, aryl, heteroaryl or heterocyclyl is optionally substituted with one to four Z$^{1b}$ groups, or R$^{13}$ and R$^{14}$ together with the nitrogen to which they are attached form a heterocyclyl, wherein said heterocyclyl is optionally substituted with one to four Z$^{1b}$ groups;

each $R^{15}$ is independently halo, —CN, —NO$_2$, —O—R$^7$, —N(R$^8$)(R$^9$), —S(O)—R$^7$, —S(O)$_2$R$^7$, —S(O)$_2$N(R$^7$)$_2$, —C(O)R$^7$, —OC(O)—R$^7$, —C(O)O—R$^7$, —OC(O)O—R$^7$, —OC(O)N(R$^{10}$)(R$^{11}$), —C(O)N(R$^7$)$_2$, —N(R$^7$)C(O)(R$^7$), C$_{1-9}$ alkyl, C$_{2-6}$ alkenyl, C$_{2-6}$ alkynyl, C$_{1-9}$ alkylthio, C$_{1-6}$ haloalkyl, C$_{3-15}$ cycloalkyl, aryl, heterocyclyl, or heteroaryl; and each $Z^{1b}$ is independently oxo, thioxo, hydroxy, halo, —NO$_2$, —N$_3$, —CN, C$_{1-9}$ alkyl, C$_{2-6}$ alkenyl, C$_{2-6}$ alkynyl, C$_{3-15}$ cycloalkyl, C$_{1-8}$ haloalkyl, aryl, heteroaryl, heterocyclyl, —O(C$_{1-9}$ alkyl), —O(C$_{2-6}$ alkenyl), —O(C$_{2-6}$ alkynyl), —O(C$_{3-15}$ cycloalkyl), —O(C$_{1-8}$ haloalkyl), —O(aryl), —O(heteroaryl), —O(heterocyclyl), —NH$_2$, —NH(C$_{1-9}$ alkyl), —NH(C$_{2-6}$ alkenyl), —NH(C$_{2-6}$ alkynyl), —NH(C$_{3-15}$ cycloalkyl), —NH(C$_{1-8}$ haloalkyl), —NH(aryl), —NH(heteroaryl), —NH(heterocyclyl), —N(C$_{1-9}$ alkyl)$_2$, —N(C$_{2-6}$ alkenyl)$_2$, —N(C$_{2-6}$ alkynyl)$_2$, —N(C$_{3-15}$ cycloalkyl)$_2$, —N(C$_{1-8}$ haloalkyl)$_2$, —N(aryl)$_2$, —N(heteroaryl)$_2$, —N(heterocyclyl)$_2$, —N(C$_{1-9}$ alkyl)(C$_{2-6}$ alkenyl), —N(C$_{1-9}$ alkyl)(C$_{2-6}$ alkynyl), —N(C$_{1-9}$ alkyl)(C$_{3-15}$ cycloalkyl), —N(C$_{1-9}$ alkyl)(C$_{1-8}$ haloalkyl), —N(C$_{1-9}$ alkyl)(aryl), —N(C$_{1-9}$ alkyl)(heteroaryl), —N(C$_{1-9}$ alkyl)(heterocyclyl), —C(O)(C$_{1-9}$ alkyl), —C(O)(C$_{2-6}$ alkenyl), —C(O)(C$_{2-6}$ alkynyl), —C(O)(C$_{3-15}$ cycloalkyl), —C(O)(C$_{1-8}$ haloalkyl), —C(O)(aryl), —C(O)(heteroaryl), —C(O)(heterocyclyl), —C(O)O(C$_{1-9}$ alkyl), —C(O)O(C$_{2-6}$ alkenyl), —C(O)O(C$_{2-6}$ alkynyl), —C(O)O(C$_{3-15}$ cycloalkyl), —C(O)O(C$_{1-8}$ haloalkyl), —C(O)O(aryl), —C(O)O(heteroaryl), —C(O)O(heterocyclyl), —C(O)NH$_2$, —C(O)NH(C$_{1-9}$ alkyl), —C(O)NH(C$_{2-6}$ alkenyl), —C(O)NH(C$_{2-6}$ alkynyl), —C(O)NH(C$_{3-15}$ cycloalkyl), —C(O)NH(C$_{1-8}$ haloalkyl), —C(O)NH(aryl), —C(O)NH(heteroaryl), —C(O)NH(heterocyclyl), —C(O)N($C_{1-9}$ alkyl)$_2$, —C(O)N($C_{3-15}$ cycloalkyl)$_2$, —C(O)N($C_{2-6}$ alkenyl)$_2$, —C(O)N($C_{2-6}$ alkynyl)$_2$, —C(O)N($C_{1-8}$ haloalkyl)$_2$, —C(O)N(aryl)$_2$, —C(O)N(heteroaryl)$_2$, —C(O)N(heterocyclyl)$_2$, —NHC(O)($C_{1-9}$ alkyl), —NHC(O)($C_{2-6}$ alkenyl), —NHC(O)($C_{2-6}$ alkynyl), —NHC(O)($C_{3-15}$ cycloalkyl), —NHC(O)($C_{1-8}$ haloalkyl), —NHC(O)(aryl), —NHC(O)(heteroaryl), —NHC(O)(heterocyclyl), —NHC(O)O($C_{1-9}$ alkyl), —NHC(O)O($C_{2-6}$ alkenyl), —NHC(O)O($C_{2-6}$ alkynyl), —NHC(O)O($C_{3-15}$ cycloalkyl), —NHC(O)O($C_{1-8}$ haloalkyl), —NHC(O)O(aryl), —NHC(O)O(heteroaryl), —NHC(O)O(heterocyclyl), —NHC(O)NH($C_{1-9}$ alkyl), —NHC(O)NH($C_{2-6}$ alkenyl), —NHC(O)NH($C_{2-6}$ alkynyl), —NHC(O)NH($C_{3-15}$ cycloalkyl), —NHC(O)NH($C_{1-8}$ haloalkyl), —NHC(O)NH(aryl), —NHC(O)NH(heteroaryl), —NHC(O)NH(heterocyclyl), —SH, —S($C_{1-9}$ alkyl), —S($C_{2-6}$ alkenyl), —S($C_{2-6}$ alkynyl), —S($C_{3-15}$ cycloalkyl), —S($C_{1-8}$ haloalkyl), —S(aryl), —S(heteroaryl), —S(heterocyclyl), —NHS(O)($C_{1-9}$ alkyl), —N($C_{1-9}$ alkyl)(S(O)($C_{1-9}$ alkyl), —S(O)N($C_{1-9}$ alkyl)$_2$, —S(O)($C_{1-9}$ alkyl), —S(O)(NH)($C_{1-9}$ alkyl), —S(O)($C_{2-6}$ alkenyl), —S(O)($C_{2-6}$ alkynyl), —S(O)($C_{3-15}$ cycloalkyl), —S(O)($C_{1-8}$ haloalkyl), —S(O)(aryl), —S(O)(heteroaryl), —S(O)(heterocyclyl), —S(O)$_2$($C_{1-9}$ alkyl), —S(O)$_2$($C_{2-6}$ alkenyl), —S(O)$_2$($C_{2-6}$ alkynyl), —S(O)$_2$($C_{3-15}$ cycloalkyl), —S(O)$_2$($C_{1-8}$ haloalkyl), —S(O)$_2$(aryl), —S(O)$_2$(heteroaryl), —S(O)$_2$(heterocyclyl), —S(O)$_2$NH($C_{1-9}$ alkyl), or —S(O)$_2$N($C_{1-9}$ alkyl)$_2$;

wherein any alkyl, cycloalkyl, aryl, heteroaryl, or heterocyclyl is optionally substituted with one to four halo, $C_{1-9}$ alkyl, $C_{1-8}$ haloalkyl, —OH, —NH$_2$, —NH($C_{1-9}$ alkyl), —NH($C_{3-15}$ cycloalkyl), —NH($C_{1-8}$ haloalkyl), —NH(aryl), —NH(heteroaryl), —NH(heterocyclyl), —N($C_{1-9}$ alkyl)$_2$, —N($C_{3-15}$ cycloalkyl)$_2$, —NHC(O)($C_{3-15}$ cycloalkyl), —NHC(O)($C_{1-8}$ haloalkyl), —NHC(O)(aryl), —NHC(O)(heteroaryl), —NHC(O)(heterocyclyl), —NHC(O)O($C_{1-9}$ alkyl), —NHC(O)O($C_{2-6}$ alkynyl), —NHC(O)O($C_{3-15}$ cycloalkyl), —NHC(O)O($C_{1-8}$ haloalkyl), —NHC(O)O(aryl), —NHC(O)O(heteroaryl), —NHC(O)O(heterocyclyl), —NHC(O)NH($C_{1-9}$ alkyl), —S(O)(NH)($C_{1-9}$ alkyl), S(O)$_2$($C_{1-9}$ alkyl), —S(O)$_2$($C_{3-15}$ cycloalkyl), —S(O)$_2$($C_{1-8}$ haloalkyl), —S(O)$_2$(aryl), —S(O)$_2$(heteroaryl), —S(O)$_2$(heterocyclyl), —S(O)$_2$NH($C_{1-9}$ alkyl), —S(O)$_2$N($C_{1-9}$ alkyl)$_2$, —O($C_{3-15}$ cycloalkyl), —O($C_{1-8}$ haloalkyl), —O(aryl), —O(heteroaryl), —O(heterocyclyl), or —O($C_{1-9}$ alkyl);

m is 0, 1, or 2;

or a pharmaceutically acceptable salt, stereoisomer, mixture of stereoisomers, or deuterated analog thereof and a pharmaceutically acceptable carrier.

2. The method of claim 1, wherein the subject is a mammal.

3. The method according to claim 1, wherein the disease or condition is selected from systemic lupus erythematosus (SLE), myestenia gravis, rheumatoid arthritis (RA), acute disseminated encephalomyelitis, idiopathic thrombocytopenic purpura, multiple sclerosis (MS), inflammatory bowel disease (IBMD), sepsis, psoriasis, Sjoegren's syndrome, autoimmune hemolytic anemia, asthma, or chronic obstructive pulmonary disease (COPD), ankylosing spondylitis, reactive arthritis, monoarticular arthritis, osteoarthritis, gouty arthritis, juvenile arthritis, juvenile onset rheumatoid arthritis, juvenile rheumatoid arthritis, and psoriatic arthritis.

4. The method according to claim 1 wherein said disease or condition is selected from diversion colitis, ischemic colitis, infectious colitis, chemical colitis, microscopic colitis (including collagenous colitis and lymphocytic colitis), atypical colitis, pseudomembranous colitis, fulminant colitis, autistic enterocolitis, indeterminate colitis, Behçet's disease, gastroduodenal CD, jejunoileitis, ileitis, ileocolitis, Crohn's (granulomatous) colitis, irritable bowel syndrome, mucositis, radiation induced enteritis, short bowel syndrome, celiac disease, stomach ulcers, diverticulitis, pouchitis, proctitis, and chronic diarrhea.

5. The method according to claim 1 wherein said disease or condition is selected from systemic lupus erythematosus (SLE), lupus nephritis, lupus-related, and autoimmune disorders or a symptom of SLE.

6. The method according to claim 5 wherein said symptom of SLE is selected from joint pain, joint swelling, arthritis, fatigue, hair loss, mouth sores, swollen lymph nodes, sensitivity to sunlight, skin rash, headaches, numbness, tingling, seizures, vision problems, personality changes, abdominal pain, nausea, vomiting, abnormal heart rhythms, coughing up blood and difficulty breathing, patchy skin color and Raynaud's phenomenon.

7. The method of claim 1, wherein the disease or condition is inflammatory bowel disease (IBD).

8. The method of claim 7, wherein the disease or condition is ulcerative colitis.

9. The method of claim 7, wherein the disease or condition is Crohn's disease.

\* \* \* \* \*

UNITED STATES PATENT AND TRADEMARK OFFICE
CERTIFICATE OF CORRECTION

PATENT NO. : 11,066,414 B2
APPLICATION NO. : 16/717074
DATED : July 20, 2021
INVENTOR(S) : Elizabeth M. Bacon et al.

It is certified that error appears in the above-identified patent and that said Letters Patent is hereby corrected as shown below:

In the Claims

Column 805, Line 57, Claim 1, delete "—$CH_2P(O)(R^2)(OR^{12})$," and insert -- —$CH_2P(O)(R^{12})(OR^{12})$ --;

Column 805, Lines 59-60, Claim 1, delete "—$OCH_2P(O)(N(R^2)_2)_2$," and insert -- —$OCH_2P(O)(N(R^{12})_2)_2$, --;

Column 805, Line 60, Claim 1, delete "—$C(O))OCH_2P(O)(N(R^{12})_2)_2$," and insert -- —$C(O)OCH_2P(O)(N(R^{12})_2)_2$, --;

Column 807, Lines 20-21, Claim 1, delete "-$N(C_{1-9}$ alkyl$)(S(O)(C_{1-9}$ alkyl)" and insert -- , "-$N(C_{1-9}$ alkyl$)S(O)(C_{1-9}$ alkyl)" --;

Column 808, Line 9, Claim 3, delete "myestenia" and insert -- myasthenia --;

Column 808, Line 12, Claim 3, delete "(IBMD)" and insert -- (IBD) --.

Signed and Sealed this
Second Day of November, 2021

Drew Hirshfeld
*Performing the Functions and Duties of the*
*Under Secretary of Commerce for Intellectual Property and*
*Director of the United States Patent and Trademark Office*